US012643849B2

(12) United States Patent
Takahashi et al.

(10) Patent No.: US 12,643,849 B2
(45) Date of Patent: Jun. 2, 2026

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Yusuke Takahashi, Sodegaura (JP); Tasuku Haketa, Sodegaura (JP); Shota Tanaka, Sodegaura (JP); Hirokatsu Ito, Sodegaura (JP); Yu Kudo, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 1046 days.

(21) Appl. No.: 17/767,602

(22) PCT Filed: Oct. 9, 2020

(86) PCT No.: PCT/JP2020/038399
§ 371 (c)(1),
(2) Date: Apr. 8, 2022

(87) PCT Pub. No.: WO2021/070964
PCT Pub. Date: Apr. 15, 2021

(65) Prior Publication Data

US 2023/0227397 A1 Jul. 20, 2023

(30) Foreign Application Priority Data

Oct. 11, 2019 (JP) ................................ 2019-187783
Feb. 4, 2020 (JP) ................................ 2020-017406
(Continued)

(51) Int. Cl.
*C07C 211/54* (2006.01)
*C07D 307/91* (2006.01)
(Continued)

(52) U.S. Cl.
CPC .......... *C07C 211/54* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS 9,590,186 B2 3/2017 Itoi et al.
10,079,348 B2 9/2018 Jin et al.
(Continued)

FOREIGN PATENT DOCUMENTS

CN 106831313 A 6/2017
CN 108250083 A 7/2018
(Continued)

OTHER PUBLICATIONS

Machine translation of JP-2017022195-A (publication date Jan. 2017). (Year: 2017).*
(Continued)

*Primary Examiner* — Dawn L Garrett
(74) *Attorney, Agent, or Firm* — Oblon, McClelland, Maier & Neustadt, L.L.P.

(57) ABSTRACT

A compound may improve the capability of an organic EL device, and an organic electroluminescent device including such compound may have improved capability and may be included in electronic devices. Such compounds may be of formula (1A) or formula (1B) (wherein the symbols are as defined in the description)
(Continued)

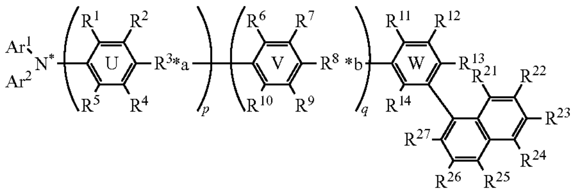

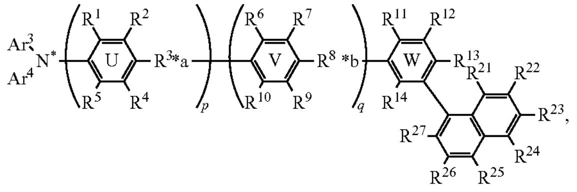

organic electroluminescent device(s) may contain such compound(s), and electronic device(s) may include such organic electroluminescent device(s).

14 Claims, 1 Drawing Sheet

(30) Foreign Application Priority Data

Mar. 25, 2020 (JP) ................................ 2020-054254
Jun. 5, 2020 (JP) ................................ 2020-098420

(51) Int. Cl.

*C07D 333/76* (2006.01)
*C07D 409/12* (2006.01)
*H10K 50/11* (2023.01)
*H10K 50/15* (2023.01)
*H10K 85/60* (2023.01)

(52) U.S. Cl.

CPC ........... *C07D 409/12* (2013.01); *H10K 50/11* (2023.02); *H10K 50/15* (2023.02); *H10K 85/615* (2023.02); *H10K 85/622* (2023.02); *H10K 85/626* (2023.02); *H10K 85/631* (2023.02); *H10K 85/633* (2023.02); *H10K 85/636* (2023.02); *H10K 85/6574* (2023.02); *H10K 85/6576* (2023.02); *C07B 2200/05* (2013.01)

(56) References Cited

U.S. PATENT DOCUMENTS

| | | | |
|---|---|---|---|
| 10,270,041 | B2 | 4/2019 | Suzuki et al. |
| 10,388,900 | B2 | 8/2019 | Seo et al. |
| 2016/0372677 | A1 | 12/2016 | Miyake |
| 2017/0012204 | A1 | 1/2017 | Jin et al. |
| 2017/0244047 | A1 | 8/2017 | Lee et al. |
| 2018/0331290 | A1 | 11/2018 | Miyake et al. |
| 2019/0237668 | A1 | 8/2019 | Miyake et al. |
| 2019/0237676 | A1 | 8/2019 | Miyake et al. |
| 2021/0066597 | A1 | 3/2021 | Miyake et al. |
| 2023/0055036 | A1 | 2/2023 | Miyake et al. |

FOREIGN PATENT DOCUMENTS

| | | | | |
|---|---|---|---|---|
| CN | 108863813 | A | 11/2018 | |
| CN | 106632185 | B | 4/2019 | |
| CN | 110078705 | A | 8/2019 | |
| EP | 3 401 313 | A1 | 11/2018 | |
| EP | 3 518 304 | A1 | 7/2019 | |
| JP | 2014-17389 | A | 1/2014 | |
| JP | 2017-22194 | A | 1/2017 | |
| JP | 2017-22195 | A | 1/2017 | |
| JP | 6085354 | B2 | 2/2017 | |
| JP | 2019-57484 | A | 4/2019 | |
| KR | 10-2017-0094665 | A | 8/2017 | |
| KR | 10-2017-0100709 | A | 9/2017 | |
| KR | 10-2017-0134163 | A | 12/2017 | |
| KR | 10-1961346 | B1 | 3/2019 | |
| WO | WO 2009/139358 | A1 | 11/2009 | |
| WO | WO-2016072691 | A1 * | 5/2016 | ............. C09K 11/06 |
| WO | WO 2018/168991 | A1 | 9/2018 | |
| WO | WO 2019/146781 | A1 | 8/2019 | |
| WO | WO 2019/168320 | A1 | 9/2019 | |
| WO | WO 2019/168367 | A1 | 9/2019 | |

OTHER PUBLICATIONS

Machine translation of KR 10-2017-0134163 A (publication date Dec. 2017). (Year: 2017).*
European Office Action issued Nov. 13, 2024, in European Patent Application No. 20875400.2, 6 pages.
International Search Report issued Dec. 15, 2020 in PCT/JP2020/038399 filed Oct. 9, 2020, 2 pages.
Combined Chinese Office Action and Search Report issued Oct. 28, 2023 in Chinese Patent Application No. 202080070566.5 (with unedited computer-generated English Translation), 32 pages.
Chinese Office Action issued Jul. 24, 2024 in Chinese Patent Application No. 202080070566.5 (with English translation), 9 pages.
Extended European Search Report issued Oct. 4, 2023 in European Application 20875400.2, 11 pages.
Officail Communication issued Feb. 13, 2026, in Korean Patent Application No. 10-2024-7028734 with English translation, 22 pages.

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

CROSS-REFERENCE TO RELATED APPLICATIONS

The present application is the national stage of international application PCT/JP2020/038399, filed on Oct. 9, 2020, and claims the benefit of the filing date of Japanese Appl. No. 2019-187783, 2020-017406, 2020-054254, and 2020-098420, respectively filed on Oct. 11, 2019, and Feb. 4, Mar. 25, and Jun. 5, 2020.

TECHNICAL FIELD

The present invention relates to a compound, a material for organic electroluminescent devices, an organic electroluminescent device, and an electronic device including the organic luminescent device.

BACKGROUND ART

In general, an organic electroluminescent device (which may be hereinafter referred to as an "organic EL device") is constituted by an anode, a cathode, and an organic layer intervening between the anode and the cathode. In application of a voltage between both the electrodes, electrons from the cathode side and holes from the anode side are injected into a light emitting region, and the injected electrons and holes are recombined in the light emitting region to generate an excited state, which then returns to the ground state to emit light. Accordingly, development of a material that efficiently transports electrons or holes into the light emitting region, and promotes recombination of the electrons and holes is important for providing a high-performance organic EL device.

PTLs 1 to 16 describe compounds used for materials for organic electroluminescent devices.

CITATION LIST

Patent Literatures

PTL 1: WO2019/146781A1
PTL 2: US2017/244047A1

PTL 6: JP06085354B2
PTL 7: U.S. Pat. No. 9,590,186B2
PTL 8: U.S. Pat. No. 10,079,348B2
PTL 9: JP2017022194A
PTL 10: WO2018/168991A1
PTL 11: KR10-2017-0094665
PTL 12: CN106831313A
PTL 13: WO2009/139358A1
PTL 14: U.S. Pat. No. 10,388,900B2
PTL 15: U.S. Pat. No. 10,270,041B2
PTL 16: US2019/0237668A1

SUMMARY OF INVENTION

Technical Problem

Heretofore, various compounds for organic EL devices have been reported, but a compound that further enhances the capability of an organic EL device has been still demanded.

The present invention has been made for solving the problem, and an object thereof is to provide a compound that further improves the capability of an organic EL device, an organic EL device having a further improved device capability, and an electronic device including the organic EL device.

Solution to Problem

As a result of the continued investigations by the present inventors on the capabilities of organic EL devices containing the compounds described in PTLs 1 to 16 and other compounds, it has been found that a monoamine in which one having a group that has an m-(1-naphthyl)phenyl group at the terminal bonds to the central nitrogen atom, and the remaining two each having a specific aryl group bonds thereto, or a monoamine in which one having a group that has an m-(1-naphthyl)phenyl group at the terminal bonds to the central nitrogen atom, and one of the remaining two having a specific aryl group and the other having a specific heteroaryl group bond thereto, or both the remaining two each having a specific heteroaryl group bond to the central nitrogen atom, can provide an organic EL device having a further improved capability.

In one embodiment, the present invention provides a compound represented by the following formula (1A):

(1A)

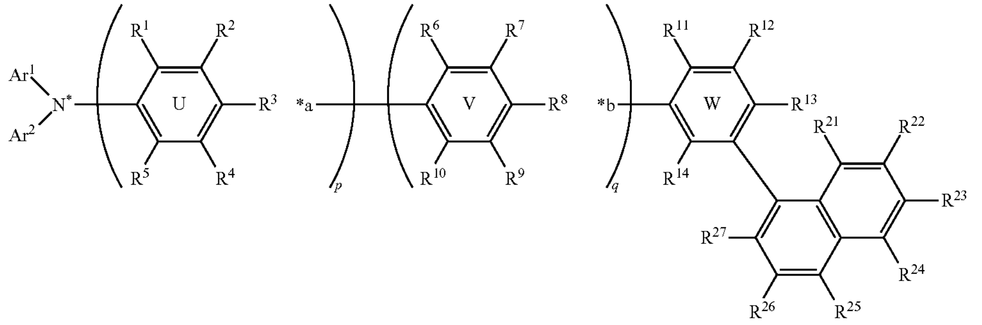

PTL 3: KR10-1961346
PTL 4: CN108250083A
PTL 5: CN106632185B

In the formula (1A),

N* is a central nitrogen atom, p represents 0 or 1, q represents 0 or 1, provided that p+q≥1, when p is 0 and q is 1, *a bonds to the nitrogen atom N*, one selected from $R^6$ to $R^{10}$ is a single bond bonding to *b, when p is 1 and q is 0, one selected from $R^1$ to $R^5$ is a single bond bonding to *b, when p is 1 and q is 1, one selected from $R^1$ to $R^5$ is a single bond bonding to *a, and one selected from $R^6$ to $R^{10}$ is a single bond bonding to *b, $R^1$ to $R^5$ that are not a single bond bonding to *a or *b, $R^6$ to $R^{10}$ that are not a single bond bonding to *b, $R^{11}$ to $R^{14}$, and $R^{21}$ to $R^{27}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, adjacent two selected from $R^1$ to $R^5$ that are not a single bond, adjacent two selected from $R^6$ to $R^{10}$ that are not a single bond, adjacent two selected from $R^{11}$ to $R^{14}$ that are not a single bond, and adjacent two selected from $R^{21}$ to $R^{27}$ do not bond to each other and therefore do not form a cyclic structure, provided that one or more pairs of two benzene rings bonding to each other selected from the benzene ring U, the benzene ring V and the benzene ring W may be crosslinked with $CR^xR^y$ to form a substituted or unsubstituted fluorene structure, or may not be crosslinked and may not form a fluorene structure, $R^x$ and $R^y$ each independently represent a substituted or unsubstituted alkyl group having 1 to 50 carbon atoms or a substituted or unsubstituted aryl group having 6 to 50 ring carbon atoms, and $R^x$ and $R^y$ may bond via a single bond, $Ar^1$ and $Ar^2$ each are independently represented by any of the following formulae (1-a) to (1-e):

(1-a)

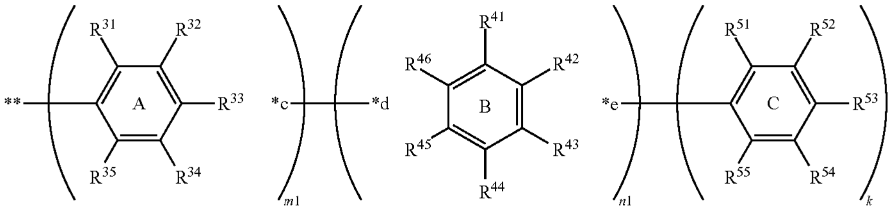

(1-b)

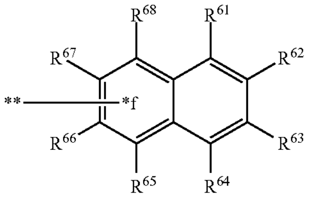

(1-c)

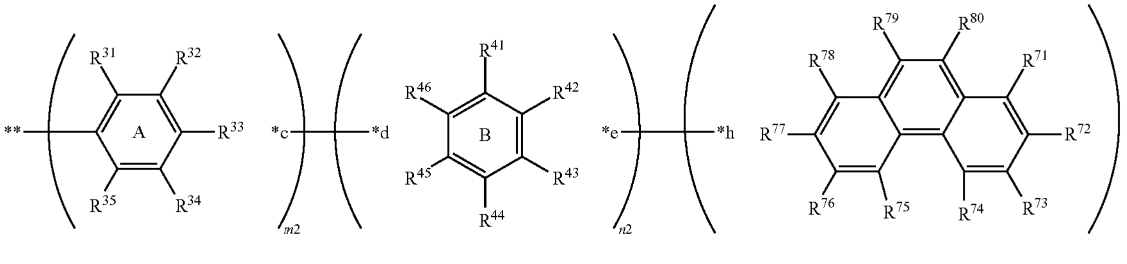

-continued (1-d)

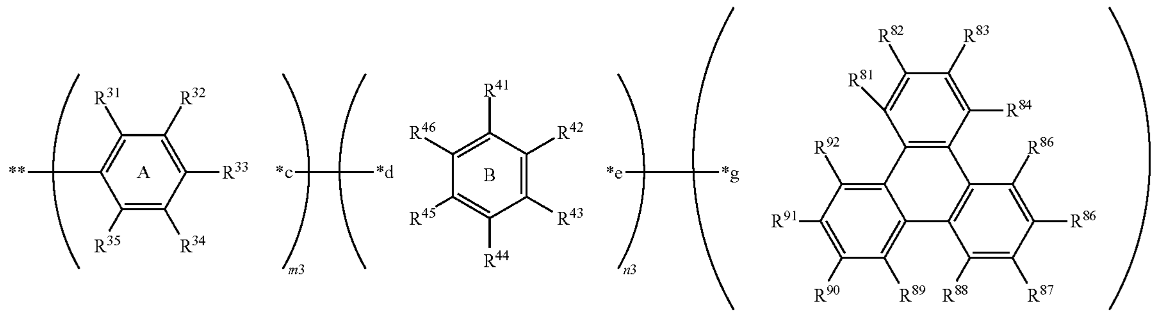

(1-e)

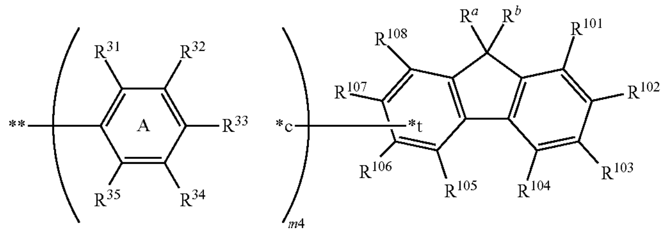

In the formula (1-a), $R^{31}$ to $R^{35}$, $R^{41}$ to $R^{46}$, and $R^{51}$ to $R^{55}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{31}$ to $R^{35}$ is a single bond bonding to *c, one selected from $R^{41}$ to $R^{46}$ is a single bond bonding to *d, and the other one selected from $R^{41}$ to $R^{46}$ is a single bond bonding to *e,

* is a bonding position to the nitrogen atom N*, m1 represents 0 or 1, and n1 represents 0 or 1, when m1 is 0 and n1 is 0, *e bonds to the nitrogen atom N*, when m1 is 0 and n1 is 1, *c bonds to the nitrogen atom N*, when m1 is 1 and n1 is 0, one selected from $R^{31}$ to $R^{35}$ is a single bond bonding to *e, k represents 1 or 2, adjacent two selected from $R^{31}$ to $R^{35}$ that are not a single bond, adjacent two selected from $R^{41}$ to $R^{46}$ that are not a single bond, and adjacent two selected from $R^{51}$ to $R^{55}$ do not bond to each other and therefore do not form a cyclic structure, the benzene ring A and the benzene ring B, the benzene ring A and the benzene ring C, and the benzene ring B and the benzene ring C do not crosslink;

In the formula (1-b), $R^{61}$ to $R^{68}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that one selected from $R^{61}$ to $R^{68}$ is a single bond bonding to *f, ** represents a bonding position to the nitrogen atom N*, adjacent two selected from $R^{61}$ to $R^{68}$ that are not a single bond do not bond to each other and therefore do not form a cyclic structure;

In the formula (1-c), $R^{31}$ to $R^{35}$, $R^{41}$ to $R^{46}$, **, *c, *d, and *e are the same as above, $R^{71}$ to $R^{80}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{71}$ to $R^{80}$ is a single bond bonding to *h, m2 represents 0 or 1, n2 represents 0 or 1, when m2 is 0 and n2 is 0, *e bonds to the nitrogen atom N*, when m2 is 0 and n2 is 1, *c bonds to the nitrogen atom N*, when m2 is 1 and n2 is 0, one selected from $R^{31}$ to $R^{35}$ is a single bond bonding to *e, adjacent two selected from $R^{31}$ to $R^{35}$ that are not a single bond, adjacent two selected from $R^{41}$ to $R^{46}$ that are not a single bond, and adjacent two selected from $R^{71}$ to $R^{80}$ do not bond to each other and therefore do not form a cyclic structure, the benzene ring A and the benzene ring B do not crosslink;

In the formula (1-d), $R^{31}$ to $R^{35}$, $R^{41}$ to $R^{46}$, *c, *d, and *e are the same as above, $R^{81}$ to $R^{92}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{81}$ to $R^{92}$ is a single bond bonding to *g, m3 represents 0 or 1, n3 represents 0 or 1, when m3 is 0 and n3 is 0, *e bonds to the nitrogen atom N*, when m3 is 0 and n3 is 1, *c bonds to the nitrogen atom N*, when m3 is 1 and n3 is 0, one selected from $R^{31}$ to $R^{35}$ is a single bond bonding to *e, adjacent two selected from $R^{31}$ to $R^{35}$ that are not a single bond, adjacent two selected from $R^{41}$ to $R^{46}$ that are not a single bond, and adjacent two selected from $R^{81}$ to $R^{92}$ do not bond to each other and therefore do not form a cyclic structure, the benzene ring A and the benzene ring B do not crosslink;

In the formula (1-e), $R^{31}$ to $R^{35}$, **, and *c are the same as above, $R^{101}$ to $R^{108}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{101}$ to $R^{108}$ is a single bond bonding to *i, m4 represents 0 or 1, one of $R^a$ and $R^b$ is a substituted or unsubstituted aryl group having 6 to 50 ring carbon atoms, and the other is a substituted or unsubstituted alkyl group having 1 to 50 carbon atoms, or $R^a$ and $R^b$ each are independently a substituted or unsubstituted alkyl group having 1 to 50 ring carbon atoms, or a substituted or unsubstituted aryl group having 6 to 50 ring carbon atoms, adjacent two selected from $R^{101}$ to $R^{104}$ and $R^{105}$ to $R^{108}$ that are not a single bond do not bond to each other and therefore do not form a cyclic structure, provided that when $Ar^1$ is represented by the formula (1-e), m4 is 1, and when $Ar^2$ is represented by the formula (1-e), m4 is 0 or 1,

** represents a bonding position to the nitrogen atom N*.

Also in one embodiment, the present invention provides a compound represented by the following formula (1B):

(1B)

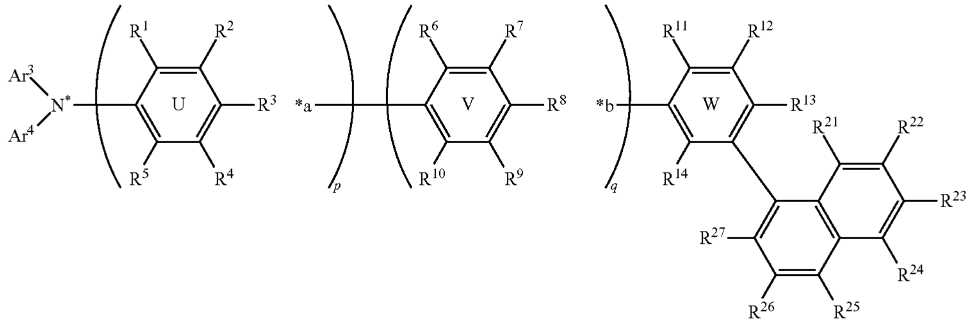

In the formula (1B),

N* is a central nitrogen atom, p represents 0 or 1, q represents 0 or 1, provided that p+q≥1, when p is 0 and q is 1, *a bonds to the nitrogen atom N*, and one selected from $R^6$ to $R^{10}$ is a single bond bonding to *b, when p is 1 and q is 0, one selected from $R^1$ to $R^5$ is a single bond bonding to *b, when p is 1 and q is 1, one selected from $R^1$ to $R^5$ is a single bond bonding to *a, and one selected from $R^6$ to $R^{10}$ is a single bond bonding to *b, $R^1$ to $R^5$ that are not a single bond bonding to *a or *b, and $R^6$ to $R^{10}$, $R^{11}$ to $R^{14}$, and $R^{21}$ to $R^{27}$ that are not a single bond bonding to *b each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, adjacent two selected from $R^1$ to $R^5$ that are not a single bond, adjacent two selected from $R^6$ to $R^{10}$ that are not a single bond, adjacent two selected from $R^{11}$ to $R^{14}$ that are not a single bond, and adjacent two selected from $R^{21}$ to $R^{27}$ do not bond to each other and therefore do not form a cyclic structure, provided that one or more pairs of two benzene rings bonding to each other selected from the benzene ring U, the benzene ring V and the benzene ring W may be crosslinked with $CR^xR^y$ to form a substituted or unsubstituted fluorene structure, or may not be crosslinked and may not form a fluorene structure, $R^x$ and $R^y$ each independently represent a substituted or unsubstituted alkyl group having 1 to 50 carbon atoms or a substituted or unsubstituted aryl group having 6 to 50 ring carbon atoms, and $R^x$ and $R^y$ may bond via a single bond, $Ar^3$ is represented by the following formula (1-f):

(1-f)

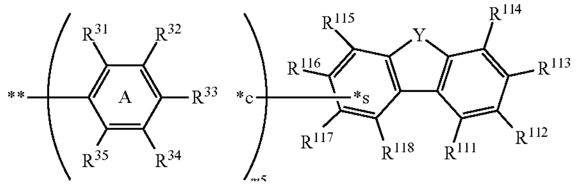

In the formula (1-f), $R^{31}$ to $R^{35}$ and $R^{111}$ to $R^{118}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{31}$ to $R^{35}$ is a single bond bonding to *c, and one selected from $R^{111}$ to $R^{118}$ is a single bond bonding to *s, X represents an oxygen atom or a sulfur atom, adjacent two selected from 111 to $R^{114}$ and $R^{115}$ to $R^{118}$ that are not a single bond do not bond to each other and therefore do not form a cyclic structure,

* represents a bonding position to the nitrogen atom N*, m5 represents 0 or 1, $Ar^4$ is represented by any of the following formulae (1-a), (1-b), (1-c), (1-d) and (1-g):

a substituted or unsubstituted haloalkyl group having 1 to 50 carbon atoms, a substituted or unsubstituted alkoxy group having 1 to 50 carbon atoms, (1-a)

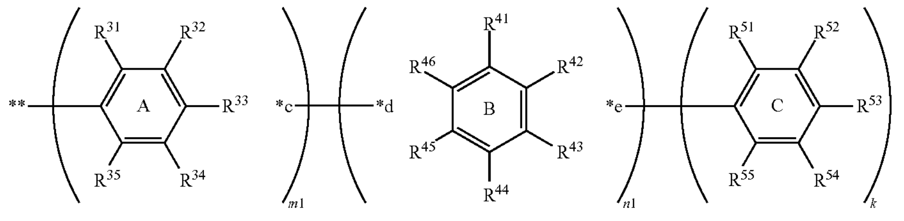

(1-b)

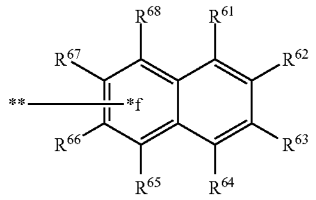

(1-c)

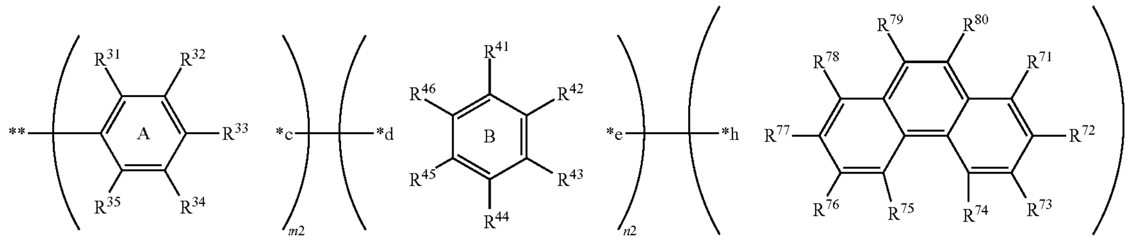

(1-d)

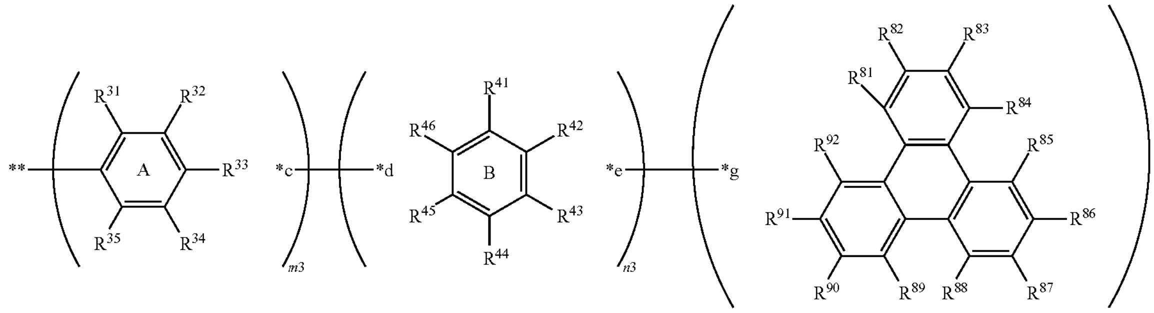

(1-g)

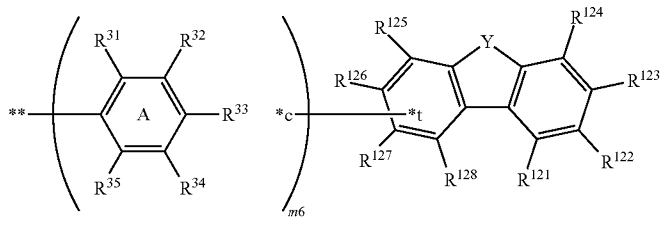

In the formula (1-a), $R^{31}$ to $R^{35}$, **, and *c are the same as above, $R^{41}$ to $R^{46}$, and $R^{51}$ to $R^{55}$ each independently represent, a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{41}$ to $R^{46}$ is a single bond bonding to *d, and the other one selected from $R^{41}$ to $R^{46}$ is a single bond bonding to *e, m1 represents 0 or 1, and n1 represents 0 or 1, when m1 is 0 and n1 is 0, *e bonds to the nitrogen atom N*, when m1 is 0 and n1 is 1, *c bonds to the nitrogen atom N*, when m1 is 1 and n1 is 0, one selected from $R^{31}$ to $R^{35}$ is a single bond bonding to *e, k represents 1 or 2, adjacent two selected from $R^{31}$ to $R^{35}$ that are not a single bond, adjacent two selected from $R^{41}$ to $R^{46}$ that are not a single bond, and adjacent two selected from $R^{51}$ to $R^{55}$ do not bond to each other and therefore do not form a cyclic structure, the benzene ring A and the benzene ring B, the benzene ring A and the benzene ring C, and the benzene ring B and the benzene ring C do not crosslink;

In the formula (1-b), $R^{61}$ to $R^{68}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that one selected from $R^{61}$ to $R^{68}$ is a single bond bonding to *f, ** represents a bonding position to the nitrogen atom N*, adjacent two selected from $R^{61}$ to $R^{68}$ that are not a single bond do not bond to each other and therefore do not form a cyclic structure;

In the formula (1-c), $R^{31}$ to $R^{35}$, $R^{41}$ to $R^{46}$, *c, *d, and *e are the same as above, $R^{71}$ to $R^{80}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{71}$ to $R^{80}$ is a single bond bonding to *h, m2 represents 0 or 1, n2 represents 0 or 1, when m2 is 0 and n2 is 0, *e bonds to the nitrogen atom N*, when m2 is 0 and n2 is 1, *c bonds to the nitrogen atom N*, when m2 is 1 and n2 is 0, one selected from $R^{31}$ to $R^{35}$ is a single bond bonding to *e, adjacent two selected from $R^{31}$ to $R^{35}$ that are not a single bond, adjacent two selected from $R^{41}$ to $R^{46}$ that are not a single bond, and adjacent two selected from $R^{71}$ to $R^{80}$ do not bond to each other and therefore do not form a cyclic structure, the benzene ring A and the benzene ring B do not crosslink;

In the formula (1-d), $R^{31}$ to $R^{35}$, $R^{41}$ to $R^{46}$, **, *c, *d, and *e are the same as above, $R^{81}$ to $R^{92}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{81}$ to $R^{92}$ is a single bond bonding to *g, m3 represents 0 or 1, n3 represents 0 or 1, when m3 is 0 and n3 is 0, *e bonds to the nitrogen atom N*, when m3 is 0 and n3 is 1, *c bonds to the nitrogen atom N*, when m3 is 1 and n3 is 0, one selected from $R^{31}$ to $R^{35}$ is a single bond bonding to *e, adjacent two selected from $R^{31}$ to $R^{35}$ that are not a single bond, adjacent two selected from $R^{41}$ to $R^{46}$ that are not a single bond, and adjacent two selected from $R^{81}$ to $R^{92}$ do not bond to each other and therefore do not form a cyclic structure, the benzene ring A and the benzene ring B do not crosslink;

In the formula (1-g), $R^{31}$ to $R^{35}$, **, *c and *i are the same as above, $R^{121}$ to $R^{128}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{121}$ to $R^{128}$ is a single bond bonding to *t, m6 represents 0 or 1, Y represents an oxygen atom, a sulfur atom, or $CR^cR^d$, one of $R^c$ and $R^d$ is a substituted or unsubstituted aryl group having 6 to 50 ring carbon atoms, and the other is a substituted or unsubstituted alkyl group having 1 to 50 carbon atoms, or $R^c$ and $R^d$ each are independently a substituted or unsubstituted alkyl group having 1 to 50 ring carbon atoms, or a substituted or unsubstituted aryl group having 6 to 50 ring carbon atoms, and the two aryl groups may bond to each other via a single bond, provided that when Y is $CR^cR^d$, $R^{121}$ to $R^{128}$ do not contain a substituted or unsubstituted aryl group having 6 to 50 ring carbon atoms, adjacent two selected from $R^{121}$ to $R^{124}$ and $R^{125}$ to $R^{128}$ that are not a single bond do not bond to each other and therefore do not form a cyclic structure.

In another embodiment, the present invention provides a material for an organic EL device containing the compound represented by the formula (1A) or the formula (1B).

In still another embodiment, the present invention provides an organic electroluminescent device including an anode, a cathode, and organic layers intervening between the anode and the cathode, the organic layers including a light emitting layer, at least one layer of the organic layers containing the compound represented by the formula (1A) or the formula (1B).

In a further embodiment, the present invention provides an electronic device including the organic electroluminescent device.

Advantageous Effects of Invention

An organic EL device containing the compound represented by the formula (1A) or the formula (1B) shows an improved device capability.

DESCRIPTION OF EMBODIMENTS

Definitions

Figure 1:
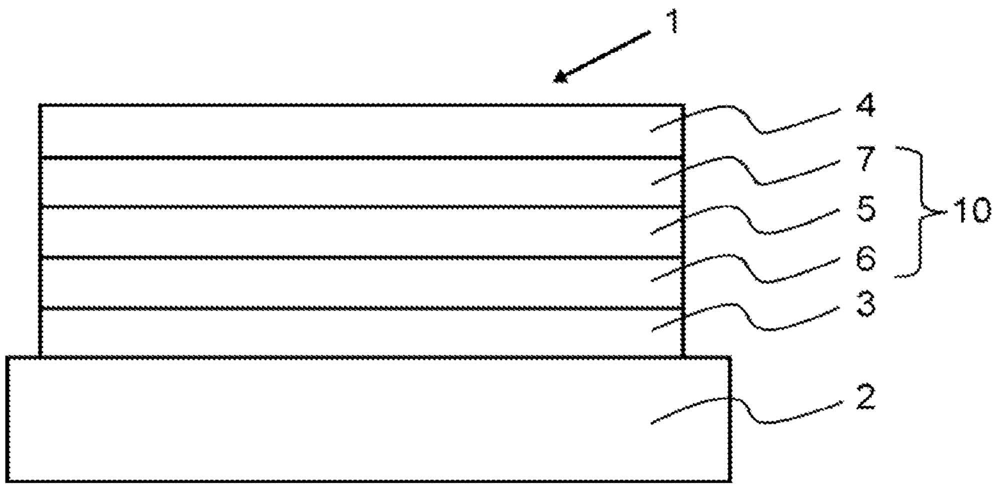
FIG. 1 is a schematic illustration showing an example of the layer configuration of the organic EL device according to one embodiment of the present invention.

In the description herein, the hydrogen atom encompasses isotopes thereof having different numbers of neutrons, i.e., a light hydrogen atom (protium), a heavy hydrogen atom (deuterium), and tritium.

In the description herein, the bonding site where the symbol, such as "R", or "D" representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly, a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly, a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms" described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly, a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly, a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A):

a phenyl group,
a p-biphenyl group,
a m-biphenyl group,
an o-biphenyl group, a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenarenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
monovalent aryl groups derived by removing one hydrogen atom from each of the ring structures represented by the following general formulae (TEMP-1) to (TEMP-15):

(TEMP-1)

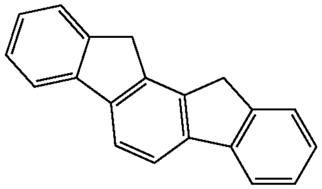

(TEMP-2)

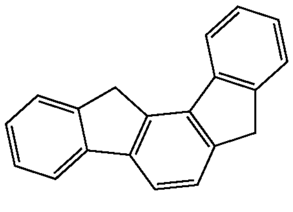

(TEMP-3)

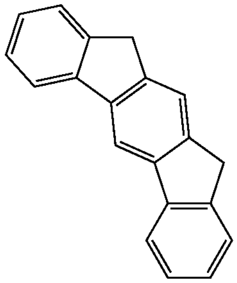

-continued (TEMP-4)

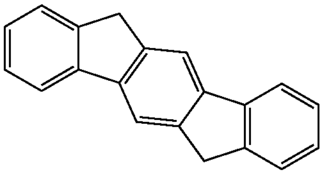

(TEMP-5)

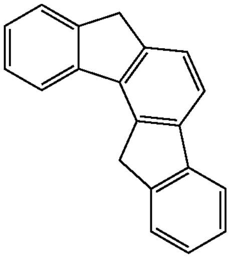

(TEMP-6)

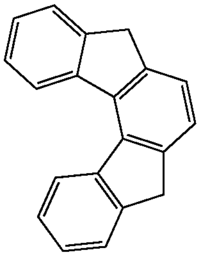

(TEMP-7)

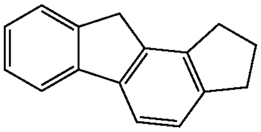

(TEMP-8)

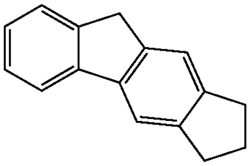

(TEMP-9)

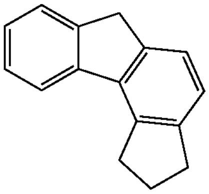

(TEMP-10)

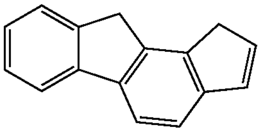

(TEMP-11)

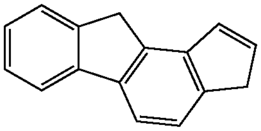

-continued (TEMP-12)

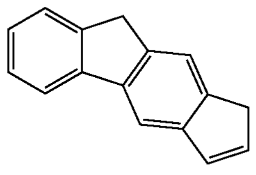

(TEMP-13)

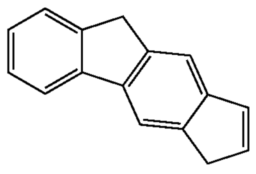

(TEMP-14)

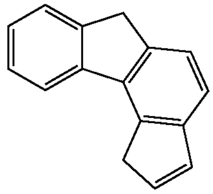

(TEMP-15)

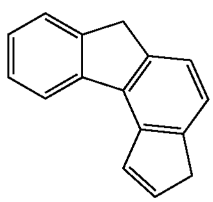

Substituted Aryl Group (Set of Specific Examples G1B)

- an o-tolyl group,
- a m-tolyl group,
- a p-tolyl group,
- a p-xylyl group,
- a m-xylyl group,
- an o-xylyl group,
- a p-isopropylphenyl group,
- a m-isopropylphenyl group,
- an o-isopropylphenyl group,
- a p-t-butylphenyl group,
- a m-t-butylphenyl group,
- a o-t-butylphenyl group,
- a 3,4,5-trimethylphenyl group,
- a 9,9-dimethylfluorenyl group,
- a 9,9-diphenylfluorenyl group,
- a 9,9-bis(4-methylphenyl)fluorenyl group,
- a 9,9-bis(4-isopropylphenyl)fluorenyl group,
- a 9,9-bis(4-t-butylphenyl)fluorenyl group,
- a cyanophenyl group,
- a triphenylsilylphenyl group,
- a trimethylsilylphenyl group,
- a phenylnaphthyl group,
- a naphthylphenyl group, and
- groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the "heterocyclic group" means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the "heterocyclic group" is a monocyclic group or a condensed ring group.

In the description herein, the "heterocyclic group" is an aromatic heterocyclic group or a non-aromatic heterocyclic group.

In the description herein, specific examples (set of specific examples G2) of the "substituted or unsubstituted heterocyclic group" include the unsubstituted heterocyclic groups (set of specific examples G2A) and the substituted heterocyclic groups (set of specific examples G2B) shown below. (Herein, the unsubstituted heterocyclic group means the case where the "substituted or unsubstituted heterocyclic group" is an "unsubstituted heterocyclic group", and the substituted heterocyclic group means the case where the "substituted or unsubstituted heterocyclic group" is a "substituted heterocyclic group".) In the description herein, the simple expression "heterocyclic group" encompasses both the "unsubstituted heterocyclic group" and the "substituted heterocyclic group".

The "substituted heterocyclic group" means a group formed by substituting one or more hydrogen atom of the "unsubstituted heterocyclic group" by a substituent. Specific examples of the "substituted heterocyclic group" include groups formed by substituting a hydrogen atom of each of the "unsubstituted heterocyclic groups" in the set of specific examples G2A by a substituent, and the examples of the substituted heterocyclic groups in the set of specific examples G2B. The examples of the "unsubstituted heterocyclic group" and the examples of the "substituted heterocyclic group" enumerated herein are mere examples, and the "substituted heterocyclic group" in the description herein encompasses groups formed by substituting a hydrogen atom bonded to the ring atom of the heterocyclic group itself of each of the "substituted heterocyclic groups" in the set of specific examples G2B by a substituent, and groups formed by substituting a hydrogen atom of the substituent of each of the "substituted heterocyclic groups" in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G2B4).

Unsubstituted Heterocyclic Group Containing Nitrogen Atom (Set of Specific Examples G2A1)

- a pyrrolyl group,
- an imidazolyl group,
- a pyrazolyl group,
- a triazolyl group,
- a tetrazolyl group,
- an oxazolyl group, an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolinyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing Oxygen Atom (Set of Specific Examples G2A2)

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing Sulfur Atom (Set of Specific Examples G2A3)

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group Derived by Removing One Hydrogen Atom from Ring Structures Represented by General Formulae (TEMP-16) to (TEMP-33) (Set of Specific Examples G2A4)

(TEMP-16)

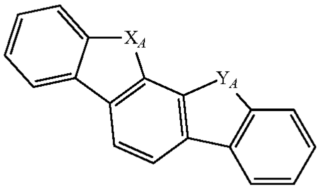

(TEMP-17)

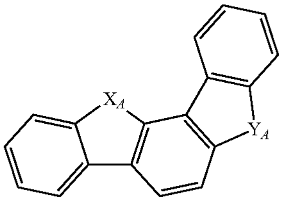

(TEMP-18)

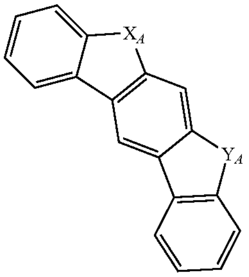

(TEMP-19)

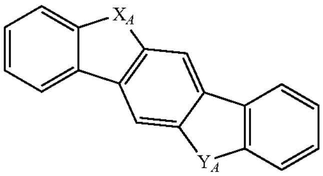

(TEMP-20)

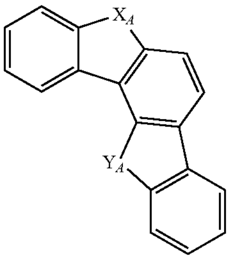

-continued (TEMP-21)

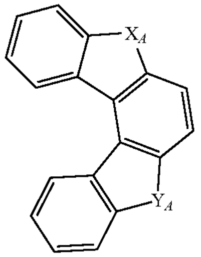

(TEMP-22)

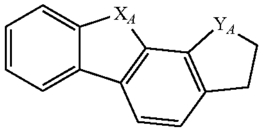

(TEMP-23)

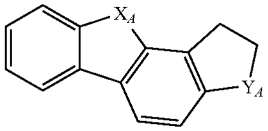

(TEMP-24)

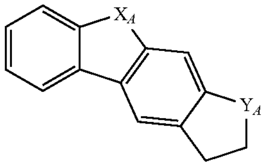

(TEMP-25)

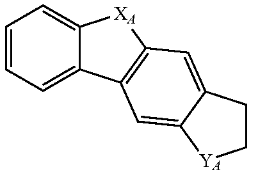

(TEMP-26)

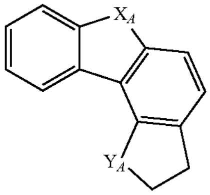

(TEMP-27)

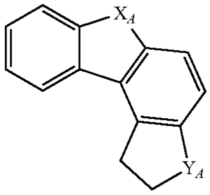

(TEMP-28)

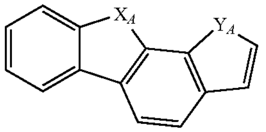

(TEMP-29)

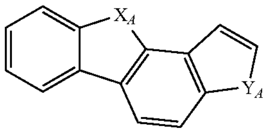

-continued (TEMP-30)'

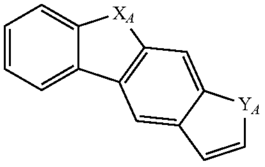

(TEMP-31)

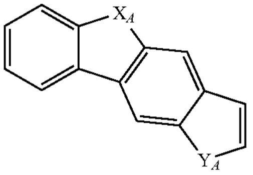

(TEMP-32)

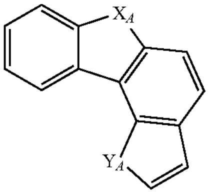

(TEMP-33)

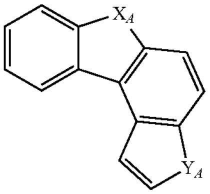

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-33), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group Containing Nitrogen Atom (Set of Specific Examples G2B1)

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenyltriazinyl group,
a diphenyltriazinyl group,
a phenylquinazolinyl group, and
a biphenylquinazolinyl group.

Substituted Heterocyclic Group Containing Oxygen Atom (Set of Specific Examples G2B2)

a phenyldibenzofuranyl group,
a methyldibenzofuranyl group,
a t-butyldibenzofuranyl group, and
a monovalent residual group of spiro[9H-xanthene-9,9'-[9H]fluorene].

Substituted Heterocyclic Group Containing Sulfur Atom (Set of Specific Examples G2B3)

a phenyldibenzothiophenyl group,
a methyldibenzothiophenyl group,
a t-butyldibenzothiophenyl group, and
a monovalent residual group of spiro[9H-thioxanthene-9, 9'-[9H]fluorene].

Group Formed by Substituting One or More Hydrogen Atom of Monovalent Heterocyclic Group Derived from Ring Structures Represented by General Formulae (TEMP-16) to (TEMP-33) by Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$ represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3A) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3A) by a substituent, and the examples of the substituted alkyl groups (set of specific examples G3B). In the description herein, the alkyl group in the "unsubstituted alkyl group" means a chain-like alkyl group. Accordingly, the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific Examples G3A)

a methyl group,
an ethyl group,
a n-propyl group,
an isopropyl group,
a n-butyl group,
an isobutyl group,
a s-butyl group, and
a t-butyl group.

Substituted Alkyl Group (Set of Specific Examples G3B)

a heptafluoropropyl group (including isomers),
a pentafluoroethyl group,
a 2,2,2-trifluoroethyl group, and
a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4A) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific Examples G4A)

a vinyl group,
an allyl group,
a 1-butenyl group,
a 2-butenyl group, and
a 3-butenyl group.

Substituted Alkenyl Group (Set of Specific Examples G4B)

a 1,3-butanedienyl group,
a 1-methylvinyl group,
a 1-methylallyl group,
a 1,1-dimethylallyl group,
a 2-methylallyl group, and
a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples GSA) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The "substituted alkynyl group" means a group formed by substituting one or more hydrogen atom of the "unsubstituted alkynyl group" by a substituent. Specific examples of the "substituted alkenyl group" include groups formed by substituting one or more hydrogen atom of the "unsubstituted alkynyl group" (set of specific examples G5A) by a substituent.

Unsubstituted Alkynyl Group (Set of Specific Examples G5A)

an ethynyl group.

Substituted or Unsubstituted Cycloalkyl Group

In the description herein, specific examples (set of specific examples G6) of the "substituted or unsubstituted cycloalkyl group" include the unsubstituted cycloalkyl groups (set of specific examples G6A) and the substituted cycloalkyl group (set of specific examples G6B) shown below. (Herein, the unsubstituted cycloalkyl group means the case where the "substituted or unsubstituted cycloalkyl group" is an "unsubstituted cycloalkyl group", and the substituted cycloalkyl group means the case where the "substituted or unsubstituted cycloalkyl group" is a "substituted cycloalkyl group".) In the description herein, the simple expression "cycloalkyl group" encompasses both the "unsubstituted cycloalkyl group" and the "substituted cycloalkyl group".

The "substituted cycloalkyl group" means a group formed by substituting one or more hydrogen atom of the "unsubstituted cycloalkyl group" by a substituent. Specific examples of the "substituted cycloalkyl group" include groups formed by substituting one or more hydrogen atom of each of the "unsubstituted cycloalkyl groups" (set of specific examples G6A) by a substituent, and the example of the substituted cycloalkyl group (set of specific examples G6B). The examples of the "unsubstituted cycloalkyl group" and the examples of the "substituted cycloalkyl group" enumerated herein are mere examples, and the "substituted cycloalkyl group" in the description herein encompasses groups formed by substituting one or more hydrogen atom bonded to the carbon atoms of the cycloalkyl group itself of the "substituted cycloalkyl group" in the set of specific examples G6B by a substituent, and groups formed by substituting a hydrogen atom of the substituent of the "substituted cycloalkyl group" in the set of specific examples G6B by a substituent.

Unsubstituted Cycloalkyl Group (Set of Specific Examples G6A)

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Set of Specific Examples G6B):

a 4-methylcyclohexyl group.

Group Represented by —Si($R_{901}$)($R_{902}$)($R_{903}$)

In the description herein, specific examples (set of specific examples G7) of the group represented by —Si($R^{901}$)($R^{902}$)($R^{903}$) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group Represented by —O—($R_{904}$)

In the description herein, specific examples (set of specific examples G8) of the group represented by —O—($R_{904}$) include:

—O(G1),
—O(G2),
—O(G3), and
—O(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and GG represents the "substituted or unsubstituted cycloalkyl group" described in the set of specific examples G6.

Group Represented by —S—($R_{905}$)

In the description herein, specific examples (set of specific examples G9) of the group represented by —S—($R^{905}$) include:

—S(G1),
—S(G2),
—S(G3), and
—S(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group Represented by —N($R^{906}$)($R^{907}$)

In the description herein, specific examples (set of specific examples G10) of the group represented by —N($R^{906}$)($R^{907}$) include:

—N(G1)(G1),
—N(G2)(G2),
—N(G1)(G2),
—N(G3)(G3), and
—N(G6)(G6).

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and GG represents the "substituted or unsubstituted cycloalkyl group" described in the set of specific examples GG.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)(G3)(G3), wherein G3 represents the "substituted or unsubstituted alkyl group" described in the set of specific examples G3. Plural groups represented by G3 in —Si(G3)(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly, the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α- naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranly group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl)carbazol-3-yl group, or a (9-phenyl) carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

(TEMP-Cz1)

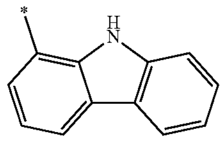

(TEMP-Cz2)

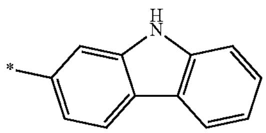

(TEMP-Cz3)

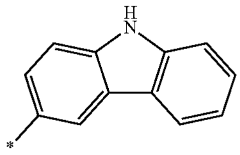

-continued (TEMP-Cz4)

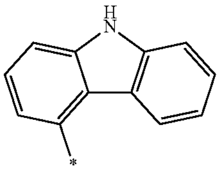

(TEMP-Cz5)

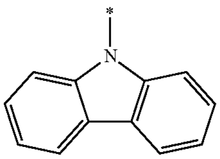

In the description herein, the (9-phenyl)carbazolyl group is specifically any one of the following groups unless otherwise indicated in the description.

(TEMP-Cz6)

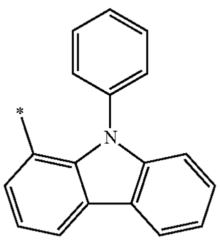

(TEMP-Cz7)

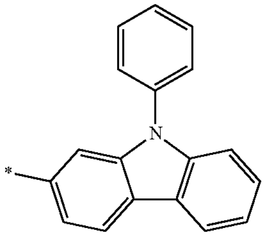

(TEMP-Cz8)

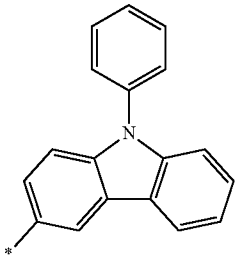

(TEMP-Cz9)

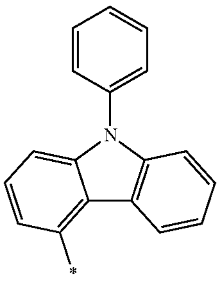

In the general formulae (TEMP-Cz1) to (TEMP-Cz9), * represents a bonding site.

In the description herein, the dibenzofuranyl group and the dibenzothiophenyl group are specifically any one of the following groups unless otherwise indicated in the description.

(TEMP-34)

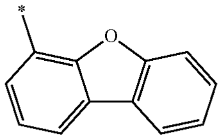

(TEMP-35)

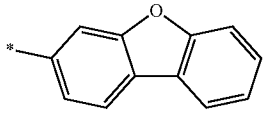

(TEMP-36)

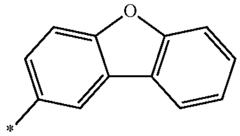

(TEMP-37)

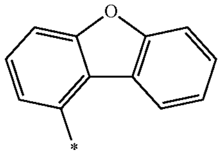

(TEMP-38)

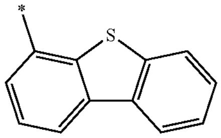

(TEMP-39)

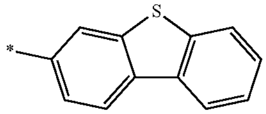

(TEMP-40)

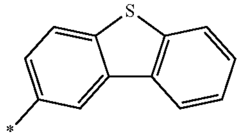

(TEMP-41)

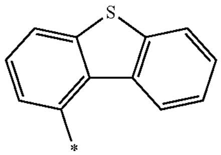

In the general formulae (TEMP-34) to (TEMP-41), * represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the “substituted or unsubstituted arylene group” is a divalent group derived by removing one hydrogen atom on the aryl ring from the “substituted or unsubstituted aryl group” described above unless otherwise indicated in the description. Specific examples (set of specific examples G12) of the “substituted or unsubstituted arylene group” include divalent groups derived by removing one hydrogen atom on the aryl ring from the “substituted or unsubstituted aryl groups” described in the set of specific examples G1.

Substituted or Unsubstituted Divalent Heterocyclic Group

In the description herein, the “substituted or unsubstituted divalent heterocyclic group” is a divalent group derived by removing one hydrogen atom on the heterocyclic ring from the “substituted or unsubstituted heterocyclic group” described above unless otherwise indicated in the description. Specific examples (set of specific examples G13) of the “substituted or unsubstituted divalent heterocyclic group” include divalent groups derived by removing one hydrogen atom on the heterocyclic ring from the “substituted or unsubstituted heterocyclic groups” described in the set of specific examples G2.

Substituted or Unsubstituted Alkylene Group

In the description herein, the “substituted or unsubstituted alkylene group” is a divalent group derived by removing one hydrogen atom on the alkyl chain from the “substituted or unsubstituted alkyl group” described above unless otherwise indicated in the description. Specific examples (set of specific examples G14) of the “substituted or unsubstituted alkylene group” include divalent groups derived by removing one hydrogen atom on the alkyl chain from the “substituted or unsubstituted alkyl groups” described in the set of specific examples G3.

In the description herein, the substituted or unsubstituted arylene group is preferably any one of the groups represented by the following general formulae (TEMP-42) to (TEMP-68) unless otherwise indicated in the description.

(TEMP-42)

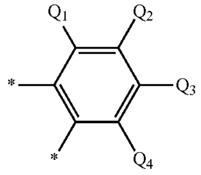

(TEMP-43)

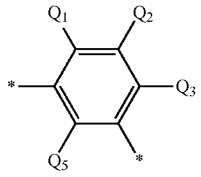

(TEMP-44)

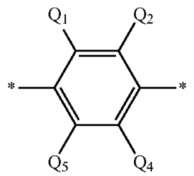

-continued
(TEMP-45)
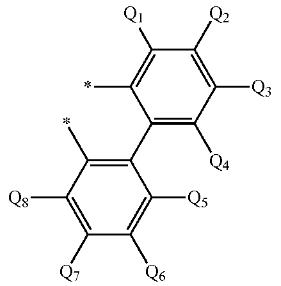
(TEMP-46)
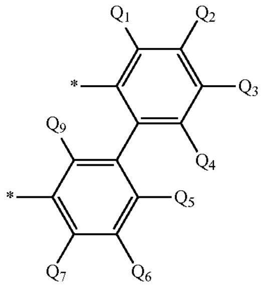
(TEMP-47)
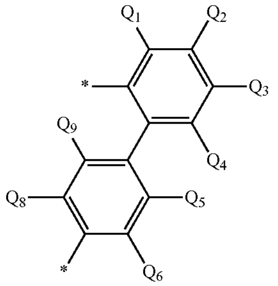
(TEMP-48)
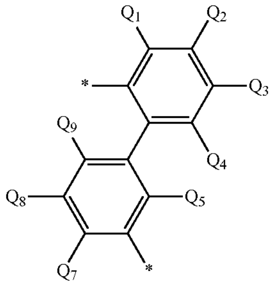
(TEMP-49)
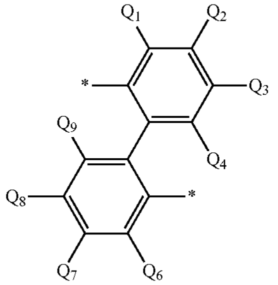
-continued
(TEMP-50)
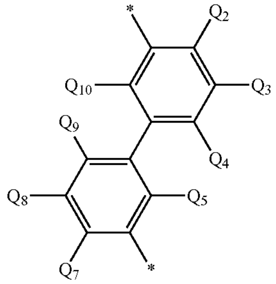
(TEMP-51)
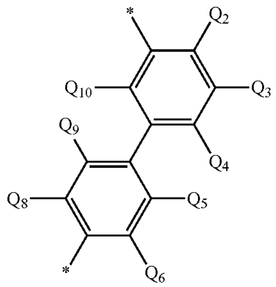
(TEMP-52)
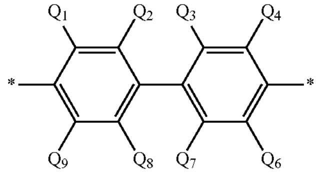
In the general formulae (TEMP-42) to (TEMP-52), $Q_1$ to $Q_{10}$ each independently represent a hydrogen atom or a substituent.
In the general formulae (TEMP-42) to (TEMP-52), * represents a bonding site.
(TEMP-53)
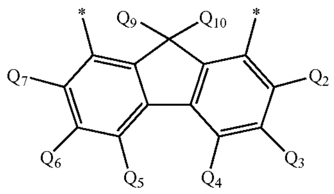
(TEMP-54)
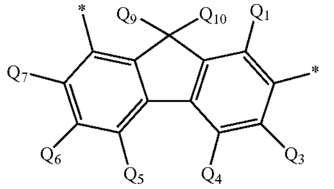
(TEMP-55)
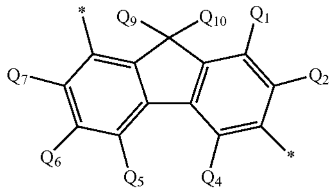

-continued (TEMP-56)

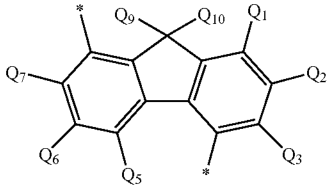

(TEMP-57)

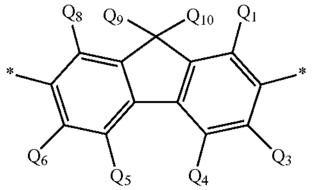

(TEMP-58)

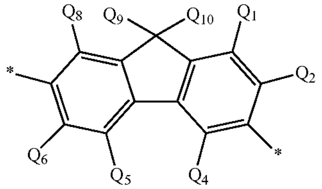

(TEMP-59)

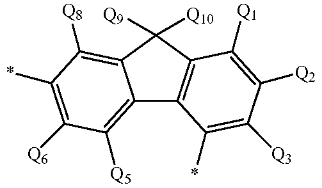

(TEMP-60)

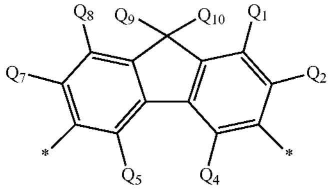

(TEMP-61)

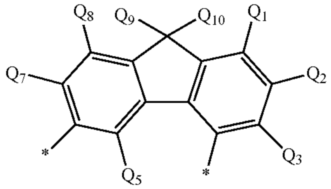

(TEMP-62)

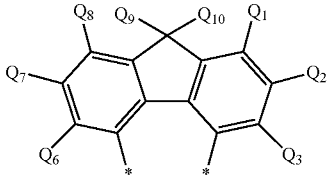

In the general formulae (TEMP-53) to (TEMP-62), $Q_1$ to $Q_{10}$ each independently represent a hydrogen atom or a substituent.

The formulae $Q_9$ and $Q_{10}$ may be bonded to each other to form a ring via a single bond.

In the general formulae (TEMP-53) to (TEMP-62), * represents a bonding site.

(TEMP-63)

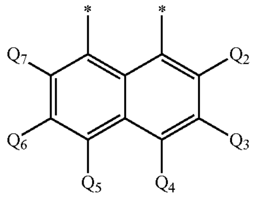

(TEMP-64)

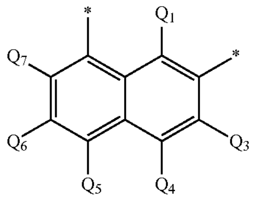

(TEMP-65)

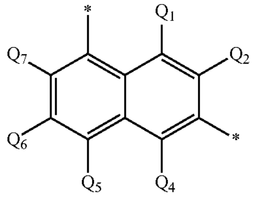

(TEMP-66)

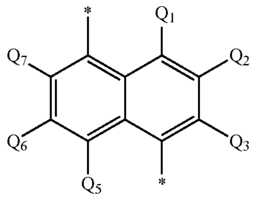

(TEMP-67)

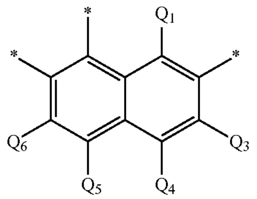

(TEMP-68)

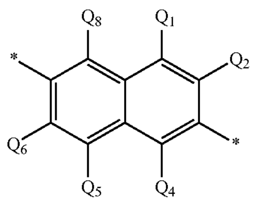

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae (TEMP-69) to (TEMP-102) unless otherwise indicated in the description.

-continued
(TEMP-69)
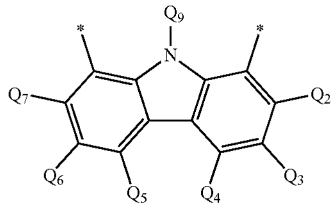
(TEMP-70)
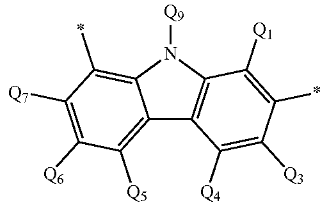
(TEMP-71)
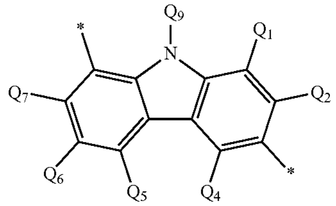
(TEMP-72)
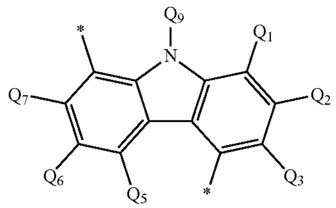
(TEMP-73)
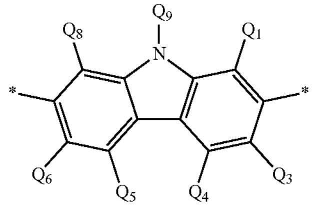
(TEMP-74)
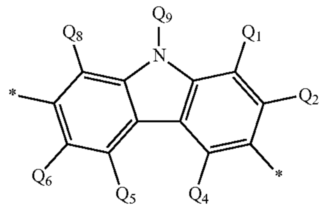
(TEMP-75)
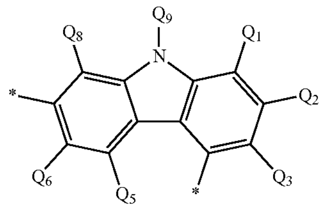
(TEMP-76)
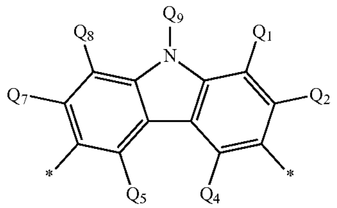
(TEMP-77)
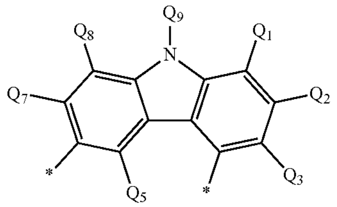
(TEMP-78)
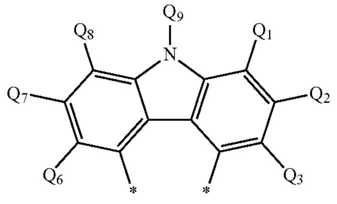
(TEMP-79)
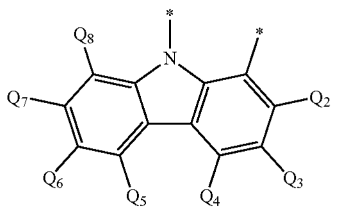
(TEMP-80)
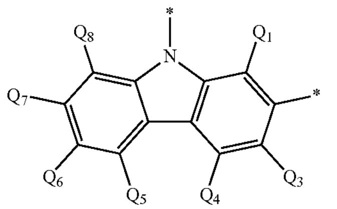
(TEMP-81)
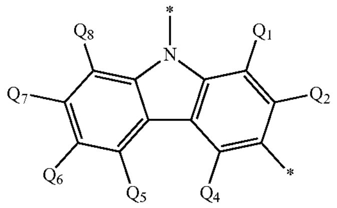
(TEMP-82)
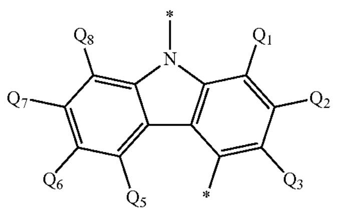
In the general formulae (TEMP-69) to (TEMP-82), $Q_1$ to $Q_9$ each independently represent a hydrogen atom or a substituent.

(TEMP-83)
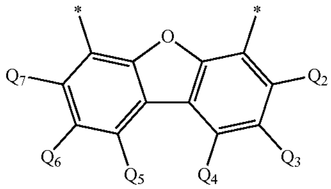
(TEMP-84)
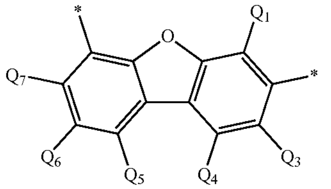
(TEMP-85)
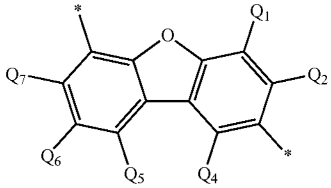
(TEMP-86)
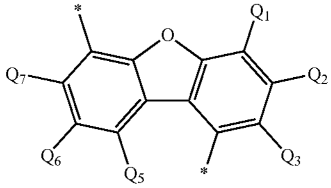
(TEMP-87)
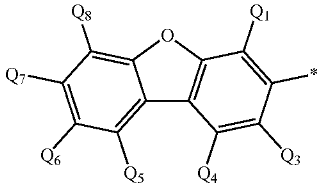
(TEMP-88)
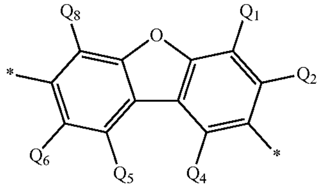
(TEMP-89)
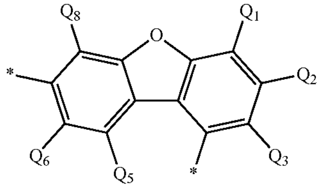
(TEMP-90
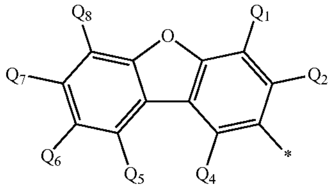
-continued
(TEMP-91)
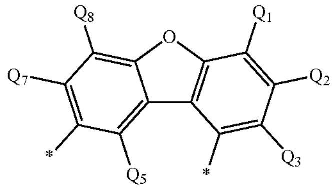
(TEMP-92)
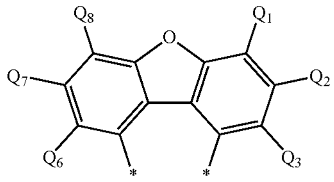
9TEMP-93)
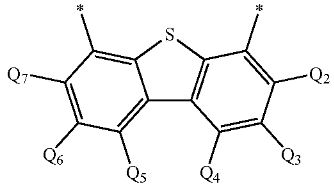
(TEMP-94)
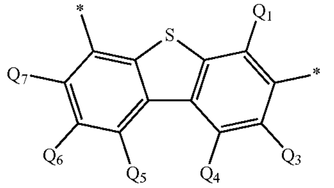
(TEMP-95)
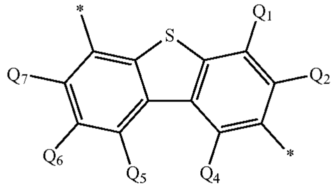
(TEMP-96)
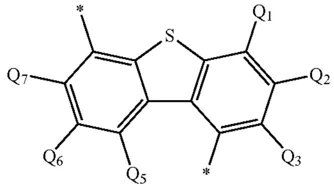
(TEMP-97)
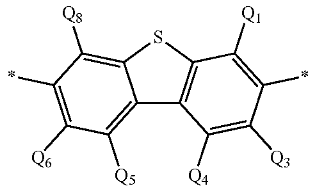
(TEMP-98)
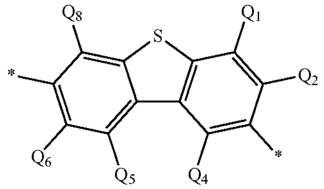

-continued (TEMP-99)

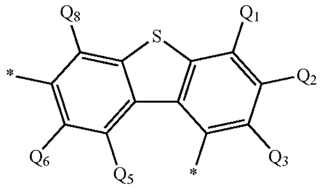

(TEMP-100)

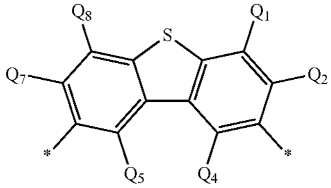

(TEMP-101)

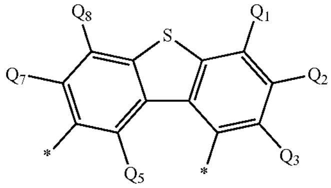

(TEMP-102)

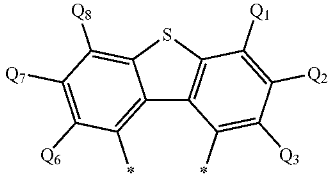

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

(TEMP-103)

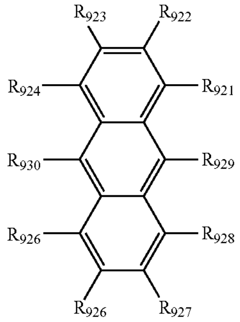

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

(TEMP-104)

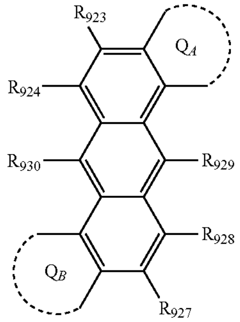

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

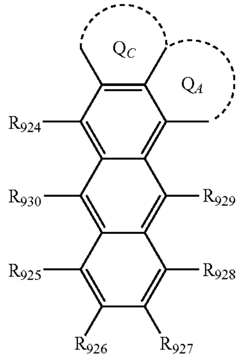

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TMEP-104) is a benzene ring, the ring $Q_A$ is a monocyclic ring. In the case where the ring $Q_A$ in the general formula (TMEP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to $R_{922}$, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms, wherein $R_{901}$ to 8907 each independently represent a hydrogen atom, a substituted or unsubstituted alkyl group having 1 to 50 carbon atoms a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the case where two or more groups each represented by $R_{901}$ exist, the two or more groups each represented by $R_{901}$ are the same as or different from each other, in the case where two or more groups each represented by $R_{902}$ exist, the two or more groups each represented by $R_{902}$ are the same as or different from each other, in the case where two or more groups each represented by $R_{903}$ exist, the two or more groups each represented by $R_{903}$ are the same as or different from each other, in the case where two or more groups each represented by $R_{904}$ exist, the two or more groups each represented by $R_{904}$ are the same as or different from each other, in the case where two or more groups each represented by $R_{905}$ exist, the two or more groups each represented by $R_{905}$ are the same as or different from each other, in the case where two or more groups each represented by $R_{903}$ exist, the two or more groups each represented by $R_{903}$ are the same as or different from each other, and in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of an alkyl group having 1 to 50 carbon atoms, an aryl group having 6 to 50 ring carbon atoms, and a heterocyclic group having 5 to 50 ring atoms.

In one embodiment, the substituent for the case of "substituted or unsubstituted" may be a group selected from the group consisting of an alkyl group having 1 to 18 carbon atoms, an aryl group having 6 to 18 ring carbon atoms, and a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the present invention will be described below.

The compound of the present invention is represented by the following formula (1A).

In the following description, the compounds of the present invention represented by the formula (1A) and the subordinate formulae of the formula (1A) described later each may be referred simply to as an "inventive compound A". Also, the compound of the present invention is represented by the following formula (1B). In the following description, the compounds of the present invention represented by the formula (1B) and the subordinate formulae of the formula (1B) described later each may be referred simply to as an "inventive compound B". Further, those including both the "inventive compound A" and the "inventive compound B" each may be referred simply to as an "inventive compound".

(1A)

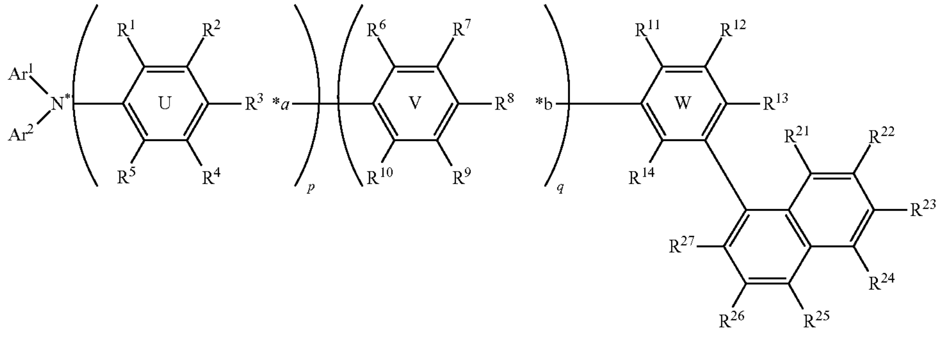

Hereinunder the symbols in the formula (1A) and in the subordinate formulae of the formula (1A) described later will be described. The same symbols have the same meanings.

In the formula (1A),

N* is a central nitrogen atom, p represents 0 or 1, q represents 0 or 1, provided that p+q≥1, when p is 0 and q is 1, *a bonds to the nitrogen atom N*, and one selected from $R^6$ to $R^{10}$ is a single bond bonding to *b, when p is 1 and q is 0, one selected from $R^1$ to $R^5$ is a single bond bonding to *b, when p is 1 and q is 1, one selected from $R^1$ to $R^5$ is a single bond bonding to *a, and one selected from $R^6$ to $R^{10}$ is a single bond bonding to *b.

$R^1$ to $R^5$ that are not a single bond bonding to *a or *b, $R^6$ to $R^{10}$ that are not a single bond bonding to *b, $R^{11}$ to $R^{14}$, and $R^{21}$ to $R^{27}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms.

Preferably, these are each independently a hydrogen atom, a substituted or unsubstituted alkyl group having 1 to 50 carbon atoms, or a substituted or unsubstituted cycloalkyl group having 3 to 50 ring carbon atoms, more preferably, each independently a hydrogen atom, or a substituted or unsubstituted alkyl group having 1 to 50 carbon atoms.

Details of the halogen atom are as described in the section of "Substituents in Description", and preferred is a fluorine atom.

Details of the substituted or unsubstituted alkyl group having 1 to 50 carbon atoms are as described in the section of "Substituents in Description".

The unsubstituted alkyl group is preferably a methyl group, an ethyl group, a n-propyl group, an isopropyl group, a n-butyl group, an isobutyl group, an s-butyl group, or a t-butyl group, more preferably a methyl group, an ethyl group, an isopropyl group, or a t-butyl group, even more preferably a methyl group or a t-butyl group.

Details of the substituted or unsubstituted cycloalkyl group having 3 to 50 ring carbon atoms are as described in the section of "Substituents in Description".

The unsubstituted cycloalkyl group is preferably a cyclopropyl group, a cyclobutyl group, a cyclopentyl group, or a cyclohexyl group, and more preferably a cyclopropyl group, a cyclopentyl group, or a cyclohexyl group.

Details of the substituted or unsubstituted haloalkyl group having 1 to 50 carbon atoms are as described in the section of "Substituents in Description", and preferred is a substituted or unsubstituted fluoroalkyl group having 1 to 50 carbon atoms.

The unsubstituted fluoroalkyl group is preferably a trifluoromethyl group, a 2,2,2-trifluoroethyl group, a pentafluoroethyl group, or a heptafluoropropyl group, more preferably a trifluoromethyl group.

Details of the substituted or unsubstituted alkoxy group having 1 to 50 carbon atoms are as described in the section of "Substituents in Description".

The unsubstituted alkoxy group is preferably a methoxy group, an ethoxy group, a propoxy group, or a t-butoxy group, more preferably a methoxy group or an ethoxy group, even more preferably a methoxy group.

The substituted or unsubstituted haloalkoxy group having 1 to 50 carbon atoms is a group represented by —O(G12), and G12 is a substituted or unsubstituted haloalkyl group described above.

The substituted or unsubstituted haloalkoxy group having 1 to 50 is preferably a substituted or unsubstituted fluoroalkoxy group having 1 to 50 carbon atoms.

The unsubstituted fluoroalkoxy group is preferably a trifluoromethoxy group, a 2,2,2-trifluoroethoxy group, a pentafluoroethoxy group, or a heptafluoropropoxy group, more preferably a trifluoromethoxy group, a 2,2,2-trifluoroethoxy group, or a pentafluoroethoxy group, even more preferably a trifluoromethoxy group.

Details of the substituted or unsubstituted aryloxy group having 6 to 50 ring carbon atoms are as described in the section of "Substituents in Description".

The unsubstituted aryloxy group is preferably a phenoxy group, a biphenyloxy group or a terphenyloxy group, more preferably a phenoxy group or a biphenyloxy group.

Details of the substituted or unsubstituted aralkyl group having 7 to 50 carbon atoms are as described in the section of "Substituents in Description".

The unsubstituted aralkyl group is preferably a benzyl group, a phenyl-t-butyl group, an α-naphthylmethyl group, a β-naphthylmethyl group, a 1-β-naphthylisopropyl group, or a 2-β-naphthylisopropyl group, more preferably a benzyl group, a phenyl-t-butyl group, an α-naphthylmethyl group or a β-naphthylmethyl group.

Details of the substituent for the mono, di or tri-substituted silyl group are as described in the section of "Substituents in Description".

The mono, di or tri-substituted silyl group is preferably a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group, more preferably a trimethylsilyl group or a triphenylsilyl group.

Adjacent two selected from $R^1$ to $R^5$ that are not a single bond, adjacent two selected from $R^6$ to $R^{10}$ that are not a single bond, adjacent two selected from $R^{11}$ to $R^{14}$ that are not a single bond, and adjacent two selected from $R^{21}$ to $R^{27}$ do not bond to each other and therefore do not form a cyclic structure.

However, in the above-mentioned formulae included in the formula (1A) and the formulae included in the formula (1) to be described later, one or more pairs of two benzene rings bonding to each other selected from the benzene ring U, the benzene ring V and the benzene ring W may be crosslinked with $CR^xR^y$ to form a substituted or unsubstituted fluorene structure, or may not be crosslinked and may not form a fluorene structure.

Namely, in the formula (1A), (1A)

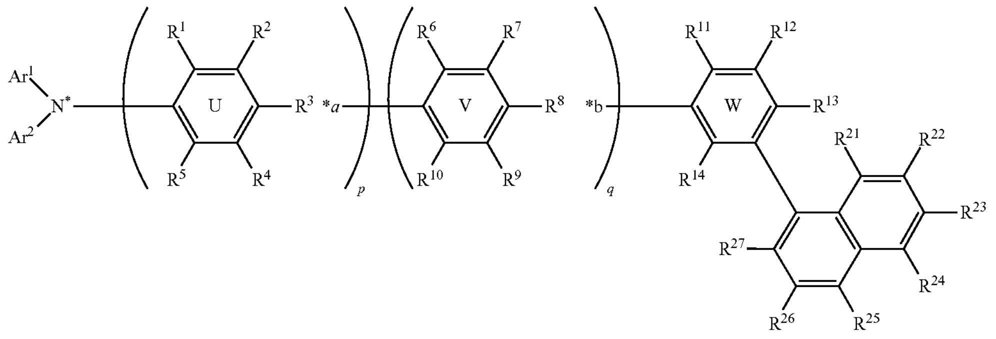

when p is 1 and q is 0, the benzene ring U and the benzene ring W bonding to each other may form a substituted or unsubstituted fluorene structure, or may not form it.

When p is 0 and q is 1, the benzene ring V and the benzene ring W bonding to each other may form a substituted or unsubstituted fluorene structure, or may not form it.

When p is 1 and q is 1, at least one pair of the two benzene rings bonding to each other selected from the benzene ring U and the benzene ring V bonding to each other, and the benzene ring V and the benzene ring W bonding to each other may form a substituted or unsubstituted fluorene structure, or may not form it.

In other words, when p is 1 and q is 0, one existing on the carbon atom adjacent to the carbon atom bonding to the benzene ring W, and selected from $R^1$ to $R^5$ may form a crosslinking group $CR^xR^y$ along with one of $R^{11}$ and $R^{44}$, or may not form $CR^xR^y$.

When p is 0 and q is 1, one existing on the carbon atom adjacent to the carbon atom bonding to the benzene ring W, and selected from $R^6$ to $R^{10}$ may form a crosslinking group $CR^xR^y$ along with one of $R^{11}$ and $R^{14}$, or may not form a crosslinking group $CR^xR^y$.

When p is 1 and q is 1, one existing on the carbon atom adjacent to the carbon atom bonding to the benzene ring V, and selected from $R^5$ to $R^9$ may form a crosslinking group $CR^xR^y$ along with one of $R^6$ and $R^{14}$, or may not form a crosslinking group $CR^xR^y$, one existing on the carbon atom adjacent to the carbon atom bonding to the benzene ring W, and selected from $R^6$ to $R^{10}$ may form a crosslinking group $CR^xR^y$ along with one of $R^{11}$ and $R^{44}$, or may not form a crosslinking group $CR^xR^y$.

In one embodiment of the present invention, preferably, two benzene rings bonding to each other are not crosslinked and do not form a substituted or unsubstituted fluorene structure. In another embodiment of the present invention, preferably, one pairs or more of two benzene rings bonding to each other are crosslinked with $CR^xR^y$ to form a substituted or unsubstituted fluorene structure.

$R^x$ and $R^y$ each independently represent a substituted or unsubstituted alkyl group having 1 to 50 carbon atoms or a substituted or unsubstituted aryl group having 6 to 50 ring carbon atoms, and $R^x$ and $R^y$ may bond via a single bond.

Details of the substituted or unsubstituted alkyl group having 1 to 50 carbon atoms are as described herein regarding $R^1$ to $R^5$ that are not a single bond bonding to *a or *b, and $R^6$ to $R^{10}$, $R^{11}$ to $R^{14}$, and $R^{21}$ to $R^{27}$ that are not a single bond bonding to *b.

Details of the substituted or unsubstituted aryl group having 6 to 50 ring carbon atoms are as described in the section of "Substituents in Description". The unsubstituted aryl group having 6 to 50 ring carbon atoms is preferably a phenyl group, a 1-naphthyl group, a 2-naphthyl group, a p-biphenyl group, an m-biphenyl group, or an o-biphenyl group, more preferably a phenyl group.

Examples of $CR^xR^y$ formed by $R^x$ and $R^y$ bonding via a single bond include the following groups.

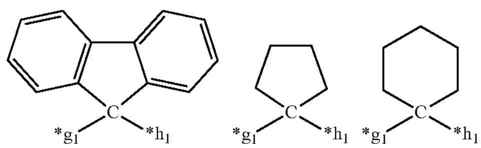

wherein $*g_1$ represents a bonding position to one benzene ring of the two benzene rings bonding to each other, and $*h_1$ represents a bonding position to the other benzene ring.

$Ar^1$ and $Ar^2$ are each independently represented by any of the following formulae (1-a) to (1-e):

(1-a)

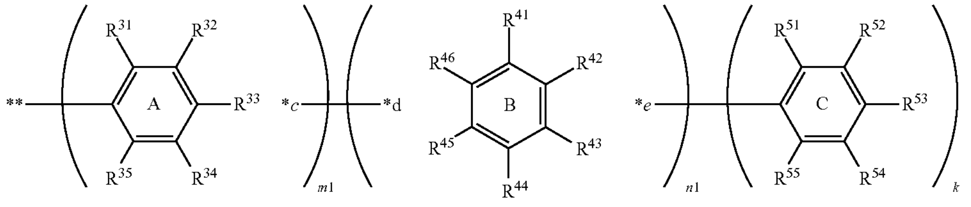

(1-b)

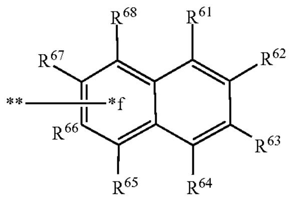

(1-c)

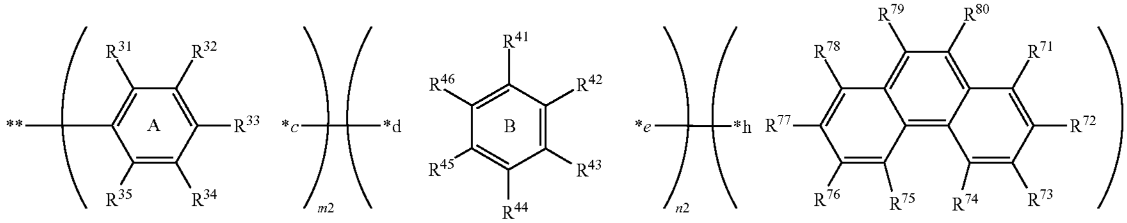

(1-d)

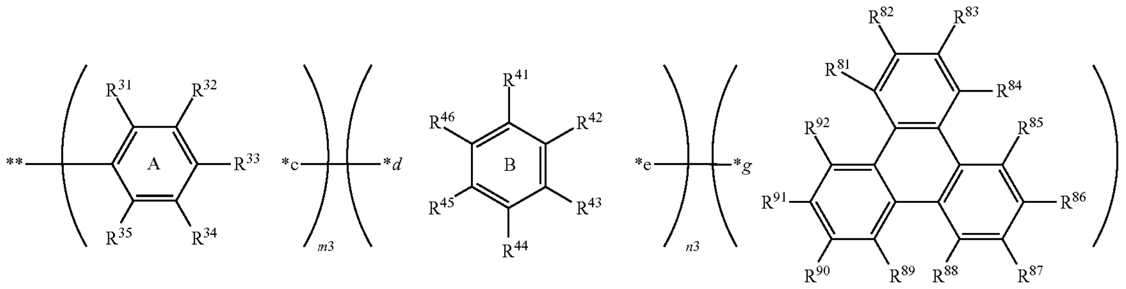

(1-e)

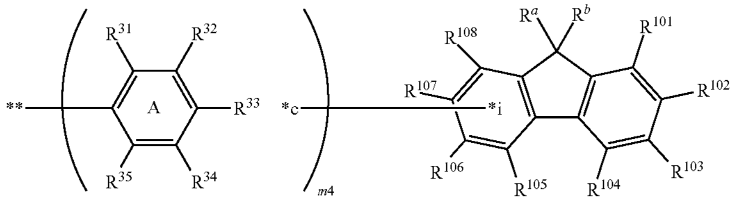

In the formula (1-a), $R^{31}$ to $R^{35}$, $R^{41}$ to $R^{46}$, and $R^{51}$ to $R^{55}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{31}$ to $R^{35}$ is a single bond bonding to *c, one selected from $R^{41}$ to $R^{46}$ is a single bond bonding to *d, and the other one selected from $R^{41}$ to $R^{46}$ is a single bond bonding to *e,

** is a bonding position to the nitrogen atom N*, m1 represents 0 or 1, and n1 represents 0 or 1, when m1 is 0 and n1 is 0, *e bonds to the nitrogen atom N*, when m1 is 0 and n1 is 1, *c bonds to the nitrogen atom N*, when m1 is 1 and n1 is 0, one selected from $R^{31}$ to $R^{35}$ is a single bond bonding to *e, k represents 1 or 2.

As one embodiment, preferably, k is 1, m1 is 0 and n1 is 0; and as another embodiment, preferably, k is 1, m1 is 0 and n1 is 1, or k is 1, m1 is 1 and n1 is 0. As still another embodiment, preferably, k is 1, m1 is 1 and n1 is 1. As still another embodiment, preferably, k is 2, m1 is 1 and n1 is 1.

Adjacent two selected from $R^{31}$ to $R^{35}$ that are not a single bond, adjacent two selected from $R^{41}$ to $R^{46}$ that are not a single bond, and adjacent two selected from $R^{51}$ to $R^{55}$ do not bond to each other and therefore do not form a cyclic structure.

The benzene ring A and the benzene ring B, the benzene ring A and the benzene ring C, and the benzene ring B and the benzene ring C do not crosslink;

In the formula (1-b), $R^{61}$ to $R^{68}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that one selected from $R^{61}$ to $R^{68}$ is a single bond bonding to *f, ** represents a bonding position to the nitrogen atom N*, adjacent two selected from $R^{61}$ to $R^{68}$ that are not a single bond do not bond to each other and therefore do not form a cyclic structure.

In the formula (1-c), $R^{31}$ to $R^{35}$, $R^{41}$ to $R^{46}$, **, *c, *d, and *e are the same as above, $R^{71}$ to $R^{80}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{71}$ to $R^{80}$ is a single bond bonding to *h, m2 represents 0 or 1, n2 represents 0 or 1, when m2 is 0 and n2 is 0, *e bonds to the nitrogen atom N*, when m2 is 0 and n2 is 1, *c bonds to the nitrogen atom N*, when m2 is 1 and n2 is 0, one selected from $R^{31}$ to $R^{35}$ is a single bond bonding to *e.

As one embodiment, preferably, m2 is 0 and n2 is 0, as another embodiment, preferably, m2 is 0 and n2 is 1, or m2 is 1 and n2 is 0. As still another embodiment, preferably, m2 is 1 and n2 is 1.

Adjacent two selected from $R^{31}$ to $R^{35}$ that are not a single bond, adjacent two selected from $R^{41}$ to $R^{46}$ that are not a single bond, and adjacent two selected from $R^{71}$ to $R^{80}$ do not bond to each other and therefore do not form a cyclic structure.

The benzene ring A and the benzene ring B do not crosslink.

In the formula (1-d), $R^{31}$ to $R^{35}$, $R^{41}$ to $R^{46}$, *c, *d, and *e are the same as above, $R^{81}$ to $R^{92}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{81}$ to $R^{92}$ is a single bond bonding to *g, m3 represents 0 or 1, n3 represents 0 or 1, when m3 is 0 and n3 is 0, *e bonds to the nitrogen atom N*, when m3 is 0 and n3 is 1, *c bonds to the nitrogen atom N*, when m3 is 1 and n3 is 0, one selected from $R^{31}$ to $R^{35}$ is a single bond bonding to *e.

As one embodiment, preferably, m3 is 0 and n3 is 0, and as another embodiment, preferably, m3 is 0 and n3 is 1, or m3 is 1 and n3 is 0. As still another embodiment, preferably, m3 is 1 and n3 is 1.

Adjacent two selected from $R^{31}$ to $R^{35}$ that are not a single bond, adjacent two selected from $R^{41}$ to $R^{46}$ that are not a single bond, and adjacent two selected from $R^{81}$ to $R^{92}$ do not bond to each other and therefore do not form a cyclic structure.

The benzene ring A and the benzene ring B do not crosslink;

In the formula (1-e), $R^{31}$ to $R^{35}$, **, and *c are the same as above, $R^{101}$ to $R^{108}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{101}$ to $R^{108}$ is a single bond bonding to *i, m4 represents 0 or 1, and as one embodiment, m4 is preferably 0, and as another embodiment, m4 is preferably 1, one of $R^a$ and $R^b$ is a substituted or unsubstituted aryl group having 6 to 50 ring carbon atoms, and the other is a substituted or unsubstituted alkyl group having 1 to 50 carbon atoms, or $R^a$ and $R^b$ each are independently a substituted or unsubstituted alkyl group having 1 to 50 ring carbon atoms, or a substituted or unsubstituted aryl group having 6 to 50 ring carbon atoms, adjacent two selected from $R^{101}$ to $R^{104}$ and $R^{105}$ to $R^{108}$ that are not a single bond do not bond to each other and therefore do not form a cyclic structure, provided that when $Ar^1$ is represented by the formula (1-e), and m4 is 1, and when $Ar^2$ is represented by the formula (1-e), and m4 is 0 or 1, ** represents a bonding position to the nitrogen atom N*.

Details of the groups that $R^{31}$ to $R^{35}$, $R^{41}$ to $R^{46}$, $R^{51}$ to $R^{55}$, $R^{61}$ to $R^{68}$, $R^{71}$ to $R^{80}$, $R^{81}$ to $R^{92}$, and $R^{101}$ to $R^{108}$ represent are the same as the details of the corresponding groups described hereinabove relating to $R^1$ to $R^5$ bonding to *a or *b that are not a single bond, and $R^6$ to $R^{10}$, $R^{11}$ to $R^{14}$, and $R^{21}$ to $R^{27}$ bonding to *b that are not a single bond.

Details of the substituted or unsubstituted alkyl group having 1 to 50 carbon atoms that $R^a$ and $R^b$ represent are the same as those described hereinabove relating to $R^1$ to $R^5$ bonding to *a or *b that are not a single bond, and $R^6$ to $R^{10}$, $R^{11}$ to $R^{14}$, and $R^{21}$ to $R^{27}$ bonding to *b that are not a single bond. Details of the substituted or unsubstituted aryl group having 6 to 50 ring carbon atoms that $R^a$ and $R^b$ represent are as described in the section of "Substituents in Description".

The unsubstituted aryl group having 6 to 50 ring carbon atoms that R. and $R^b$ represent each is independently preferably selected from a phenyl group, a biphenyl group, a naphthyl group, and a phenanthryl group, and $R^a$ and $R^b$ do not bond via a single bond.

Accordingly, the inventive compound A represented by the formula (1A) is preferably represented by any of the following formulae (1A-1) to (1A-8).

(1A-1)
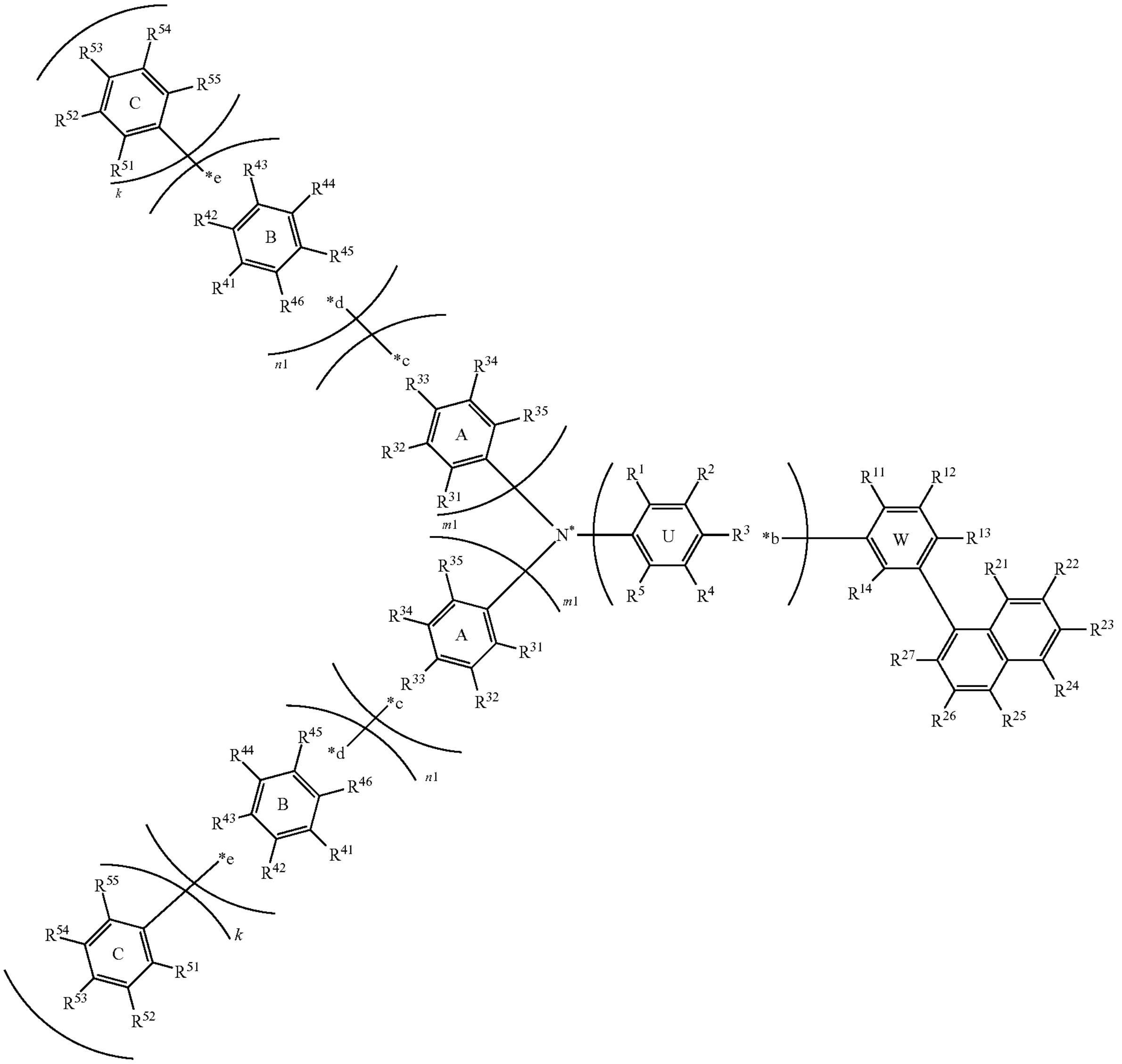

-continued
(1A-2)
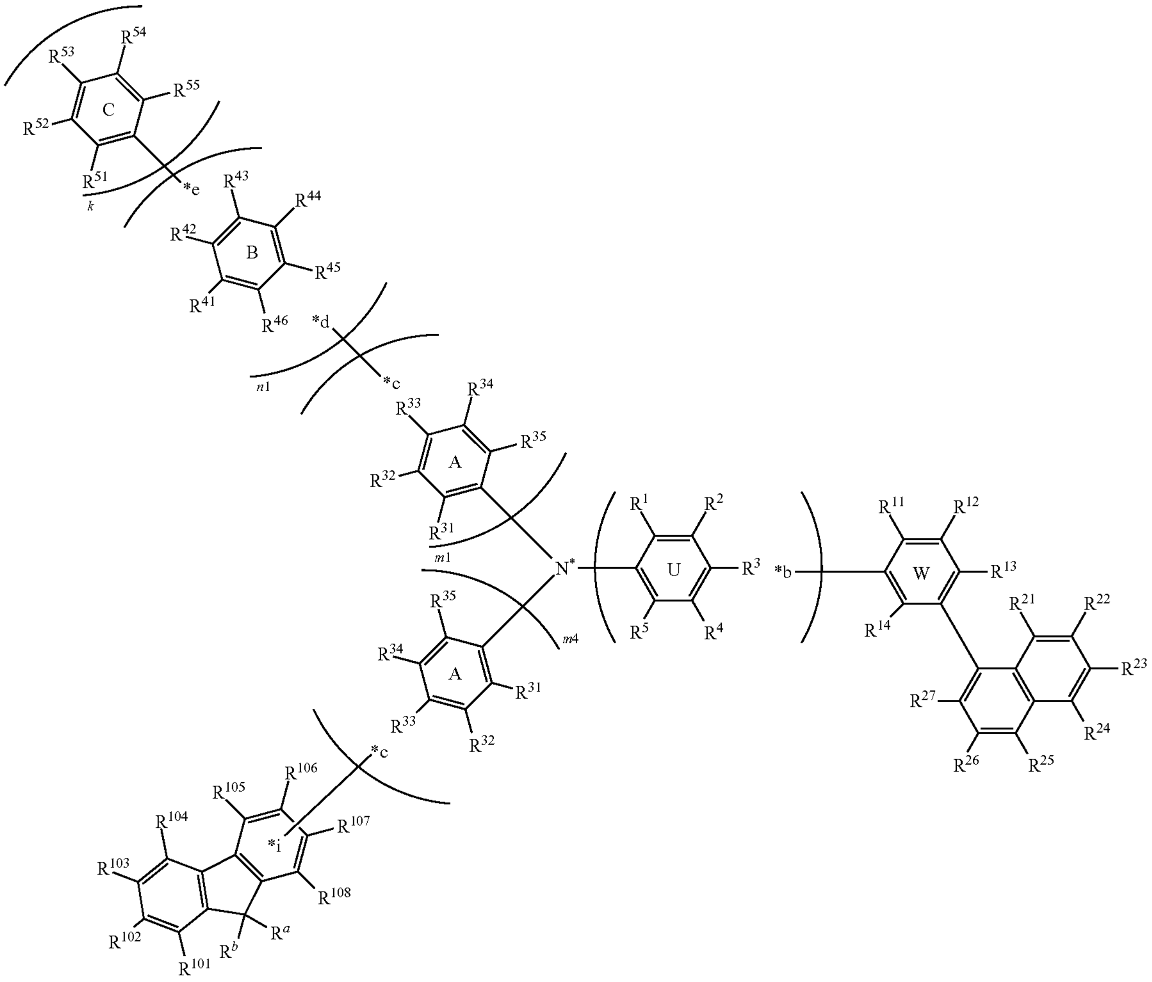
(1A-3)
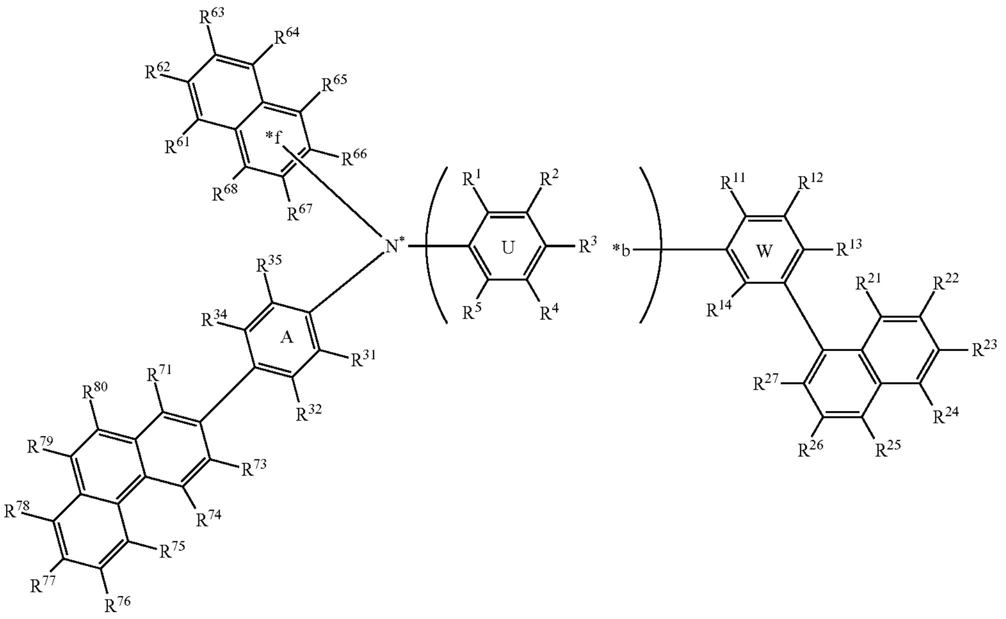

-continued
(1A-4)
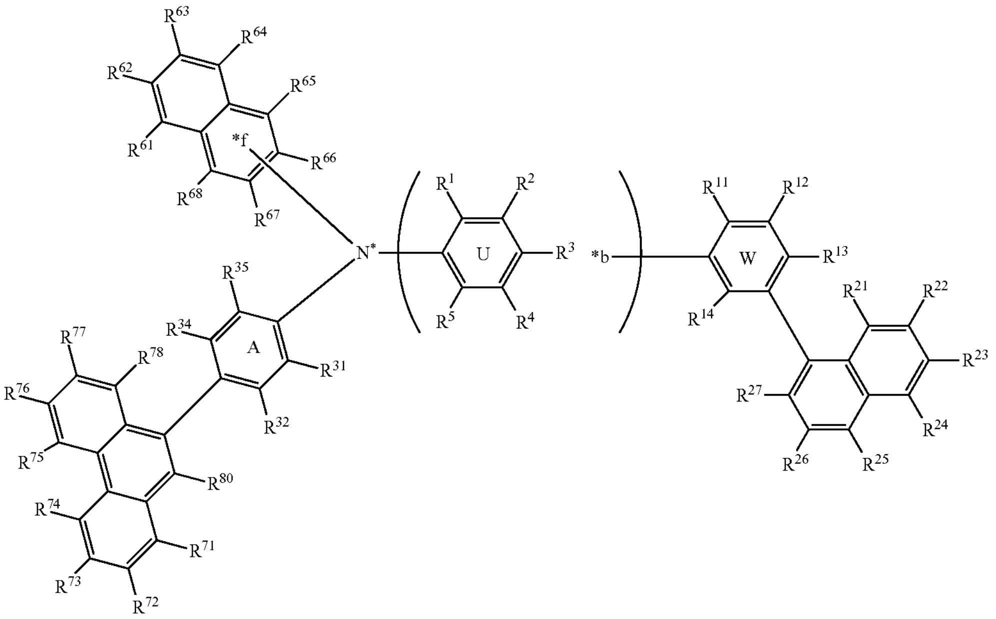
(1A-5)
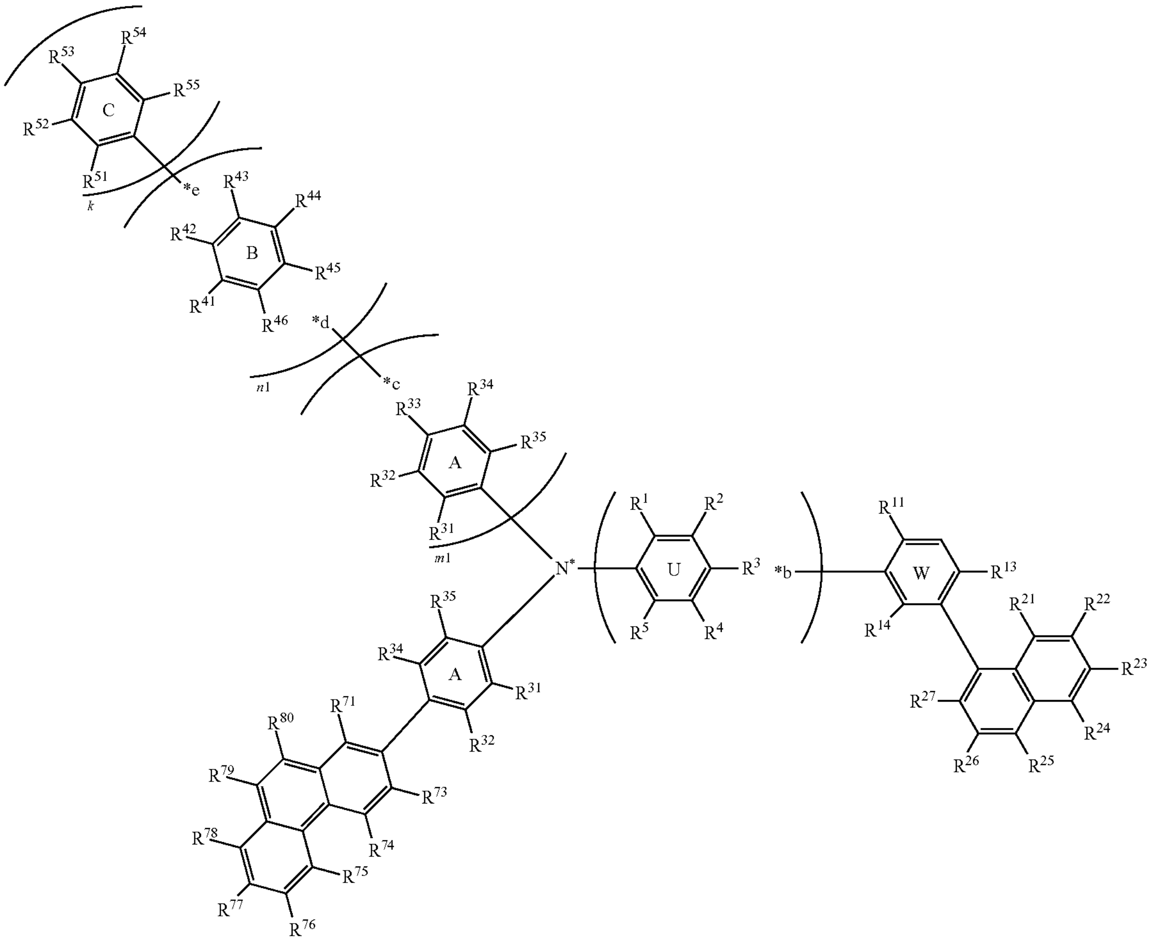

-continued
(1A-6)
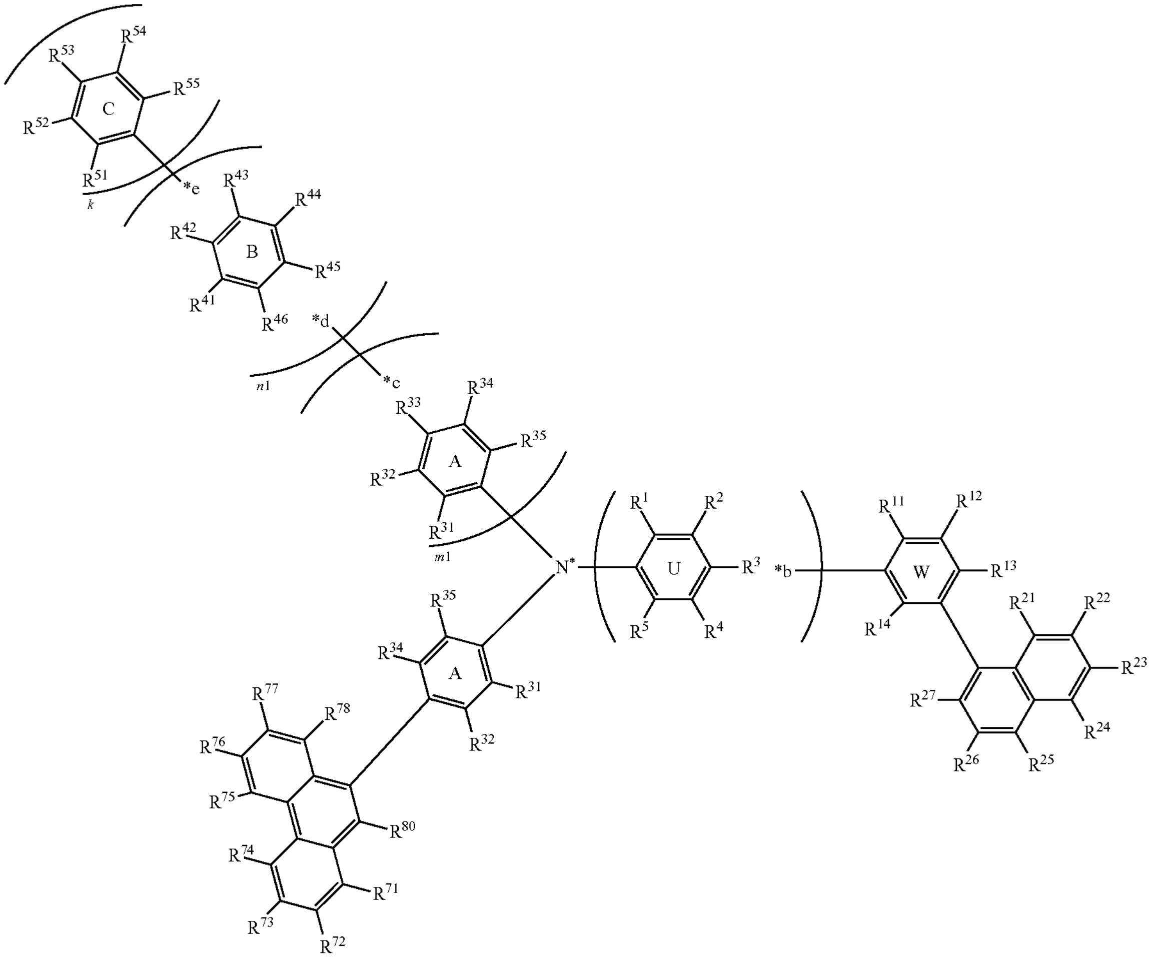

-continued
(IA-7)
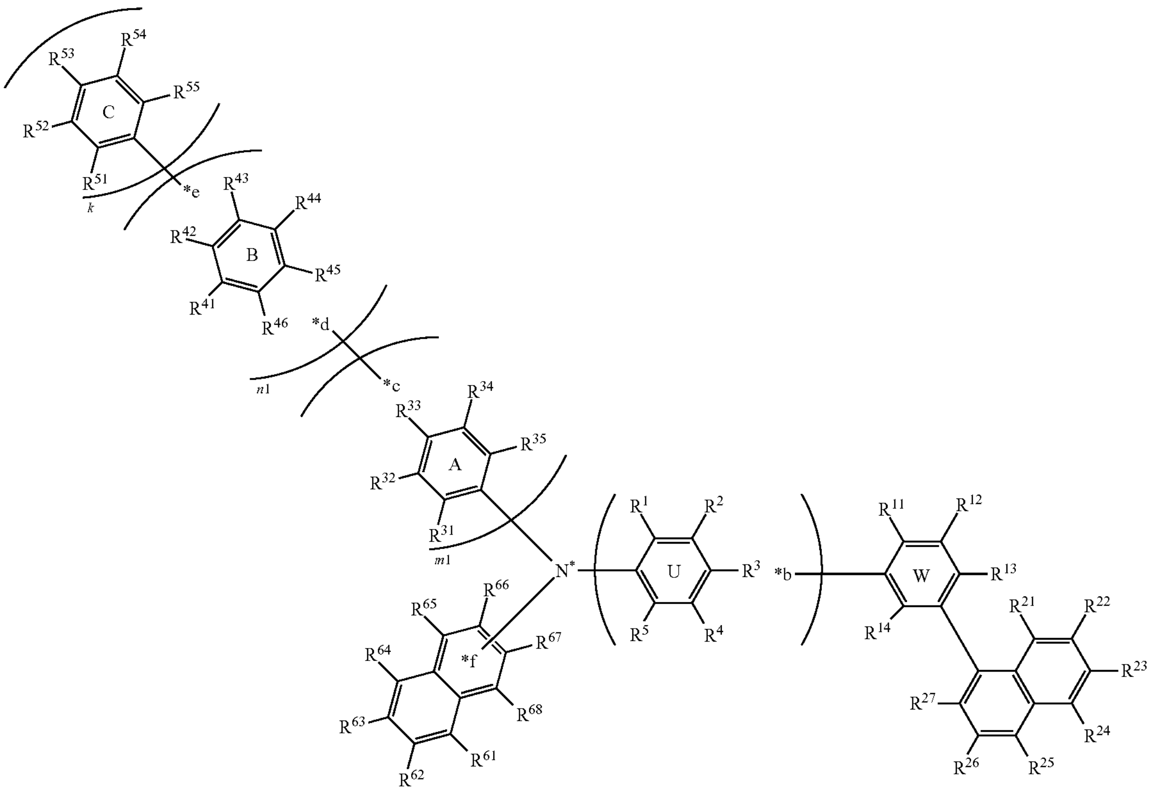
(1A-8)
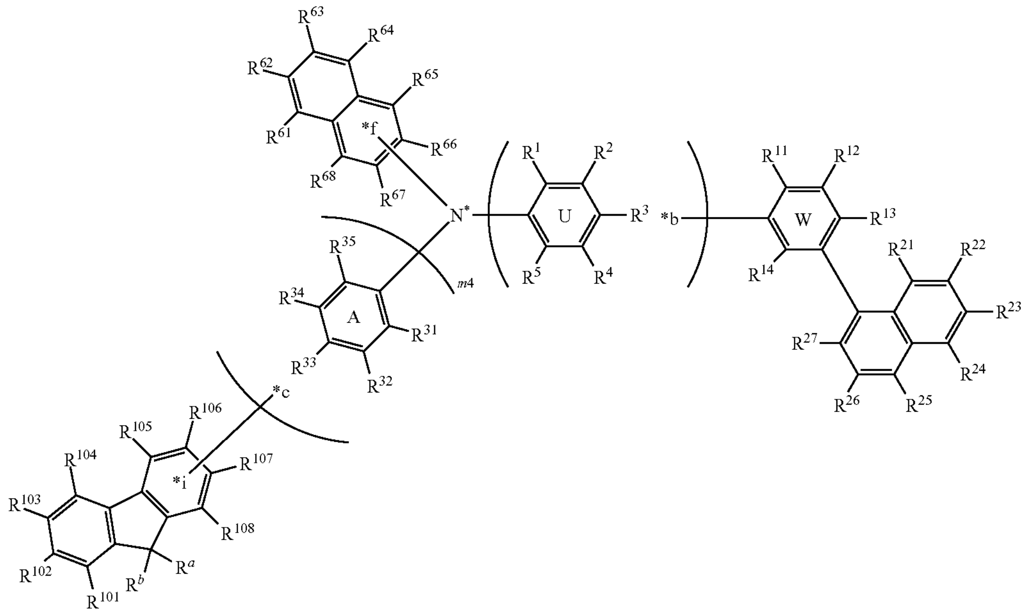
In these formulae, N*, *b, *c, *d, *e, *f, *i, k, n1, n3, m1, m3, m4, $R^a$, $R^b$, $R^1$ to $R^5$, $R^{11}$ to $R^{14}$, $R^{21}$ to $R^{27}$, $R^{31}$ to $R^{35}$, $R^{41}$ to $R^{46}$, $R^{51}$ to $R^{55}$, $R^{61}$ to $R^{68}$, $R^{71}$ to $R^{80}$, and $R^{101}$ to $R^{108}$ are as defined in the formula (1A).
The compound represented by the formula (1A-2) is preferably represented by any of the following formulae (1A-2-1) to (1A-2-4).

(1A-2-1)
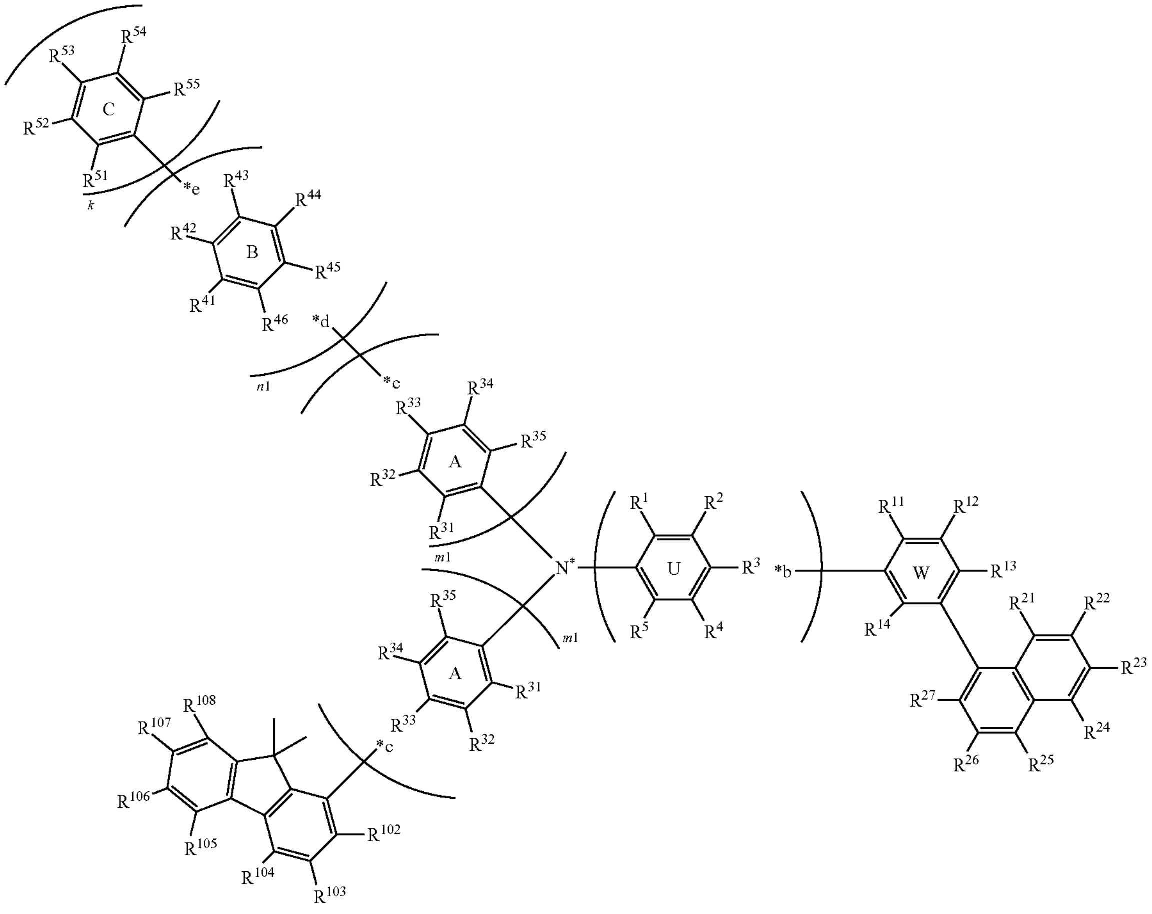

-continued
(1A-2-2)
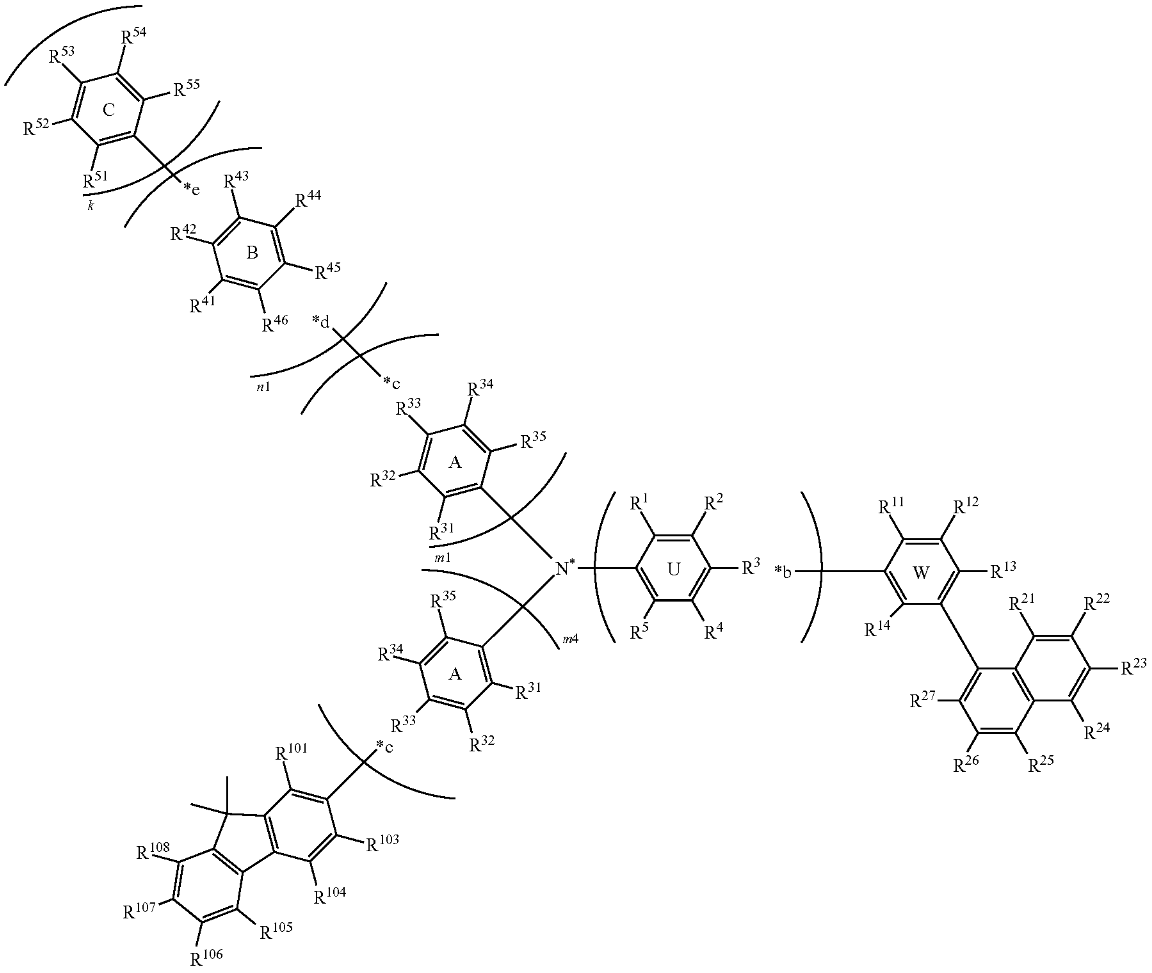

-continued
(1A-2-3)
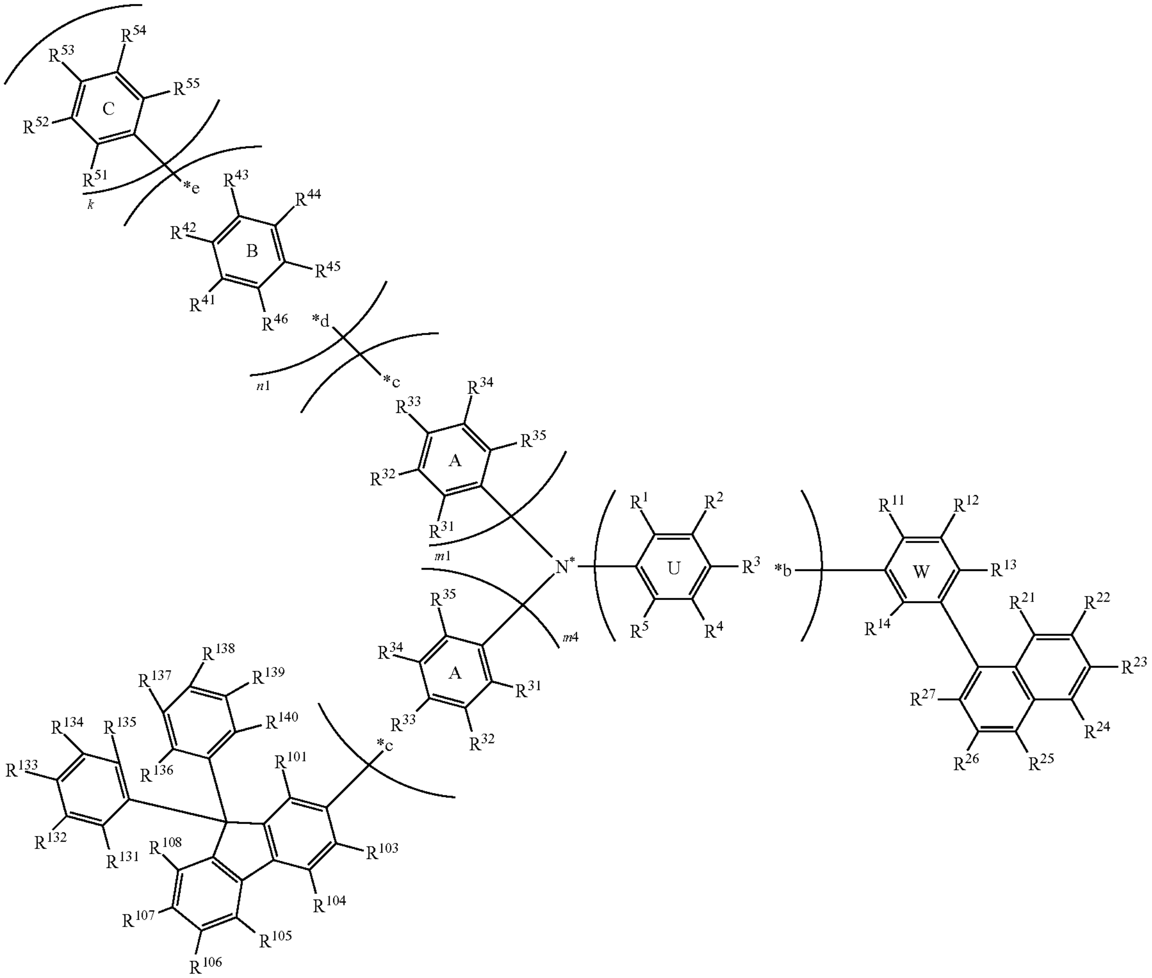

-continued (1A-2-4)

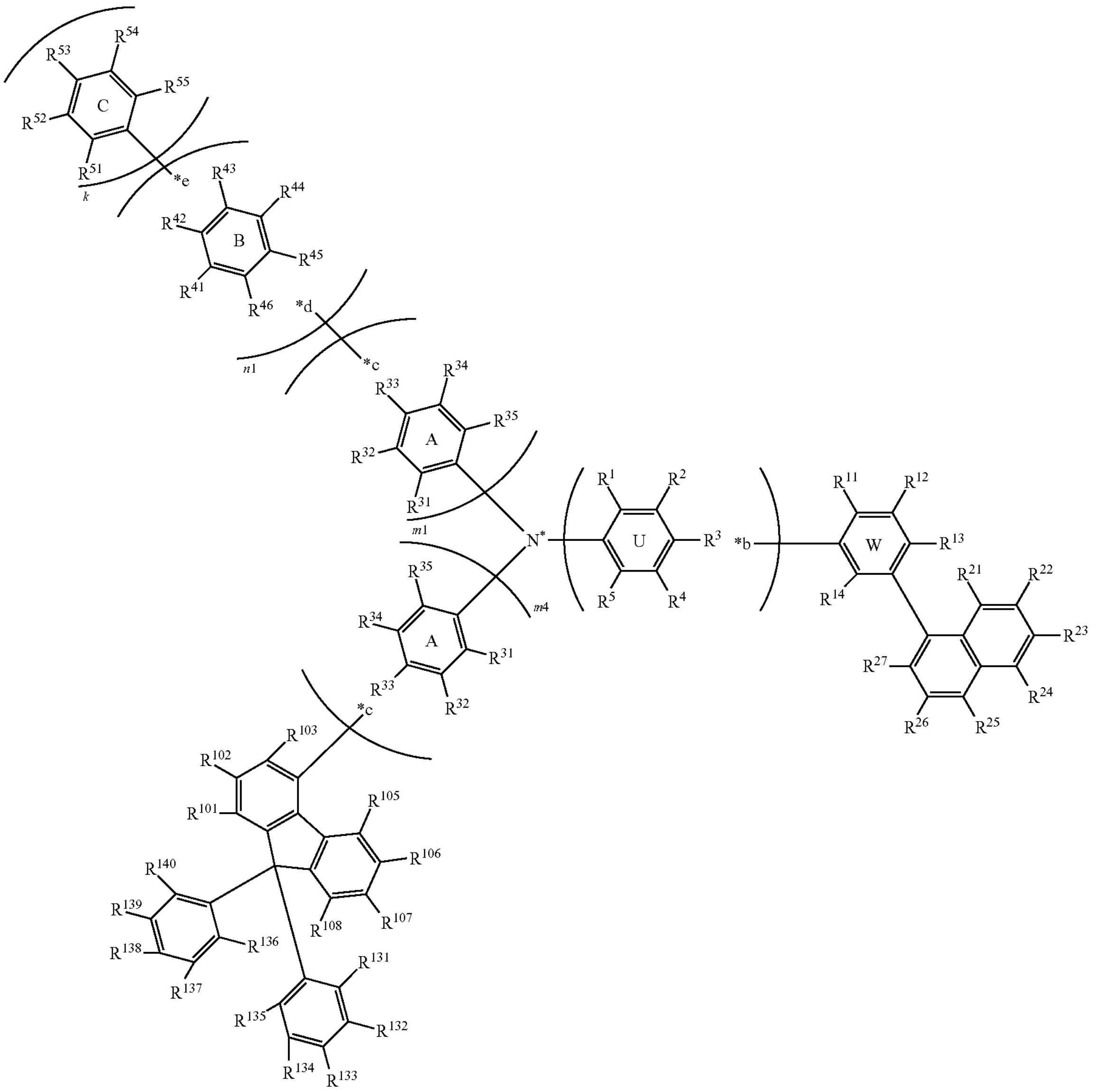

In these formulae N*, *b, *c, *d, *e, k, n1, m1, m4, $R^1$ to $R^5$, $R^{11}$ to $R^{14}$, $R^{21}$ to $R^{27}$, $R^{31}$ to $R^{35}$, $R^{41}$ to $R^{46}$, $R^{51}$ to $R^{55}$, and $R^{101}$ to $R^{108}$ are as defined in the formula (1A), $R^{131}$ to $R^{140}$ are the same as $R^{101}$ to $R^{108}$ defined in the formula (1A).

Details of the groups that $R^{131}$ to $R^{140}$ represent are the same as those of the corresponding groups described hereinabove relating to $R^1$ to $R^5$ bonding to *a or *b that are not a single bond, and $R^6$ to $R^{10}$, $R^{11}$ to $R^{14}$, and $R^{21}$ to $R^{27}$ bonding to *b that are not a single bond.

In one embodiment of the present invention, (A-1) all $R^1$ to $R^5$ bonding to *a or *b that are not a single bond may be hydrogen atoms, (A-2) all $R^{11}$ to $R^{10}$ bonding to *b that are not a single bond may be hydrogen atoms, (A-3) all $R^{11}$ to $R^{14}$ may be hydrogen atoms, (A-4) all $R^{21}$ to $R^{27}$ may be hydrogen atoms, (A-5) all $R^{31}$ to $R^{35}$ bonding to *c that are not a single bond may be hydrogen atoms, (A-6) all $R^{41}$ to $R^{46}$ bonding to *d that are not a single bond and bonding to *e that are not a single bond may be hydrogen atoms, (A-7) all $R^{51}$ to $R^{55}$ may be hydrogen atoms, (A-8) all $R^{61}$ to $R^{68}$ bonding to *f that are not a single bond may be hydrogen atoms, (A-9) all $R^{71}$ to $R^{80}$ bonding to *h that are not a single bond may be hydrogen atoms, (A-10) all $R^{81}$ to $R^{92}$ bonding to *g that are not a single bond may be hydrogen atoms, (A-11) all $R^{101}$ to $R^{108}$ bonding to *i that are not a single bond may be hydrogen atoms, (A-12) all $R^{131}$ to $R^{140}$ may be hydrogen atoms.

As described above, the "hydrogen atom" referred in the description herein encompasses a protium atom, a deuterium atom, and tritium atom. Accordingly, the inventive compound A may contain a naturally-derived deuterium atom.

A deuterium atom may be intentionally introduced into the inventive compound A by using a deuterated compound as a part or the whole of the raw material. Accordingly, in one embodiment of the present invention, the inventive compound A contains at least one deuterium atom. That is, the inventive compound A may be a compound represented by the formula (1A) in which at least one hydrogen atom contained therein is a deuterium atom.

At least one hydrogen atom selected from the following hydrogen atoms may be a deuterium atom:

a hydrogen atom that any of $R^1$ to $R^5$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^1$ to $R^5$ represents;

a hydrogen atom that any of $R^6$ to $R^{10}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^6$ to $R^{10}$ represents;

a hydrogen atom that any of $R^{11}$ to $R^{14}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{11}$ to $R^{14}$ represents;

a hydrogen atom that any of $R^{21}$ to $R^{27}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{21}$ to $R^{27}$ represents;

a hydrogen atom that any of $R^{31}$ to $R^{35}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{31}$ to $R^{35}$ represents;

a hydrogen atom that any of $R^{41}$ to $R^{46}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{41}$ to $R^{46}$ represents;

a hydrogen atom that any of $R^{51}$ to $R^{55}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{51}$ to $R^{55}$ represents;

a hydrogen atom that any of $R^{61}$ to $R^{68}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{61}$ to $R^{68}$ represents;

a hydrogen atom that any of $R^{71}$ to $R^{80}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{71}$ to $R^{80}$ represents;

a hydrogen atom that any of $R^{81}$ to $R^{92}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{81}$ to $R^{92}$ represents;

a hydrogen atom that any of Wu to $R^{108}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{101}$ to $R^{108}$ represents;

a hydrogen atom that any of $R^{131}$ to $R^{140}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{131}$ to $R^{140}$ represents;

a hydrogen atom of the substituted or unsubstituted alkyl group or aryl group that any of $R^x$ to $R^y$ represents; and a hydrogen atom of the substituted or unsubstituted alkyl group or aryl group that any of $R^a$ to $R^b$ represents.

The deuteration rate of the inventive compound A depends on the deuteration rate of the raw material compound used. Even when a raw material having a predetermined deuteration rate is used, a naturally-derived protium isotope can be contained in a certain ratio. Accordingly, an embodiment of the deuteration rate of the inventive compound A shown below includes the proportion for which a minor amount of a naturally-derived isotope is taken into consideration, relative to the proportion determined by counting the number of the deuterium atoms merely represented by a chemical formula.

The deuteration rate of the inventive compound A is preferably 1% or more, more preferably 3% or more, even more preferably 5% or more, further more preferably 10% or more, further more preferably 50% or more.

The inventive compound A may be a mixture of a deuterated compound and a non-deuterated compound, or a mixture of two or more compounds having different deuteration rates from each other. The deuteration rate of the mixture is preferably 1% or more, more preferably 3% or more, even more preferably 5% or more, further more preferably 10% or more, further more preferably 50% or more, and is less than 100%.

The proportion of the number of the deuterium atoms to the number of all the hydrogen atoms in the inventive compound A is preferably 1% or more, more preferably 3% or more, even more preferably 5% or more, further more preferably 10% or more, and is 100% or less.

Details of the substituent (arbitrary substituent) in the expression "substituted or unsubstituted" included in the definitions of the aforementioned formulae are the same as in the "substituent in the expression 'substituted or unsubstituted'".

However, the arbitrary substituent included in the definitions of the aforementioned formulae relating to the formula (1A) does not include the substituents of an aryl group, a heterocyclic group and a heterocyclic group of $R_{901}$ to $R_{907}$, among the substituents described in the section of "substituent in the expression 'substituted or unsubstituted'".

The inventive compound A can be readily produced by a person skilled in the art with reference to the following synthesis examples and known synthesis methods.

The compound of the present invention is represented by the formula (1B).

(1B)

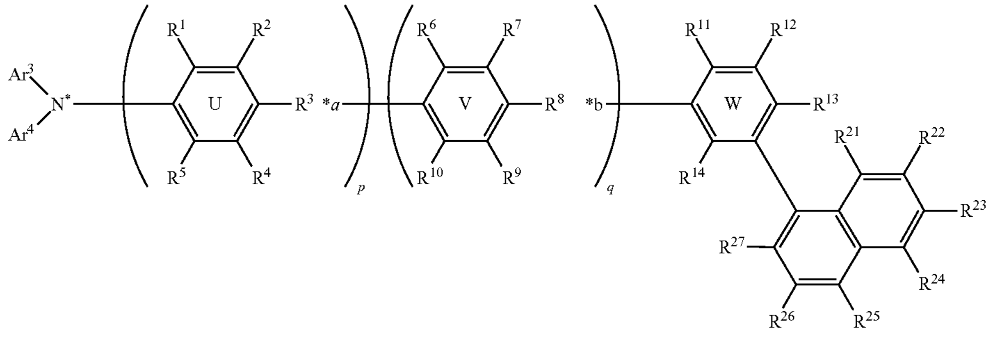

Hereinunder the symbols in the formula (1B) and in the subordinate formulae of the formula (1B) described later will be described. The same symbols have the same meanings.

In the formula (1B),

N* is a central nitrogen atom, p represents 0 or 1, q represents 0 or 1, provided that p+q≥1, when p is 0 and q is 1, *a bonds to the nitrogen atom N*, and one selected from $R^6$ to $R^{10}$ is a single bond bonding to *b, when p is 1 and q is 0, one selected from W to W is a single bond bonding to *b, when p is 1 and q is 1, one selected from $R^1$ to $R^5$ is a single bond bonding to *a, and one selected from $R^6$ to $R^{10}$ is a single bond bonding to *b.

$R^1$ to $R^5$ that are not a single bond bonding to *a or *b, and $R^6$ to $R^{10}$, $R^{11}$ to $R^{14}$, and $R^{21}$ to $R^{27}$ that are not a single bond bonding to *b each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms.

Preferably, these are each independently a hydrogen atom, a cyano group, a substituted or unsubstituted alkyl group having 1 to 50 carbon atoms, or a substituted or unsubstituted cycloalkyl group having 3 to 50 ring carbon atoms, more preferably, each independently a hydrogen atom, or a substituted or unsubstituted alkyl group having 1 to 50 carbon atoms.

Details of the halogen atom are as described in the section of "Substituents in Description", and preferred is a fluorine atom.

Details of the substituted or unsubstituted alkyl group having 1 to 50 carbon atoms are as described in the section of "Substituents in Description".

The unsubstituted alkyl group is preferably a methyl group, an ethyl group, a n-propyl group, an isopropyl group, a n-butyl group, an isobutyl group, an s-butyl group, or a t-butyl group, more preferably a methyl group, an ethyl group, an isopropyl group, or a t-butyl group, even more preferably a methyl group or a t-butyl group.

Details of the substituted or unsubstituted cycloalkyl group having 3 to 50 ring carbon atoms are as described in the section of "Substituents in Description".

The unsubstituted cycloalkyl group is preferably a cyclopropyl group, a cyclobutyl group, a cyclopentyl group, or a cyclohexyl group, and more preferably a cyclopropyl group, a cyclopentyl group, or a cyclohexyl group.

Details of the substituted or unsubstituted haloalkyl group having 1 to 50 carbon atoms are as described in the section of "Substituents in Description", and preferred is a substituted or unsubstituted fluoroalkyl group having 1 to 50 carbon atoms.

The unsubstituted fluoroalkyl group is preferably a trifluoromethyl group, a 2,2,2-trifluoroethyl group, a pentafluoroethyl group, or a heptafluoropropyl group, more preferably a trifluoromethyl group.

Details of the substituted or unsubstituted alkoxy group having 1 to 50 carbon atoms are as described in the section of "Substituents in Description".

The unsubstituted alkoxy group is preferably a methoxy group, an ethoxy group, a propoxy group, or a t-butoxy group, more preferably a methoxy group or an ethoxy group, even more preferably a methoxy group.

The substituted or unsubstituted haloalkoxy group having 1 to 50 carbon atoms is a group represented by —O(G12), and G12 is a substituted or unsubstituted haloalkyl group described above.

The substituted or unsubstituted haloalkoxy group having 1 to 50 is preferably a substituted or unsubstituted fluoroalkoxy group having 1 to 50 carbon atoms.

The unsubstituted fluoroalkoxy group is preferably a trifluoromethoxy group, a 2,2,2-trifluoroethoxy group, a pentafluoroethoxy group, or a heptafluoropropoxy group, more preferably a trifluoromethoxy group, a 2,2,2-trifluoroethoxy group, or a pentafluoroethoxy group, even more preferably a trifluoromethoxy group.

Details of the substituted or unsubstituted aryloxy group having 6 to 50 ring carbon atoms are as described in the section of "Substituents in Description".

The unsubstituted aryloxy group is preferably a phenoxy group, a biphenyloxy group or a terphenyloxy group, more preferably a phenoxy group or a biphenyloxy group.

Details of the substituted or unsubstituted aralkyl group having 7 to 50 carbon atoms are as described in the section of "Substituents in Description".

The unsubstituted aralkyl group is preferably a benzyl group, a phenyl-t-butyl group, an α-naphthylmethyl group, a β-naphthylmethyl group, a 1-β-naphthylisopropyl group, or a 2-β-naphthylisopropyl group, more preferably a benzyl group, a phenyl-t-butyl group, an α-naphthylmethyl group or a β-naphthylmethyl group.

Details of the substituent for the mono, di or tri-substituted silyl group are as described in the section of "Substituents in Description".

The mono, di or tri-substituted silyl group is preferably a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group, more preferably a trimethylsilyl group or a triphenylsilyl group.

Adjacent two selected from $R^1$ to $R^5$ that are not a single bond, adjacent two selected from $R^6$ to $R^{10}$ that are not a single bond, adjacent two selected from $R^{11}$ to $R^{14}$ that are not a single bond, and adjacent two selected from $R^{21}$ to $R^{27}$ do not bond to each other and therefore do not form a cyclic structure.

However, in the formulae included in the formula (1B) mentioned above, and in the formulae included in the formula (1B) to be mentioned later, one or more pairs of two benzene rings bonding to each other selected from the benzene ring U, the benzene ring V and the benzene ring W may be crosslinked with $CR^xR^y$ to form a substituted or unsubstituted fluorene structure, or may not be crosslinked and may not form a fluorene structure.

Namely, in the formula (1B),

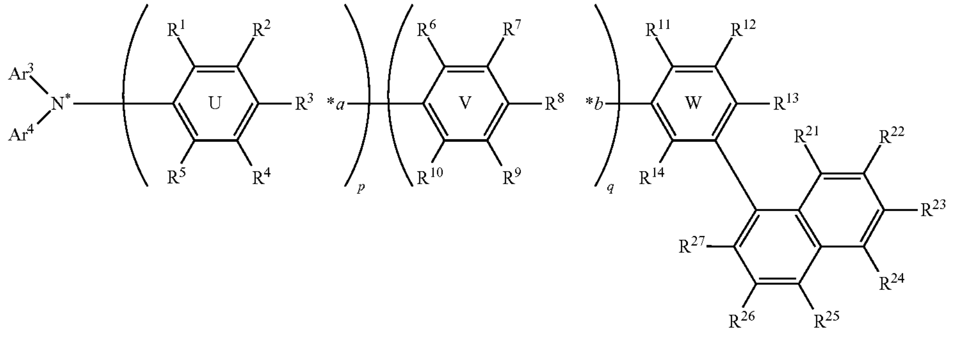

(1B)

when p is 1 and q is 0, the benzene ring U and the benzene ring W bonding to each other may form a substituted or unsubstituted fluorene structure, or may not form it.

When p is 0 and q is 1, the benzene ring V and the benzene ring W bonding to each other may form a substituted or unsubstituted fluorene structure, or may not form it.

When p is 1 and q is 1, at least one pair of the two benzene rings bonding to each other selected from the benzene ring U and the benzene ring V bonding to each other, and the benzene ring V and the benzene ring W bonding to each other may form a substituted or unsubstituted fluorene structure, or may not form it.

In other words, when p is 1 and q is 0, one existing on the carbon atom adjacent to the carbon atom bonding to the benzene ring W, and selected from $R^1$ to $R^5$ may form a crosslinking group $CR^xR^y$ along with one of $R^{11}$ and $R^{14}$, or may not form $CR^xR^y$.

When p is 0 and q is 1, one existing on the carbon atom adjacent to the carbon atom bonding to the benzene ring W, and selected from $R^6$ to $R^{10}$ may form a crosslinking group $CR^xR^y$ along with one of $R^{11}$ and $R^{14}$, or may not form a crosslinking group $CR^xR^y$.

When p is 1 and q is 1, one existing on the carbon atom adjacent to the carbon atom bonding to the benzene ring V, and selected from $R^5$ to $R^9$ may form a crosslinking group $CR^xR^y$ along with one of $R^6$ and $R^{10}$, or may not form a crosslinking group $CR^xR^y$, one existing on the carbon atom adjacent to the carbon atom bonding to the benzene ring W, and selected from $R^6$ to $R^{10}$ may form a crosslinking group $CR^xR^y$ along with one of $R^{11}$ and $R^{14}$, or may not form a crosslinking group $CR^xR^y$.

In one embodiment of the present invention, preferably, two benzene rings bonding to each other are not crosslinked and do not form a substituted or unsubstituted fluorene structure. In another embodiment of the present invention, preferably, one pairs or more of two benzene rings bonding to each other are crosslinked with $CR^xR^y$ to form a substituted or unsubstituted fluorene structure.

$R^x$ and $R^y$ each independently represent a substituted or unsubstituted alkyl group having 1 to 50 carbon atoms or a substituted or unsubstituted aryl group having 6 to 50 ring carbon atoms, and $R^x$ and $R^y$ may bond via a single bond.

Details of the substituted or unsubstituted alkyl group having 1 to 50 carbon atoms are as described herein regarding $R^1$ to W that are not a single bond bonding to *a or *b, and $R^6$ to $R^{10}$, $R^{11}$ to $R^{14}$, and $R^{21}$ to $R^{27}$ that are not a single bond bonding to *b.

Details of the substituted or unsubstituted aryl group having 6 to 50 ring carbon atoms are as described in the section of "Substituents in Description". The unsubstituted aryl group having 6 to 50 ring carbon atoms is preferably a phenyl group, a 1-naphthyl group, a 2-naphthyl group, a p-biphenyl group, an m-biphenyl group, or an o-biphenyl group, more preferably a phenyl group.

Examples of $CR^xR^y$ formed by $R^x$ and $R^y$ bonding via a single bond include the following groups.

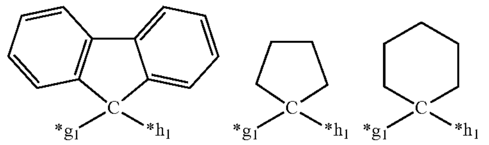

wherein $*g_1$ represents a bonding position to one benzene ring of the two benzene rings bonding to each other, and $*h_1$ represents a bonding position to the other benzene ring.

$Ar^3$ is represented by the following formula (1-f):

(1-f)

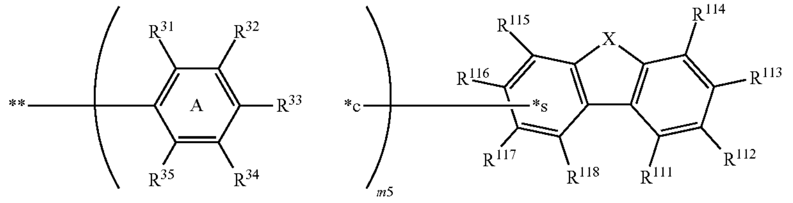

In the formula (1-0, $R^{31}$ to $R^{35}$ and $R^{111}$ to $R^{118}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{31}$ to $R^{35}$ is a single bond bonding to *c, and one selected from $R^{111}$ to $R^{118}$ is a single bond bonding to *s, X represents an oxygen atom or a sulfur atom.

As one embodiment, X is preferably an oxygen atom. As another embodiment, X is preferably a sulfur atom.

Adjacent two selected from $R^{111}$ to $R^{114}$ and $R^{115}$ to $R^{118}$ that are not a single bond do not bond to each other and therefore do not form a cyclic structure,

** represents a bonding position to the nitrogen atom N*, m5 represents 0 or 1.

As one embodiment, m5 is preferably 0, and as another embodiment, m5 is preferably 1.

$Ar^4$ is represented by any of the following formulae (1-a), (1-b), (1-c), (1-d) and (1-g):

(1-a)

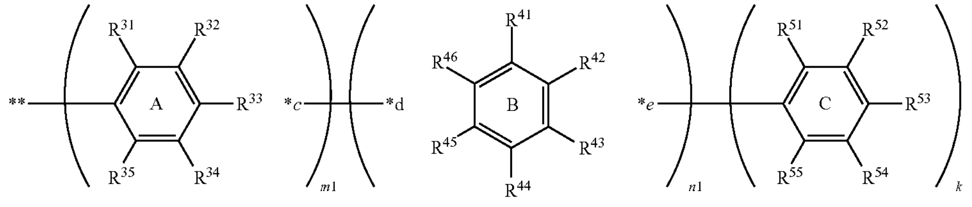

(1-b)

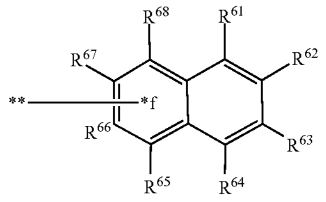

-continued (1-c)

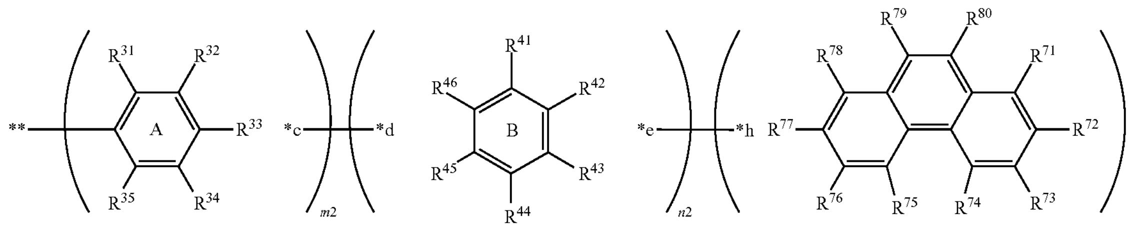

(1-d)

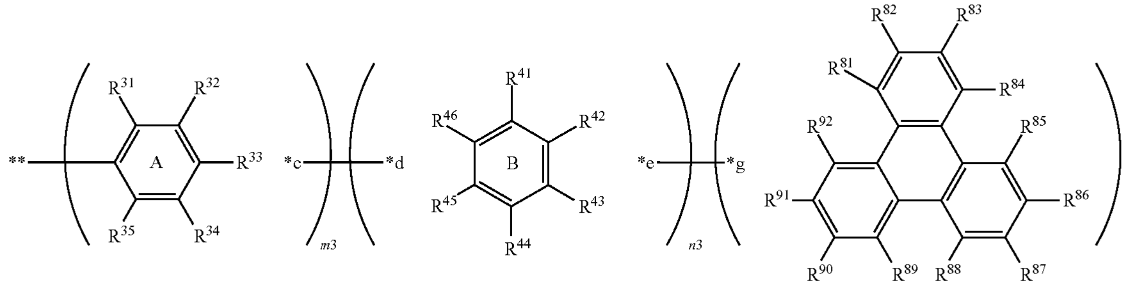

(1-g)

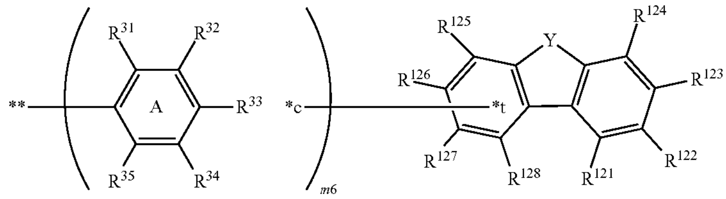

In the formula (1-a), $R^{31}$ to $R^{35}$, **, and *c are the same as above, $R^{41}$ to $R^{46}$, and $R^{51}$ to $R^{55}$ each independently represent, a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{41}$ to $R^{46}$ is a single bond bonding to *d, and the other one selected from $R^{41}$ to $R^{46}$ is a single bond bonding to *e, m1 represents 0 or 1, and n1 represents 0 or 1, when m1 is 0 and n1 is 0, *e bonds to the nitrogen atom N*, when m1 is 0 and n1 is 1, *c bonds to the nitrogen atom N*, when m1 is 1 and n1 is 0, one selected from $R^{31}$ to $R^{5}$ is a single bond bonding to *e, k represents 1 or 2.

As one embodiment, preferably, k is 1, m1 is 0 and n1 is 0, and as another embodiment, preferably, k is 1, m1 is 0 and n1 is 1, or k is 1, m1 is 1 and n1 is 1. As still another embodiment, preferably, k is 1, m1 is 1 and n1 is 1. As still another embodiment, k is 2, m1 is 1 and n1 is 1.

Adjacent two selected from $R^{31}$ to $R^{35}$ that are not a single bond, adjacent two selected from $R^{41}$ to $R^{46}$ that are not a single bond, and adjacent two selected from $R^{51}$ to $R^{55}$ do not bond to each other and therefore do not form a cyclic structure.

The benzene ring A and the benzene ring B, the benzene ring A and the benzene ring C, and the benzene ring B and the benzene ring C do not crosslink.

In the formula (1-b), $R^{61}$ to $R^{68}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{61}$ to $R^{68}$ is a single bond bonding to *f, ** represents a bonding position to the nitrogen atom N*, adjacent two selected from $R^{61}$ to $R^{68}$ that are not a single bond do not bond to each other and therefore do not form a cyclic structure.

In the formula (1-c), $R^{31}$ to $R^{35}$, $R^{41}$ to $R^{46}$, *c, *d, and *e are the same as above, $R^{71}$ to $R^{80}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{71}$ to $R^{80}$ is a single bond bonding to *h, m2 represents 0 or 1, n2 represents 0 or 1, when m2 is 0 and n2 is 0, *e bonds to the nitrogen atom N*, when m2 is 0 and n2 is 1, *c bonds to the nitrogen atom N*, when m2 is 1 and n2 is 0, one selected from $R^{31}$ to $R^{35}$ is a single bond As one embodiment, preferably, m2 is 0 and n2 is 0, and as another embodiment, preferably, m2 is 0 and n2 is 1, or m2 is 1 and n2 is 0. As still another embodiment, preferably m2 is 1 and n2 is 1.

Adjacent two selected from $R^{31}$ to $R^{35}$ that are not a single bond, adjacent two selected from $R^{41}$ to $R^{46}$ that are not a single bond, and adjacent two selected from $R^{71}$ to $R^{80}$ do not bond to each other and therefore do not form a cyclic structure.

The benzene ring A and the benzene ring B do not crosslink.

In the formula (1-d), $R^{31}$ to $R^{35}$, $R^{41}$ to $R^{46}$, *c, *d, and *e are the same as above, $R^{81}$ to $R^{92}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{81}$ to $R^{92}$ is a single bond bonding to *g, m3 represents 0 or 1, n3 represents 0 or 1, when m3 is 0 and n3 is 0, *e bonds to the nitrogen atom N*, when m3 is 0 and n3 is 1, *c bonds to the nitrogen atom N*, when m3 is 1 and n3 is 0, one selected from $R^{31}$ to $R^{35}$ is a single bond bonding to *e.

As one embodiment, preferably, m3 is 0 and n3 is 0, and as another embodiment, preferably m3 is 0 and n3 is 1, or m3 is 1 and n3 is 0. As still another embodiment, preferably, m3 is 1 and n3 is 1.

Adjacent two selected from $R^{31}$ to $R^{35}$ that are not a single bond, adjacent two selected from $R^{41}$ to $R^{46}$ that are not a single bond, and adjacent two selected from $R^{81}$ to $R^{92}$ do not bond to each other and therefore do not form a cyclic structure.

The benzene ring A and the benzene ring B do not crosslink.

In the formula (1-g), $R^{31}$ to $R^{35}$, *c and *i are the same as above, $R^{121}$ to $R^{128}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that, one selected from $R^{121}$ to $R^{128}$ is a single bond bonding to *t, m6 represents 0 or 1.

As one embodiment, preferably, m6 is 0, and as another embodiment, preferably, m6 is 1.

Y represents an oxygen atom, a sulfur atom, or $CR^cR^d$, one of $R^c$ and $R^d$ is a substituted or unsubstituted aryl group having 6 to 50 ring carbon atoms, and the other is a substituted or unsubstituted alkyl group having 1 to 50 carbon atoms, or $R^c$ and $R^d$ each are independently a substituted or unsubstituted alkyl group having 1 to 50 ring carbon atoms, or a substituted or unsubstituted aryl group having 6 to 50 ring carbon atoms, and the two aryl groups may bond to each other via a single bond, provided that when Y is $CR^cR^d$, $R^{121}$ to $R^{128}$ do not contain a substituted or unsubstituted aryl group having 6 to 50 ring carbon atoms, adjacent two selected from $R^{121}$ to $R^{124}$ and $R^{125}$ to $R^{128}$ that are not a single bond do not bond to each other and therefore do not form a cyclic structure.

Details of the groups that $R^{31}$ to $R^{35}$, $R^{41}$ to $R^{46}$, $R^{51}$ to $R^{55}$, $R^{61}$ to $R^{68}$, $R^{71}$ to $R^{80}$, $R^{81}$ to $R^{92}$, $R^{111}$ to $R^{118}$, and $R^{121}$ to $R^{128}$ represent (excluding the substituted or unsubstituted aryl group having 6 to 50 ring carbon atoms that $R^{121}$ to $R^{128}$ represent when Y is an oxygen atom or a sulfur atom) are the same as the details of the corresponding groups described hereinabove relating to $R^1$ to $R^5$ bonding to *a or *b that are not a single bond, and $R^6$ to $R^{10}$, $R^{11}$ to $R^{14}$, and $R^{21}$ to $R^{27}$ bonding to *b that are not a single bond.

Details of the substituted or unsubstituted aryl group having 6 to 50 ring carbon atoms that $R^{121}$ to $R^{128}$ represent not in the case where Y is $CR^cR^d$, that is, in the case where Y is an oxygen atom or a sulfur atom are as described above in the section of "Substituents in Description".

The substituted or unsubstituted aryl group having 6 to 50 ring carbon atoms that $R^{121}$ to $R^{128}$ represent in the case where Y is an oxygen atom or a sulfur atom each is independently preferably selected from a phenyl group, a p-biphenyl group, an m-biphenyl group, an o-biphenyl group, a 1-naphthyl group and a 2-naphthyl group.

Details of the substituted or unsubstituted alkyl group having 1 to 50 carbon atoms that $R^c$ and $R^d$ represent are the same as those described hereinabove relating to $R^1$ to $R^5$ bonding to *a or *b that are not a single bond, and $R^6$ to $R^{10}$, $R^{11}$ to $R^{14}$, and $R^{21}$ to $R^{27}$ bonding to *b that are not a single bond. Details of the substituted or unsubstituted aryl group having 6 to 50 ring carbon atoms that $R^c$ and $R^d$ represent are as described in the section of "Substituents in Description".

The unsubstituted aryl group having 6 to 50 ring carbon atoms that $R^c$ and $R^d$ represent each is independently preferably selected from a phenyl group, a biphenyl group, a naphthyl group, and a phenanthryl group.

Accordingly, the inventive compound B represented by the formula (1B) is preferably represented by any of the following formulae (1B-1) to (1B-7).

(1B-1)

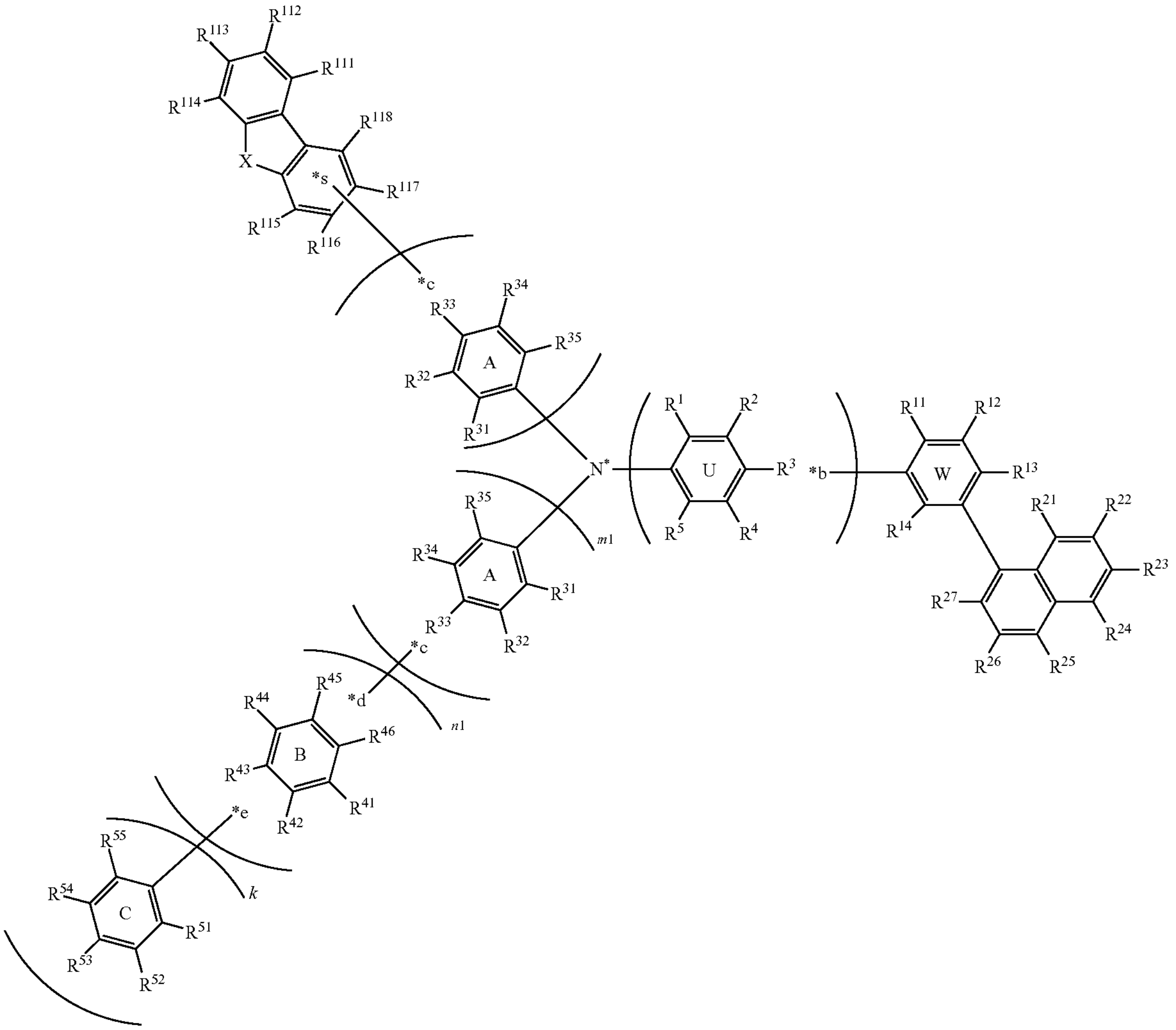

-continued
(1B-2)
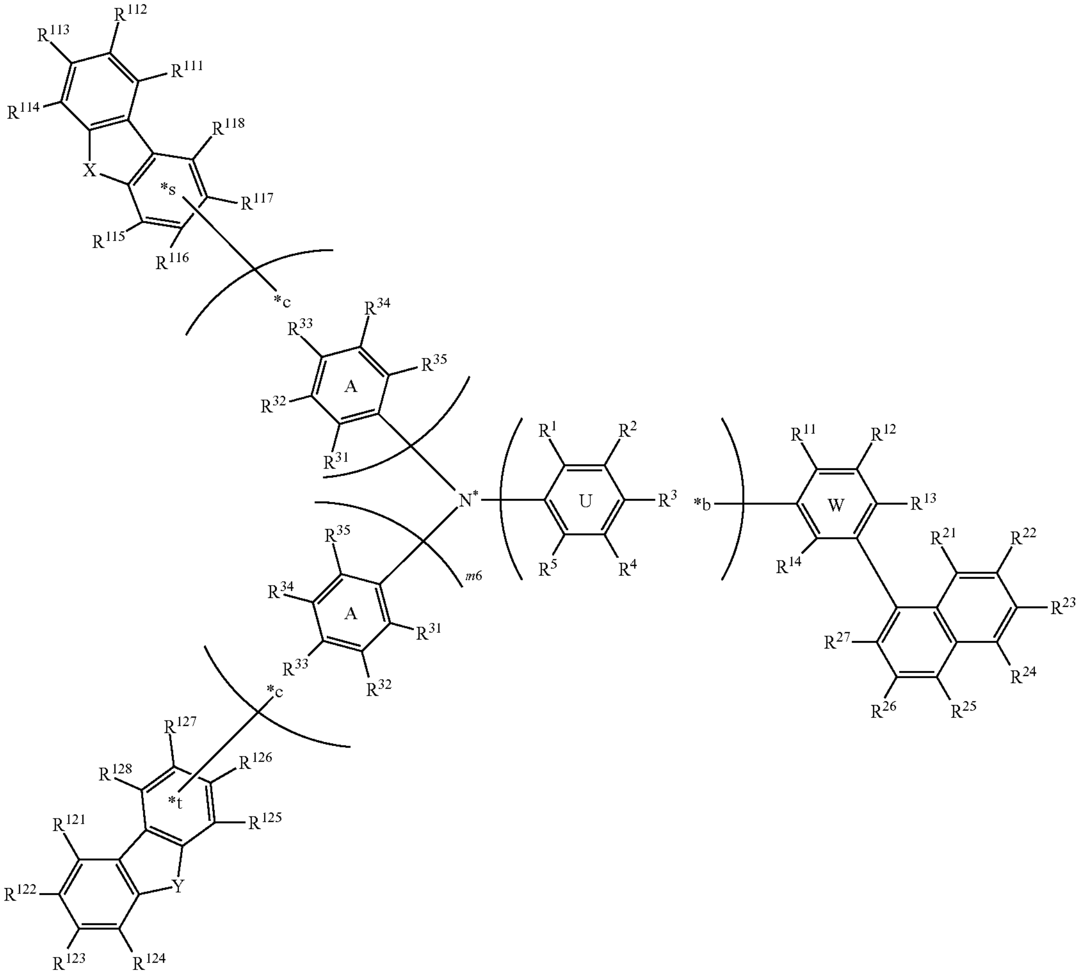
(IB-3)
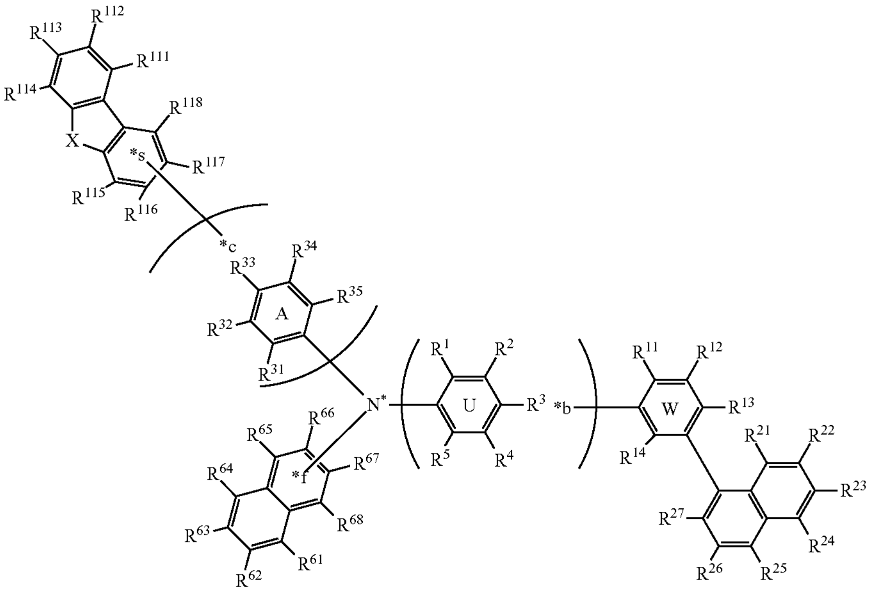

-continued
(IB-4)
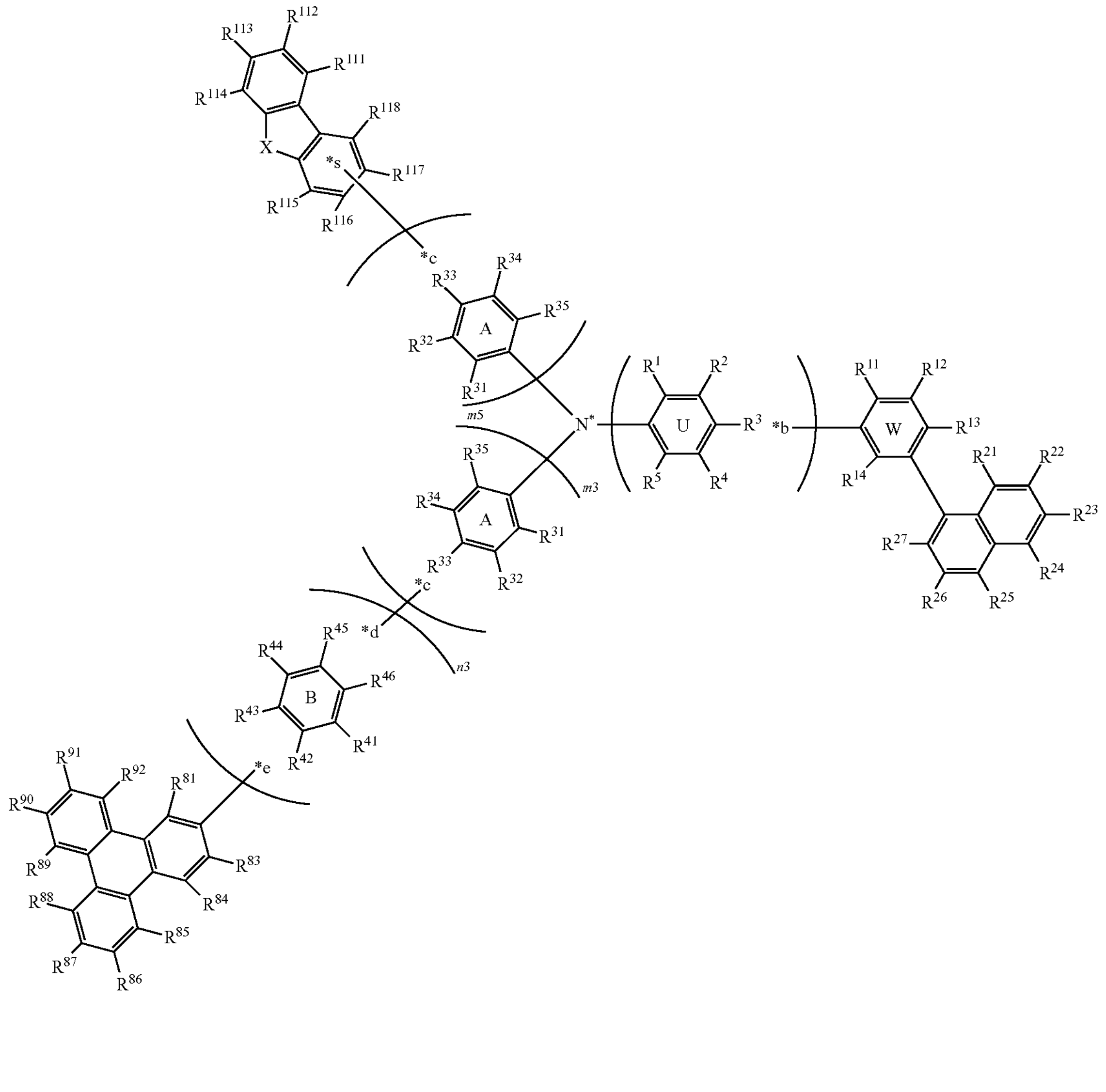

-continued
(1B-5)
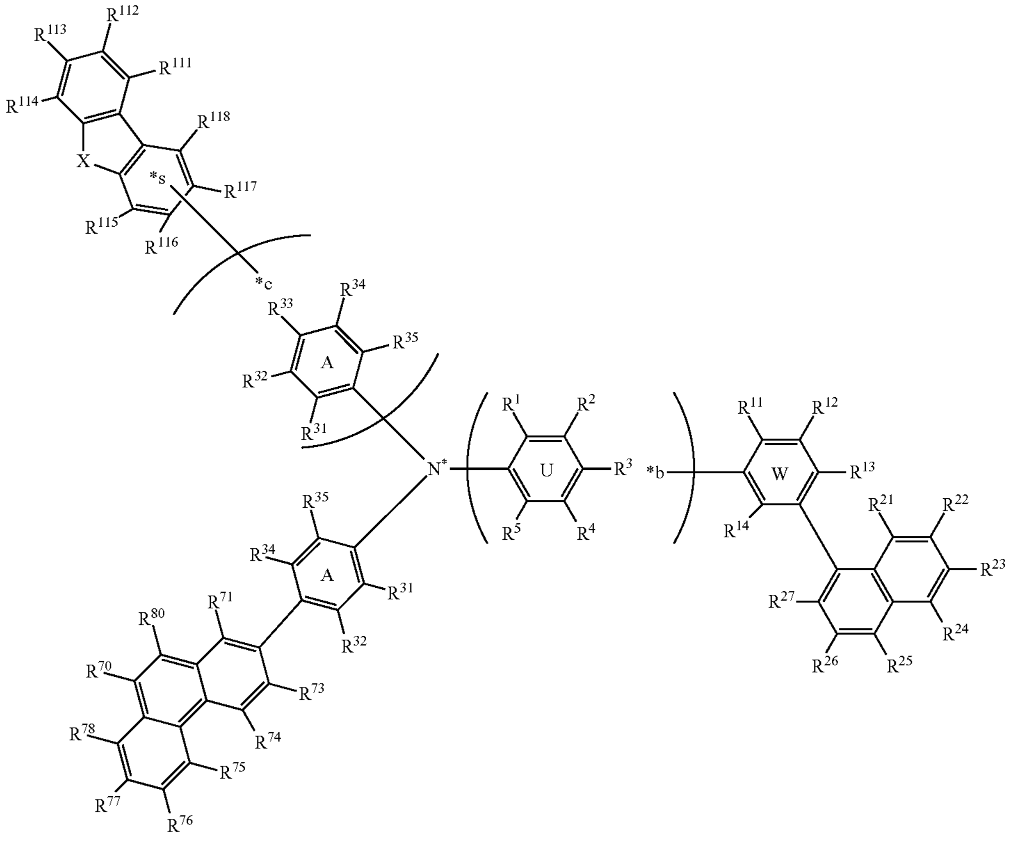

-continued
(1B-6)
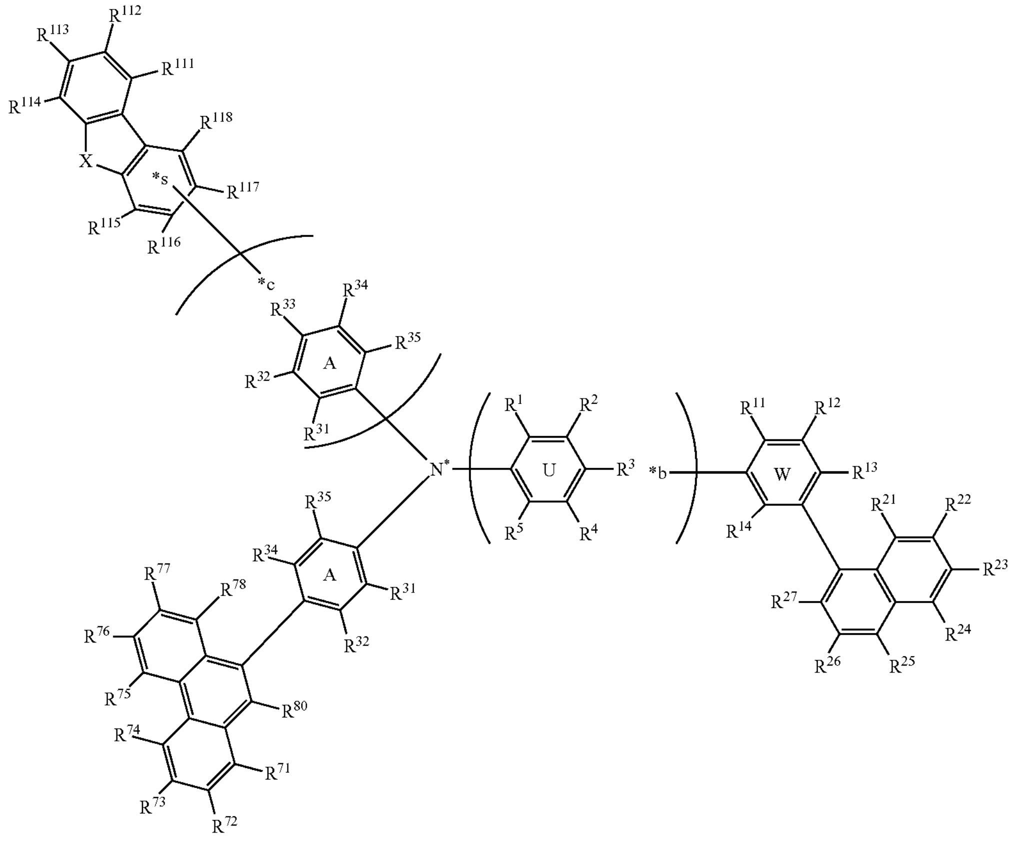
In these formulae, N*, X, Y, *b, *c, *d, *e, *f, *s, *t, k, n1, n3, m1, m3, m5, m6, $R^1$ to $R^5$, $R^{11}$ to $R^{14}$, $R^{21}$ to $R^{27}$, $R^{31}$ to $R^{35}$, $R^{41}$ to $R^{46}$, $R^{51}$ to $R^{55}$, $R^{61}$ to $R^{68}$, $R^{71}$ to $R^{80}$, $R^{81}$ to $R^{92}$, $R^{111}$ to $R^{118}$, and $R^{121}$ to $R^{128}$ are as defined in the formula (1B).

The compound represented by the formula (1B-2) is represented by the following formula (1B-2').
(1B-2')
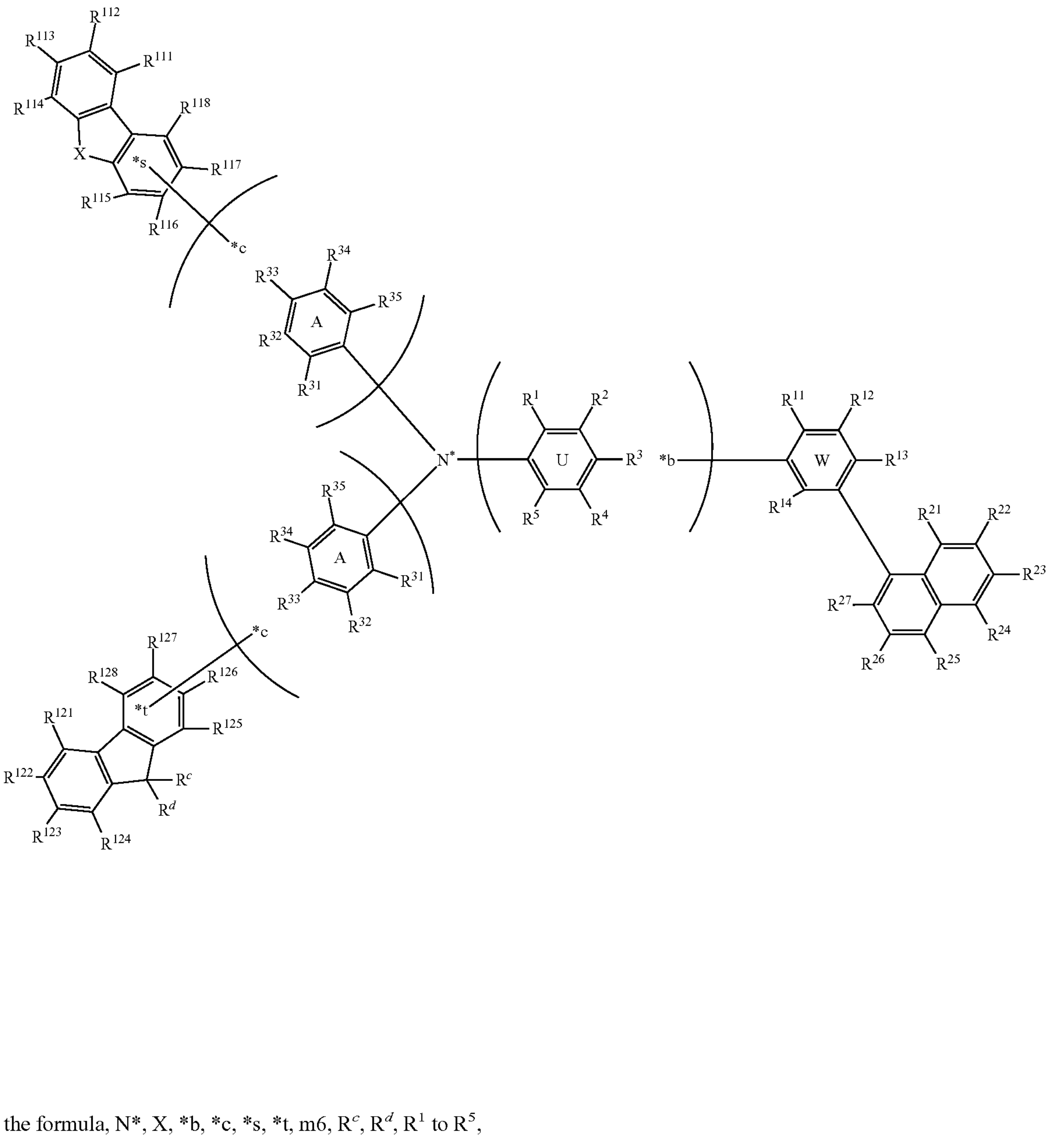
In the formula, N*, X, *b, *c, *s, *t, m6, $R^c$, $R^d$, $R^1$ to $R^5$, $R^{11}$ to $R^{14}$, $R^{21}$ to $R^{27}$, $R^{31}$ to $R^{35}$, $R^{111}$ to $R^{118}$, and $R^{121}$ to $R^{128}$ are as defined in the formula (1B).
The compound represented by the formula (1B-2') is represented by any of the following formulae (1B-2'-1) to (1B-2'-4).

(1B-2′-1)
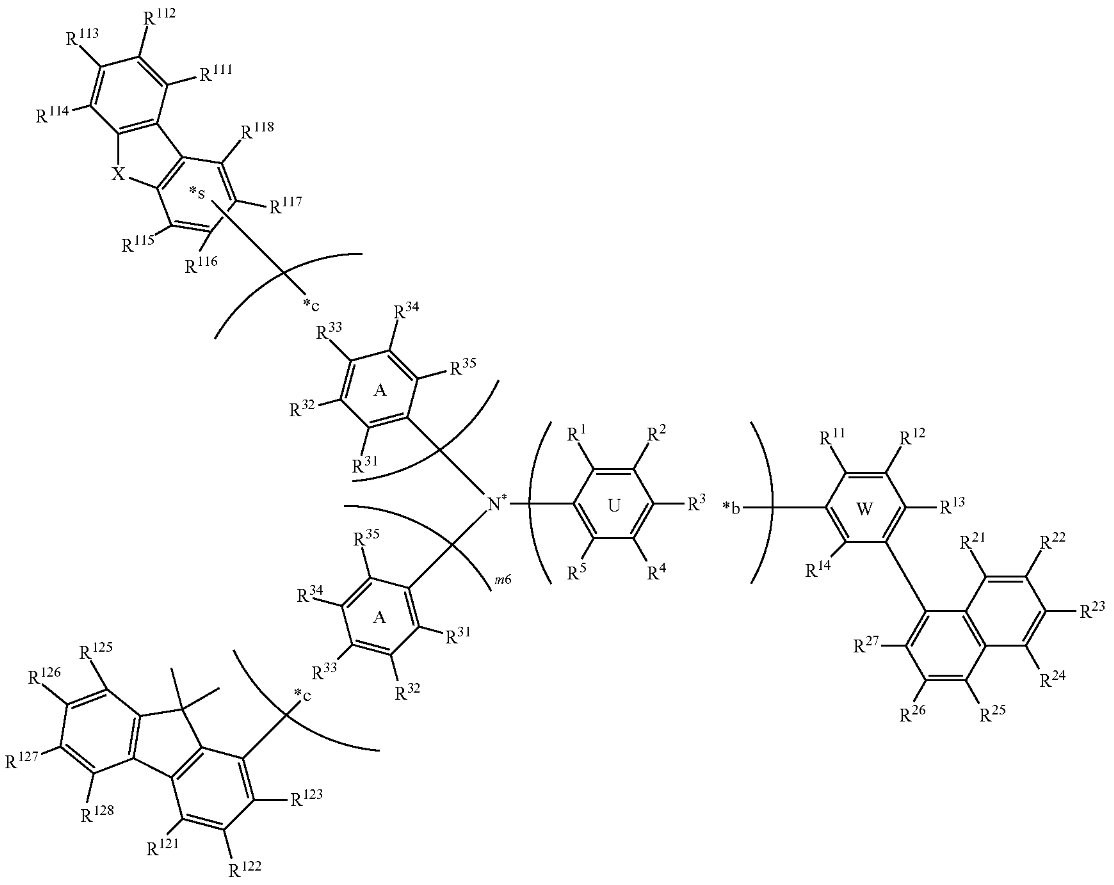

-continued
(1B-2′-2)
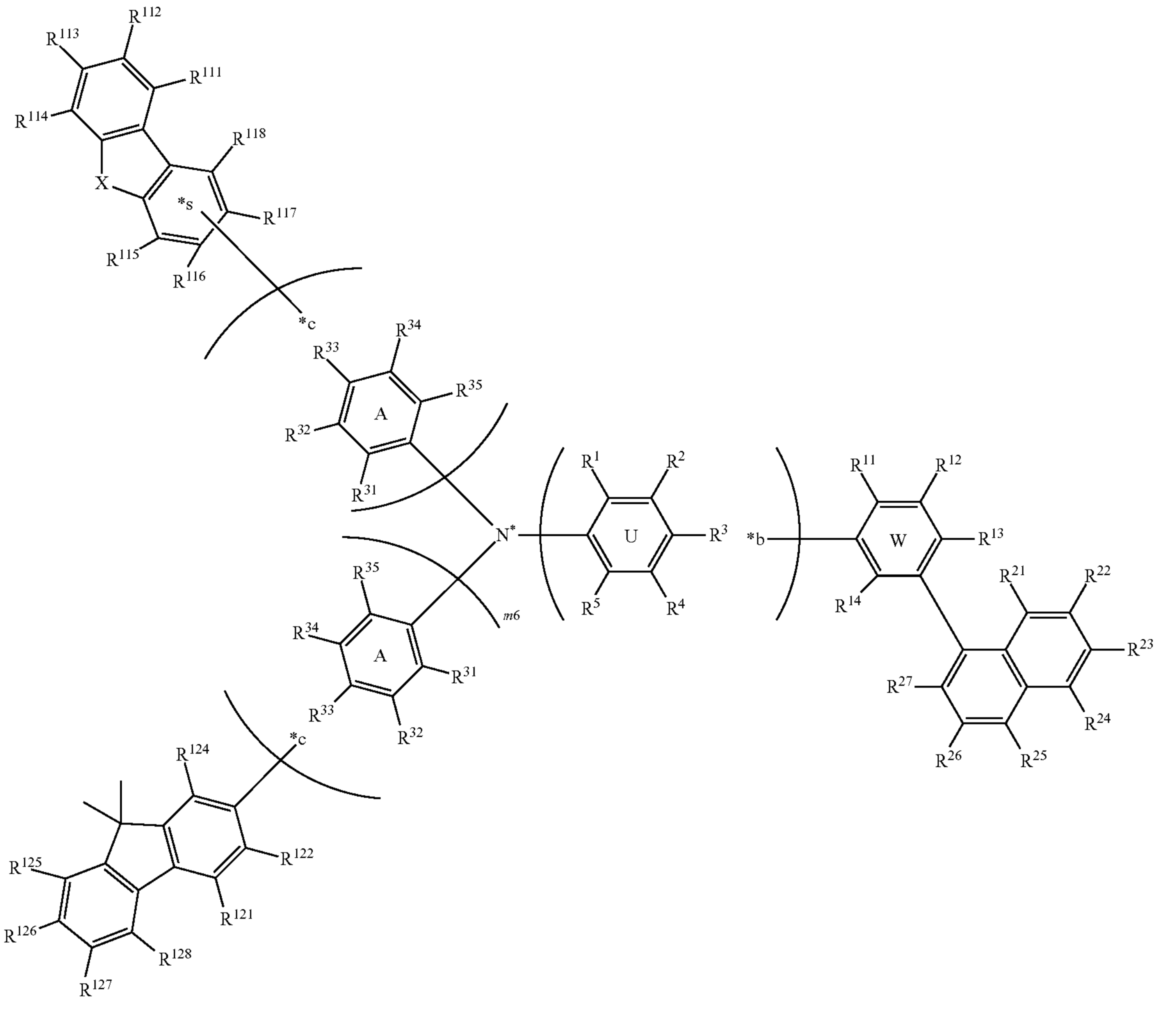

-continued
(1B-2′-3)
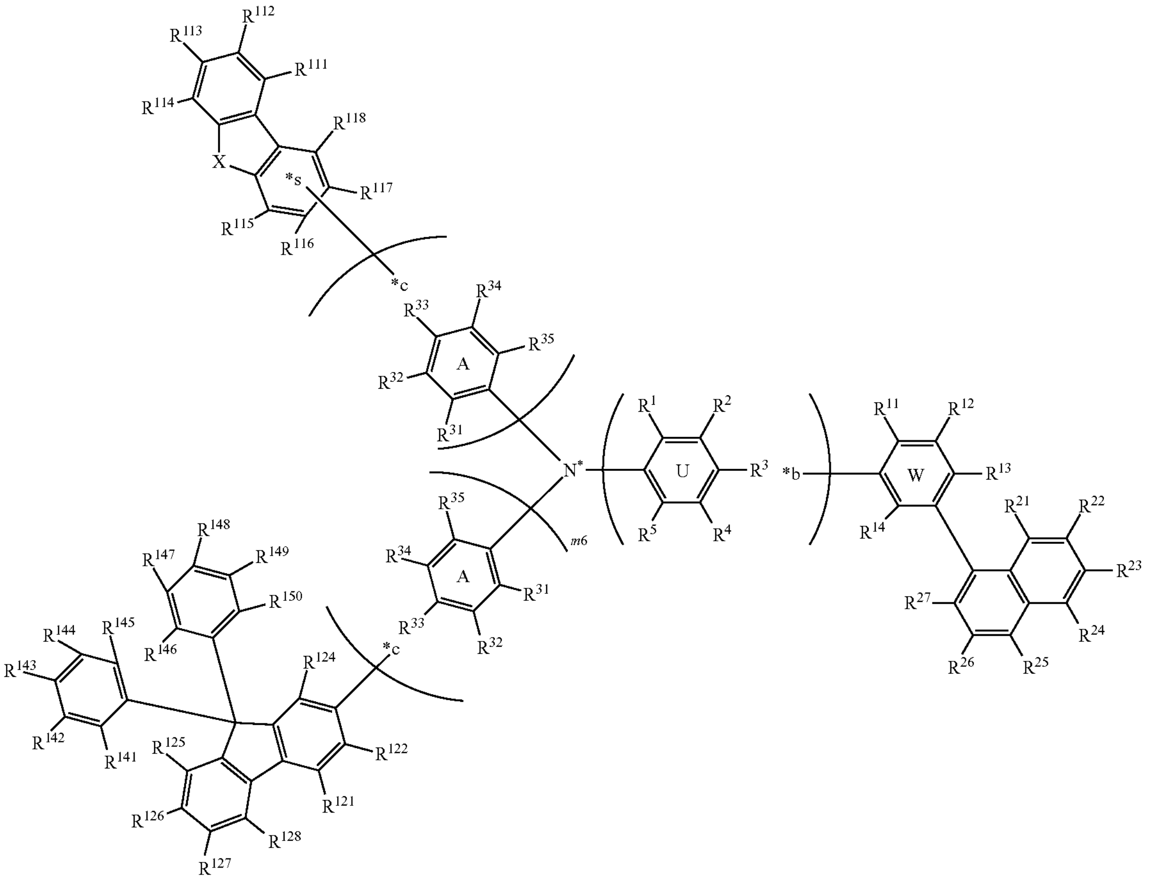

-continued (1B-2'-4)

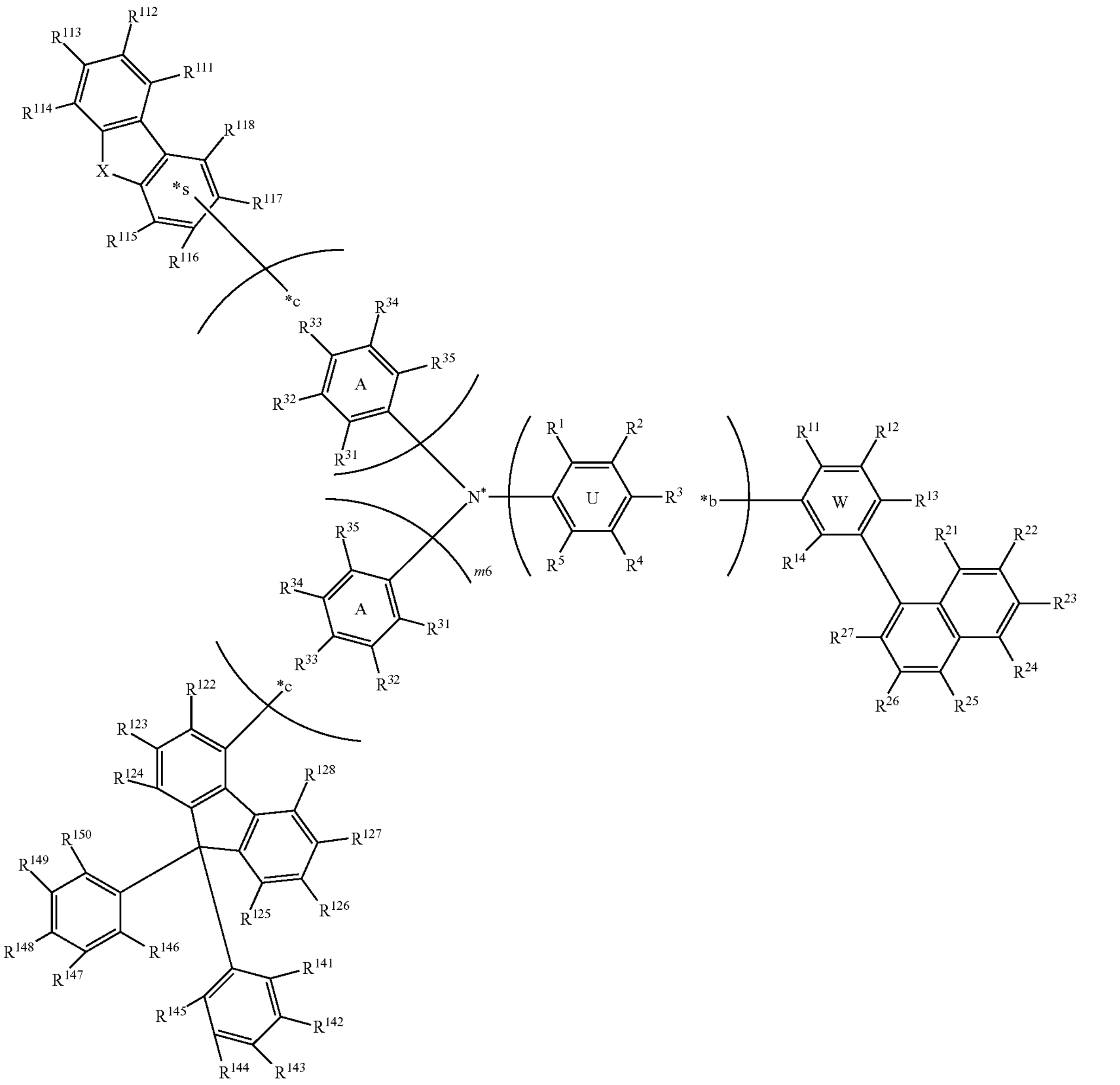

In the formulae, N*, X, *b, *c, *s, m6, $R^1$ to $R^5$, $R^{11}$ to $R^{14}$, $R^{21}$ to $R^{27}$, $R^{31}$ to $R^{35}$, $R^{111}$ to $R^{118}$, and $R^{121}$ to $R^{128}$ are as defined in the formula (1B), and $R^{141}$ to $R^{150}$ are the same as $R^{111}$ to $R^{118}$ defined in the formula (1B).

Details of the groups that $R^{141}$ to $R^{150}$ represent are the same as the details of the corresponding groups described hereinabove relating to $R^1$ to $R^5$ bonding to *a or *b that are not a single bond, and $R^6$ to $R^{10}$, $R^{11}$ to $R^{14}$, and $R^{21}$ to $R^{27}$ bonding to *b that are not a single bond.

In one embodiment of the present invention, (B-1) all $R^1$ to $R^5$ bonding to *a or *b that are not a single bond may be hydrogen atoms, (B-2) all $R^6$ to $R^{10}$ bonding to *b that are not a single bond may be hydrogen atoms, (B-3) all $R^{11}$ to $R^{14}$ may be hydrogen atoms, (B-4) all $R^{21}$ to $R^{27}$ may be hydrogen atoms, (B-5) all $R^{31}$ to $R^{35}$ bonding to *c that are not a single bond may be hydrogen atoms, (B-6) all $R^{111}$ to $R^{35}$ bonding to *s that are not a single bond may be hydrogen atoms, (B-7) all $R^{41}$ to $R^{46}$ bonding to *d that are not a single bond and bonding to *e that are not a single bond may be hydrogen atoms, (B-8) all $R^{51}$ to $R^{55}$ may be hydrogen atoms, (B-9) all $R^{61}$ to $R^{68}$ bonding to *f that are not a single bond may be hydrogen atoms, (B-10) all $R^{71}$ to $R^{80}$ bonding to *h that are not a single bond may be hydrogen atoms, (B-11) all $R^{81}$ to $R^{92}$ bonding to *g that are not a single bond may be hydrogen atoms, (B-12) all $R^{121}$ to $R^{128}$ bonding to *t that are not a single bond may be hydrogen atoms, (B-13) all $R^{141}$ to $R^{150}$ may be hydrogen atoms.

As described above, the "hydrogen atom" referred in the description herein encompasses a protium atom, a deuterium atom, and tritium atom. Accordingly, the inventive compound B may contain a naturally-derived deuterium atom.

A deuterium atom may be intentionally introduced into the inventive compound B by using a deuterated compound as a part or the whole of the raw material. Accordingly, in one embodiment of the present invention, the inventive compound B contains at least one deuterium atom. That is, the inventive compound B may be a compound represented by the formula (1B) in which at least one hydrogen atom contained therein is a deuterium atom.

At least one hydrogen atom selected from the following hydrogen atoms may be a deuterium atom:

- a hydrogen atom that any of Ru to $R^5$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^1$ to $R^5$ represents;
- a hydrogen atom that any of $R^6$ to $R^{10}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^6$ to $R^{10}$ represents;
- a hydrogen atom that any of $R^{11}$ to $R^{14}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{11}$ to $R^{14}$ represents;
- a hydrogen atom that any of $R^{21}$ to $R^{27}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{21}$ to $R^{27}$ represents;
- a hydrogen atom that any of $R^{31}$ to $R^{35}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{31}$ to $R^{35}$ represents;
- a hydrogen atom that any of $R^{41}$ to $R^{46}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{41}$ to $R^{46}$ represents;
- a hydrogen atom that any of $R^{51}$ to $R^{55}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{51}$ to $R^{55}$ represents;
- a hydrogen atom that any of $R^{61}$ to $R^{68}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{61}$ to $R^{68}$ represents;
- a hydrogen atom that any of $R^{71}$ to $R^{80}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{71}$ to $R^{80}$ represents;
- a hydrogen atom that any of $R^{81}$ to $R^{92}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{81}$ to $R^{92}$ represents;
- a hydrogen atom that any of $R^{111}$ to $R^{118}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{111}$ to $R^{118}$ represents;
- a hydrogen atom that any of $R^{121}$ to $R^{128}$ represents; a hydrogen atom of the substituted or unsubstituted alkyl group, cycloalkyl group, aryl group, haloalkyl group, alkoxy group, haloalkoxy group, aryloxy group or aralkyl group or the mono, di or tri-substituted silyl group that any of $R^{121}$ to $R^{128}$ represents;
- a hydrogen atom that any of $R^{141}$ to $R^{150}$ represents; a hydrogen atom of the substituted or unsubstituted alkyl group, cycloalkyl group, haloalkyl group, alkoxy group, haloalkoxy group, aryloxy group or aralkyl group or the mono, di or tri-substituted silyl group that any of $R^{141}$ to $R^{150}$ represents;
- a hydrogen atom of the substituted or unsubstituted alkyl group or aryl group that any of $R^x$ to $R^y$ represents; and
- a hydrogen atom of the substituted or unsubstituted alkyl group or aryl group that any of $R^c$ to $R^d$ represents.

The deuteration rate of the inventive compound B depends on the deuteration rate of the raw material compound used. Even when a raw material having a predetermined deuteration rate is used, a naturally-derived protium isotope can be contained in a certain ratio. Accordingly, an embodiment of the deuteration rate of the inventive compound B shown below includes the proportion for which a minor amount of a naturally-derived isotope is taken into consideration, relative to the proportion determined by counting the number of the deuterium atoms merely represented by a chemical formula.

The deuteration rate of the inventive compound B is preferably 1% or more, more preferably 3% or more, even more preferably 5% or more, further more preferably 10% or more, further more preferably 50% or more.

The inventive compound B may be a mixture of a deuterated compound and a non-deuterated compound, or a mixture of two or more compounds having different deuteration rates from each other. The deuteration rate of the mixture is preferably 1% or more, more preferably 3% or more, even more preferably 5% or more, further more preferably 10% or more, further more preferably 50% or more, and is less than 100%.

The proportion of the number of the deuterium atoms to the number of all the hydrogen atoms in the inventive compound B is preferably 1% or more, more preferably 3% or more, even more preferably 5% or more, further more preferably 10% or more, and is 100% or less.

Details of the substituent (arbitrary substituent) in the expression "substituted or unsubstituted" included in the definitions of the aforementioned formulae are the same as in the "substituent in the expression 'substituted or unsubstituted'".

However, the arbitrary substituent included in the definitions of the aforementioned formulae relating to the formula (1B) does not include the substituents of an aryl group and a heterocyclic group among the substituents described in the section of "substituent in the expression 'substituted or unsubstituted'".

The inventive compound B can be readily produced by a person skilled in the art with reference to the following synthesis examples and known synthesis methods.

Specific examples of the inventive compound will be described below, but the inventive compound is not limited to the following example compounds.
In the following specific examples, D represents a deuterium atom.
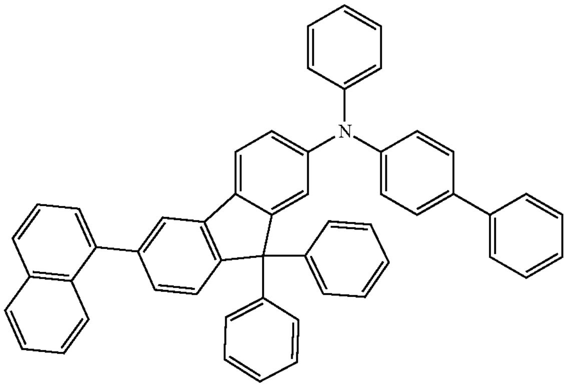
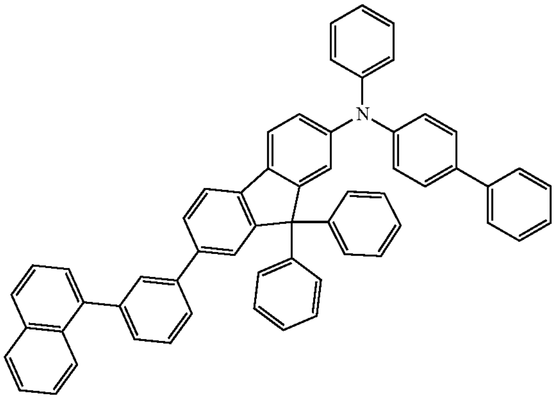
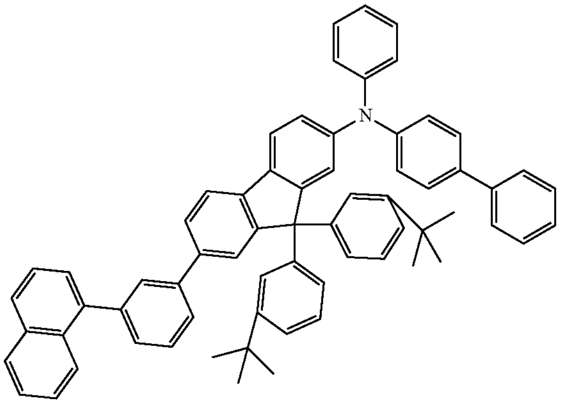
-continued
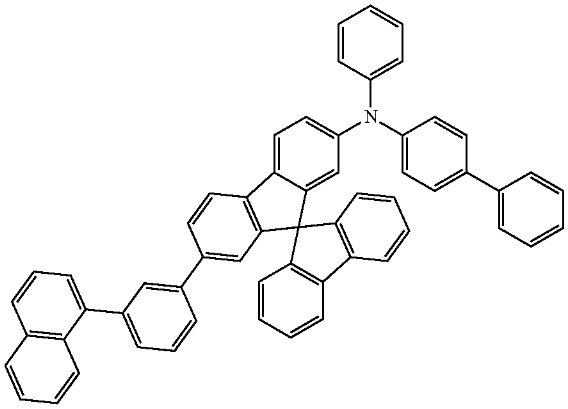
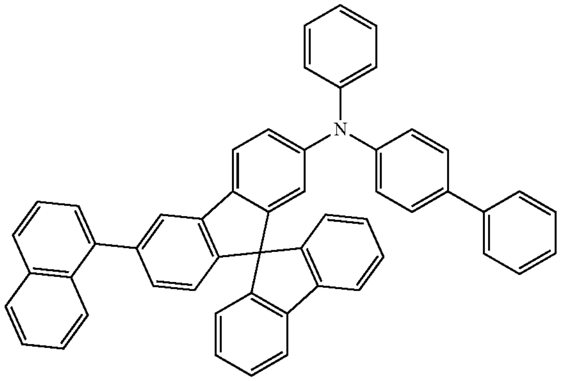
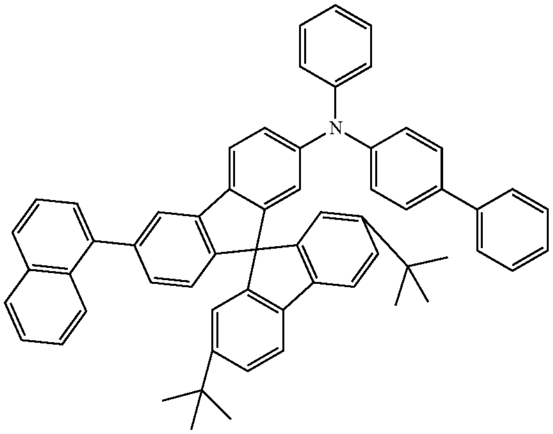
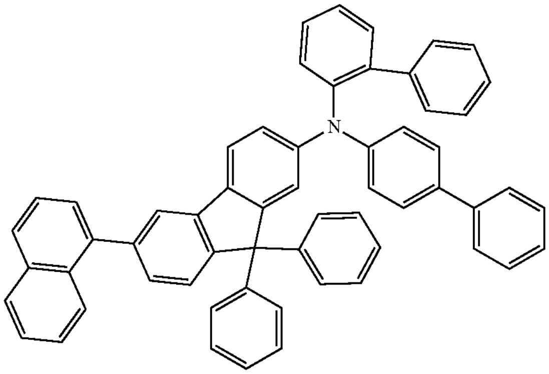

-continued
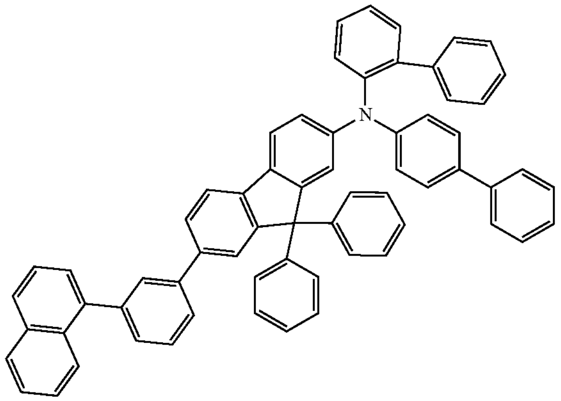
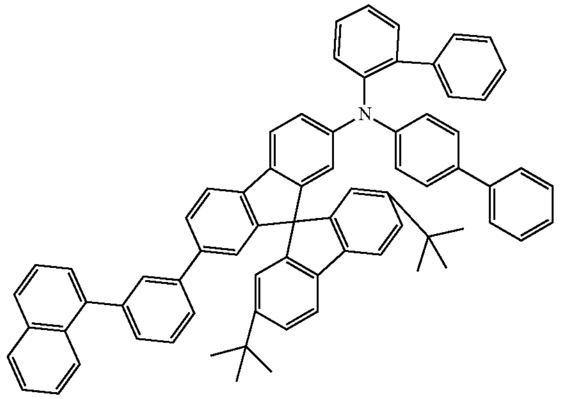
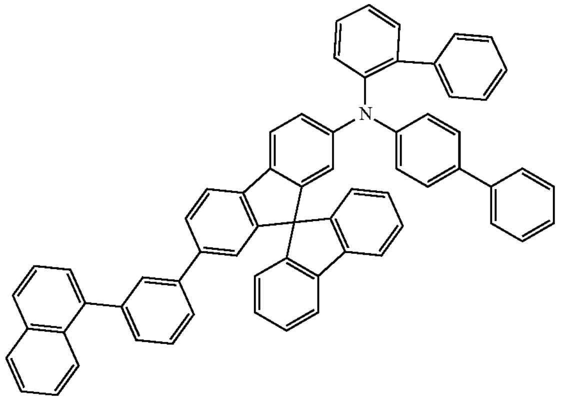
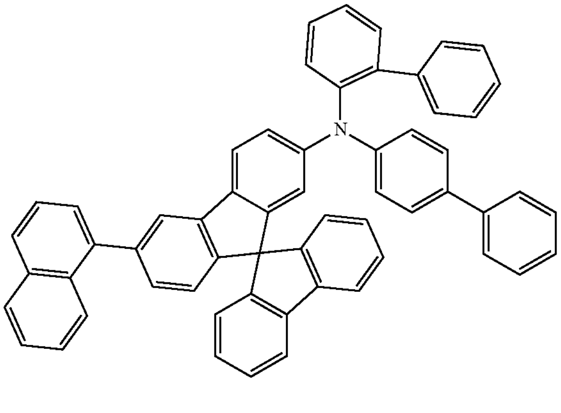
-continued
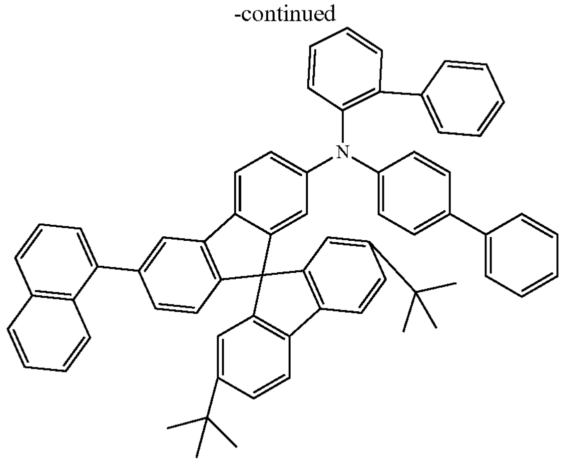
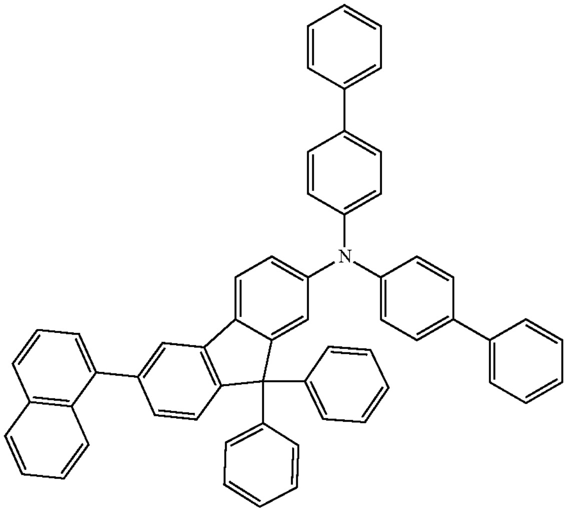
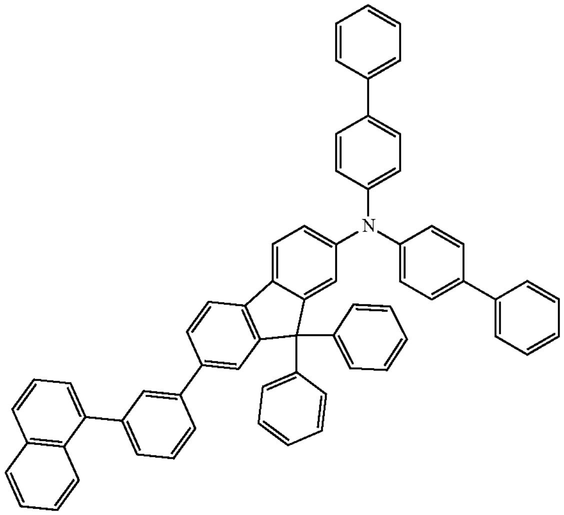

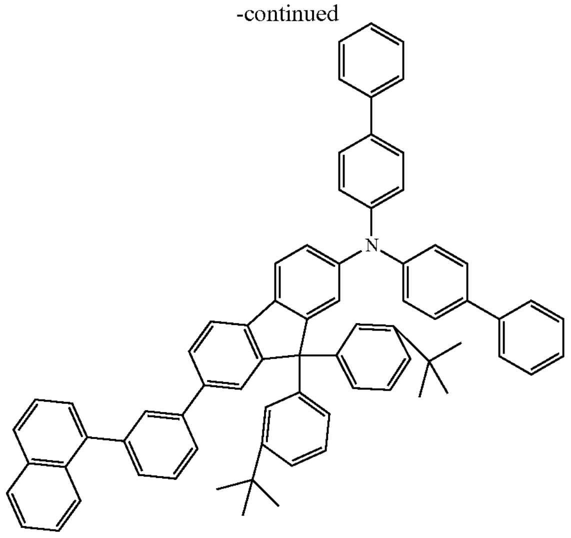
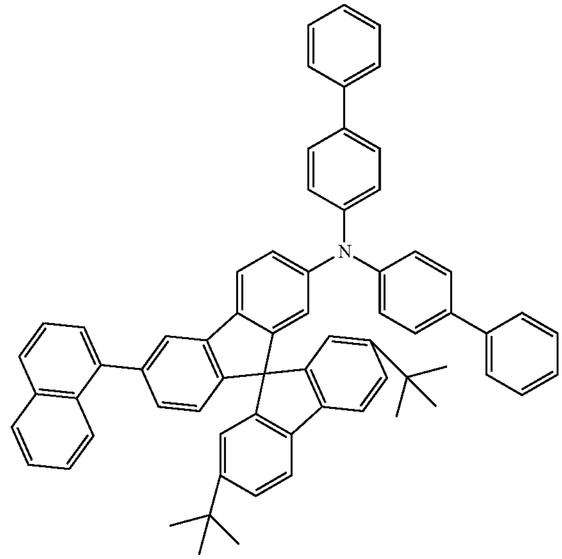
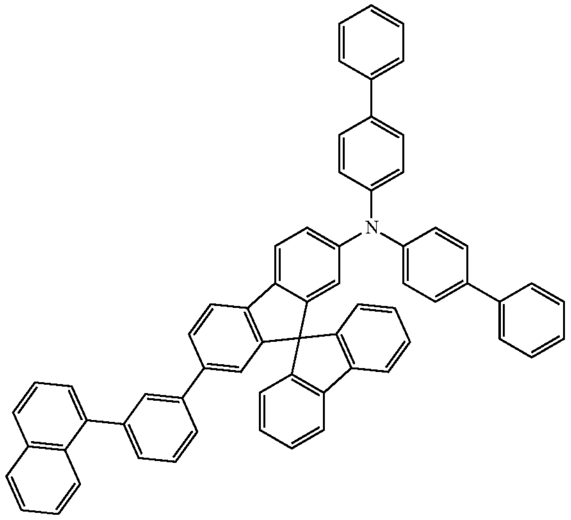 [SMILES: c1ccc(-c2ccc(N(c3ccc(-c4ccccc4)cc3)c3ccc4c(c3)C3(c5ccccc5-c5ccccc53)c3cc(-c5cccc(-c6cccc7ccccc67)c5)ccc3-4)cc2)cc1]
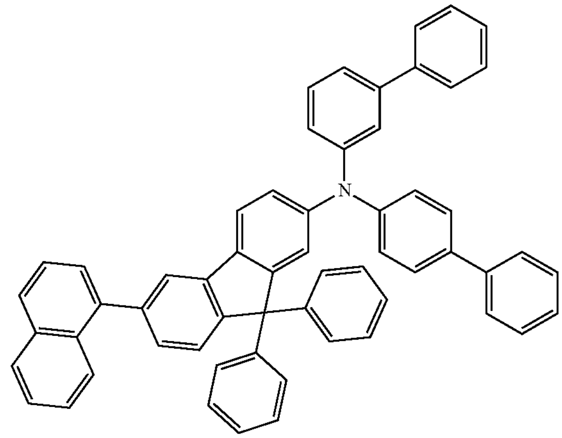
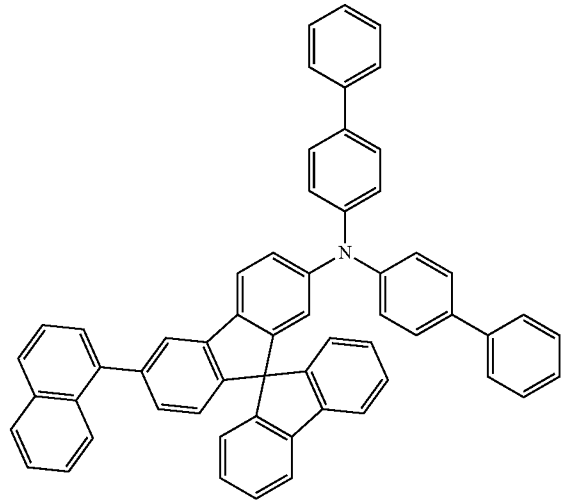
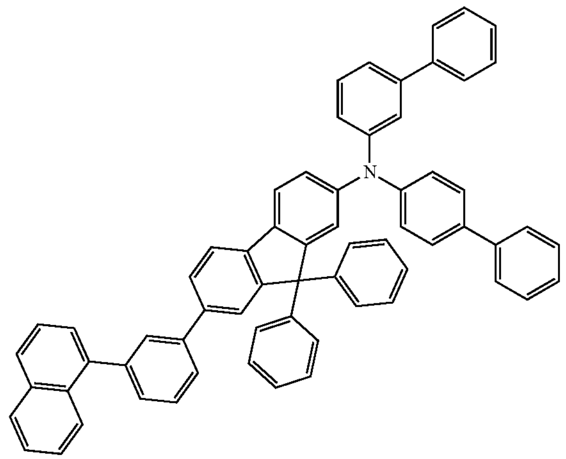

-continued
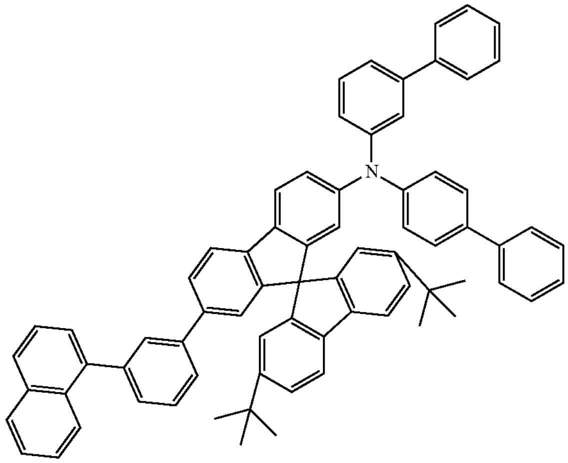
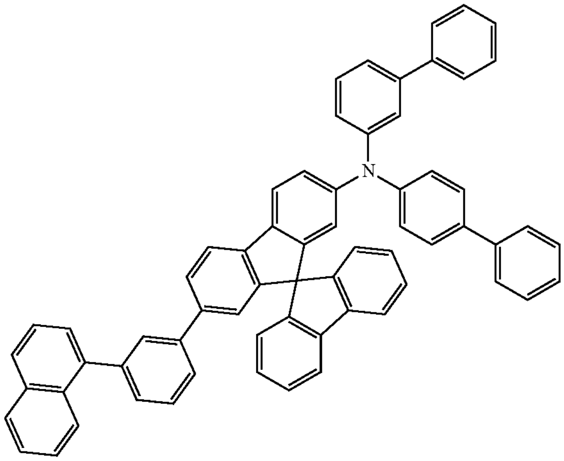
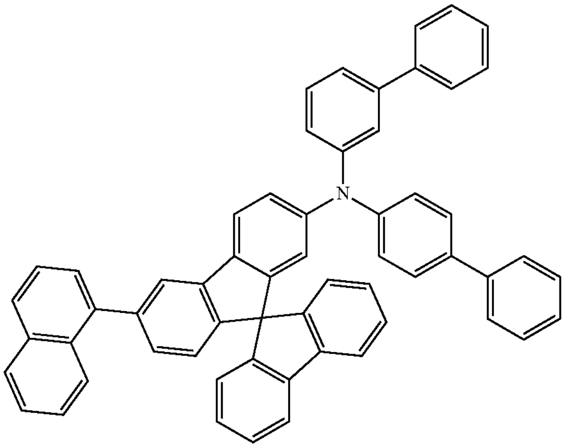
-continued
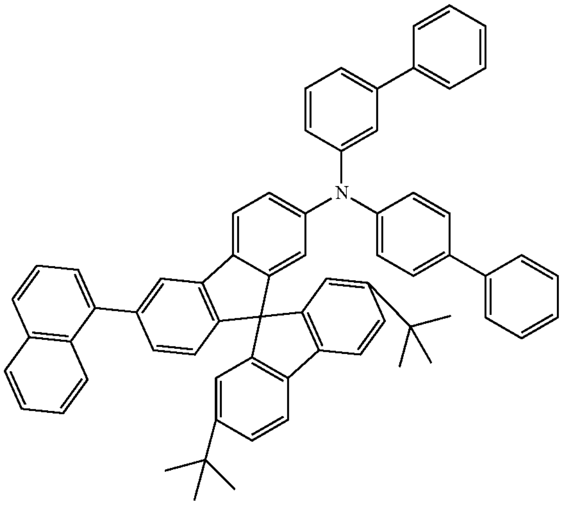
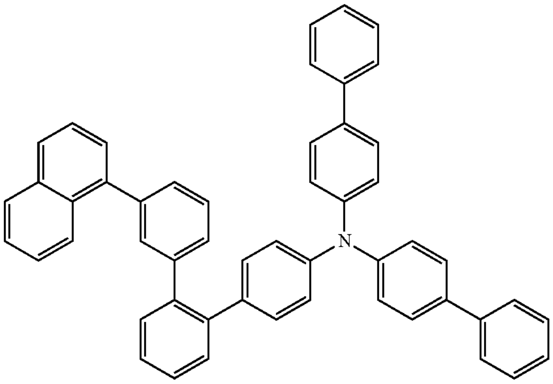
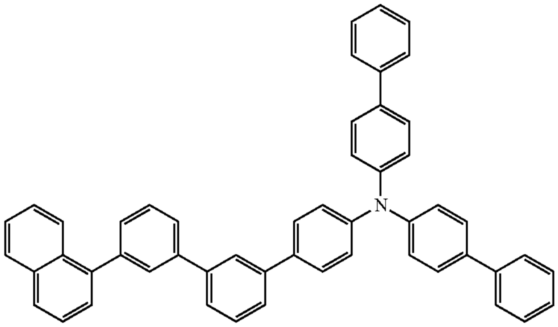
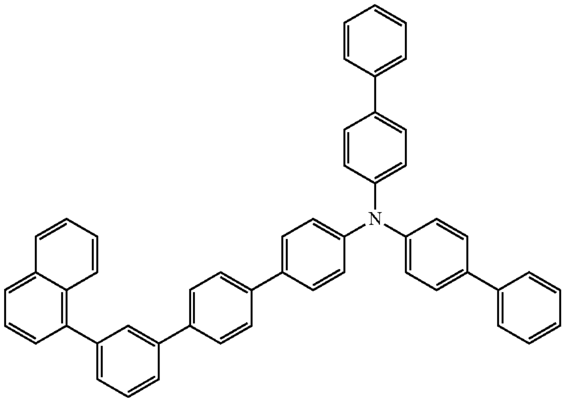

-continued
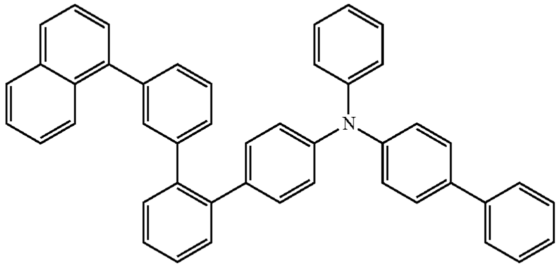
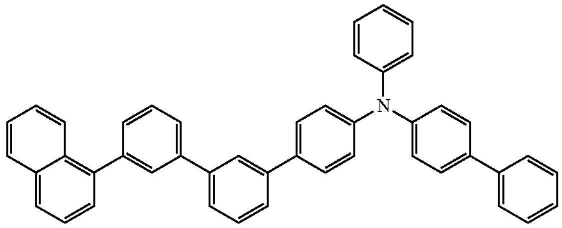
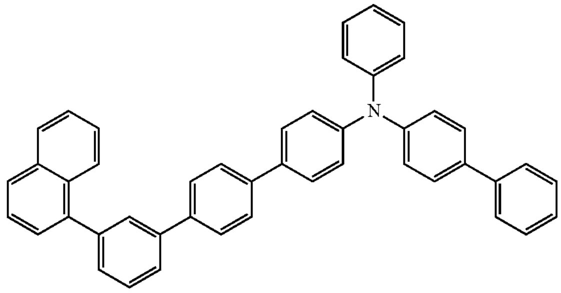
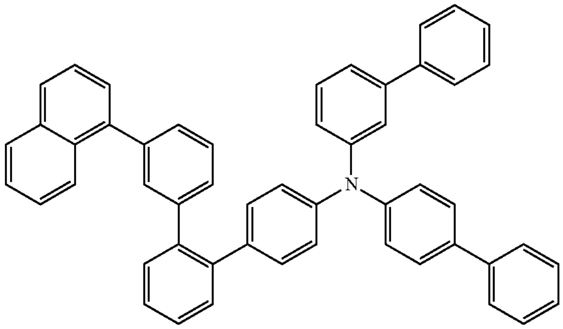
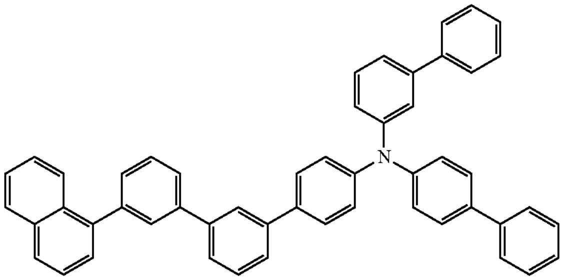
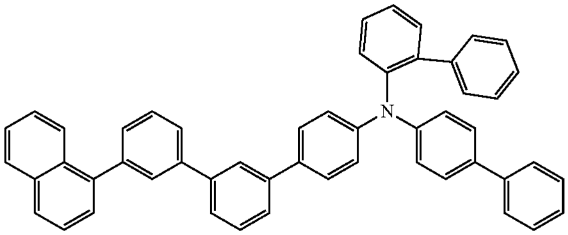
-continued
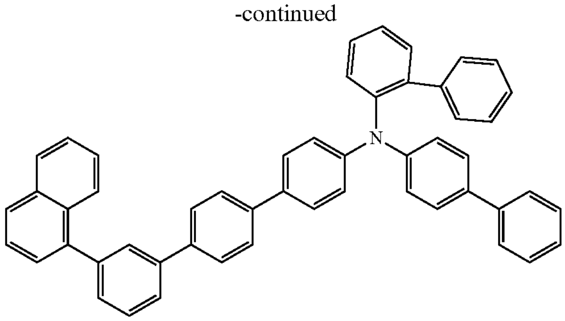
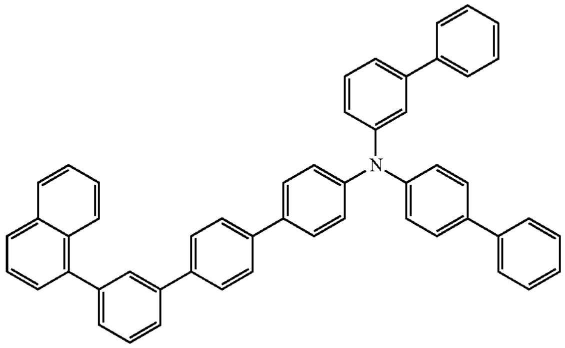
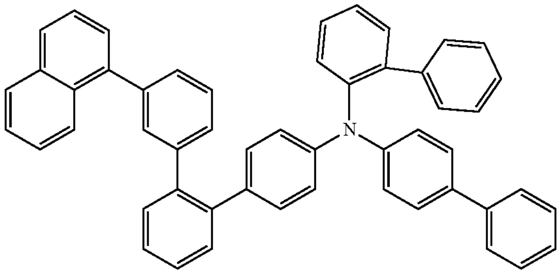
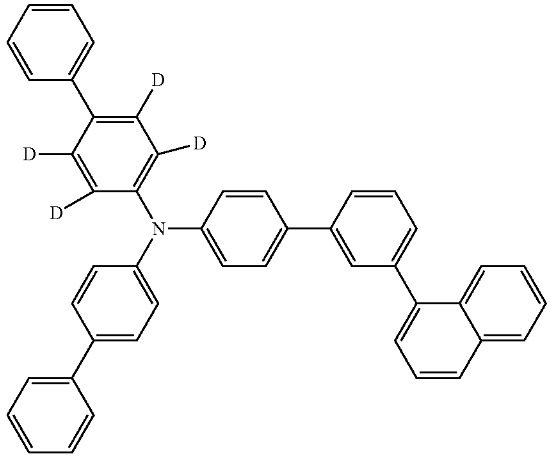
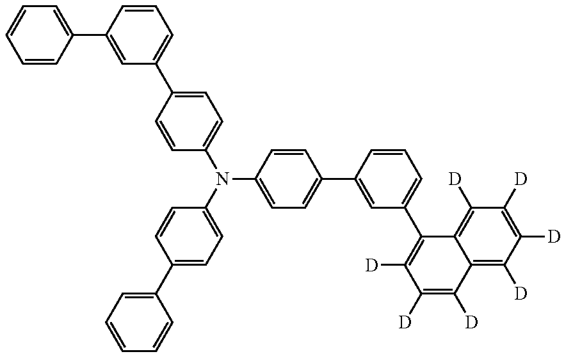

-continued
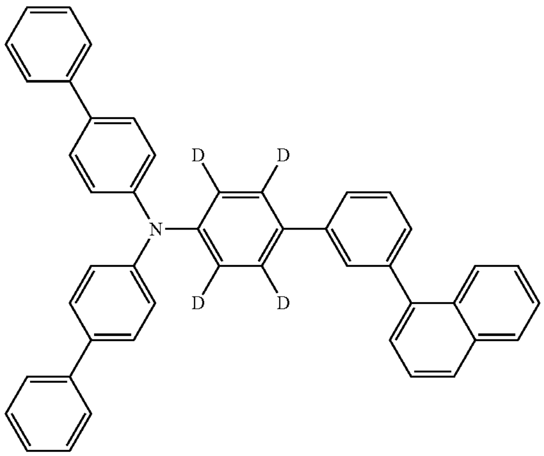
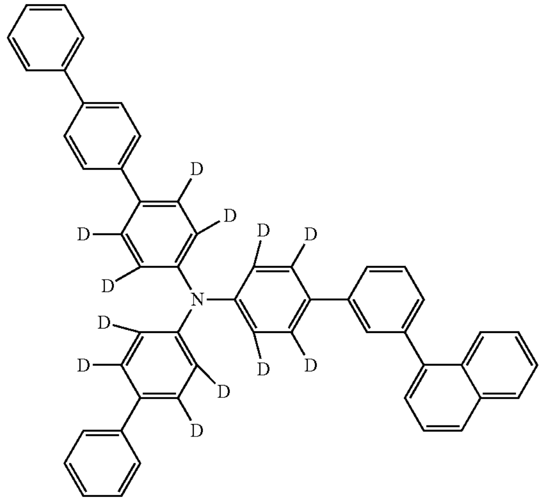
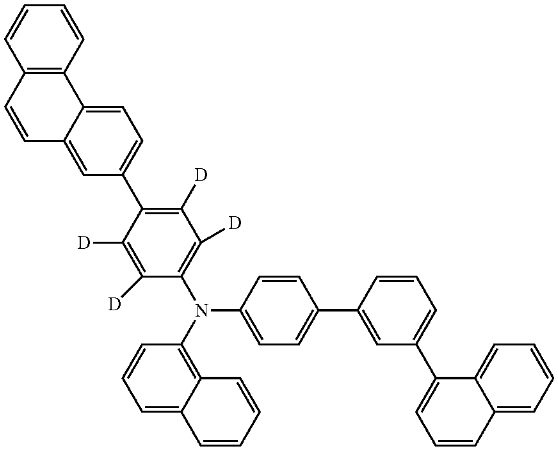
-continued
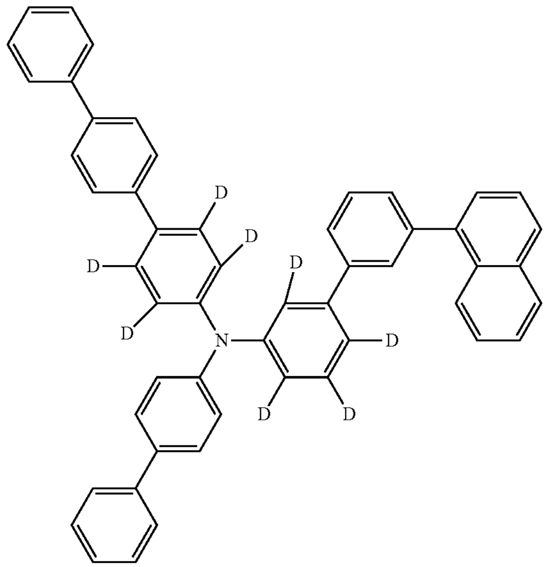 [SMILES: [2H]c1c([2H])c(-c2cccc(-c3cccc4ccccc34)c2)c([2H])c(N(c2ccc(-c3ccccc3)cc2)c2c([2H])c([2H])c(-c3ccc(-c4ccccc4)cc3)c([2H])c2[2H])c1[2H]]
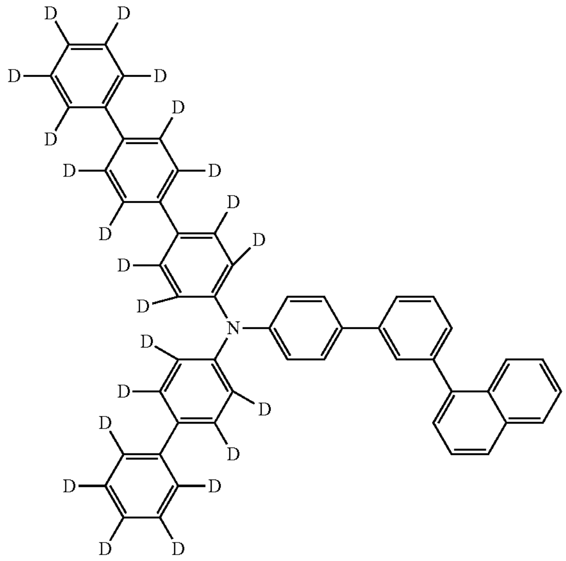
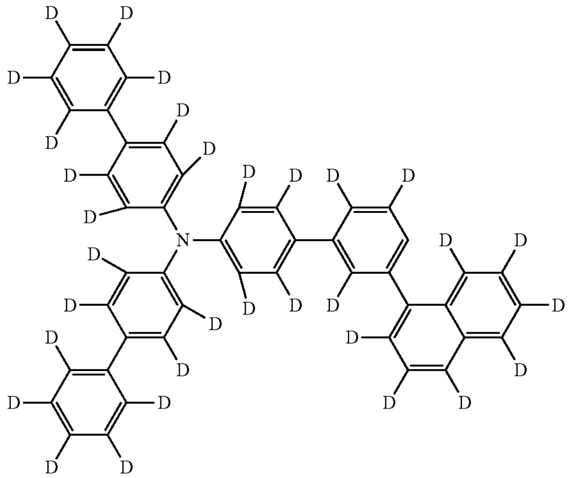

-continued
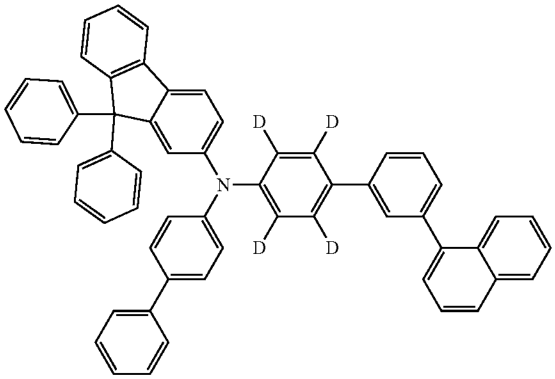
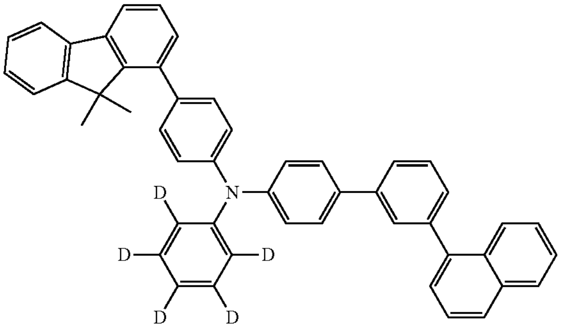
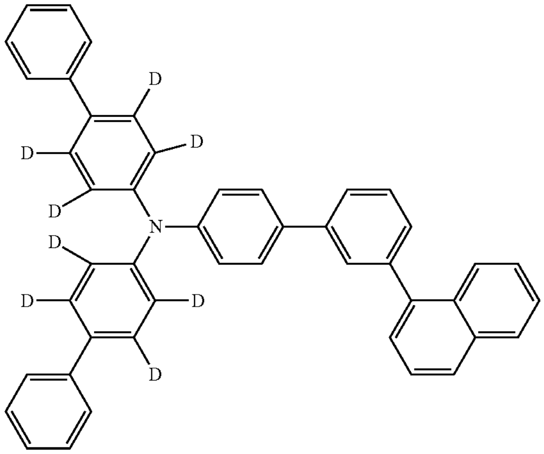
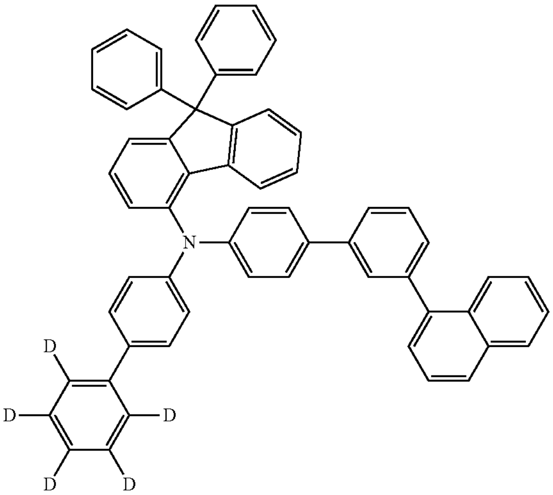
-continued
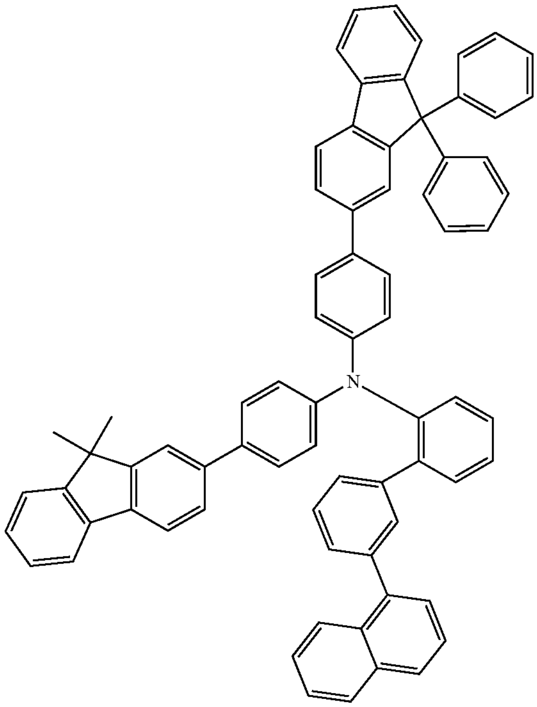
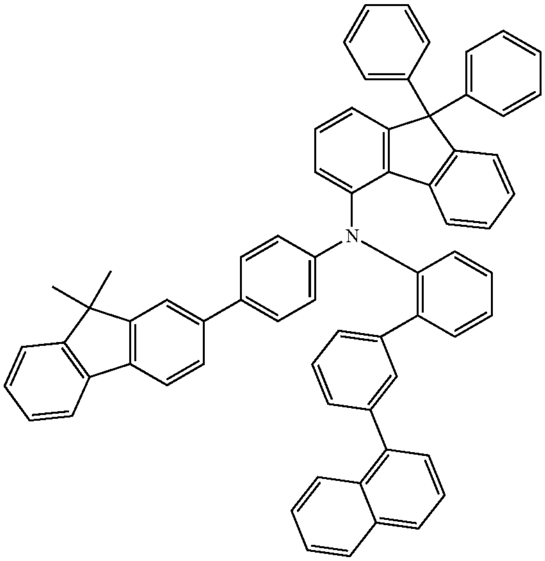

-continued
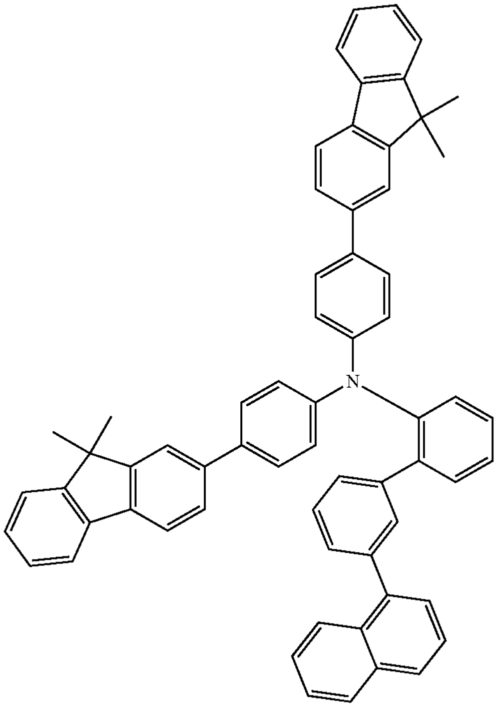
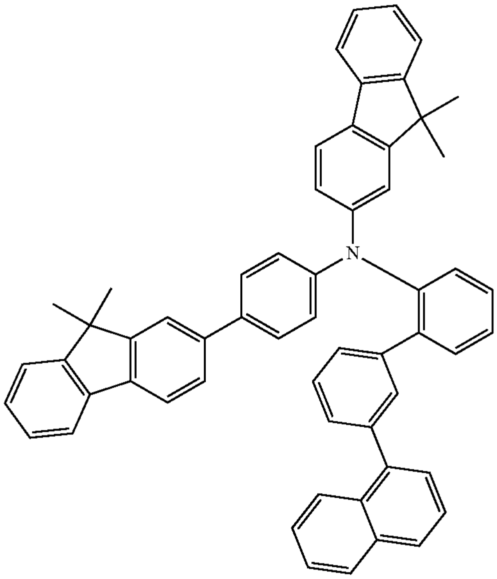
-continued
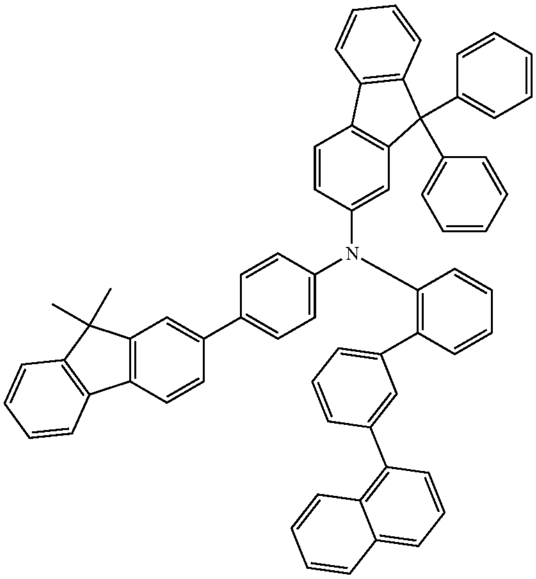
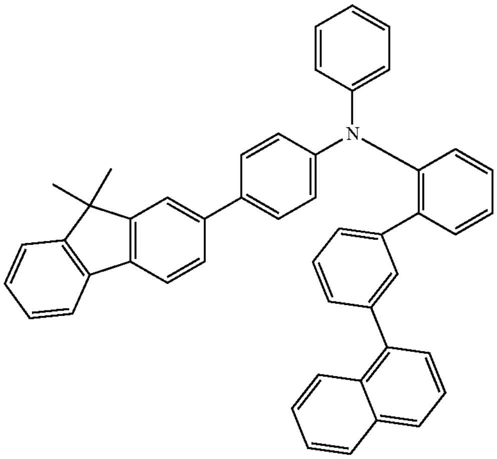
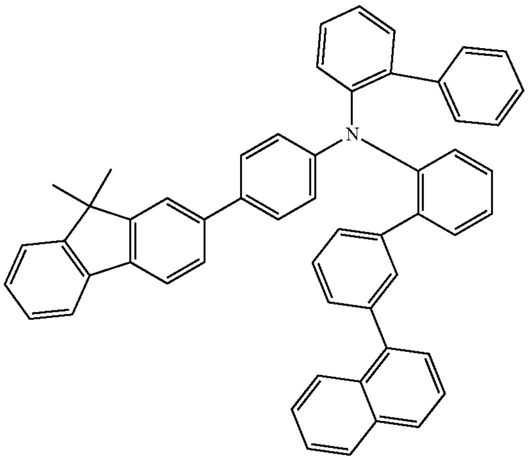

-continued
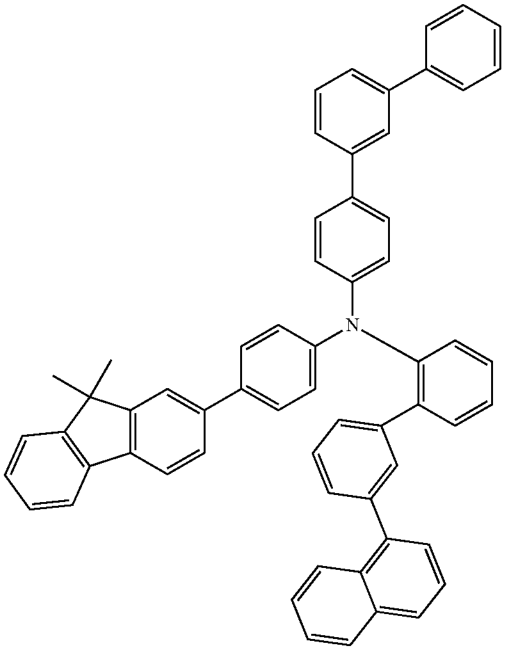
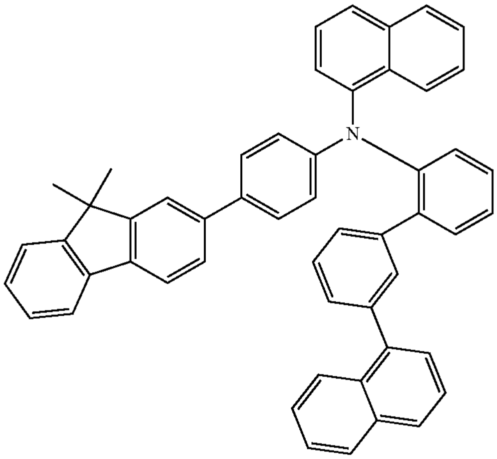
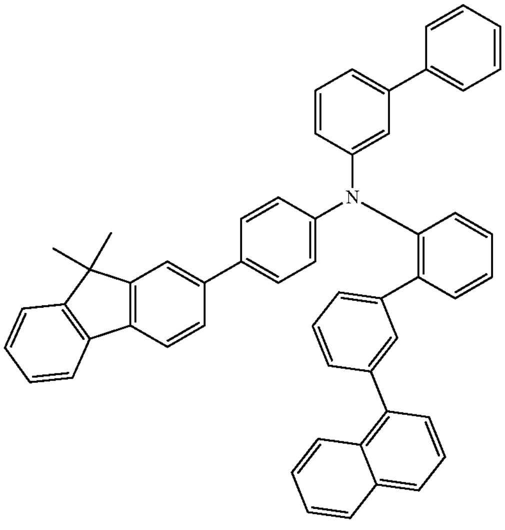
-continued
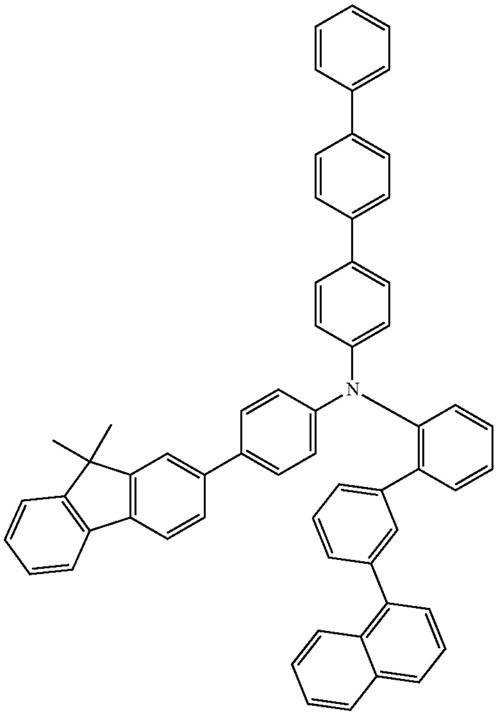
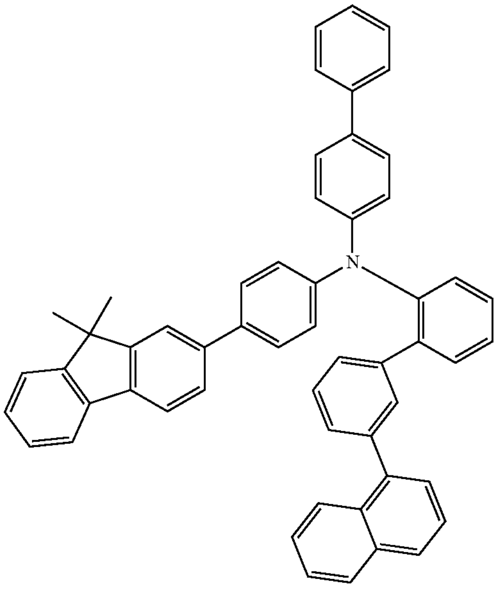

-continued
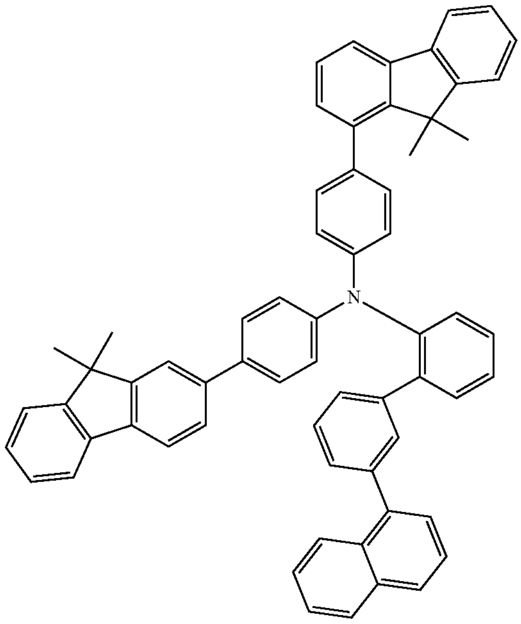
-continued
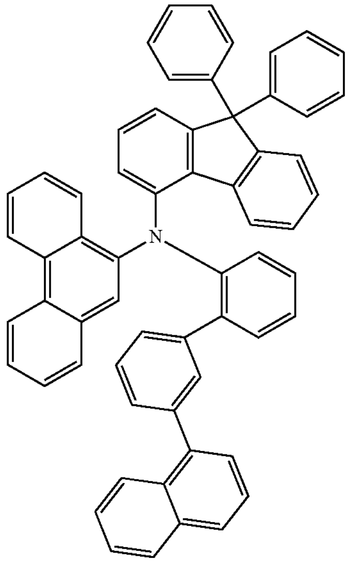
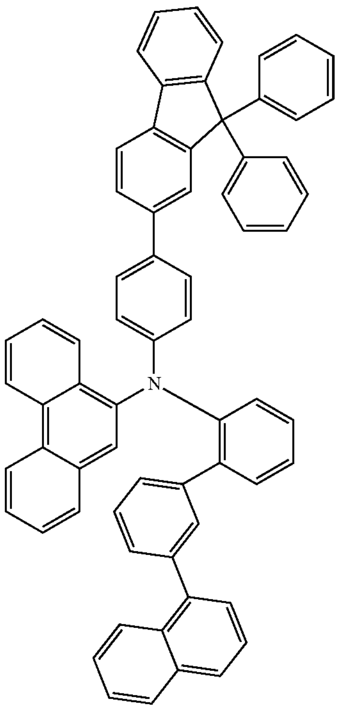
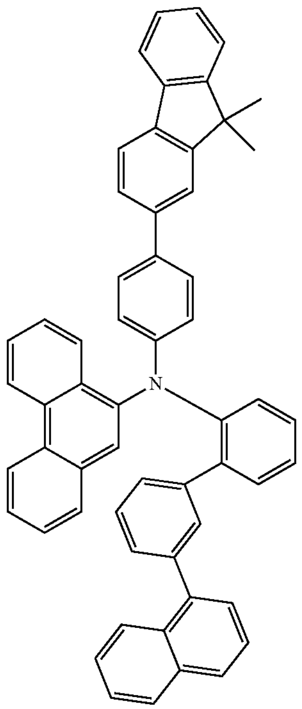

-continued
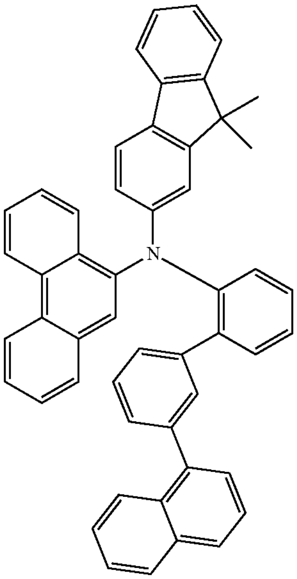
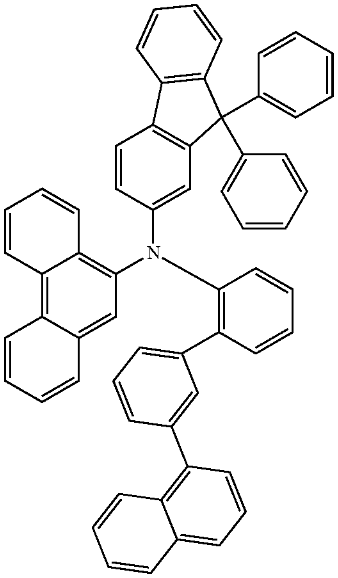
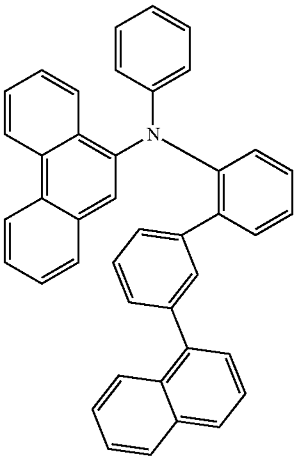
-continued
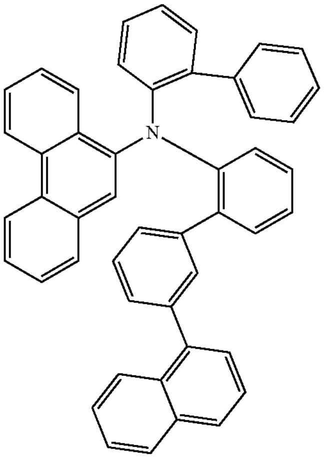
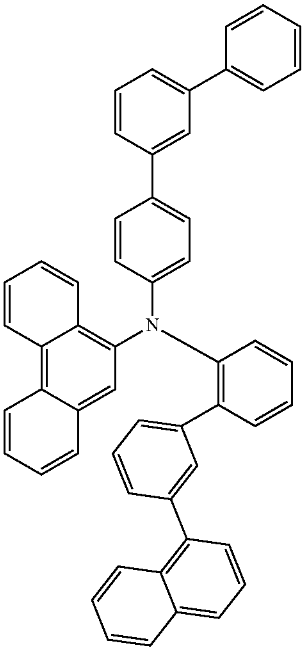
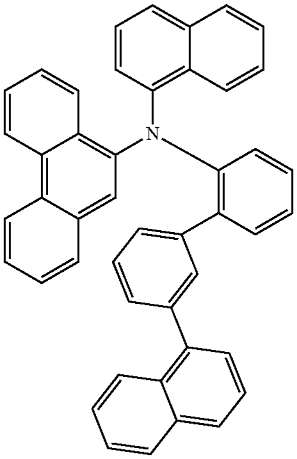

-continued
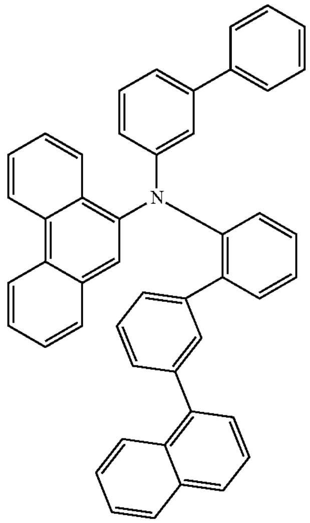
-continued
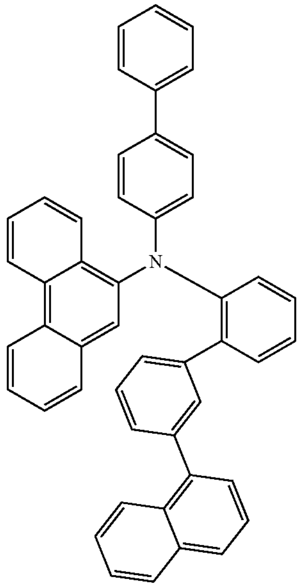
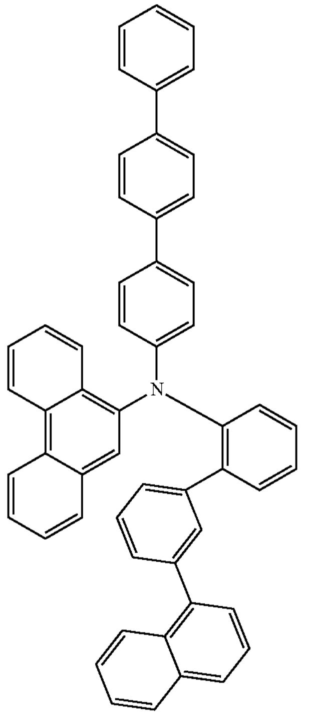
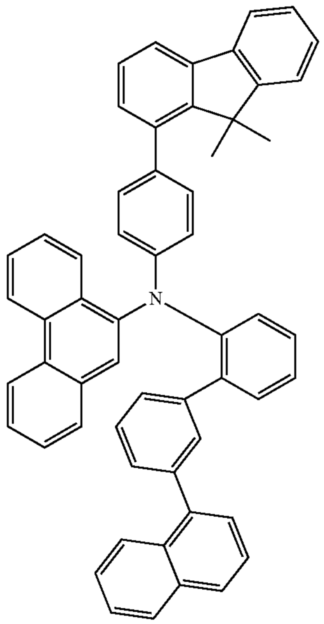

-continued
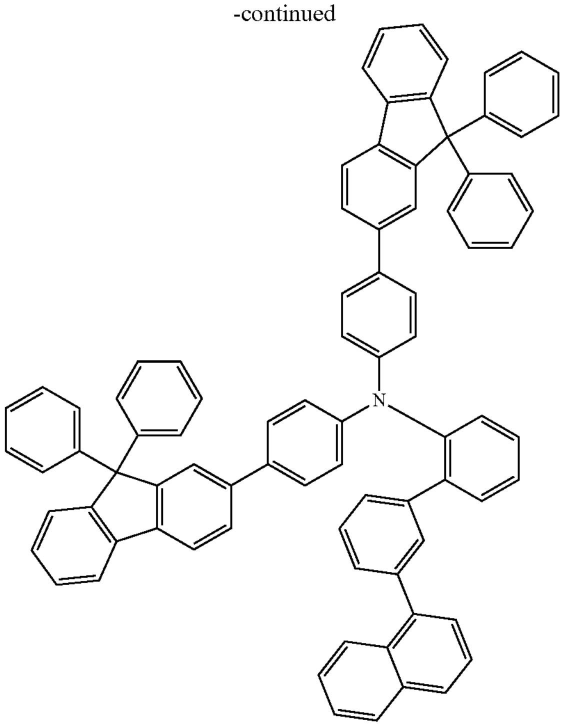
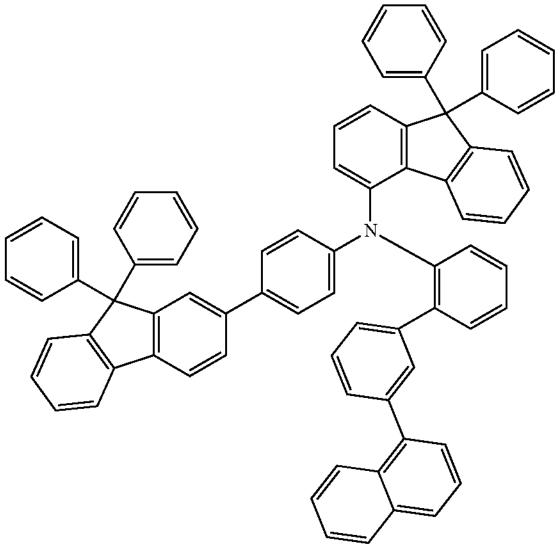
-continued
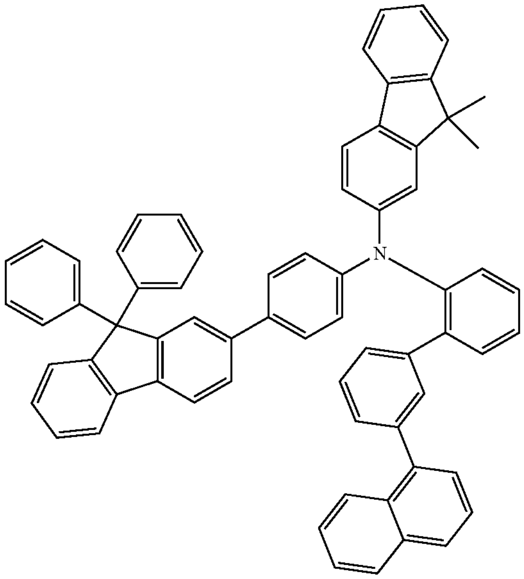
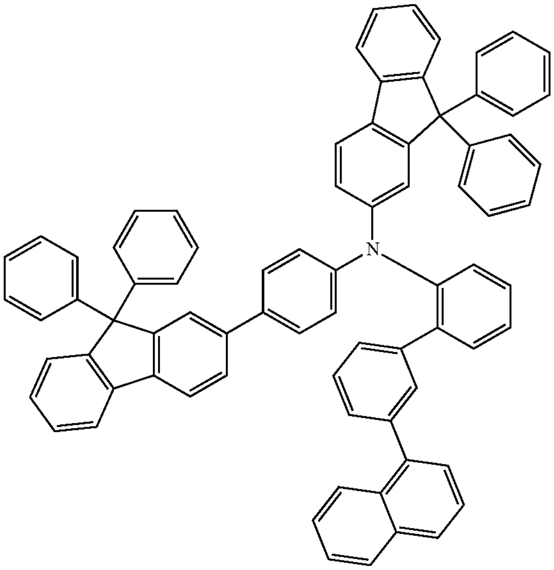
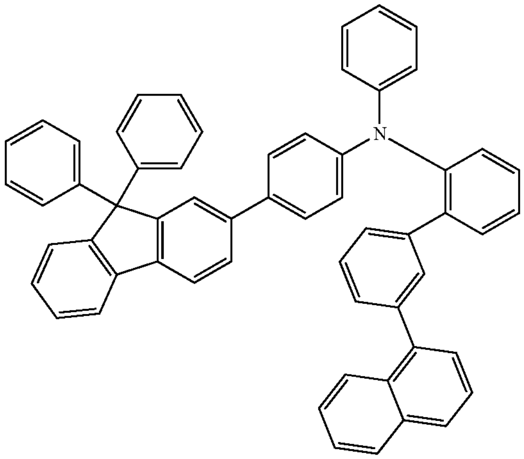

-continued
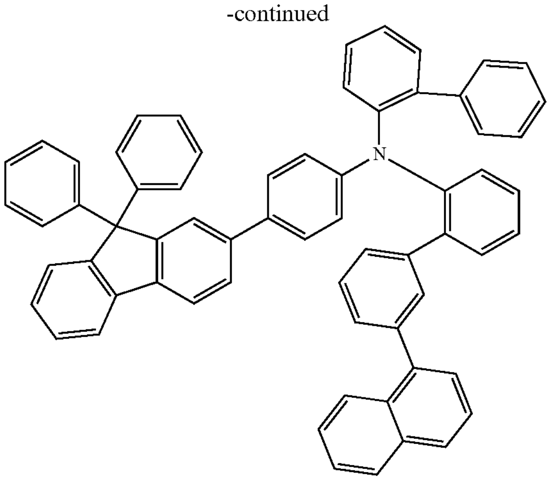
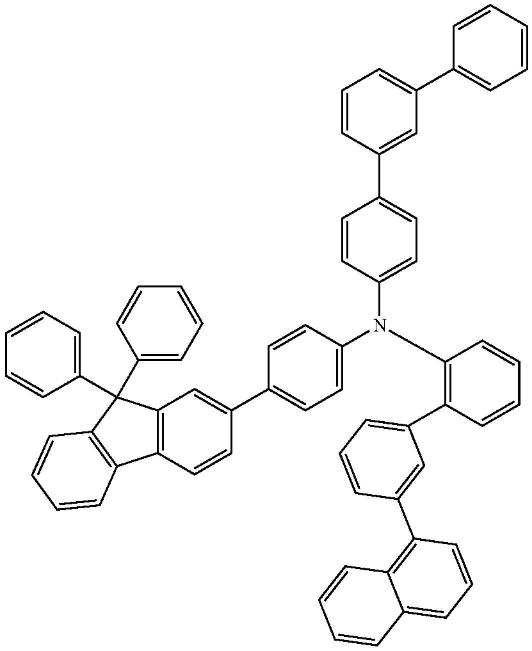
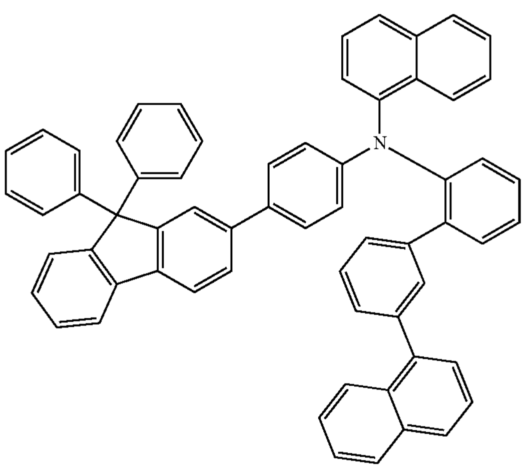
-continued
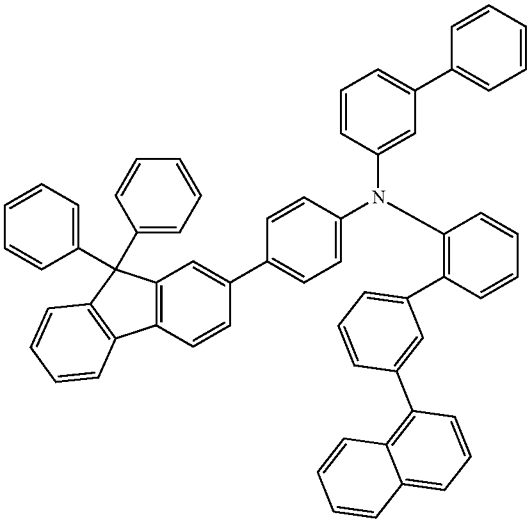
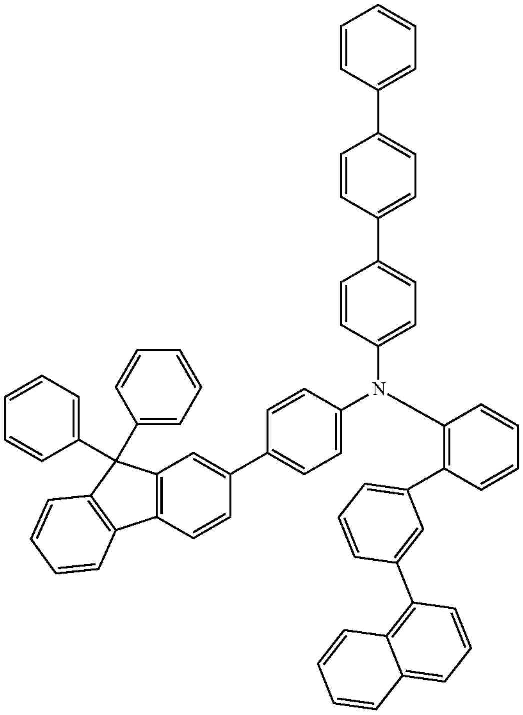

-continued
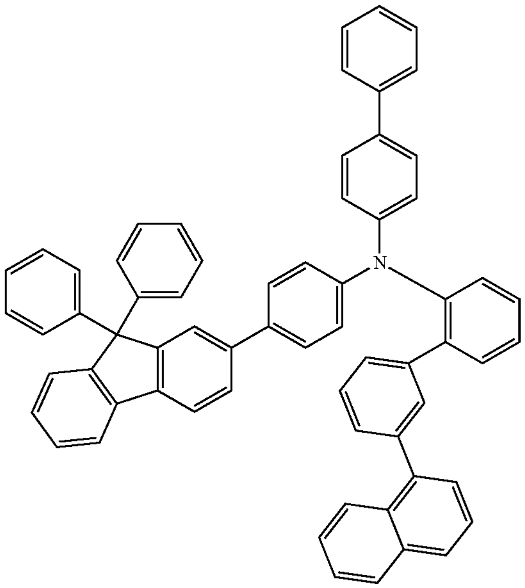
-continued
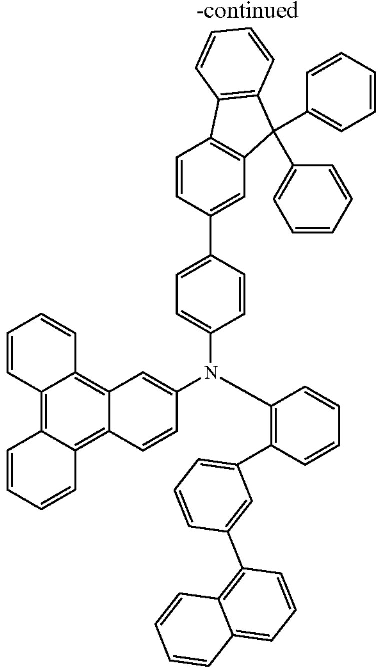
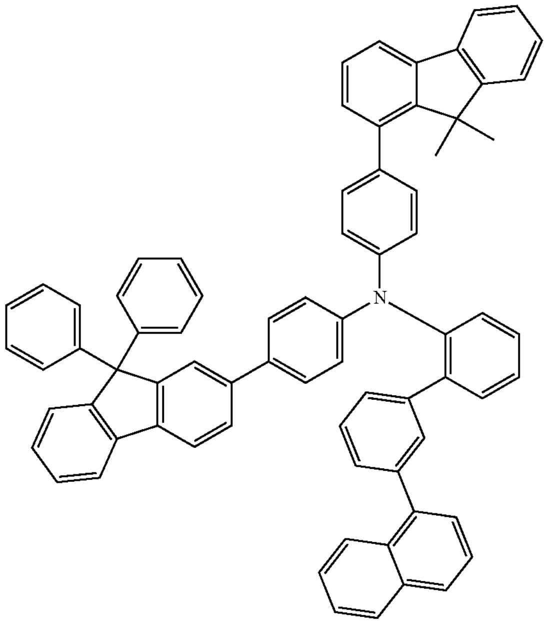
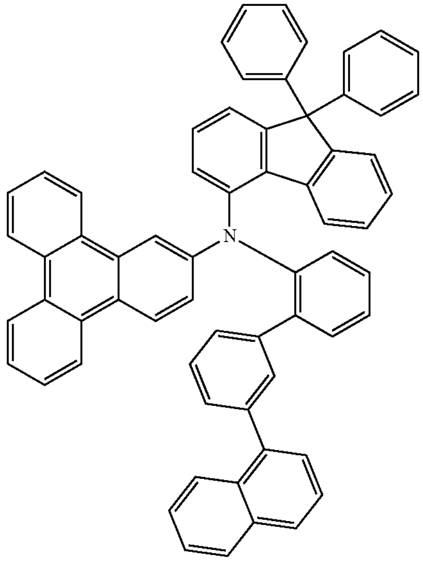

-continued
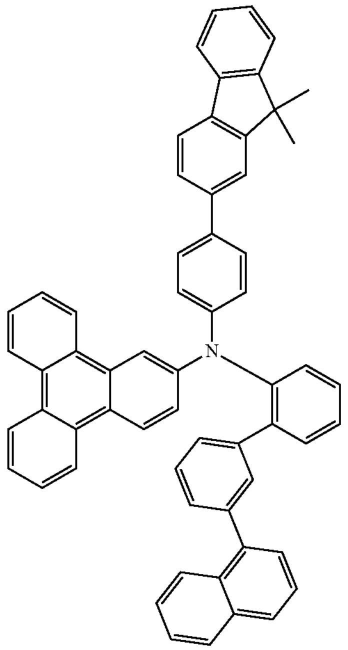
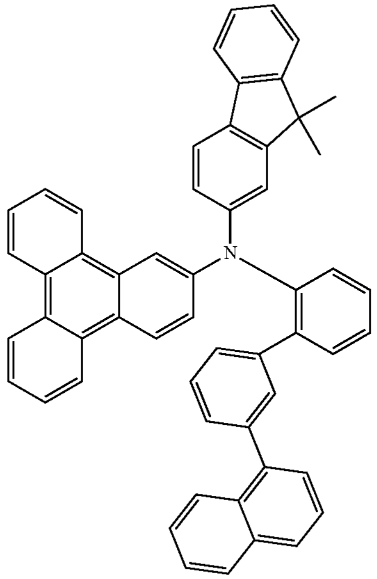
-continued
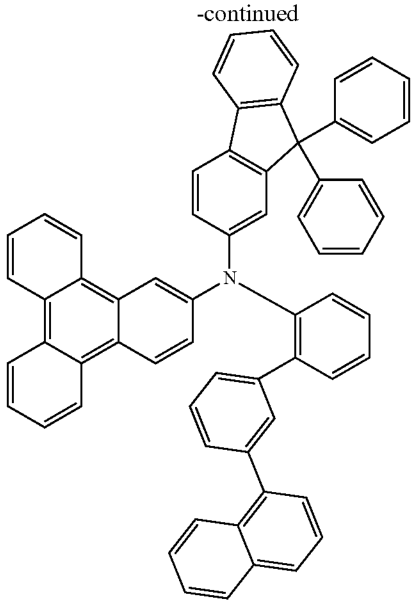
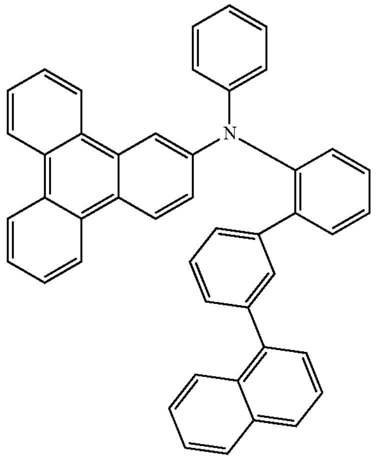
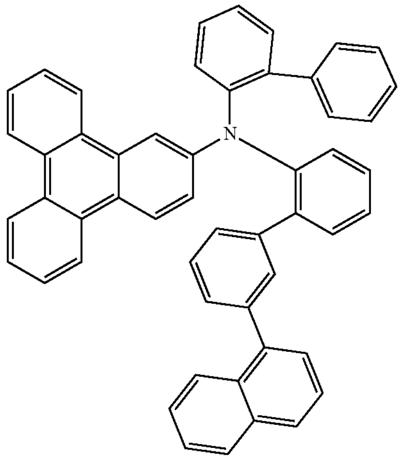

-continued
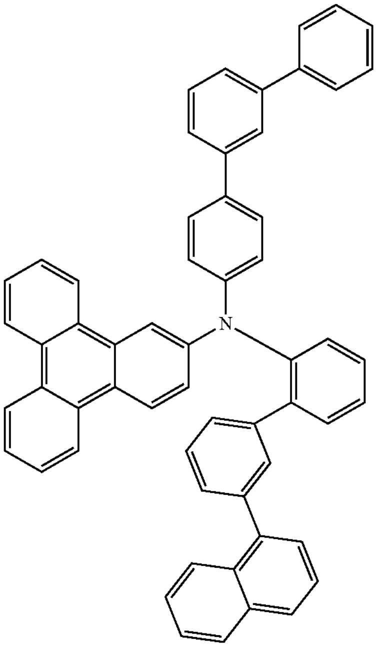
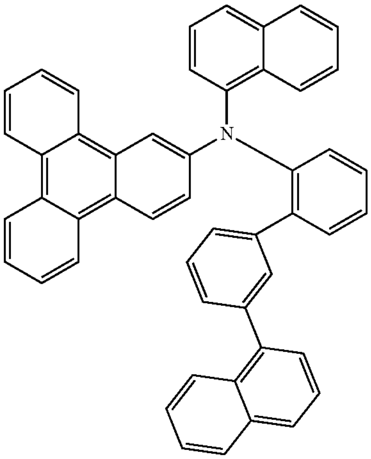
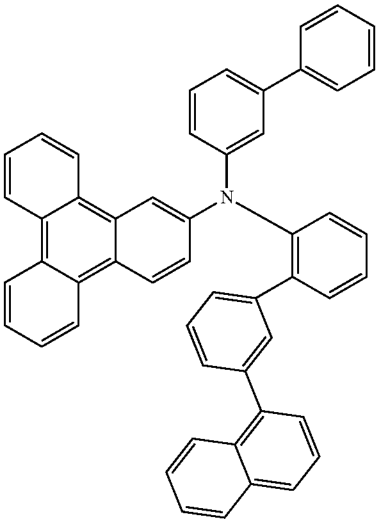
-continued
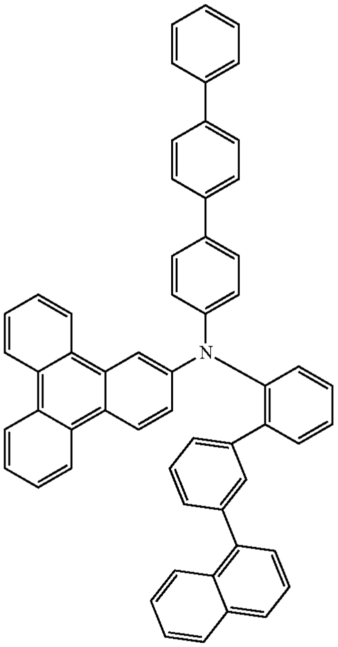
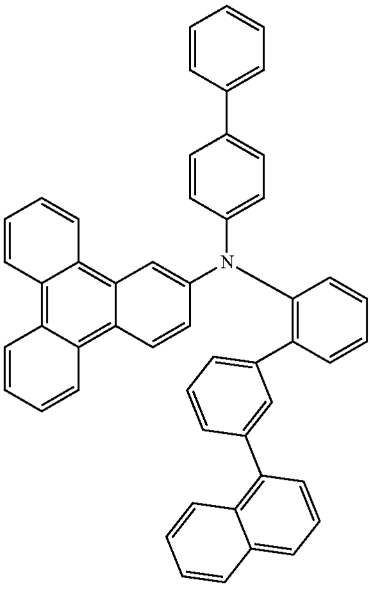

-continued
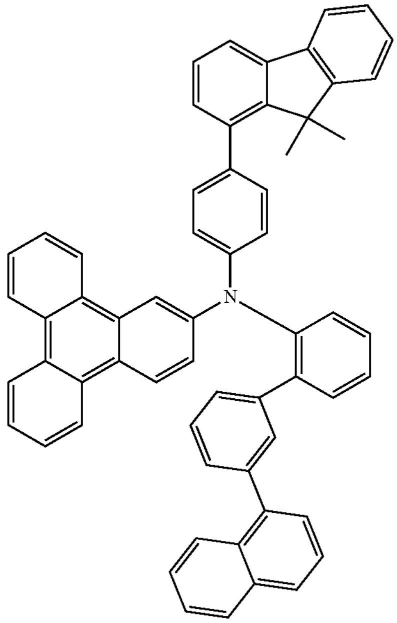
-continued
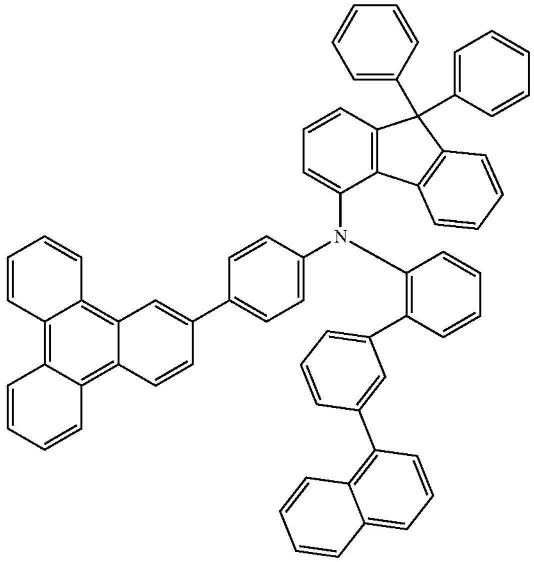 [SMILES: c1ccc(C2(c3ccccc3)c3ccccc3-c3c(N(c4ccc(-c5ccc6c7ccccc7c7ccccc7c6c5)cc4)c4ccccc4-c4cccc(-c5cccc6ccccc56)c4)cccc32)cc1]
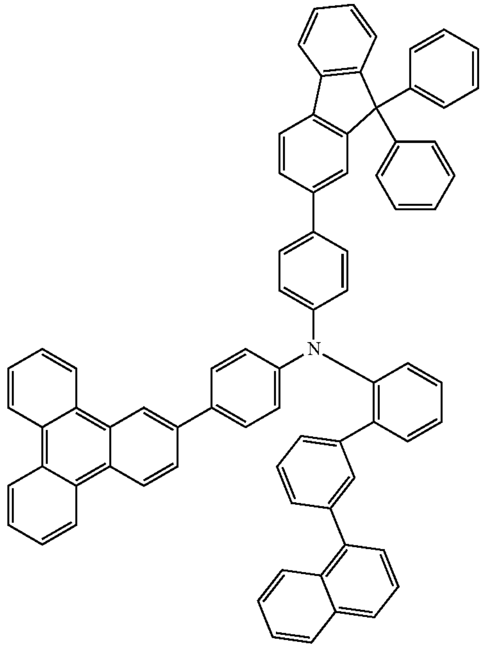
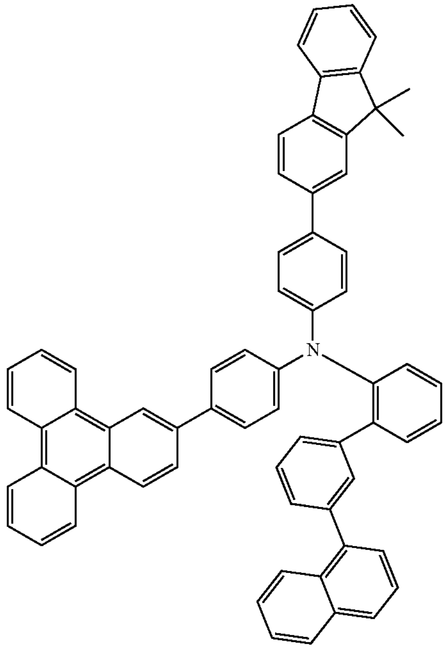

-continued
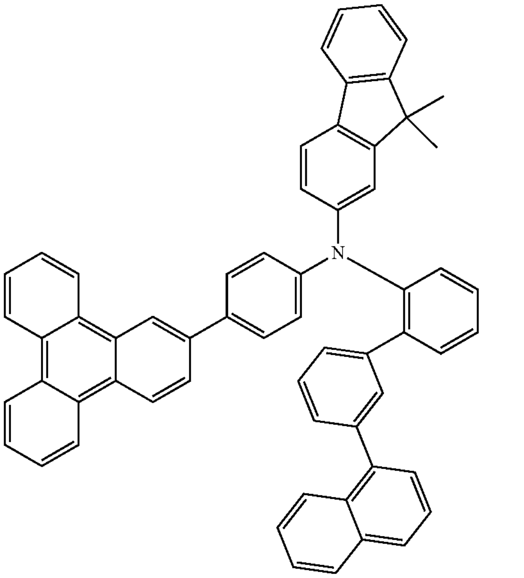
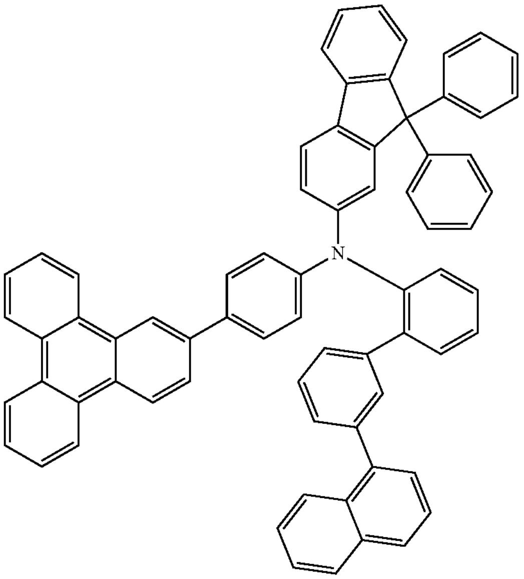
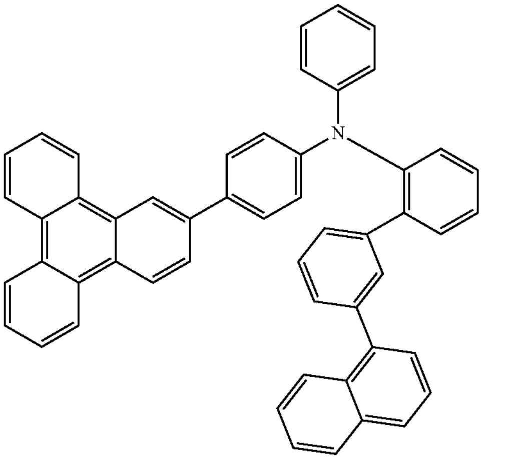
-continued
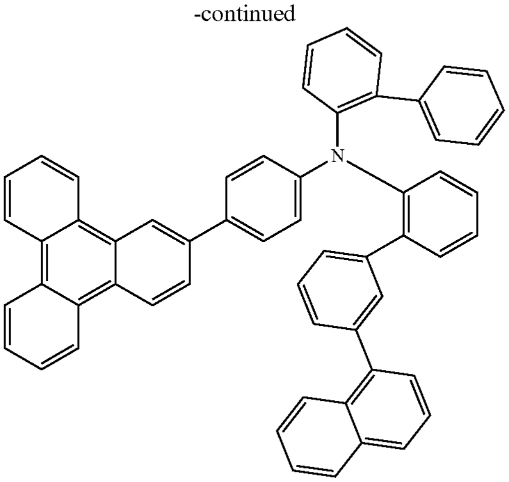
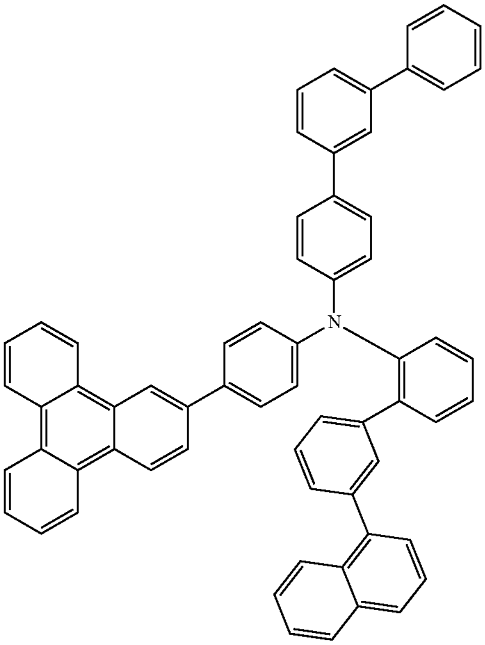 [SMILES: c1ccc(-c2cccc(-c3ccc(N(c4ccc(-c5ccc6c7ccccc7c7ccccc7c6c5)cc4)c4ccccc4-c4cccc(-c5cccc6ccccc56)c4)cc3)c2)cc1]
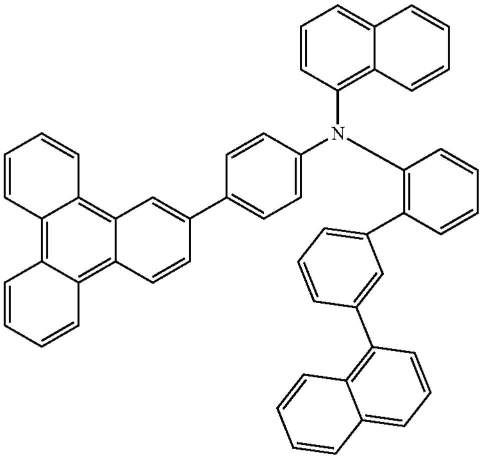

-continued
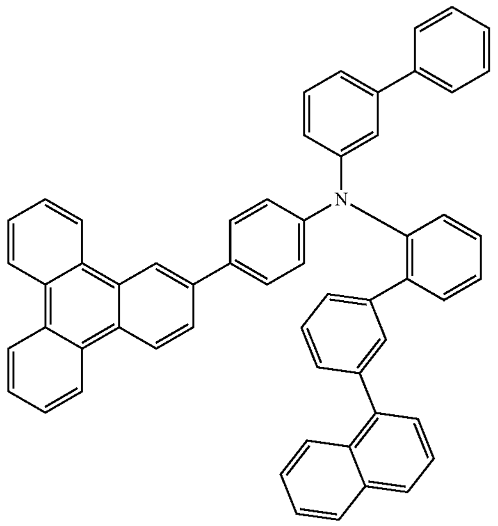
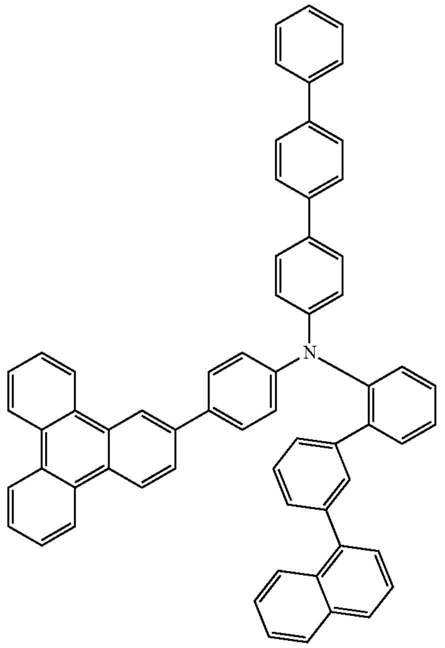
-continued
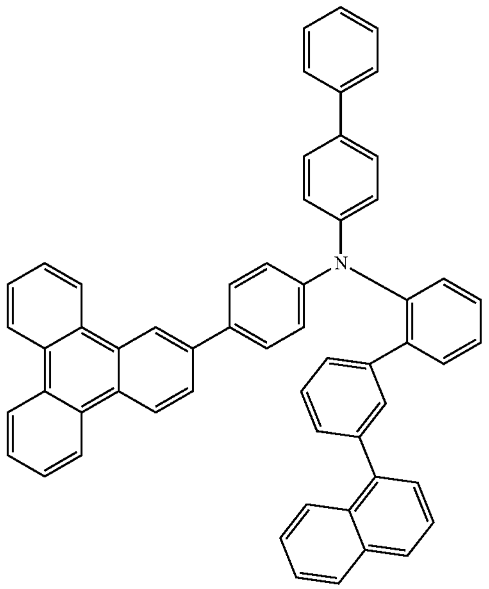
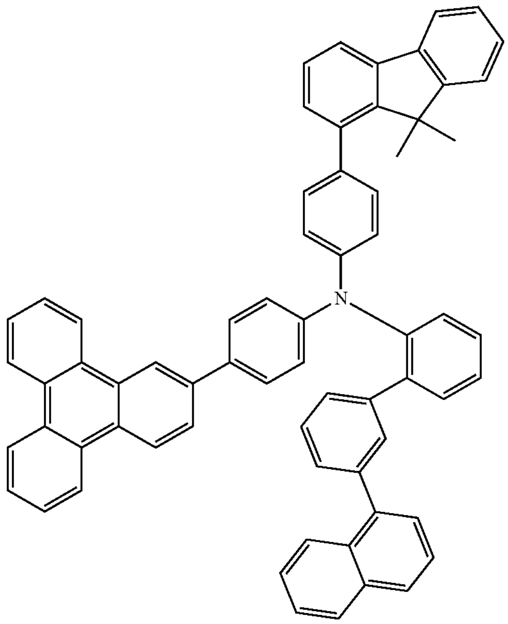

-continued
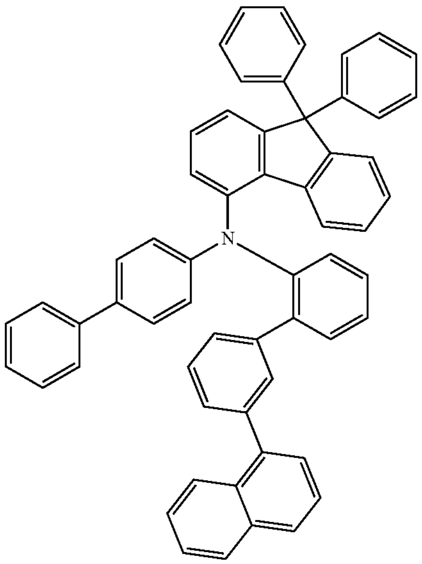
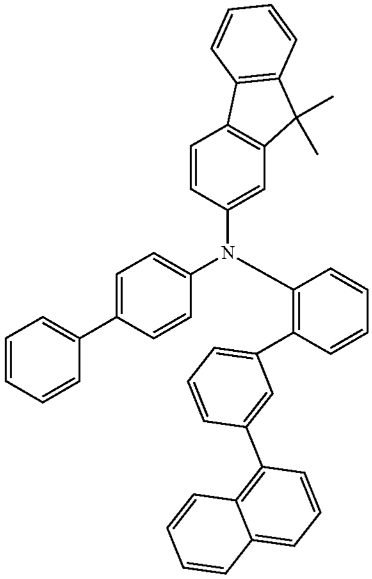
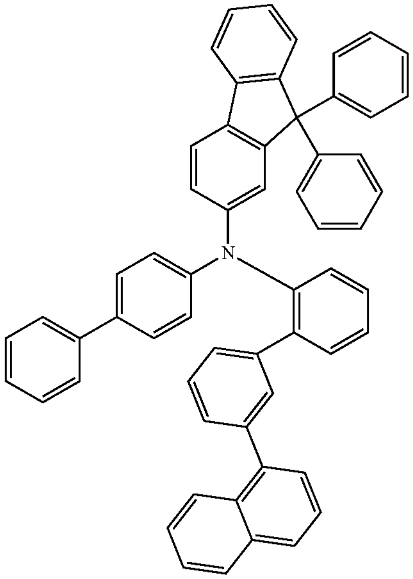
-continued
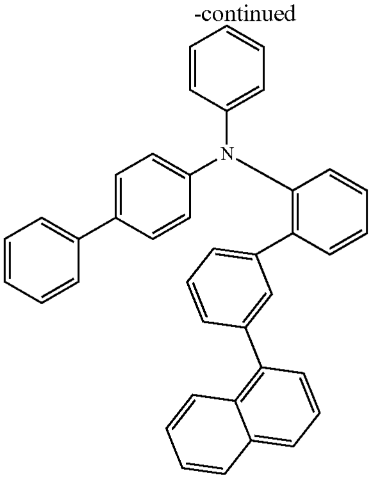
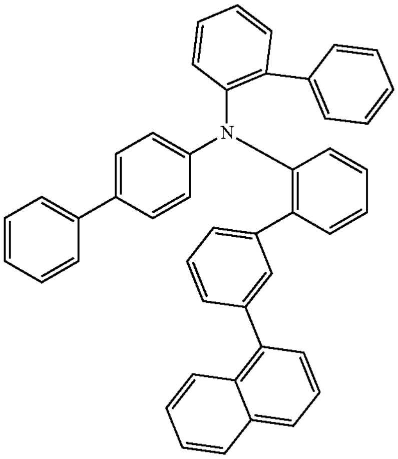
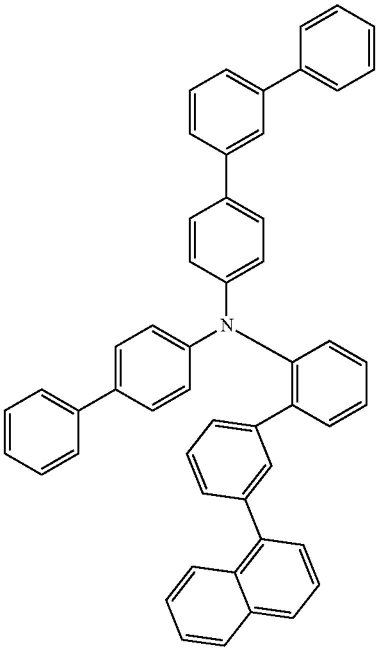

-continued
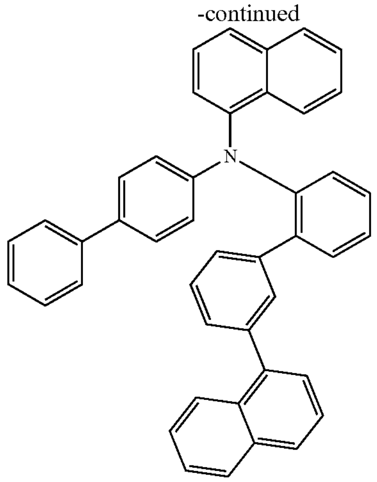
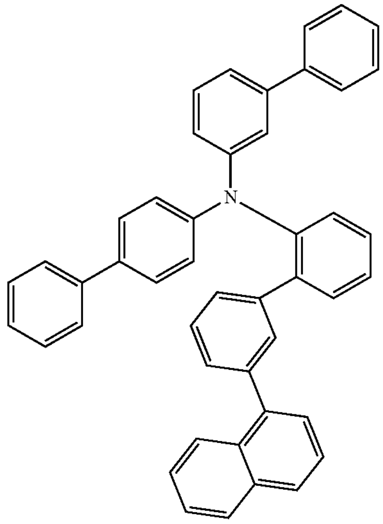
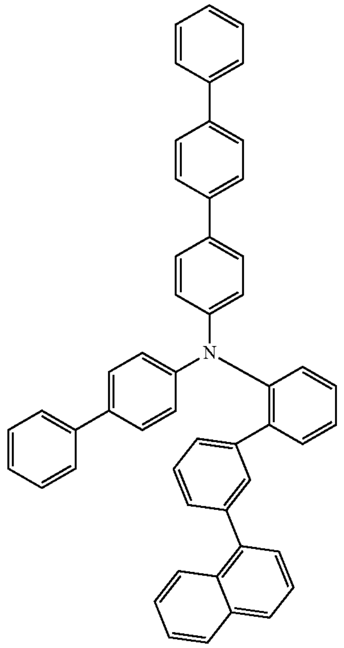
-continued
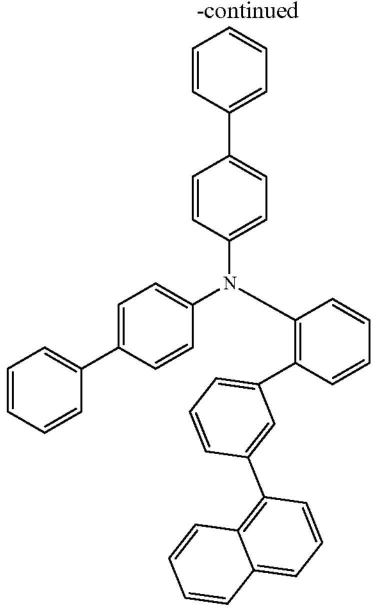
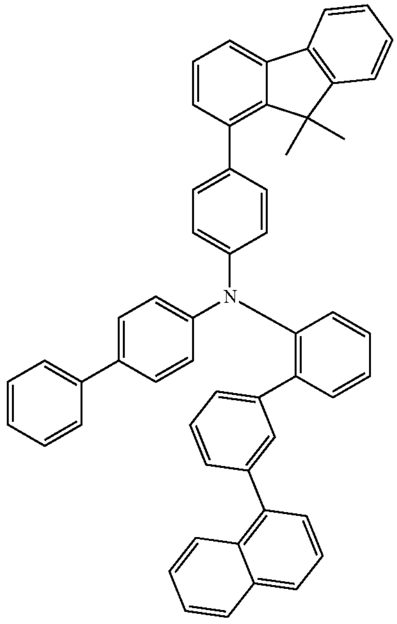 [SMILES: CC1(C)c2ccccc2-c2cccc(-c3ccc(N(c4ccc(-c5ccccc5)cc4)c4ccccc4-c4cccc(-c5cccc6ccccc56)c4)cc3)c21]

-continued
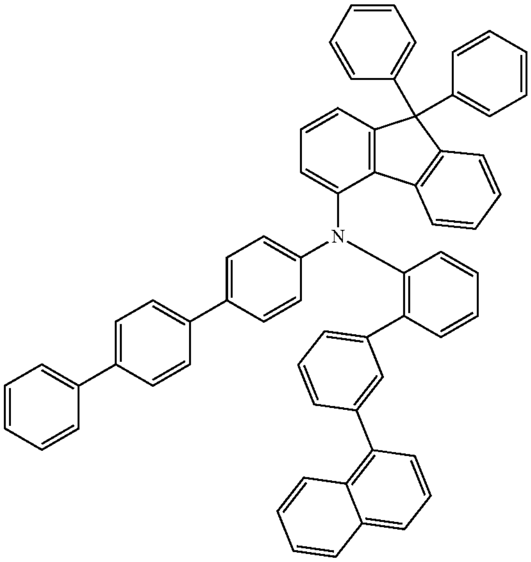
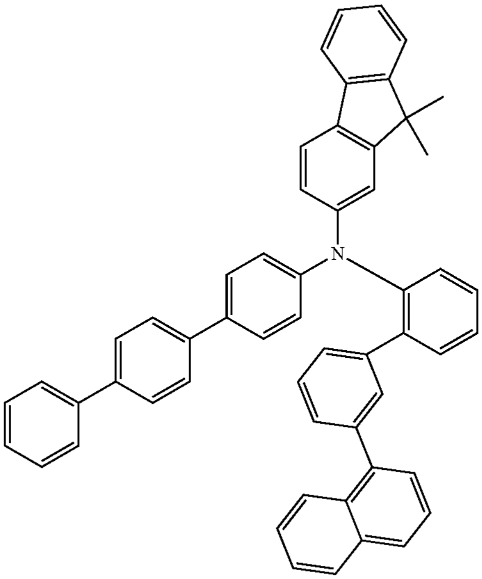
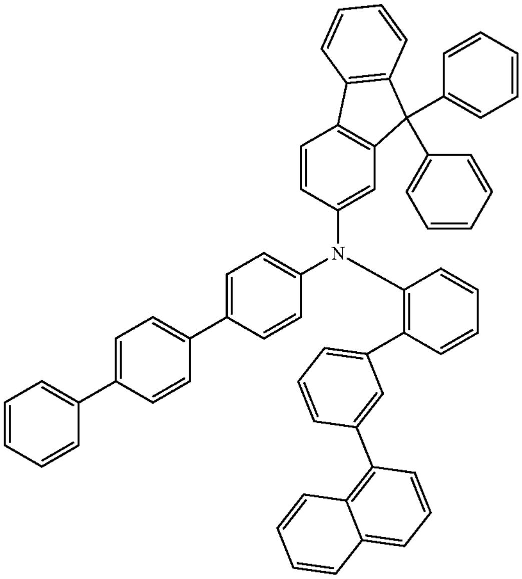
-continued
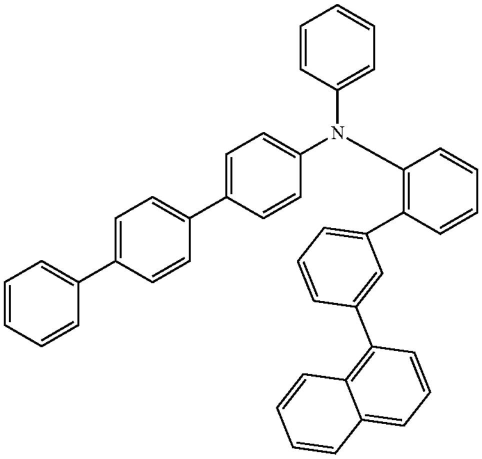
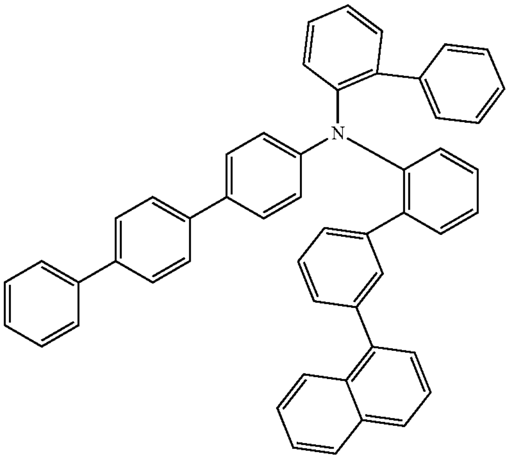
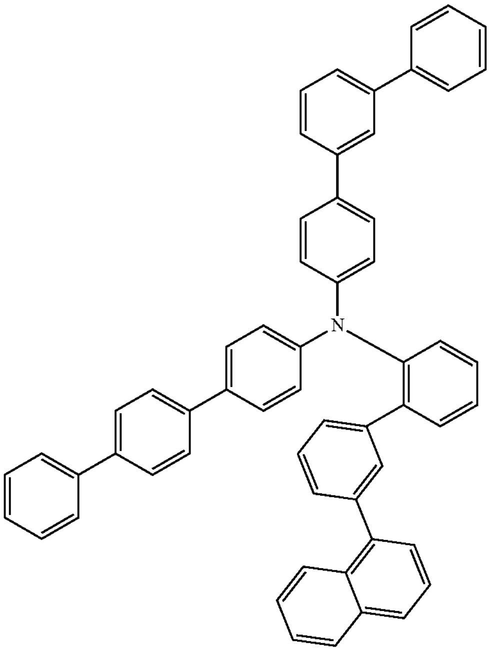

-continued
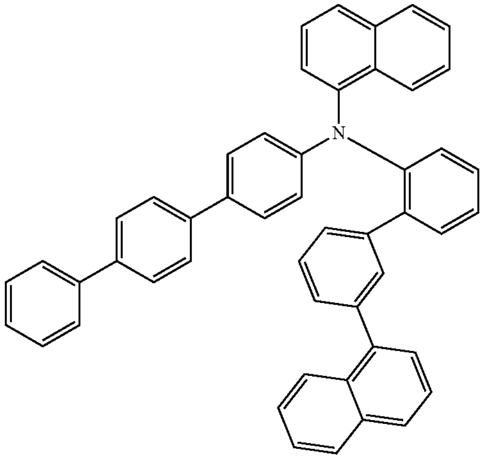
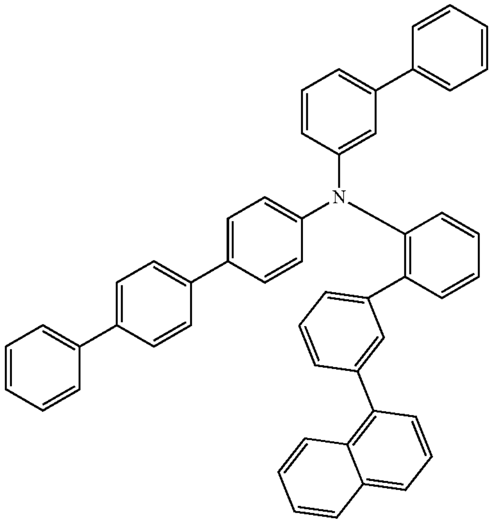
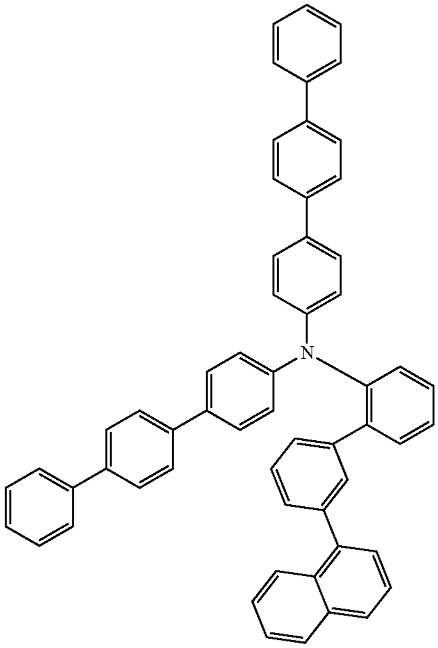
-continued
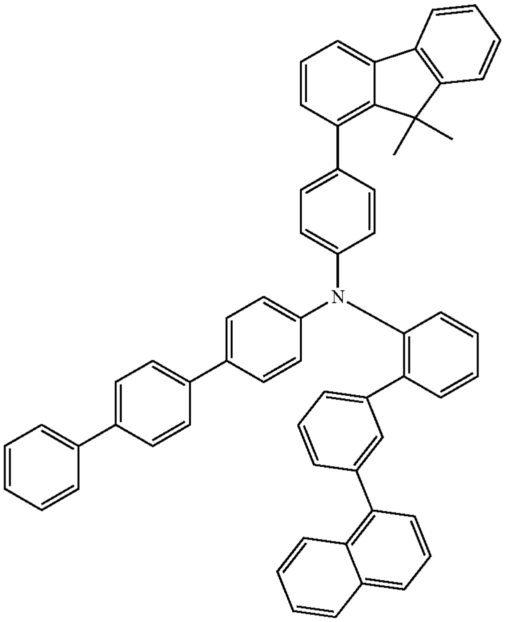
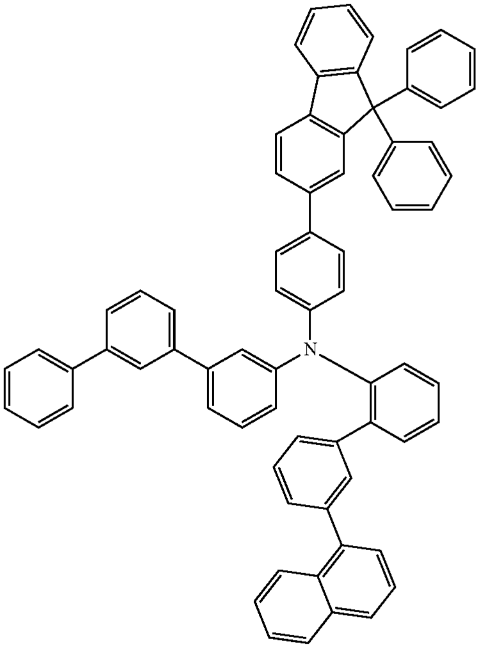

-continued
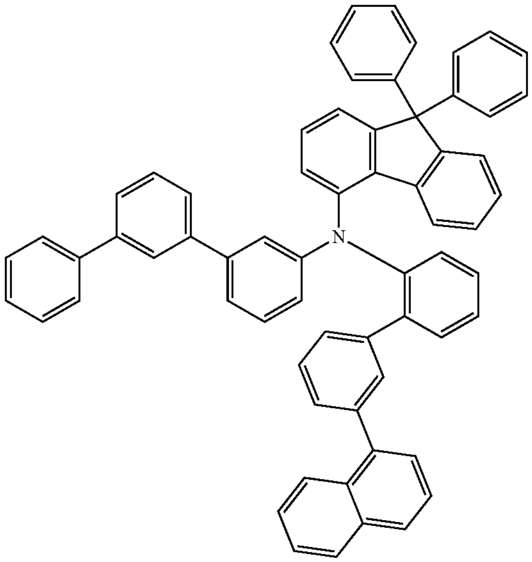 [SMILES: c1ccc(-c2cccc(-c3cccc(N(c4ccccc4-c4cccc(-c5cccc6ccccc56)c4)c4cccc5c4-c4ccccc4C5(c4ccccc4)c4ccccc4)c3)c2)cc1]
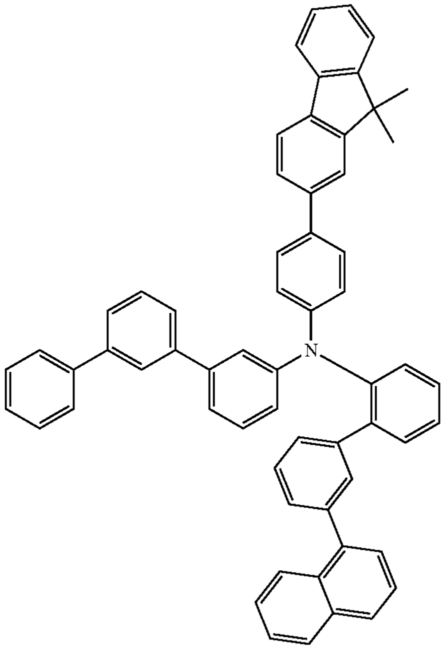
-continued
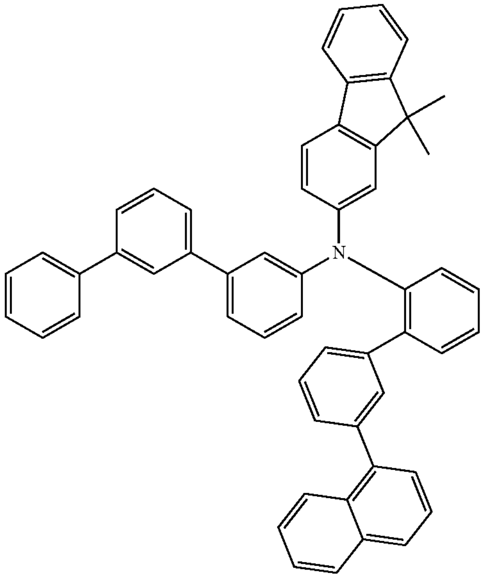
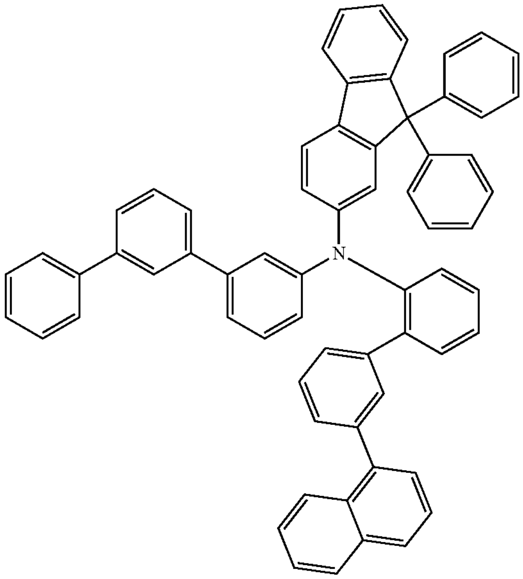
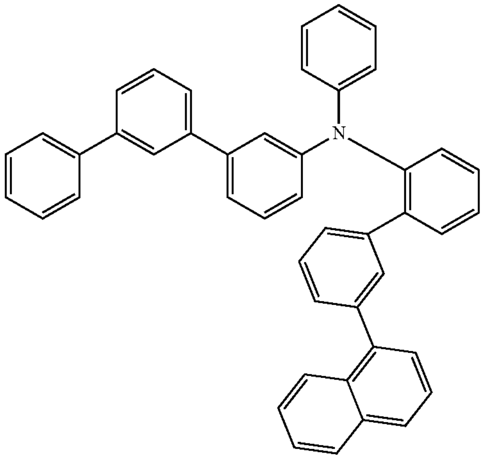

-continued
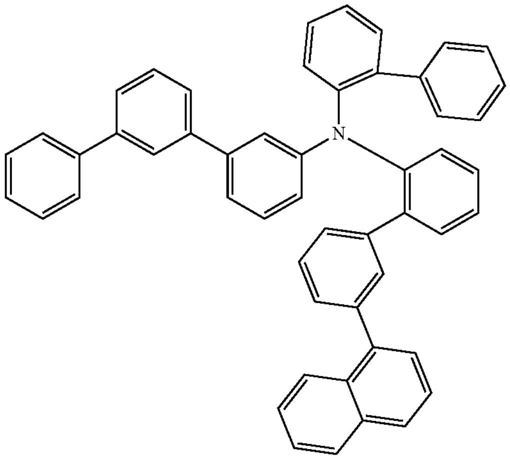
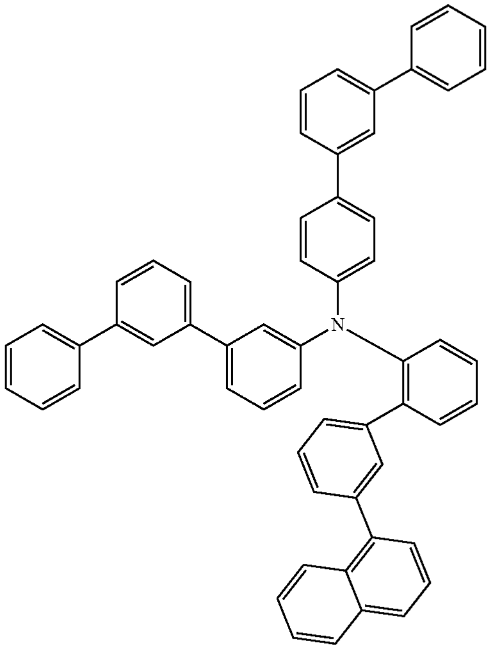 [SMILES: c1ccc(-c2cccc(-c3ccc(N(c4cccc(-c5cccc(-c6ccccc6)c5)c4)c4ccccc4-c4cccc(-c5cccc6ccccc56)c4)cc3)c2)cc1]
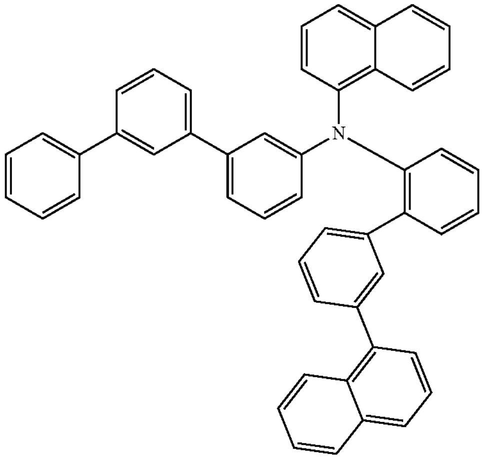
-continued
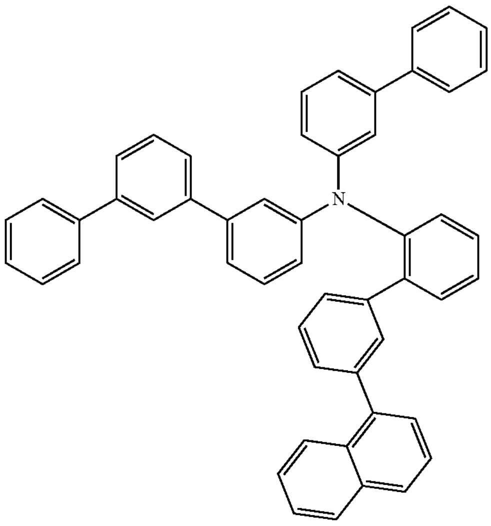
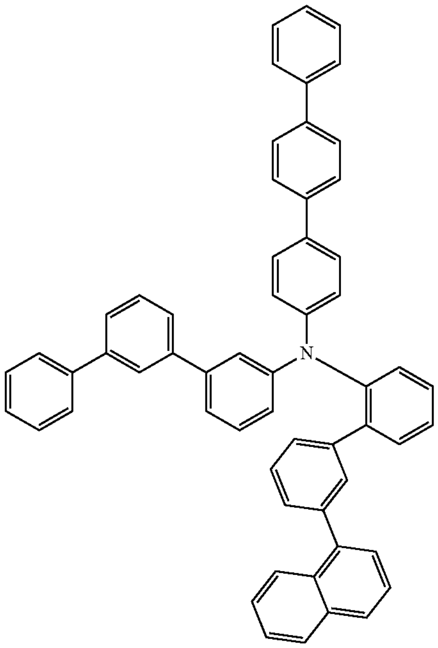

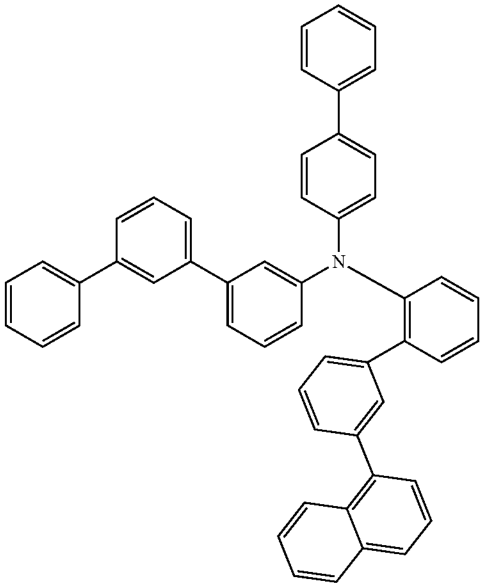
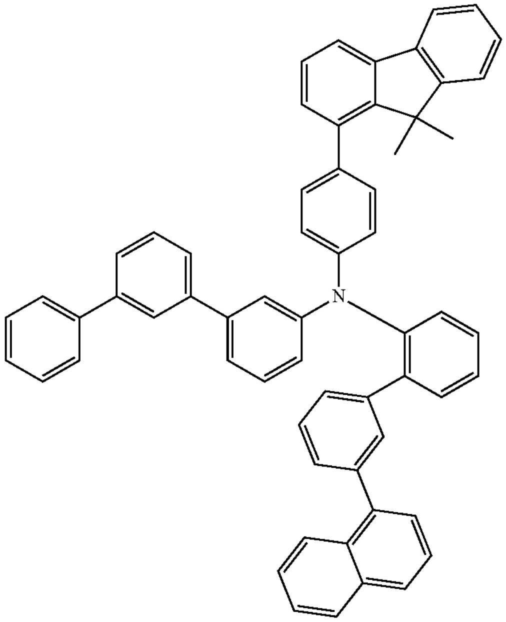
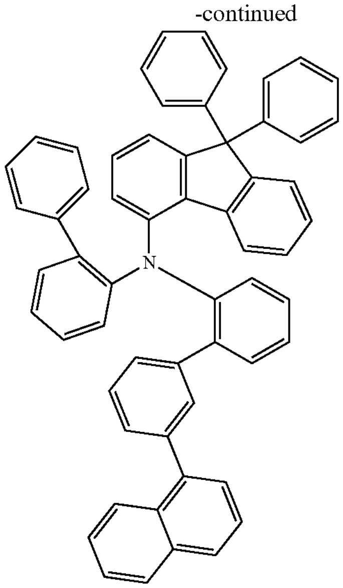
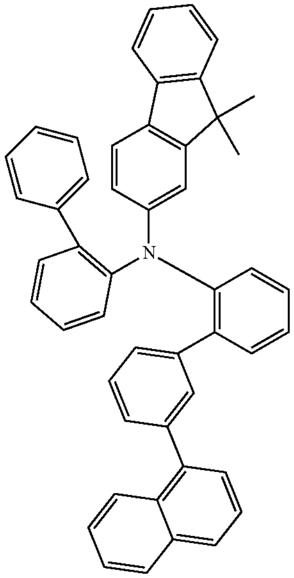
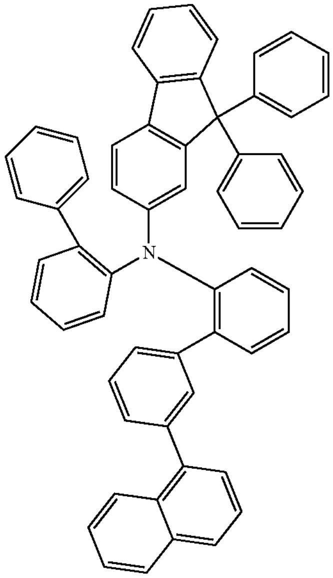

-continued
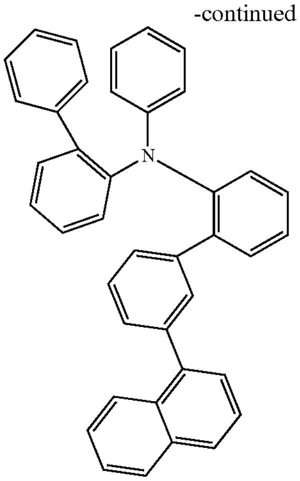
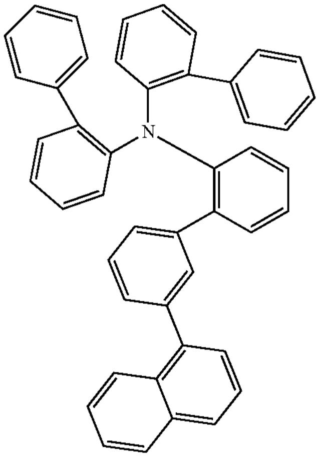
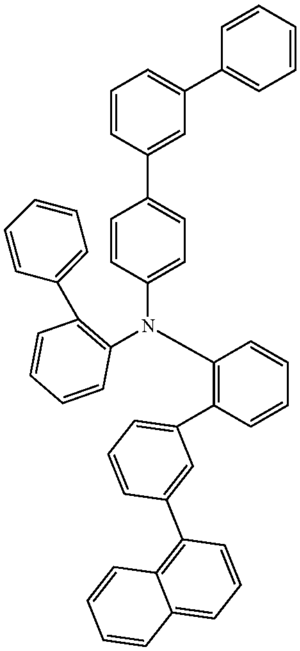
-continued
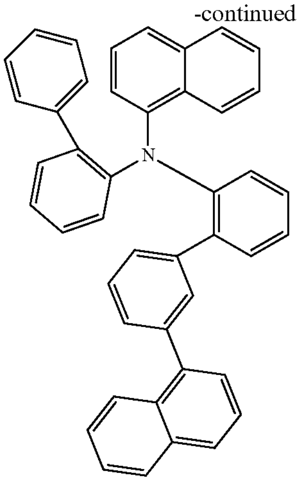
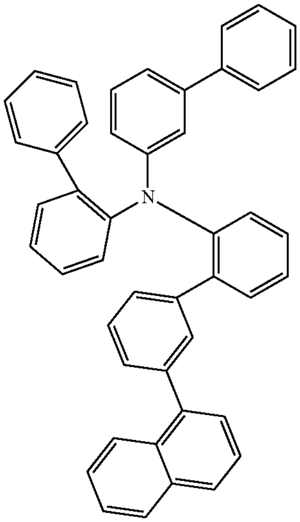
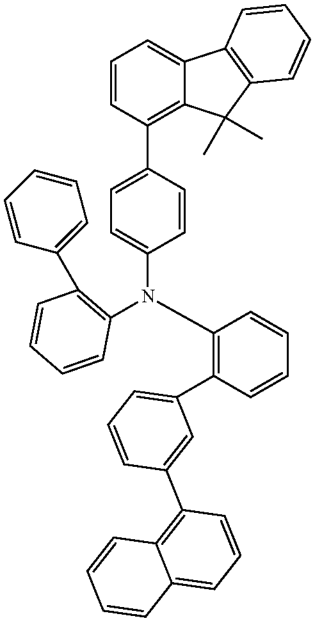

-continued
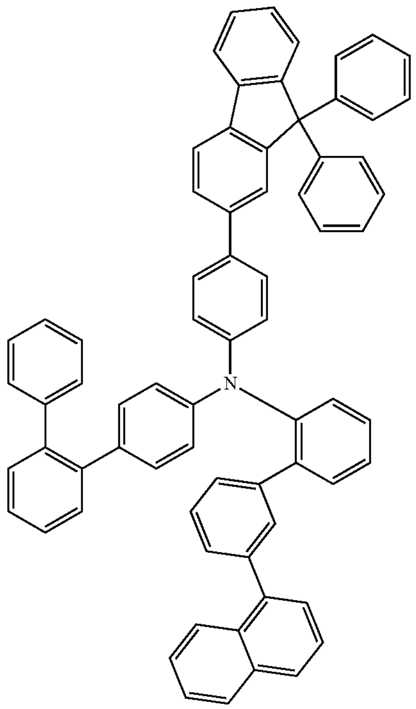
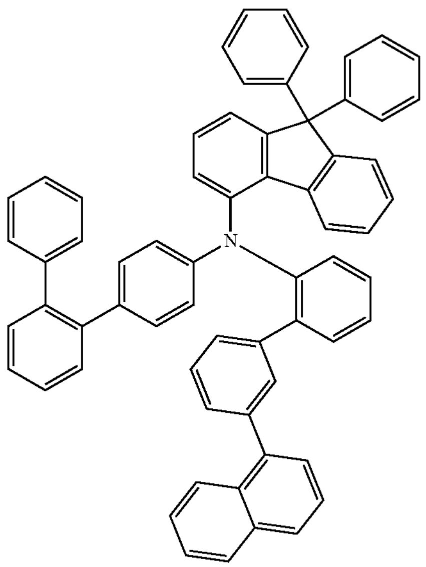
-continued
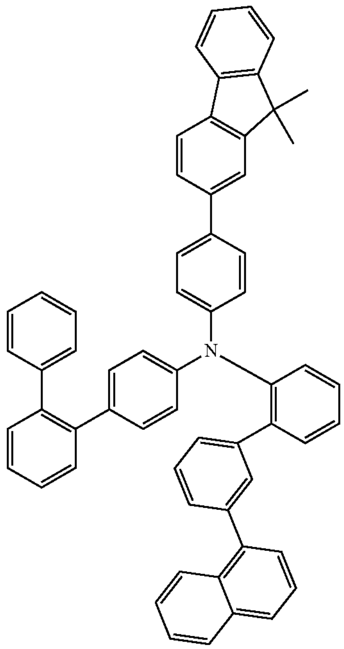
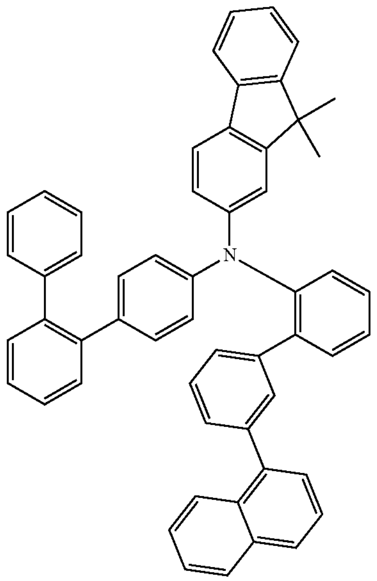

-continued
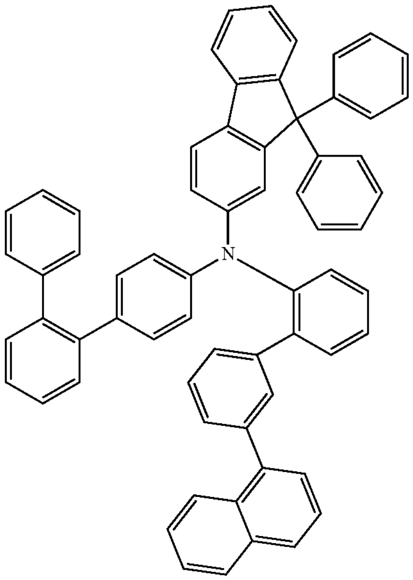
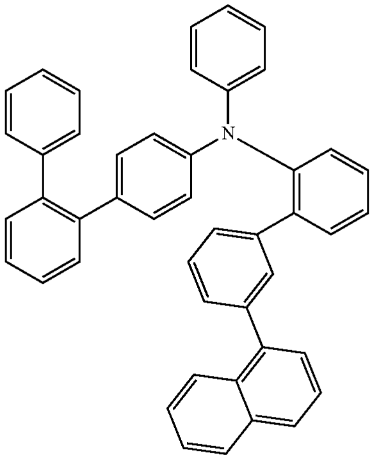
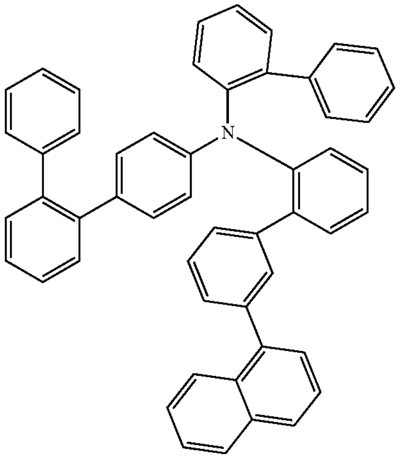
-continued
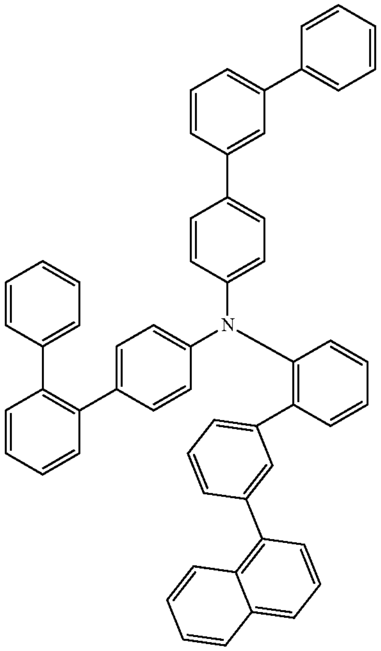
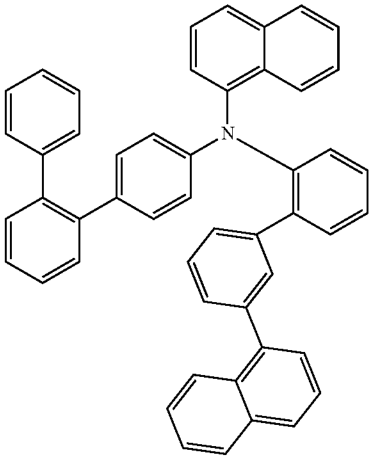
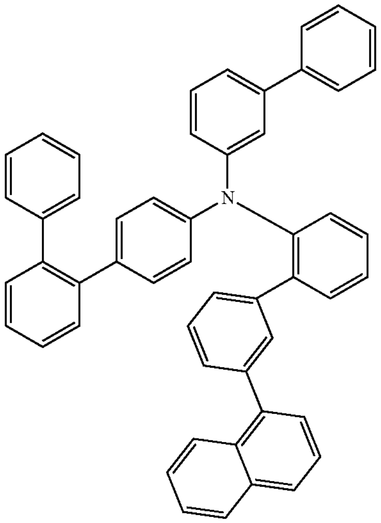

-continued
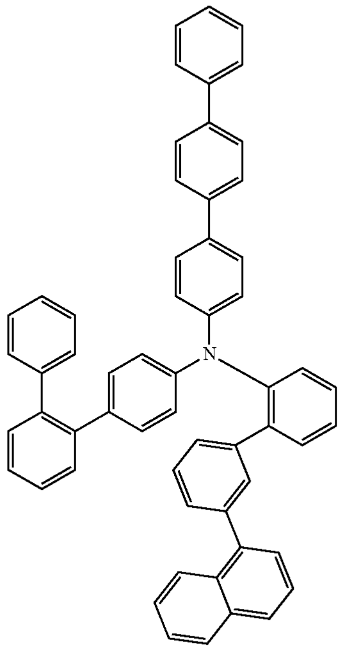
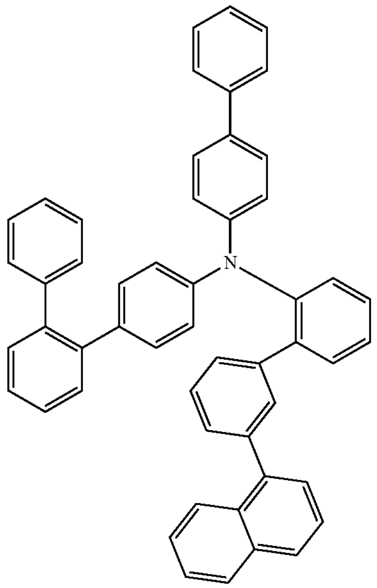
-continued
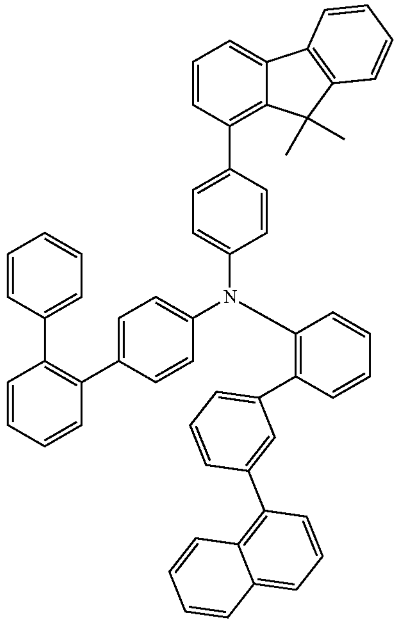 [SMILES: CC1(C)c2ccccc2-c2cccc(-c3ccc(N(c4ccc(-c5ccccc5-c5ccccc5)cc4)c4ccccc4-c4cccc(-c5cccc6ccccc56)c4)cc3)c21]
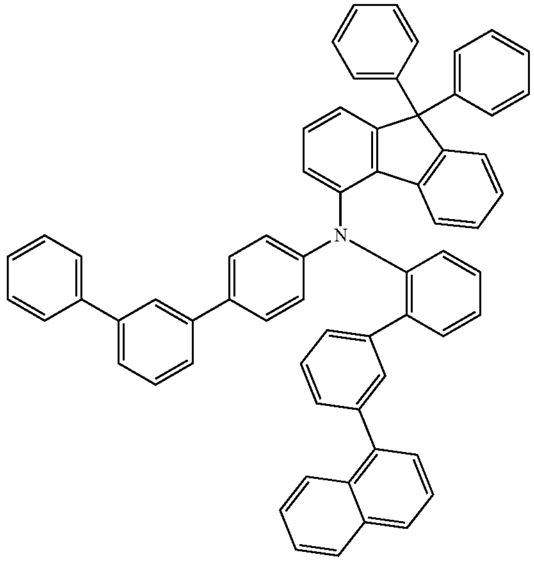

-continued
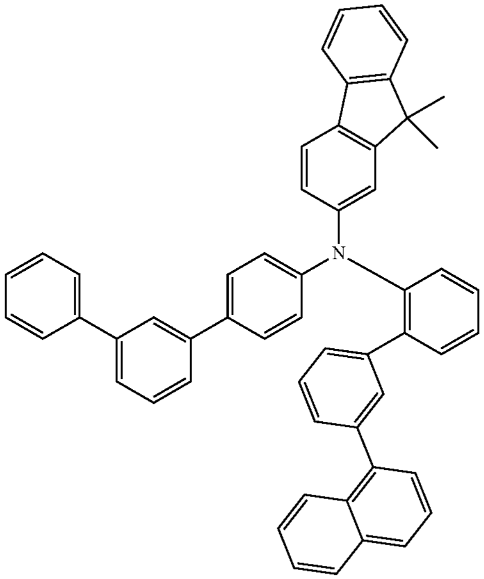
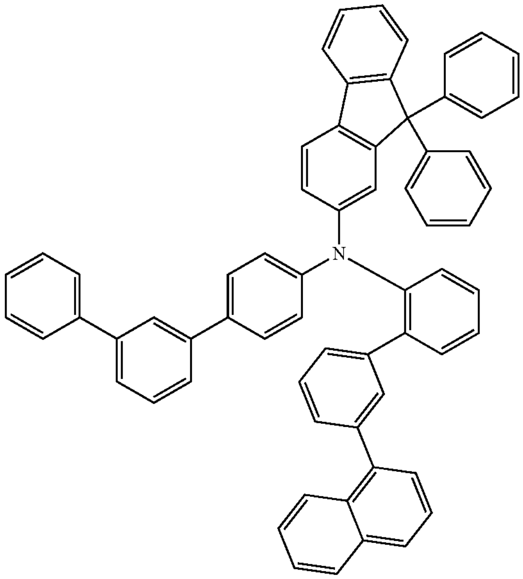
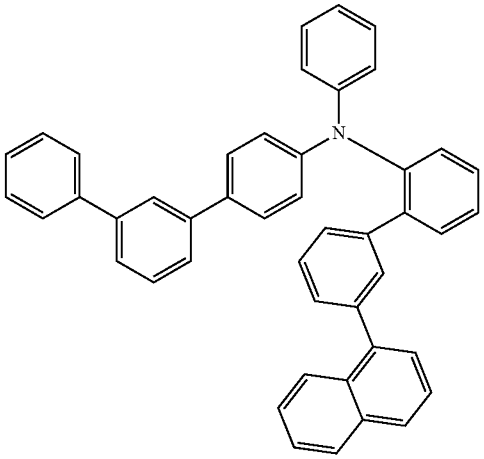
-continued
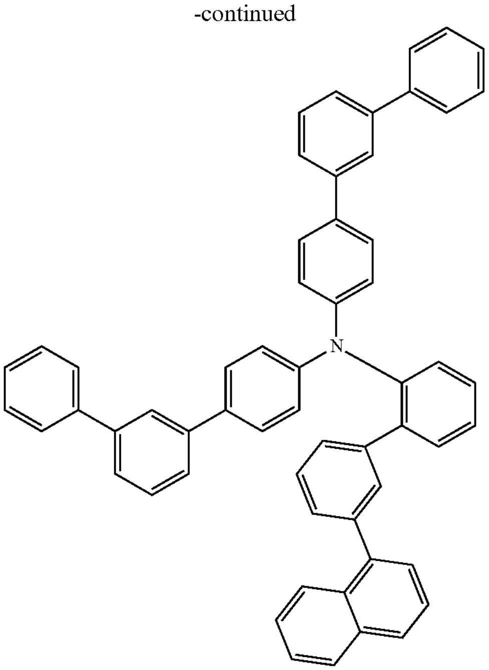
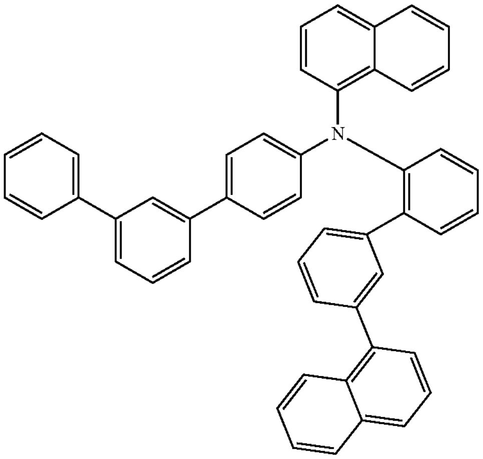
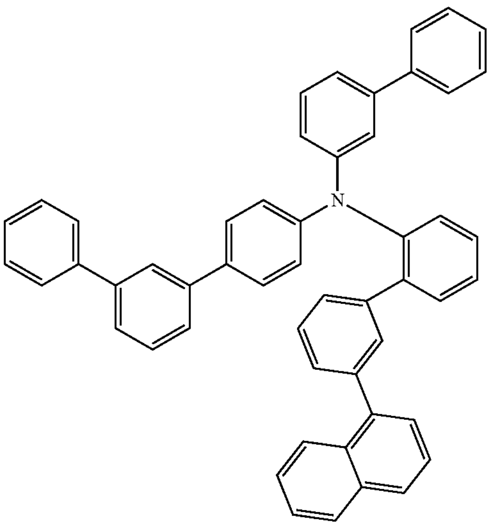

-continued
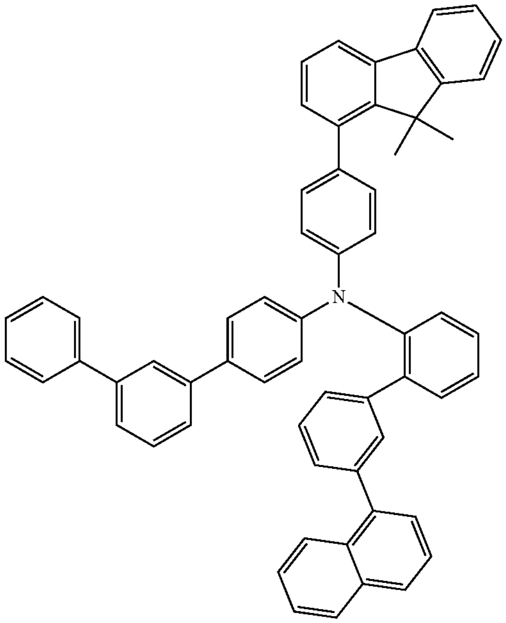
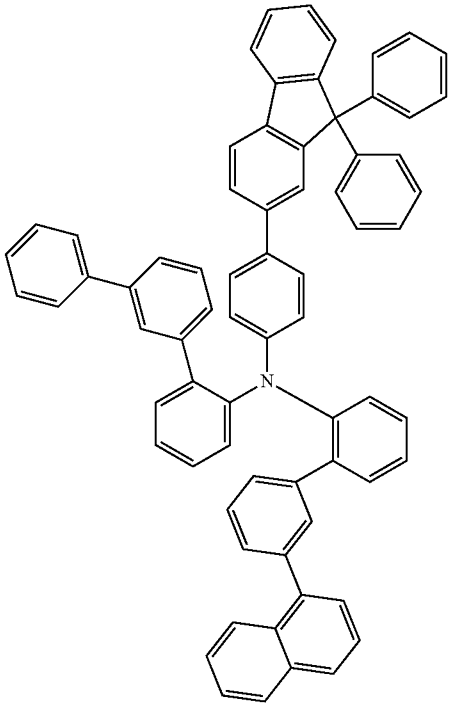
-continued
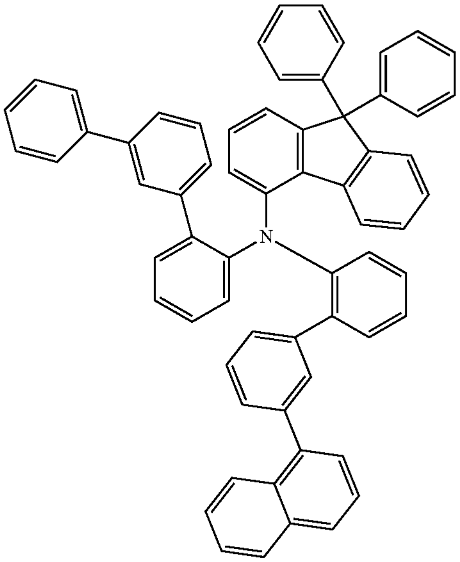
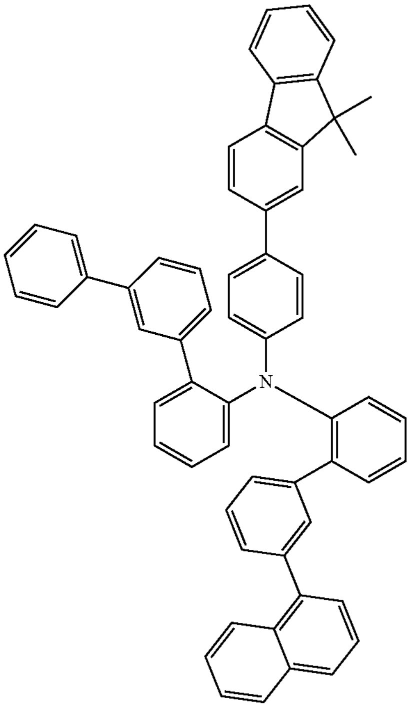

-continued
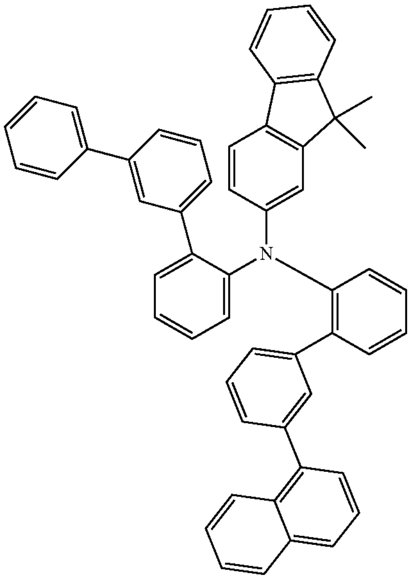
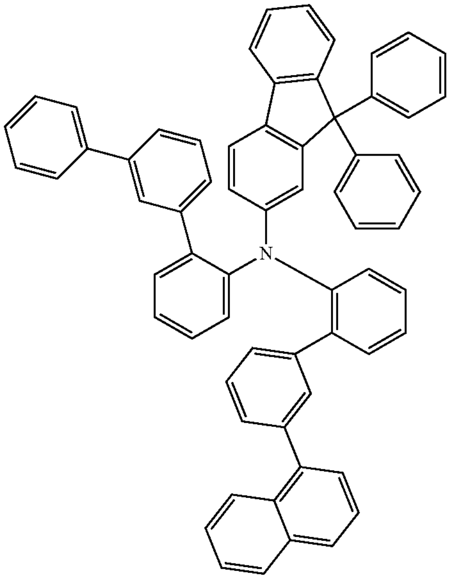
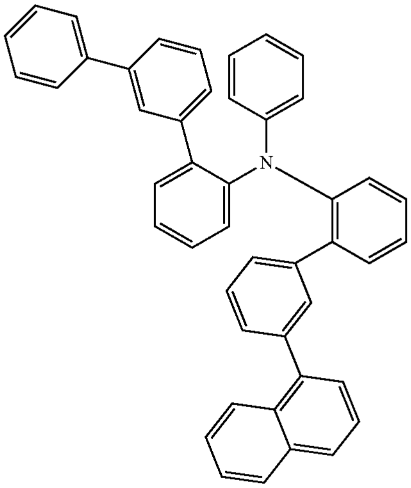
-continued
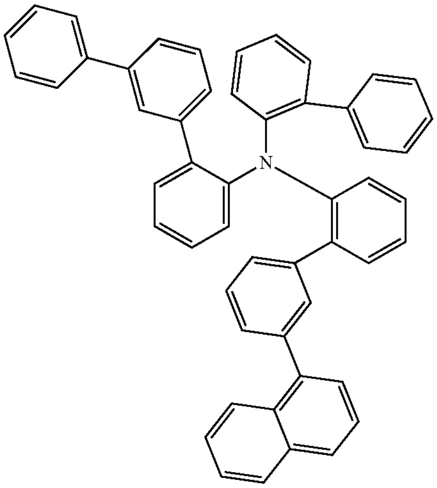 [SMILES: c1ccc(-c2cccc(-c3ccccc3N(c3ccccc3-c3ccccc3)c3ccccc3-c3cccc(-c4cccc5ccccc45)c3)c2)cc1]
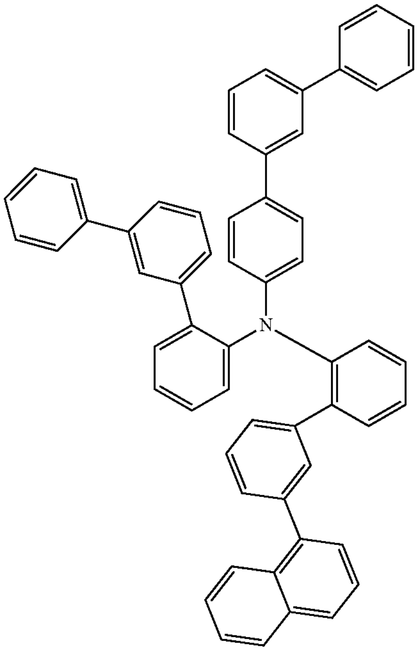
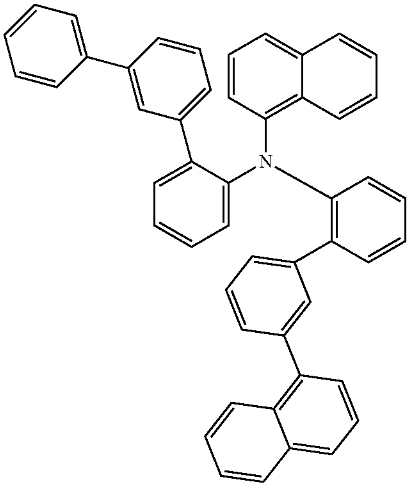

-continued
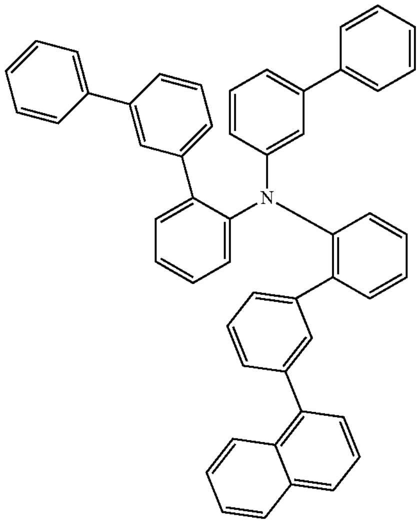
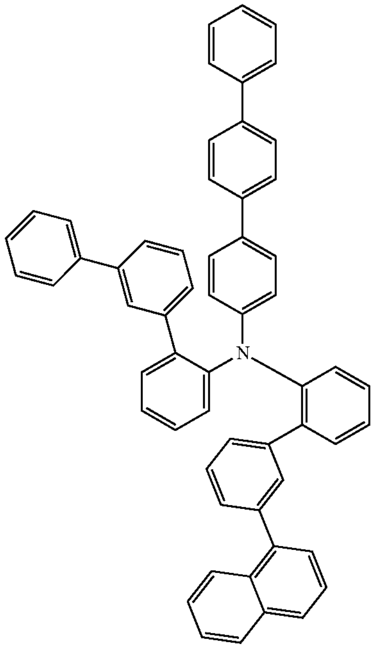
-continued
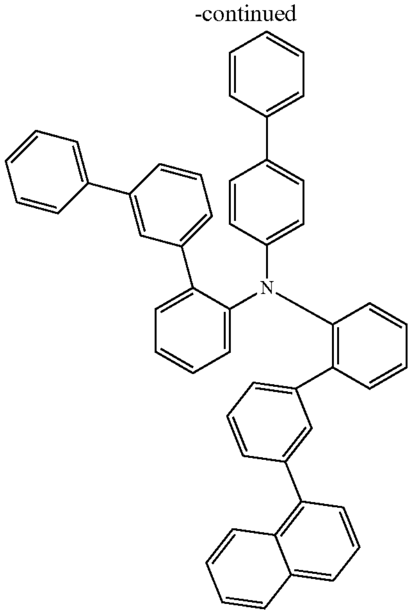
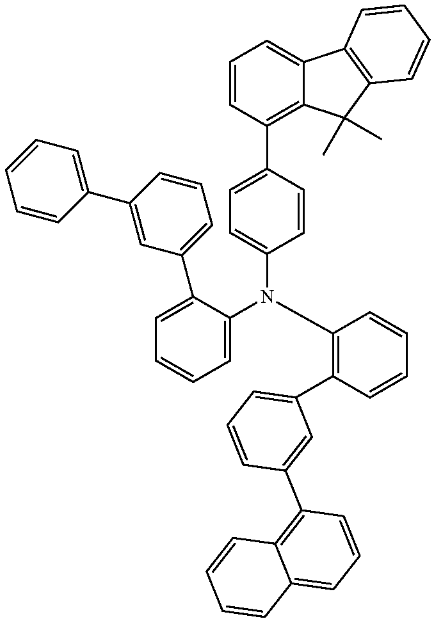

-continued
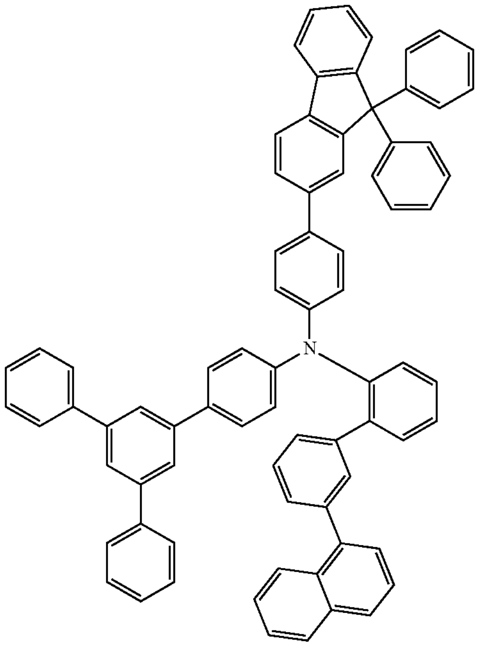
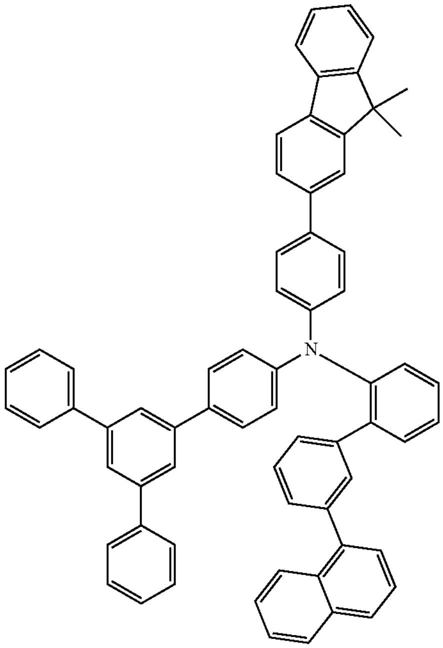
-continued
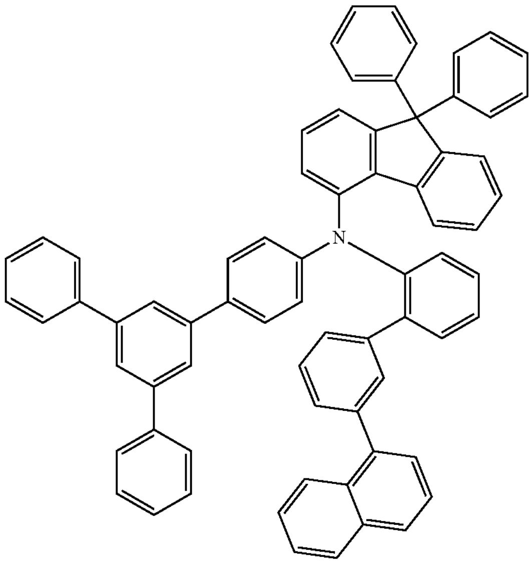 [SMILES: c1ccc(-c2cc(-c3ccccc3)cc(-c3ccc(N(c4ccccc4-c4cccc(-c5cccc6ccccc56)c4)c4cccc5c4-c4ccccc4C5(c4ccccc4)c4ccccc4)cc3)c2)cc1]
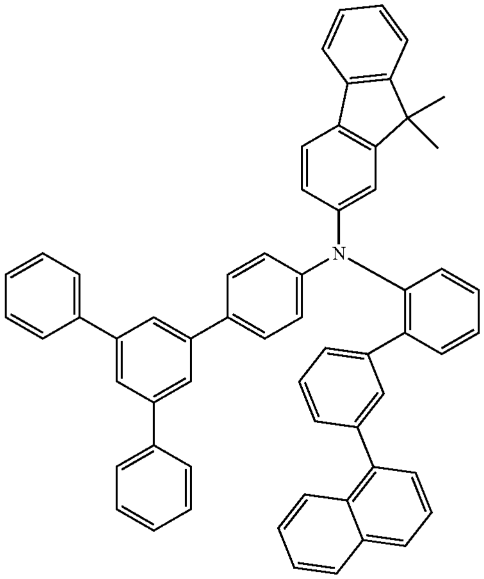

-continued
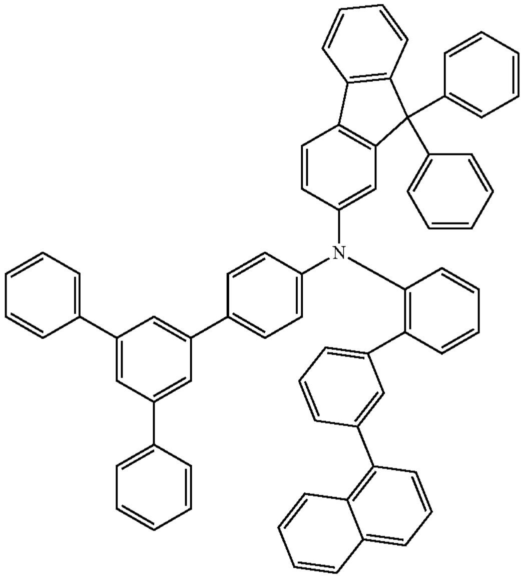
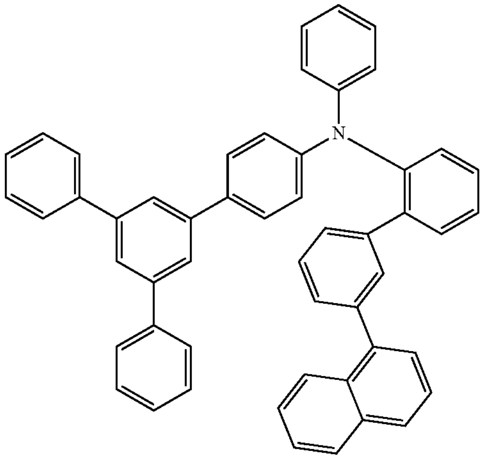
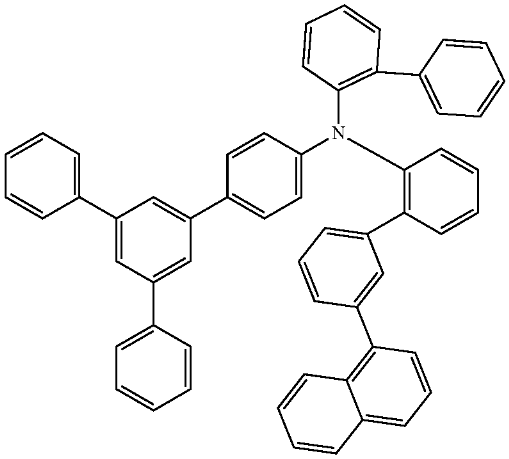
-continued
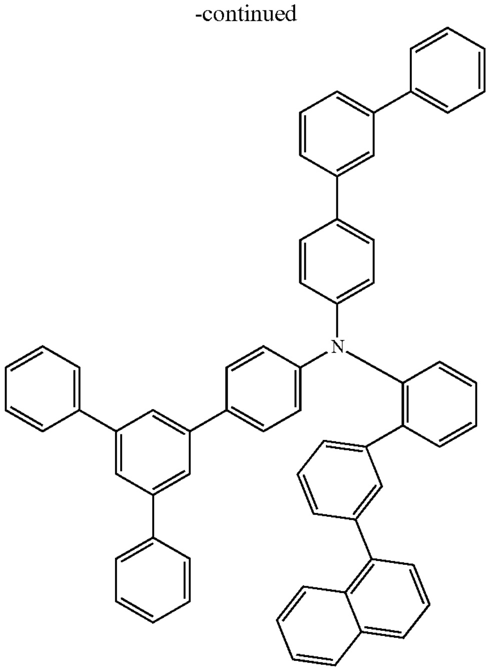
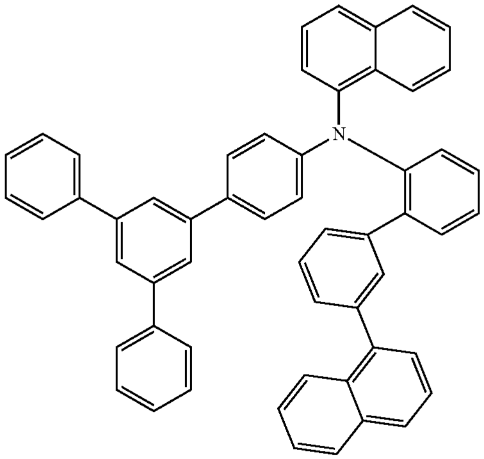
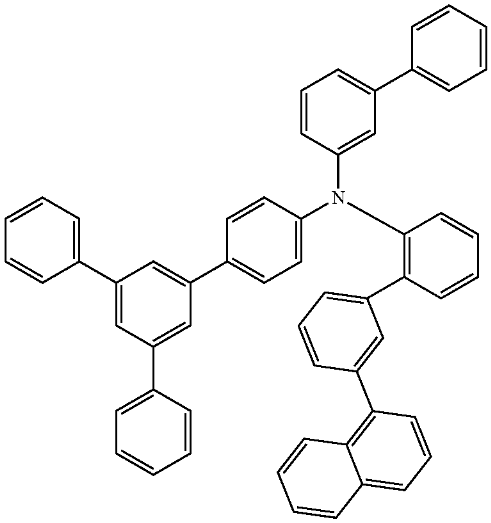

-continued
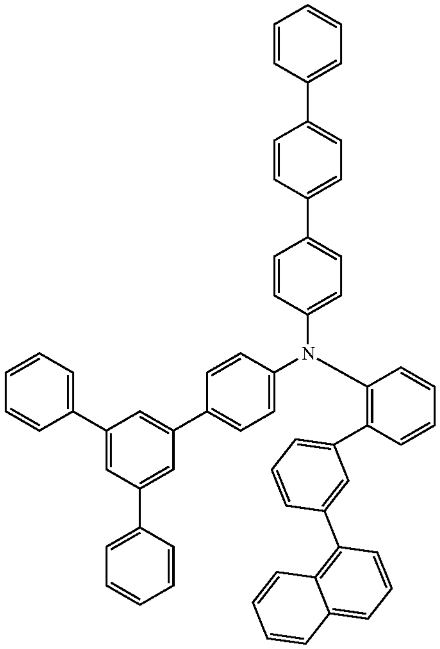
-continued
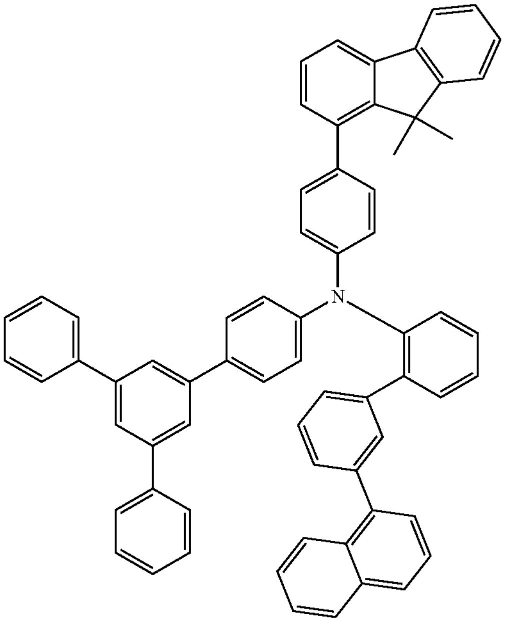
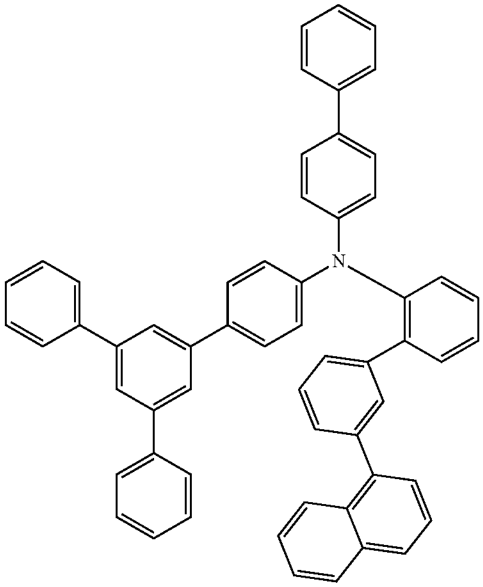
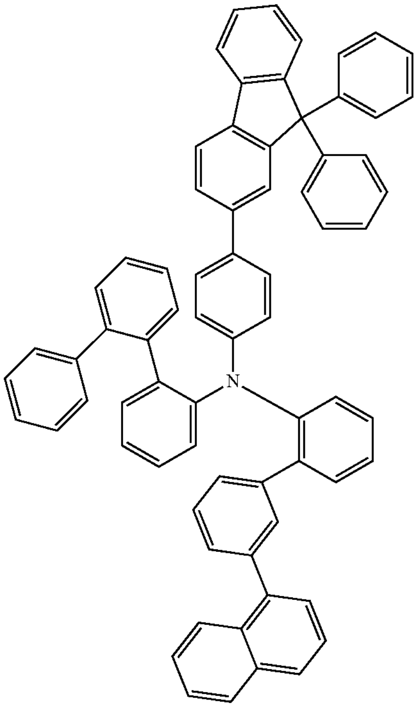

-continued
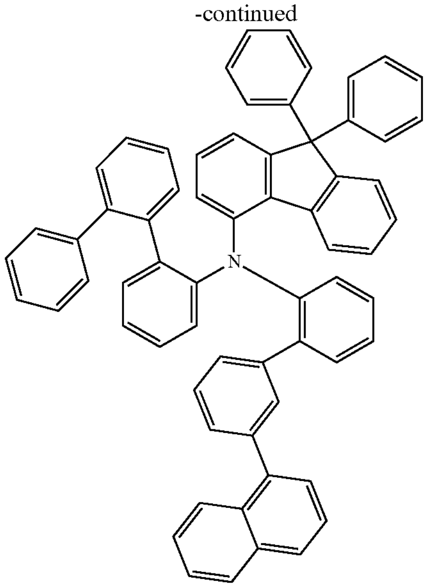
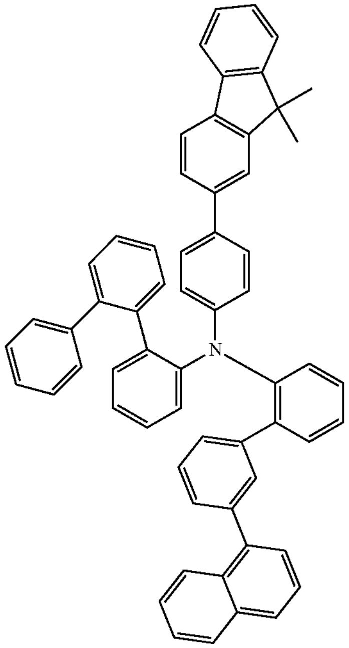
-continued
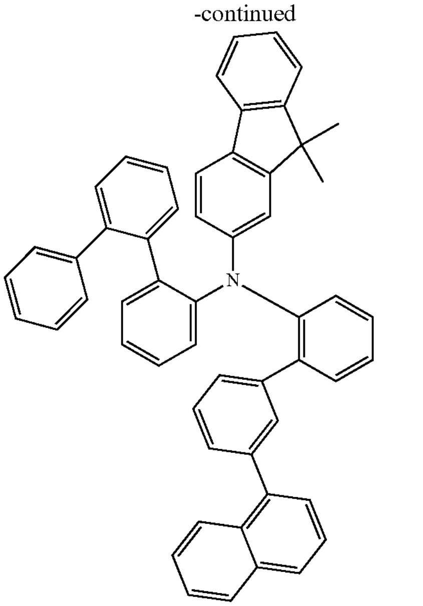
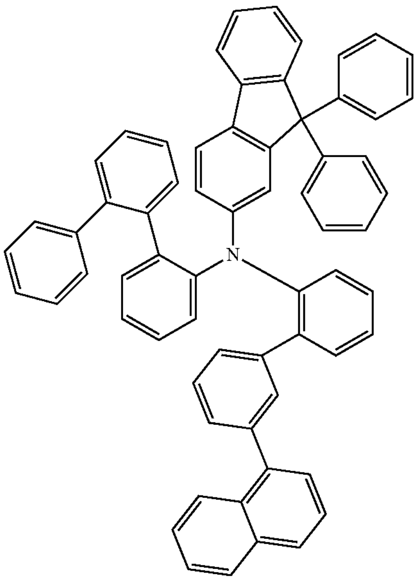
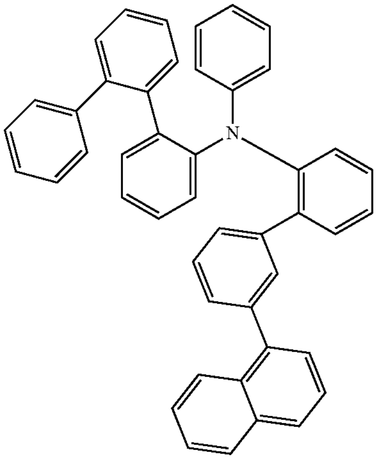

-continued
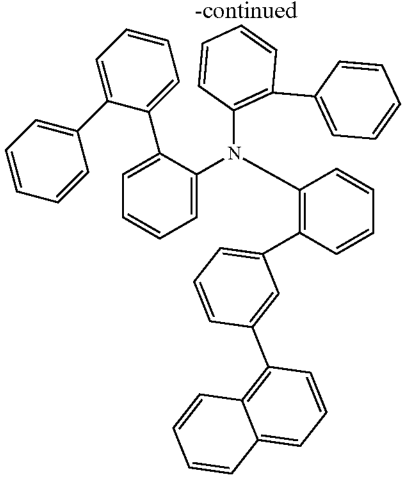
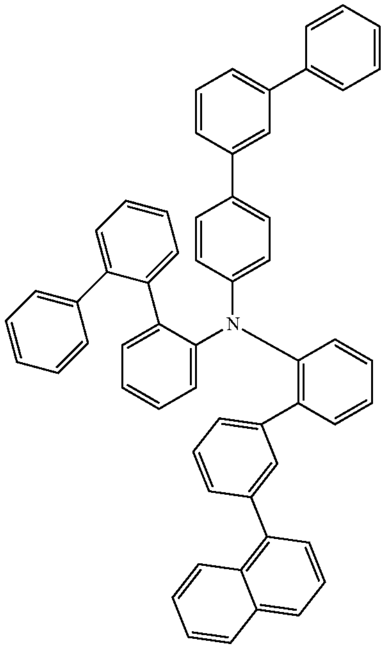
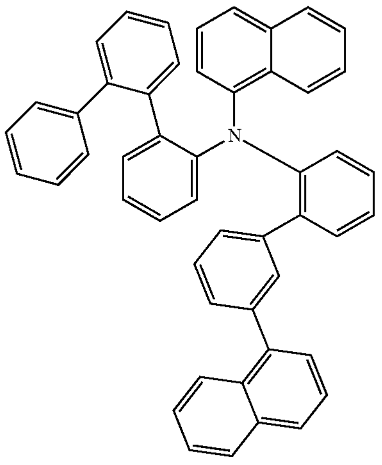
-continued
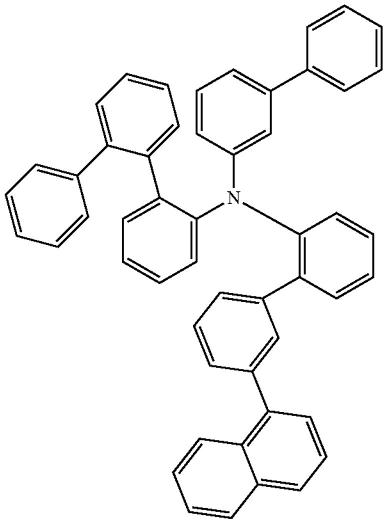
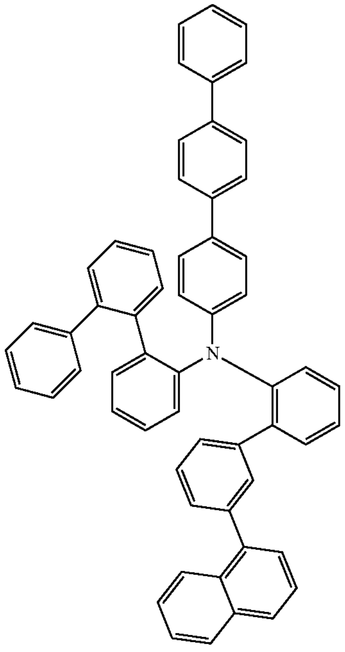 [SMILES: c1ccc(-c2ccc(-c3ccc(N(c4ccccc4-c4cccc(-c5cccc6ccccc56)c4)c4ccccc4-c4ccccc4-c4ccccc4)cc3)cc2)cc1]

-continued
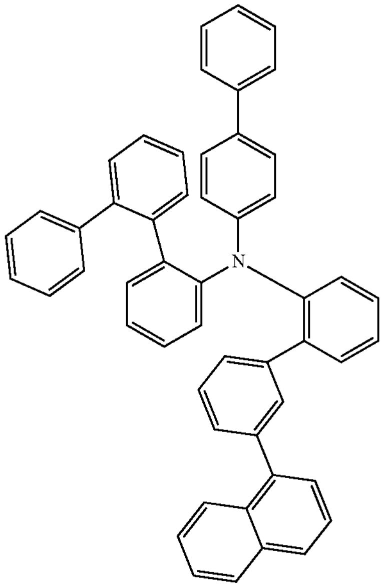
-continued
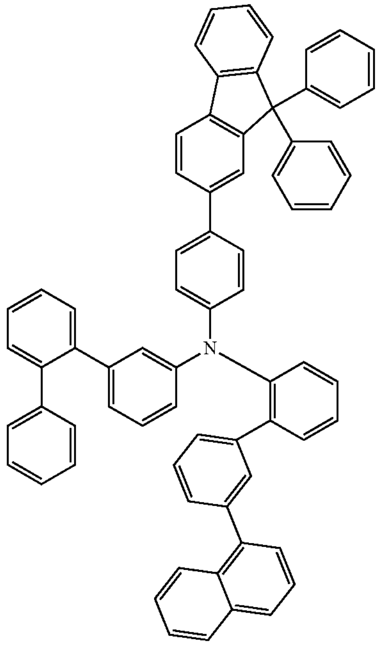
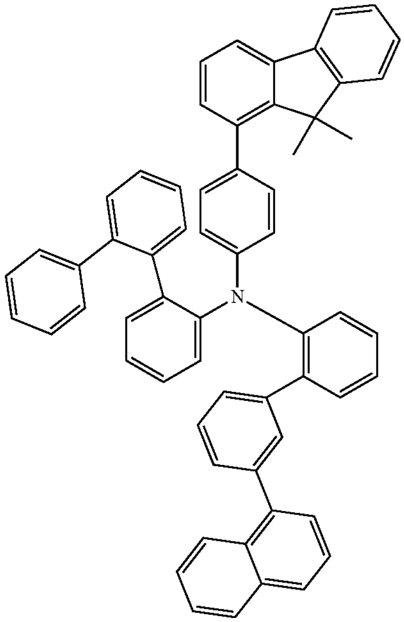
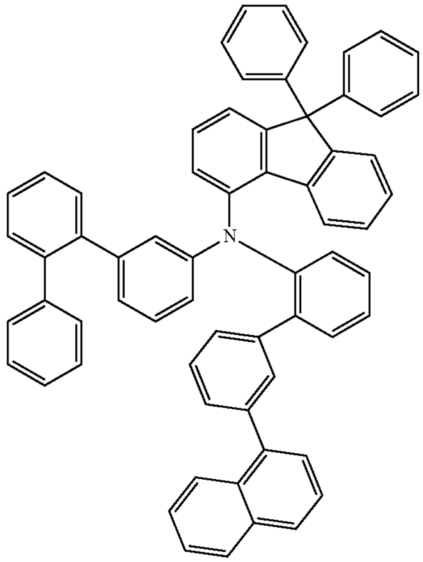

-continued
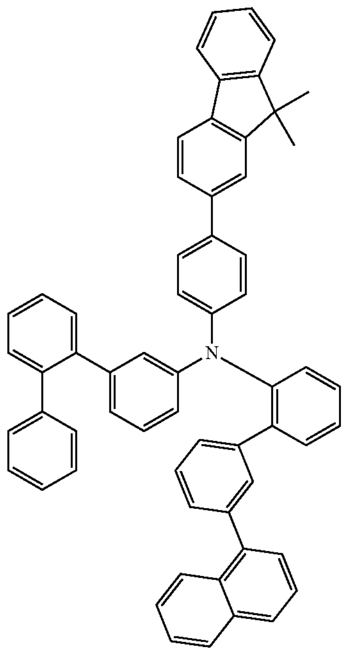
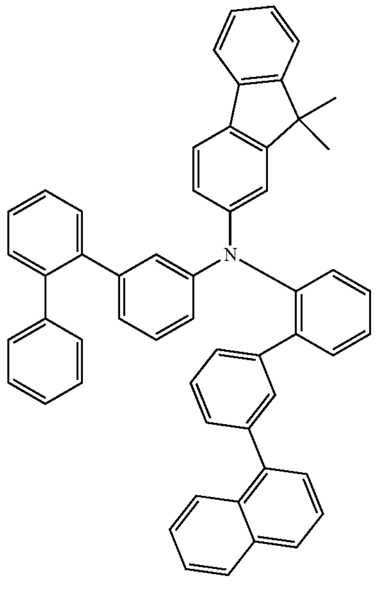
-continued
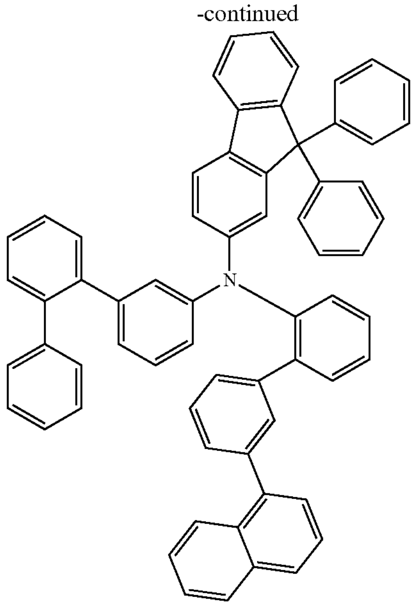
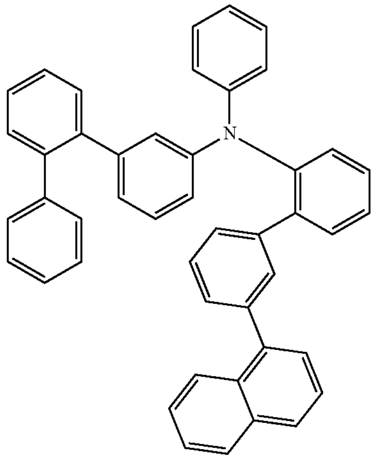
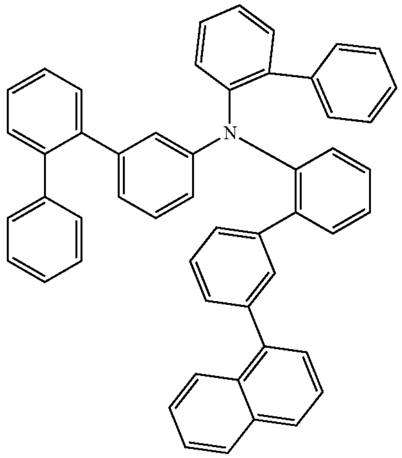

-continued
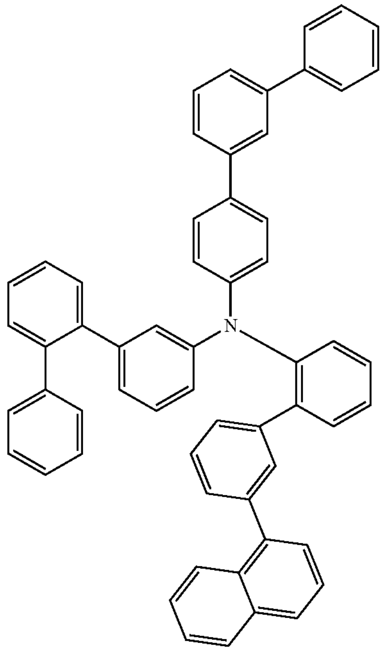
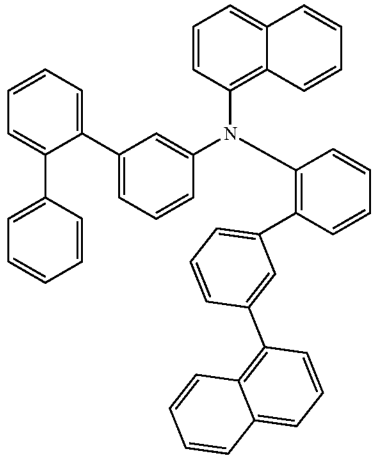
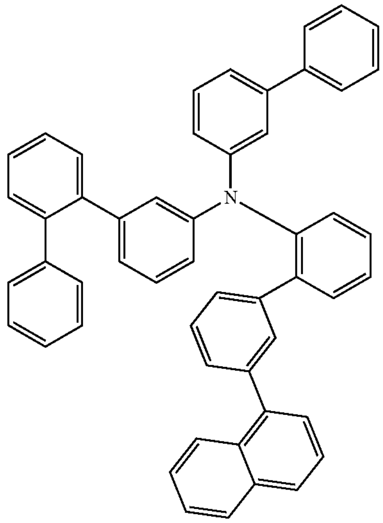
-continued
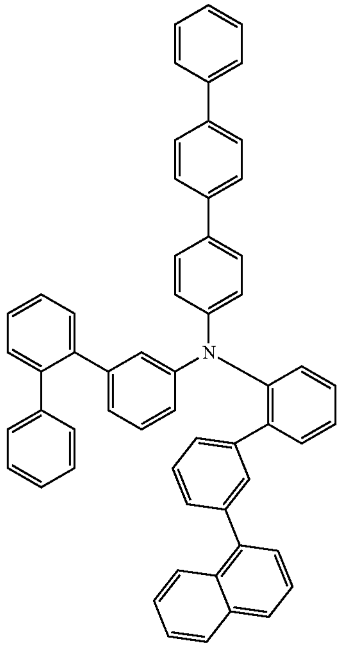
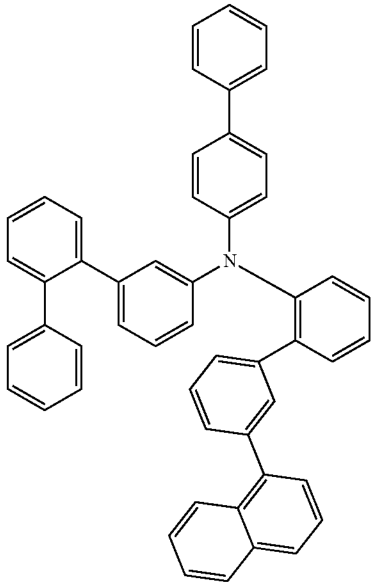

-continued
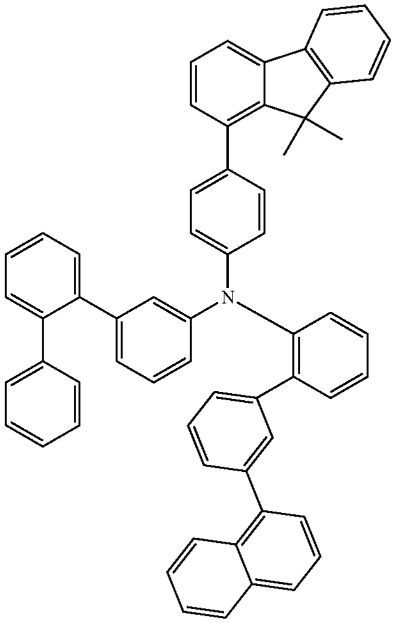
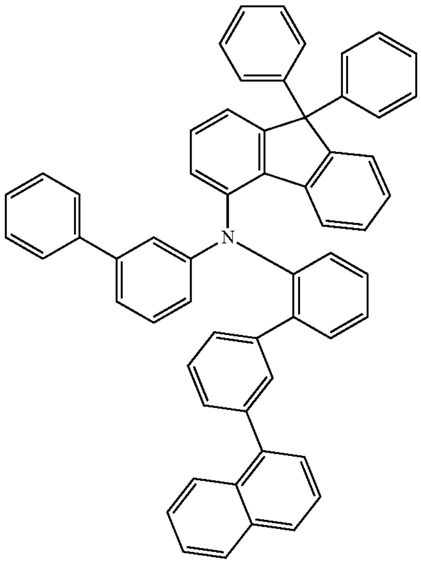
-continued
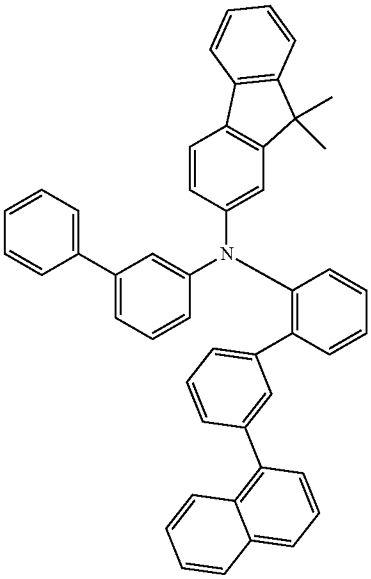
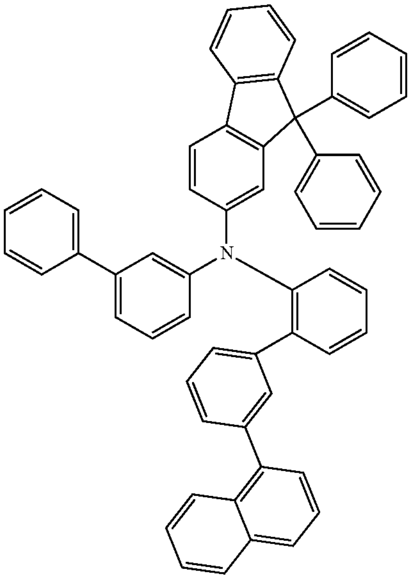
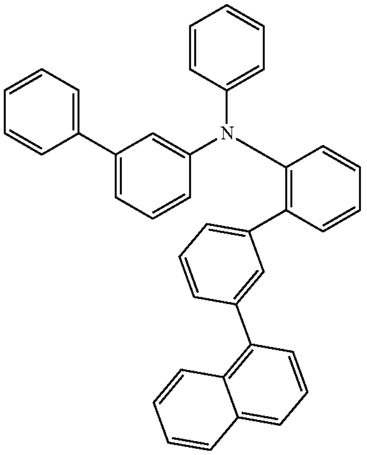

-continued
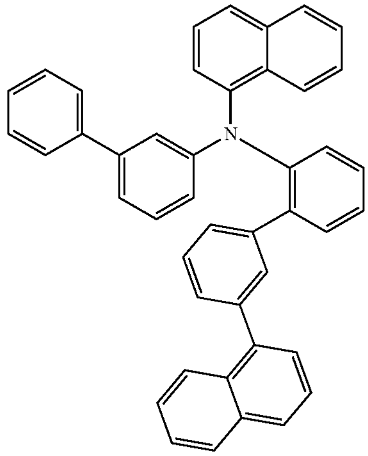
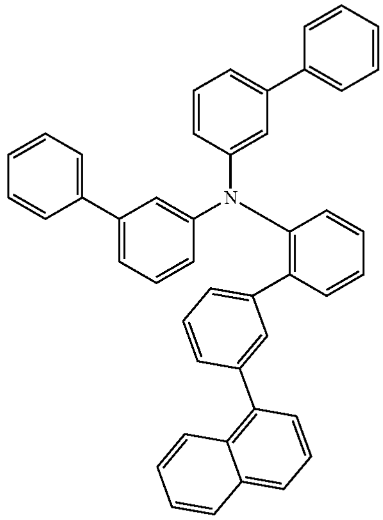
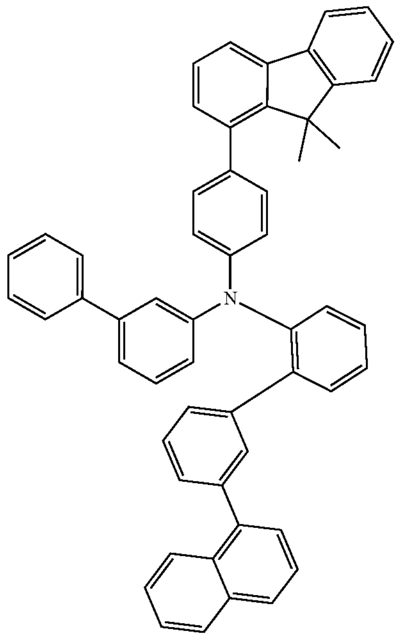
-continued
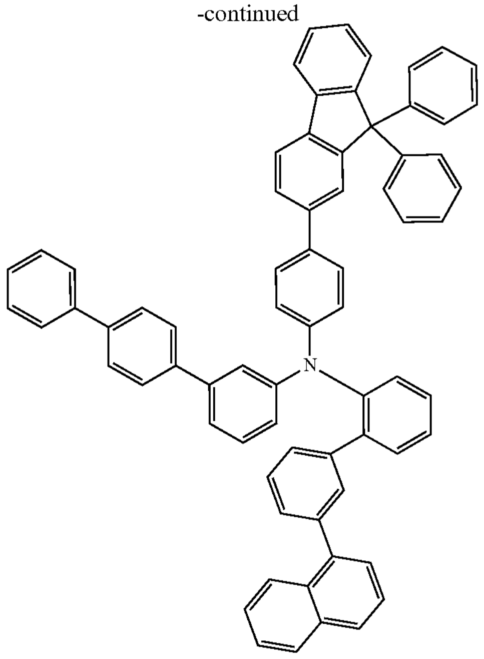
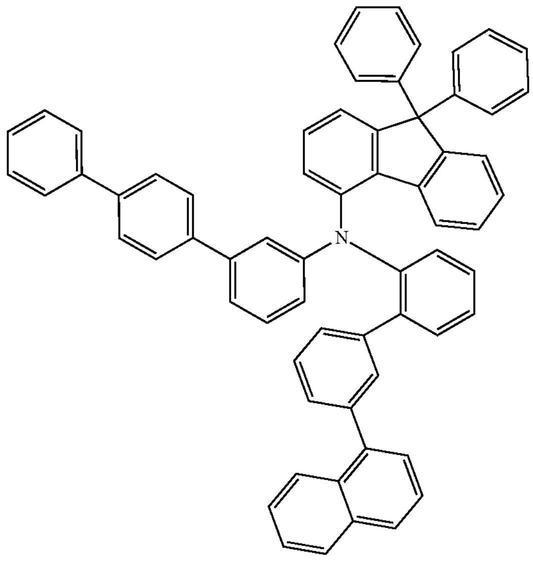

-continued
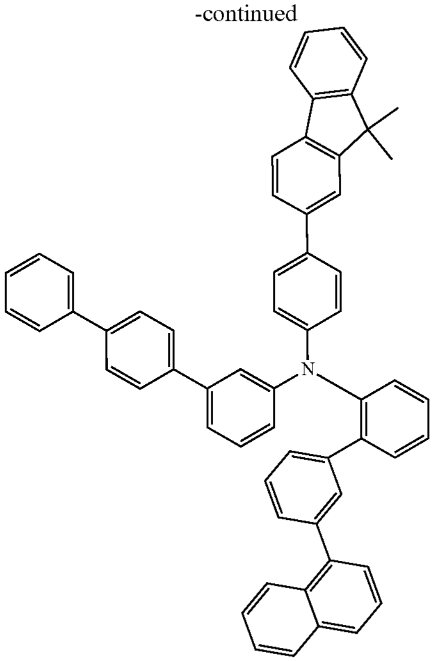
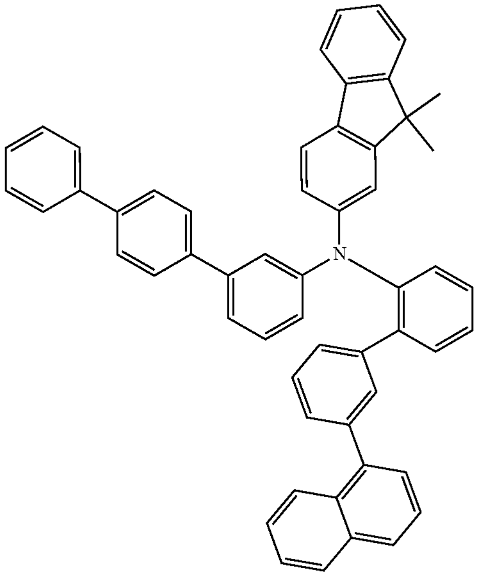
-continued
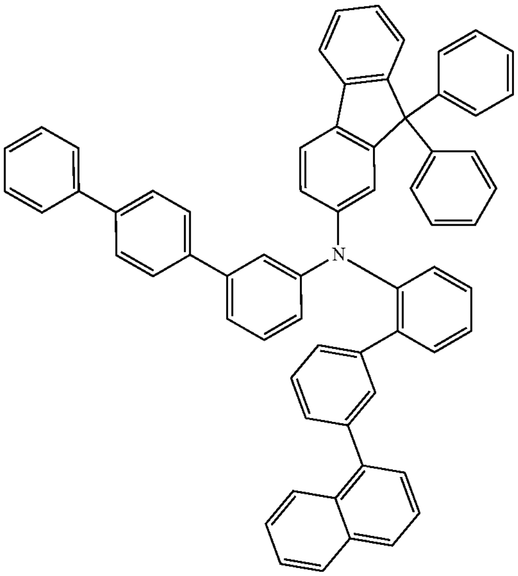
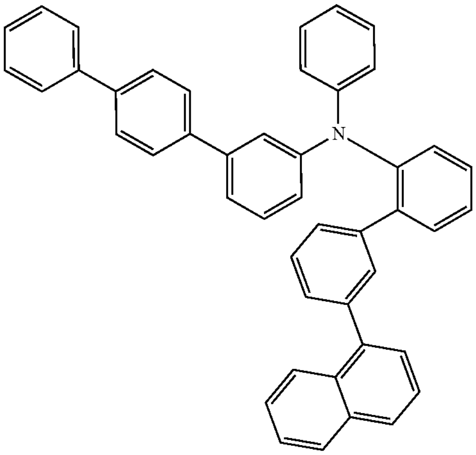
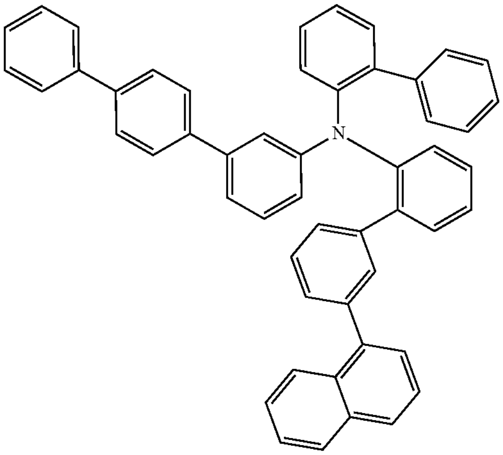

-continued
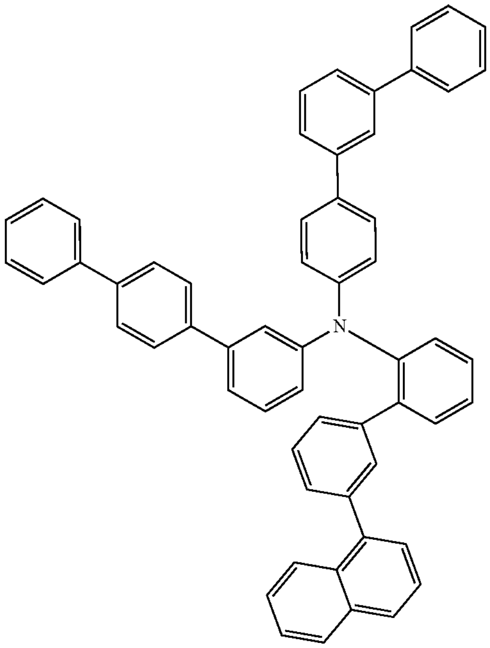
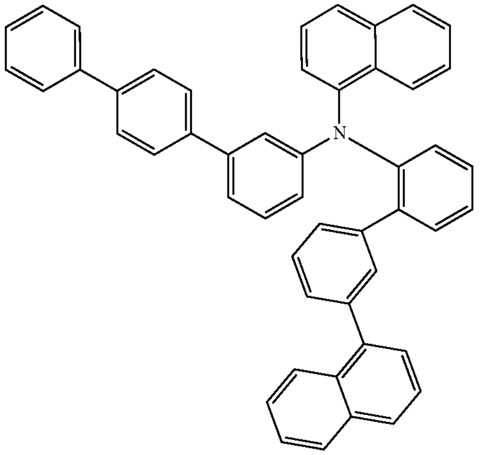
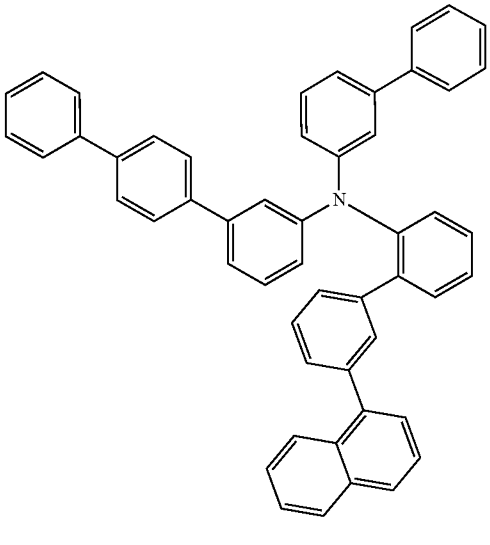
-continued
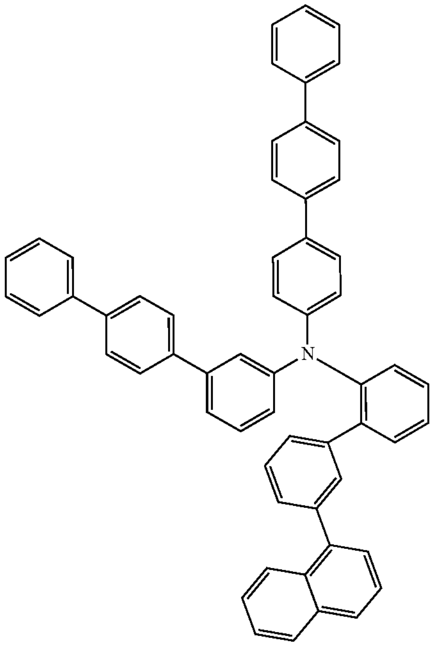
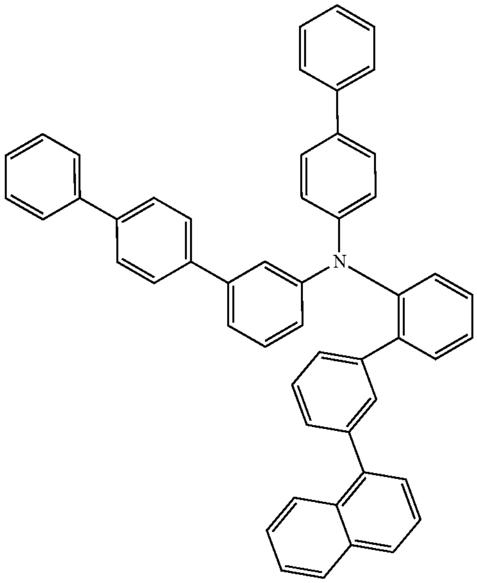

-continued
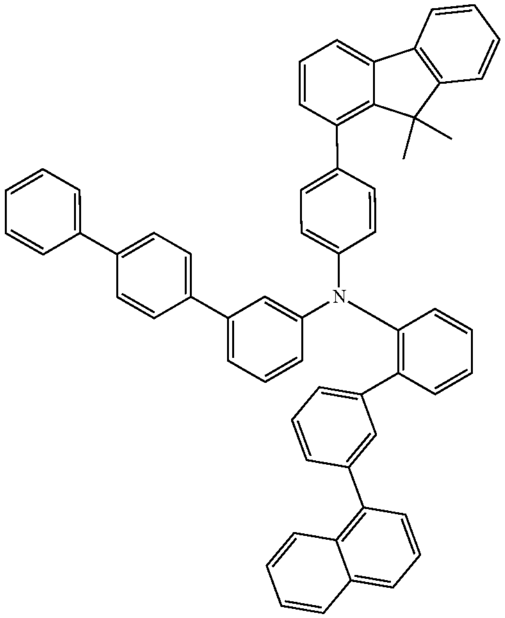
-continued
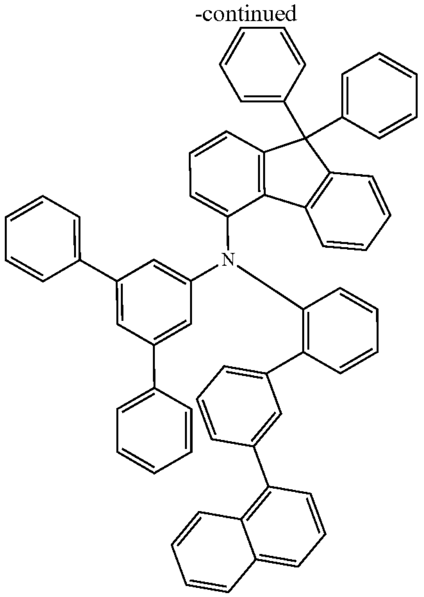
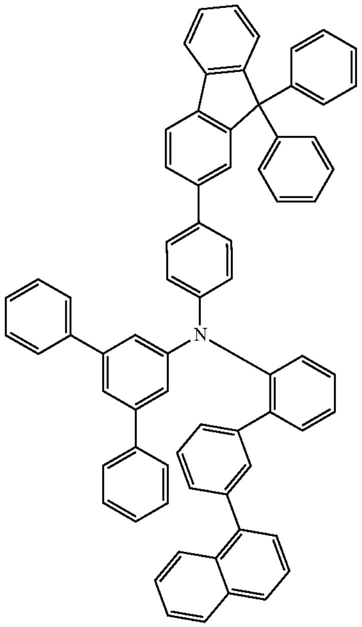
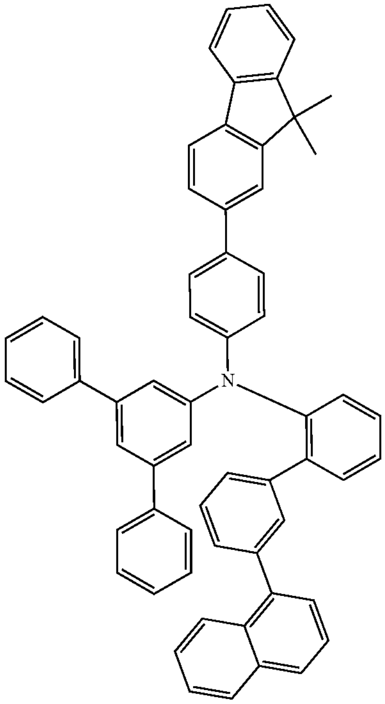

-continued
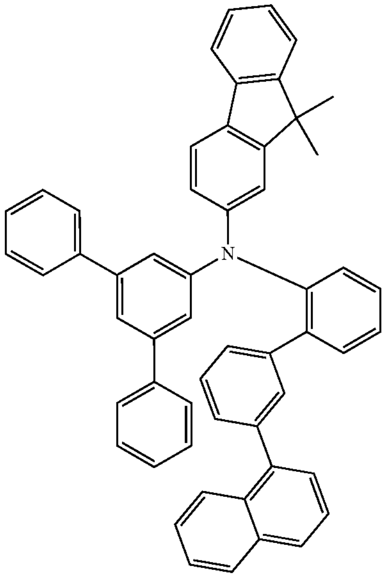
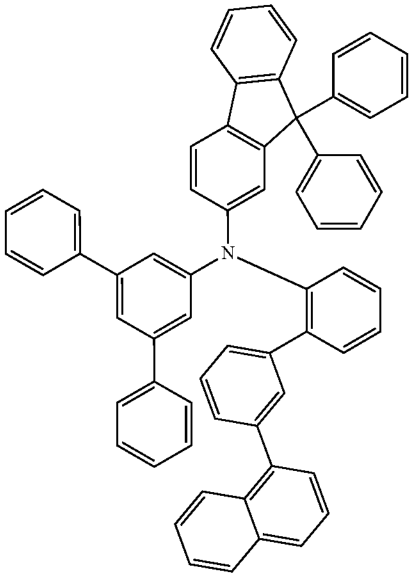
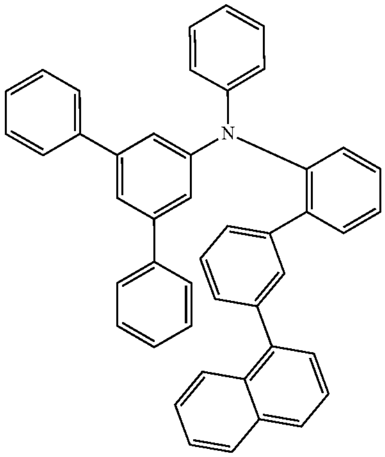
-continued
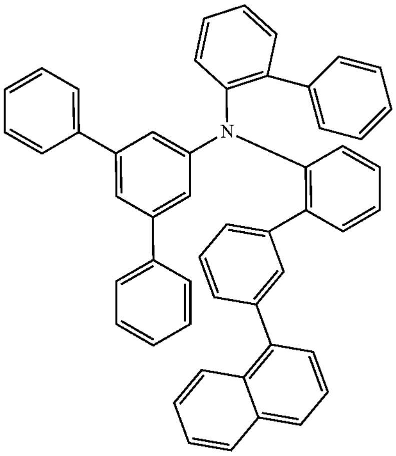
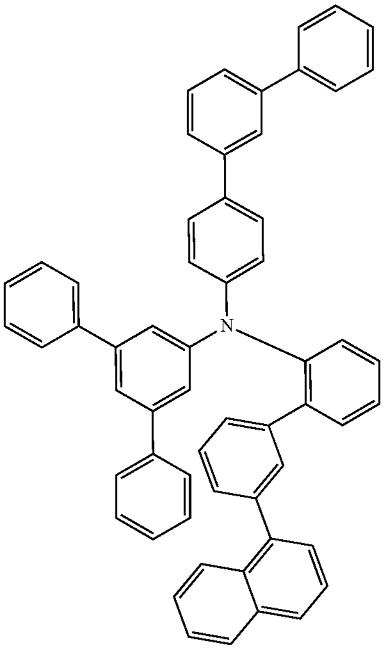
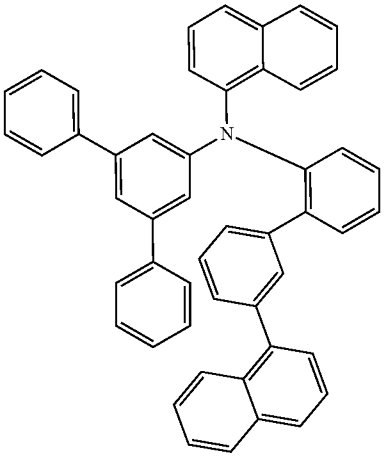

-continued
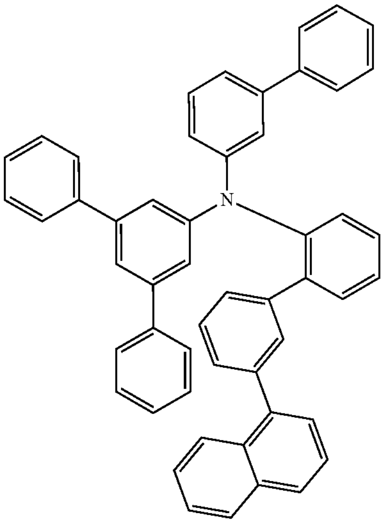
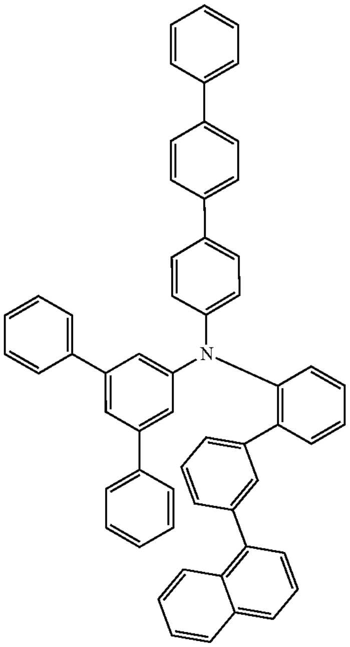
-continued
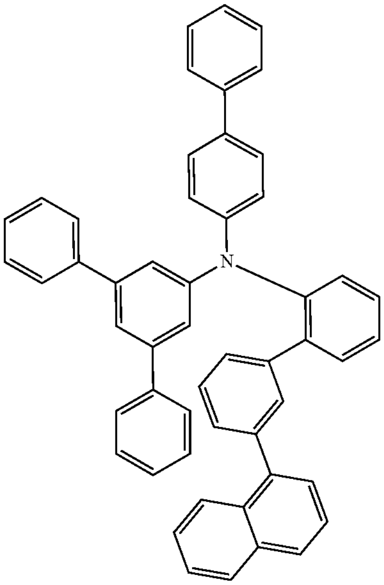
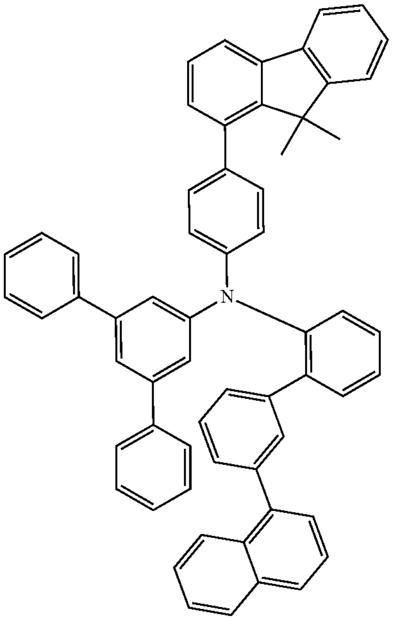

-continued
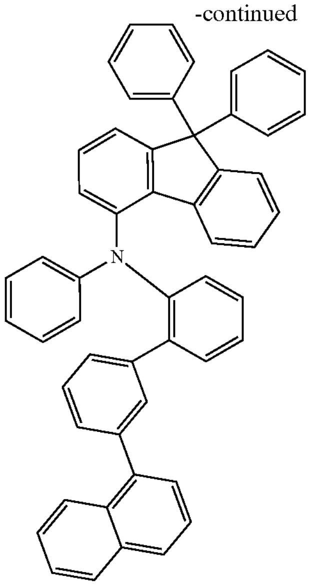
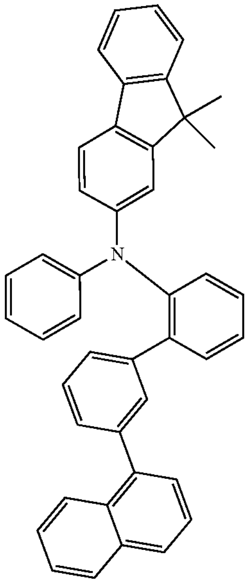
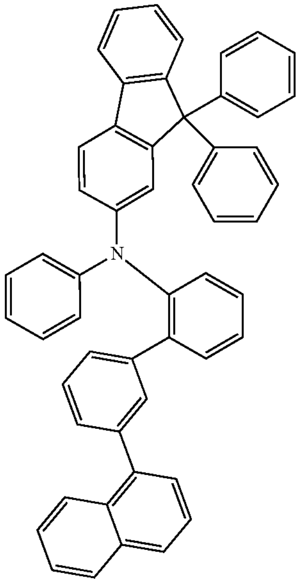
-continued
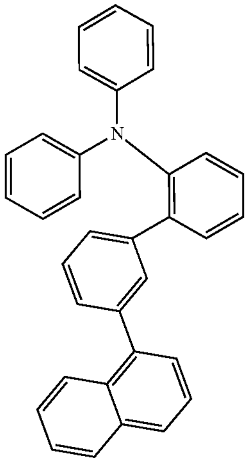
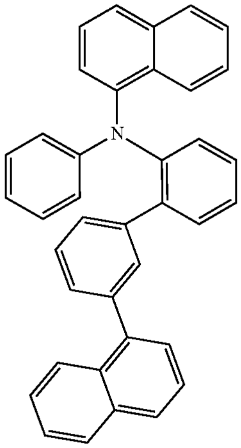
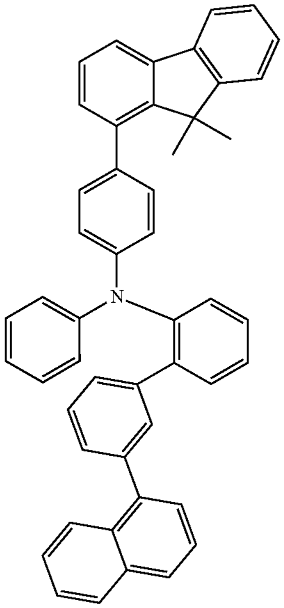

-continued
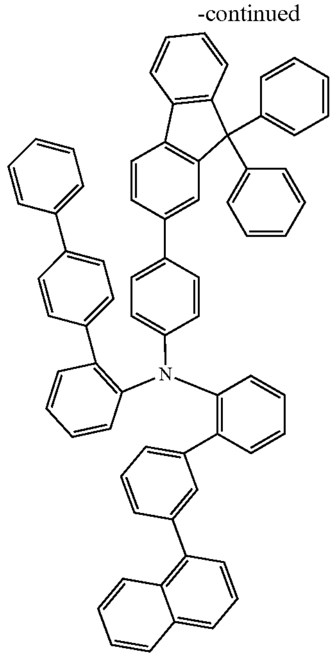
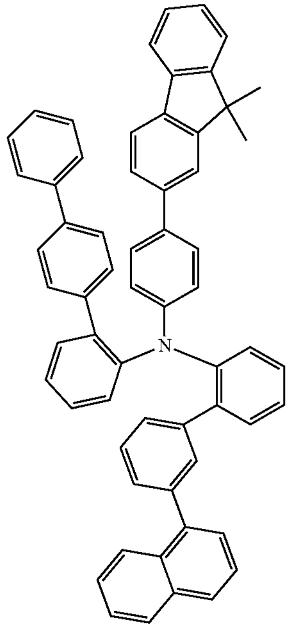
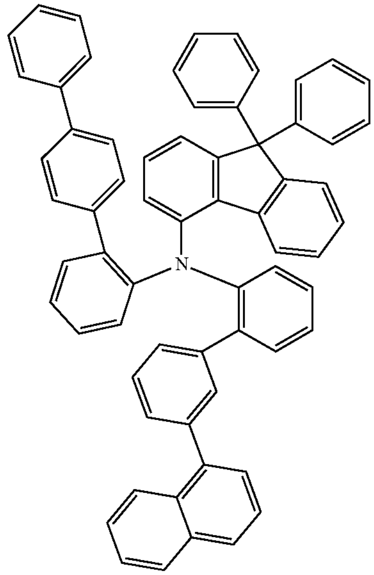
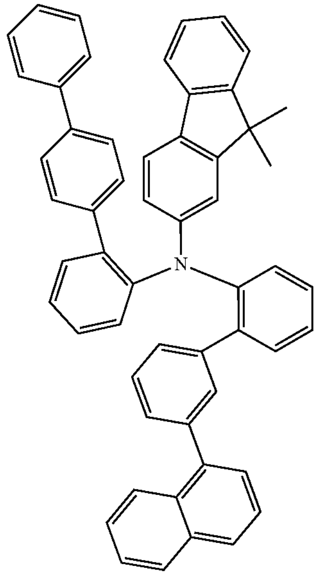

-continued
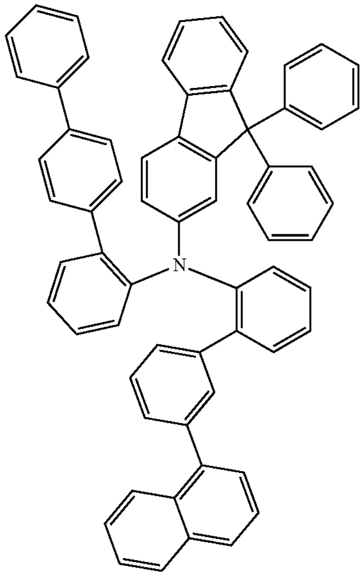
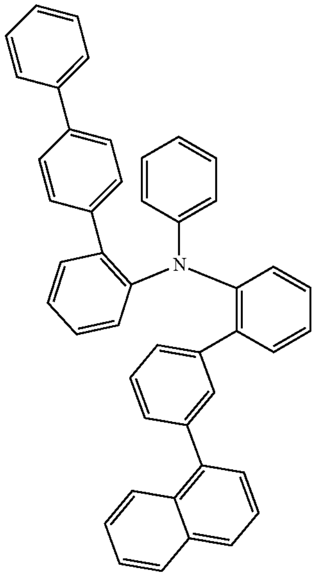
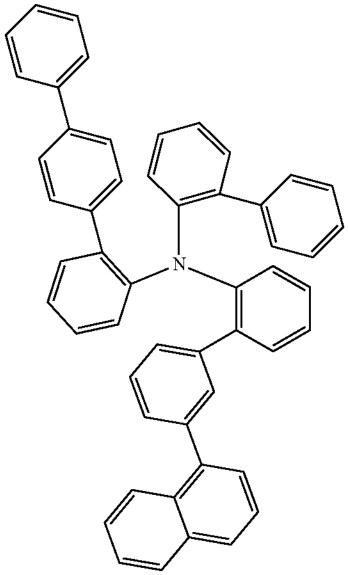
-continued
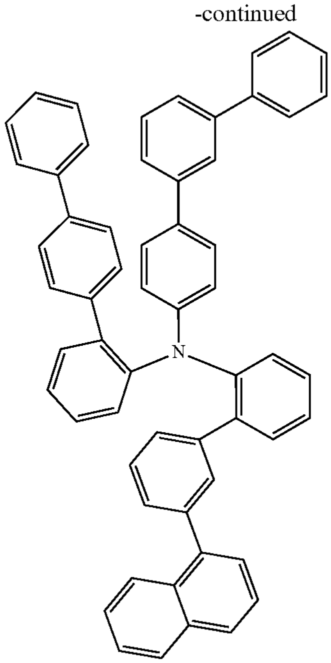
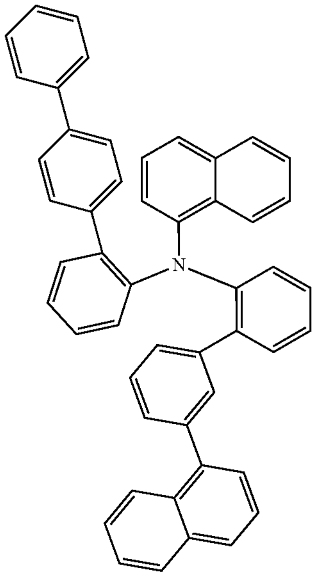

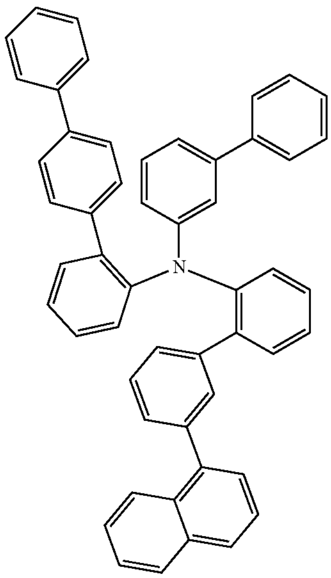
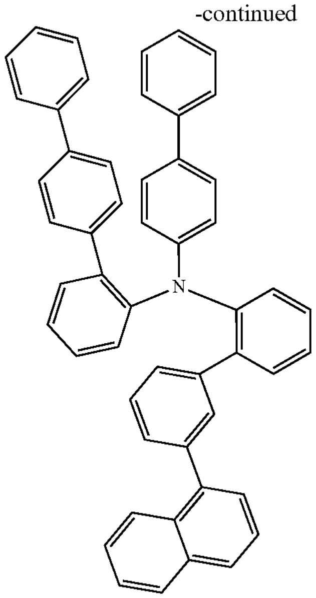
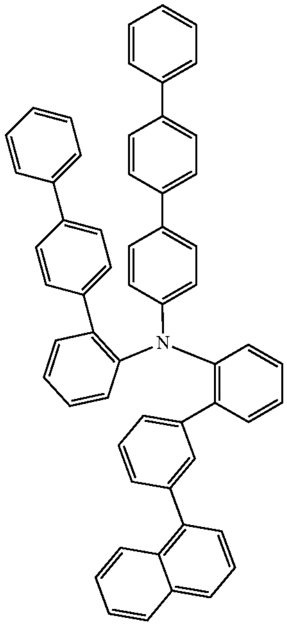
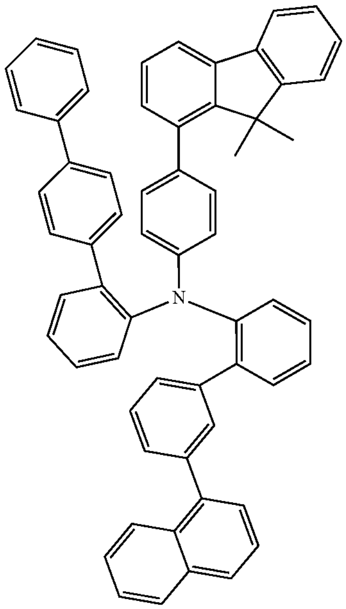

-continued
-continued
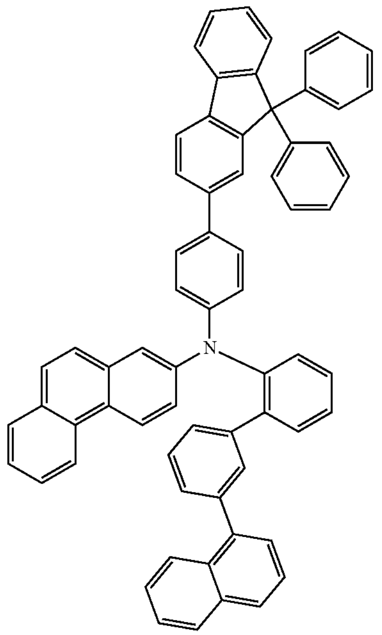
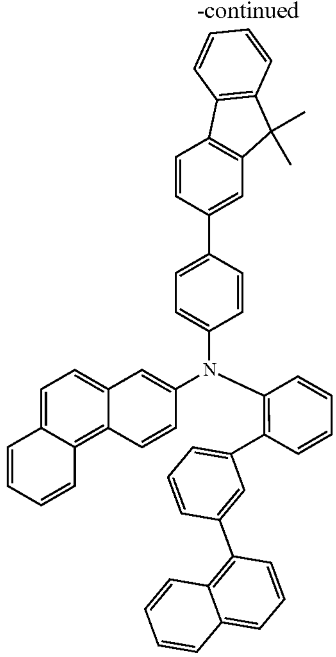
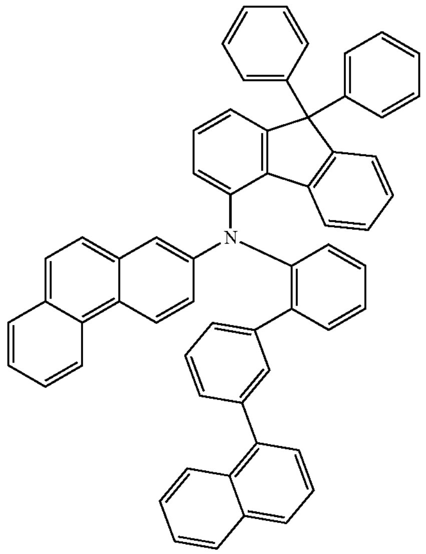
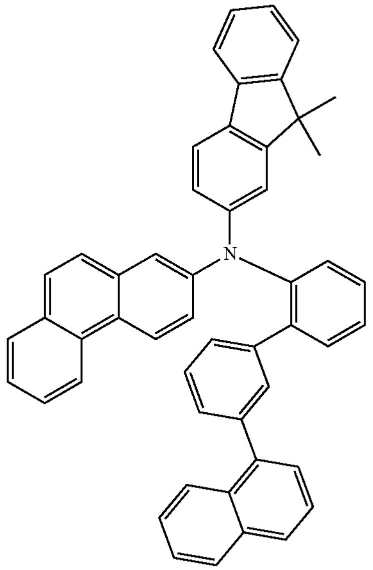

-continued
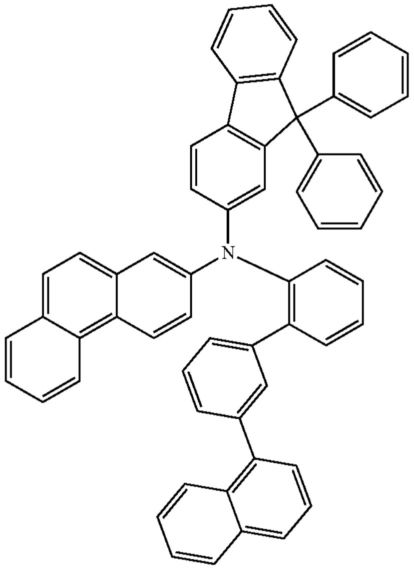
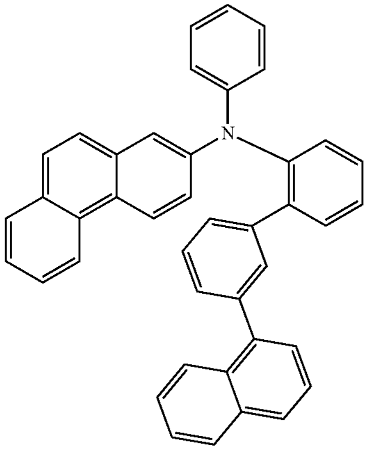
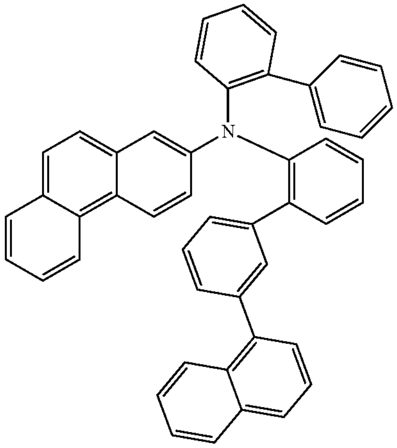
-continued
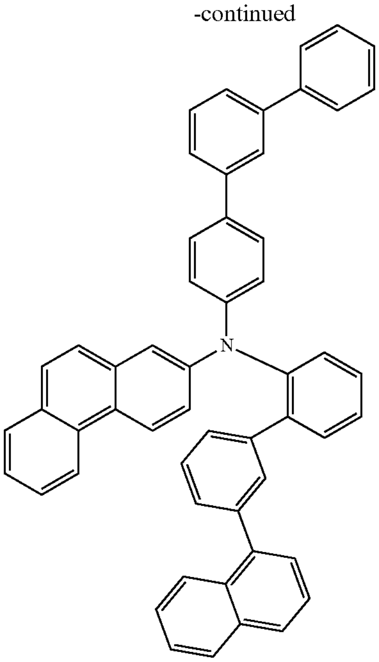
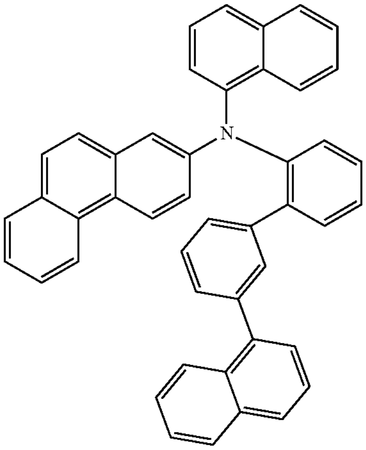
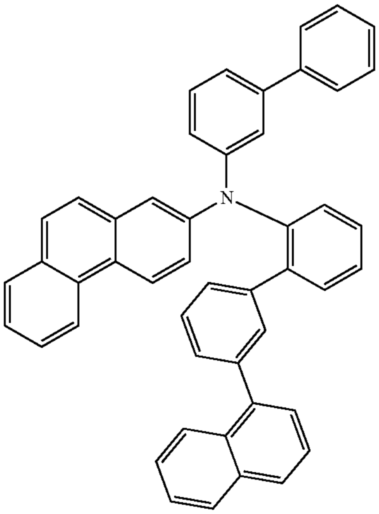

-continued
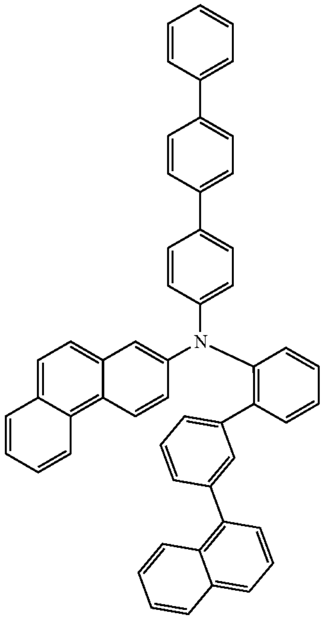
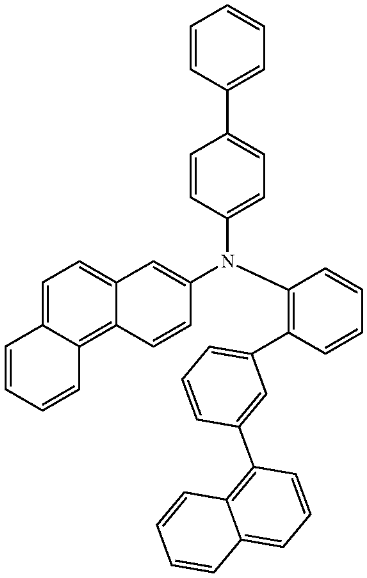
-continued
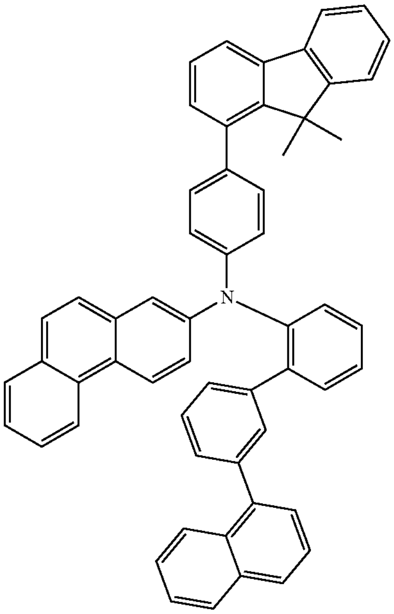
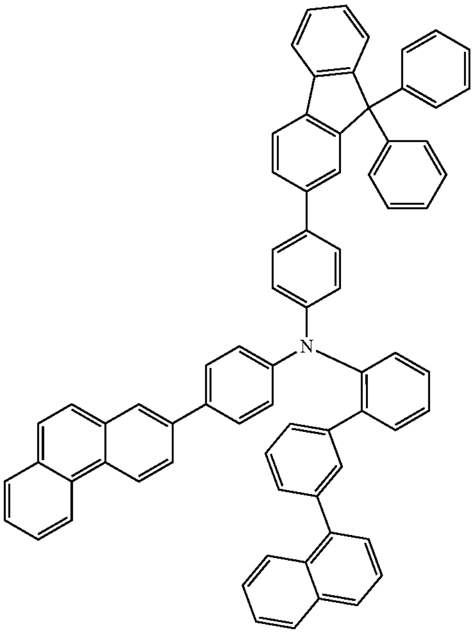

-continued
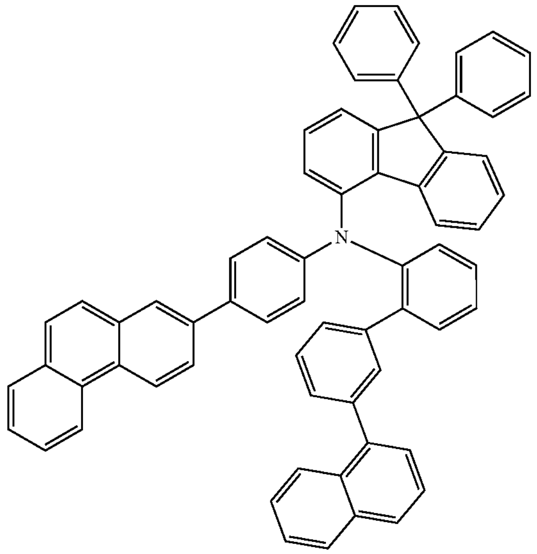
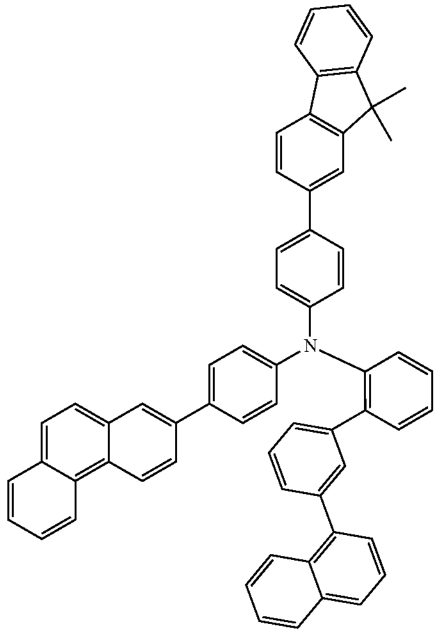
-continued
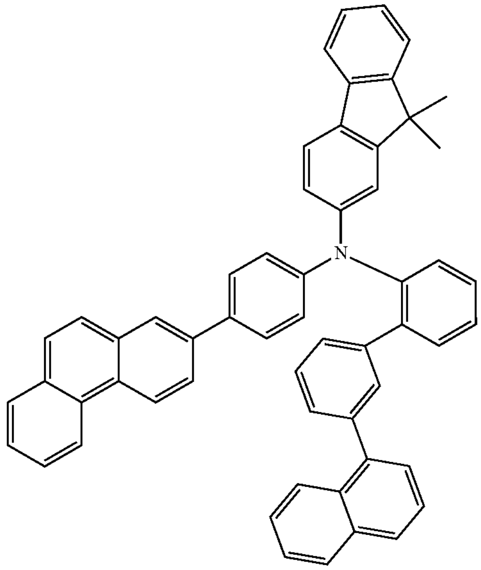
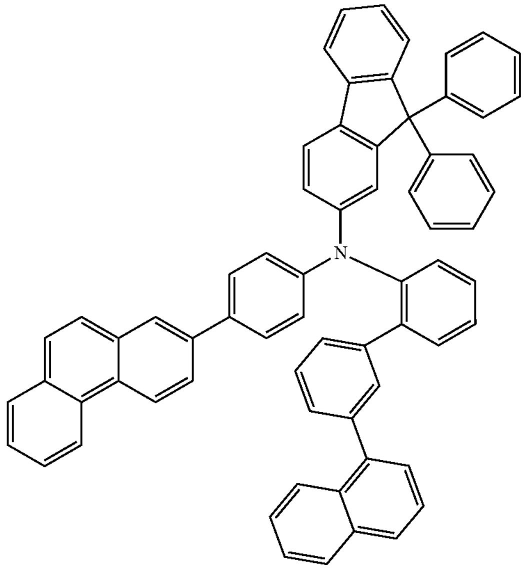
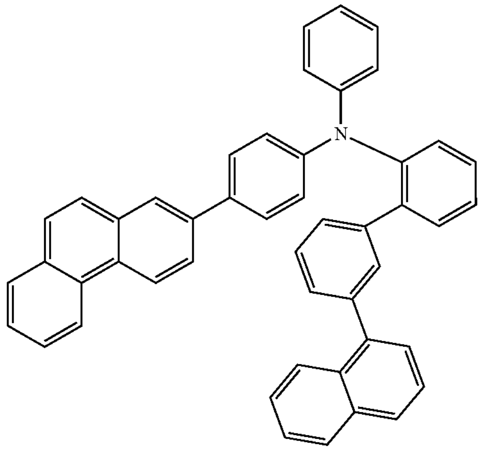

-continued
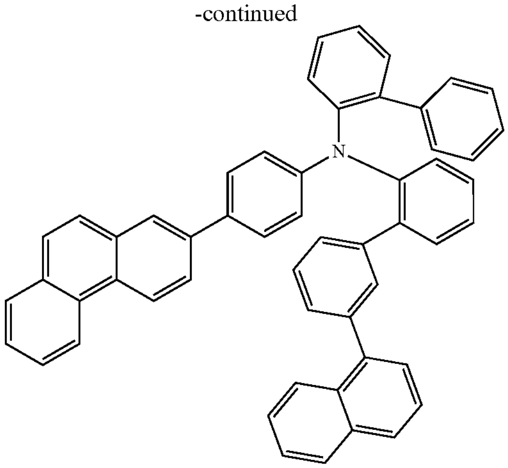
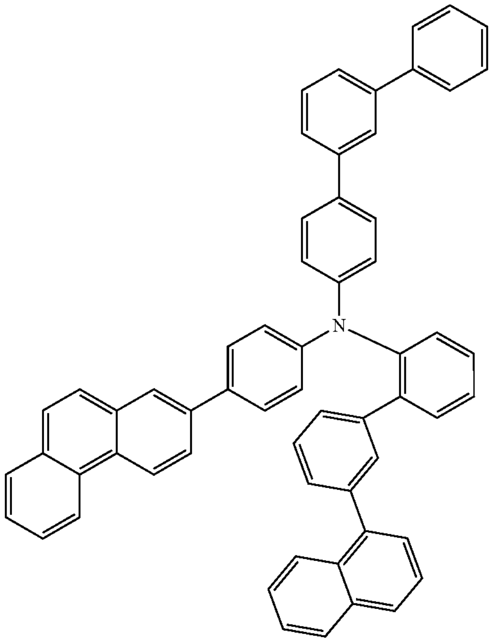
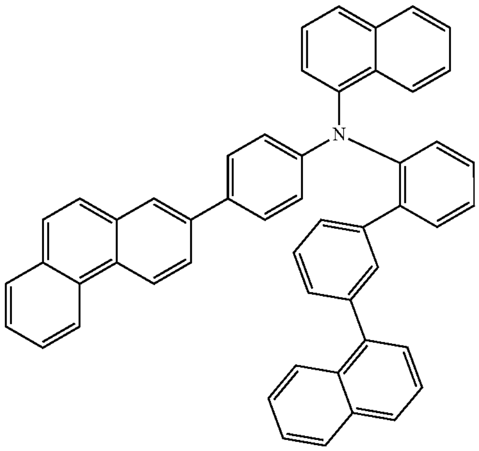
-continued
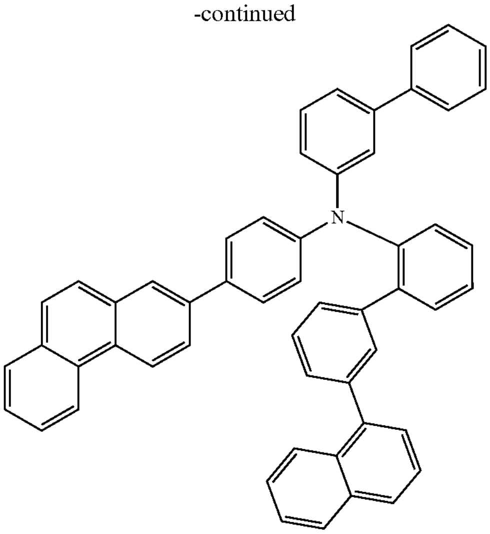
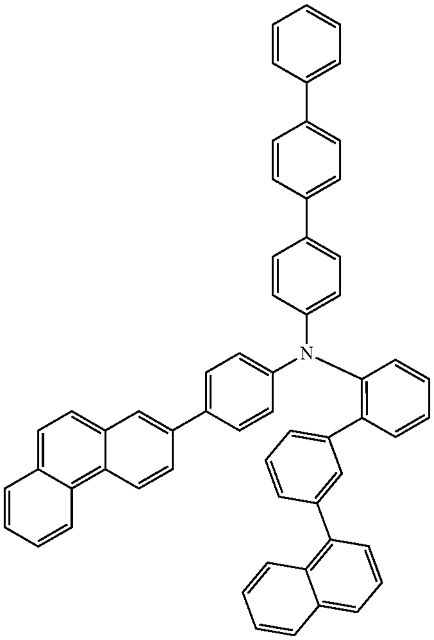
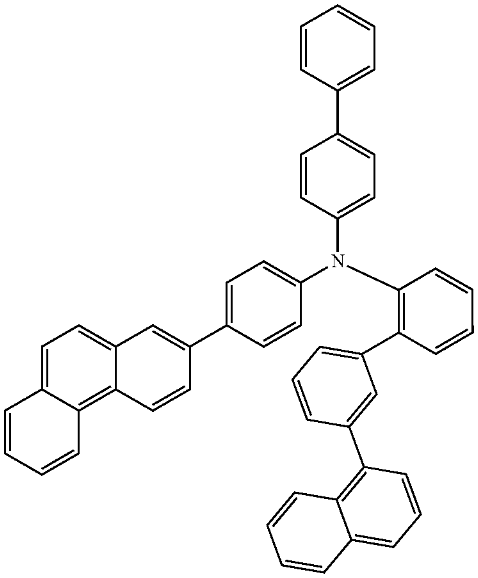

-continued
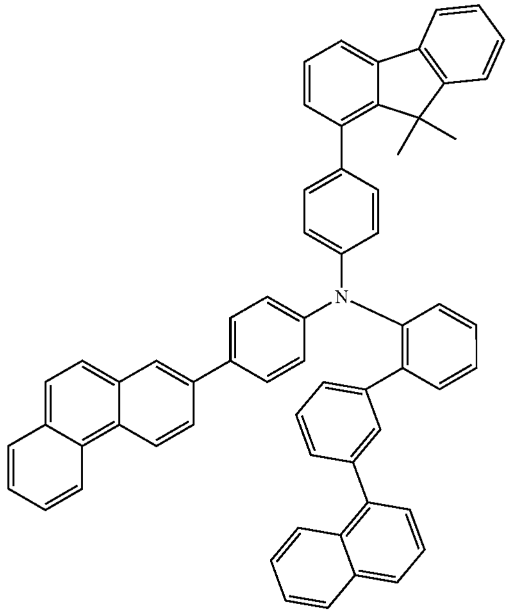
-continued
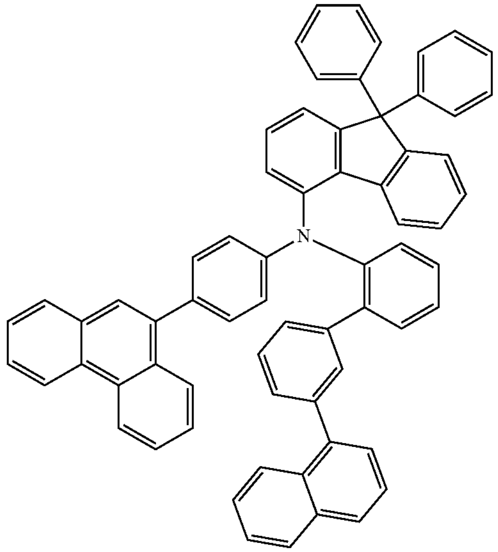
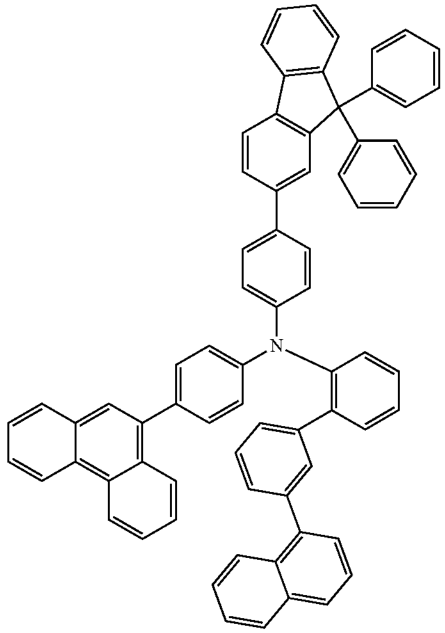
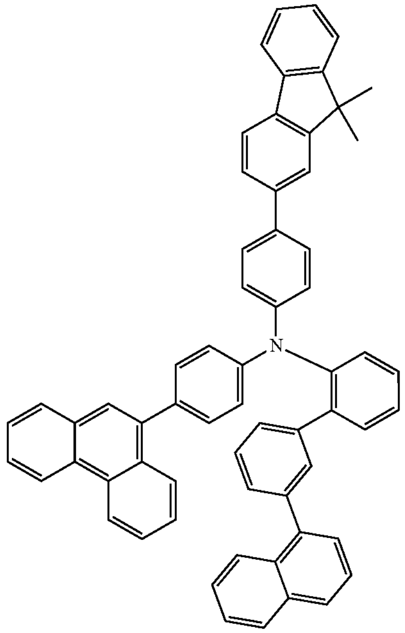

-continued
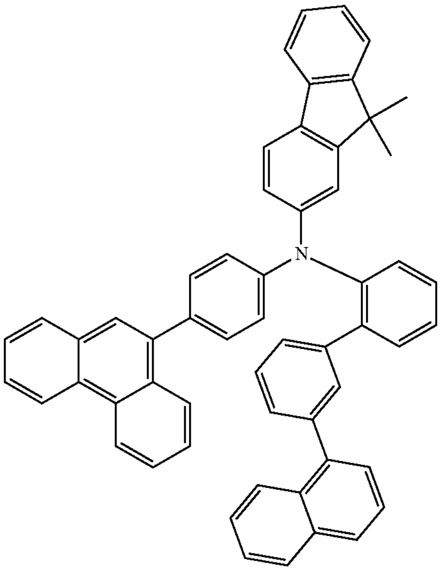
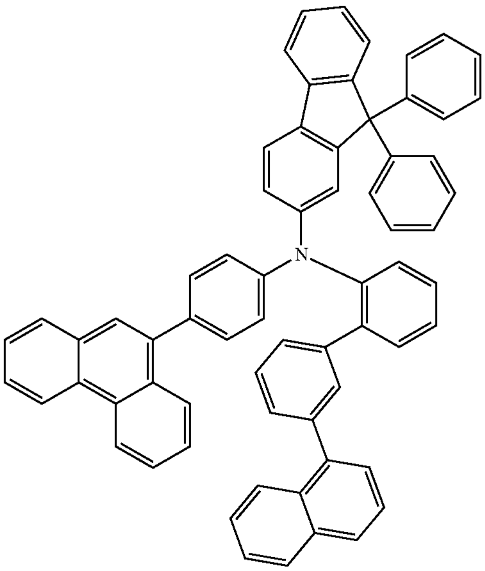
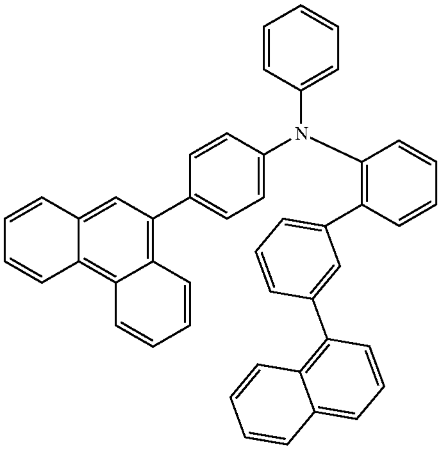
-continued
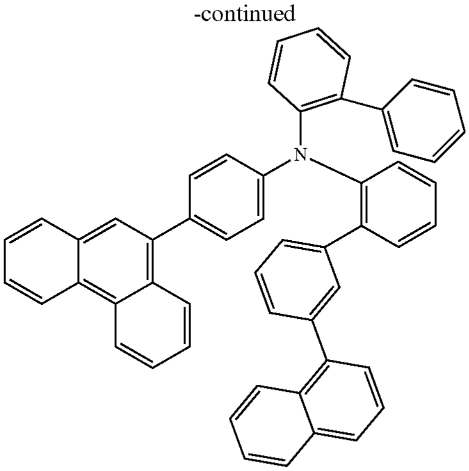
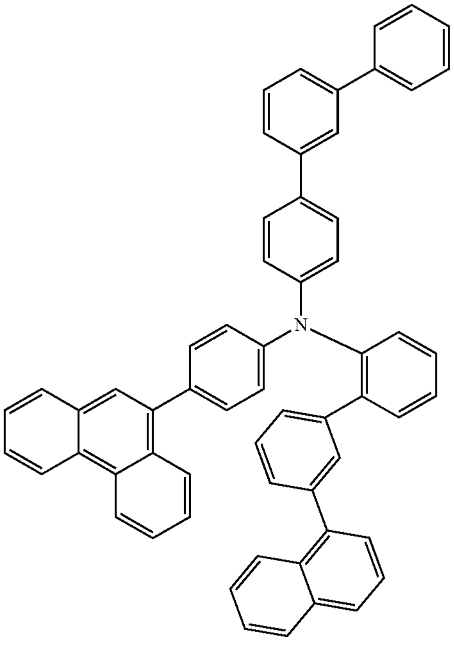
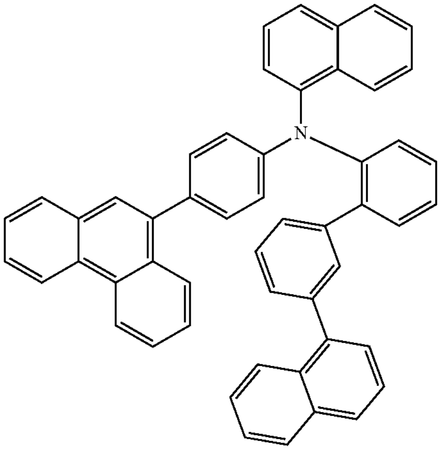

-continued
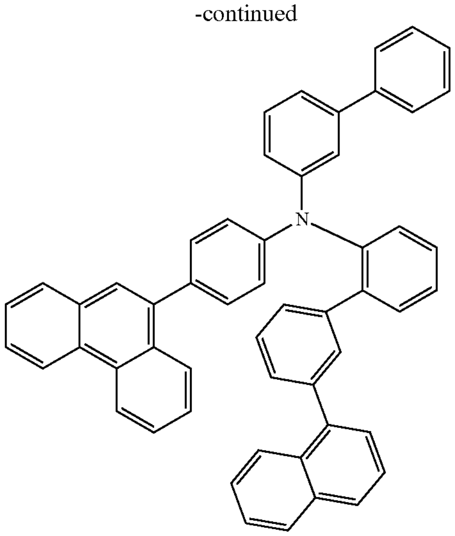
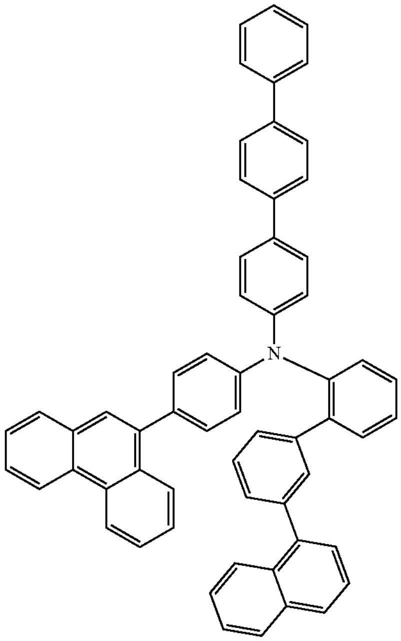
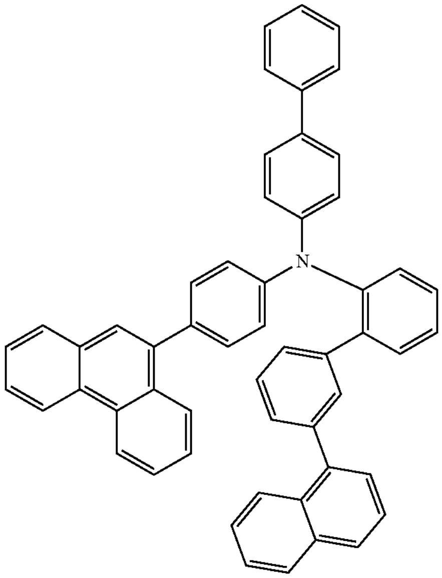
-continued
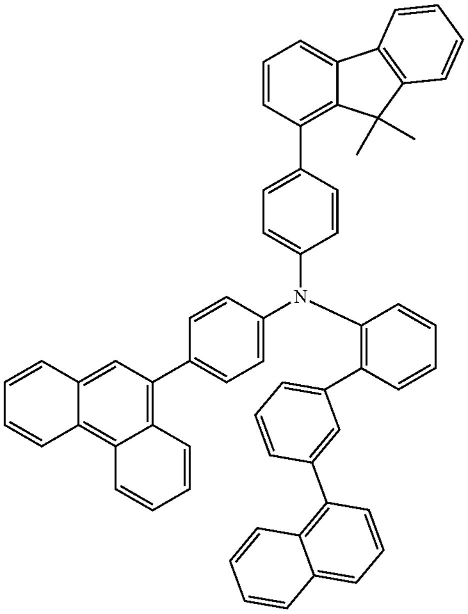
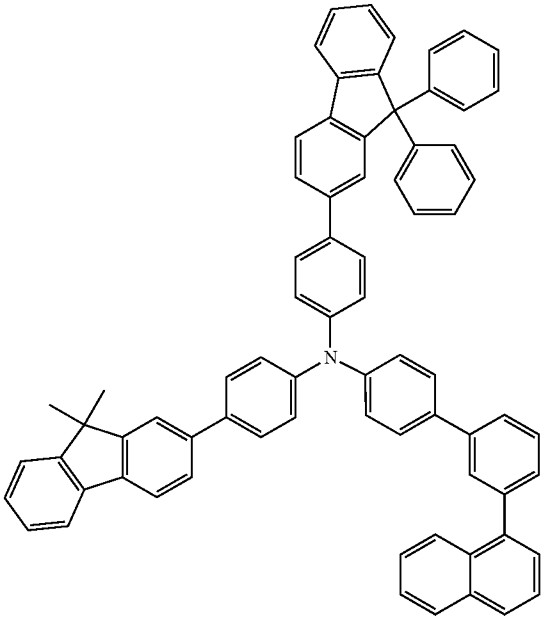
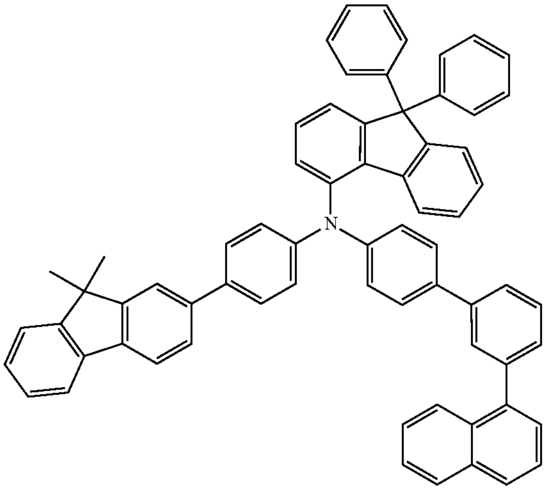

-continued
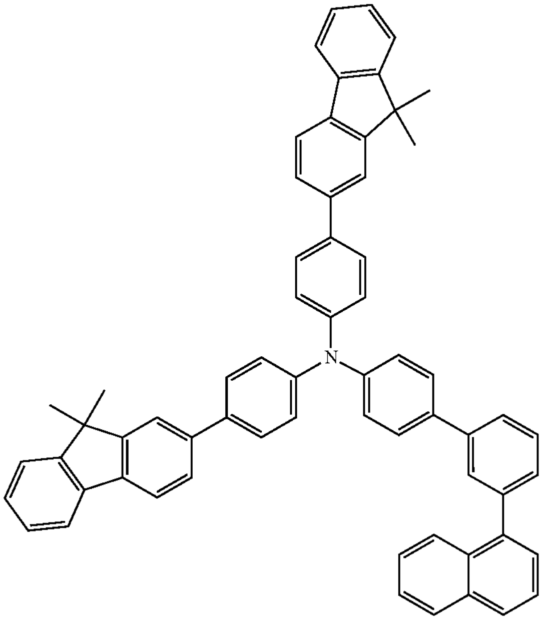
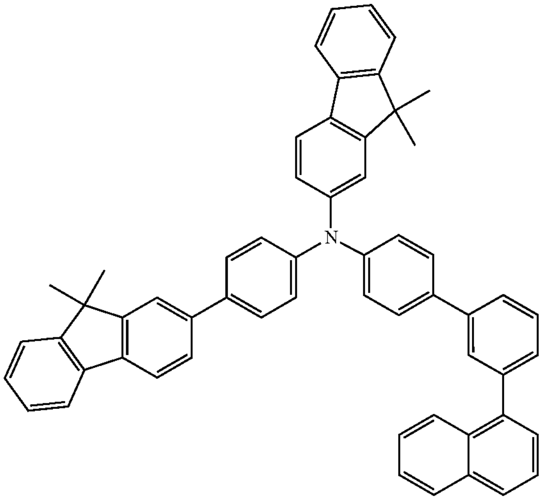
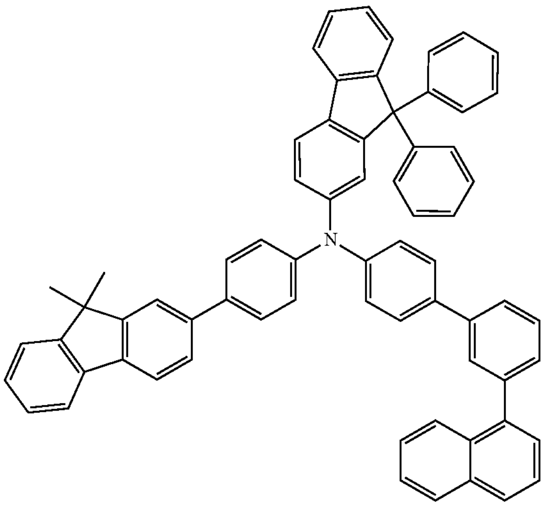
-continued
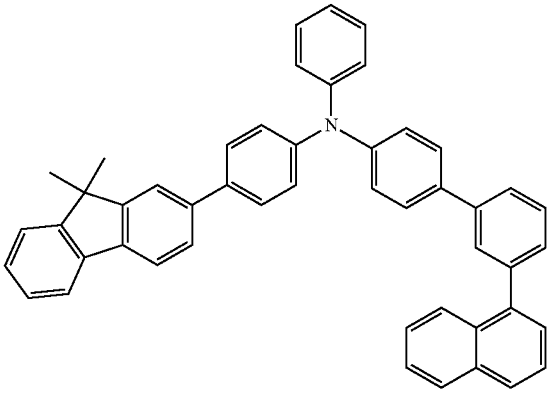
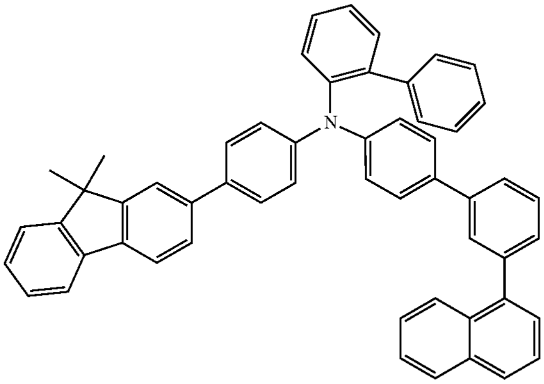
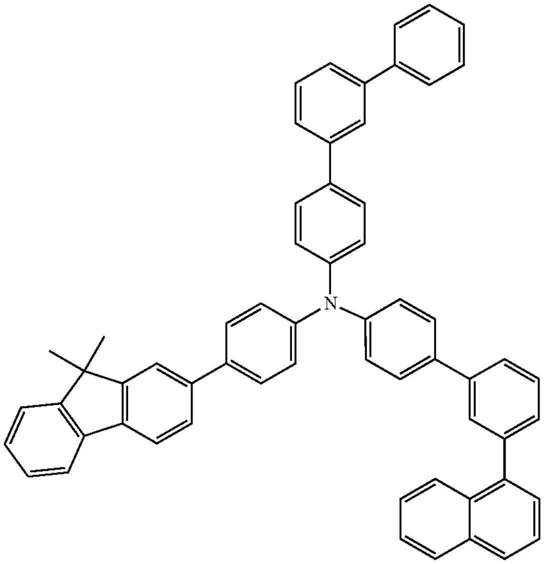
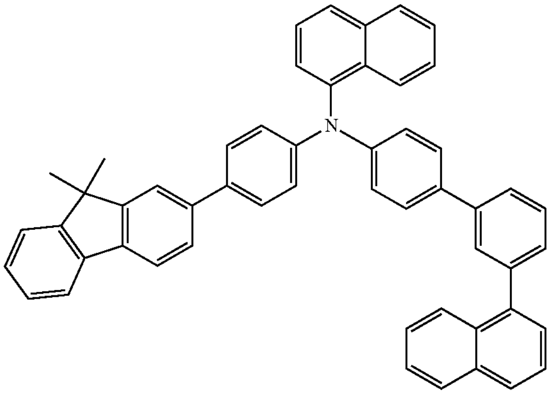

-continued
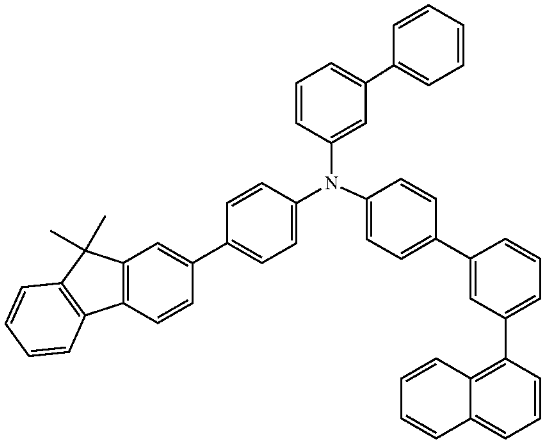
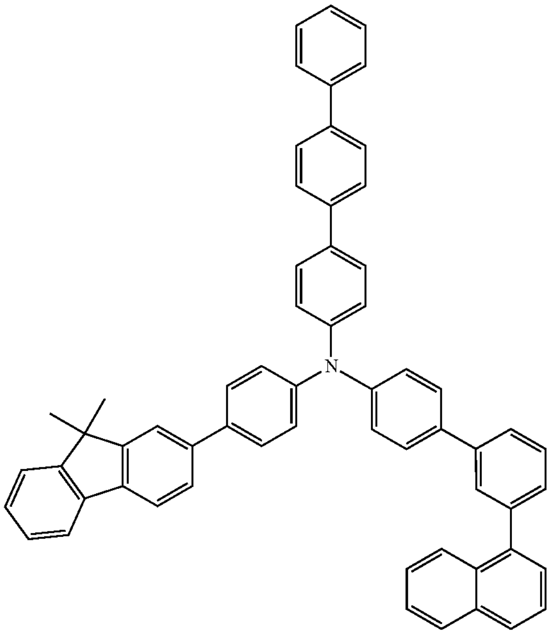
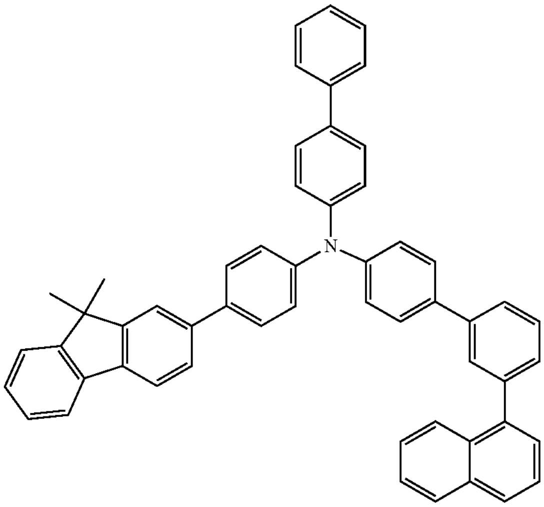
-continued
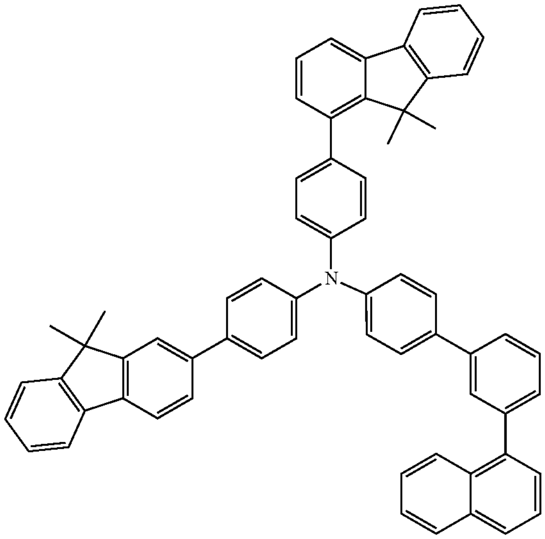
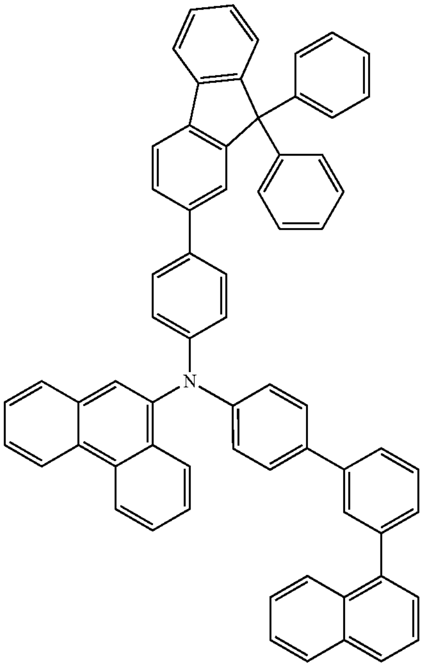
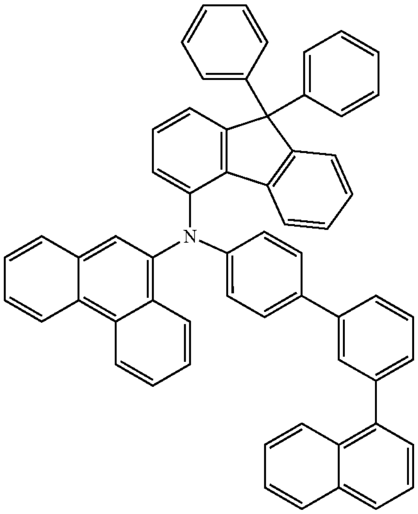

-continued
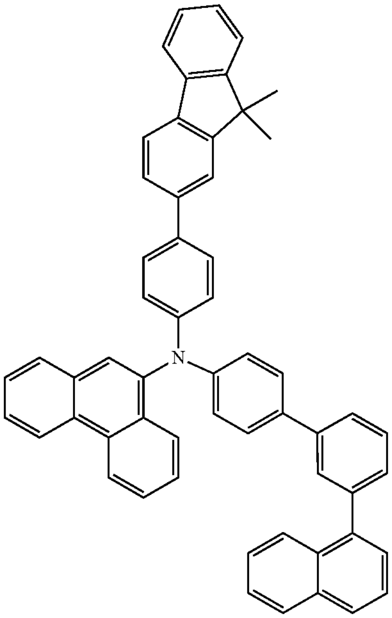
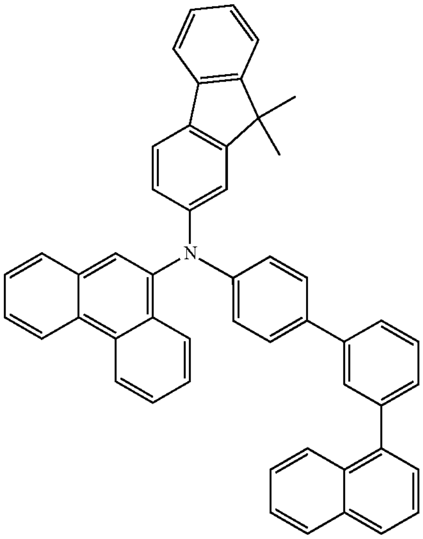
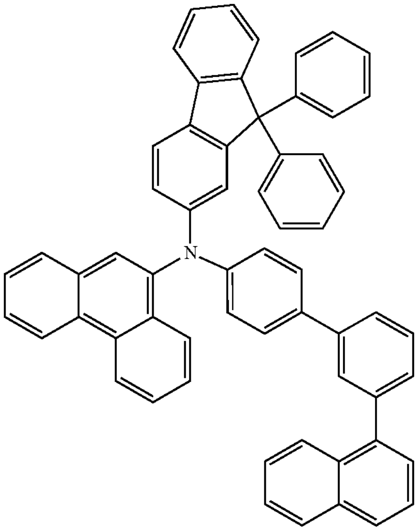
-continued
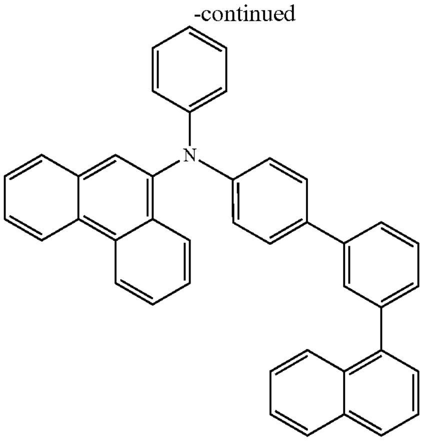
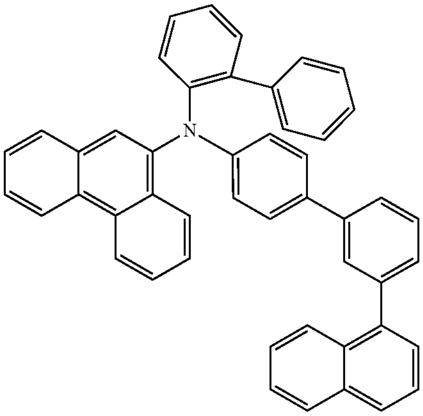
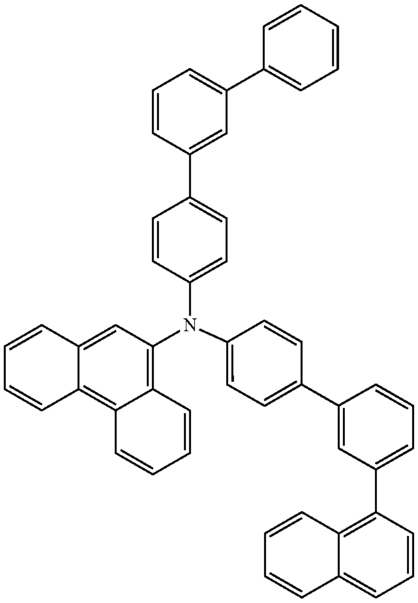

-continued
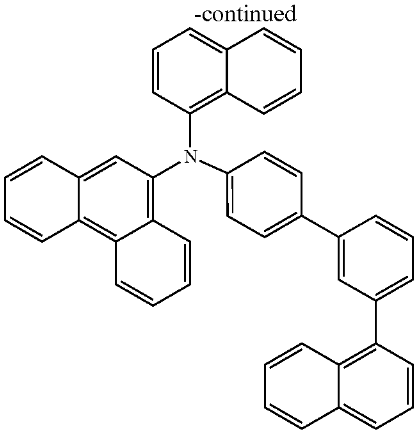
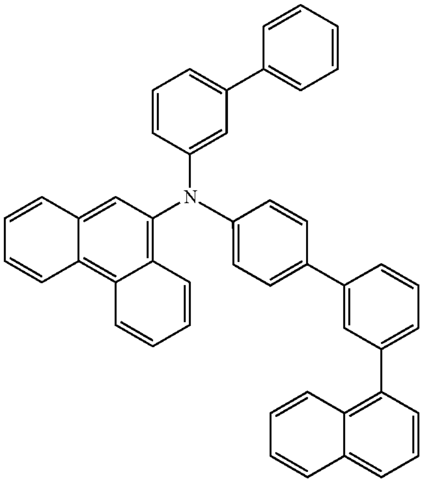
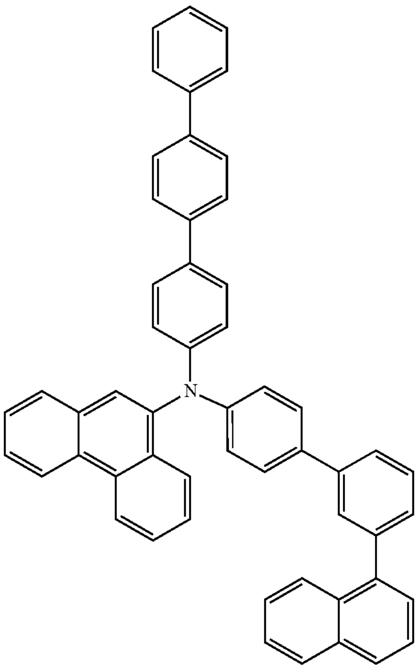
-continued
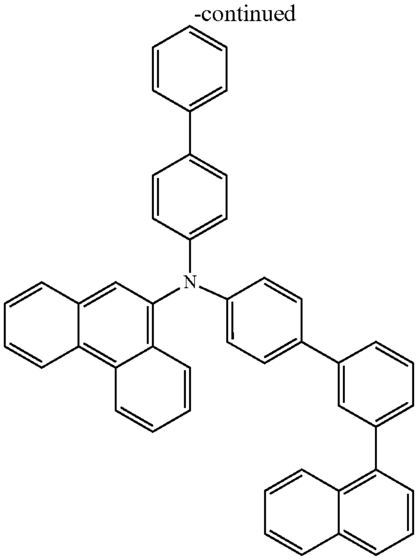
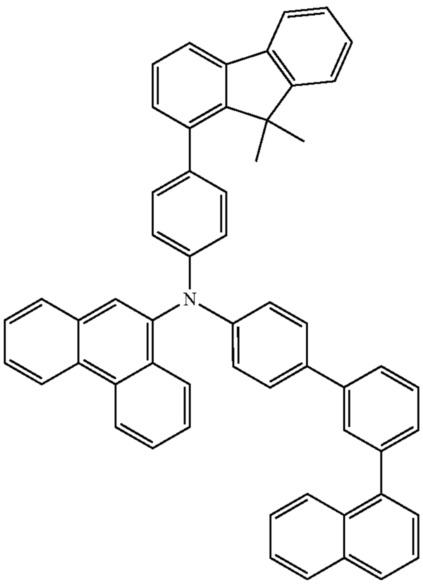

-continued
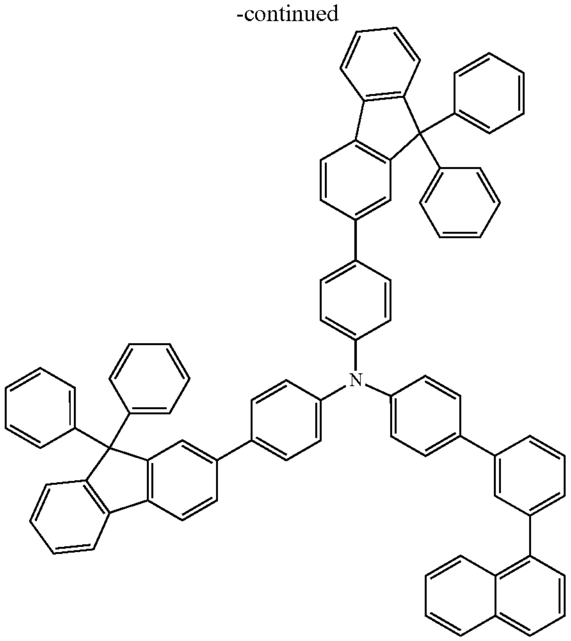
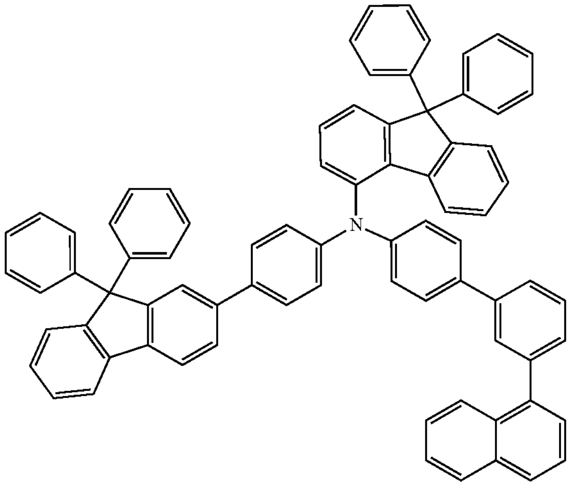
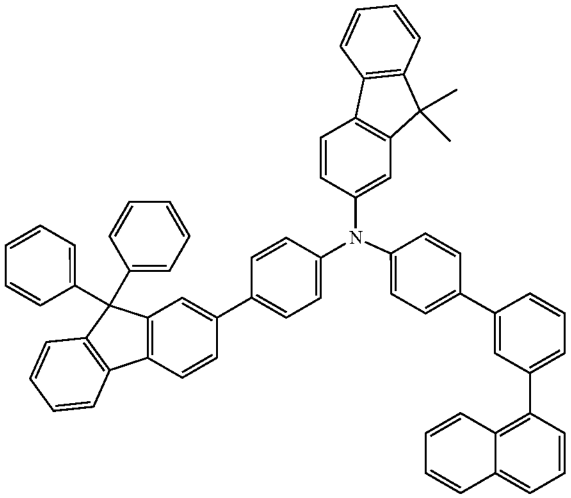
-continued
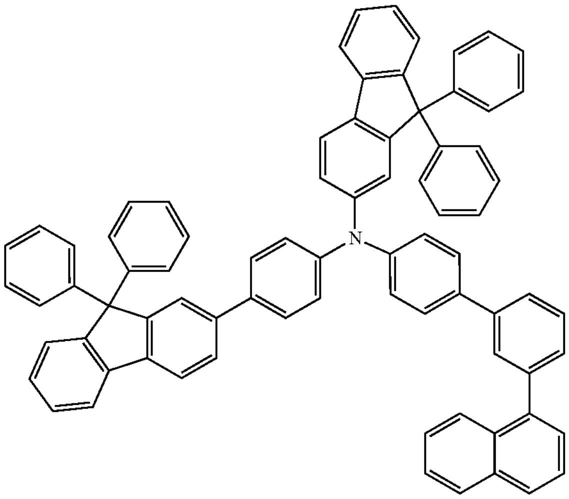
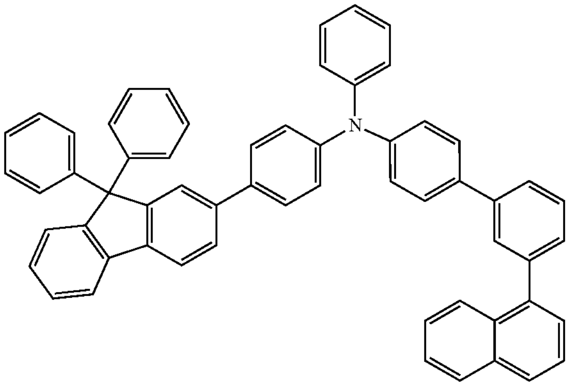
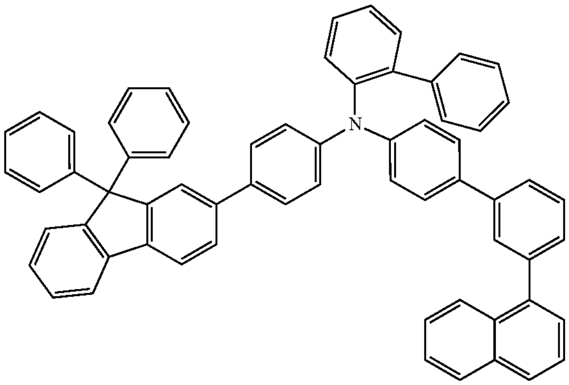

-continued
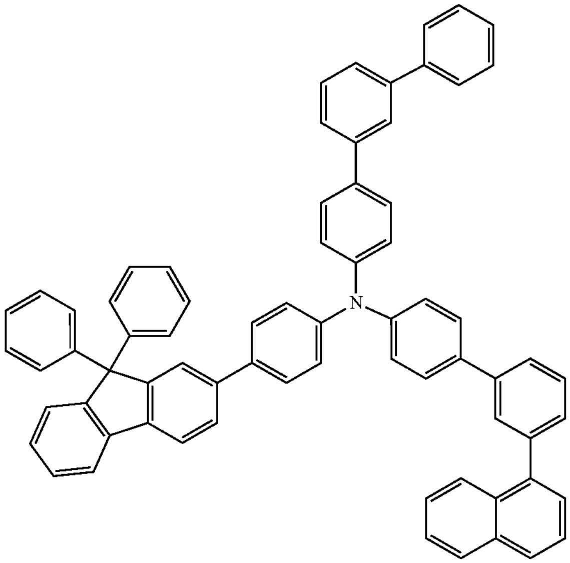
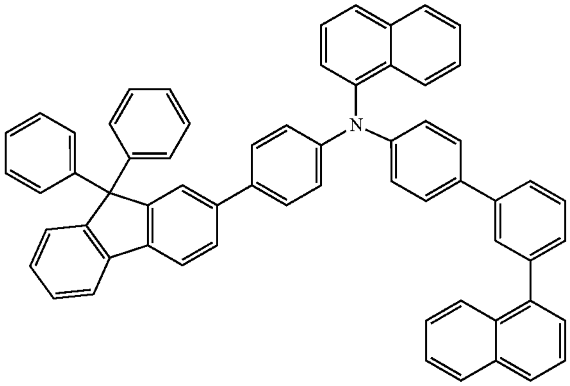
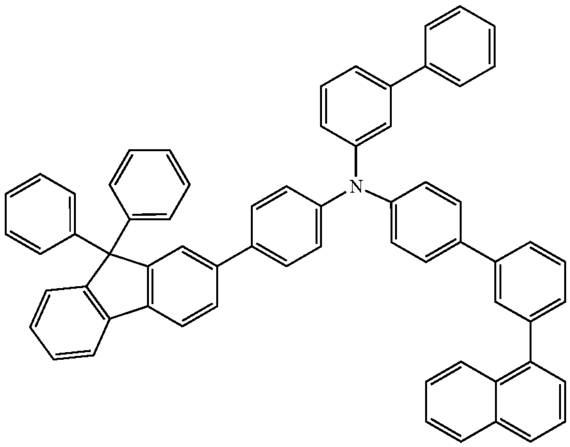 [SMILES: c1ccc(-c2cccc(N(c3ccc(-c4cccc(-c5cccc6ccccc56)c4)cc3)c3ccc(-c4ccc5c(c4)C(c4ccccc4)(c4ccccc4)c4ccccc4-5)cc3)c2)cc1]
-continued
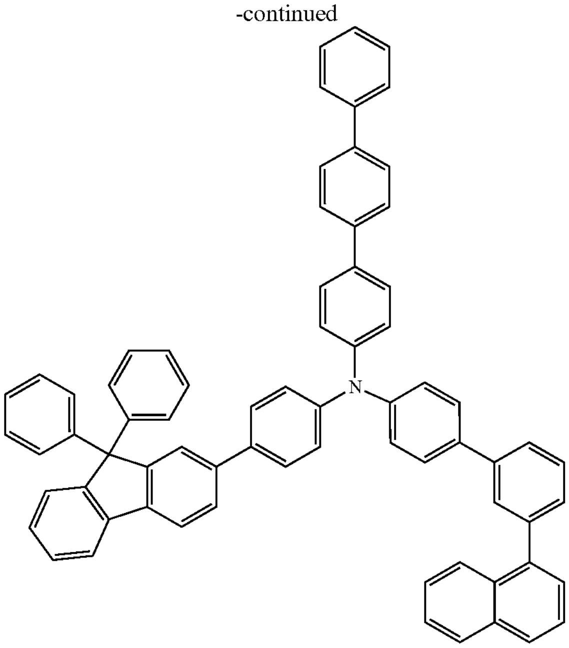
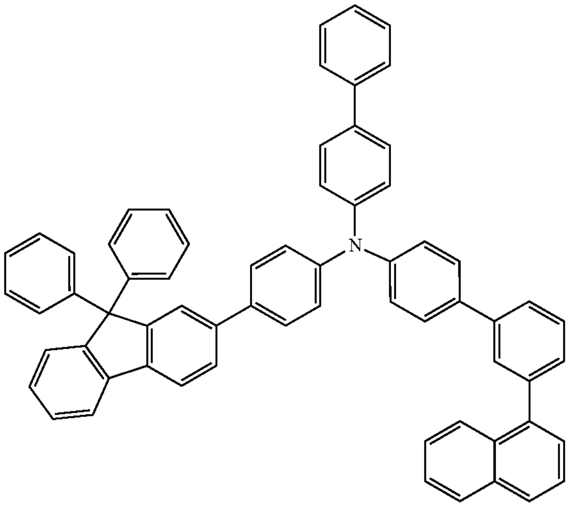
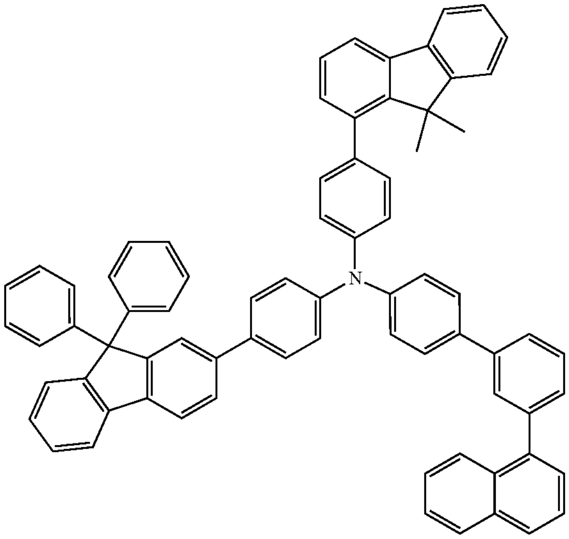

-continued
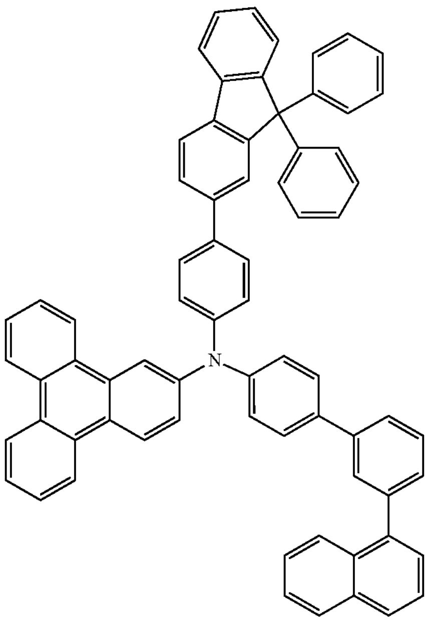
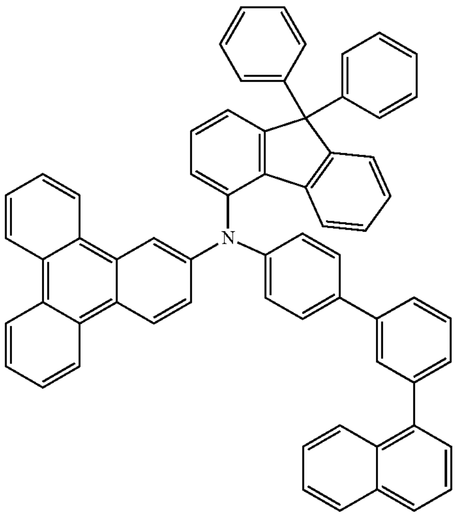
-continued
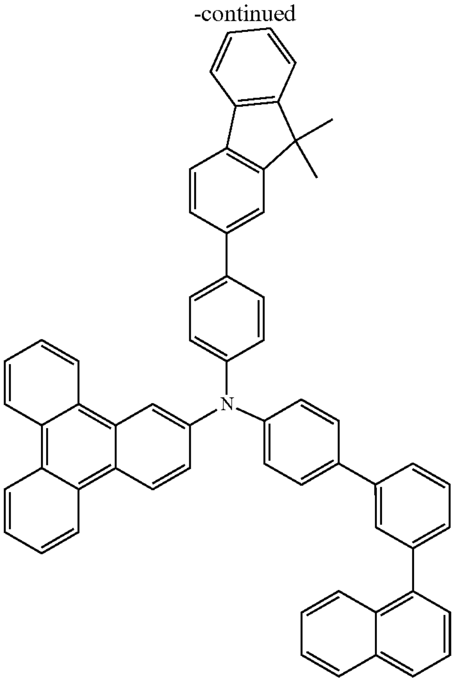
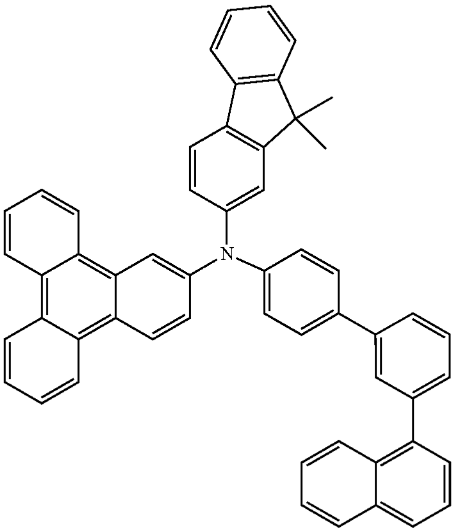
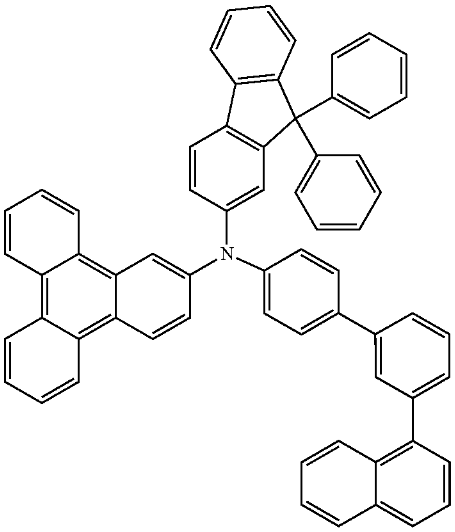

-continued
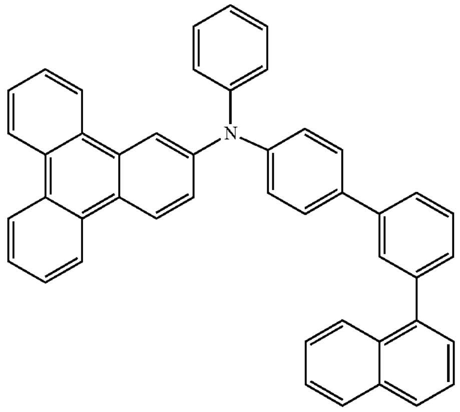
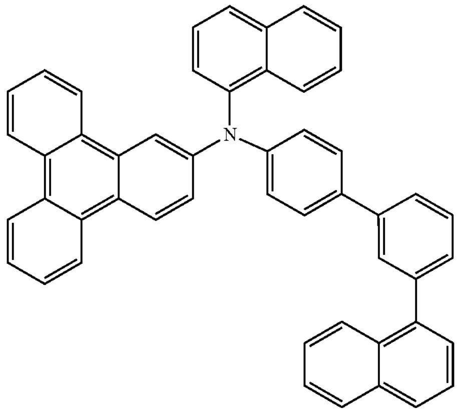
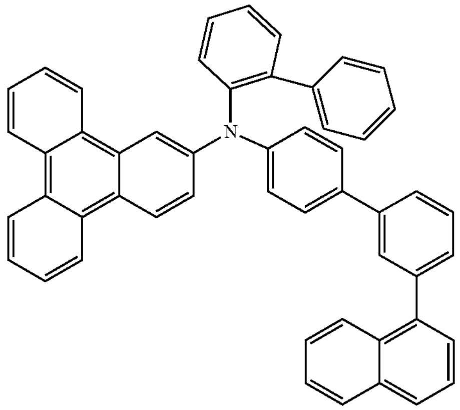
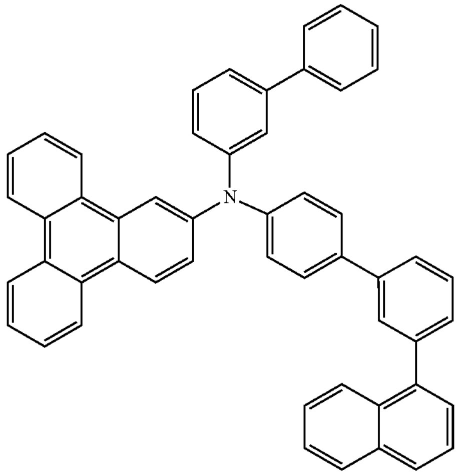
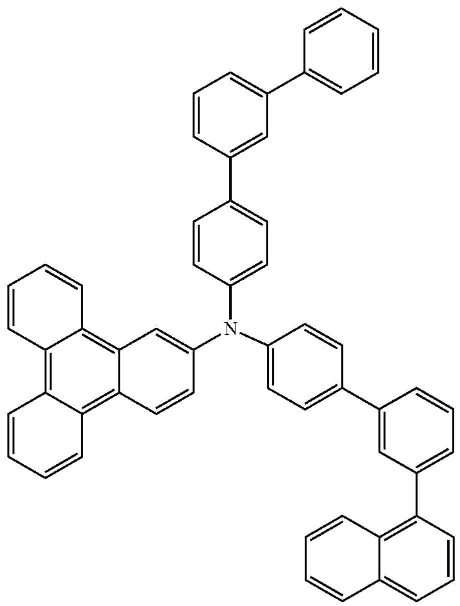
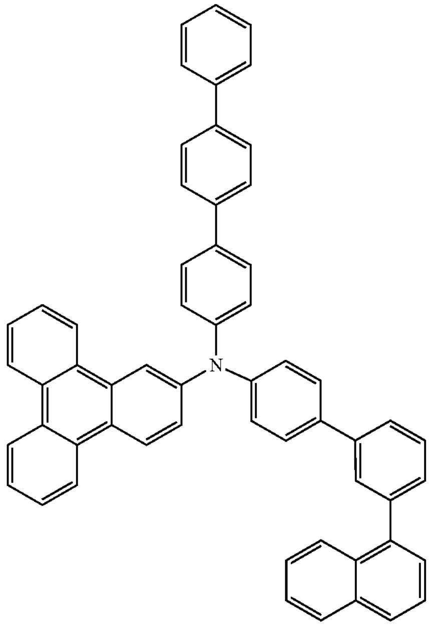
-continued -continued
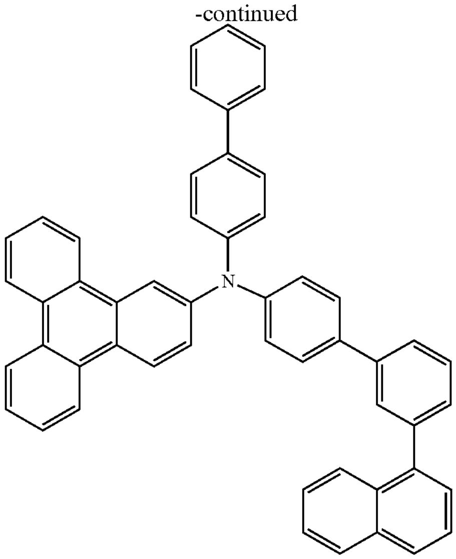
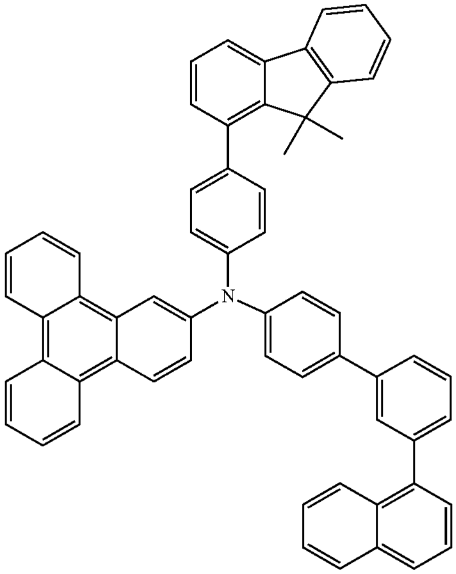
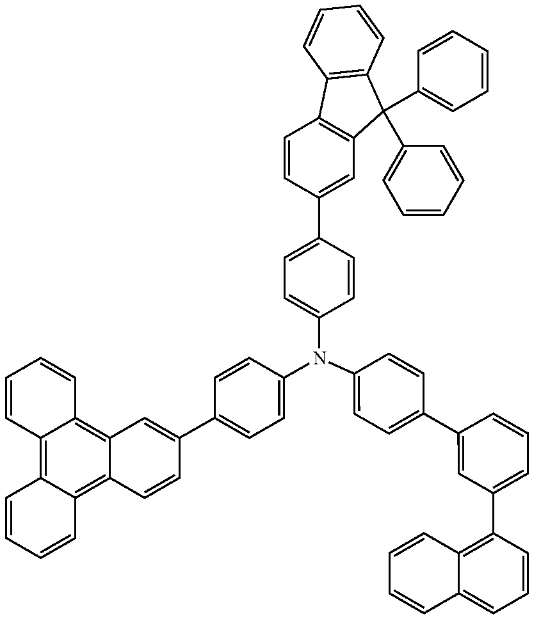
-continued
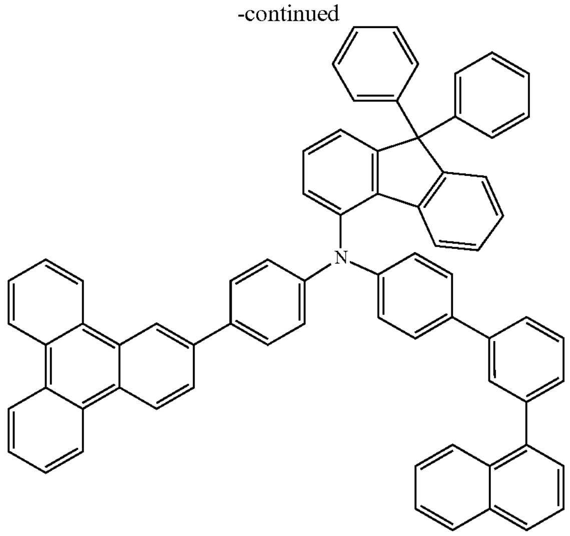
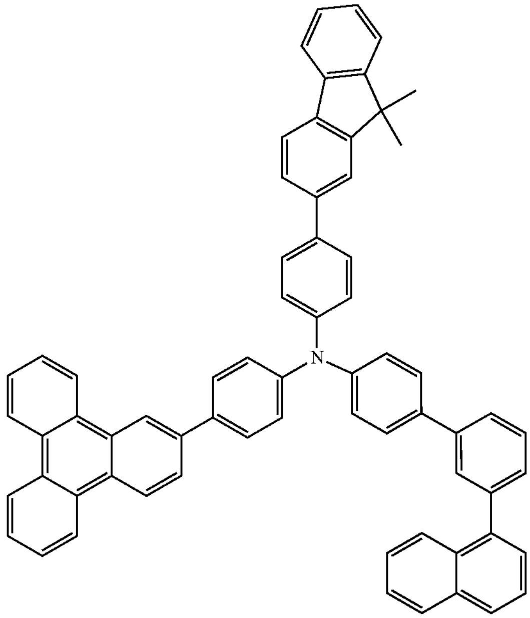
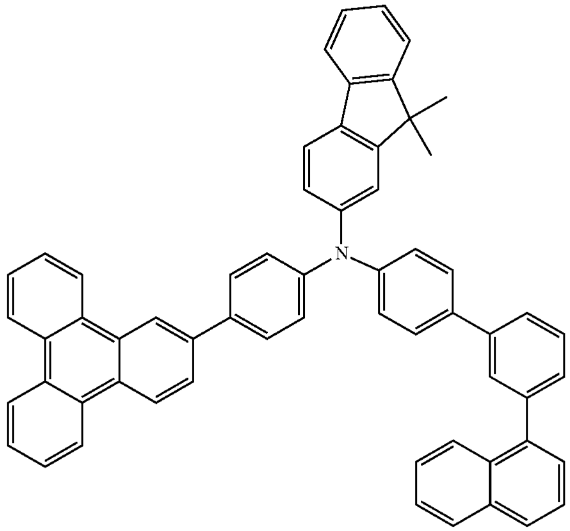

-continued
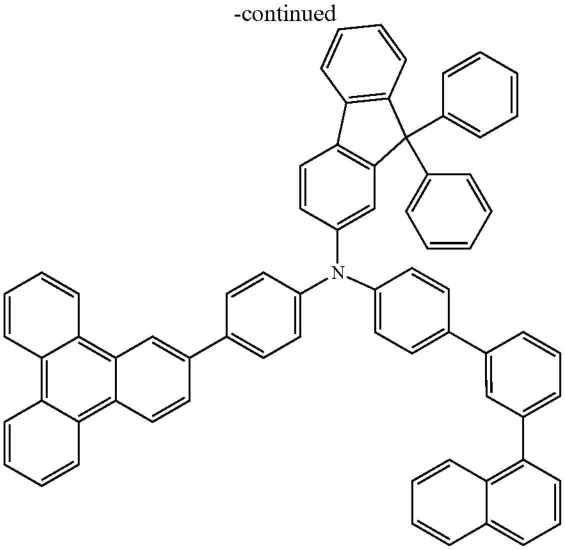
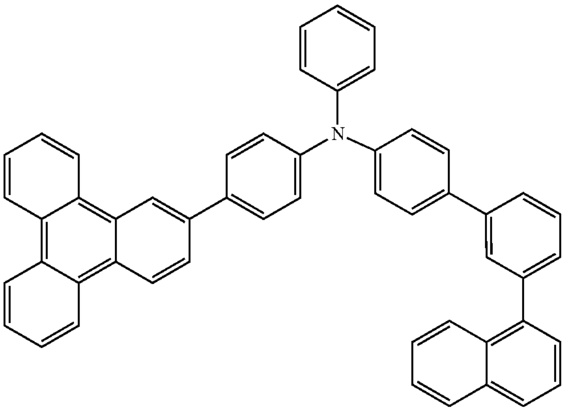
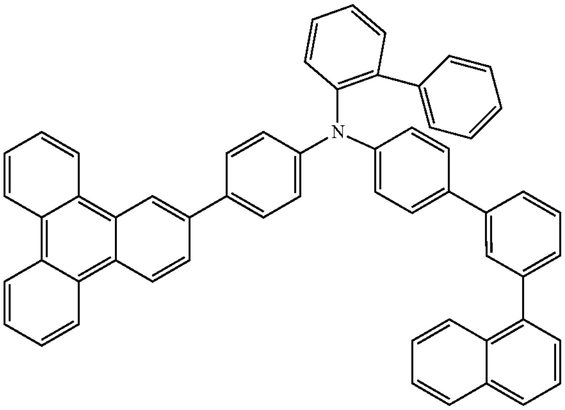
-continued
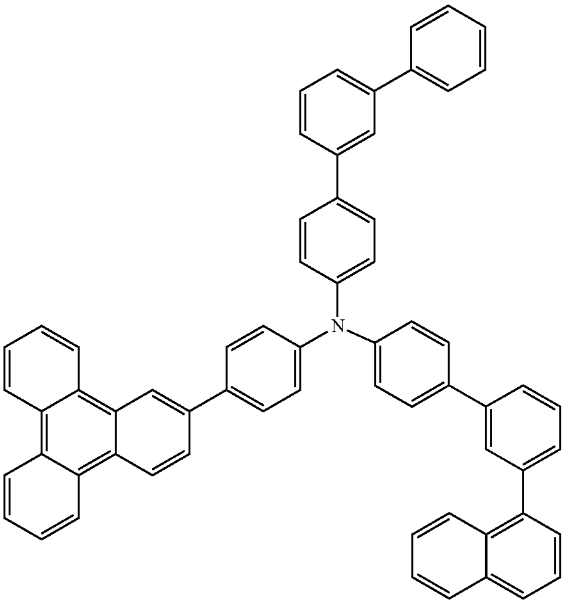
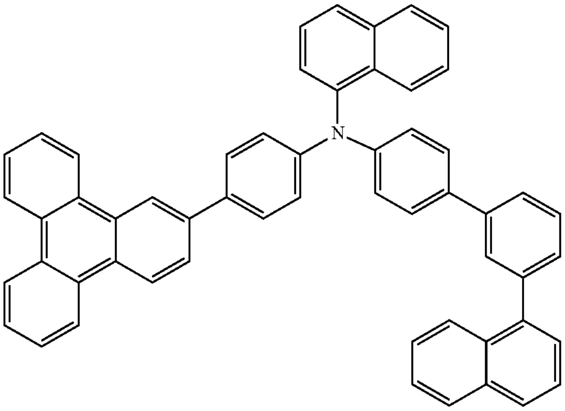
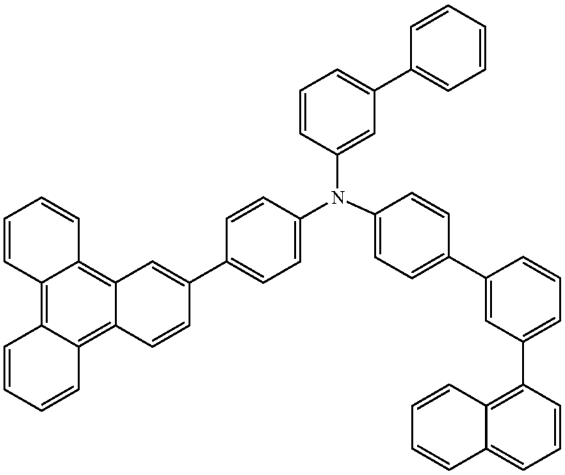

-continued
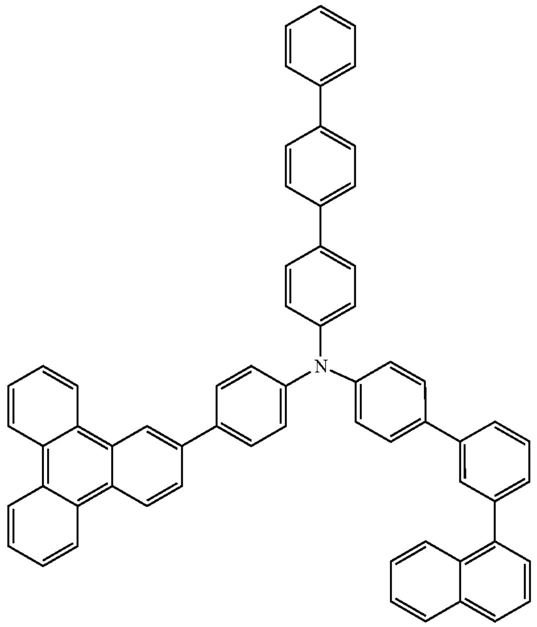
-continued
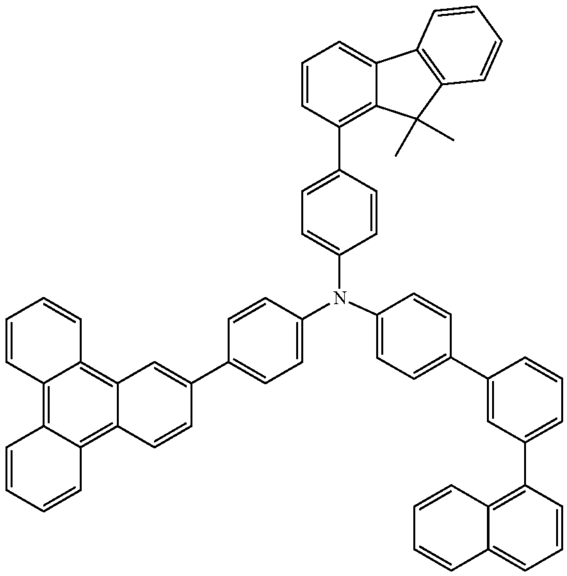
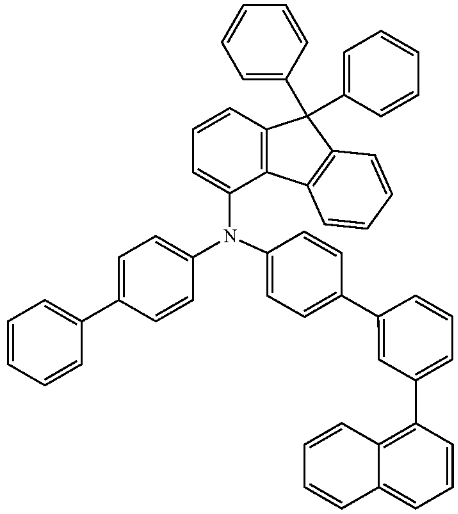
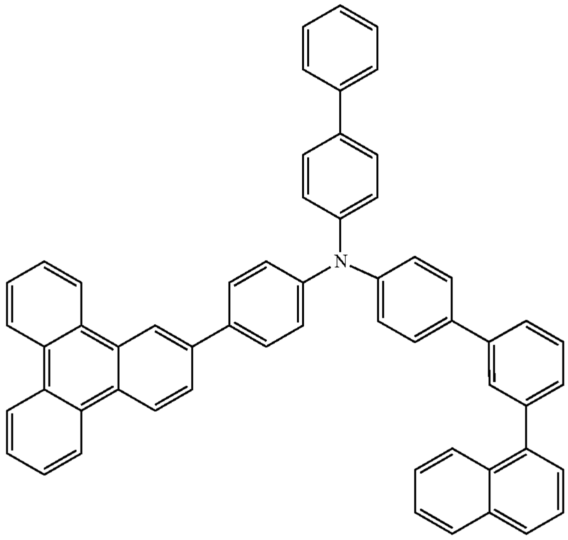
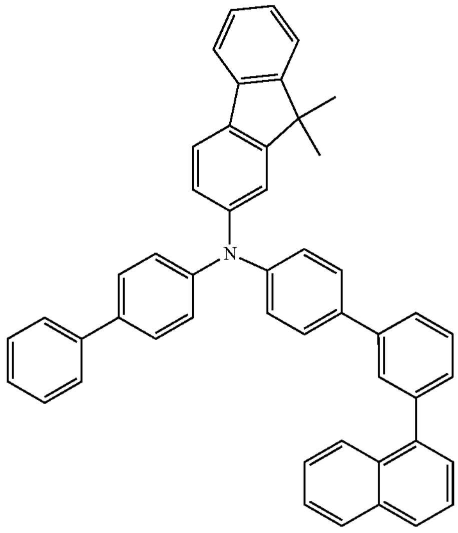

-continued
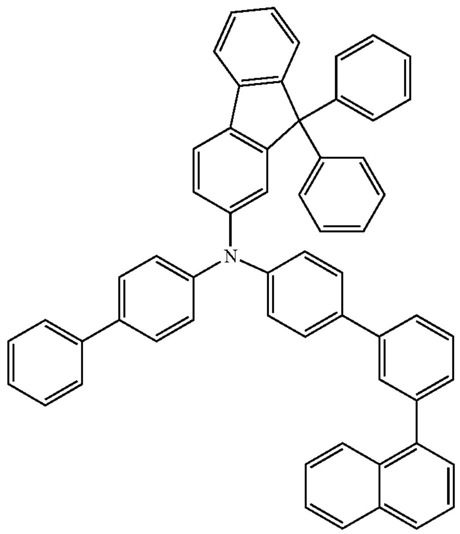
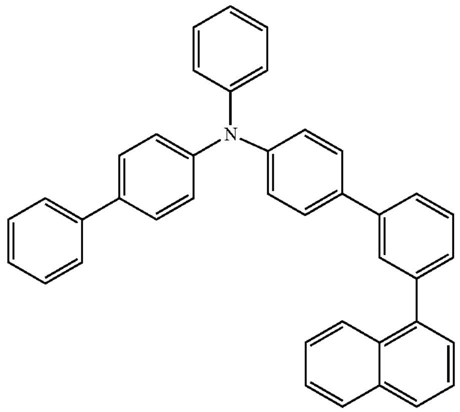
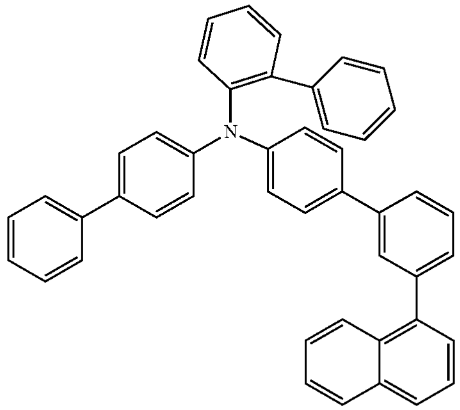
-continued
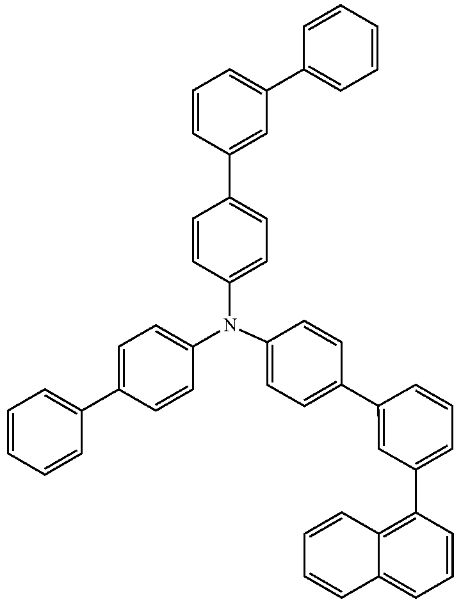
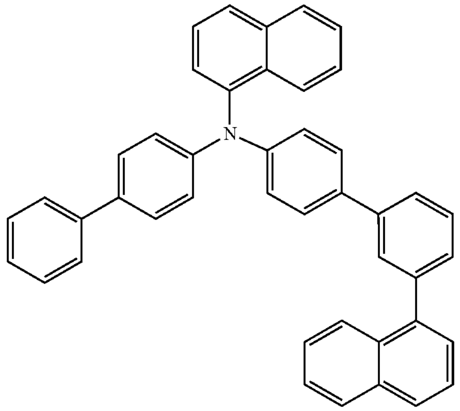
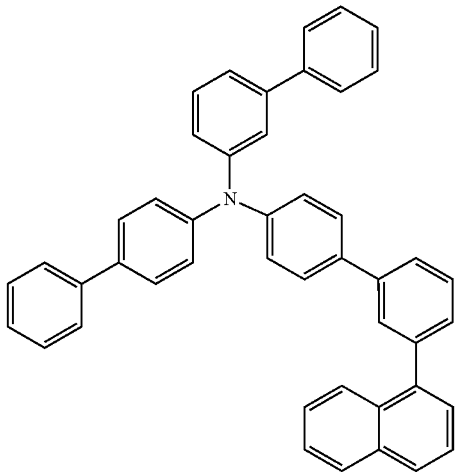

-continued
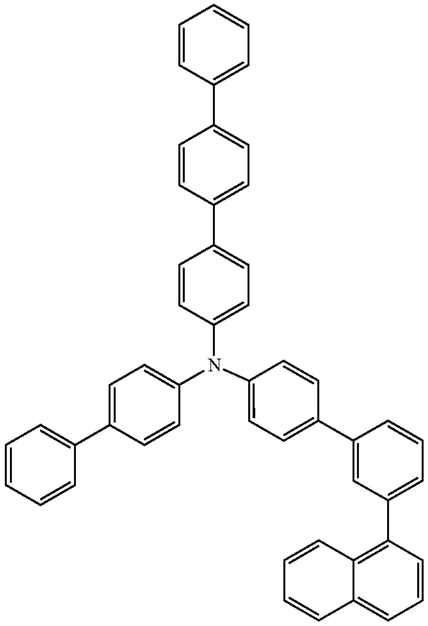
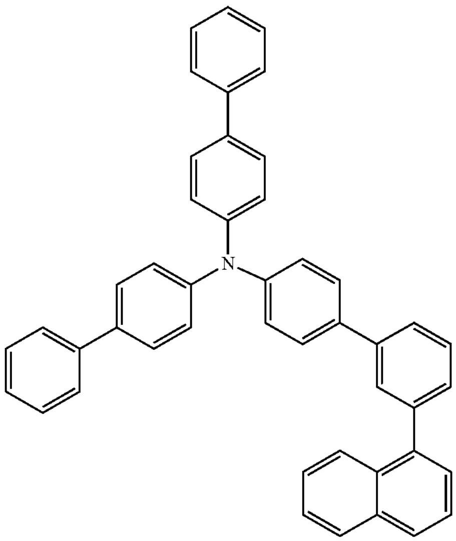
-continued
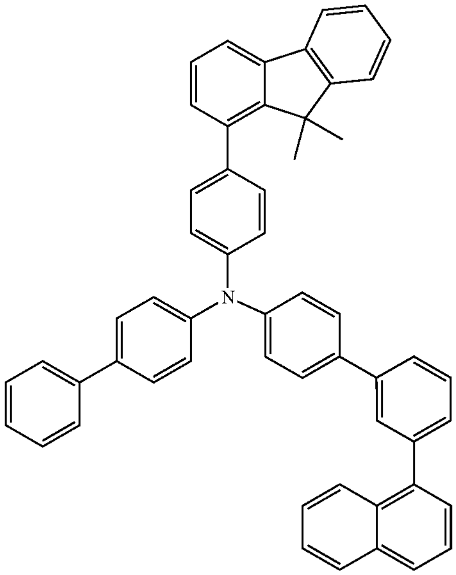
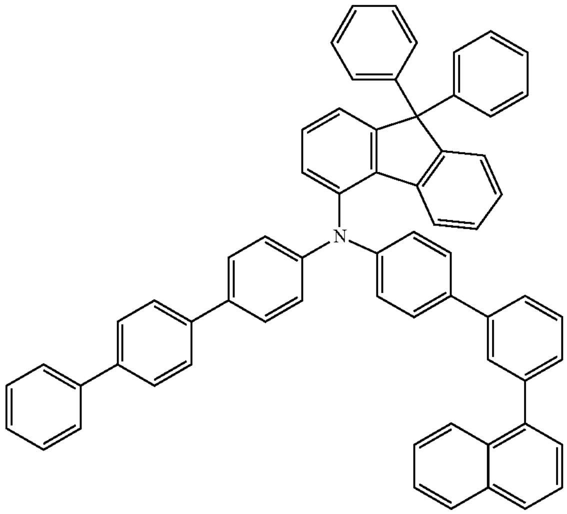
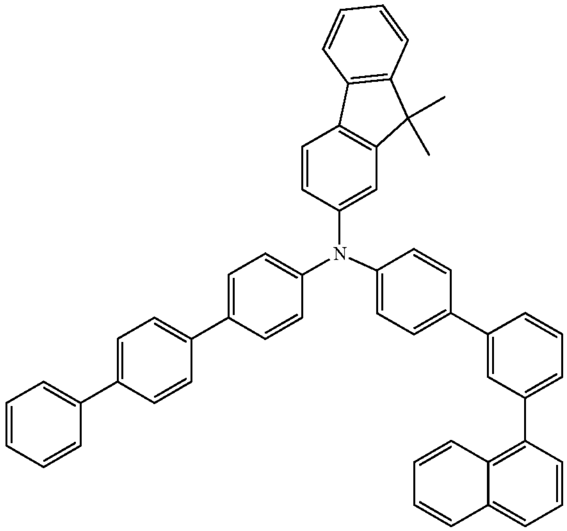

-continued
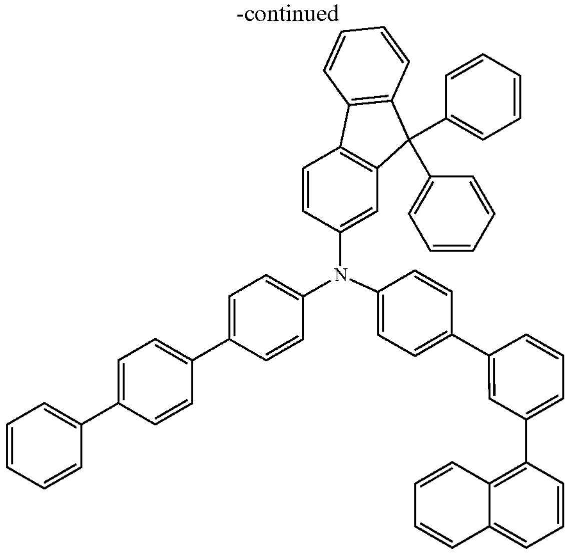
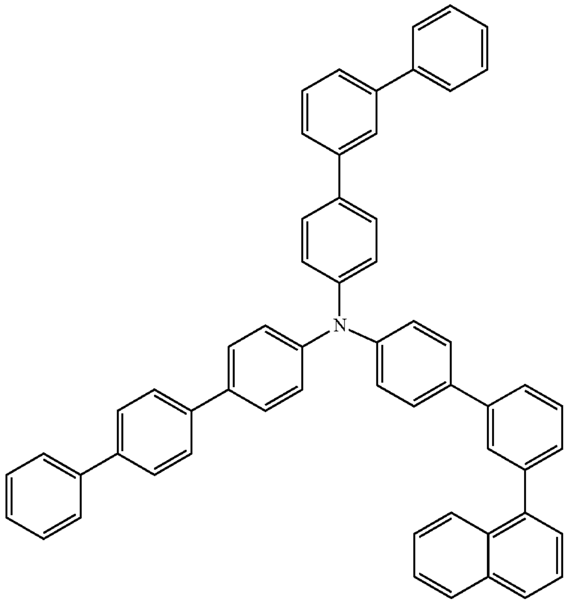
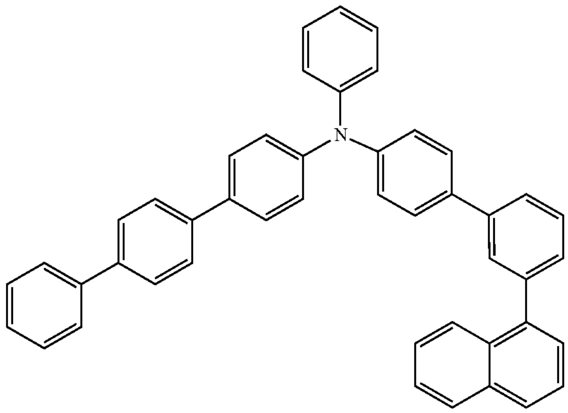
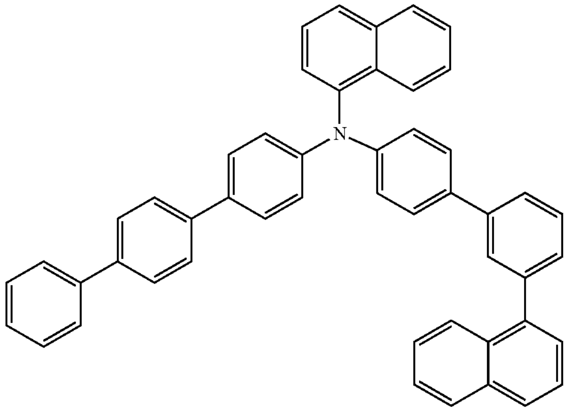
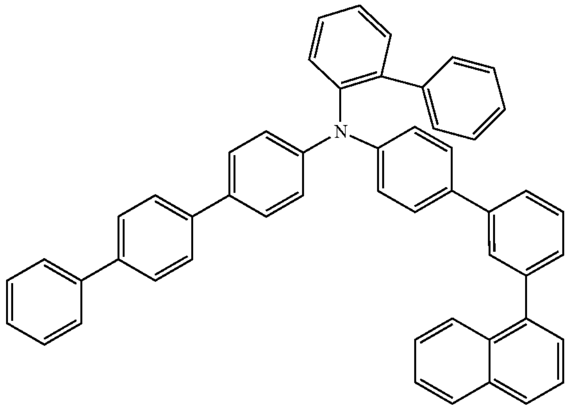
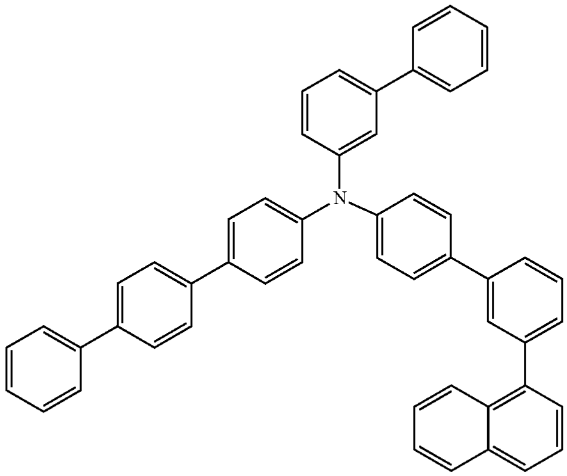
-continued -continued
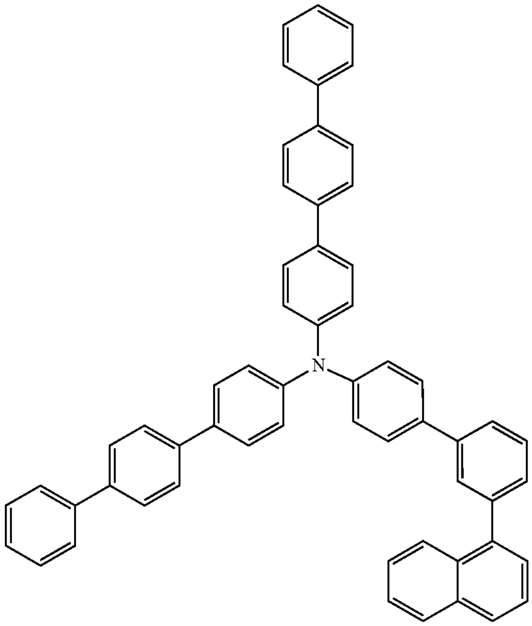
-continued
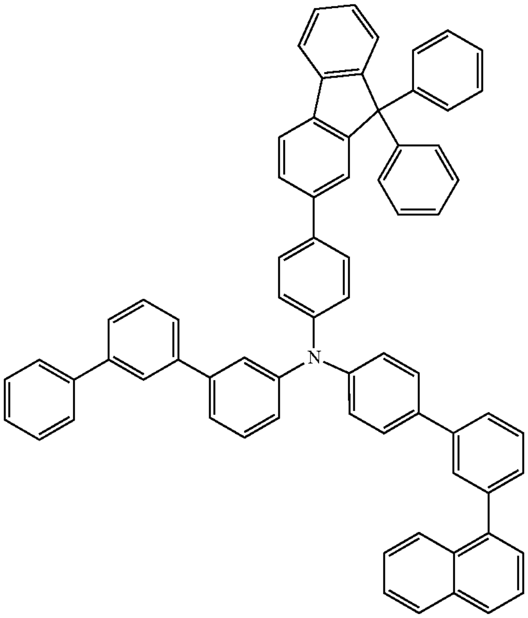
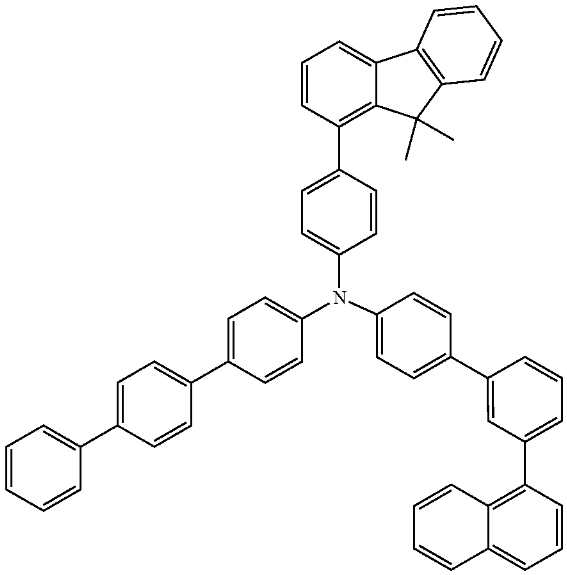
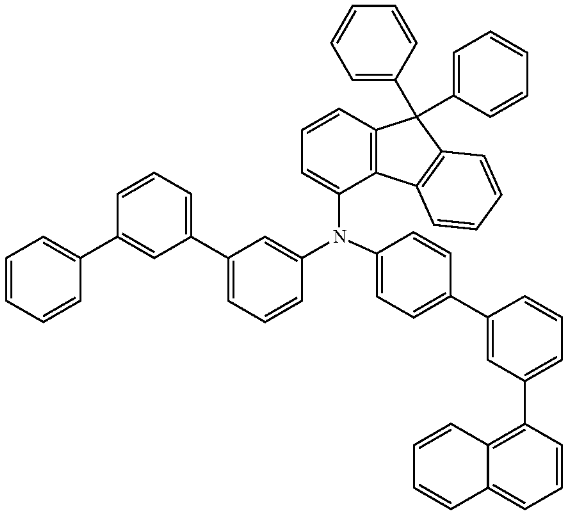

-continued
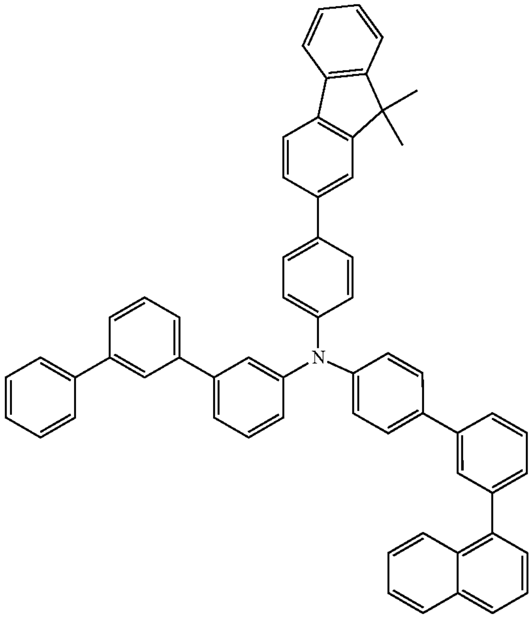
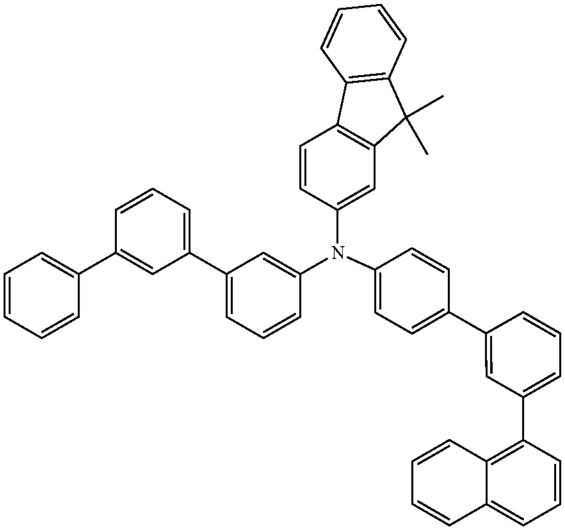
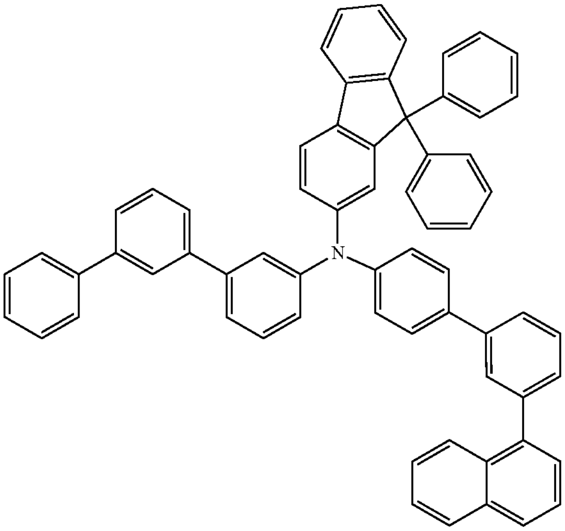
-continued
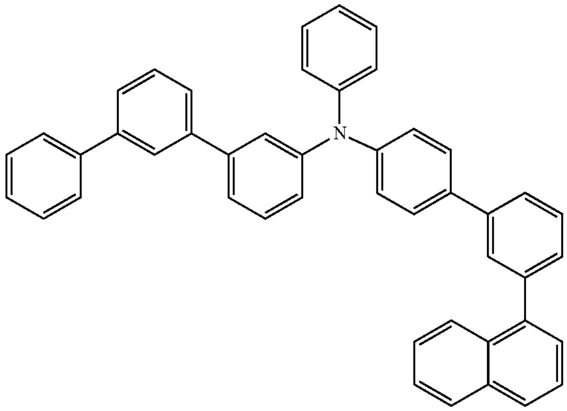
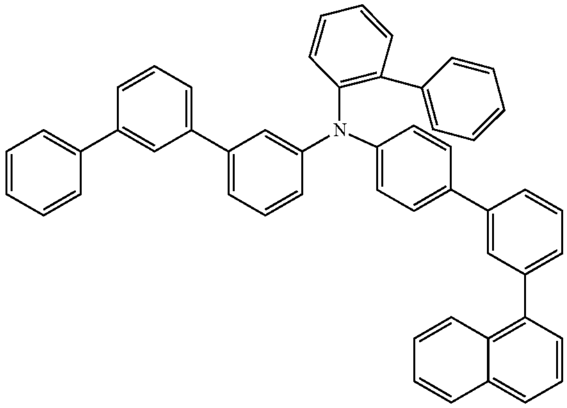
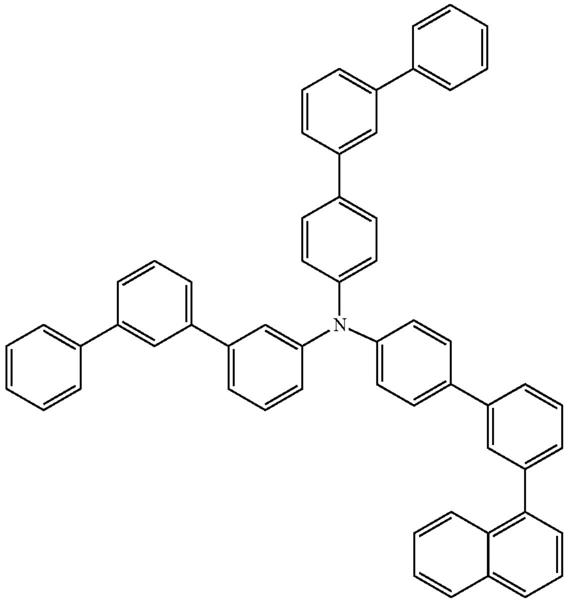

-continued
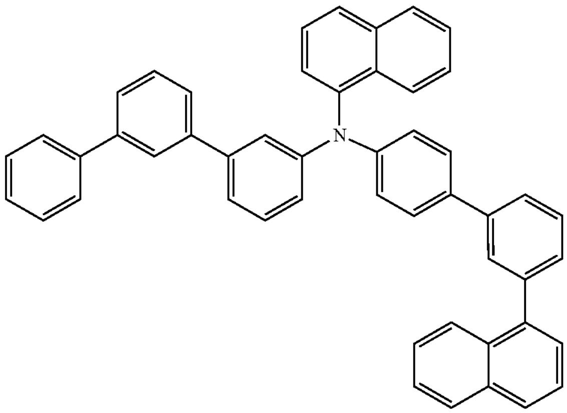
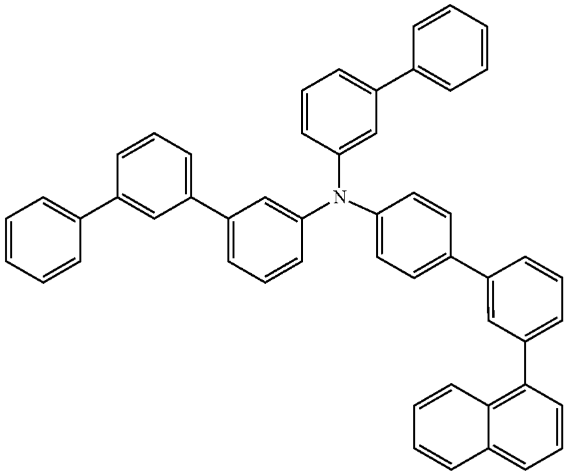
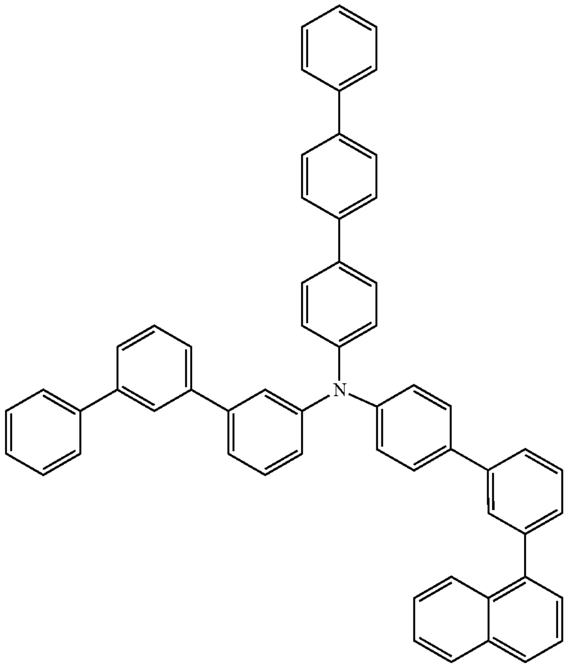
-continued
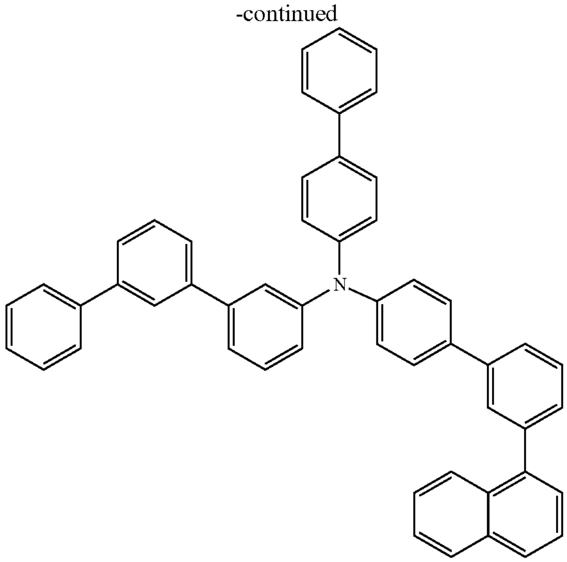
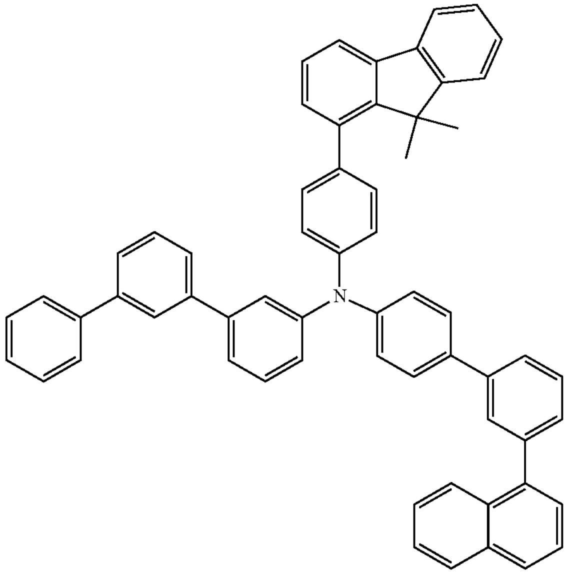
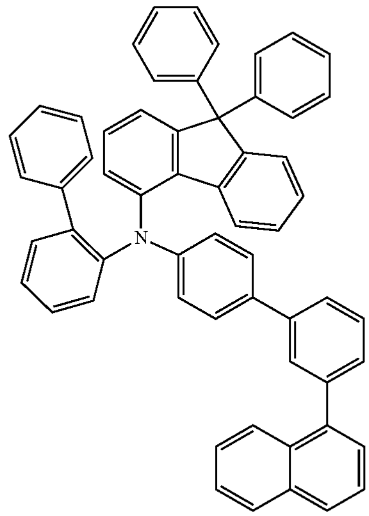

-continued
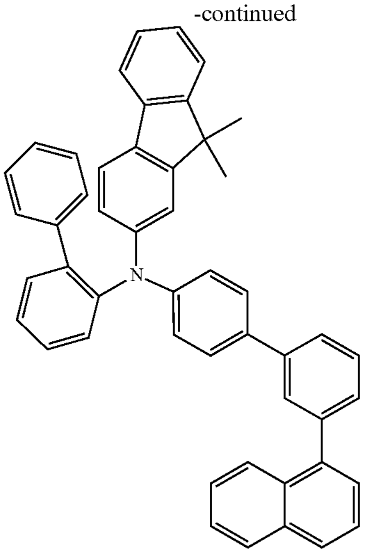
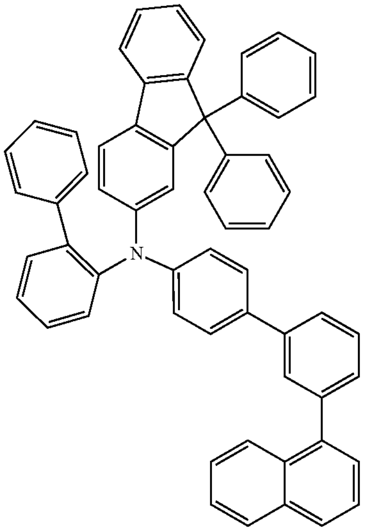
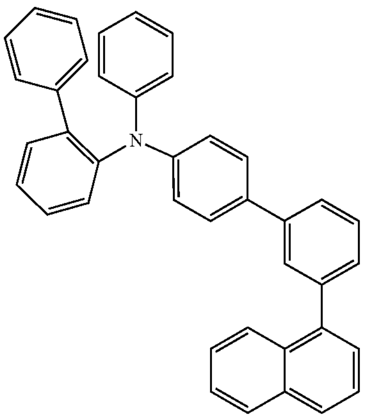
-continued
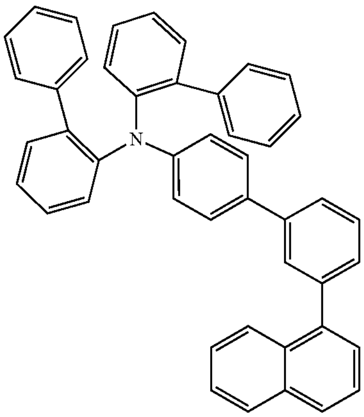
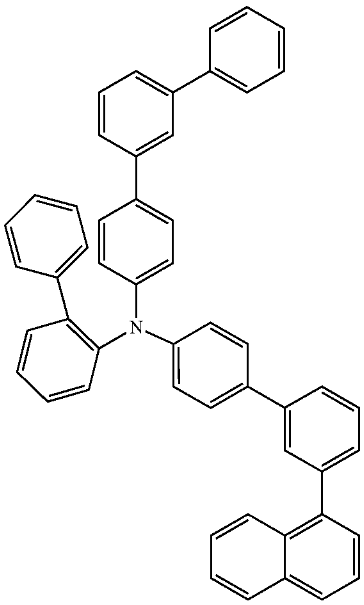
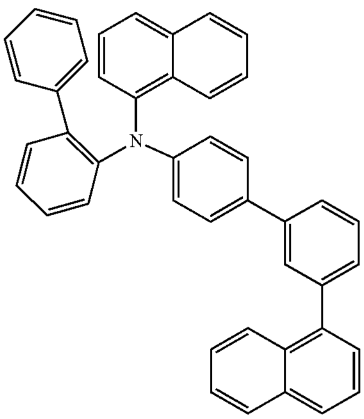

-continued
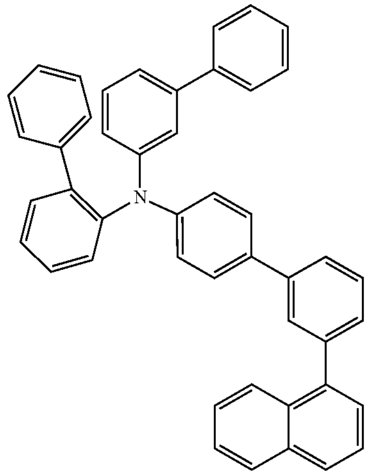
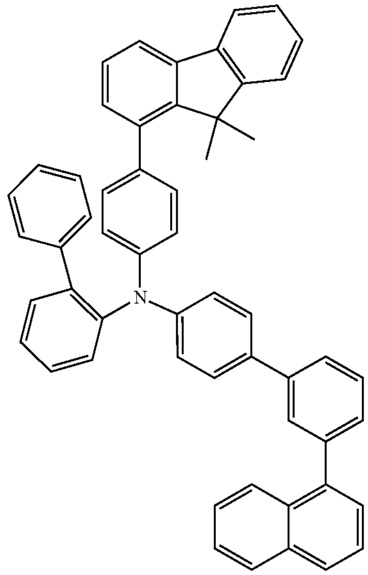
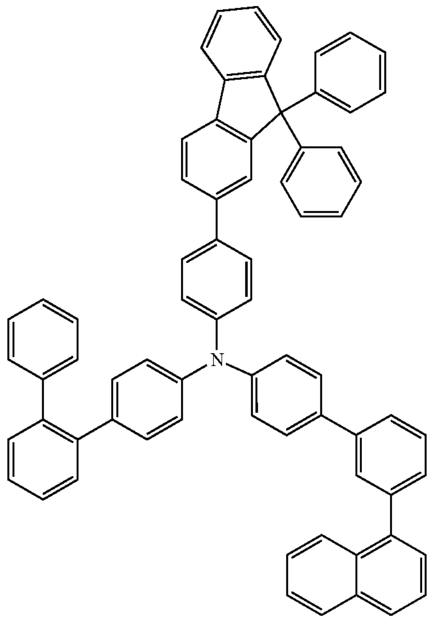
-continued
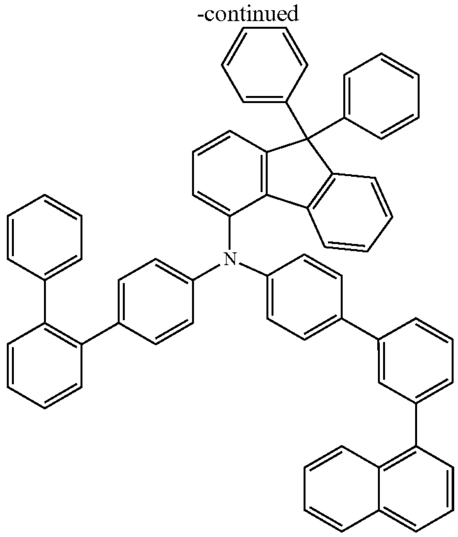
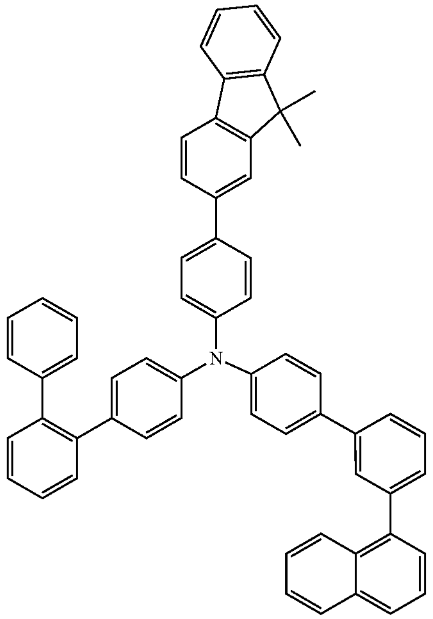
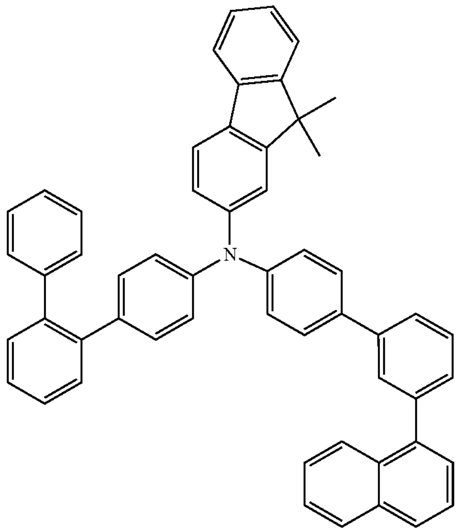

-continued
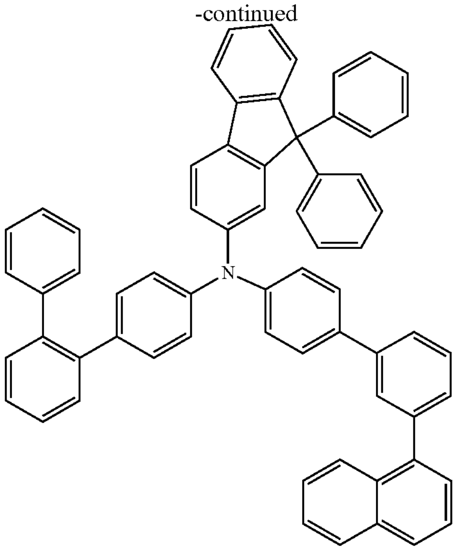
-continued
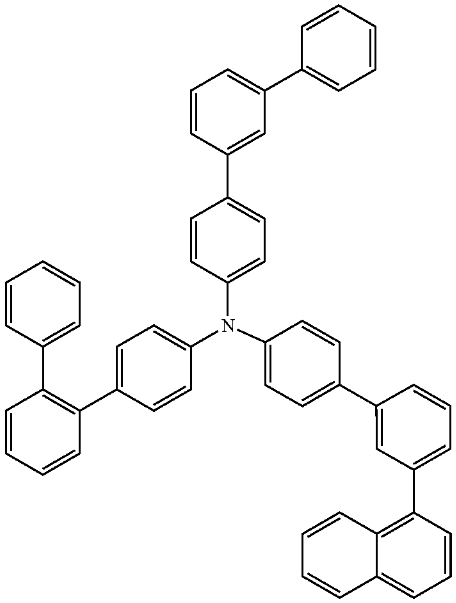
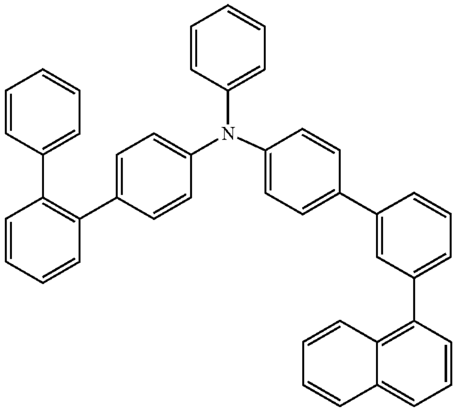
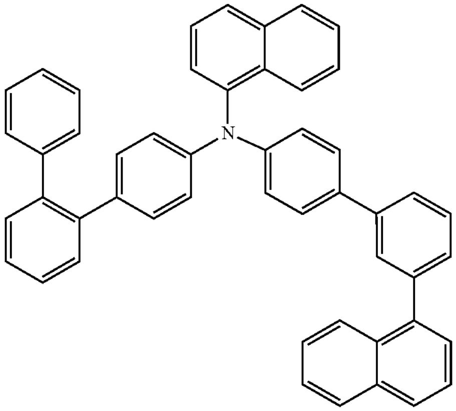
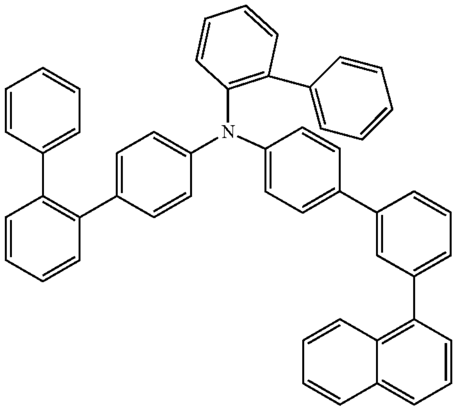
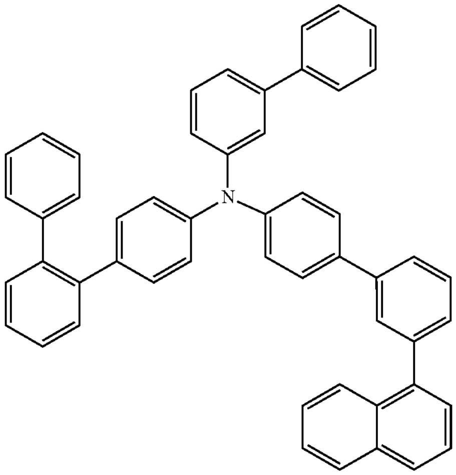

-continued
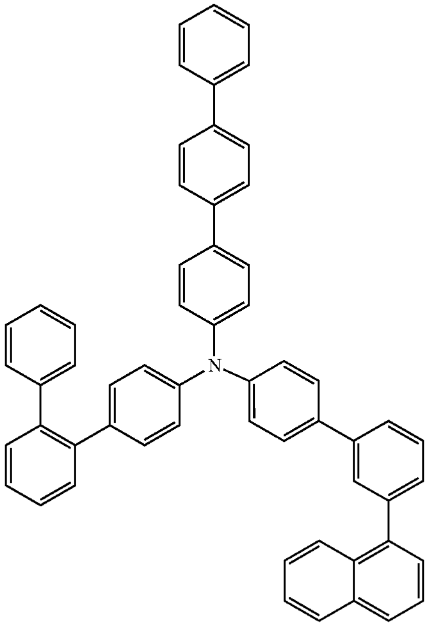
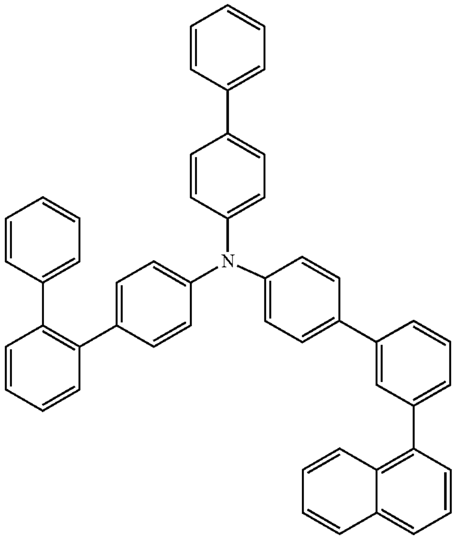
-continued
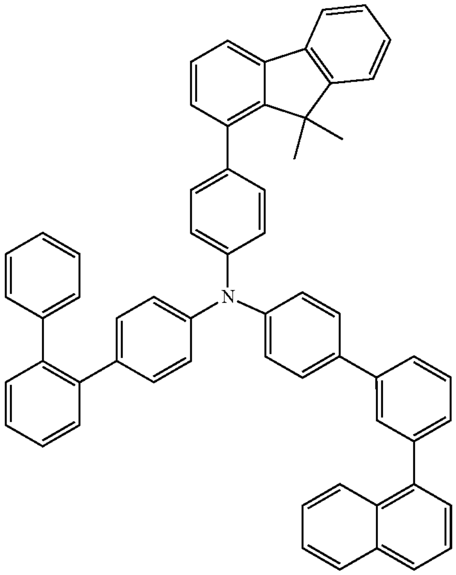
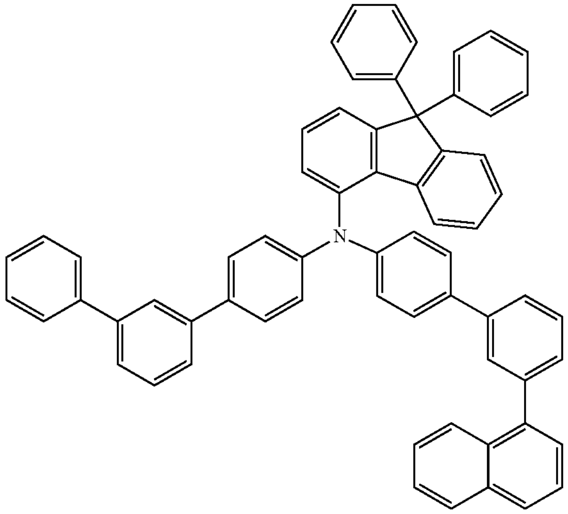
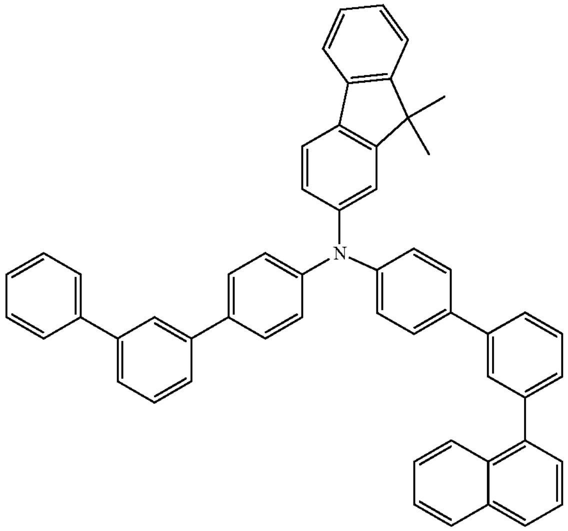

-continued
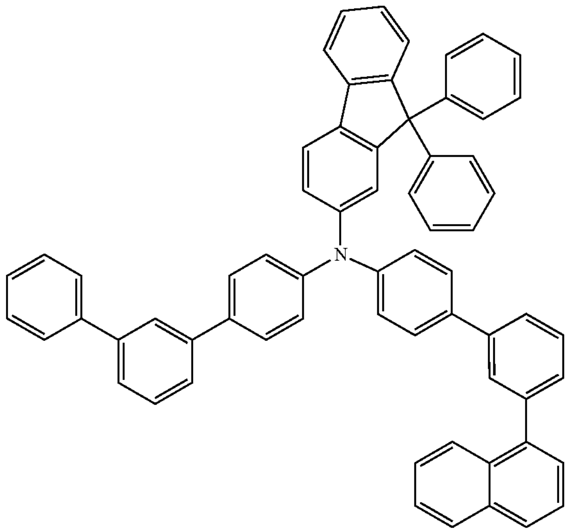
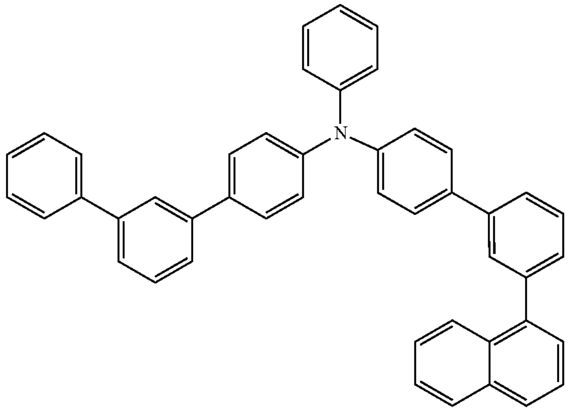
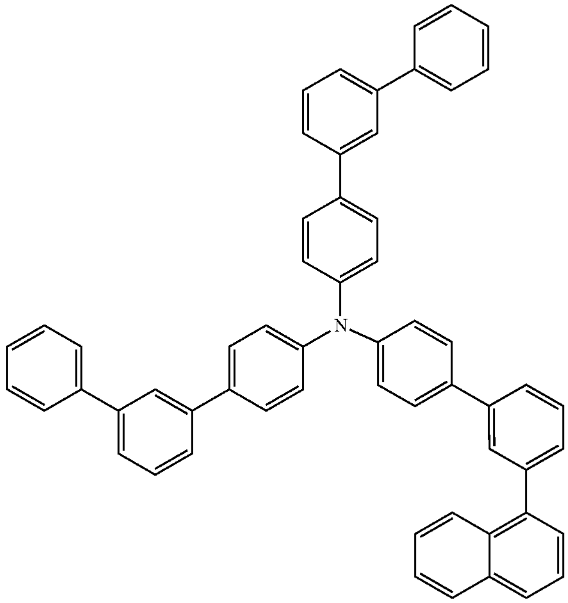
-continued
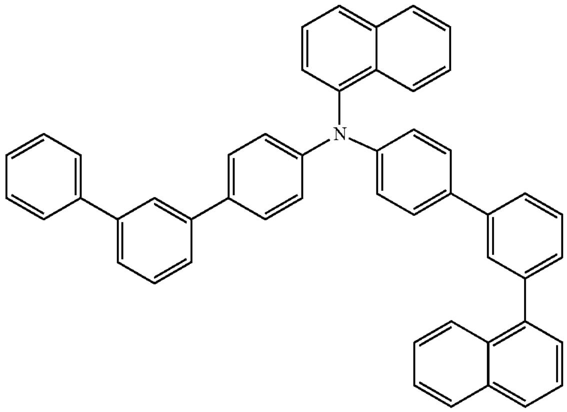
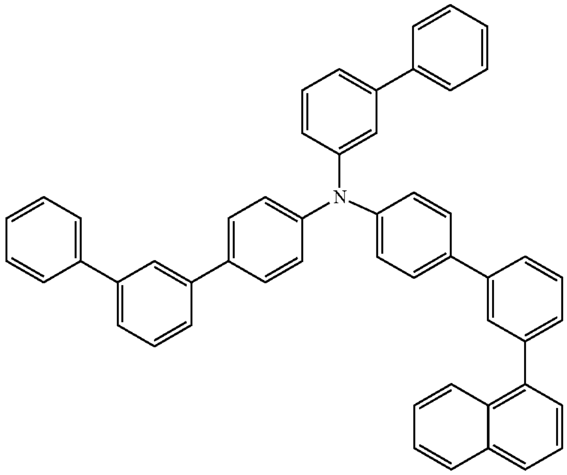
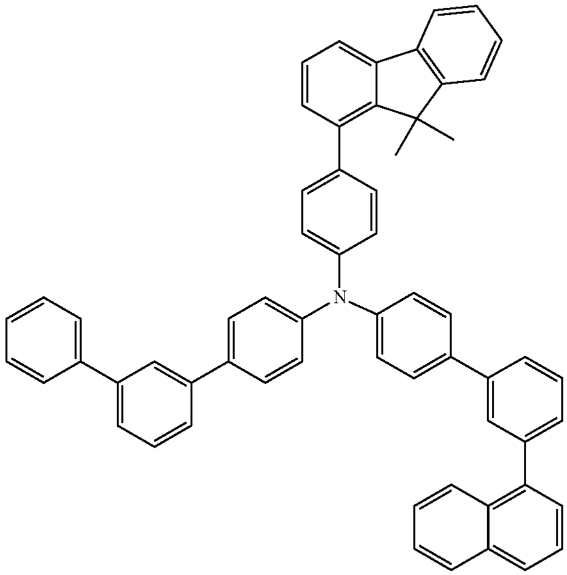

-continued
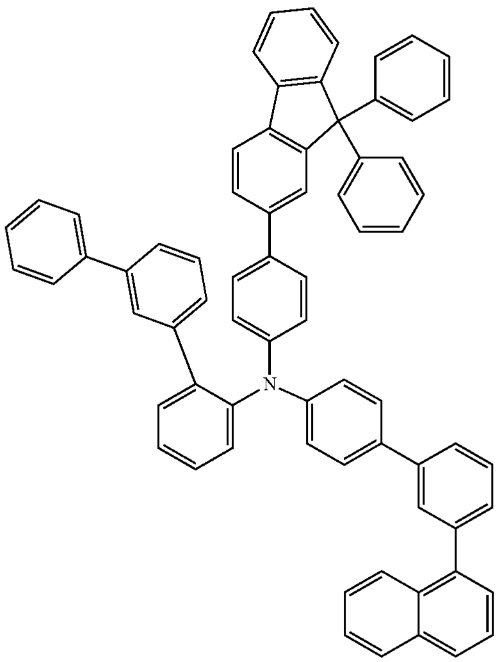
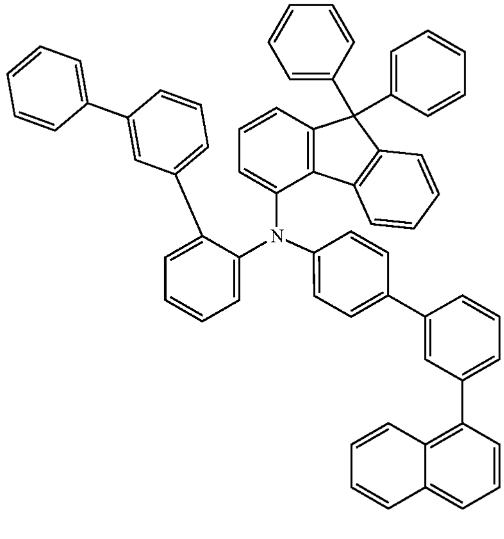
-continued
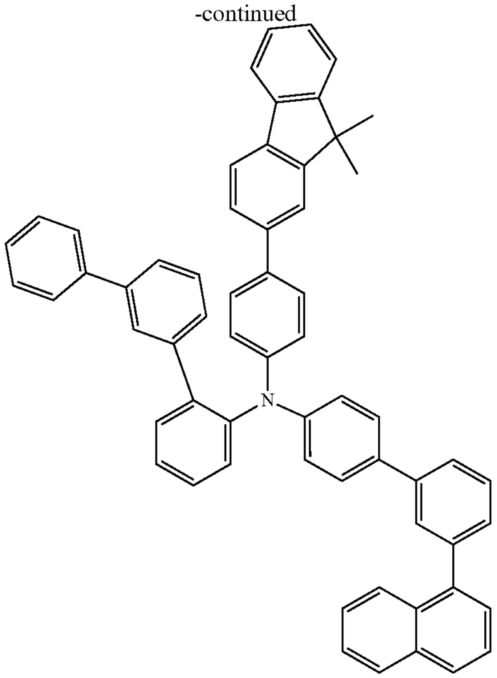
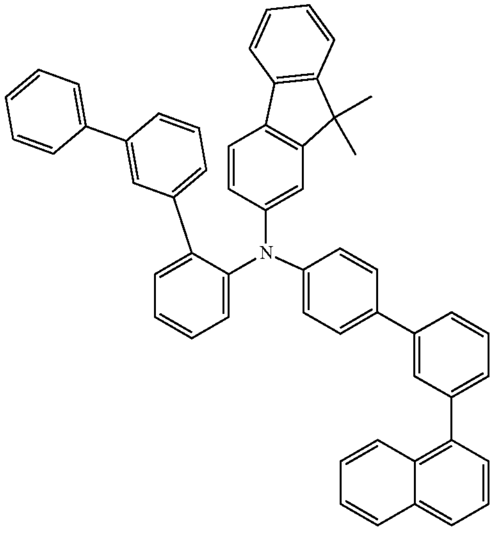

-continued
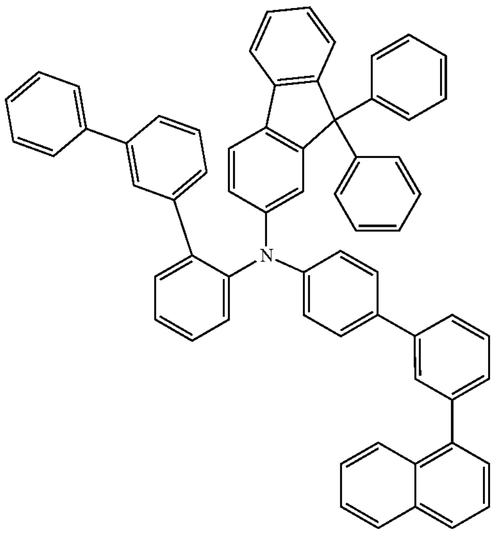
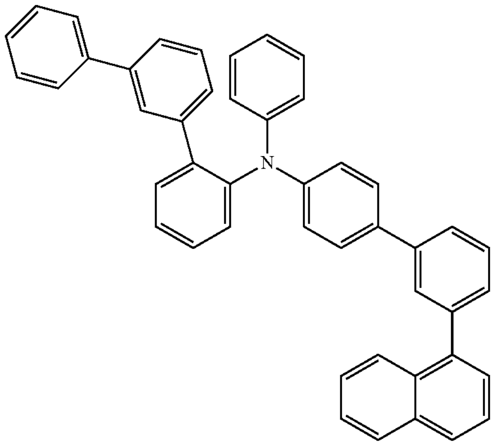
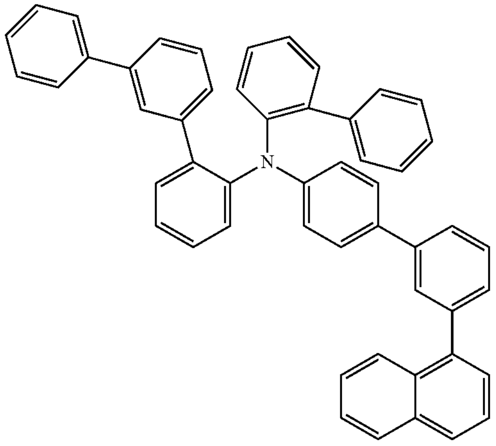
-continued
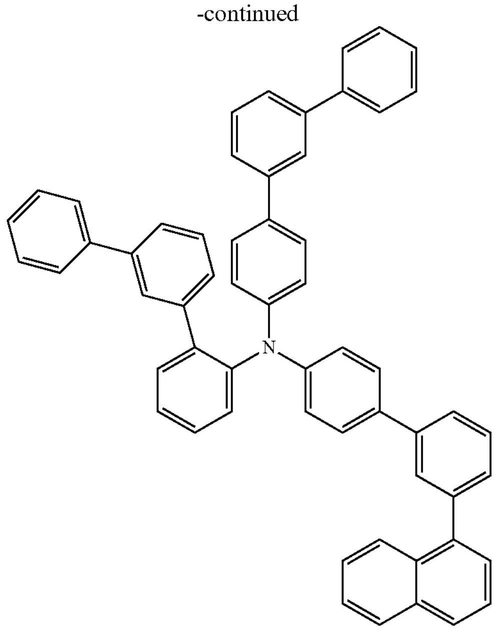
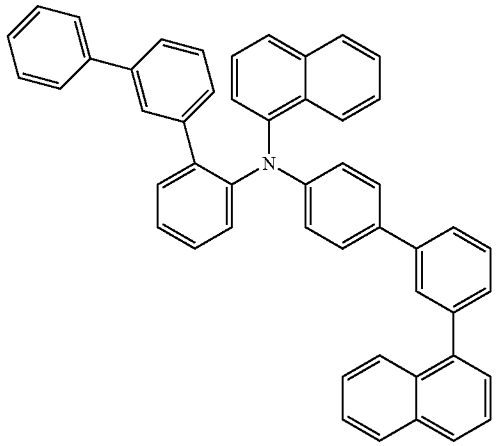
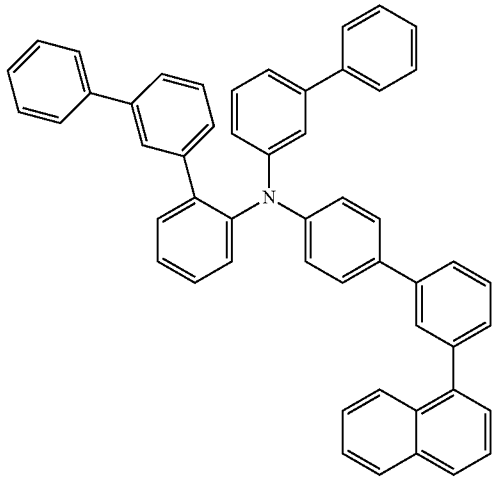

-continued
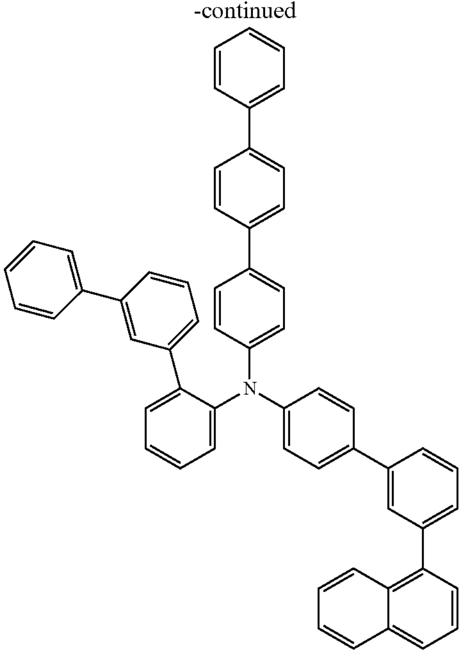
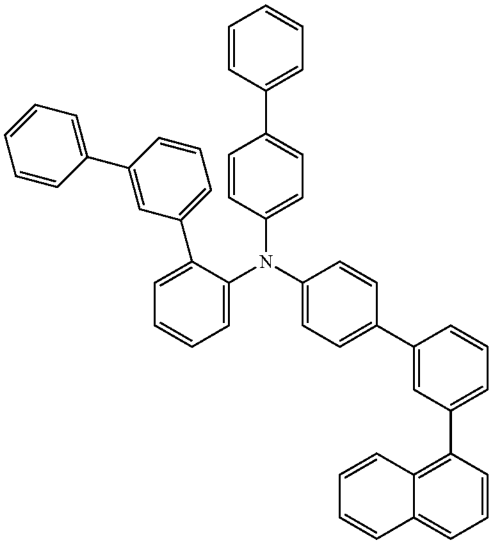
-continued
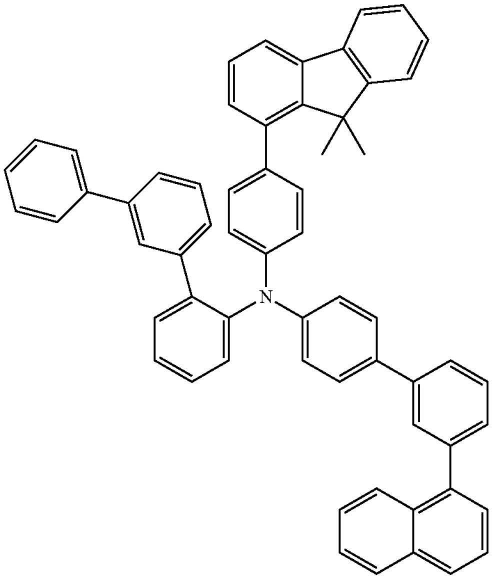
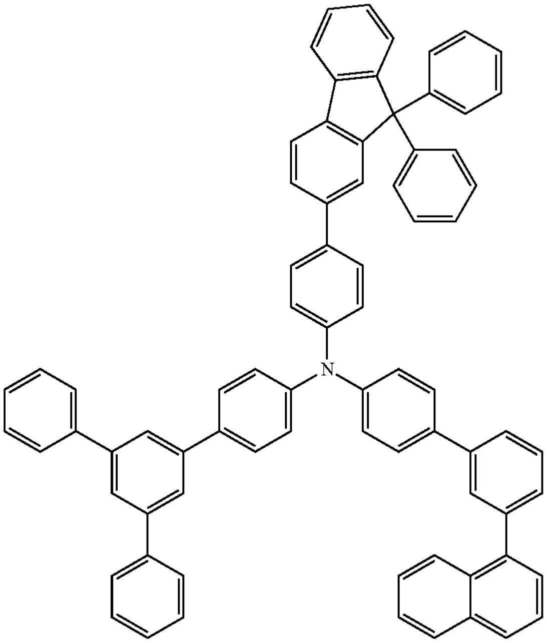

-continued
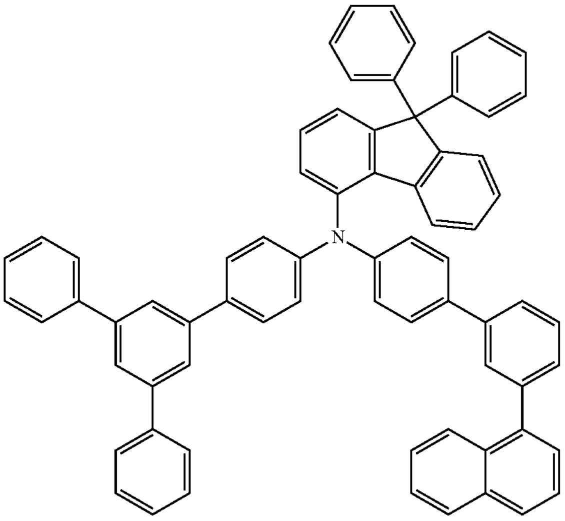
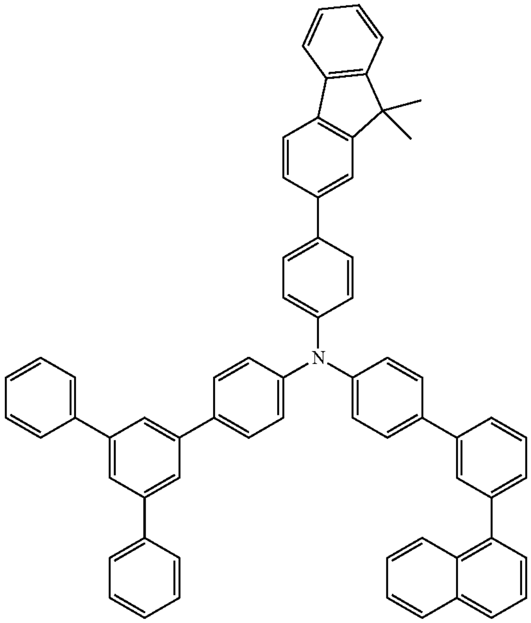
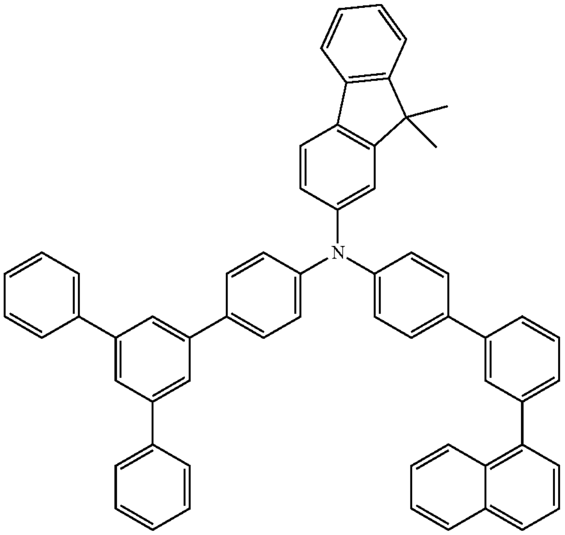
-continued
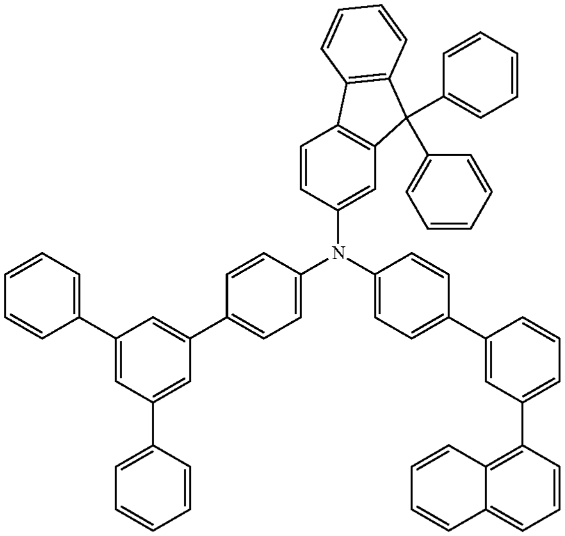
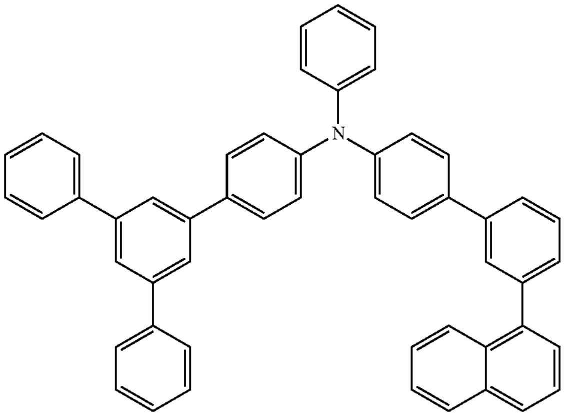
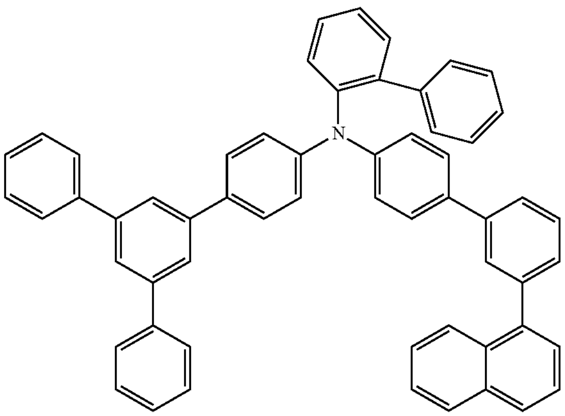

-continued
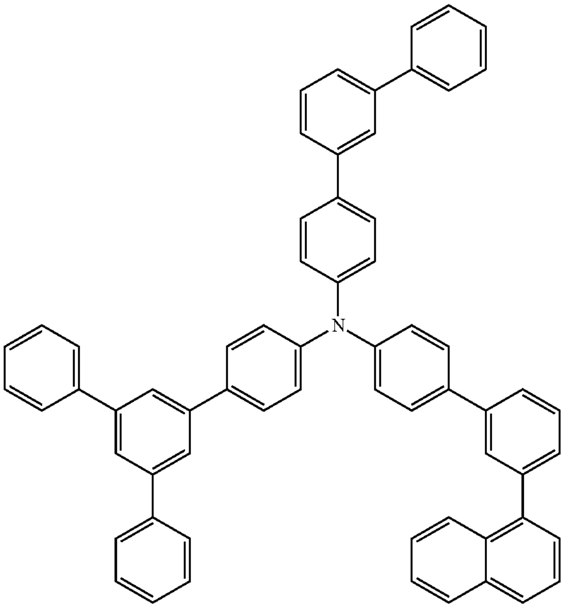
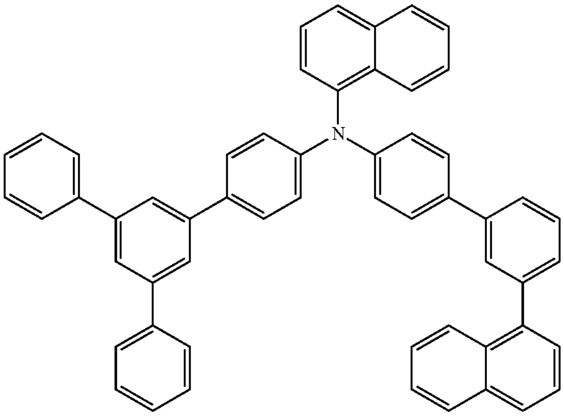
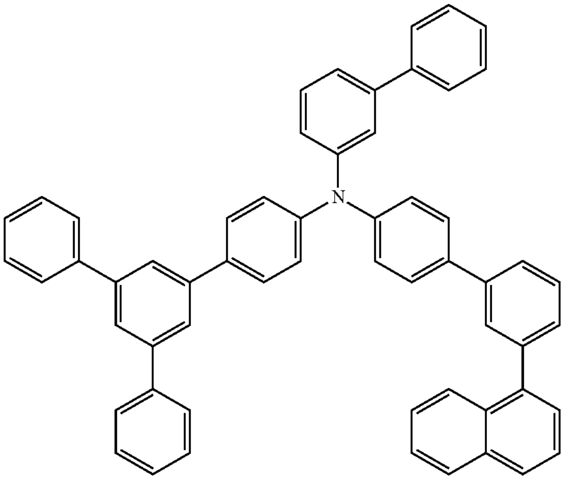
-continued
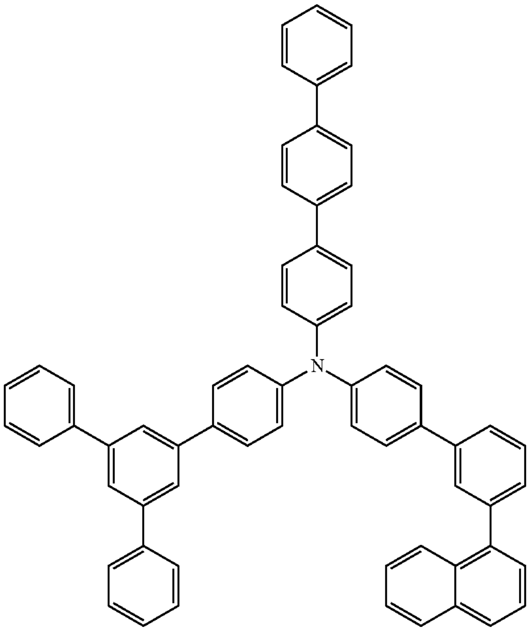
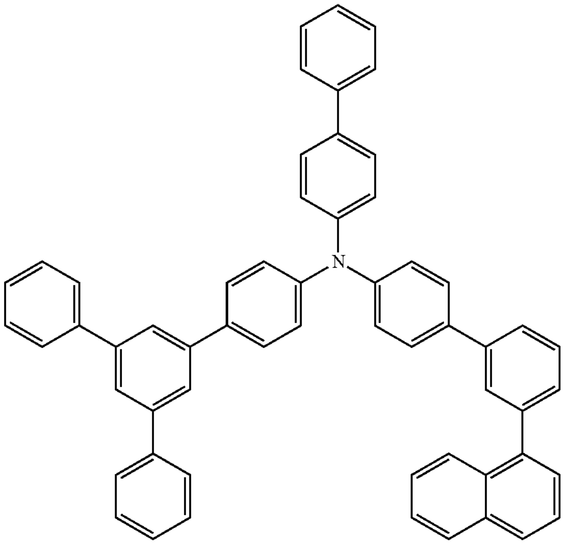

-continued
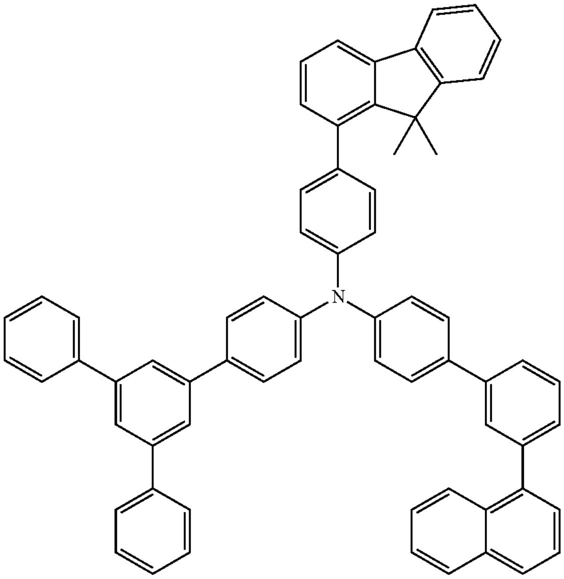
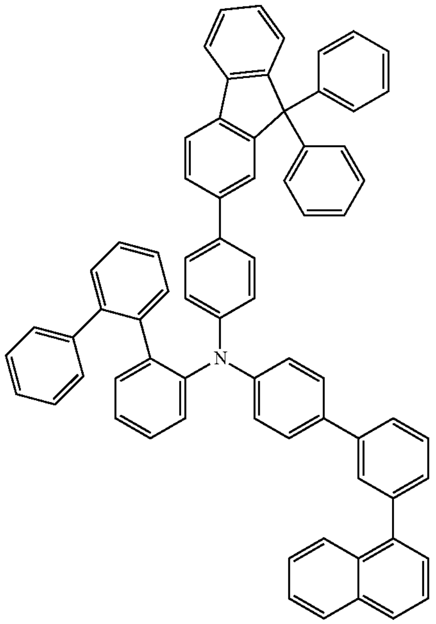
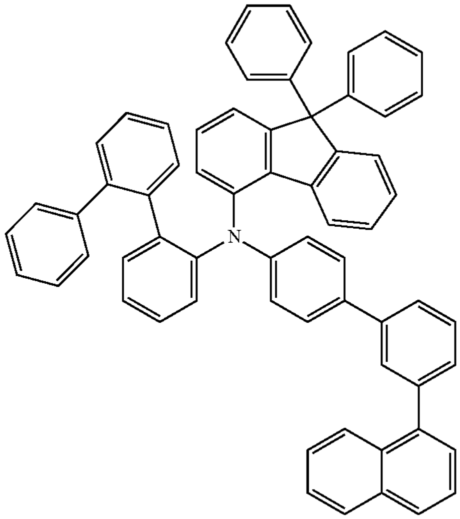
-continued
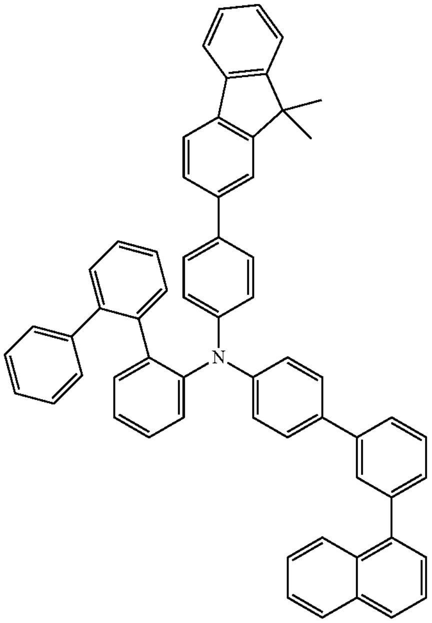
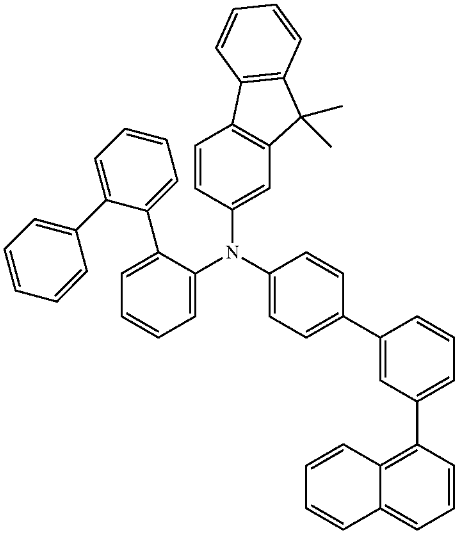
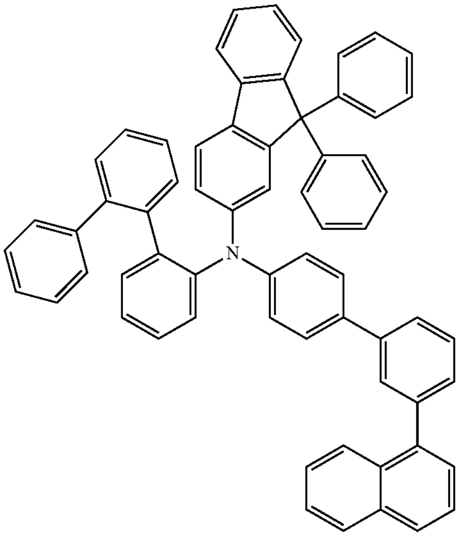

-continued
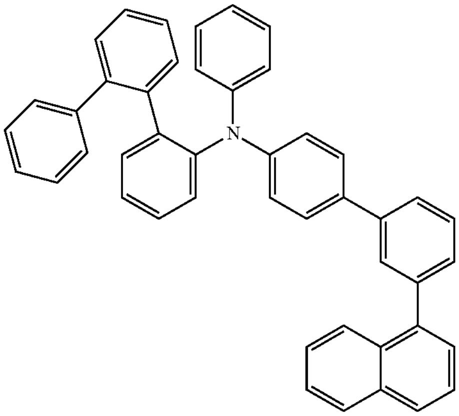
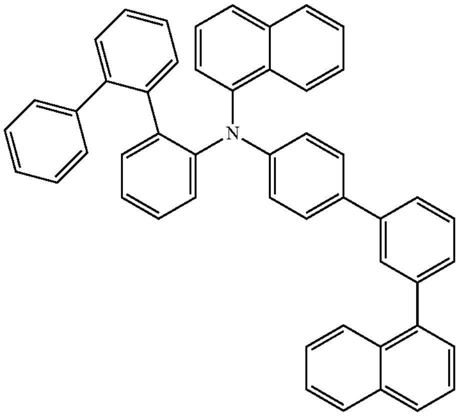
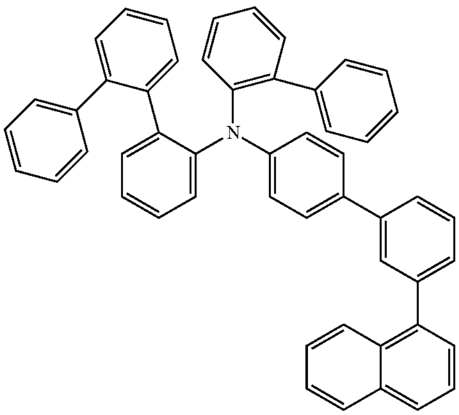
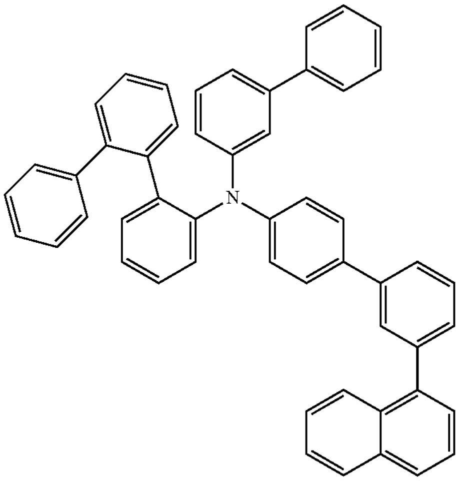
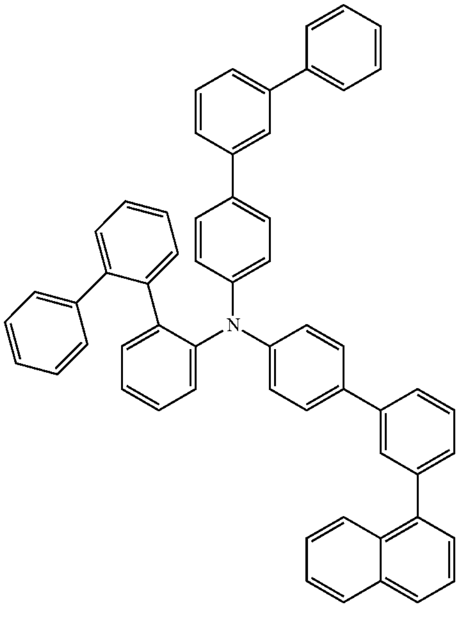
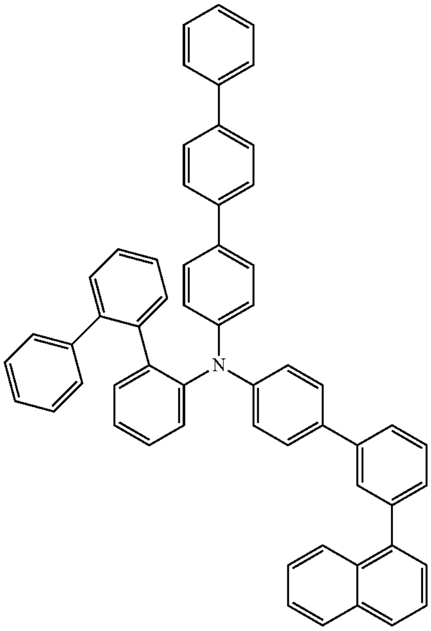

-continued
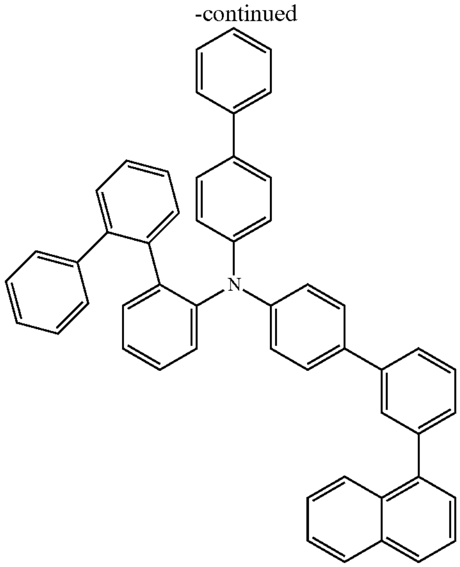
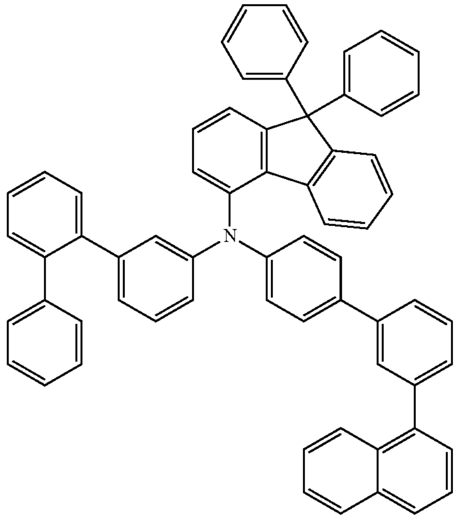
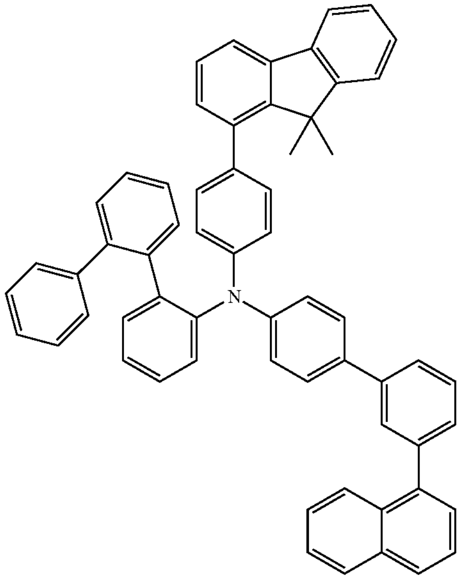
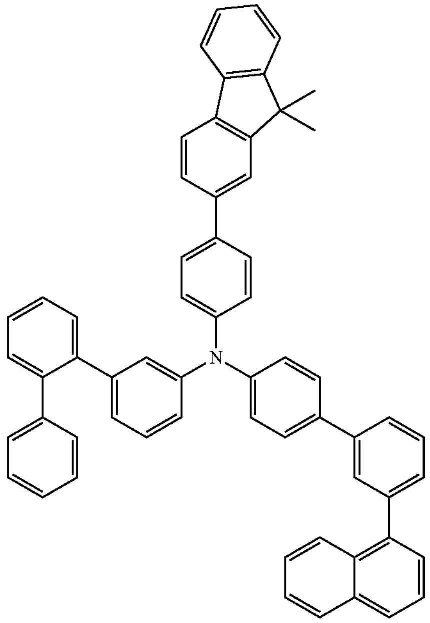
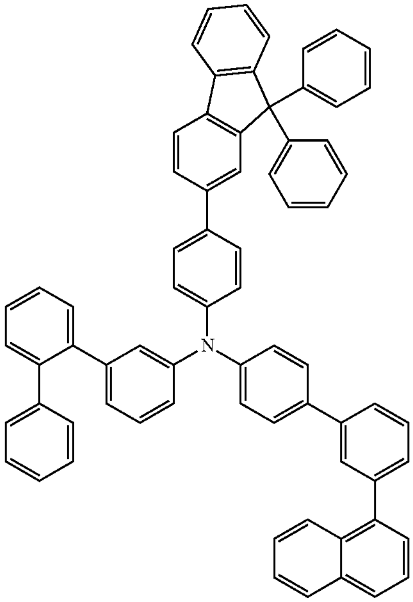
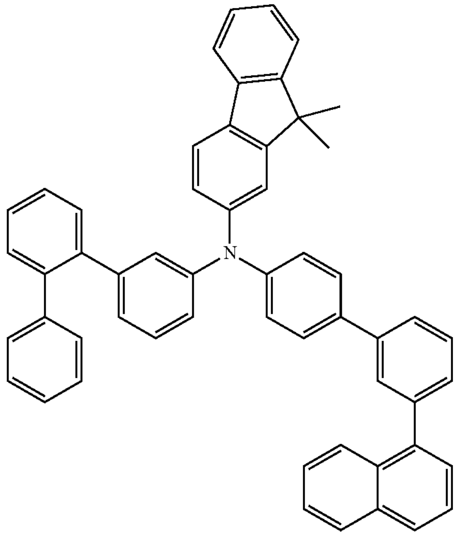
-continued -continued
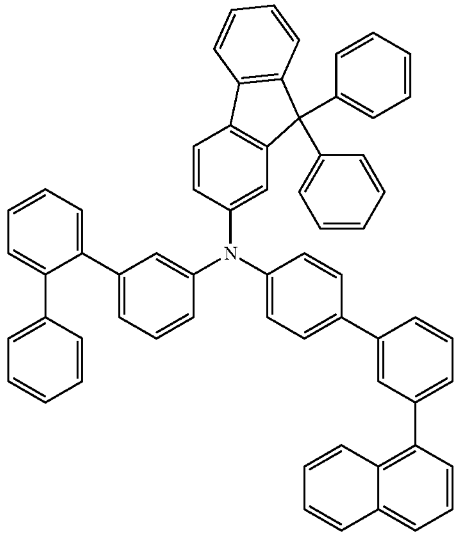
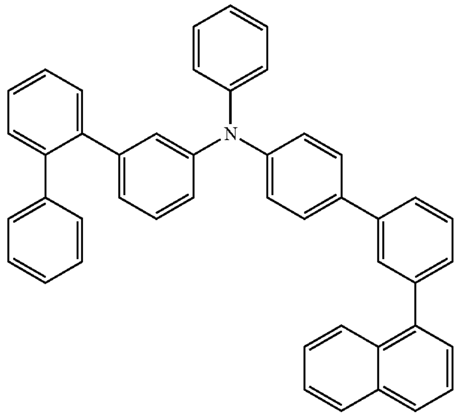
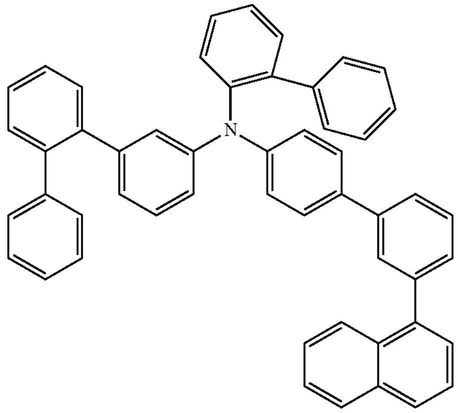
-continued
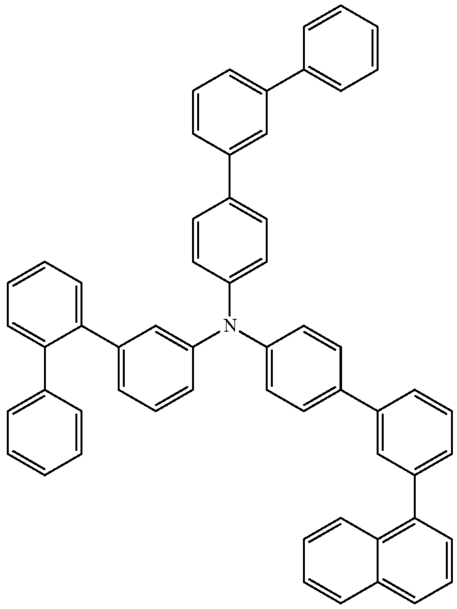
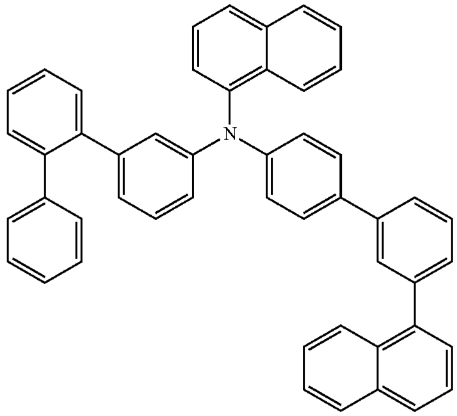
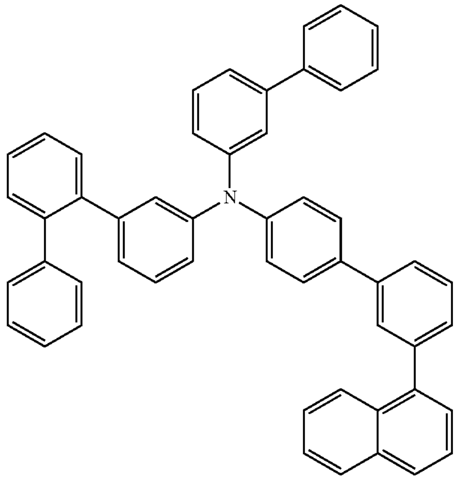

-continued
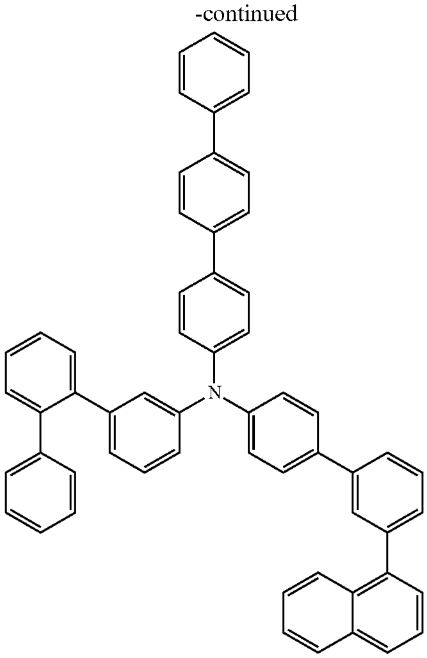
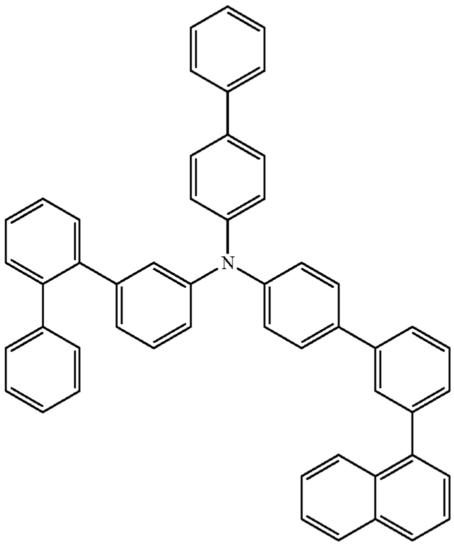
-continued
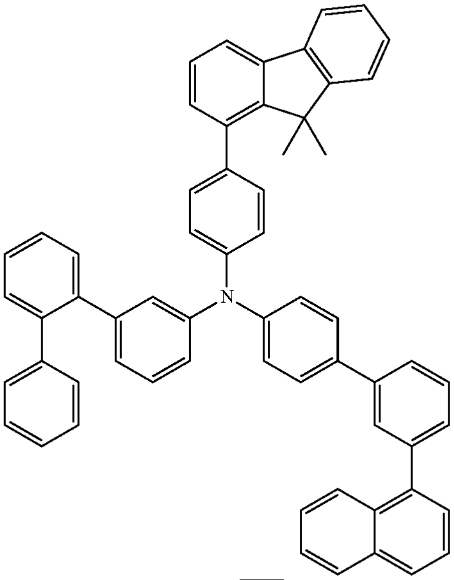
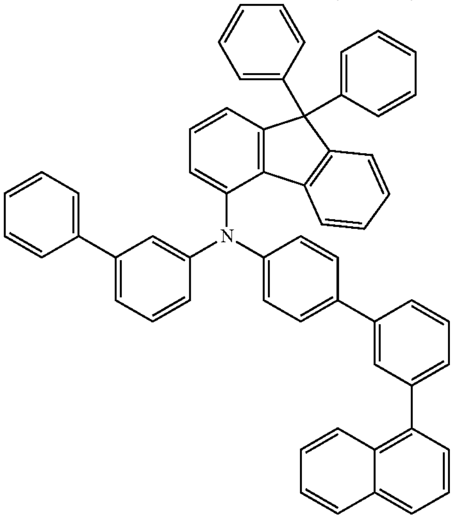
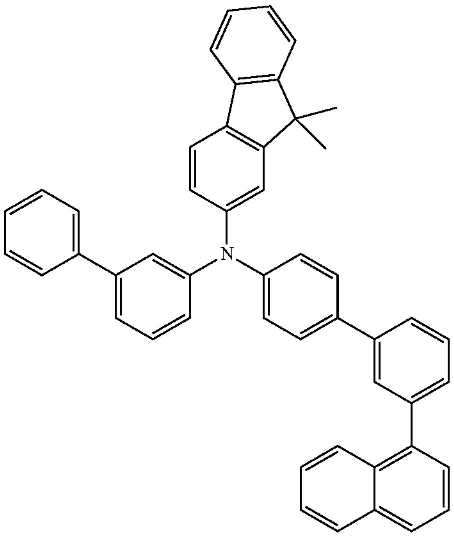

-continued
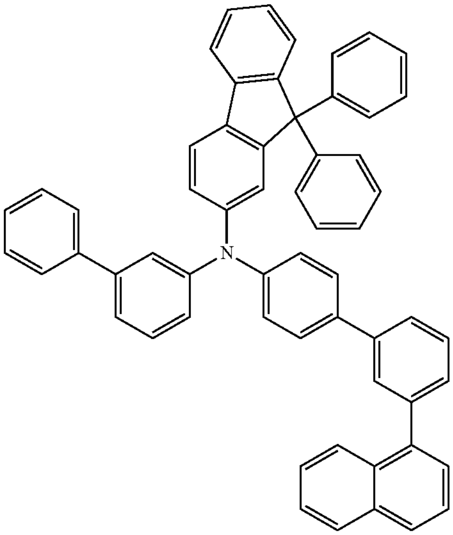
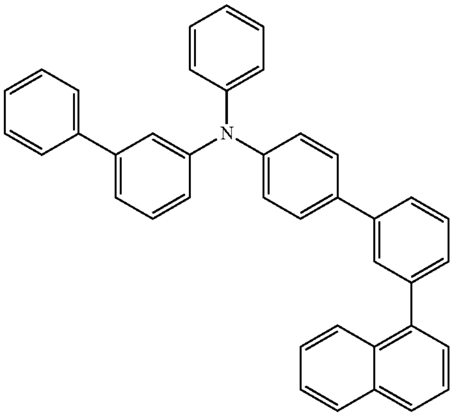
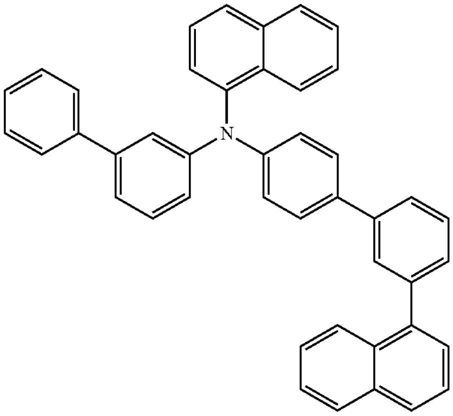
-continued
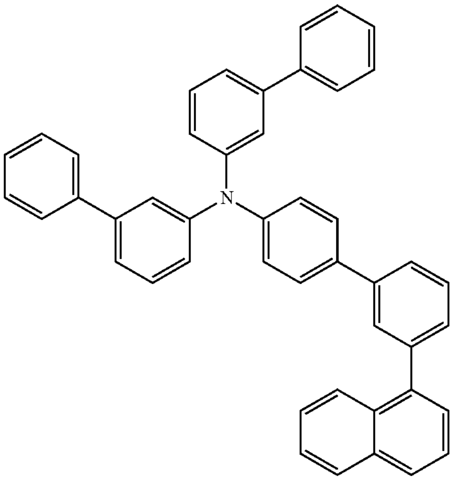
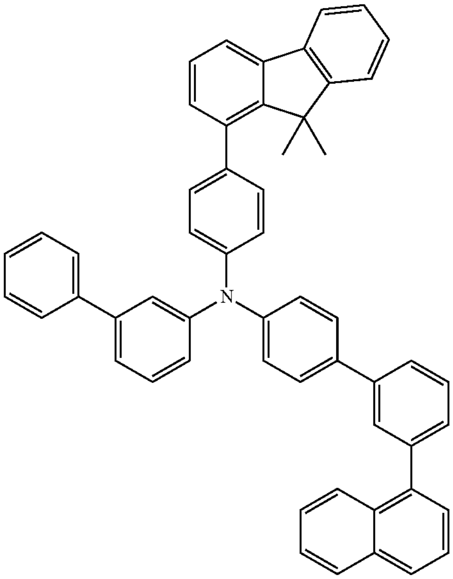
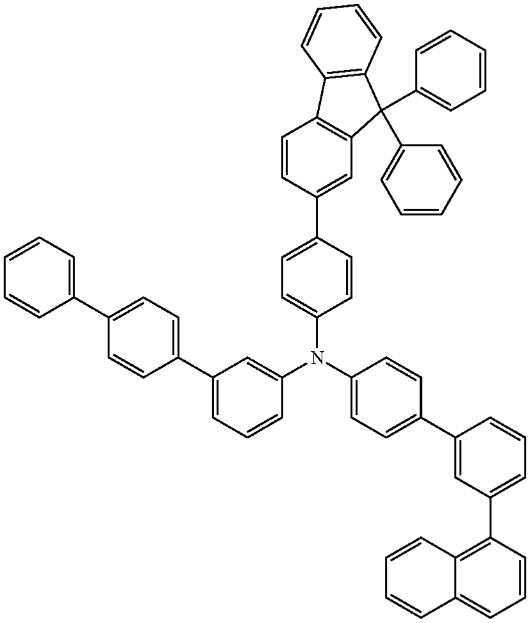

-continued
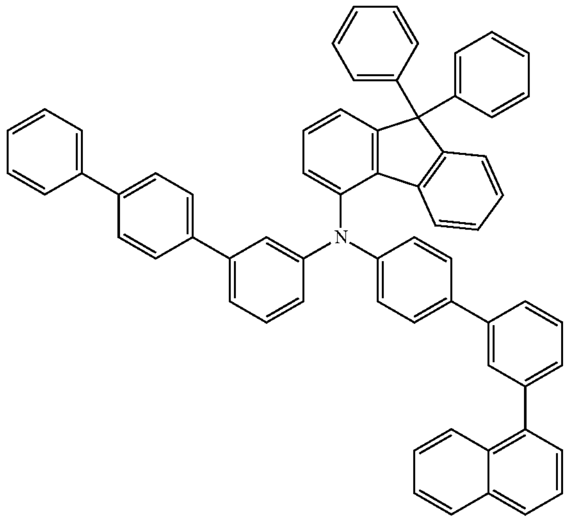
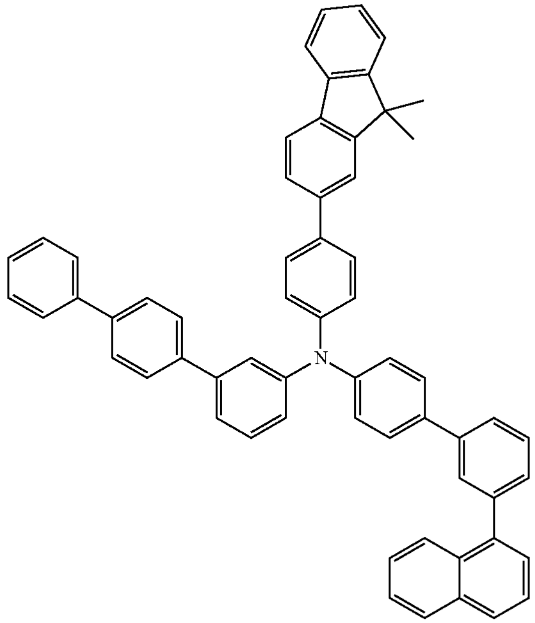
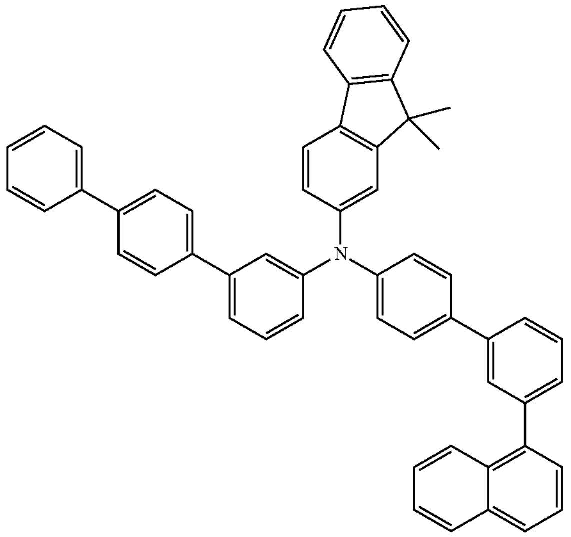
-continued
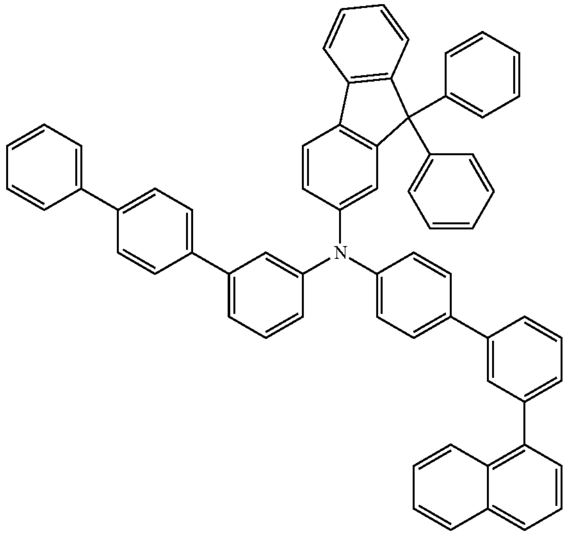
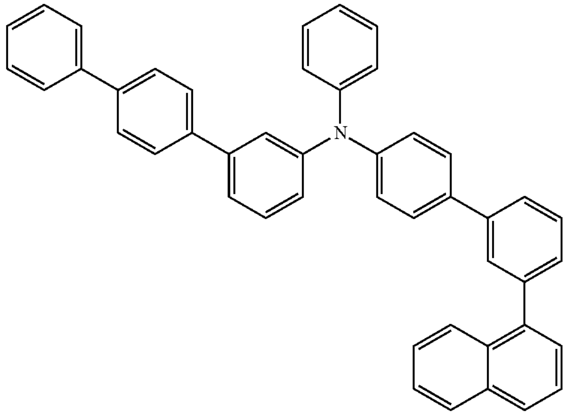
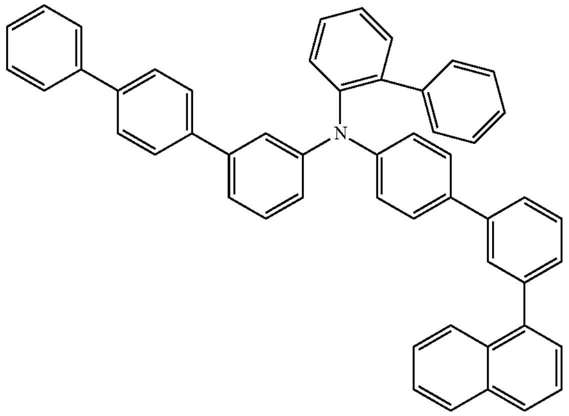

-continued
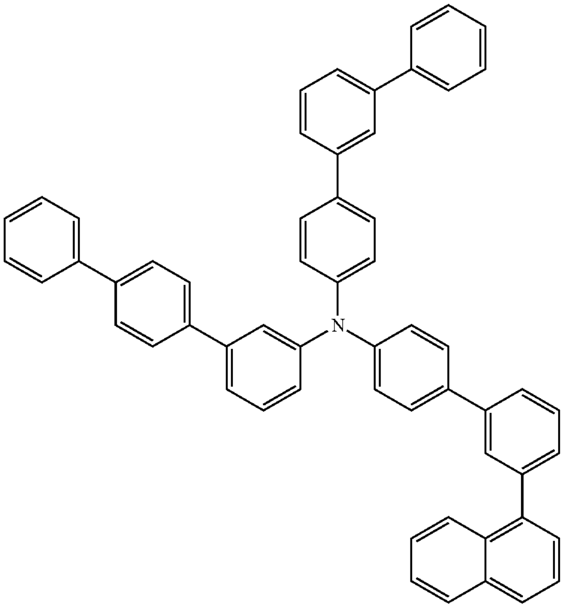
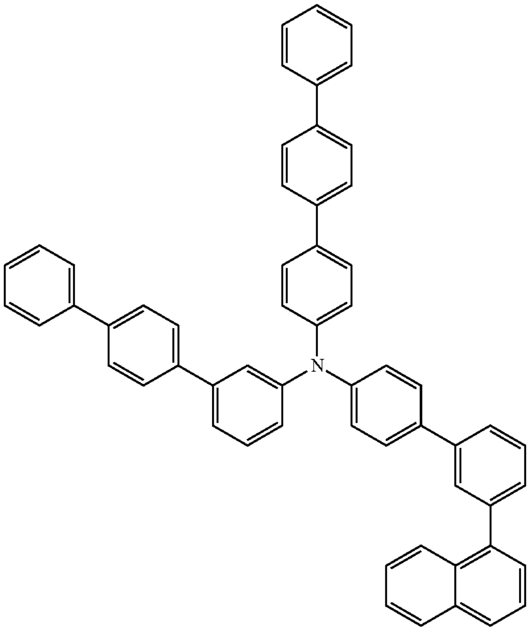
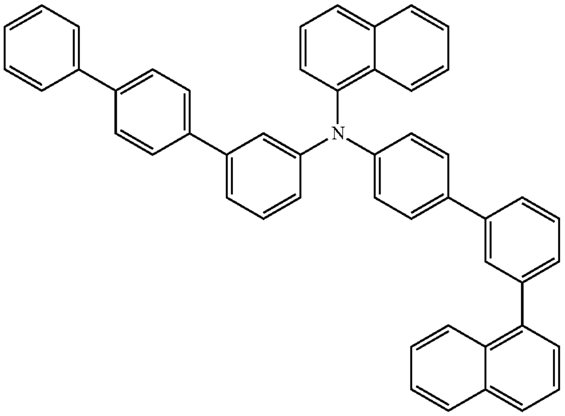
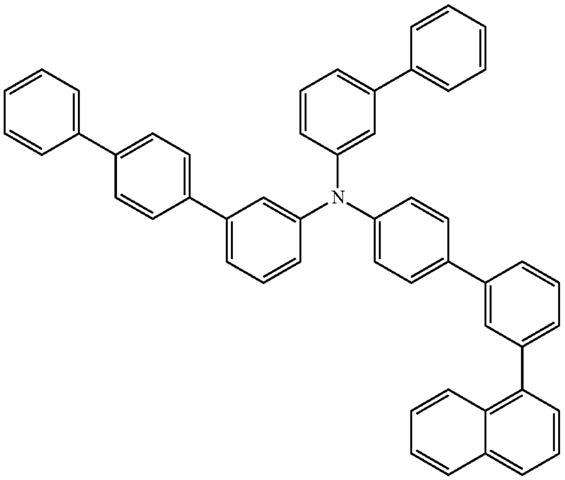
-continued
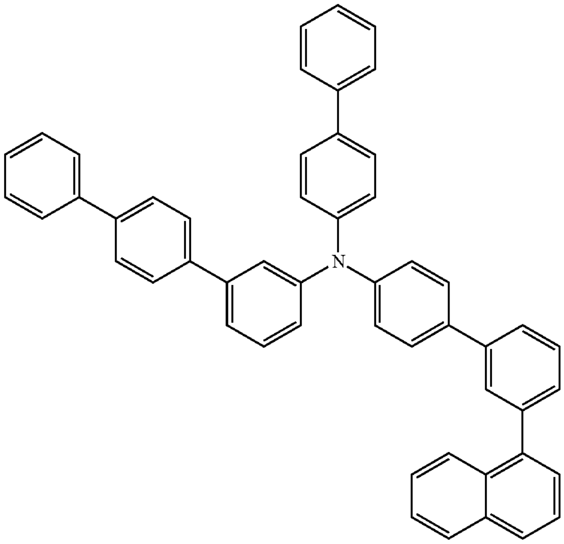

-continued
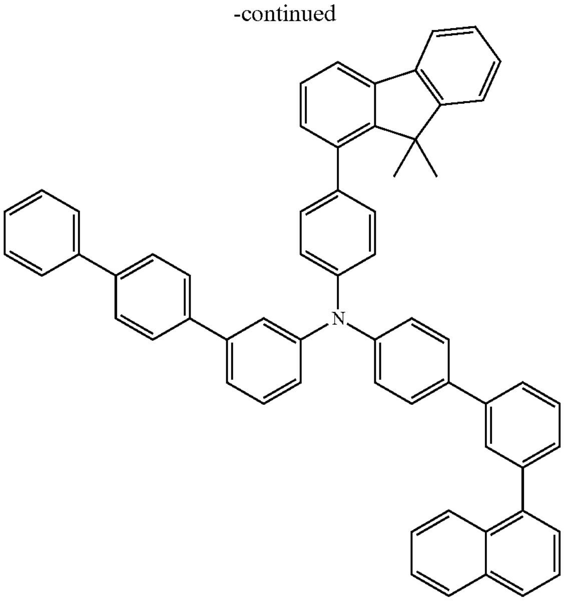
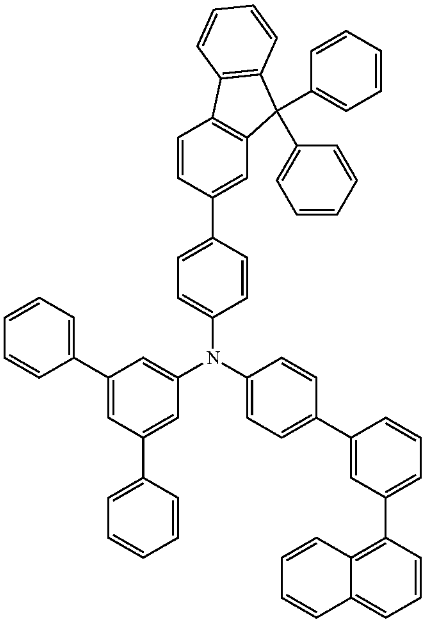
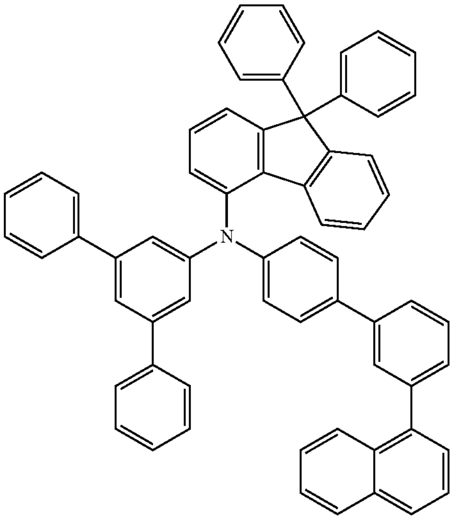
-continued
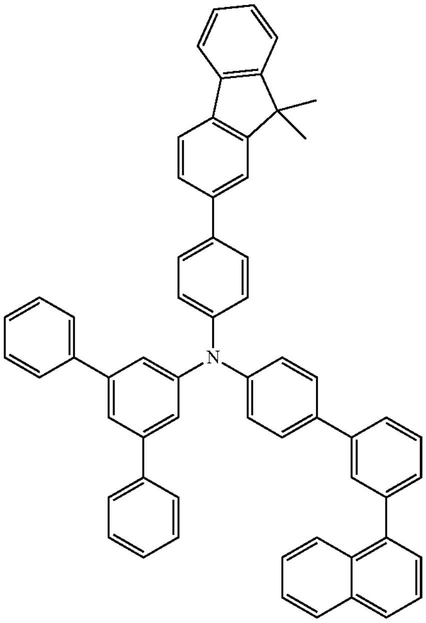
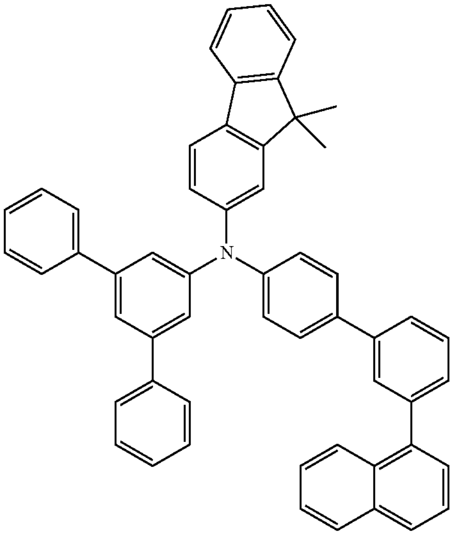
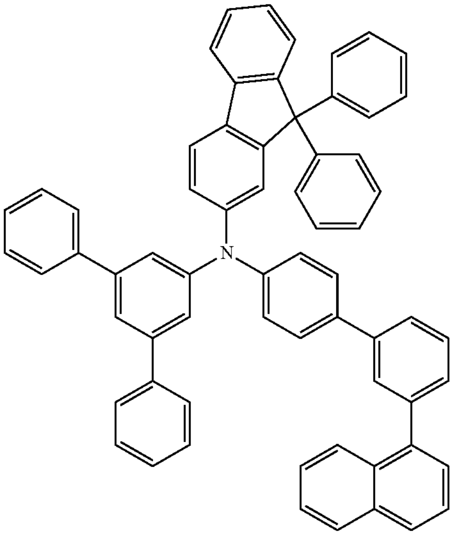

-continued
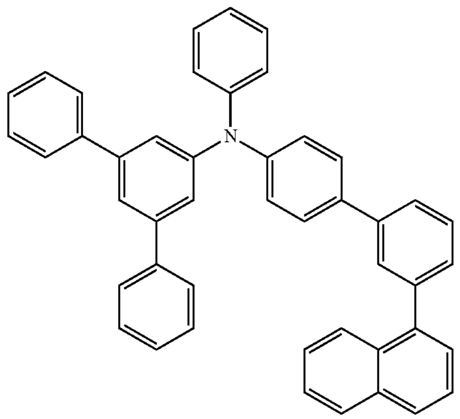
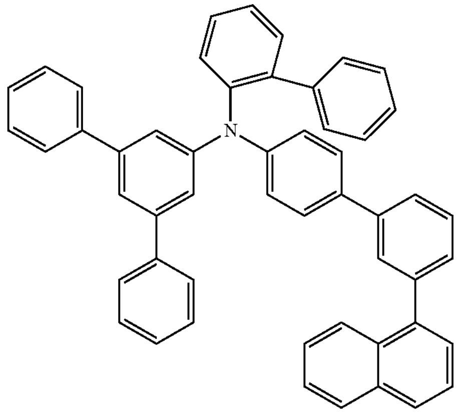
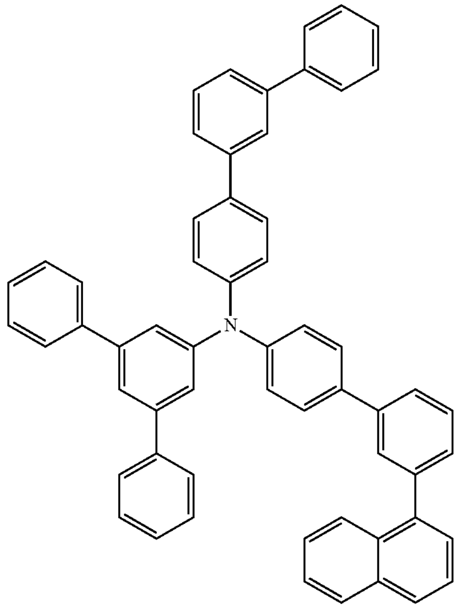
-continued
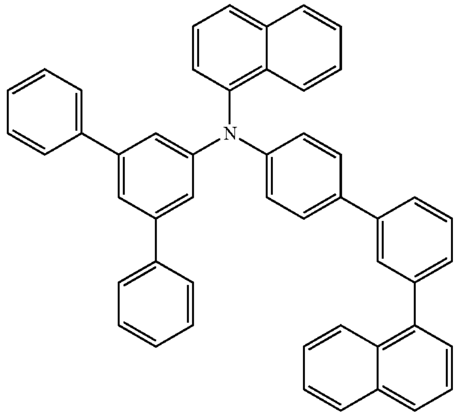
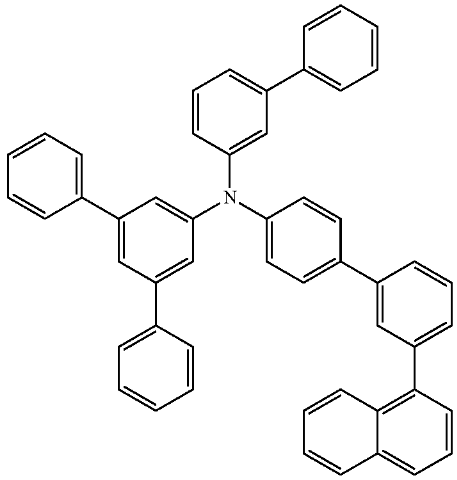
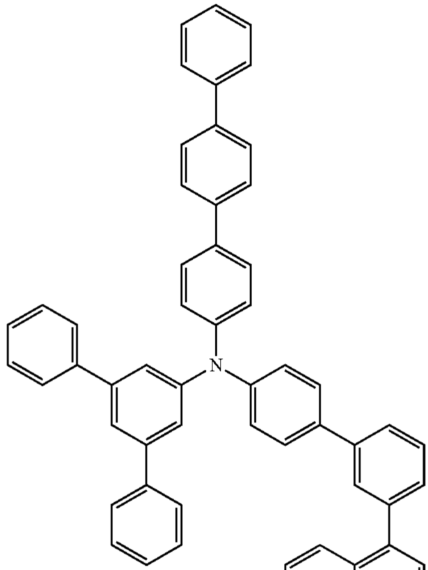

-continued
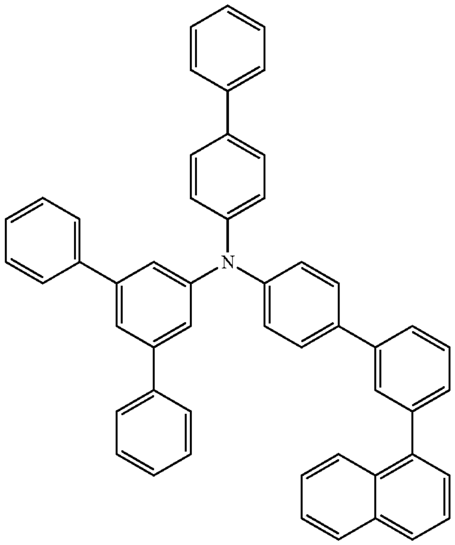
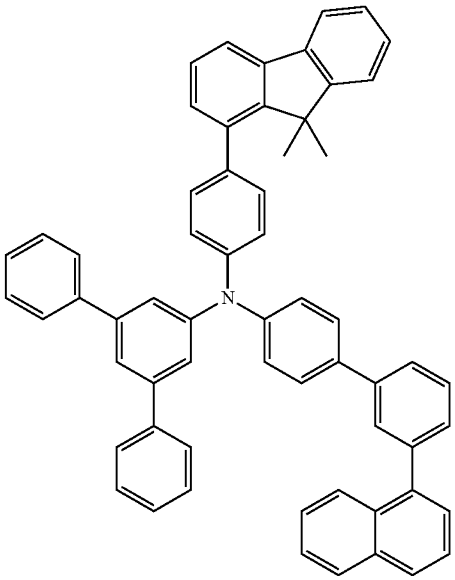
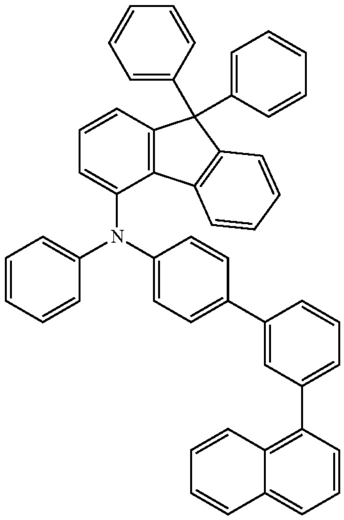
-continued
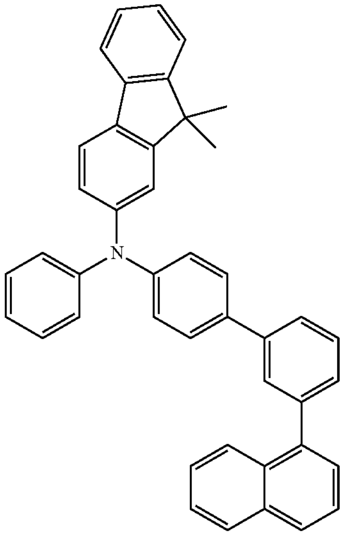
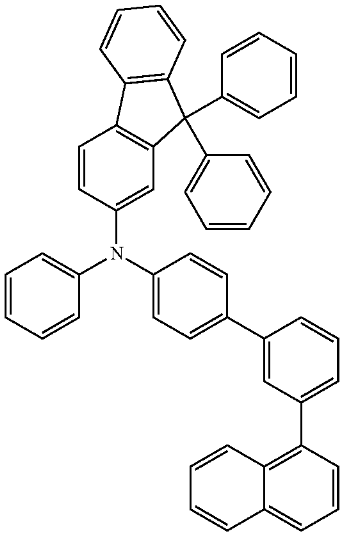
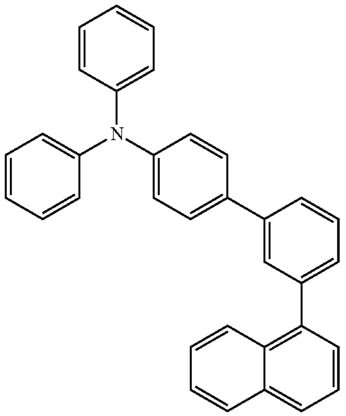

-continued
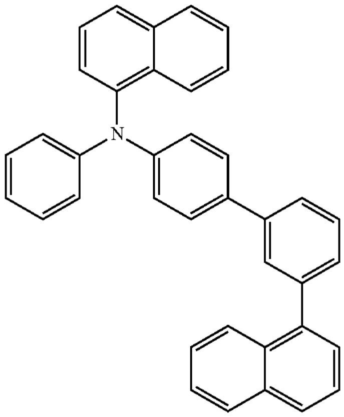
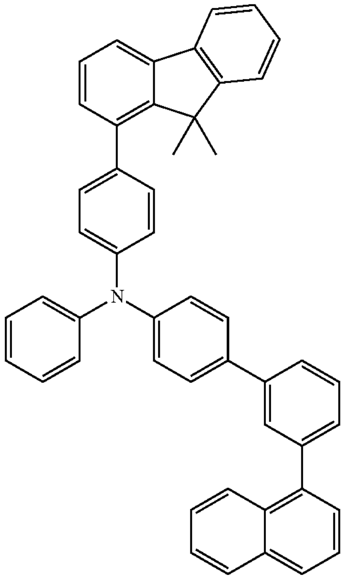
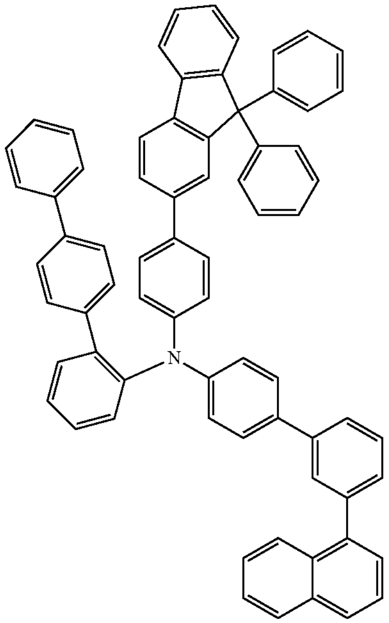
-continued
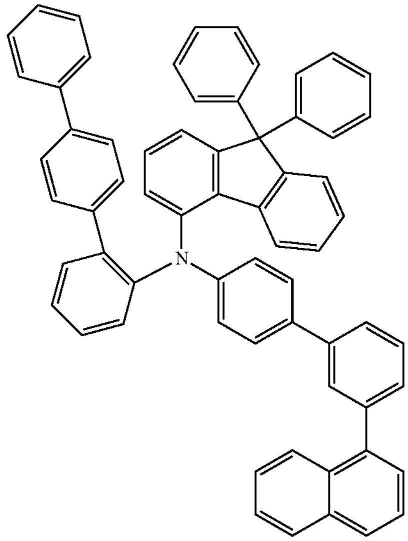
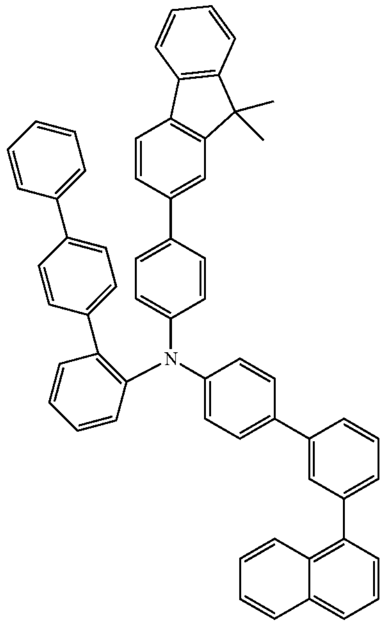
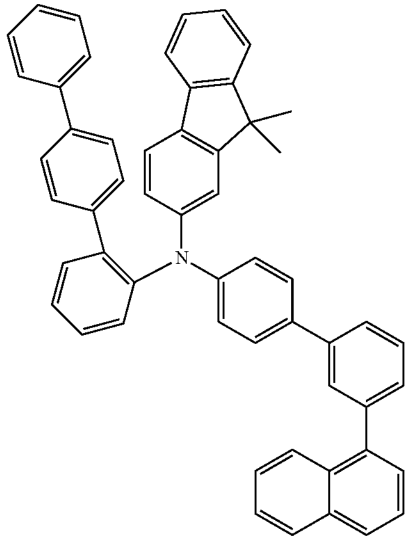

-continued
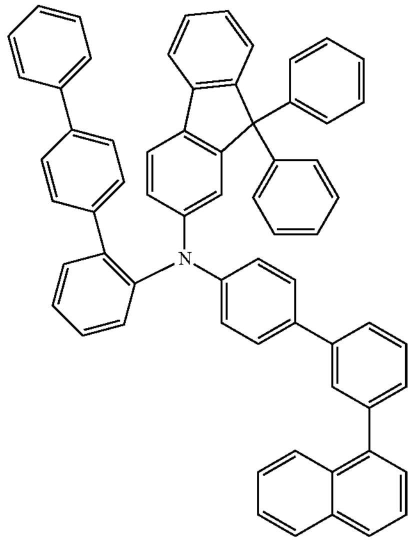
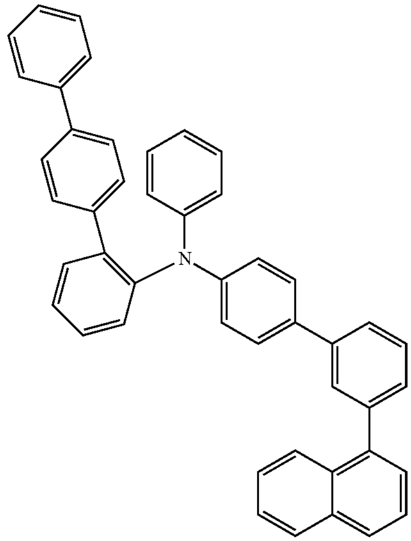
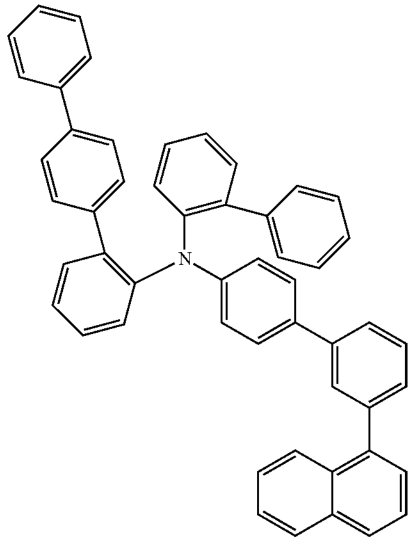
-continued
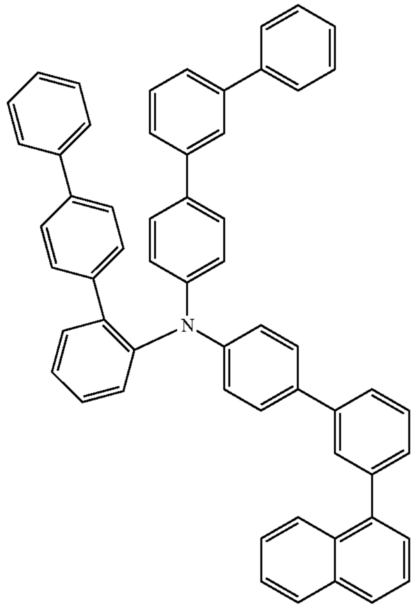
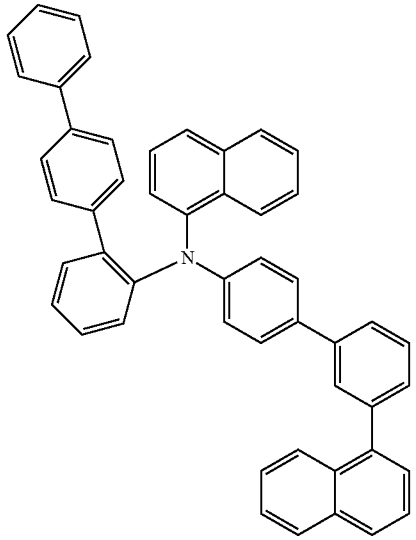
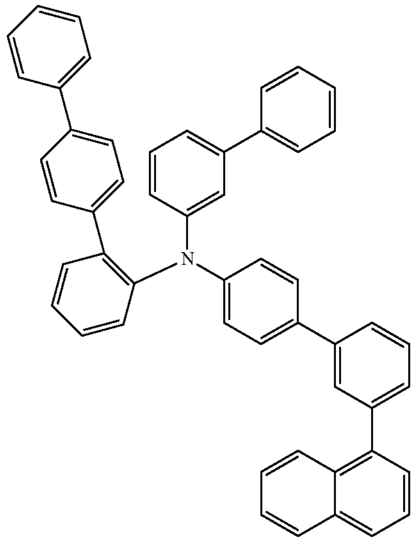

-continued
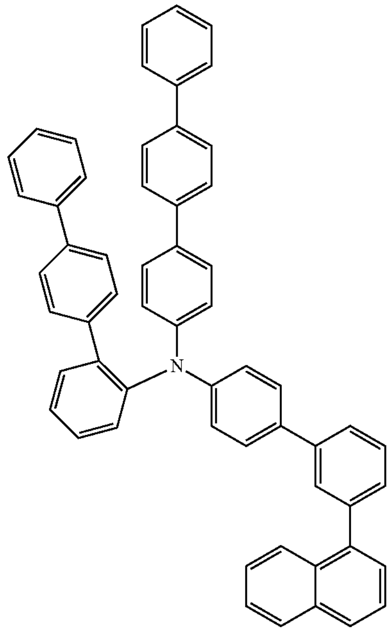
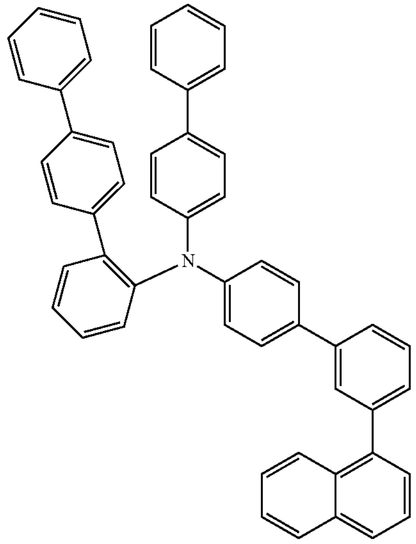
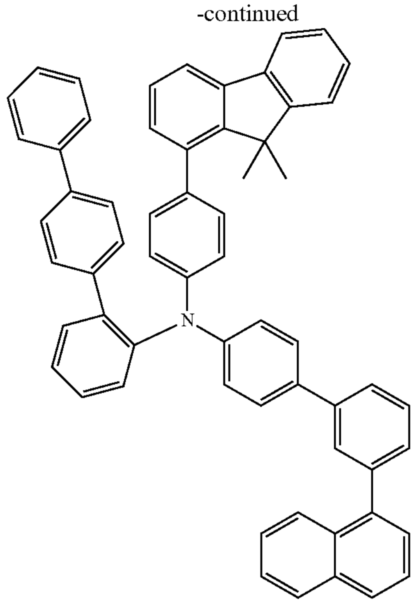
-continued
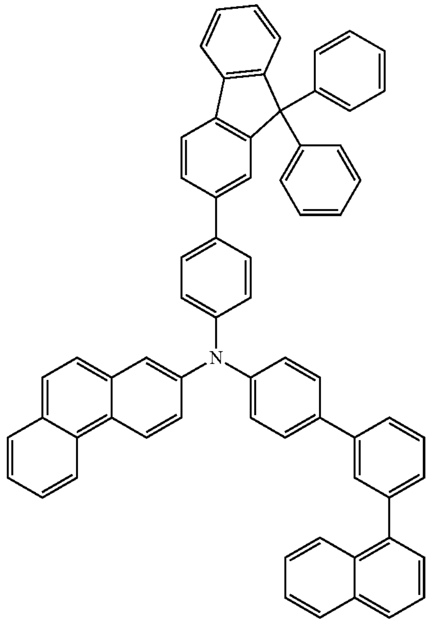
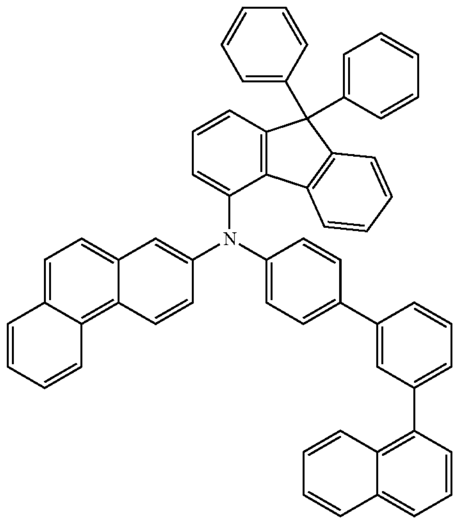

-continued
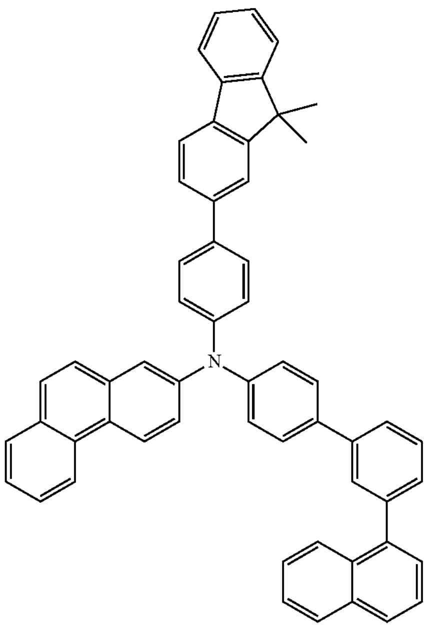
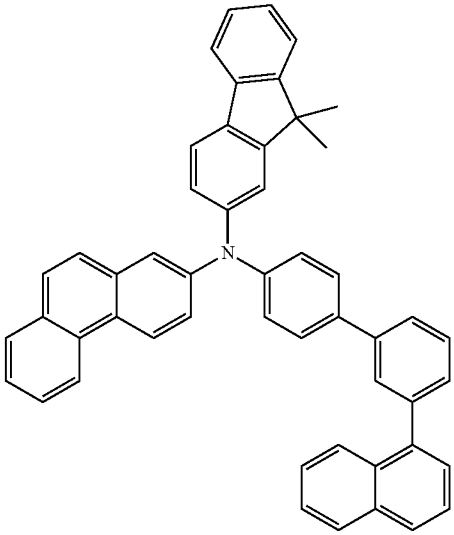
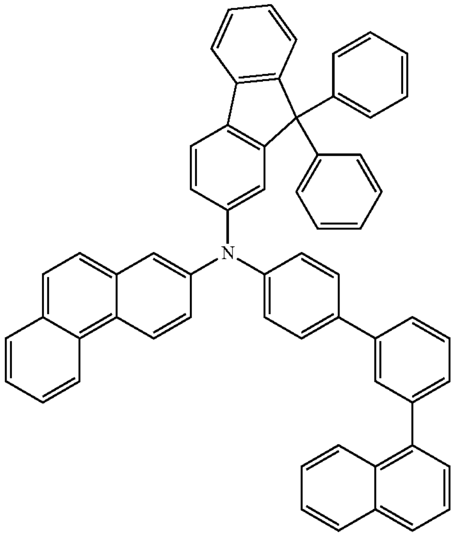
-continued
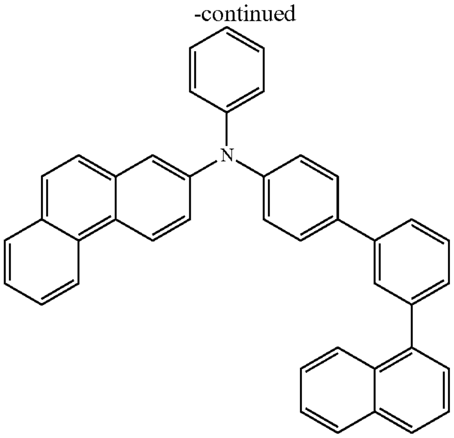
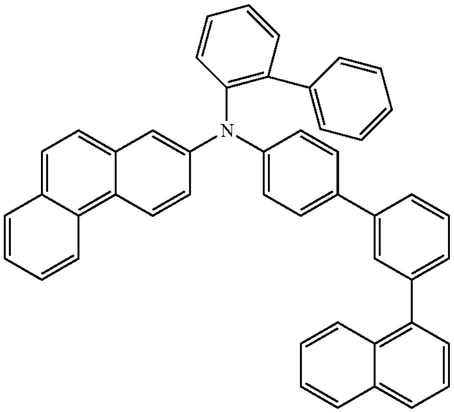
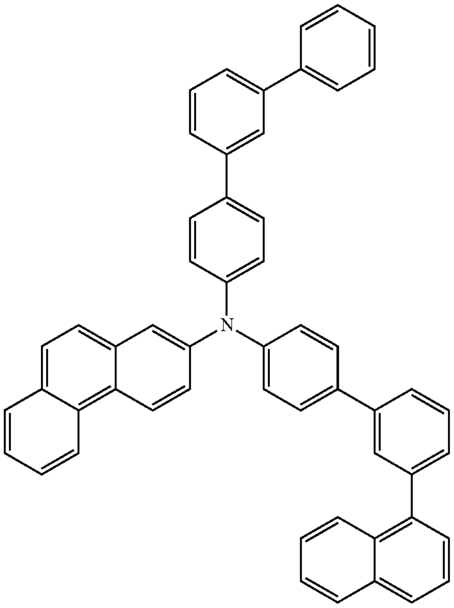

-continued
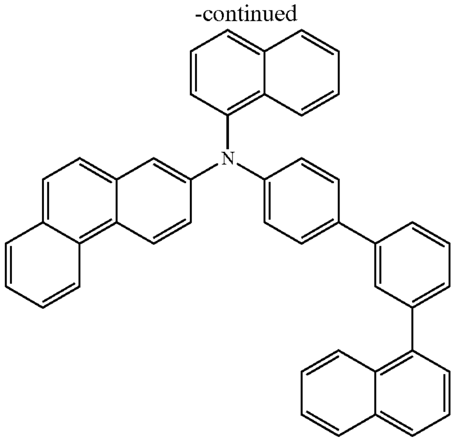
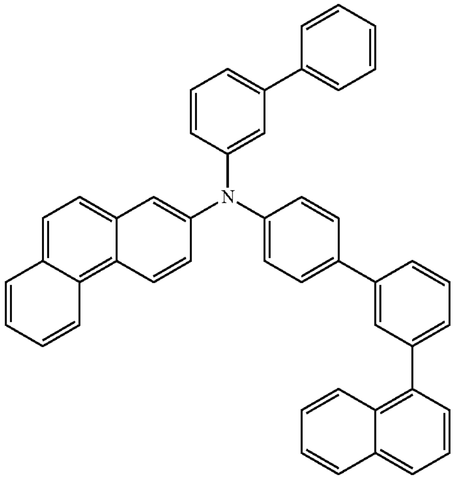
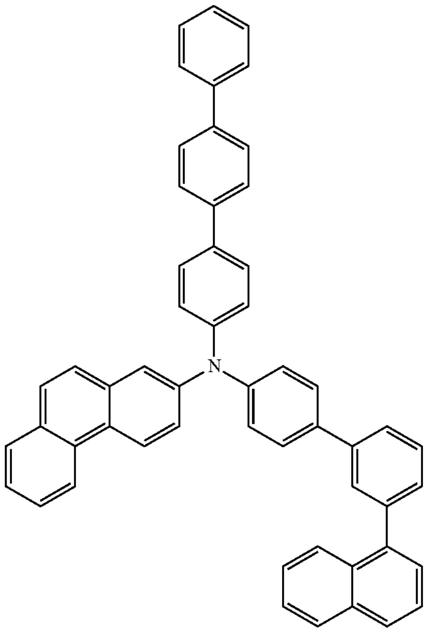
-continued
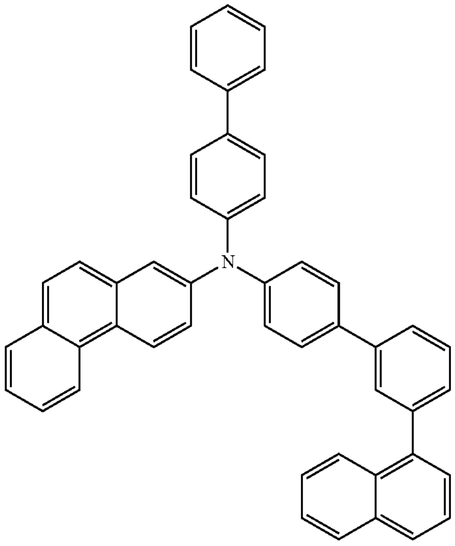
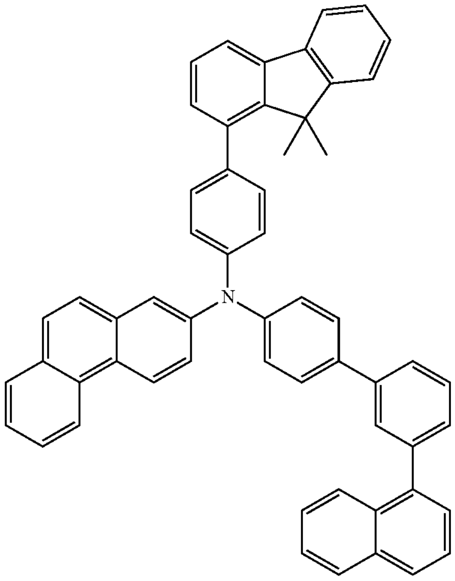

-continued
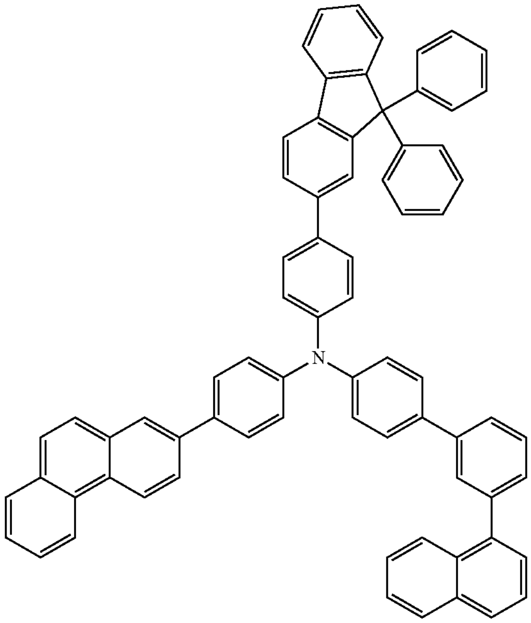
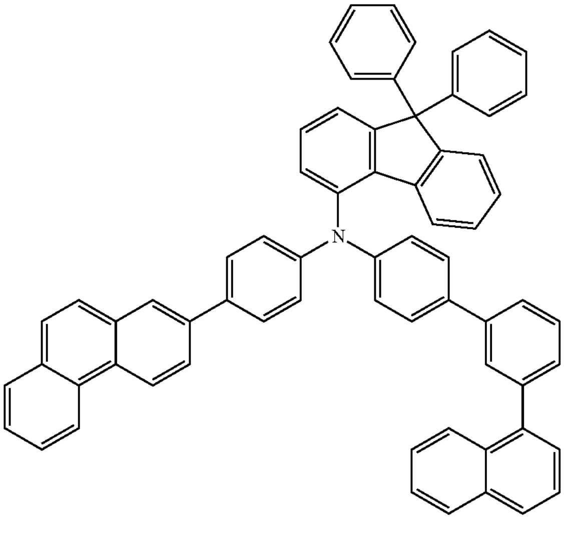
-continued
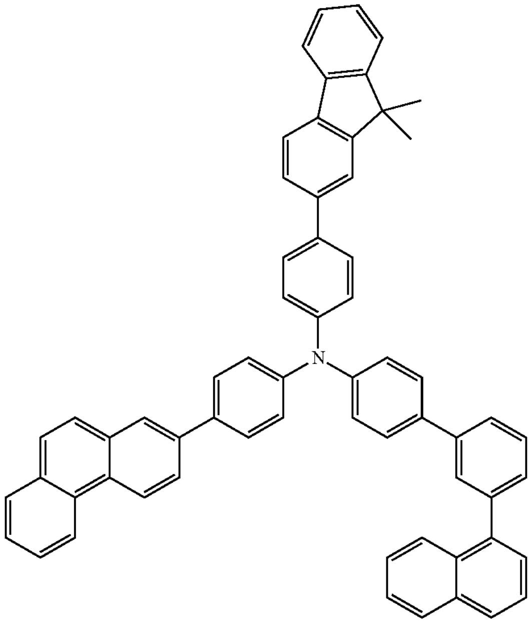
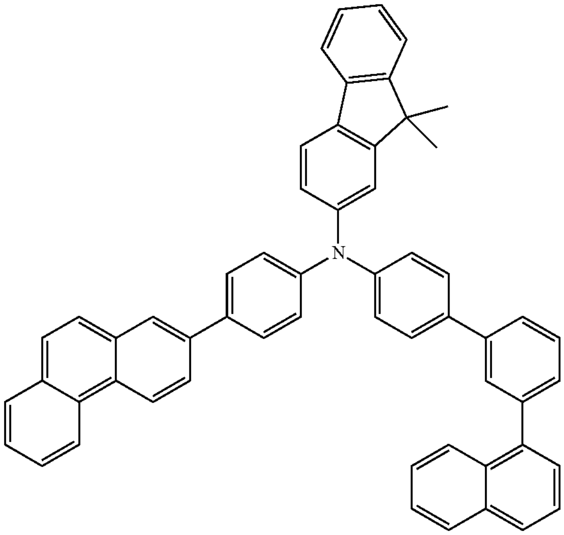
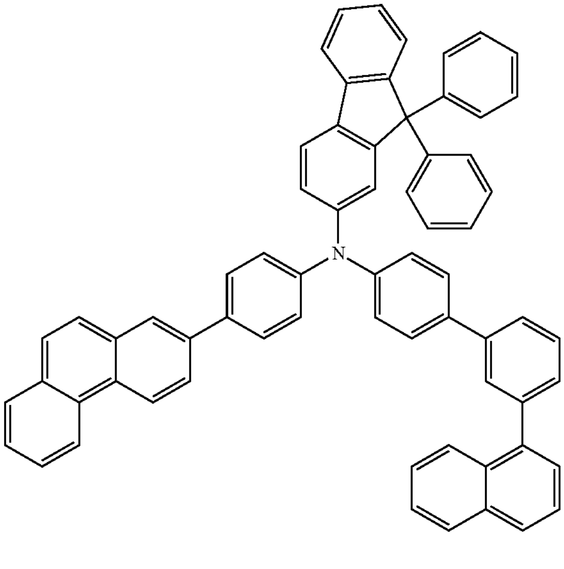

-continued
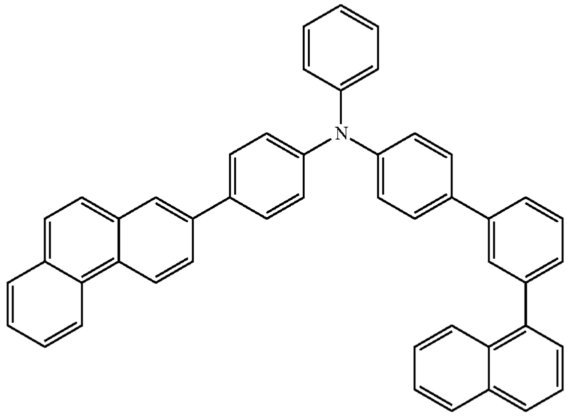
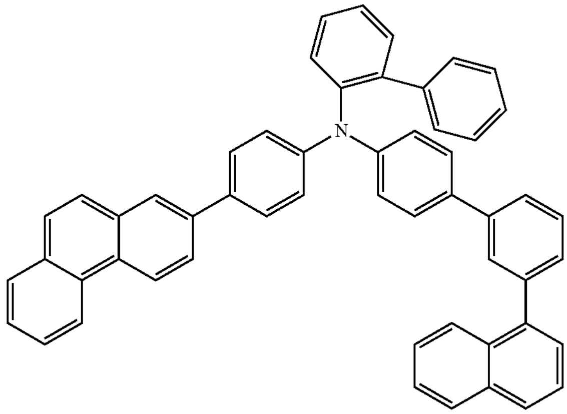
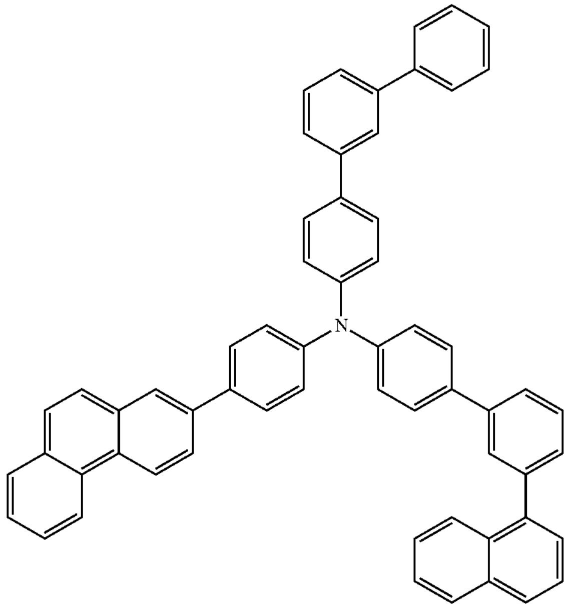
-continued
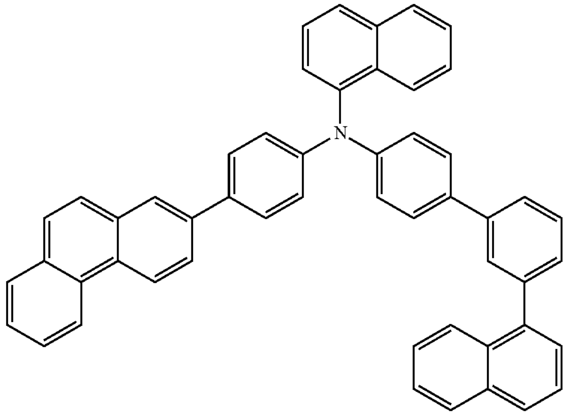
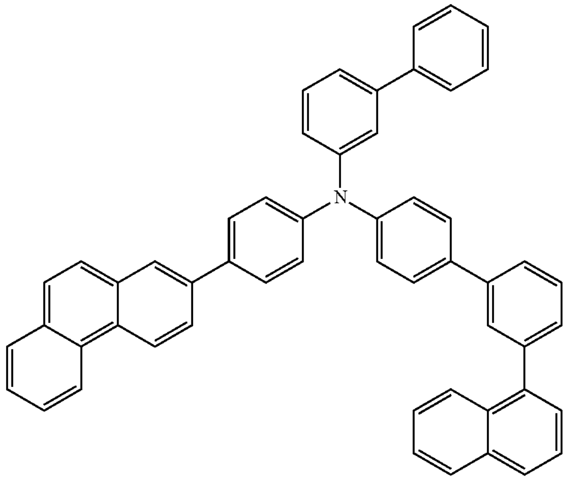
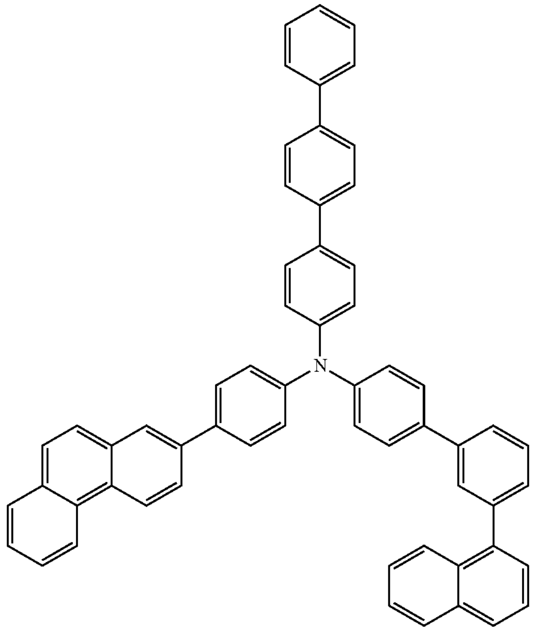

-continued
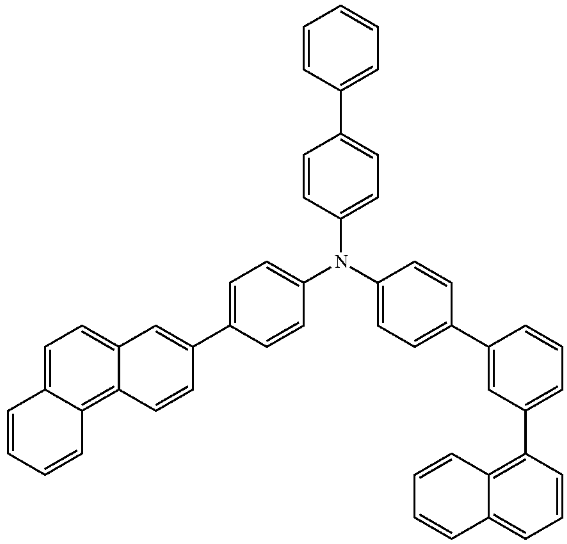
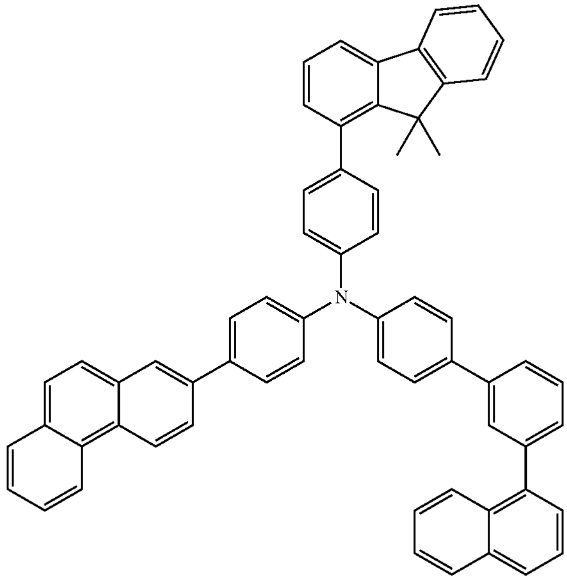
-continued
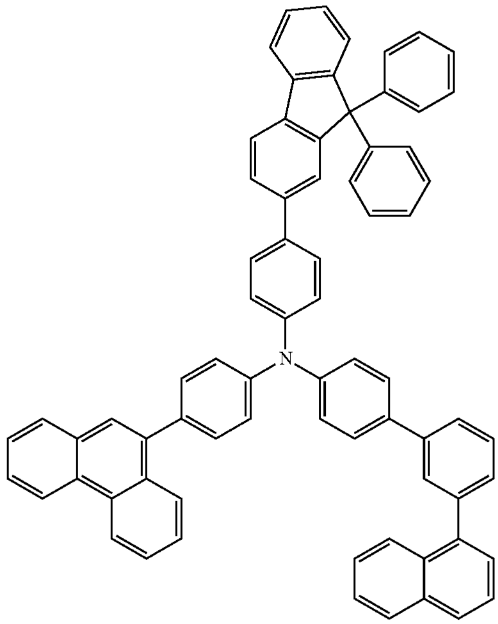
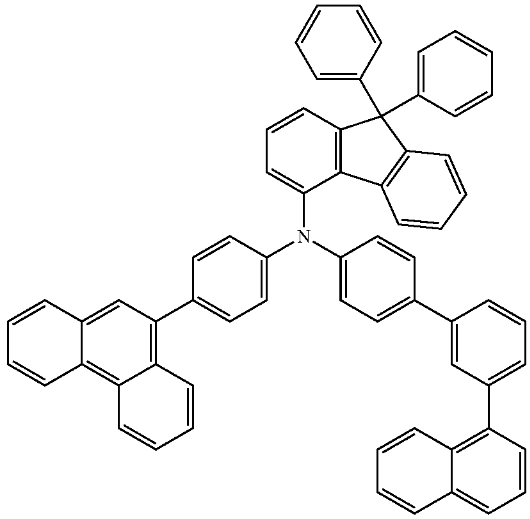

-continued
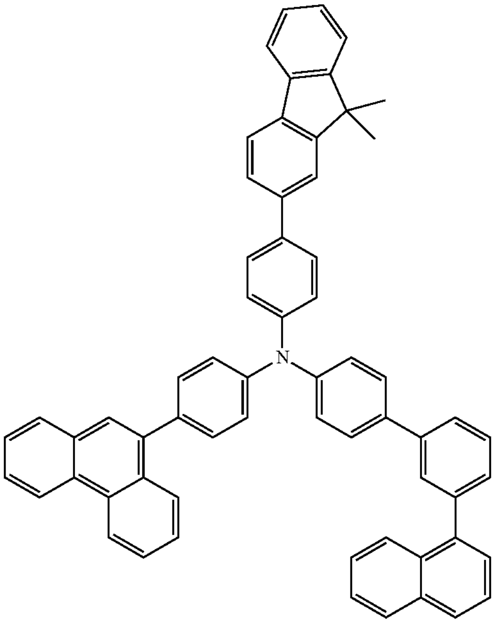
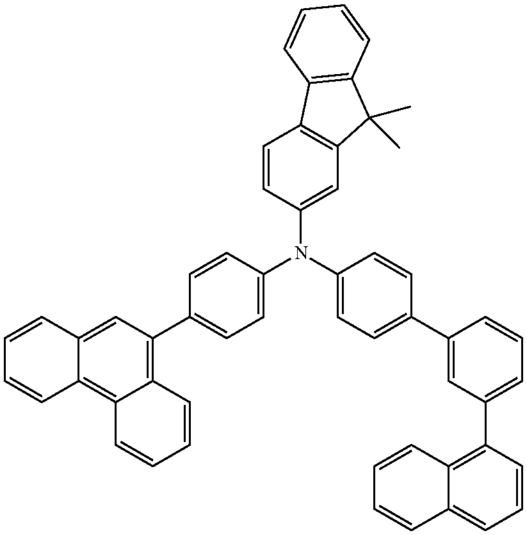
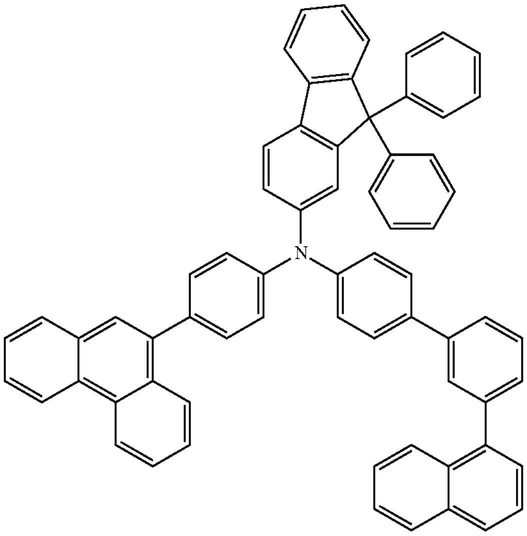
-continued
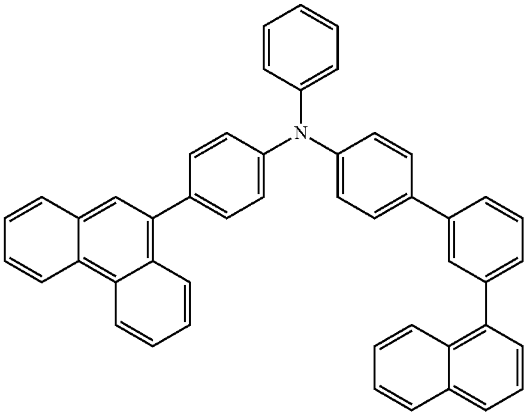
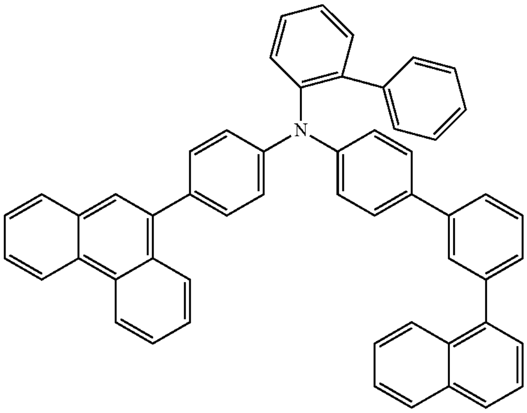
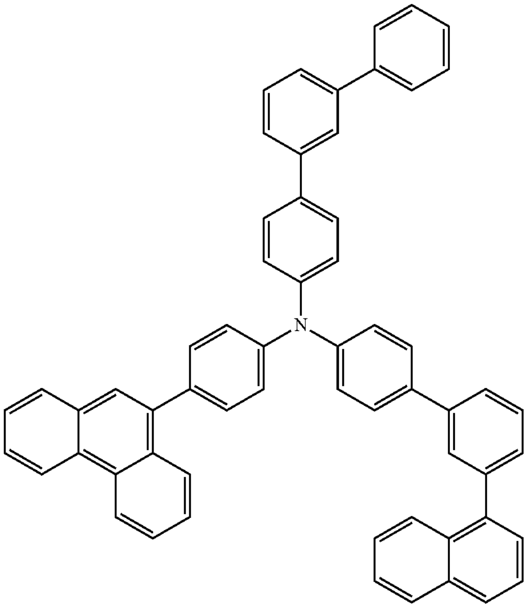

-continued
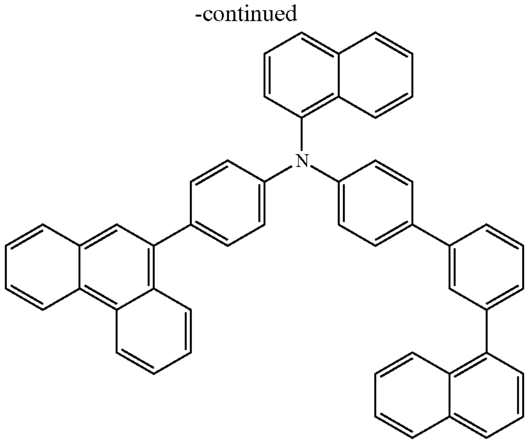
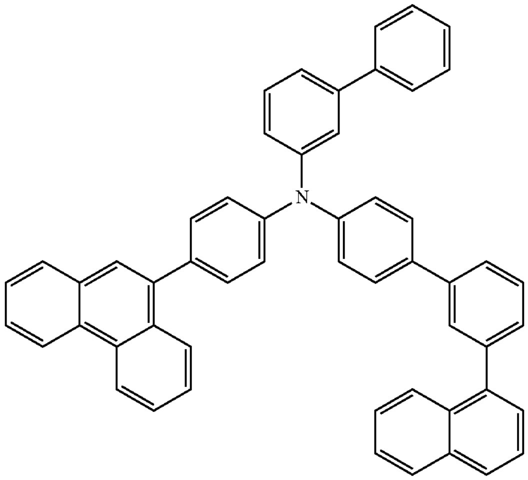
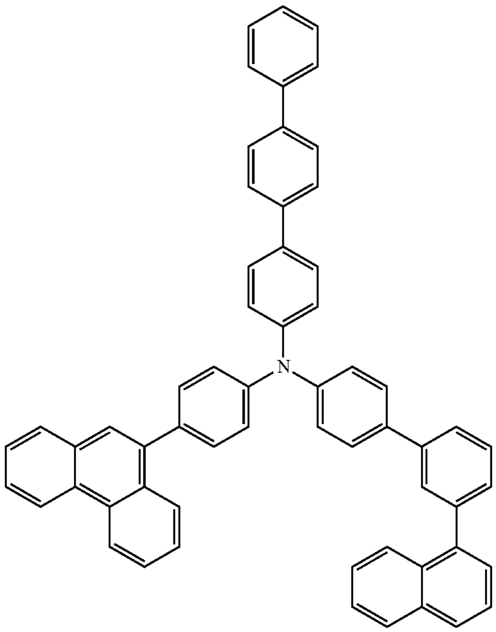
-continued
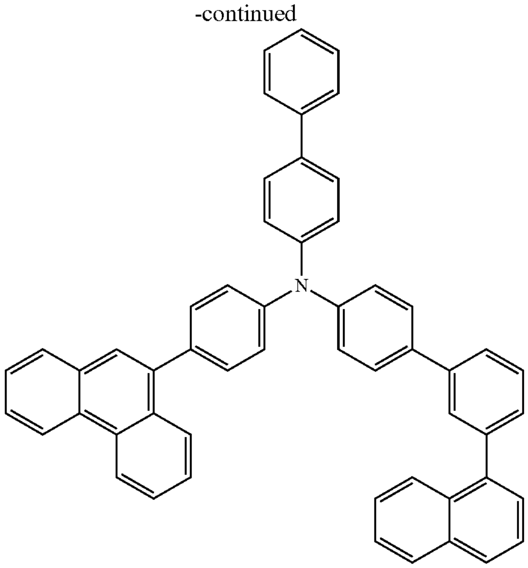
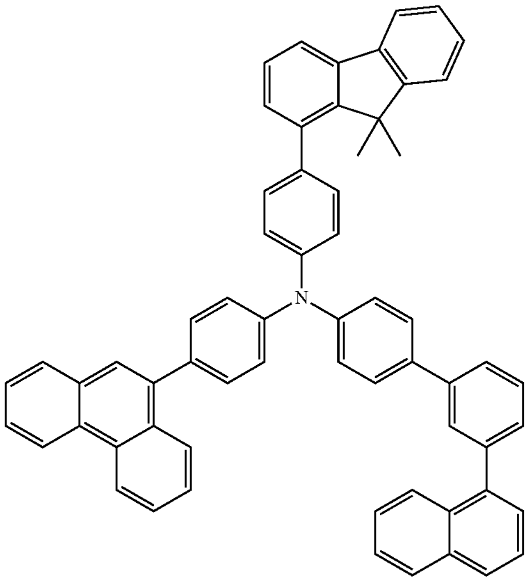

-continued
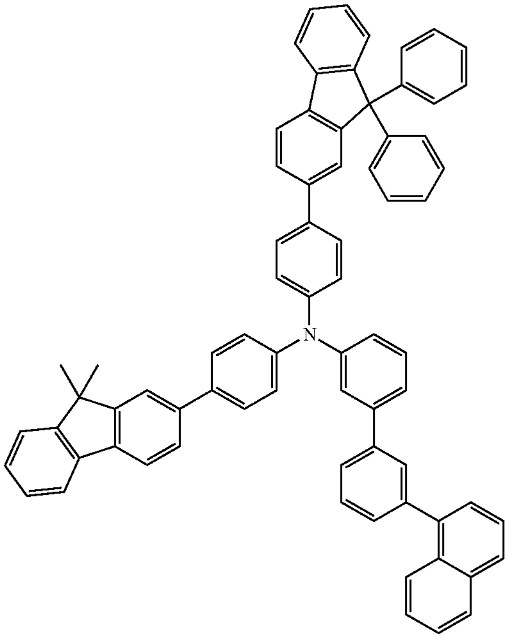
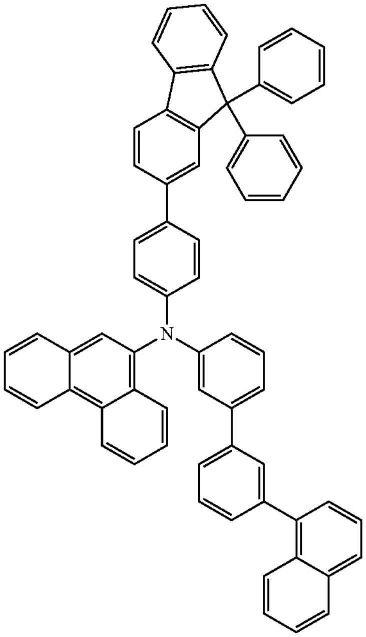
-continued
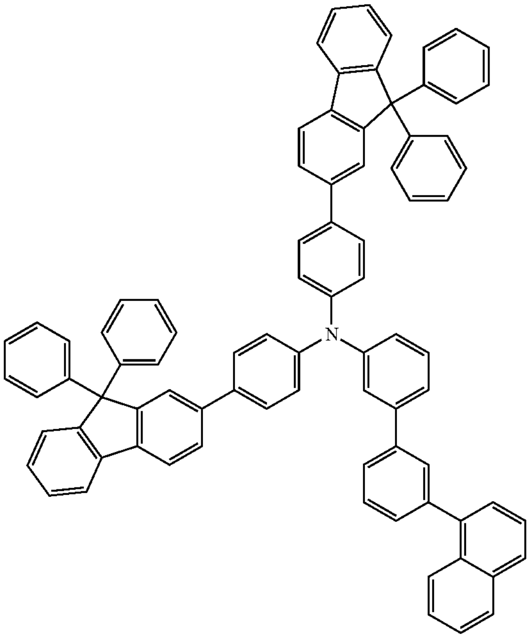
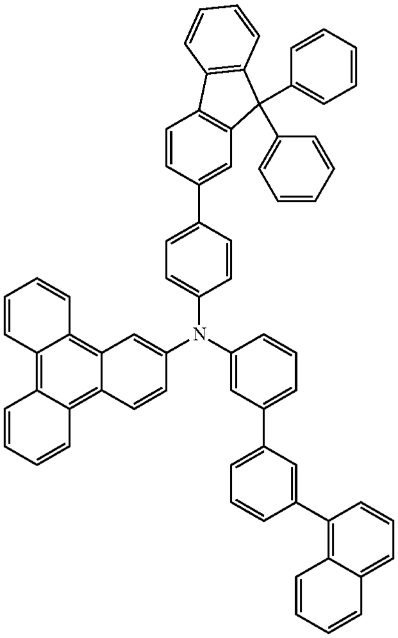

-continued
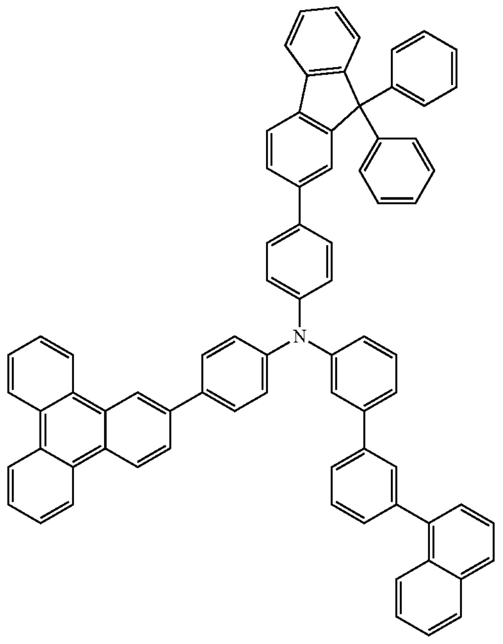
-continued
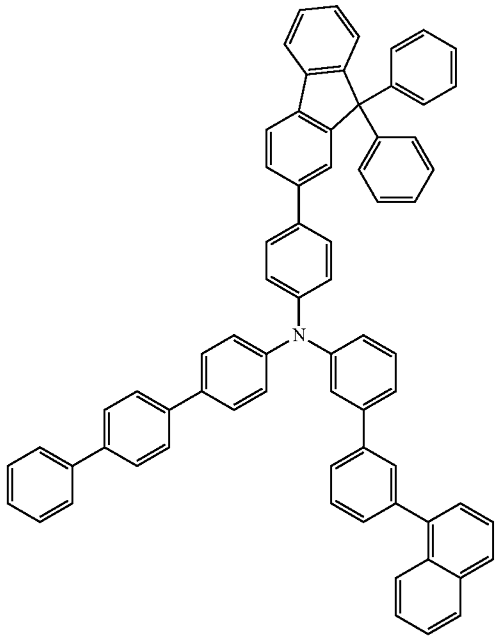
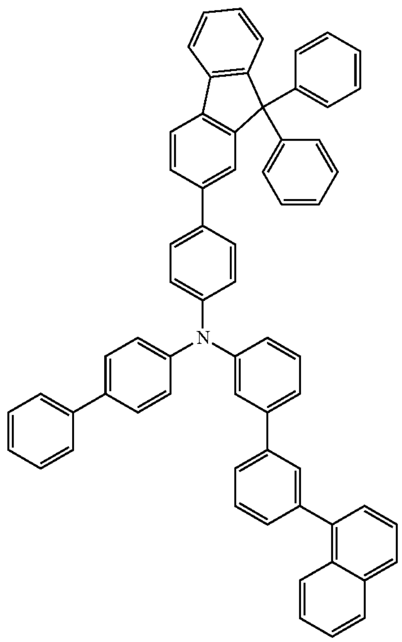
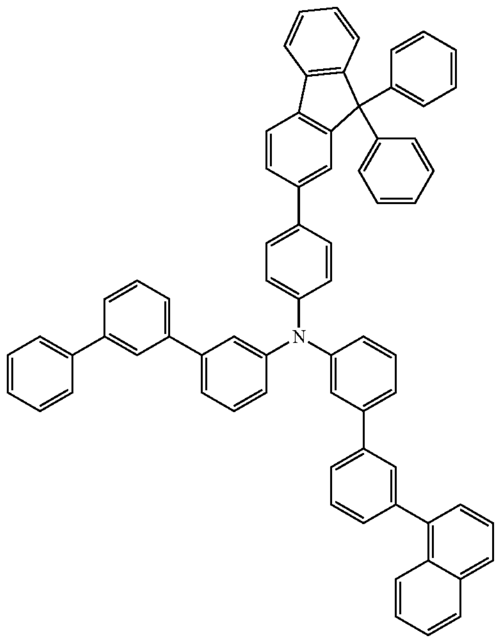

-continued
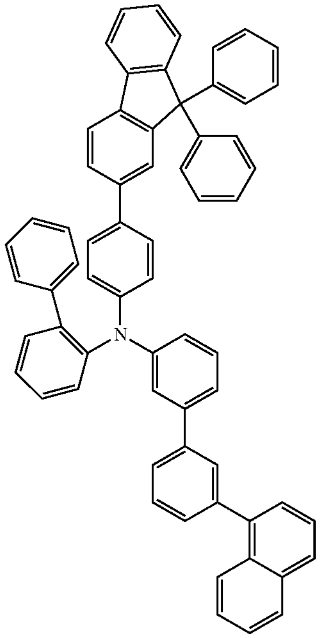
-continued
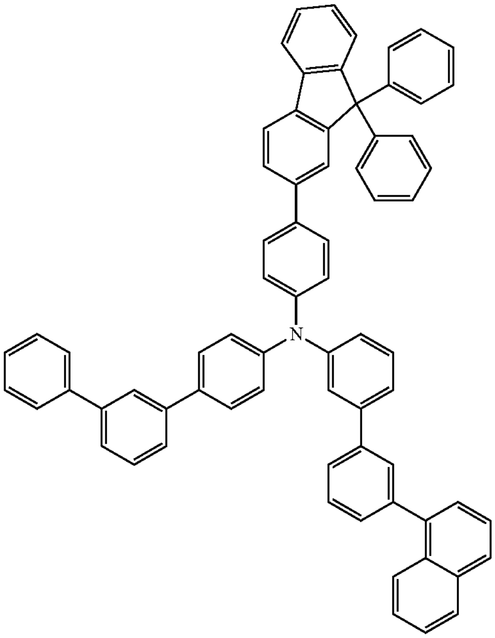
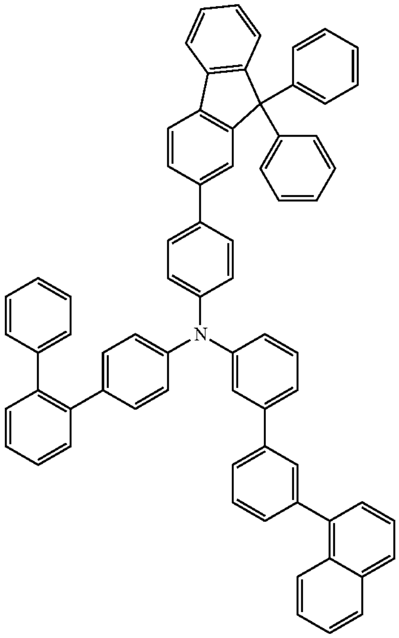
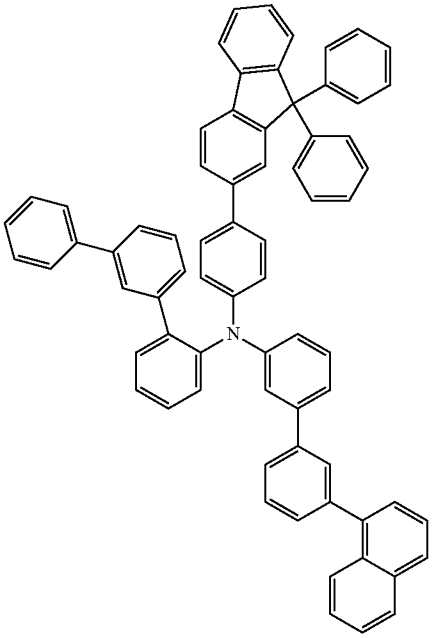

-continued
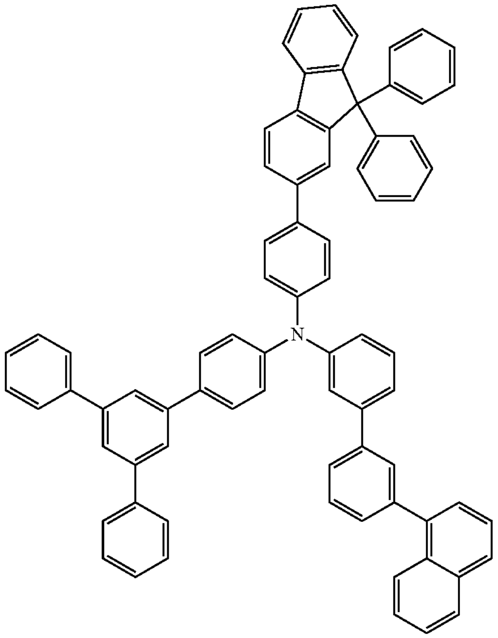 [SMILES: c1ccc(-c2cc(-c3ccccc3)cc(-c3ccc(N(c4ccc(-c5ccc6c(c5)C(c5ccccc5)(c5ccccc5)c5ccccc5-6)cc4)c4cccc(-c5cccc(-c6cccc7ccccc67)c5)c4)cc3)c2)cc1]
-continued
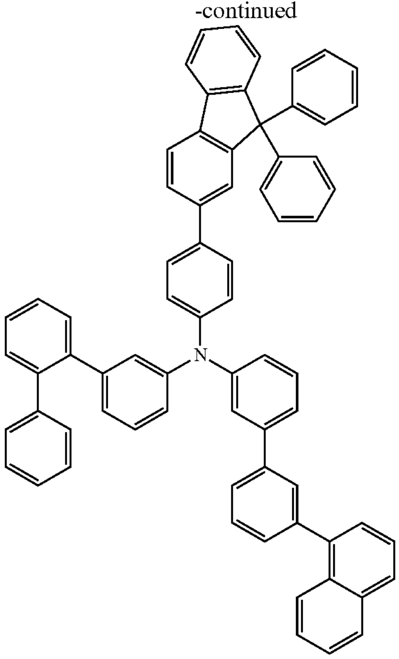
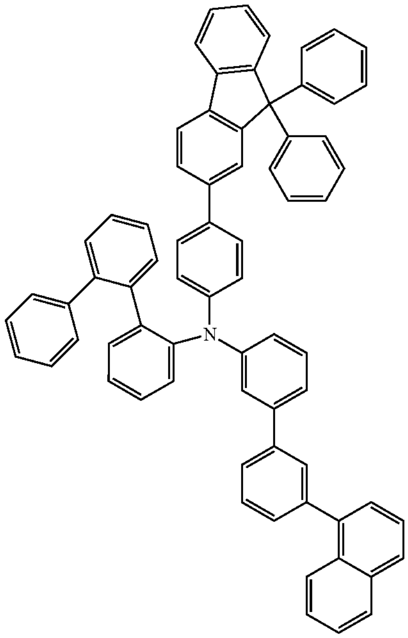
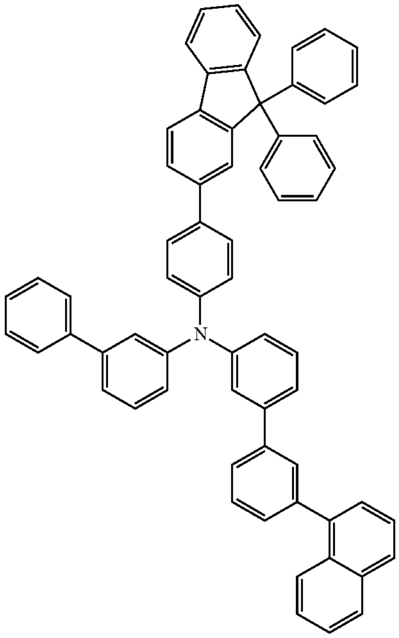

-continued
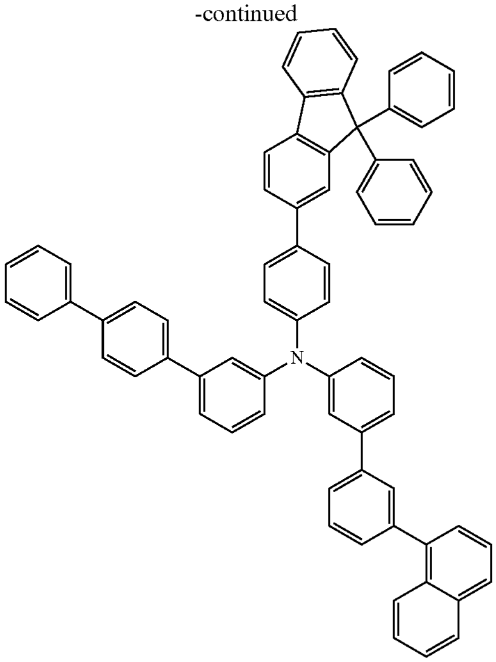
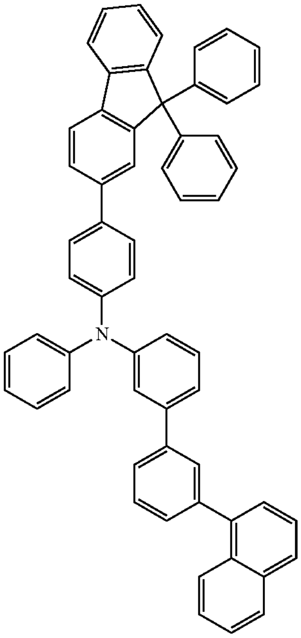
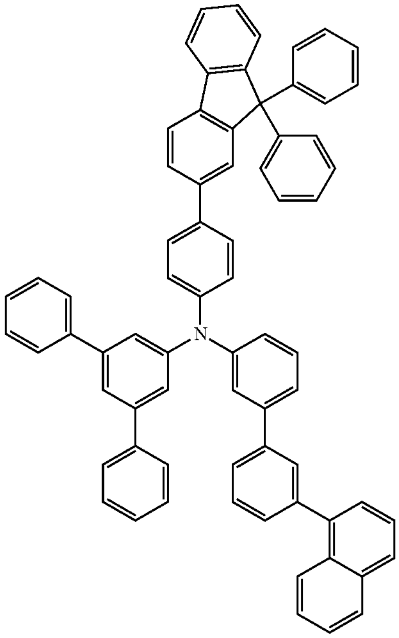
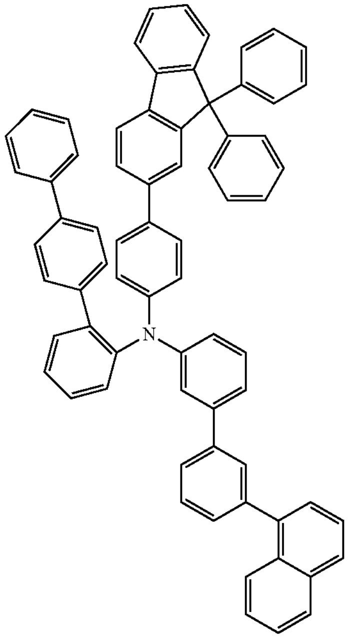

-continued
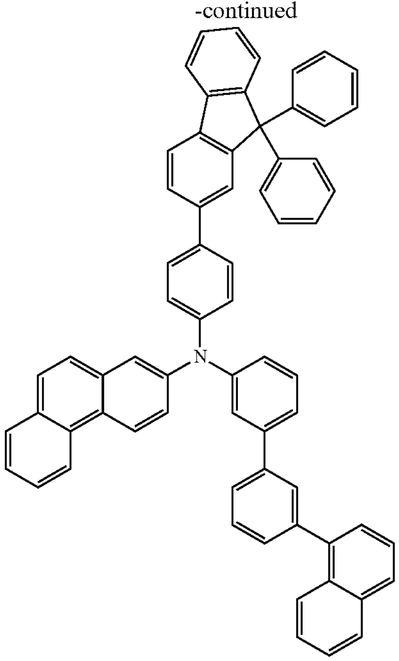
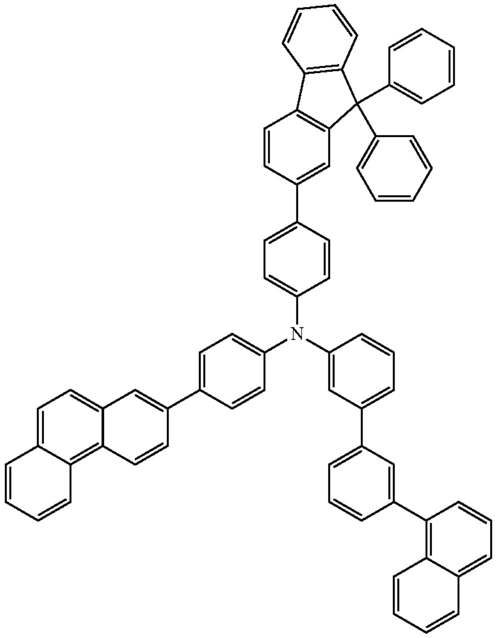
-continued
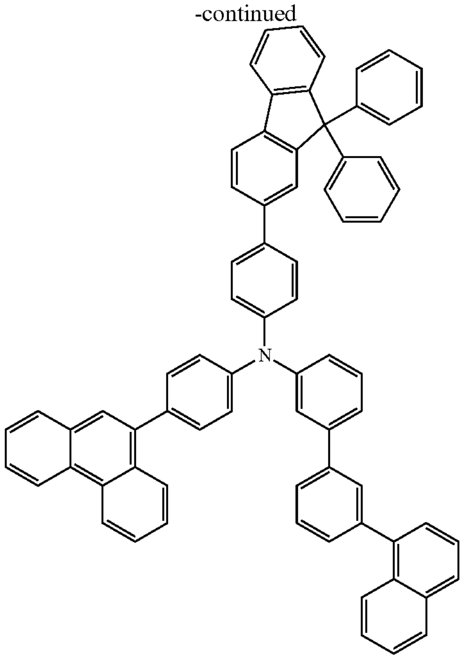
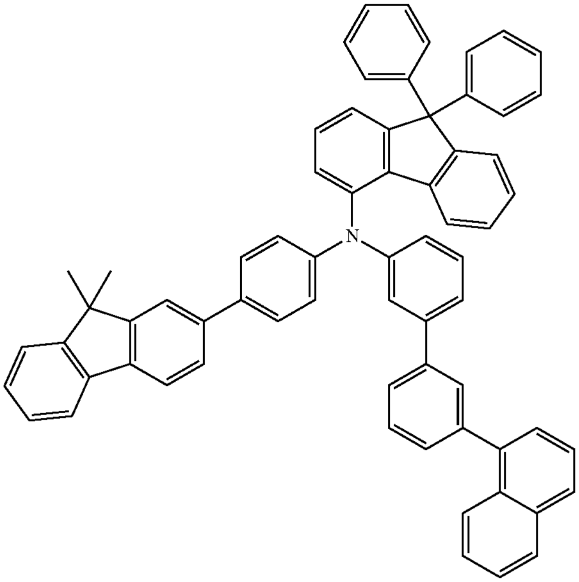

-continued
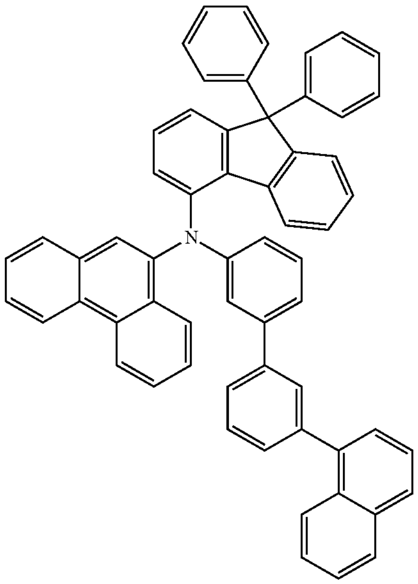
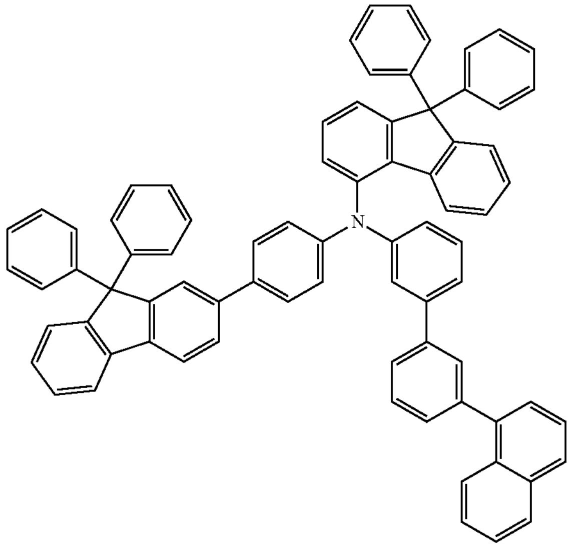
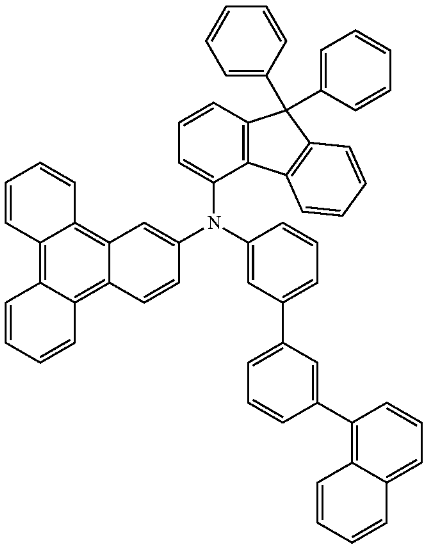
-continued
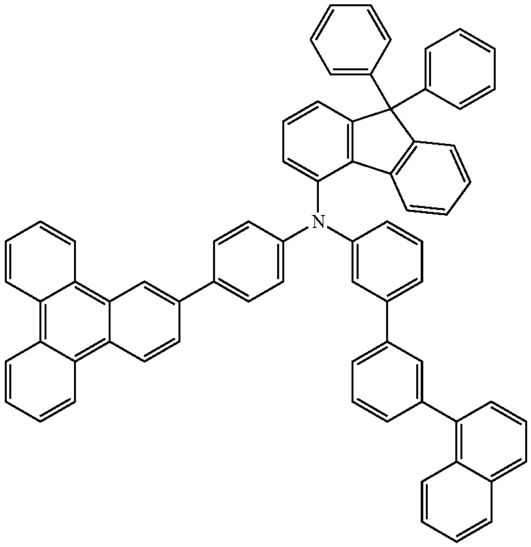
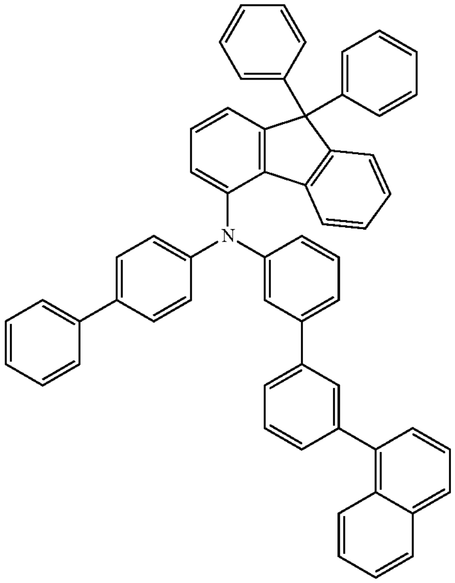
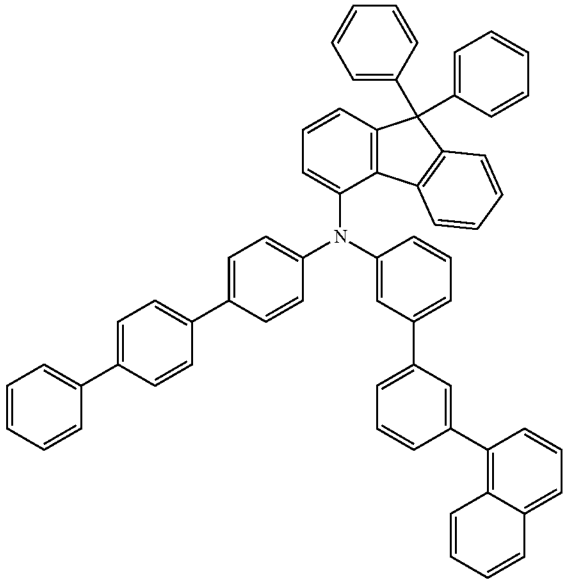

-continued
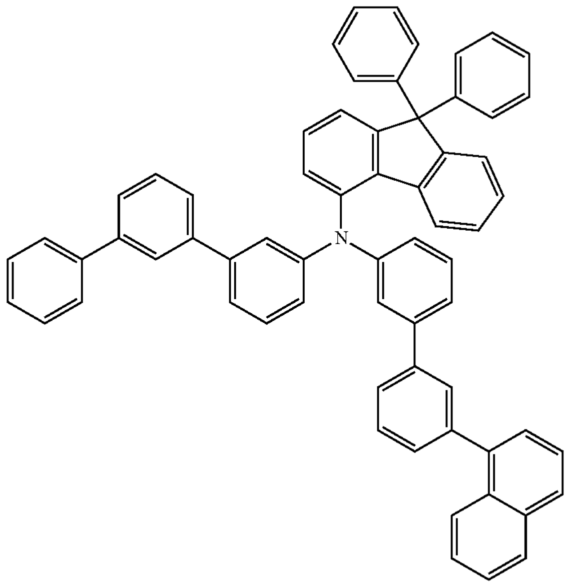
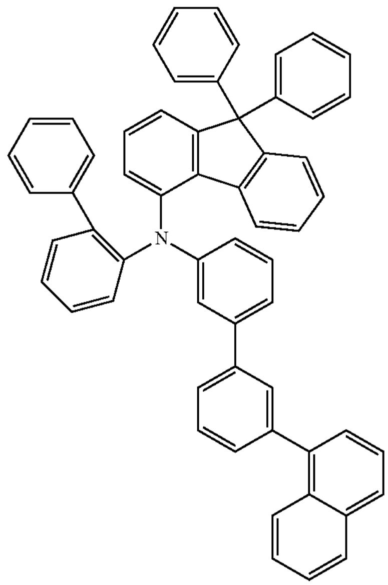
-continued
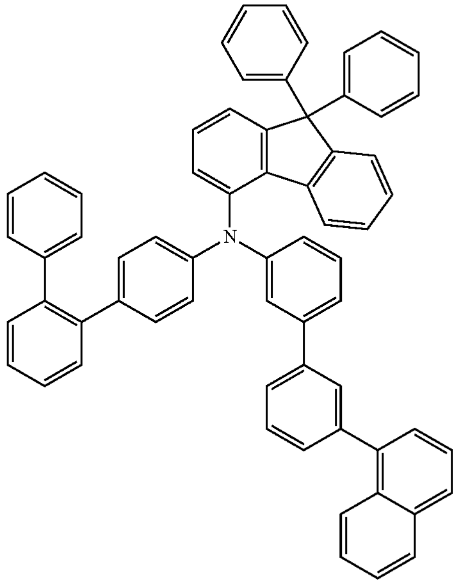
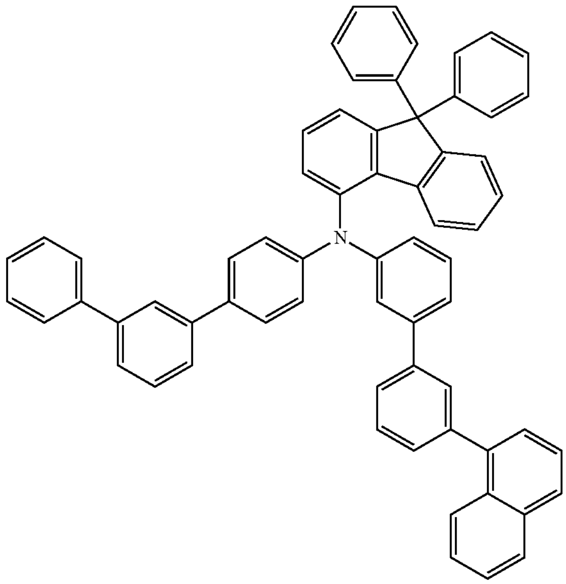

-continued
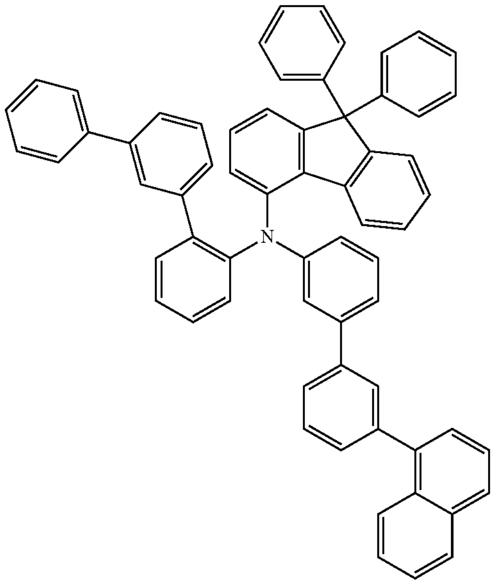
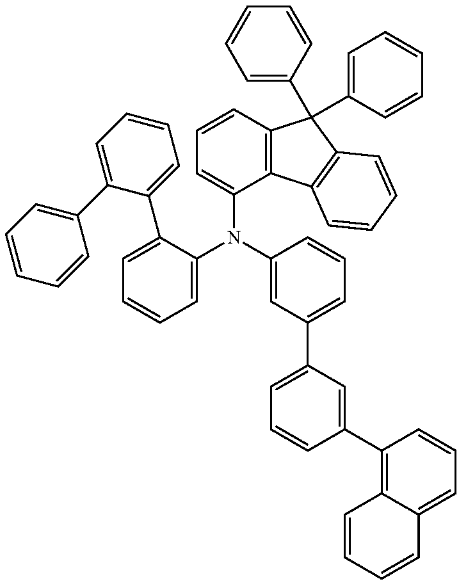
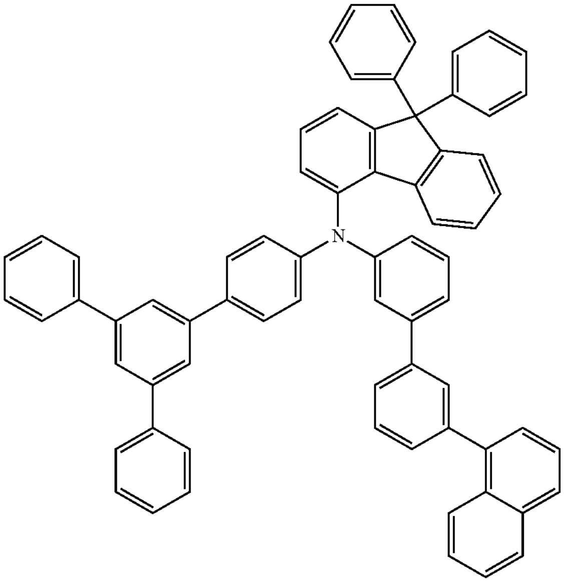
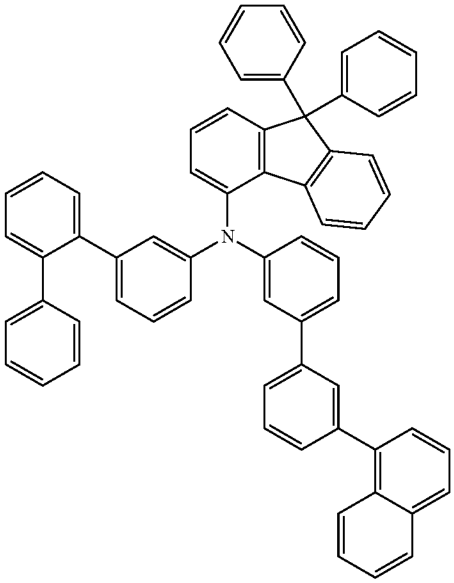
-continued

-continued
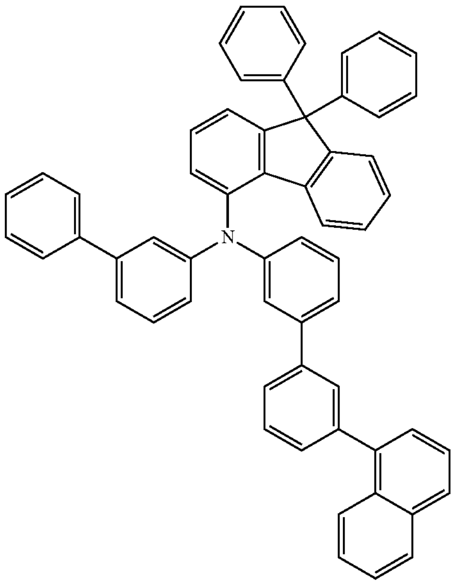
-continued
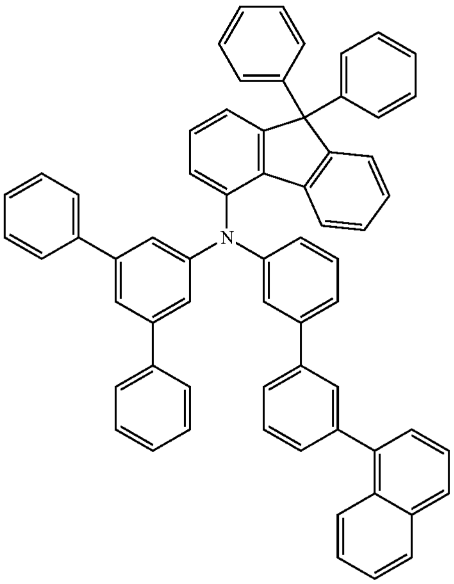
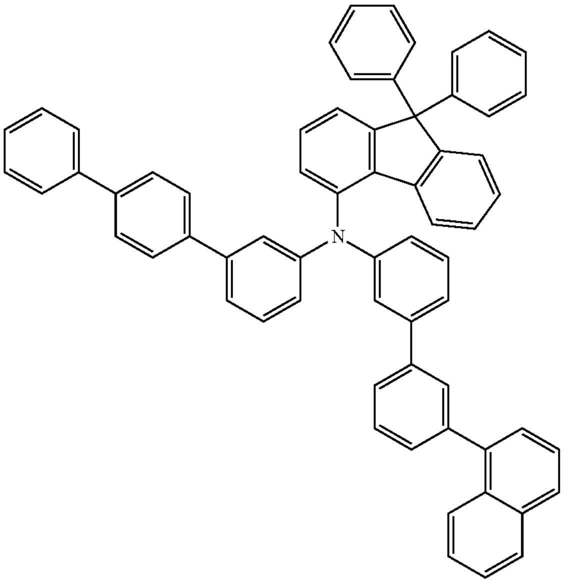
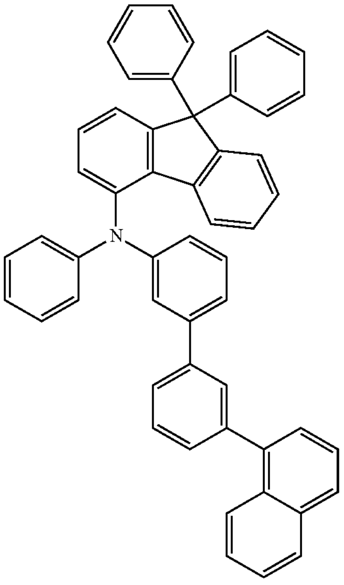

-continued
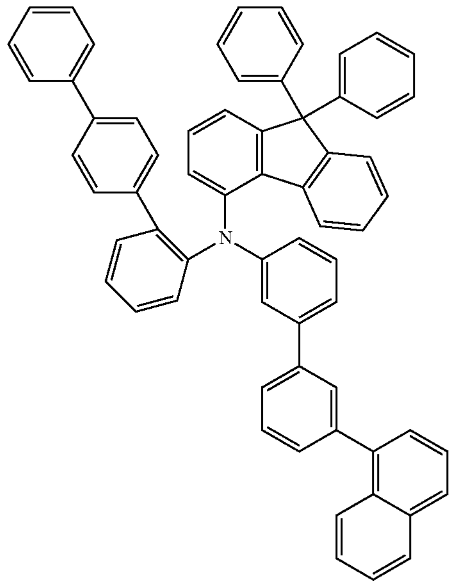
-continued
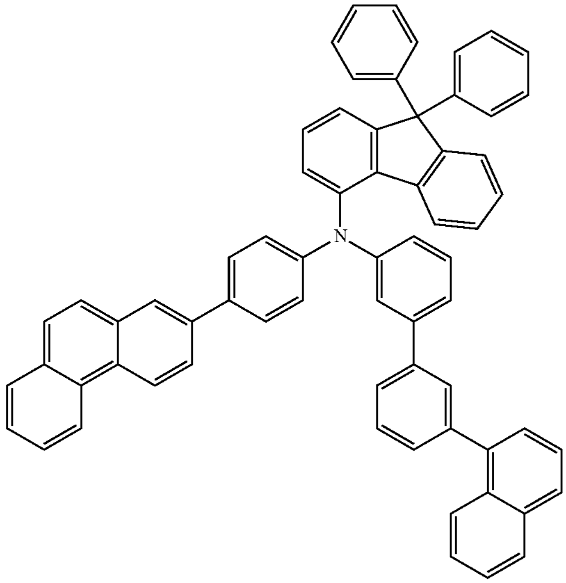
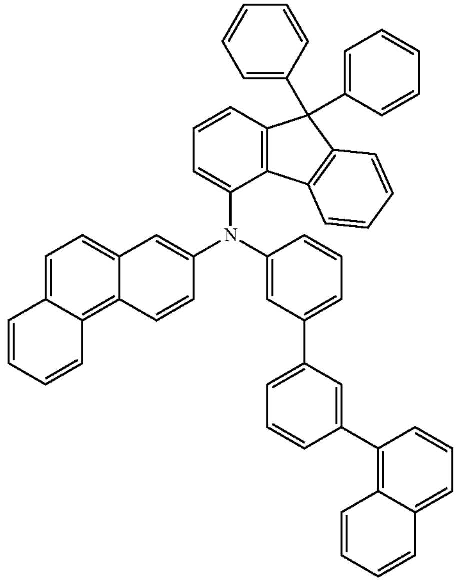
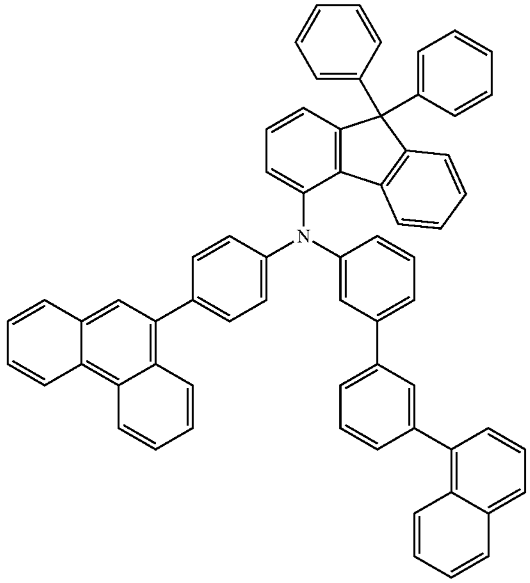

-continued
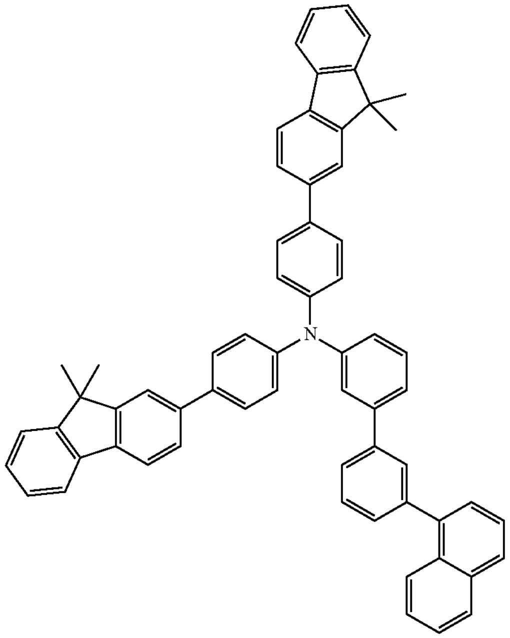
-continued
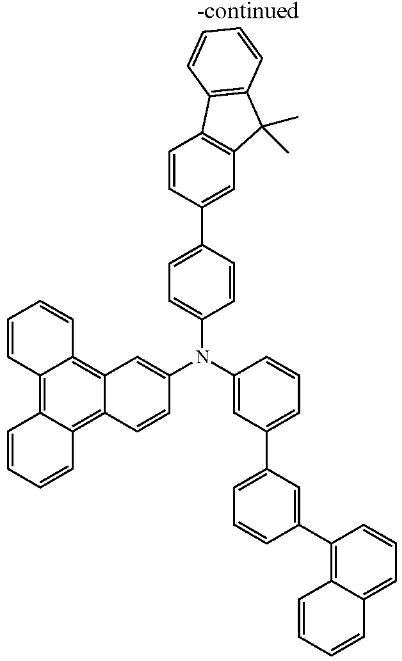
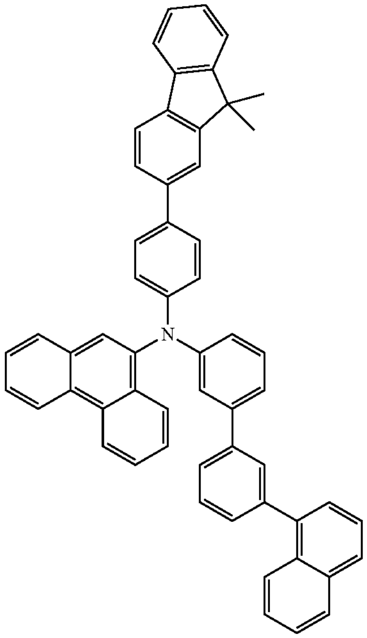
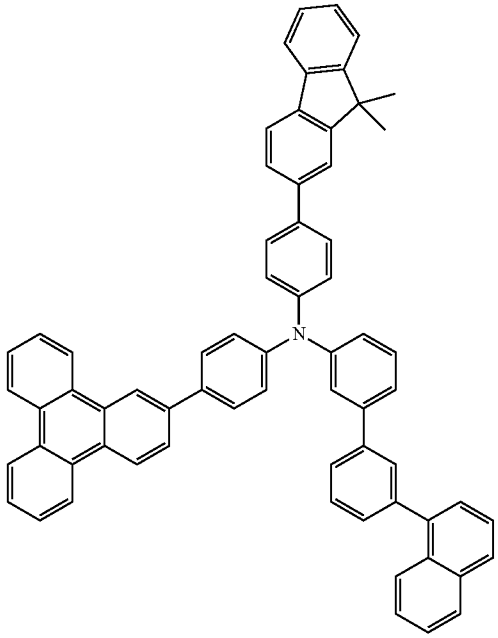

-continued
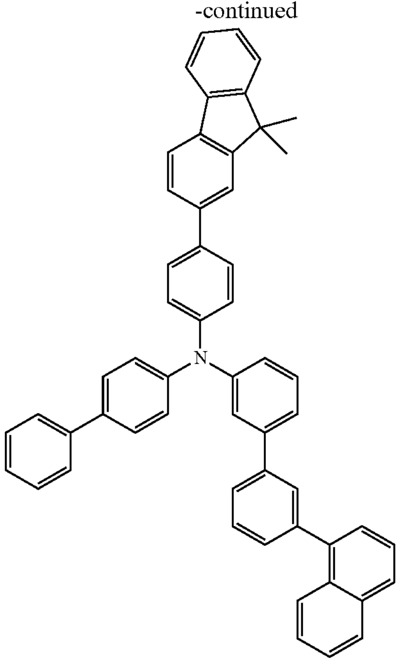
-continued
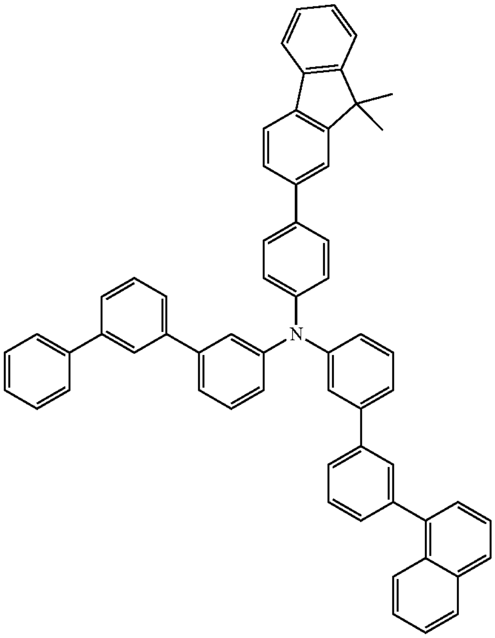
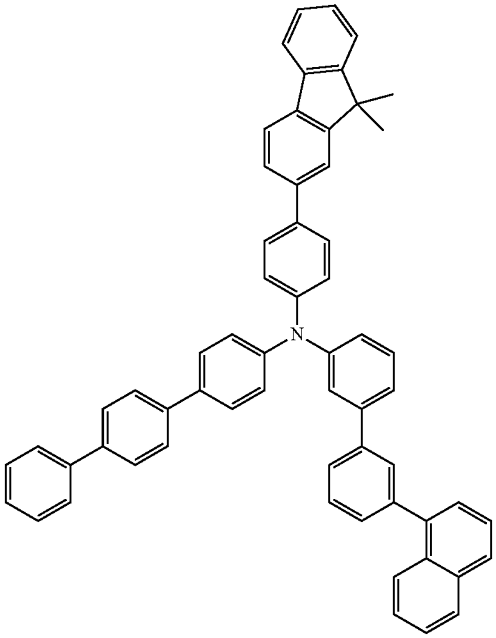
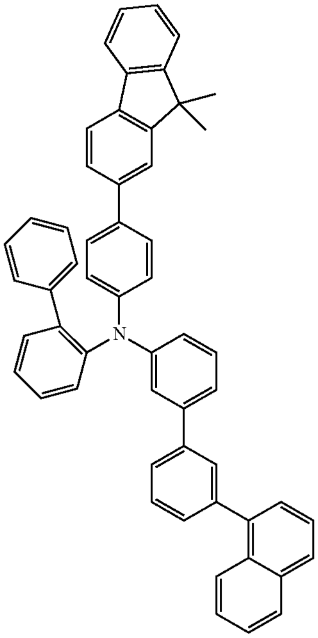

-continued
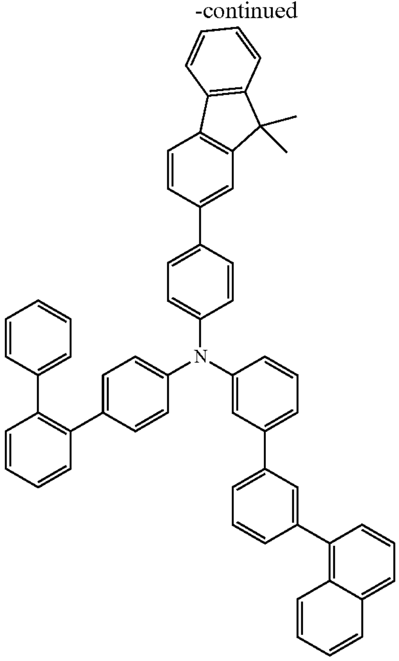
-continued
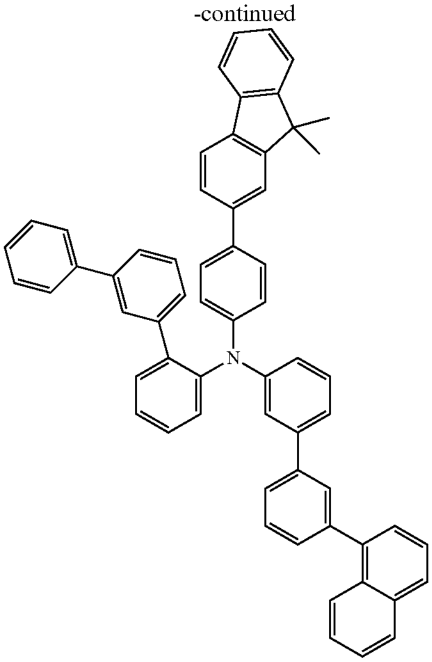
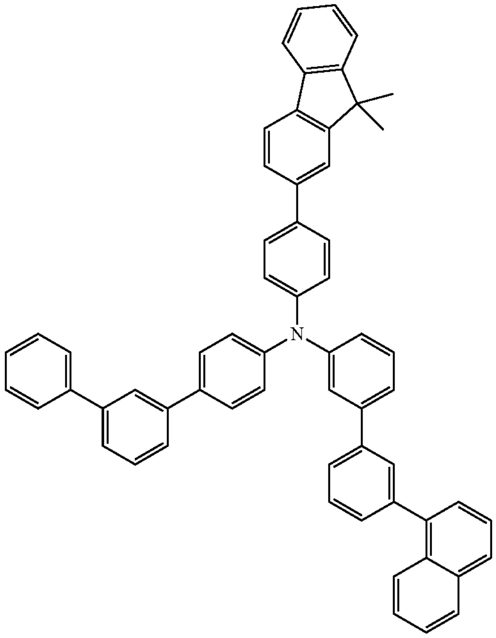
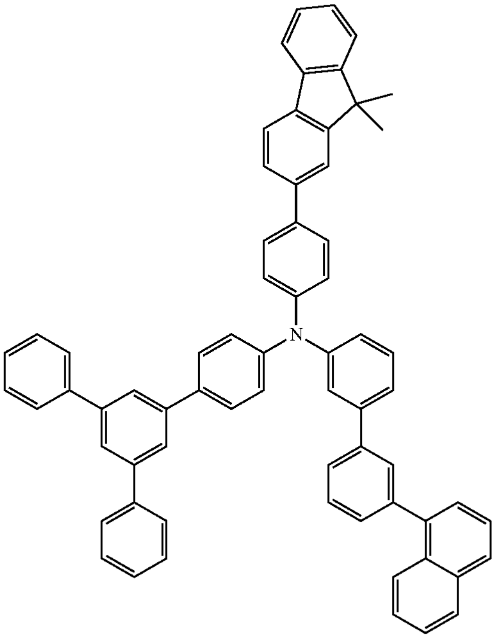

-continued
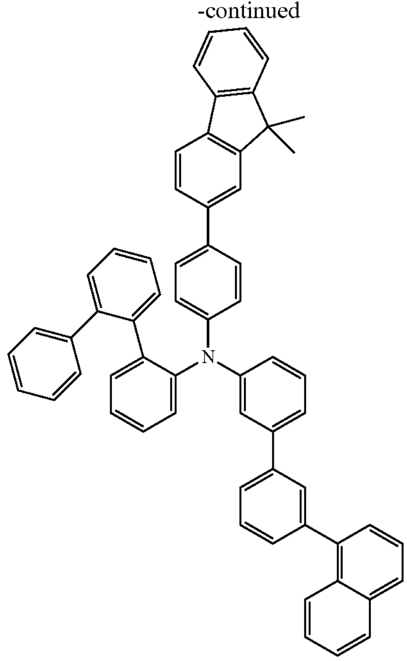
-continued
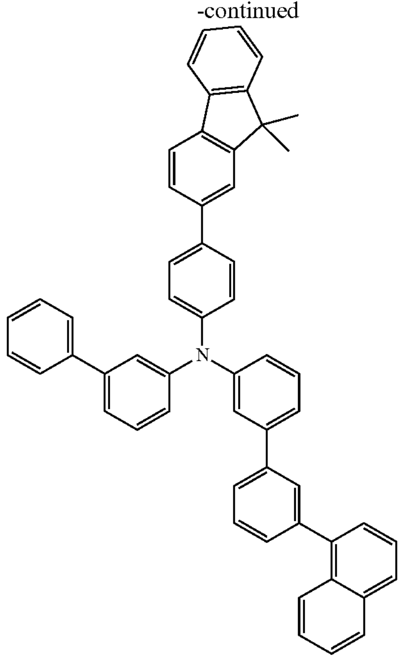
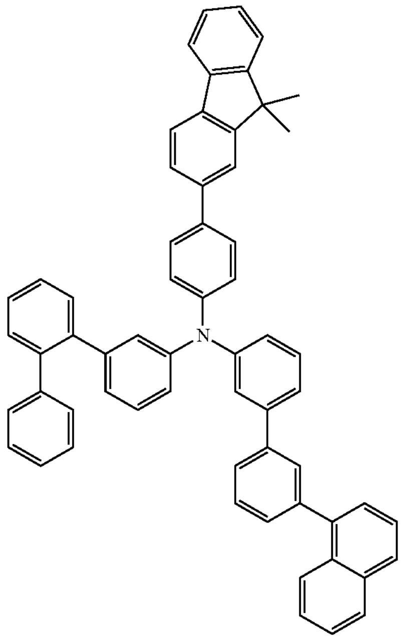
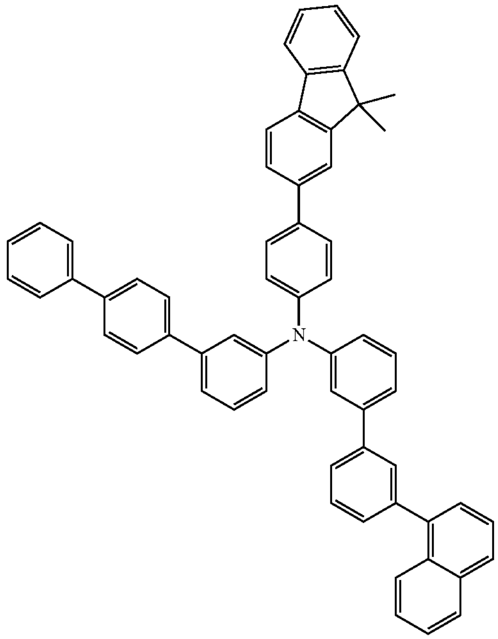

-continued
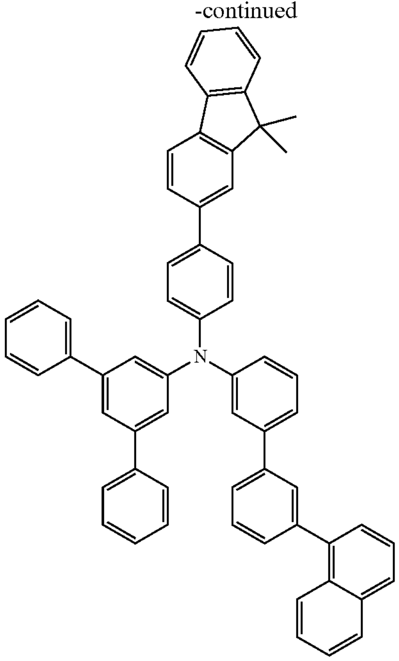
-continued
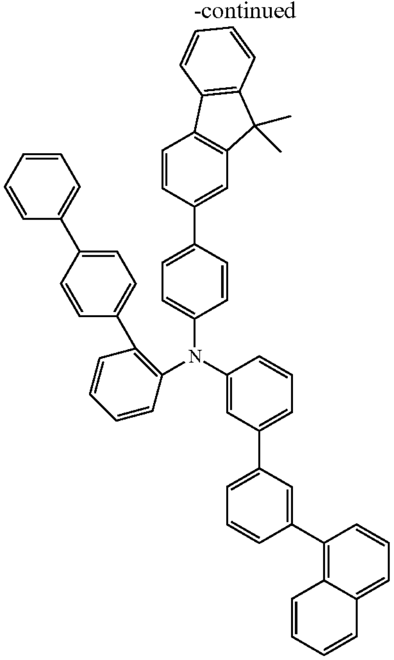
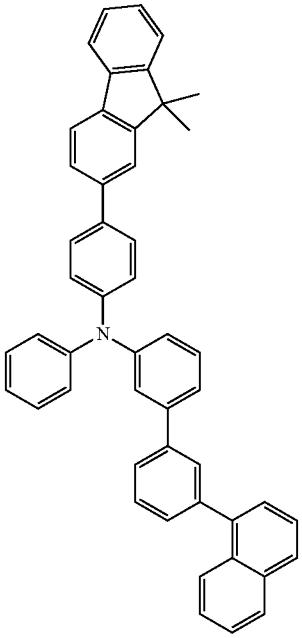
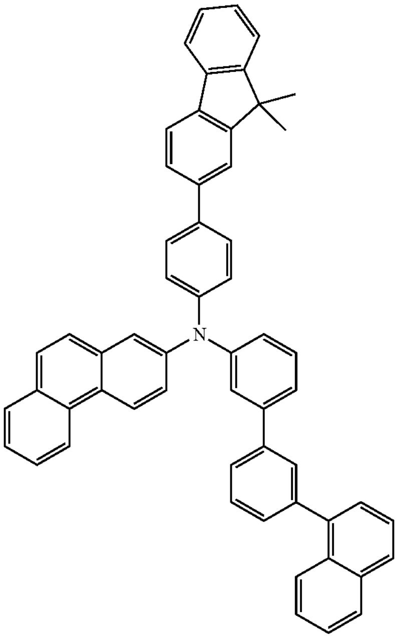

-continued
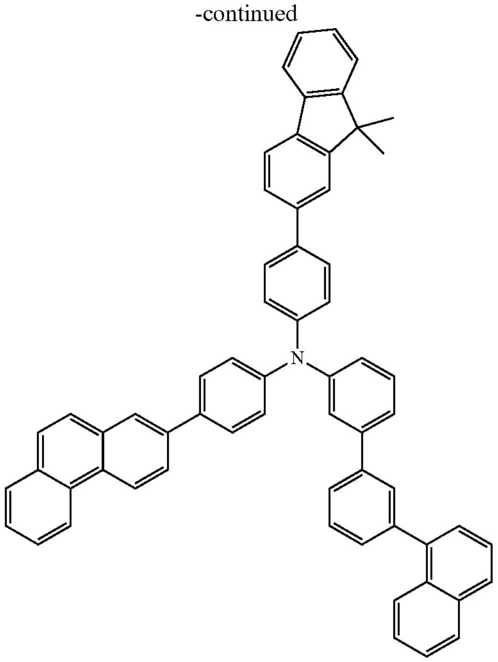
-continued
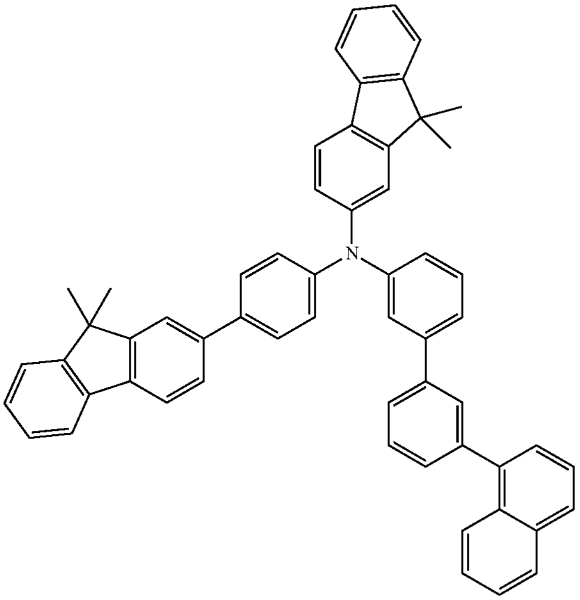
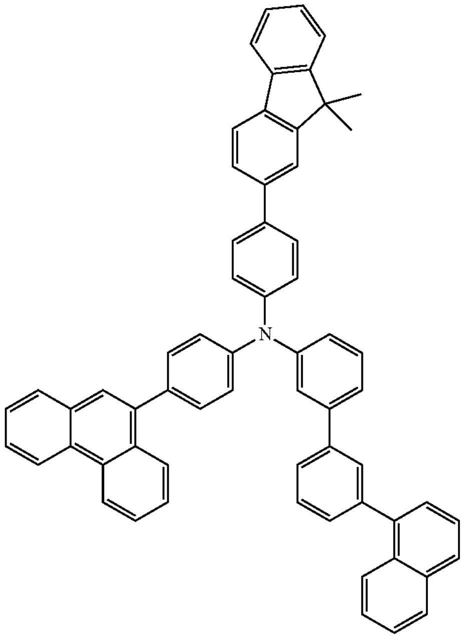
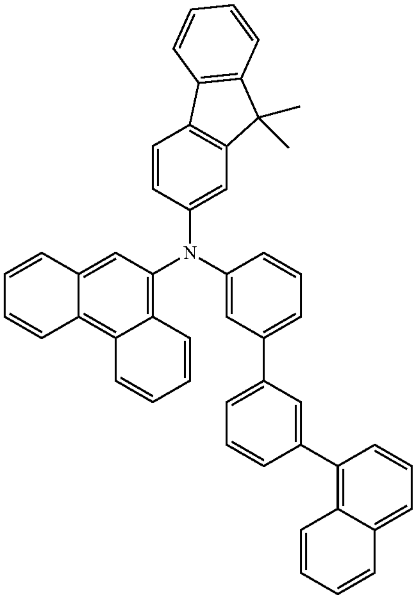

-continued
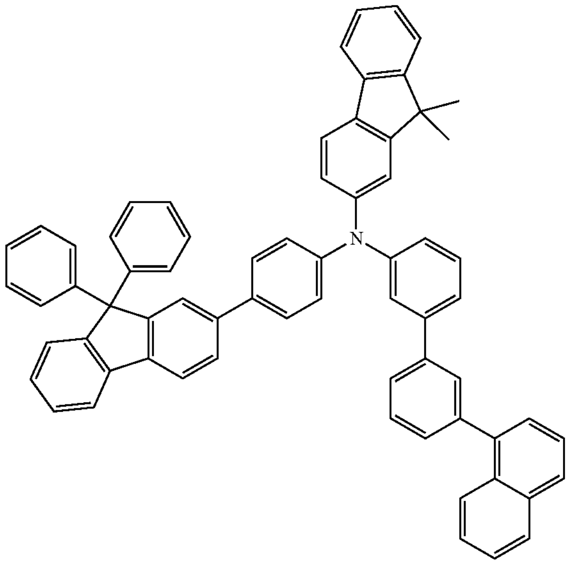
-continued
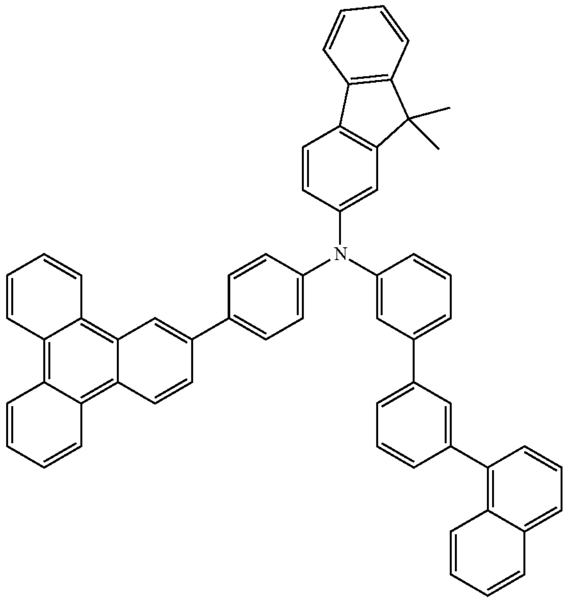
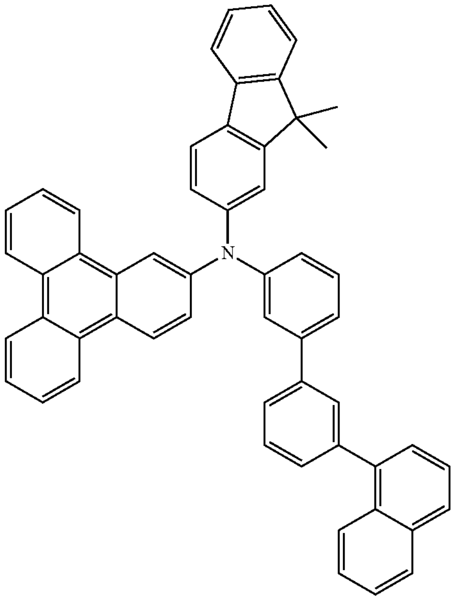
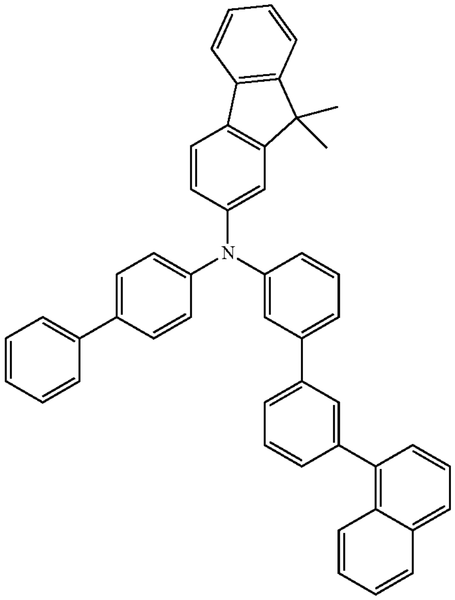

-continued
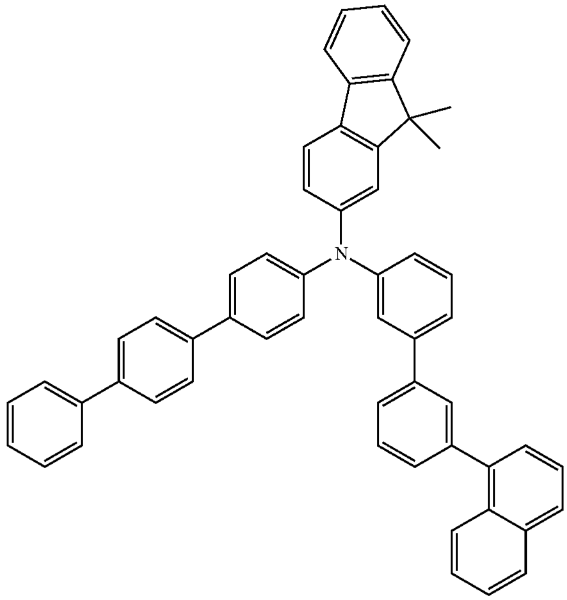
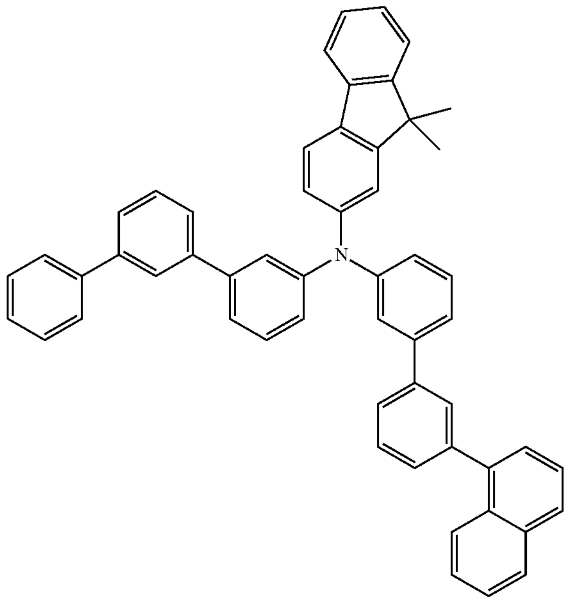
-continued
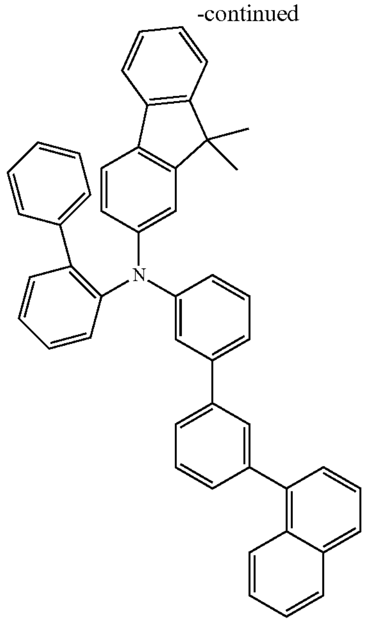
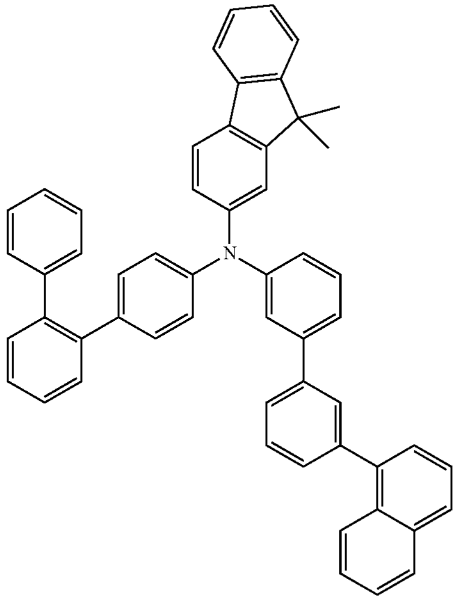

-continued
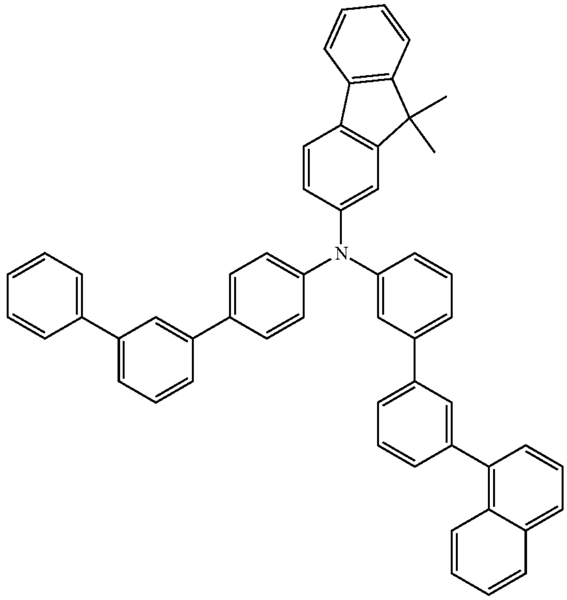
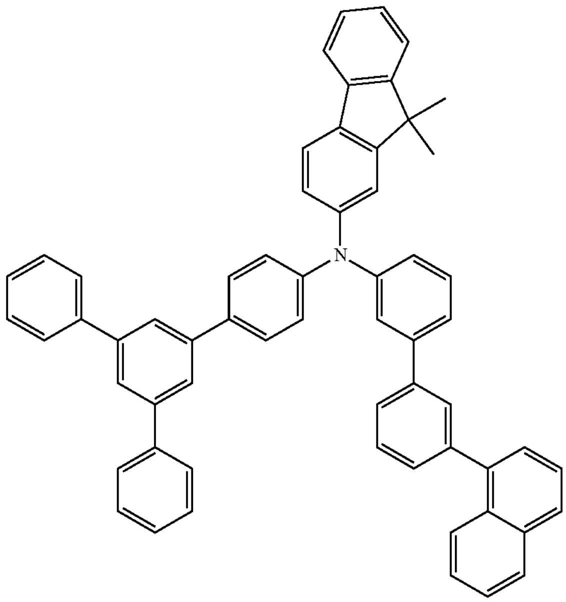
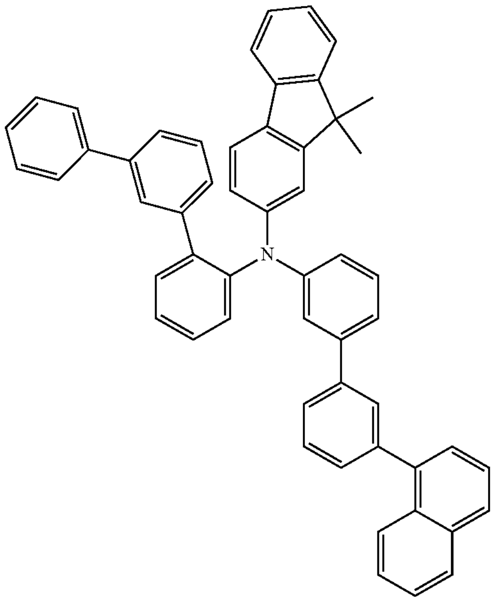
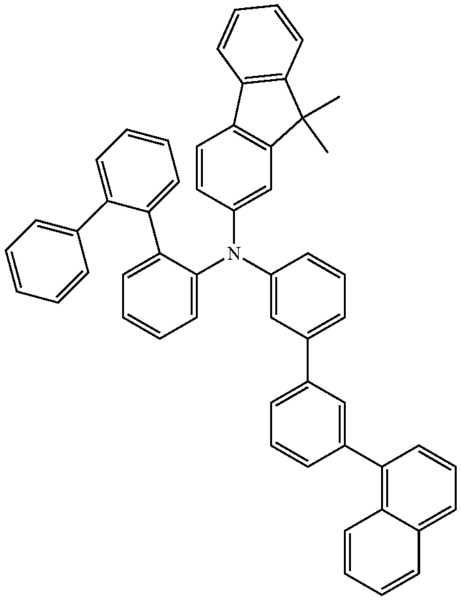

-continued
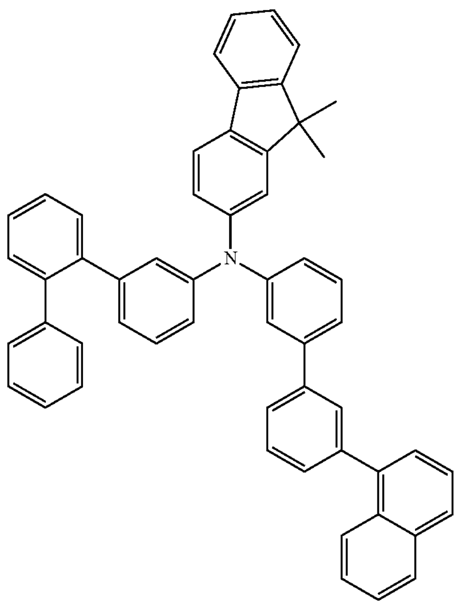
-continued
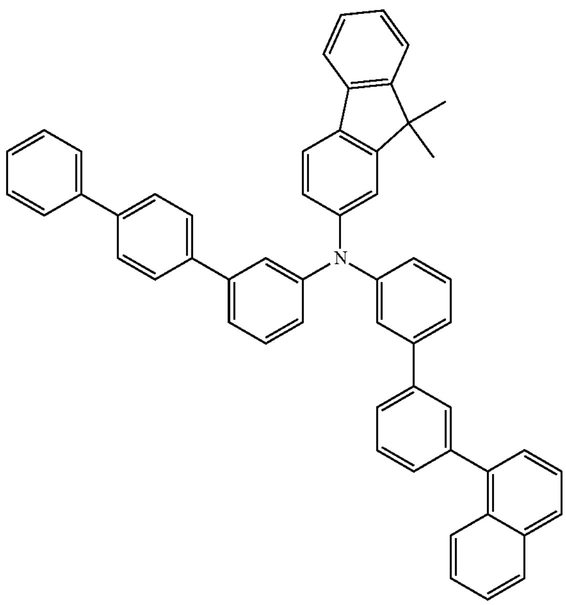
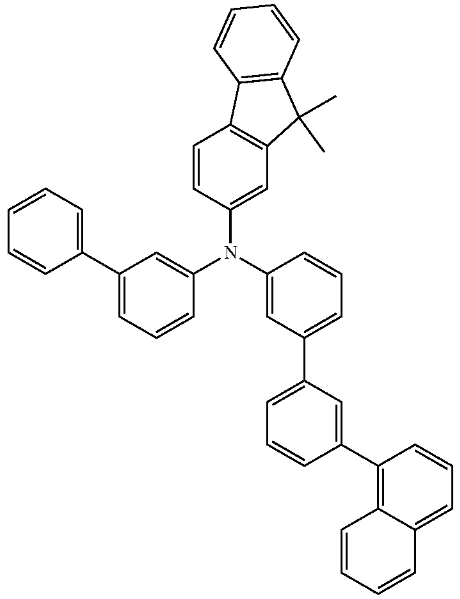
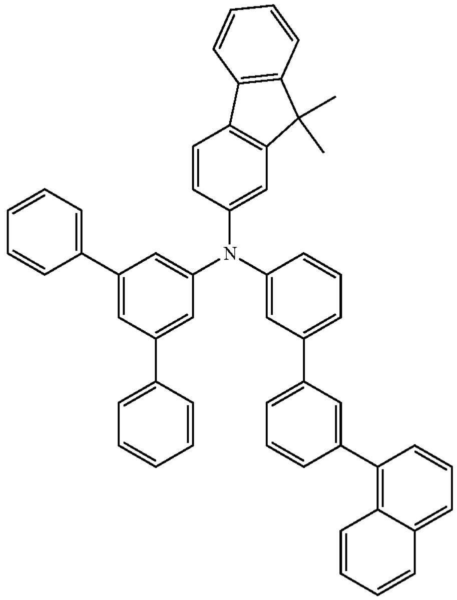

-continued
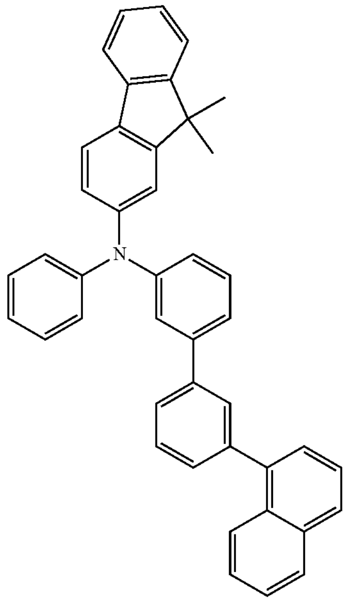
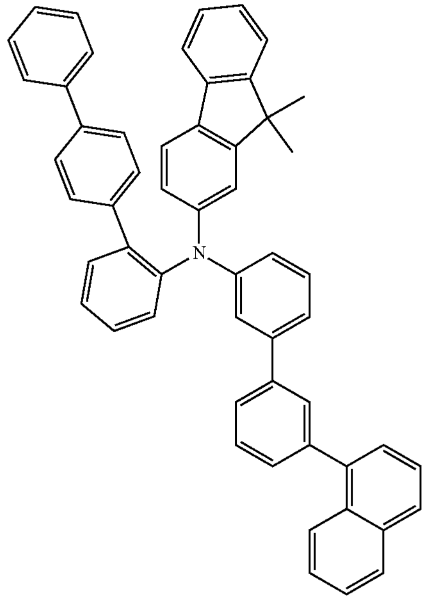
-continued
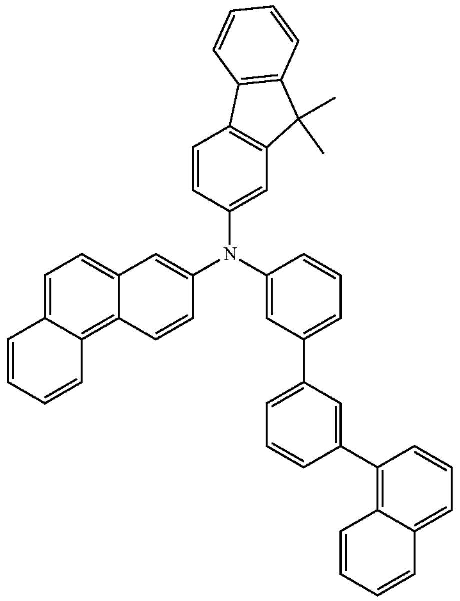
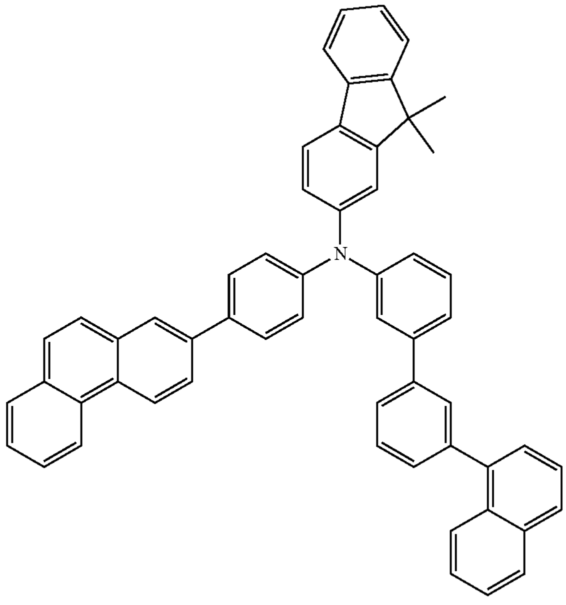

-continued
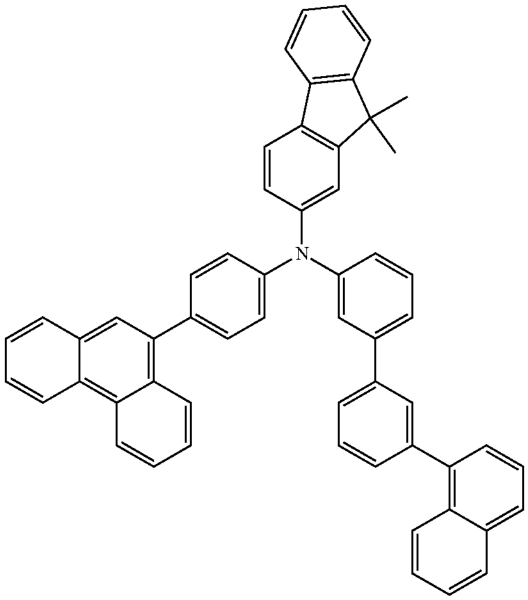
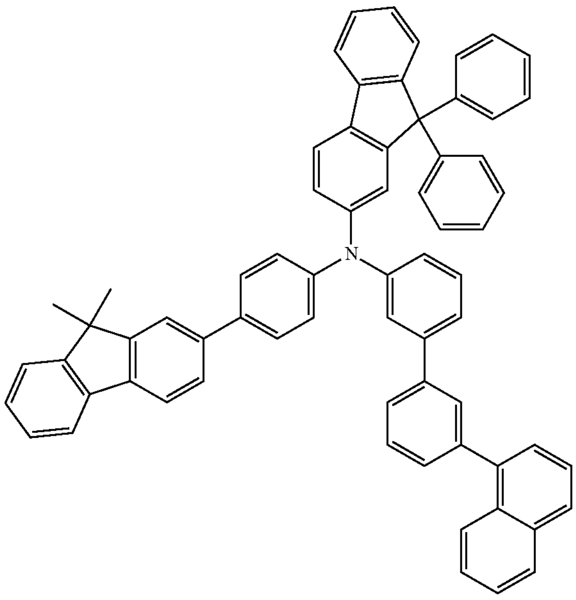
-continued
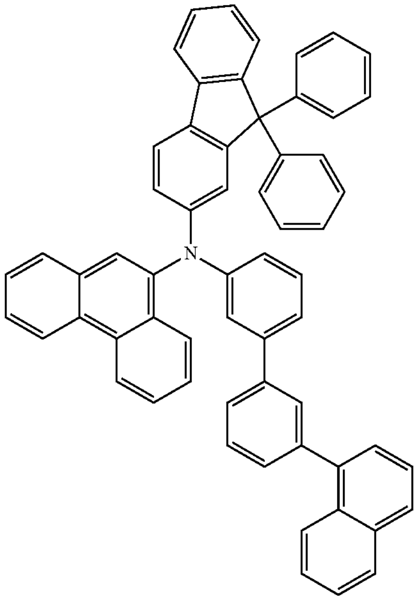
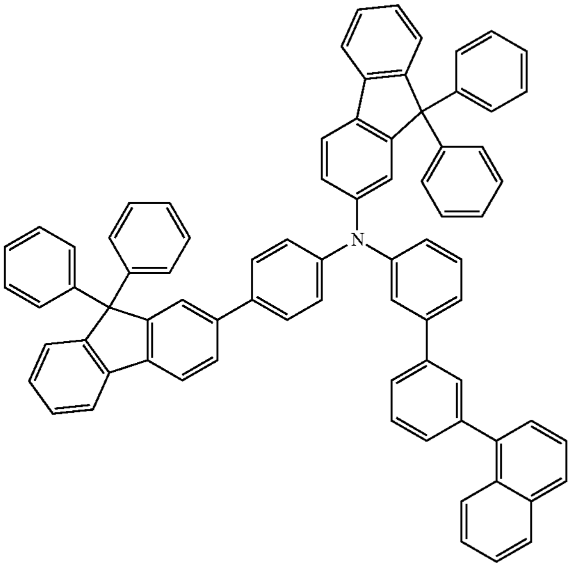

-continued
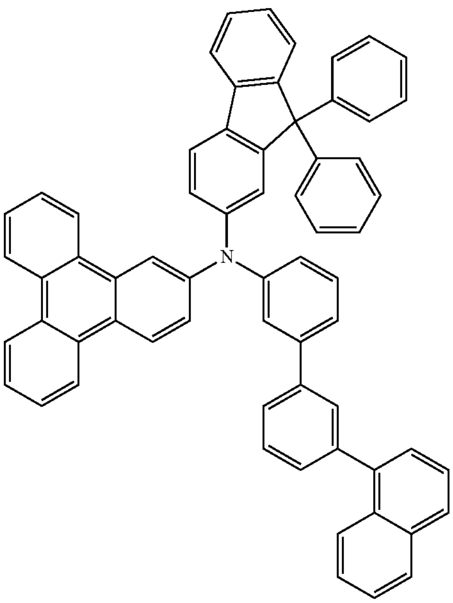
-continued
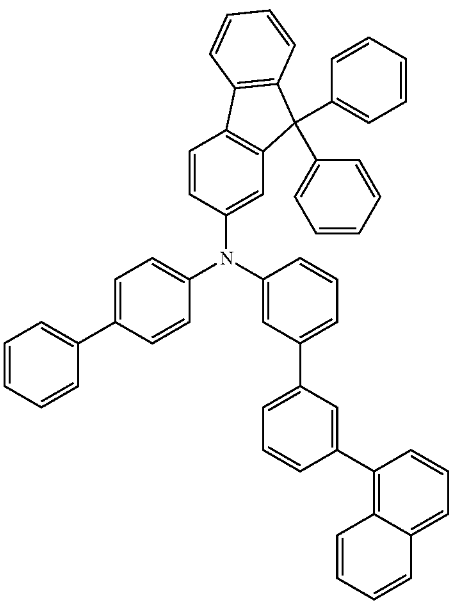
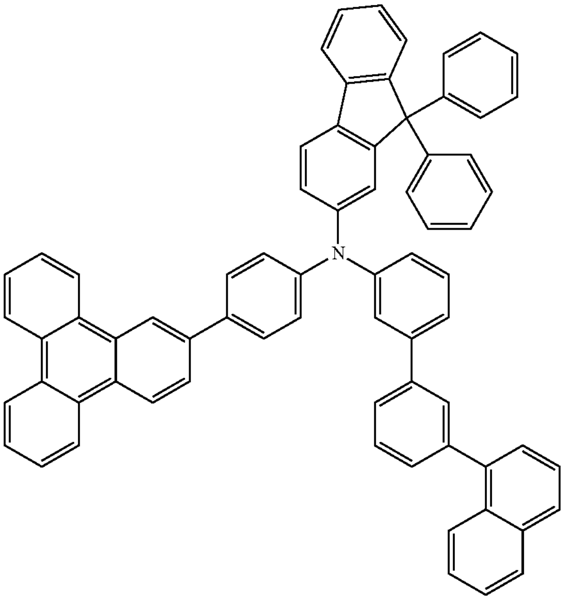
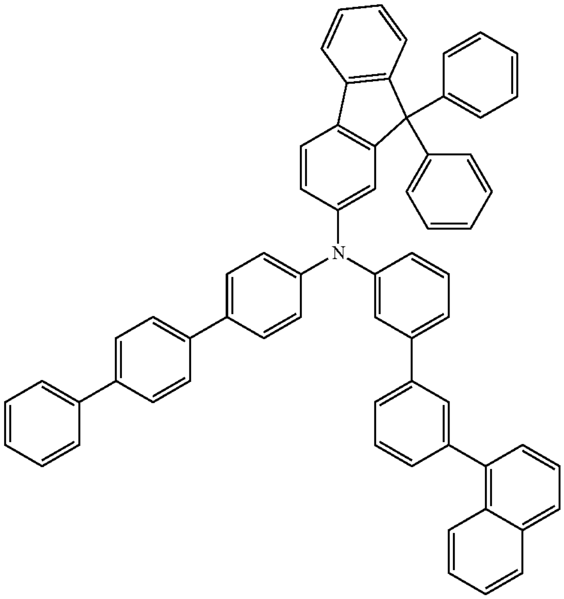

-continued
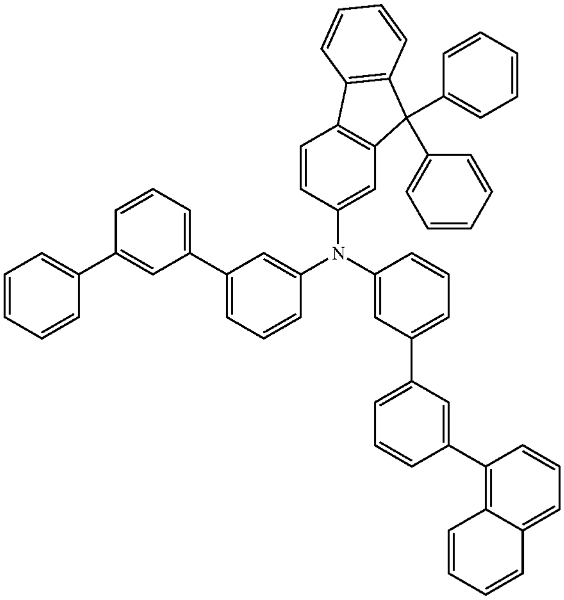
-continued
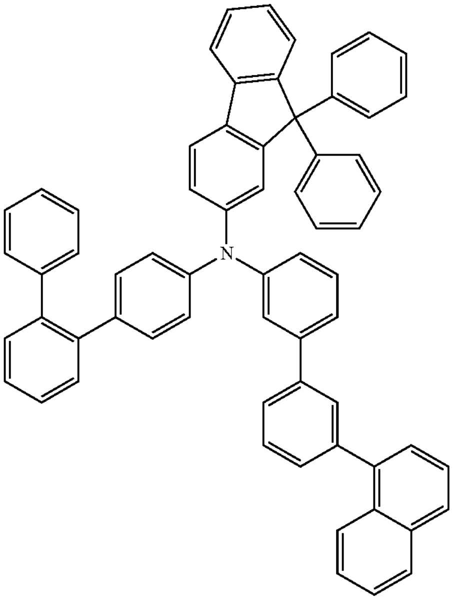
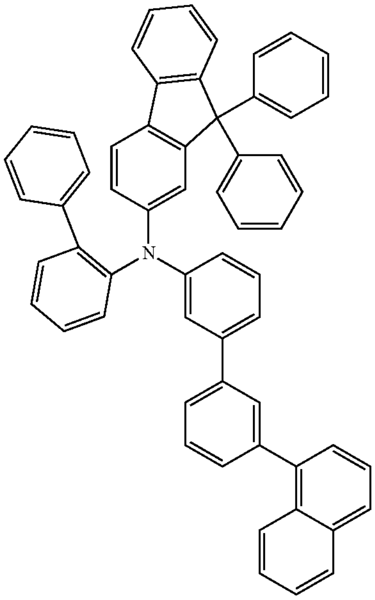
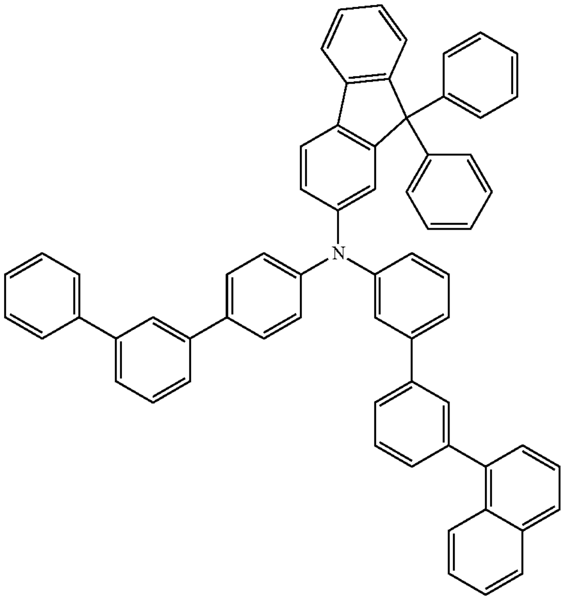

-continued
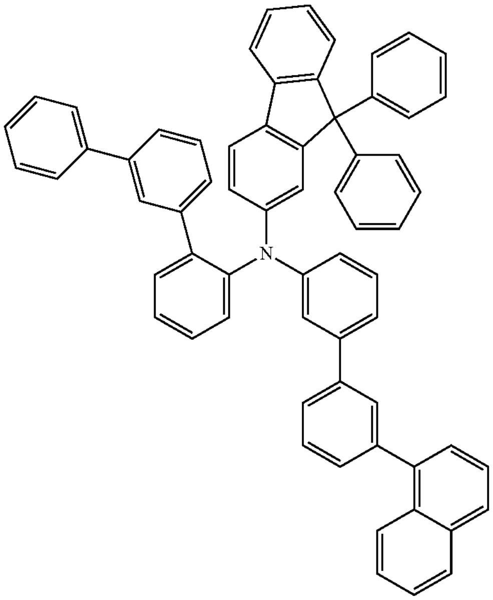
-continued
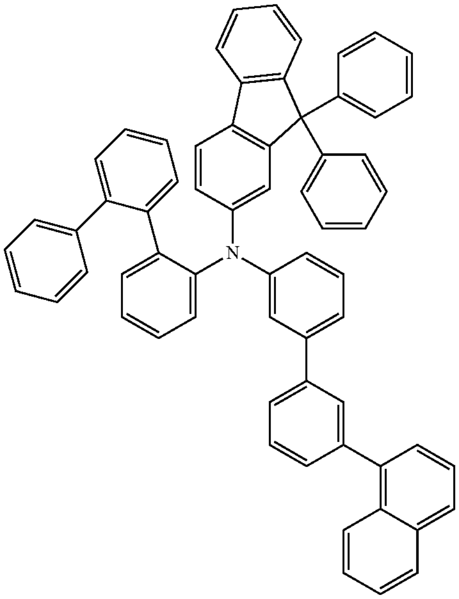
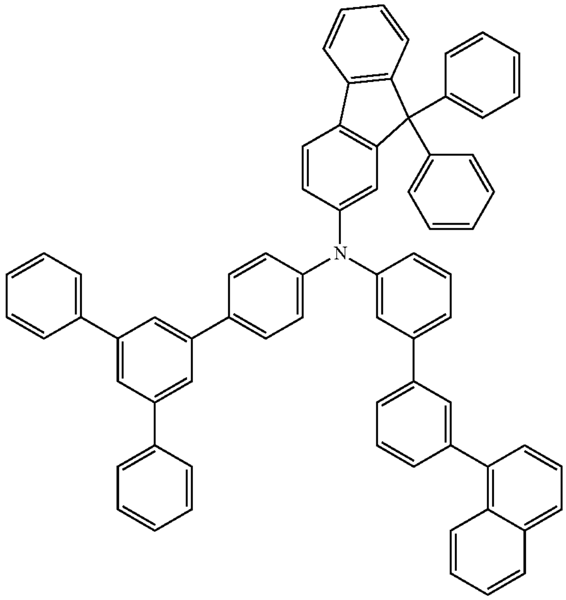
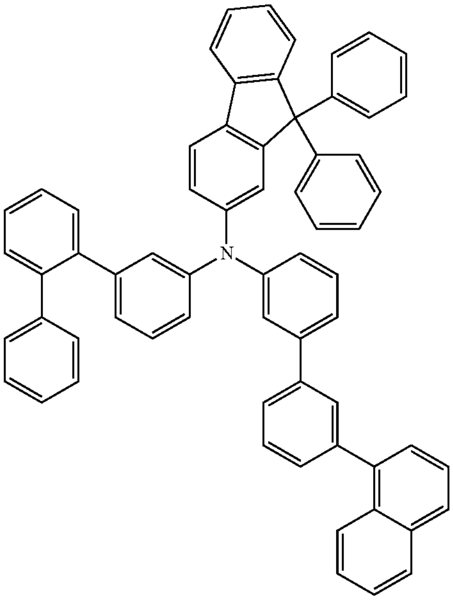

-continued
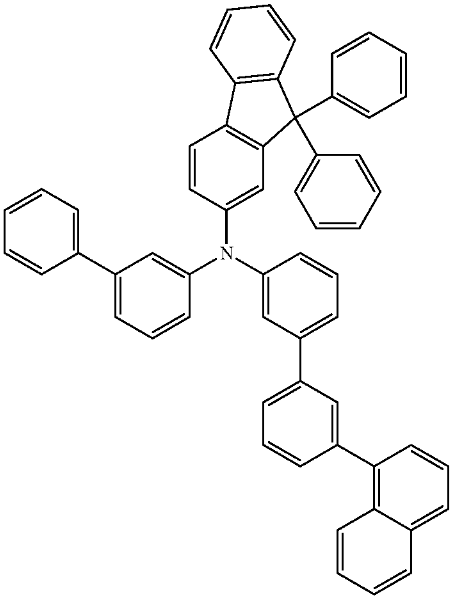
-continued
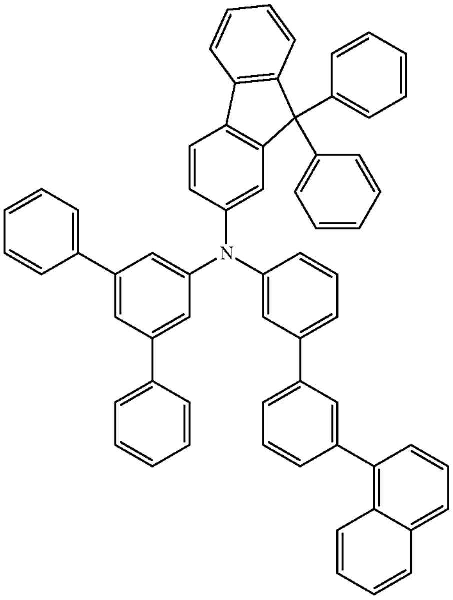
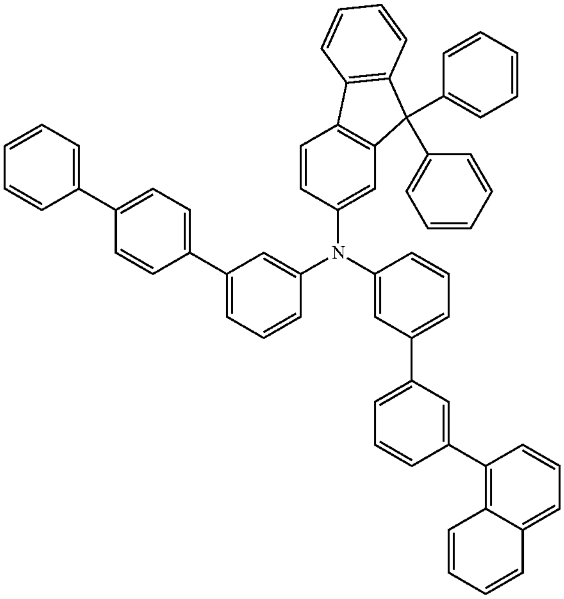
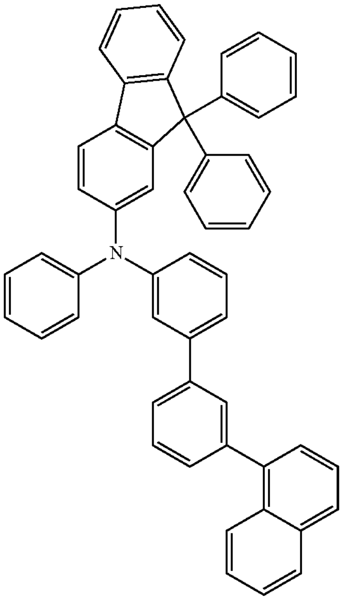

-continued
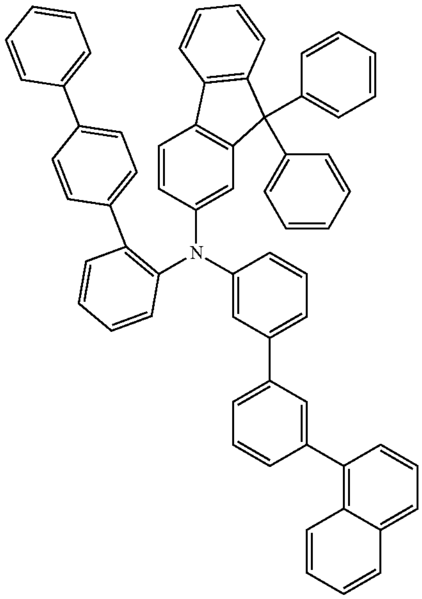
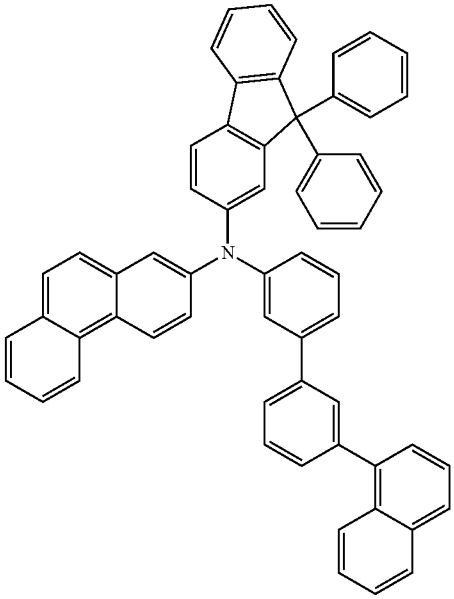
-continued
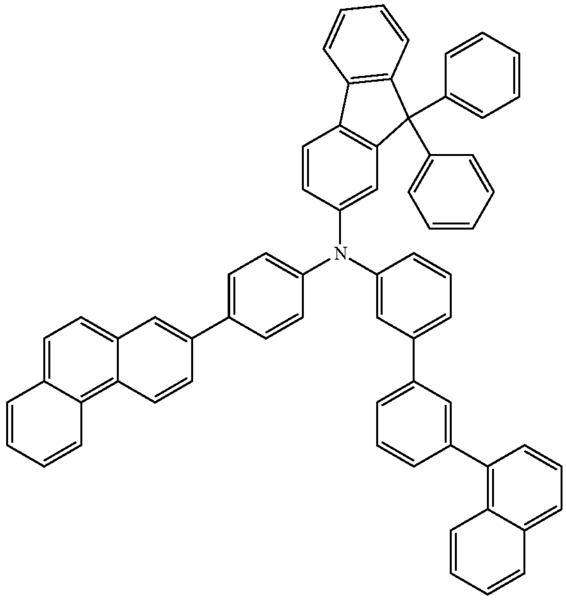
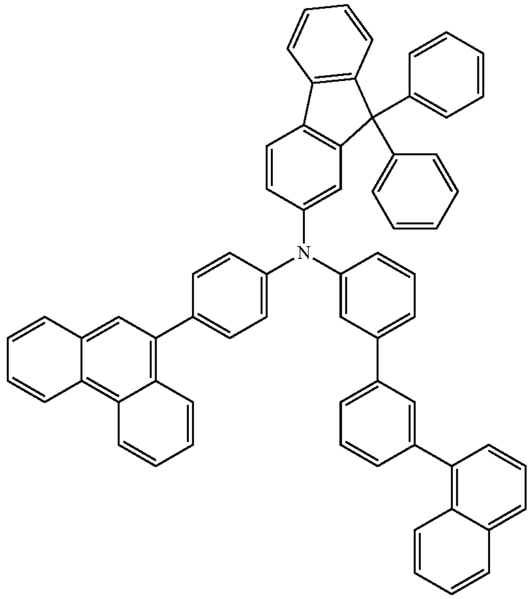
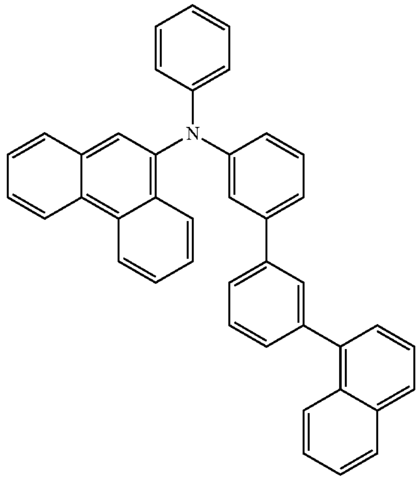

-continued
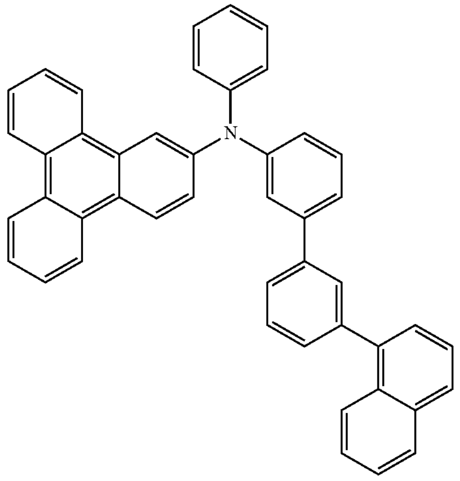
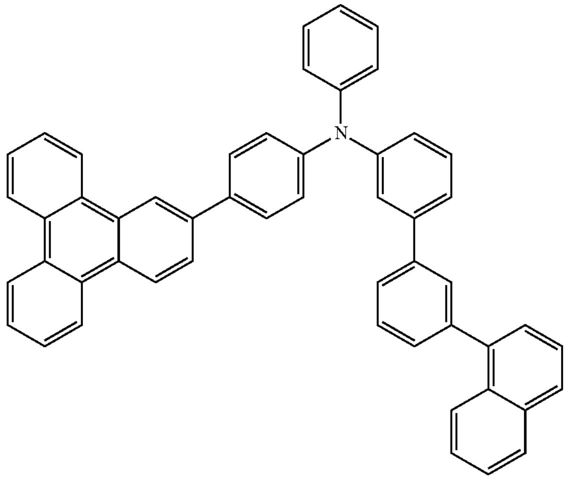
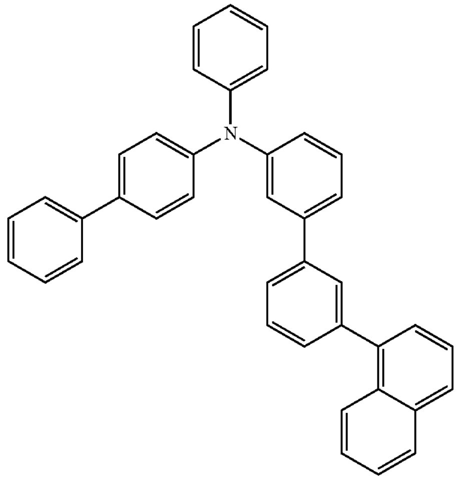
-continued
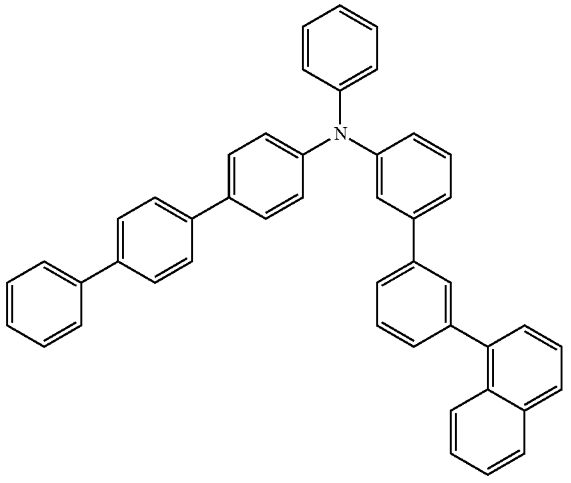
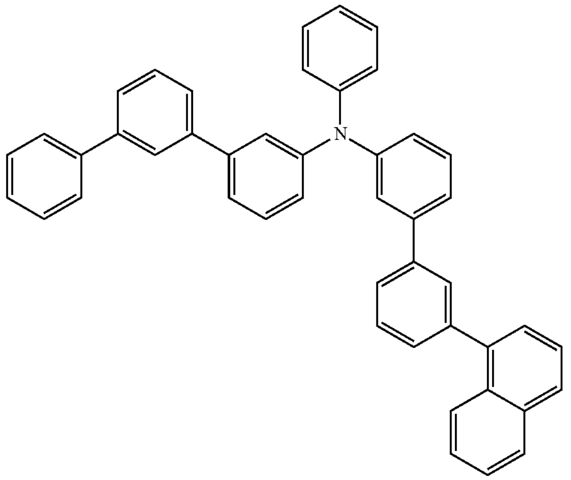
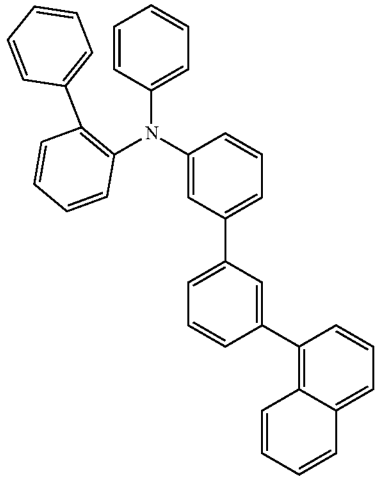

-continued
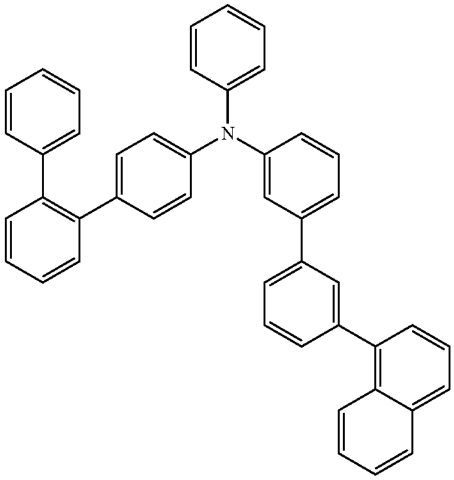
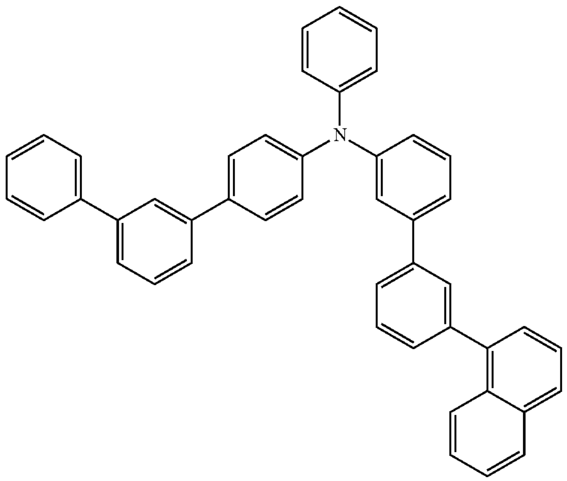
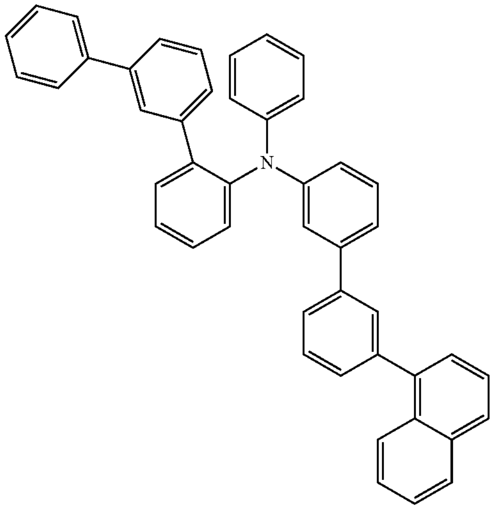
-continued
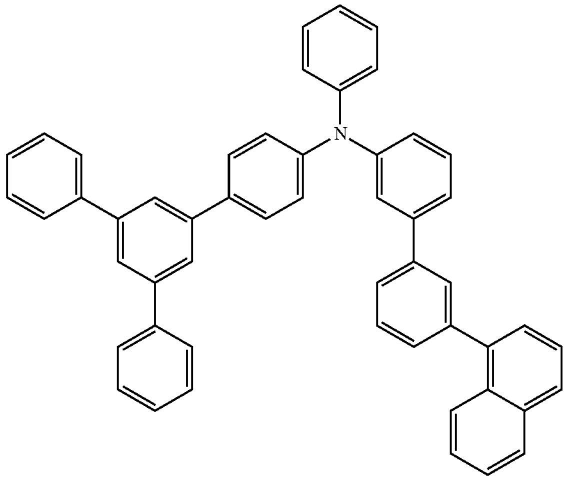
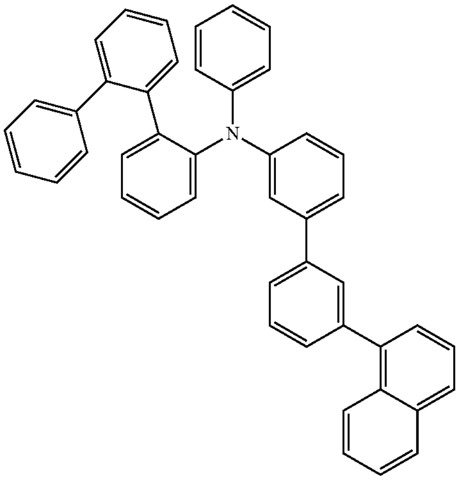
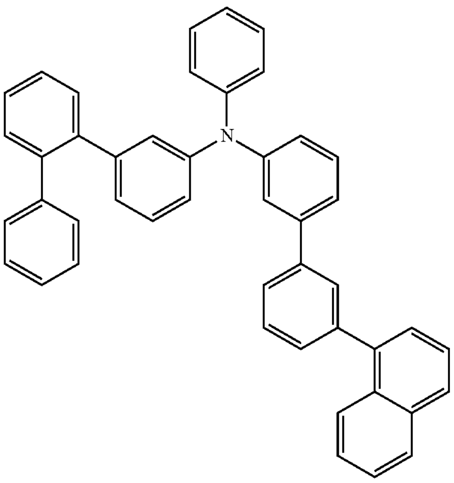

-continued
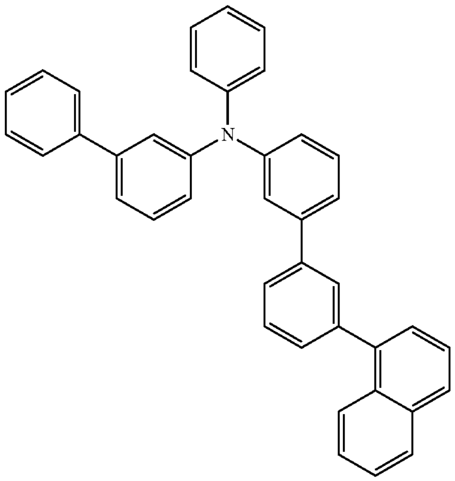
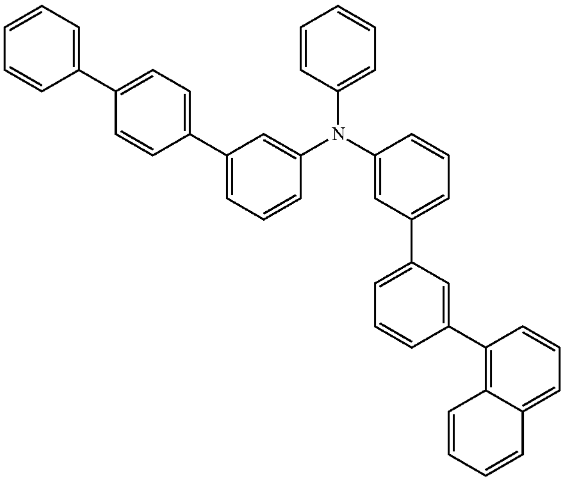
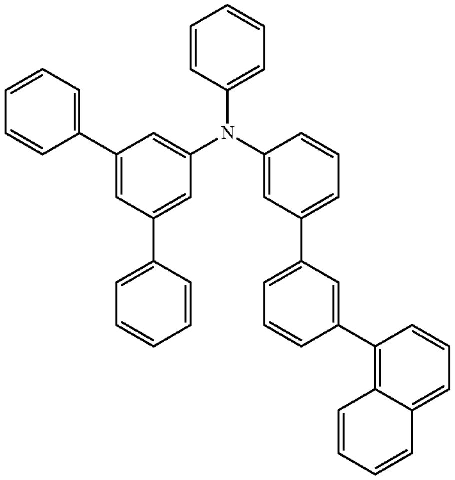
-continued
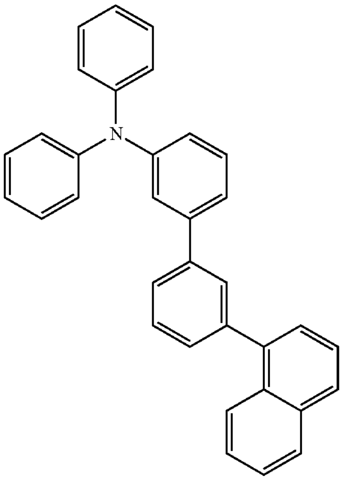
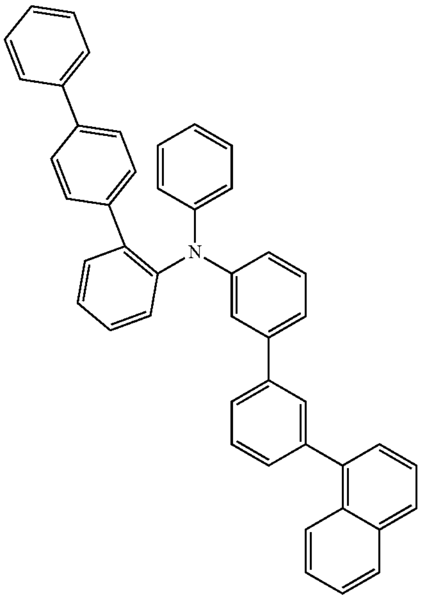
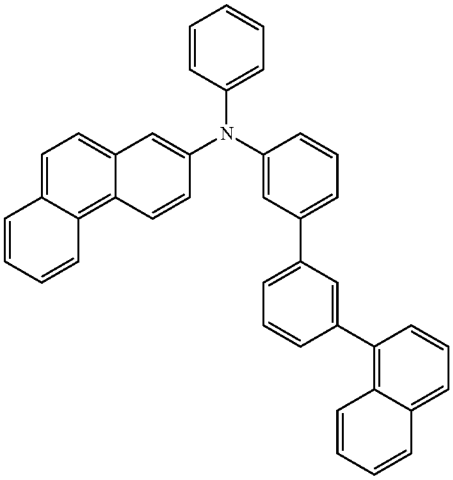

-continued
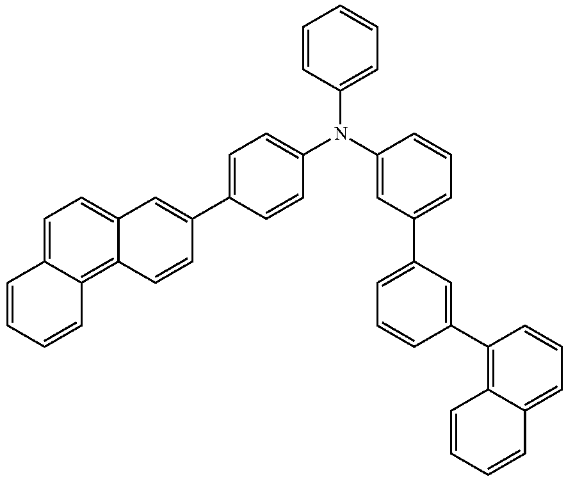
-continued
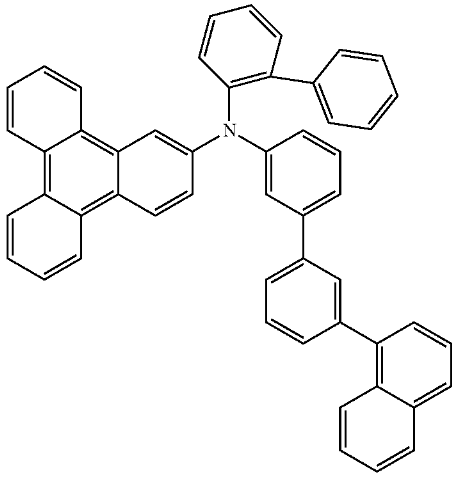
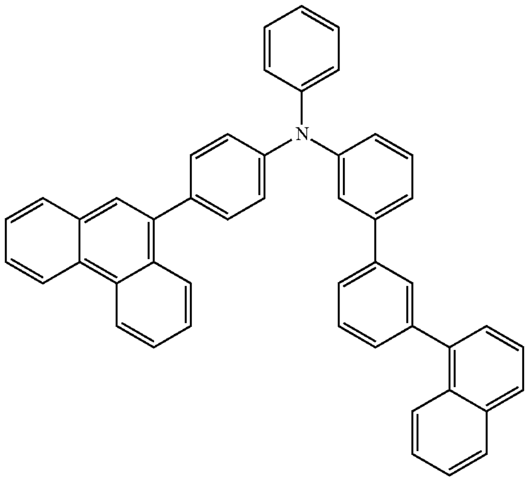
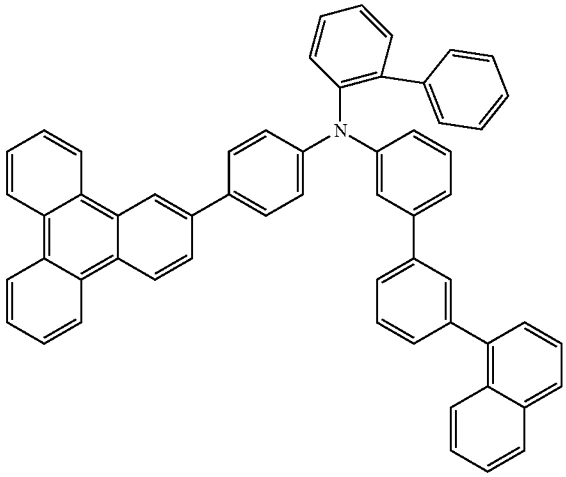
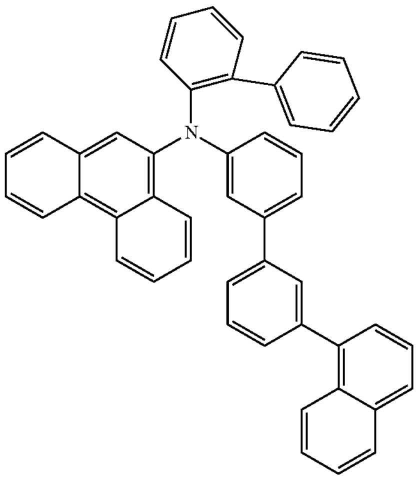
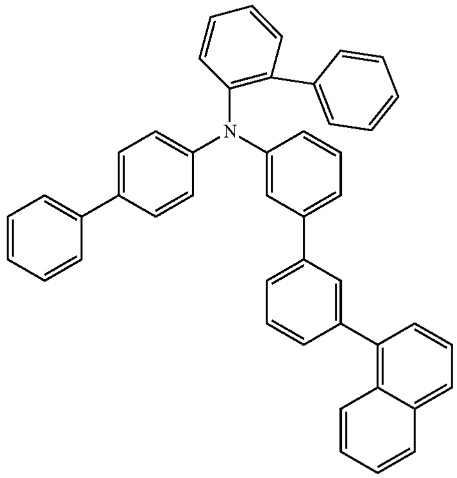

-continued
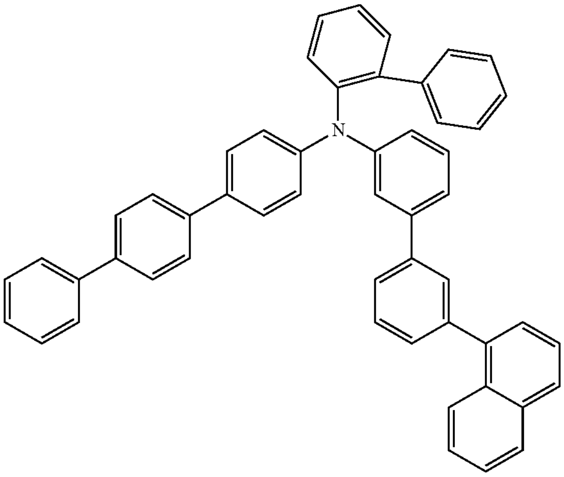
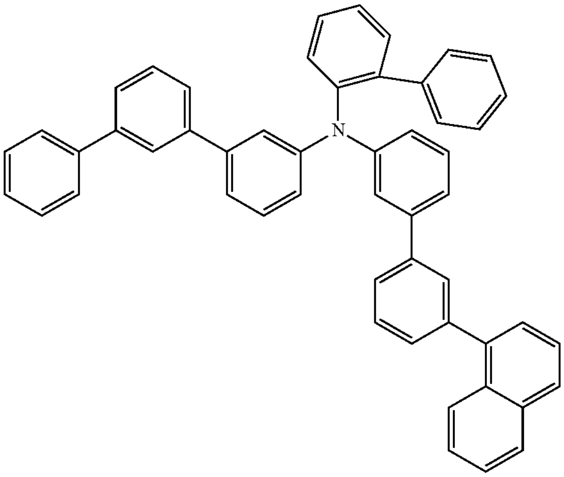
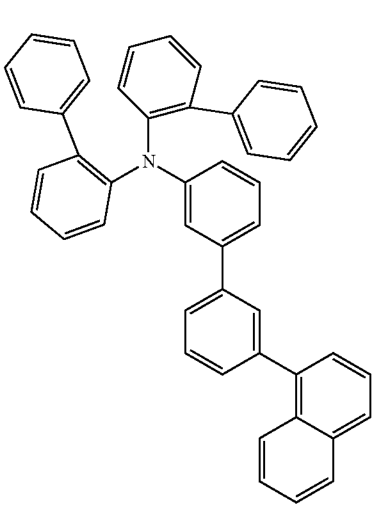
-continued
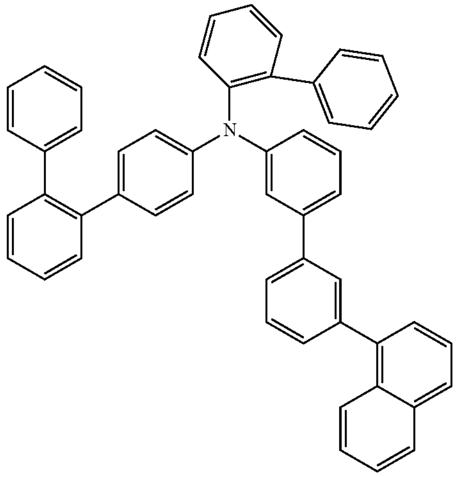
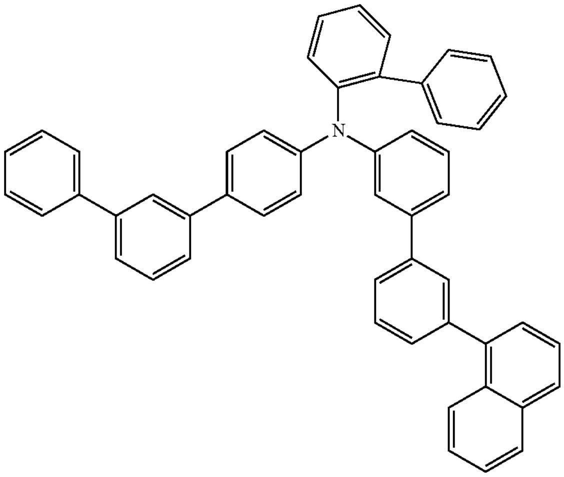
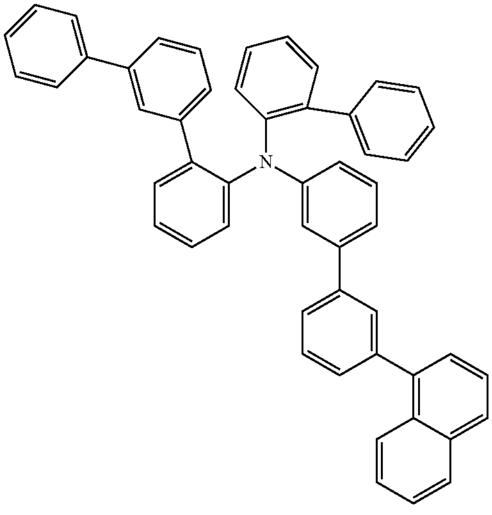

-continued
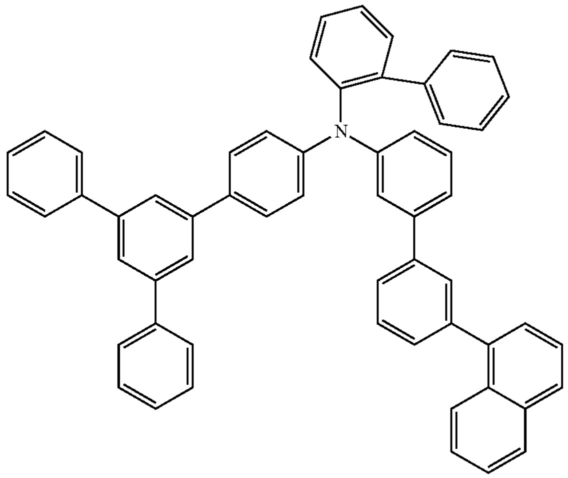
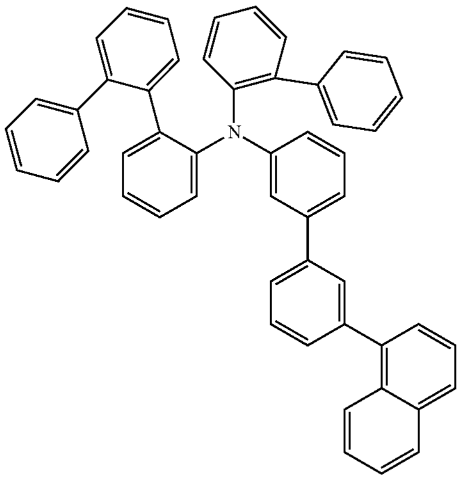
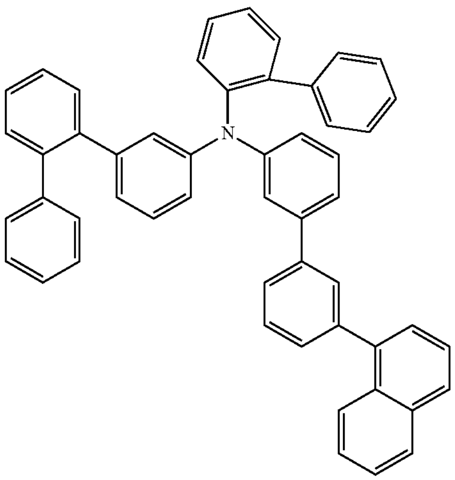
-continued
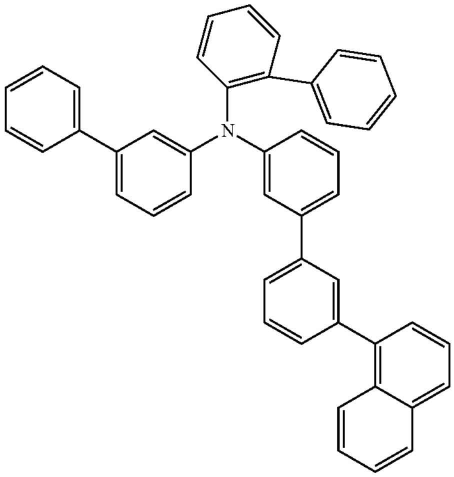
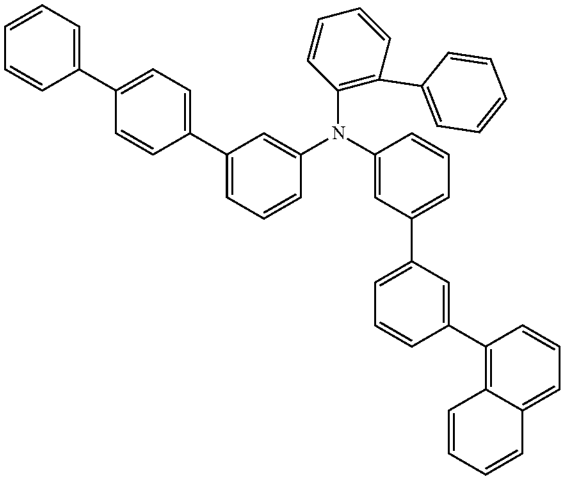
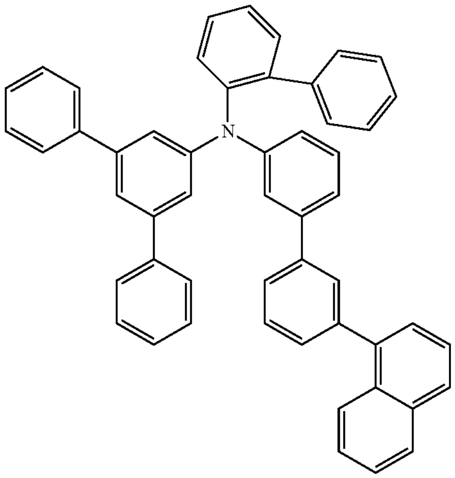

-continued
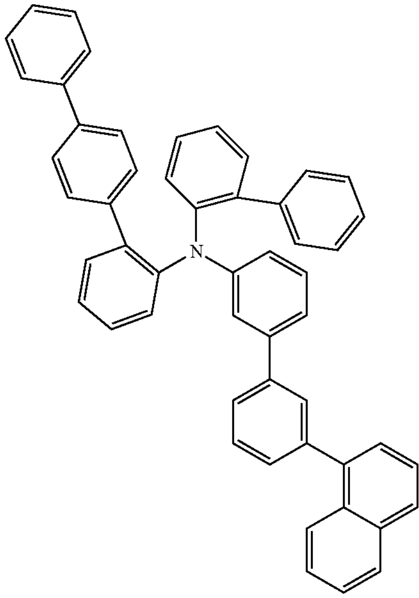
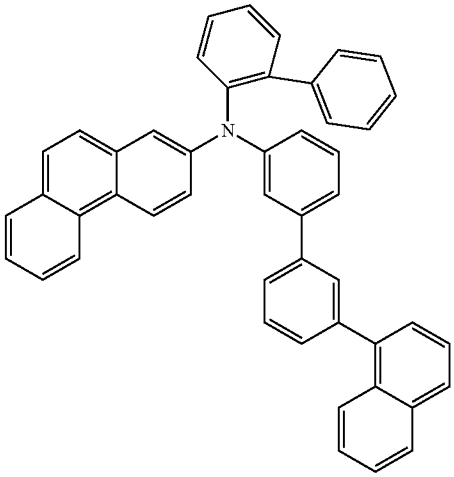
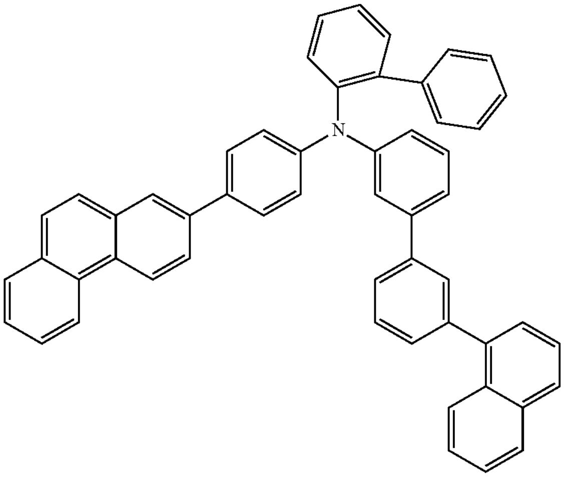
-continued
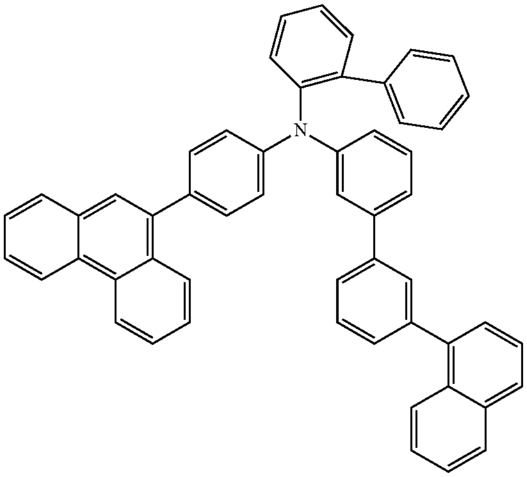
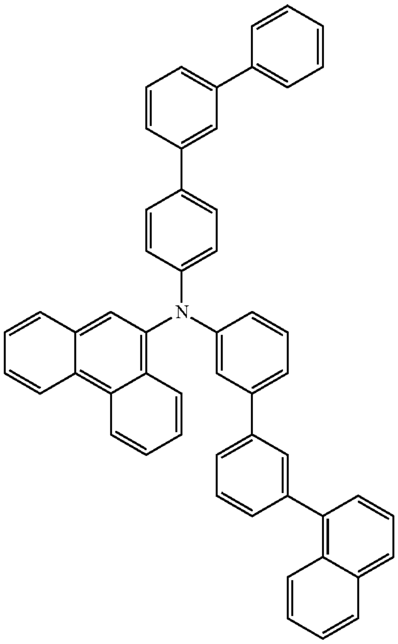

-continued
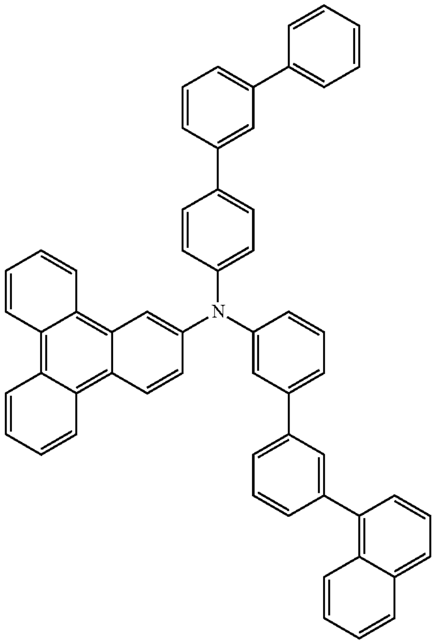
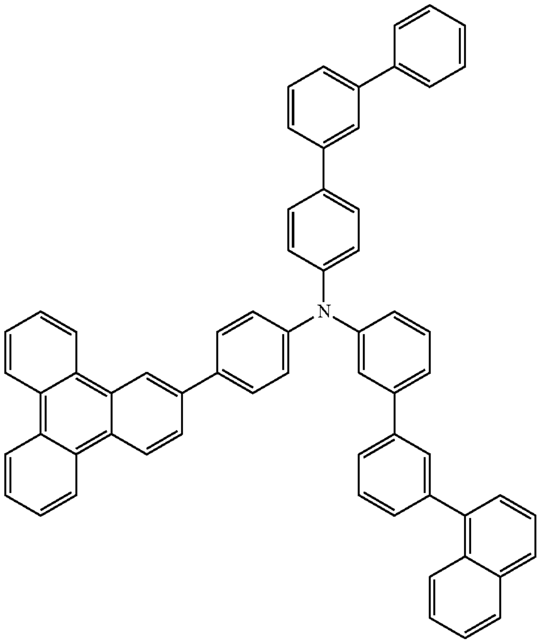
-continued
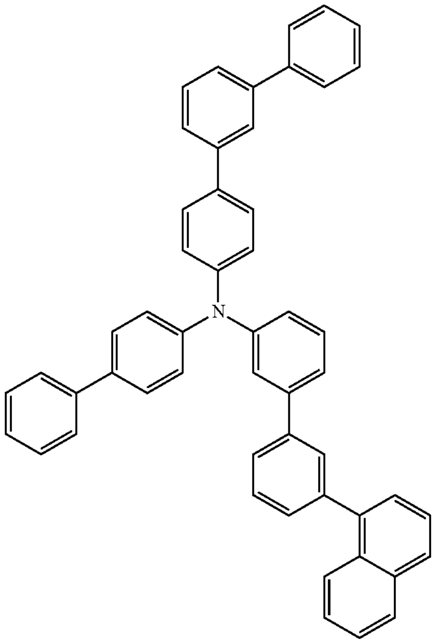
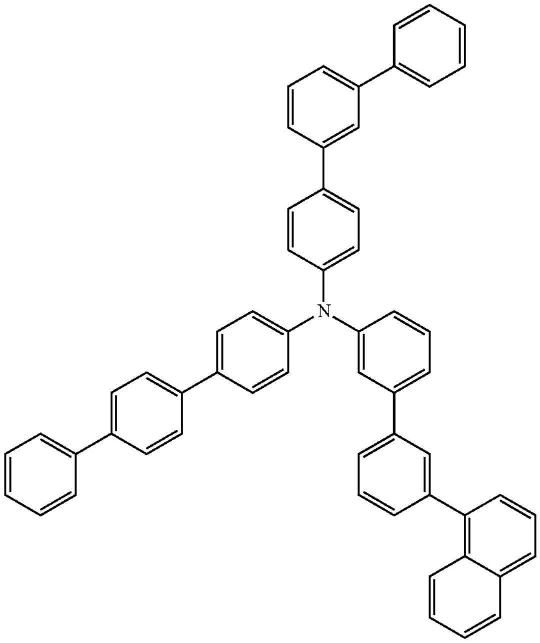

-continued
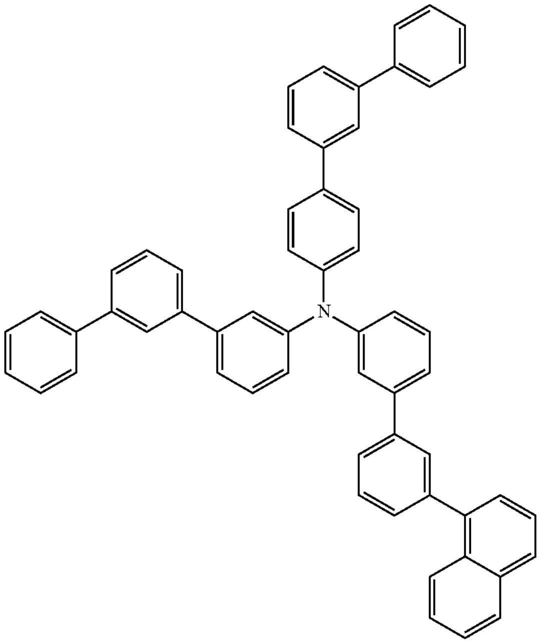
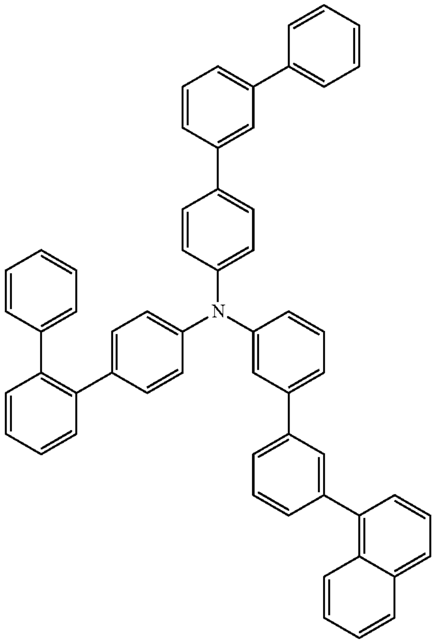
-continued
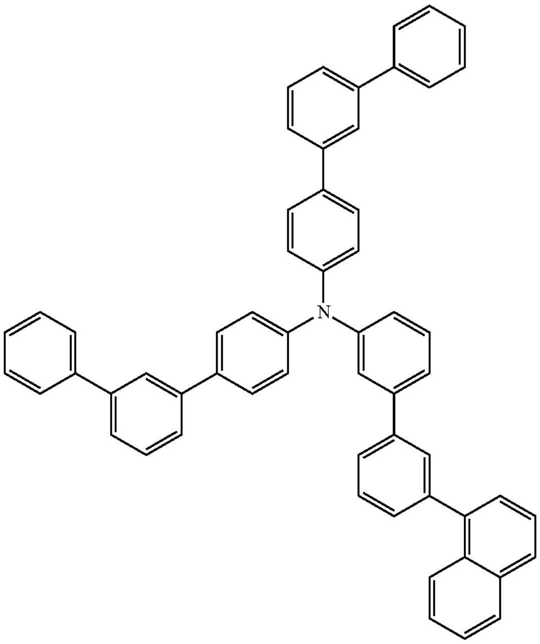
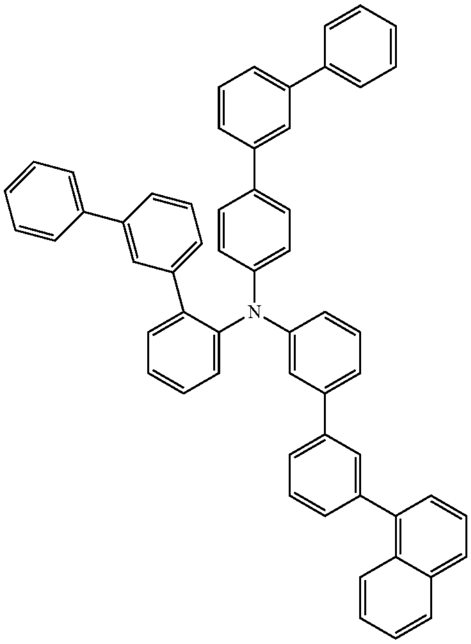

-continued
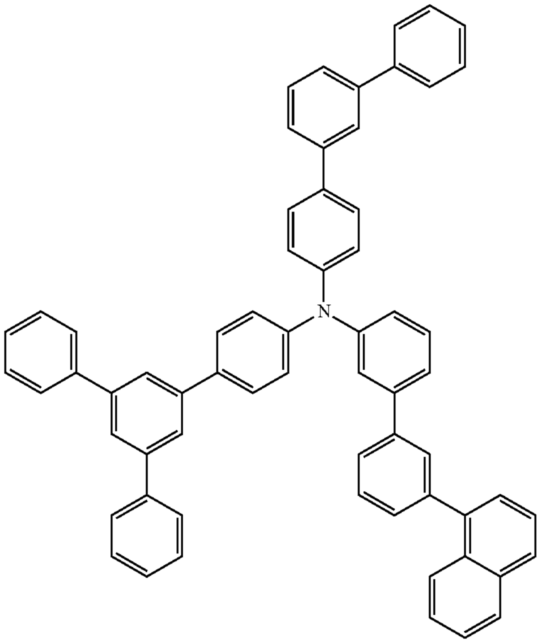
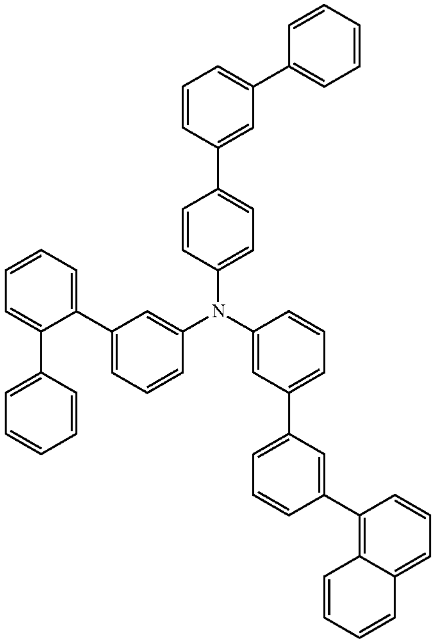
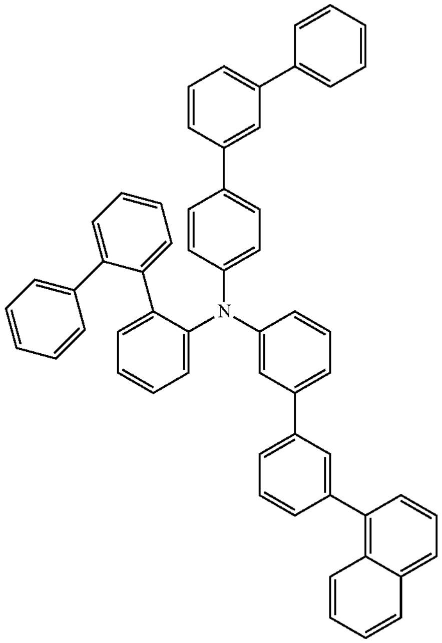
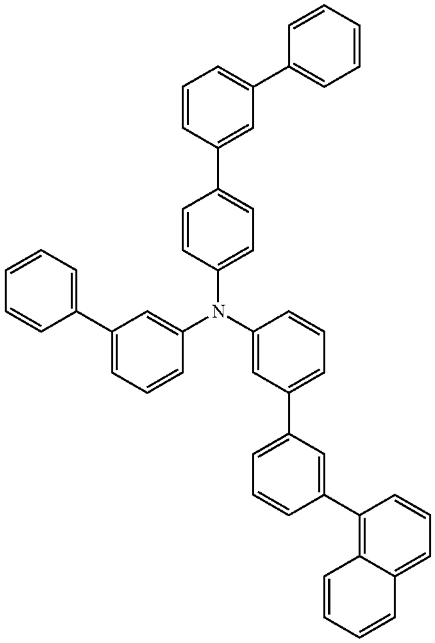
-continued

-continued
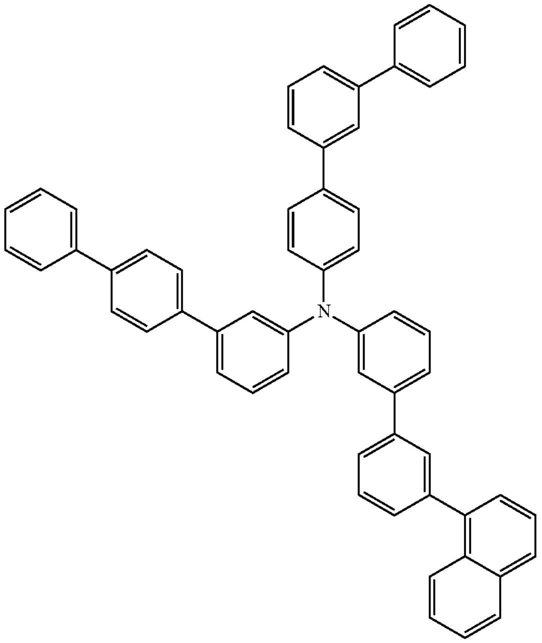
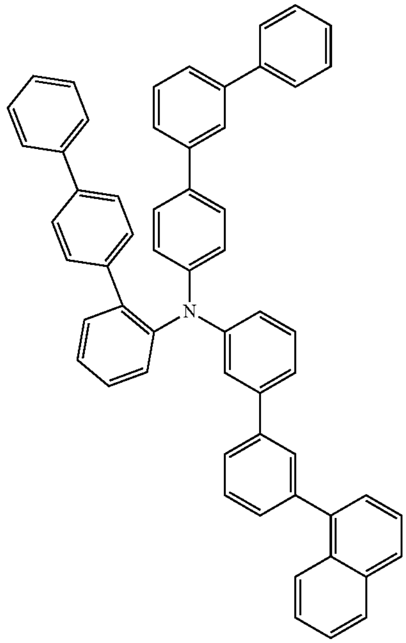
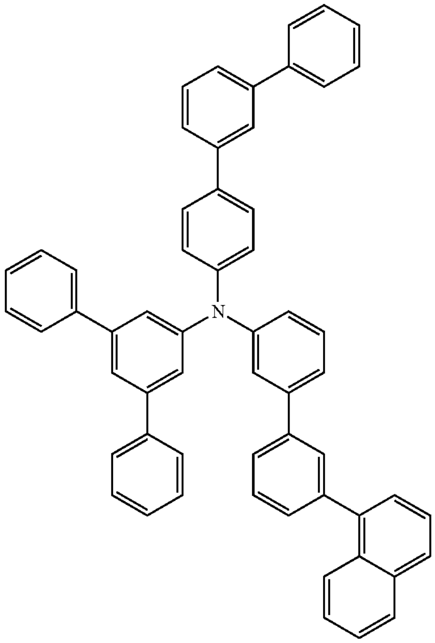
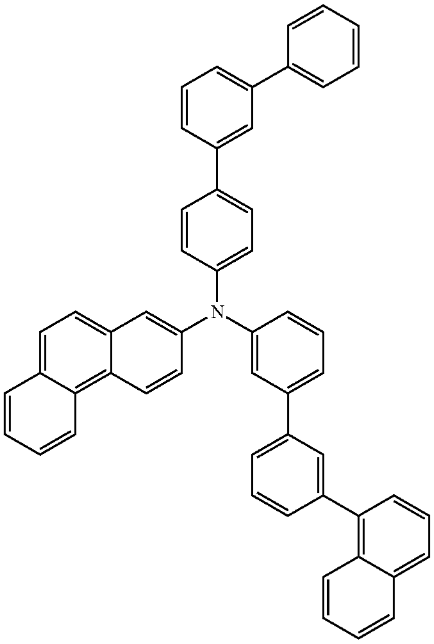
-continued

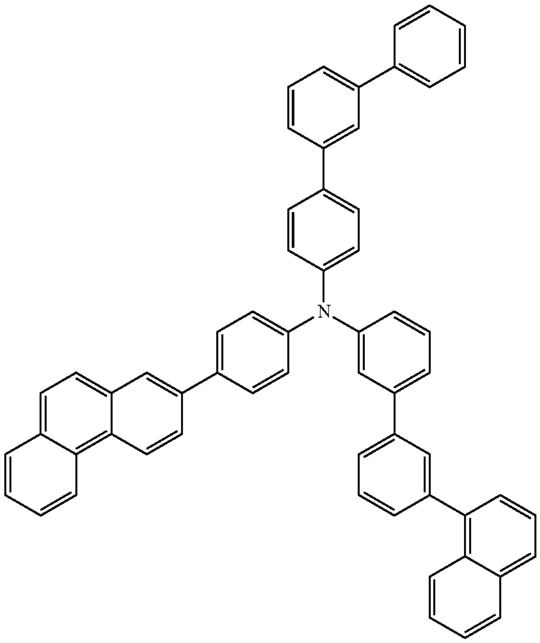
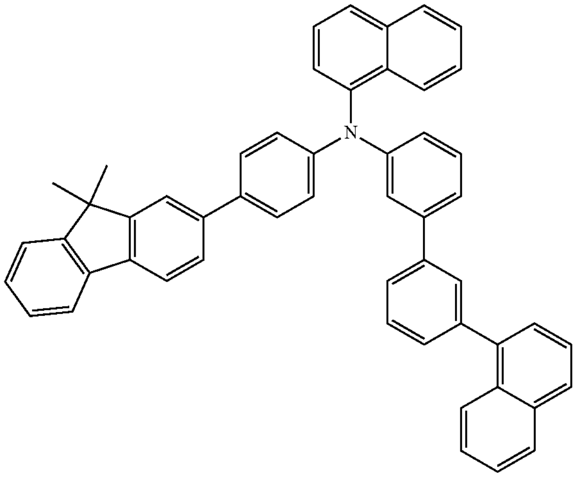
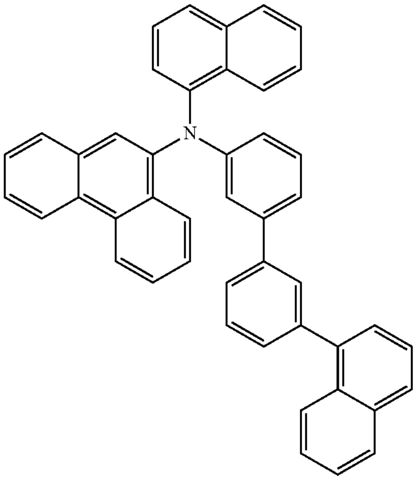
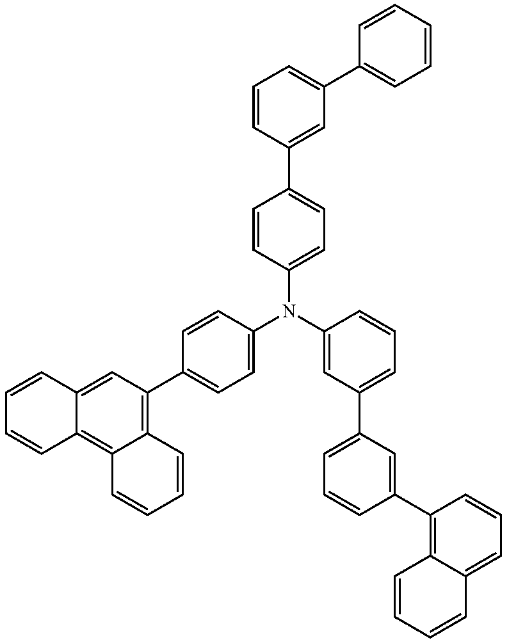
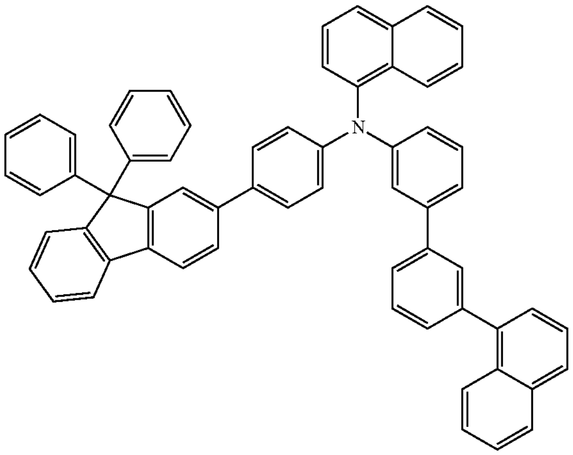

-continued
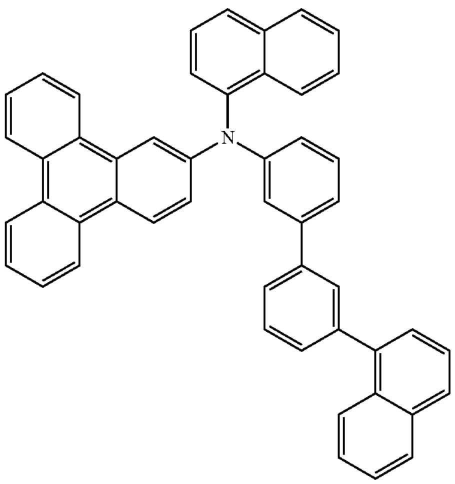
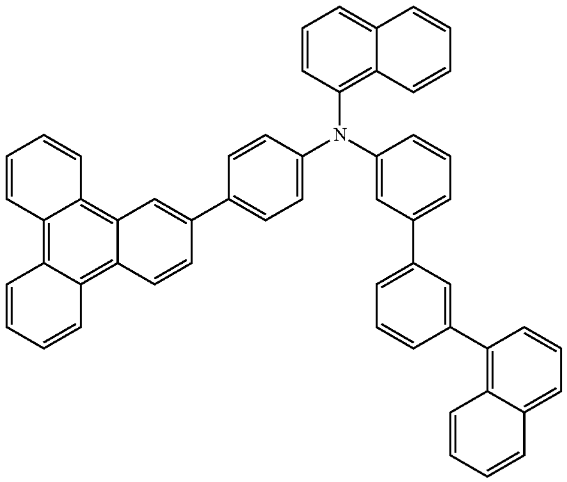
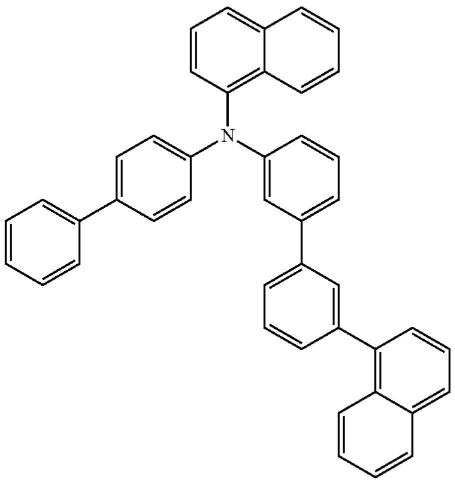
-continued
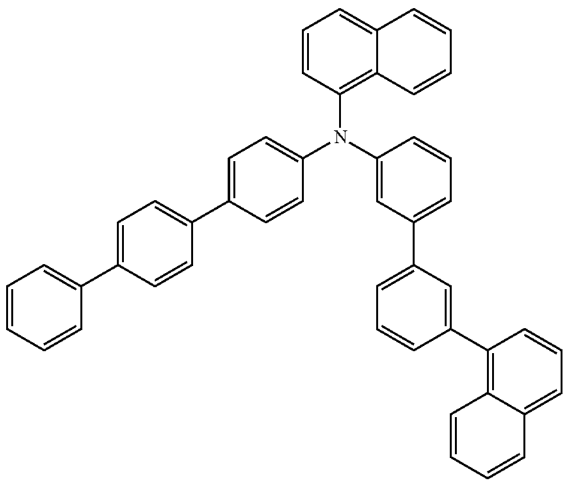
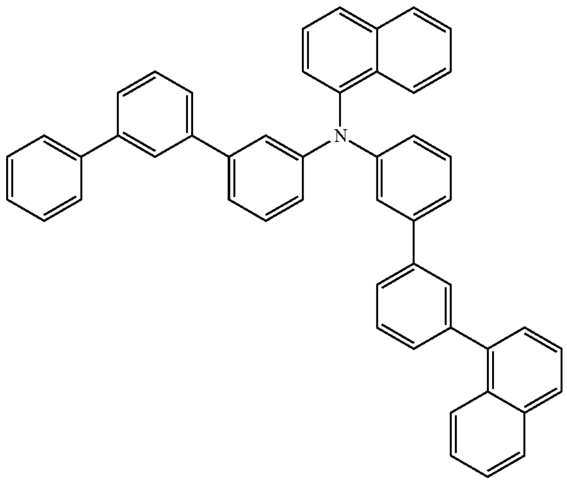
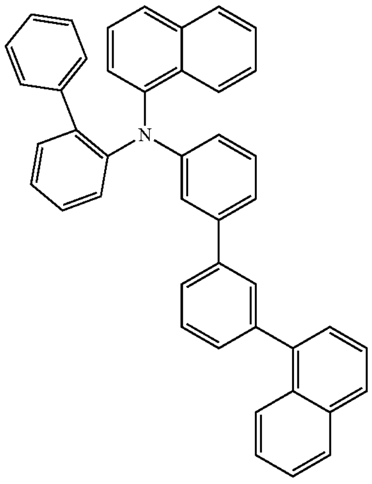

-continued
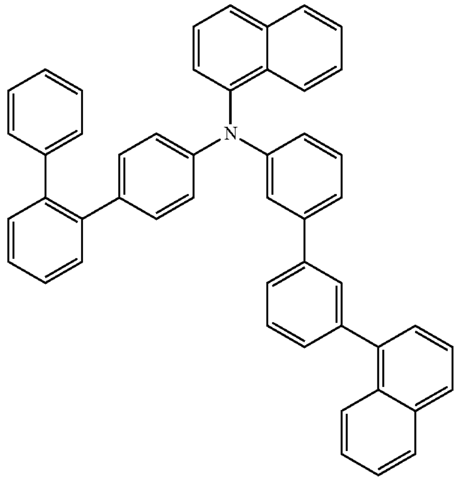
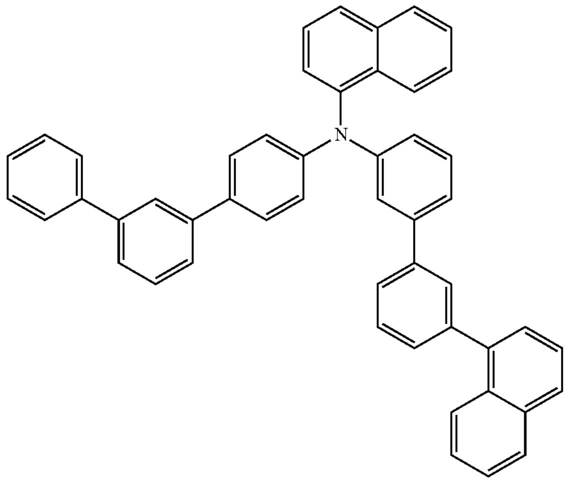
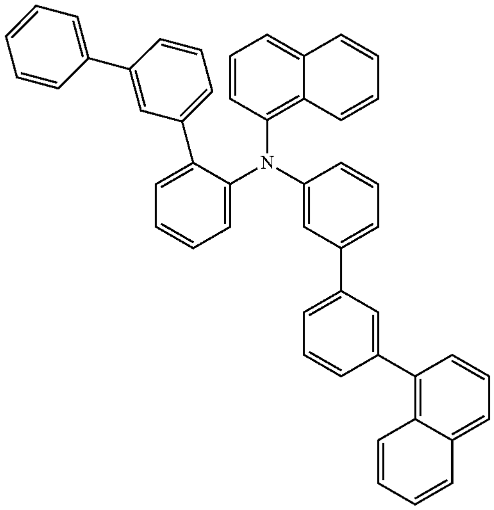
-continued
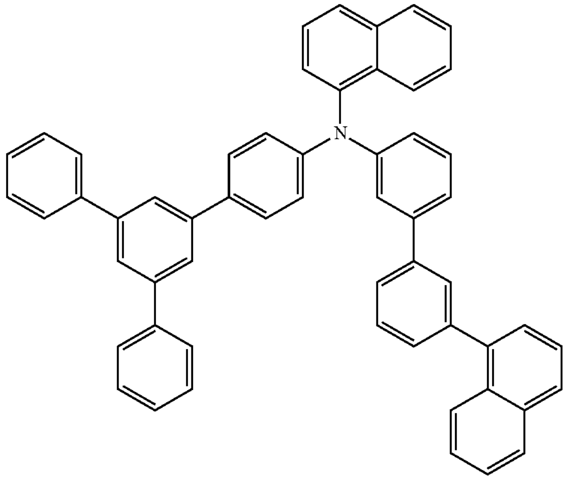
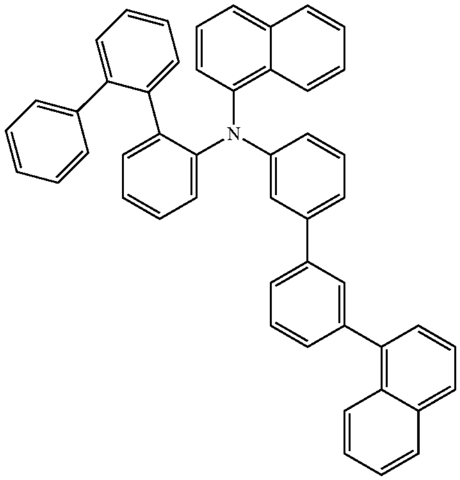
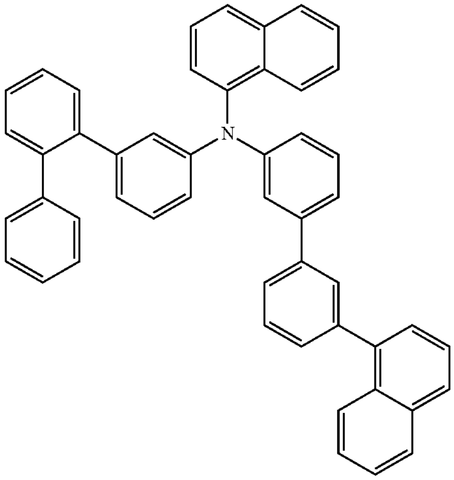

-continued
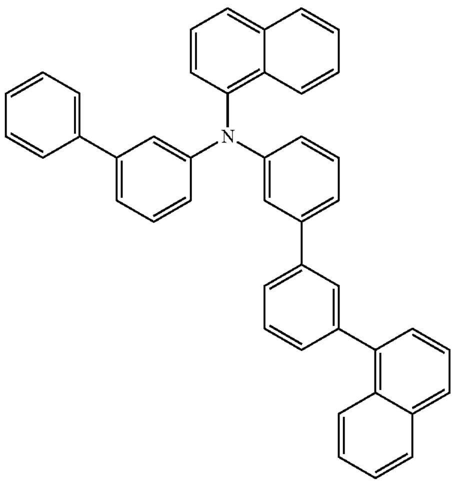
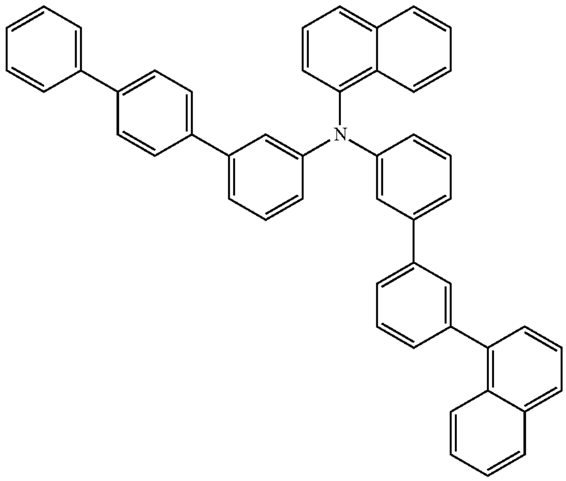
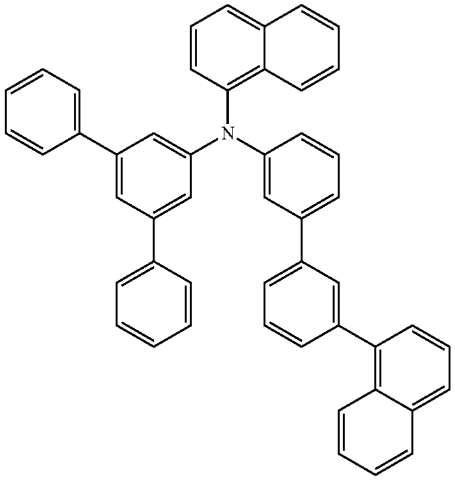
-continued
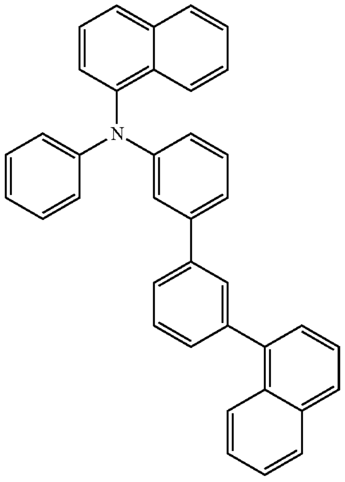
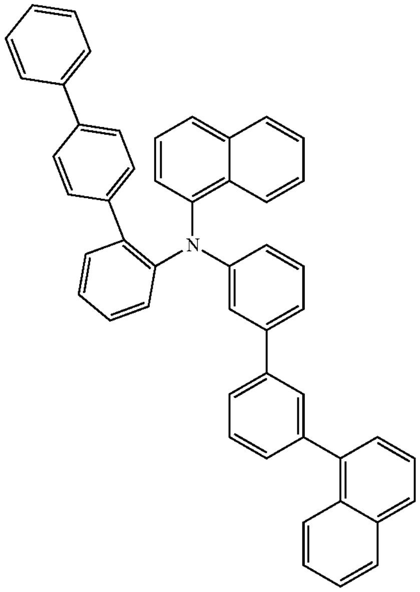
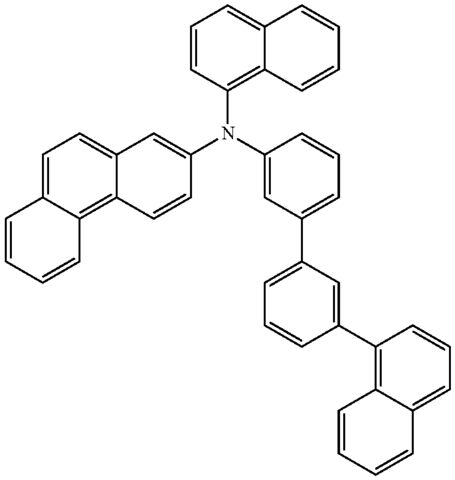

-continued
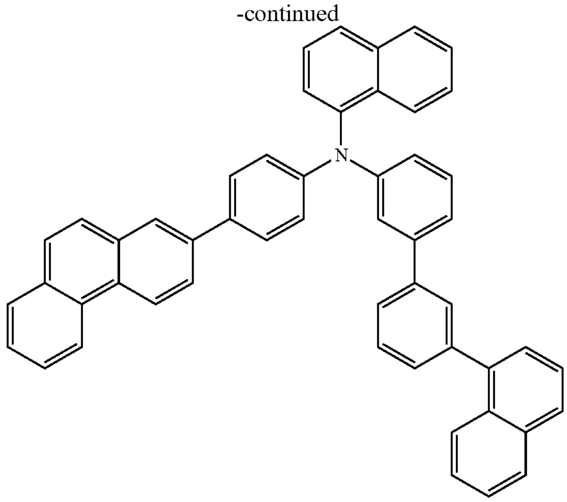
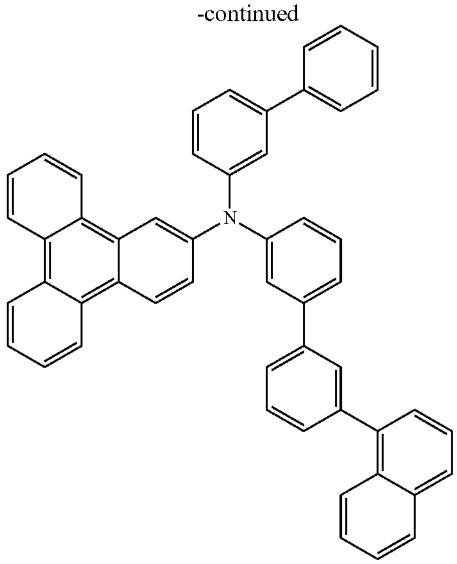
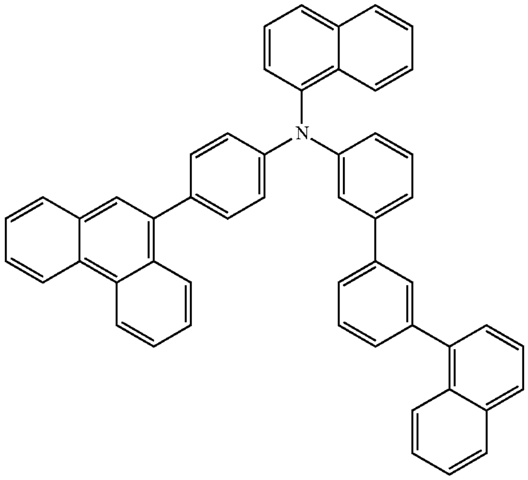
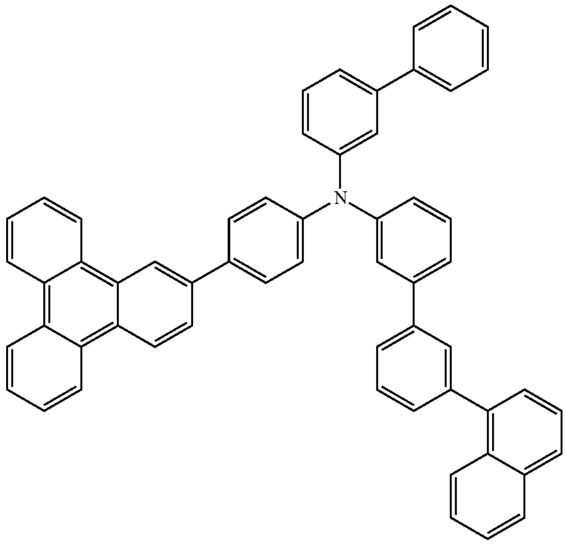
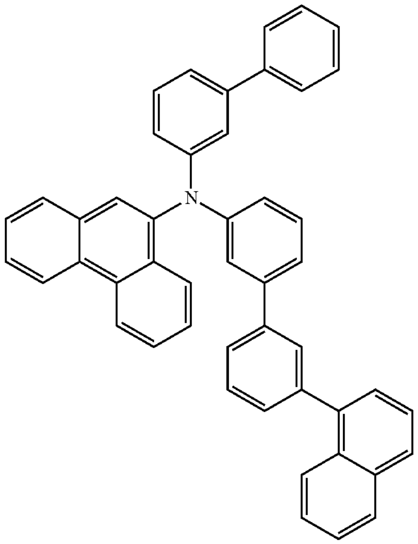
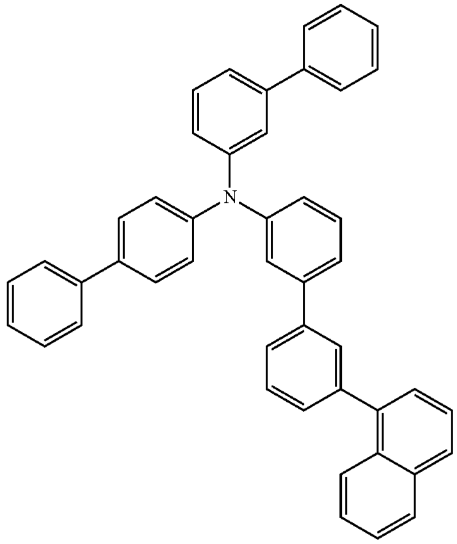

-continued
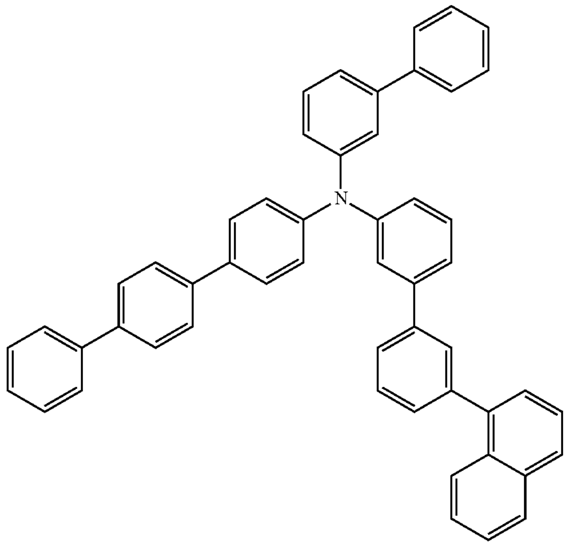
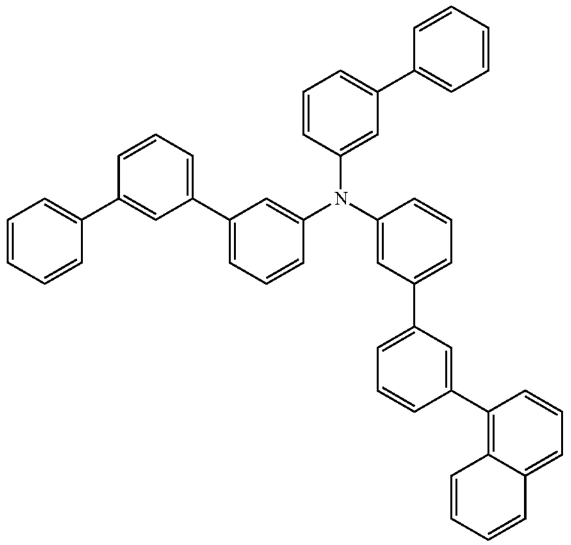
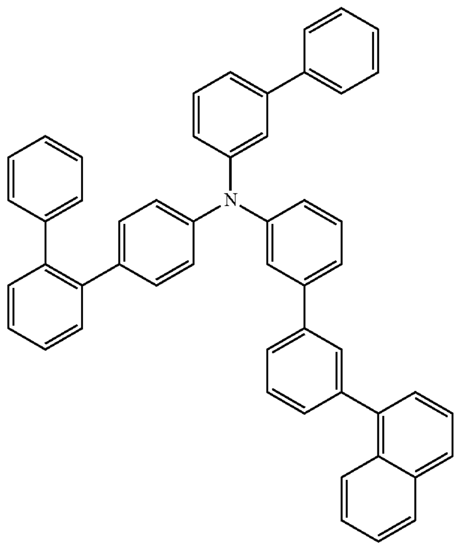
-continued
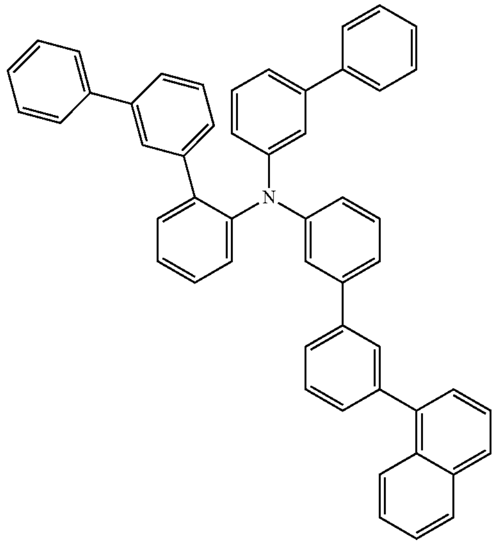
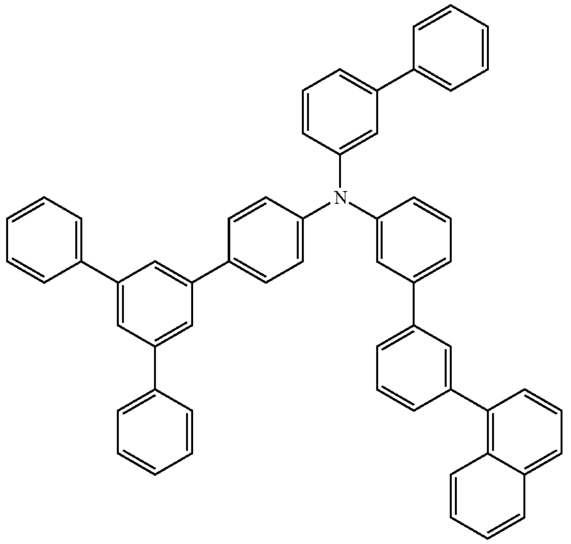
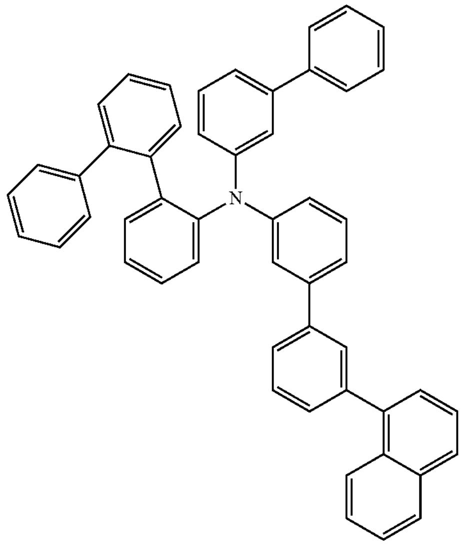

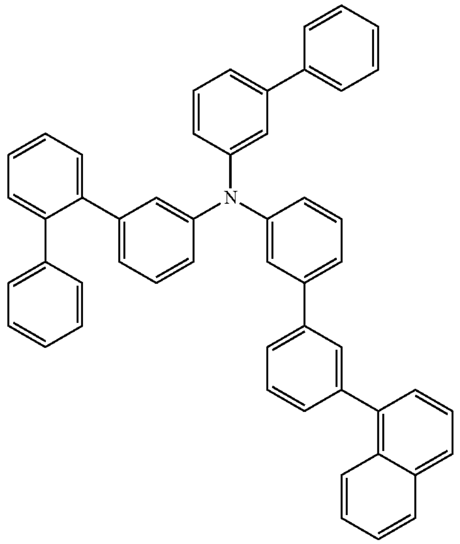
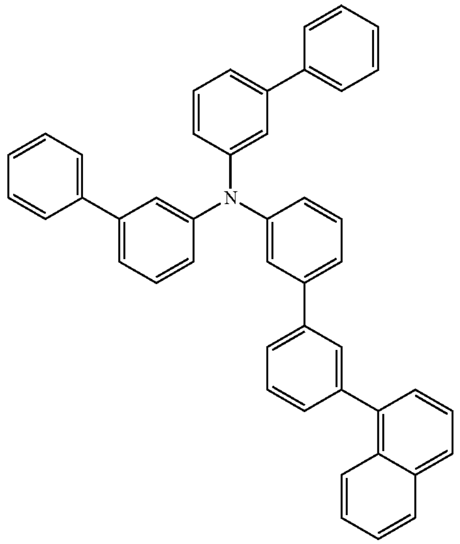
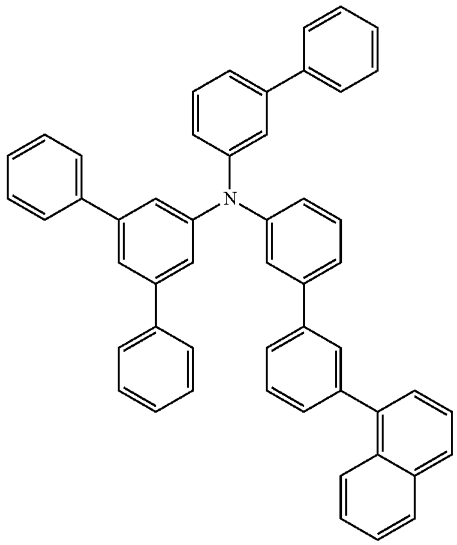
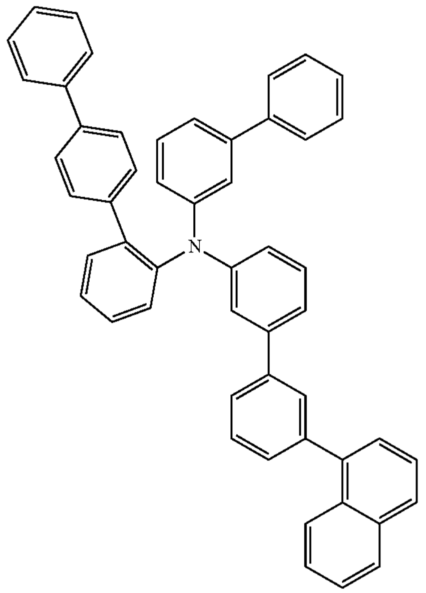
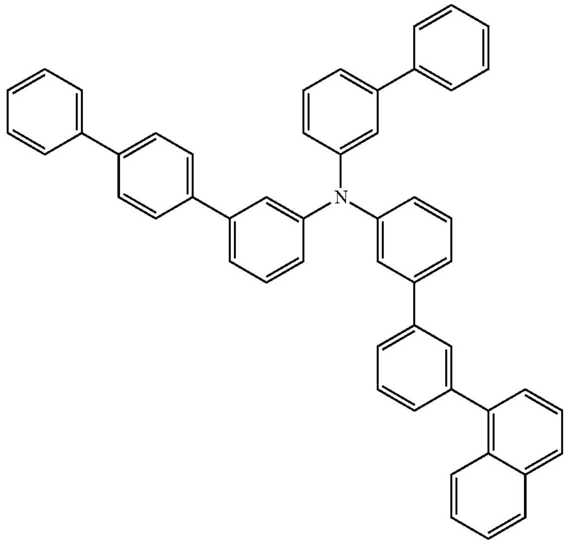
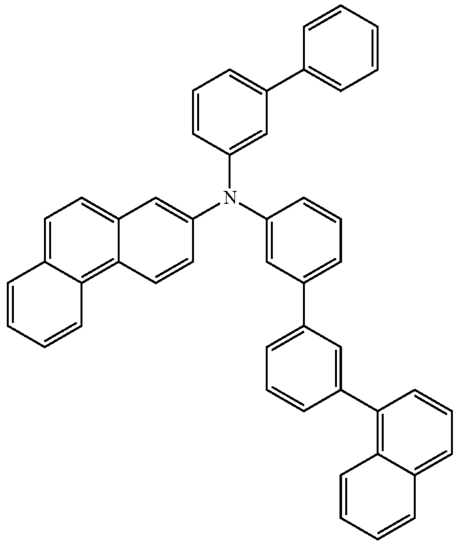

-continued
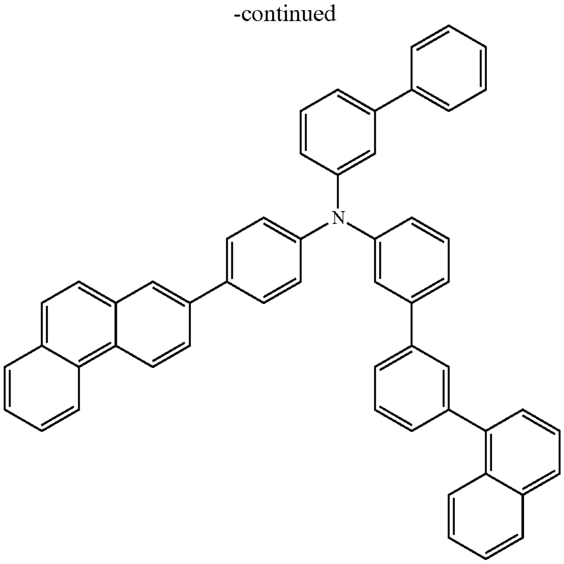
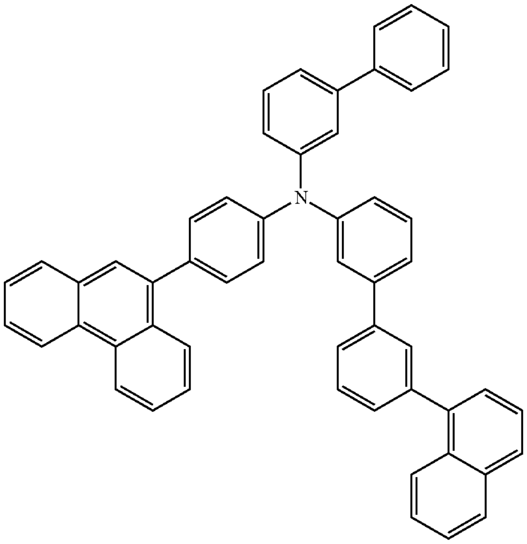
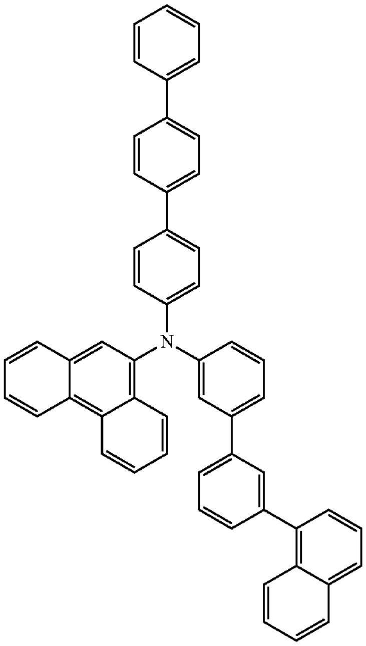
-continued
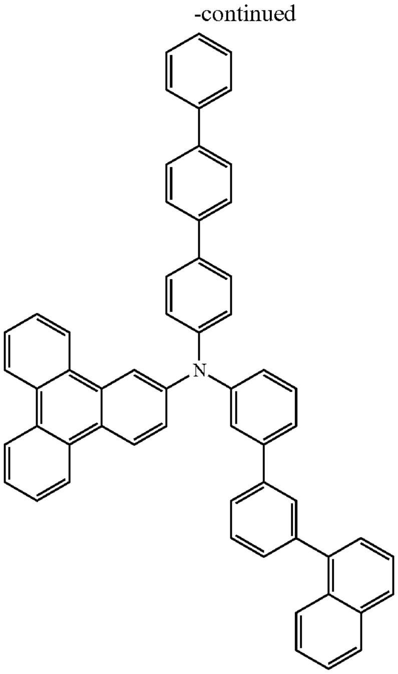
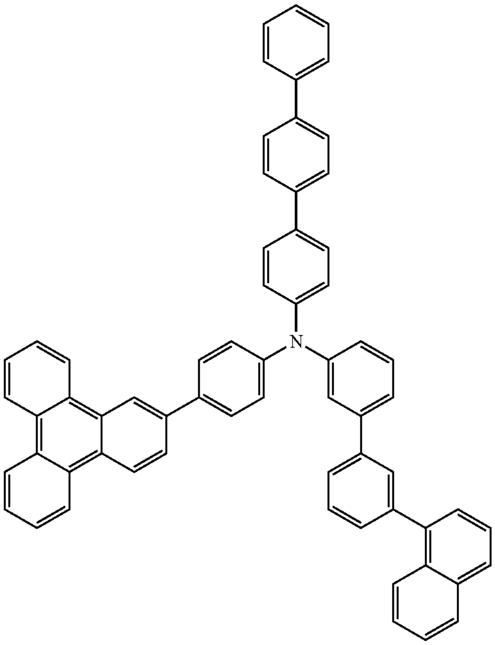

-continued
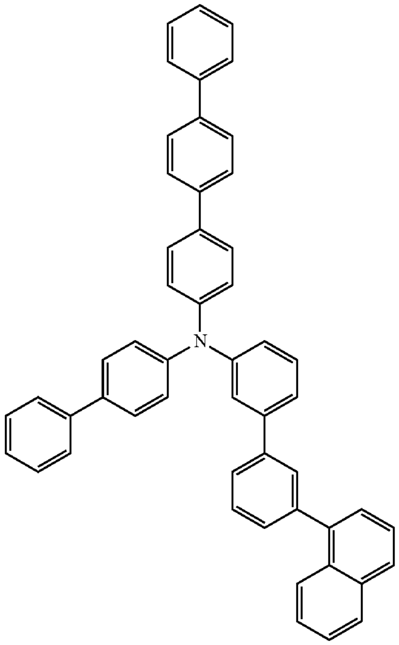
-continued
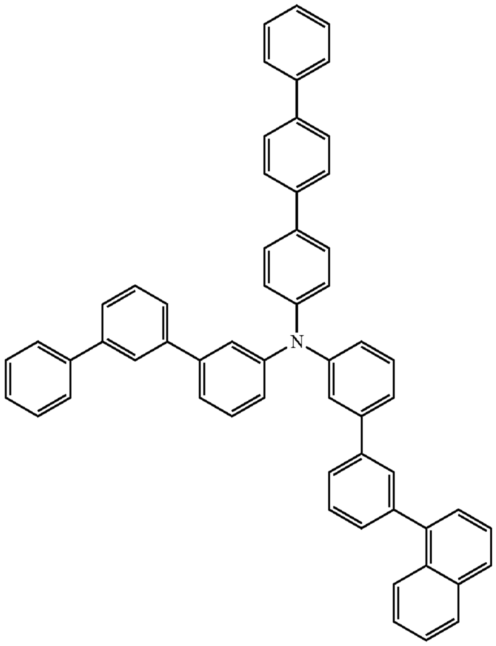
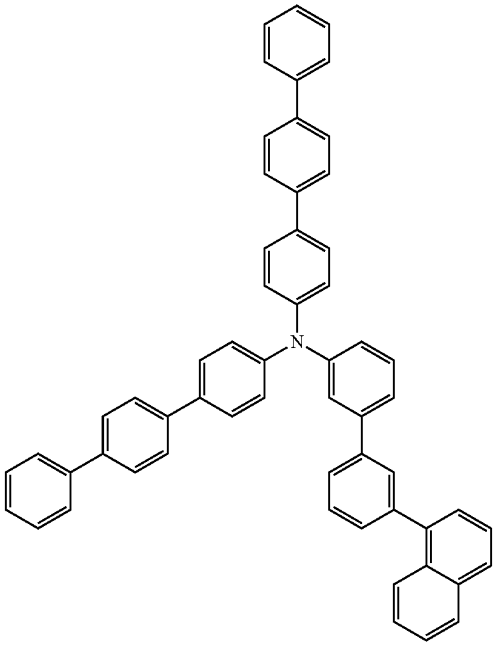
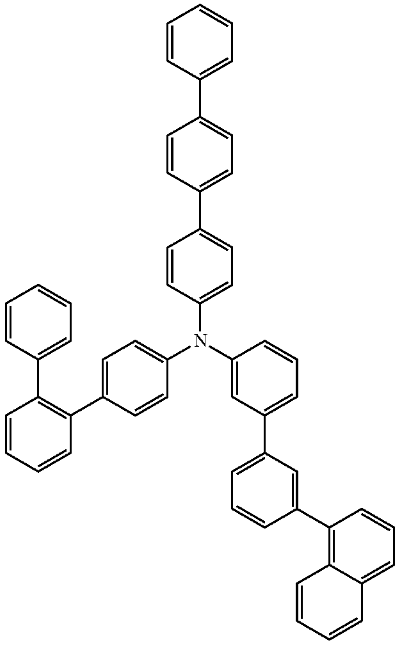

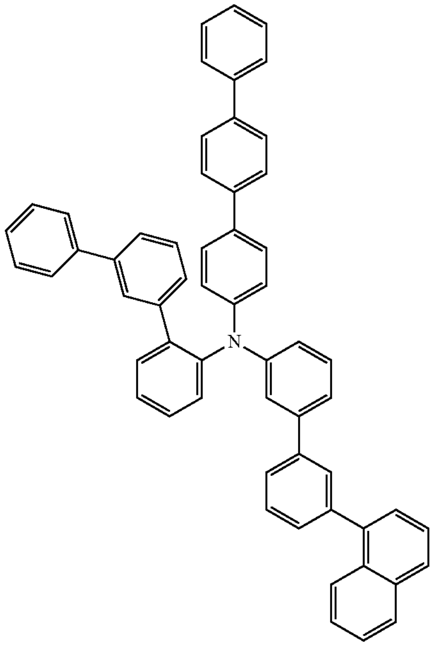
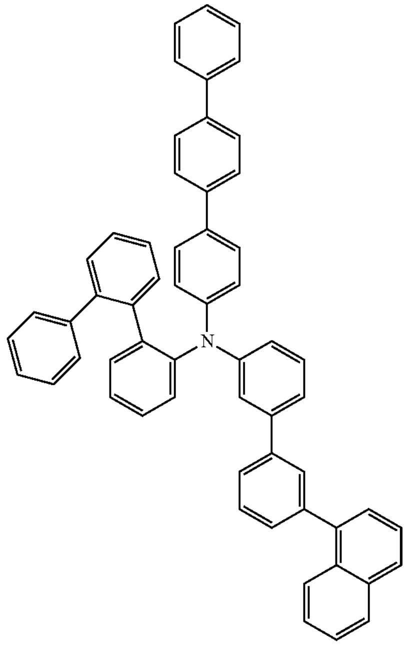
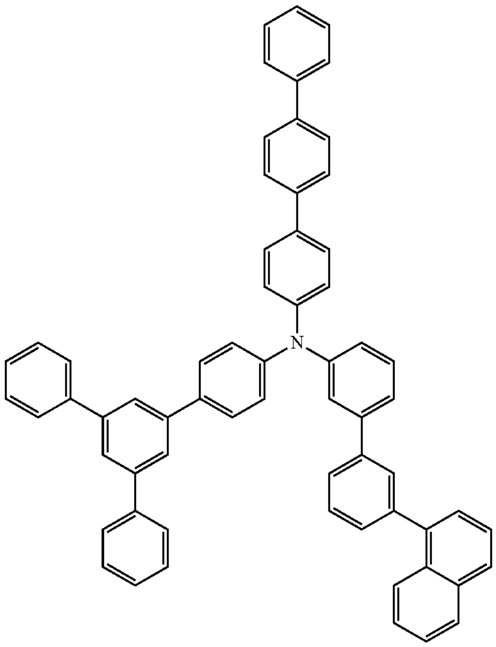
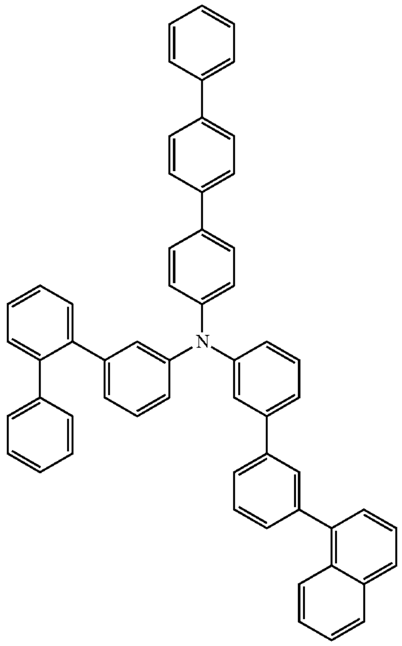

-continued
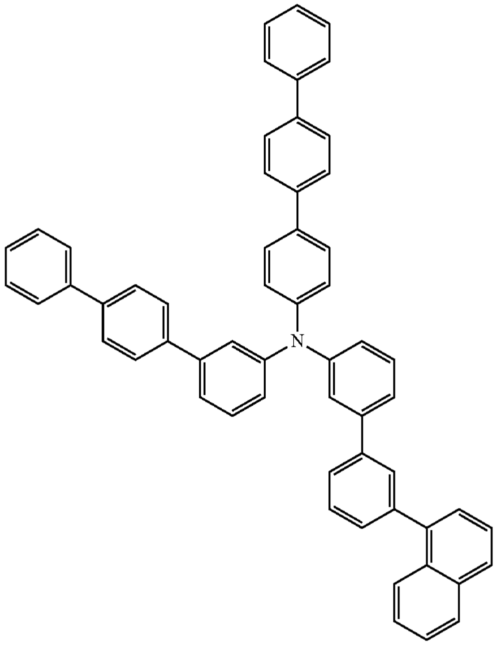
-continued
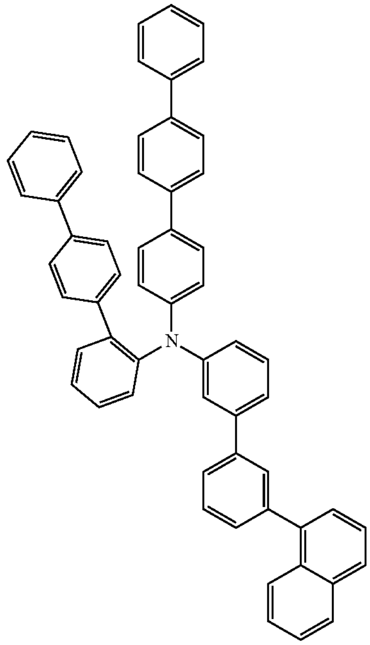
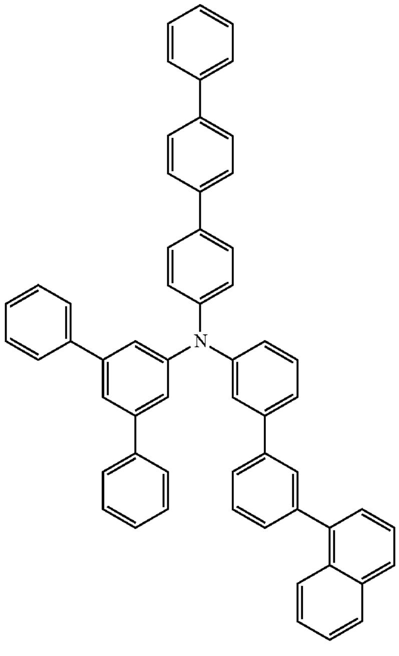
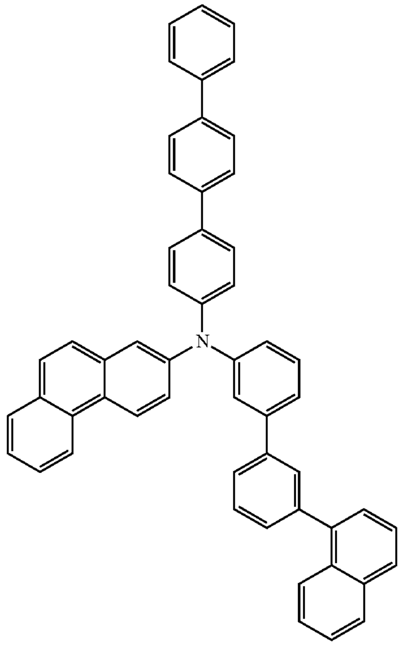

-continued
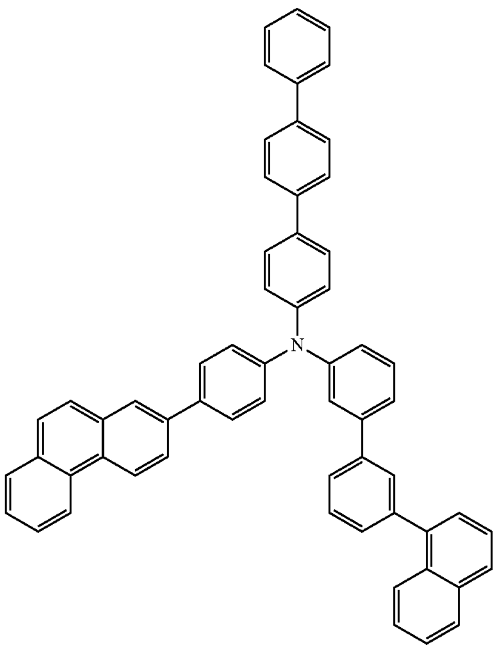
-continued
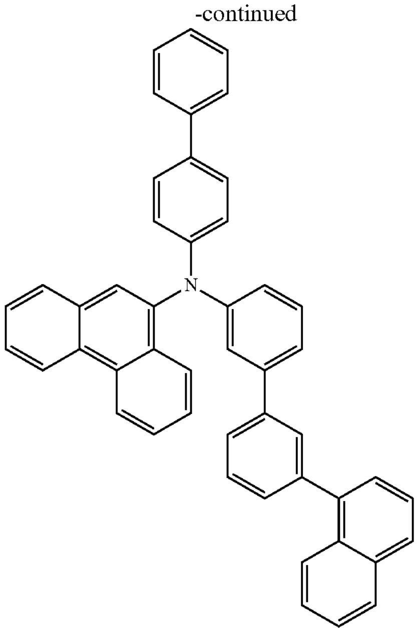
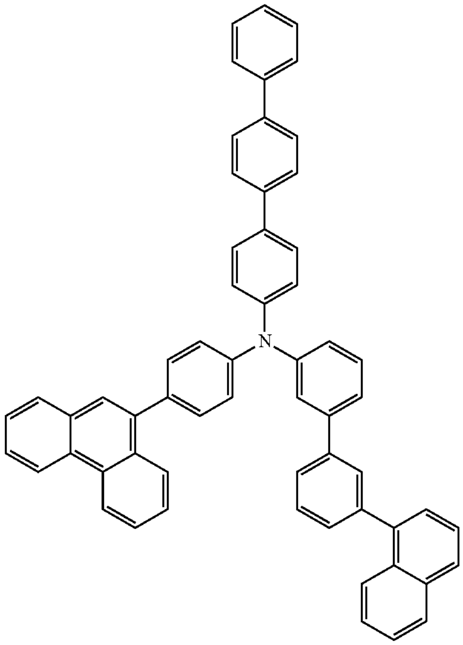
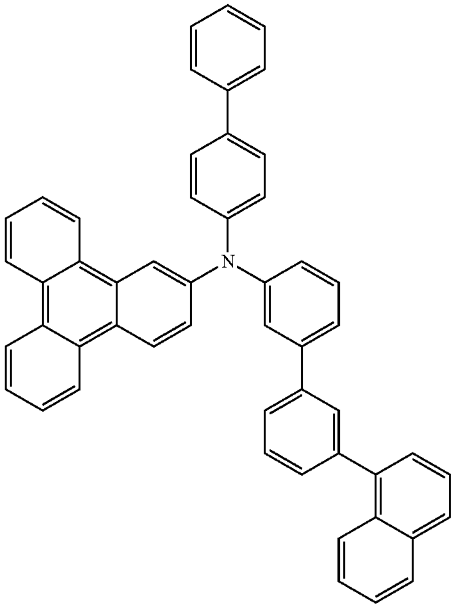

-continued
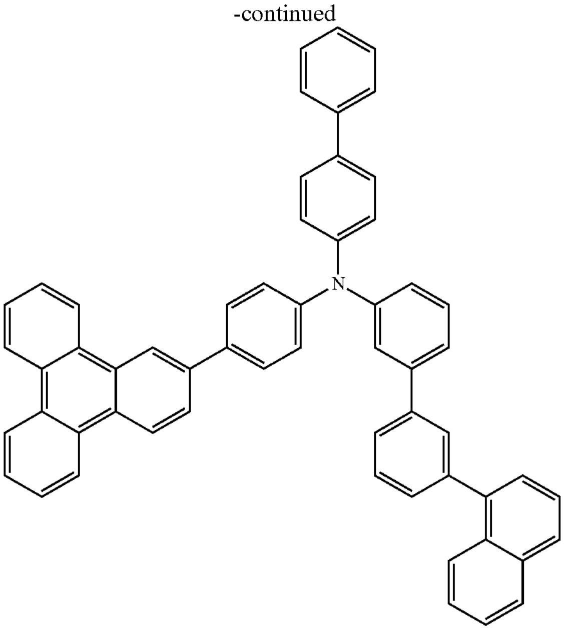
-continued
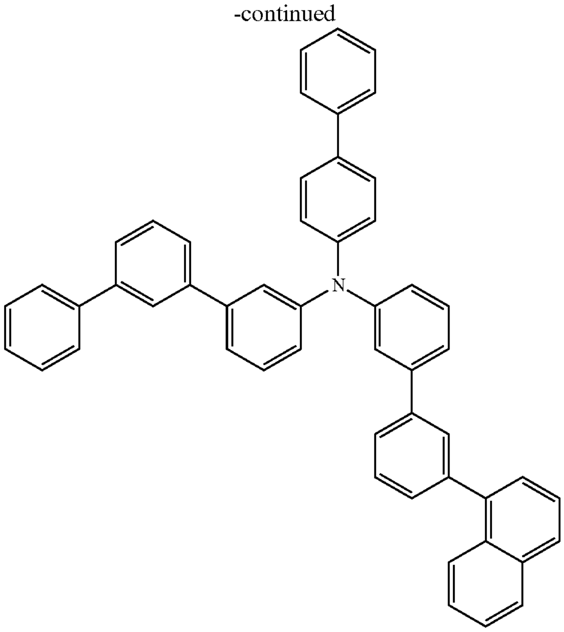
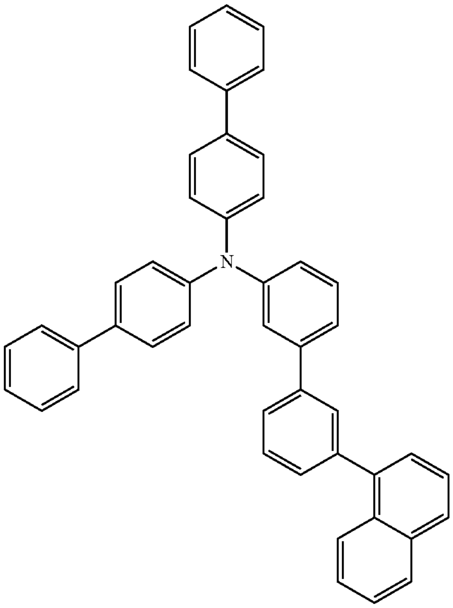
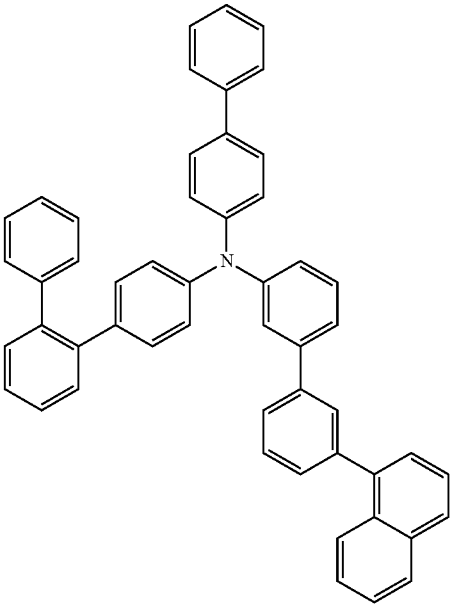

-continued
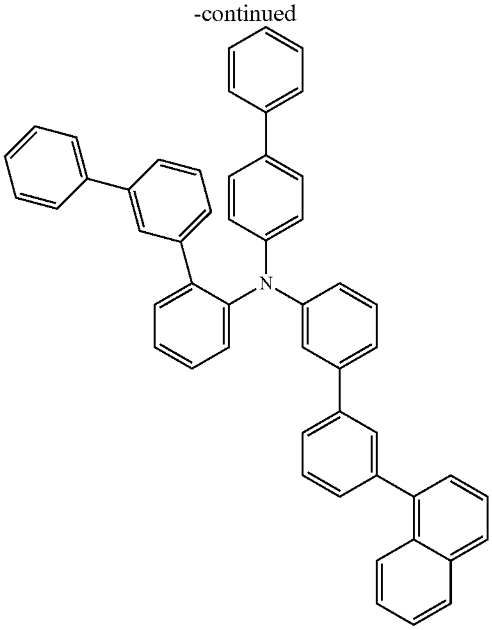
-continued
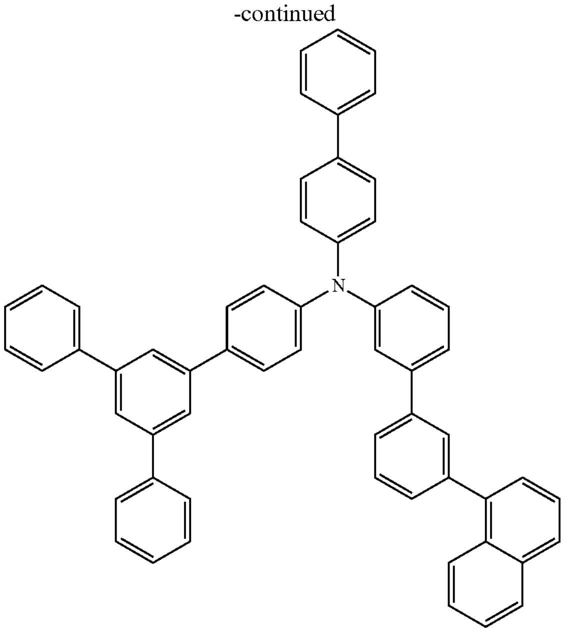
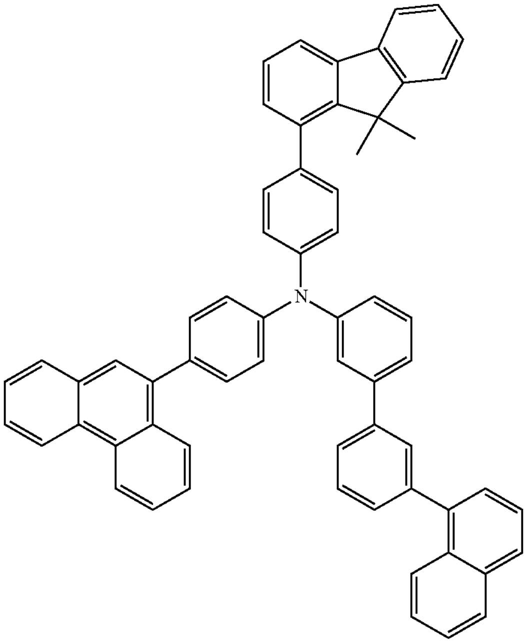
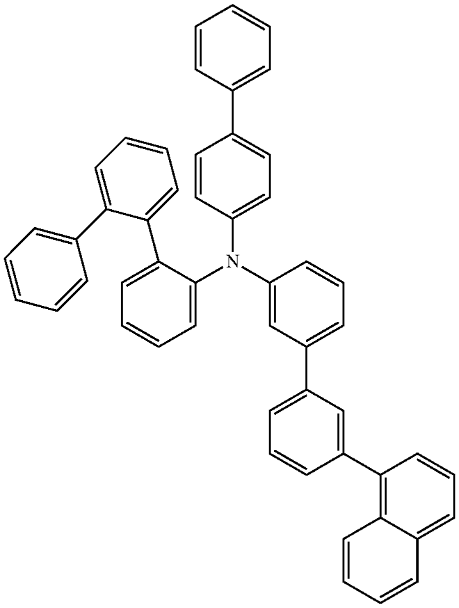

-continued
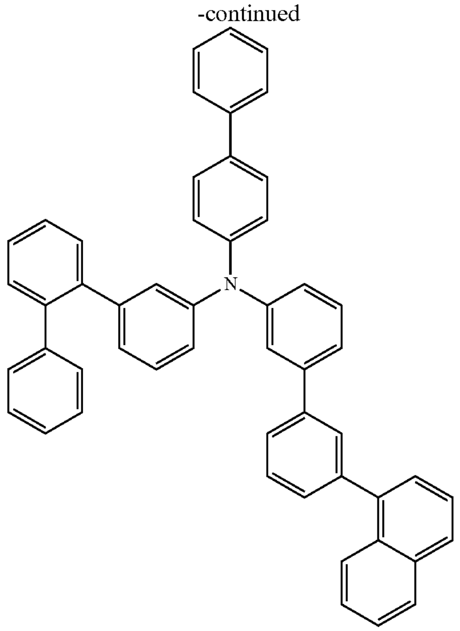
-continued
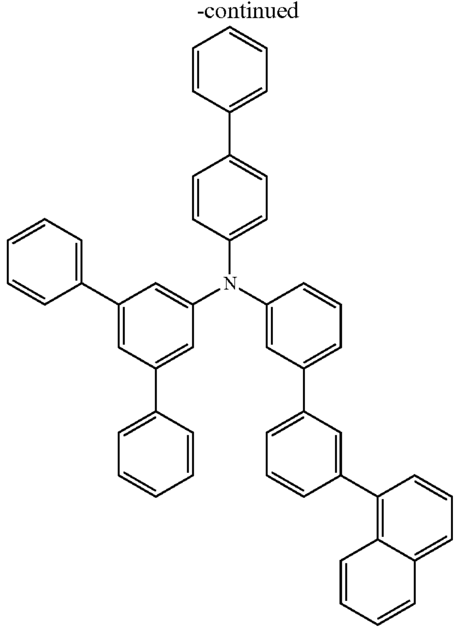
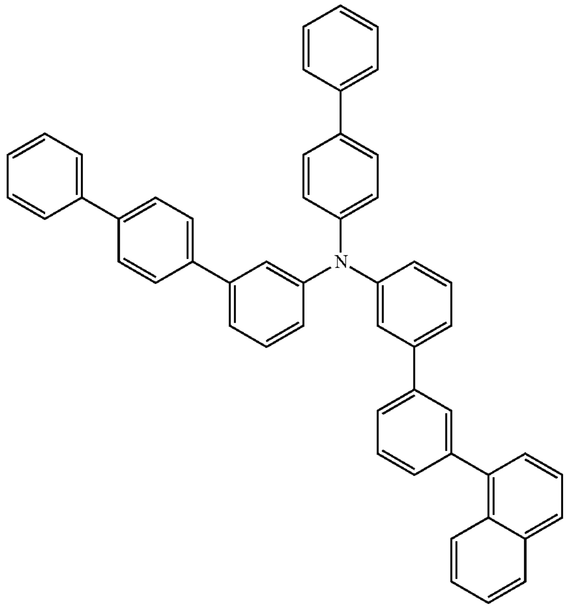
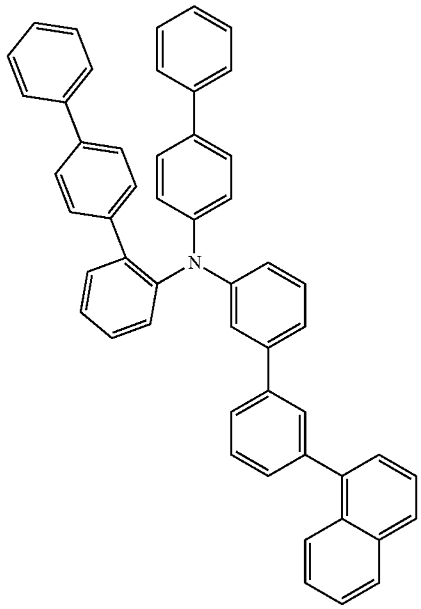

-continued
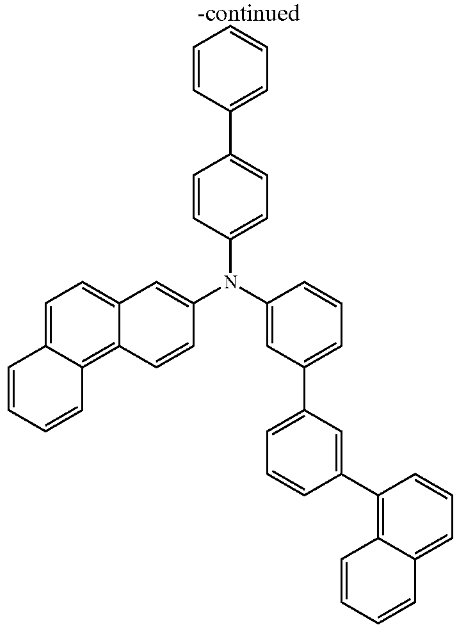
-continued
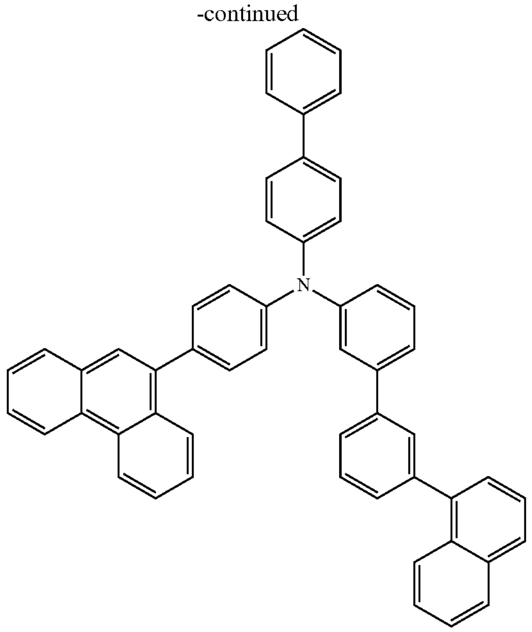
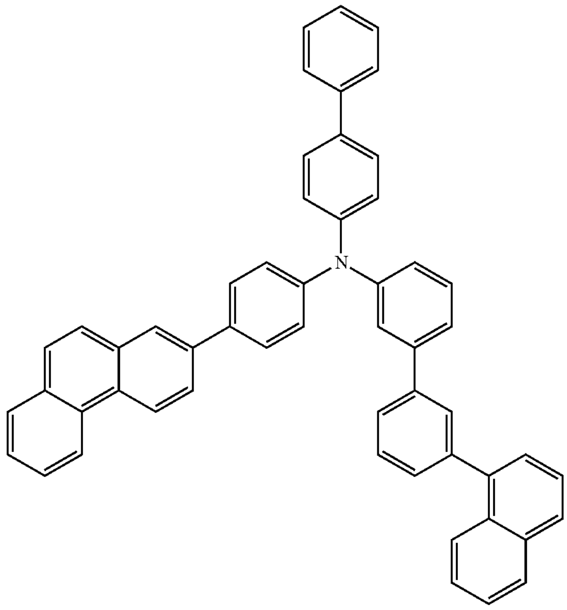
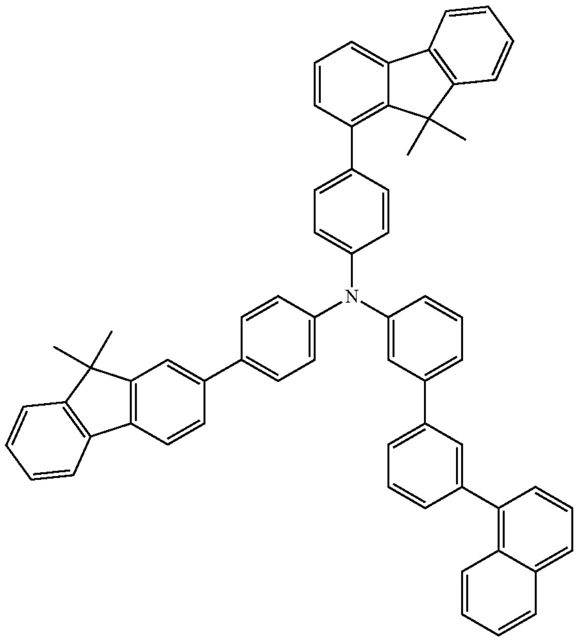

-continued
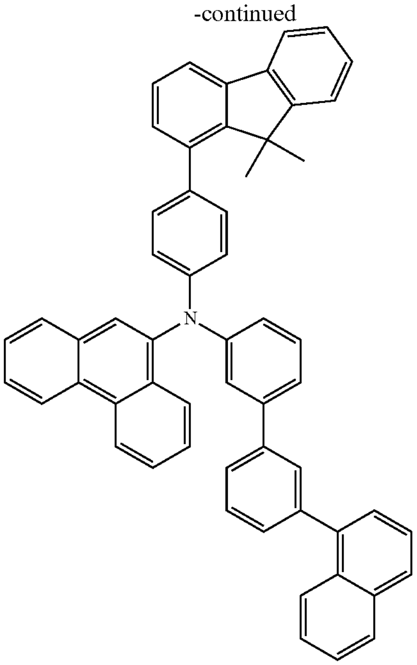
-continued
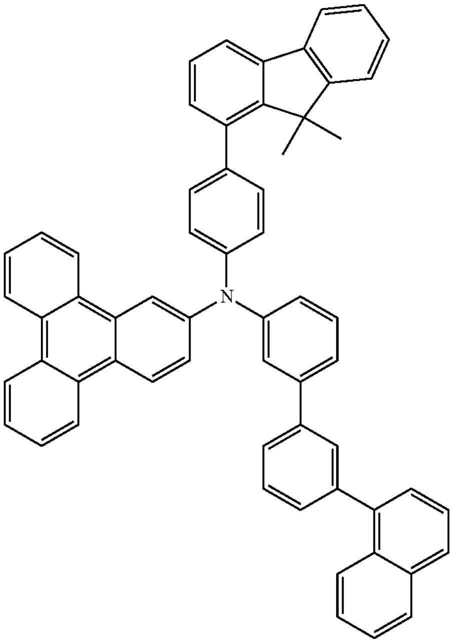
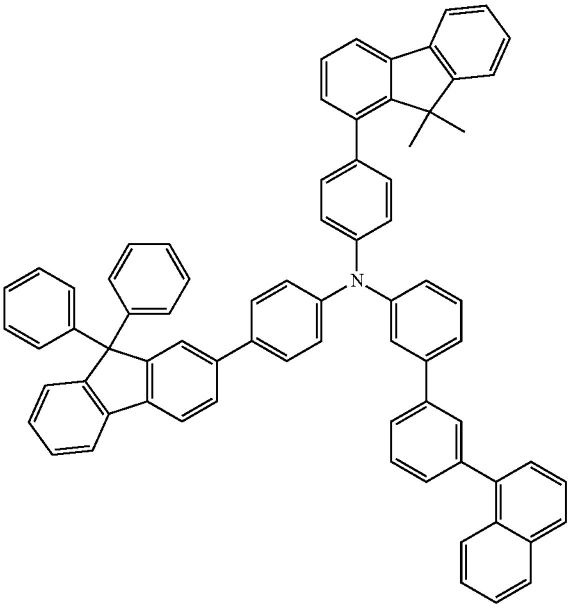
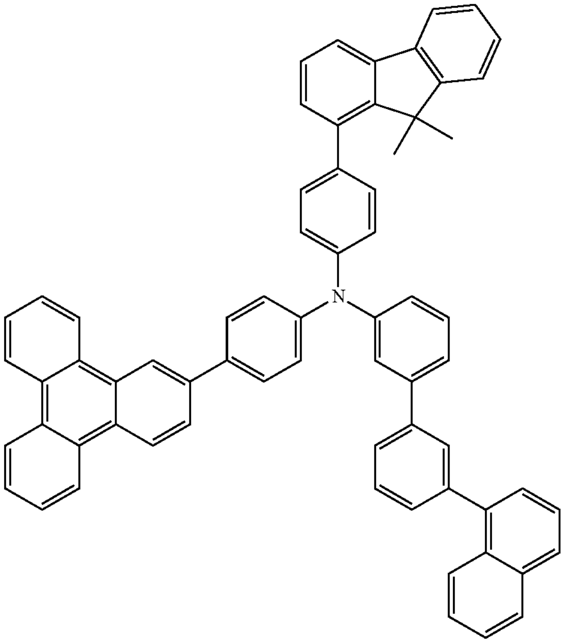

-continued
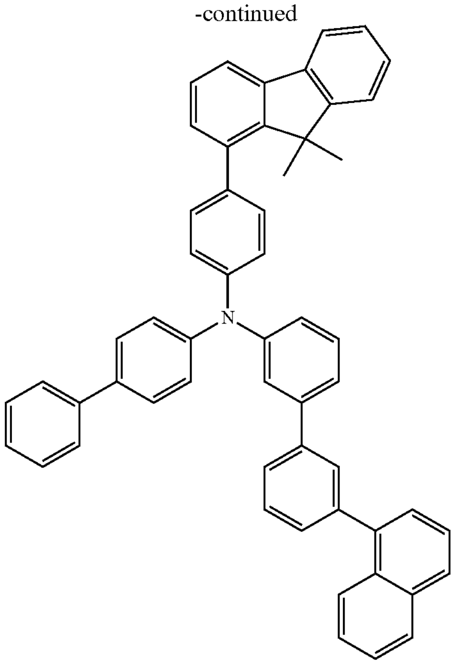
-continued
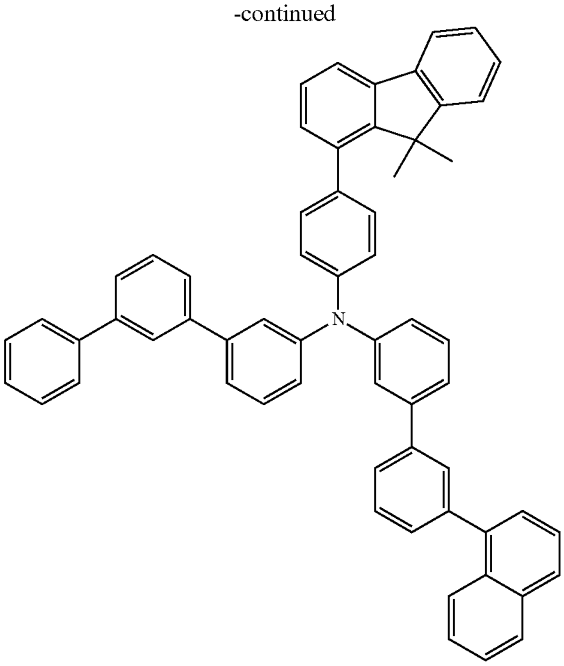
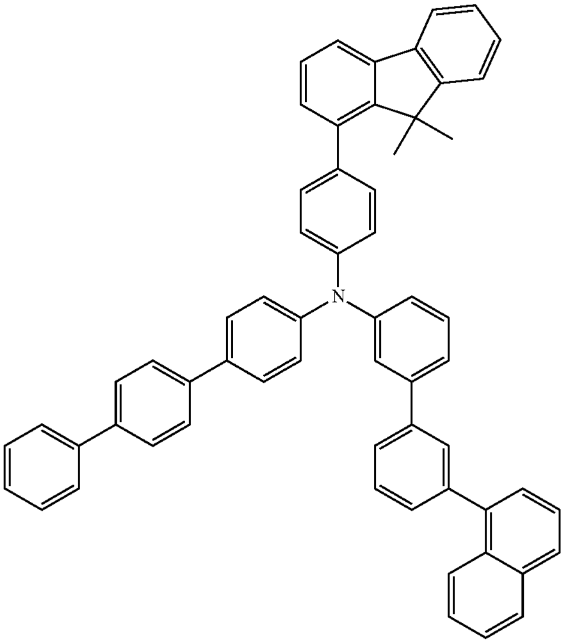
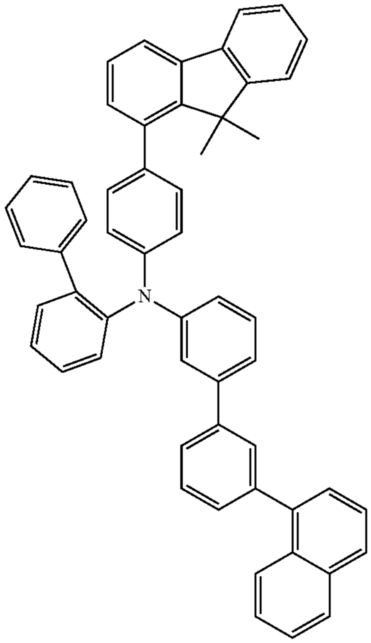

-continued
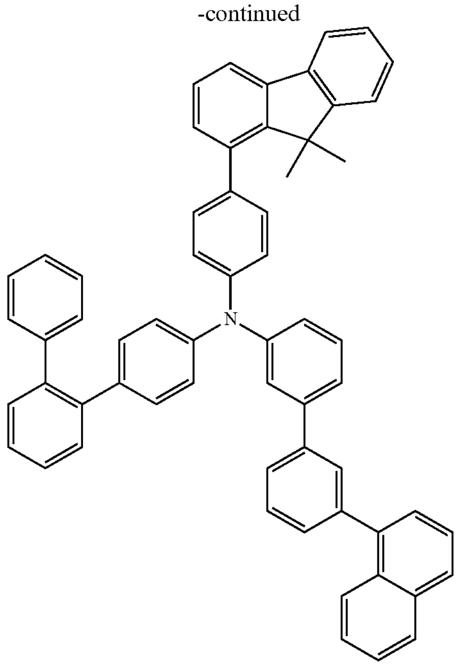
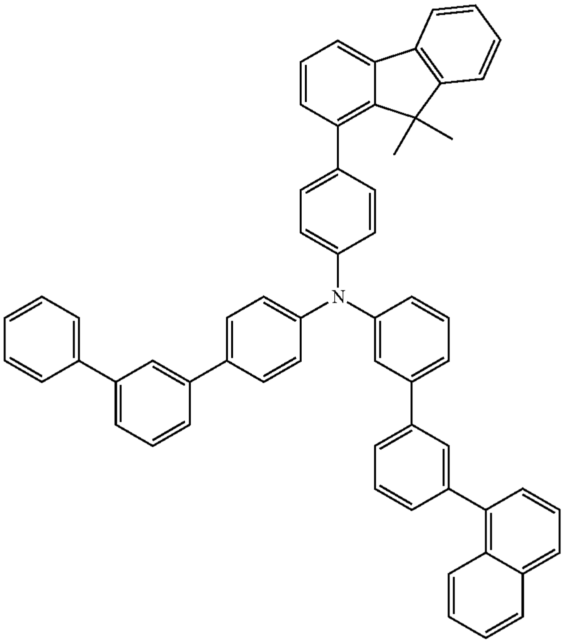
-continued
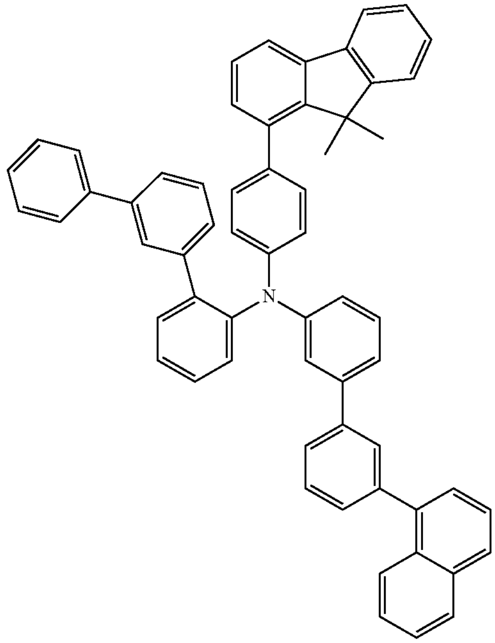
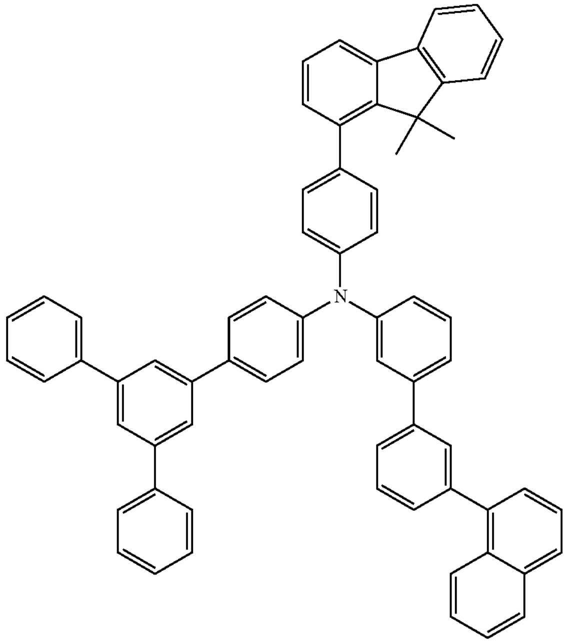

-continued
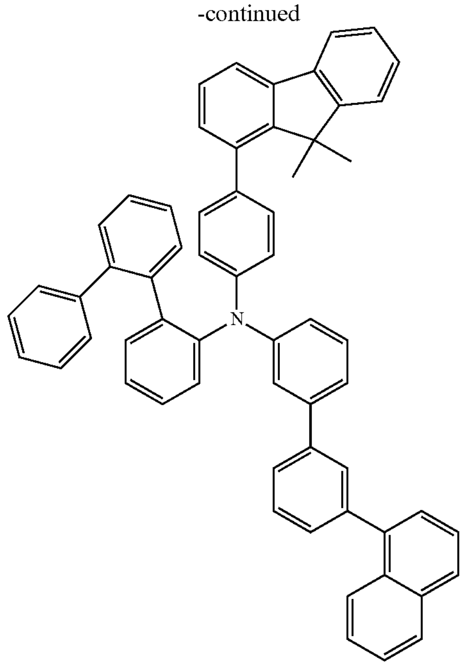
-continued
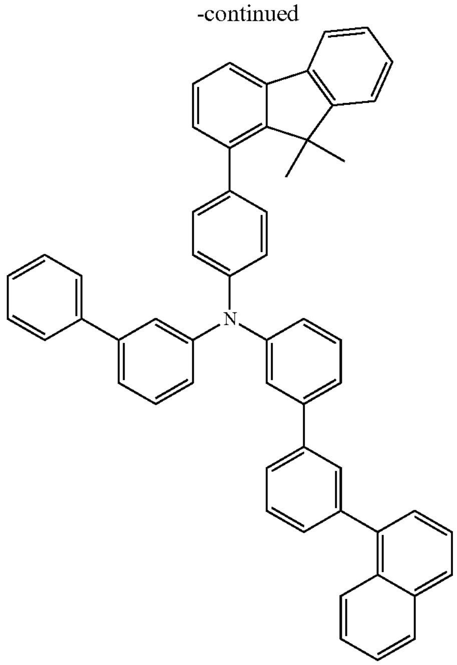
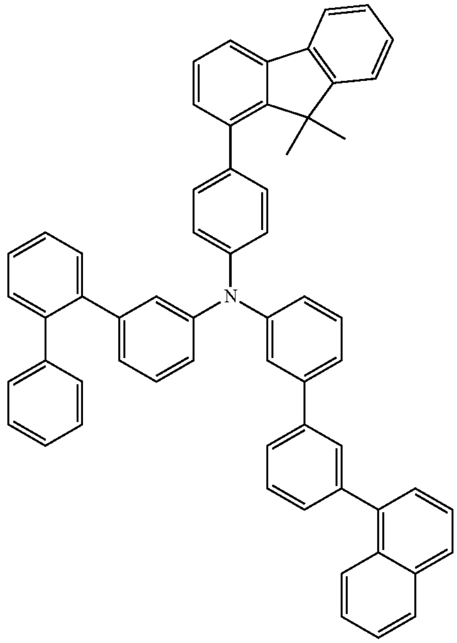
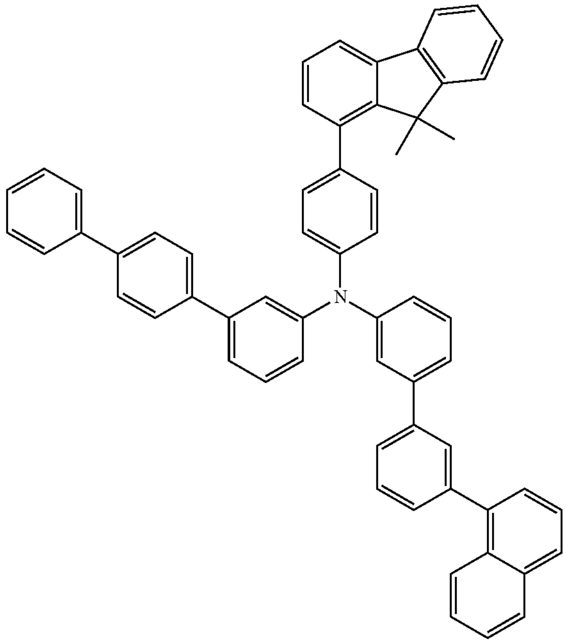

-continued
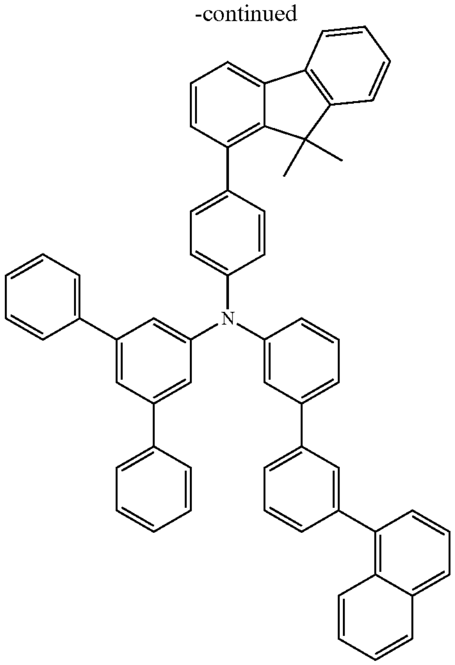
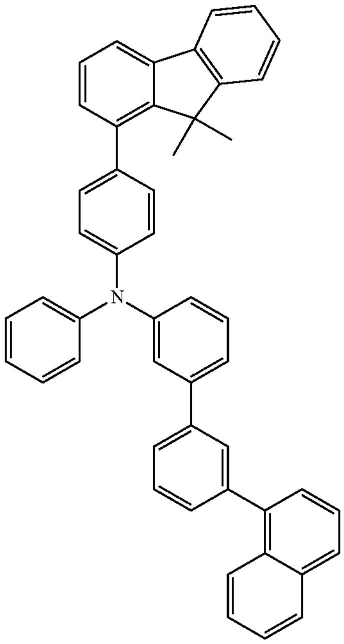
-continued
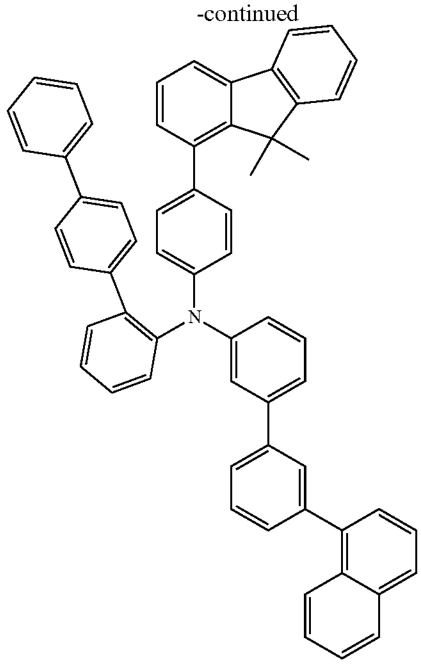
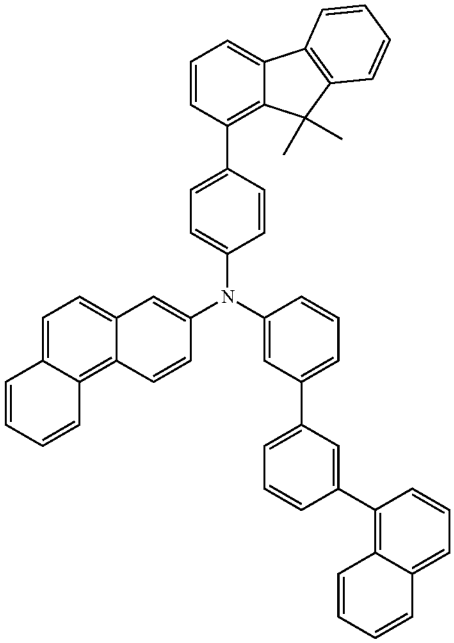

-continued
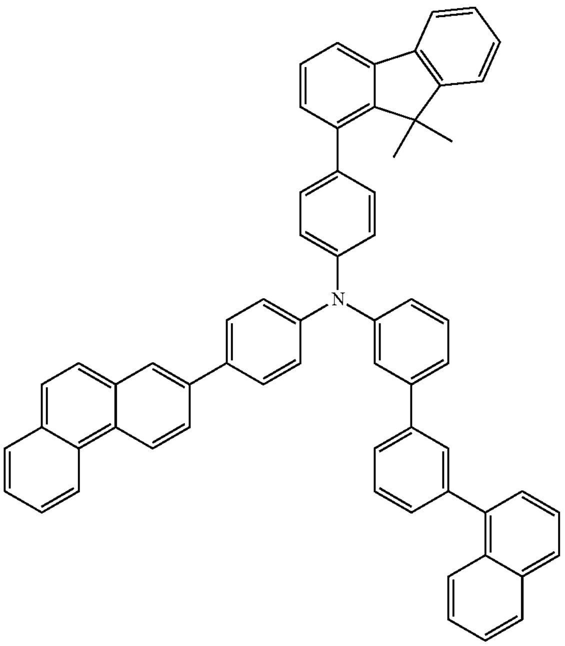
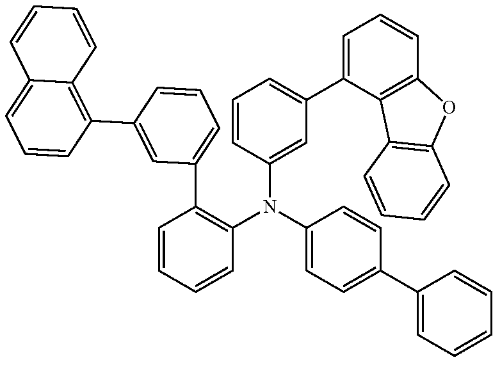
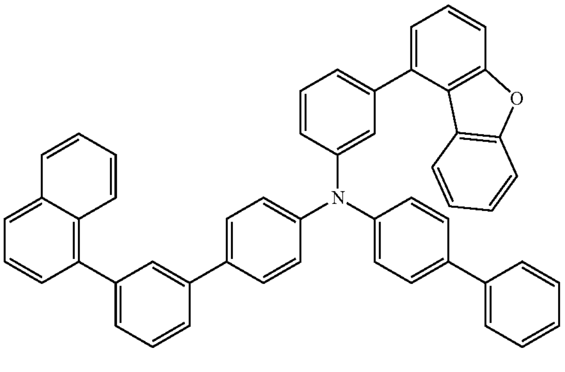
-continued
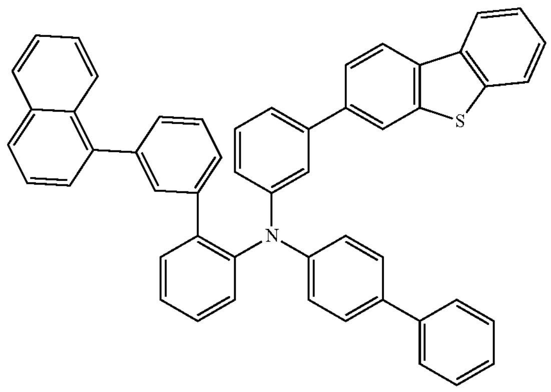
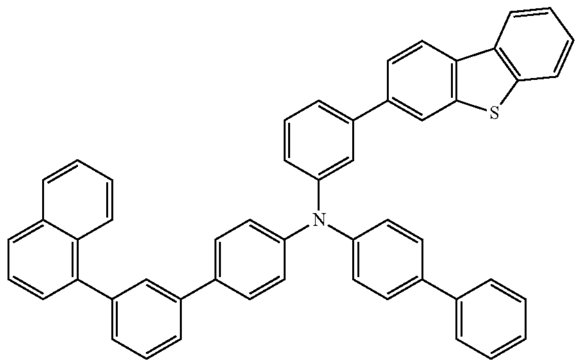
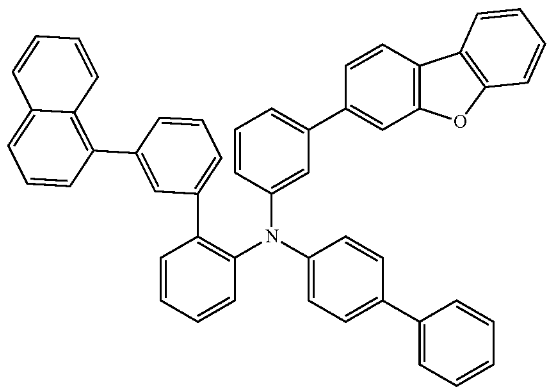
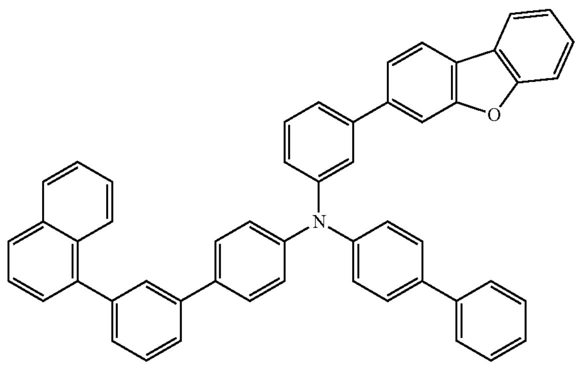

-continued
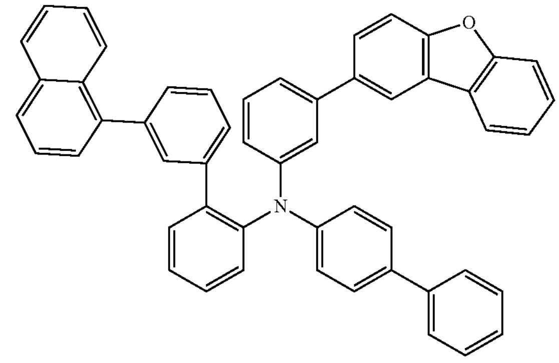
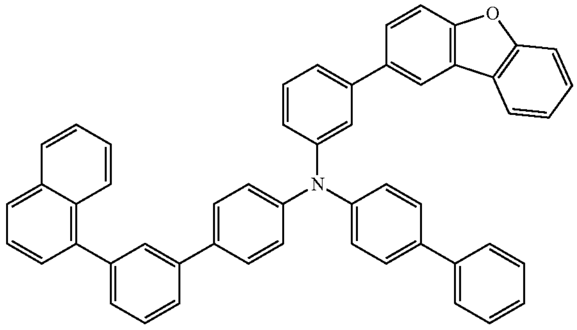
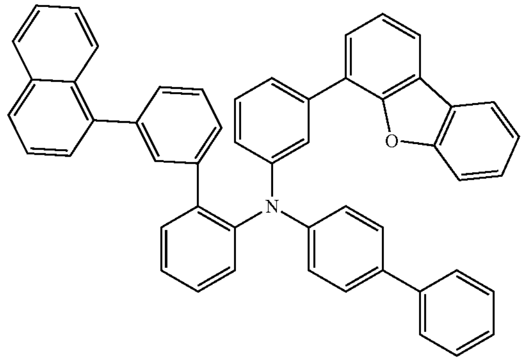
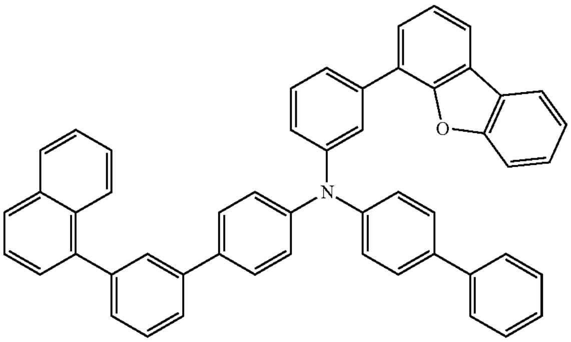
-continued
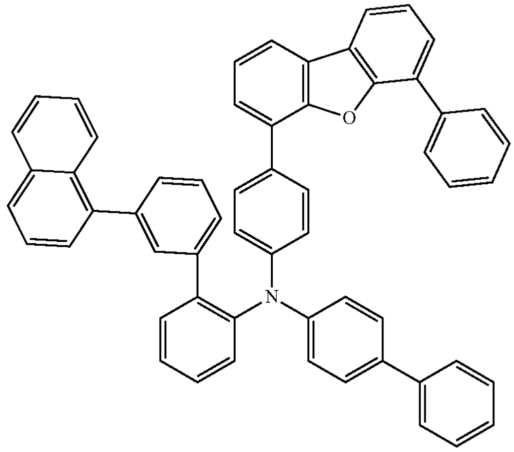
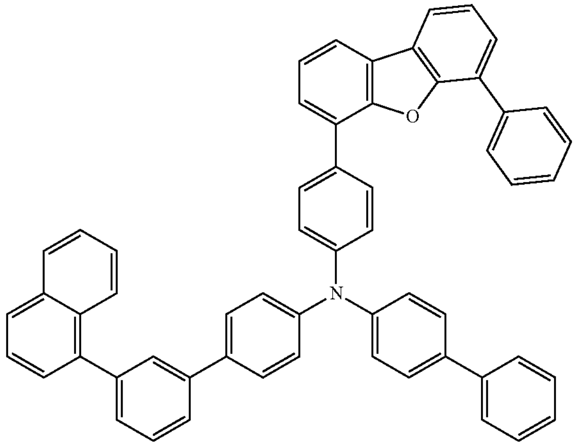
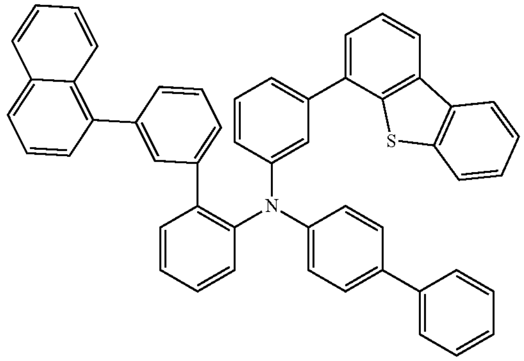
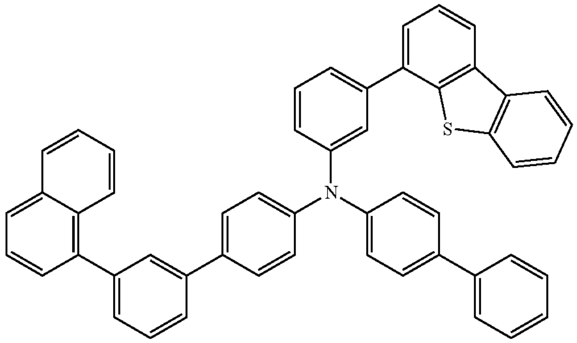

-continued
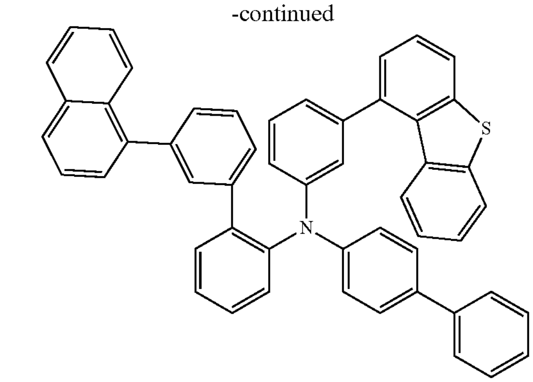
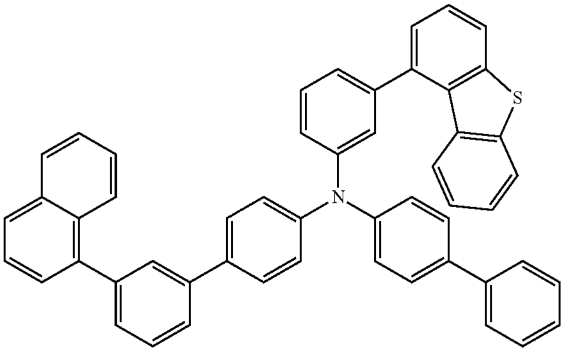
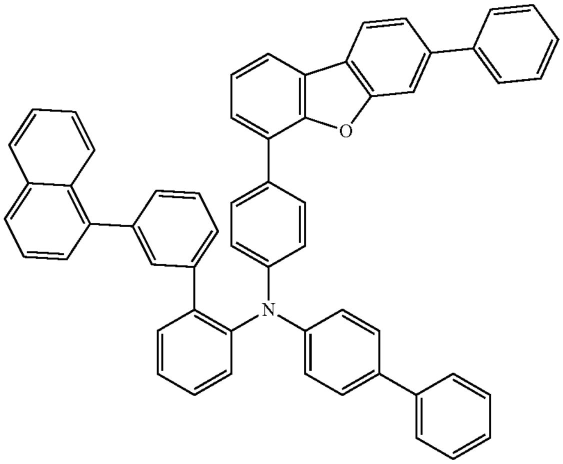
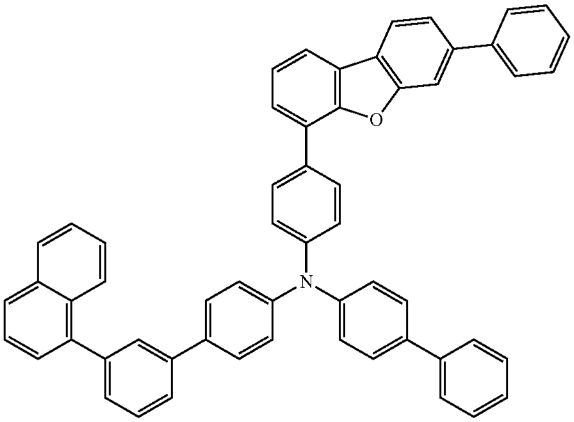
-continued
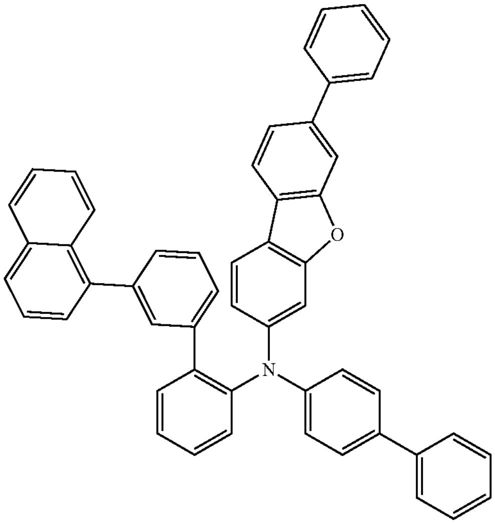
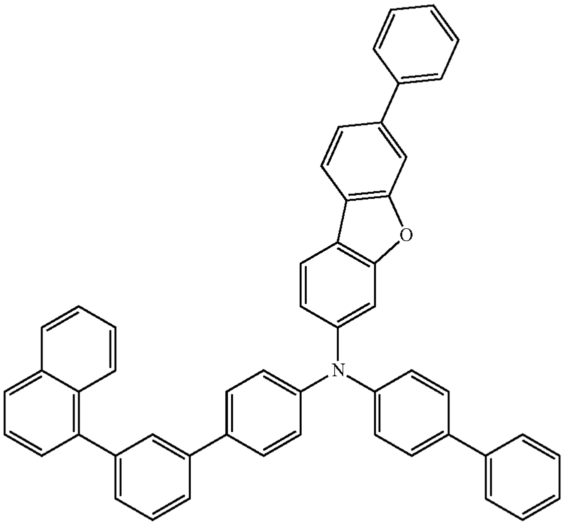
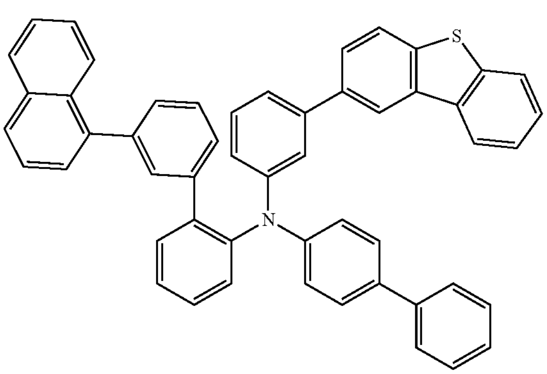

-continued
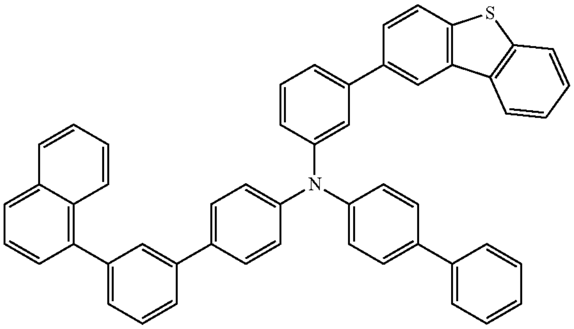
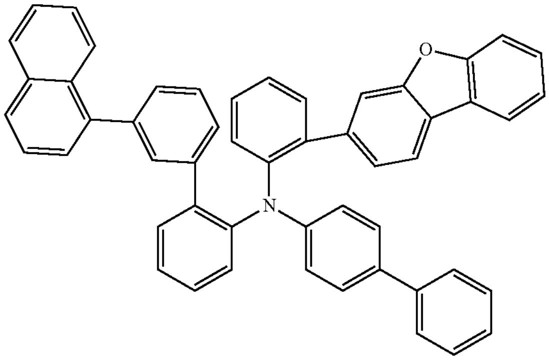
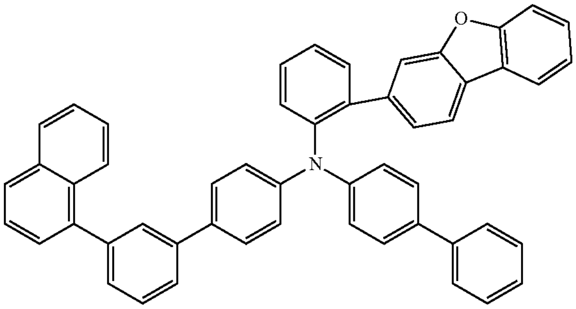
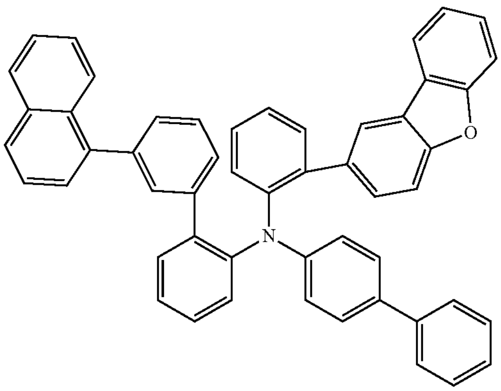
-continued
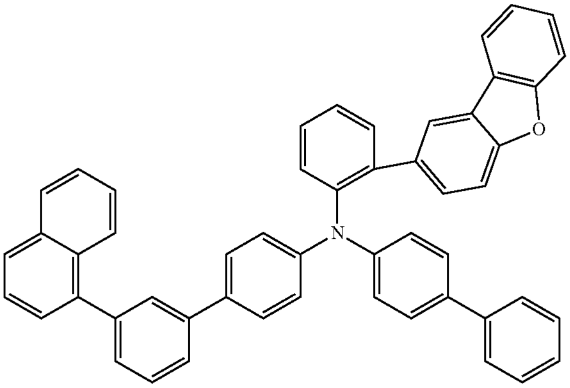
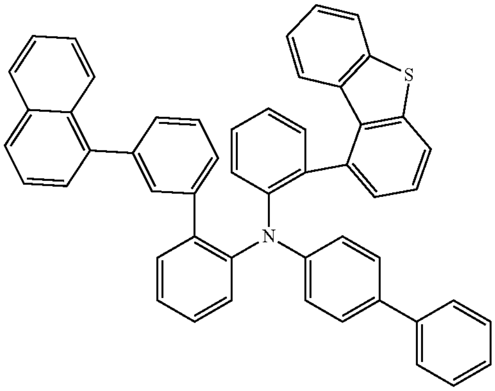
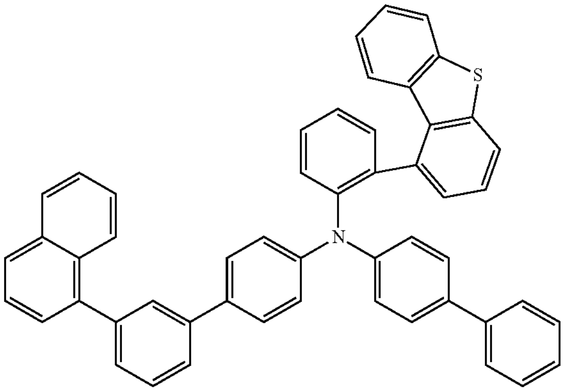 [SMILES: c1ccc(-c2ccc(N(c3ccc(-c4cccc(-c5cccc6ccccc56)c4)cc3)c3ccccc3-c3cccc4oc5ccccc5c34)cc2)cc1]
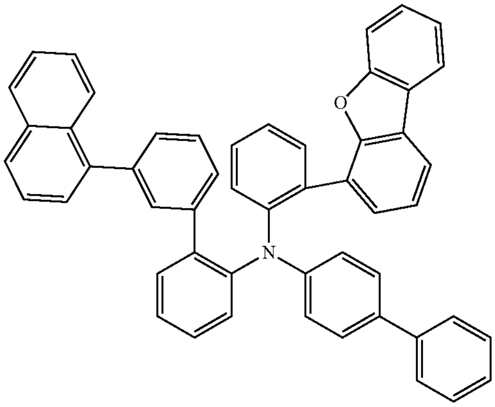

-continued
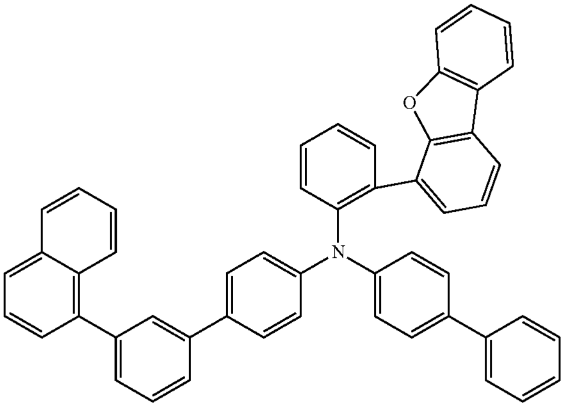
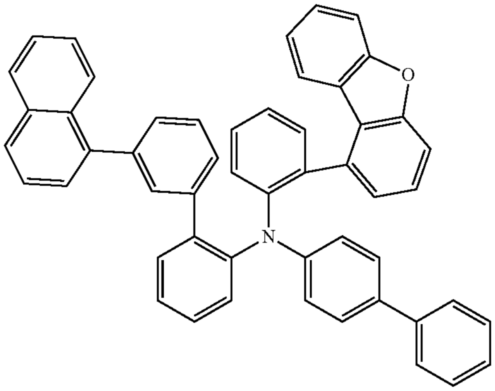
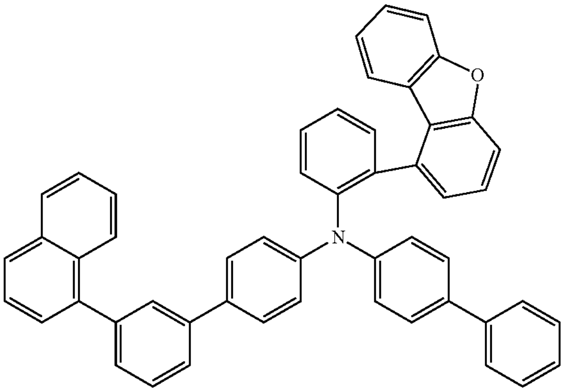
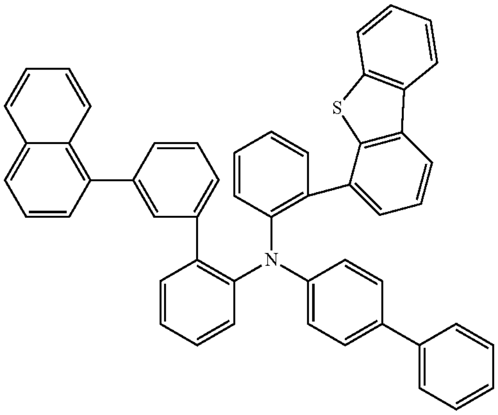
-continued
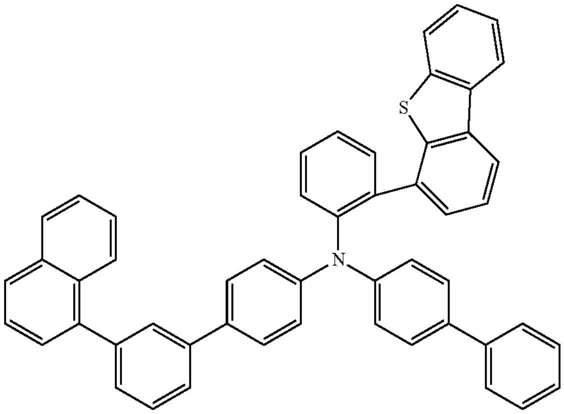
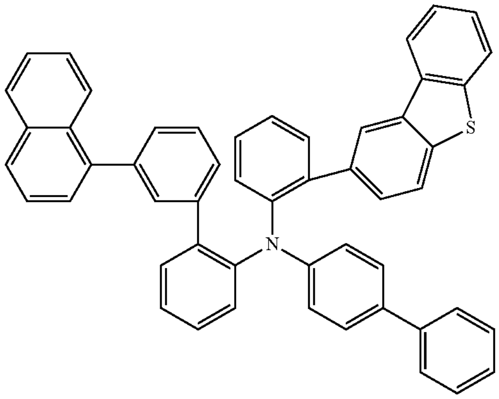
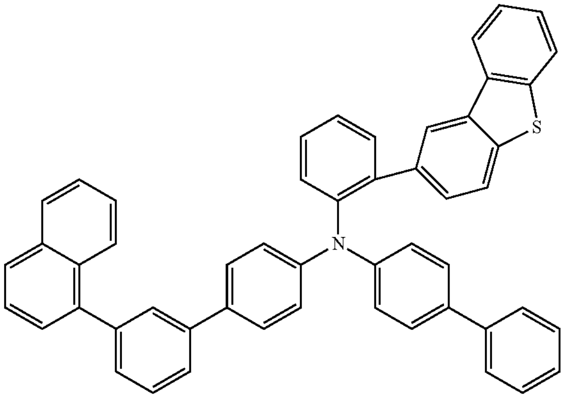
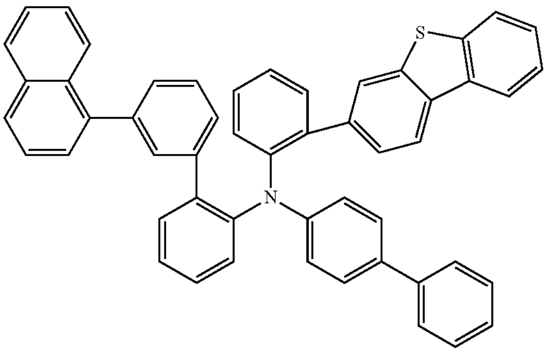

-continued
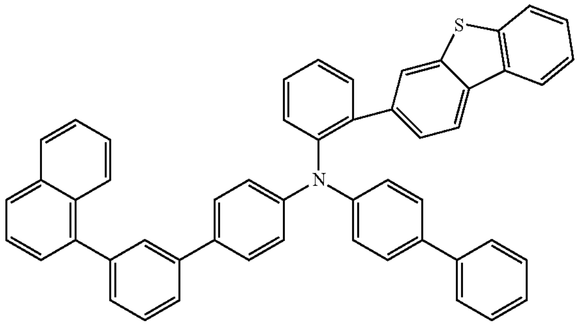
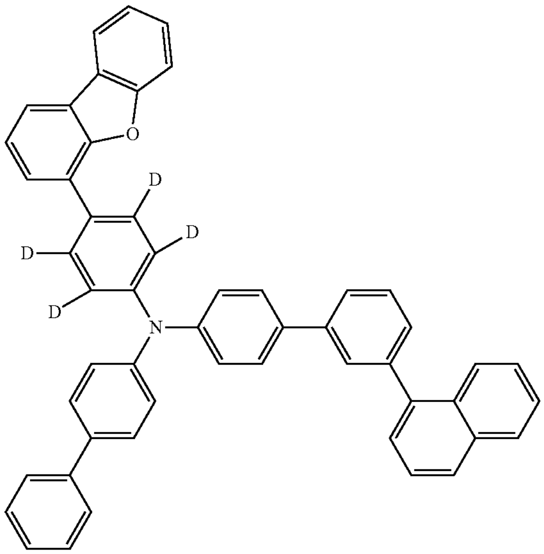
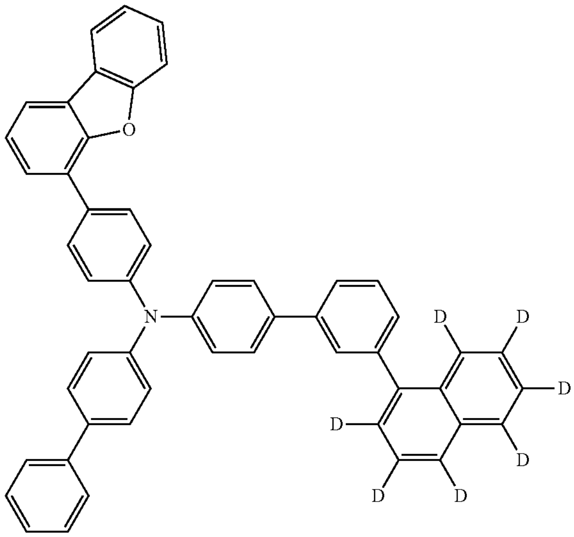
-continued
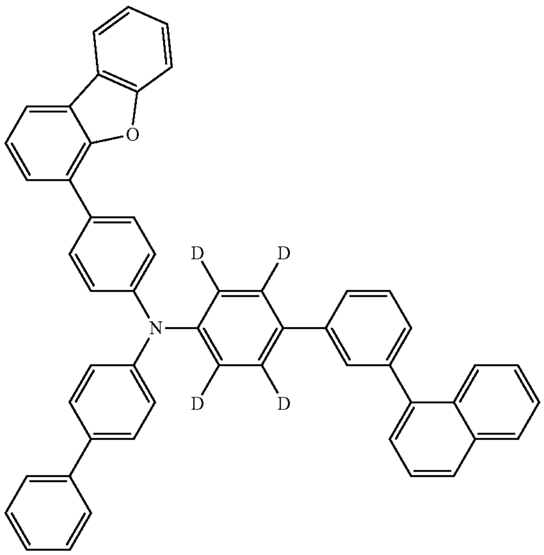
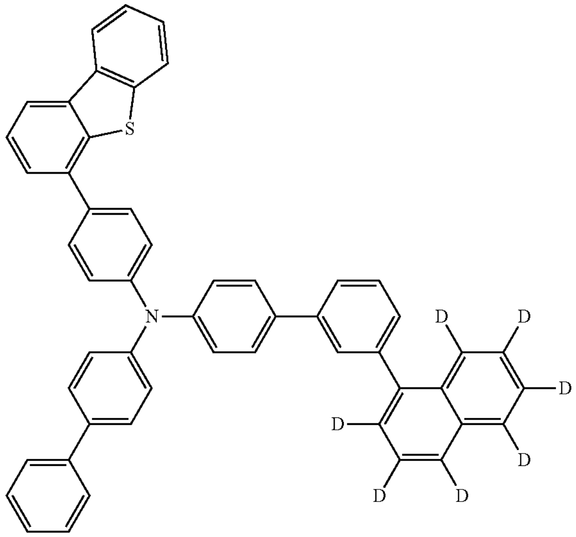
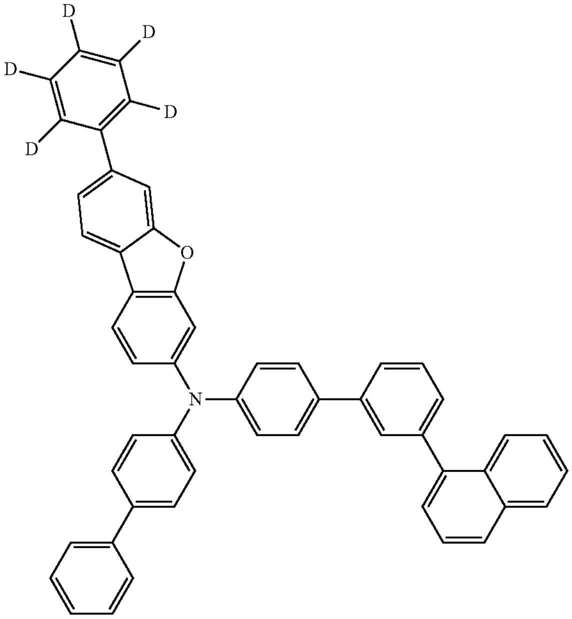

-continued
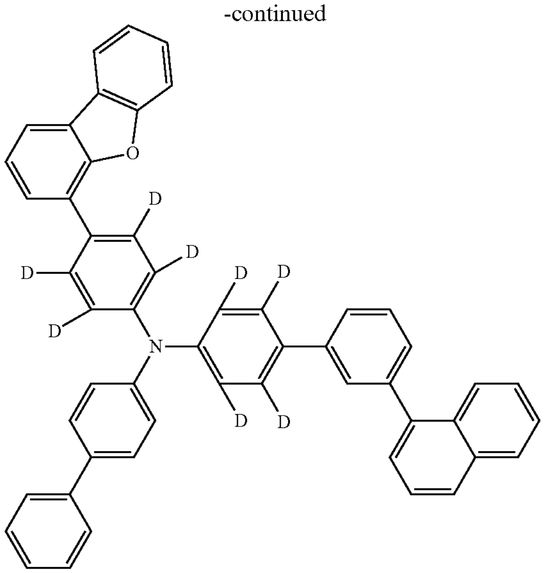
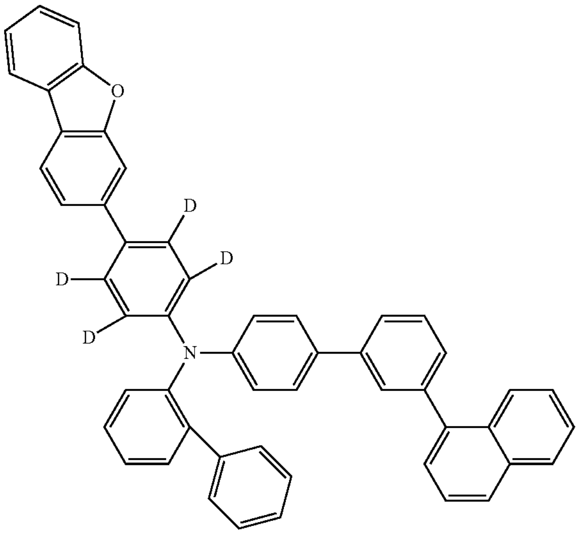
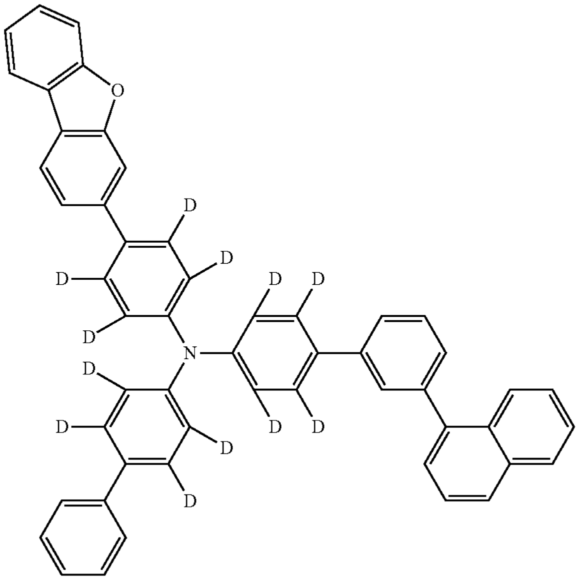
-continued
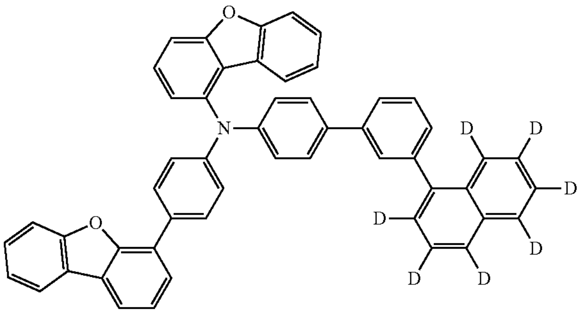
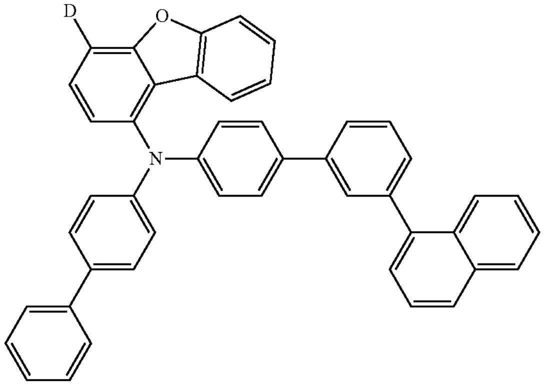
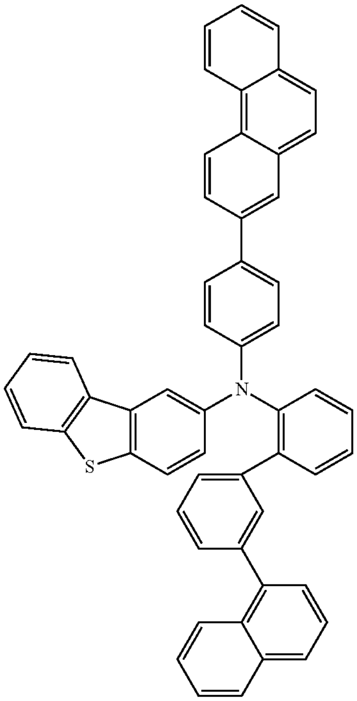

-continued
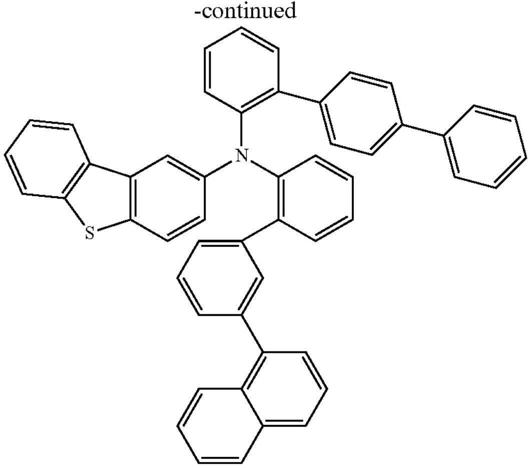
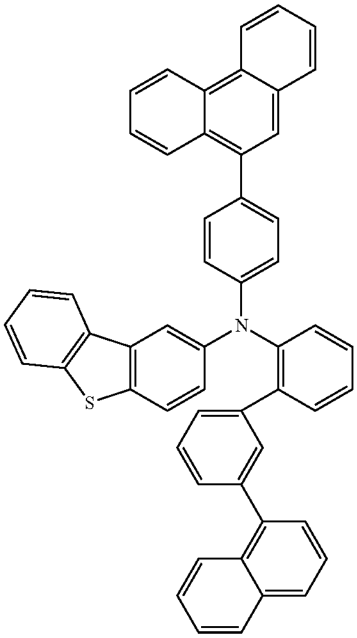
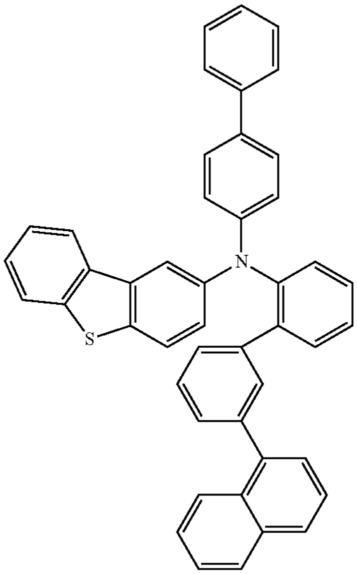
-continued
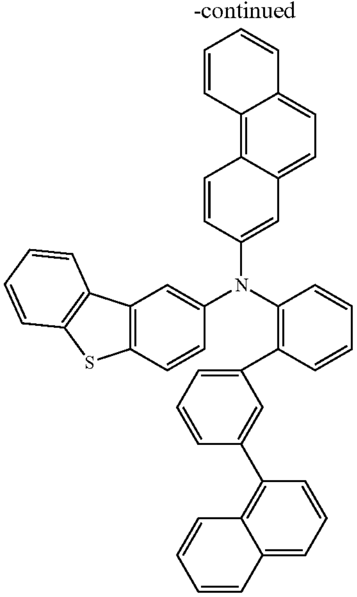
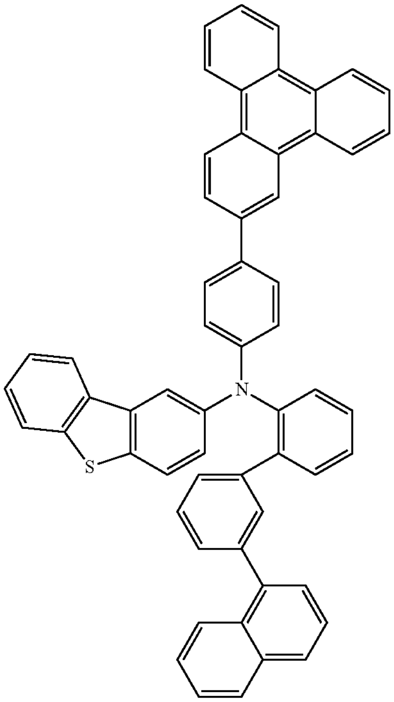

-continued
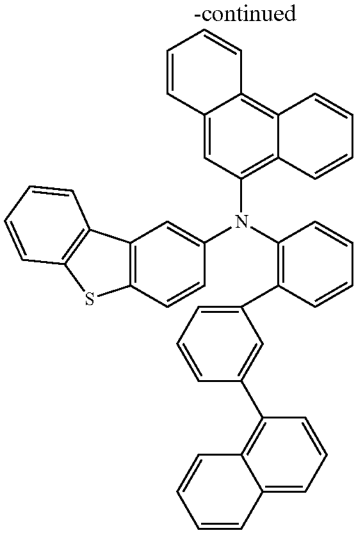
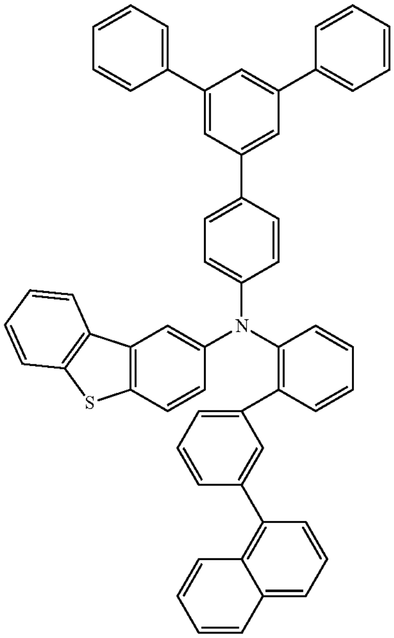
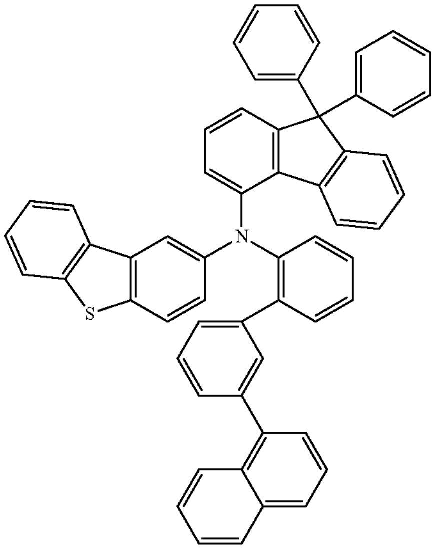
-continued
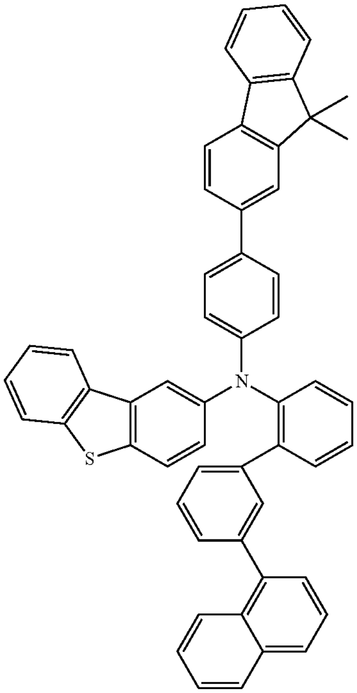
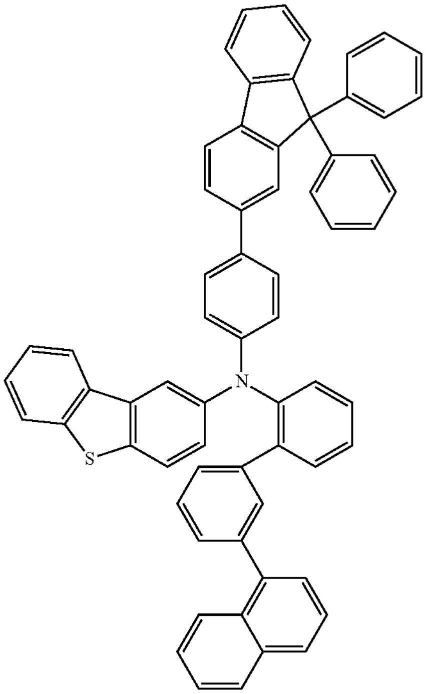

-continued
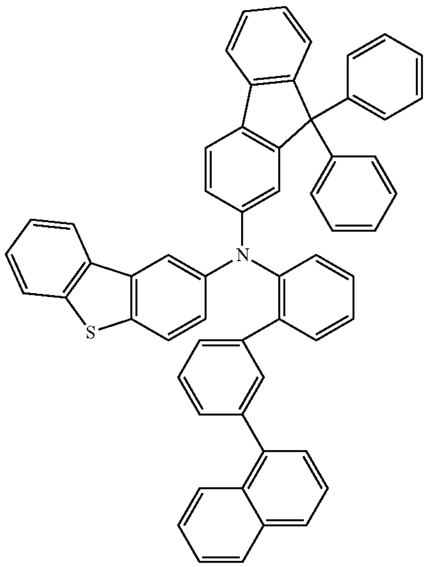
-continued
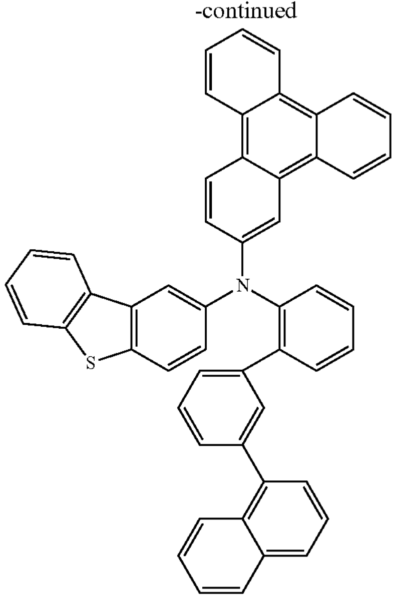
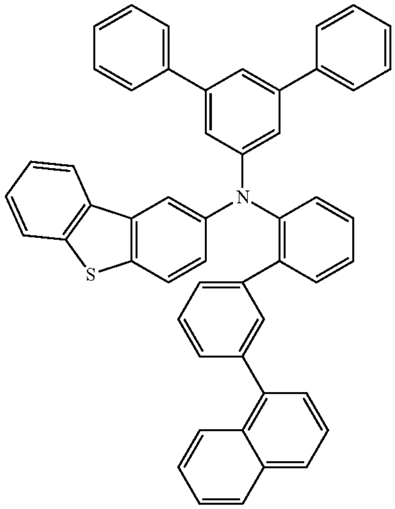
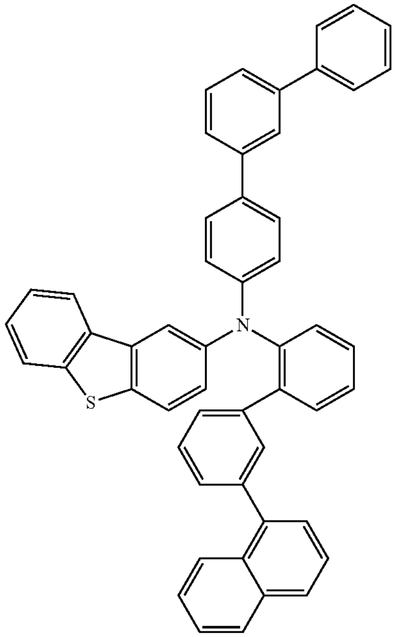
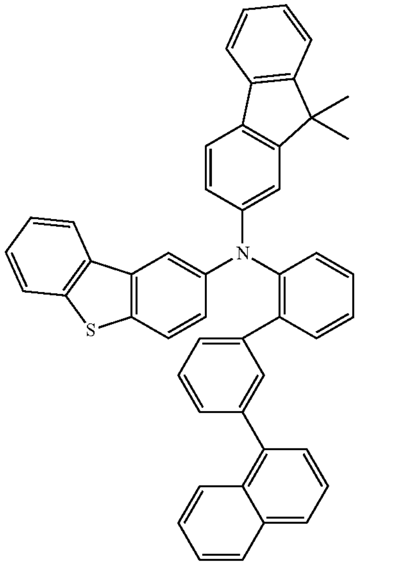

-continued
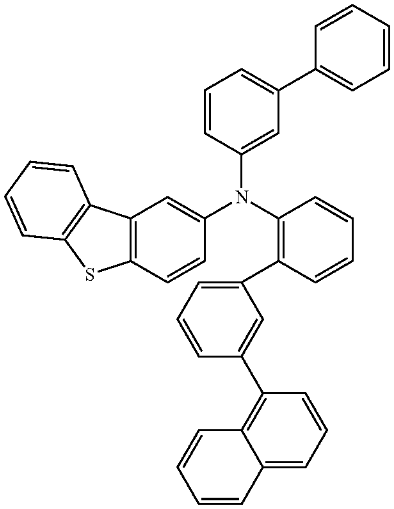
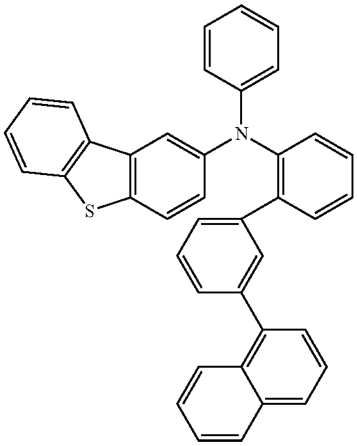
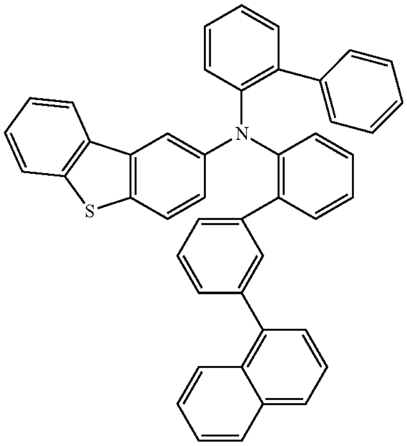
-continued
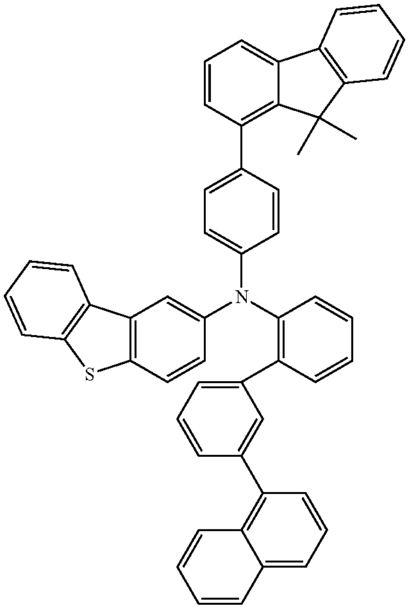
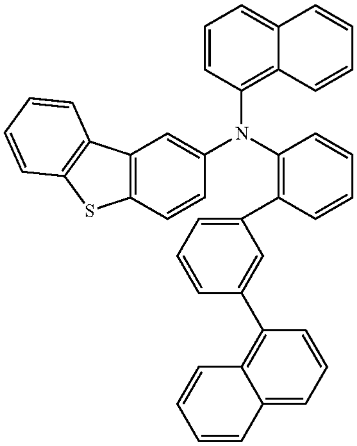

-continued
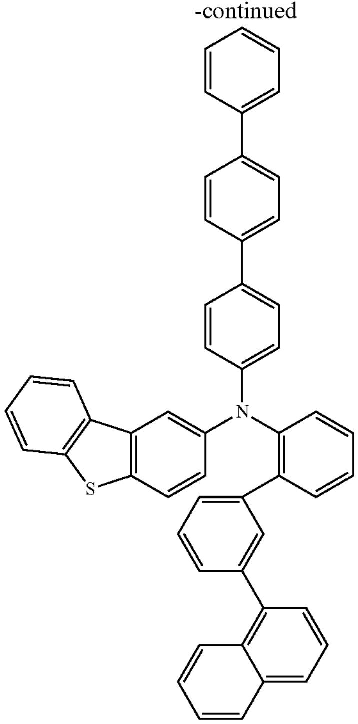
-continued
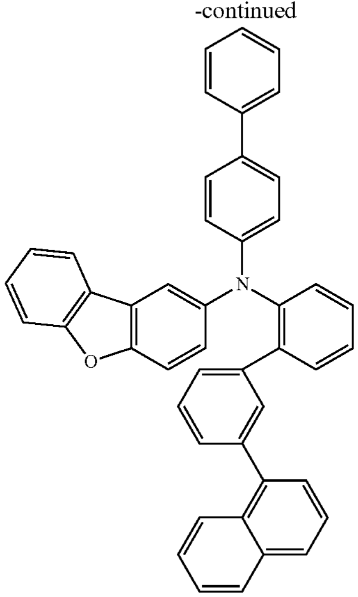
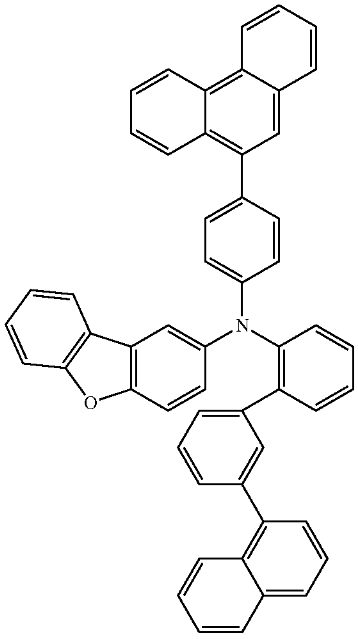
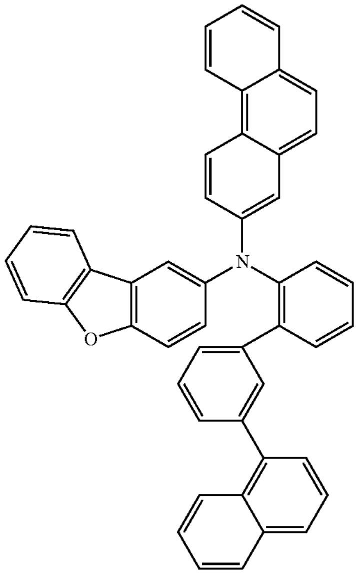

-continued
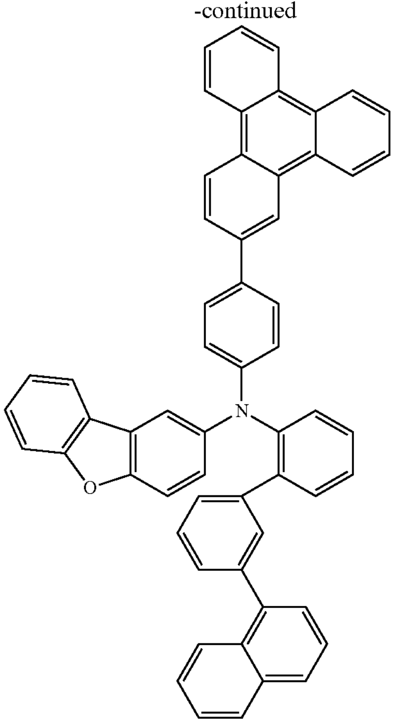
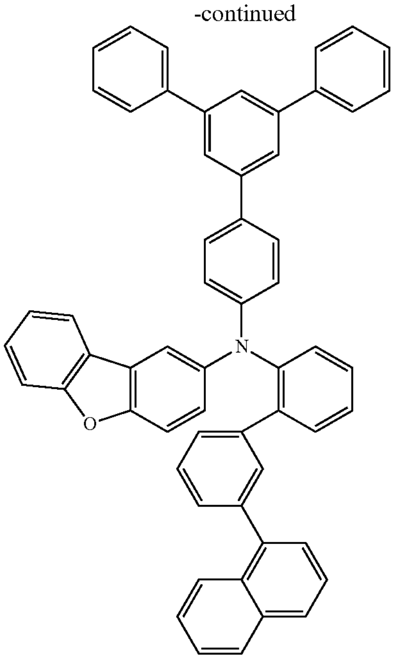
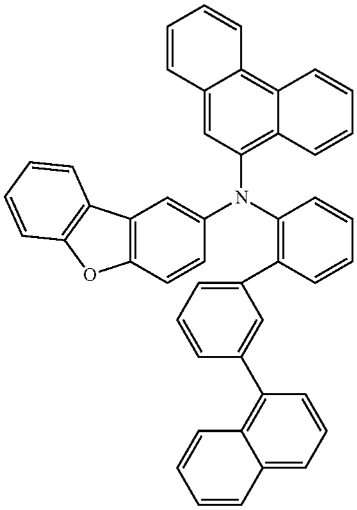
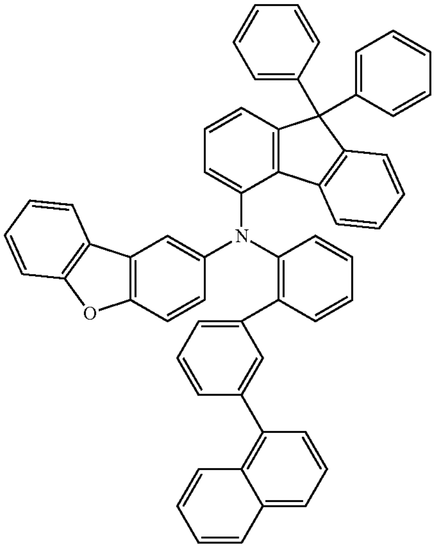

-continued
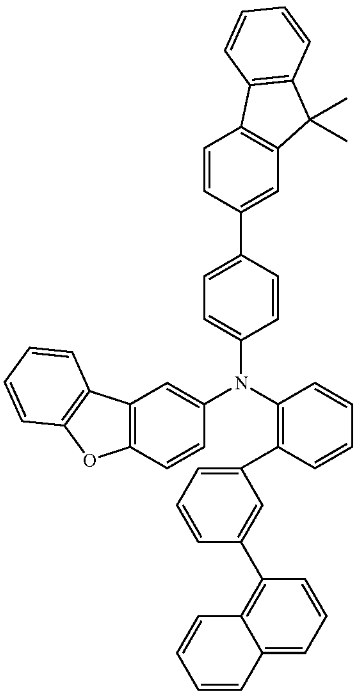
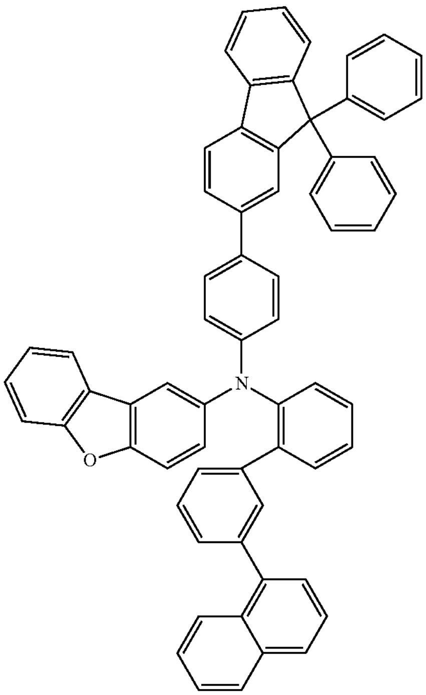
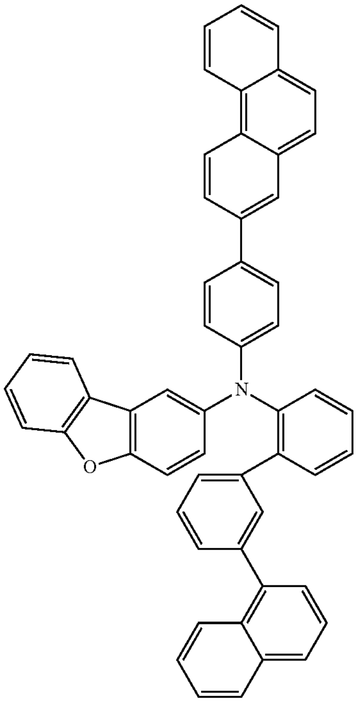
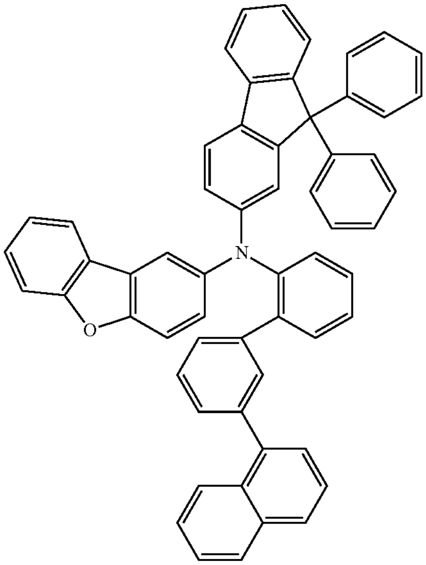

-continued
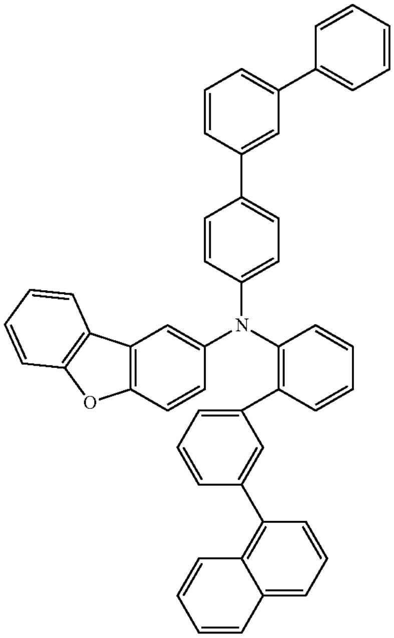
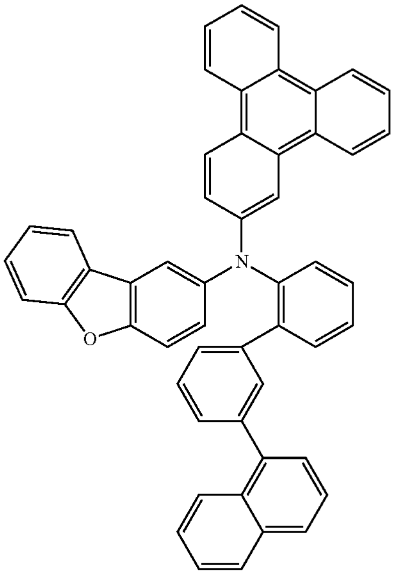
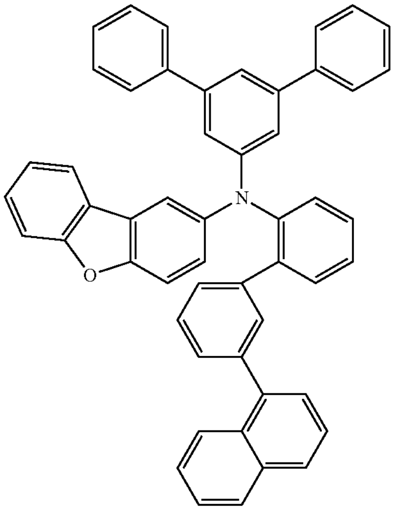
-continued
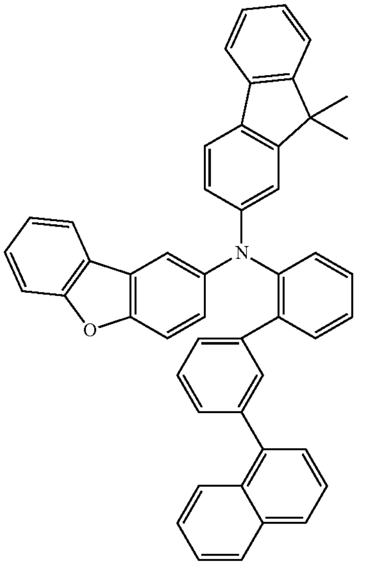
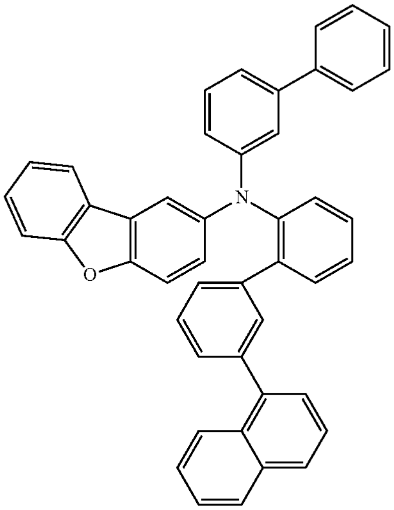
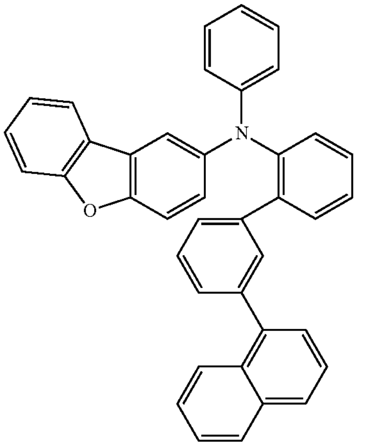

-continued
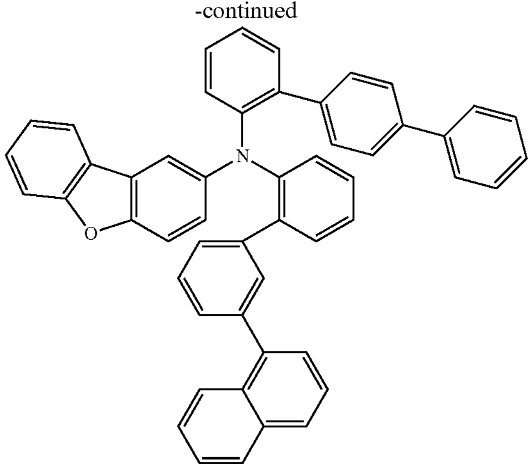
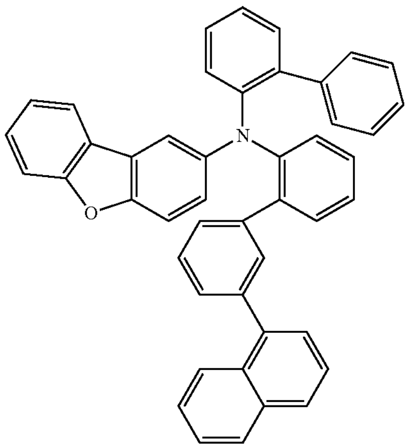
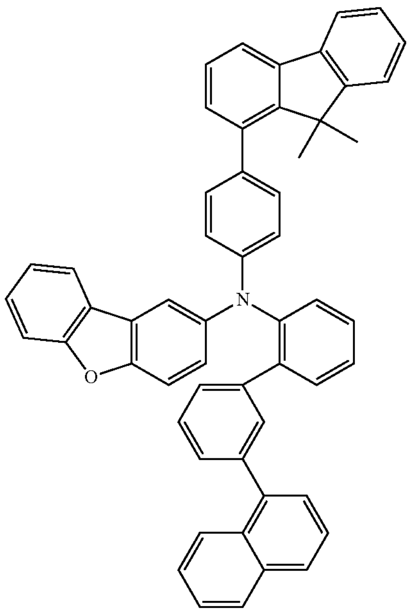
-continued
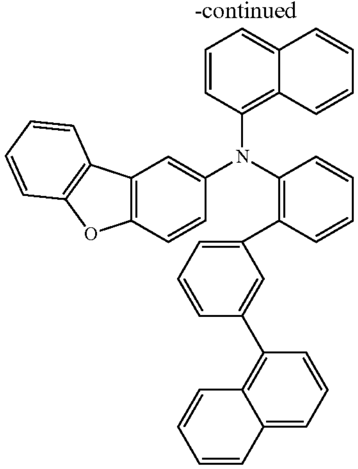
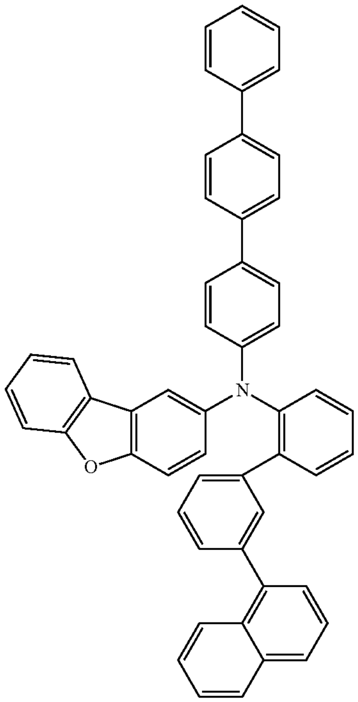 [SMILES: c1ccc(-c2ccc(-c3ccc(N(c4ccc5oc6ccccc6c5c4)c4ccccc4-c4cccc(-c5cccc6ccccc56)c4)cc3)cc2)cc1]

-continued
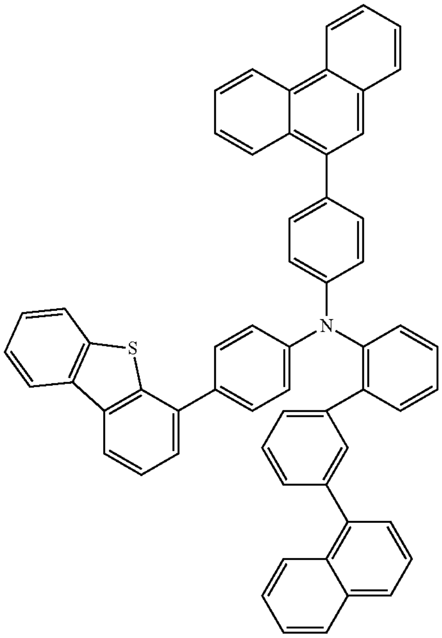
-continued
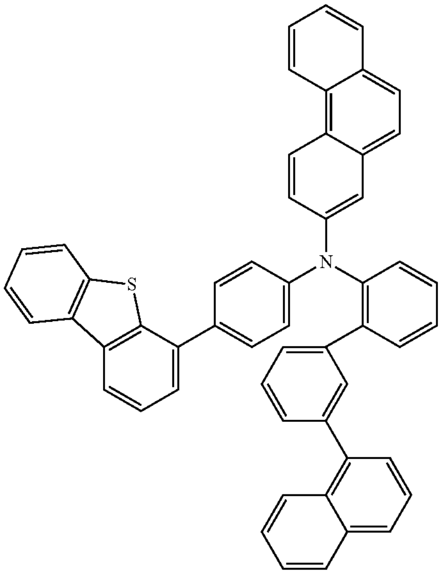
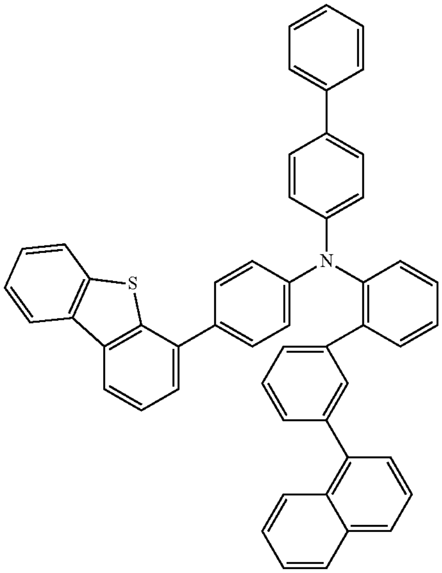
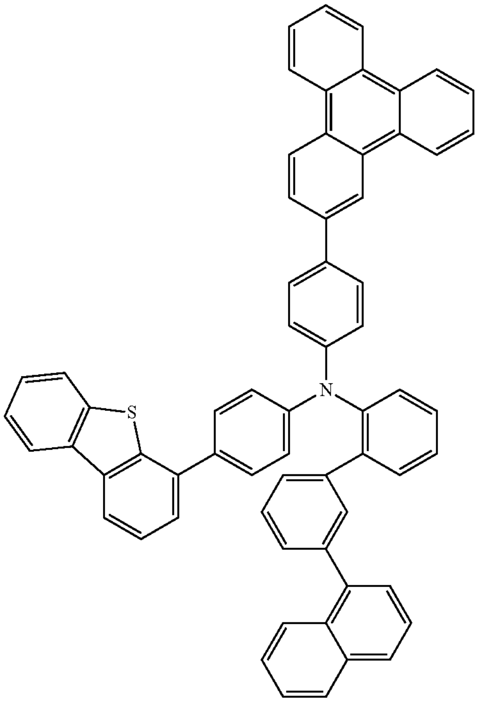

-continued
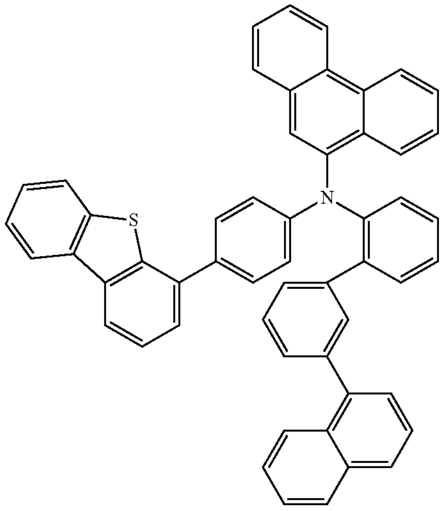
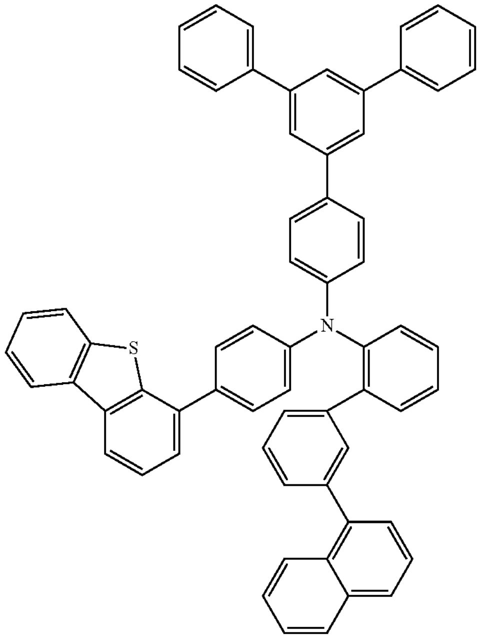
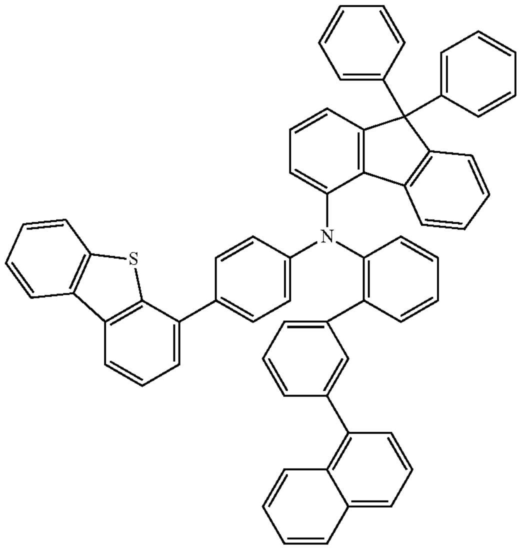
-continued
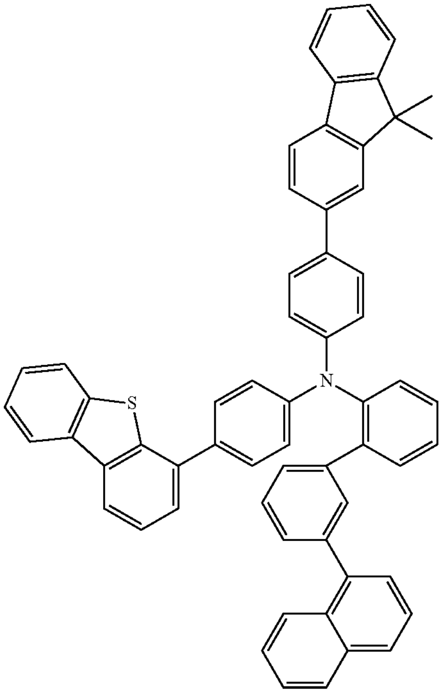
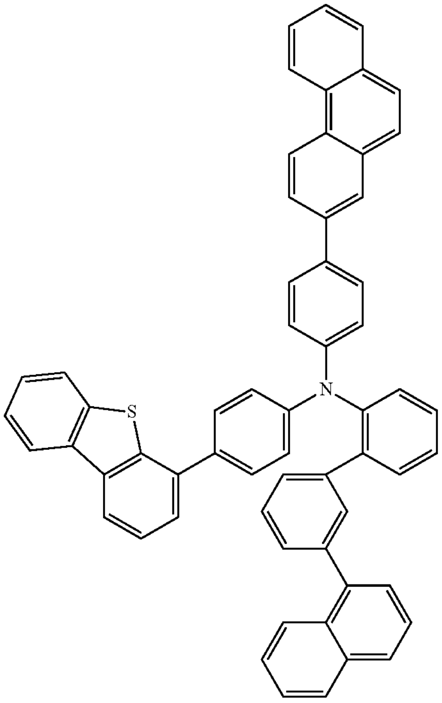 [SMILES: c1cc(-c2ccccc2N(c2ccc(-c3ccc4c(ccc5ccccc54)c3)cc2)c2ccc(-c3cccc4c3sc3ccccc34)cc2)cc(-c2cccc3ccccc23)c1]

-continued
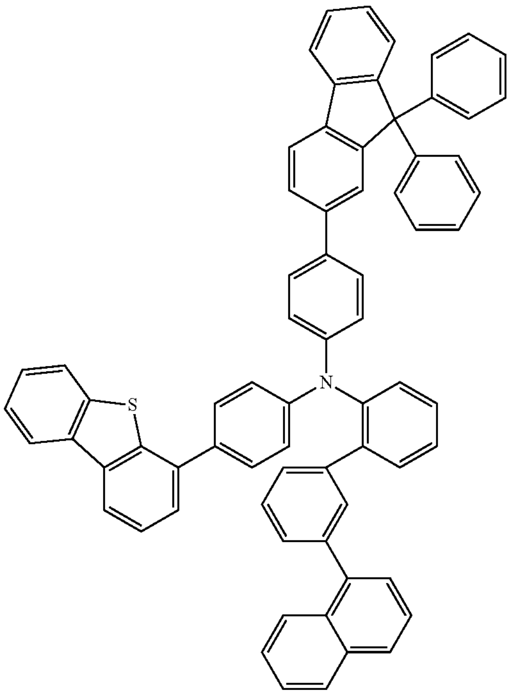
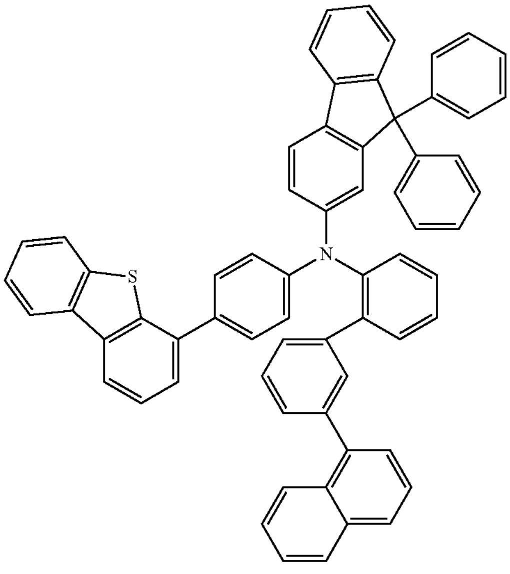
-continued
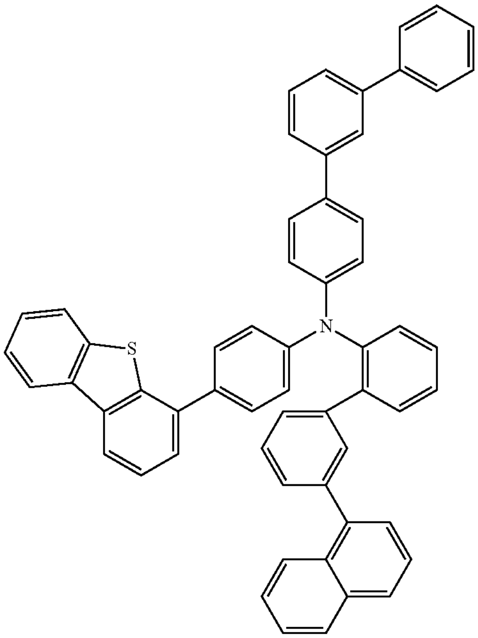
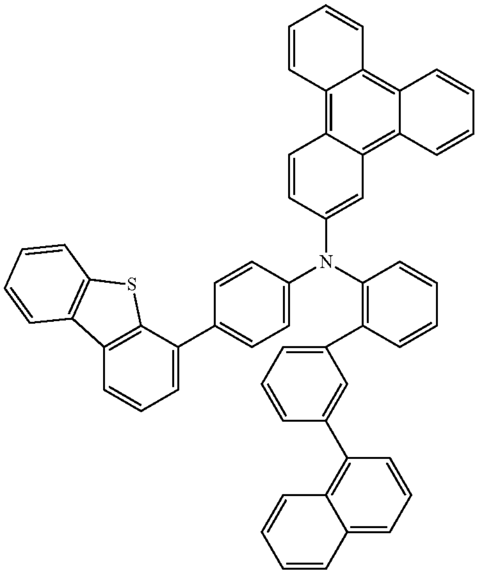
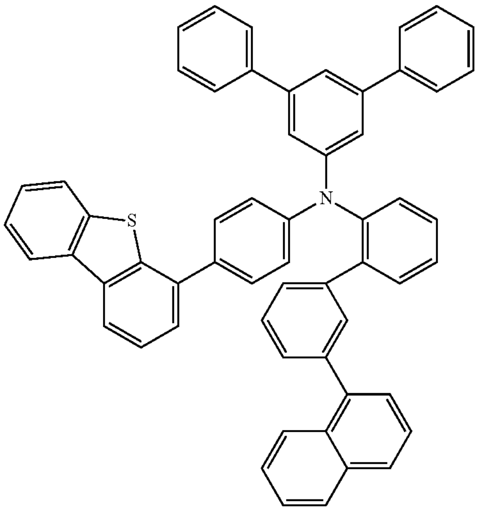

-continued
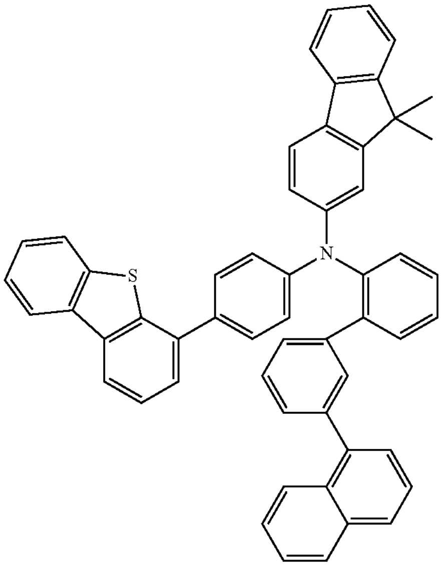
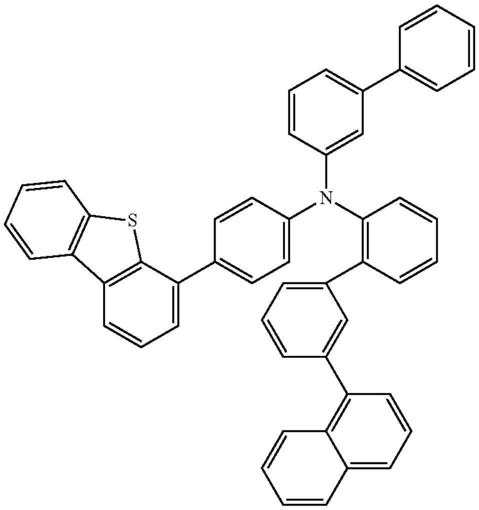
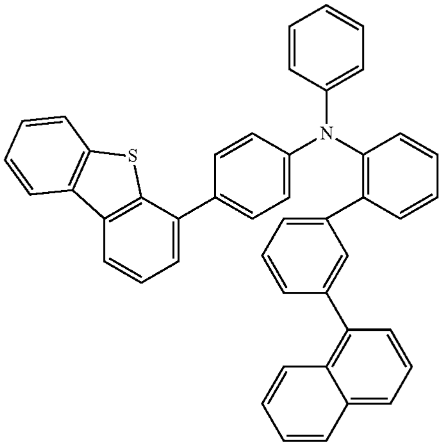
-continued
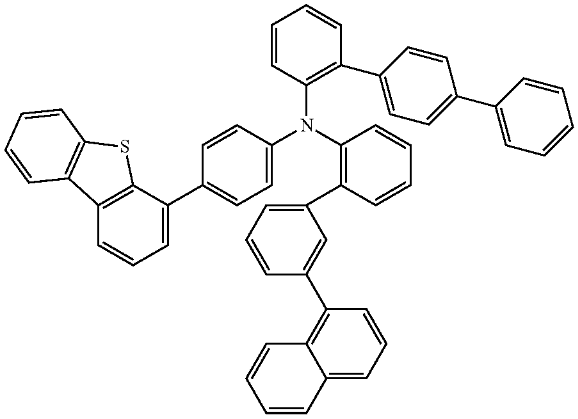
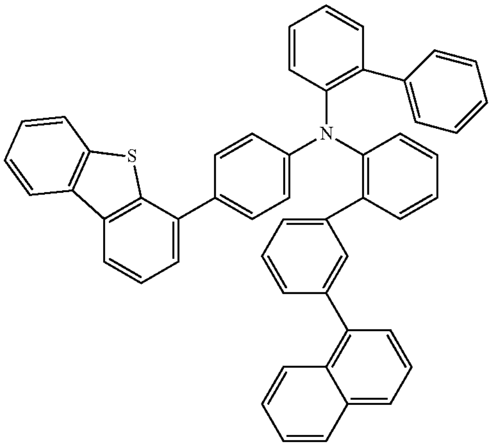
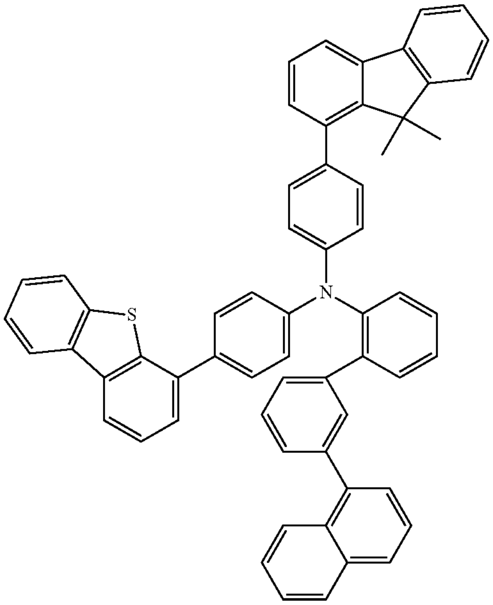

-continued
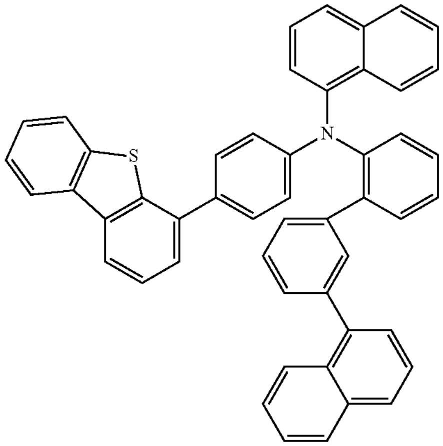
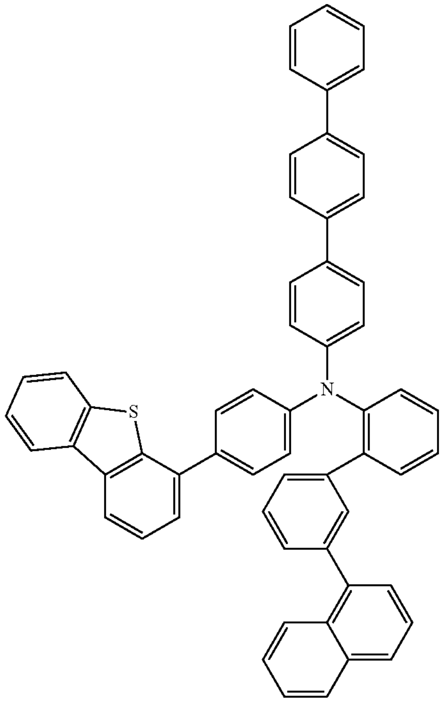
-continued
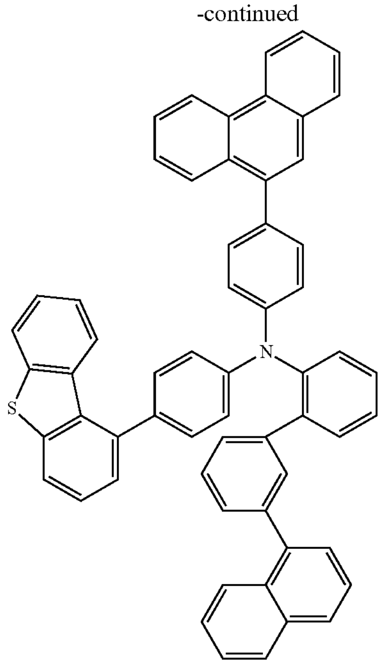
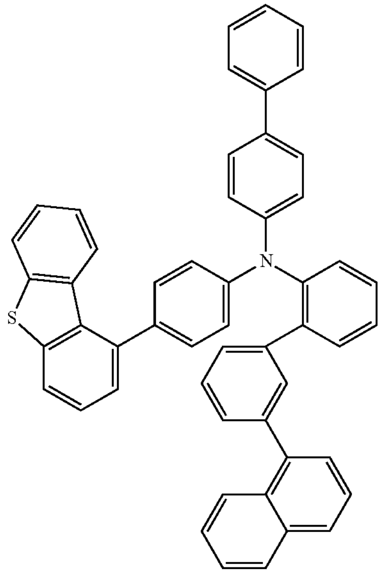

-continued
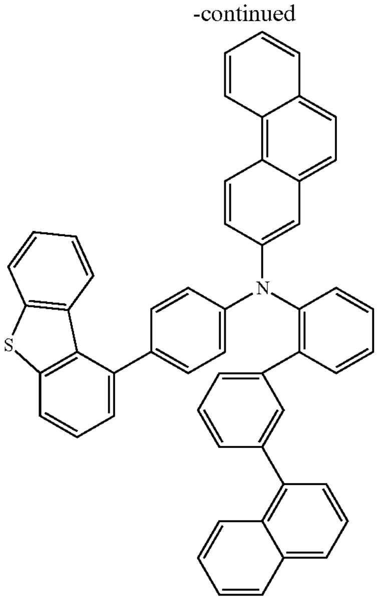
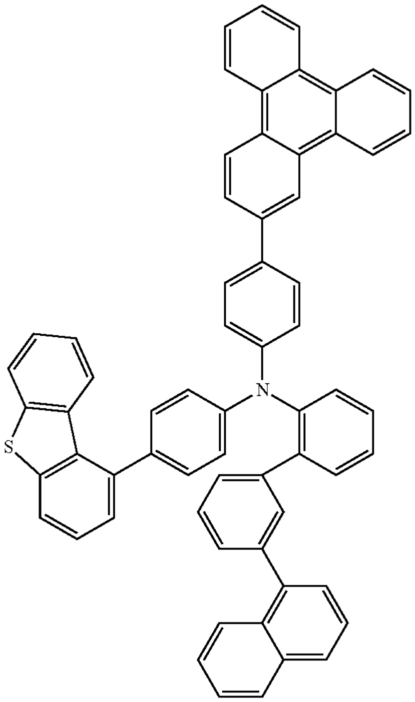
-continued
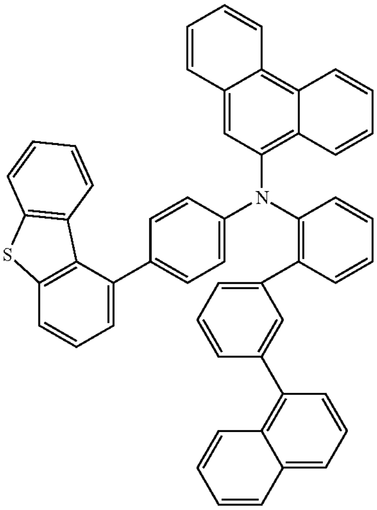
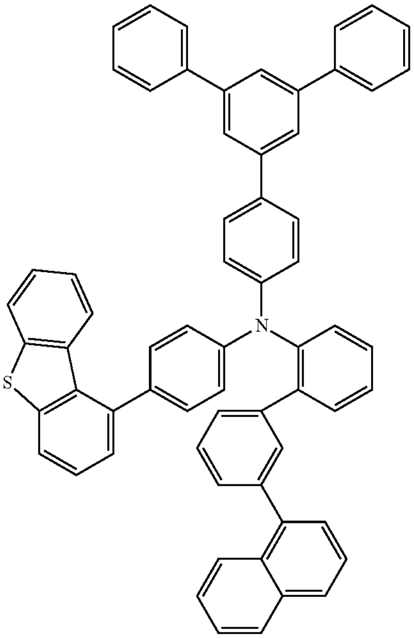
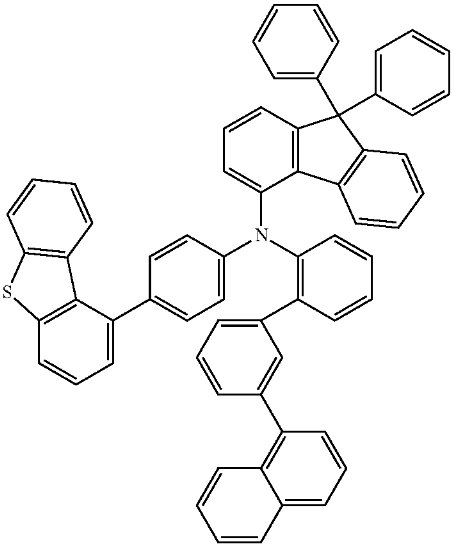

-continued
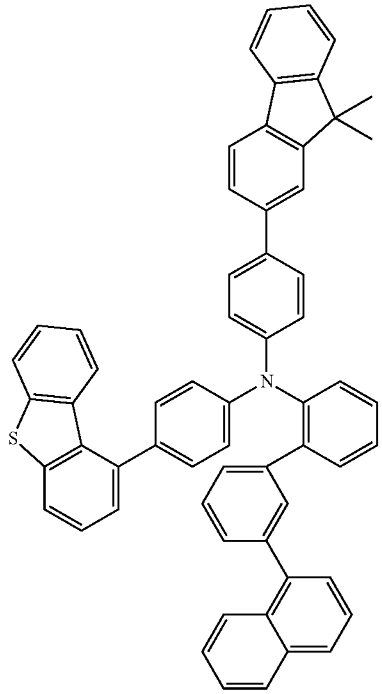
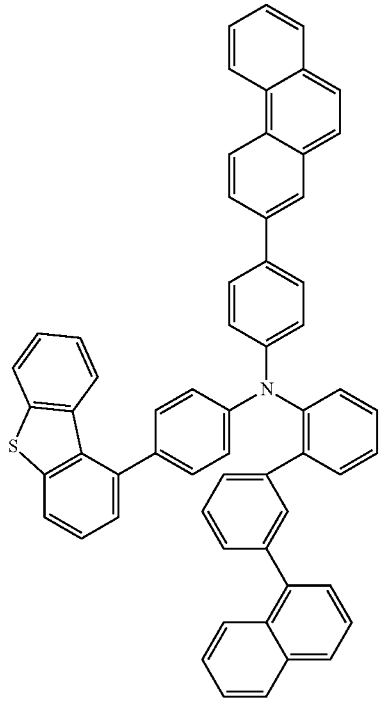 [SMILES: c1cc(-c2ccccc2N(c2ccc(-c3ccc4c(ccc5ccccc54)c3)cc2)c2ccc(-c3cccc4sc5ccccc5c34)cc2)cc(-c2cccc3ccccc23)c1]
-continued
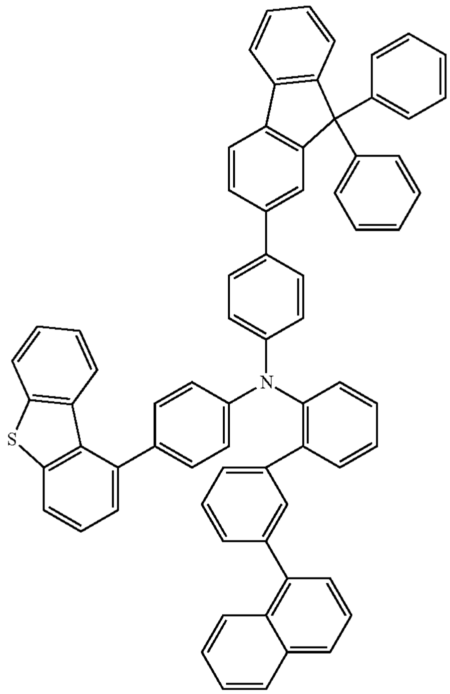
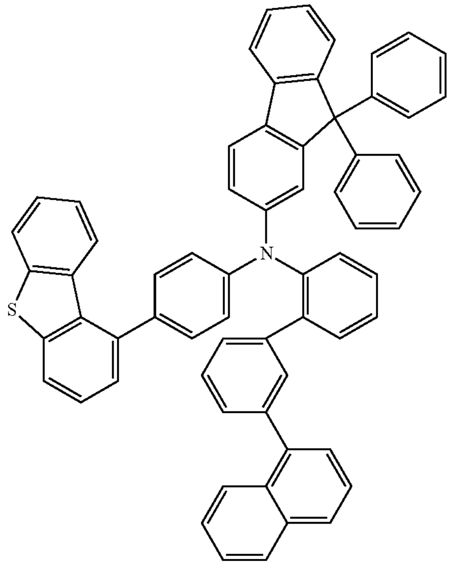

-continued
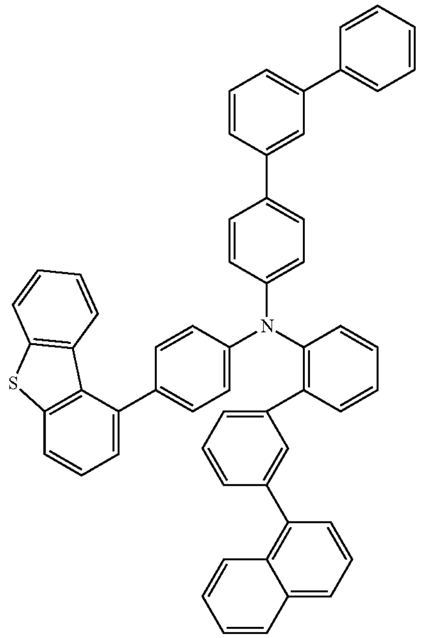
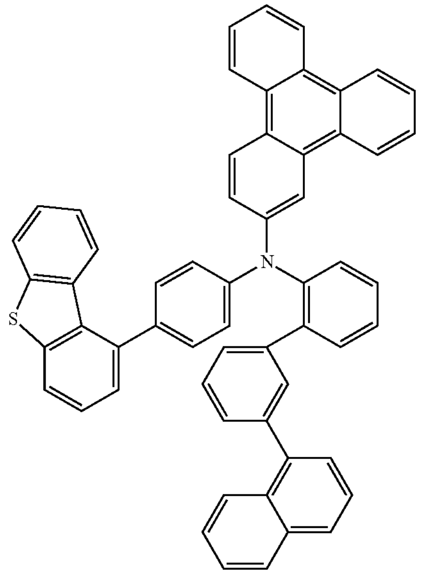
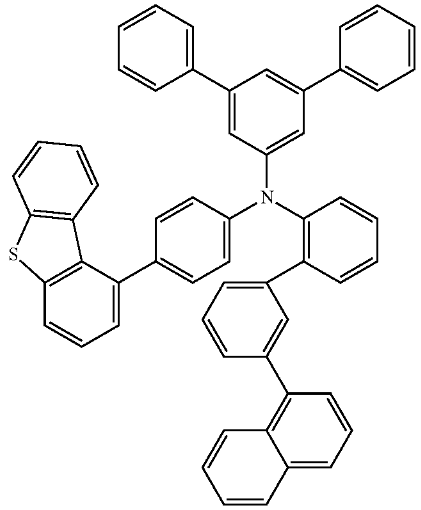
-continued
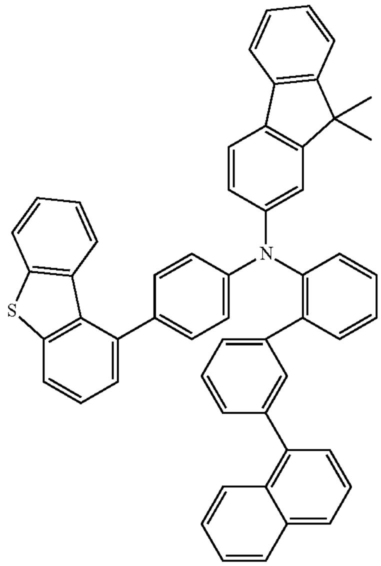
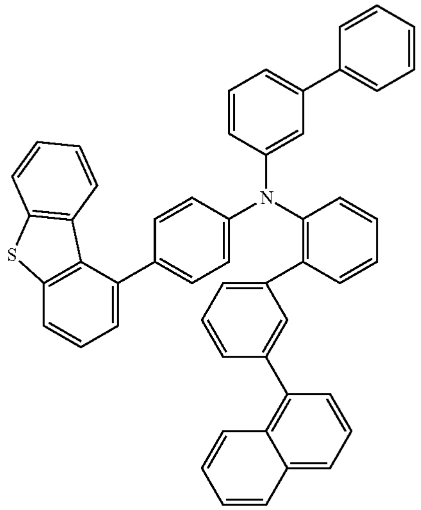
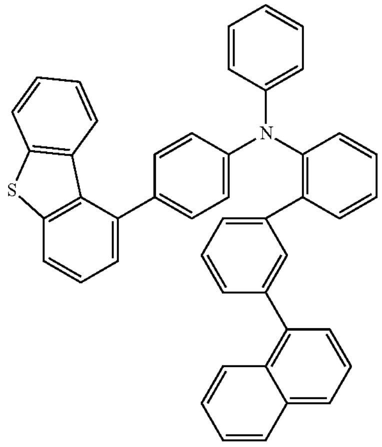

-continued
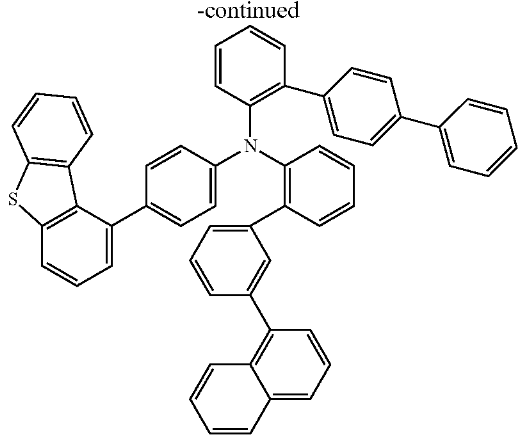
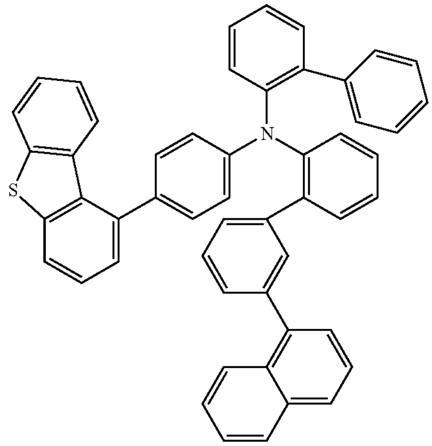
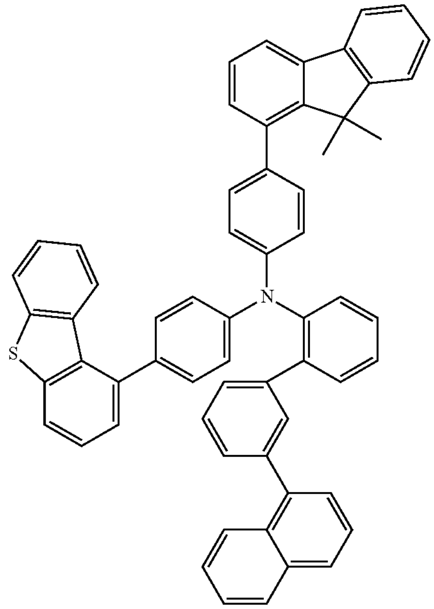
-continued
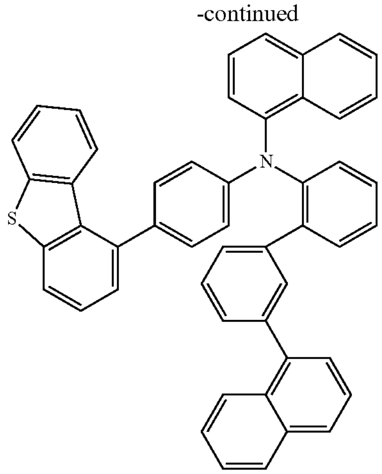
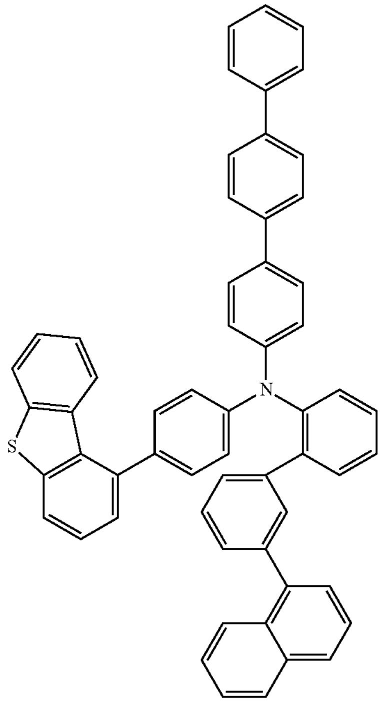

-continued
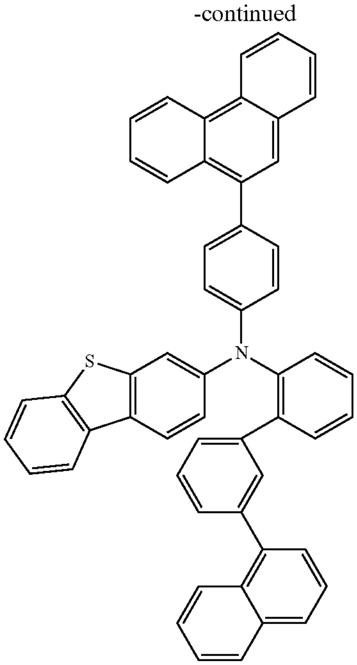
-continued
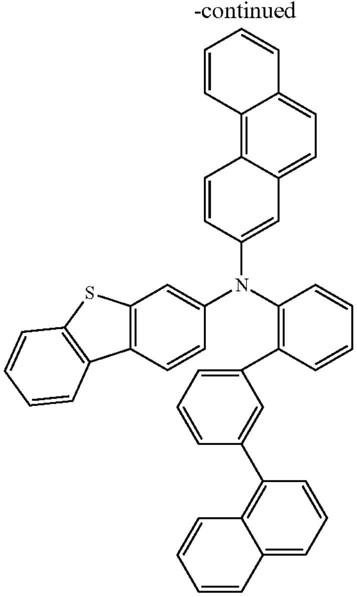
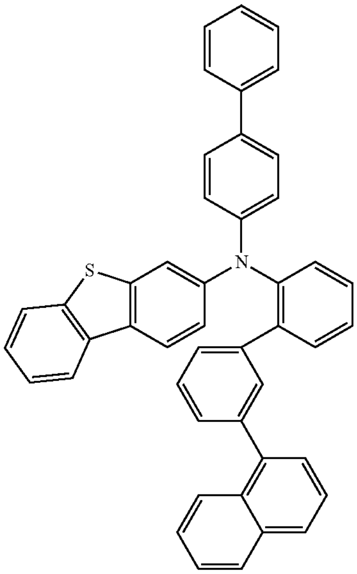
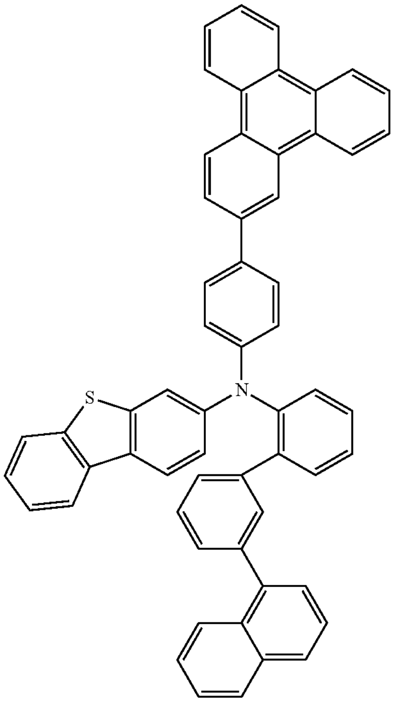

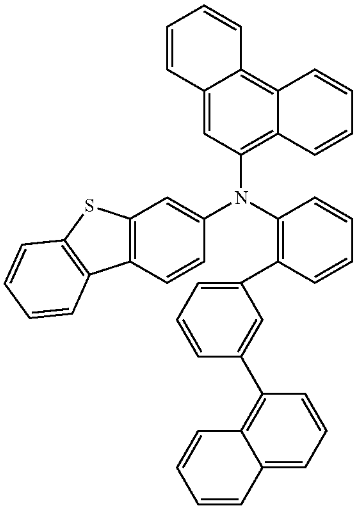
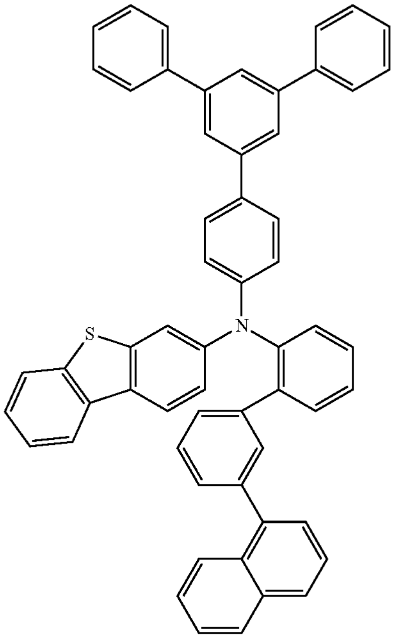
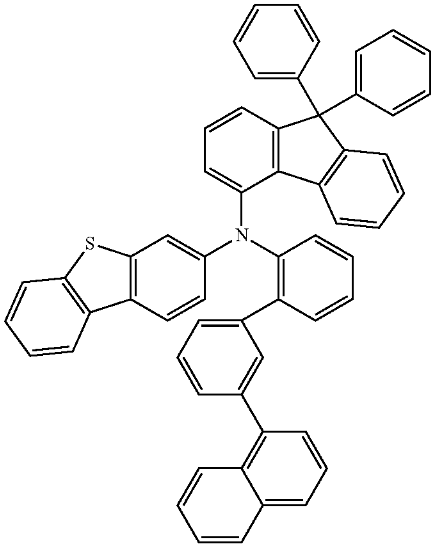
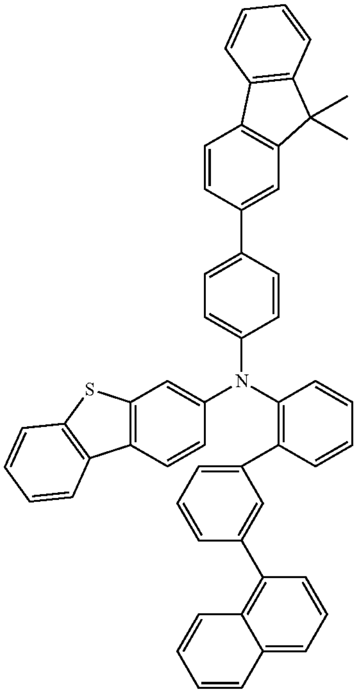
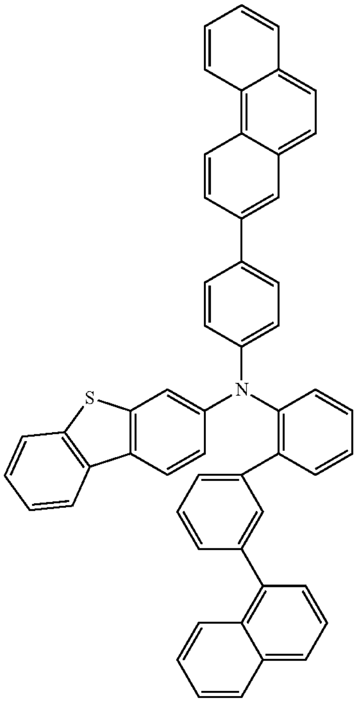 [SMILES: c1cc(-c2ccccc2N(c2ccc(-c3ccc4c(ccc5ccccc54)c3)cc2)c2ccc3c(c2)sc2ccccc23)cc(-c2cccc3ccccc23)c1]

-continued
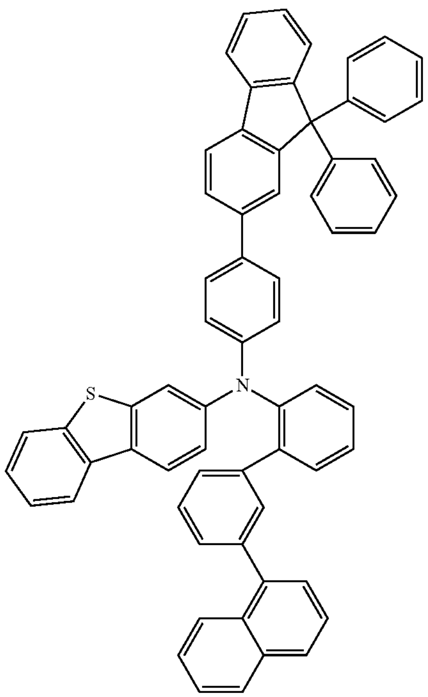
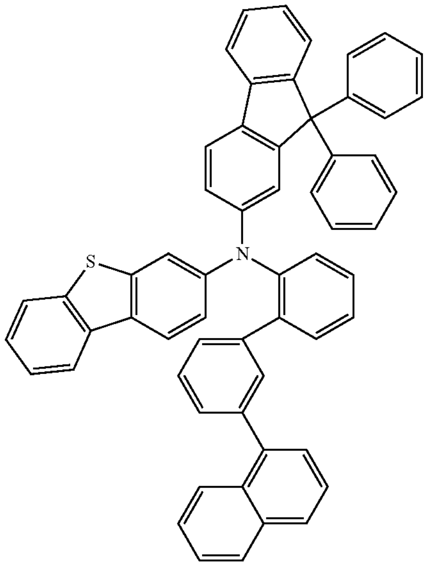
-continued
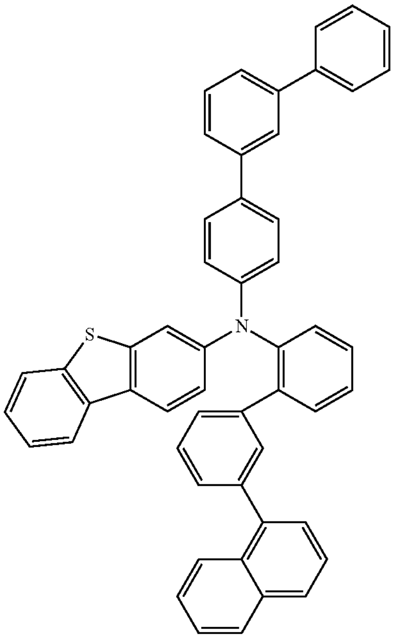
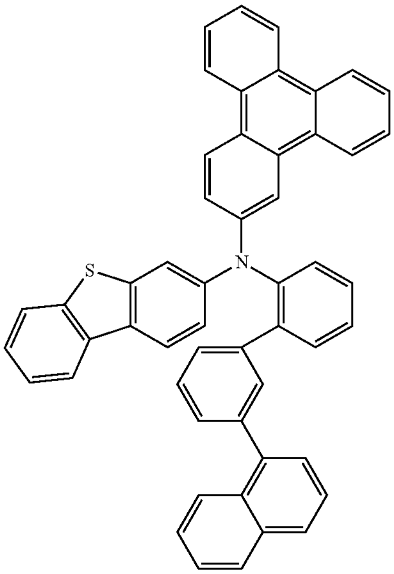
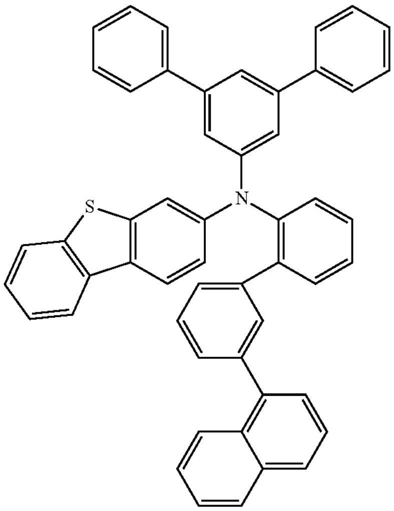

-continued
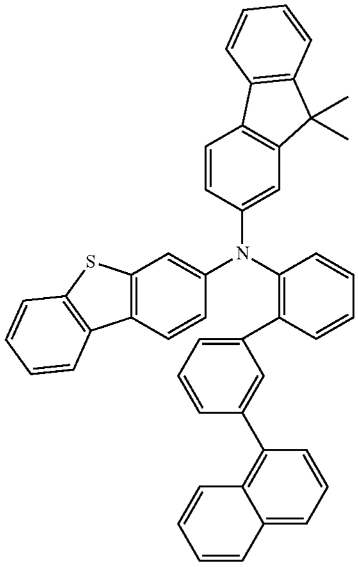
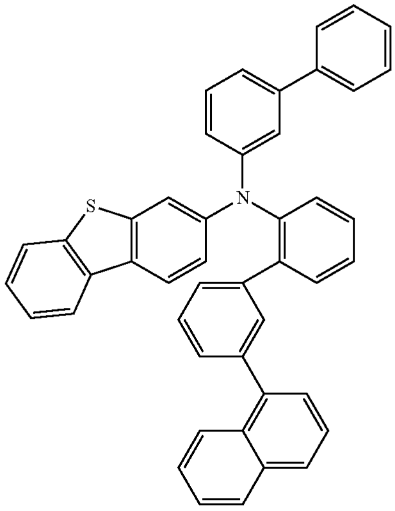
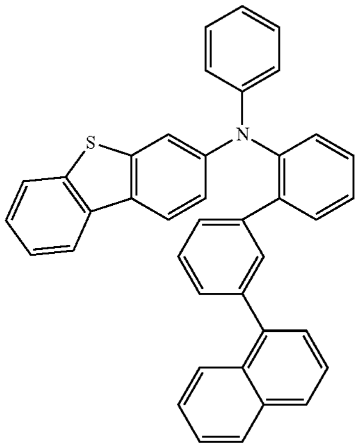
-continued
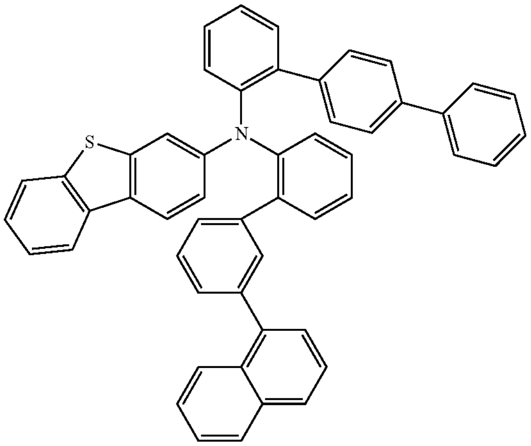
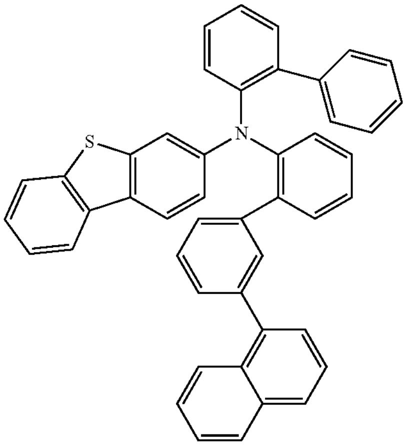
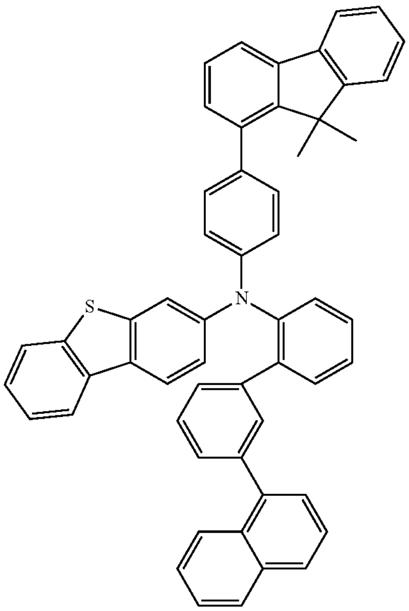

-continued
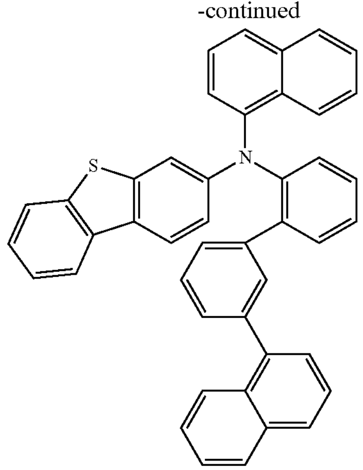
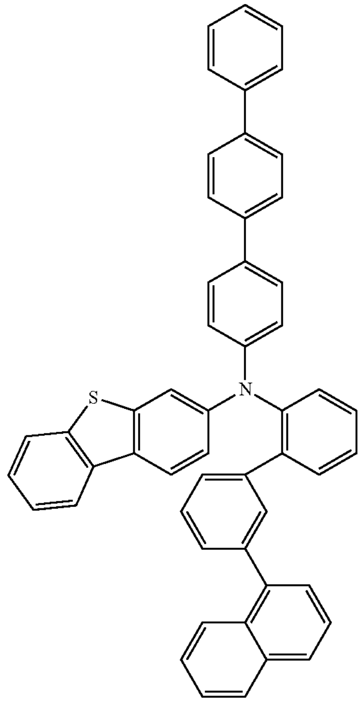
-continued
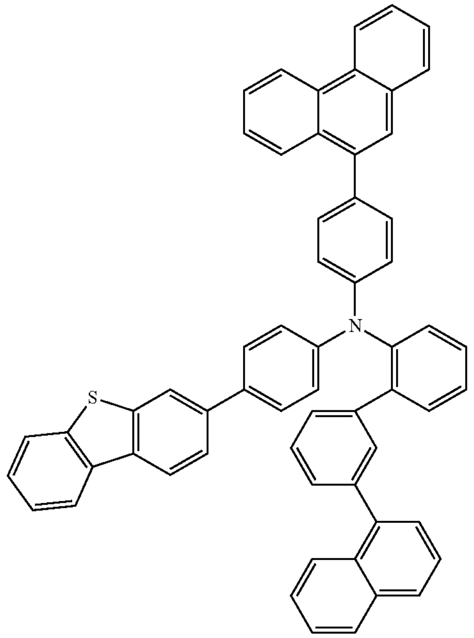
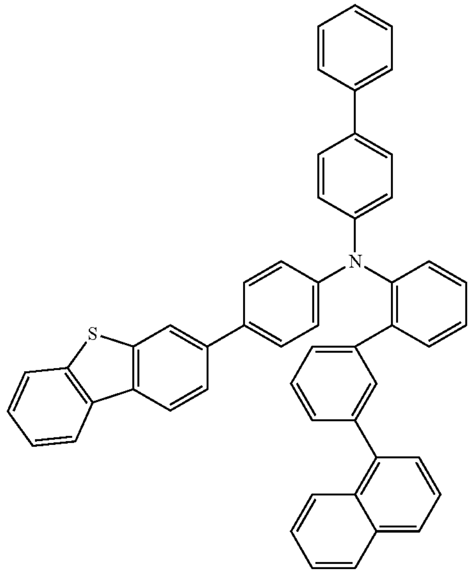

-continued
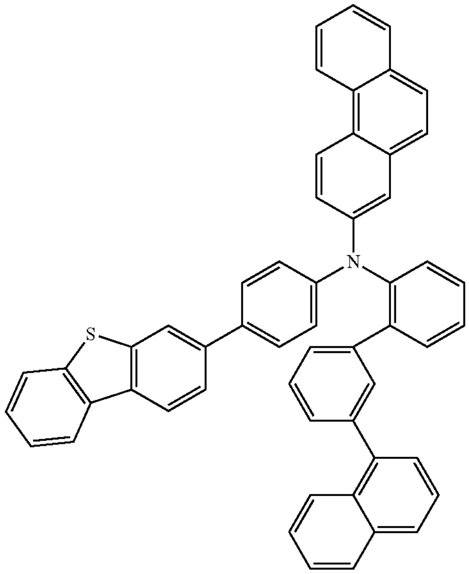
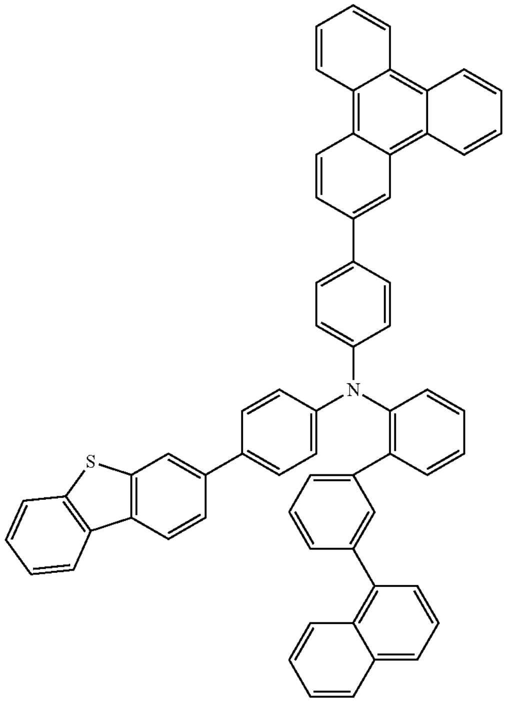
-continued
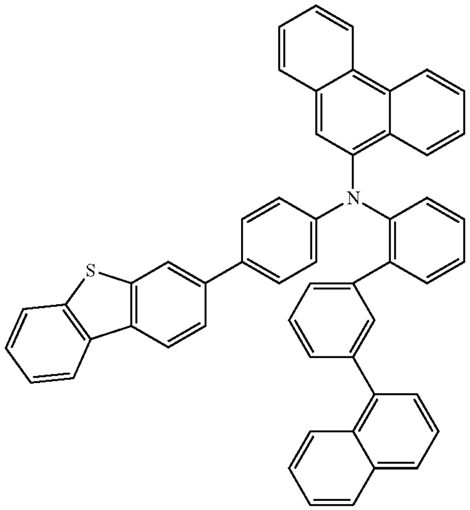
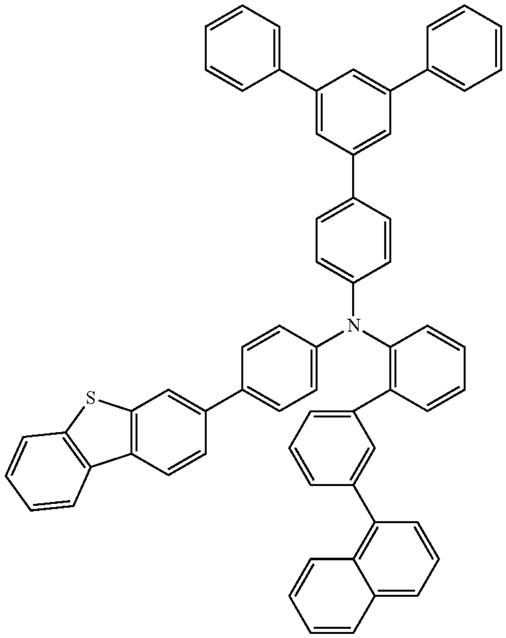
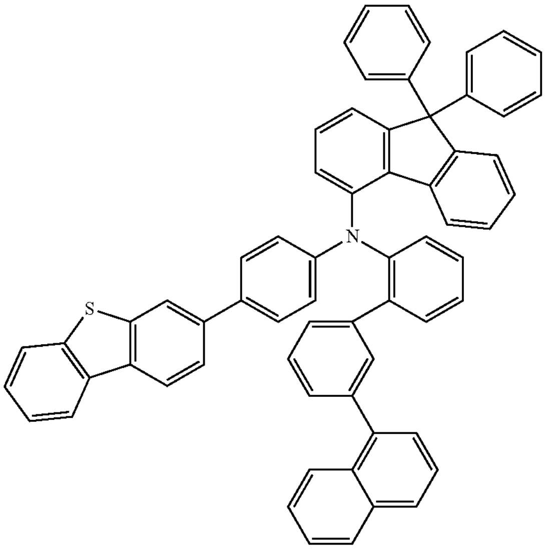

-continued
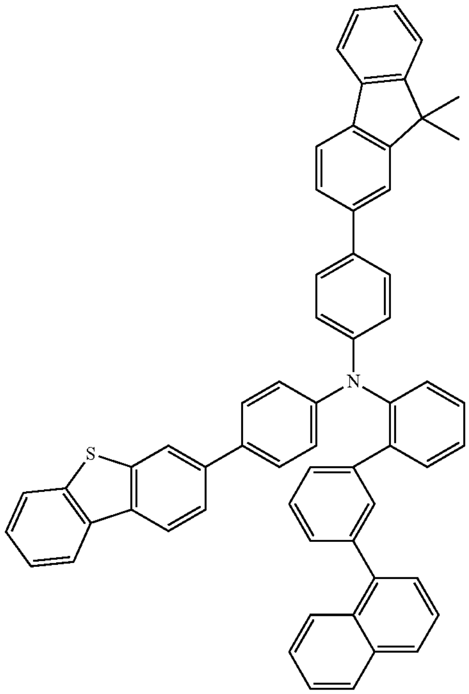
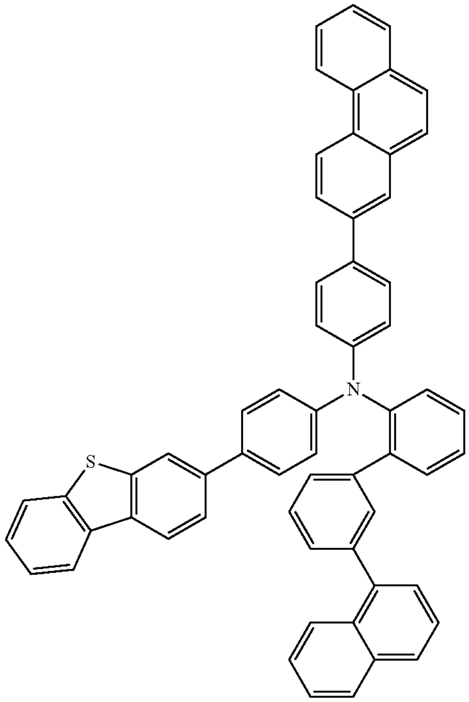 [SMILES: c1cc(-c2ccccc2N(c2ccc(-c3ccc4c(ccc5ccccc54)c3)cc2)c2ccc(-c3ccc4c(c3)sc3ccccc34)cc2)cc(-c2cccc3ccccc23)c1]
-continued
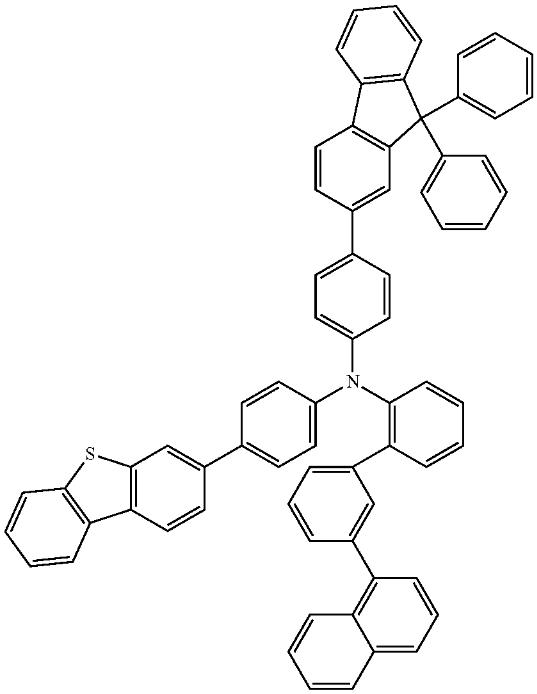
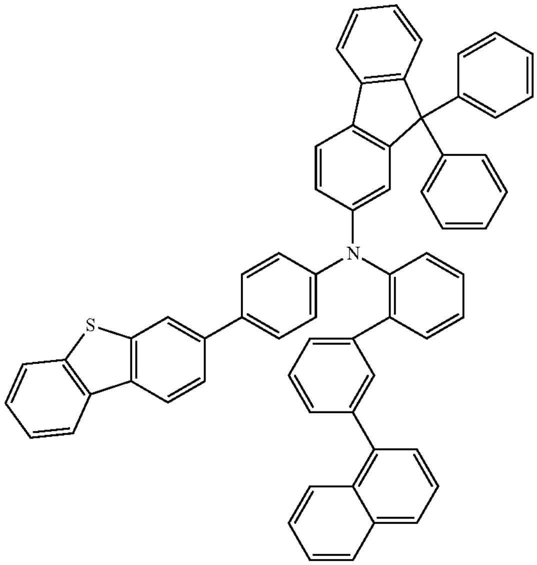

-continued
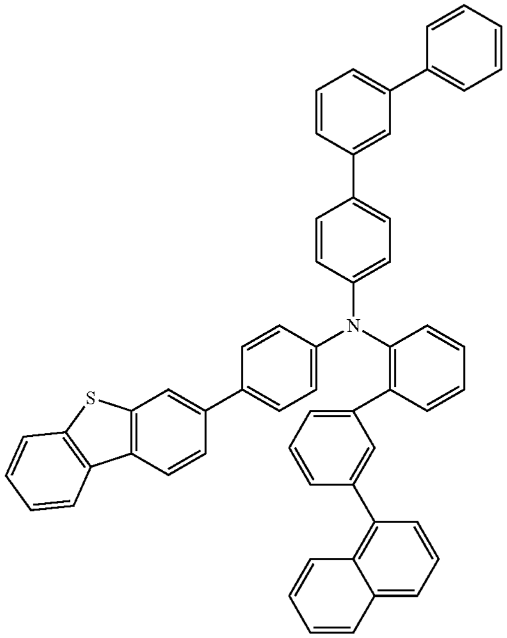
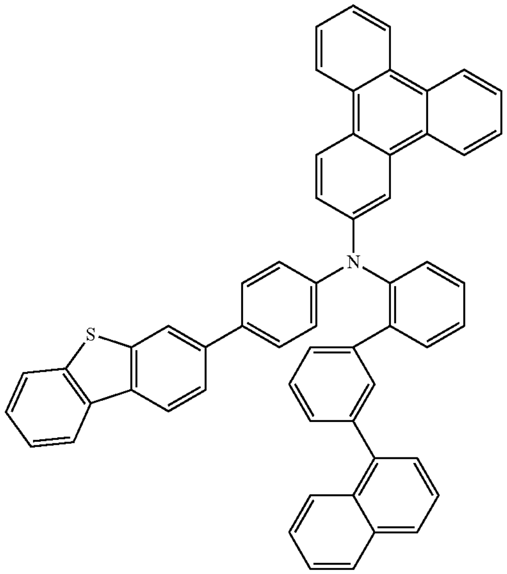
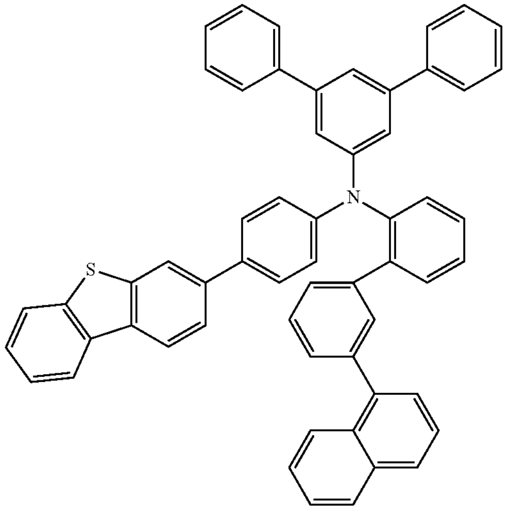
-continued
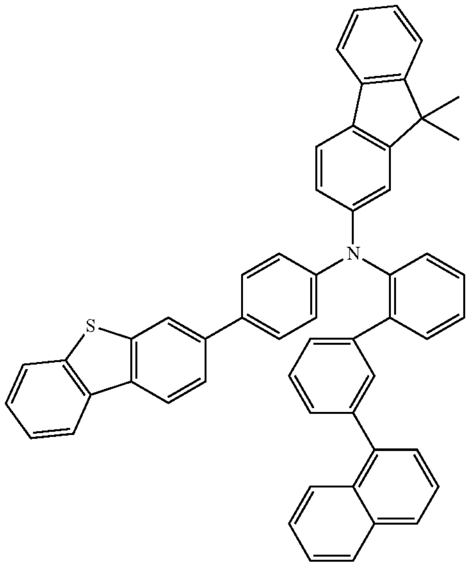
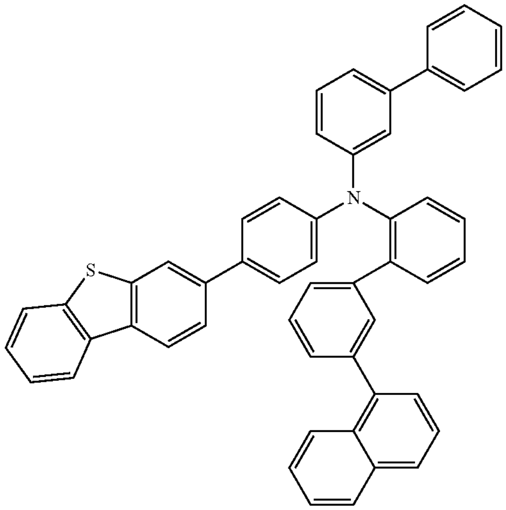
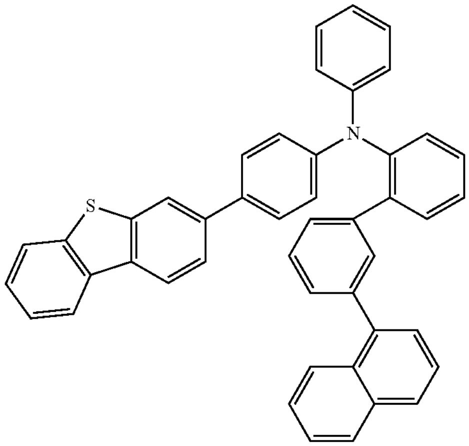

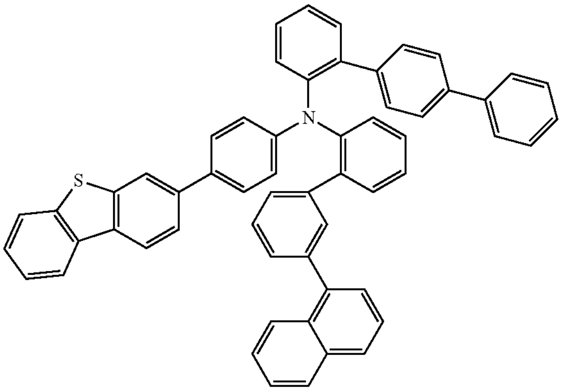
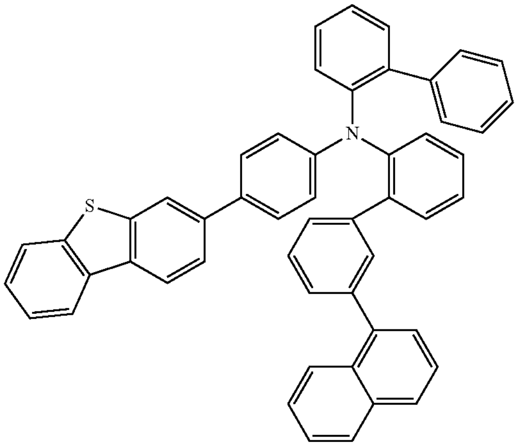
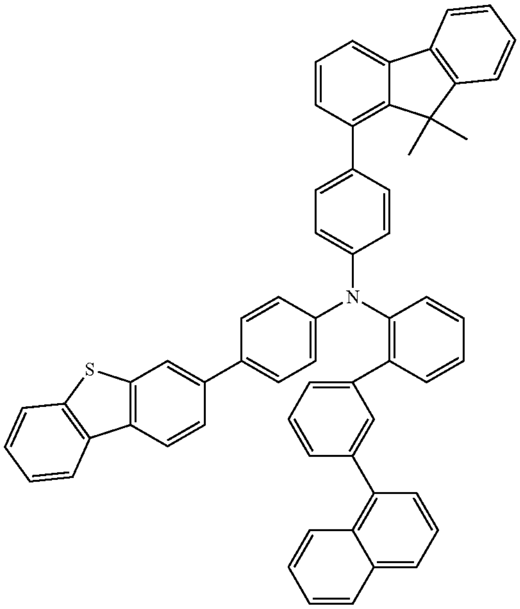
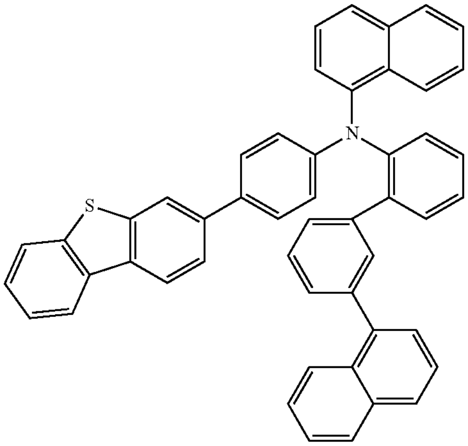
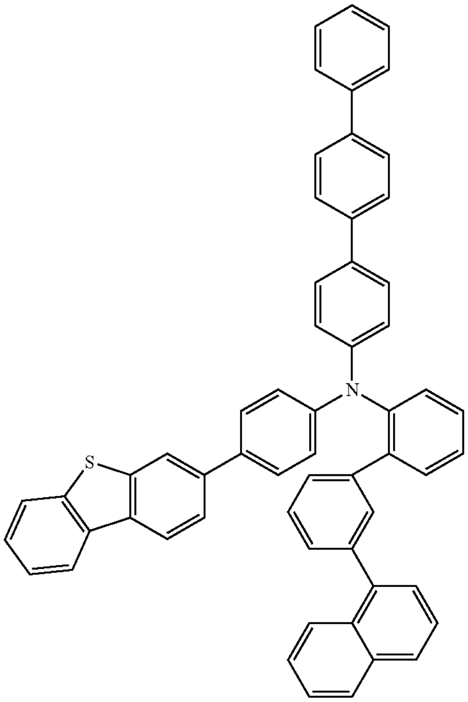

-continued
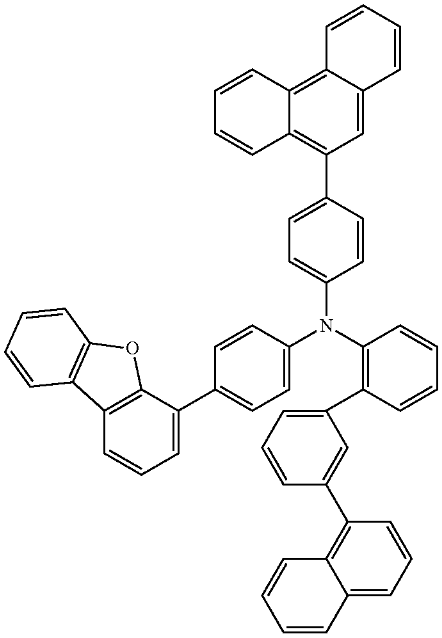
-continued
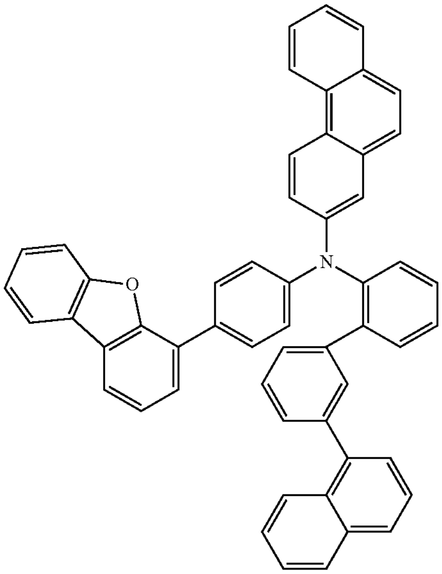
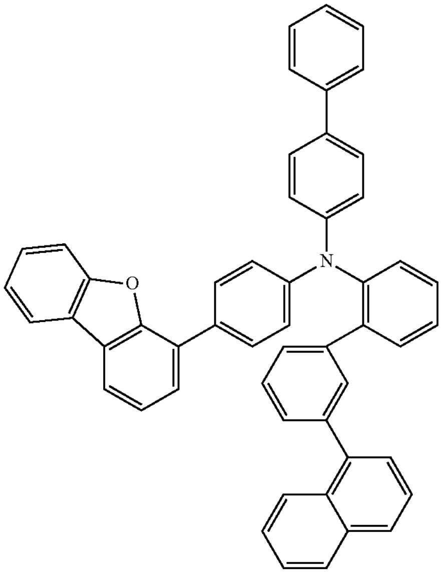
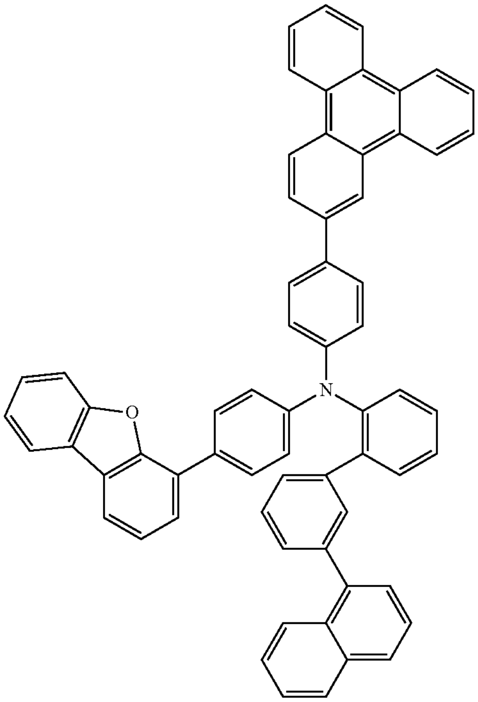

-continued
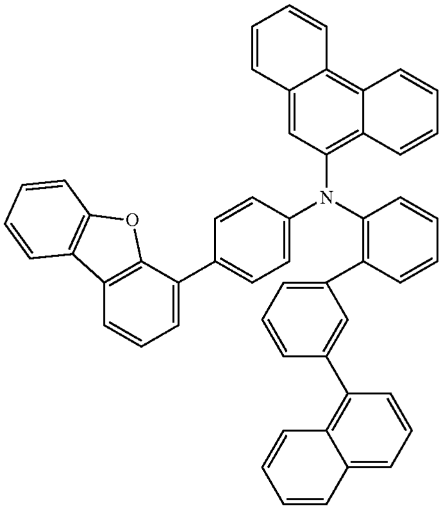
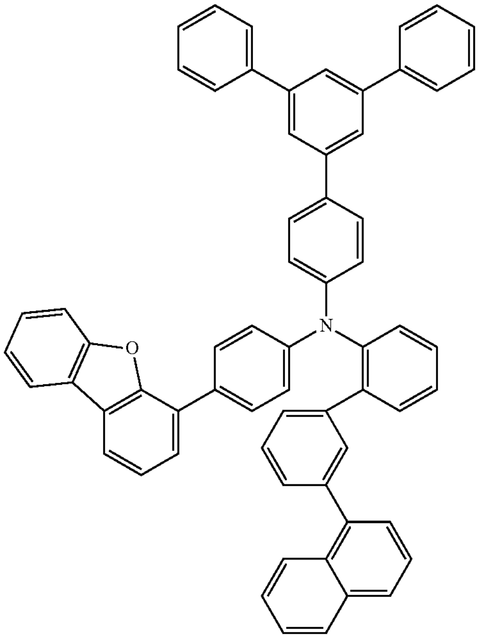
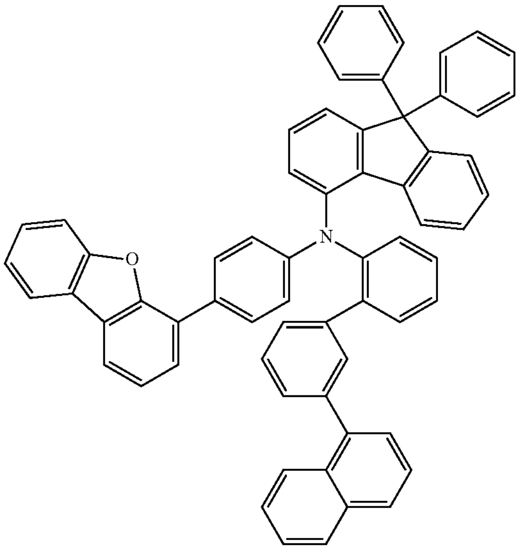
-continued
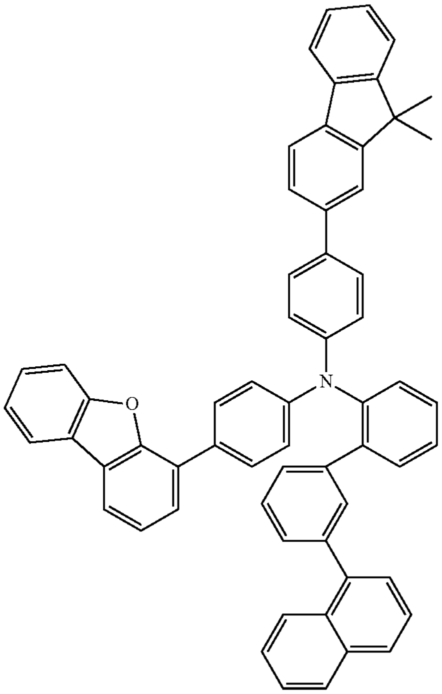
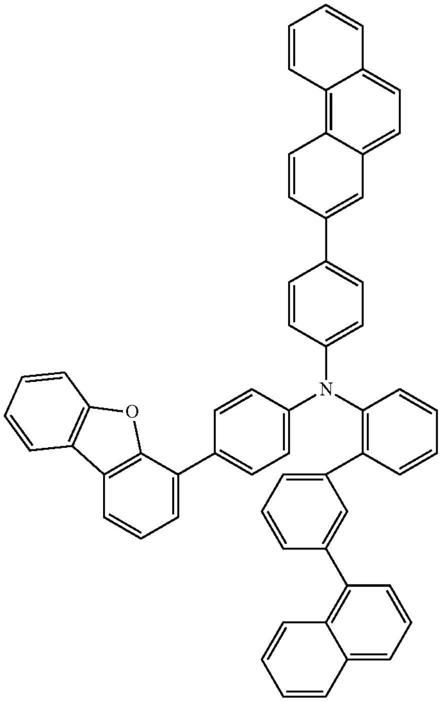 [SMILES: c1cc(-c2ccccc2N(c2ccc(-c3ccc4c(ccc5ccccc54)c3)cc2)c2ccc(-c3cccc4c3oc3ccccc34)cc2)cc(-c2cccc3ccccc23)c1]

-continued
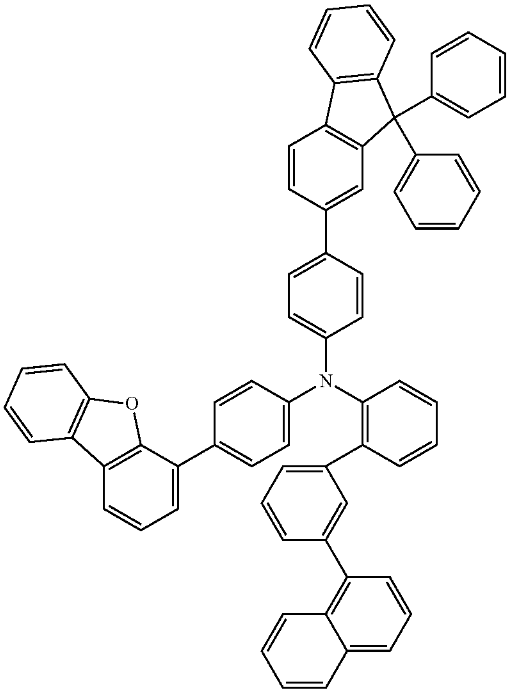
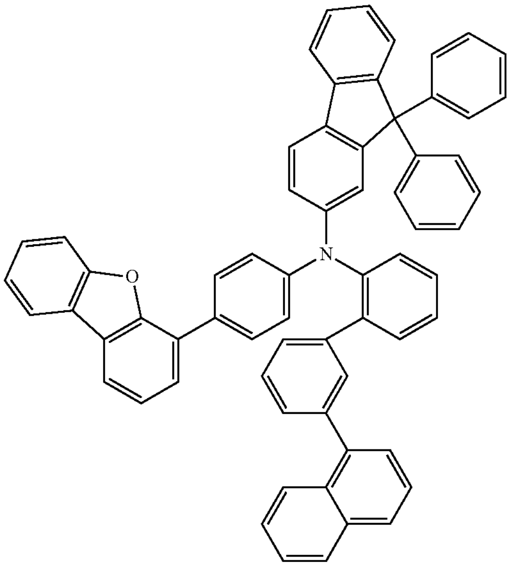
-continued
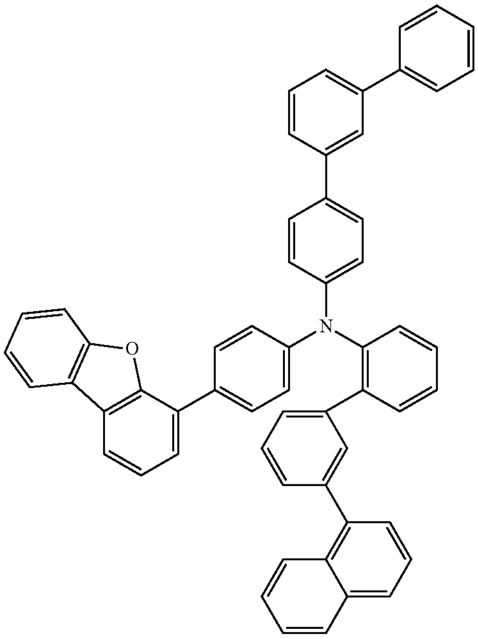
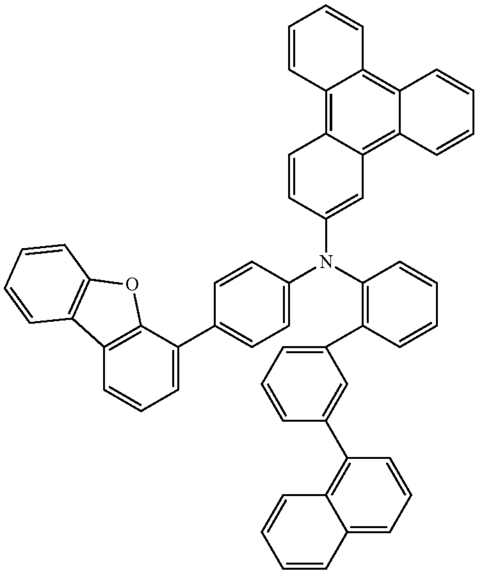
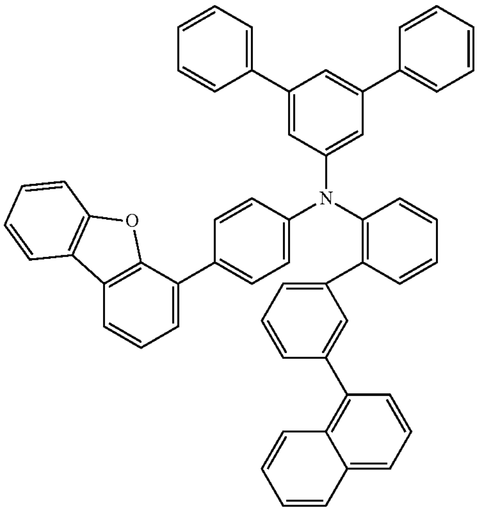

-continued
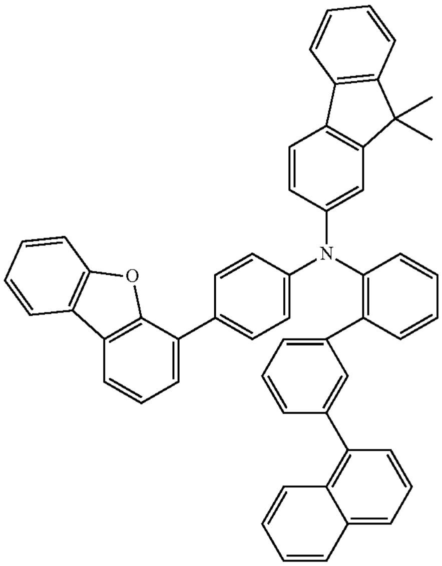
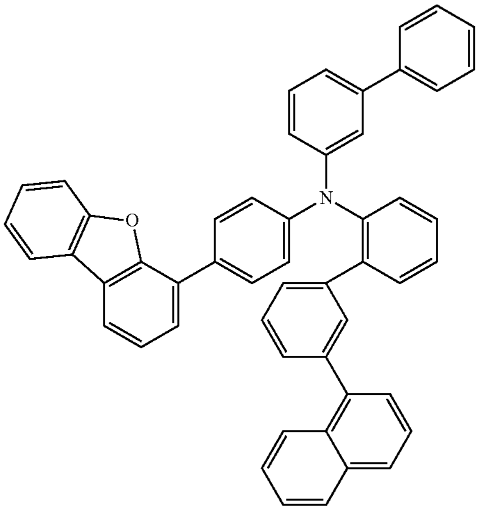
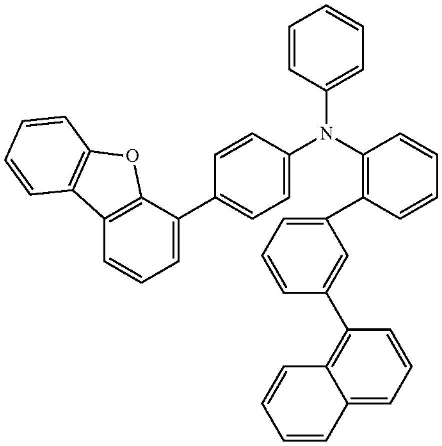
-continued
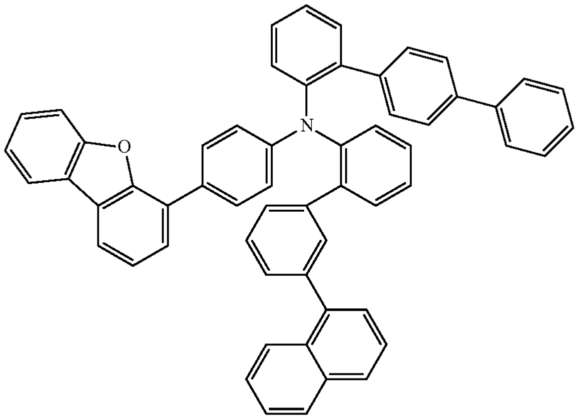
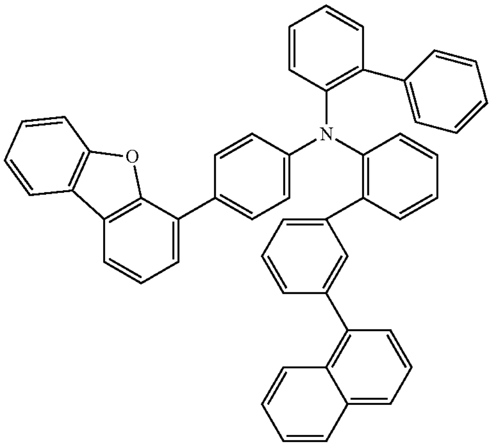
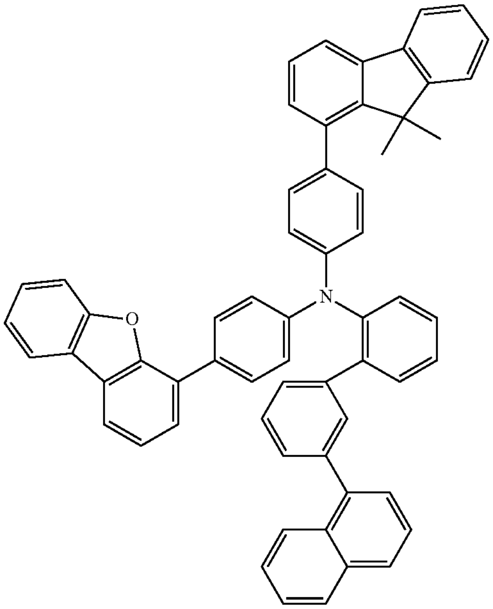

-continued
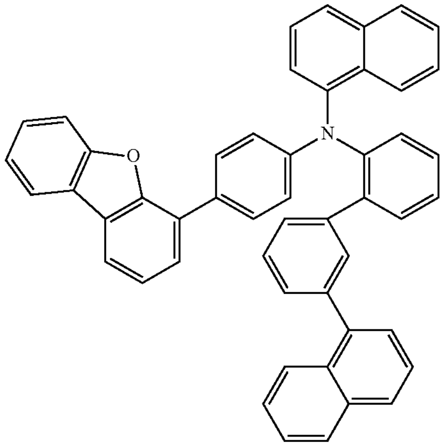
-continued
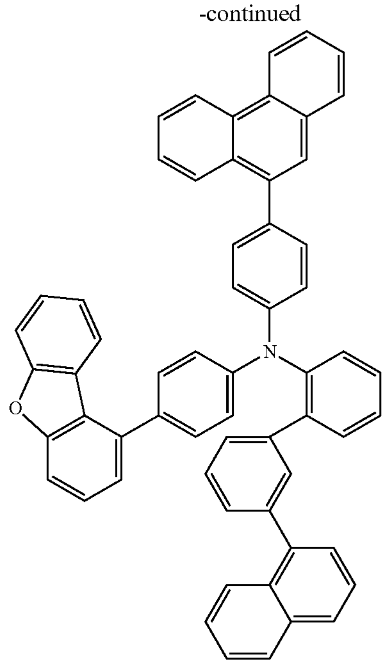
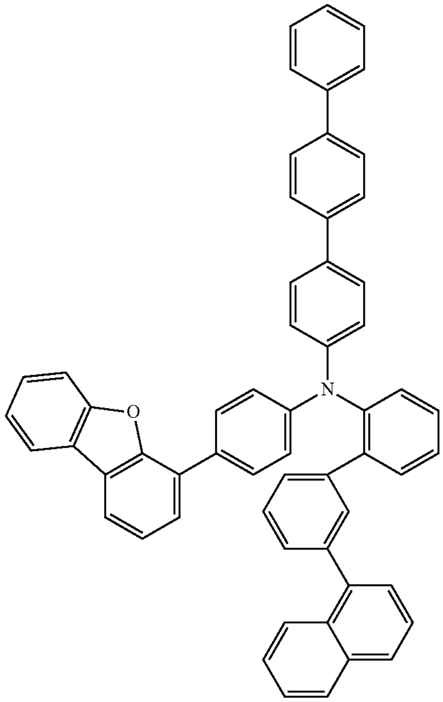
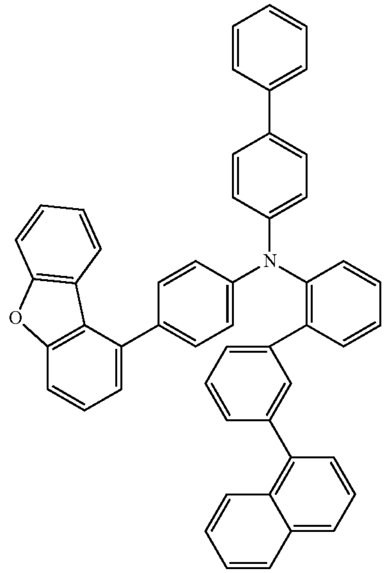

-continued
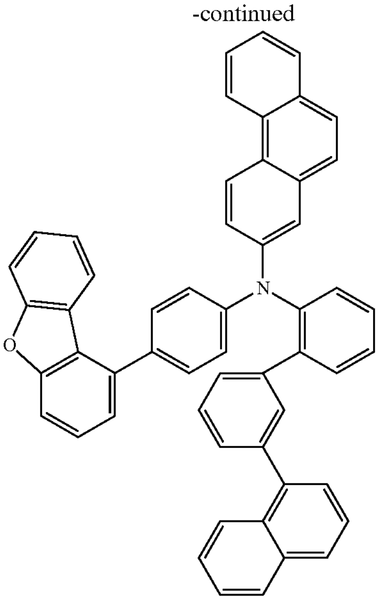
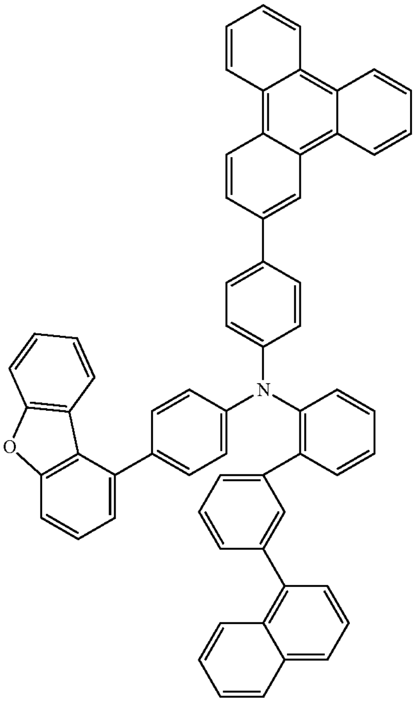
-continued
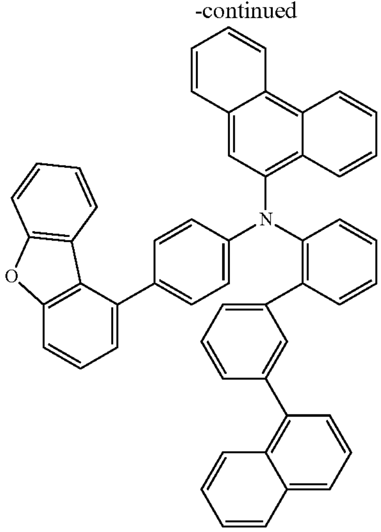
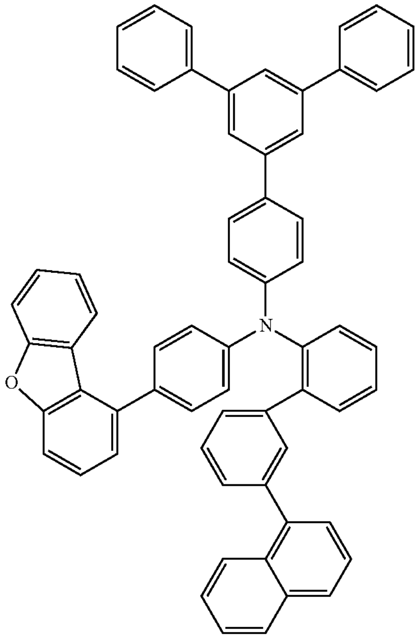
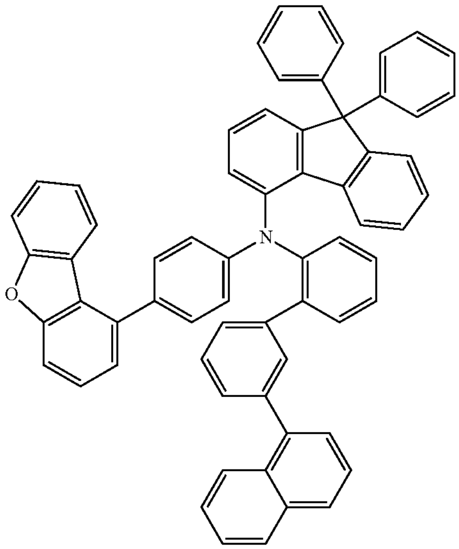

-continued
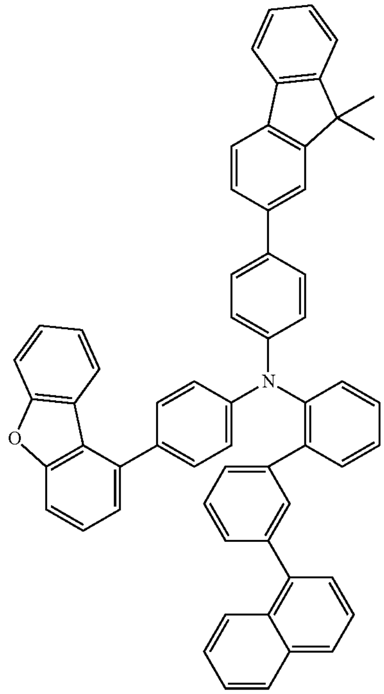
-continued
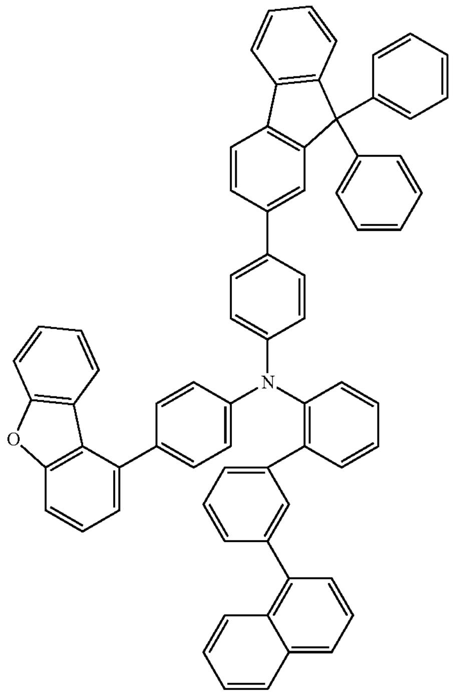
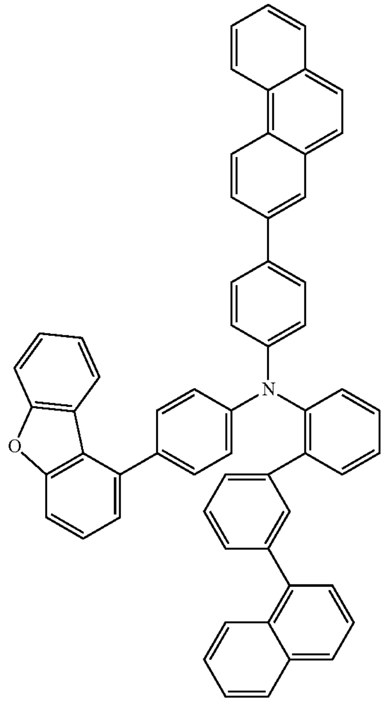 [SMILES: c1cc(-c2ccccc2N(c2ccc(-c3ccc4c(ccc5ccccc54)c3)cc2)c2ccc(-c3cccc4oc5ccccc5c34)cc2)cc(-c2cccc3ccccc23)c1]
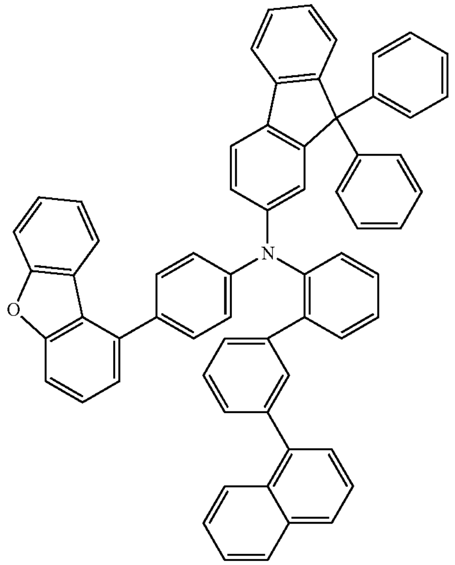

-continued
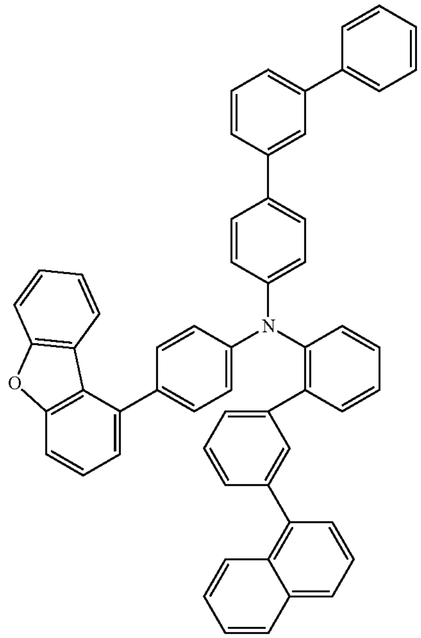
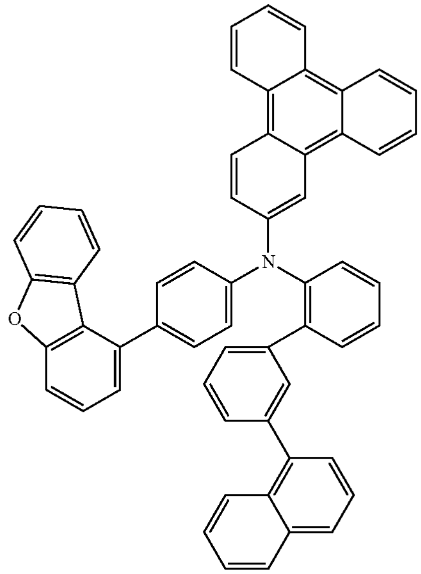
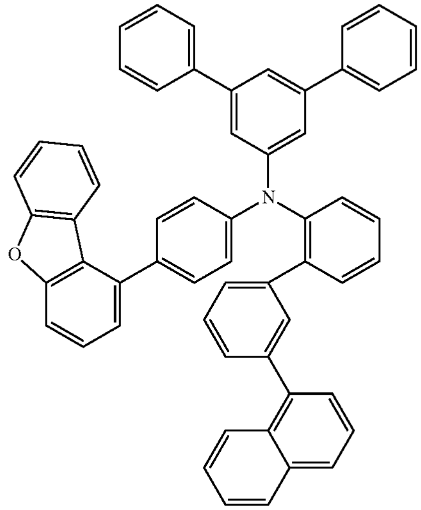
-continued
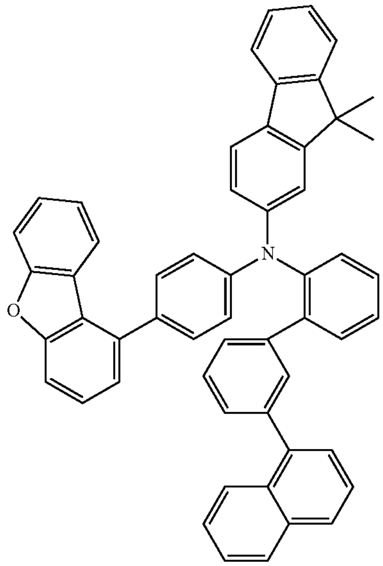
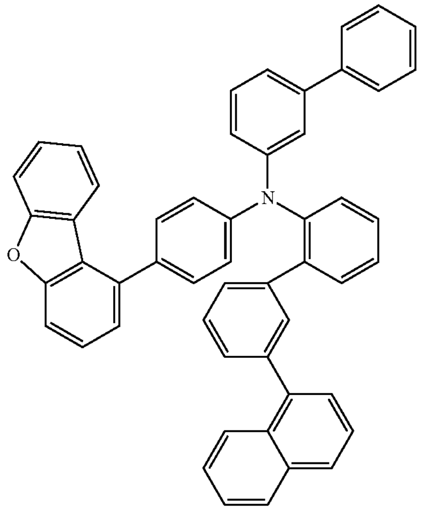
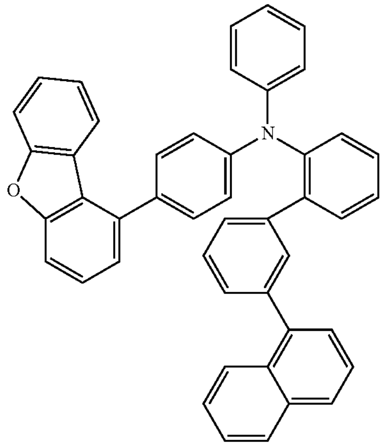

-continued
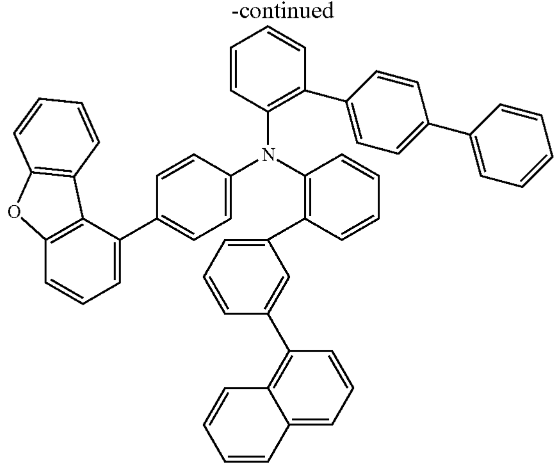
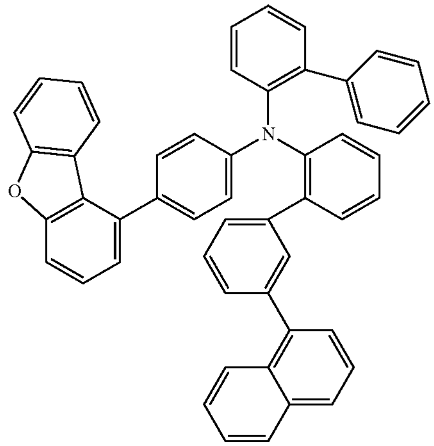
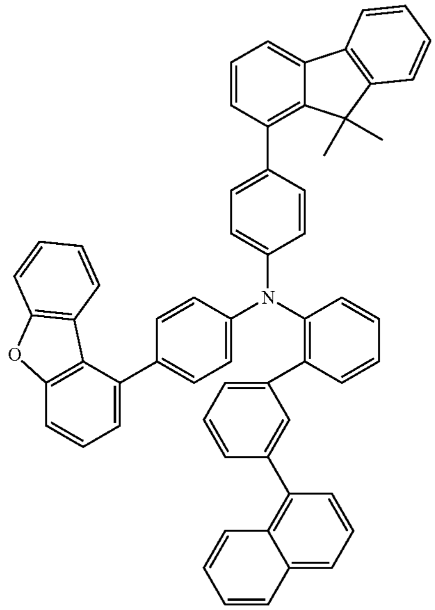
-continued
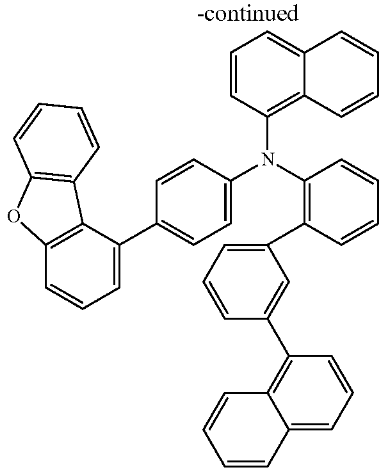
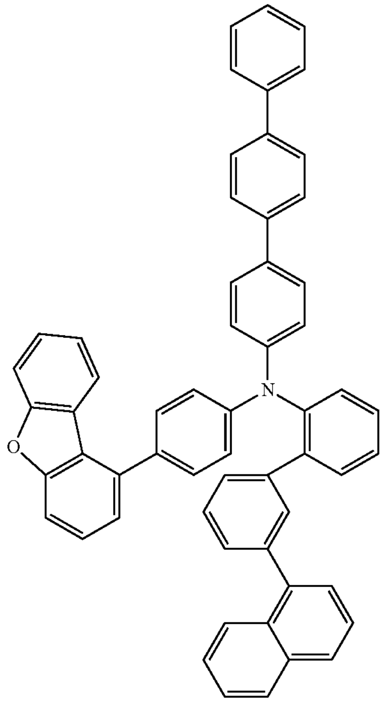

-continued
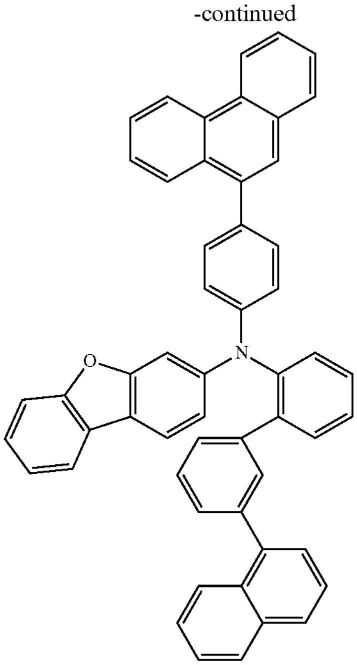
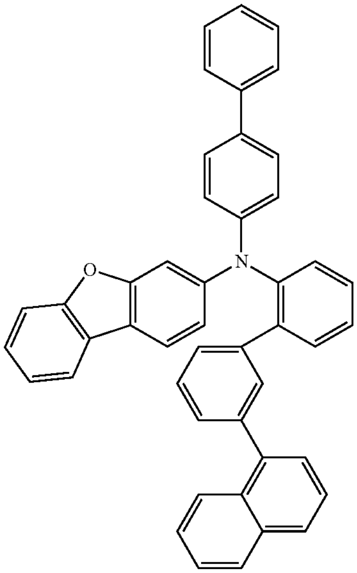
-continued
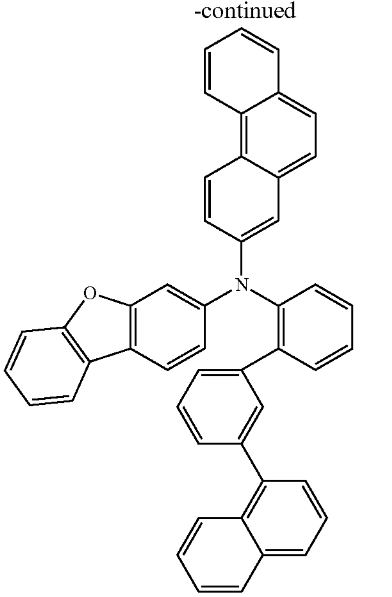
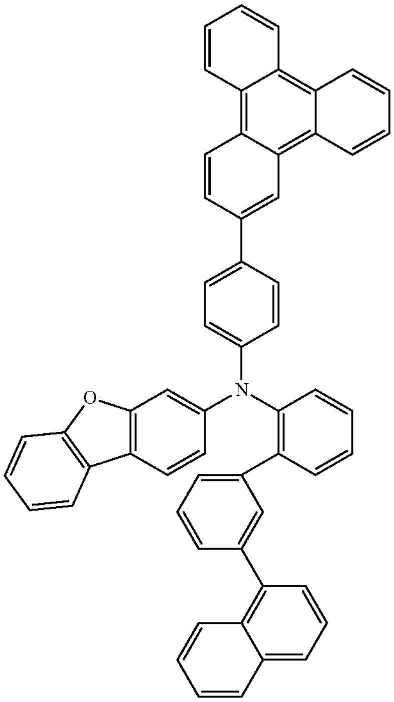

-continued
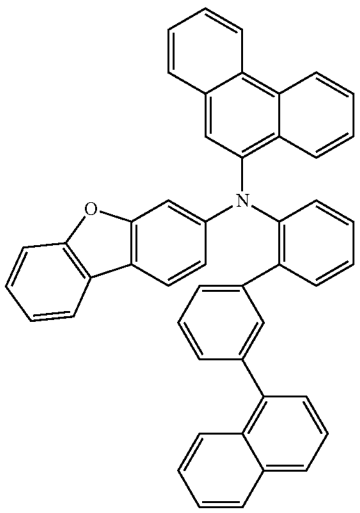
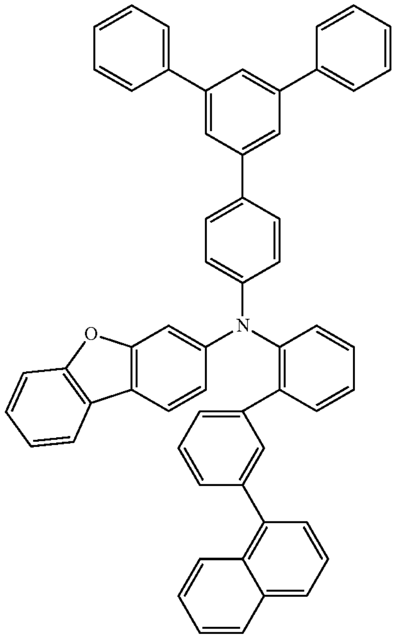
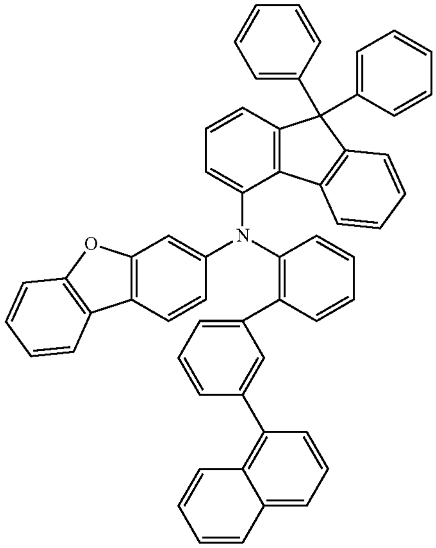
-continued
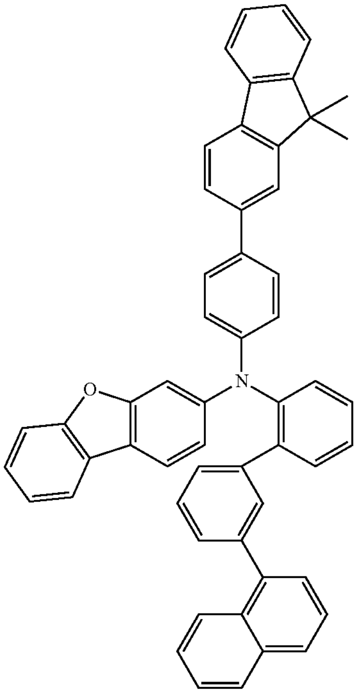
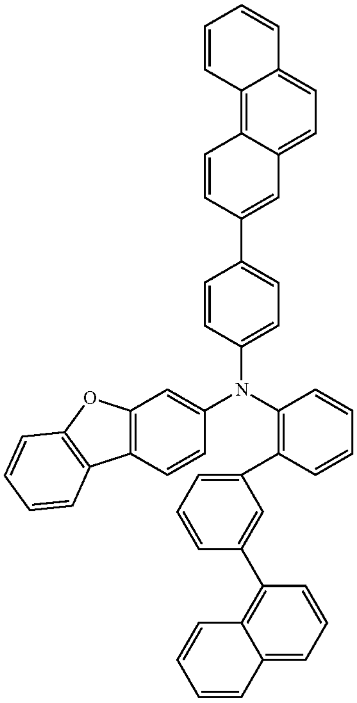

-continued
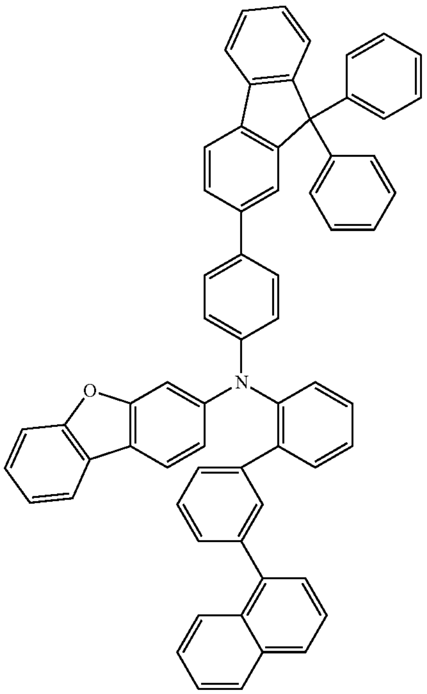
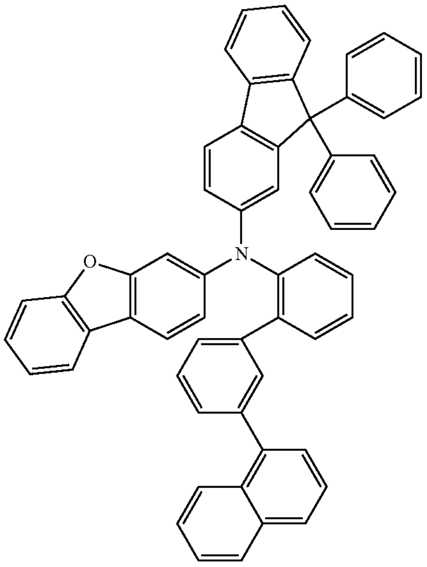
-continued
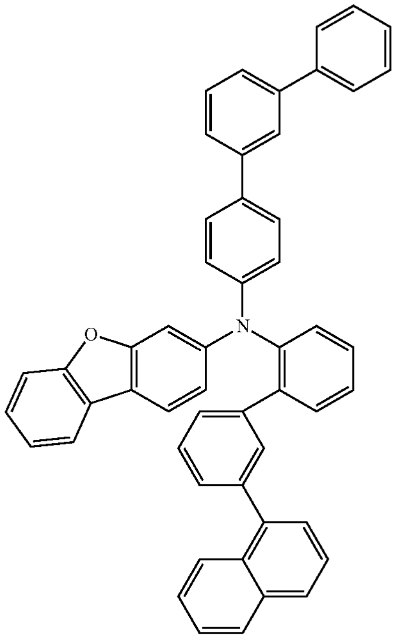
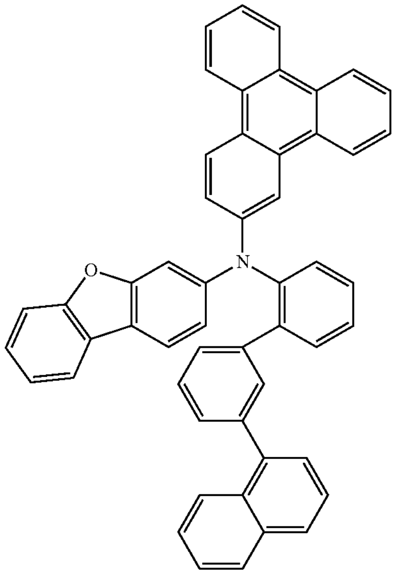
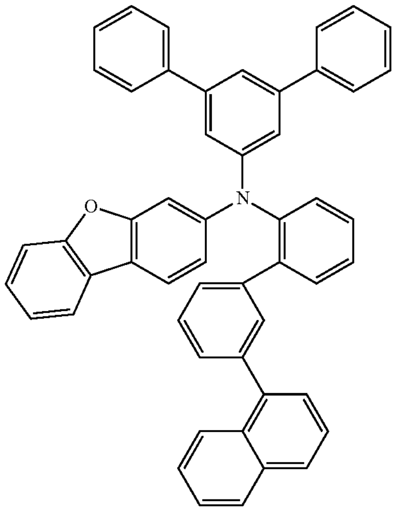

-continued
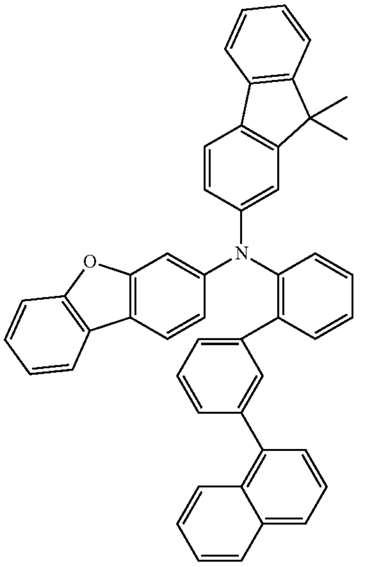
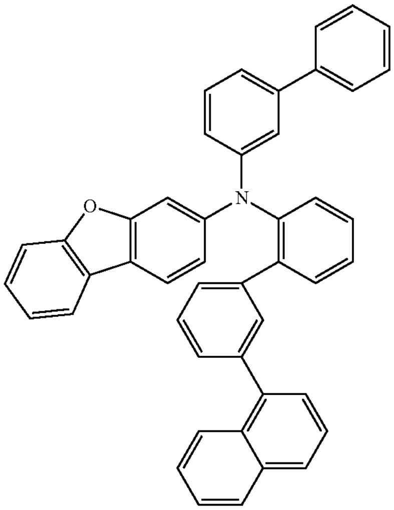
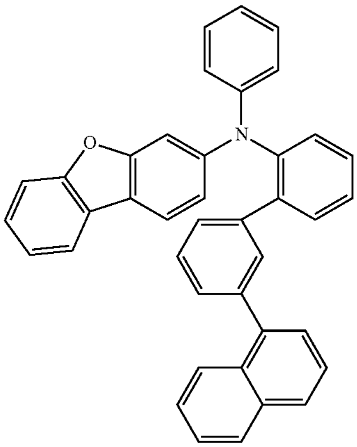
-continued
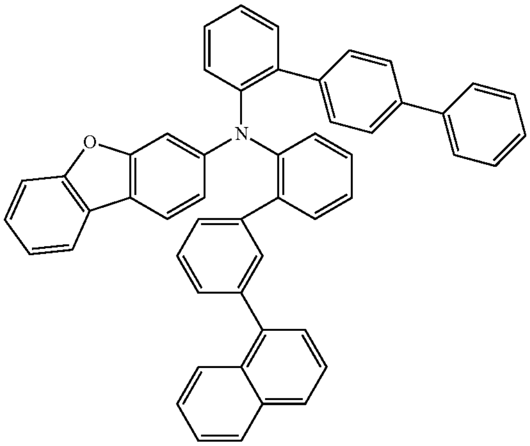
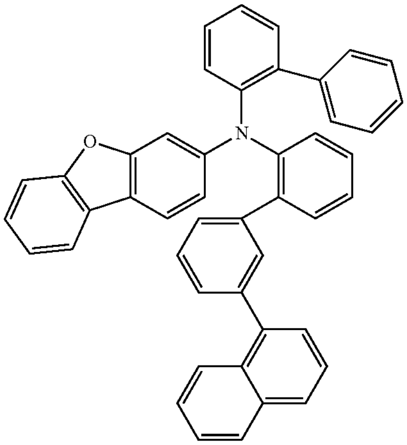
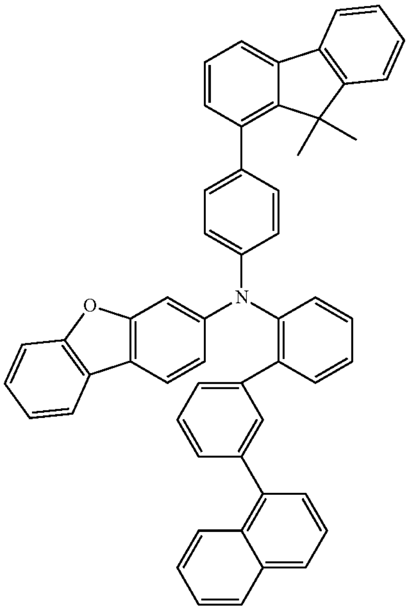

-continued
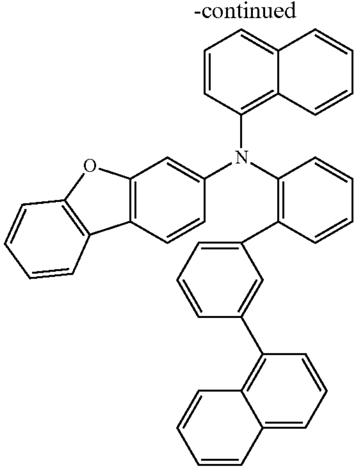
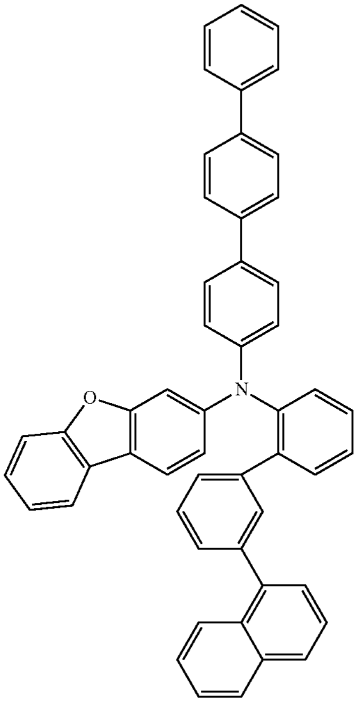
-continued
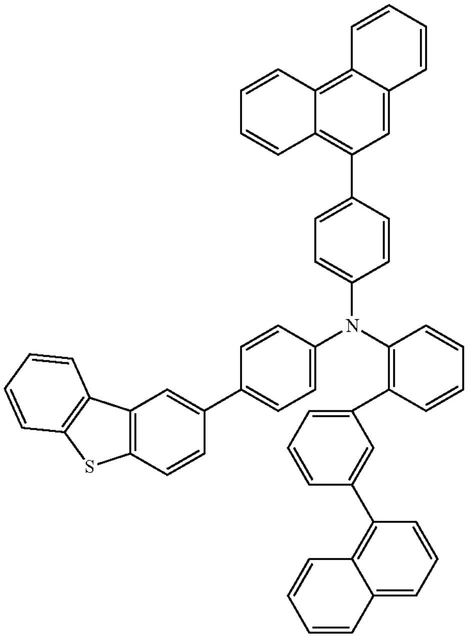
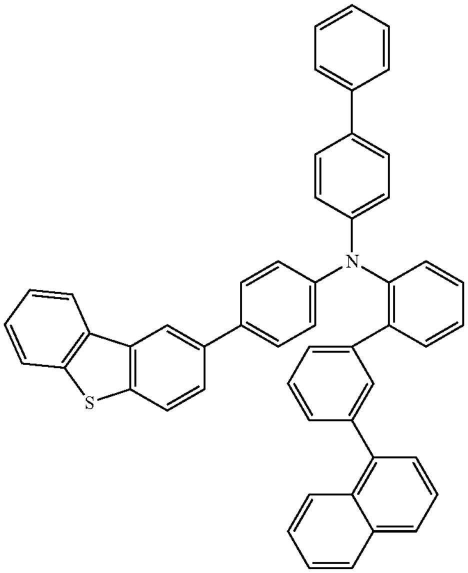

-continued
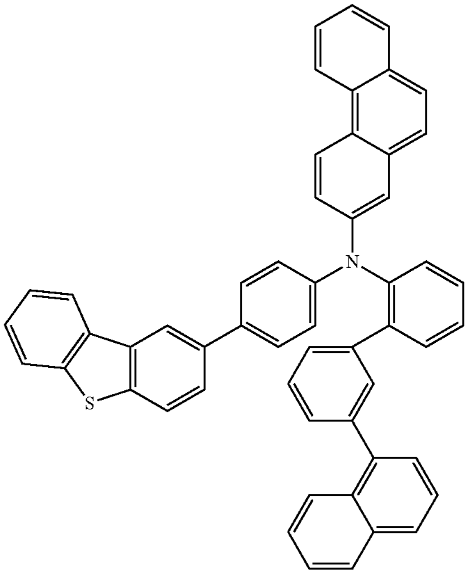
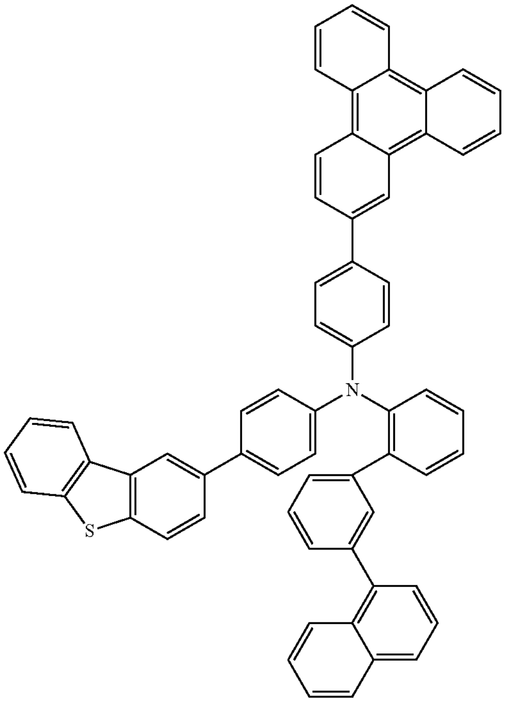
-continued
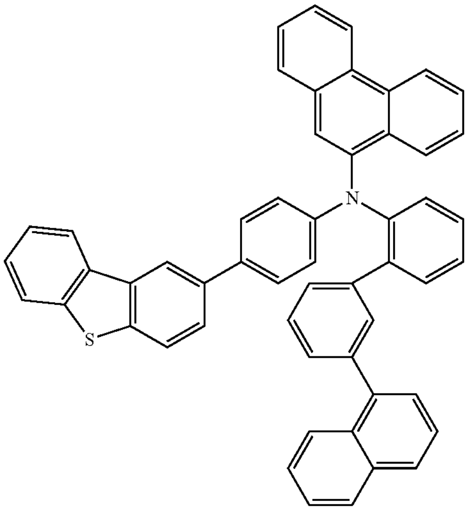
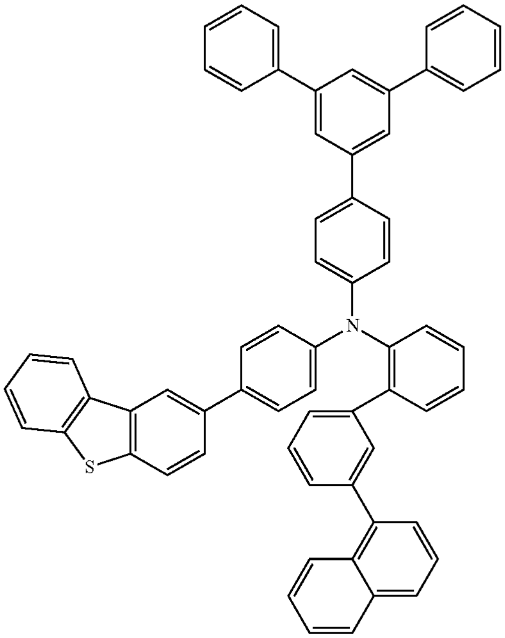
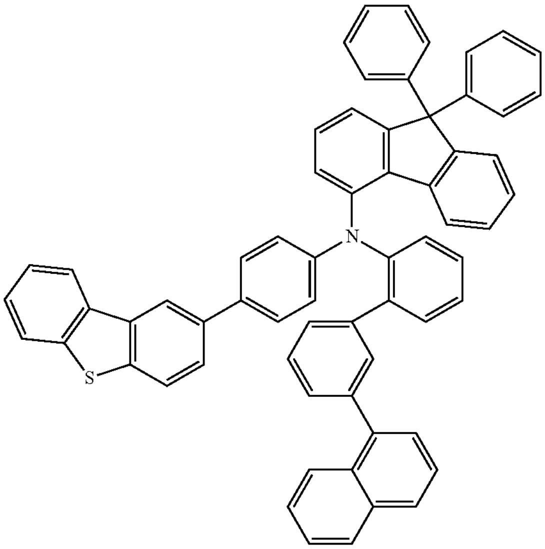

-continued
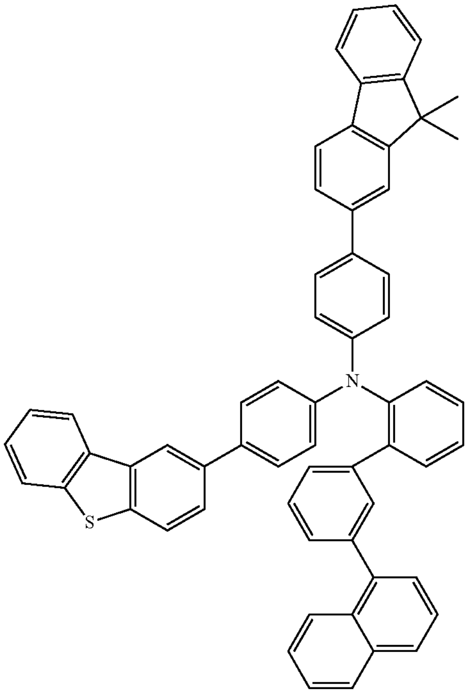
-continued
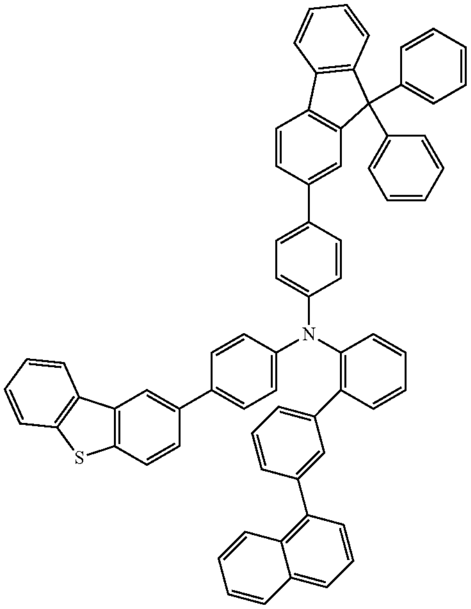
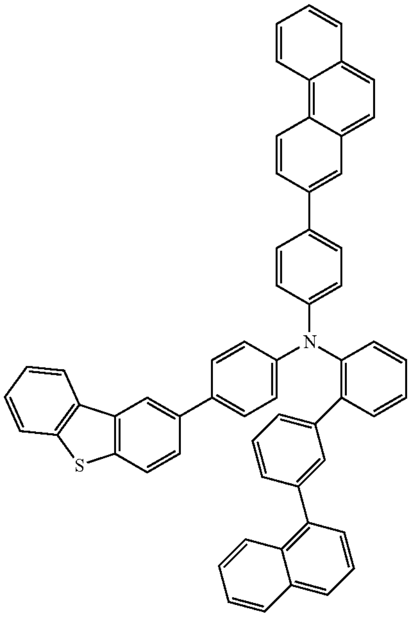
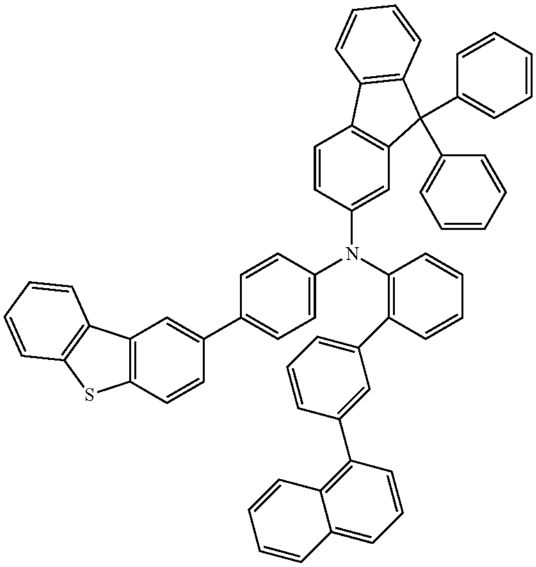

-continued
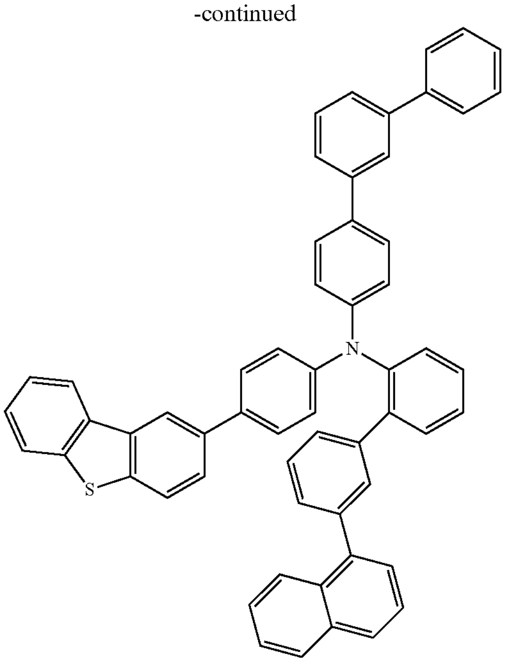
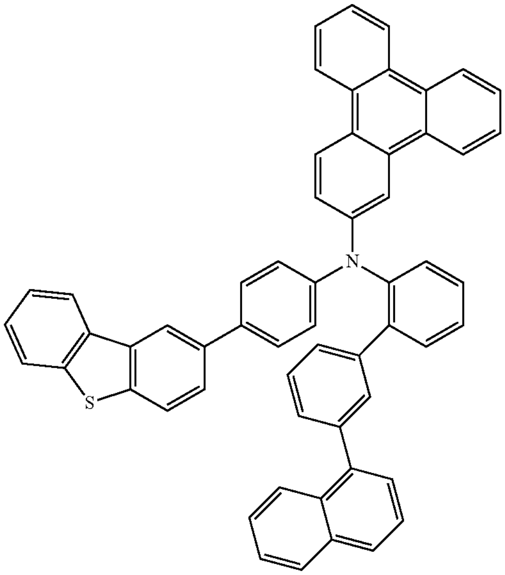
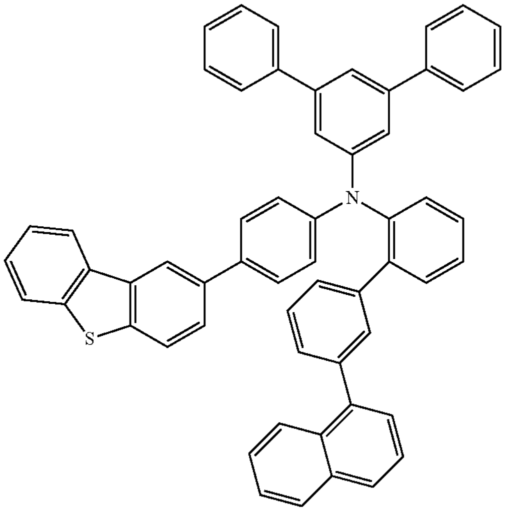
-continued
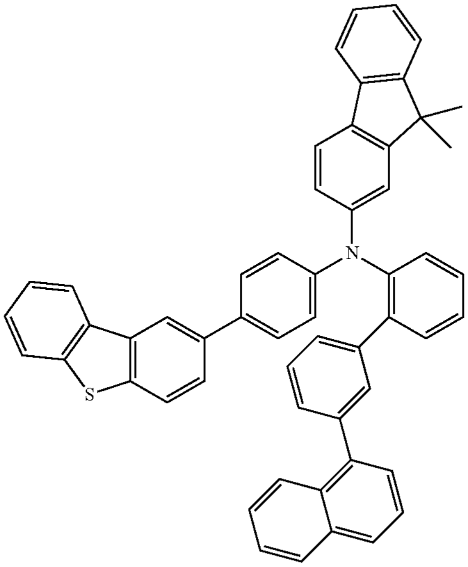
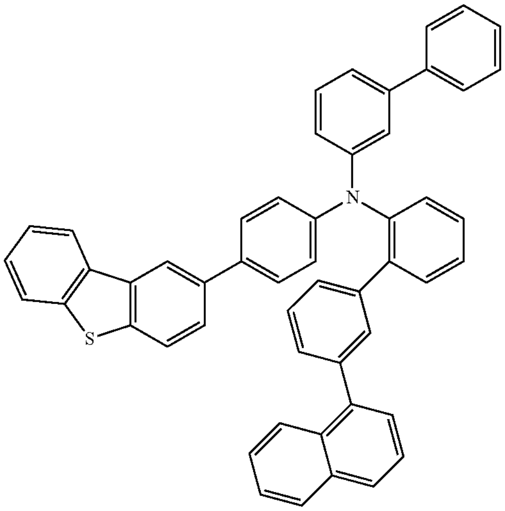
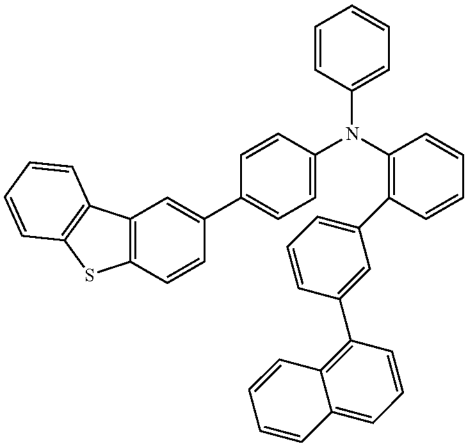

-continued
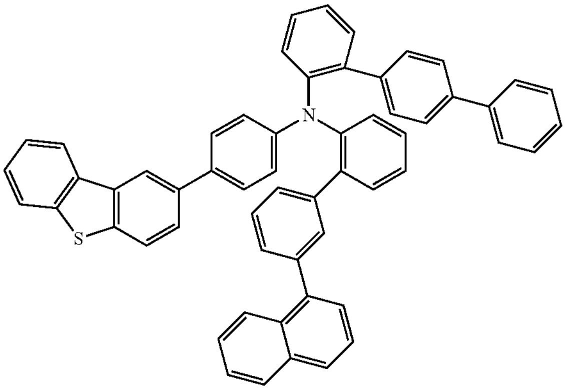
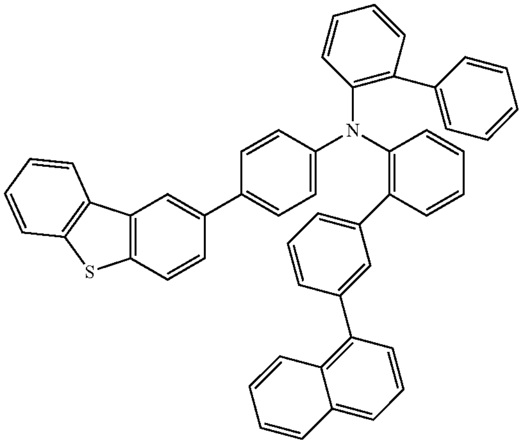
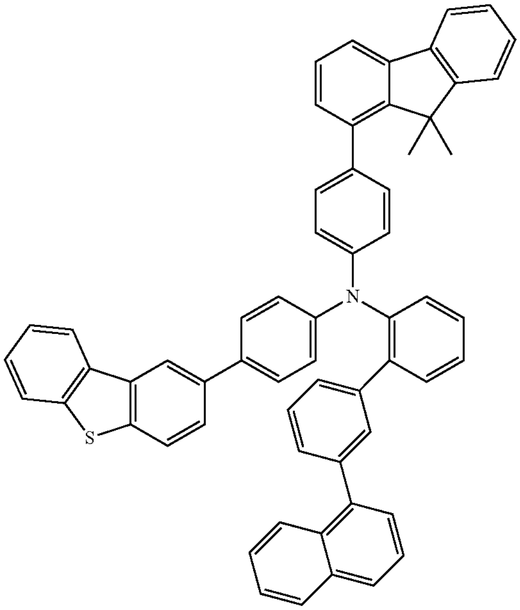
-continued
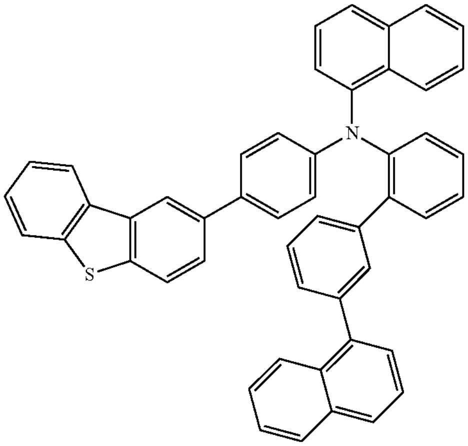
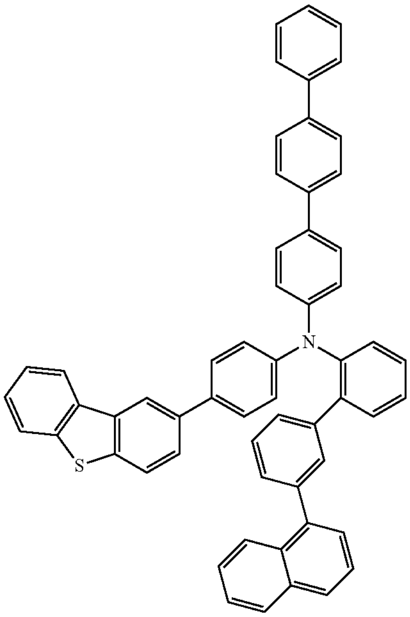
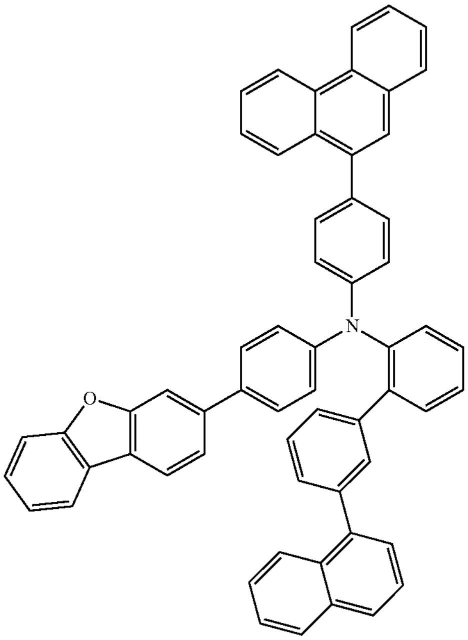

-continued
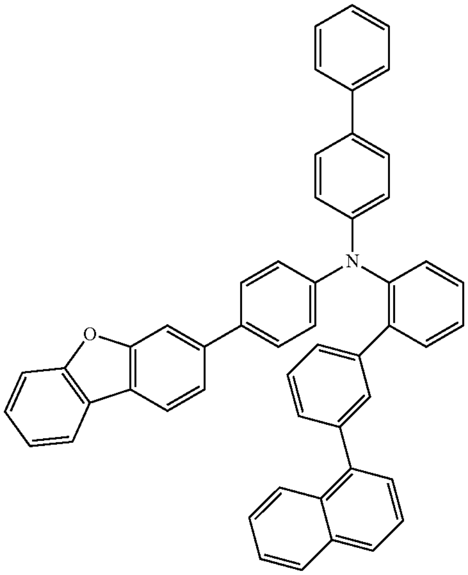
-continued
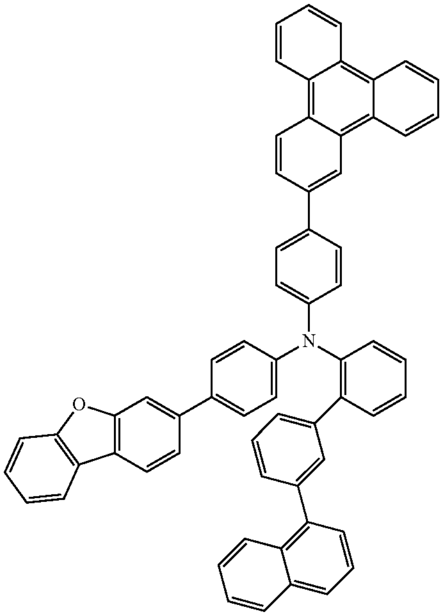
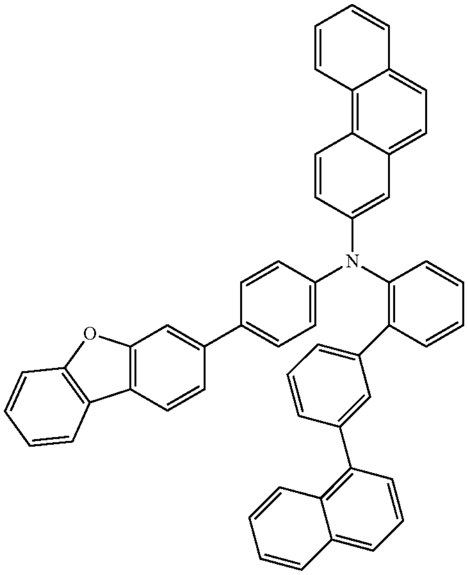
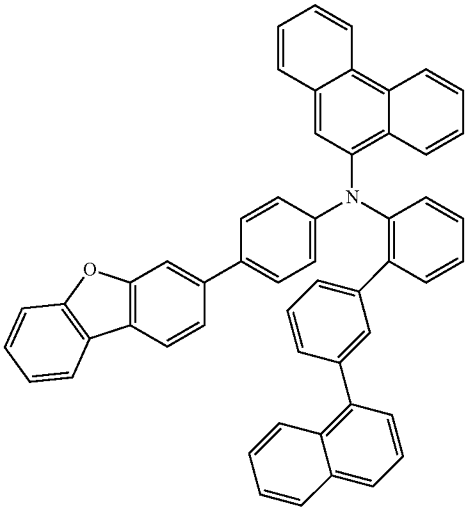

-continued
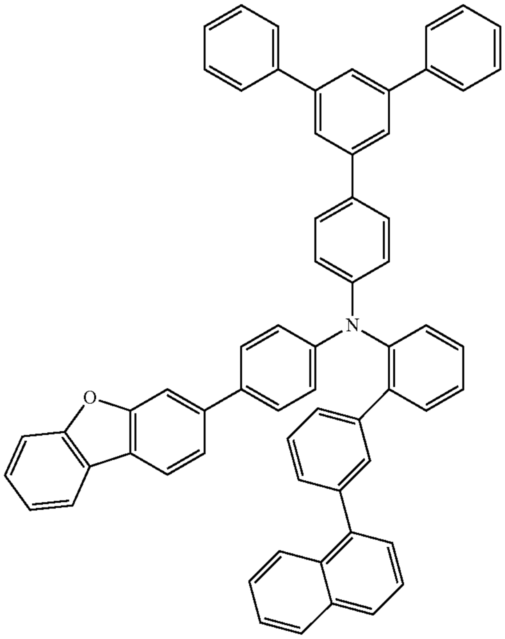
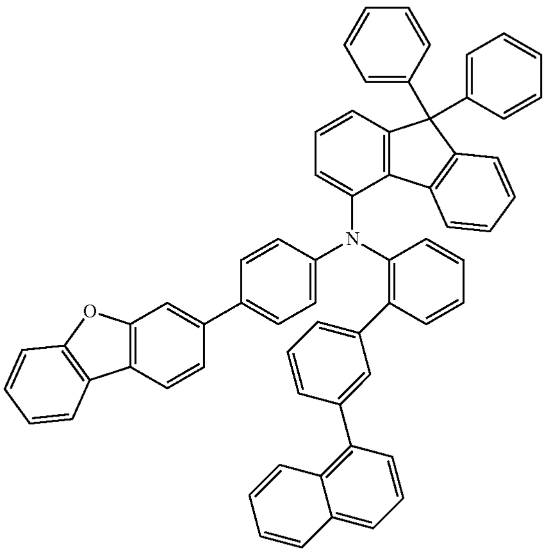
-continued
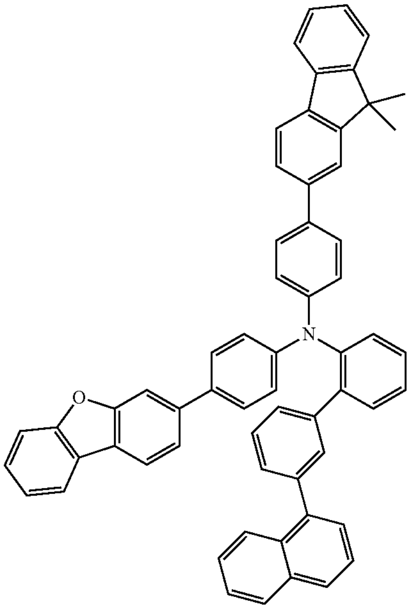
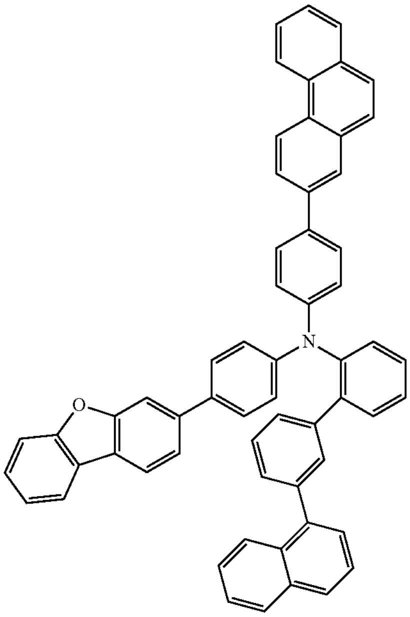

-continued
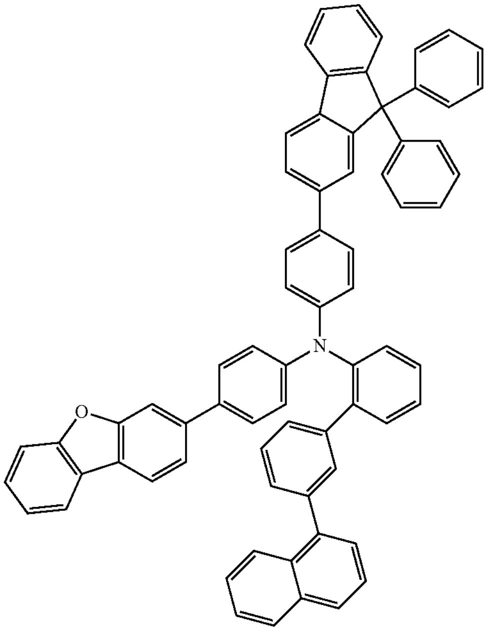
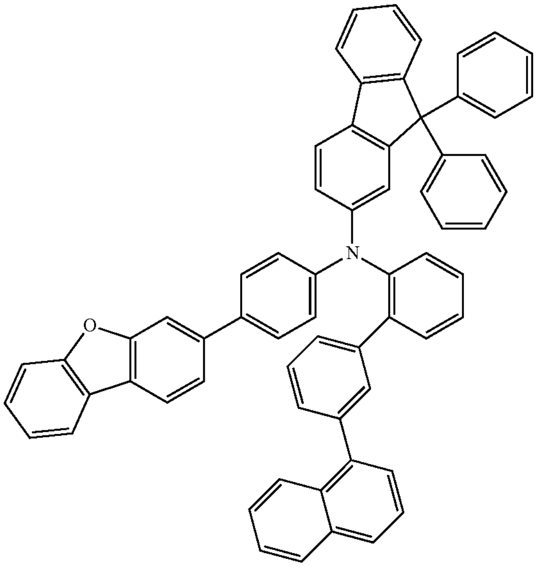
-continued
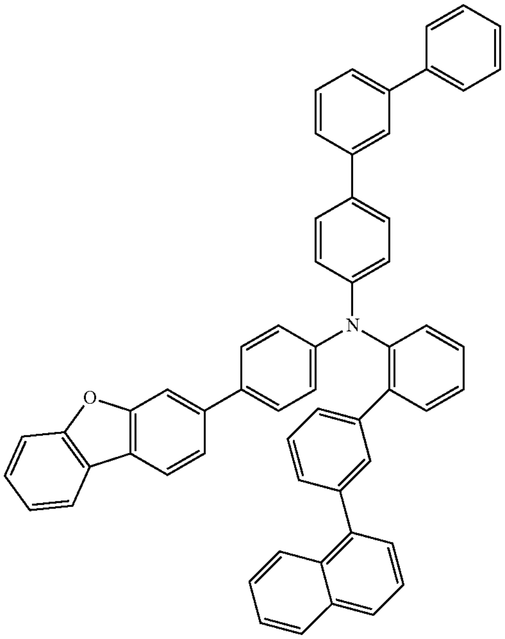
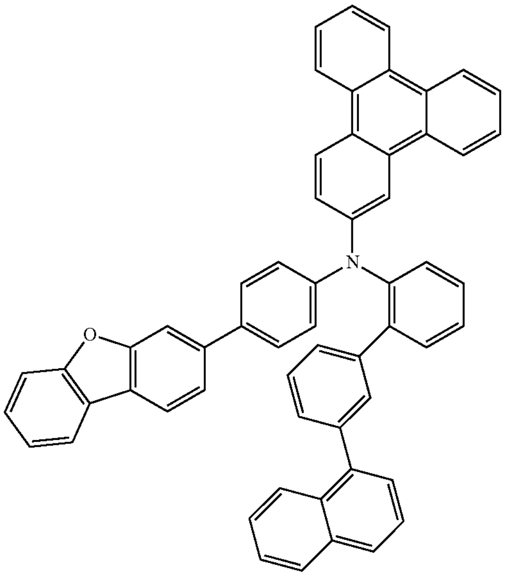
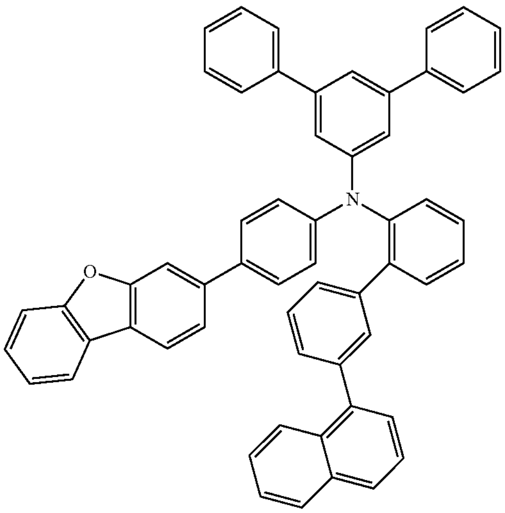

-continued
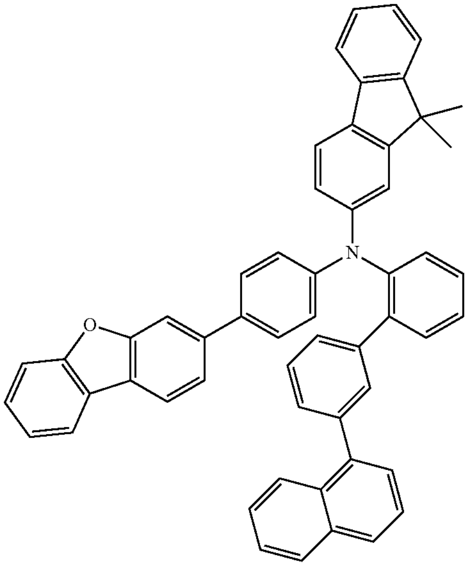
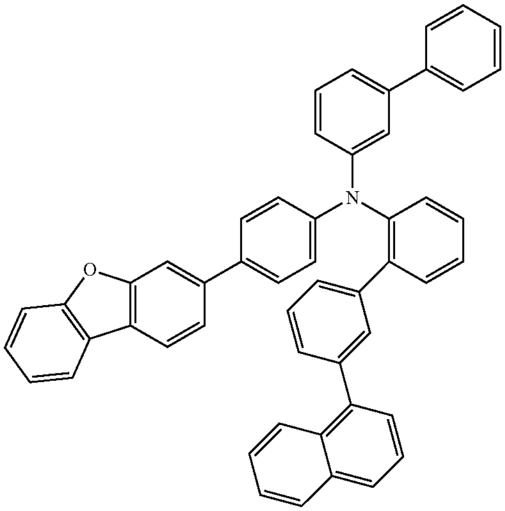
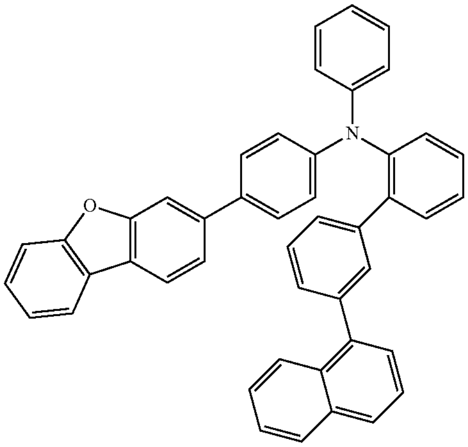
-continued
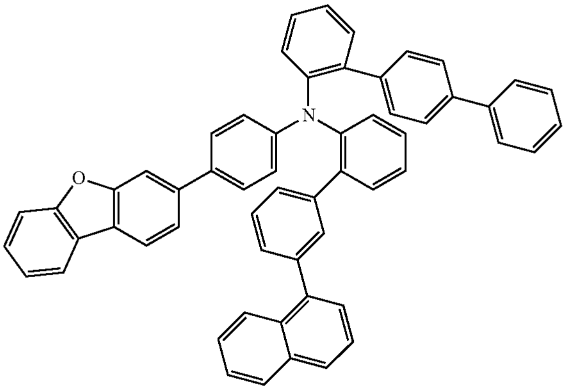
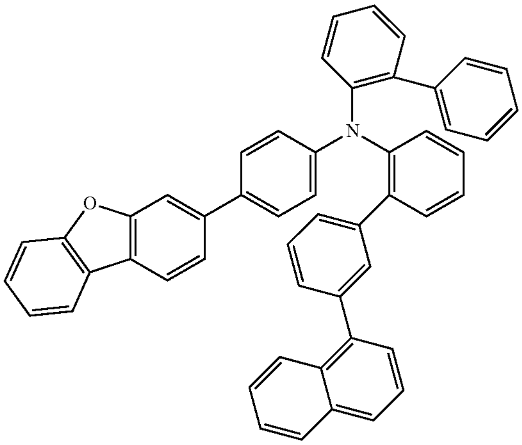
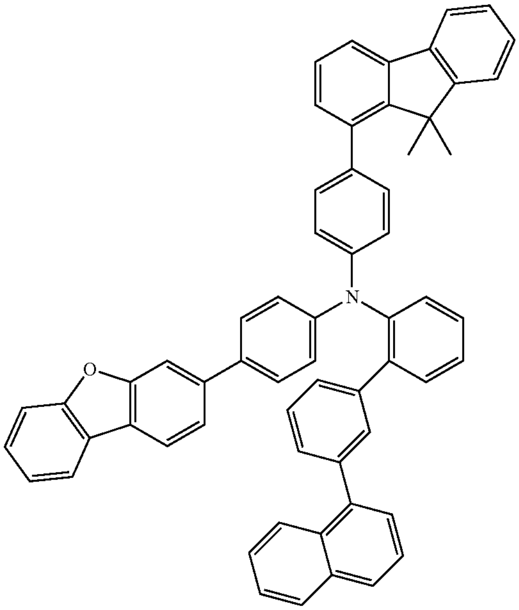

-continued
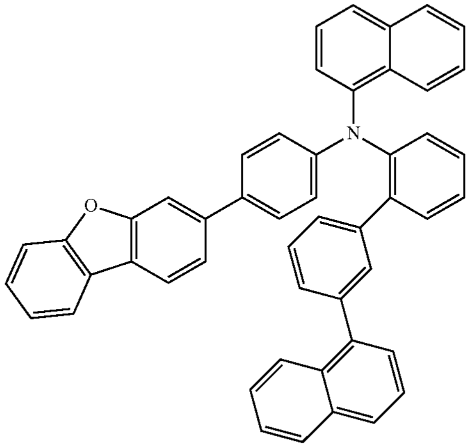
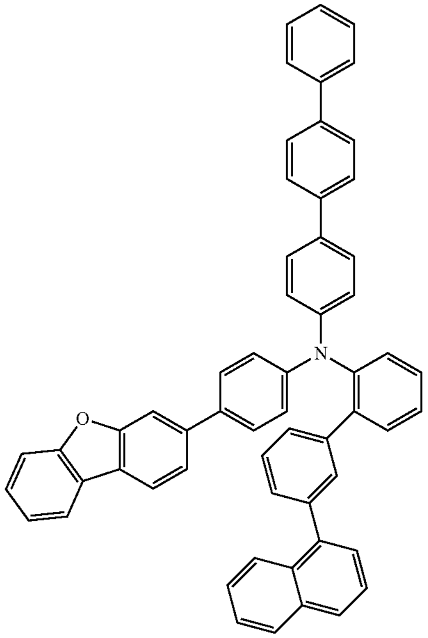
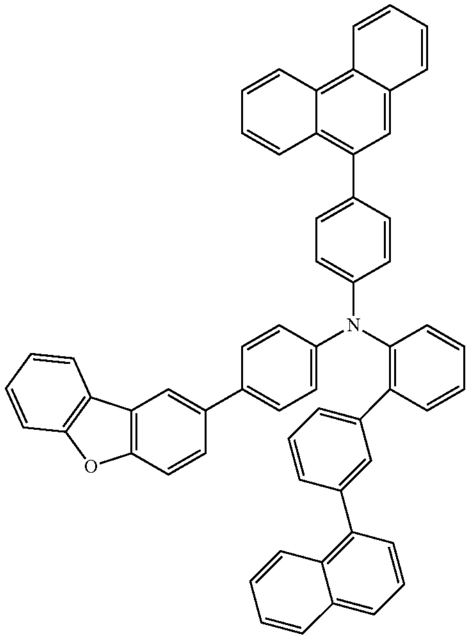
-continued
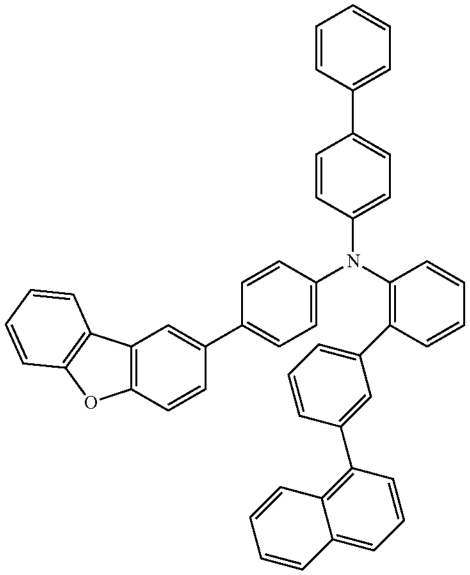
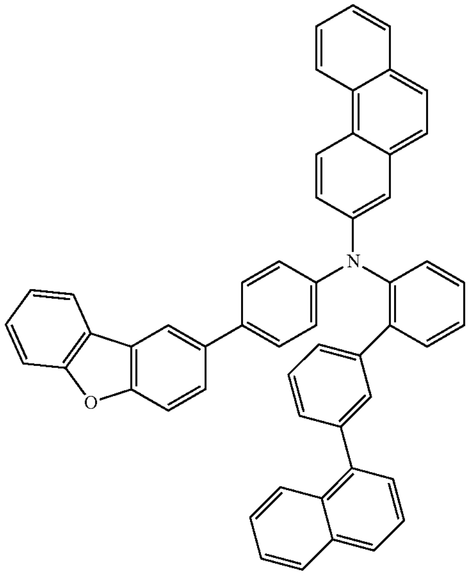

-continued
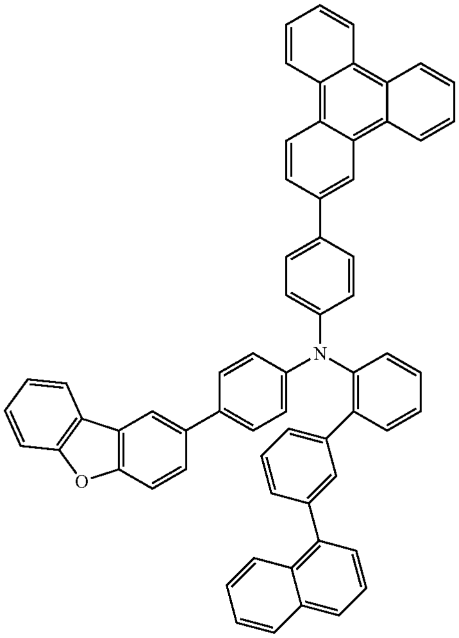
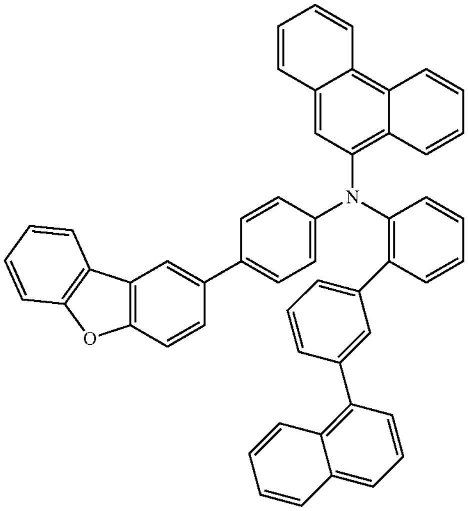
-continued
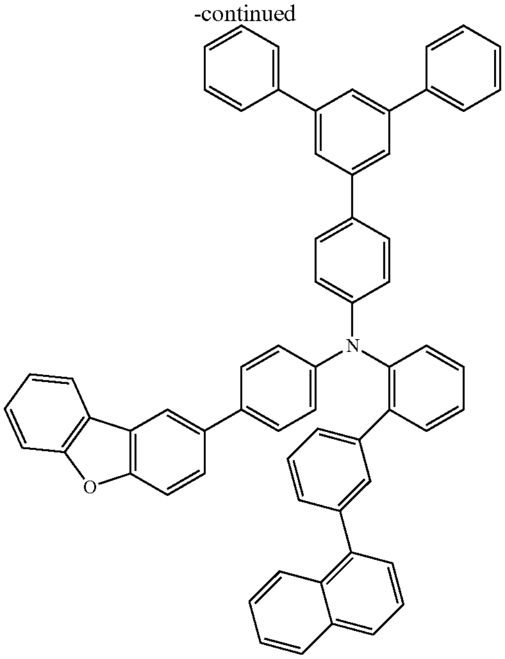
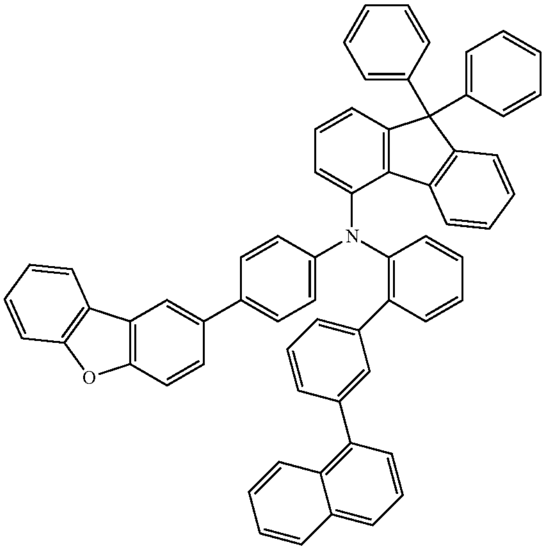

-continued
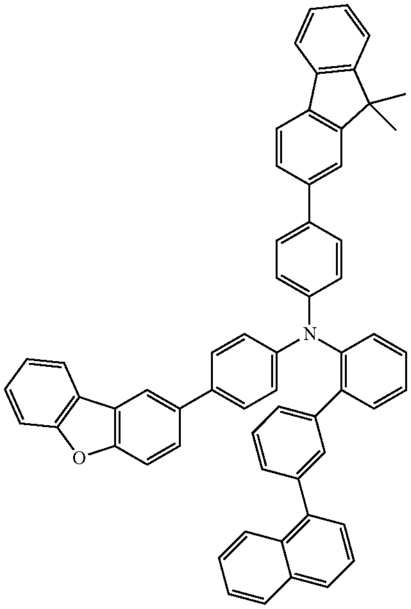
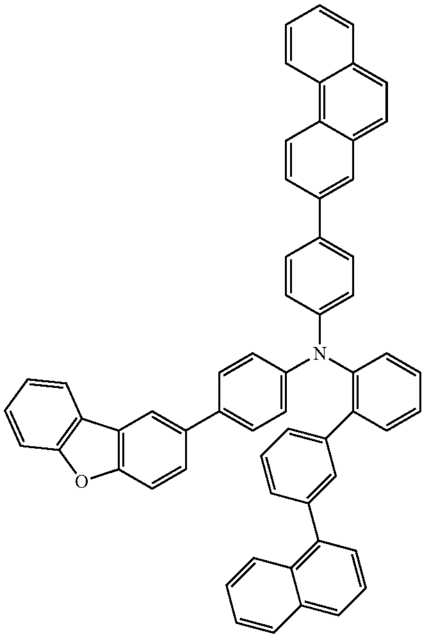
-continued
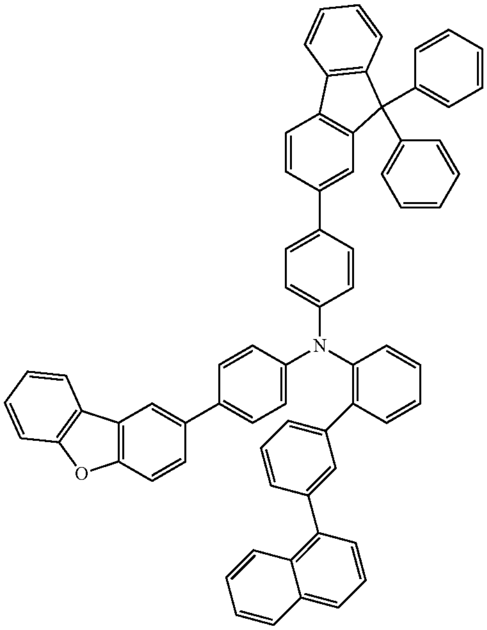
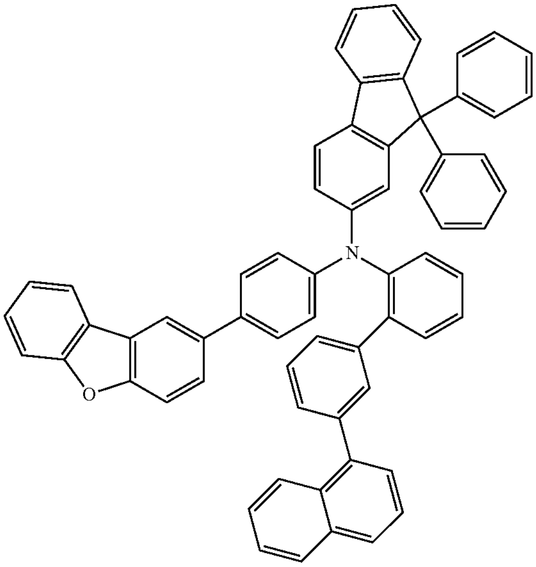

-continued
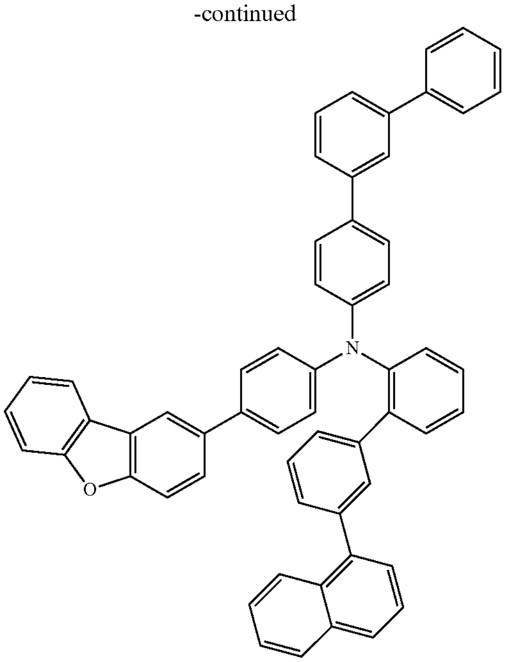
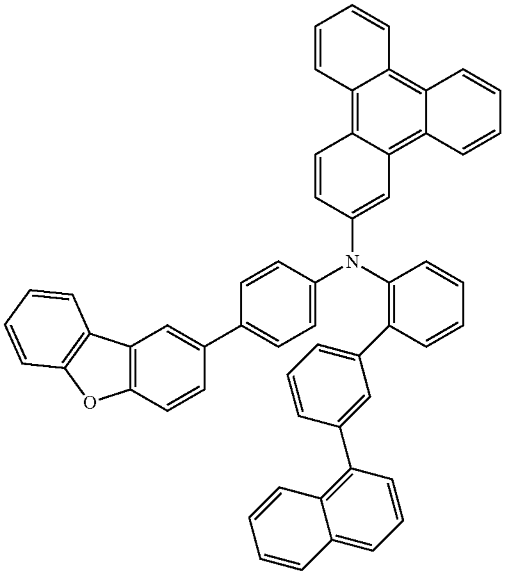
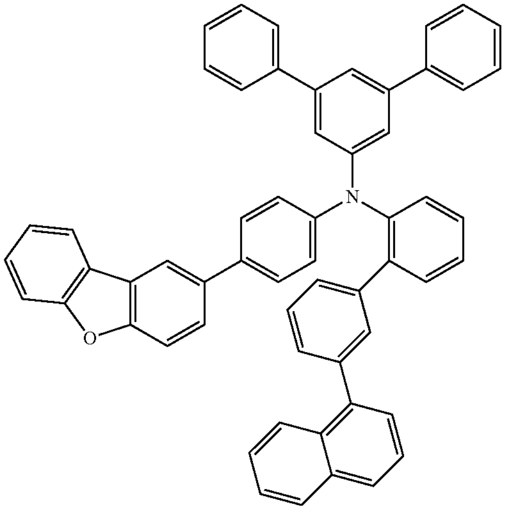
-continued
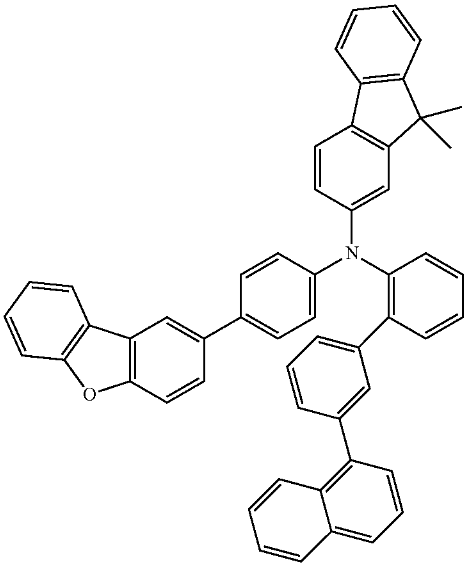
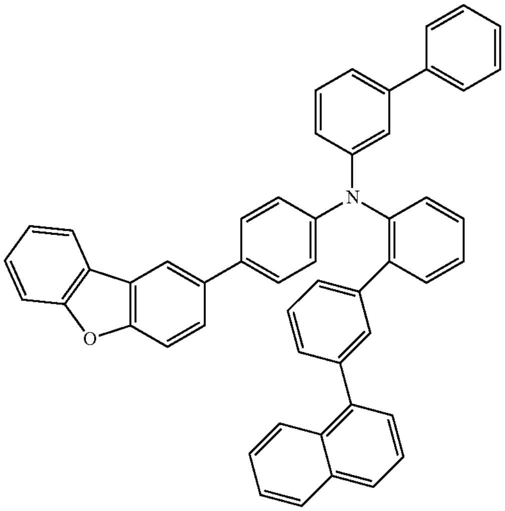
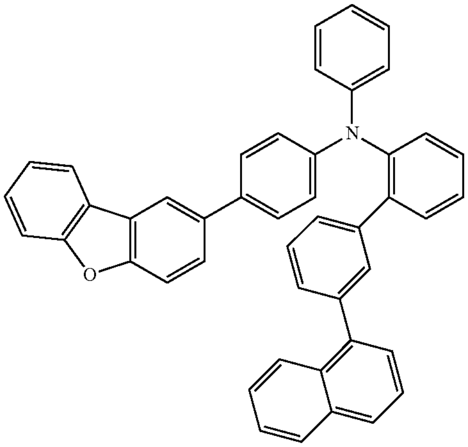

-continued
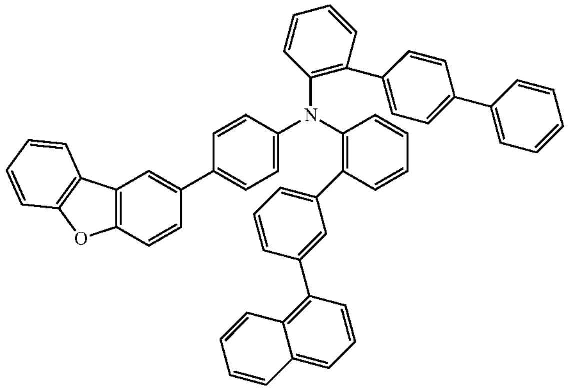
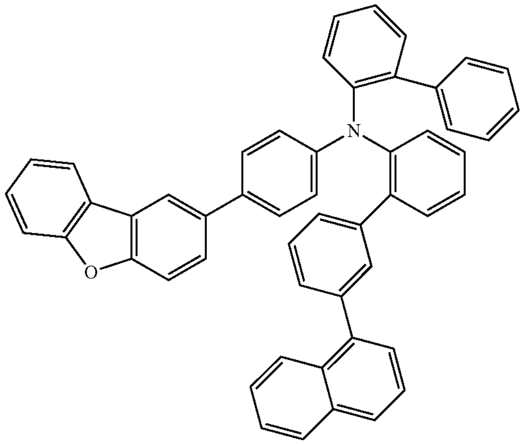
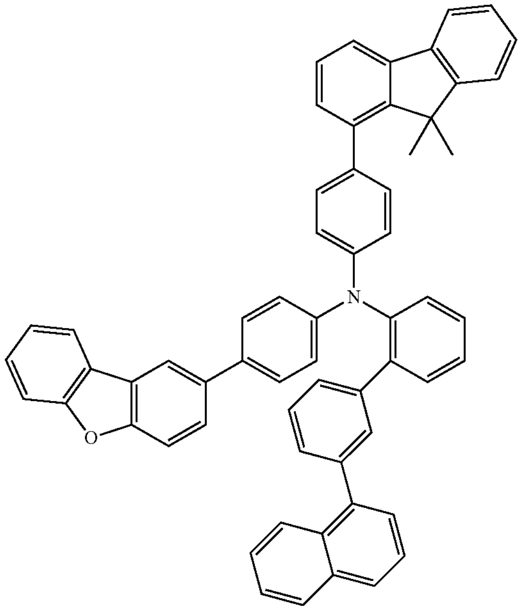
-continued
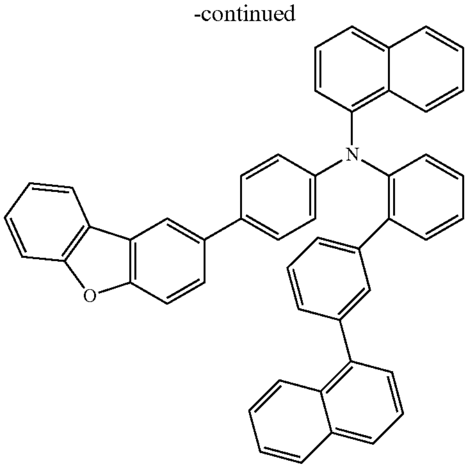
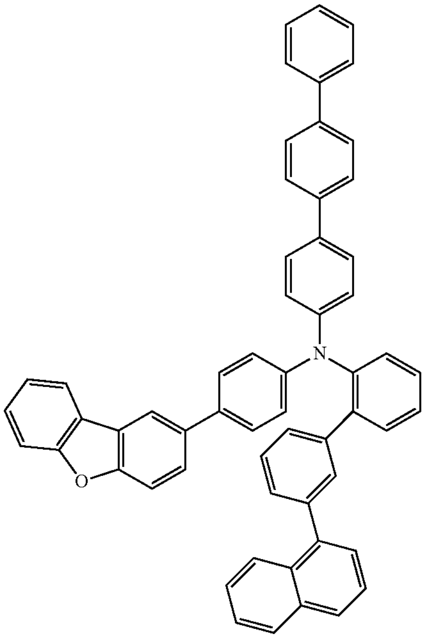
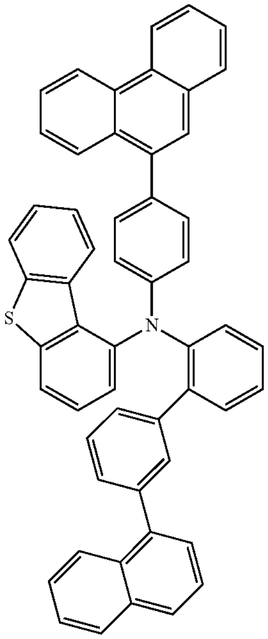

-continued
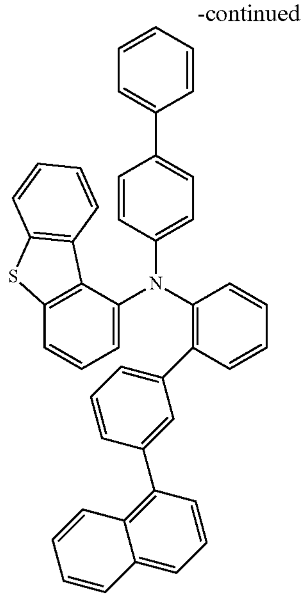
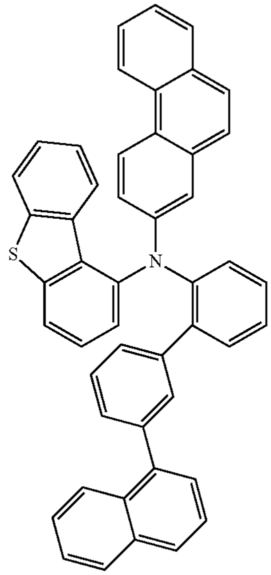
-continued
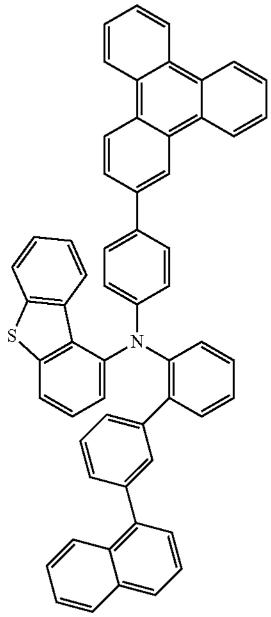
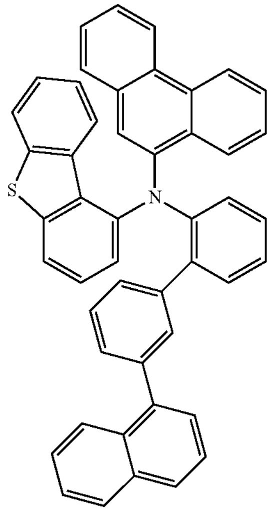

-continued
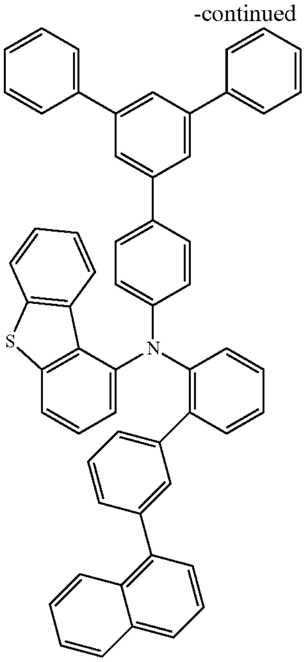
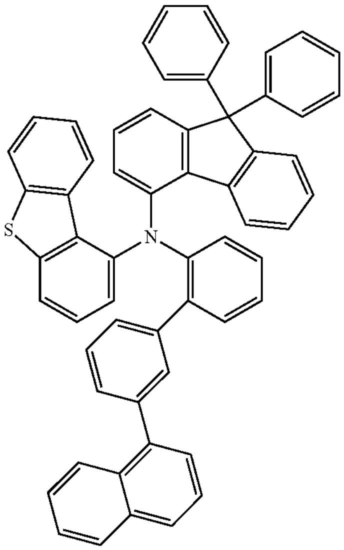
-continued
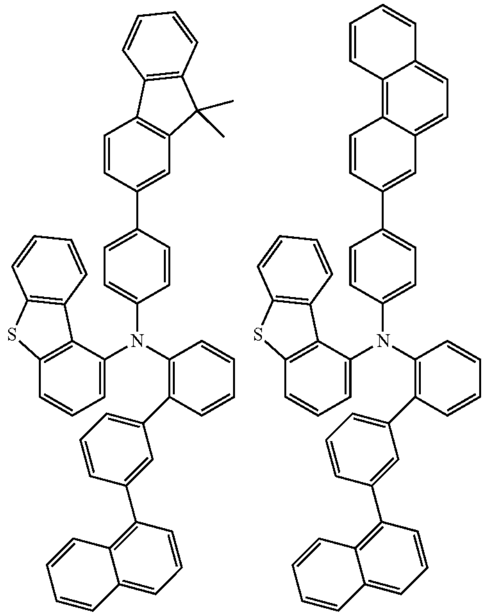
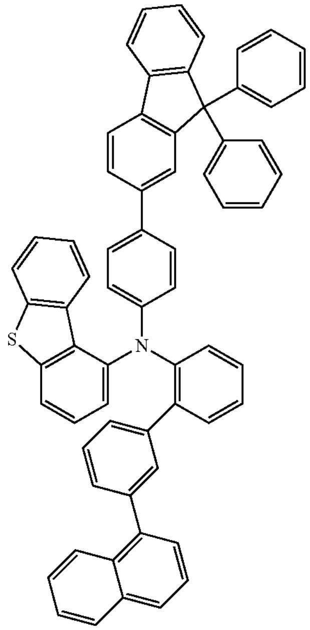

-continued
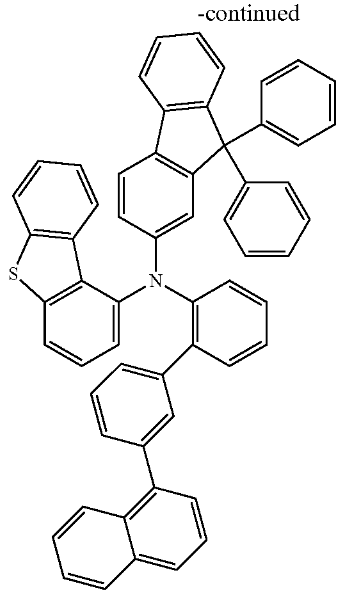
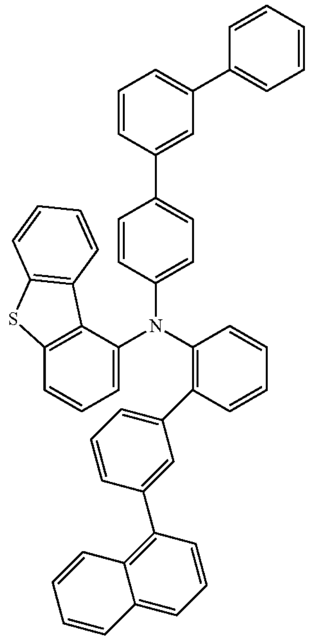
-continued
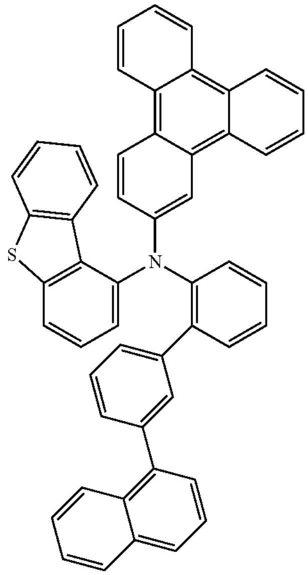
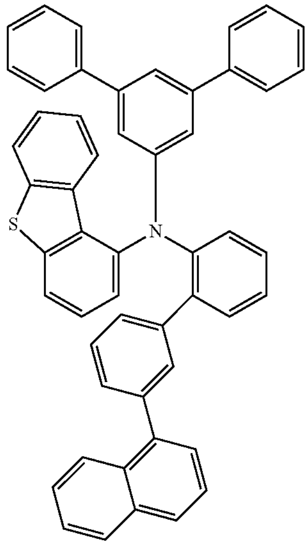
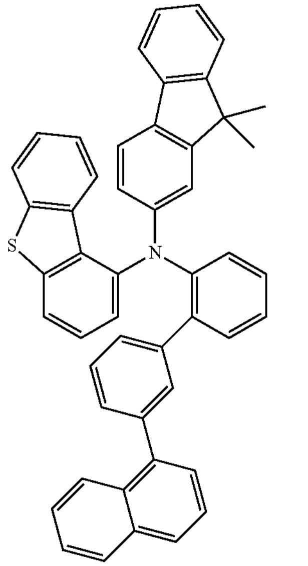

-continued
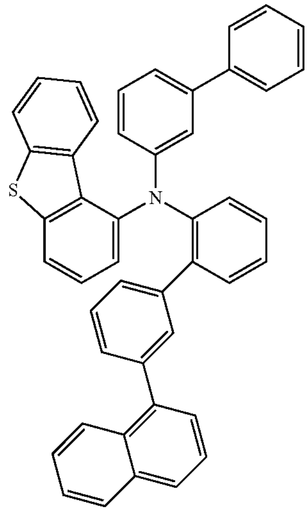
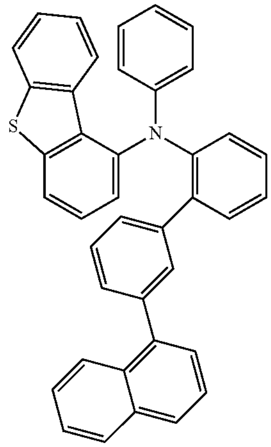
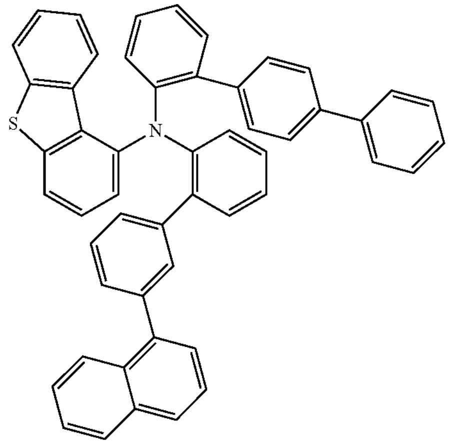
-continued
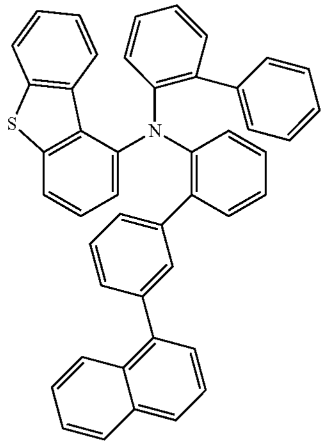
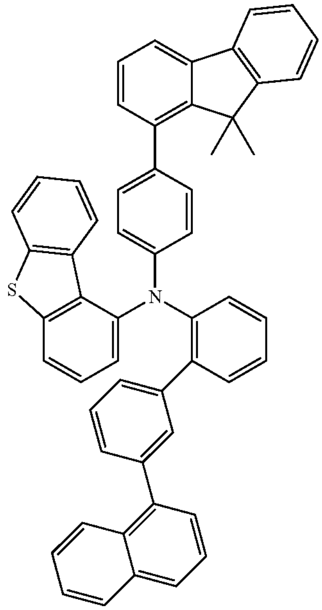
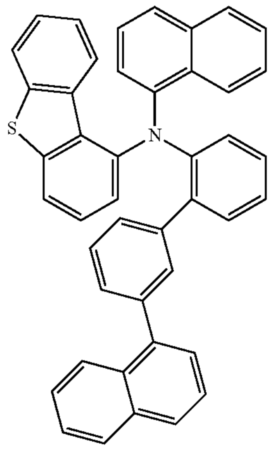
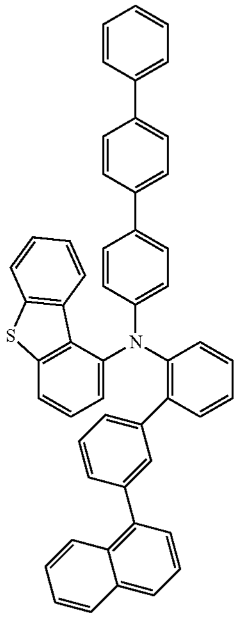

-continued
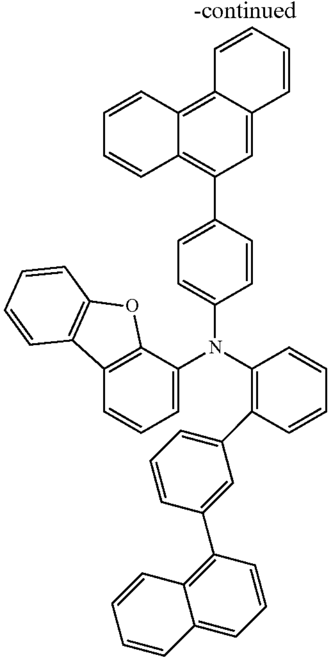
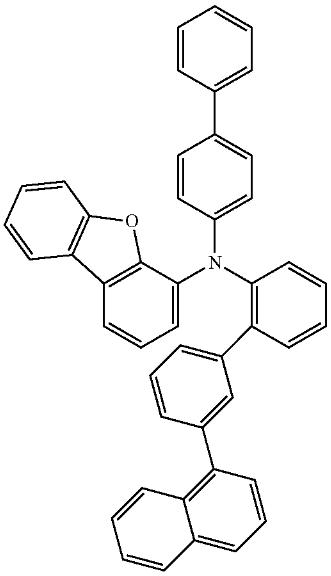
-continued
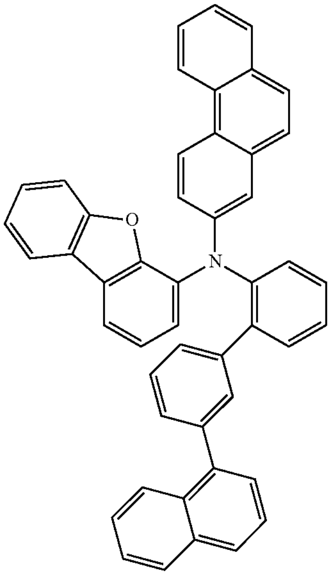
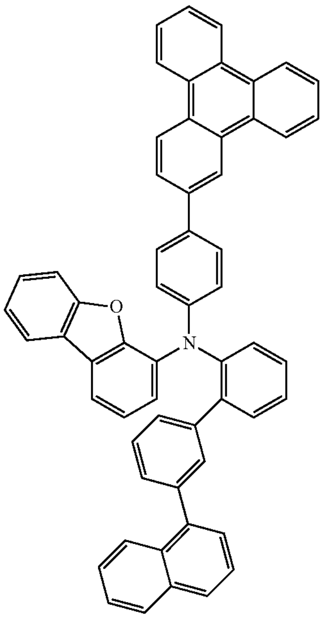
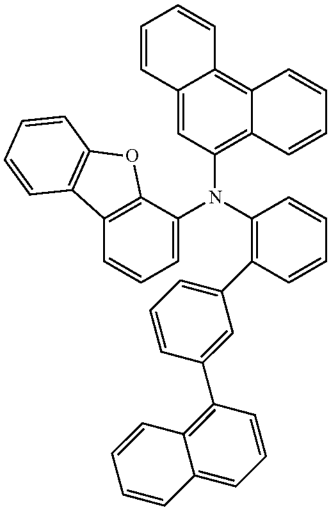

-continued
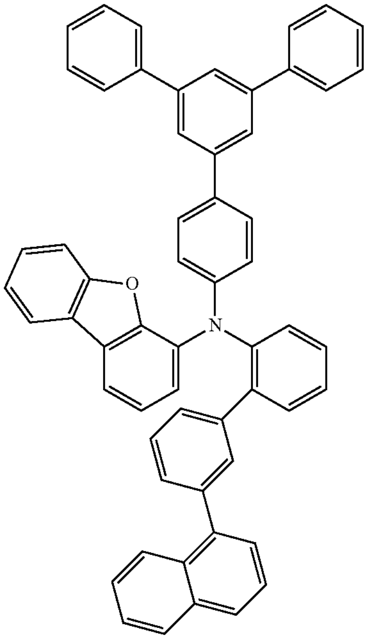
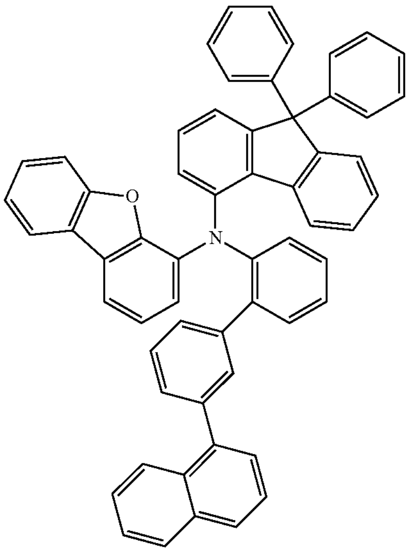
-continued
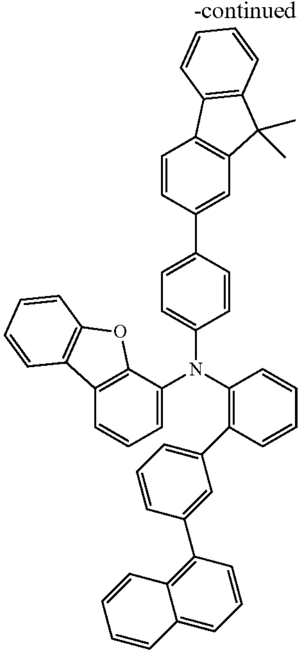
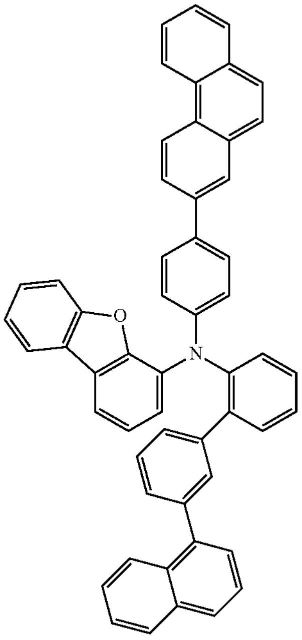

-continued
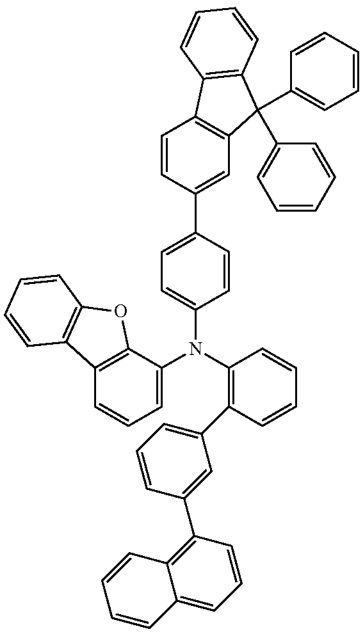
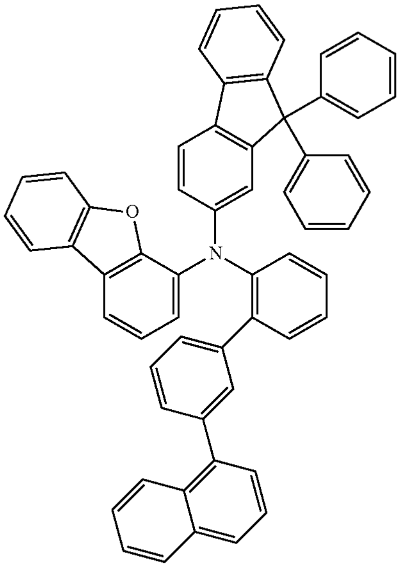
-continued
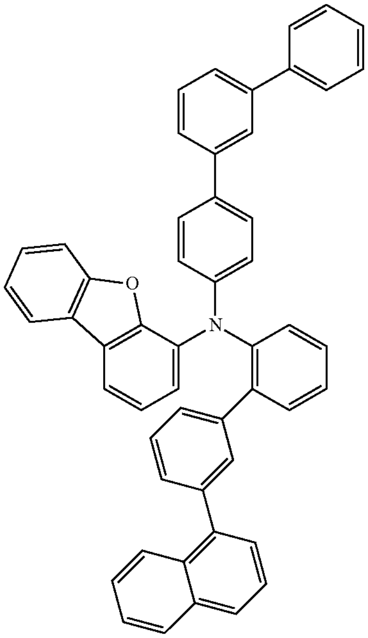
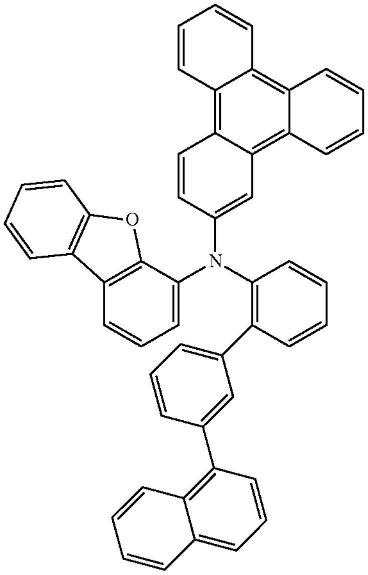
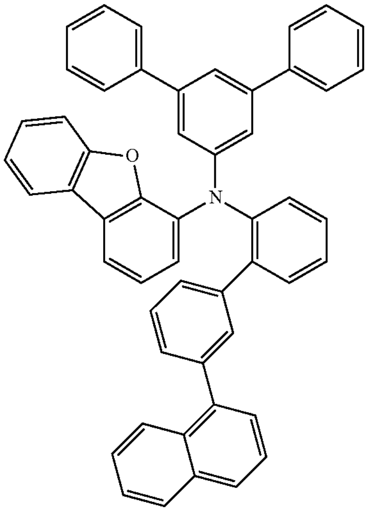

-continued
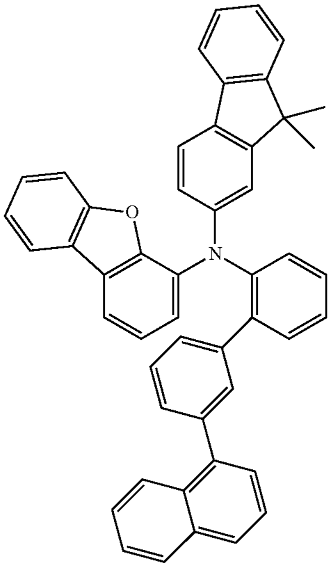
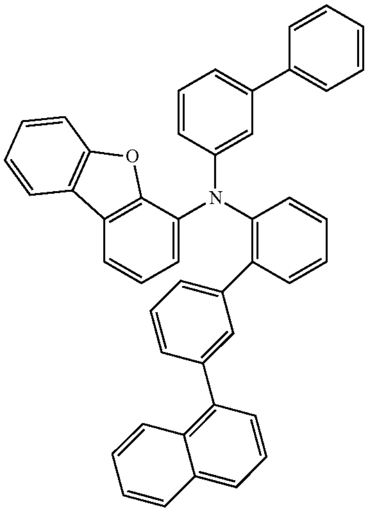
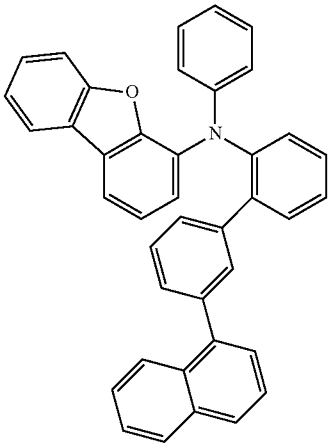
-continued
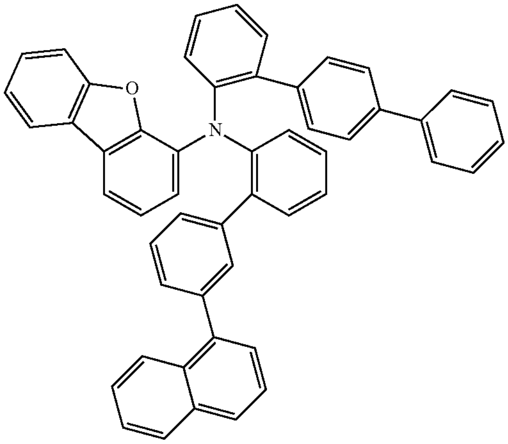
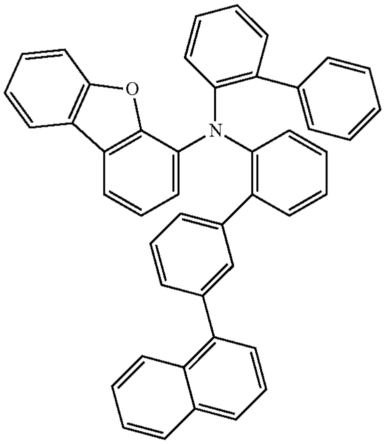
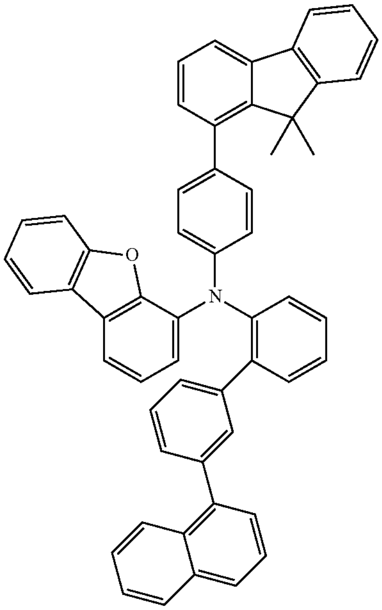

-continued
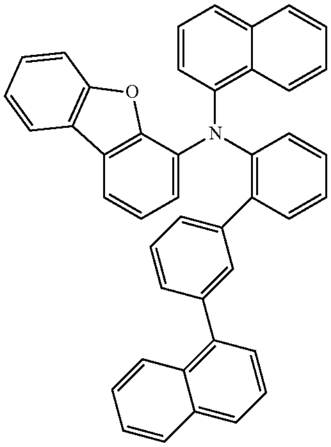
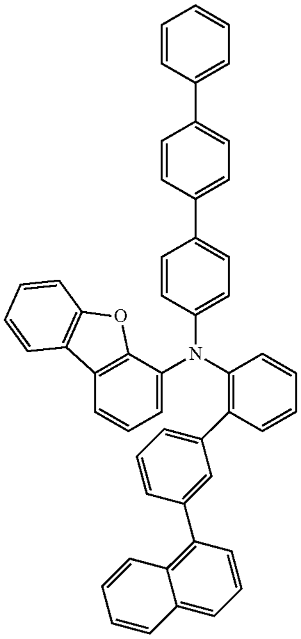
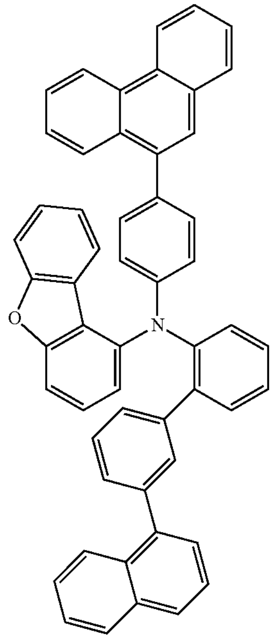
-continued
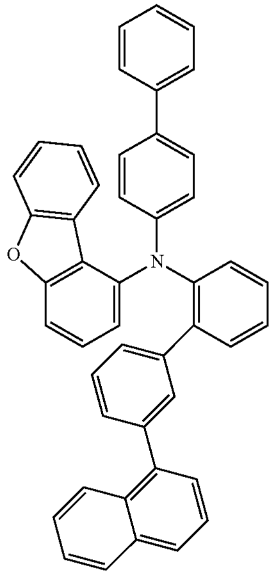
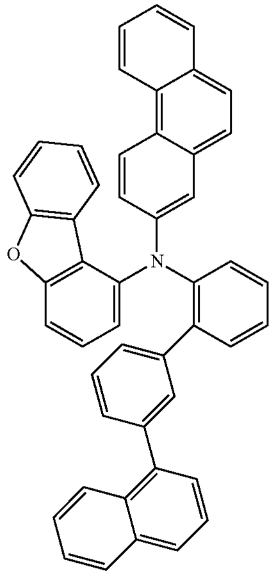
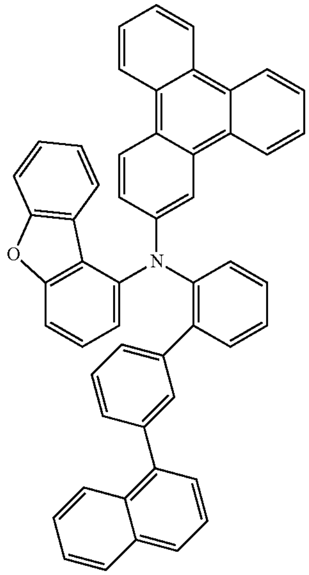

-continued
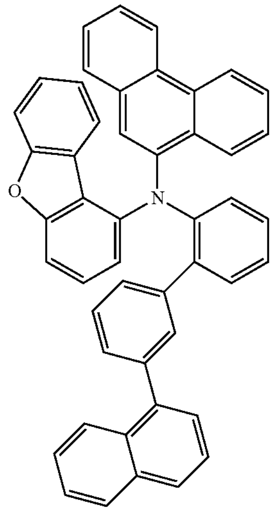
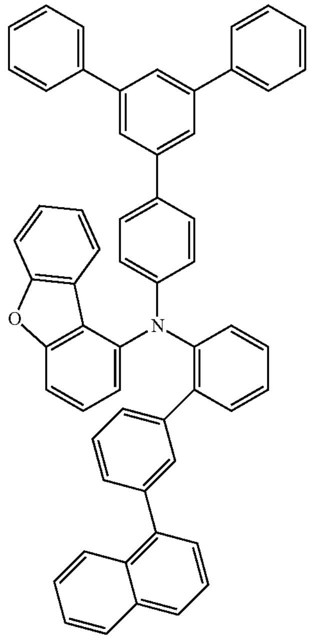
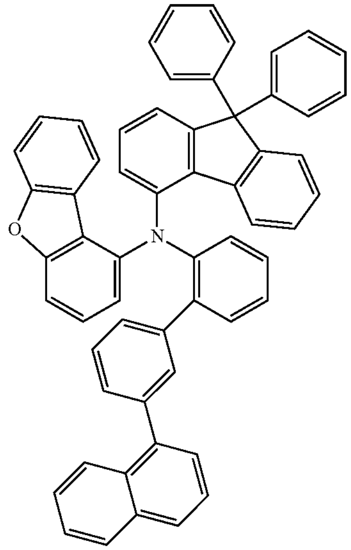
-continued
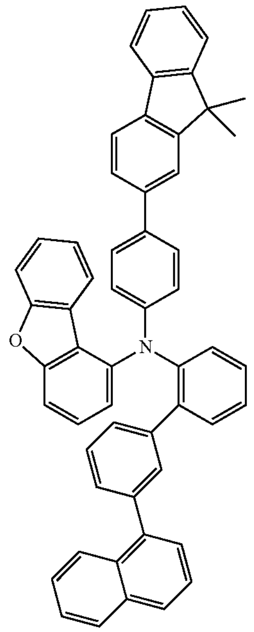
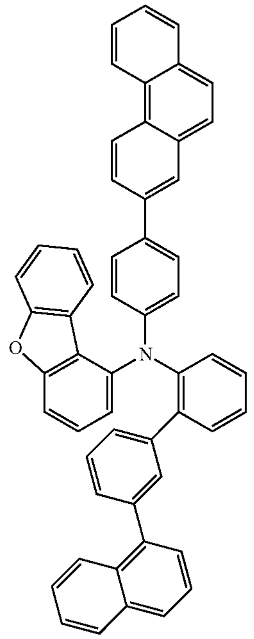

-continued
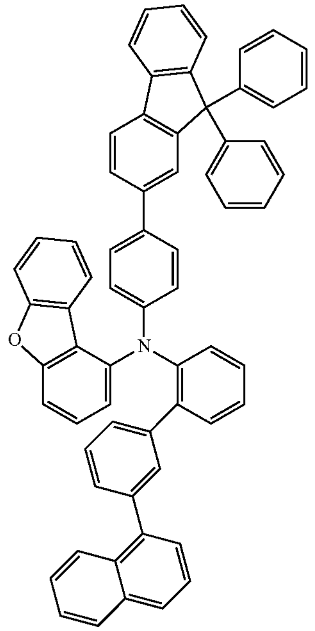
-continued
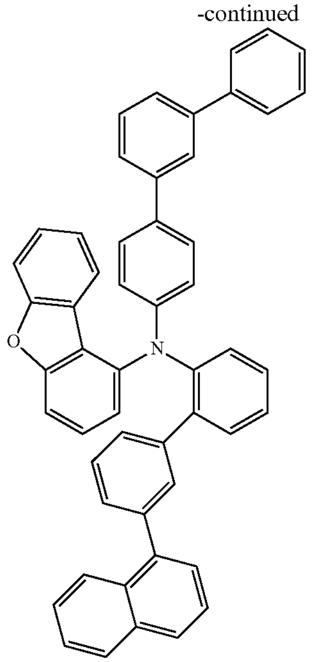
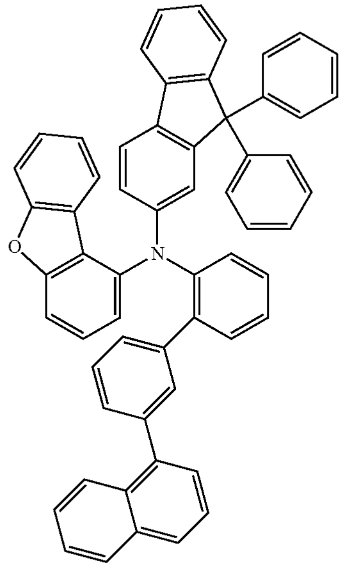
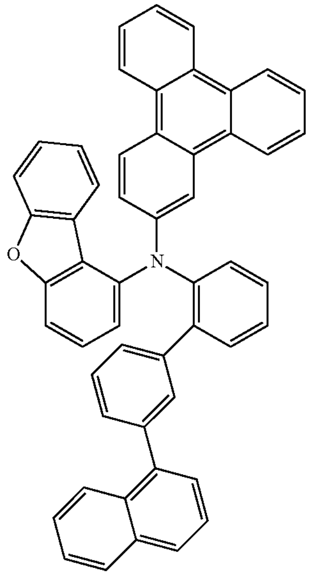

-continued
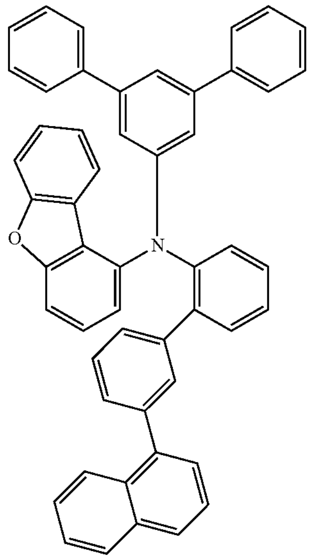
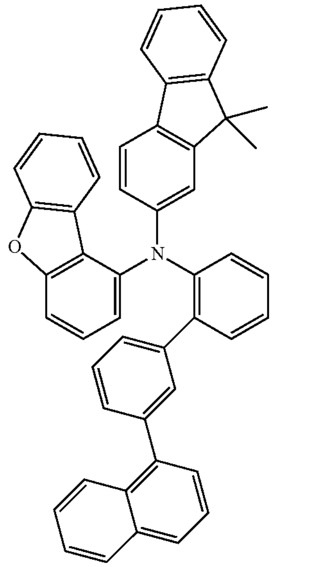
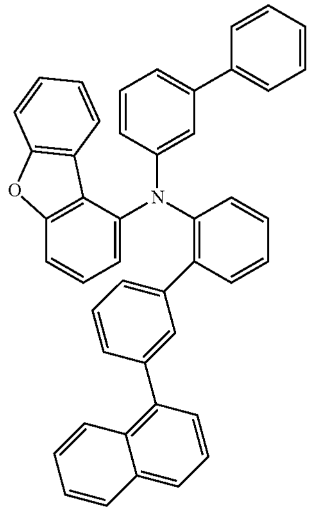
-continued
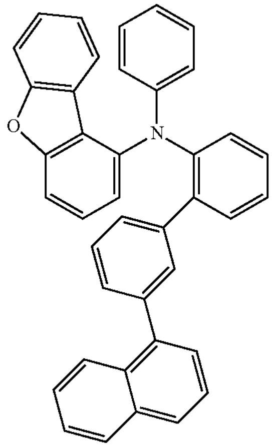
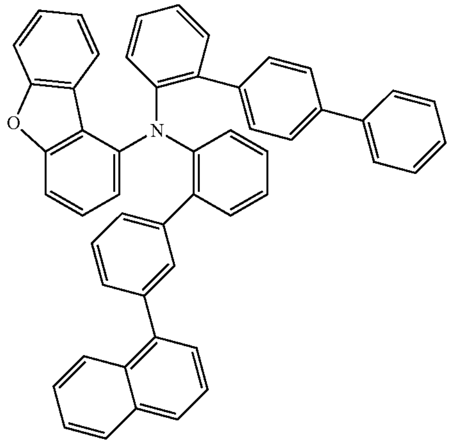
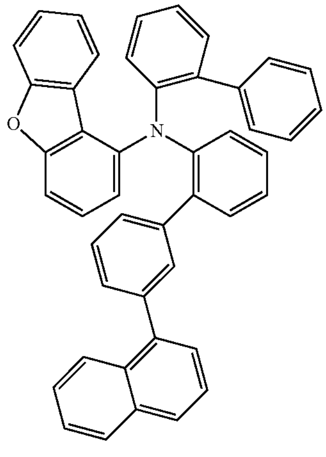

-continued
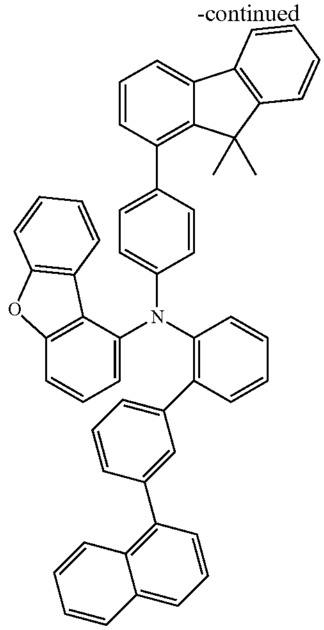
-continued
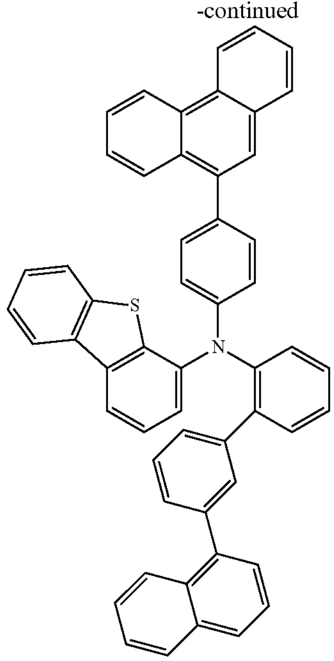
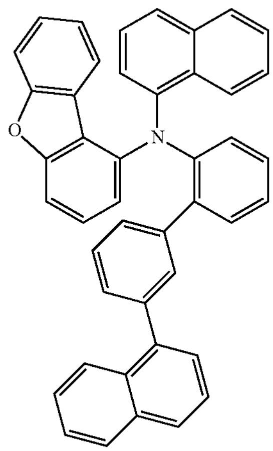
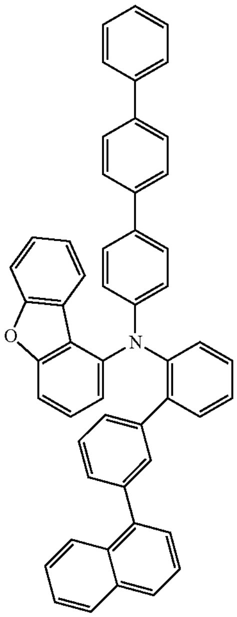
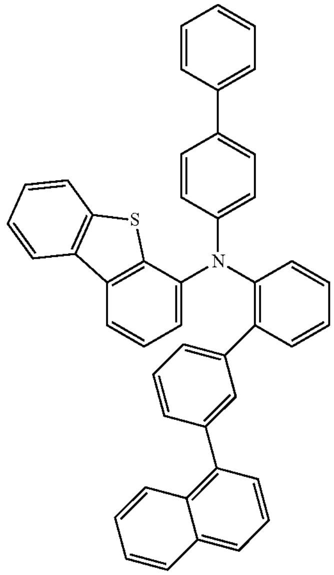

-continued
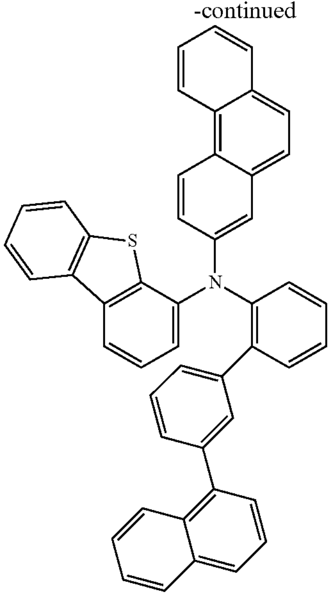
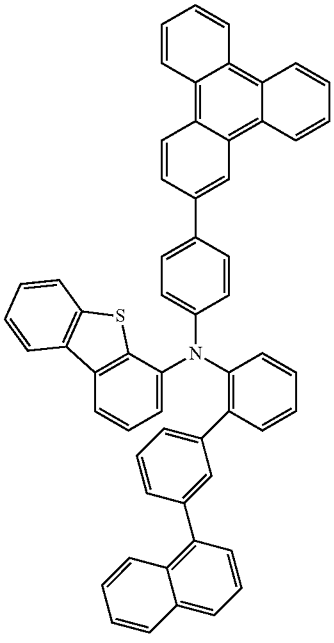
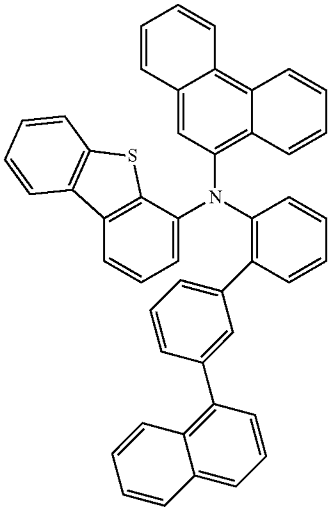
-continued
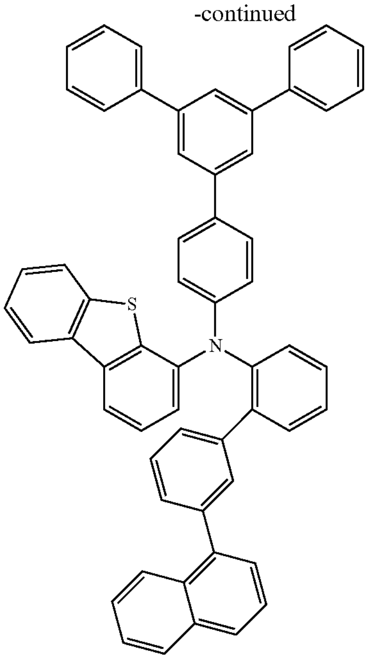
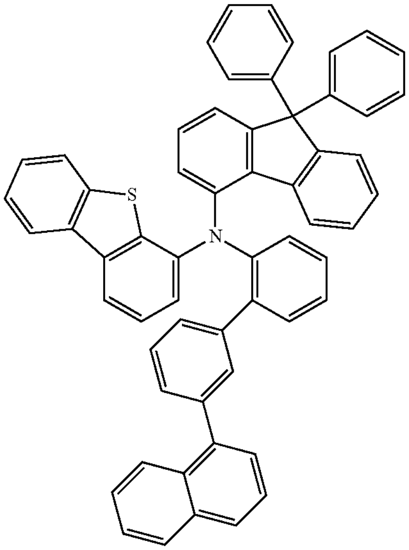

-continued
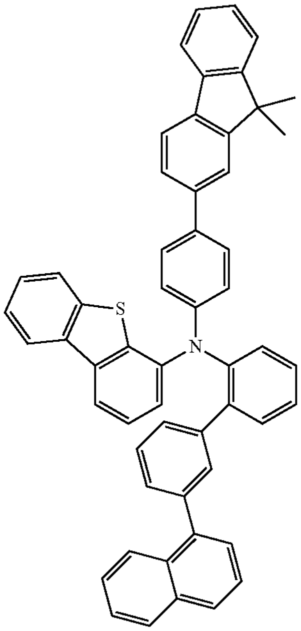
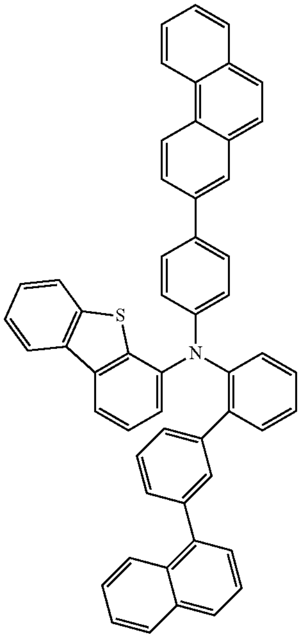
-continued
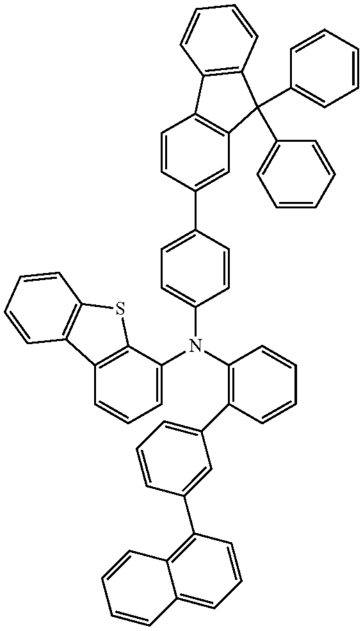
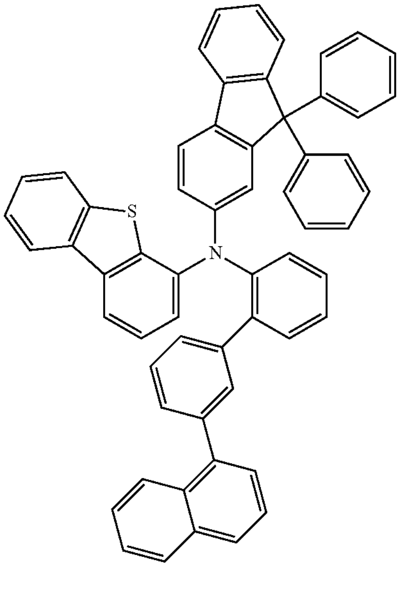

-continued
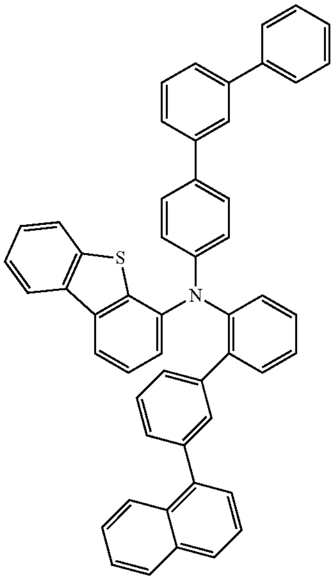
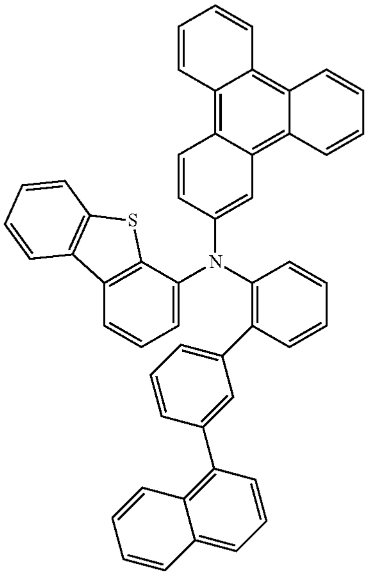
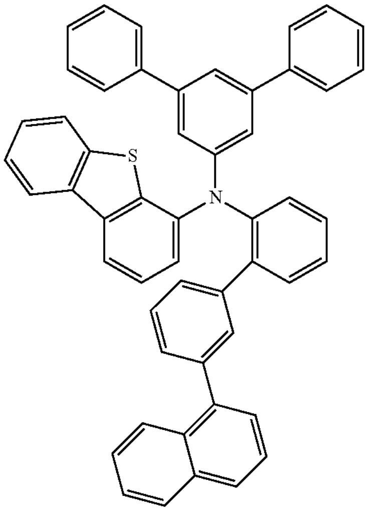
-continued
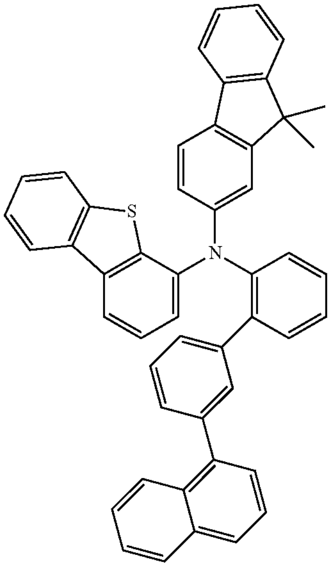
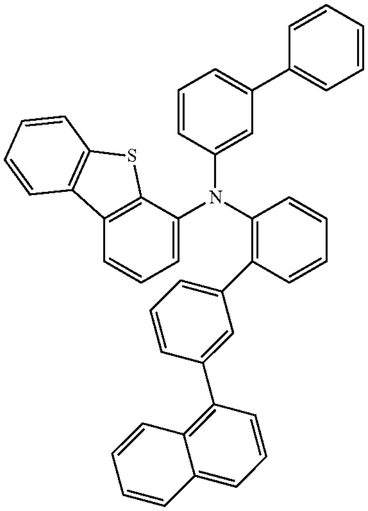
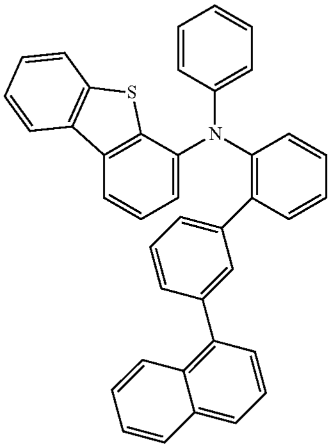

-continued
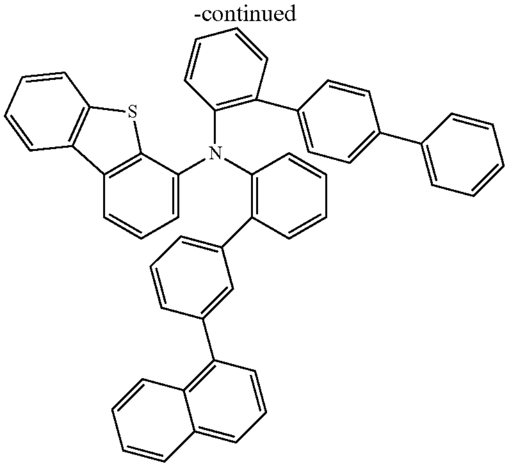
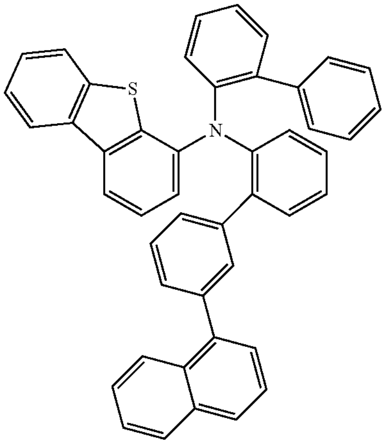
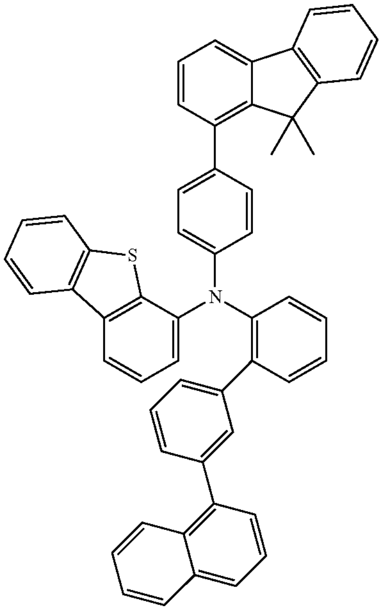
-continued
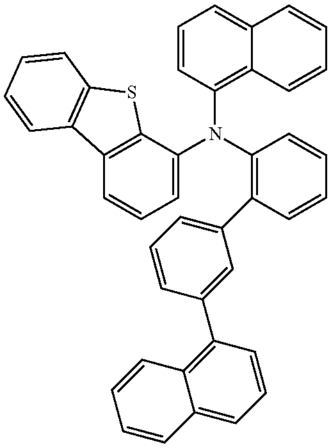
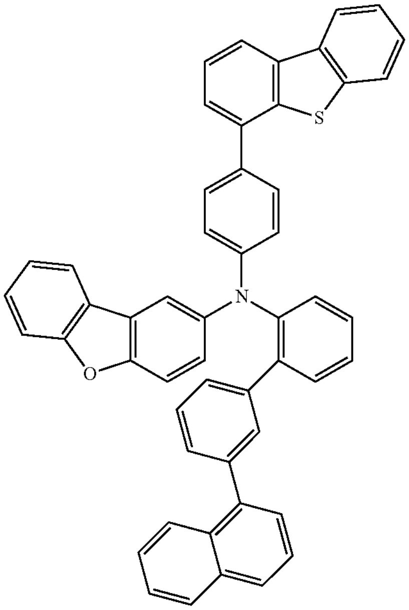
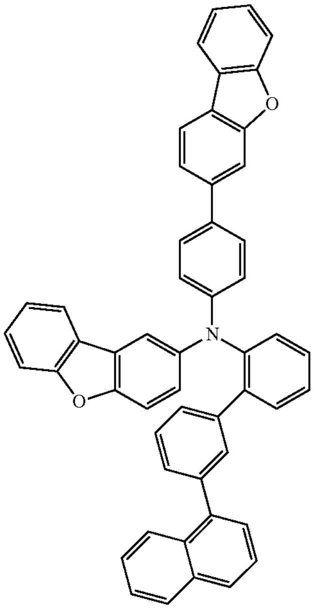

-continued
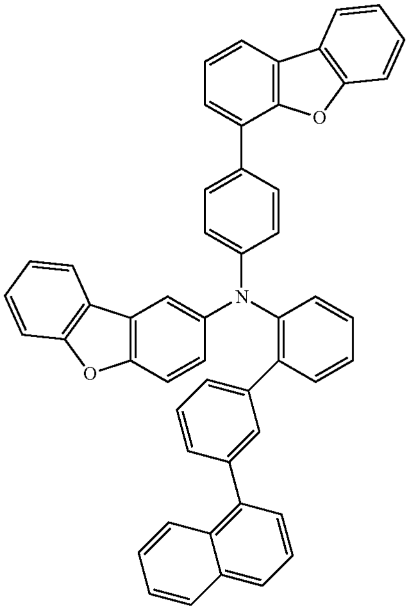
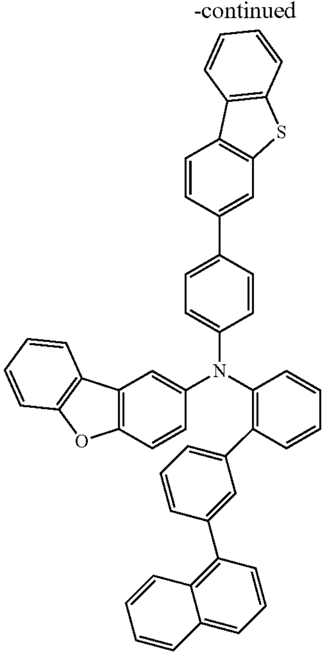
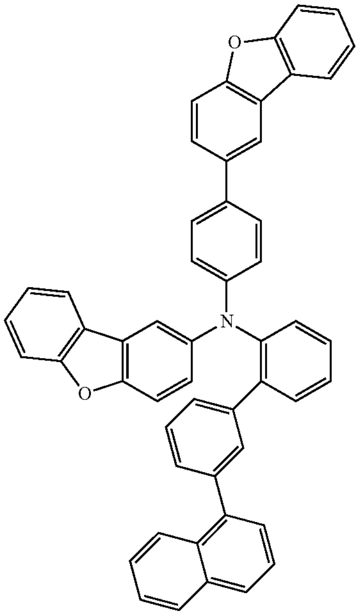
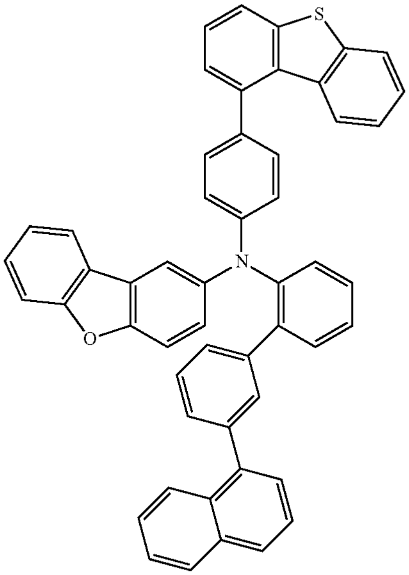

-continued
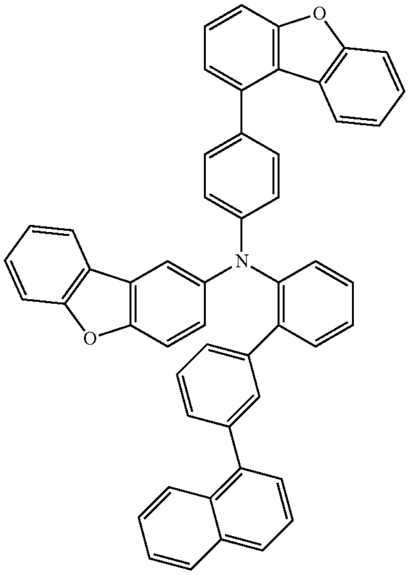
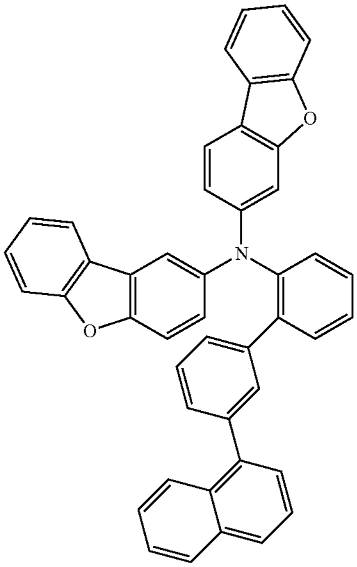
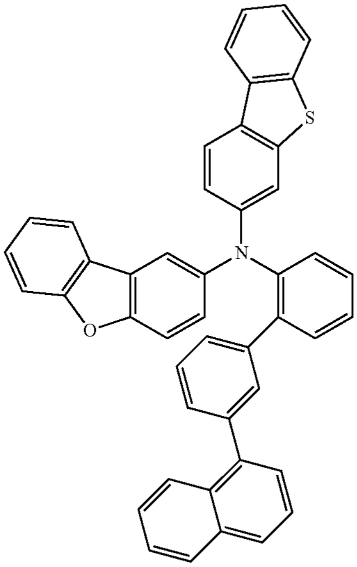
-continued
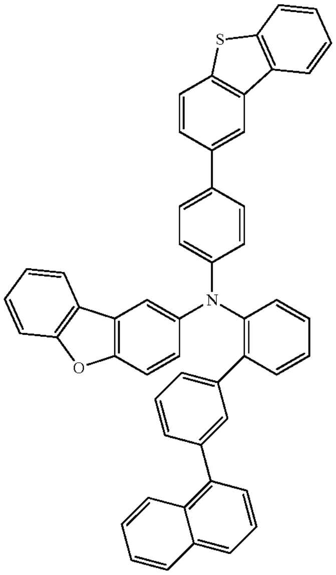
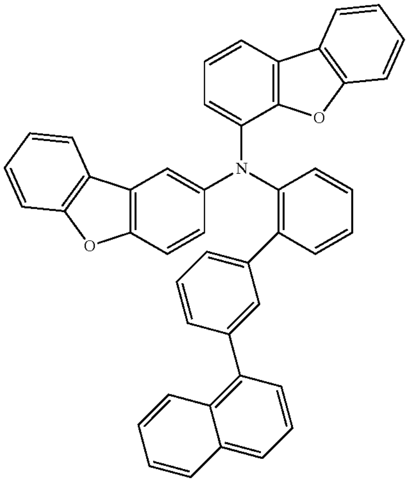
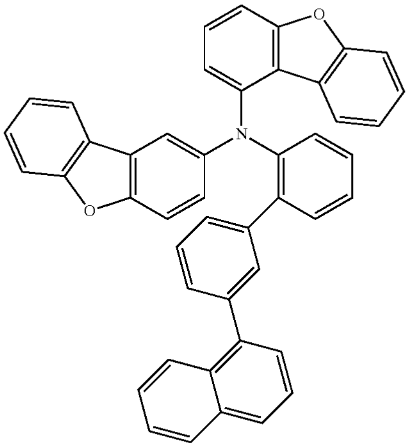

-continued
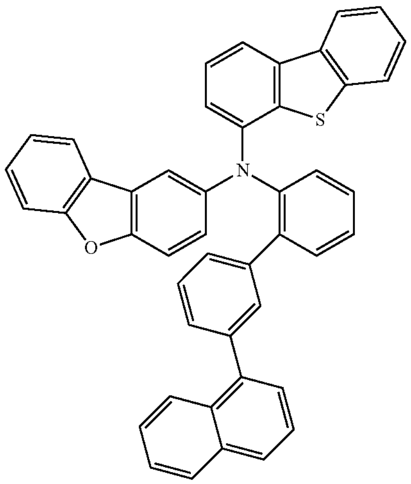
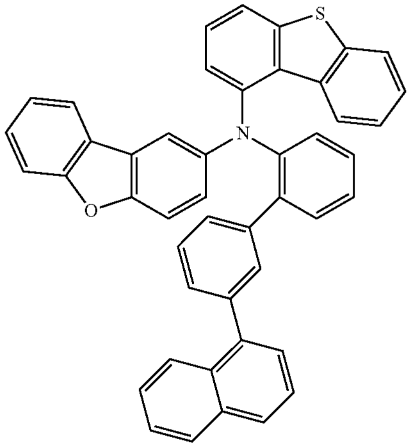
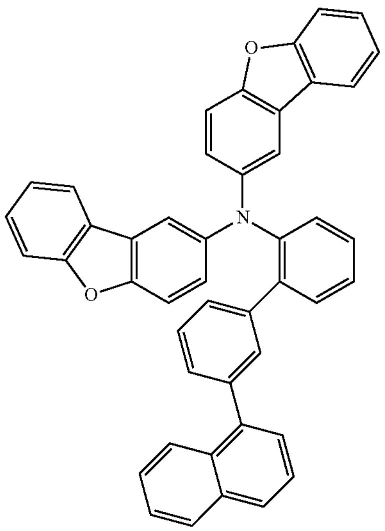
-continued
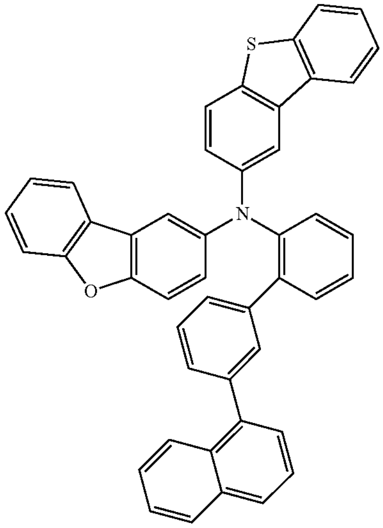
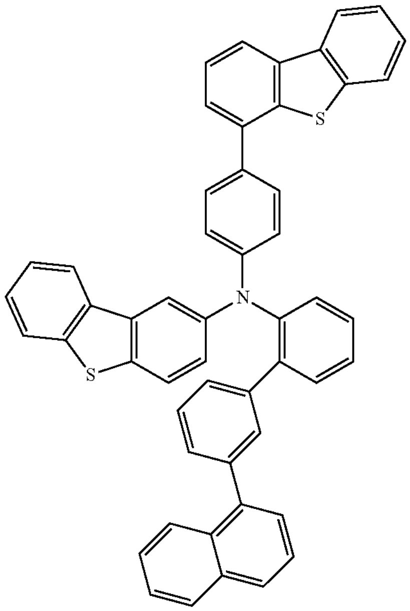

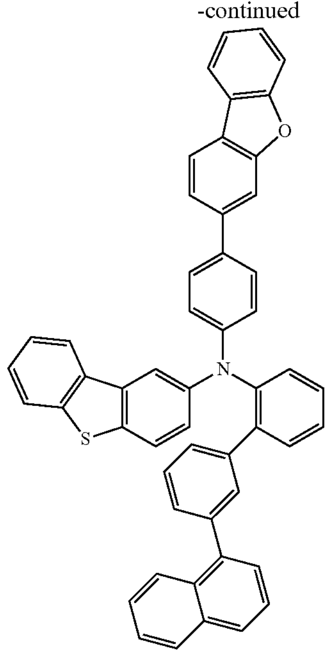
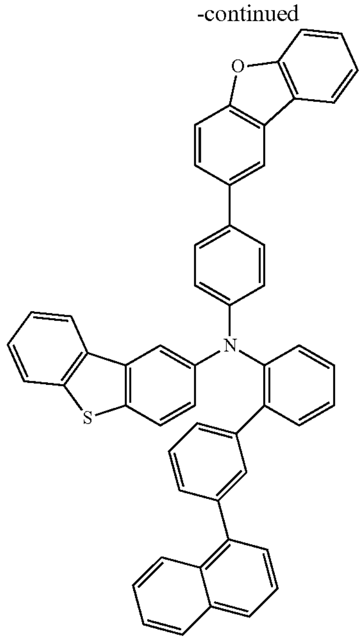
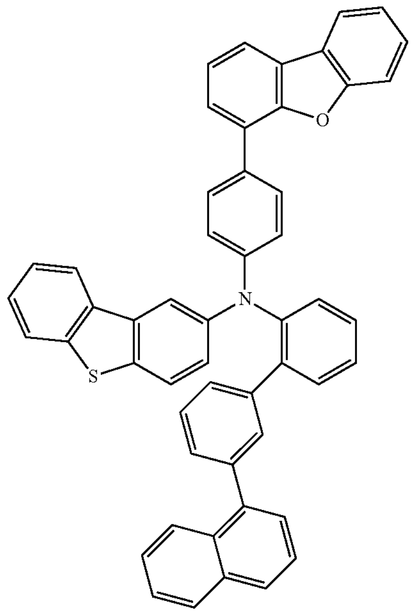
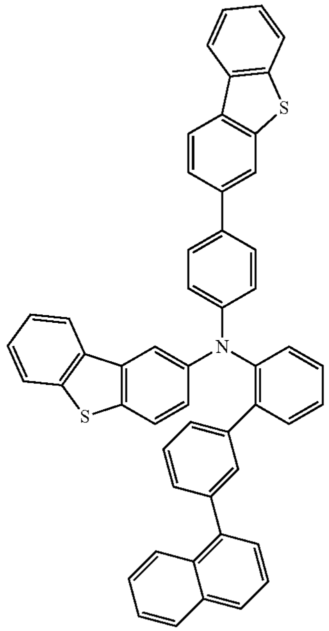

-continued
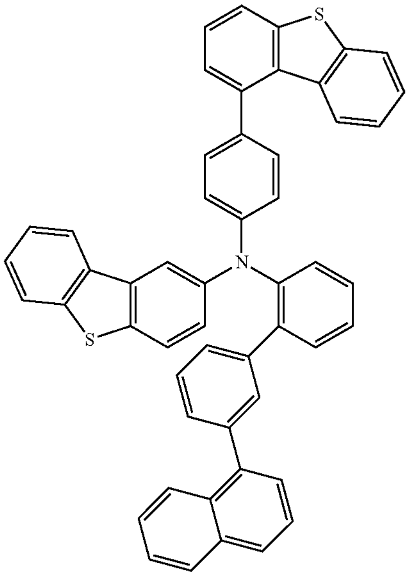
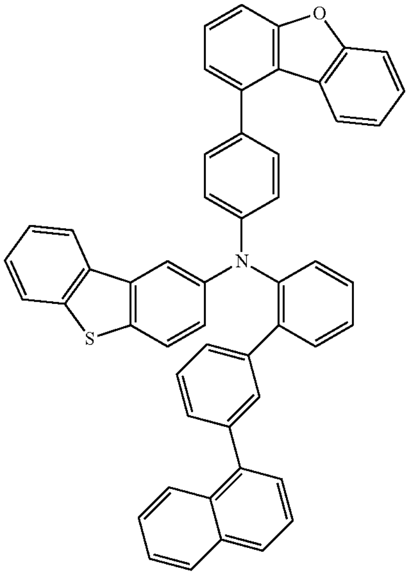
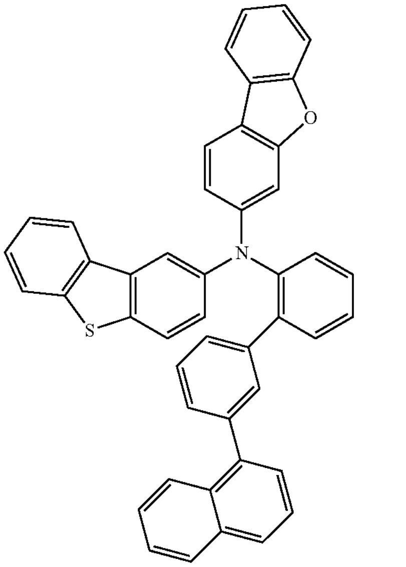
-continued
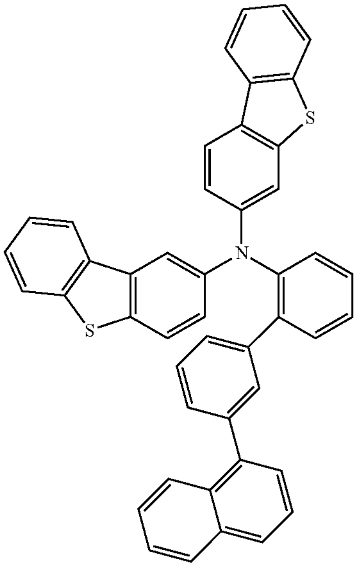
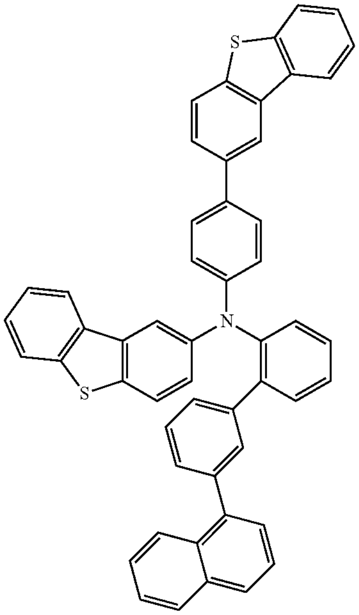
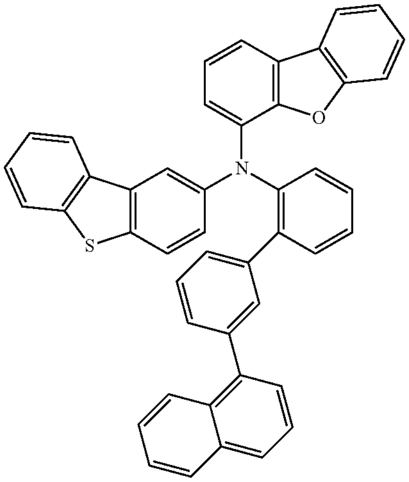

-continued
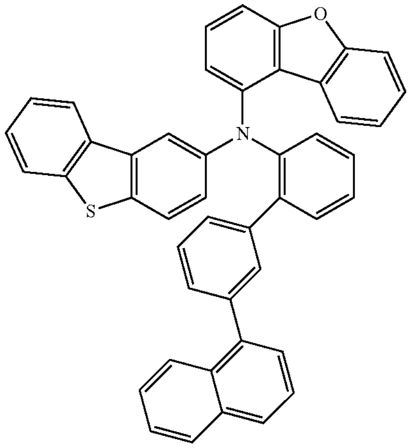
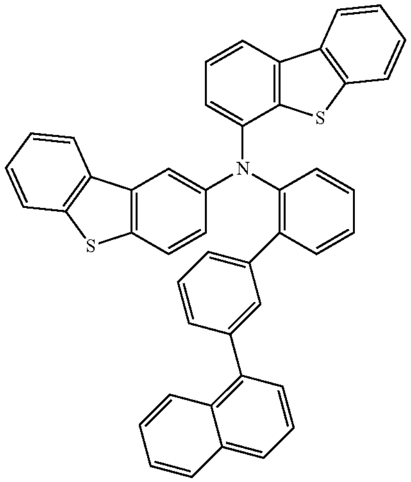
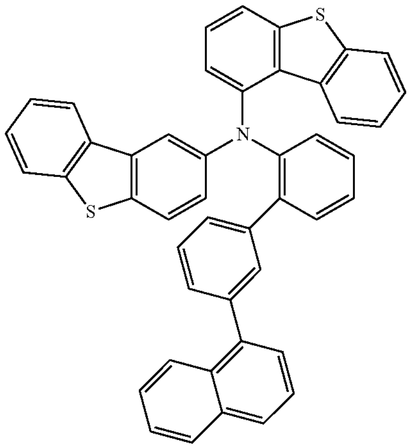
-continued
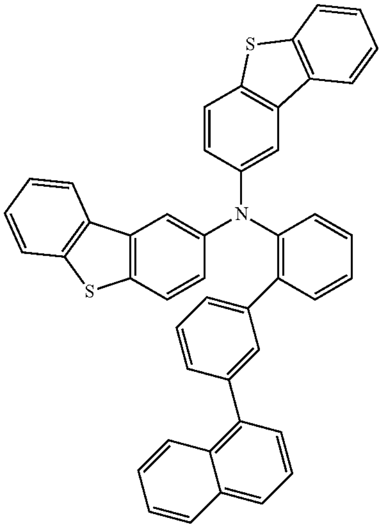
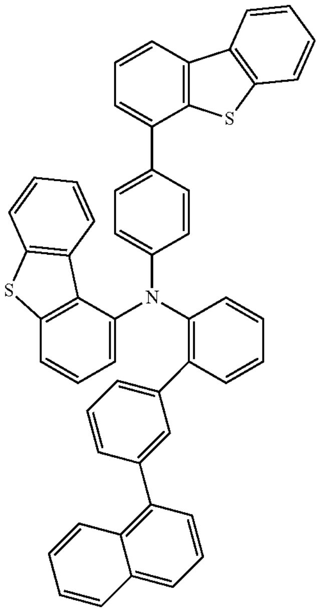

-continued
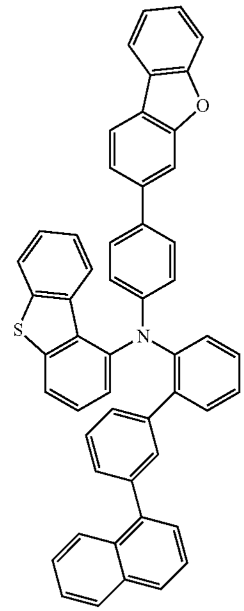
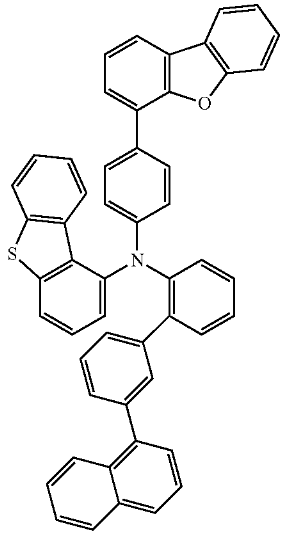
-continued
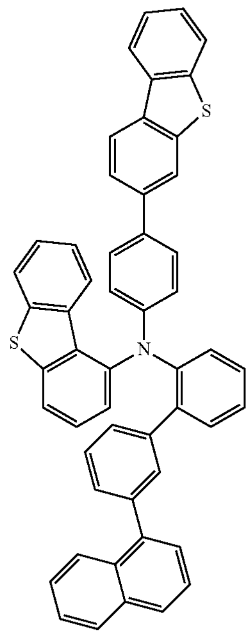
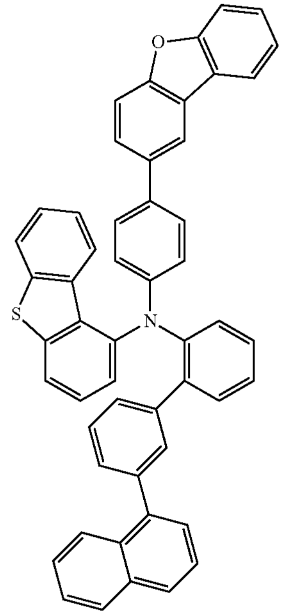
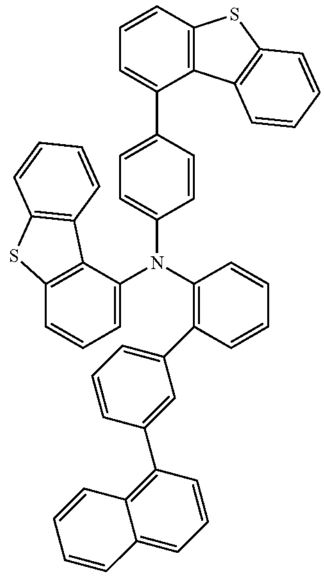

-continued
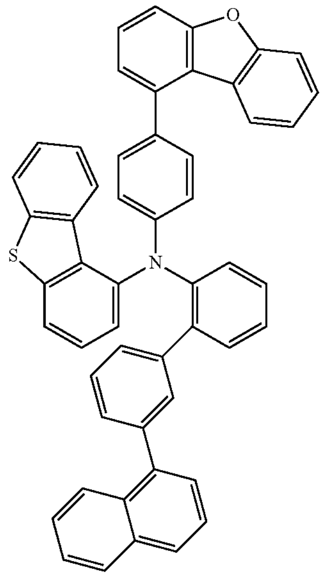
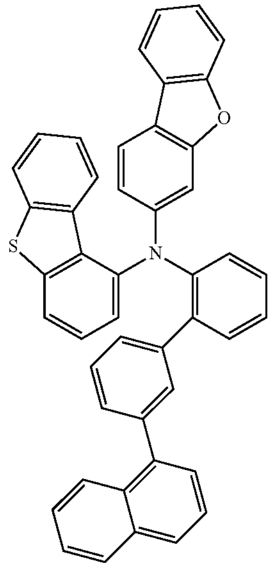
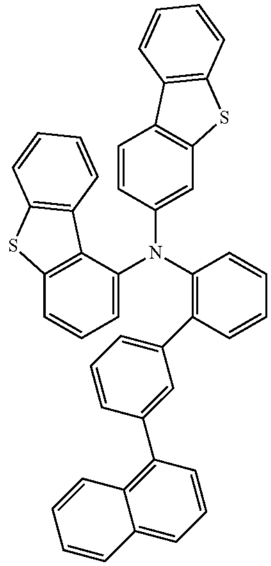
-continued
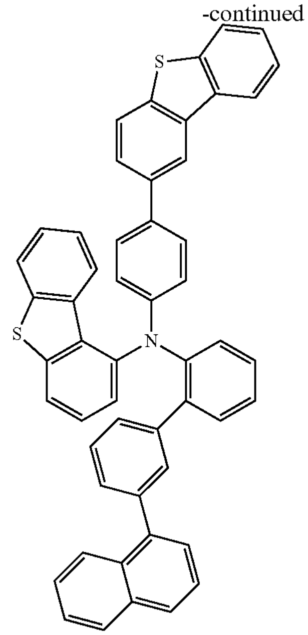
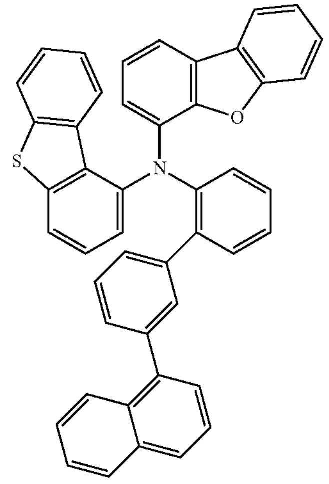
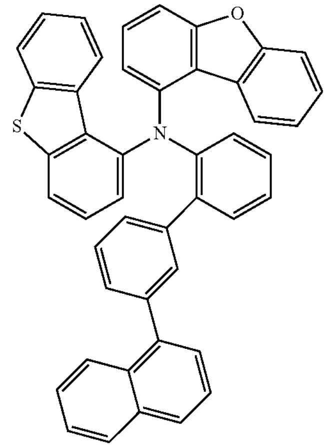

-continued
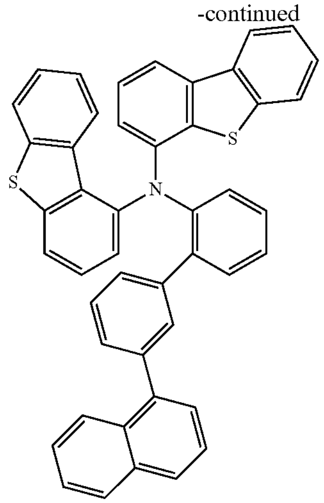
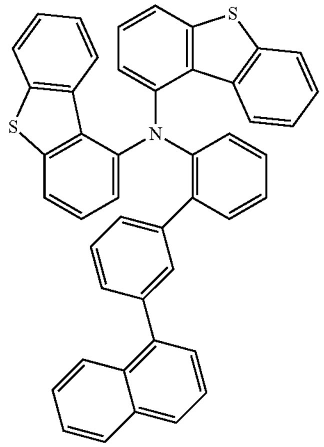
-continued
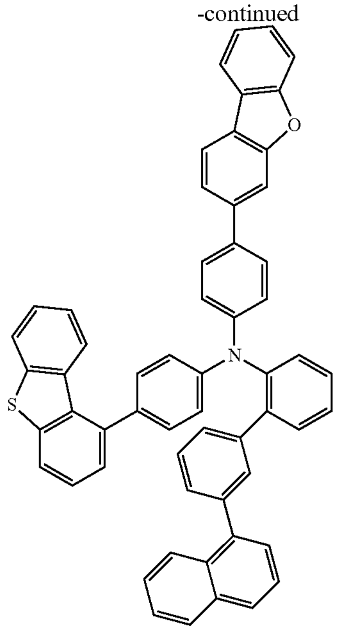
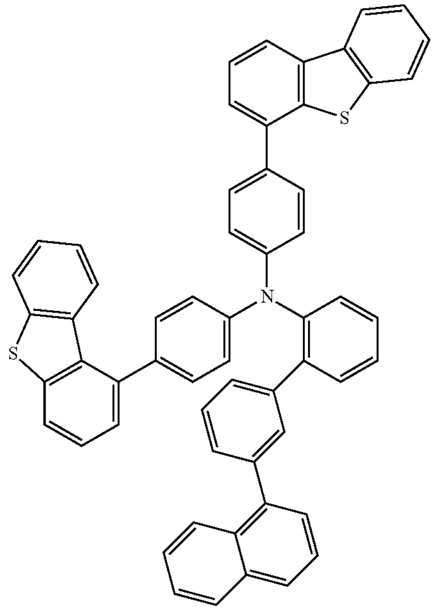
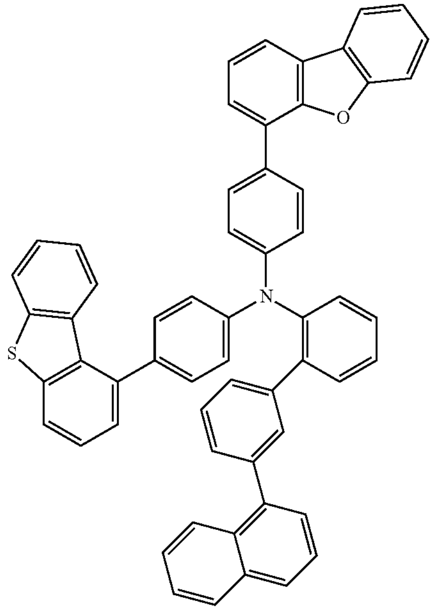

-continued
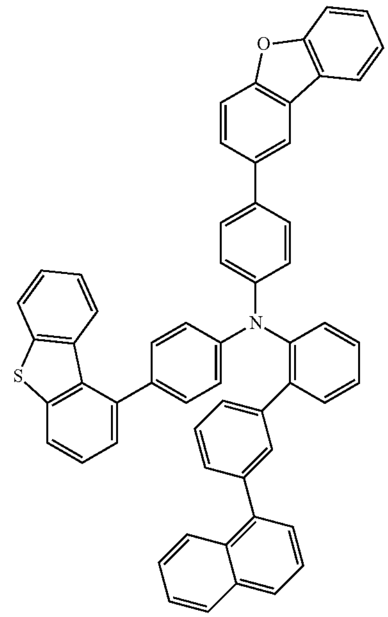
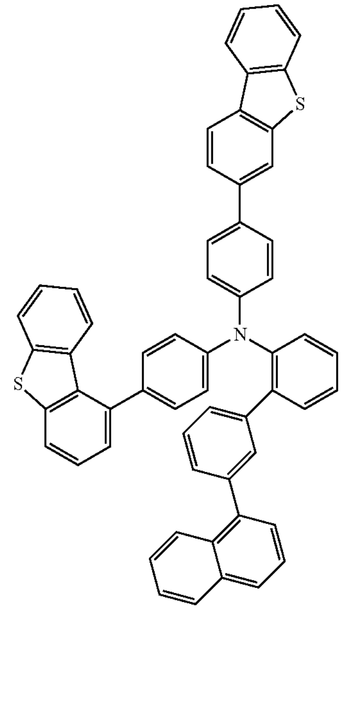
-continued
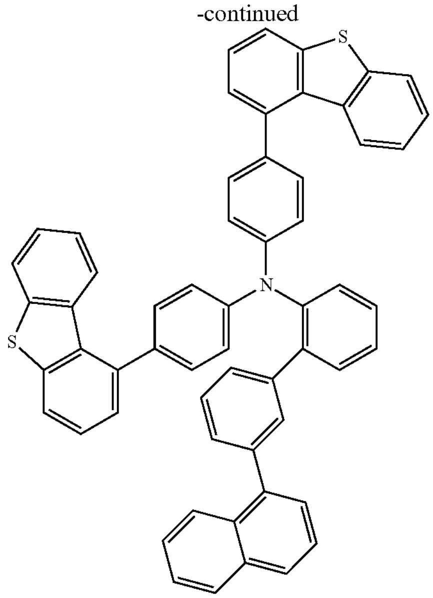
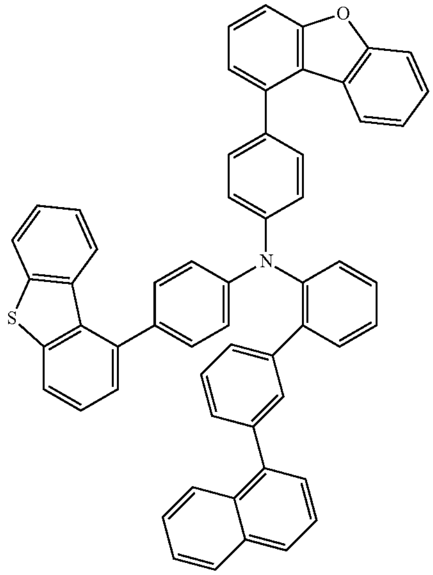
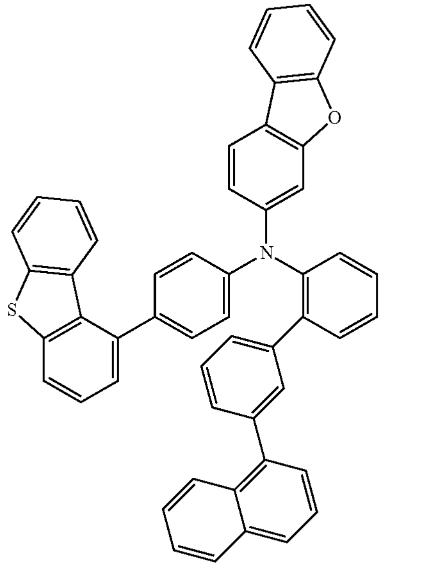

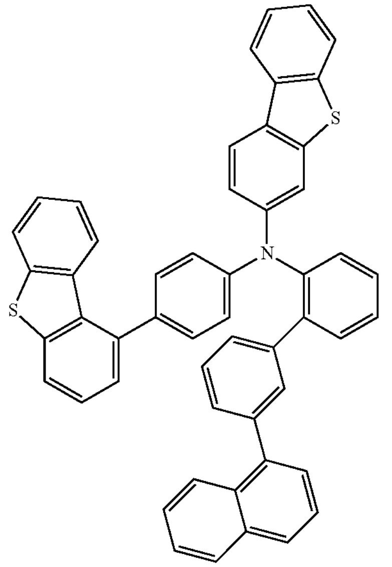
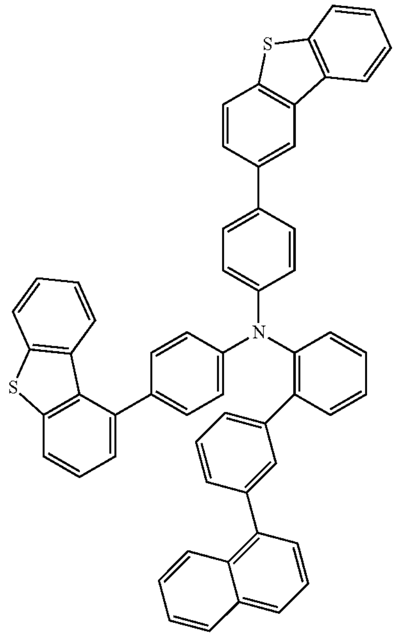
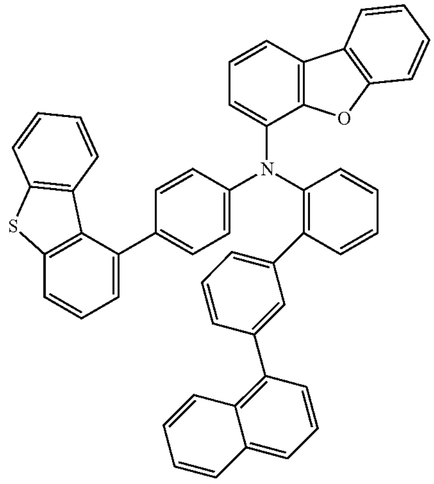
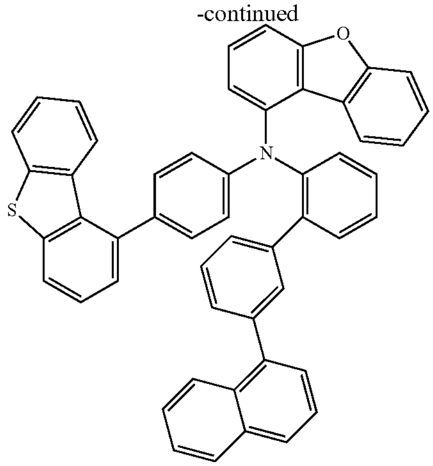
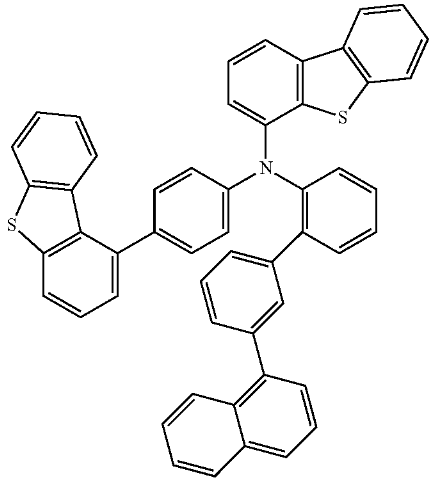
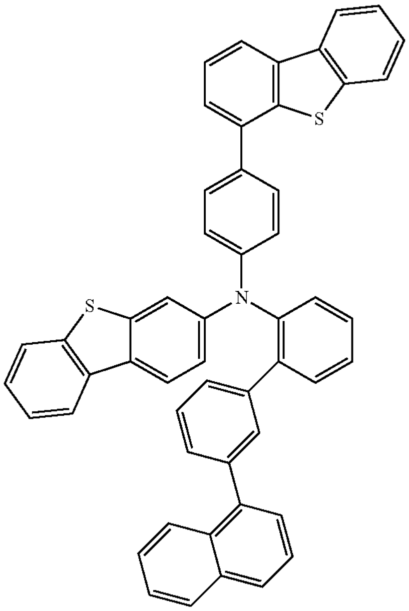

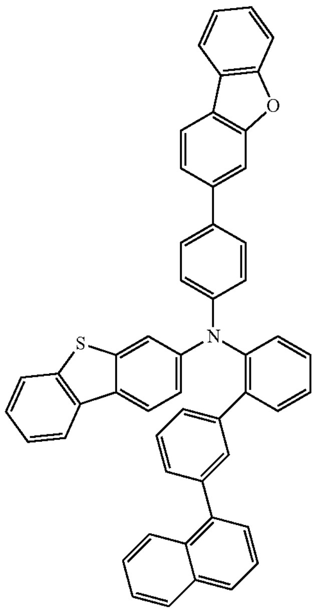
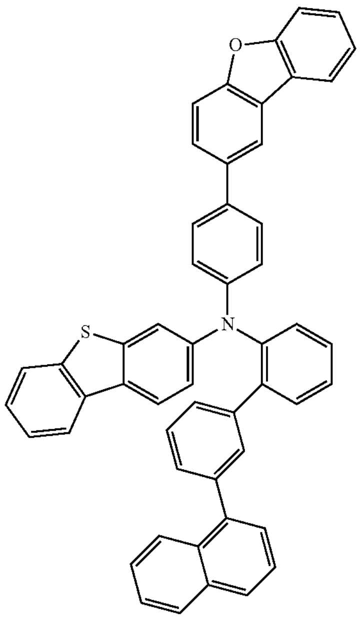
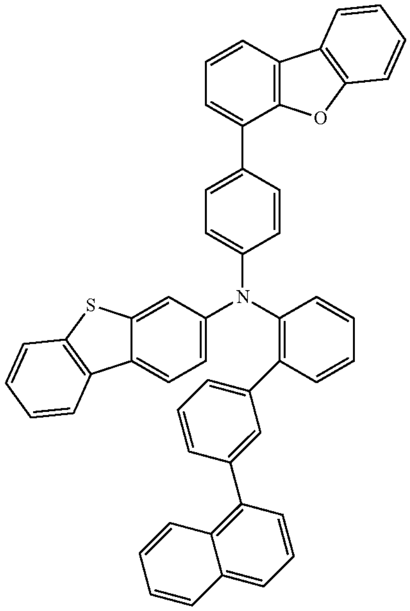
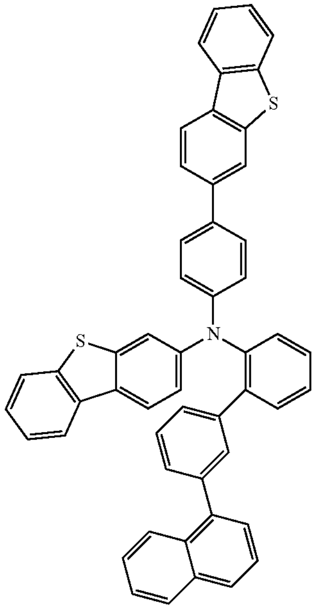

-continued
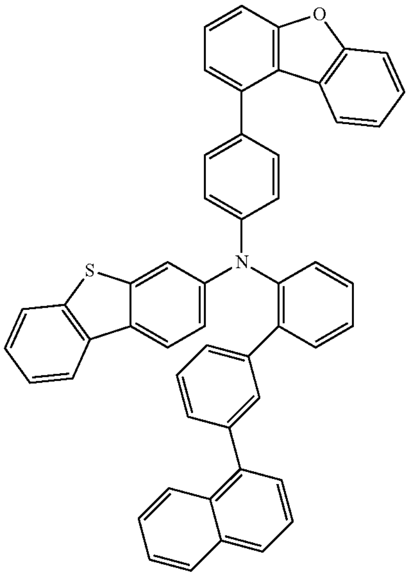
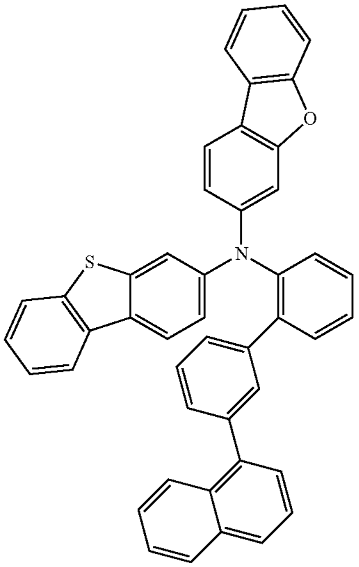
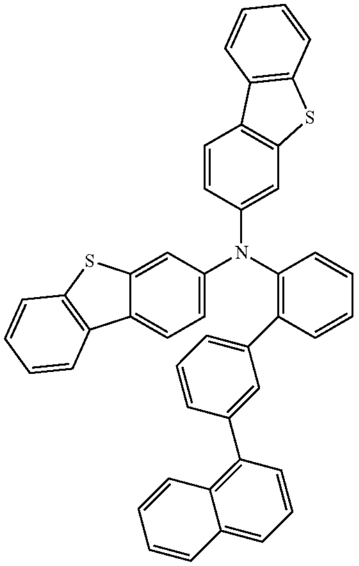
-continued
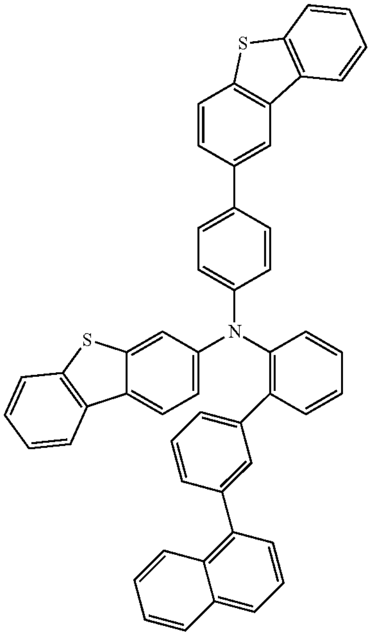
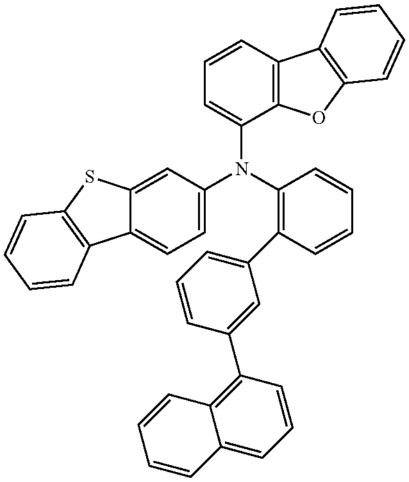
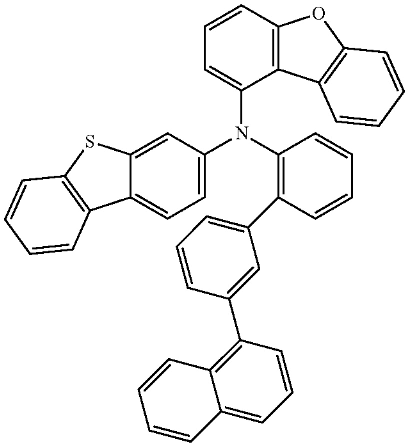

-continued
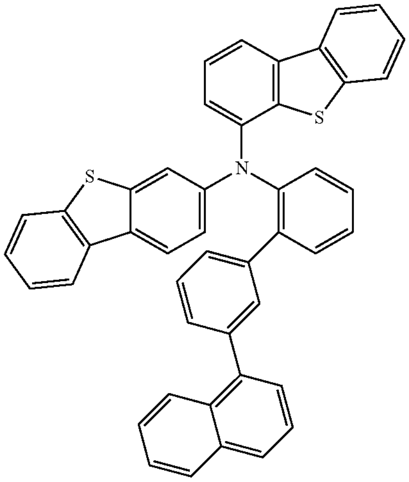
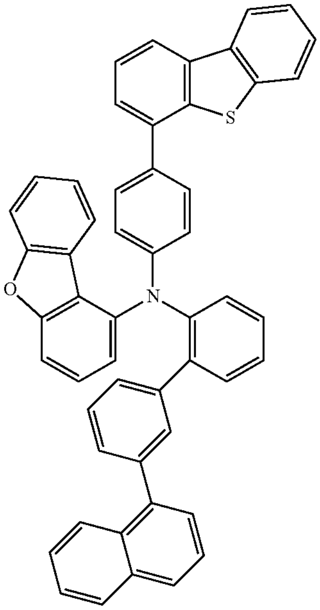
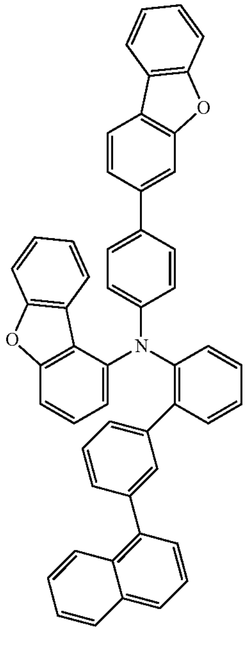
-continued
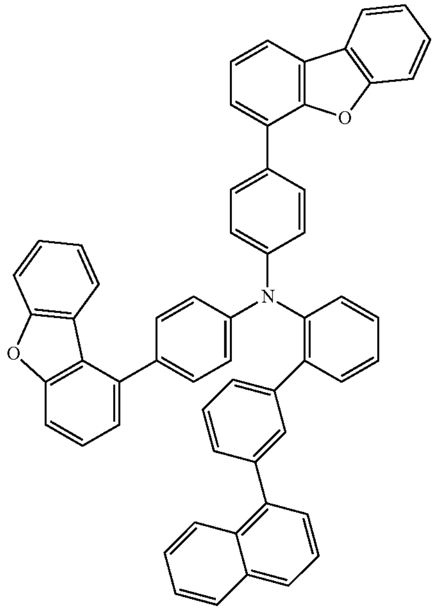
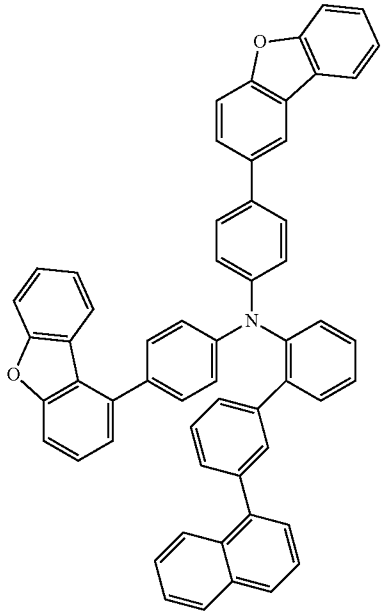

-continued
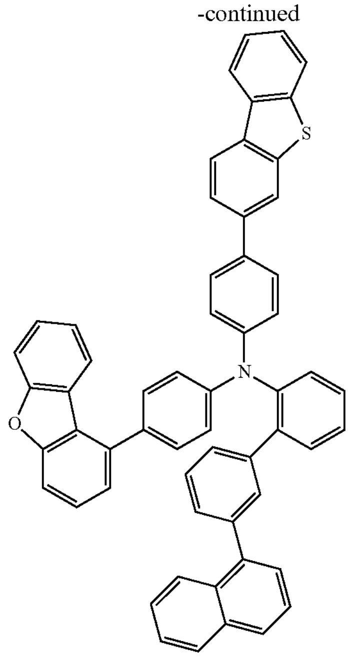
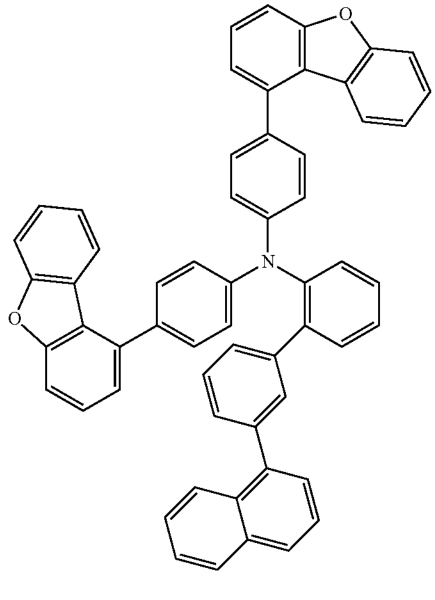
-continued
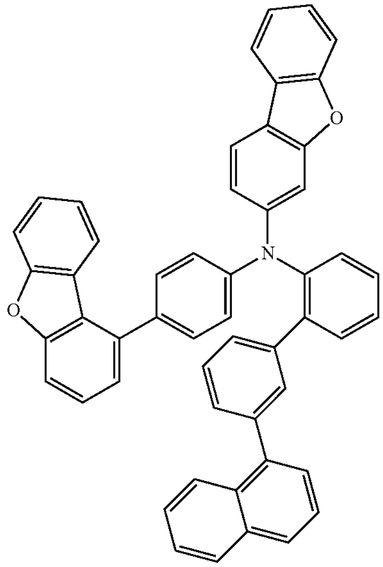
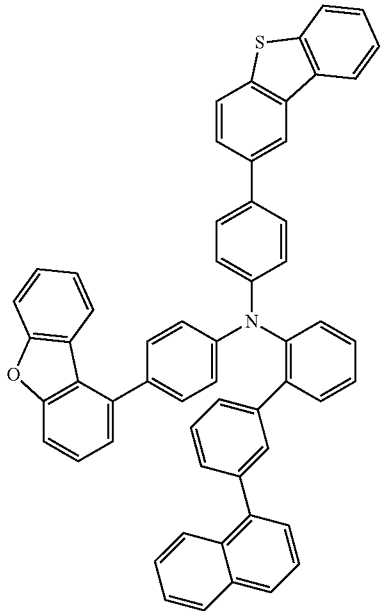
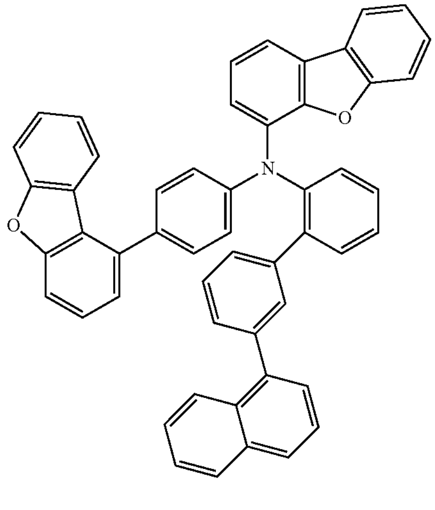

-continued
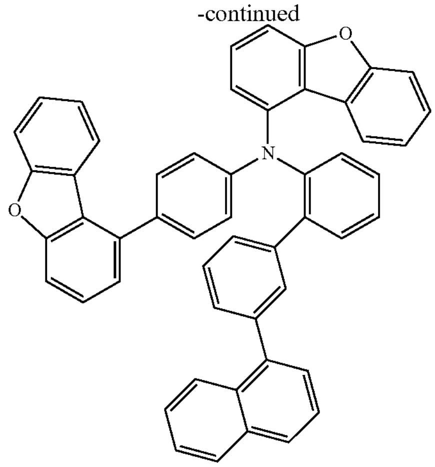
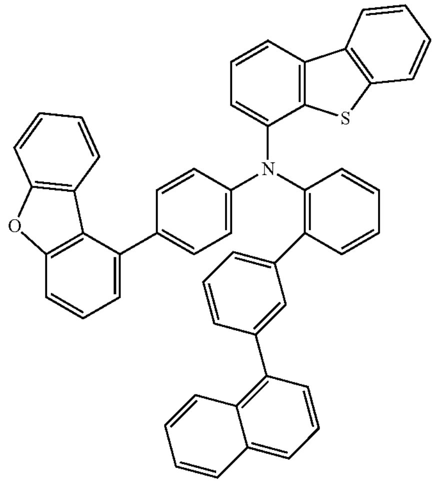
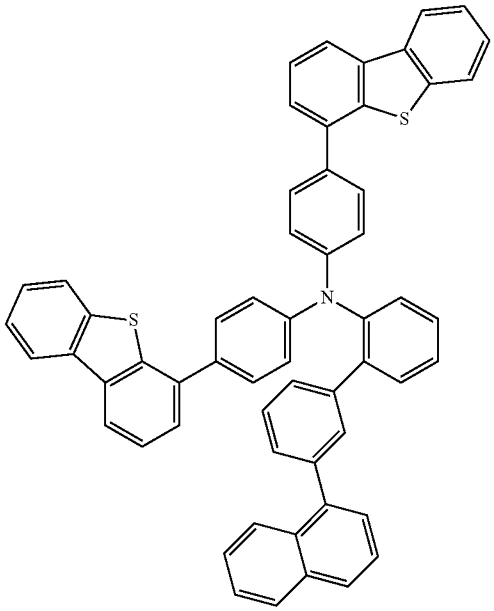
-continued
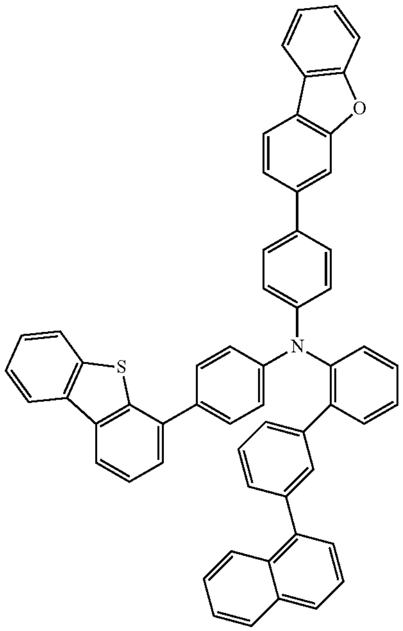
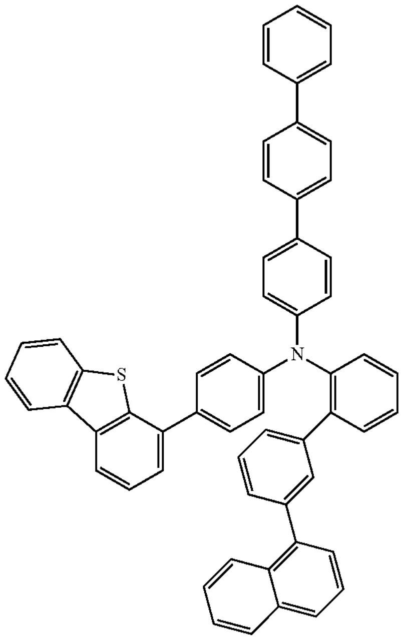

-continued
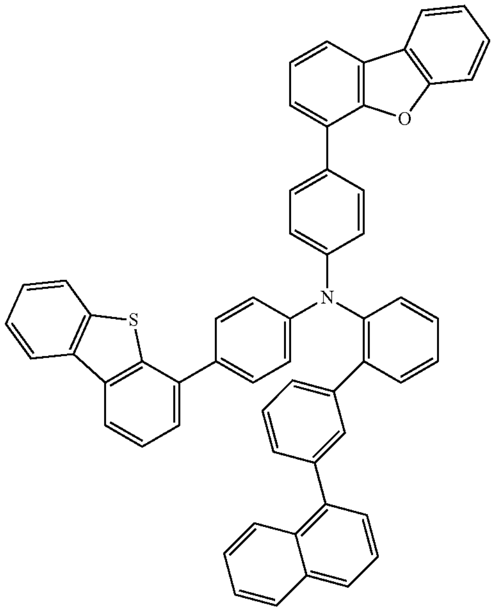
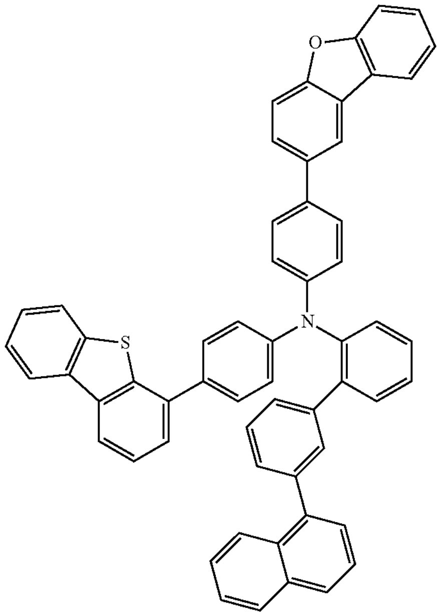
-continued
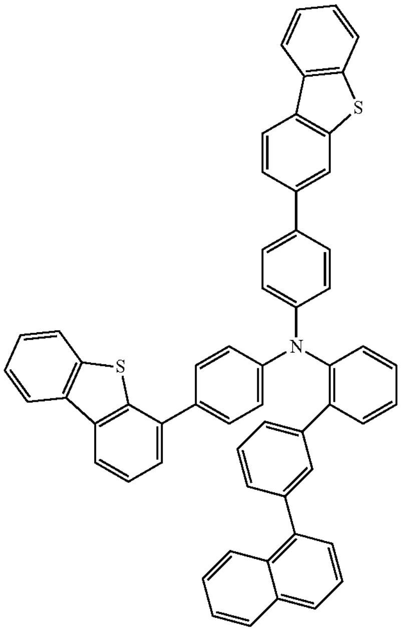
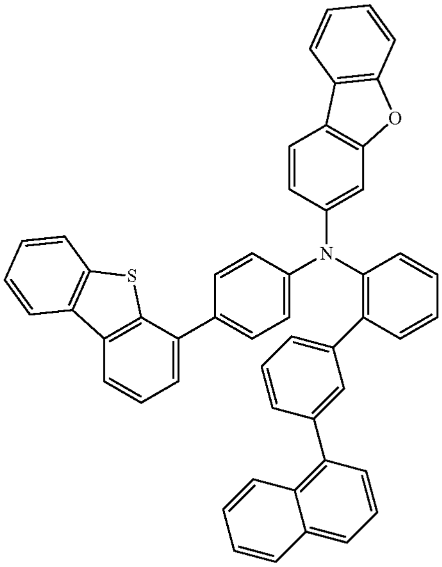

-continued
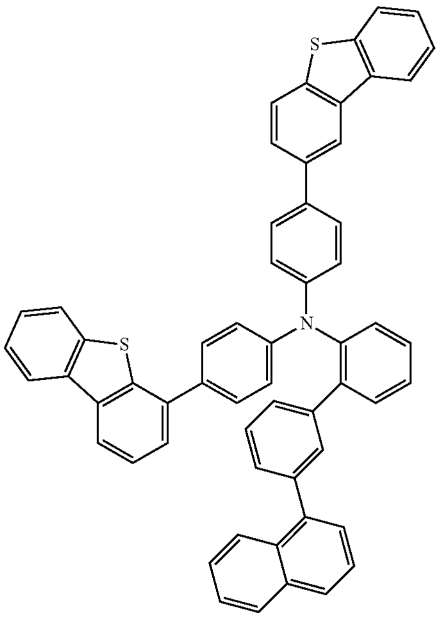
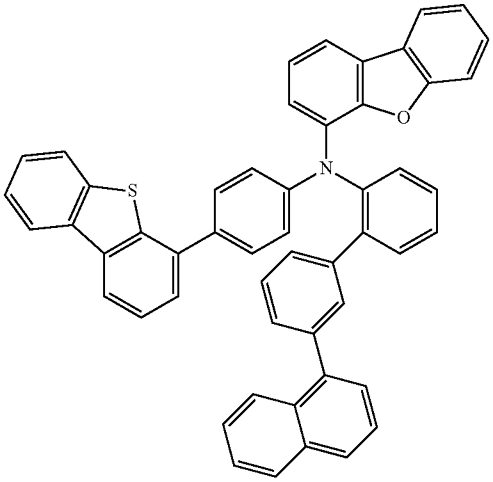
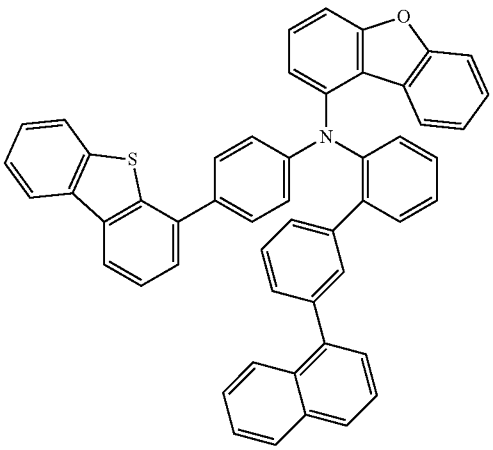
-continued
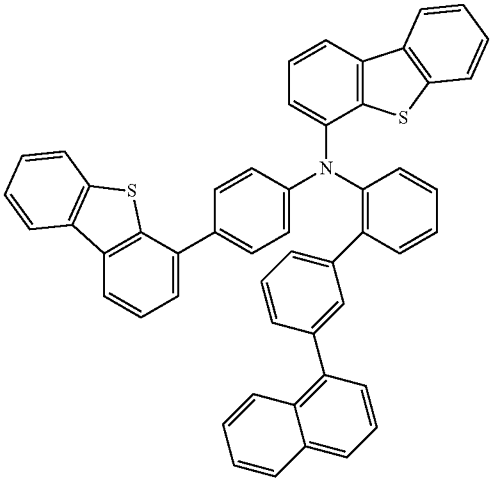
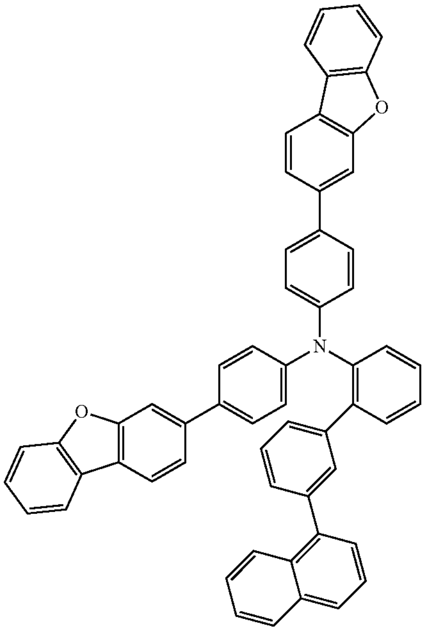
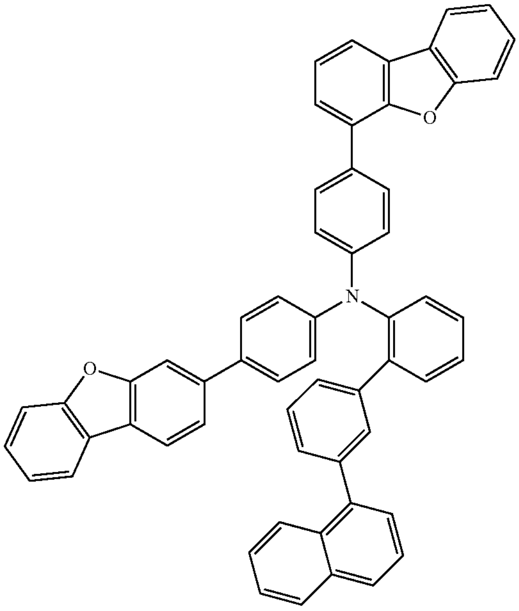

-continued
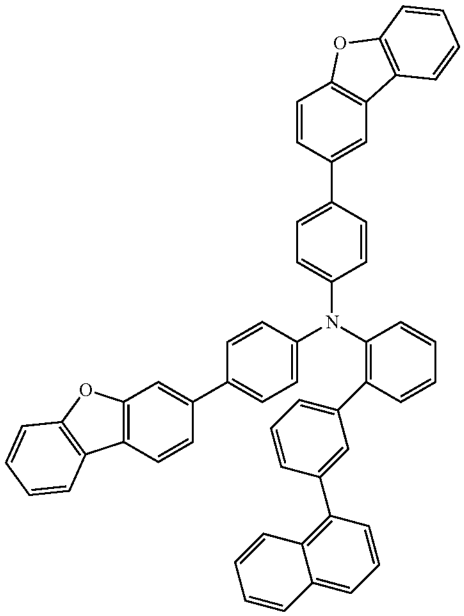
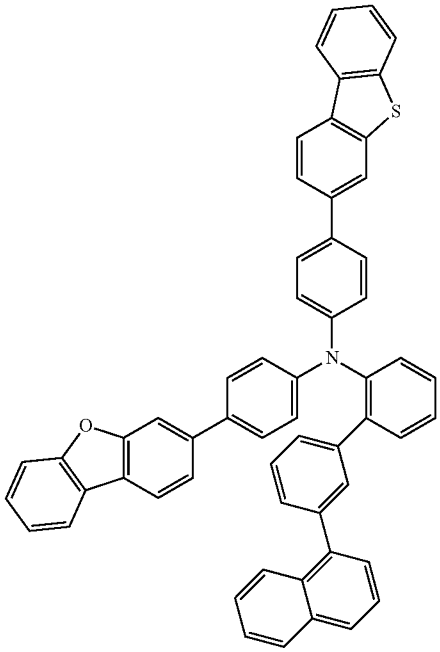
-continued
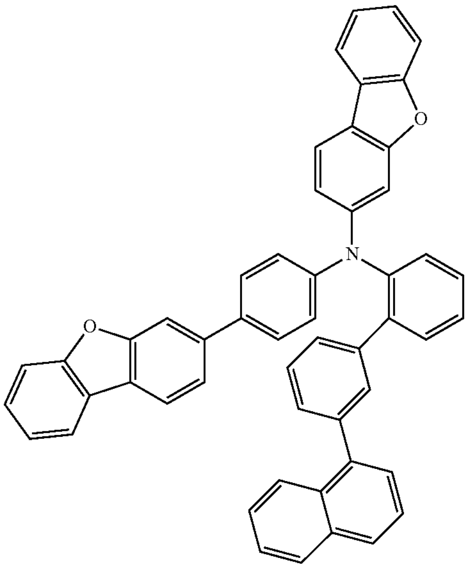
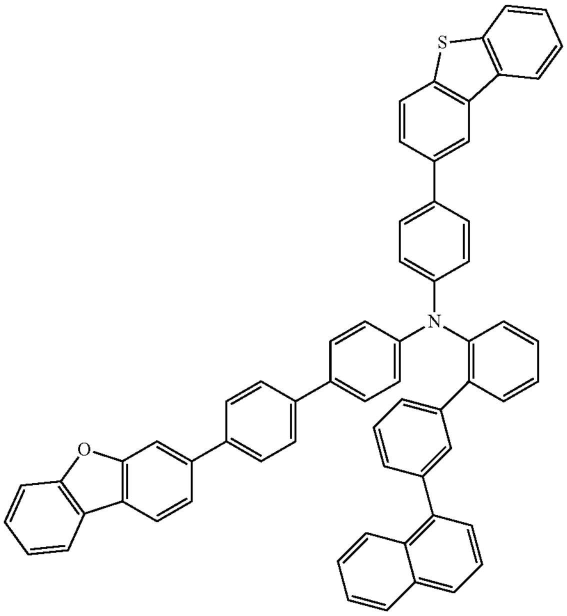
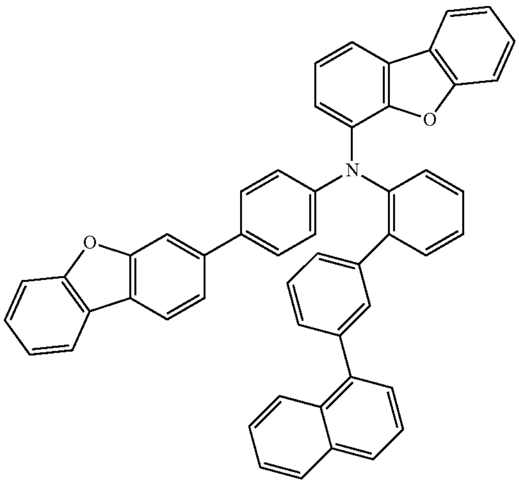

-continued
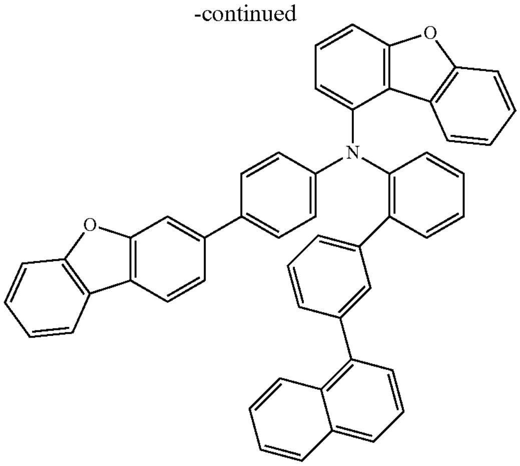
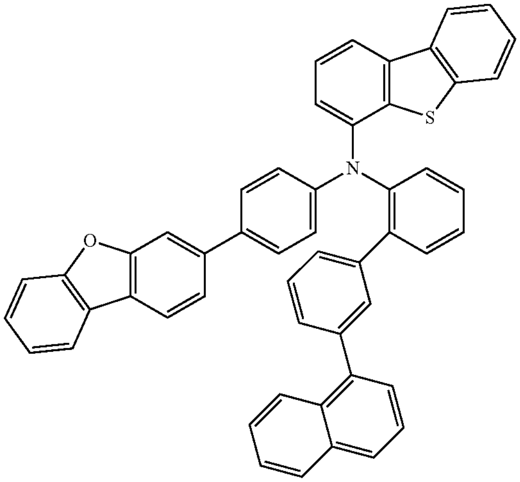
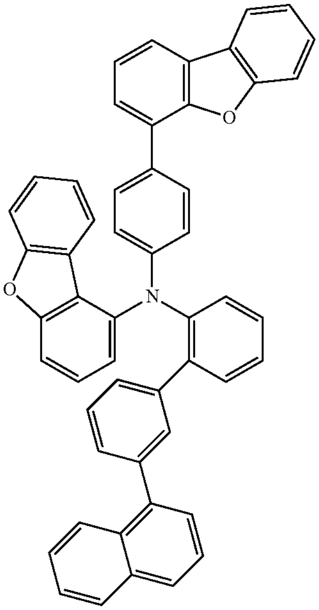
-continued
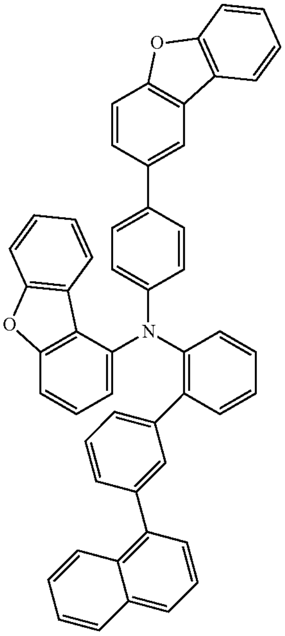
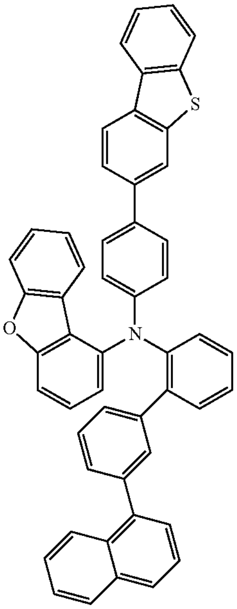
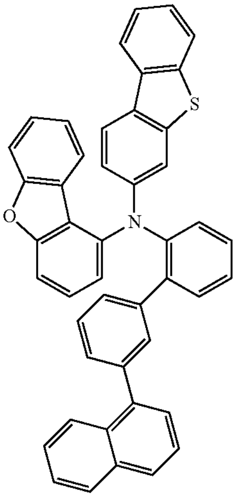

-continued
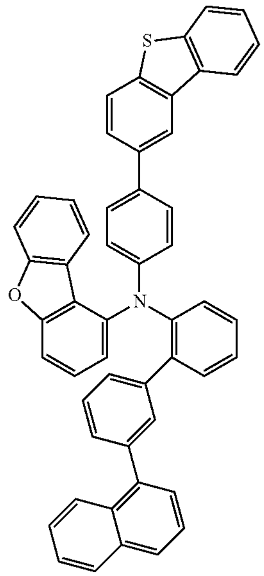
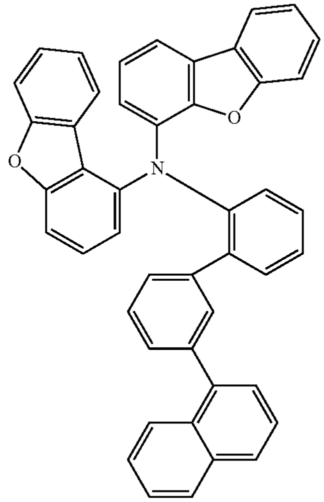
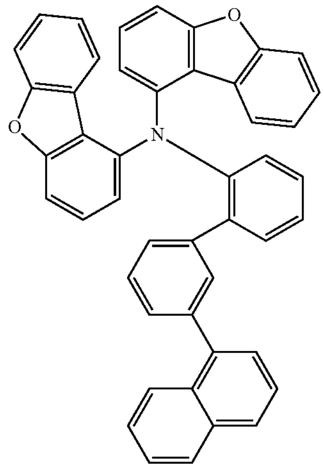
-continued
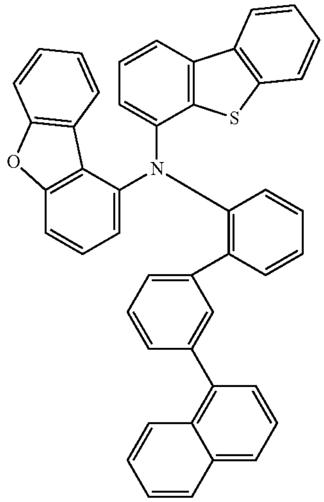
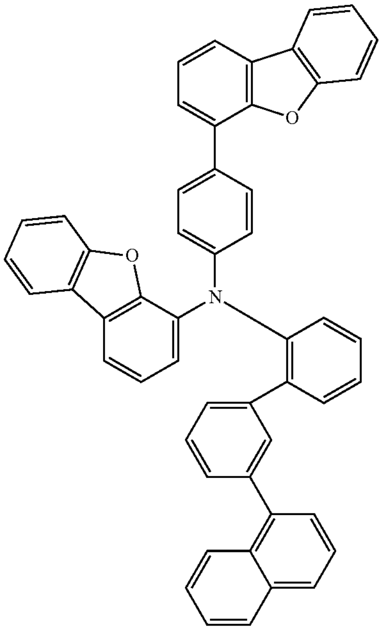

-continued
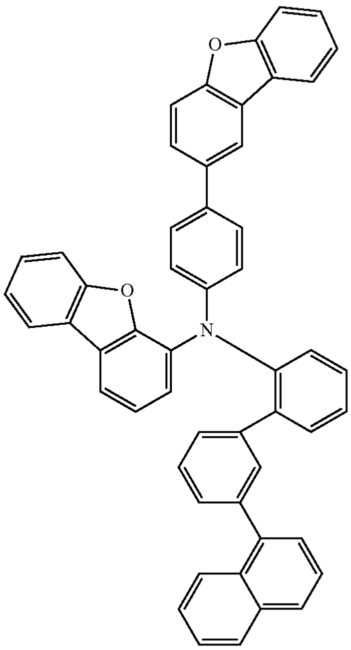
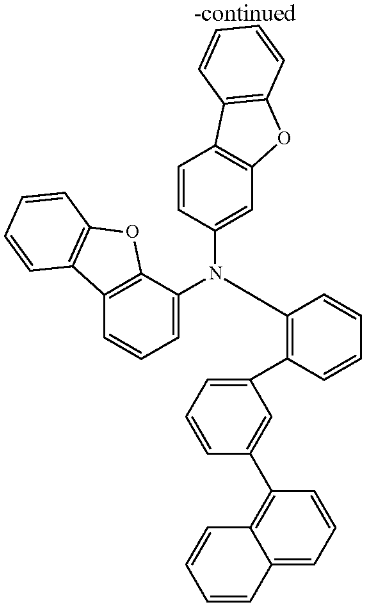
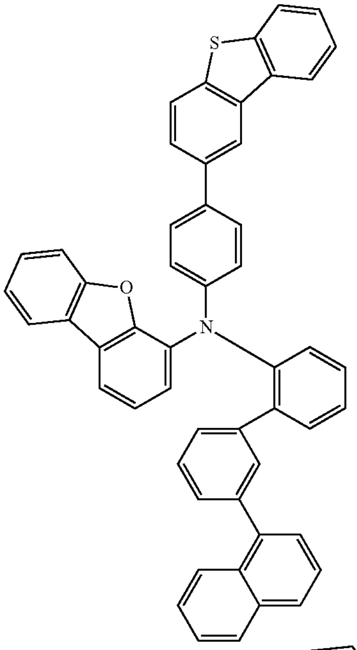
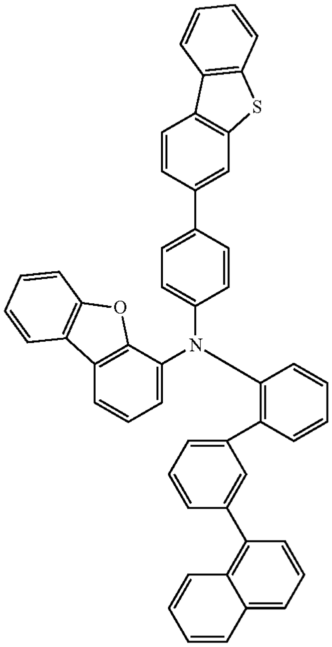
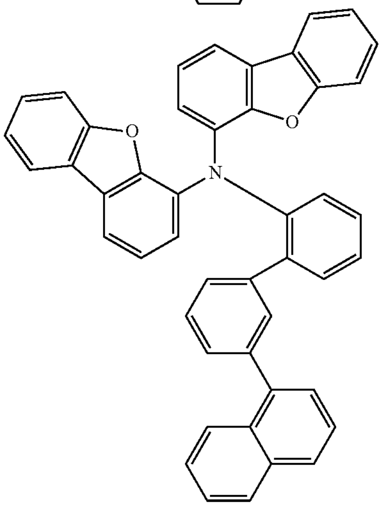

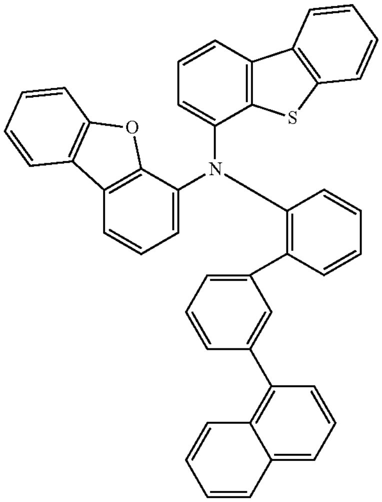
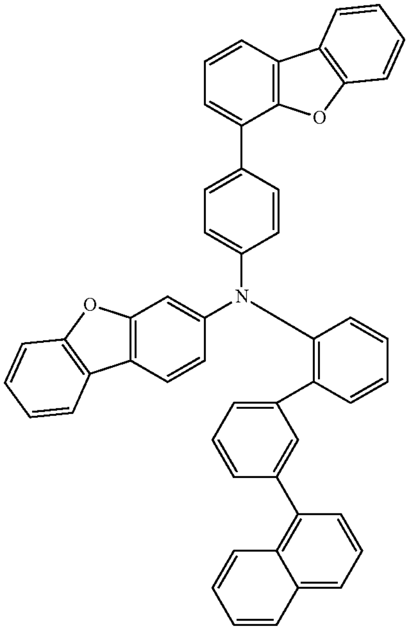
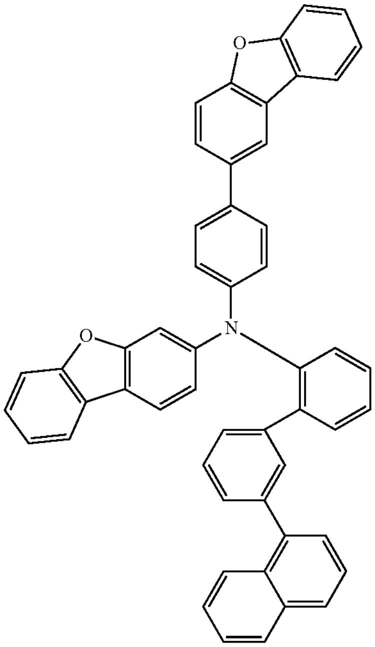
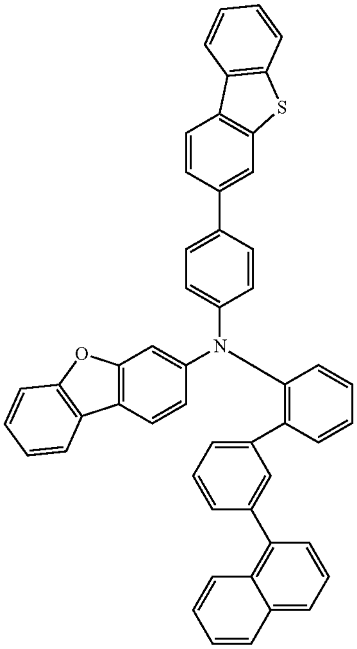

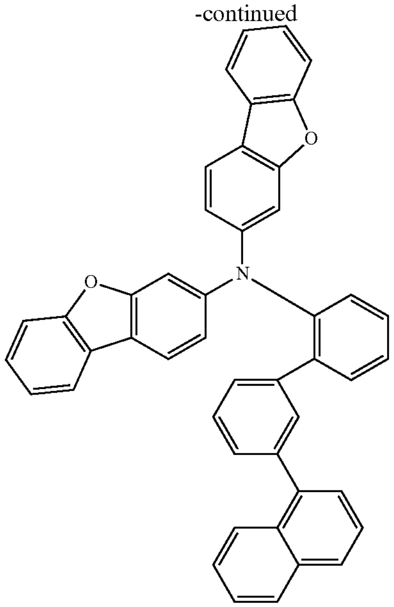
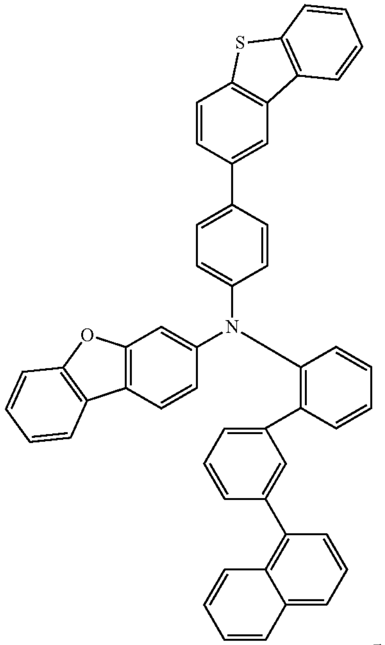
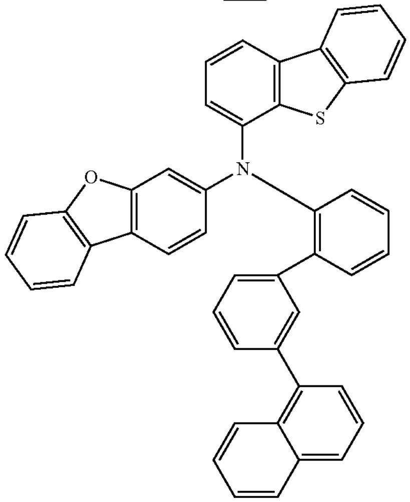
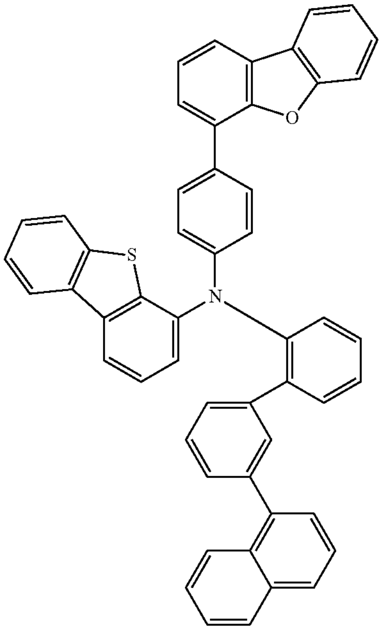
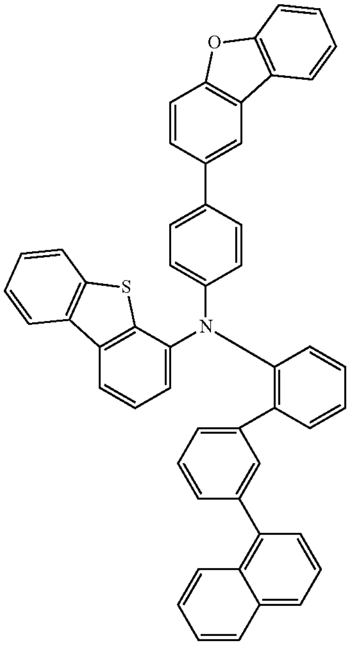

-continued
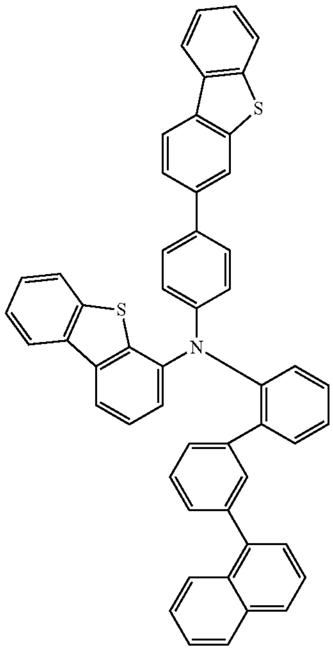 [SMILES: c1cc(-c2ccccc2N(c2ccc(-c3ccc4c(c3)sc3ccccc34)cc2)c2cccc3c2sc2ccccc23)cc(-c2cccc3ccccc23)c1]
-continued
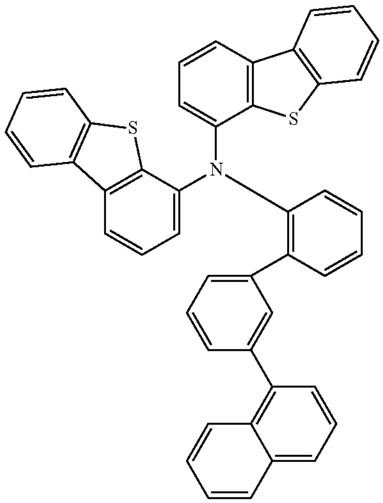
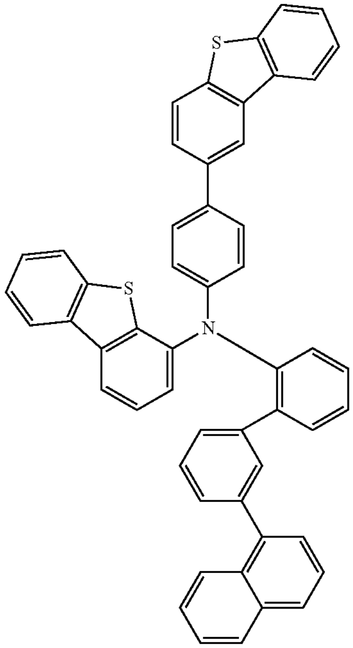
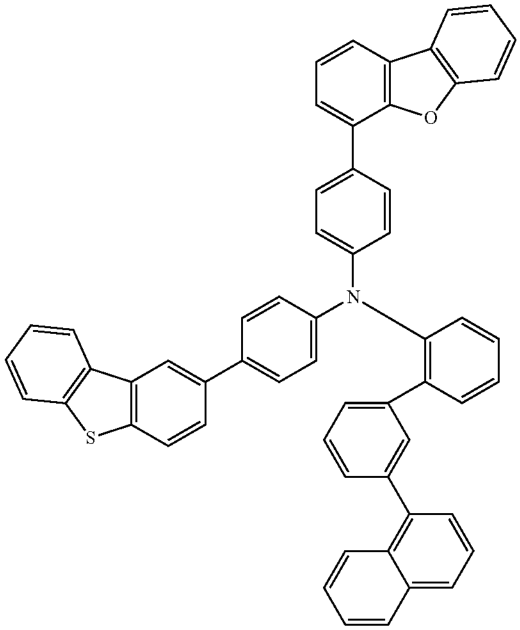

-continued
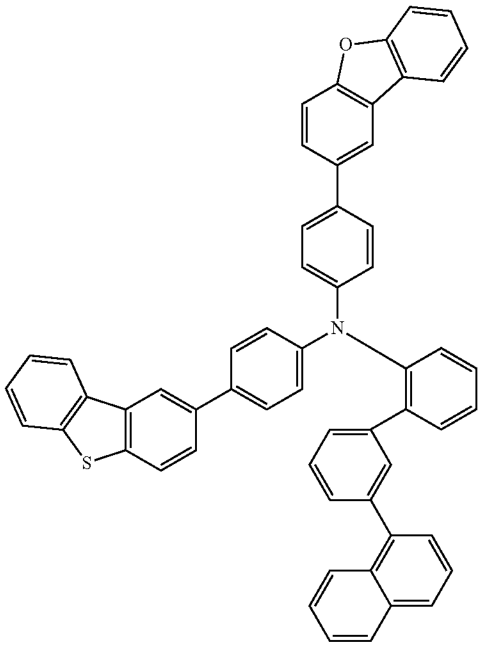
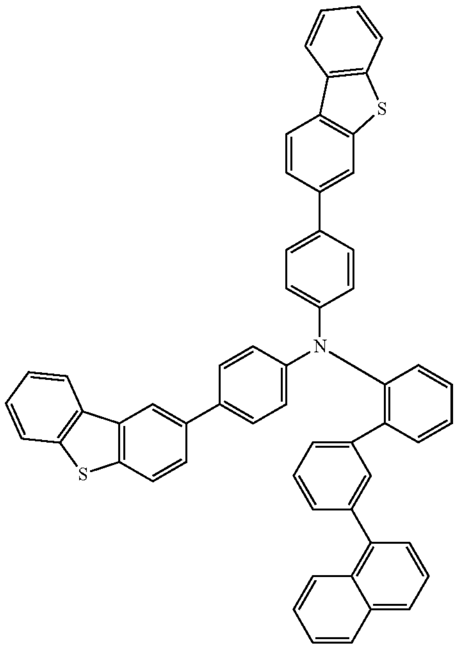
-continued
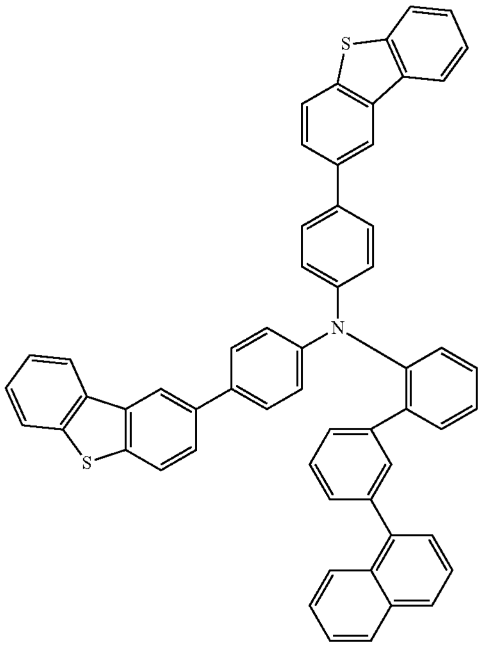
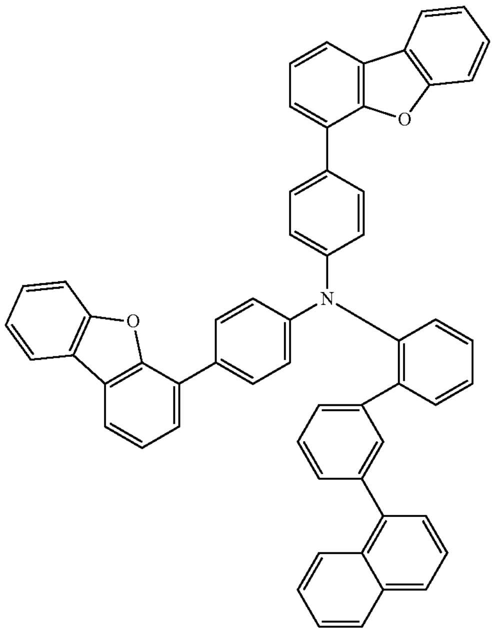

-continued
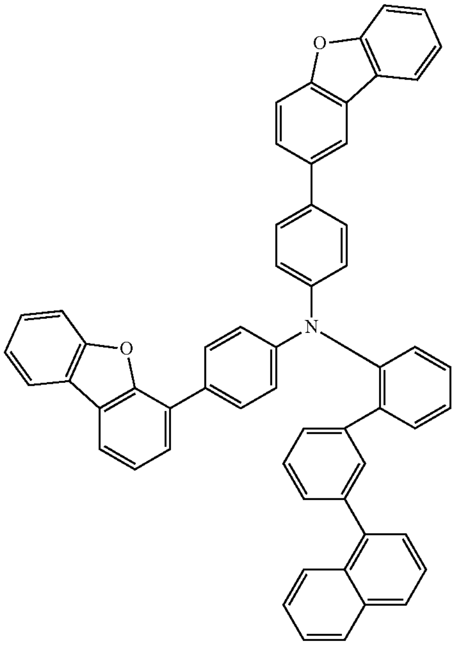
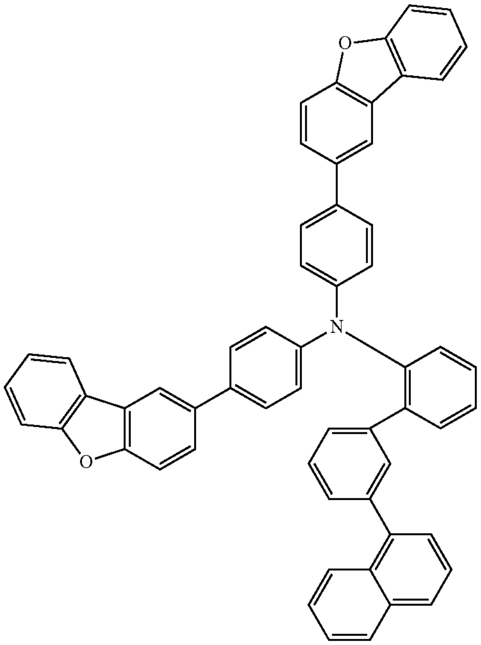
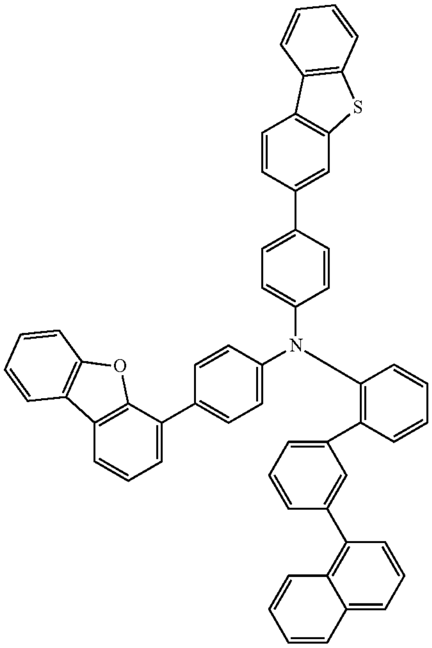
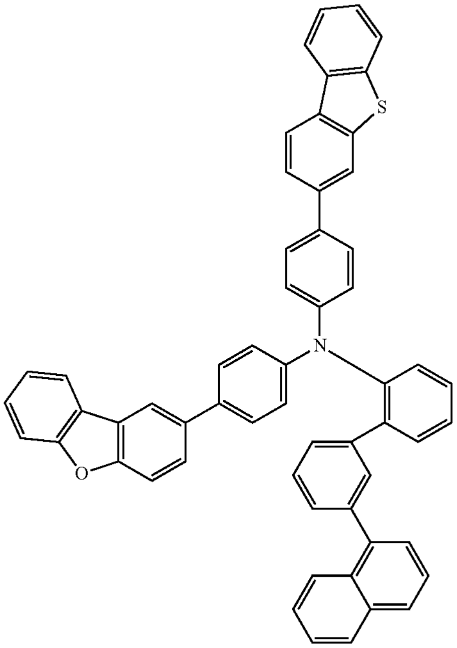
-continued

-continued
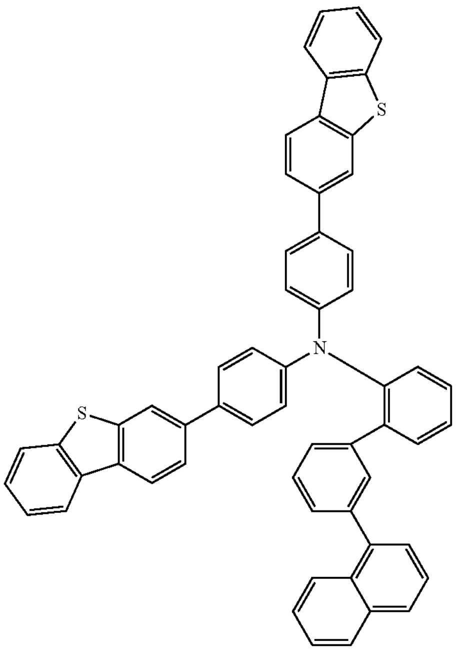 [SMILES: c1cc(-c2ccccc2N(c2ccc(-c3ccc4c(c3)sc3ccccc34)cc2)c2ccc(-c3ccc4c(c3)sc3ccccc34)cc2)cc(-c2cccc3ccccc23)c1]
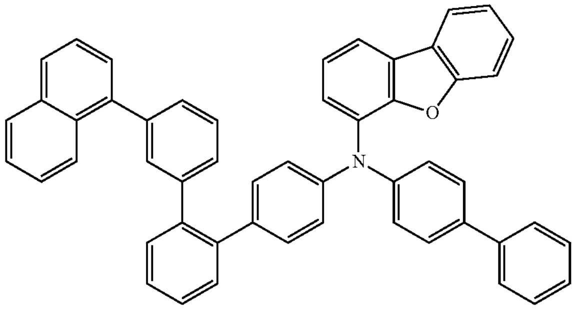
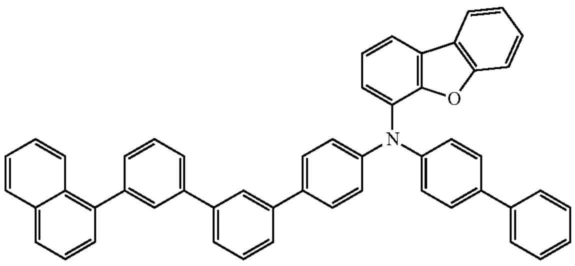
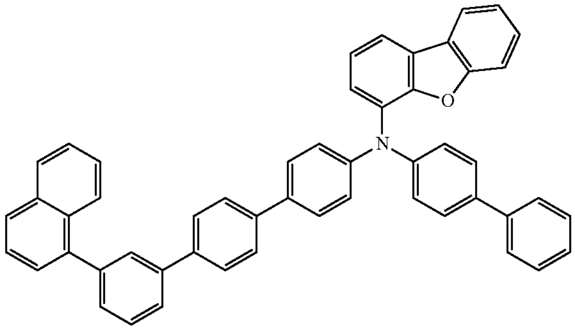
-continued
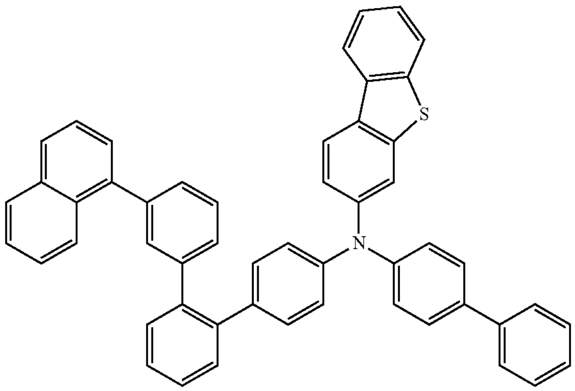
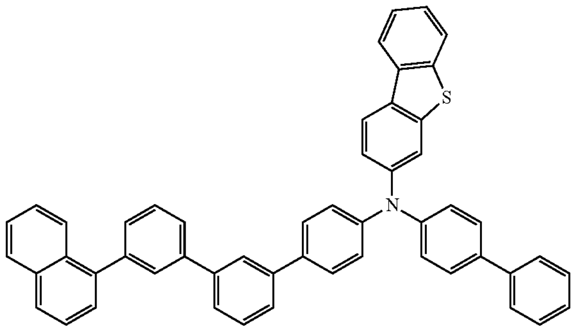
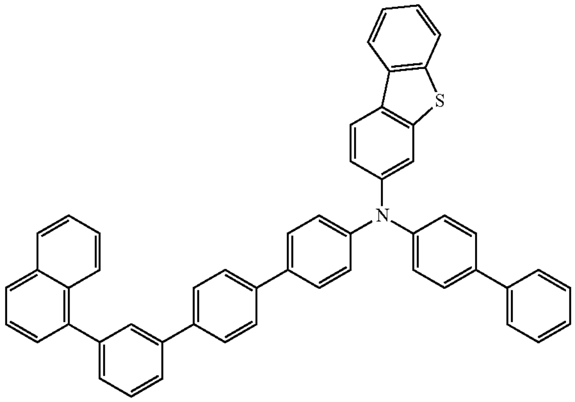
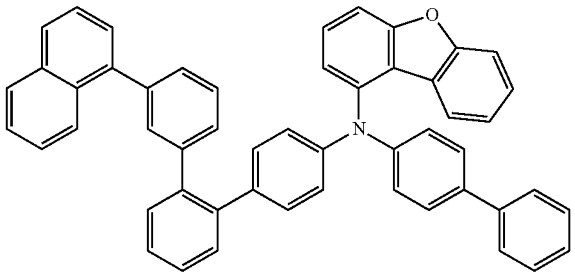
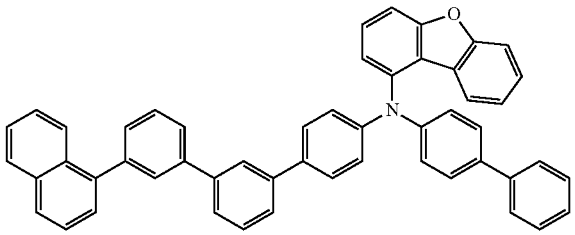

-continued
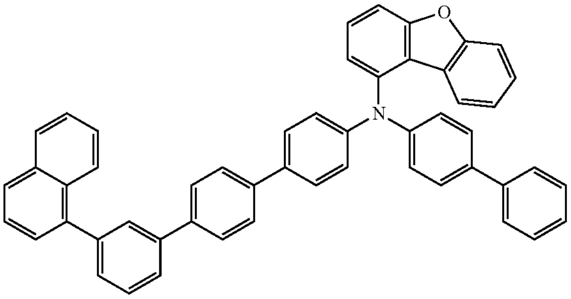
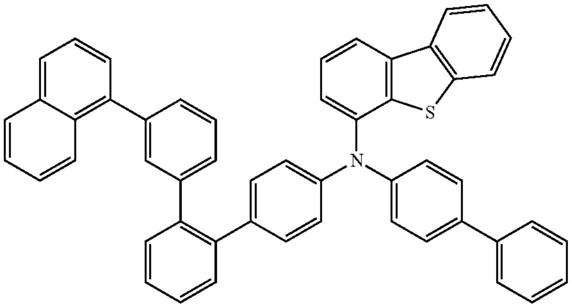
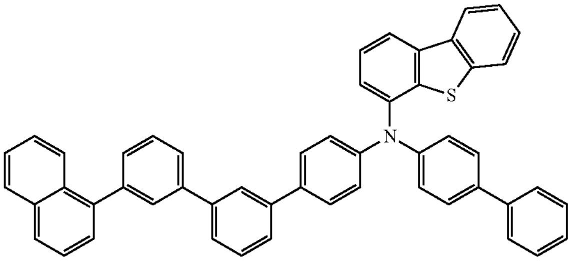
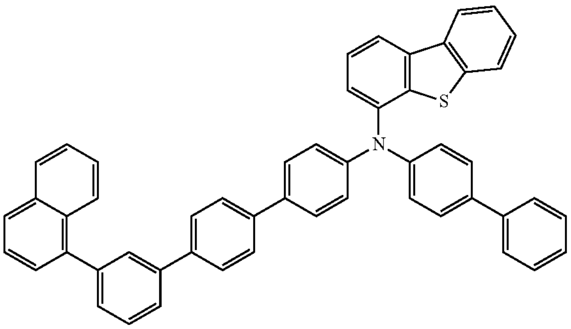
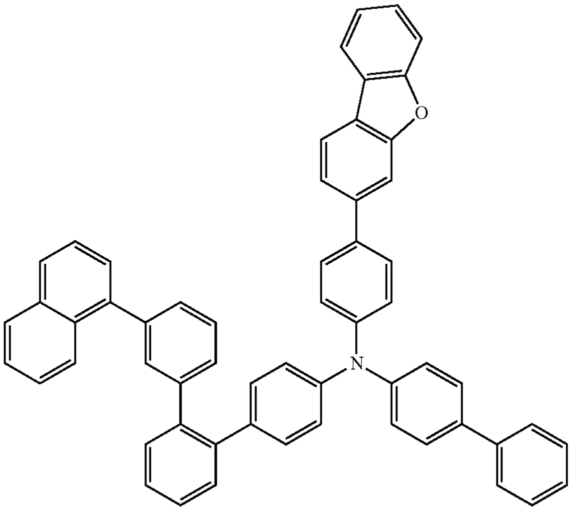
-continued
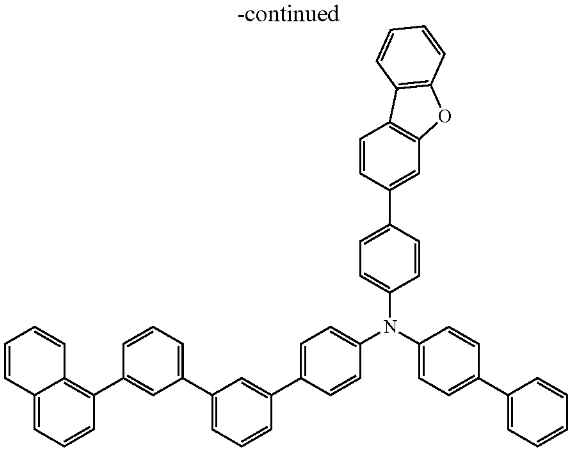
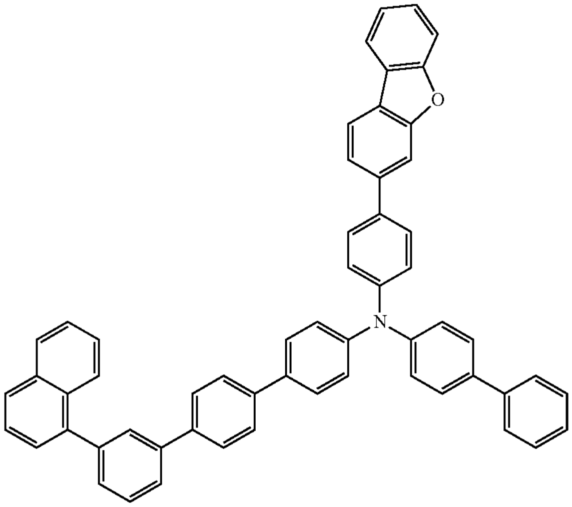
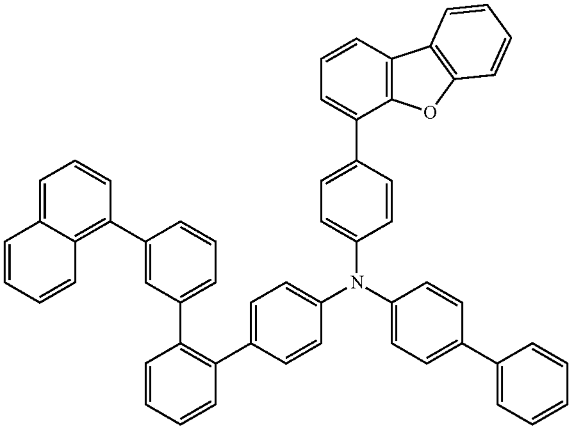
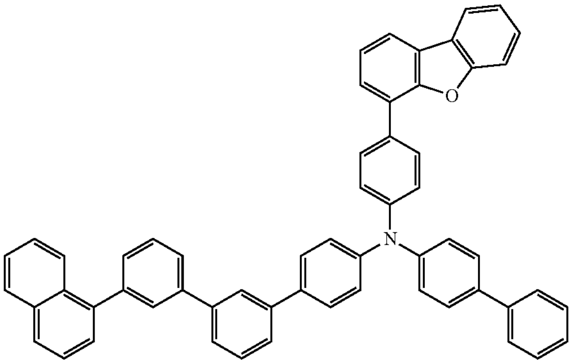

-continued
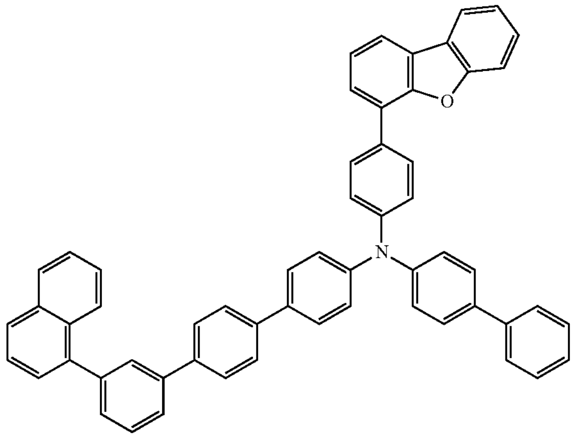
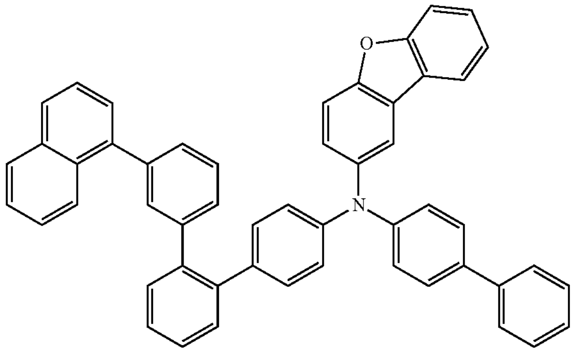
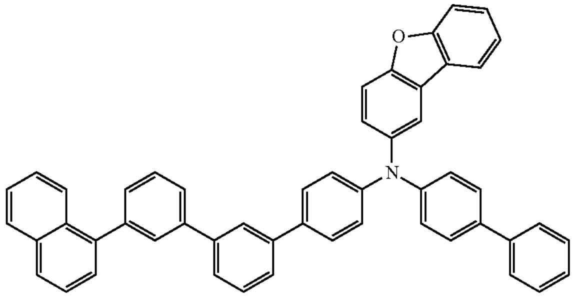
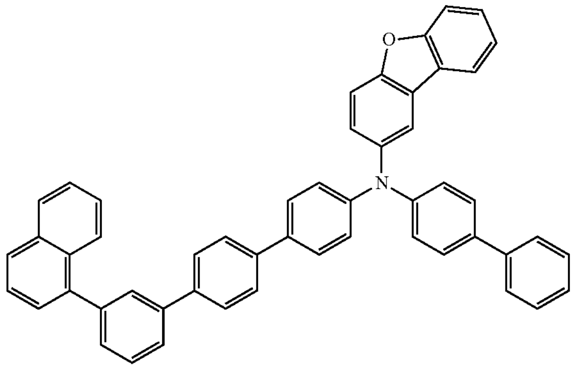
-continued
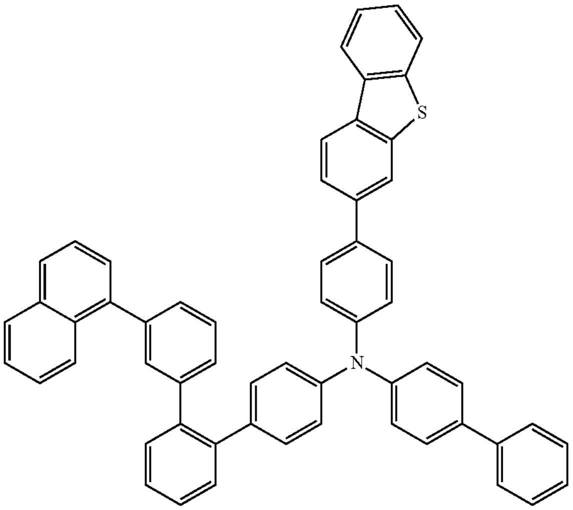
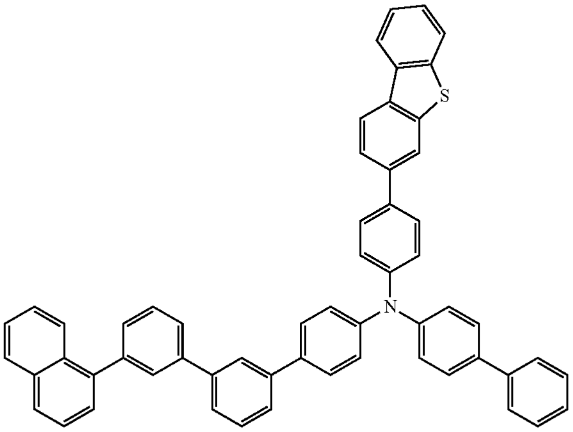
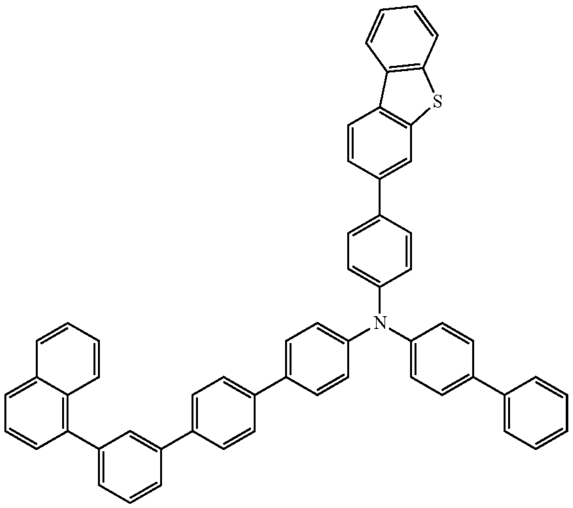

-continued
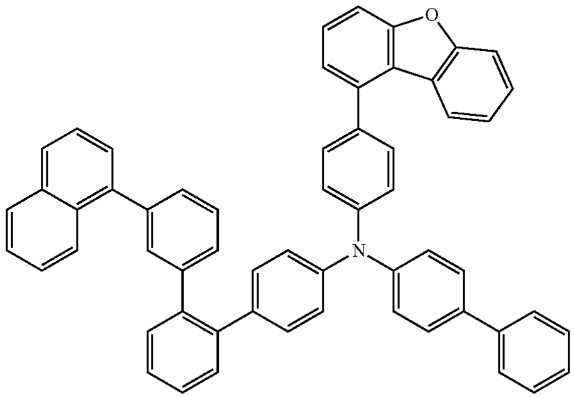
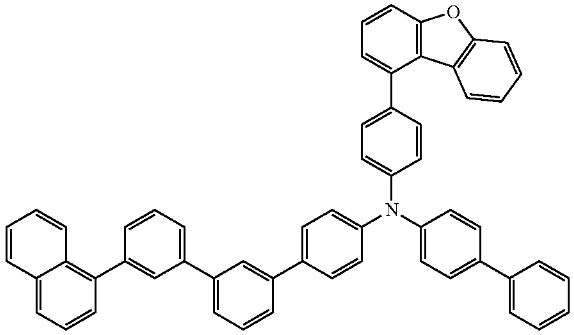
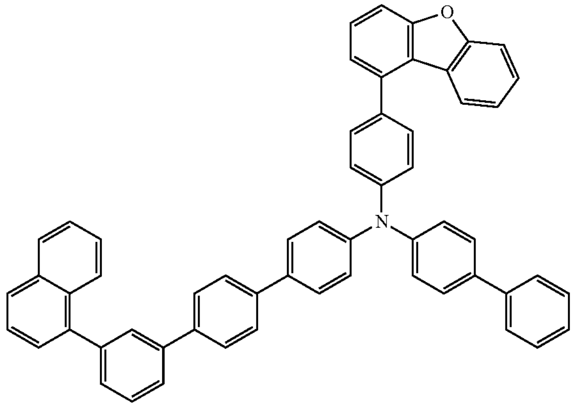
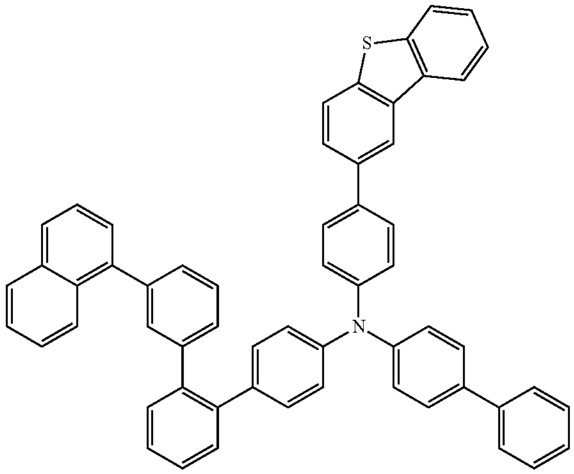
-continued
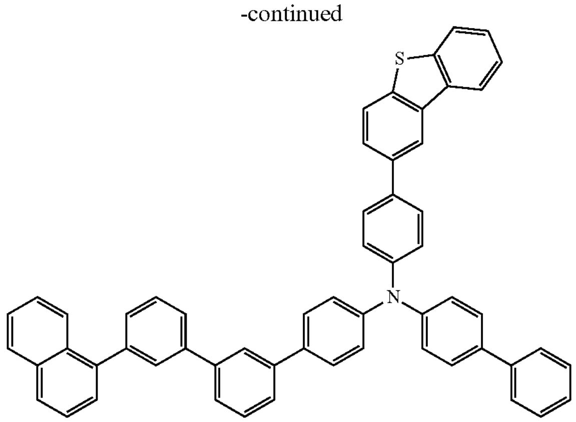
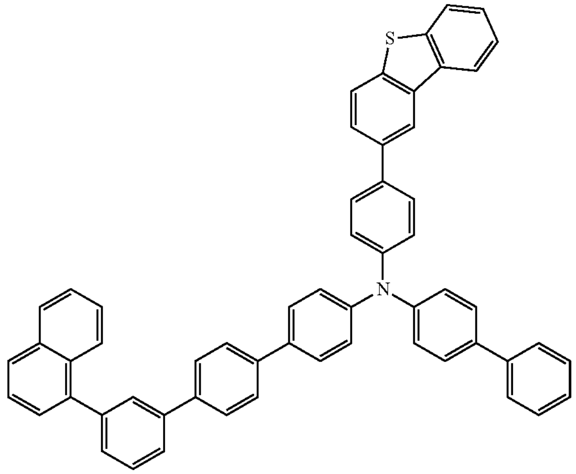
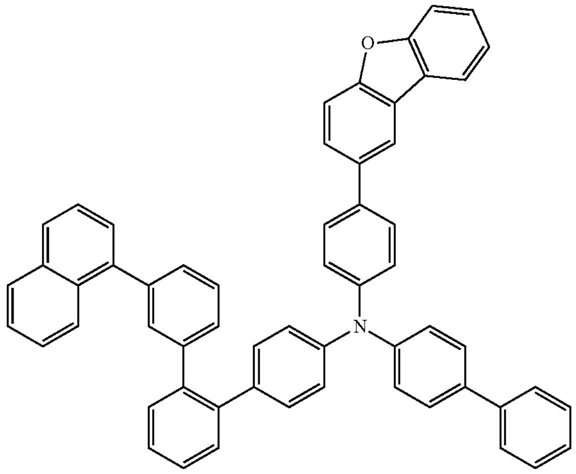

-continued
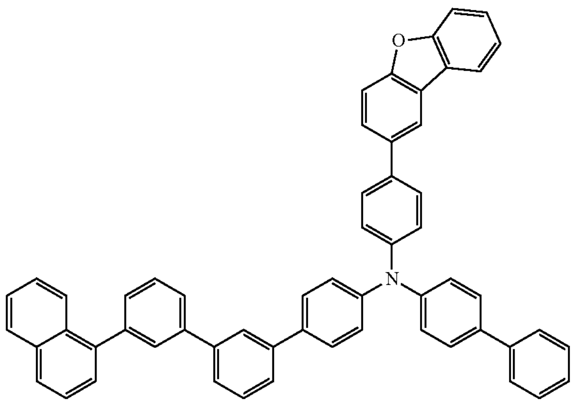
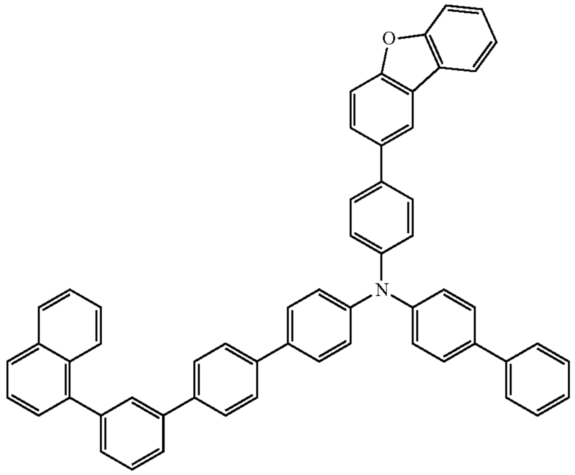
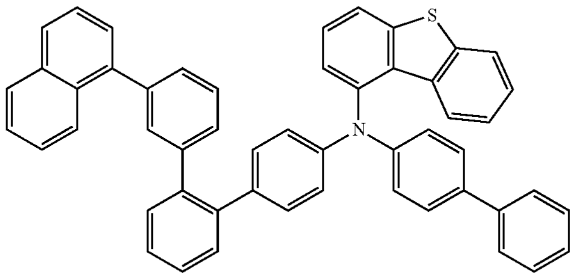
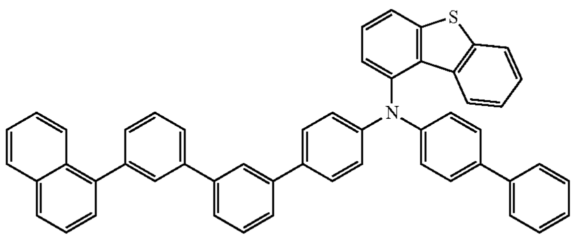
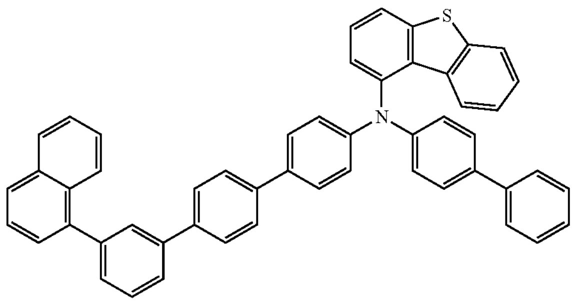
-continued
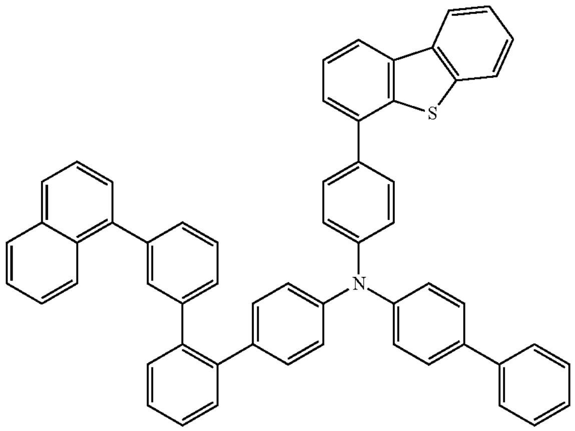
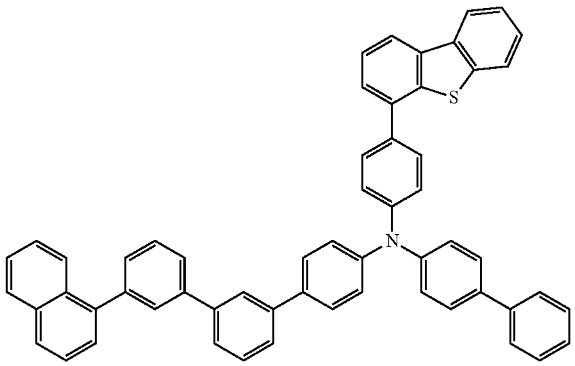
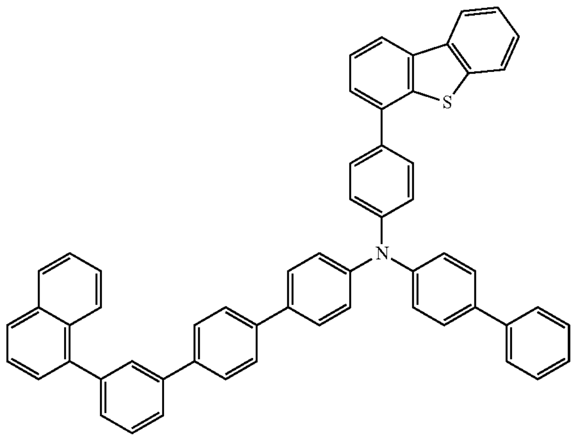
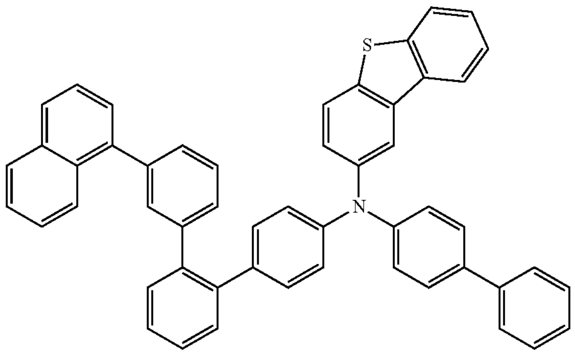

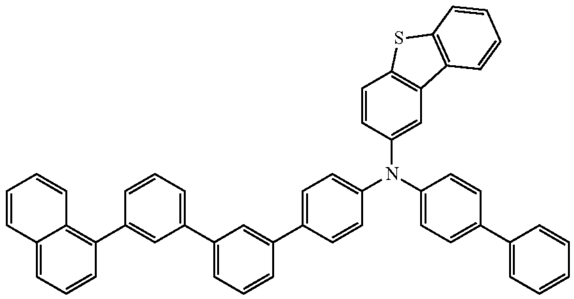
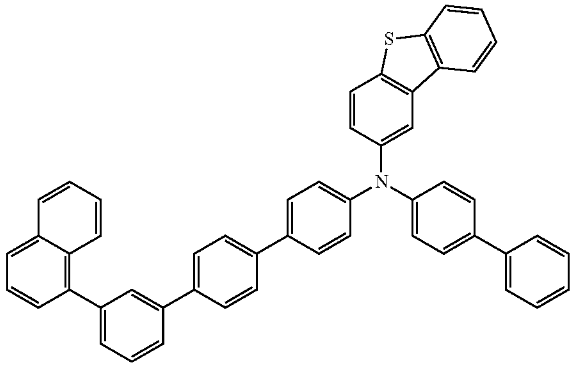
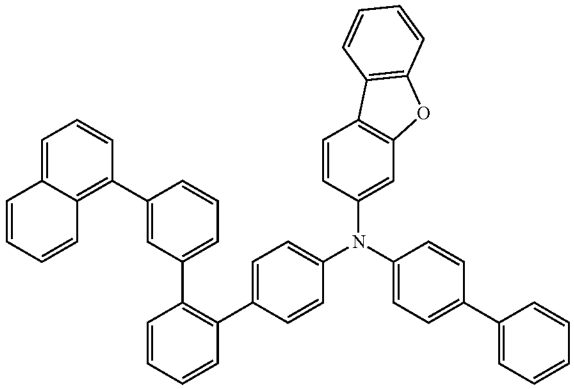
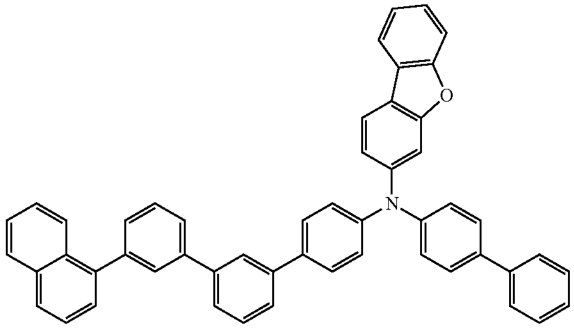
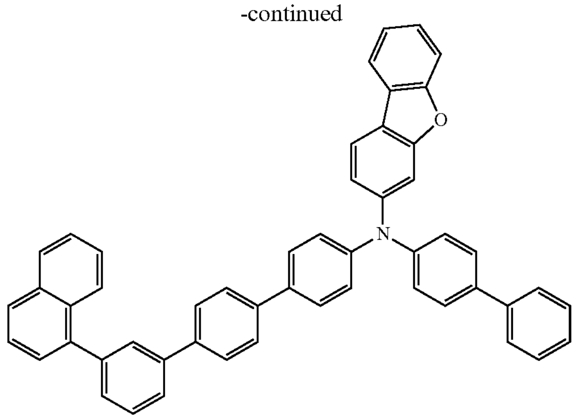
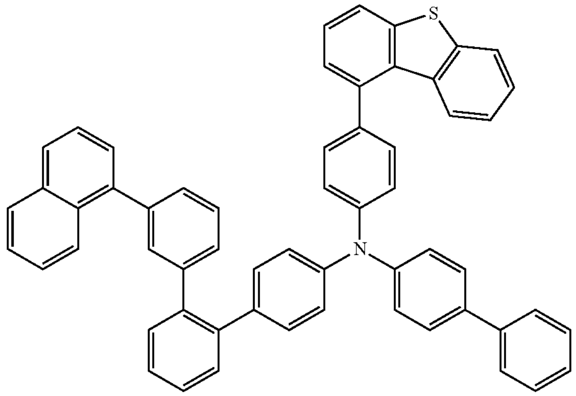
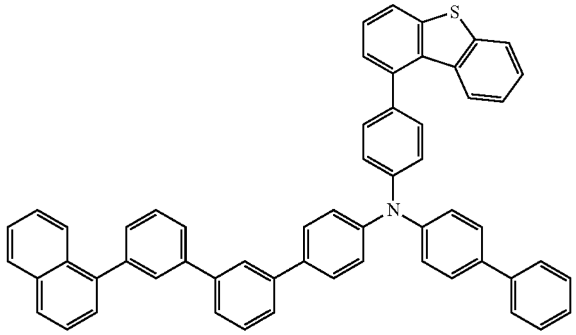
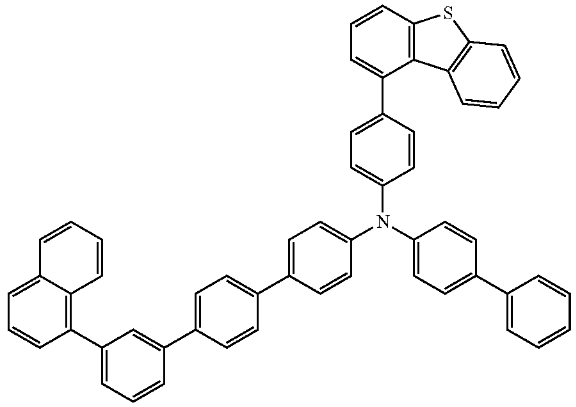

-continued
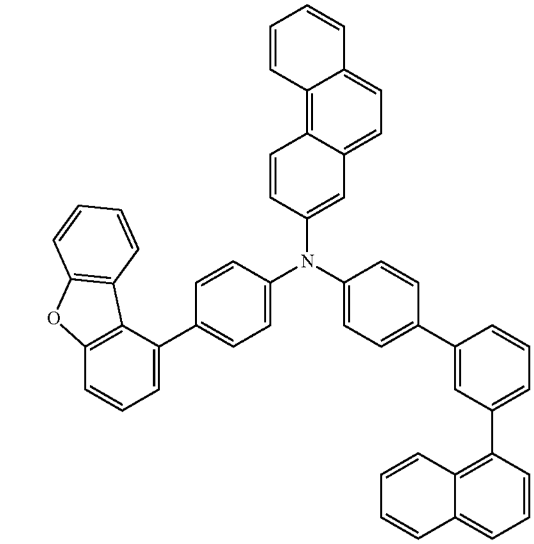
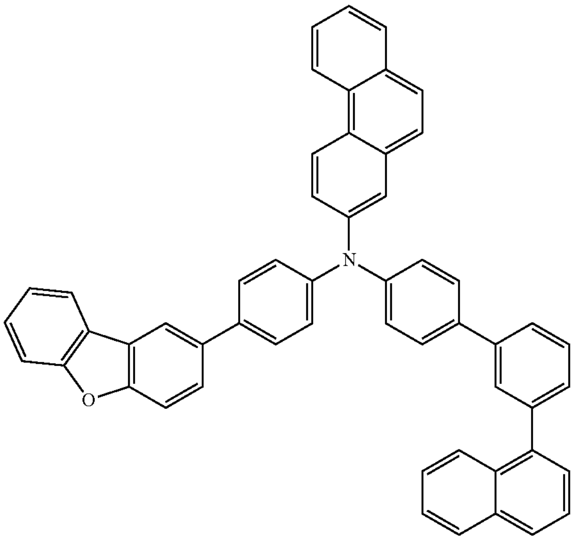
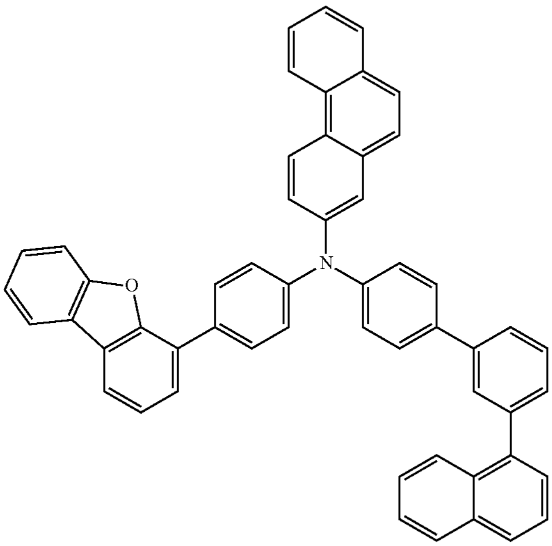
-continued
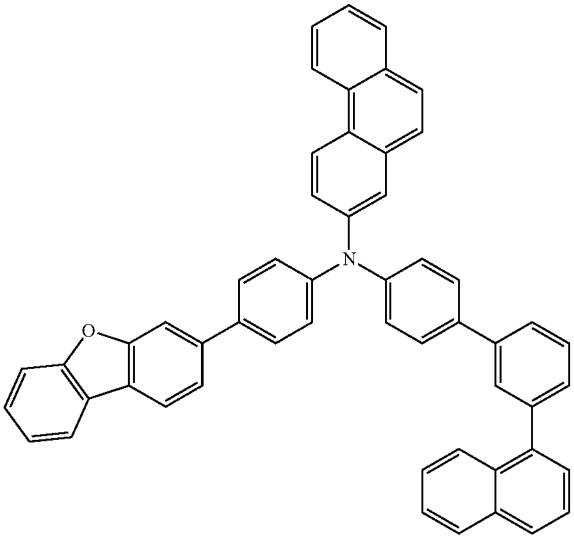
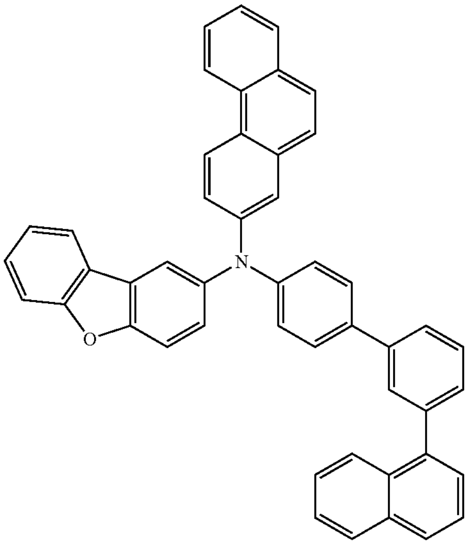
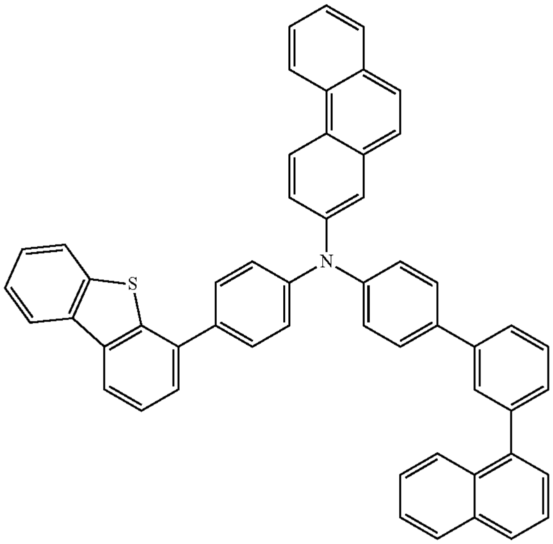

-continued
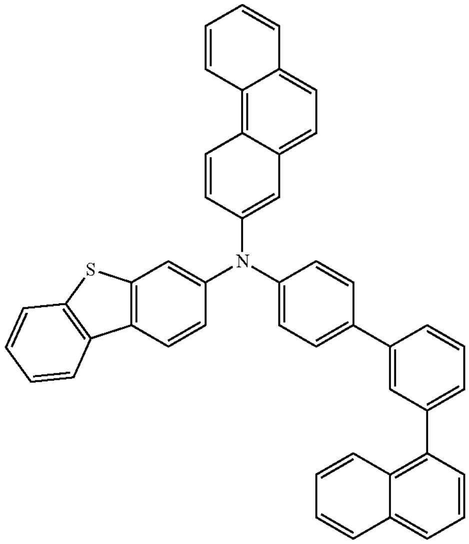
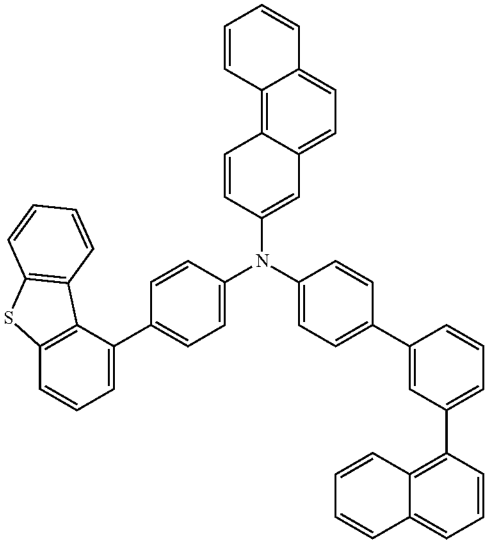
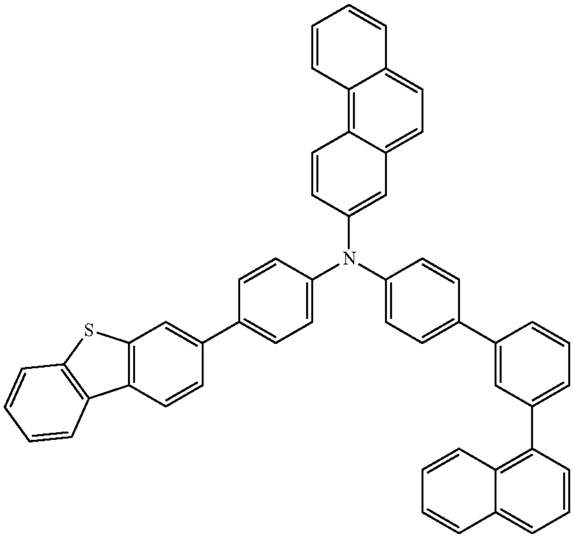
-continued
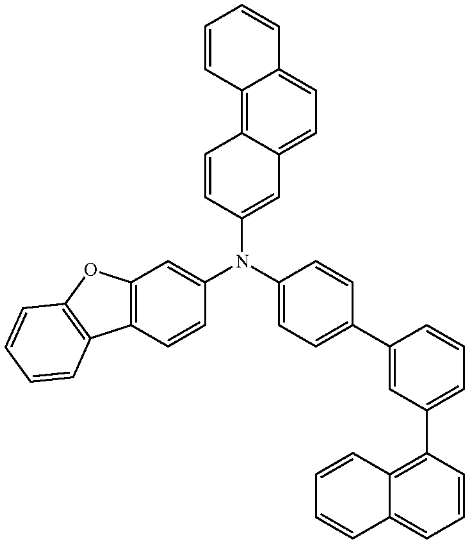
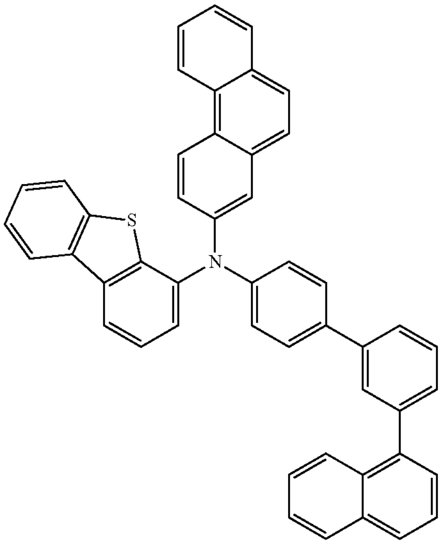
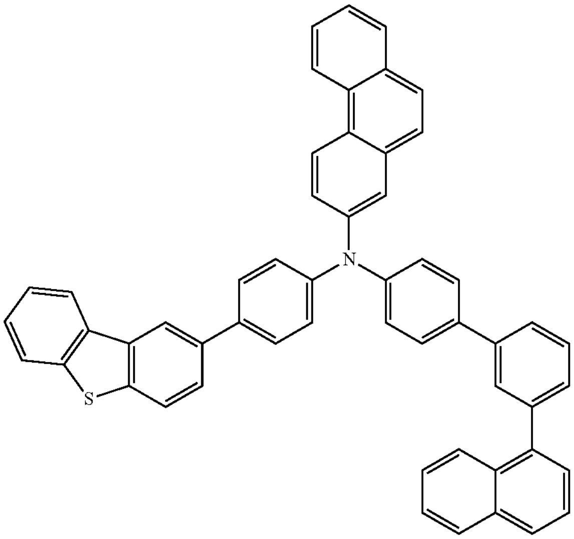

-continued
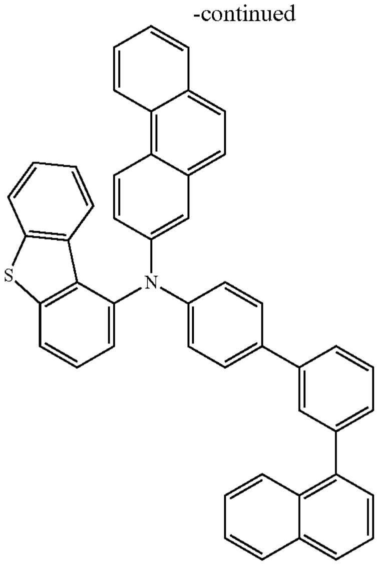
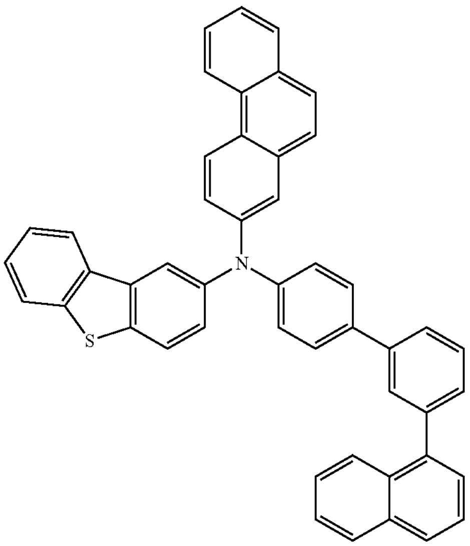
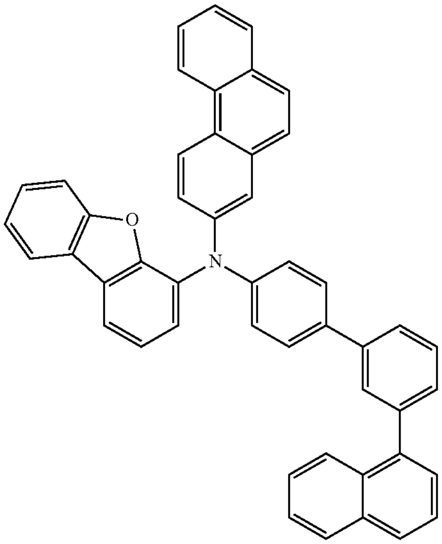
-continued
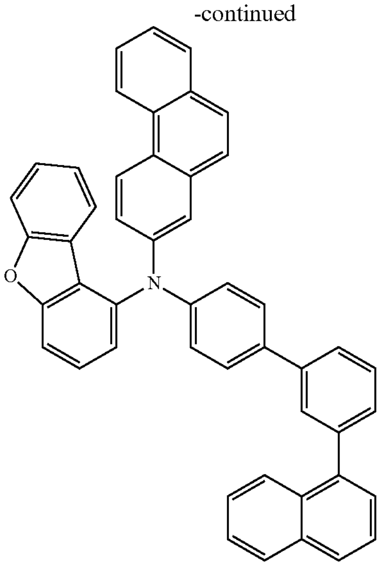
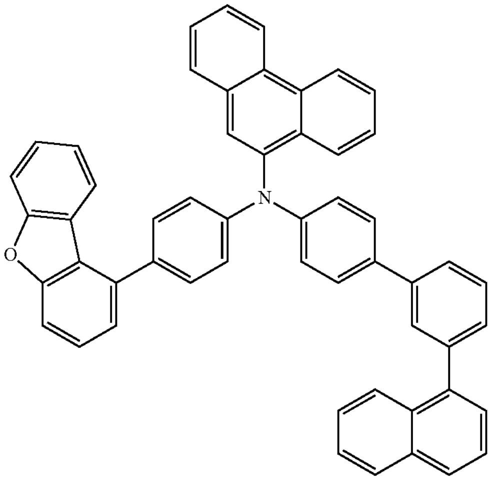
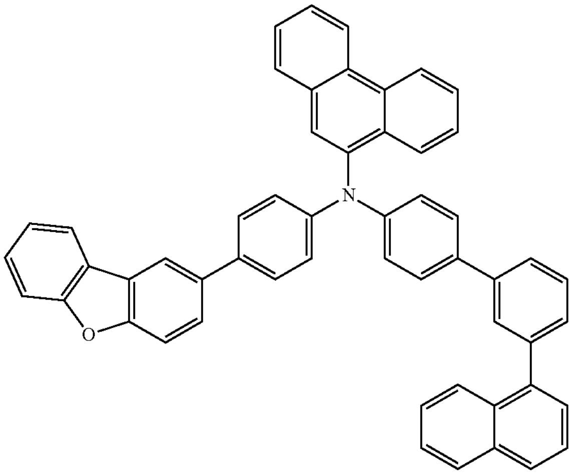

-continued
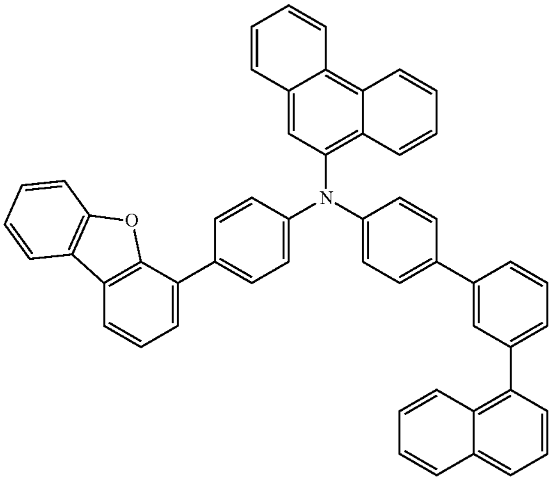
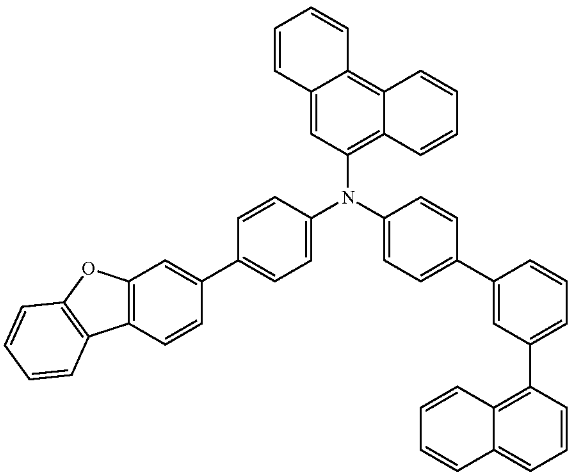 [SMILES: c1cc(-c2ccc(N(c3ccc(-c4ccc5c(c4)oc4ccccc45)cc3)c3cc4ccccc4c4ccccc34)cc2)cc(-c2cccc3ccccc23)c1]
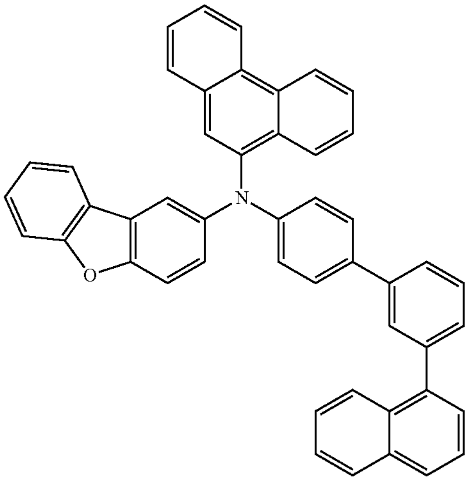
-continued
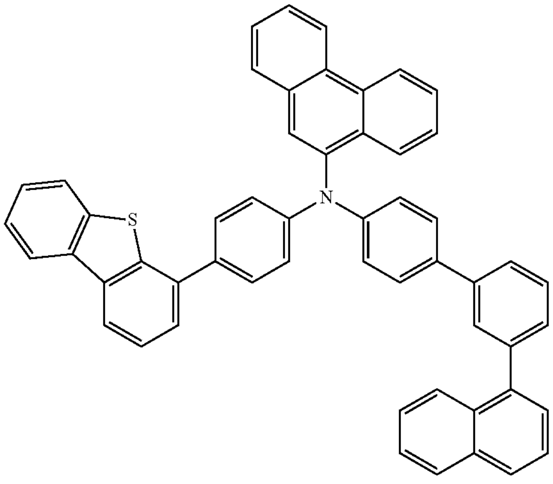
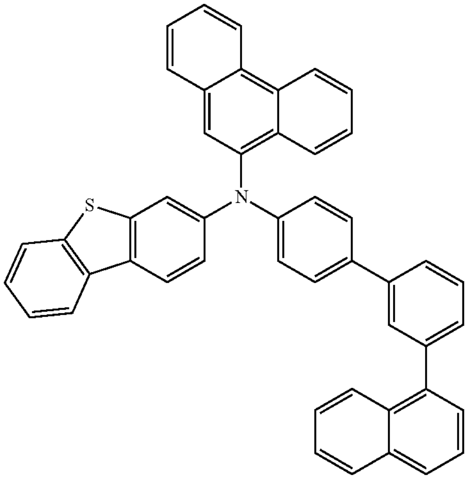
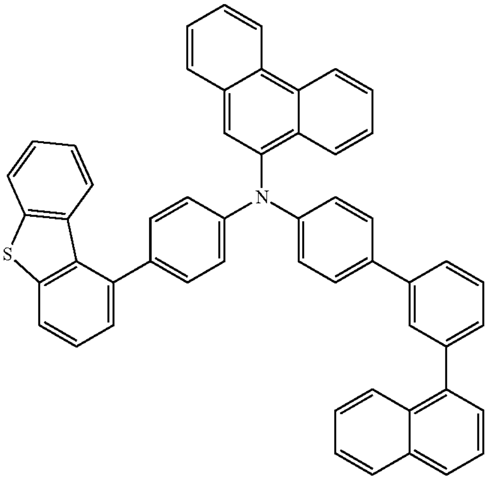

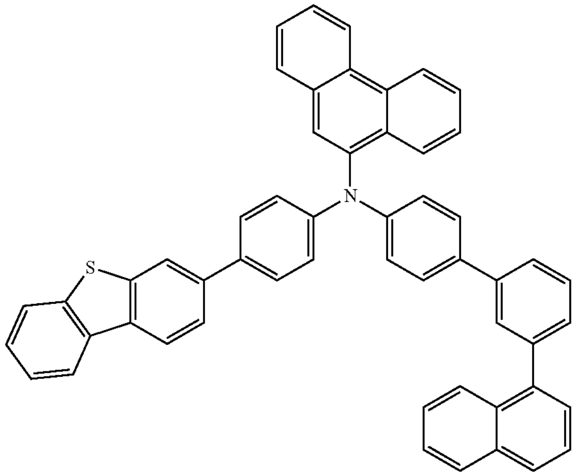
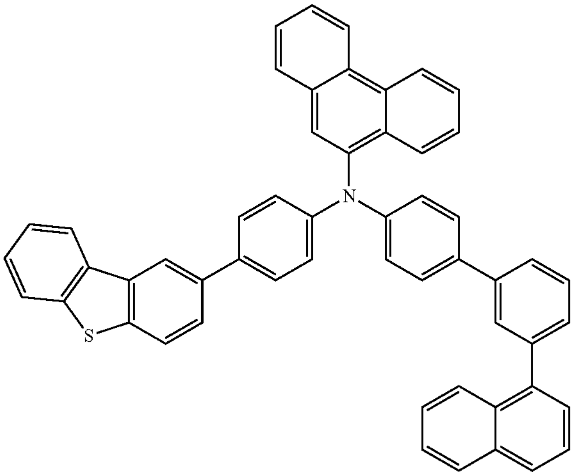
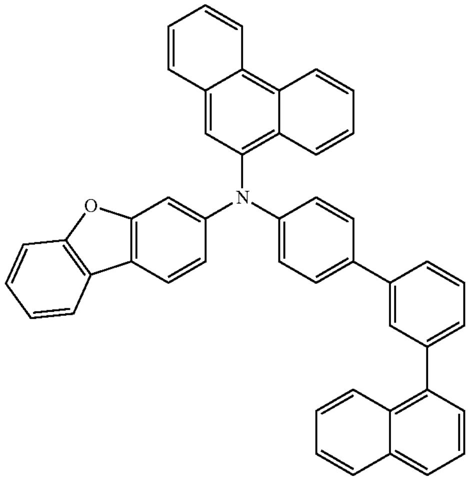
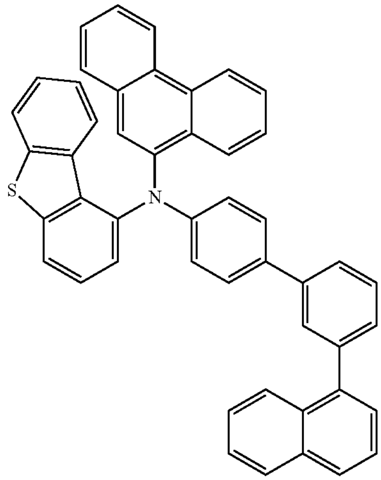
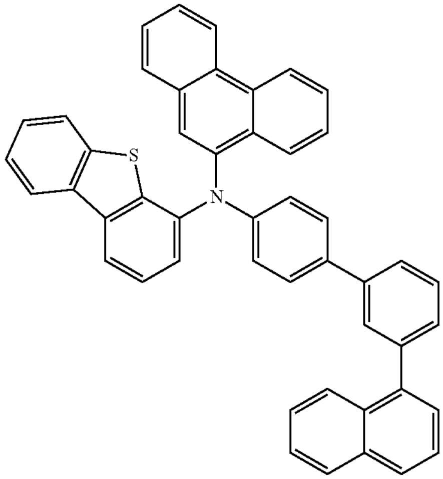
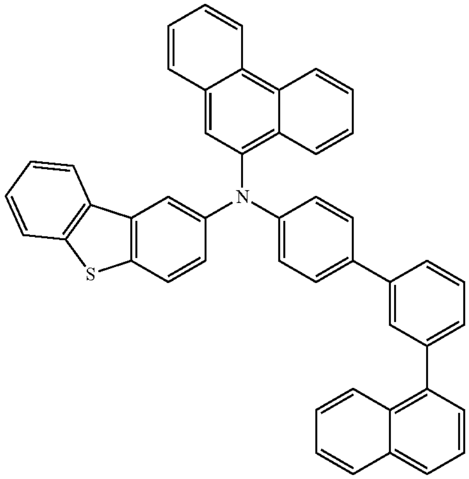

-continued
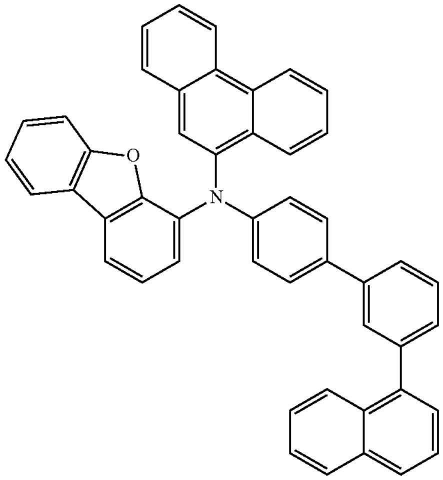
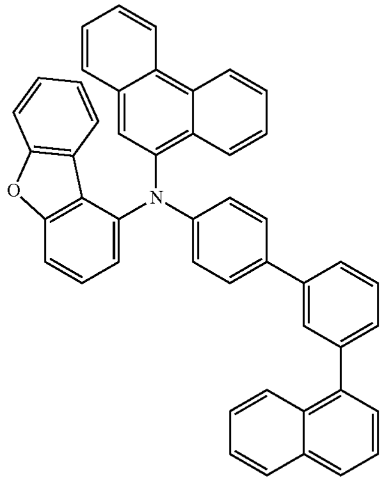
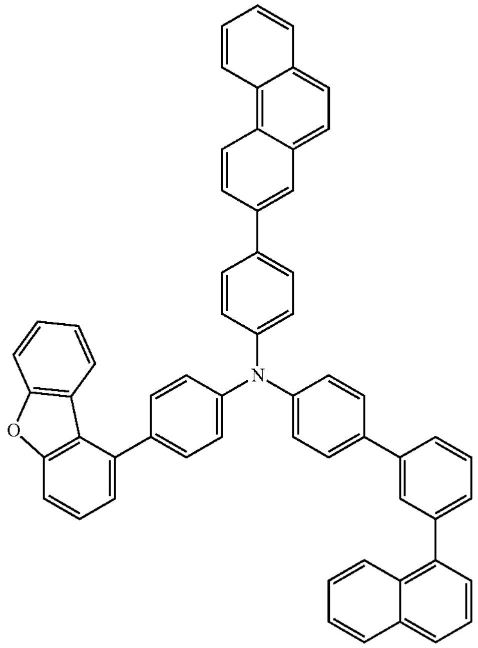
-continued
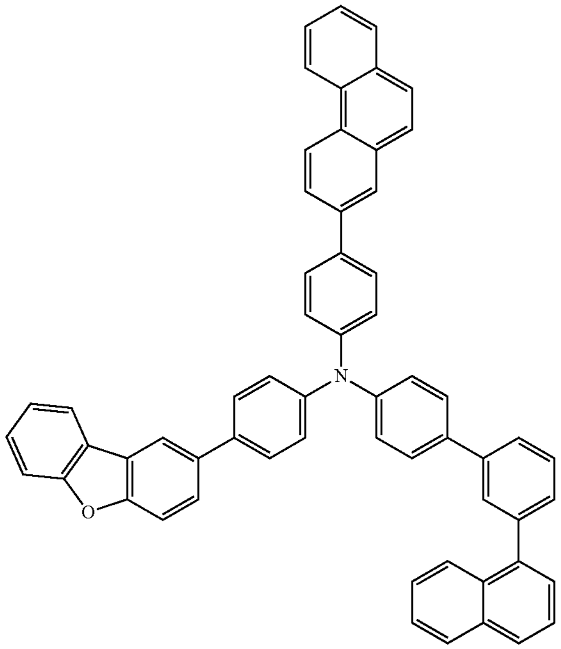
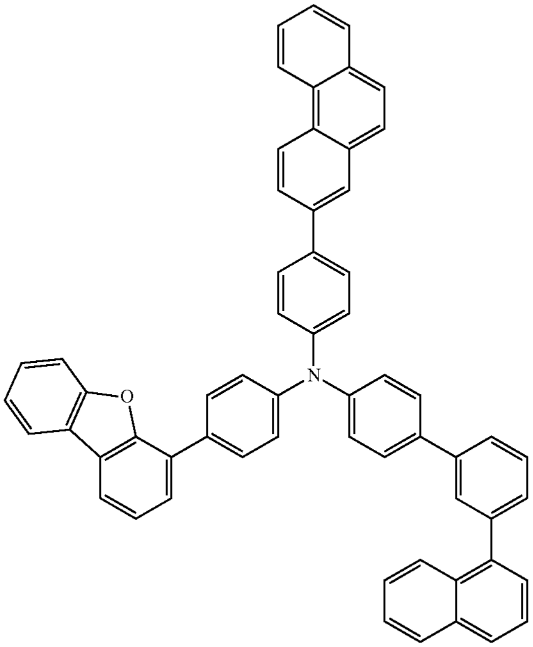

-continued
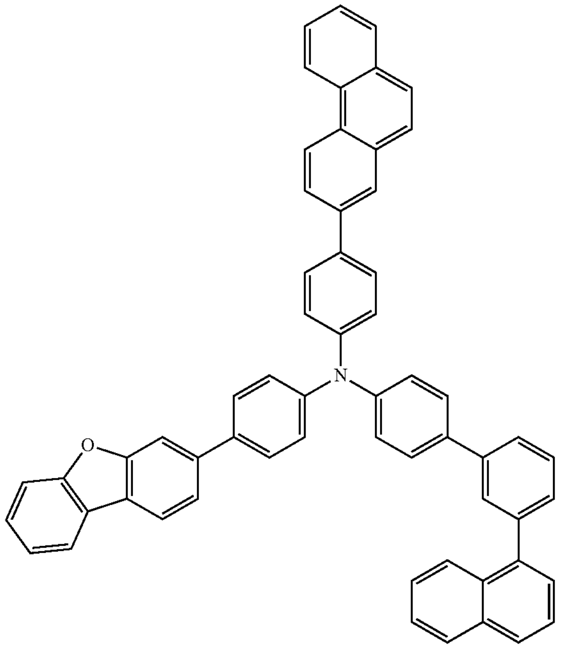
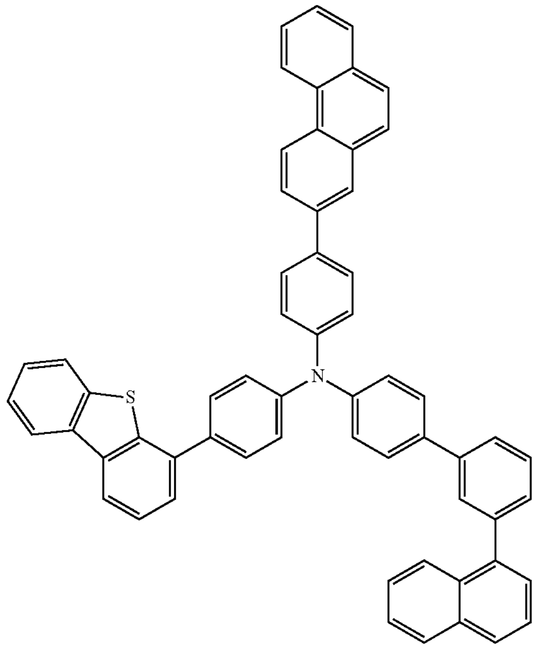
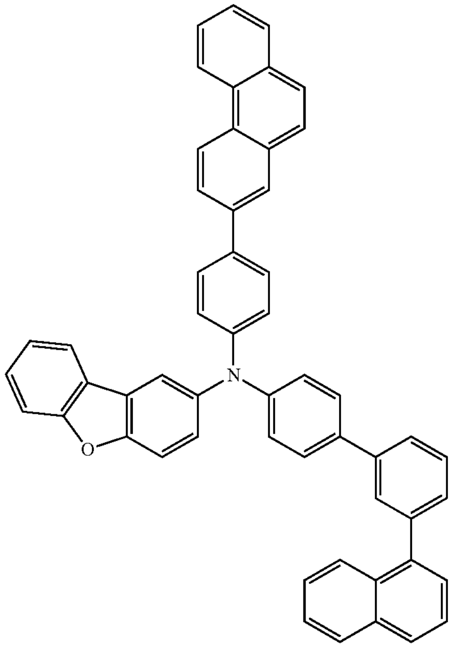
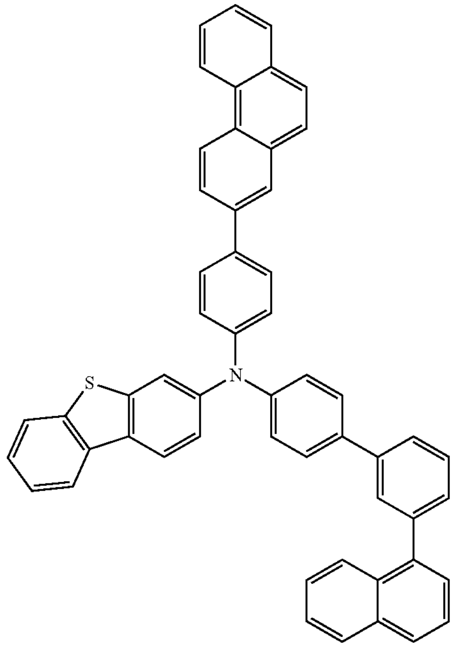

-continued
-continued
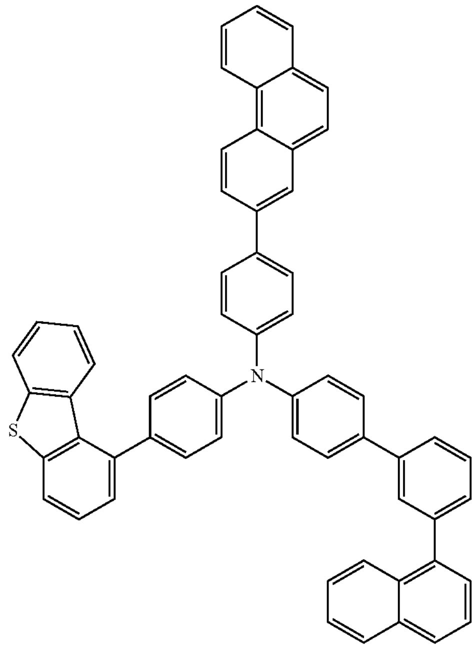
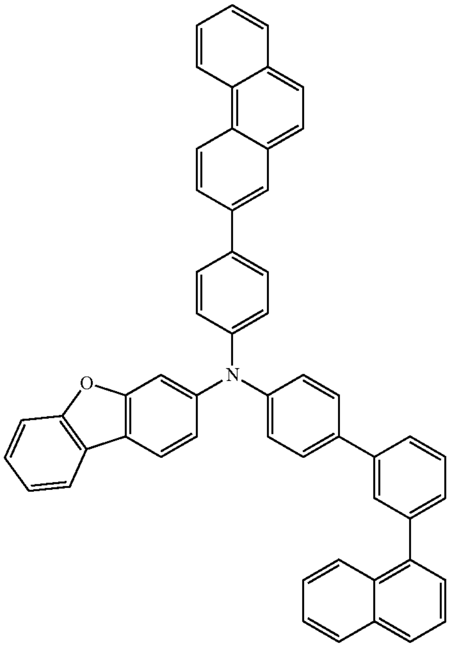
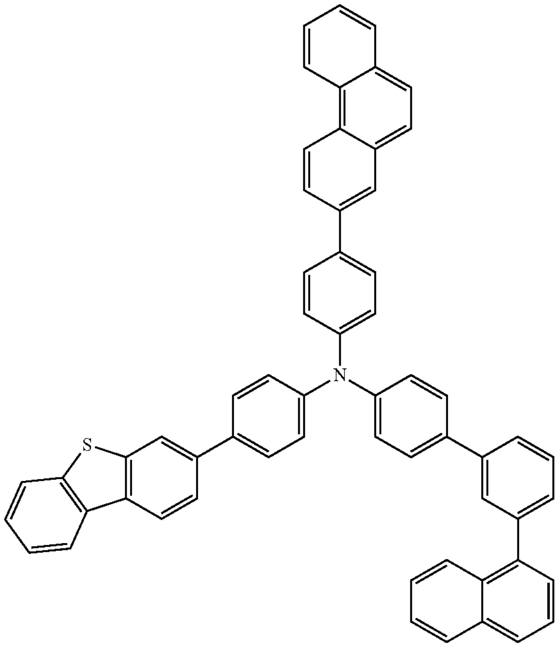
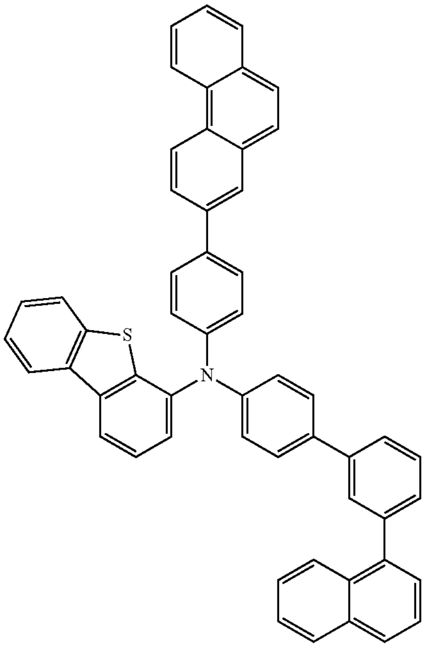

-continued
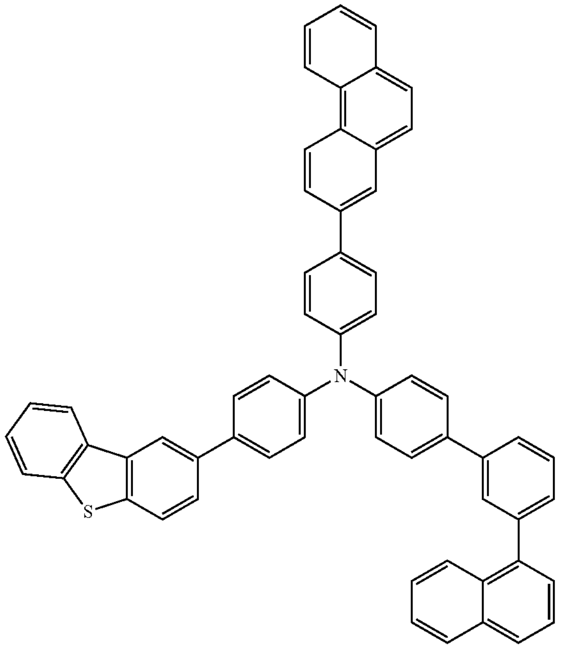
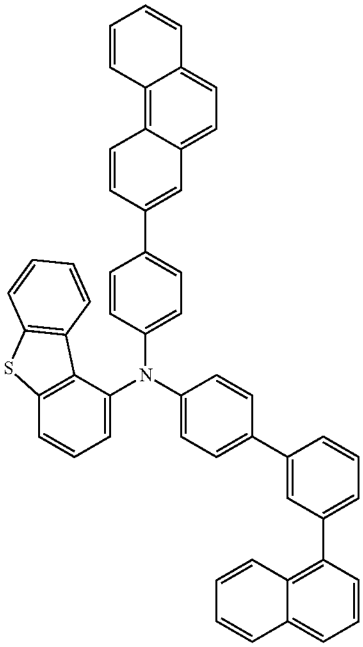
-continued
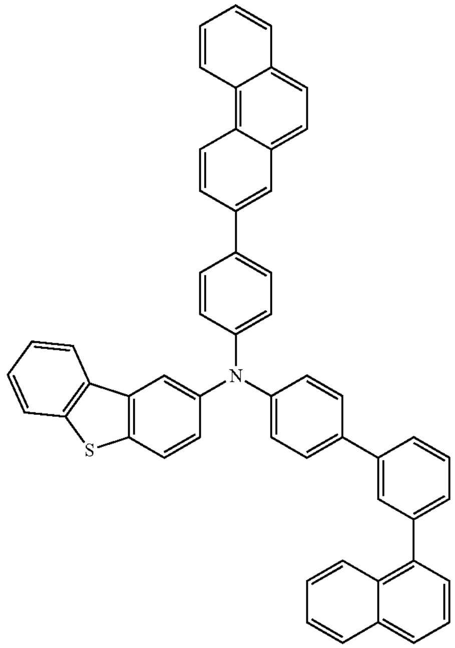
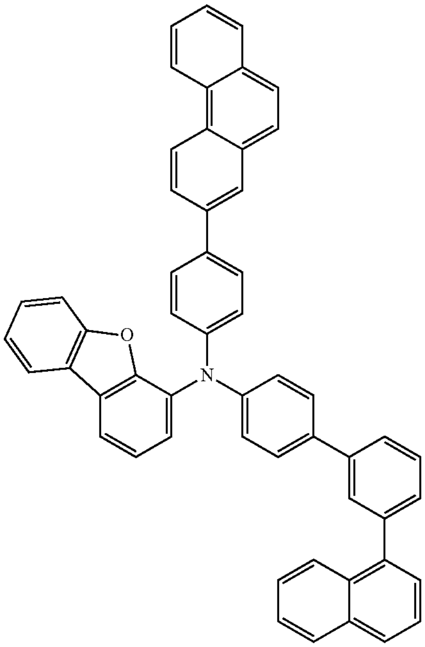

-continued
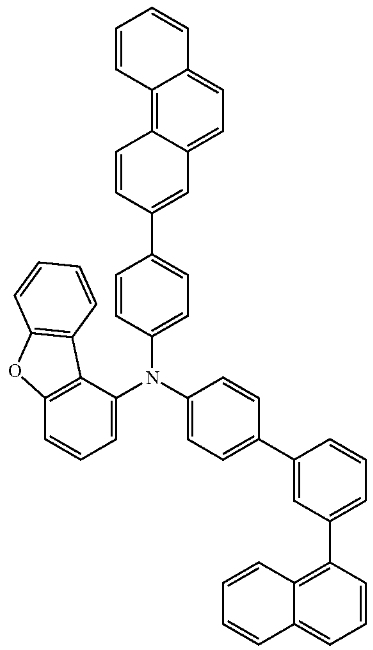
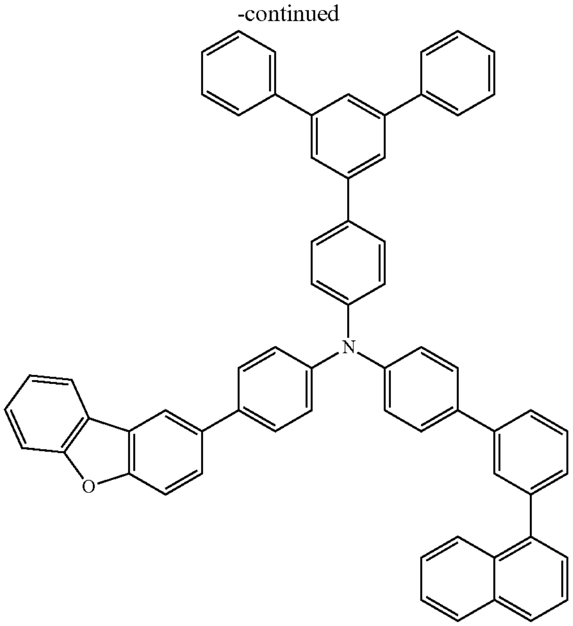
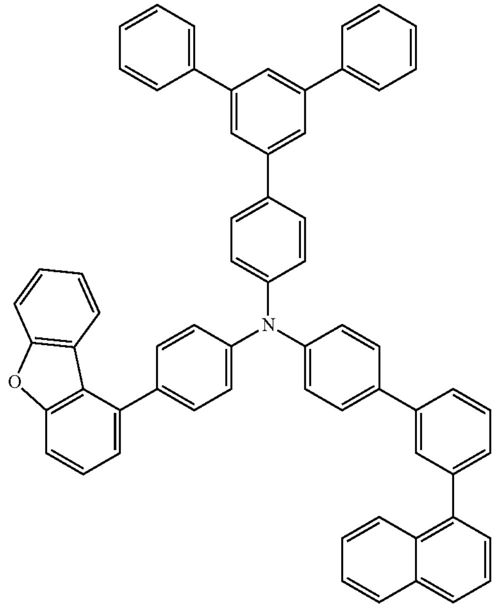
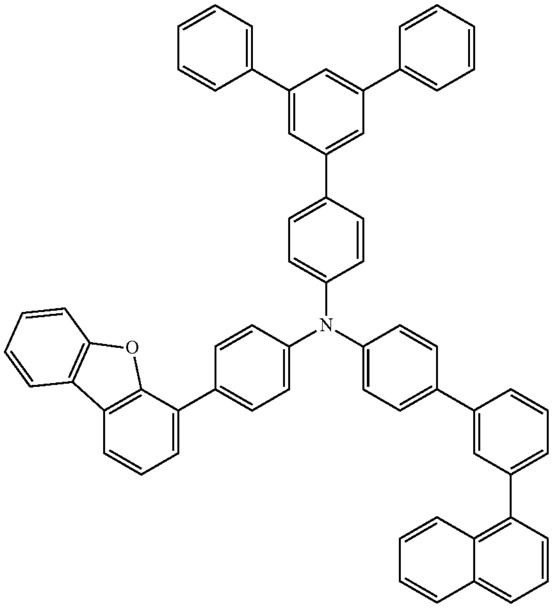

-continued
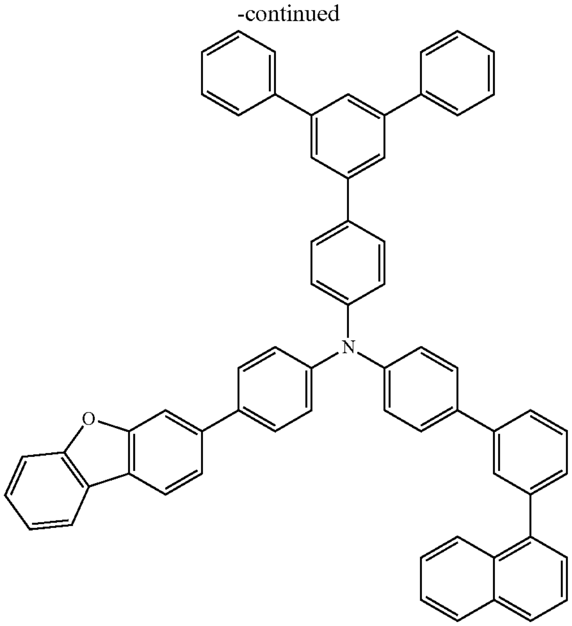
-continued
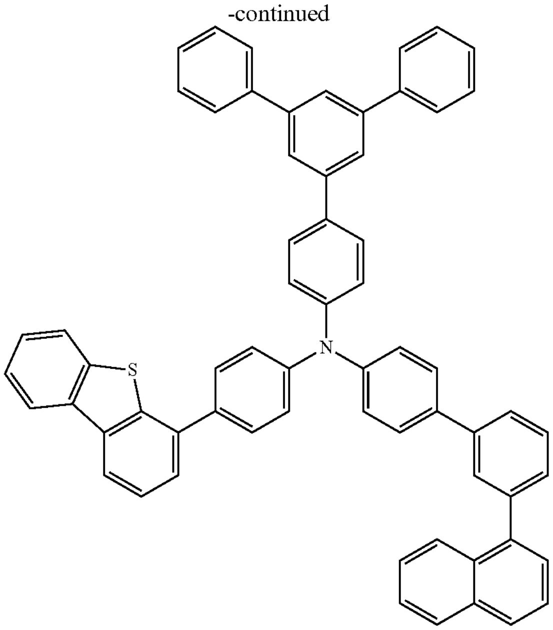
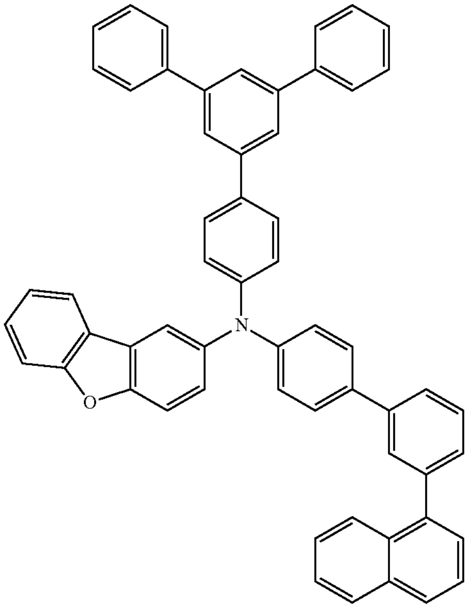
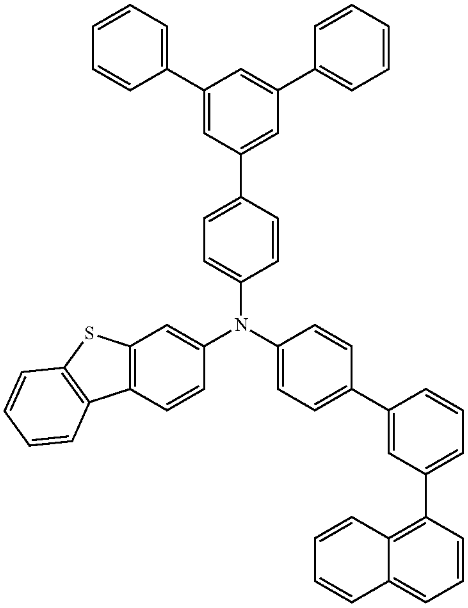

-continued
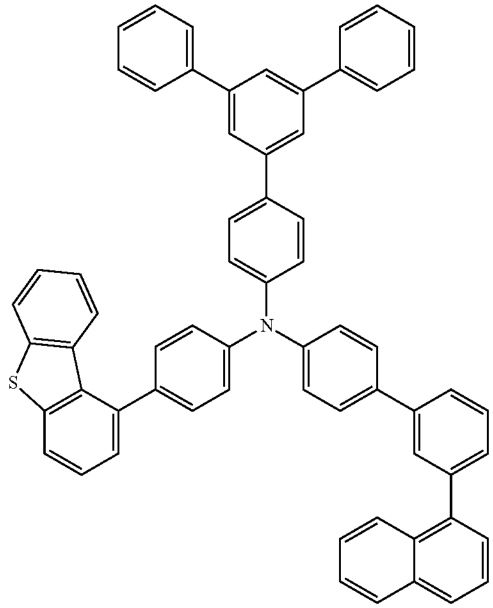
-continued
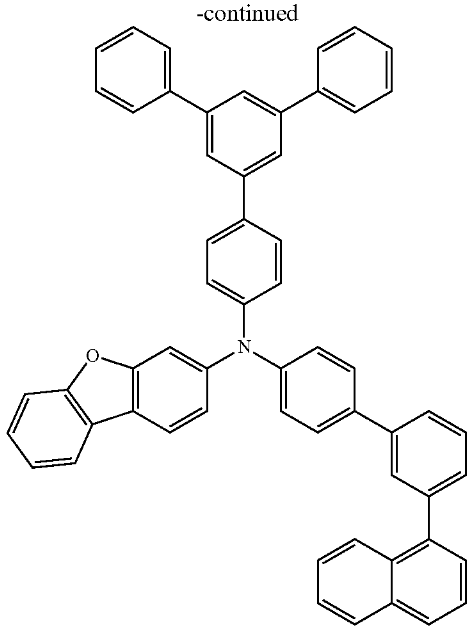
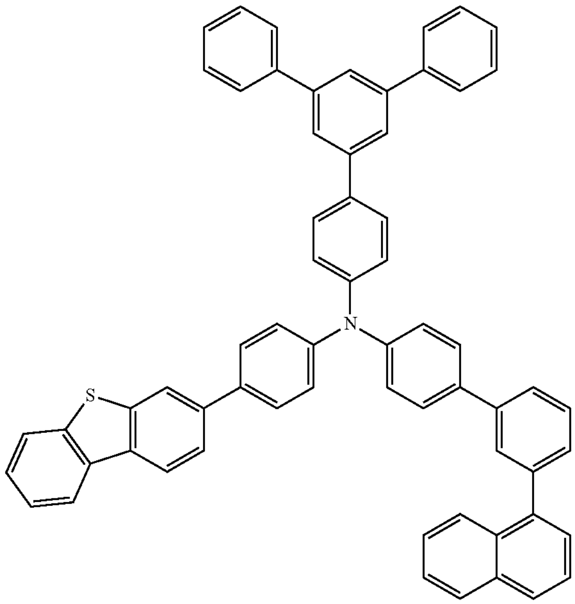
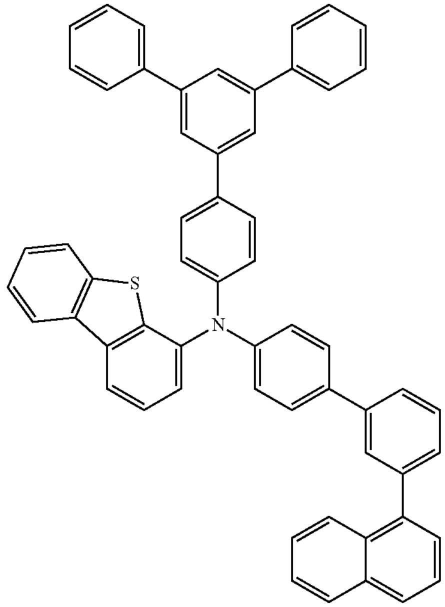

-continued
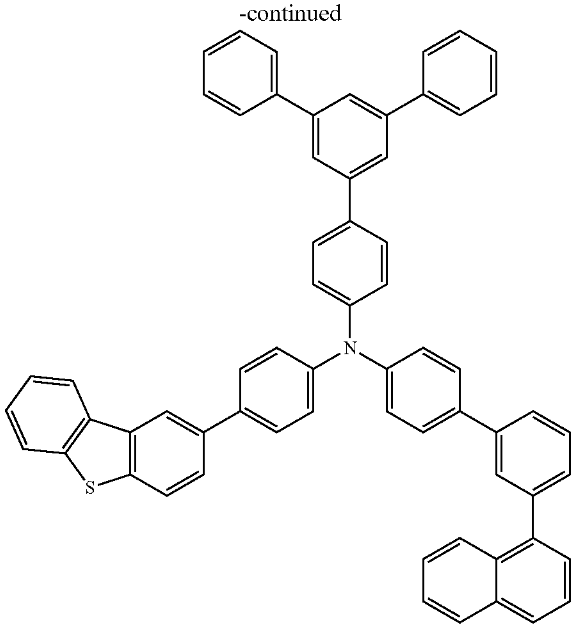
-continued
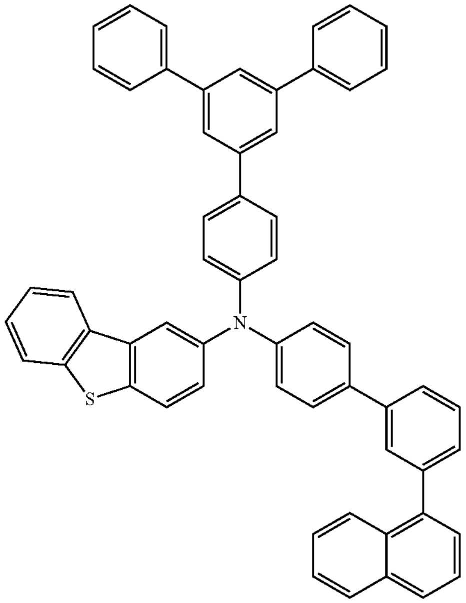
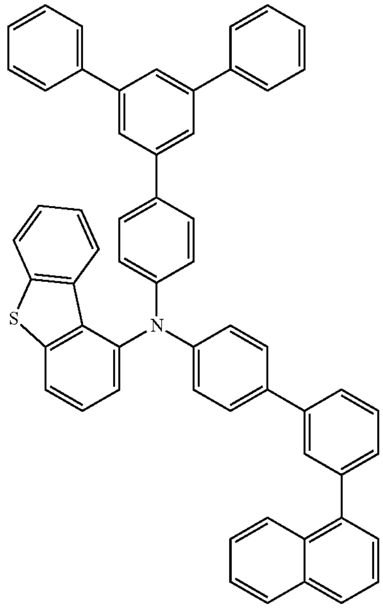
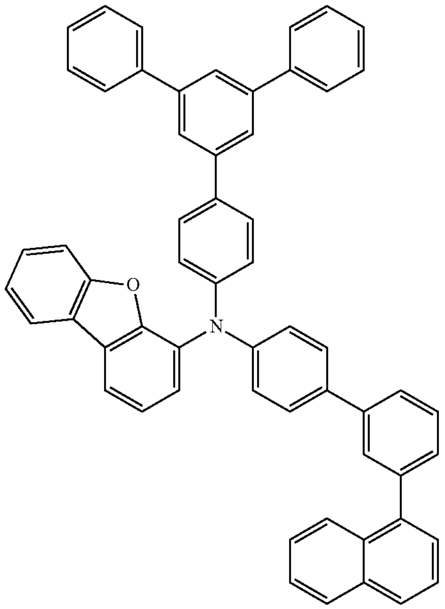

-continued
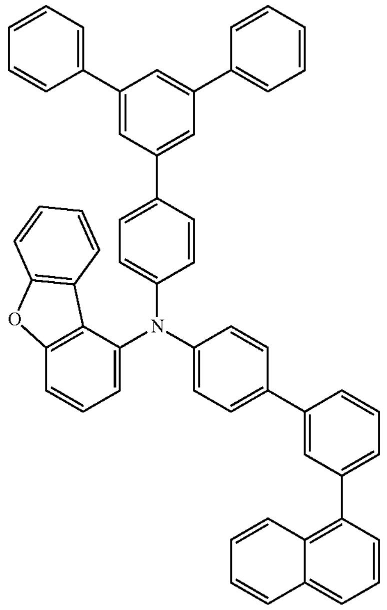
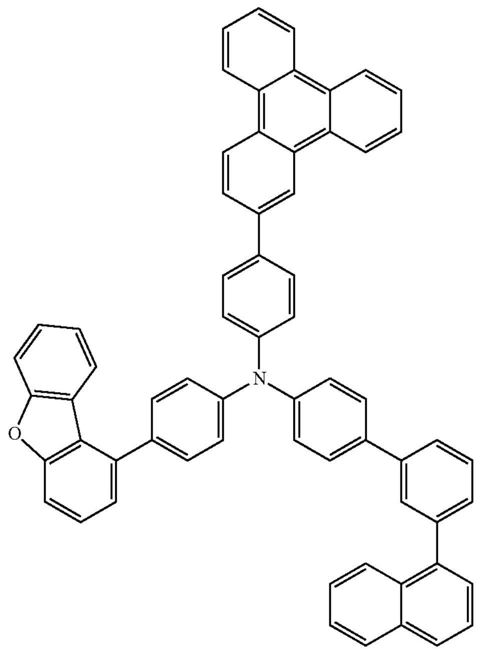
-continued
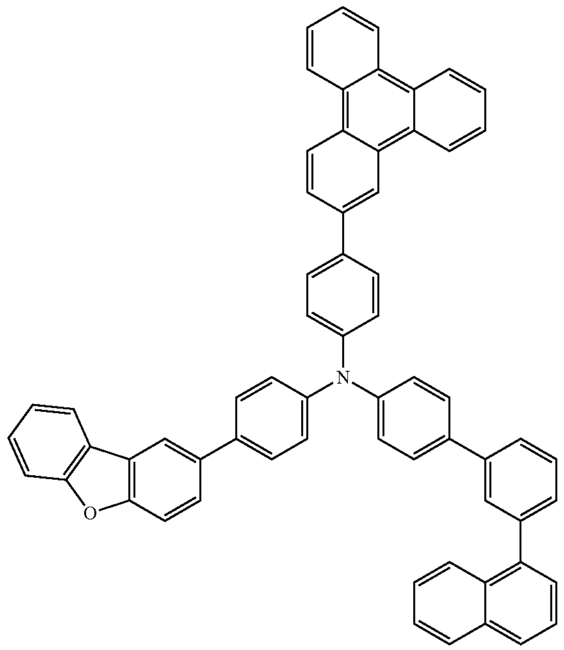
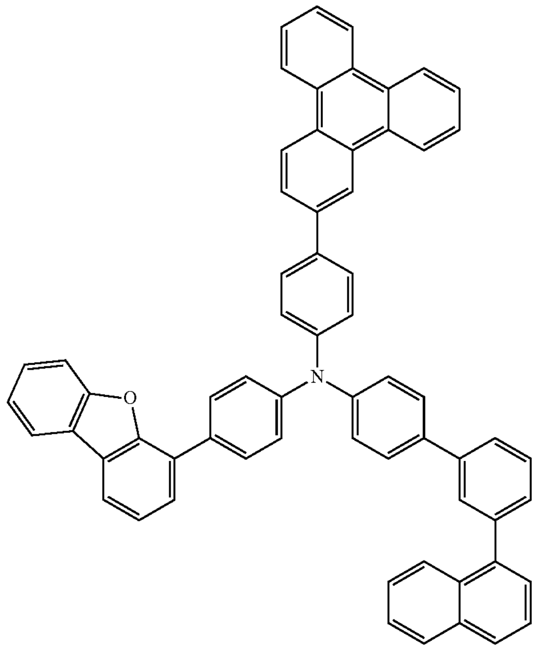

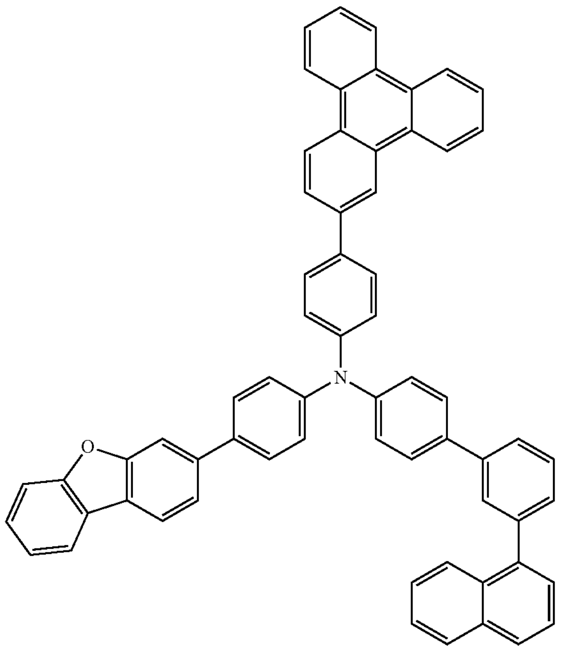
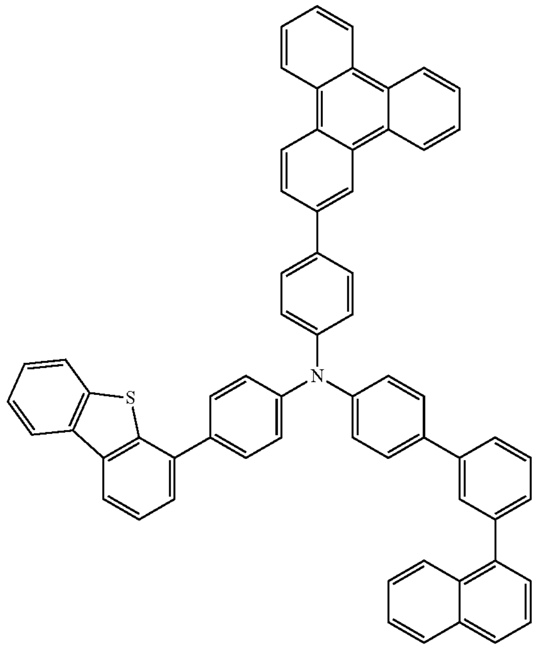
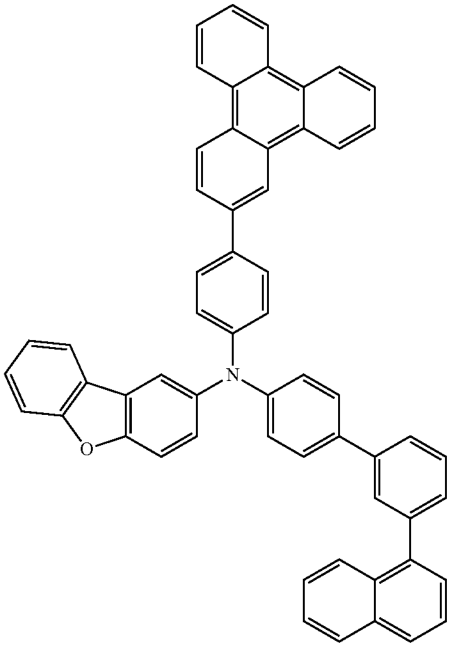
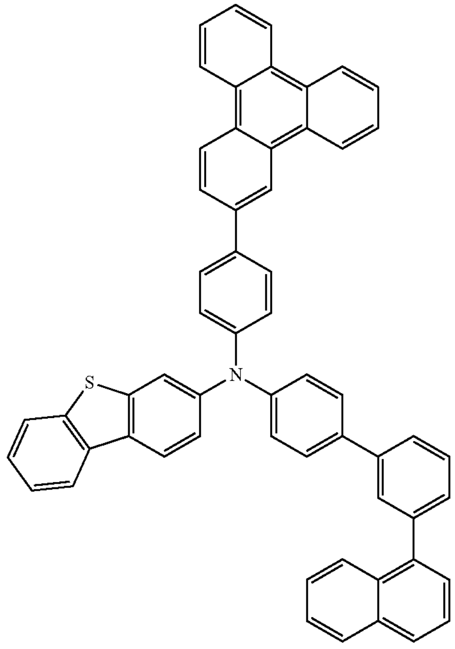

-continued
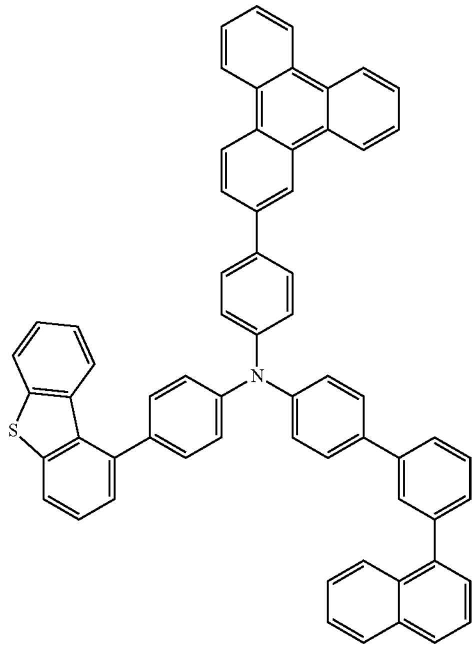
-continued
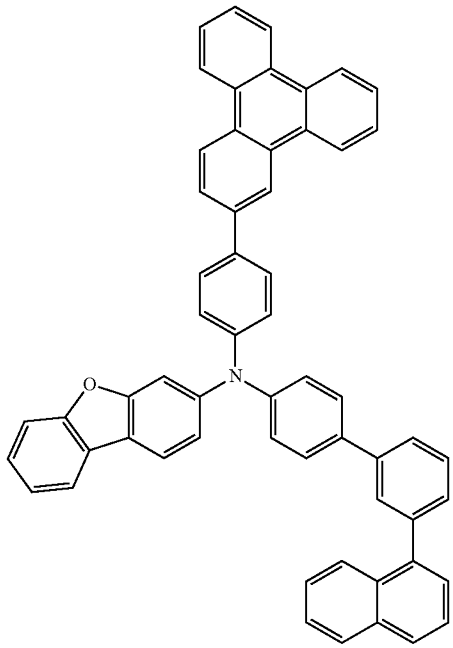
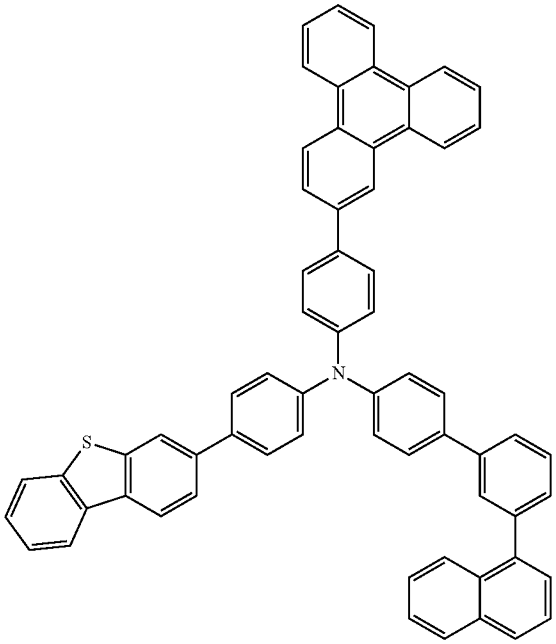
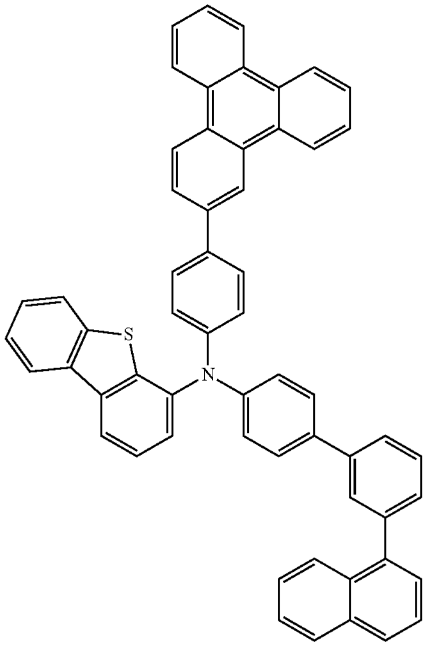

-continued
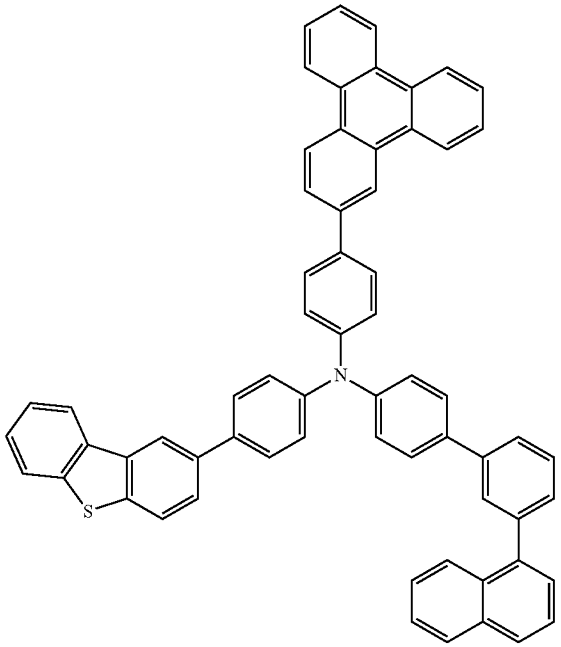
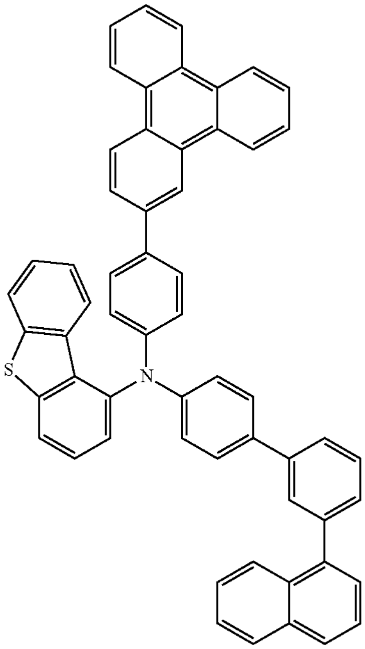
-continued
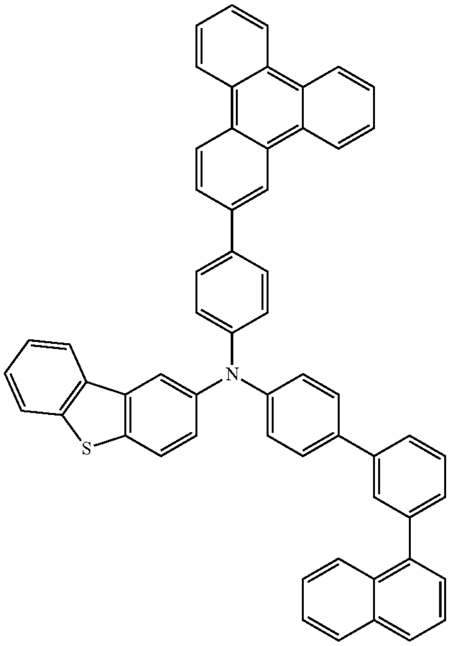
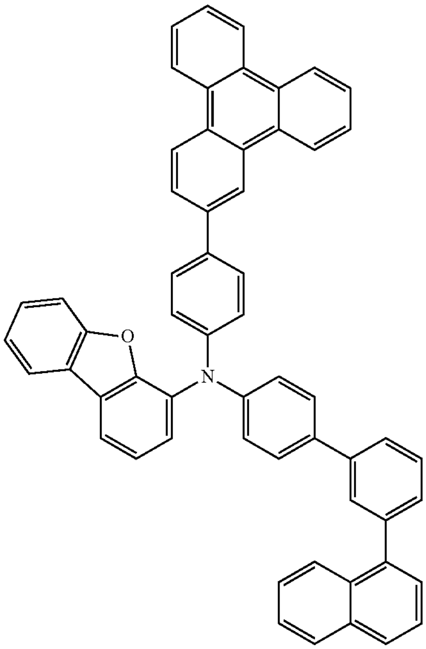

-continued
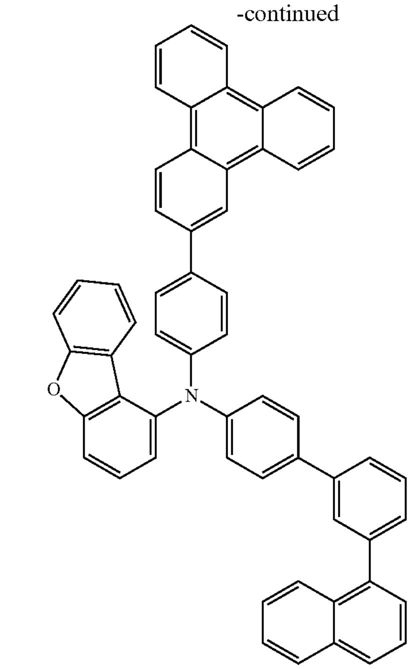
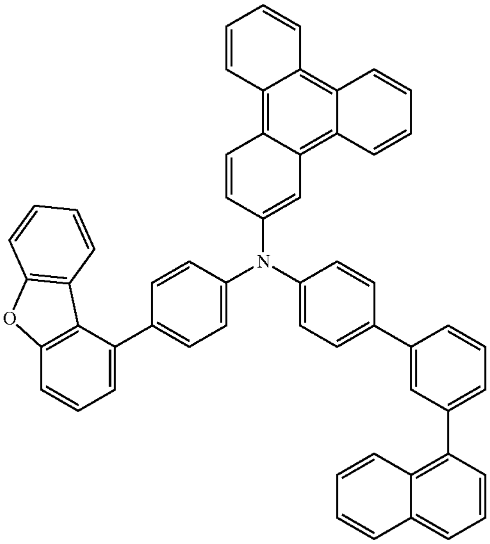
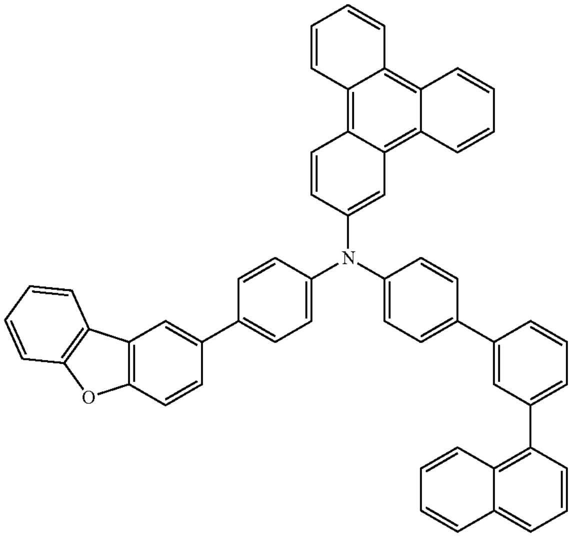
-continued
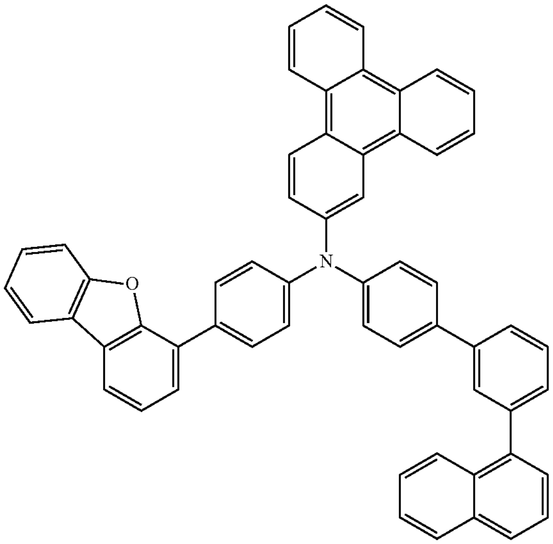
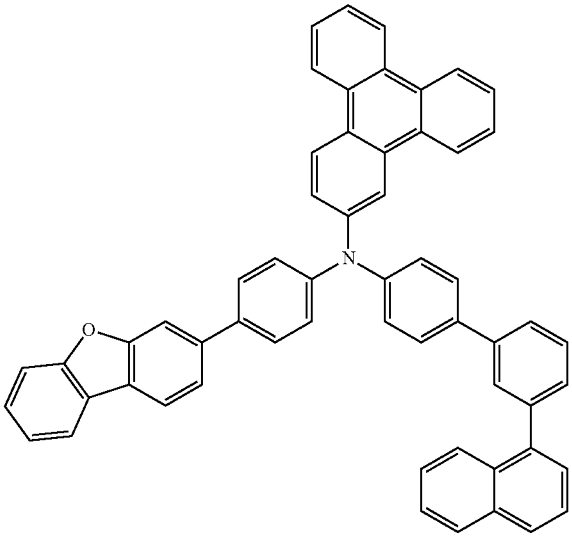
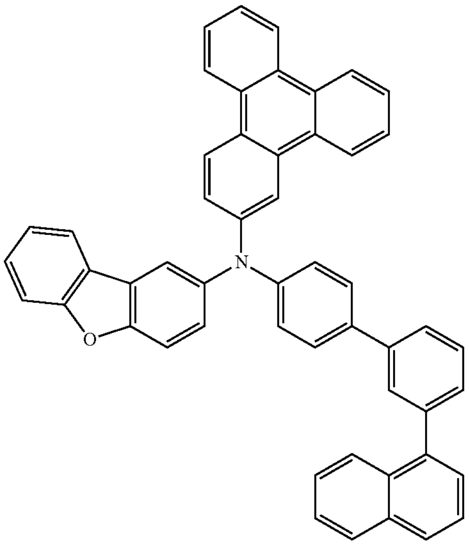

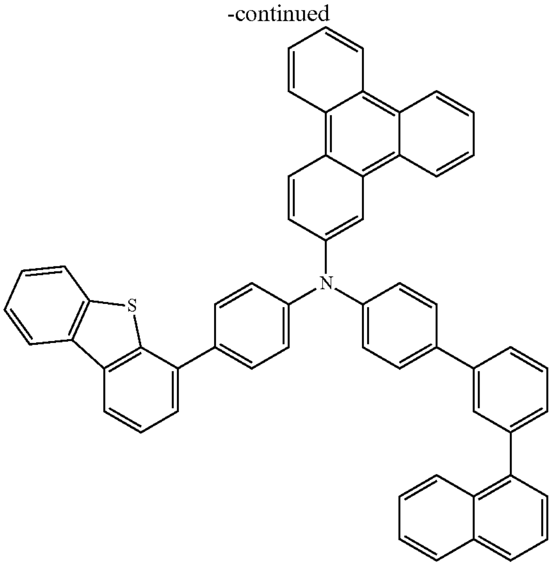
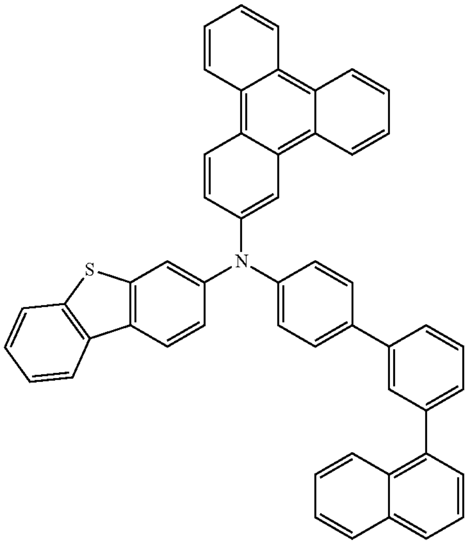
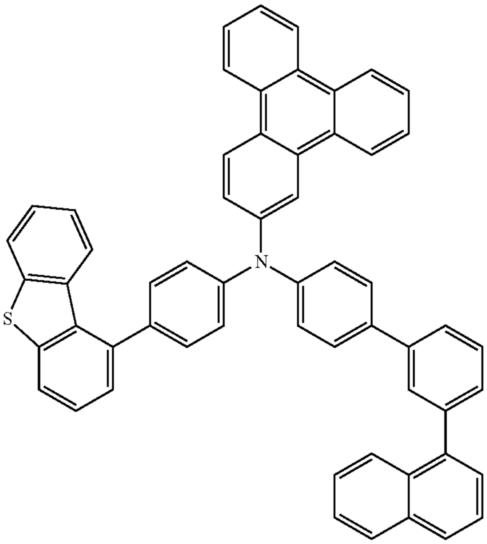
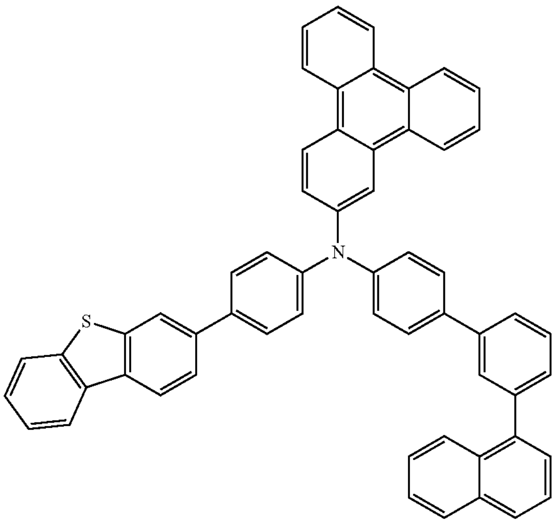
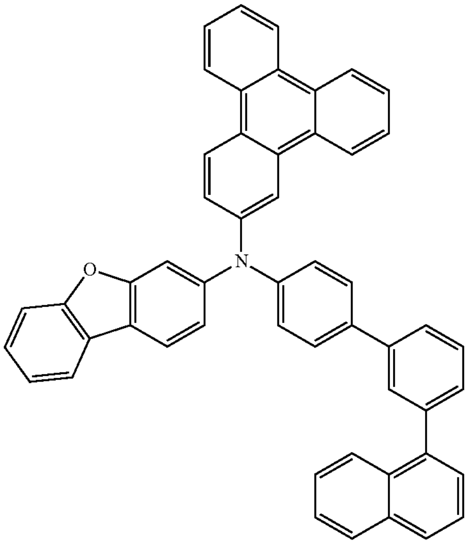
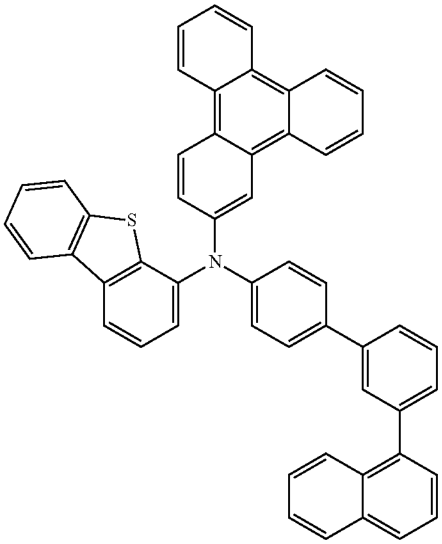

-continued
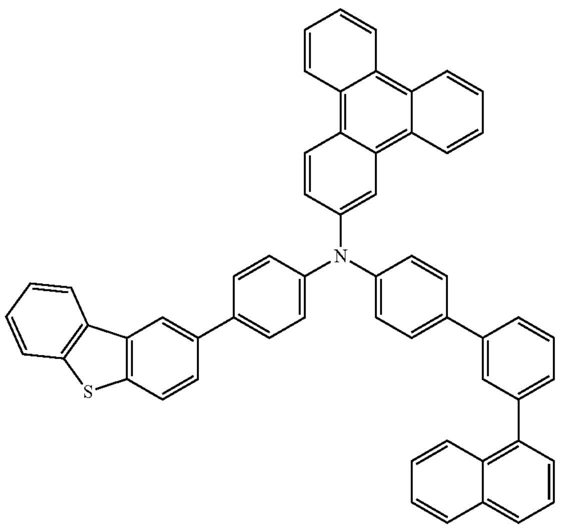
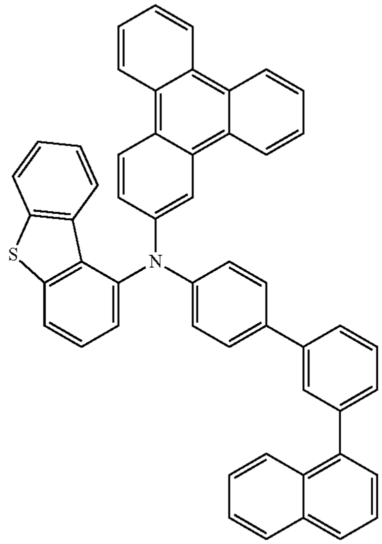
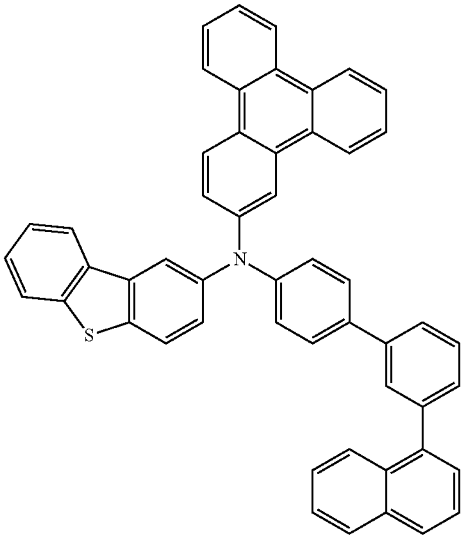
-continued
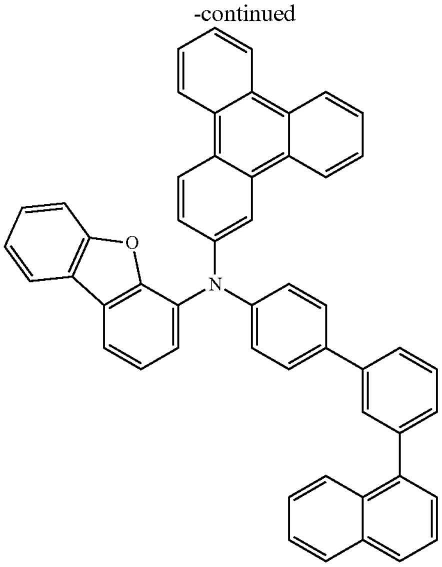
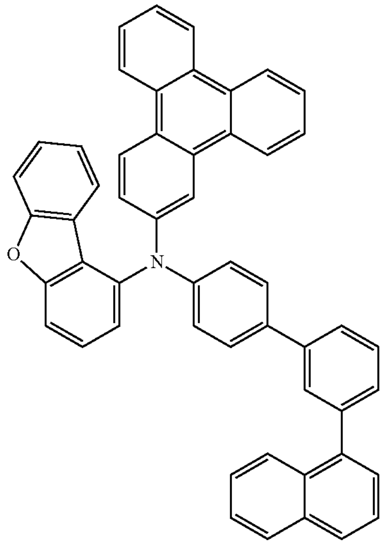
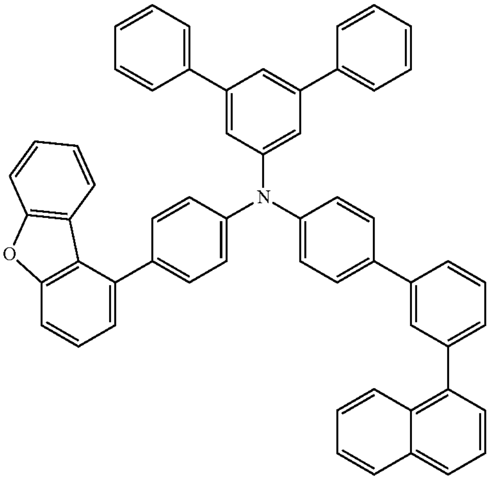

-continued
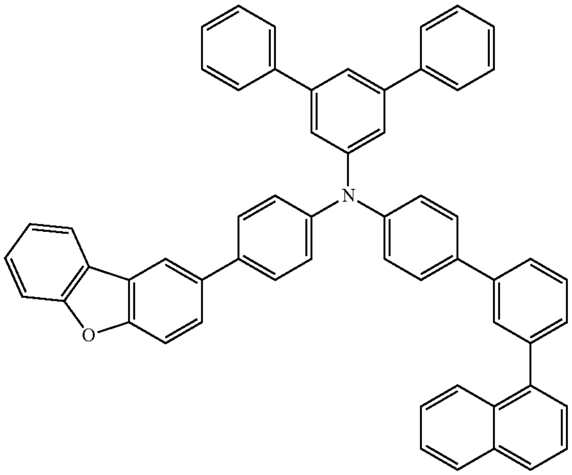
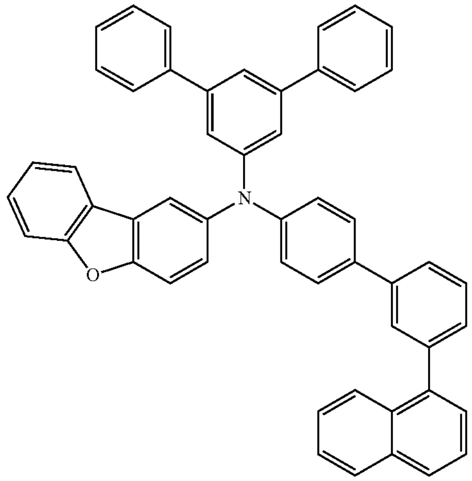
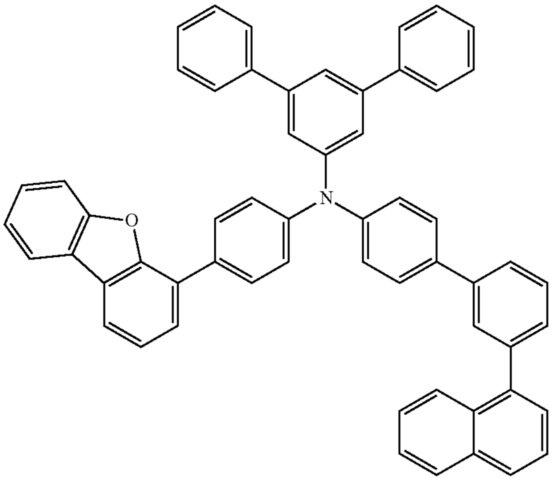
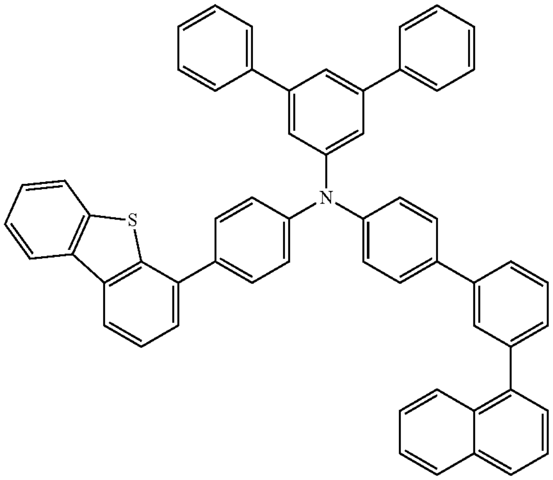
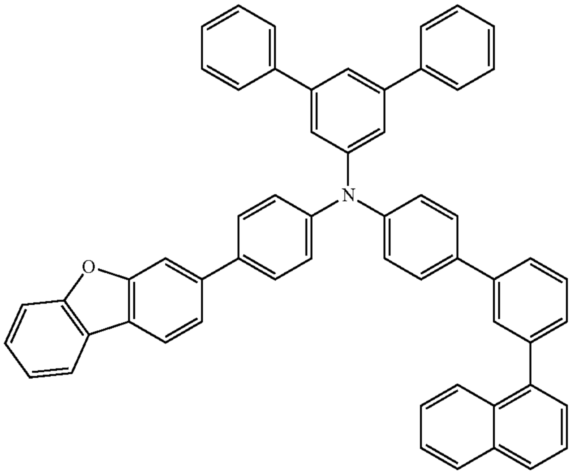
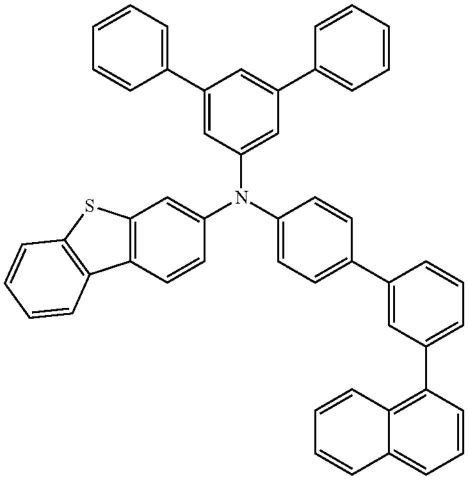
-continued

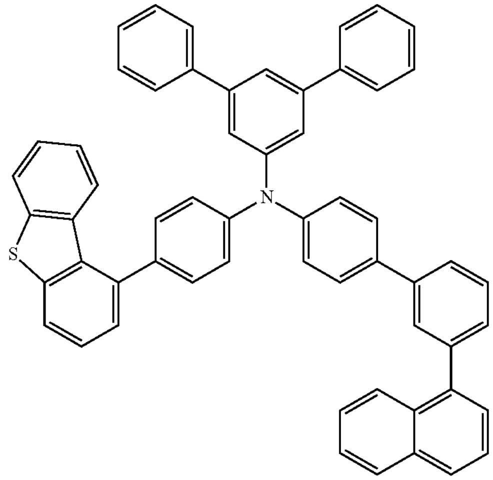
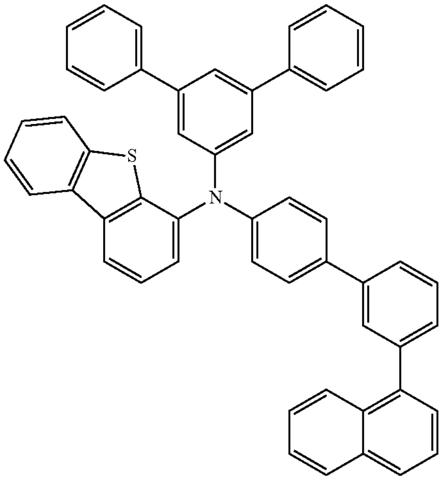
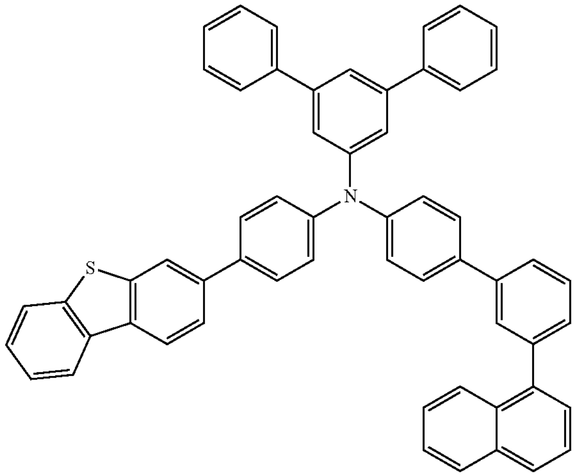
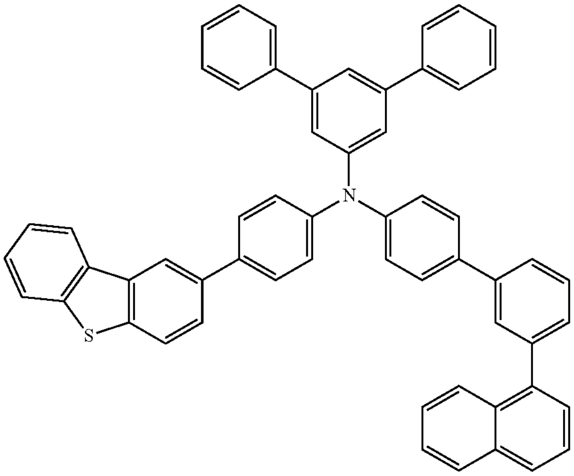
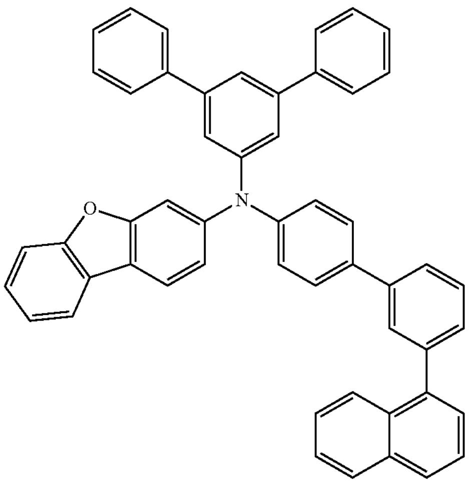
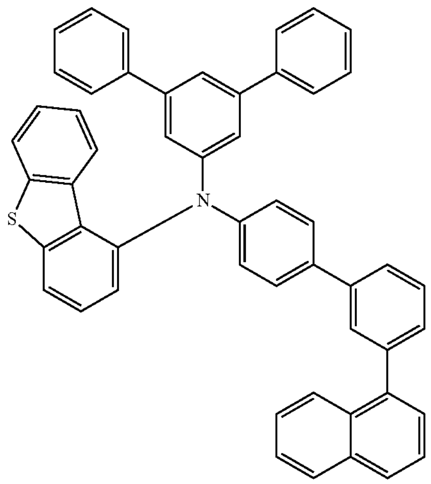

-continued
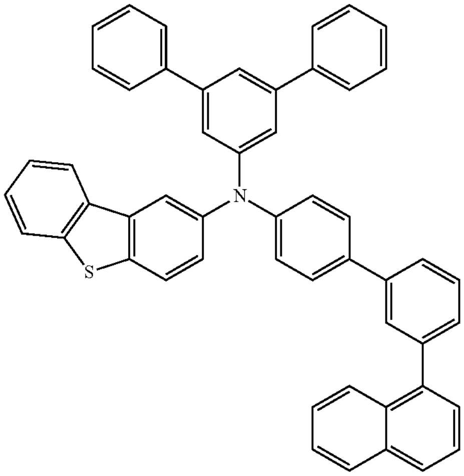
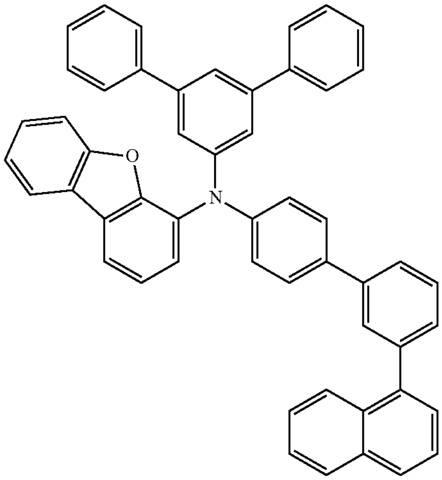
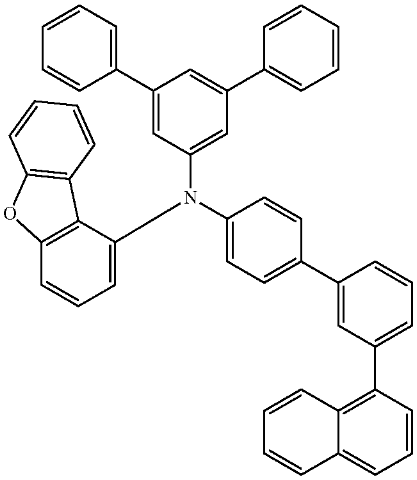
-continued
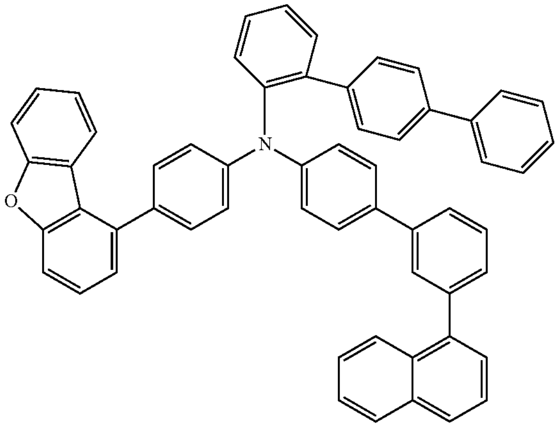
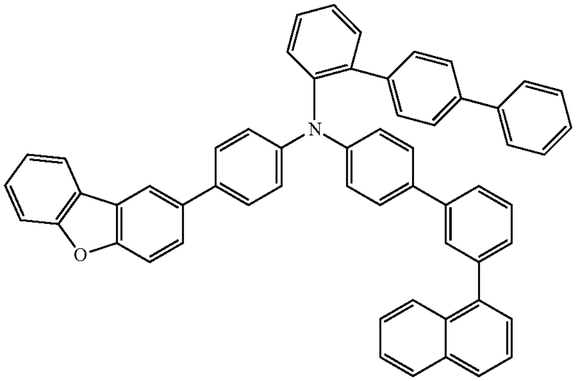
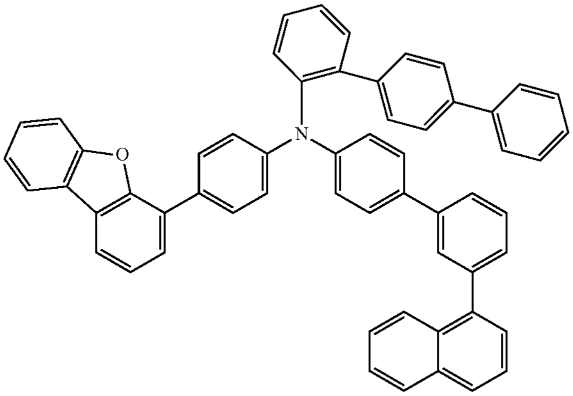
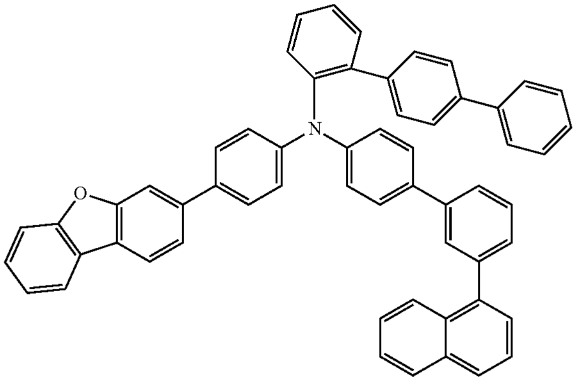

-continued
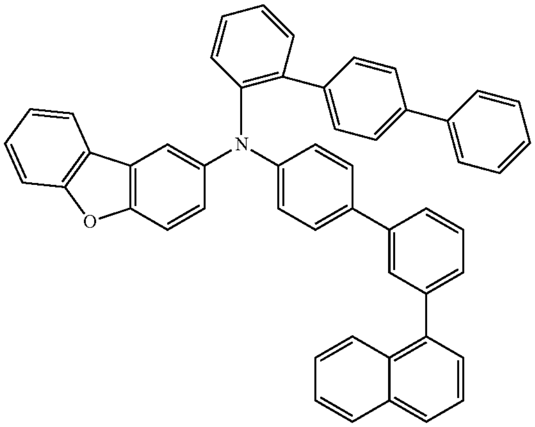
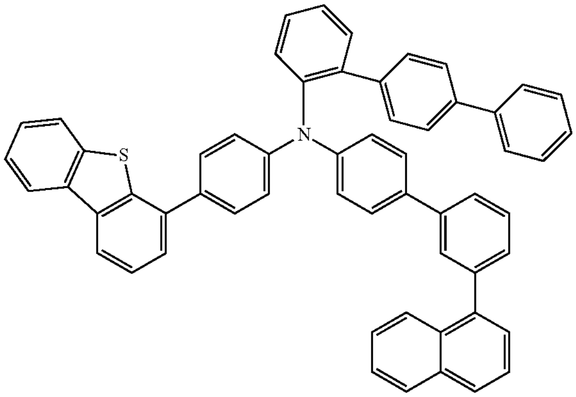
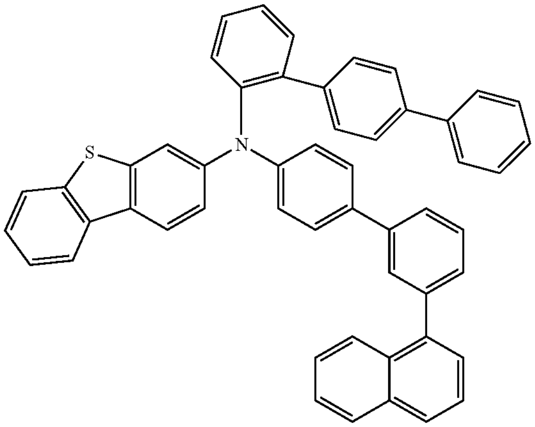
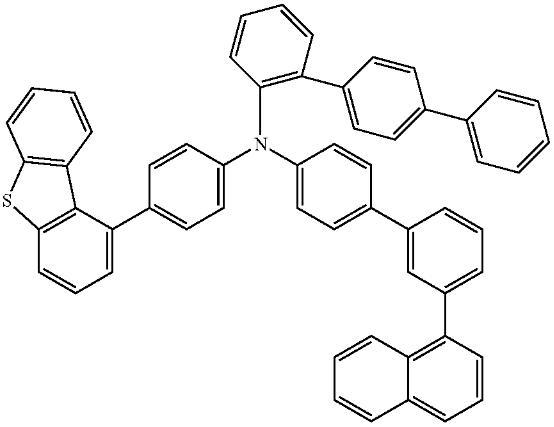
-continued
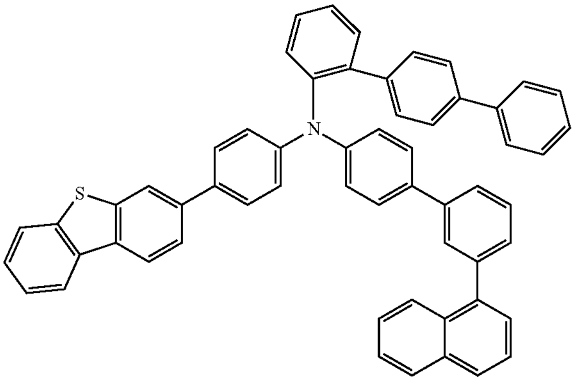
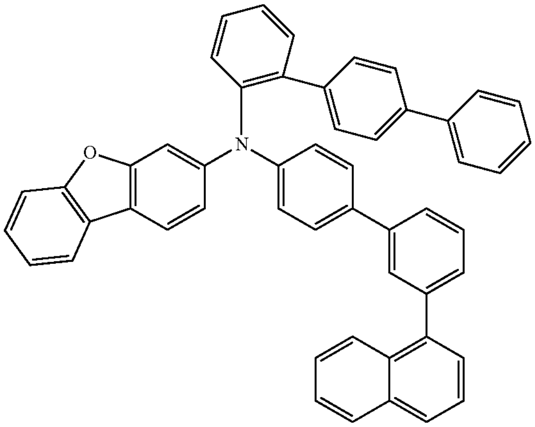
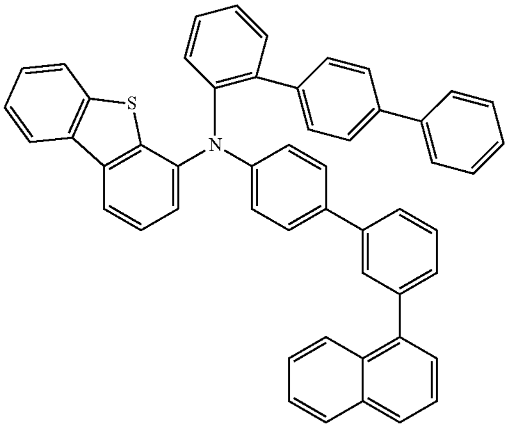
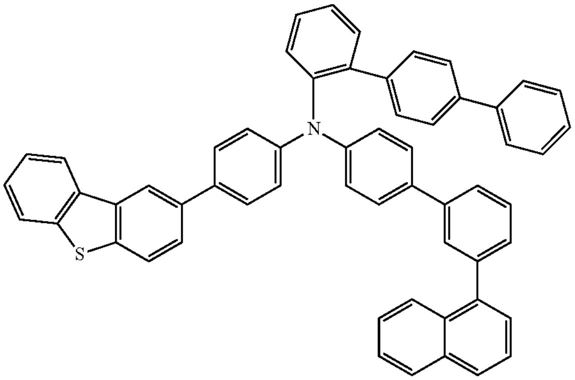

-continued
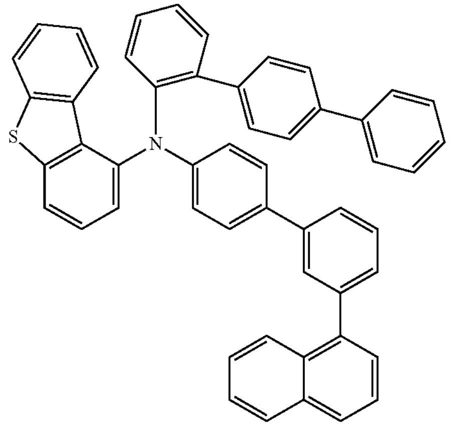
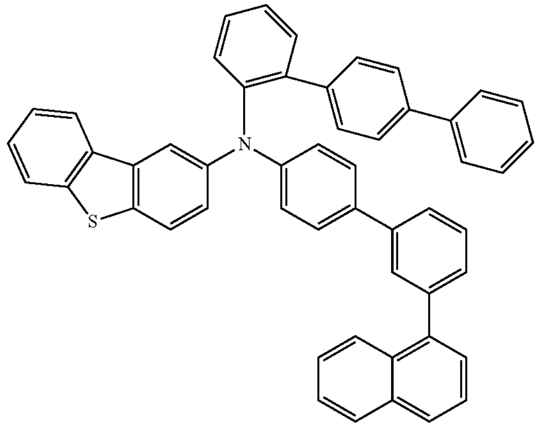
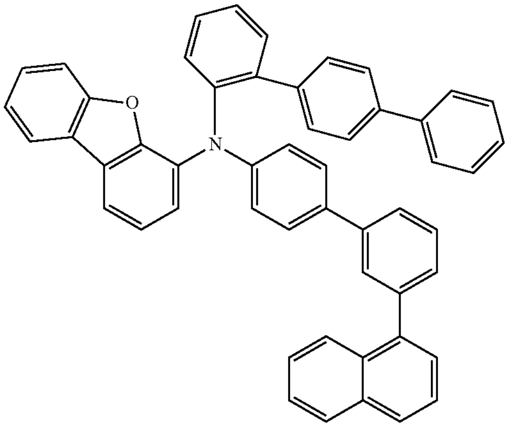
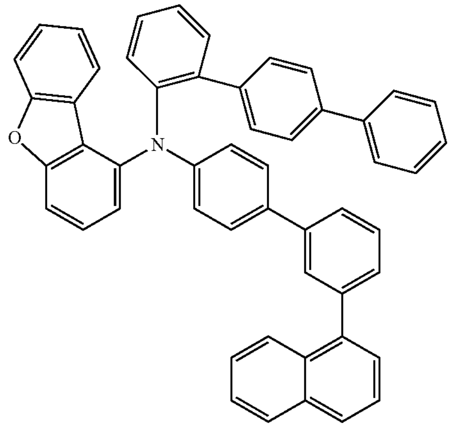
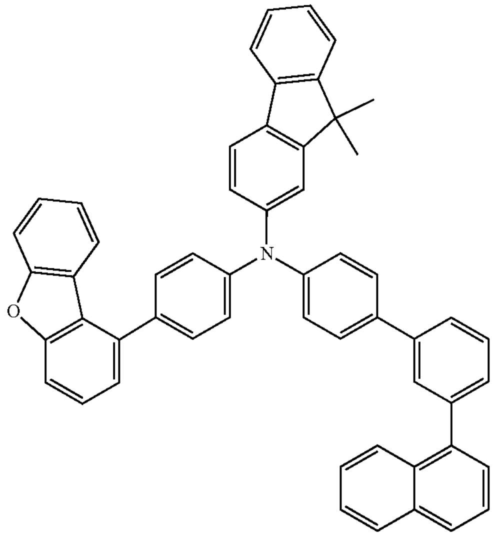
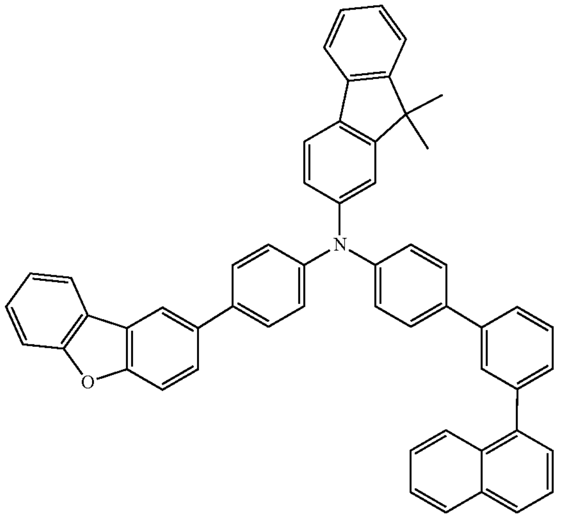
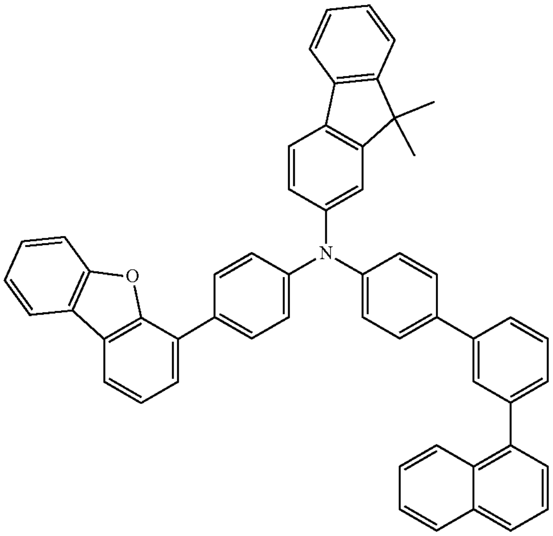

-continued
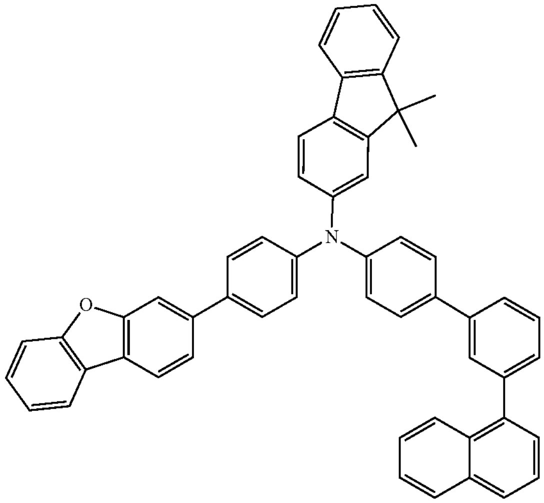
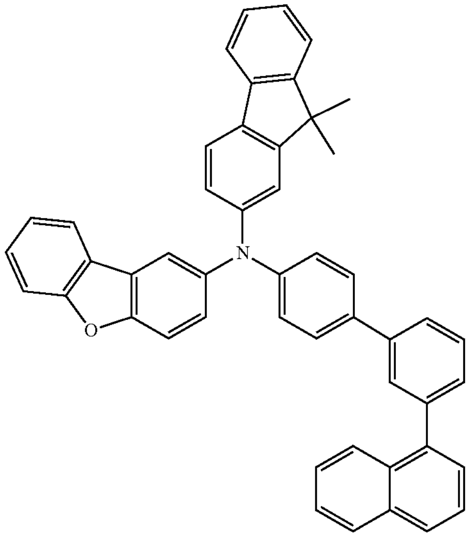
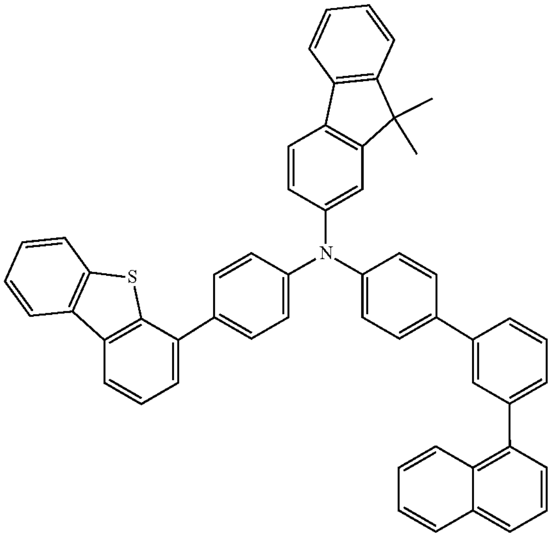
-continued
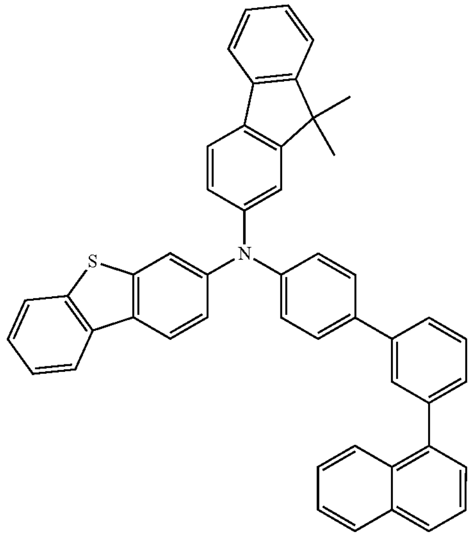
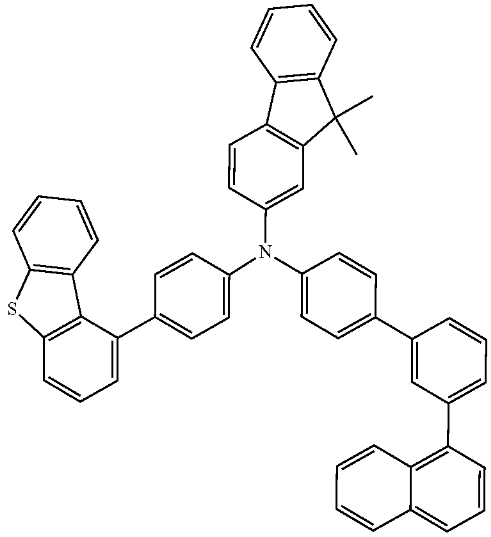
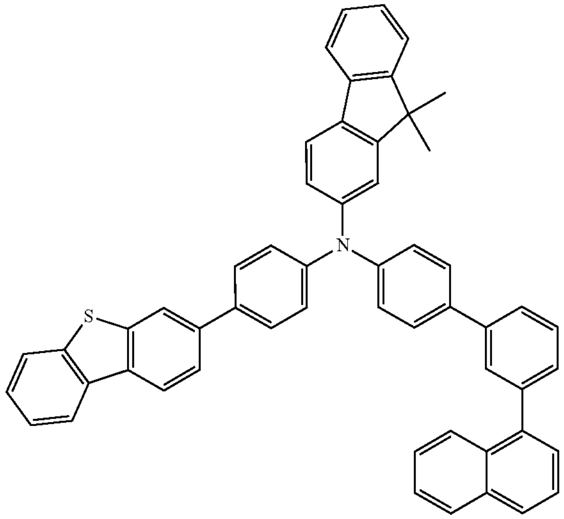

-continued
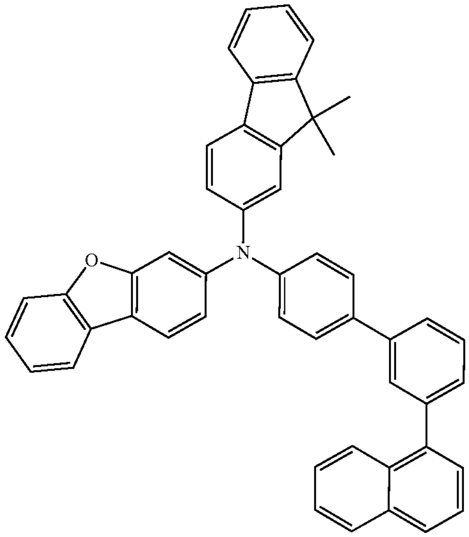
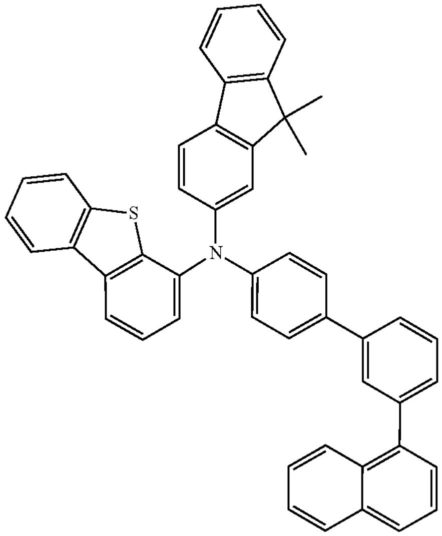
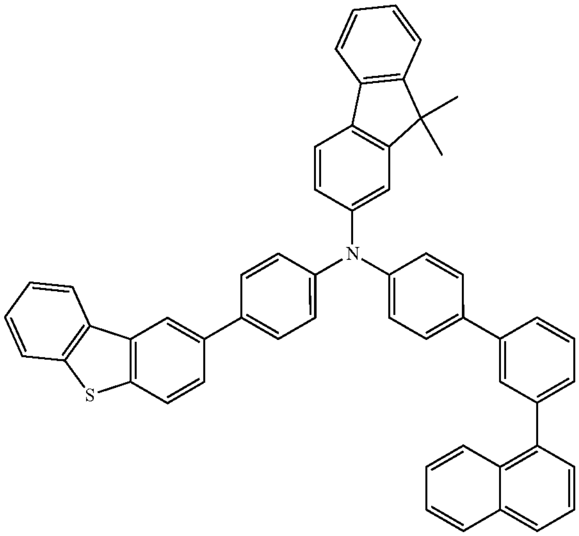
-continued
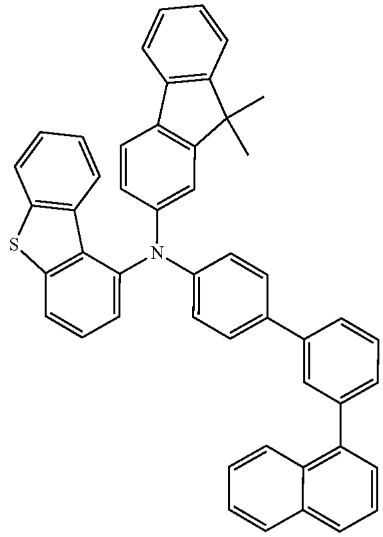 [SMILES: CC1(C)c2ccccc2-c2ccc(N(c3ccc(-c4cccc(-c5cccc6ccccc56)c4)cc3)c3cccc4sc5ccccc5c34)cc21]
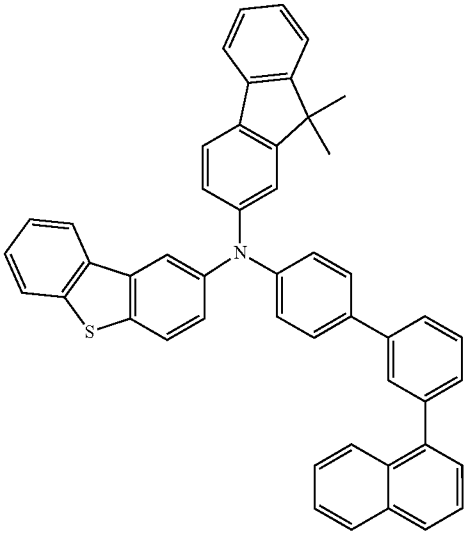
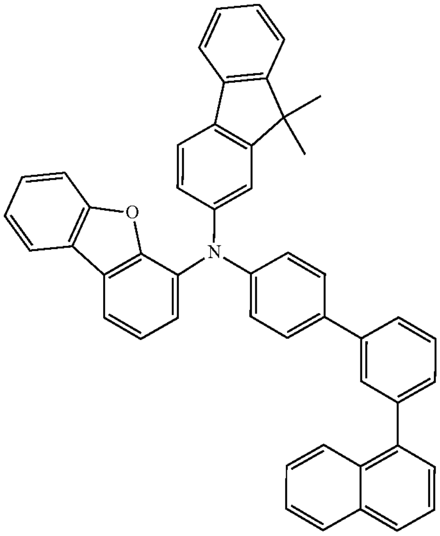

-continued
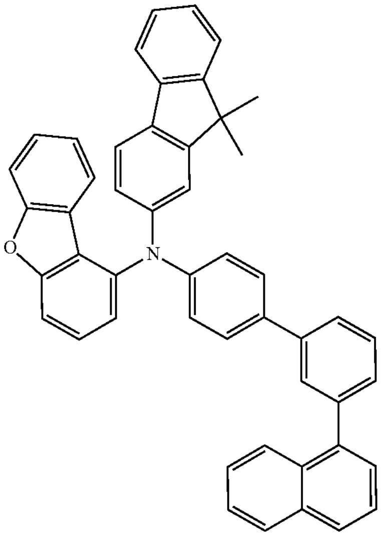
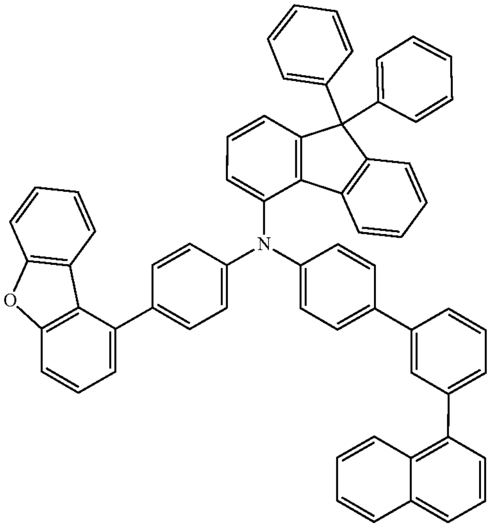
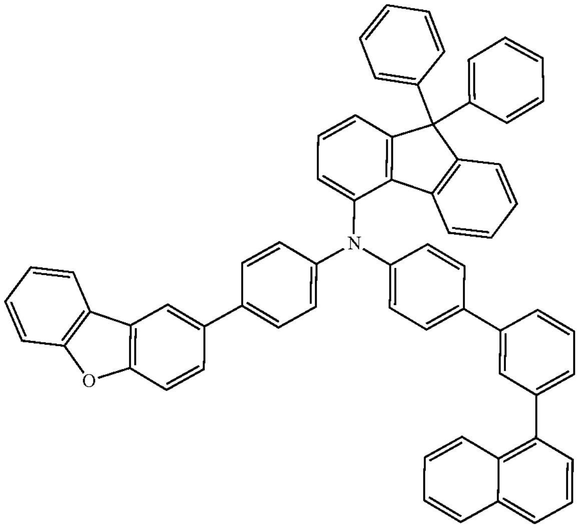
-continued
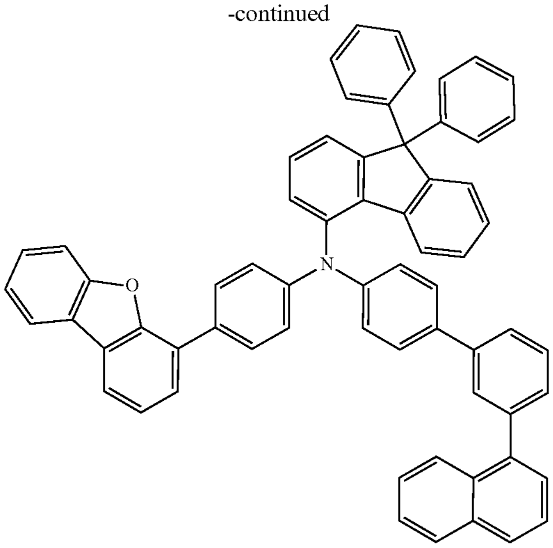
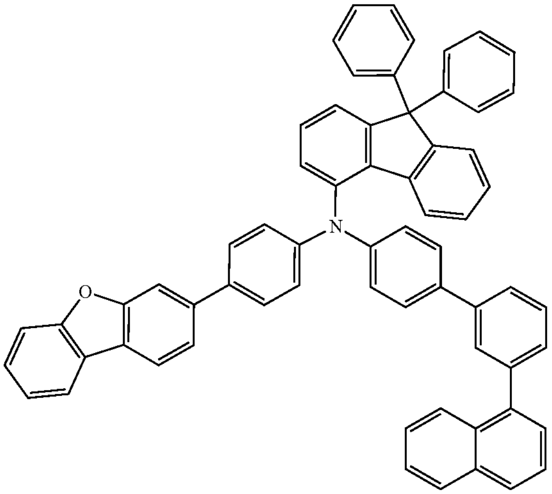 [SMILES: c1ccc(C2(c3ccccc3)c3ccccc3-c3c(N(c4ccc(-c5cccc(-c6cccc7ccccc67)c5)cc4)c4ccc(-c5ccc6c(c5)oc5ccccc56)cc4)cccc32)cc1]
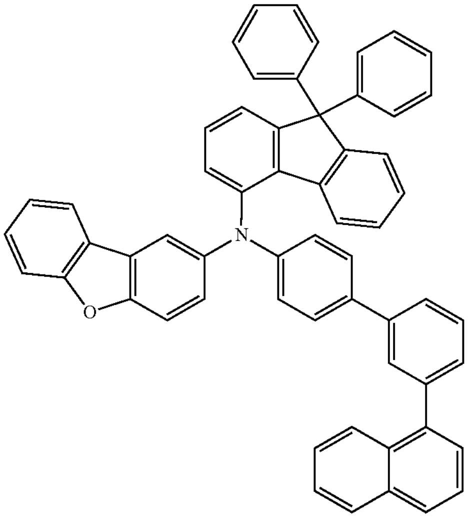

-continued
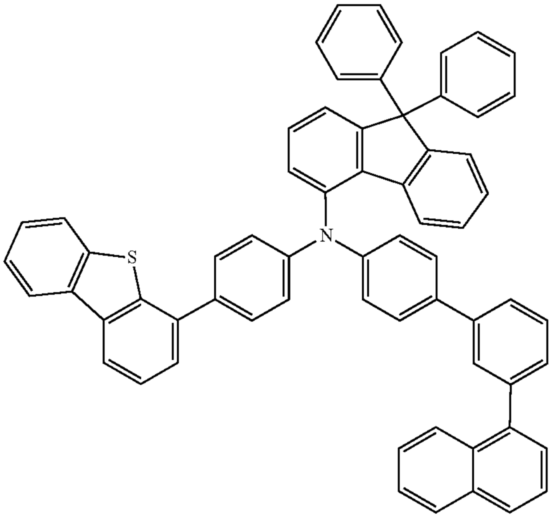
-continued
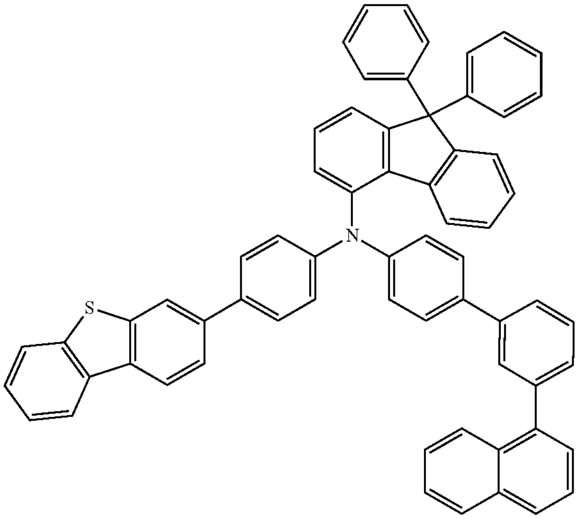
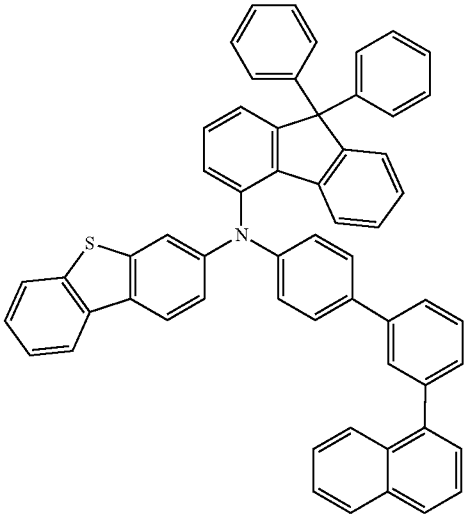
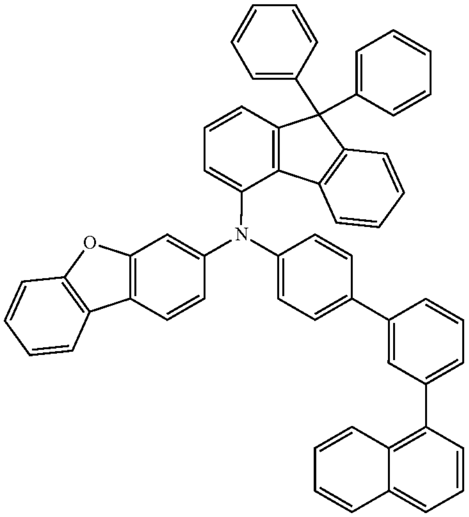
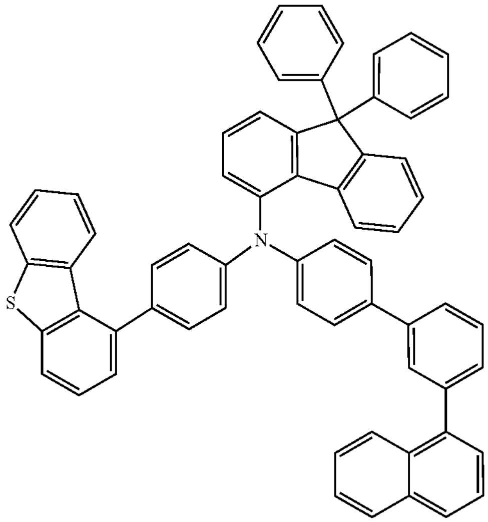
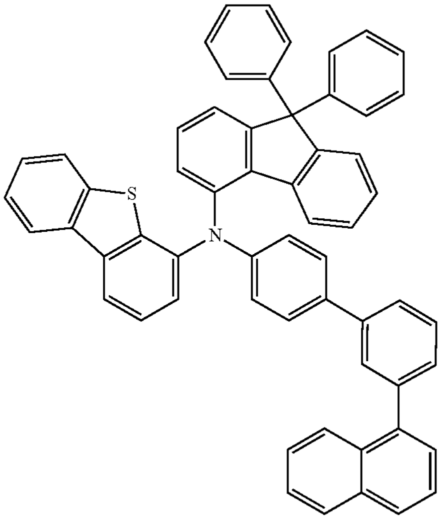

-continued
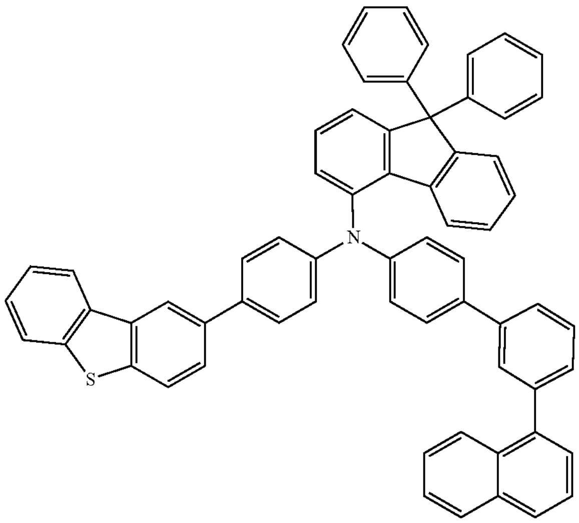
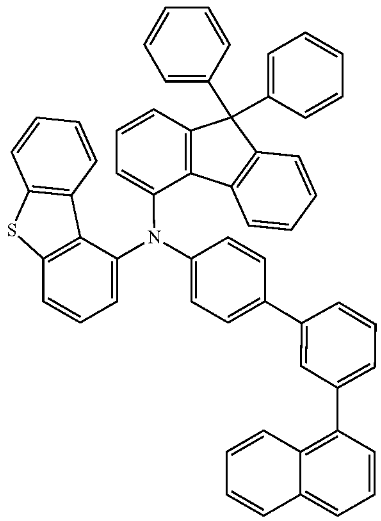
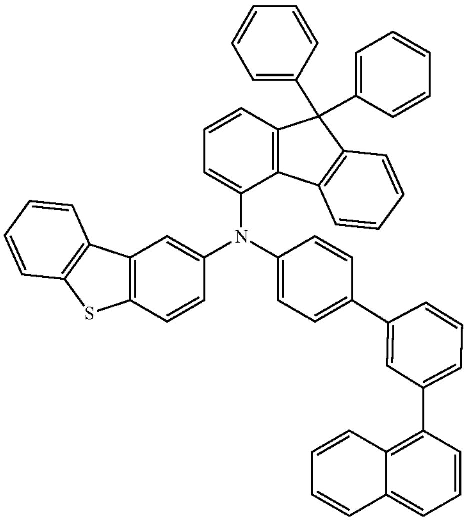
-continued
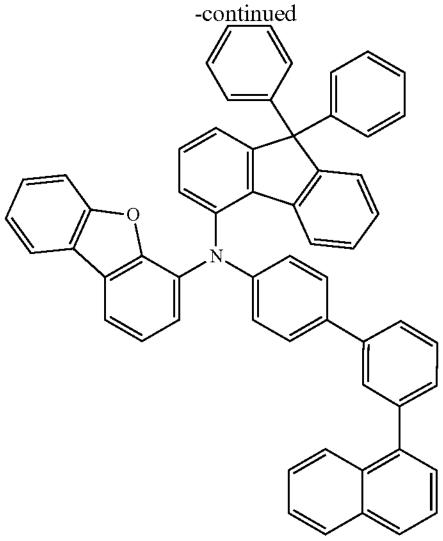
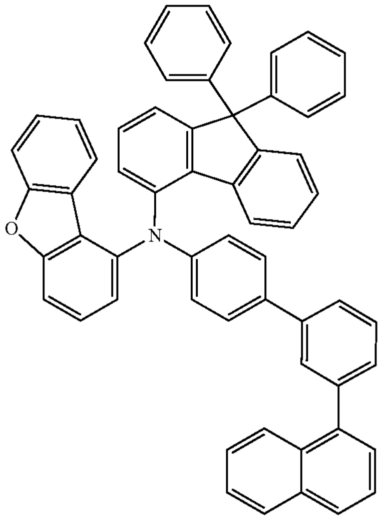
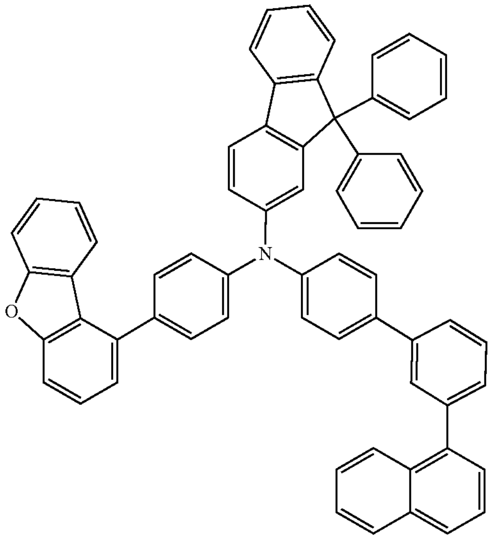

-continued
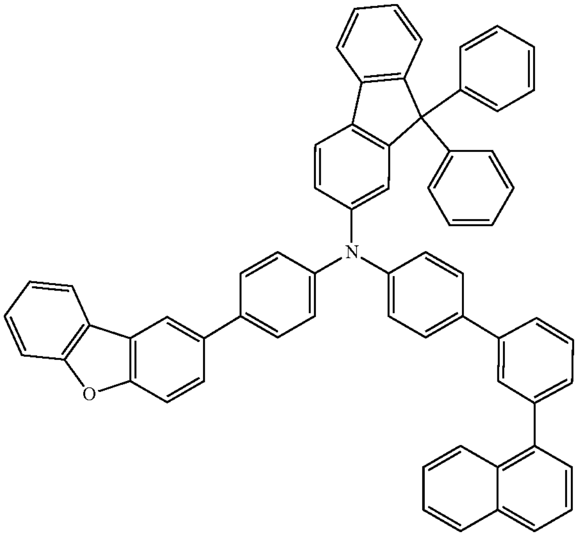
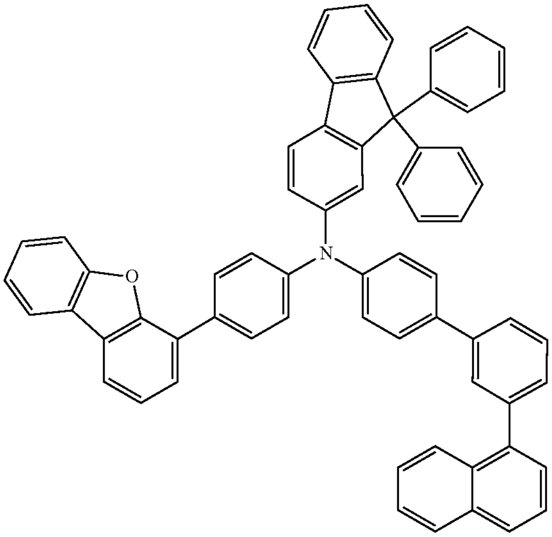
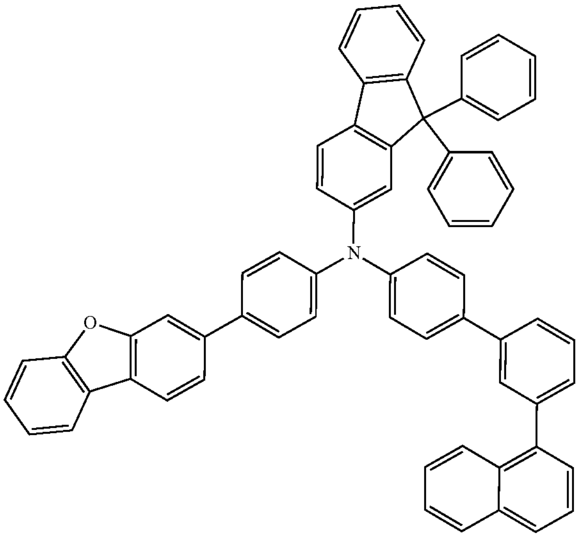
-continued
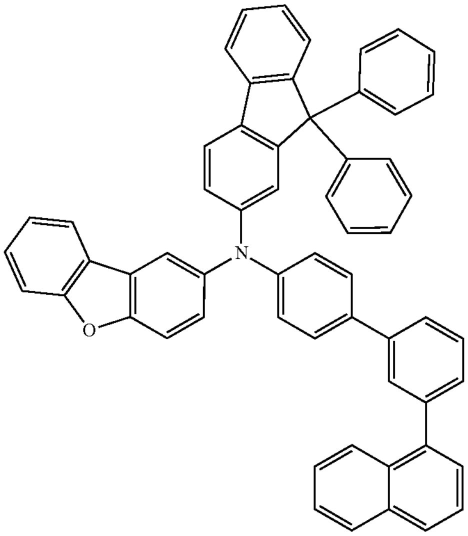
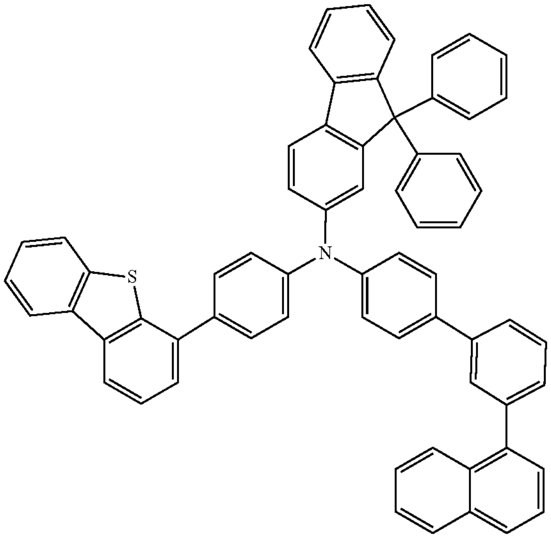
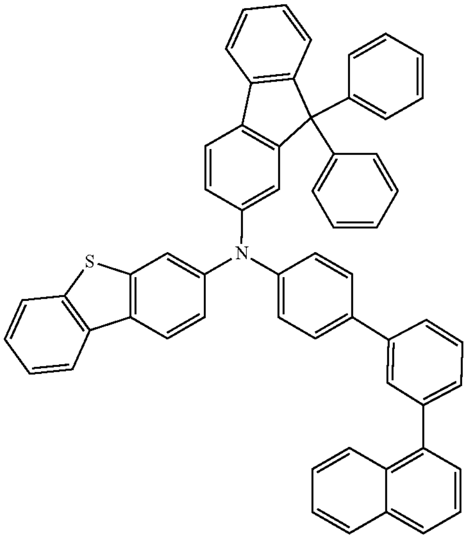

-continued
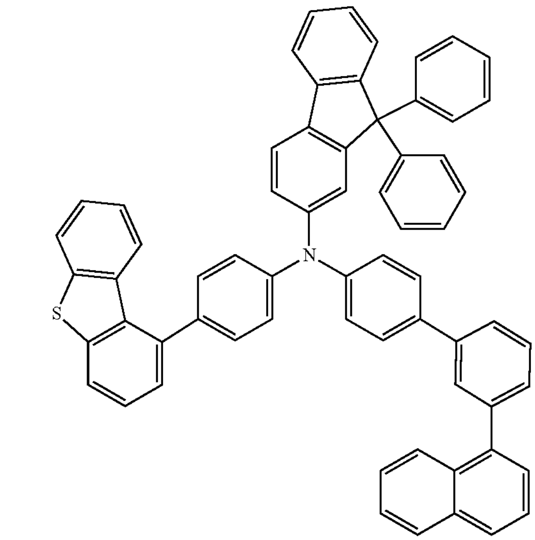
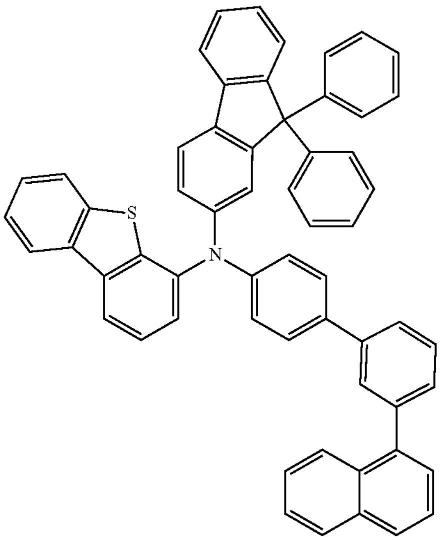
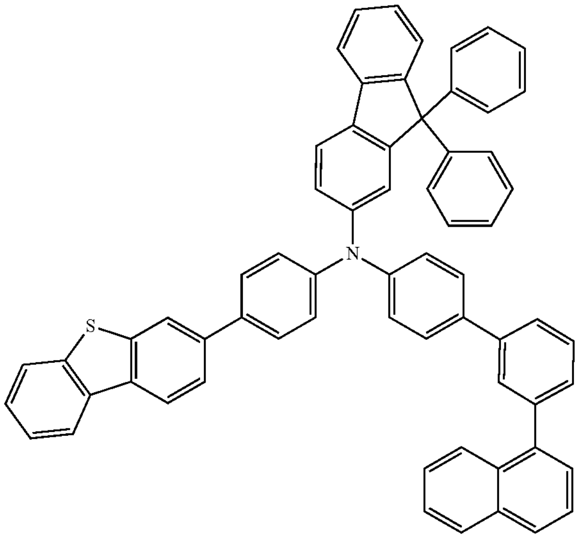
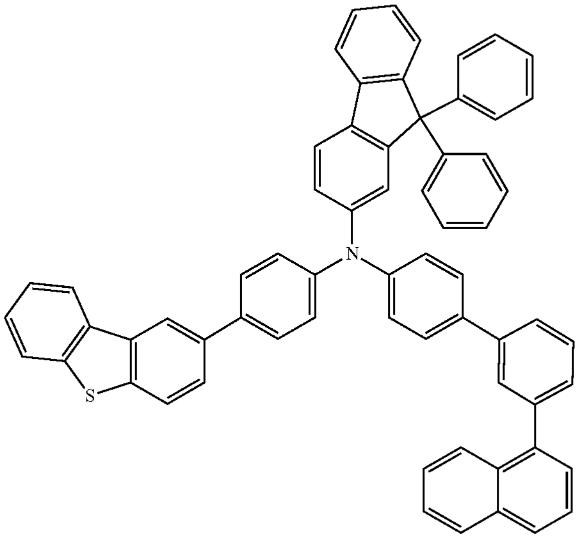
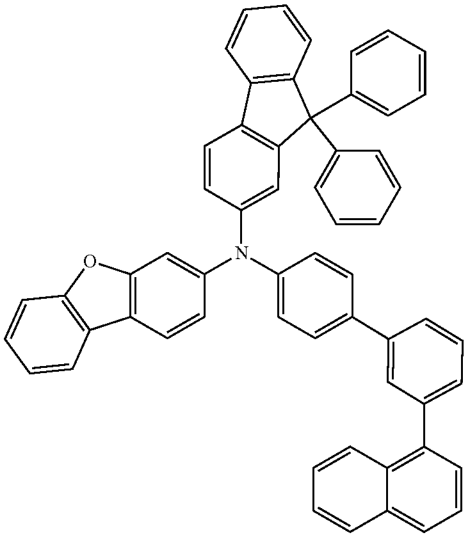
-continued
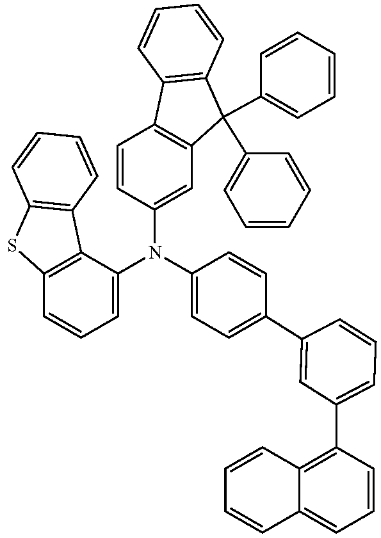

-continued
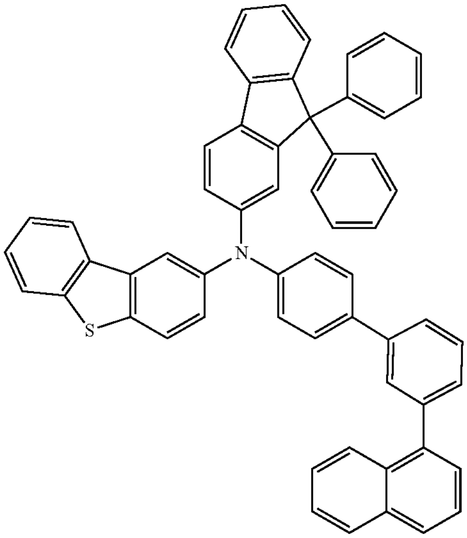
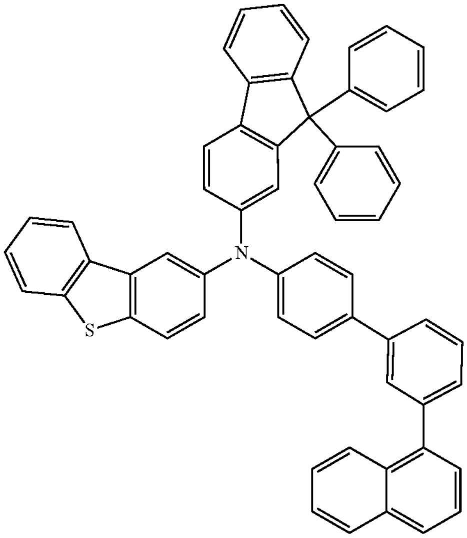
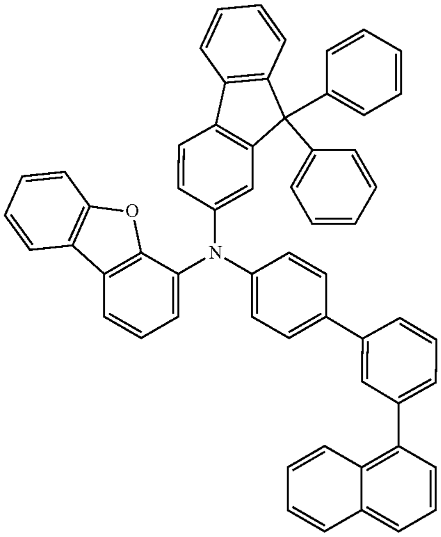
-continued
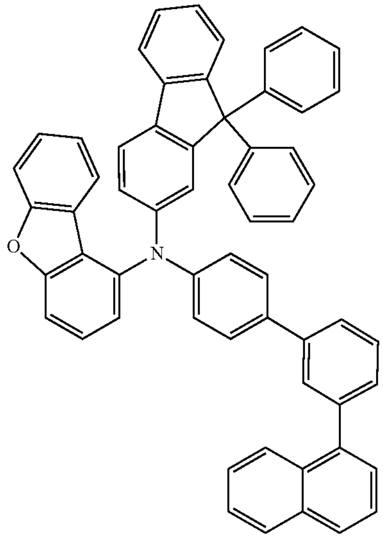
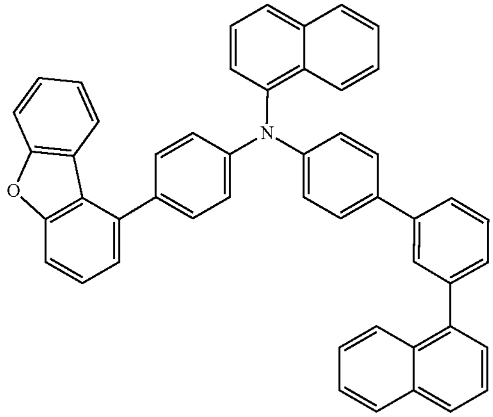
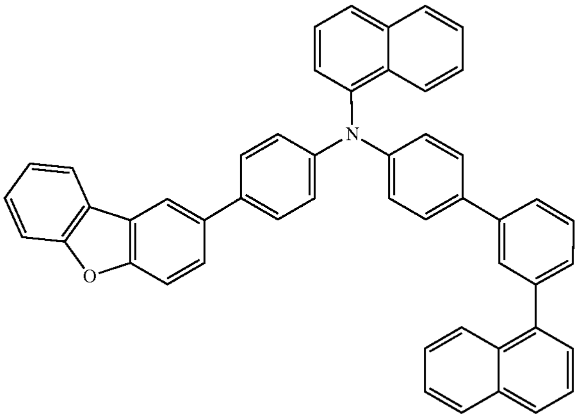

-continued
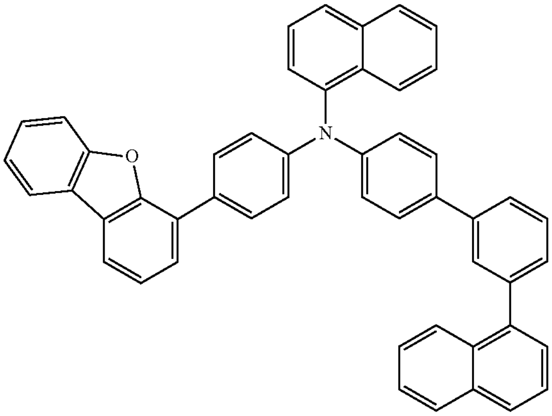
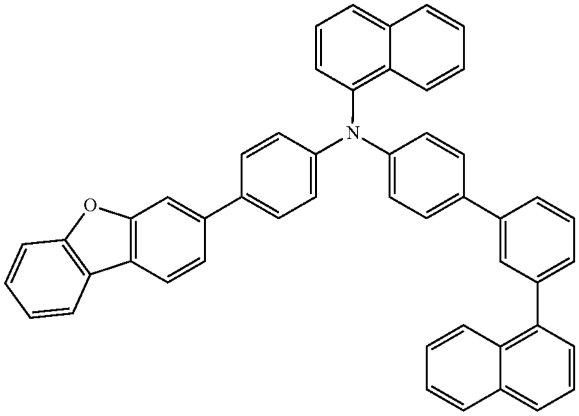
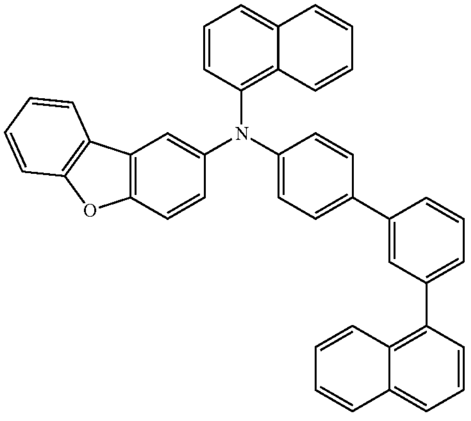
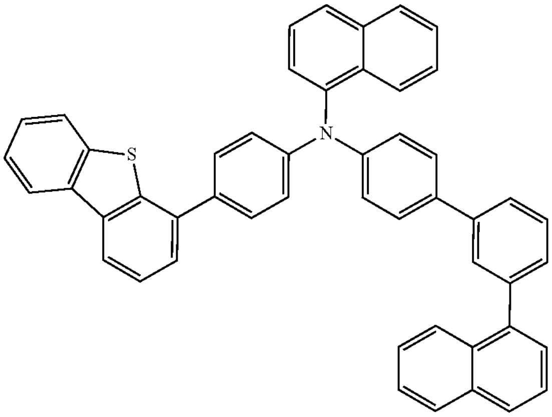
-continued
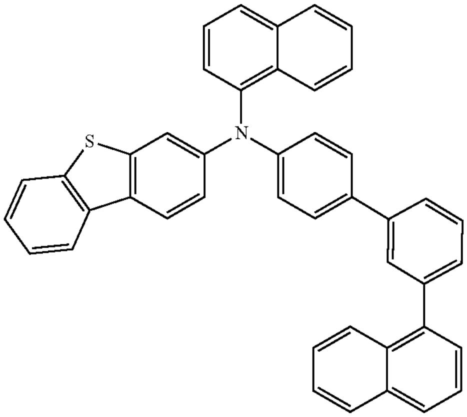
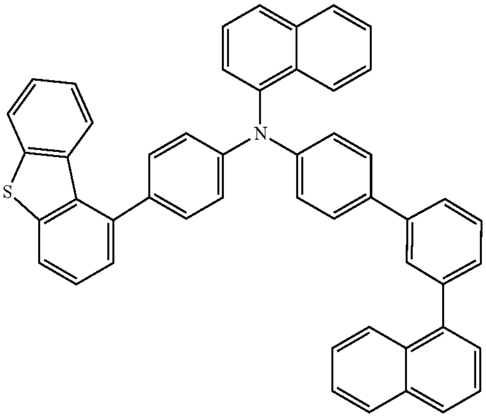
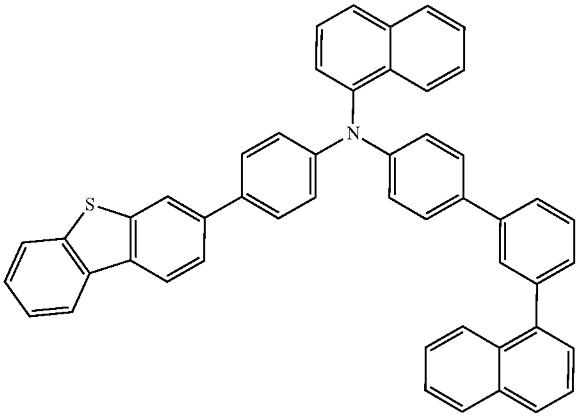
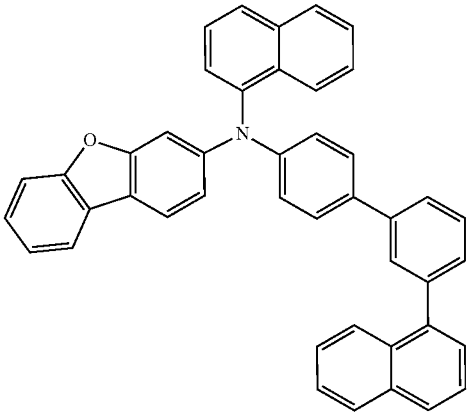

-continued
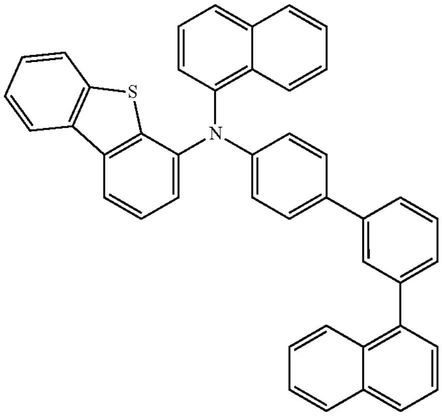
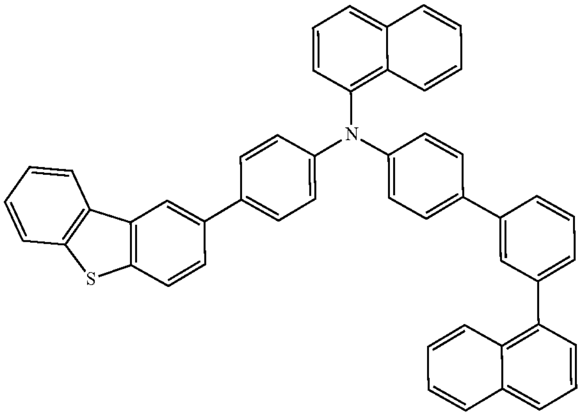
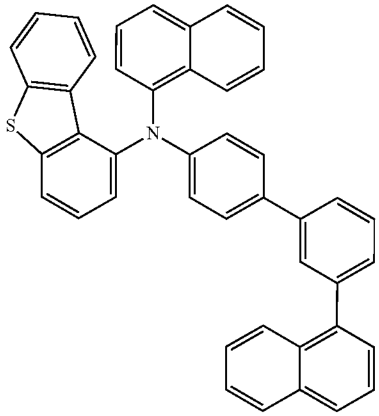
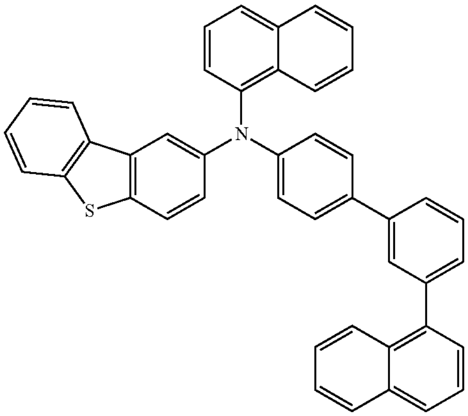
-continued
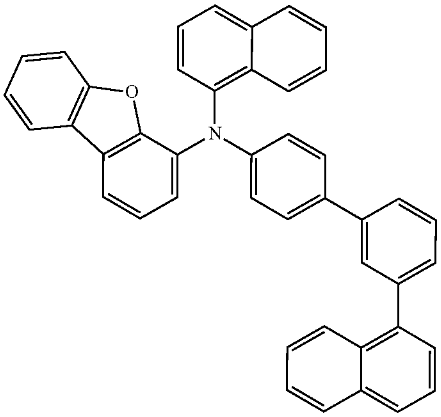
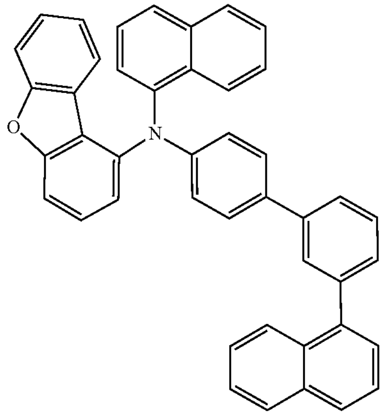
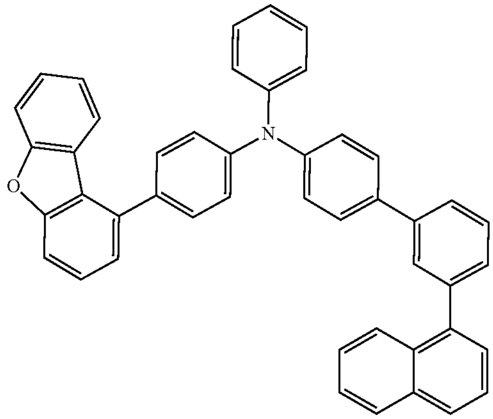
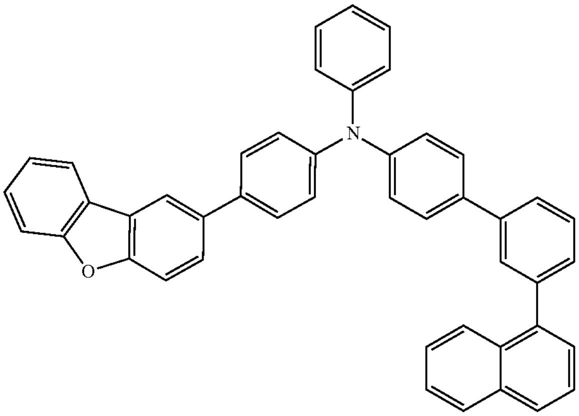

-continued
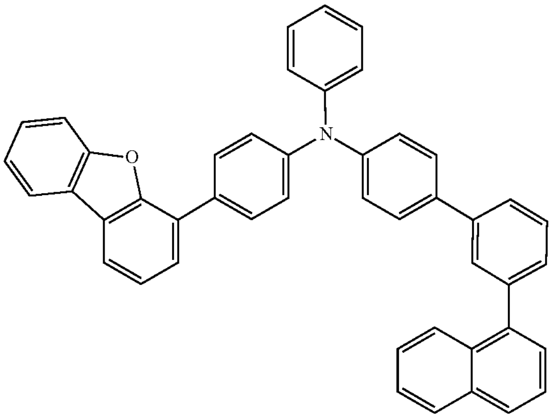
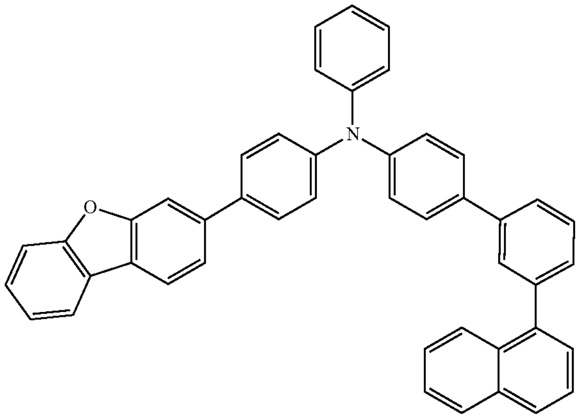
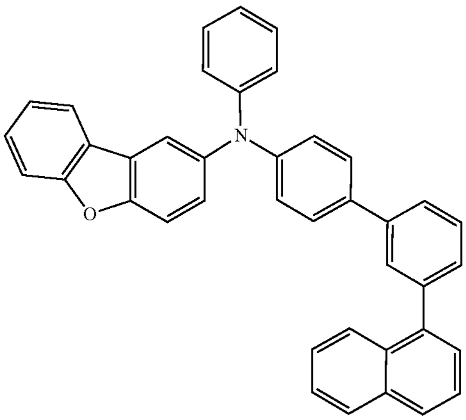
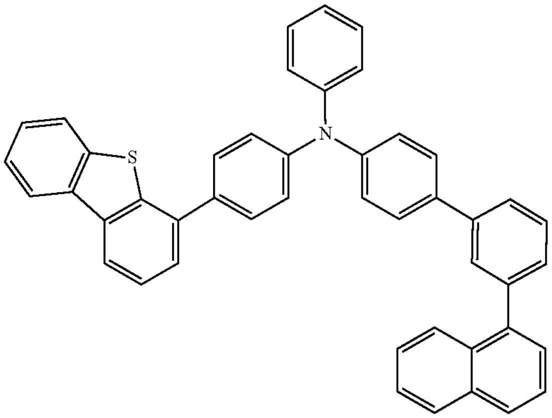
-continued
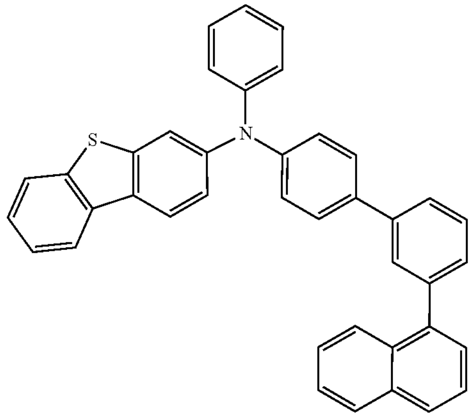
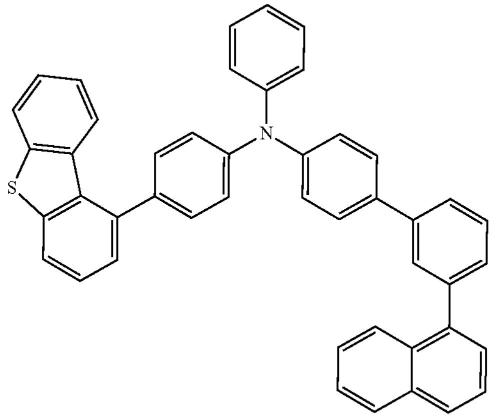
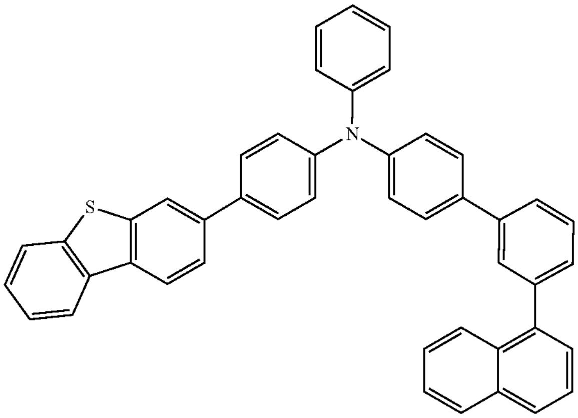
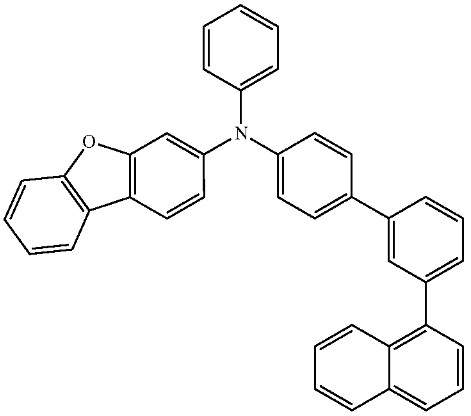

-continued
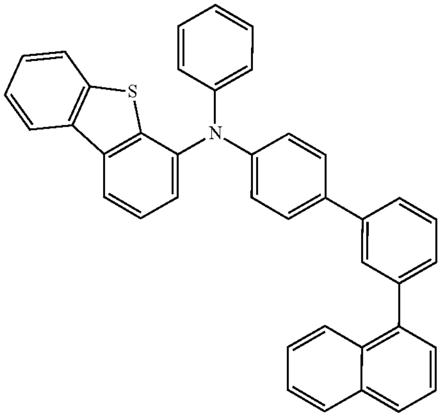
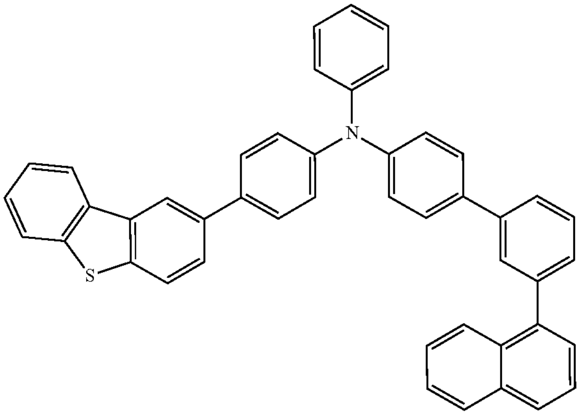
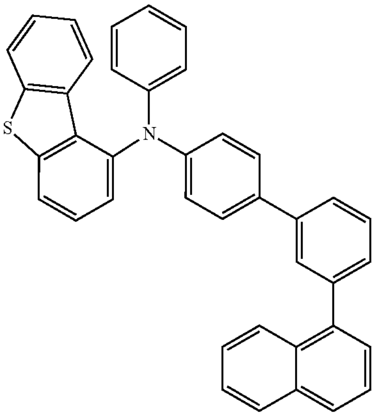
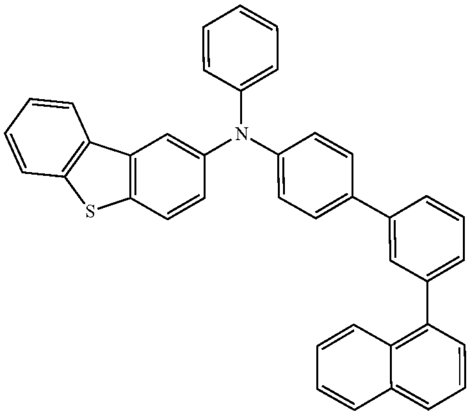
-continued
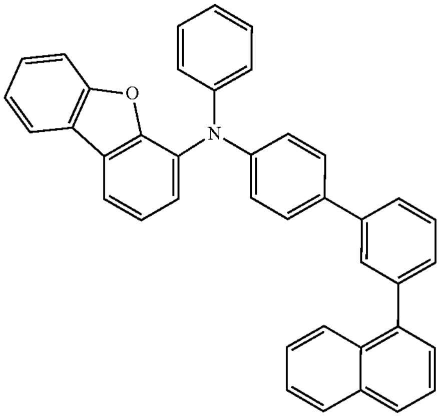
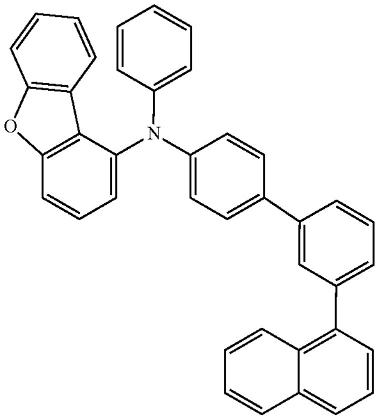
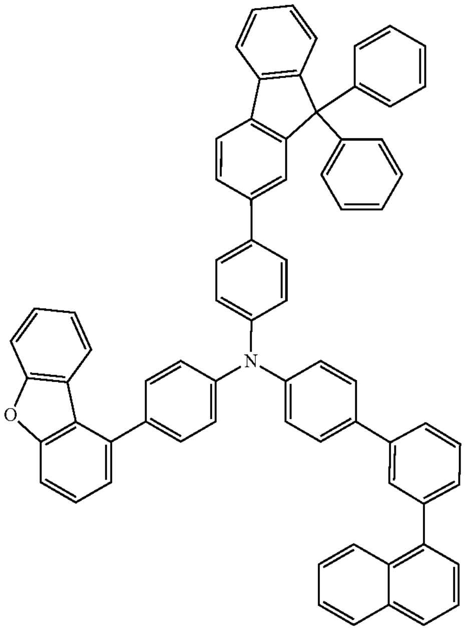

-continued
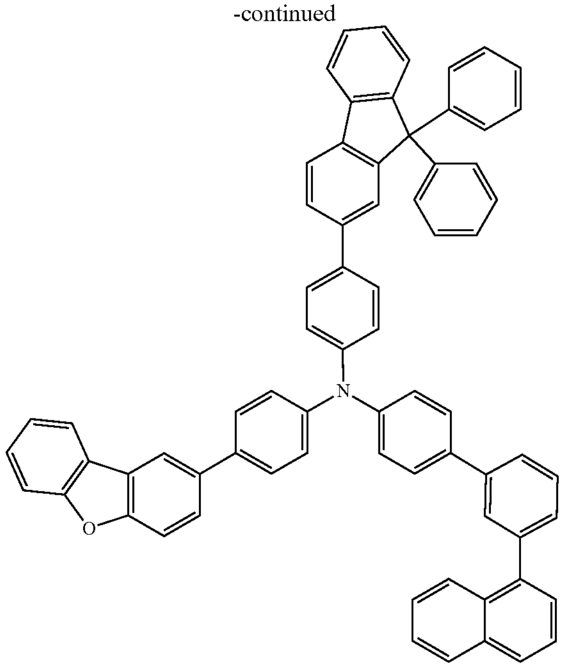
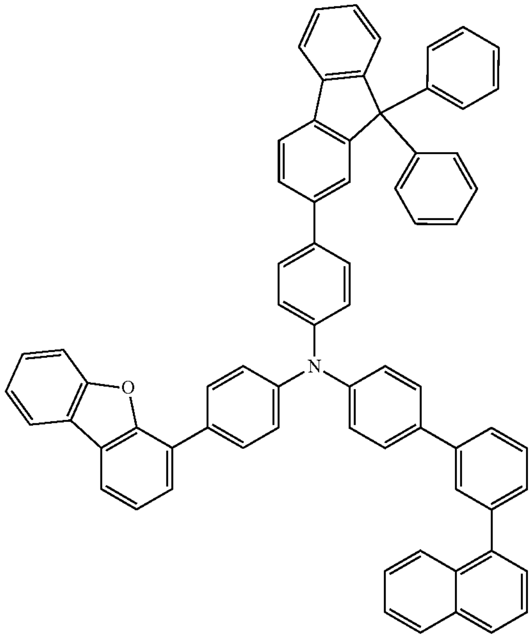
-continued
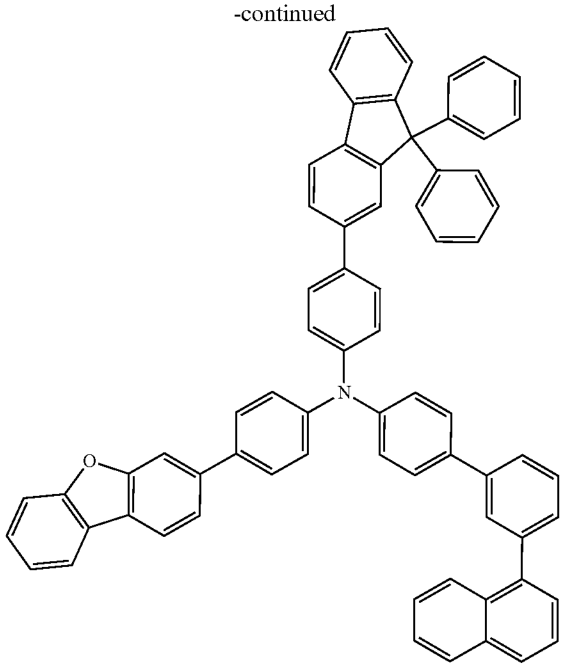
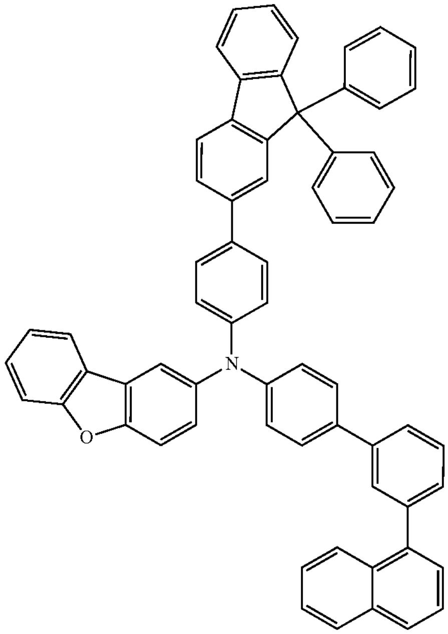

-continued
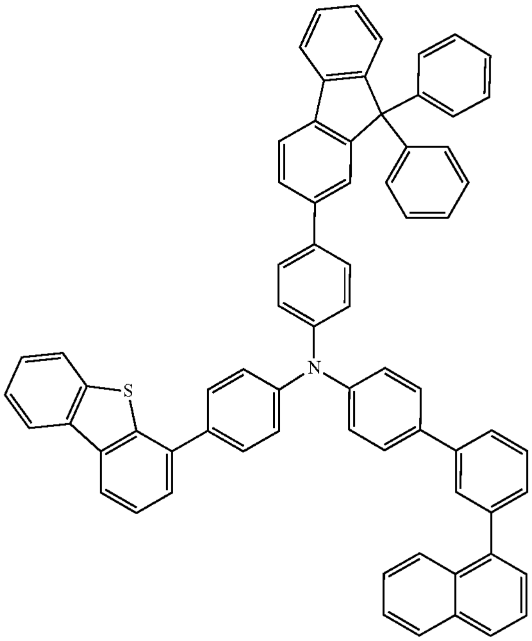
-continued
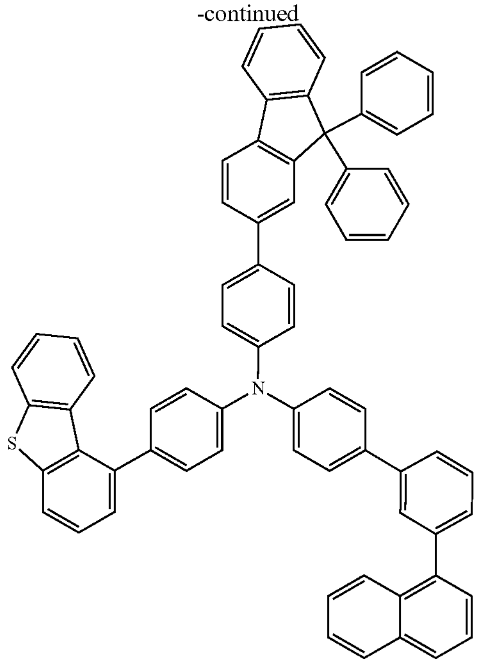
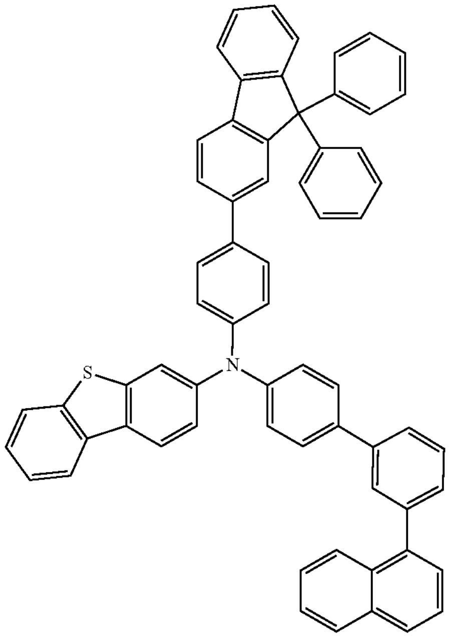
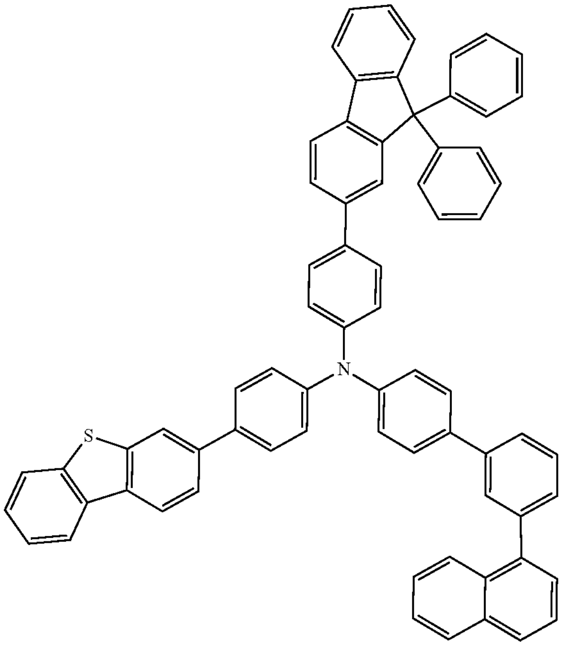

-continued
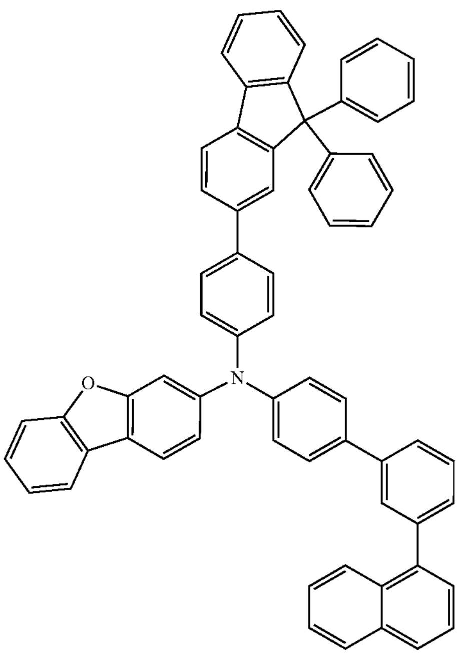
-continued
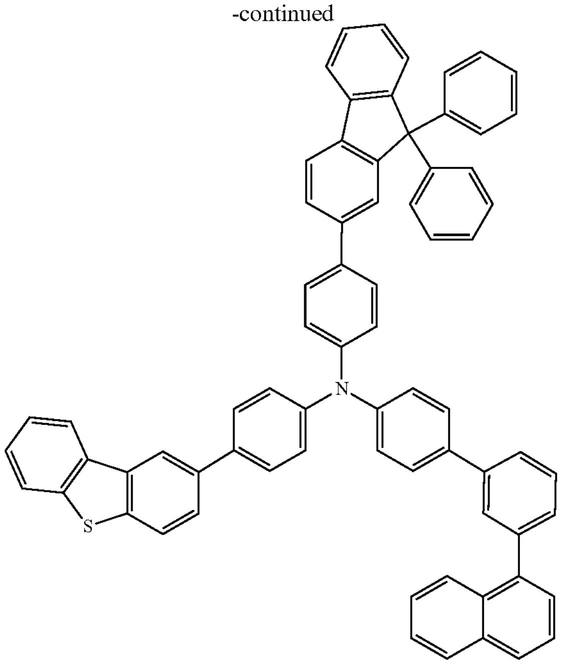
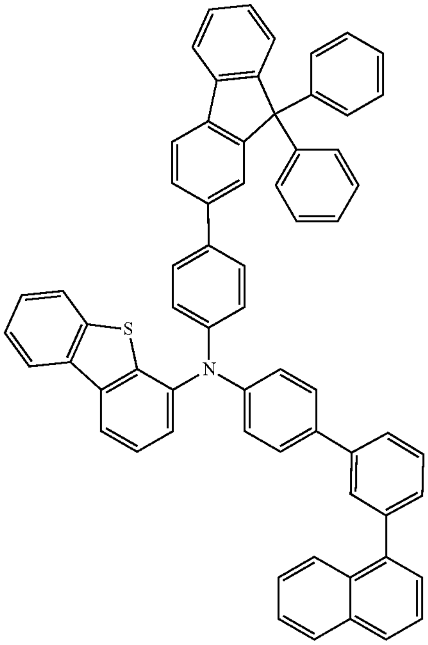
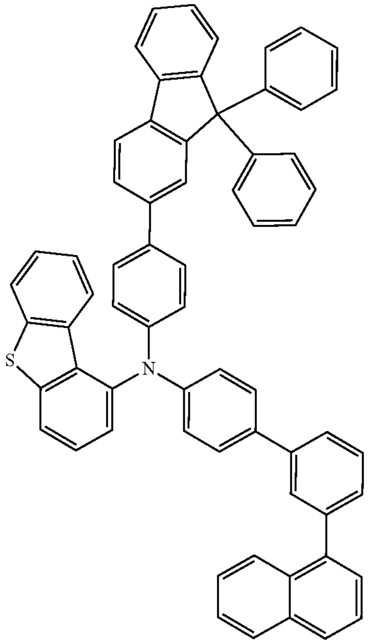

-continued
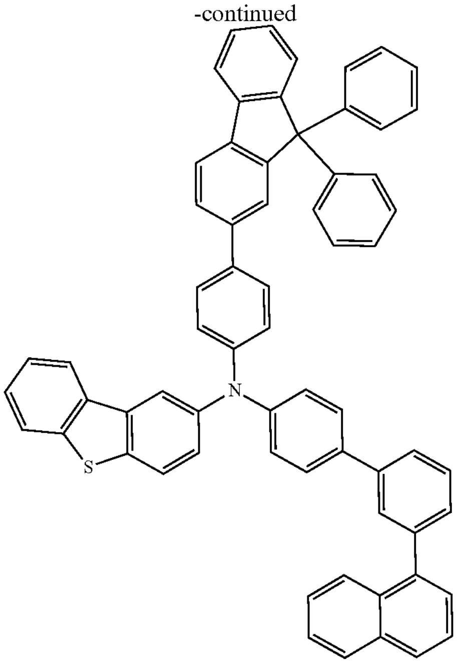
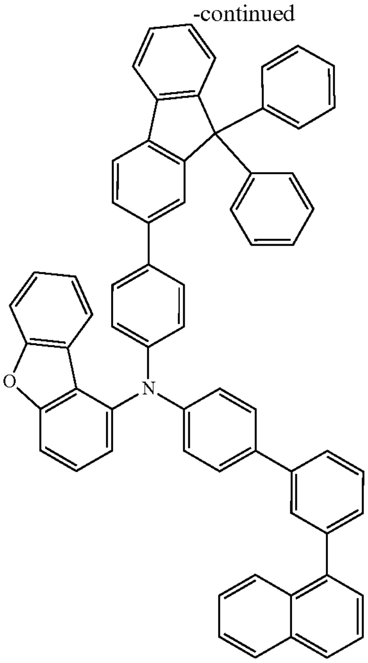
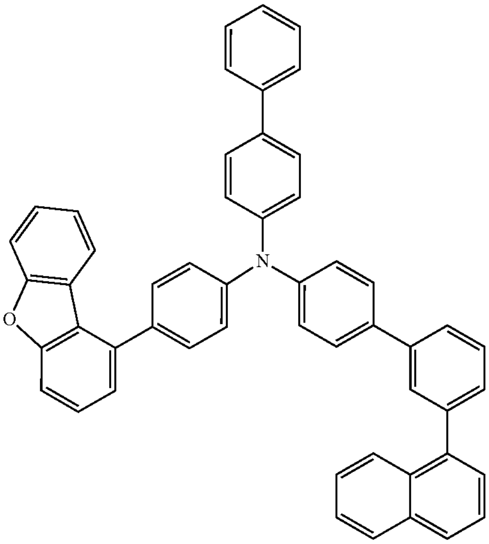
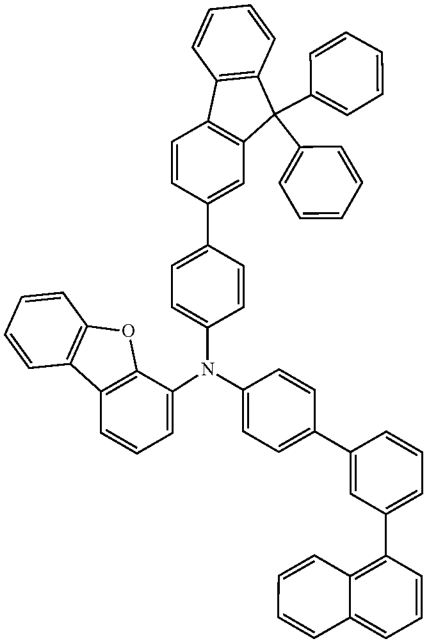
-continued
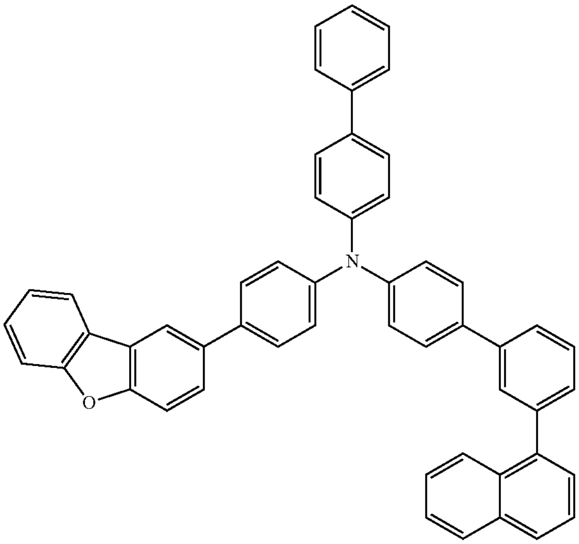

-continued
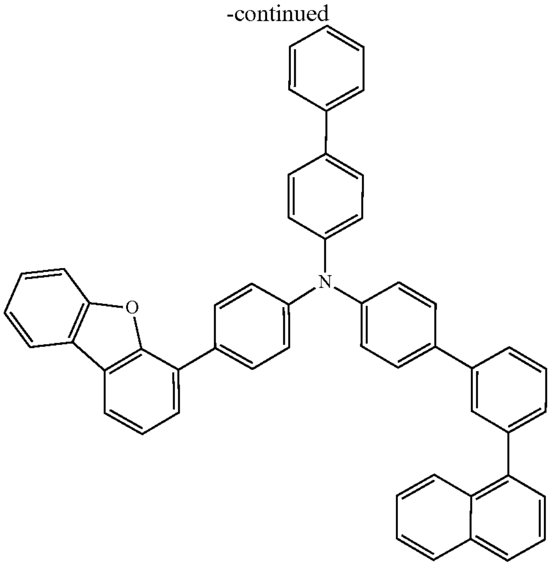
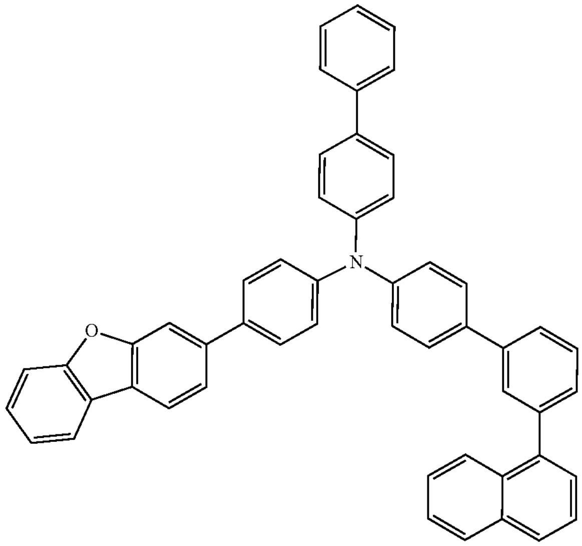
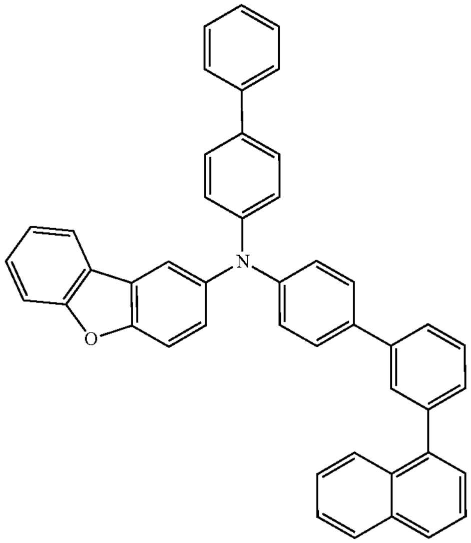
-continued
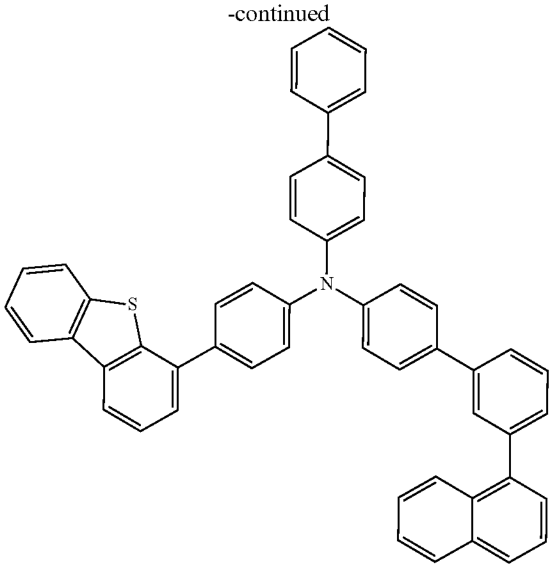
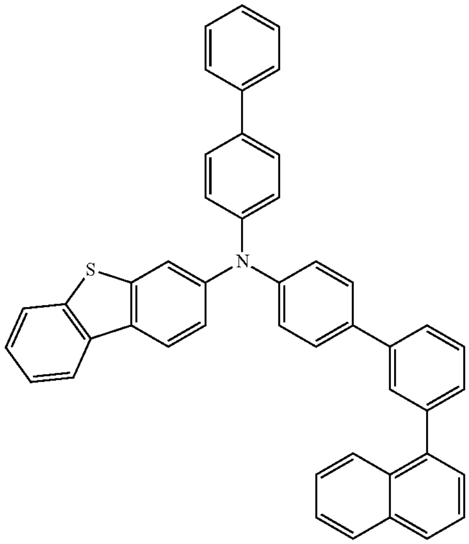
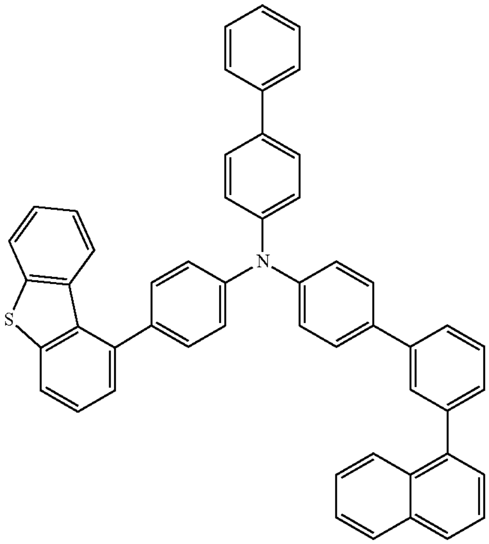

-continued
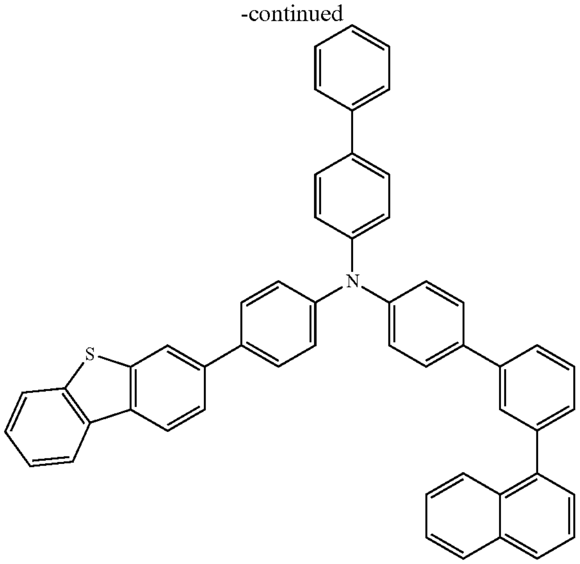
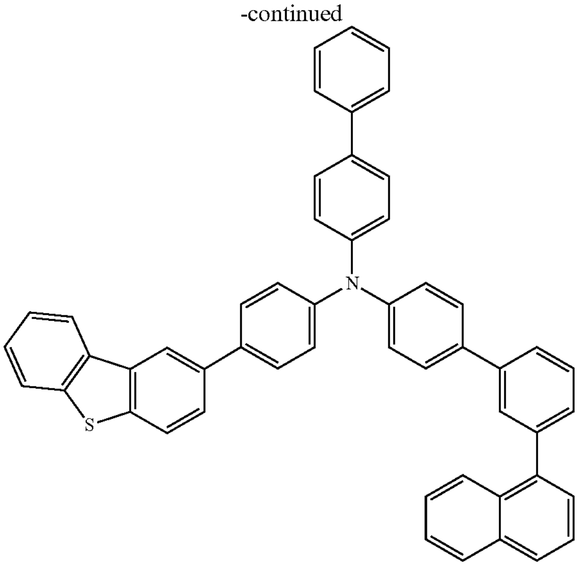
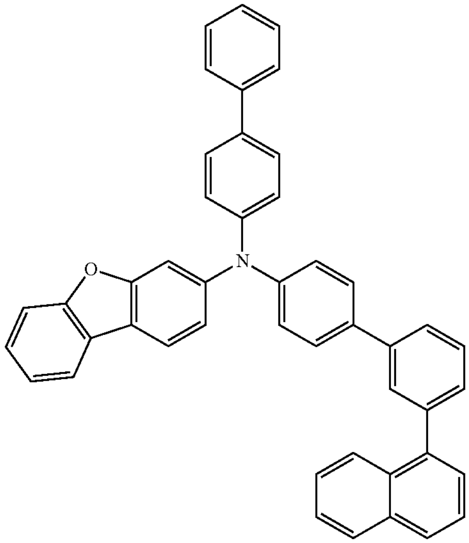
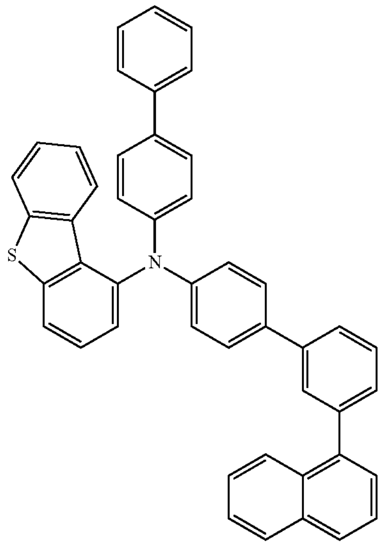 [SMILES: c1ccc(-c2ccc(N(c3ccc(-c4cccc(-c5cccc6ccccc56)c4)cc3)c3cccc4sc5ccccc5c34)cc2)cc1]
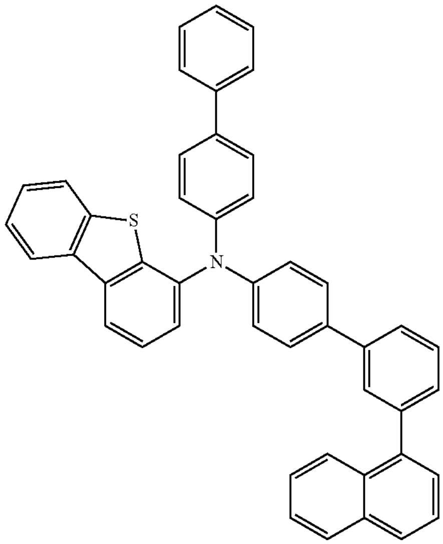
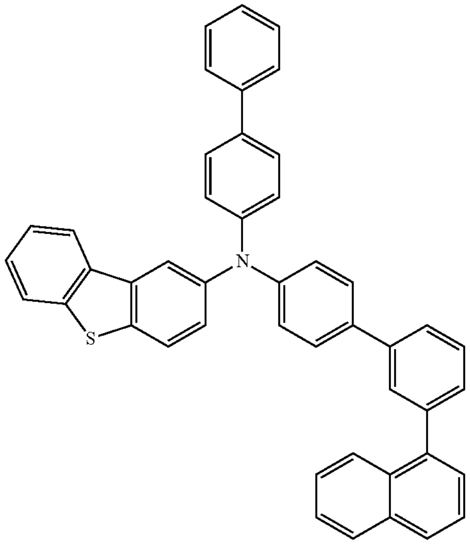
-continued

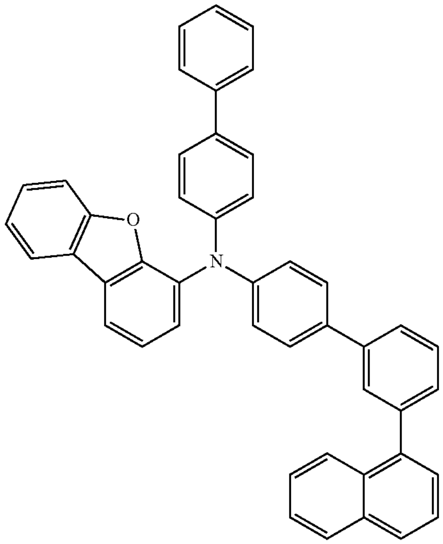
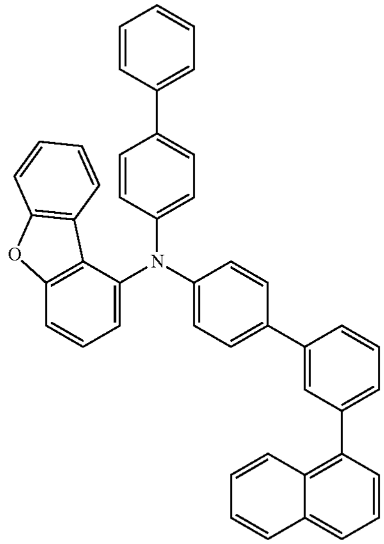
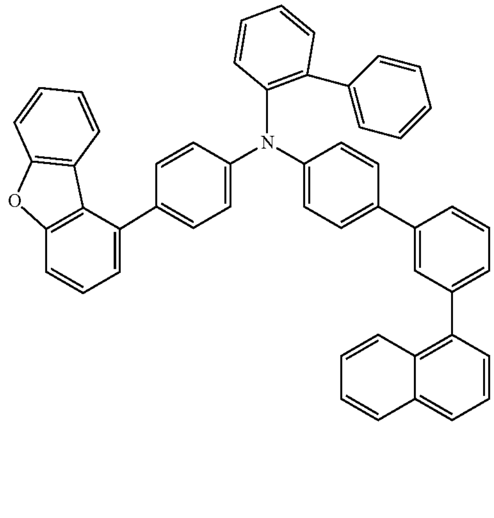
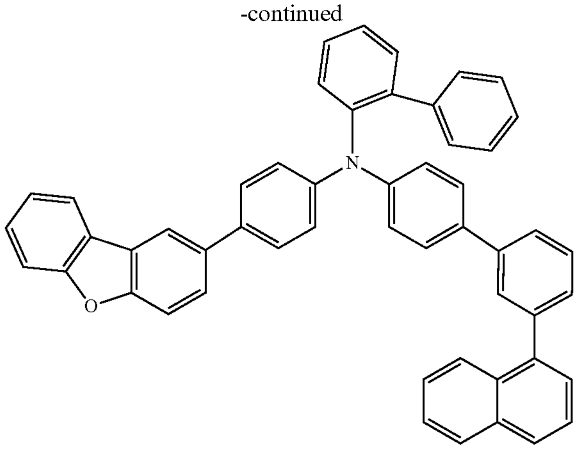
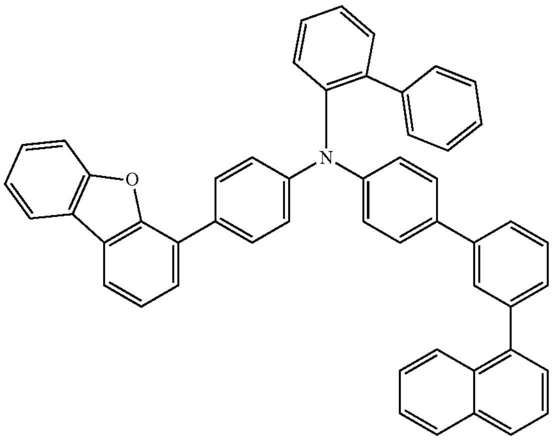
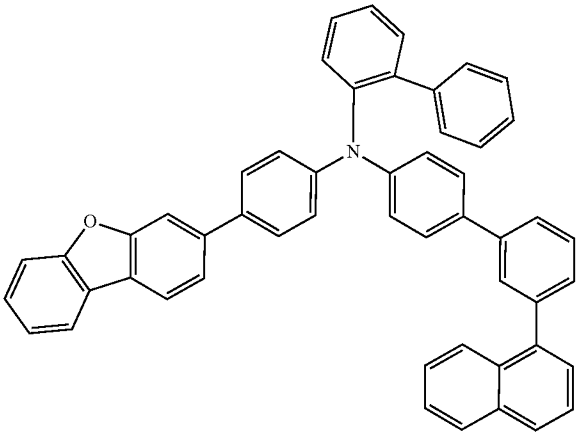
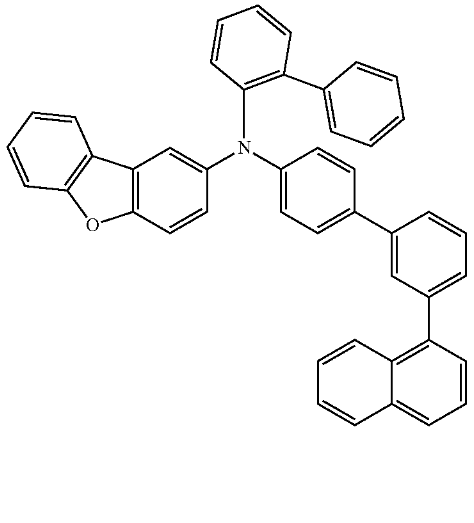

-continued
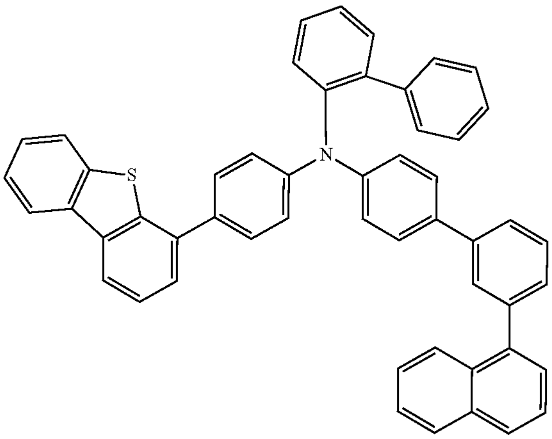
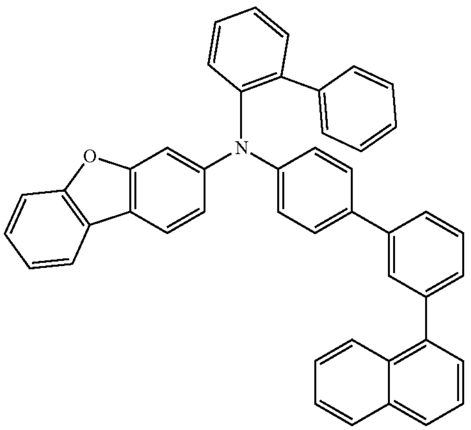
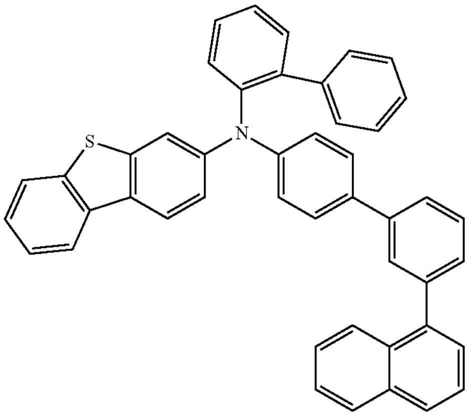
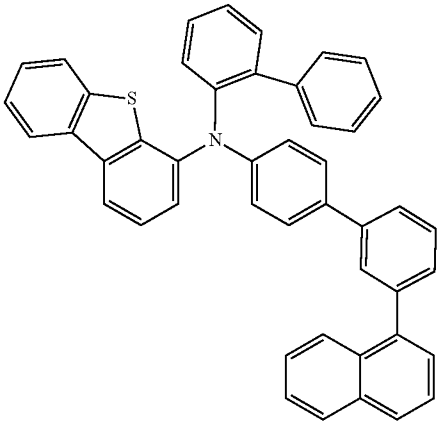
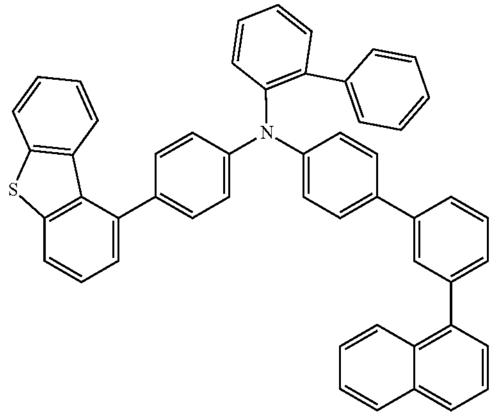
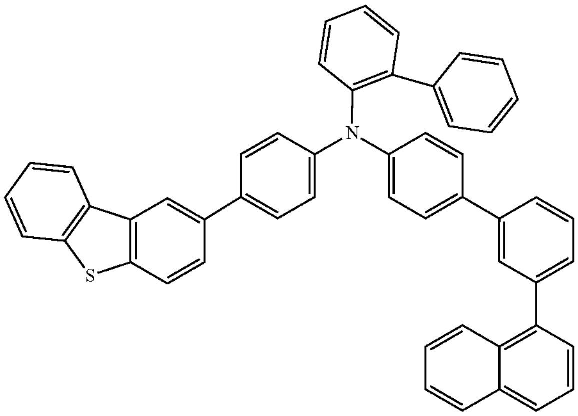
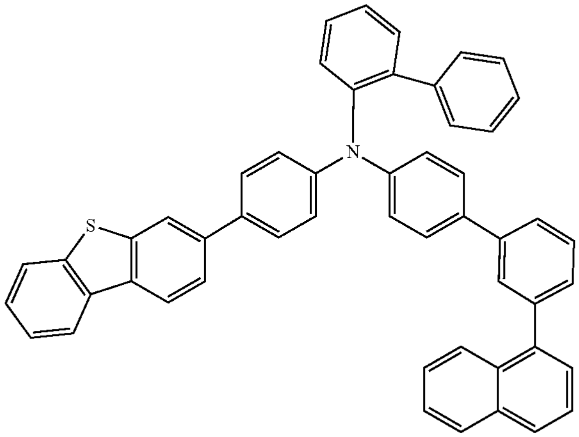
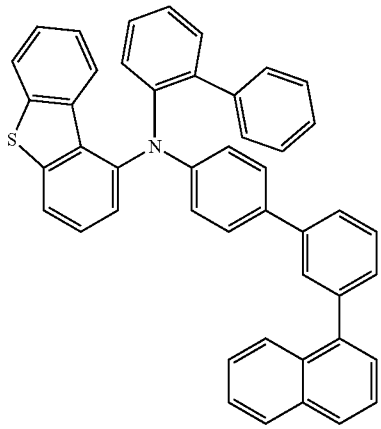
-continued -continued
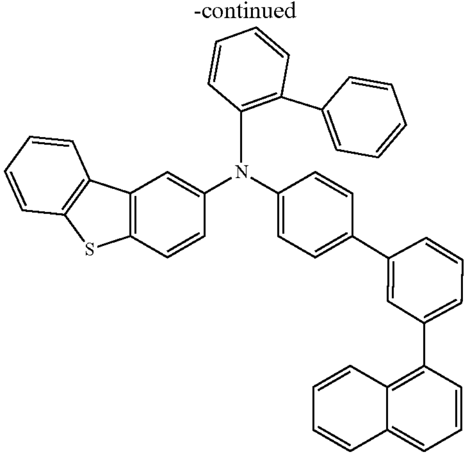
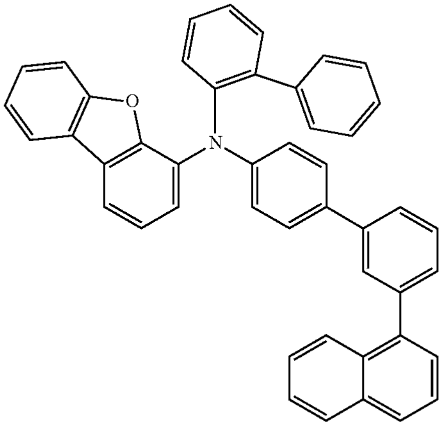
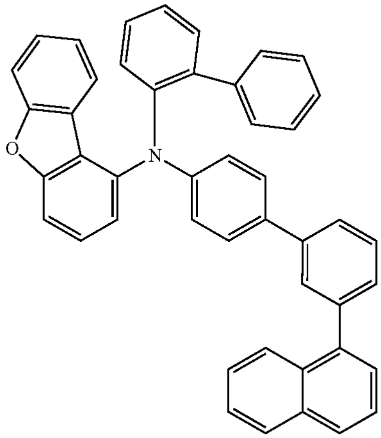
-continued
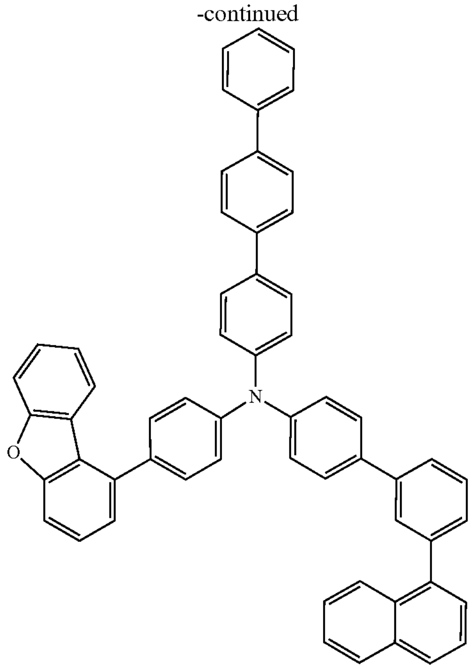
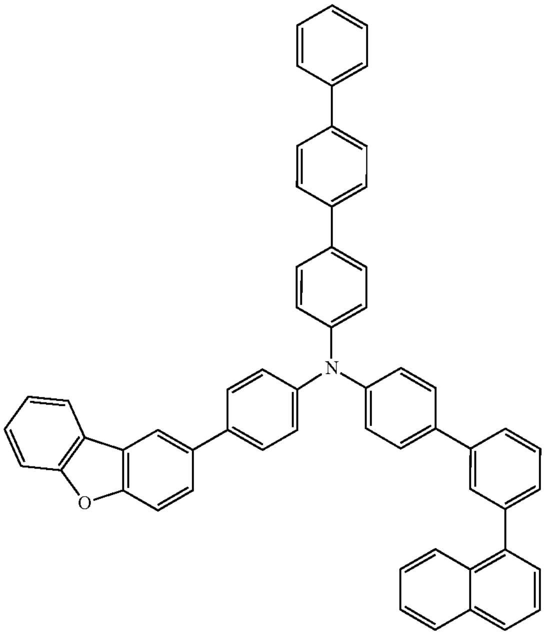

-continued
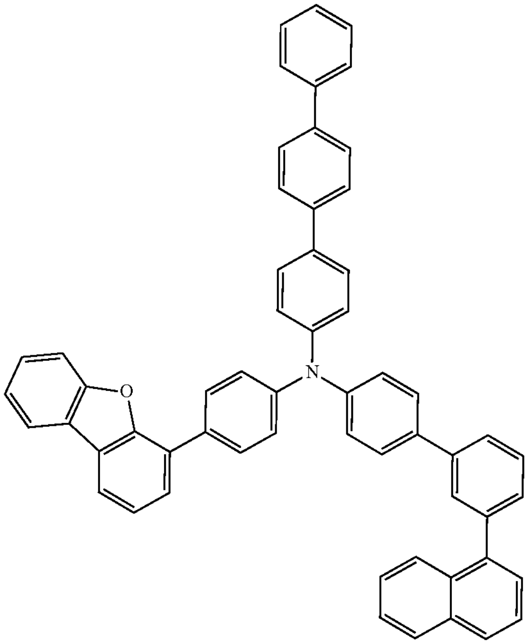
-continued
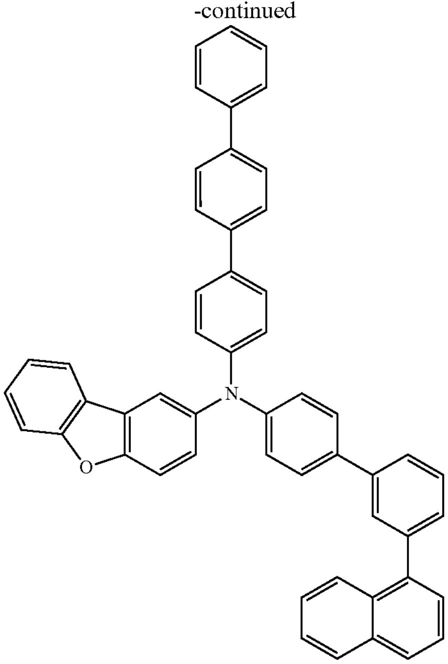
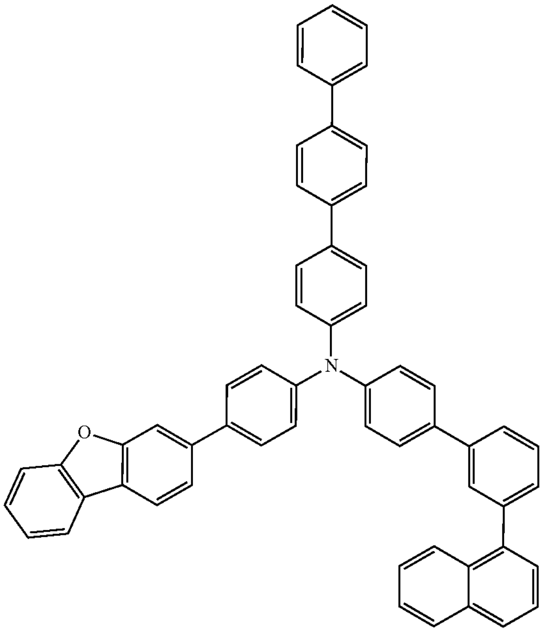
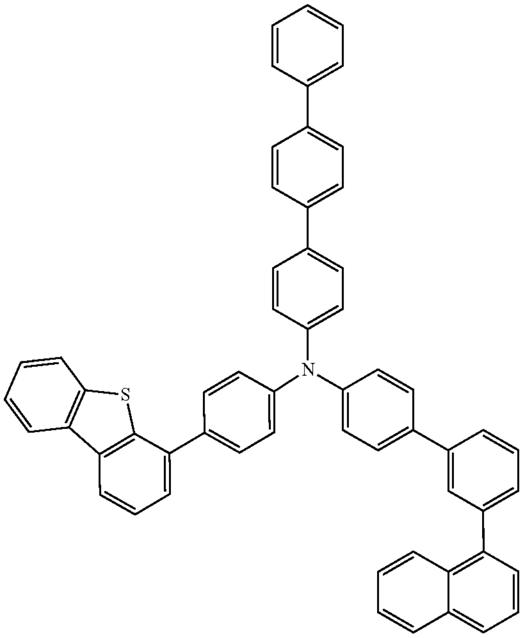

-continued
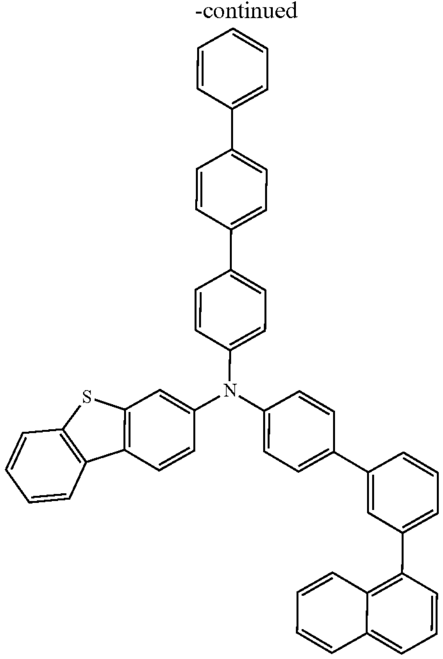
-continued
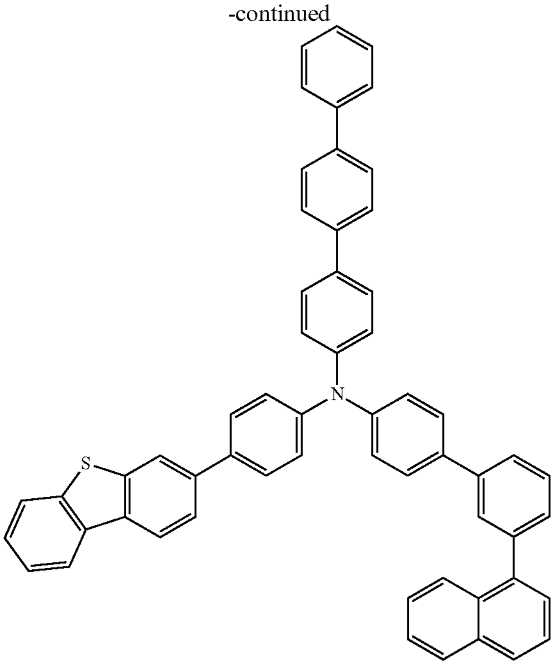
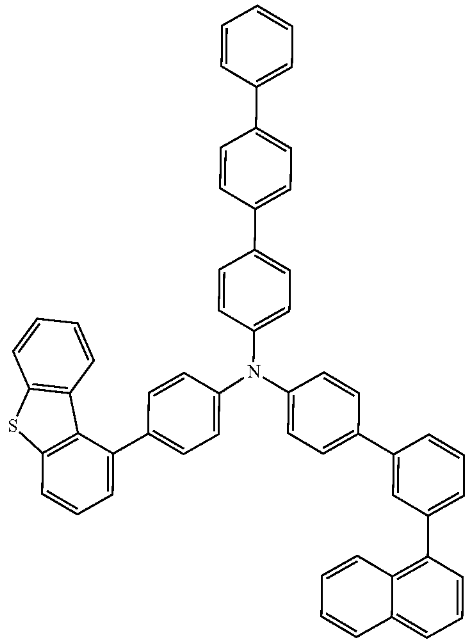
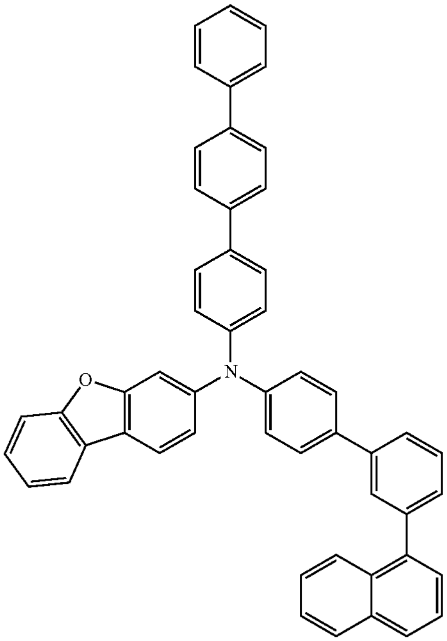

-continued
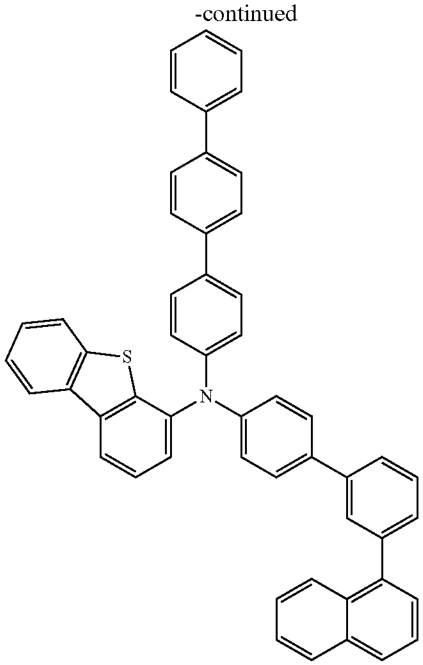
-continued
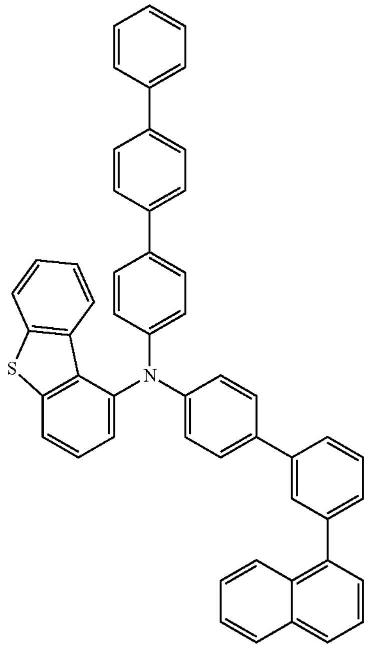 [SMILES: c1ccc(-c2ccc(-c3ccc(N(c4ccc(-c5cccc(-c6cccc7ccccc67)c5)cc4)c4cccc5sc6ccccc6c45)cc3)cc2)cc1]
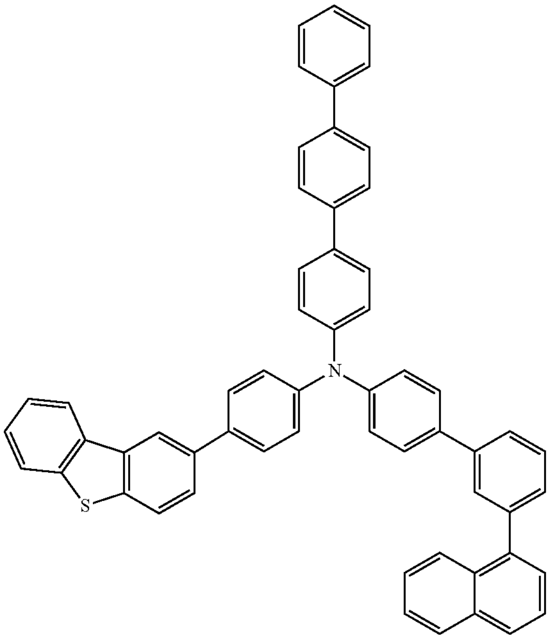
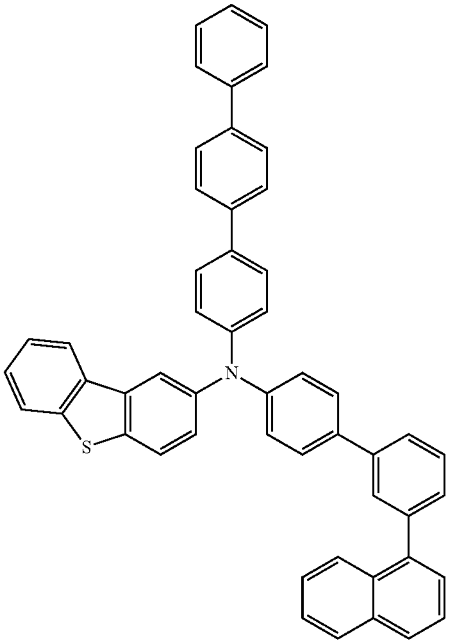

-continued
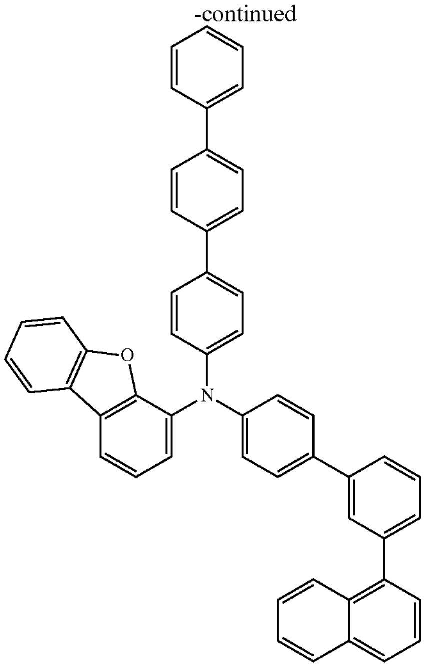
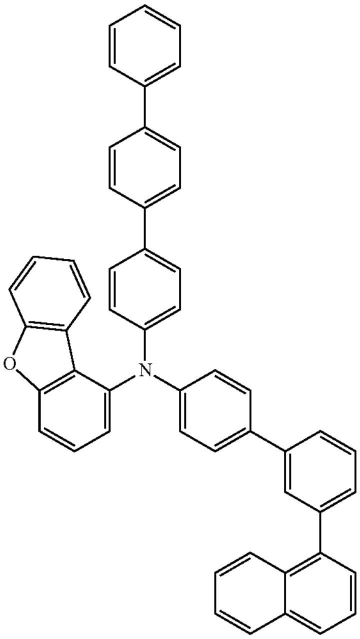
-continued
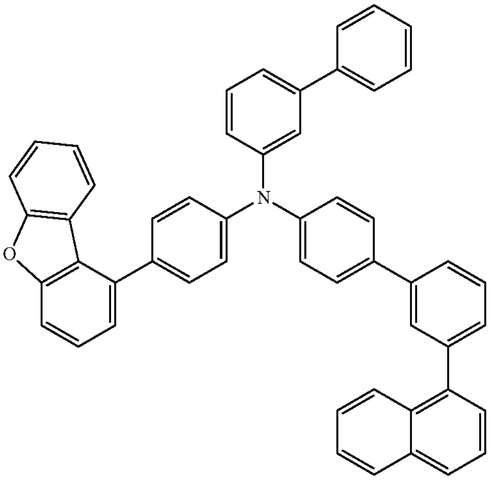
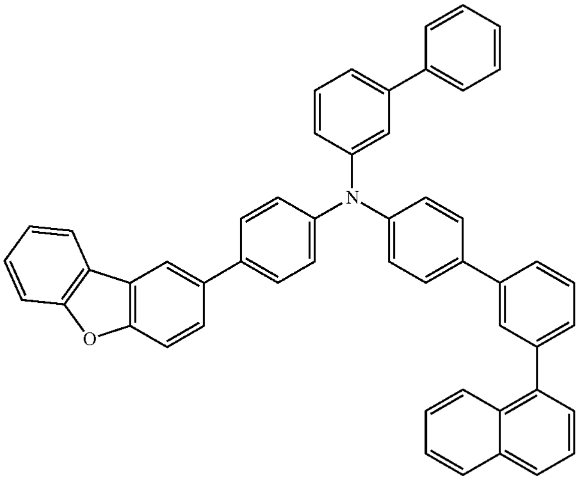
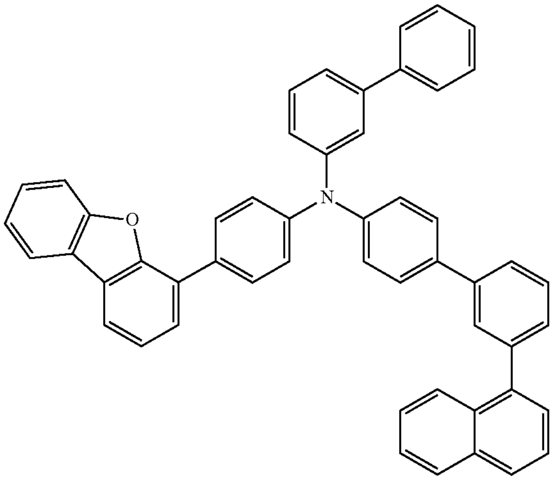

-continued
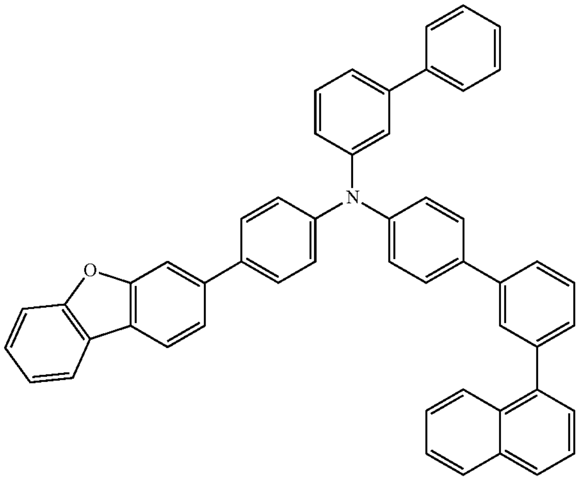
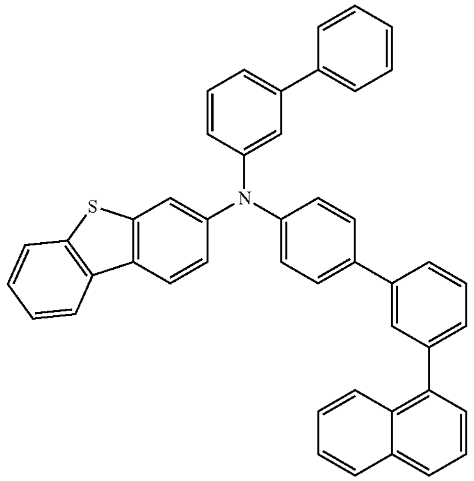
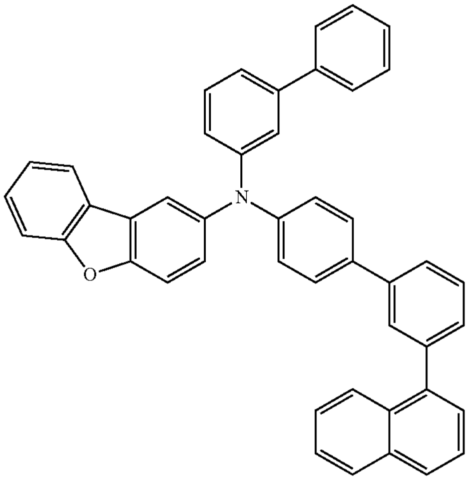
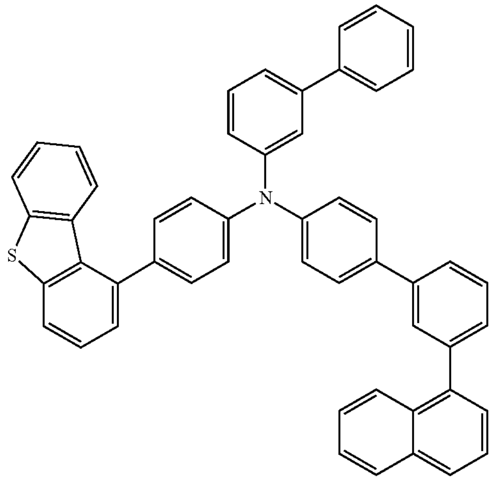
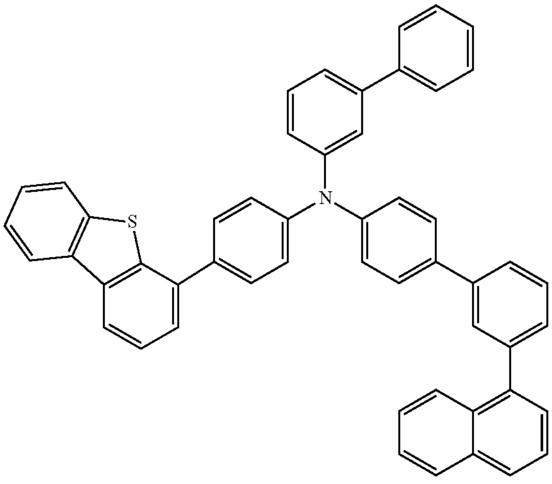
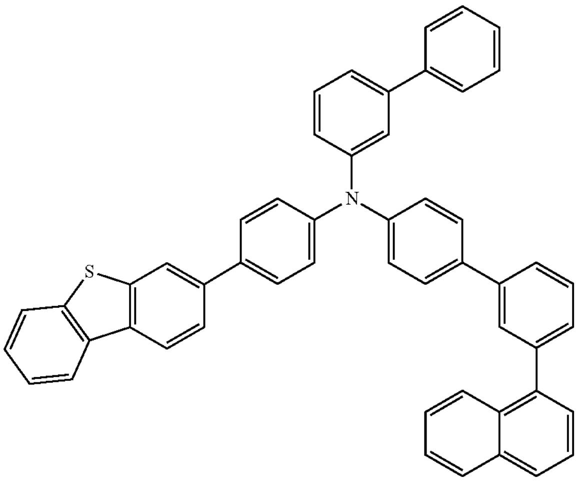
-continued -continued
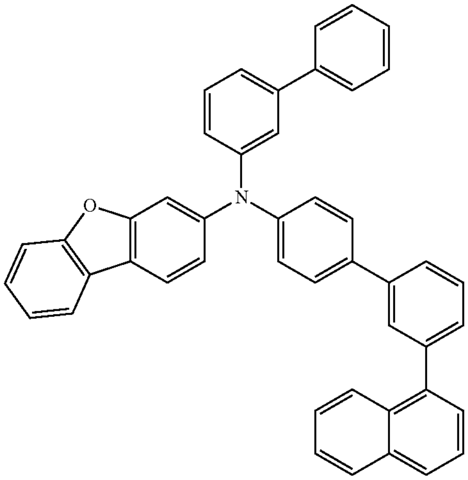
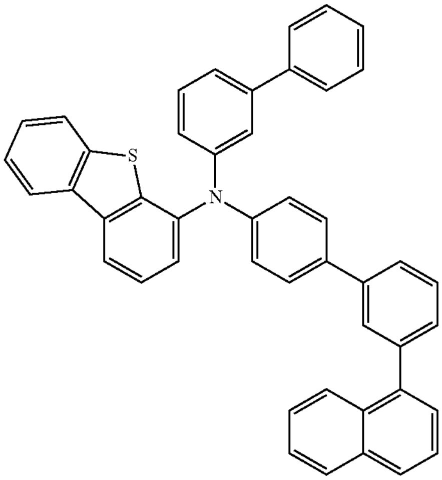
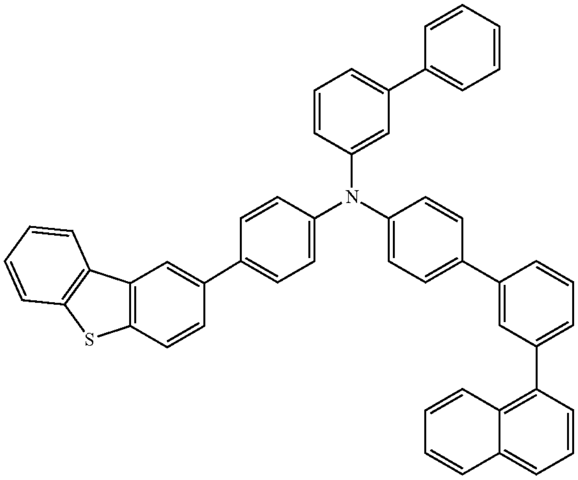
-continued
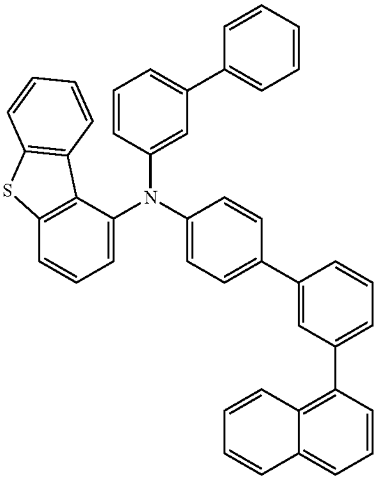
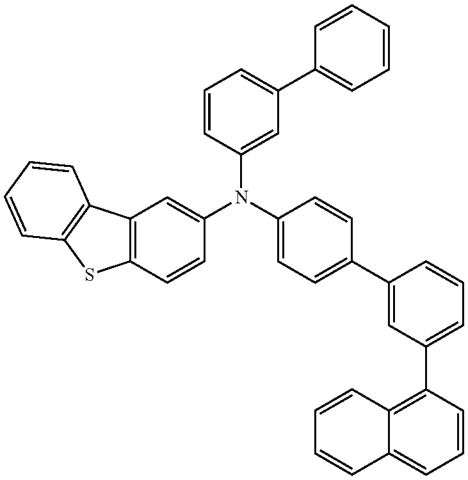
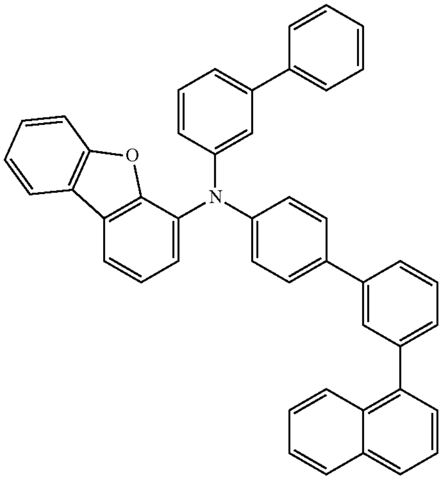

-continued
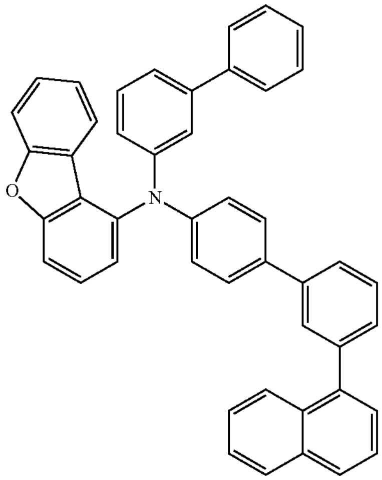
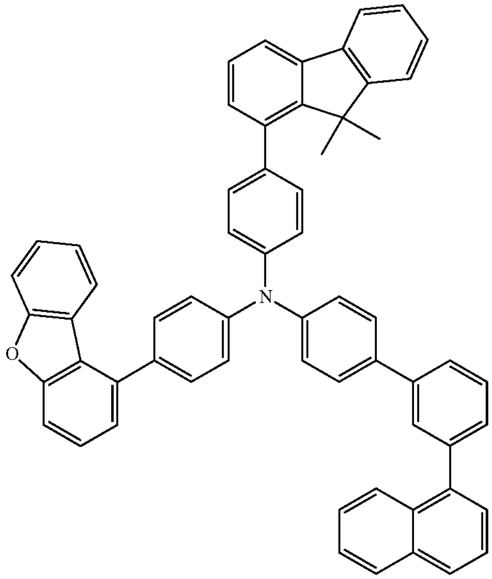
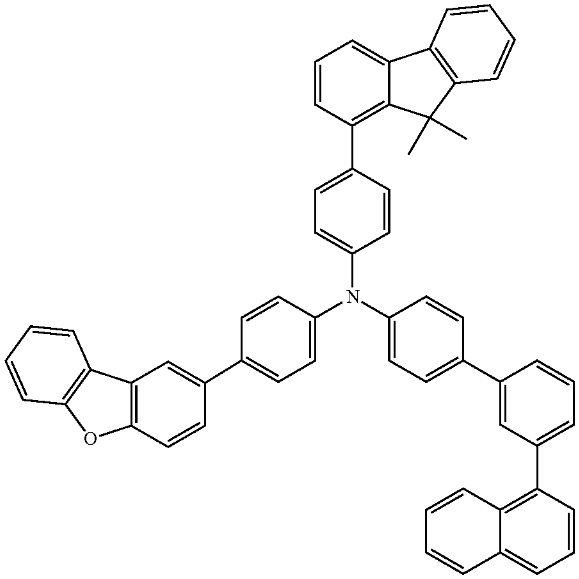
-continued
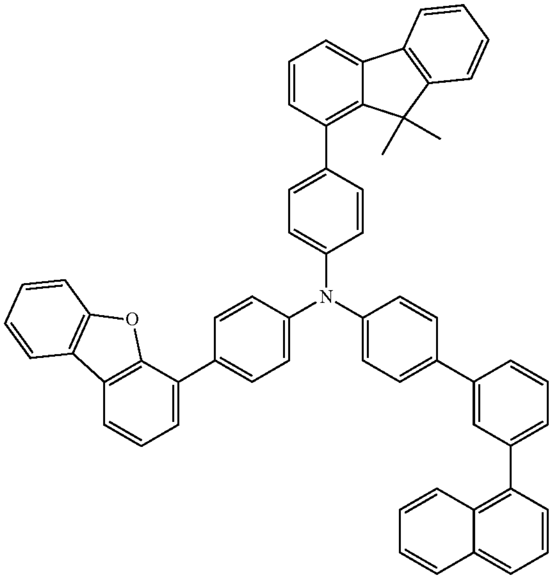
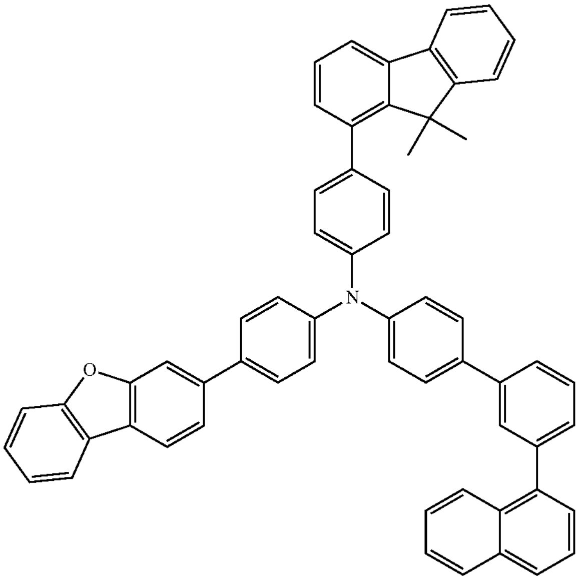

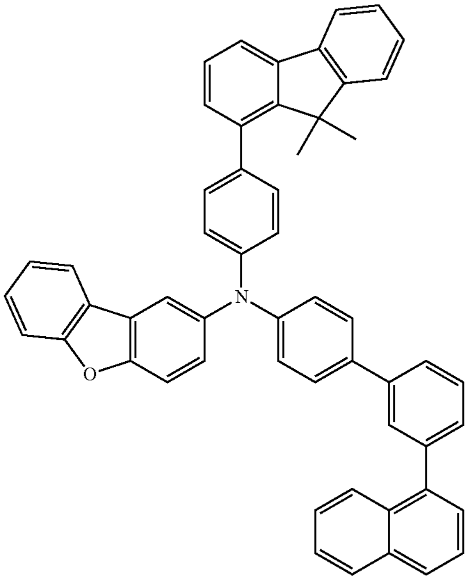
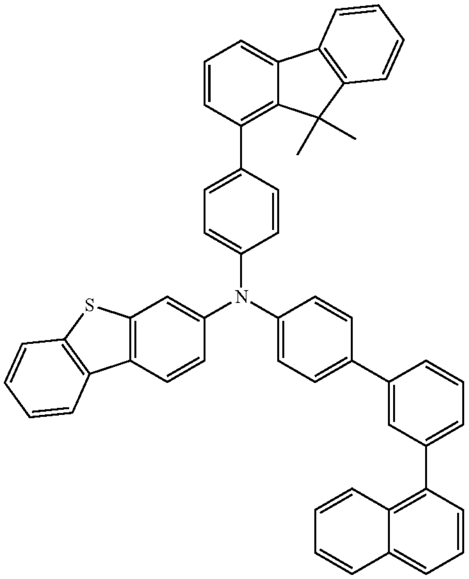
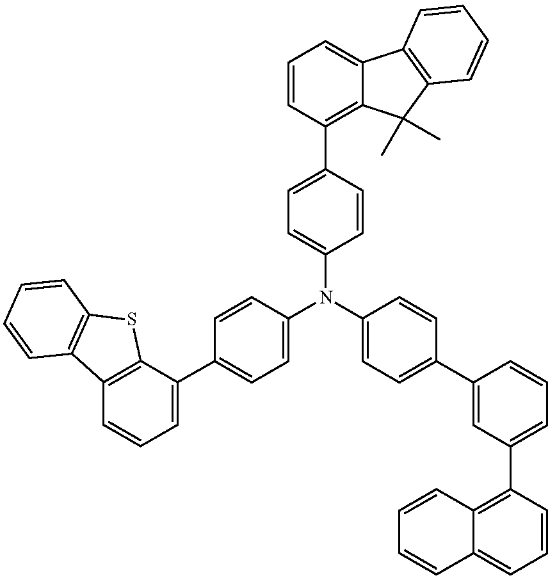
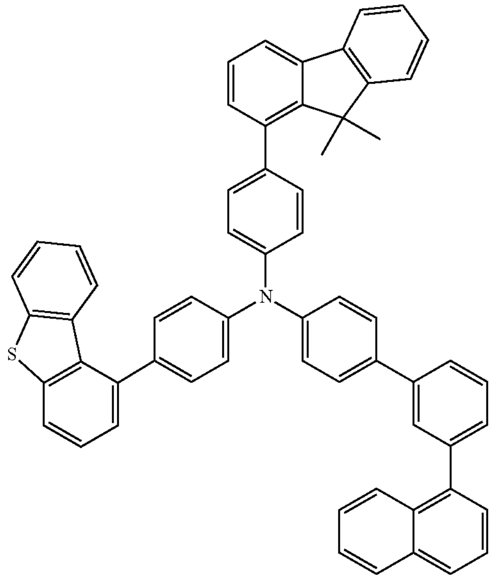

-continued
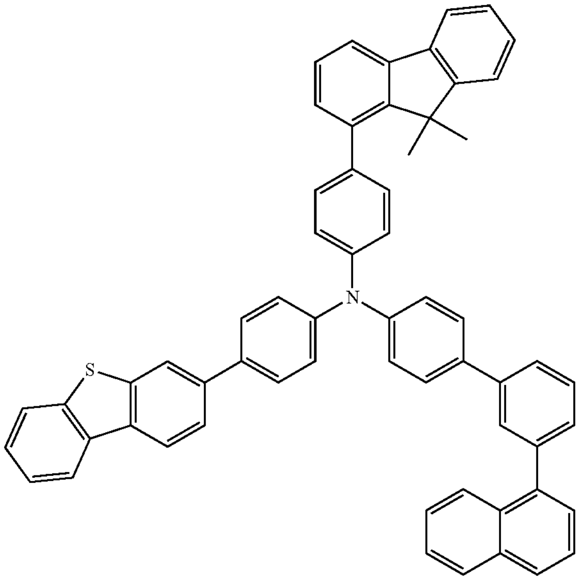
-continued
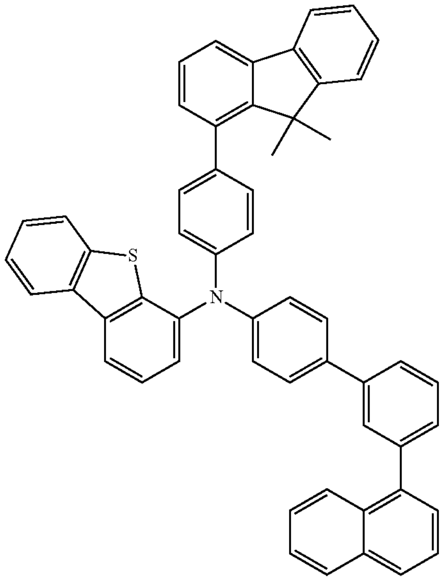
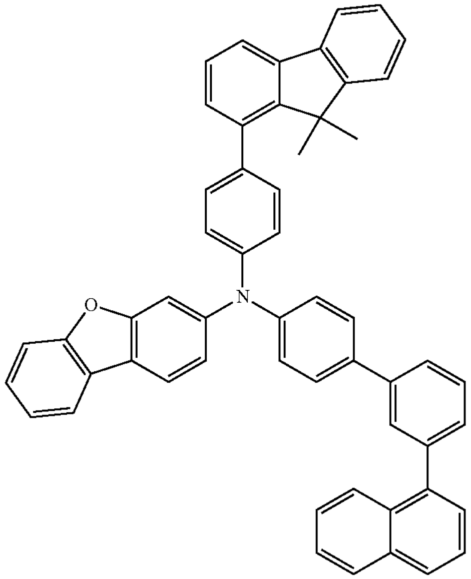
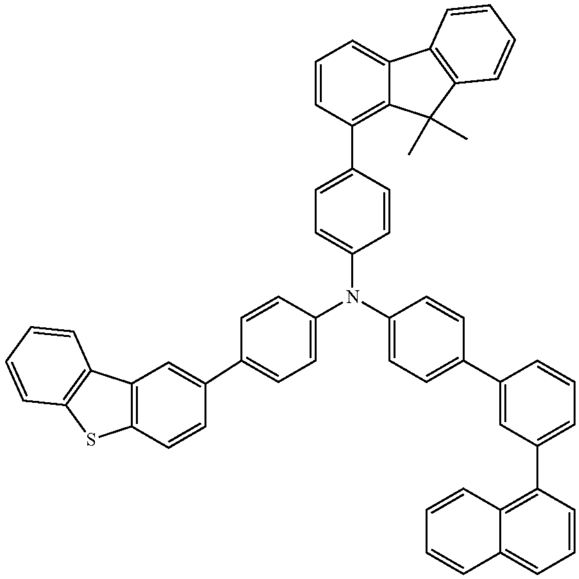

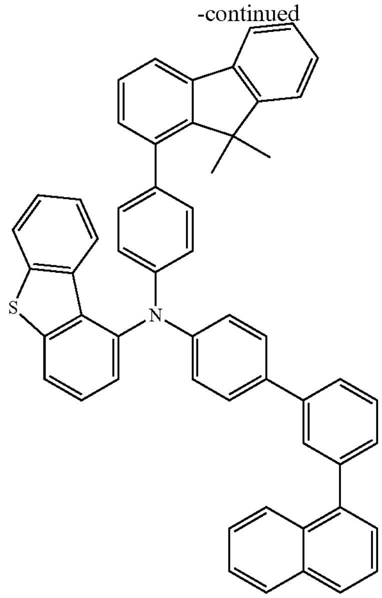
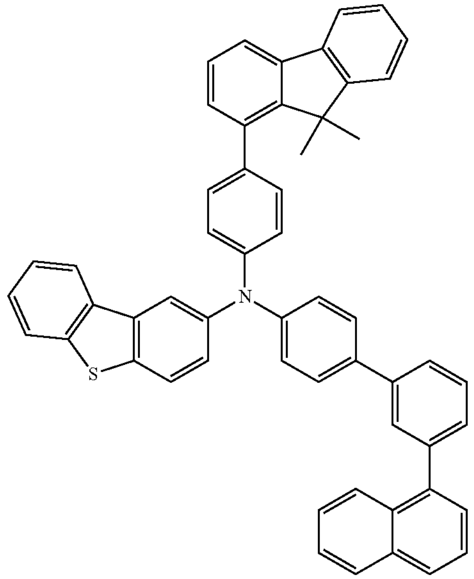
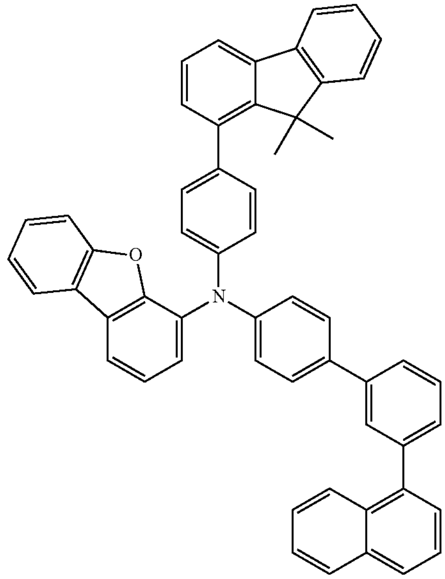
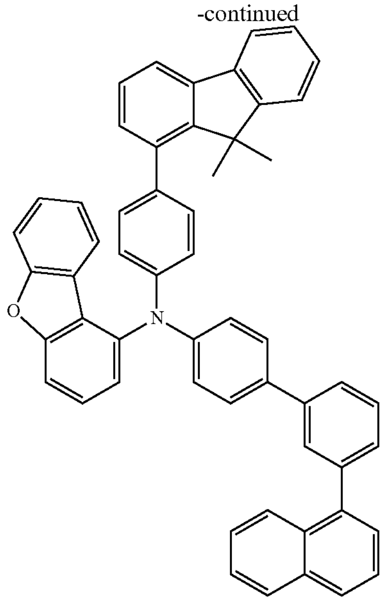
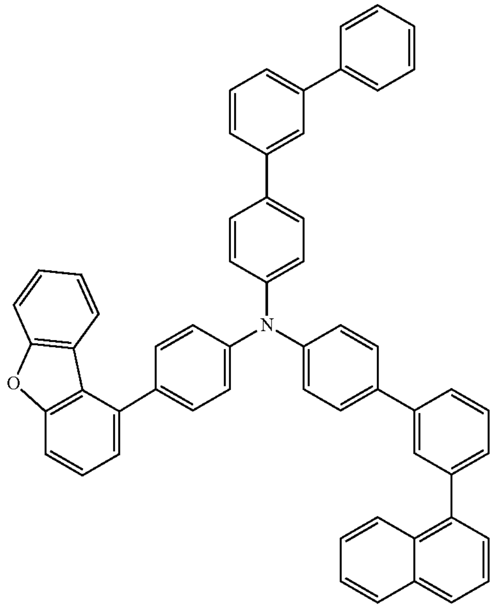

-continued
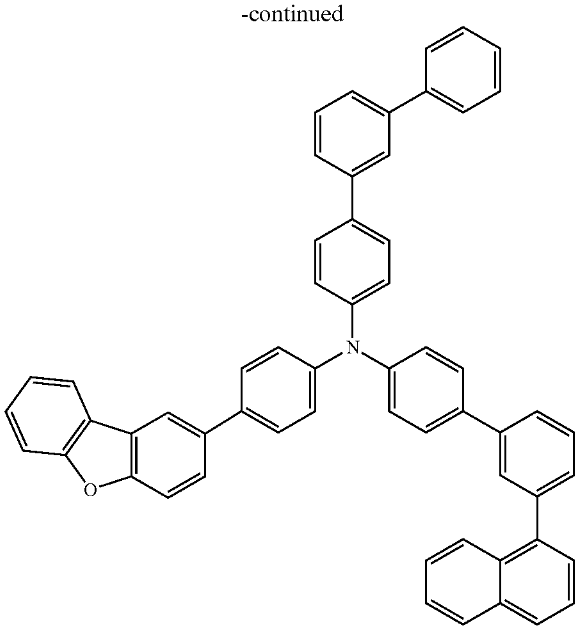
-continued
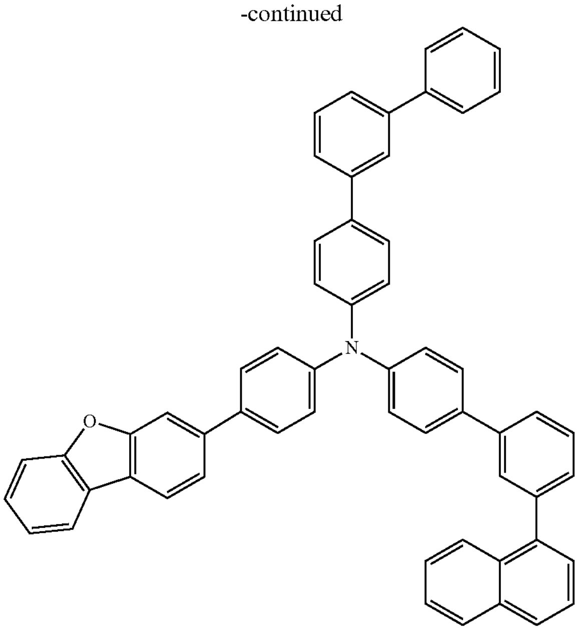
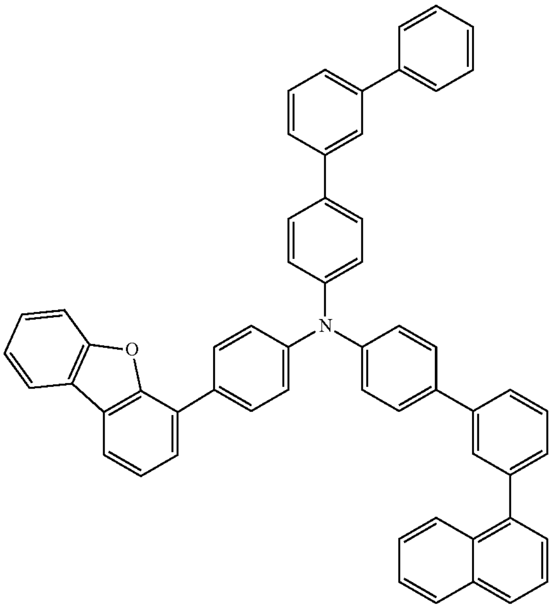
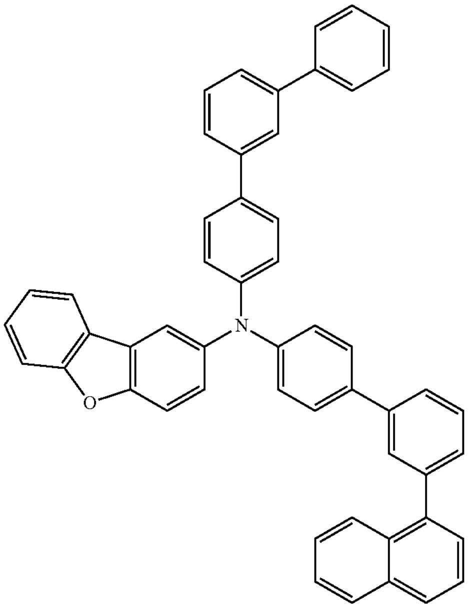

-continued
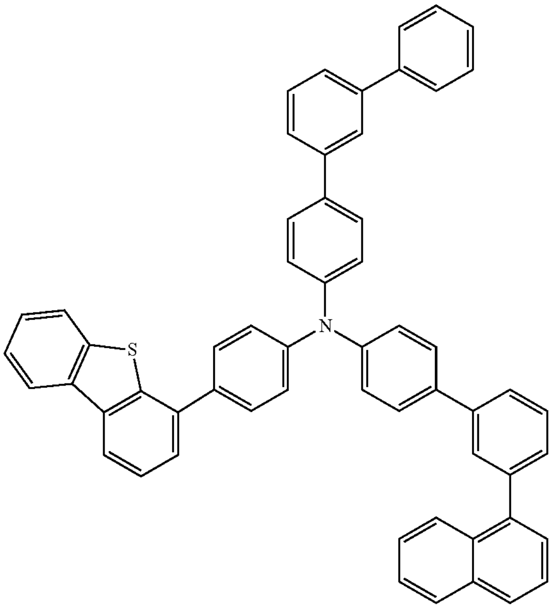
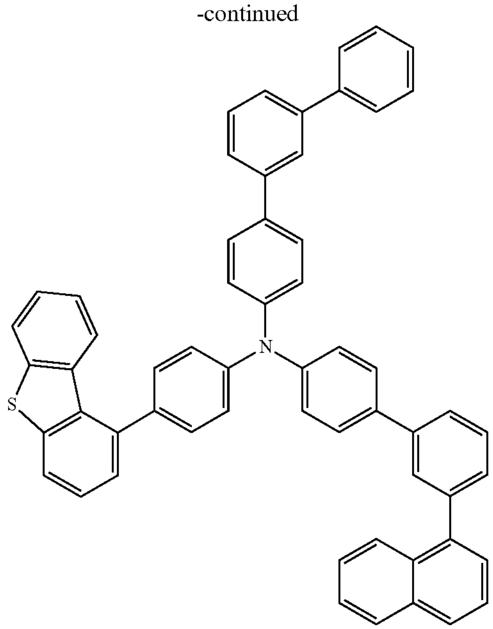
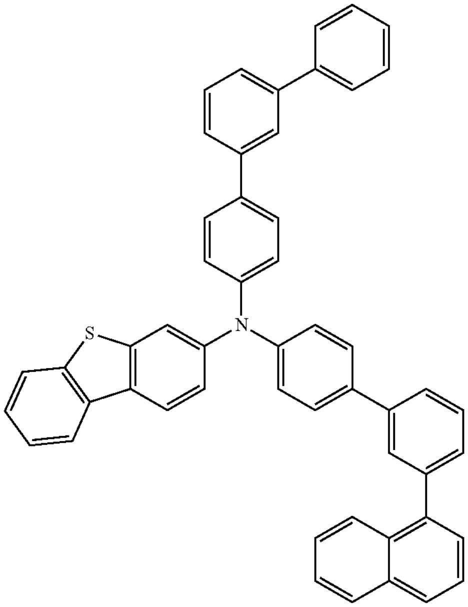
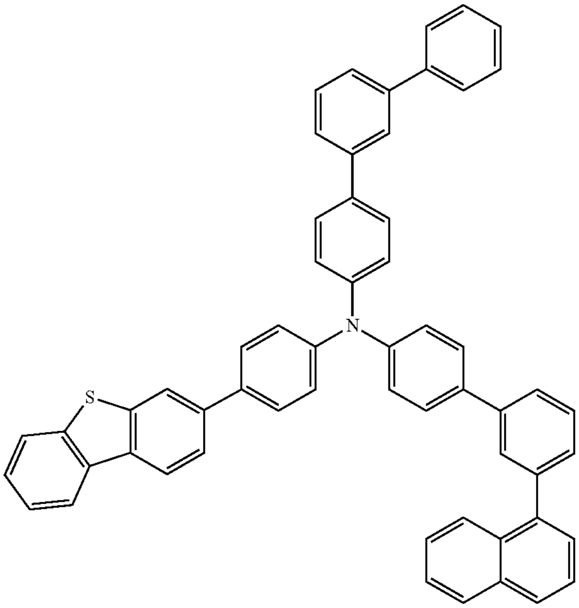

-continued
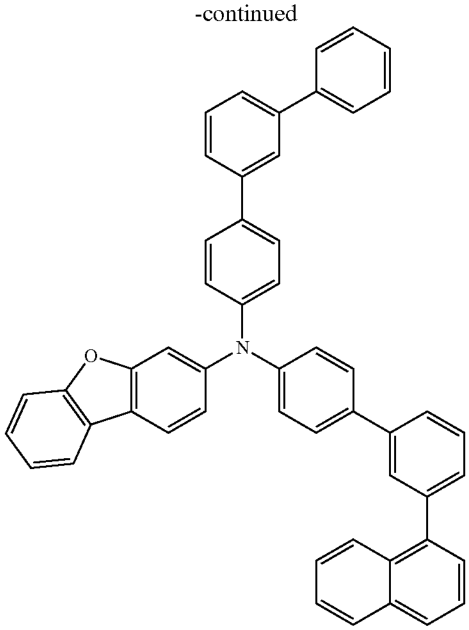
-continued
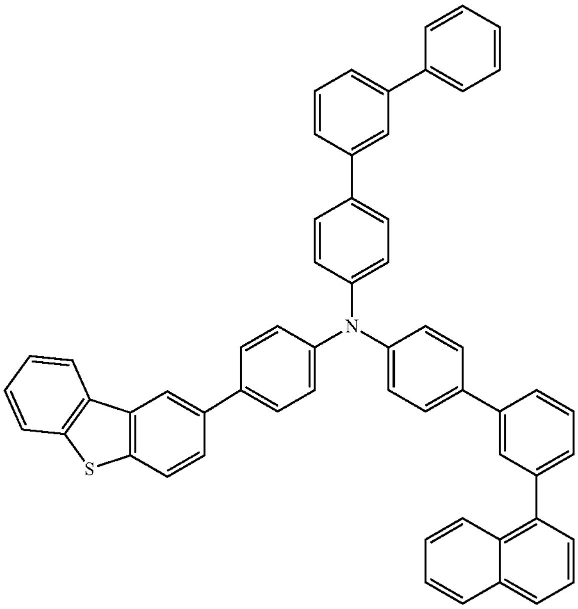
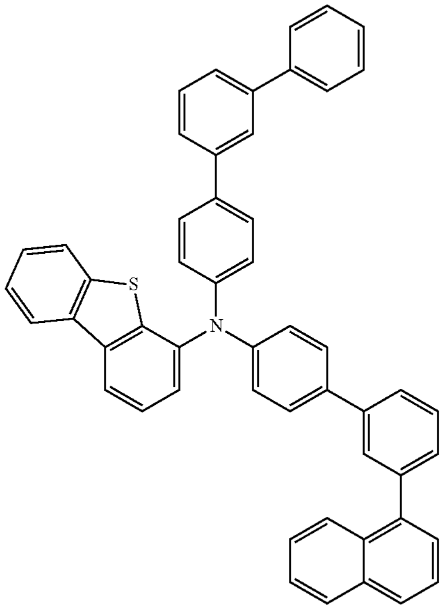
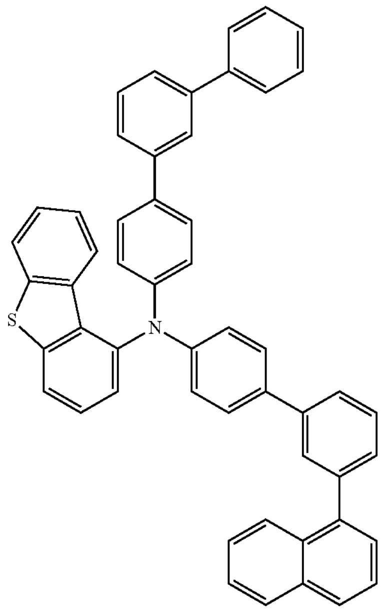

-continued
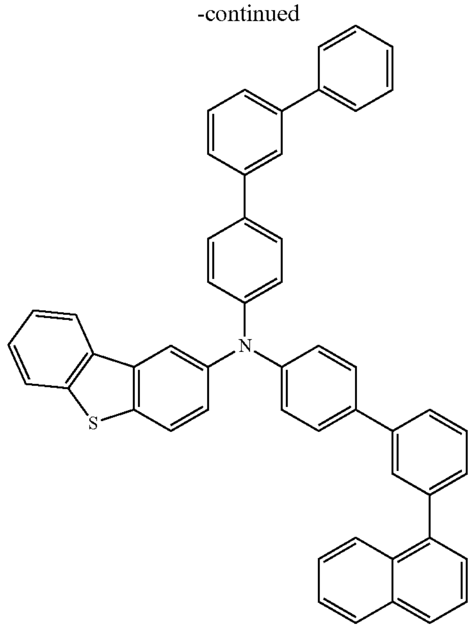
-continued
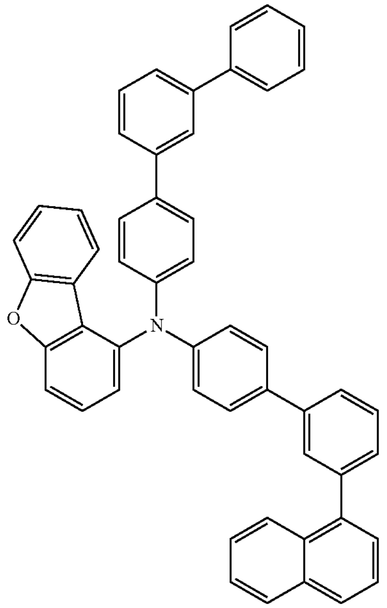
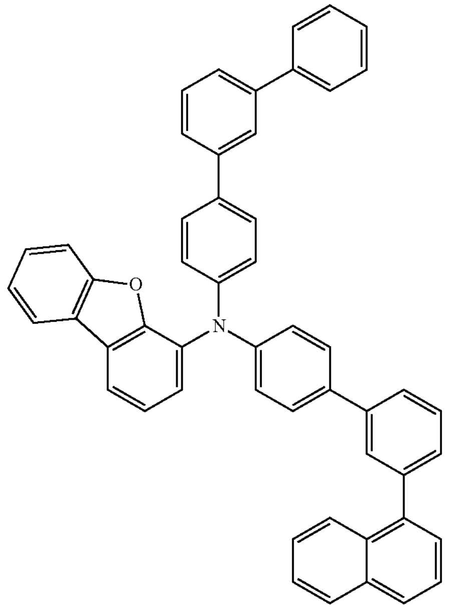
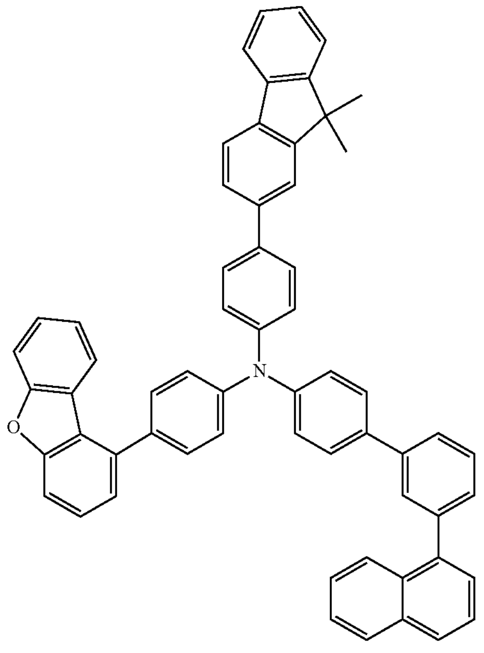

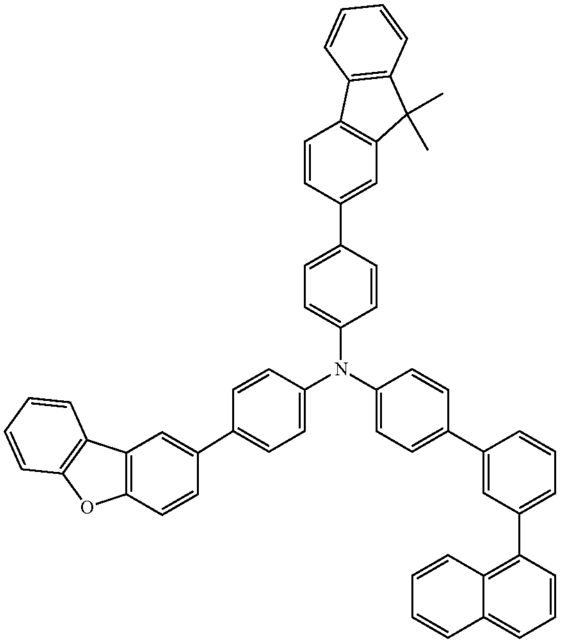
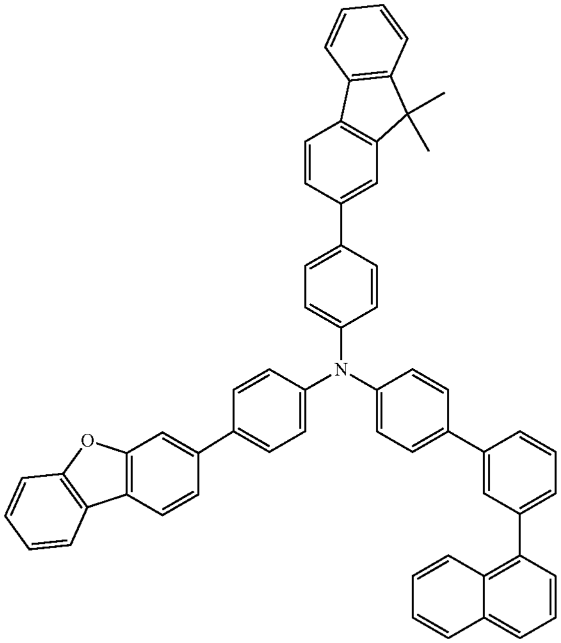
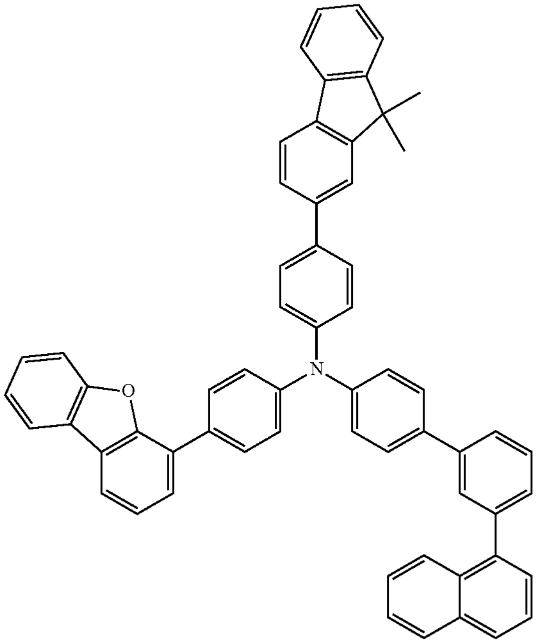
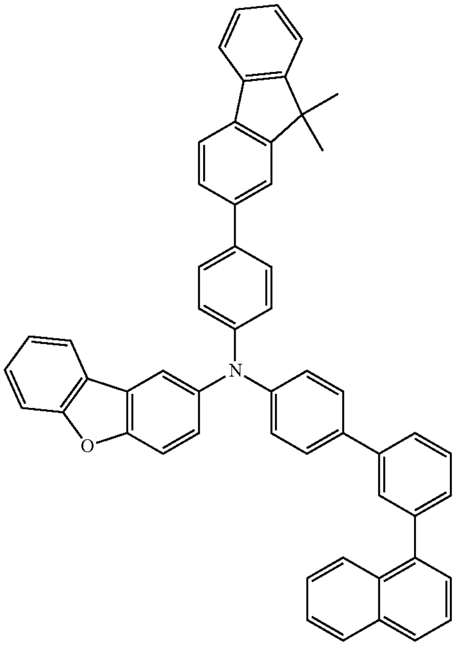

-continued
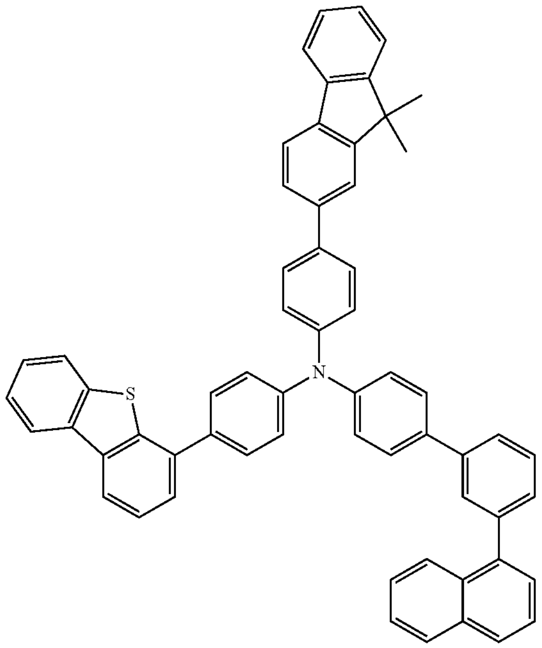
-continued
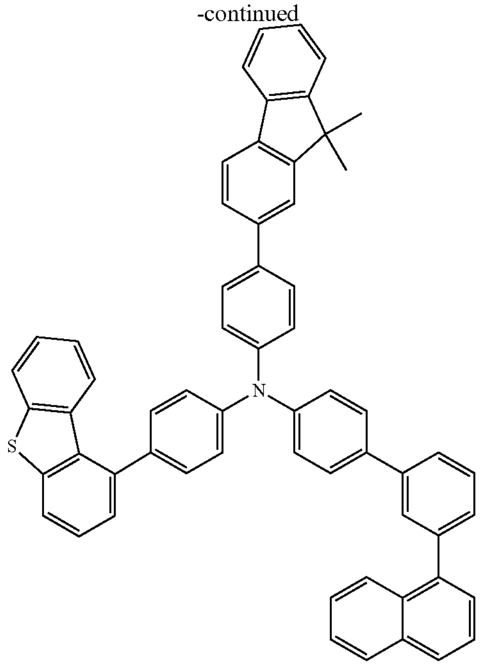
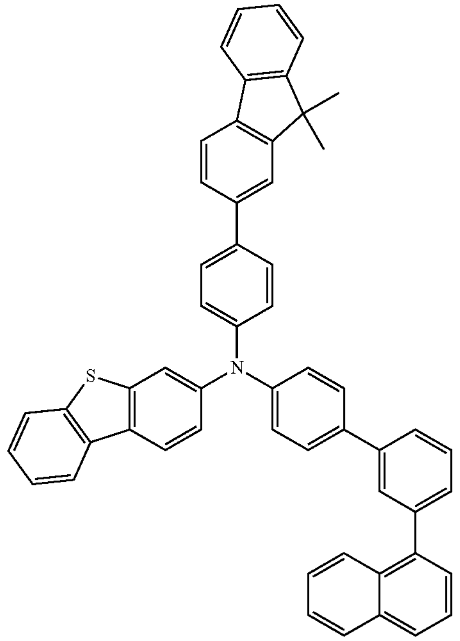
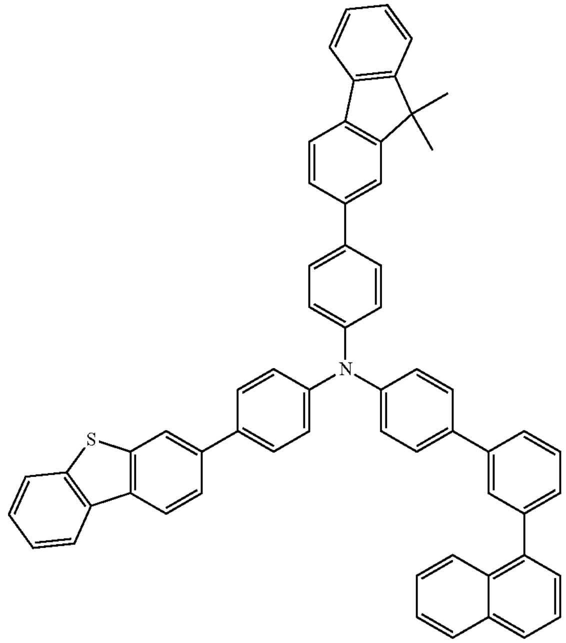

-continued
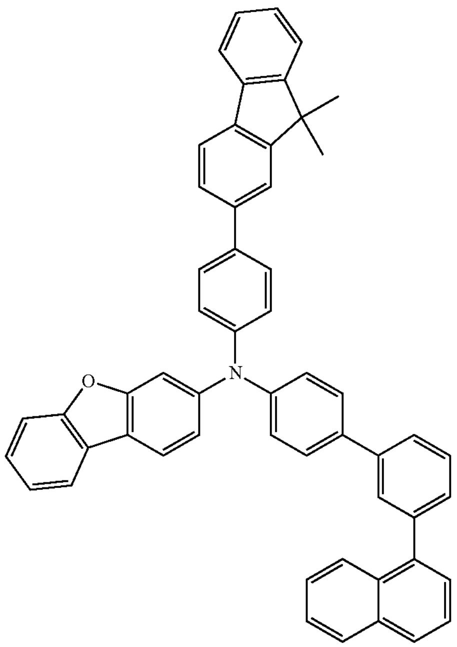
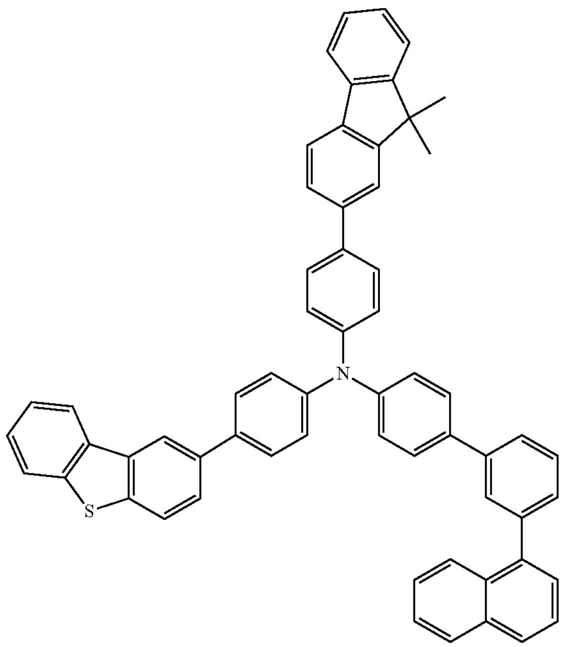
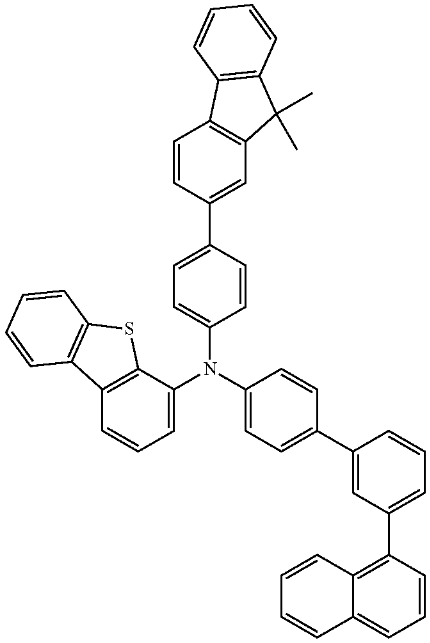
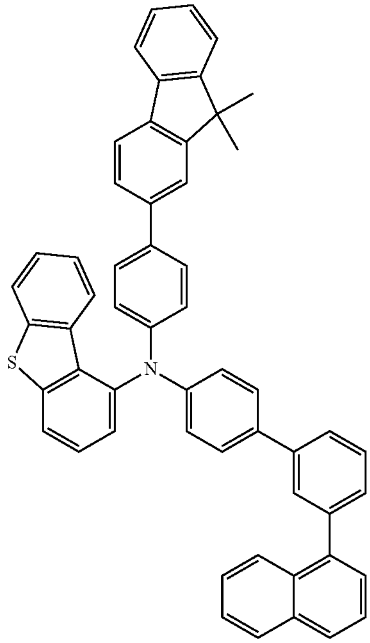 [SMILES: CC1(C)c2ccccc2-c2ccc(-c3ccc(N(c4ccc(-c5cccc(-c6cccc7ccccc67)c5)cc4)c4cccc5sc6ccccc6c45)cc3)cc21]

-continued
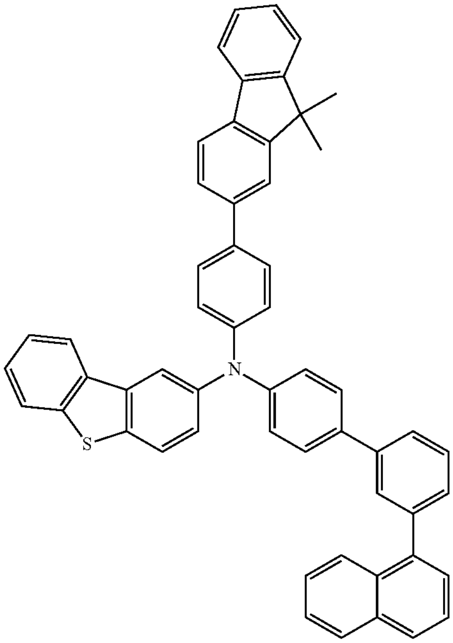
-continued
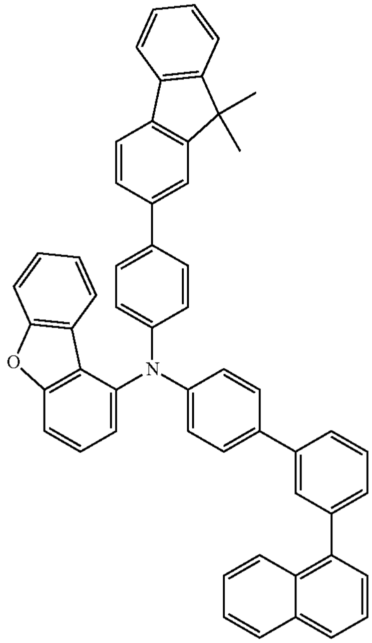
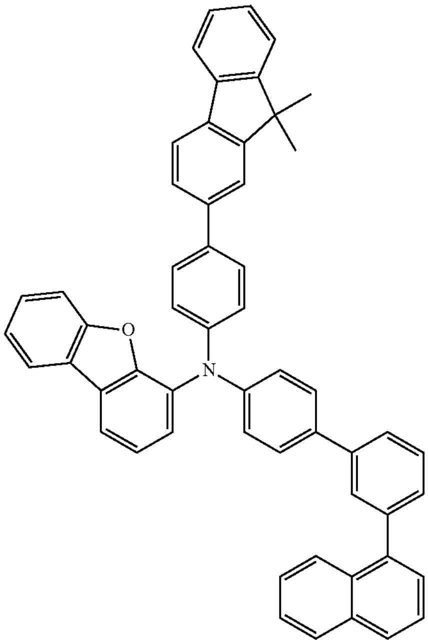
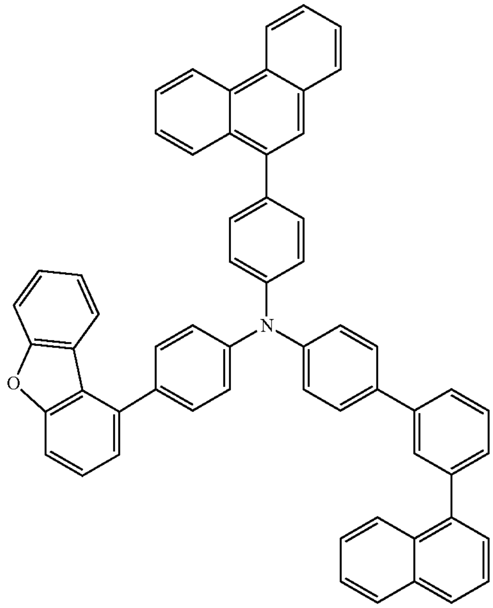

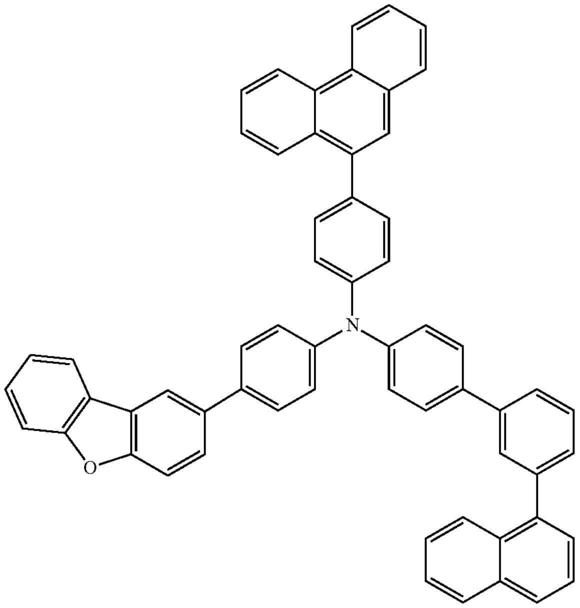
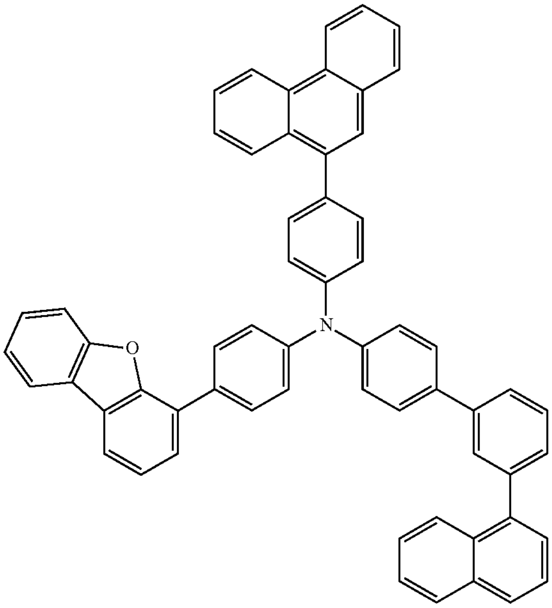
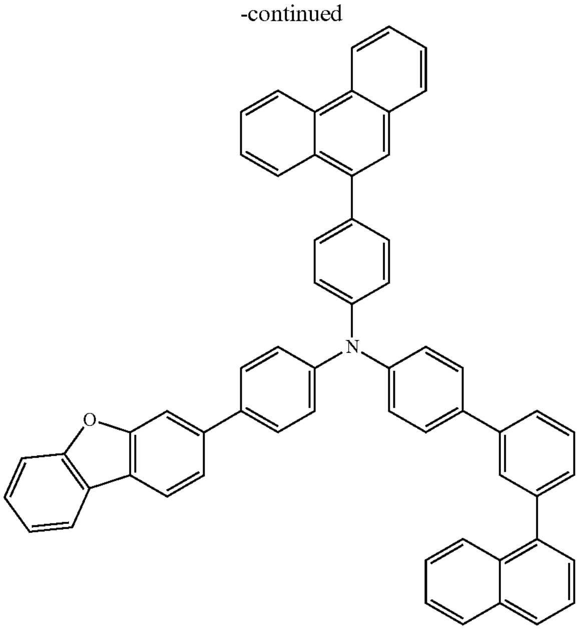
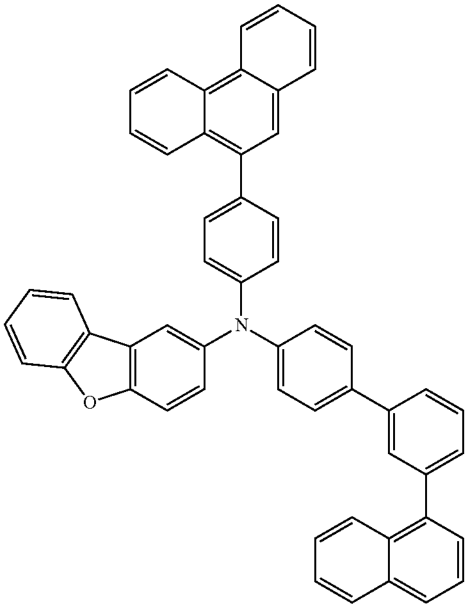

-continued
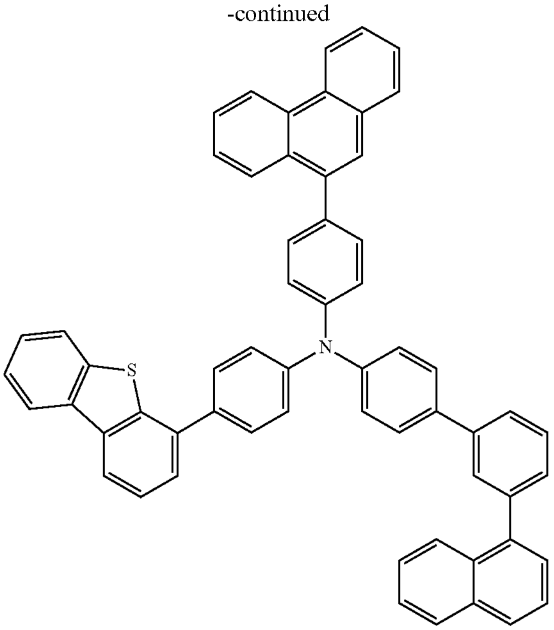
-continued
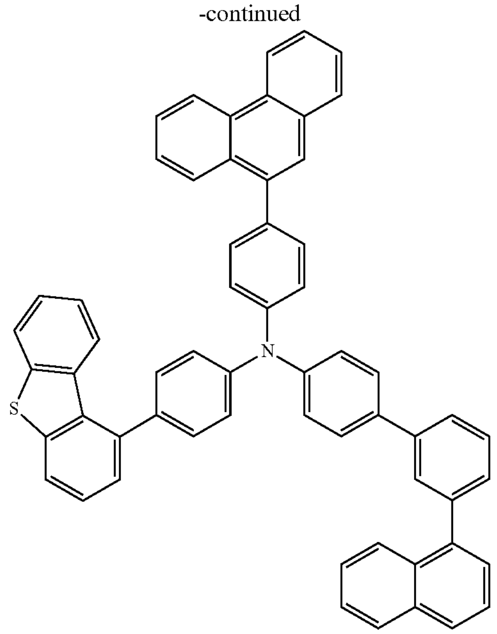
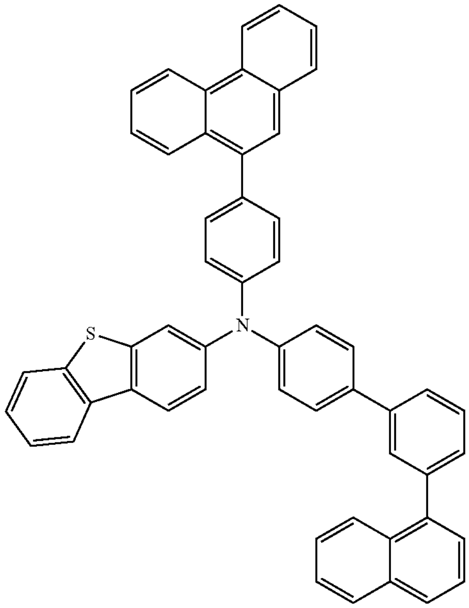
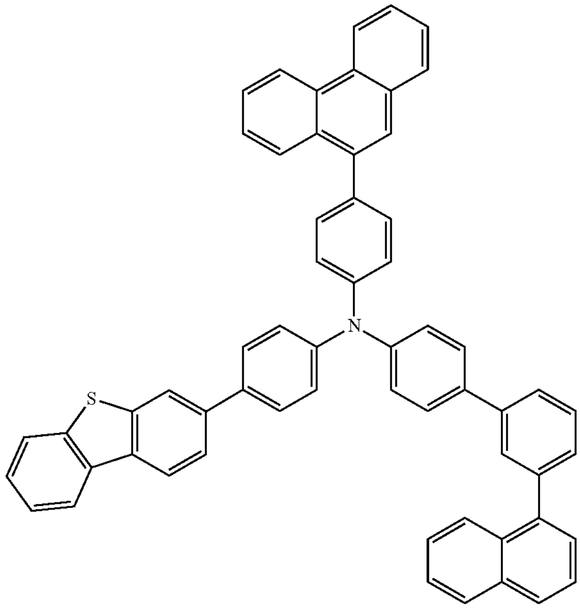

-continued
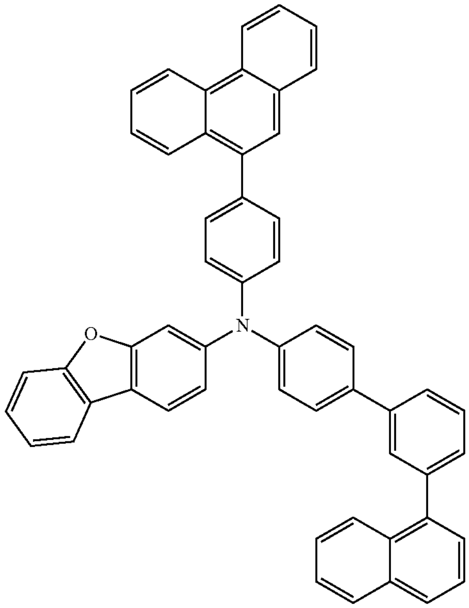
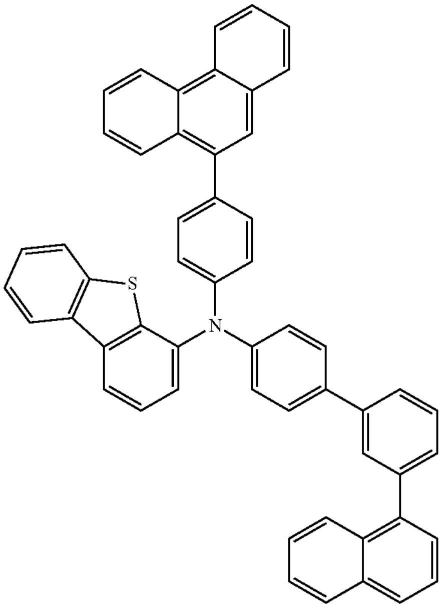
-continued
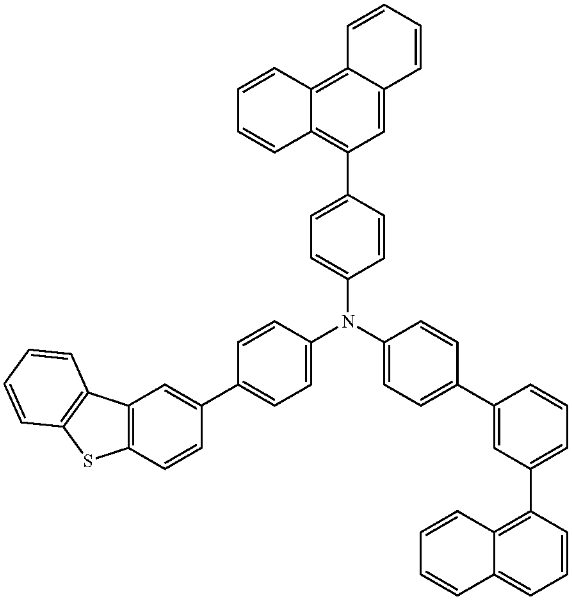
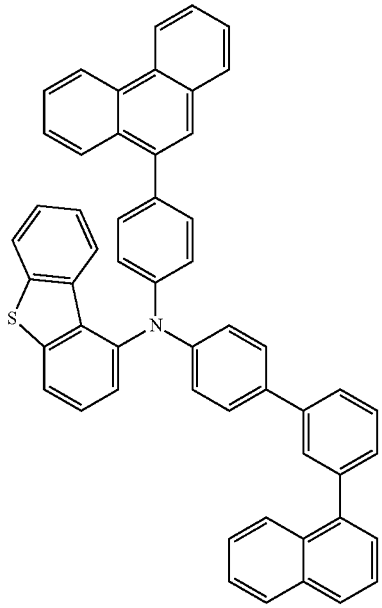

-continued
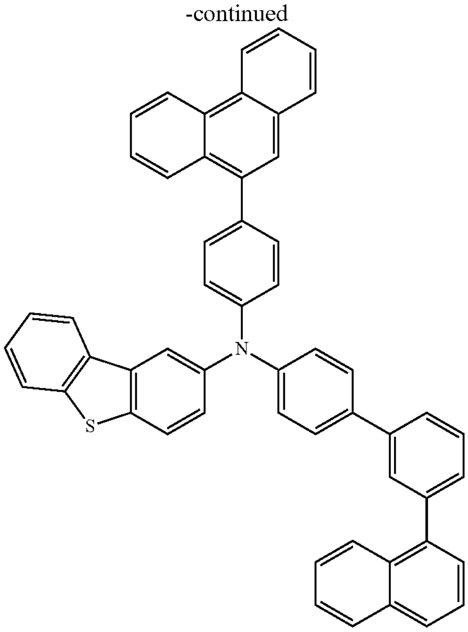
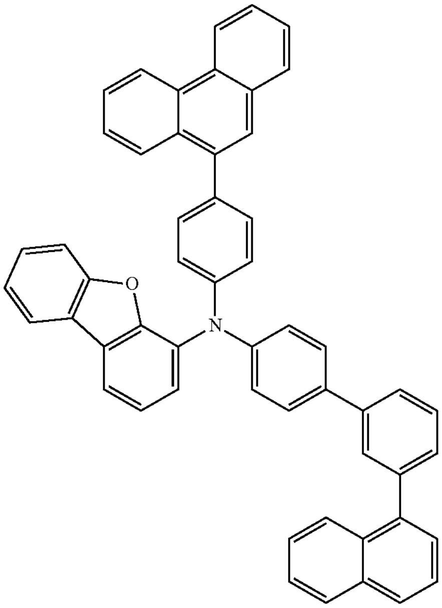
-continued
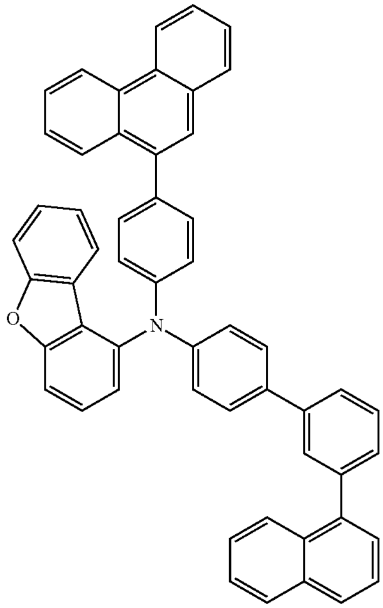
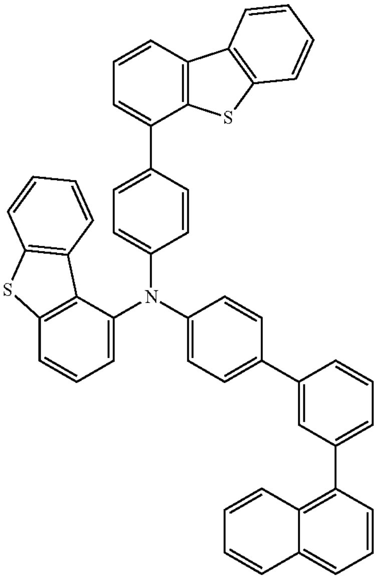

-continued
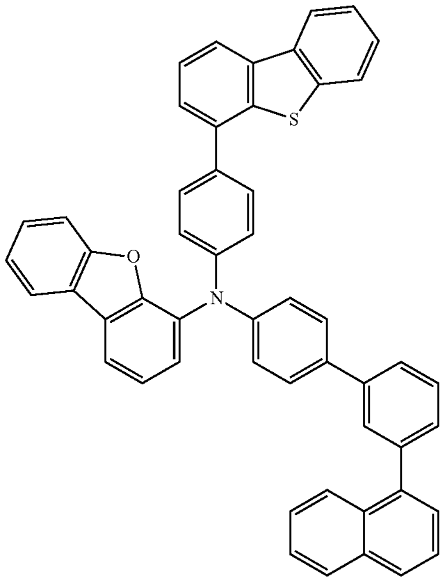
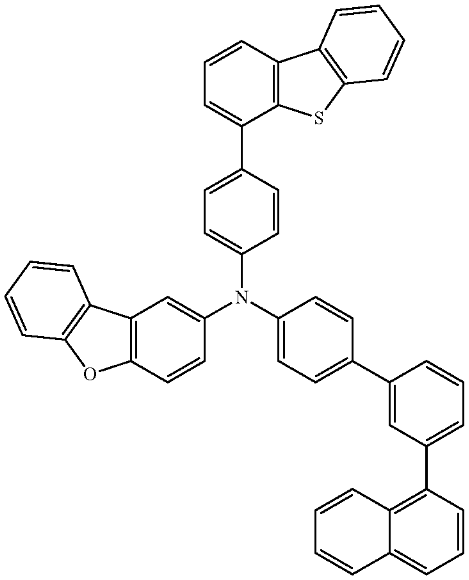
-continued
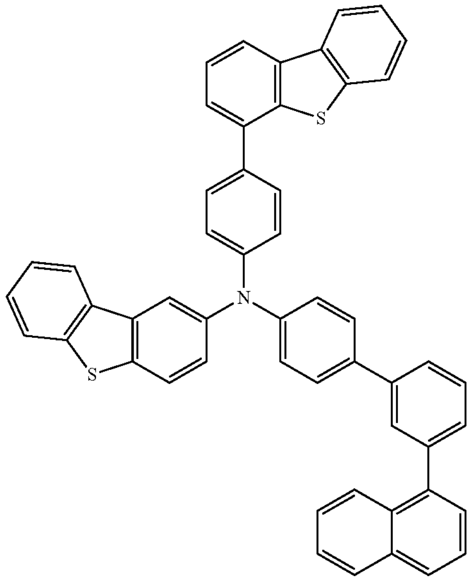
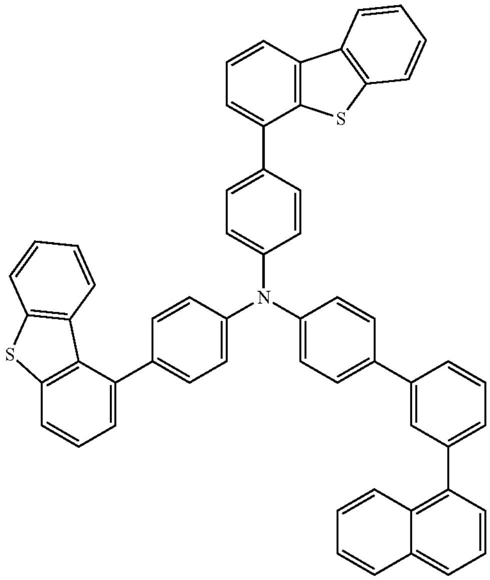

-continued
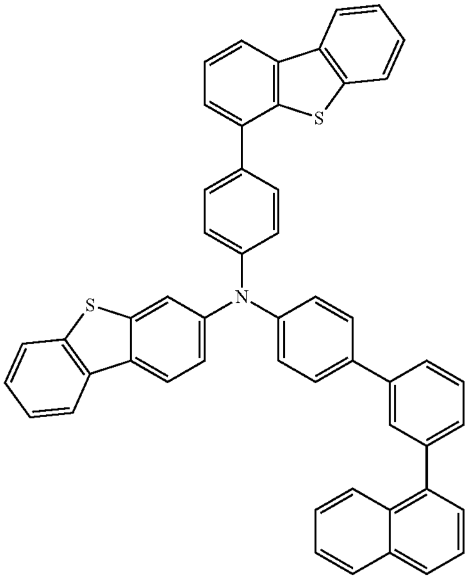
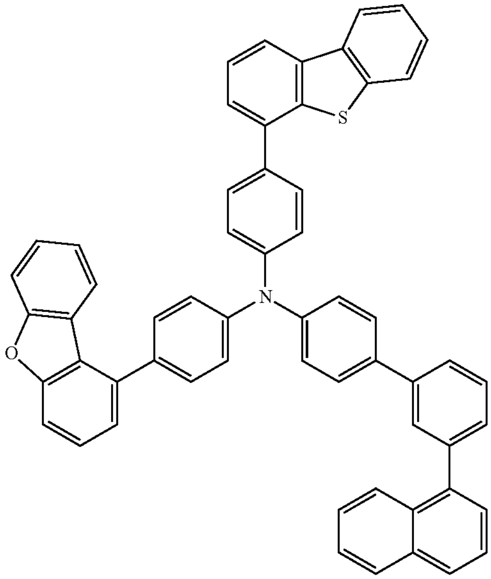
-continued
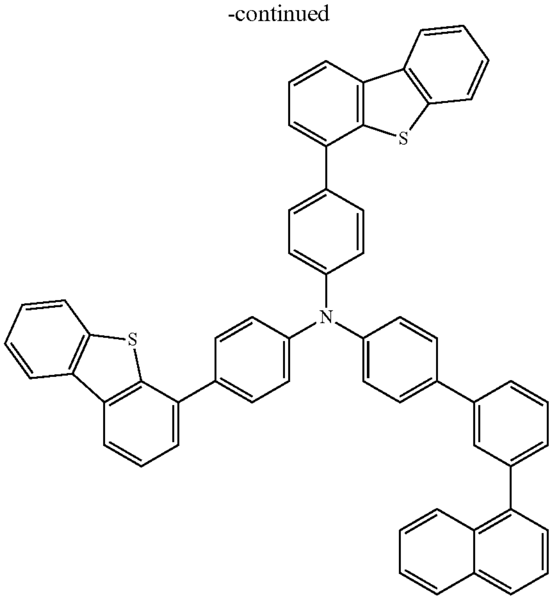
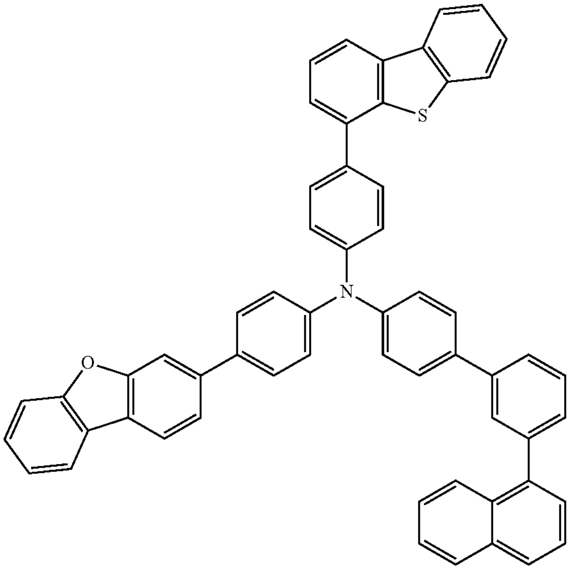
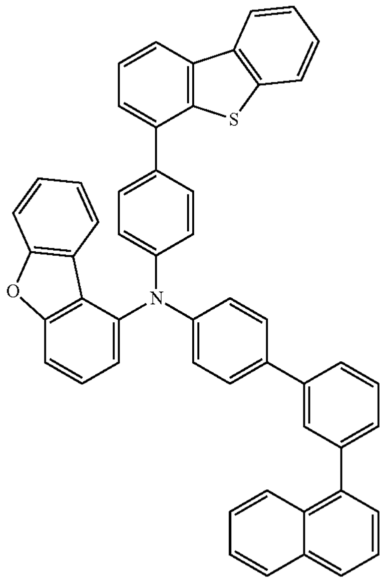

-continued
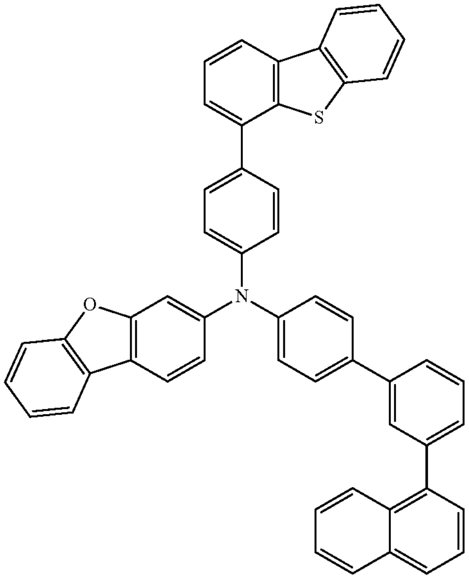
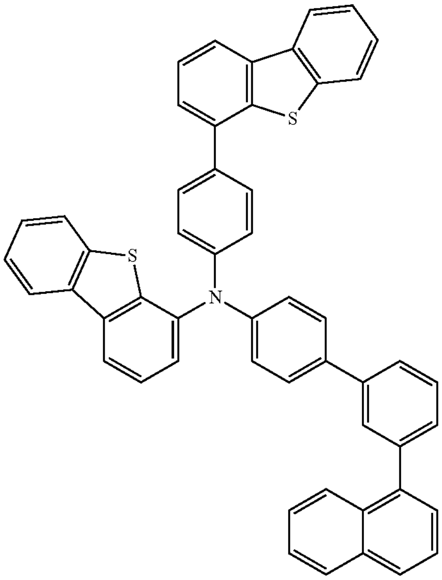
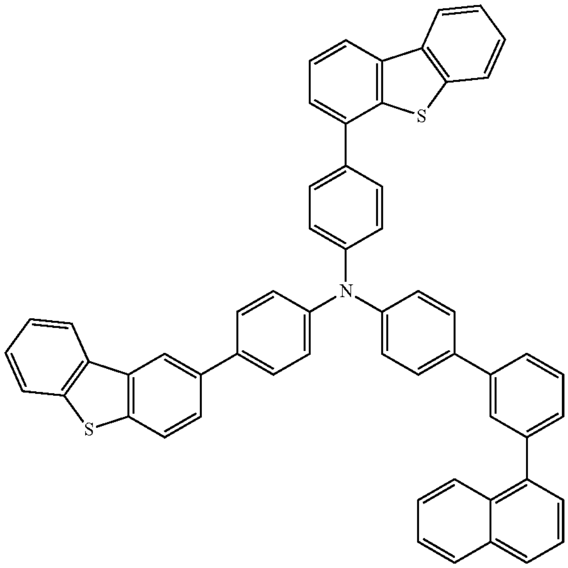
-continued
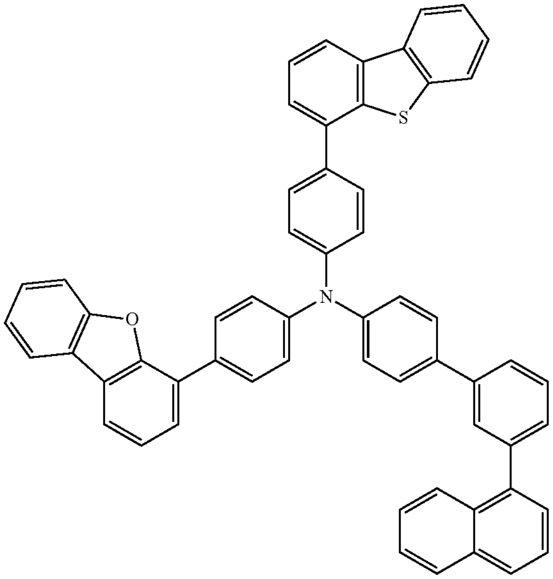
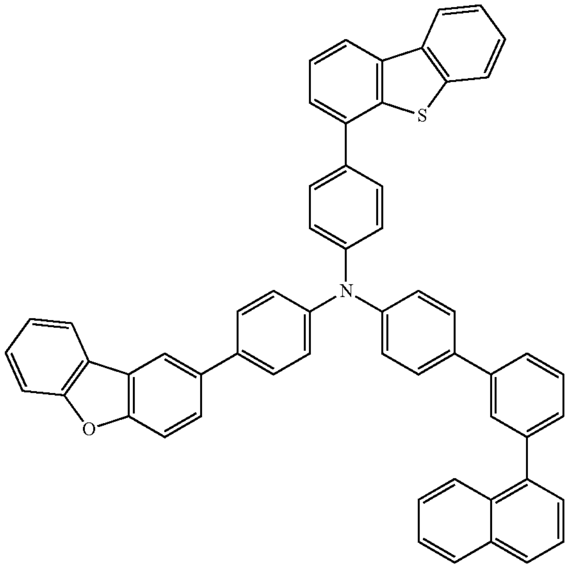
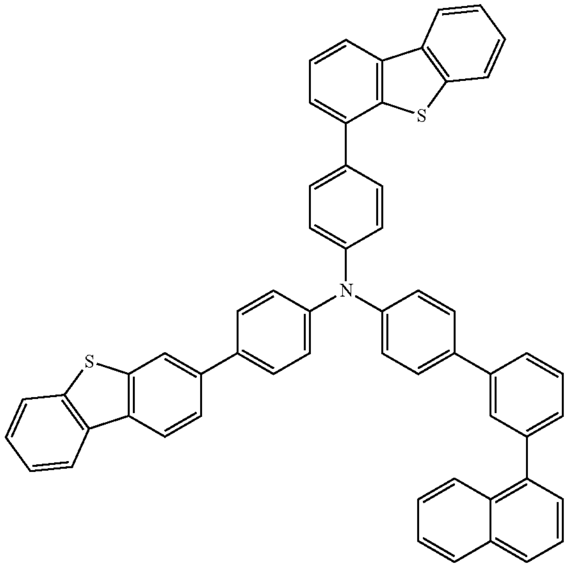

-continued
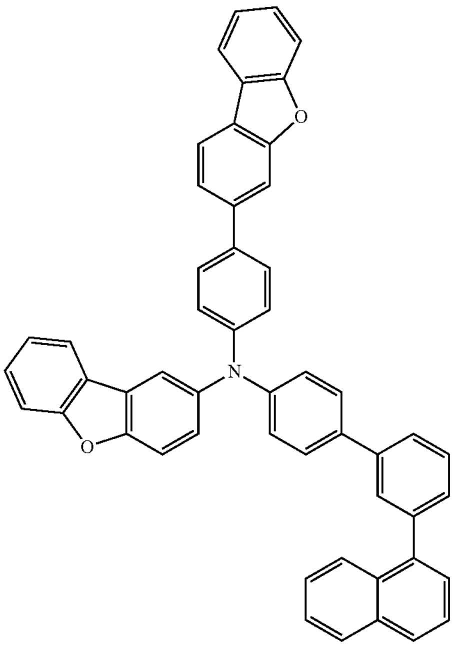
-continued
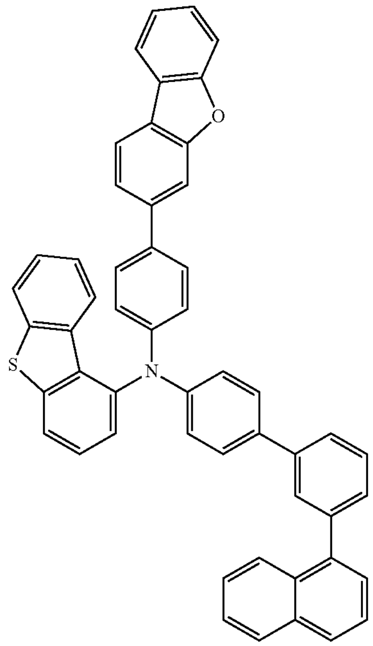
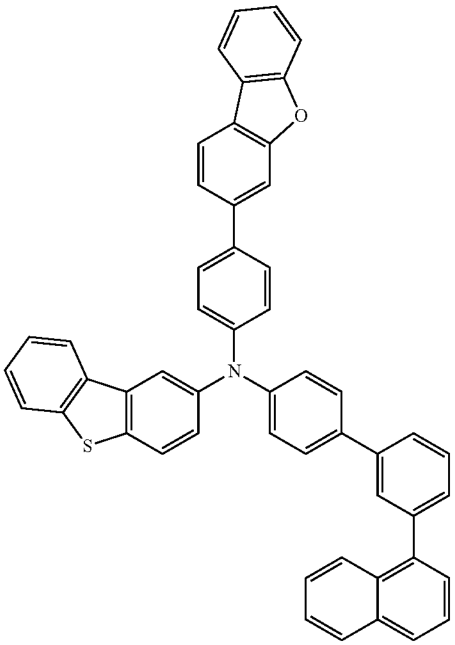
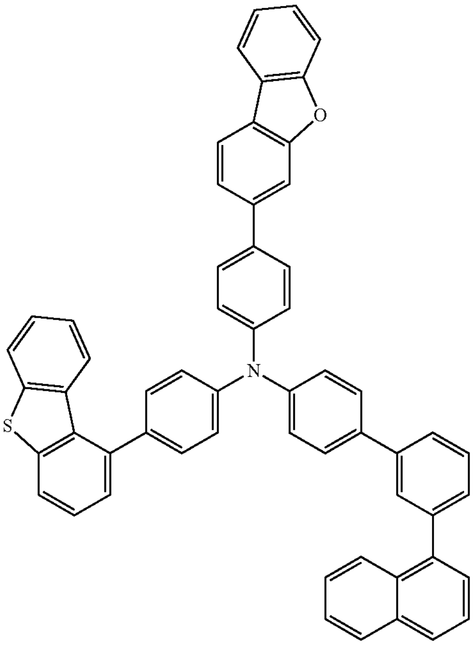

-continued
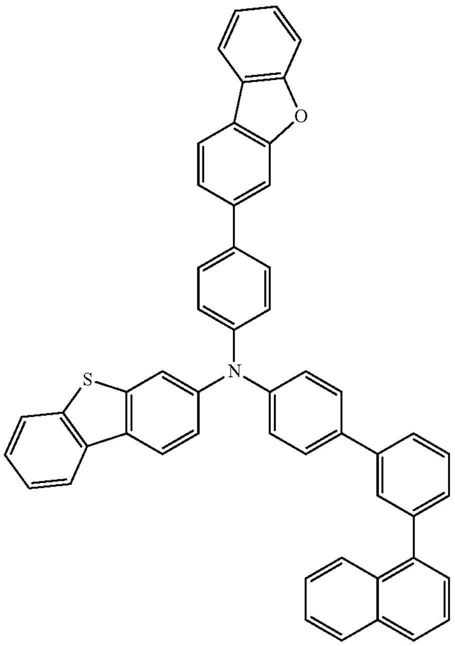
-continued
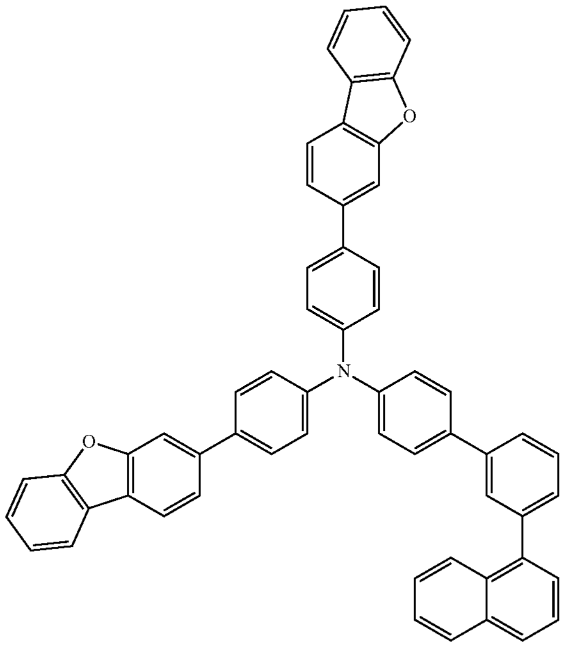
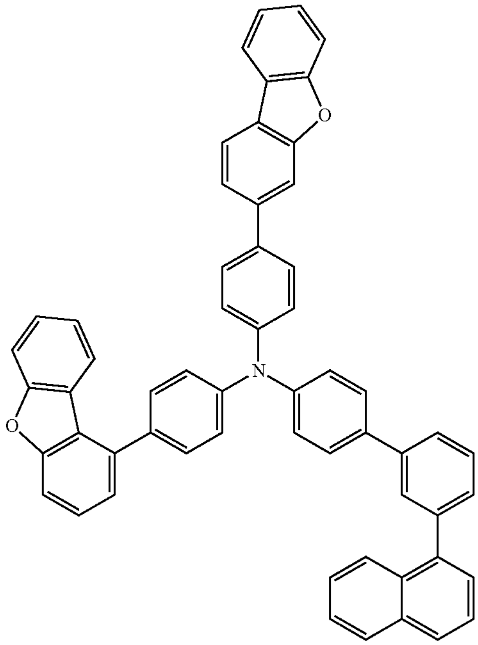
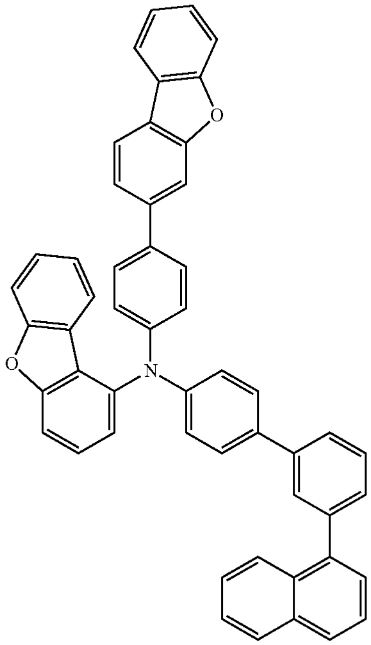

-continued
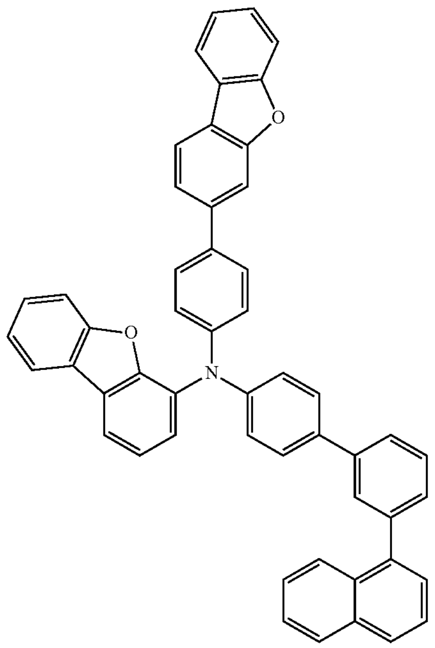
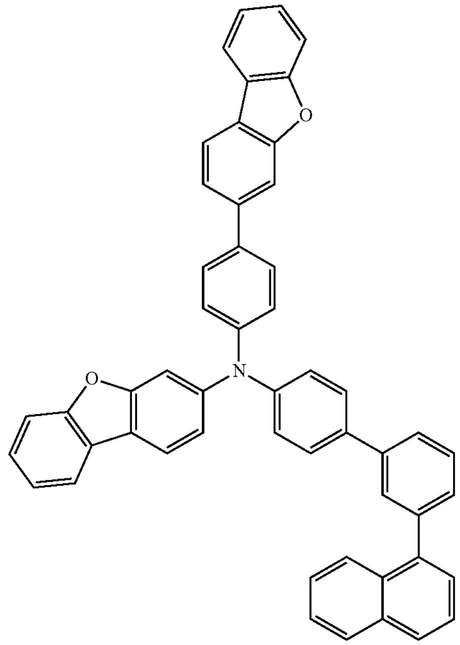
-continued
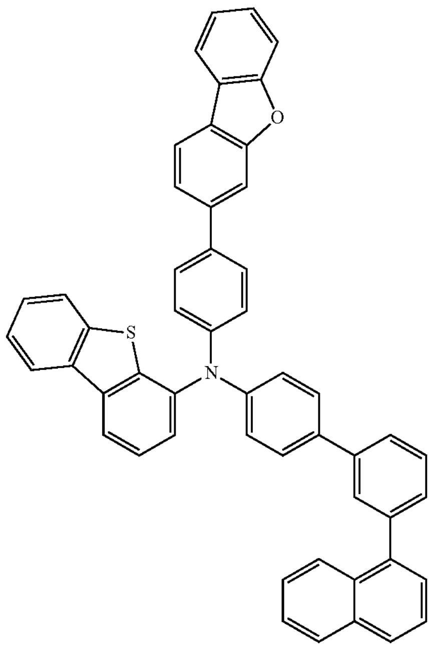
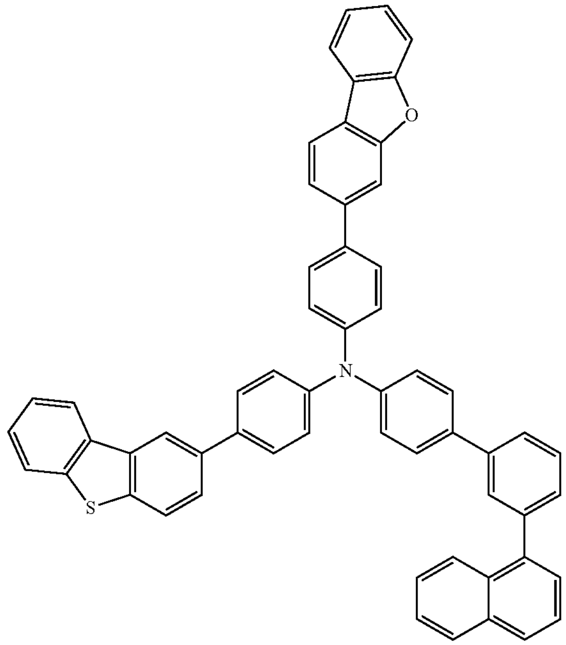

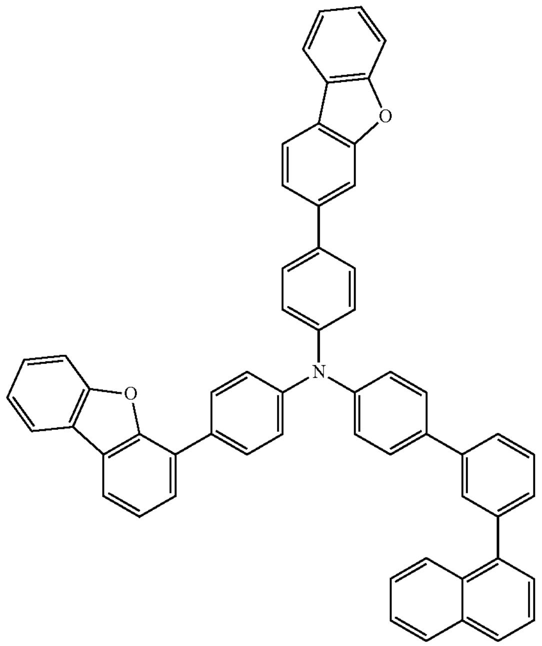
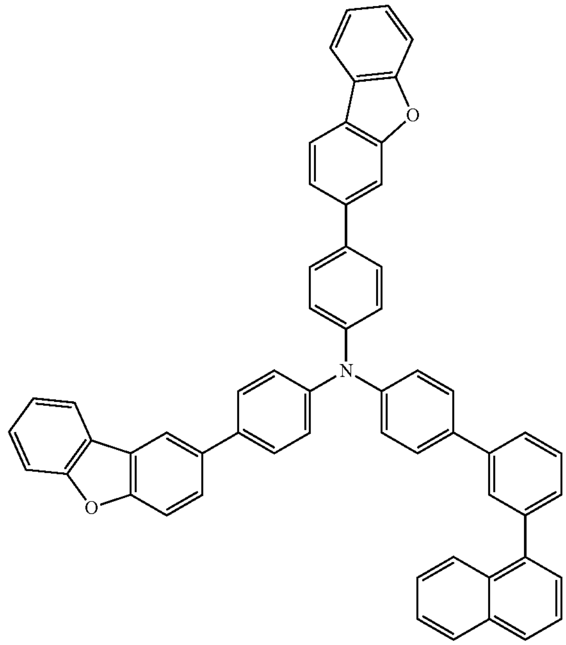
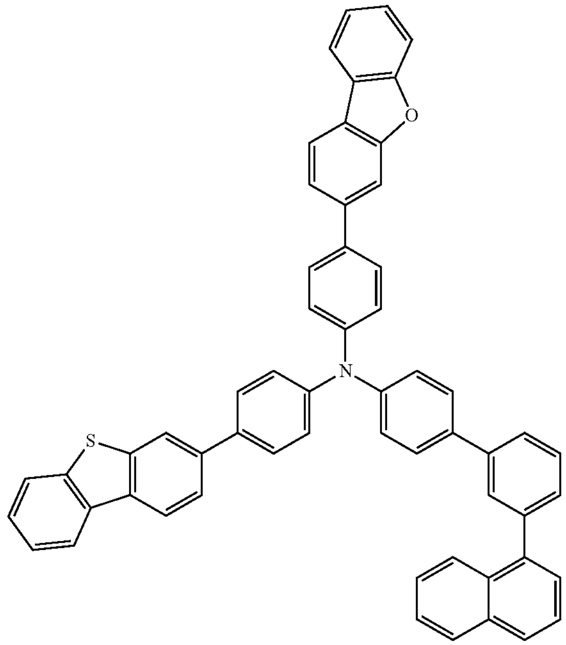
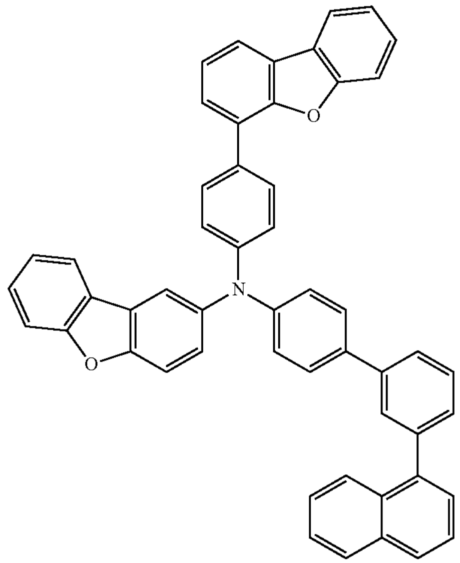

-continued
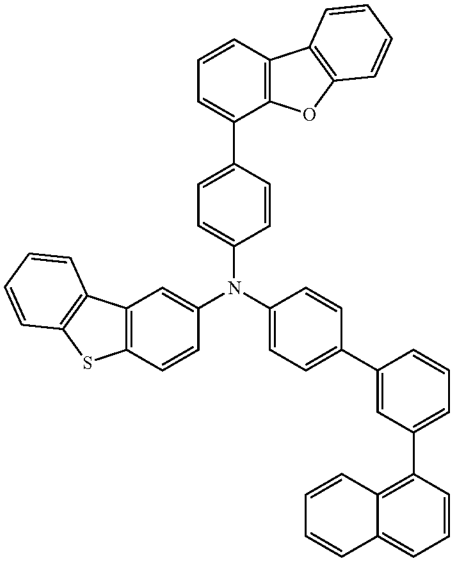
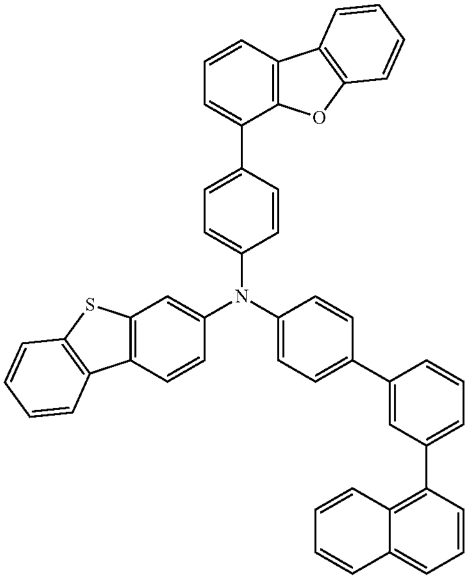
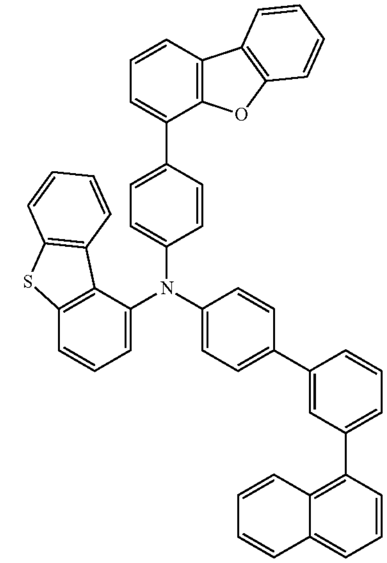
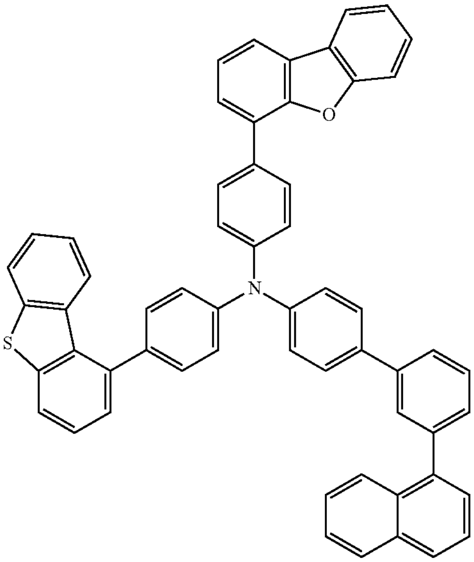
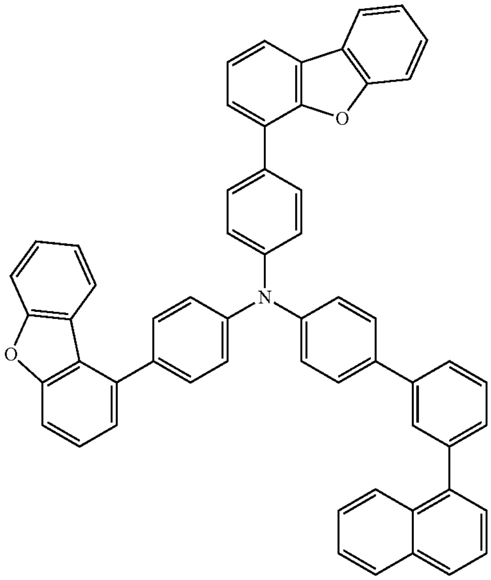

-continued
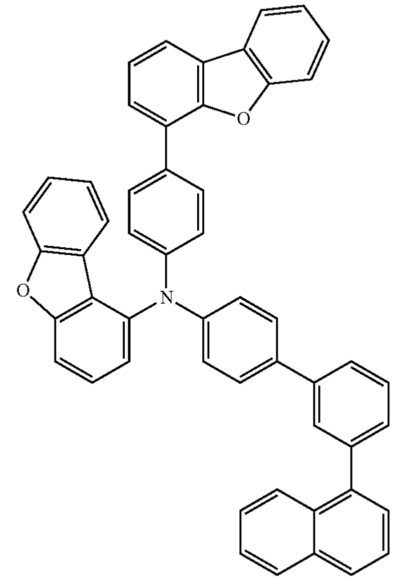
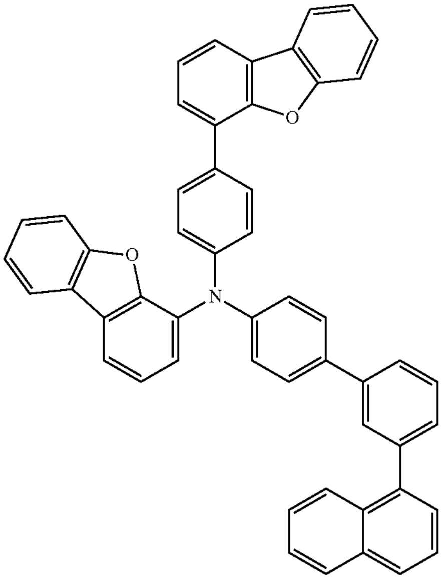
-continued
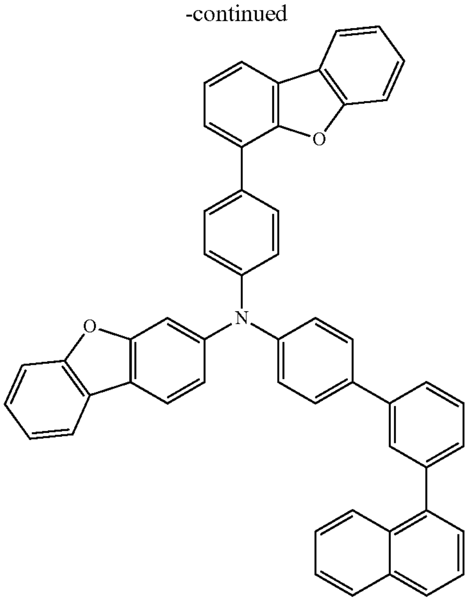
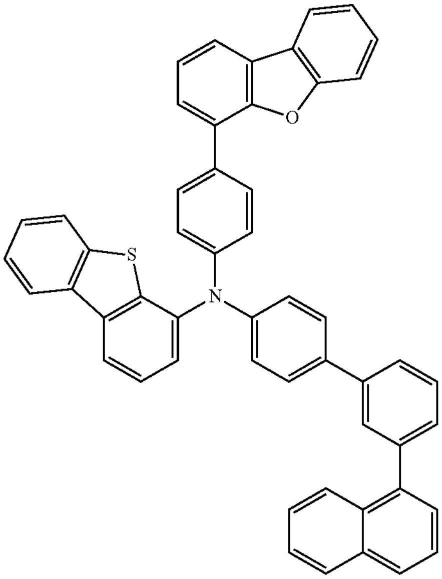
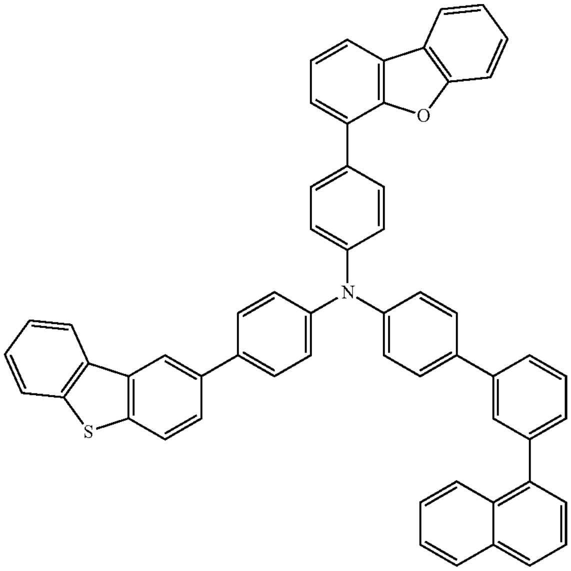

-continued
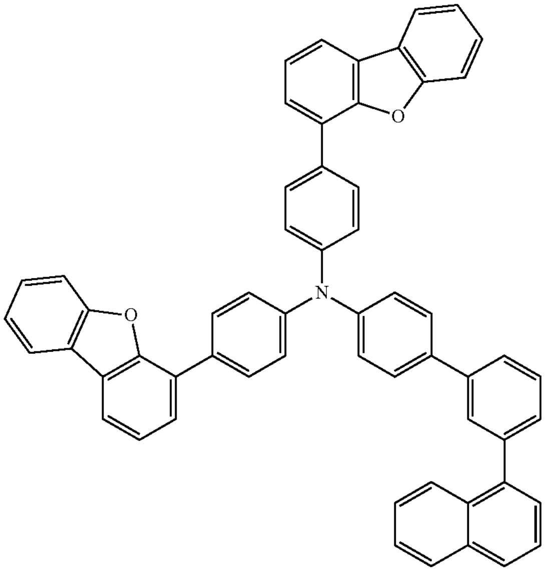
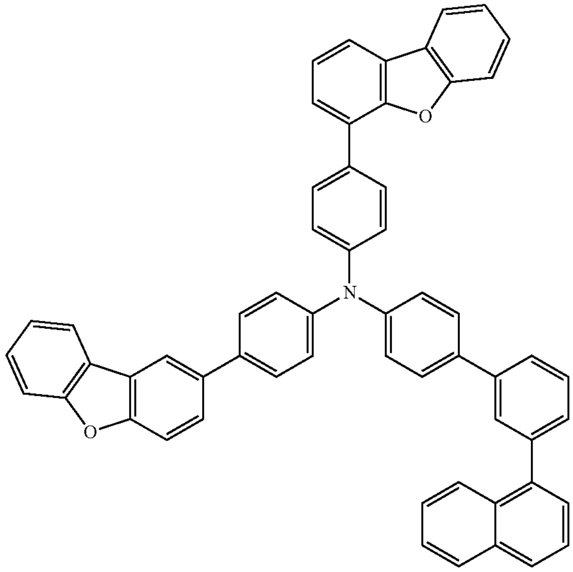
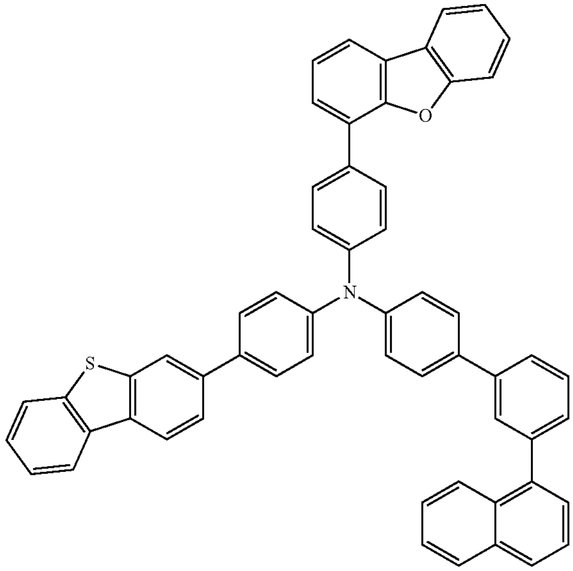
-continued
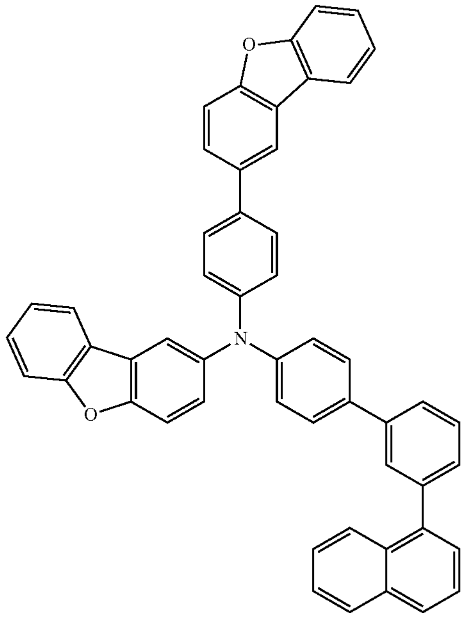
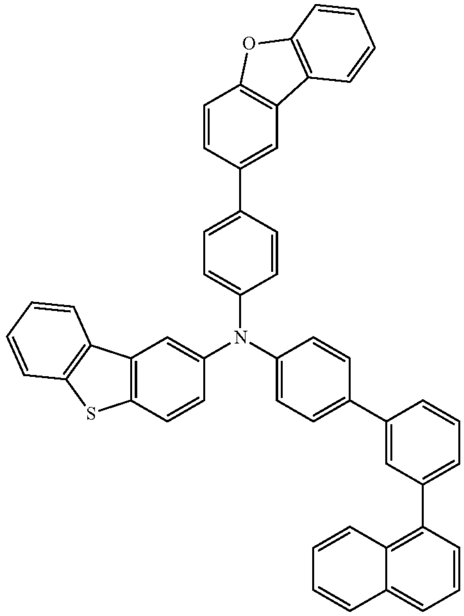

-continued
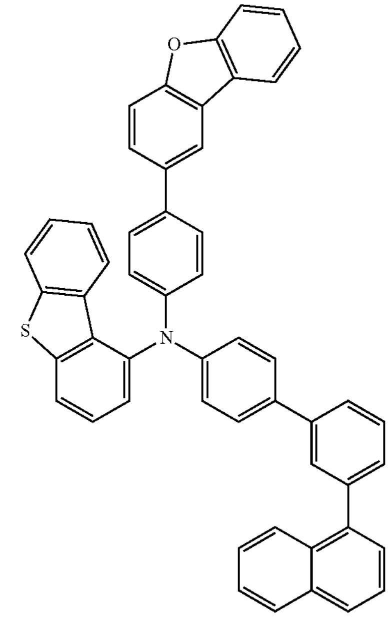
-continued
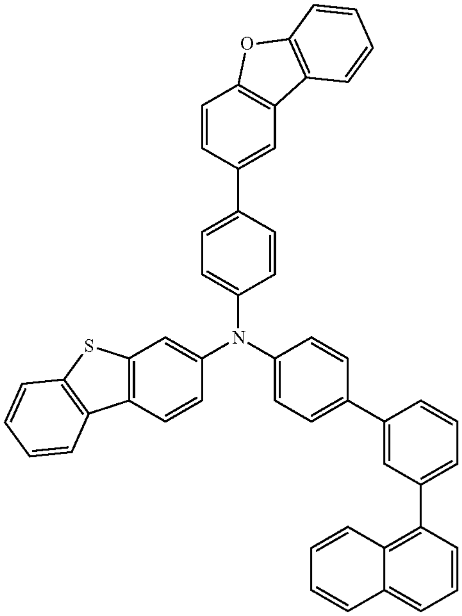
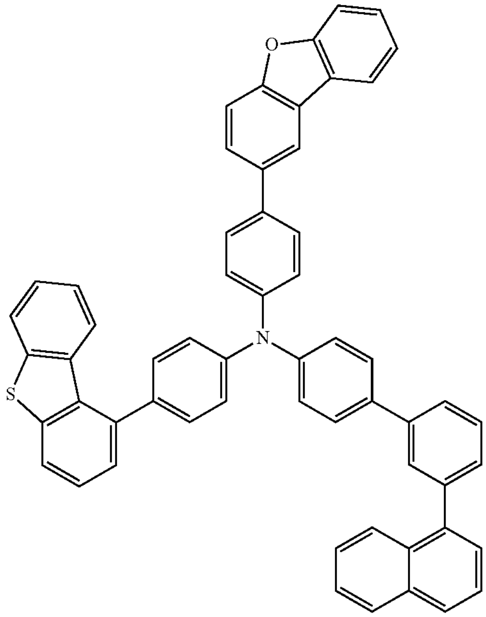
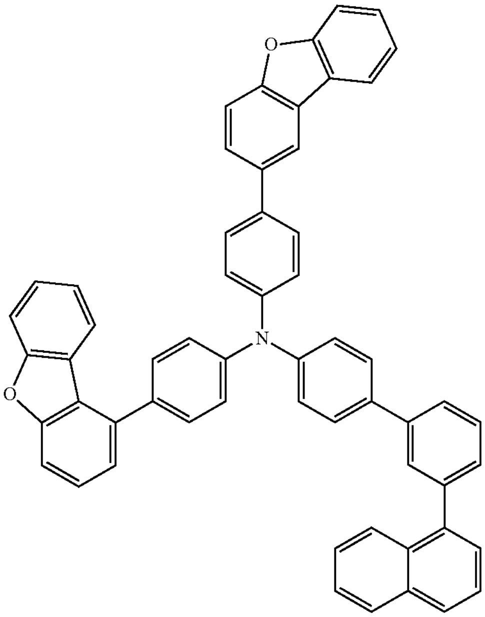

-continued
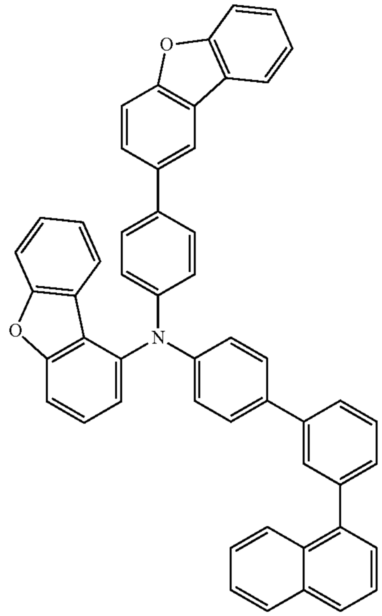
-continued
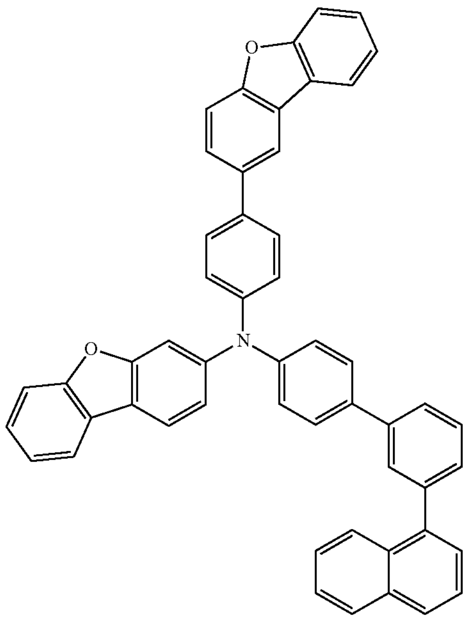
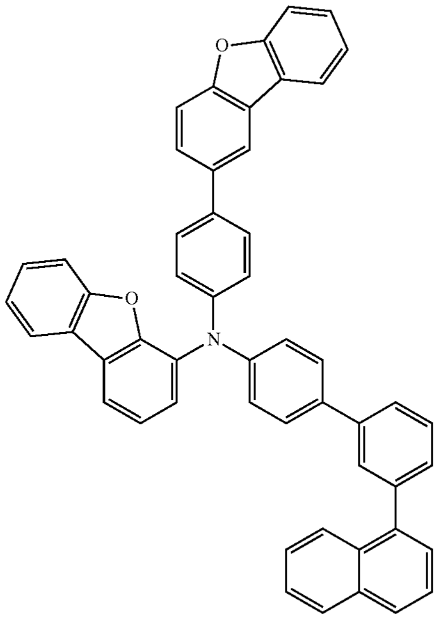
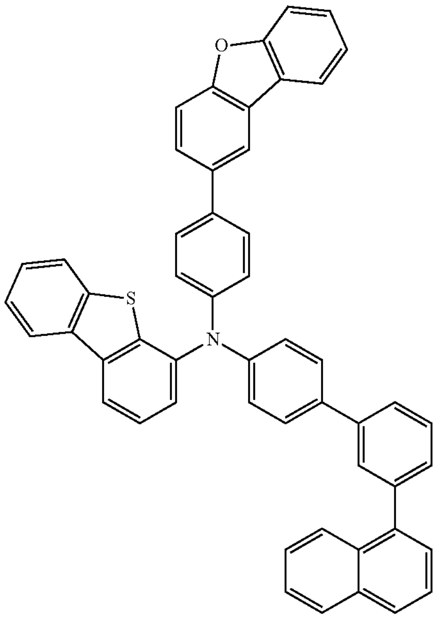

-continued
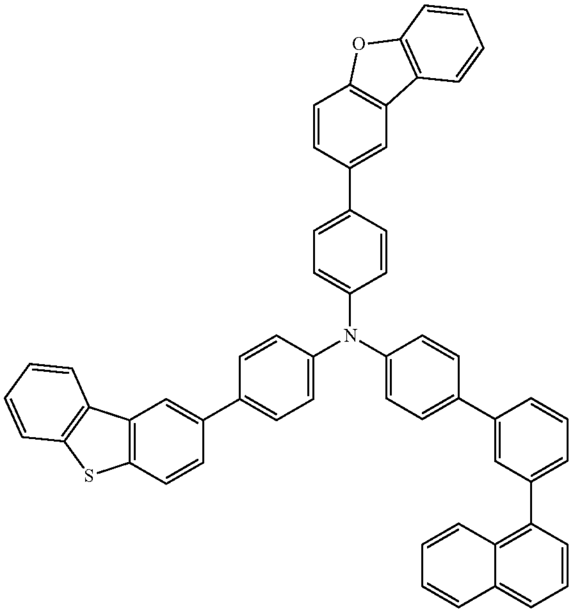
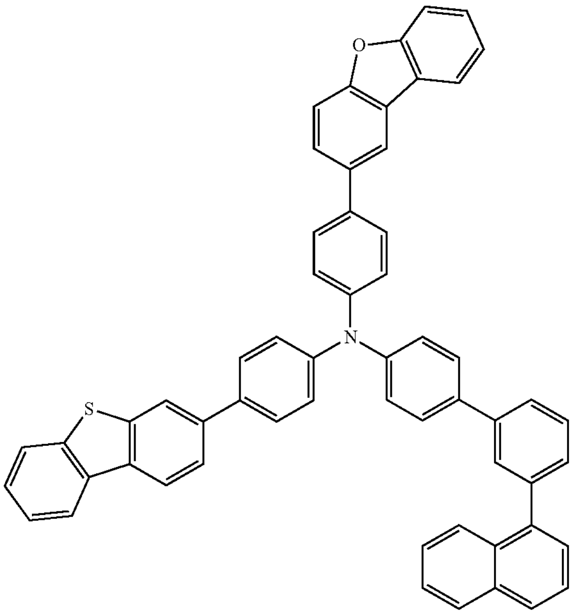
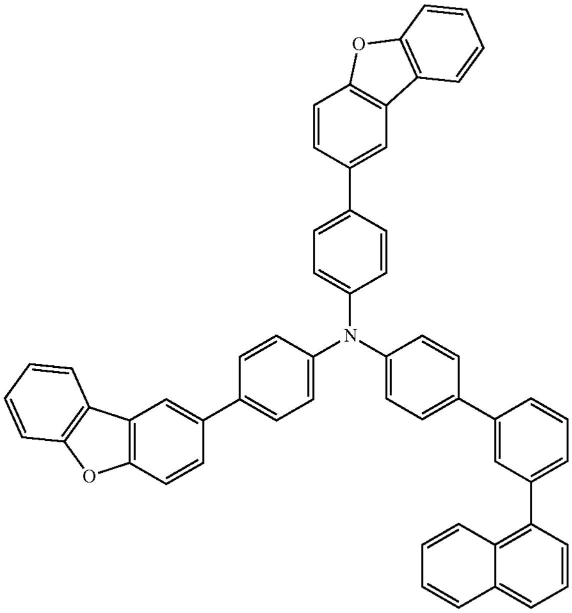
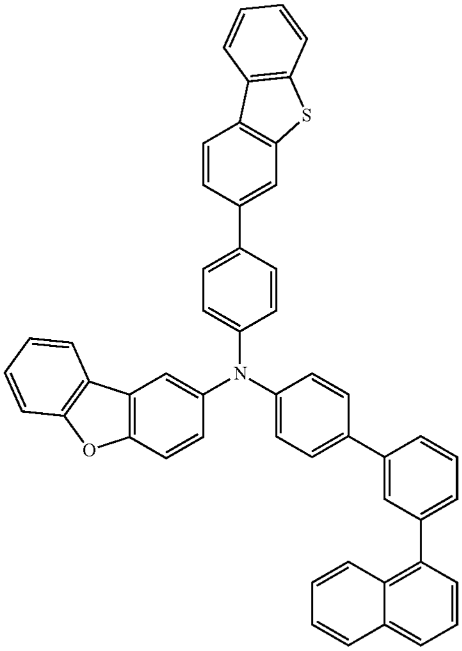
-continued

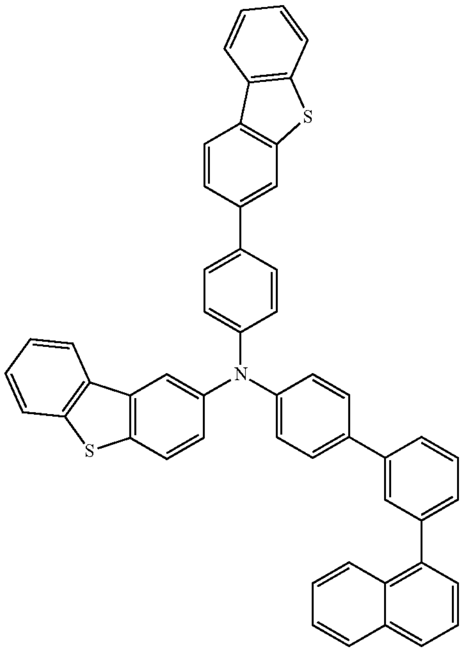
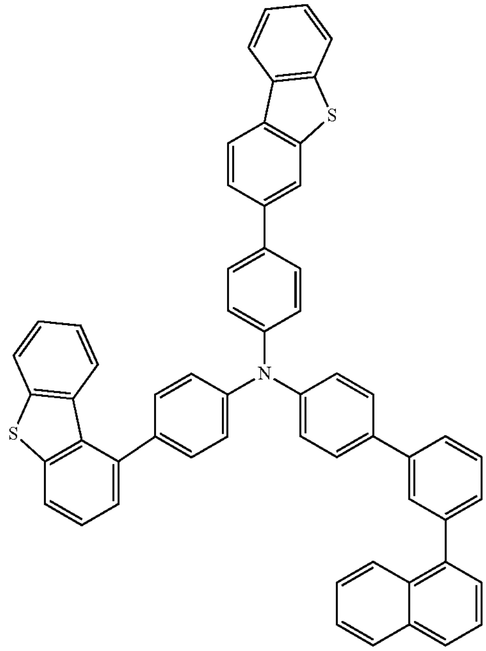 [SMILES: c1cc(-c2ccc(N(c3ccc(-c4ccc5c(c4)sc4ccccc45)cc3)c3ccc(-c4cccc5sc6ccccc6c45)cc3)cc2)cc(-c2cccc3ccccc23)c1]
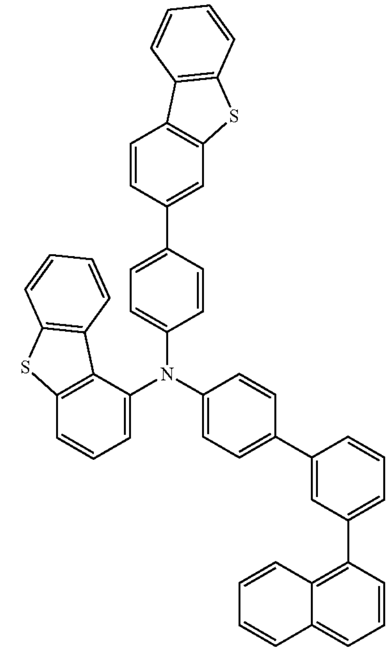
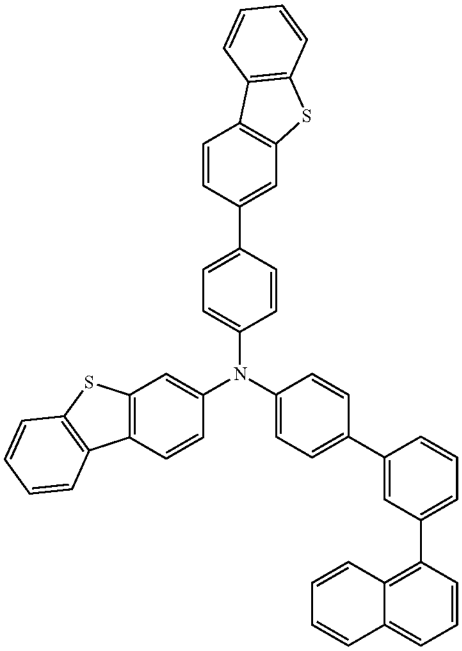

-continued
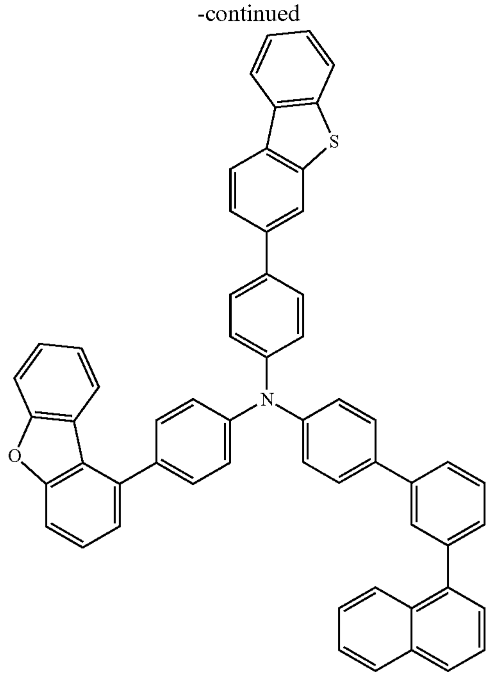
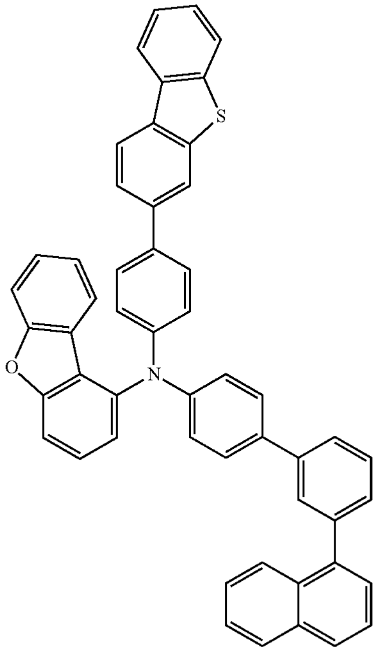
-continued
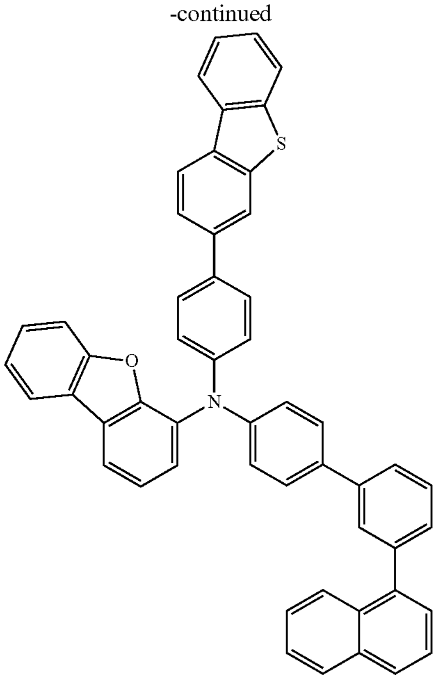
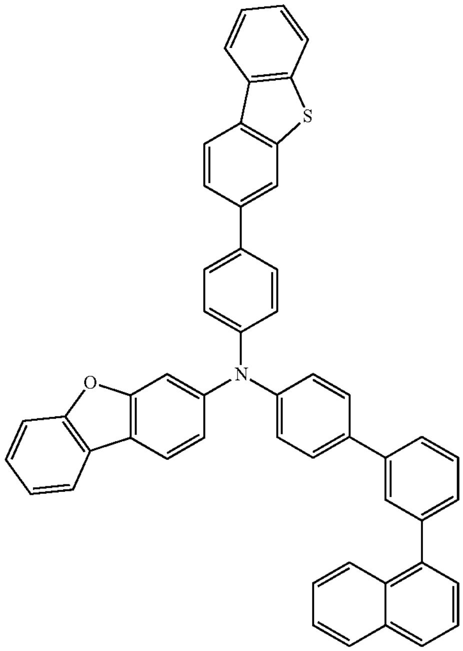

-continued
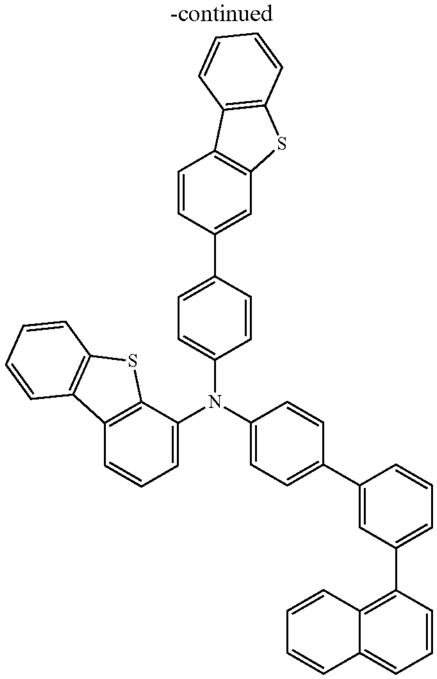
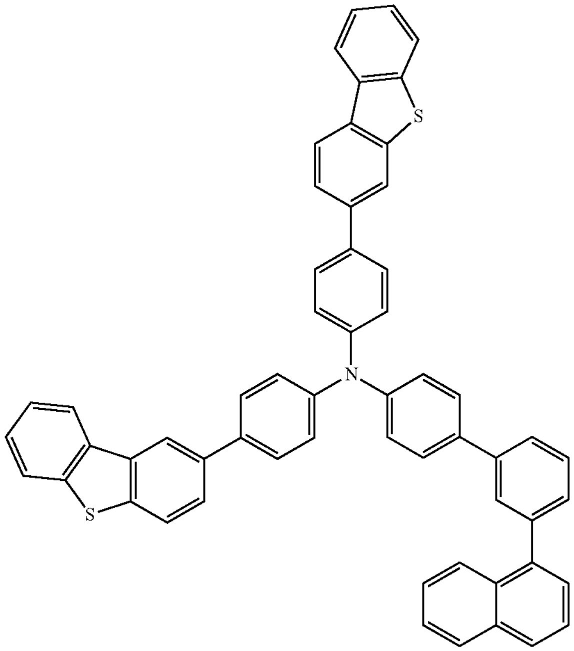
-continued
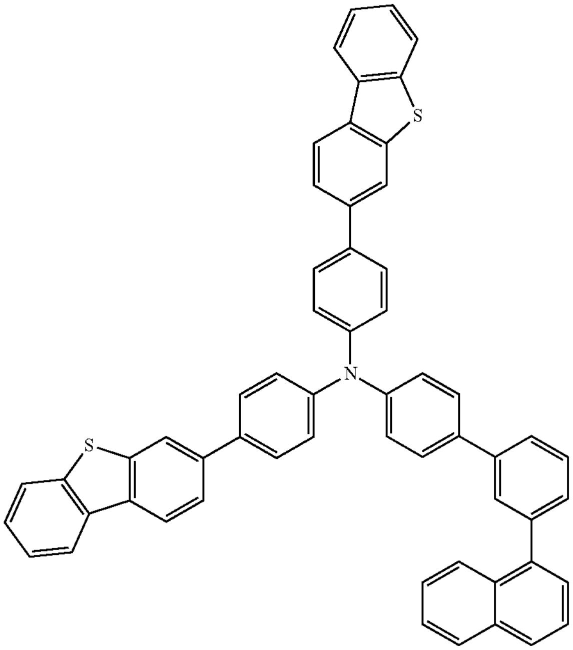
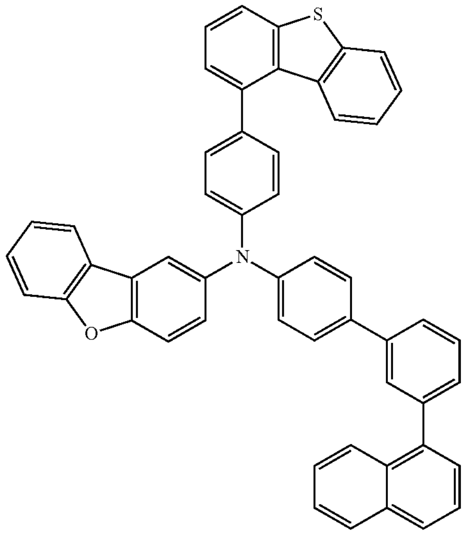
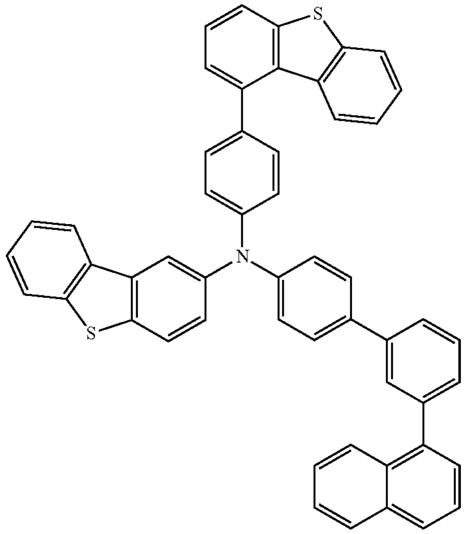

-continued
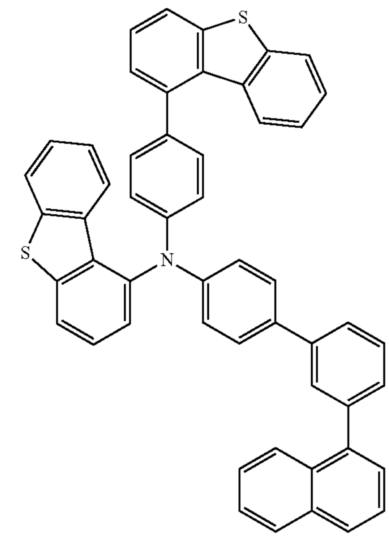
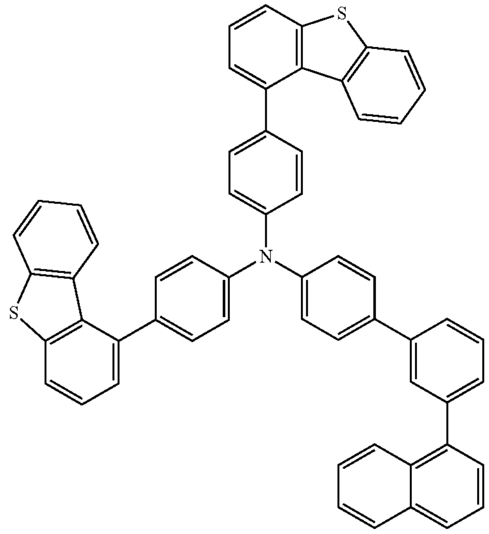
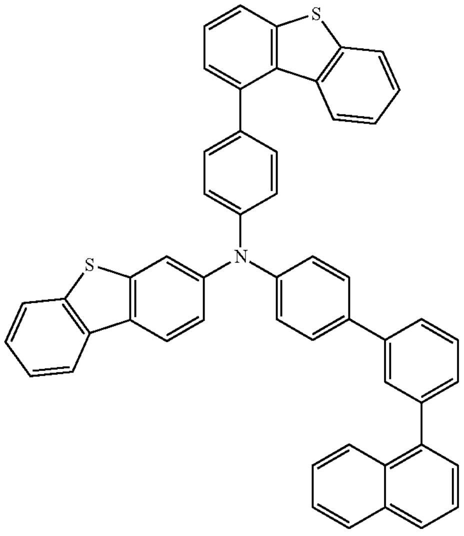
-continued
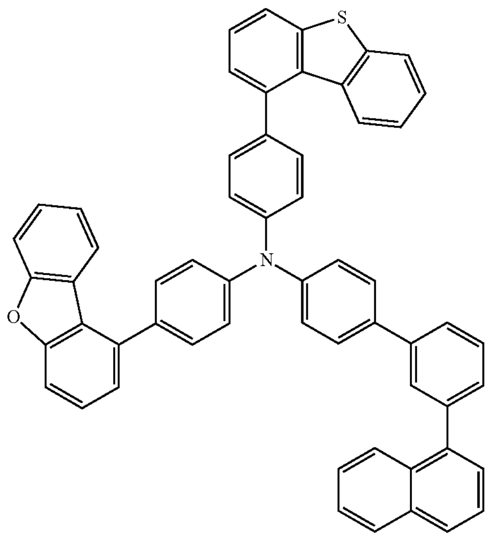
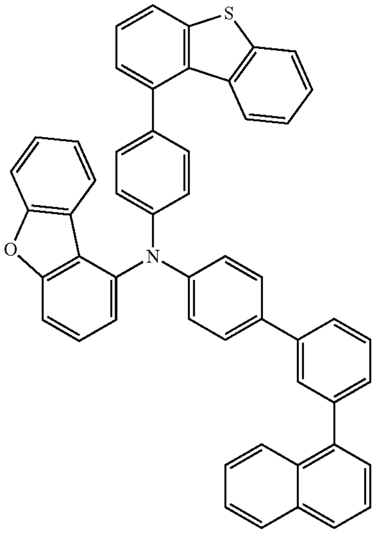
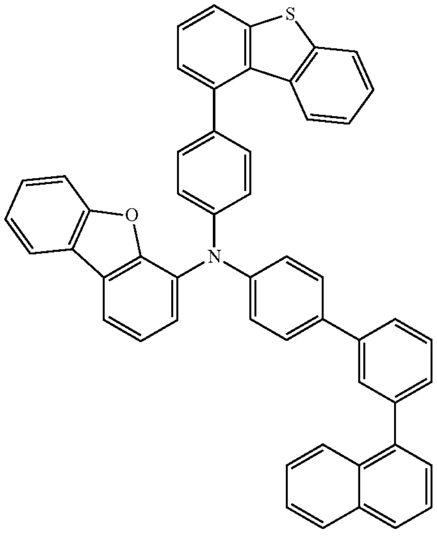 [SMILES: c1cc(-c2ccc(N(c3ccc(-c4cccc5sc6ccccc6c45)cc3)c3cccc4c3sc3ccccc34)cc2)cc(-c2cccc3ccccc23)c1]

-continued
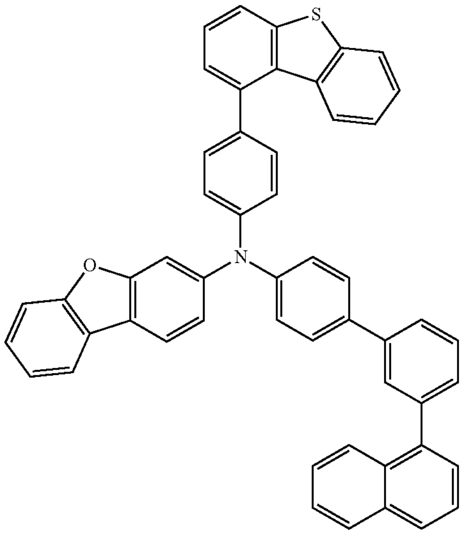
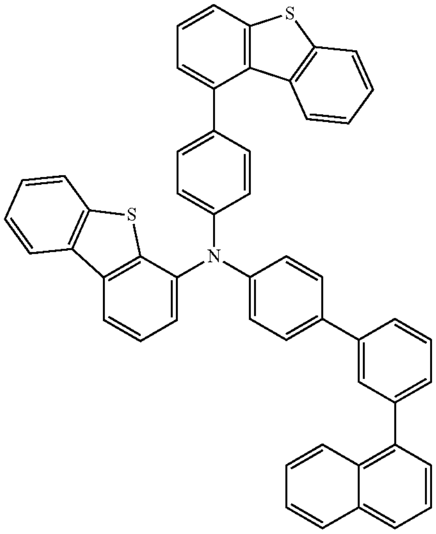
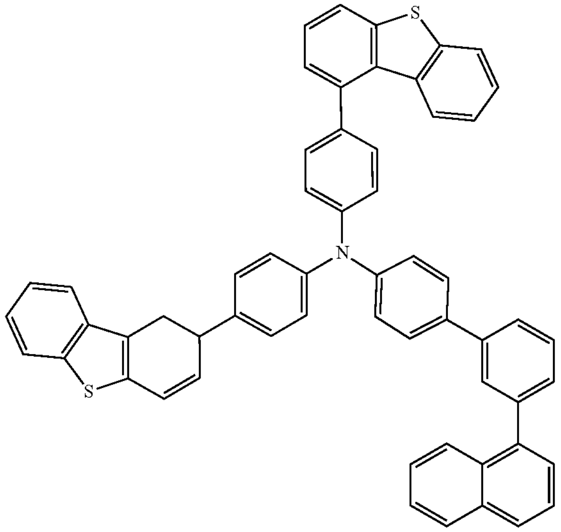
-continued
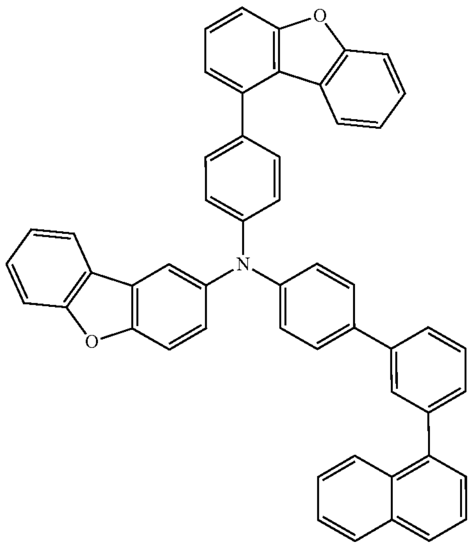
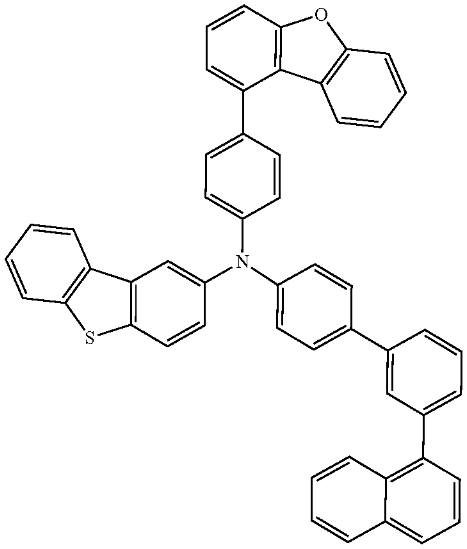
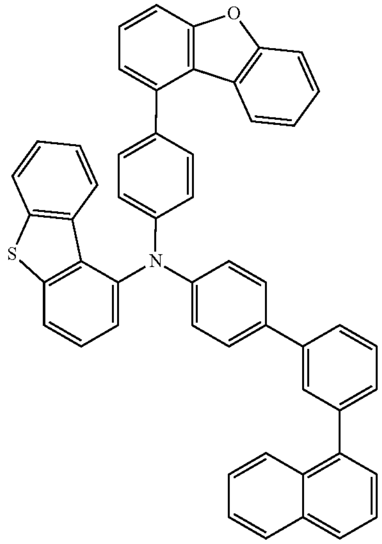

-continued
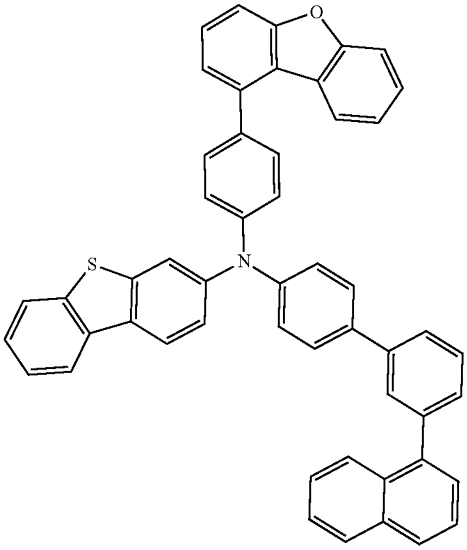
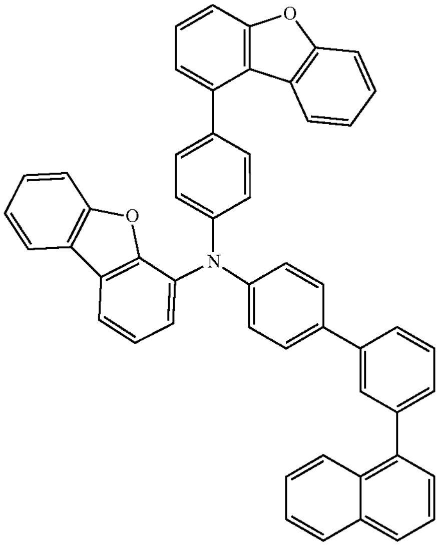
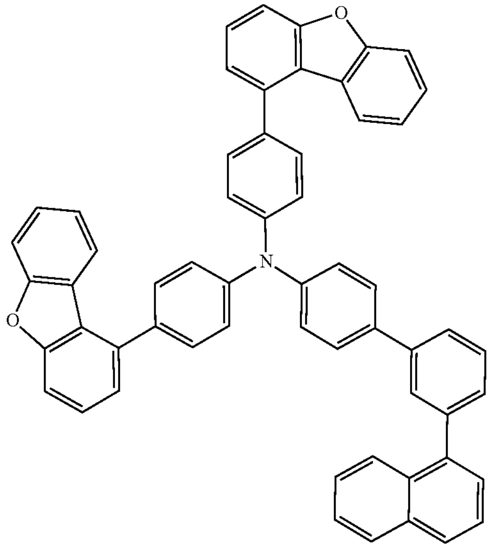
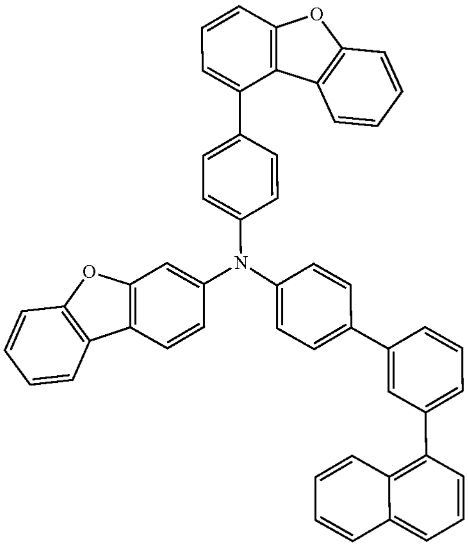
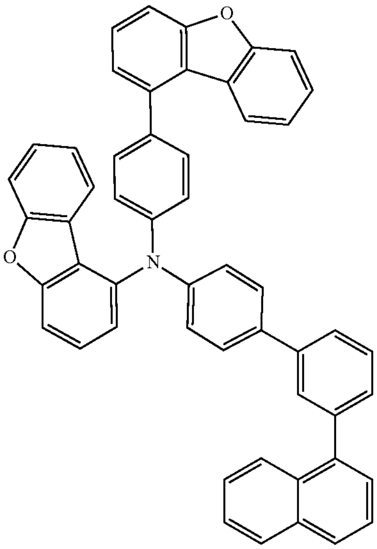
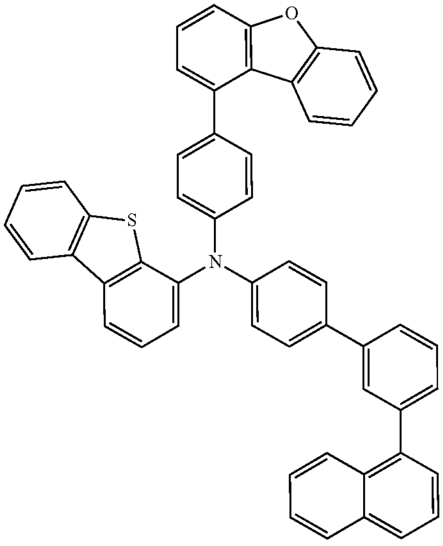
-continued -continued
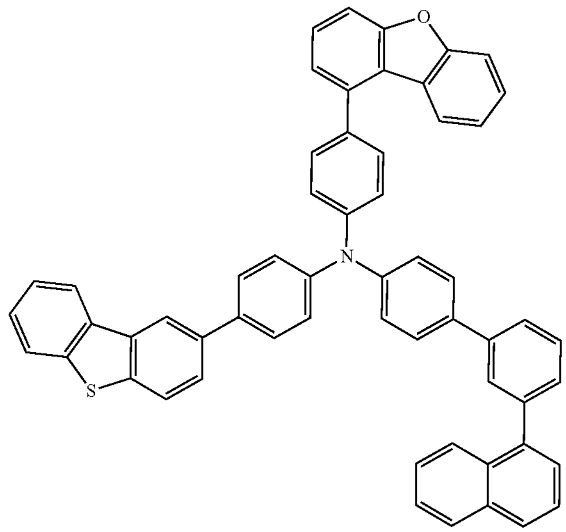
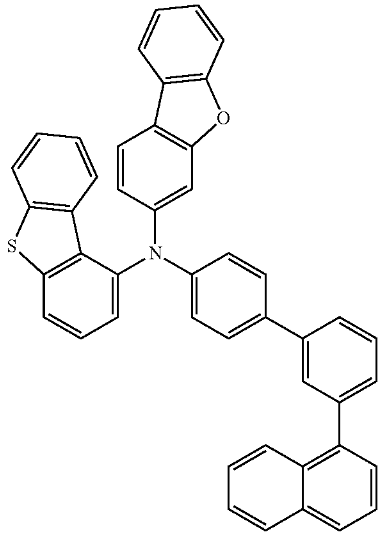
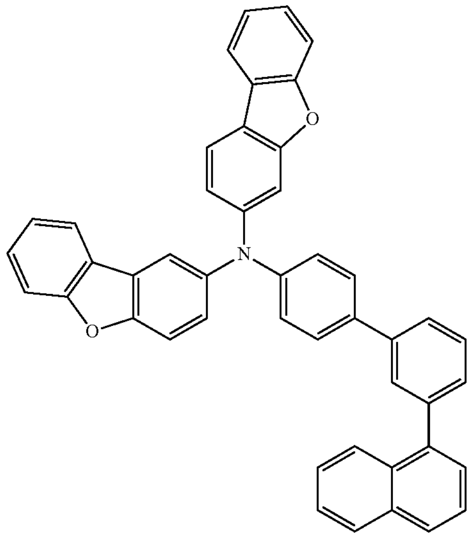
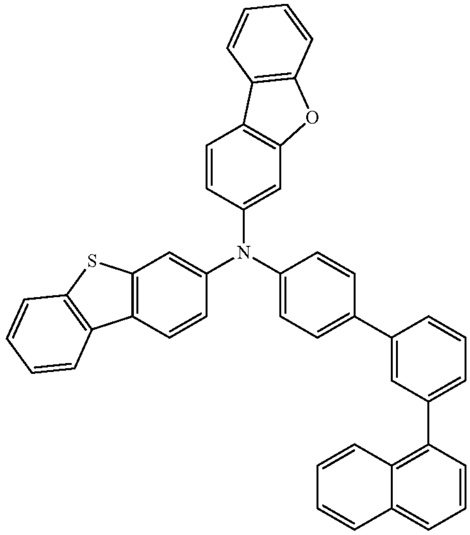
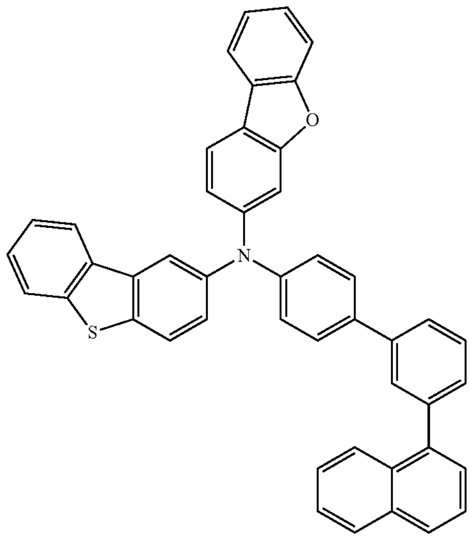
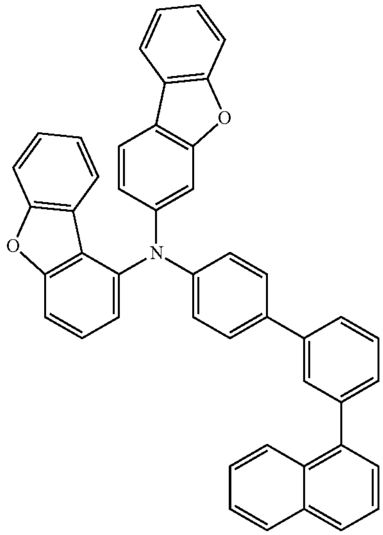
-continued -continued
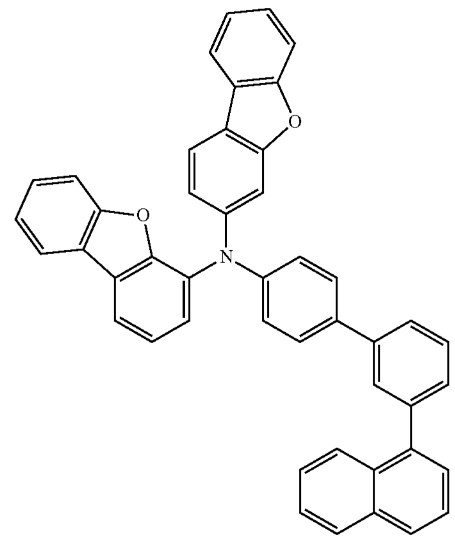
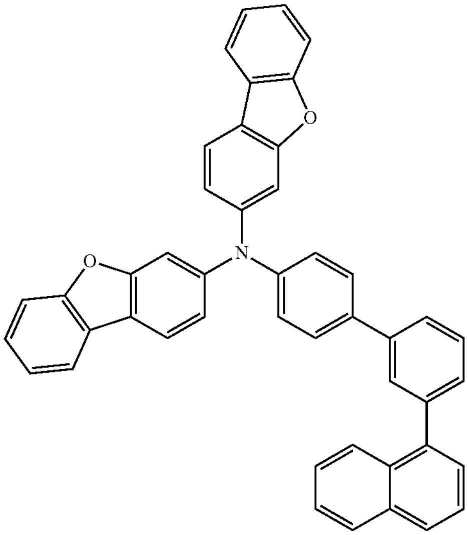
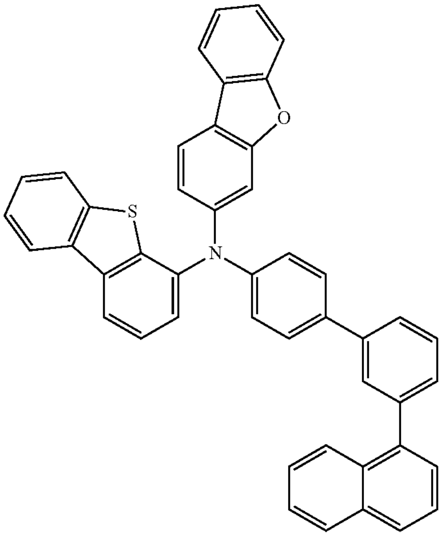
-continued
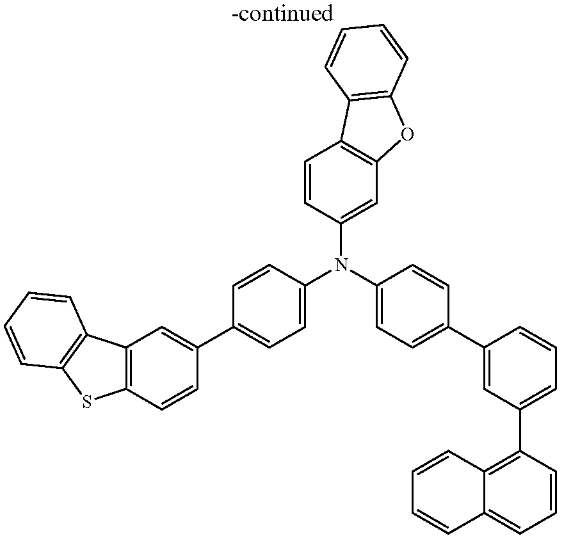
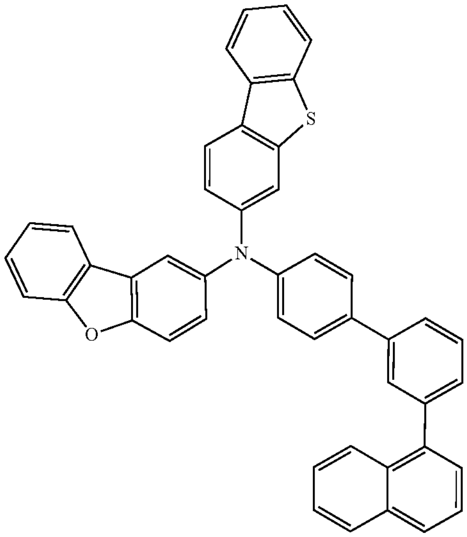
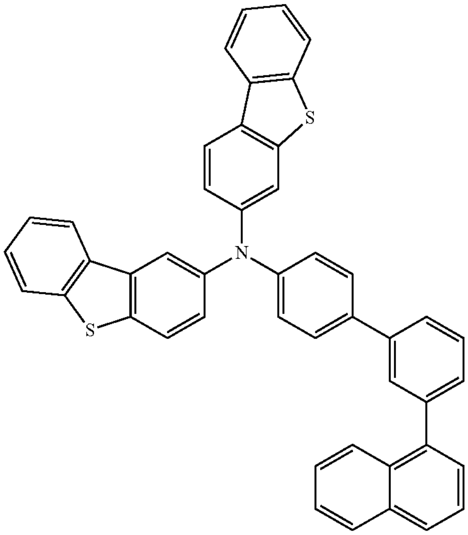

-continued
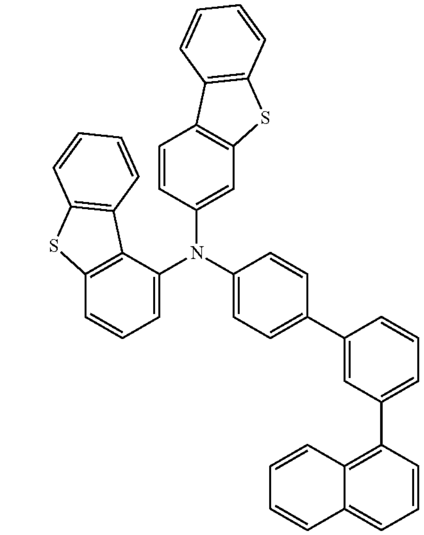
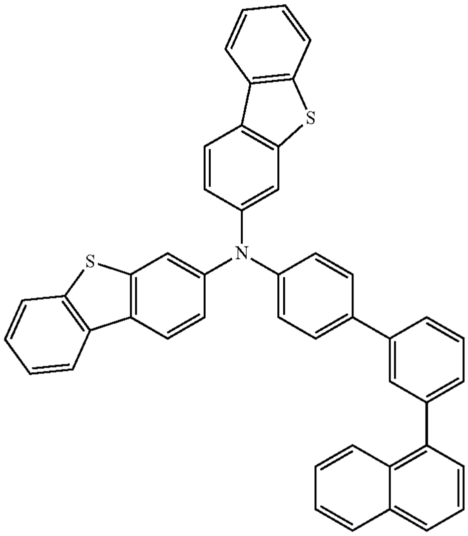 [SMILES: c1cc(-c2ccc(N(c3ccc4c(c3)oc3ccccc34)c3ccc4c(c3)sc3ccccc34)cc2)cc(-c2cccc3ccccc23)c1]
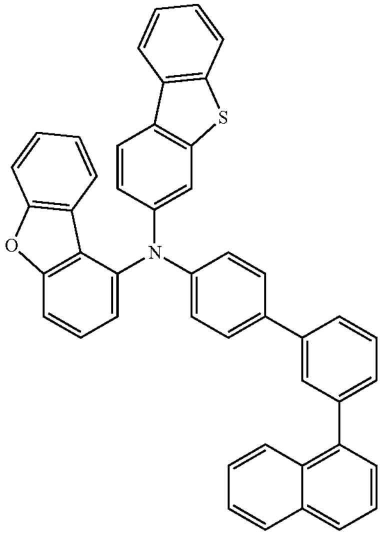
-continued
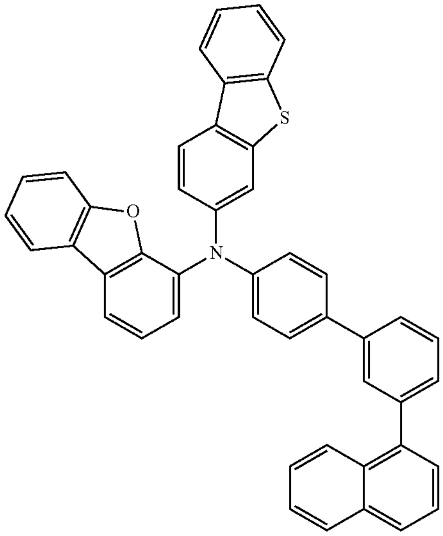
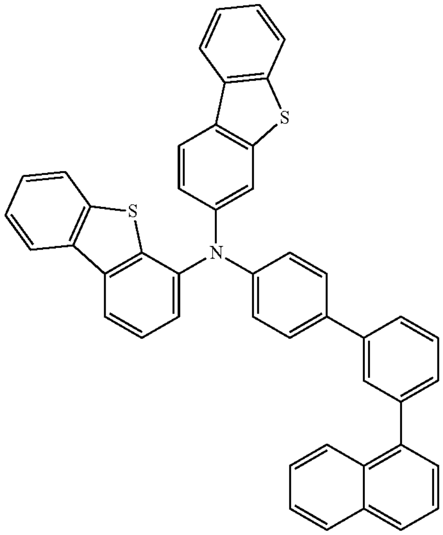
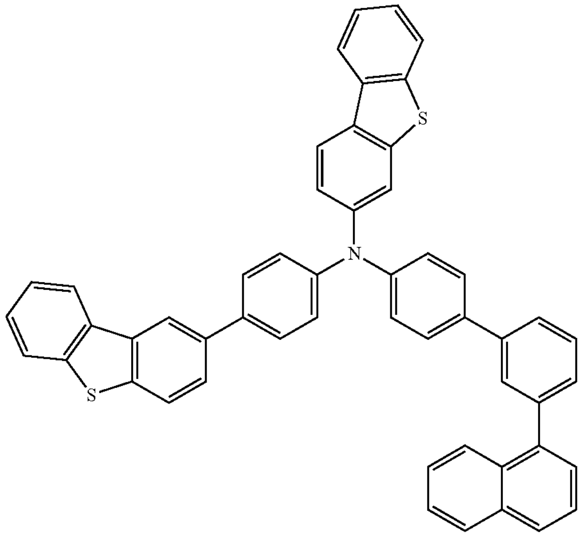

-continued
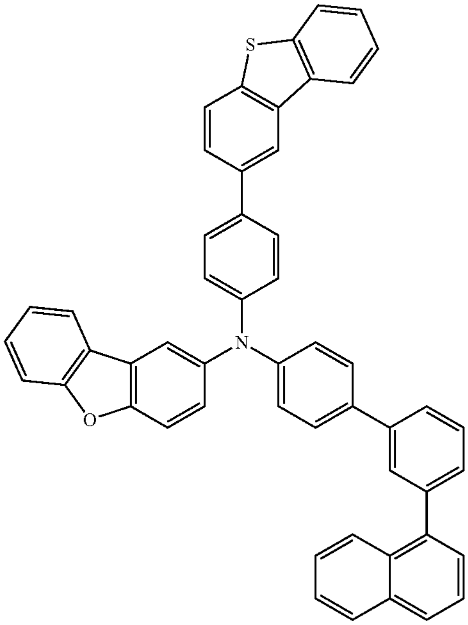
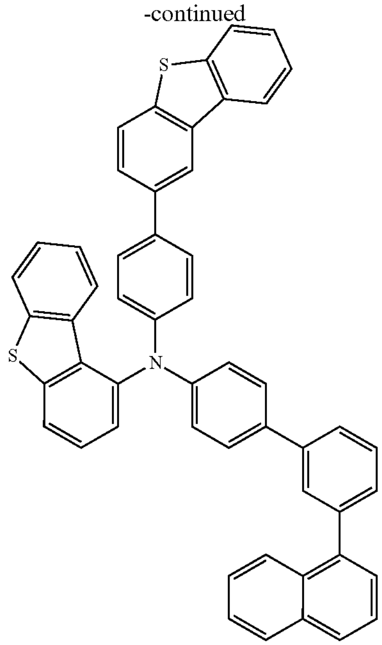
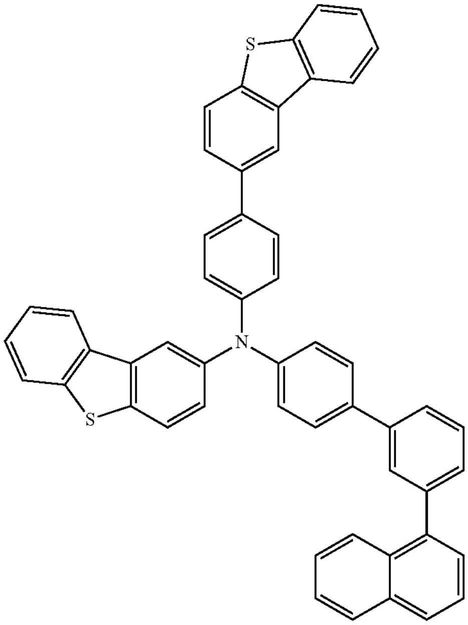
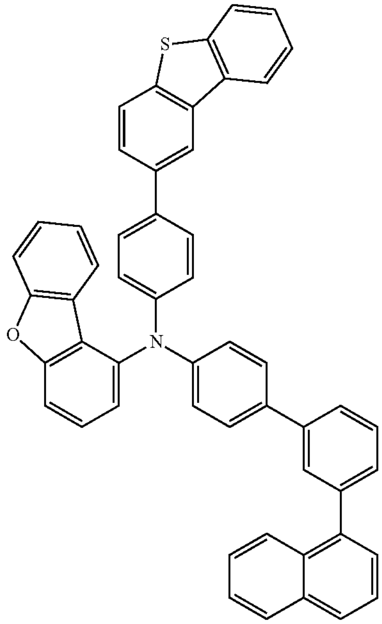

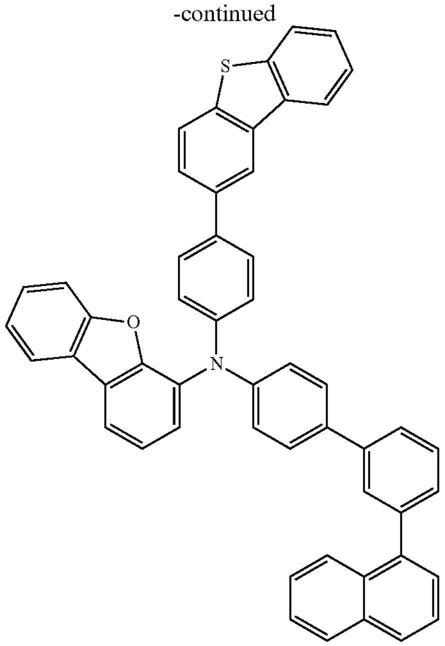
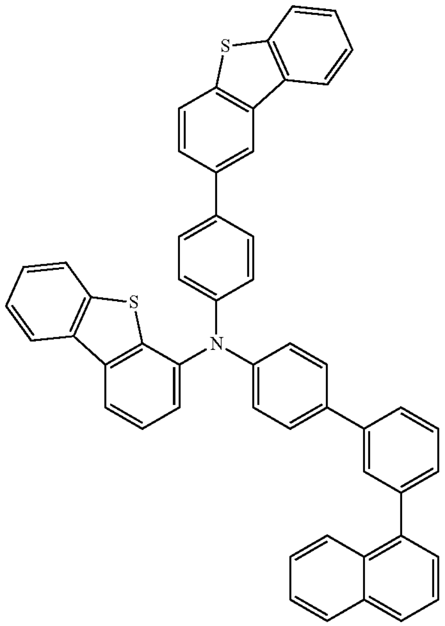
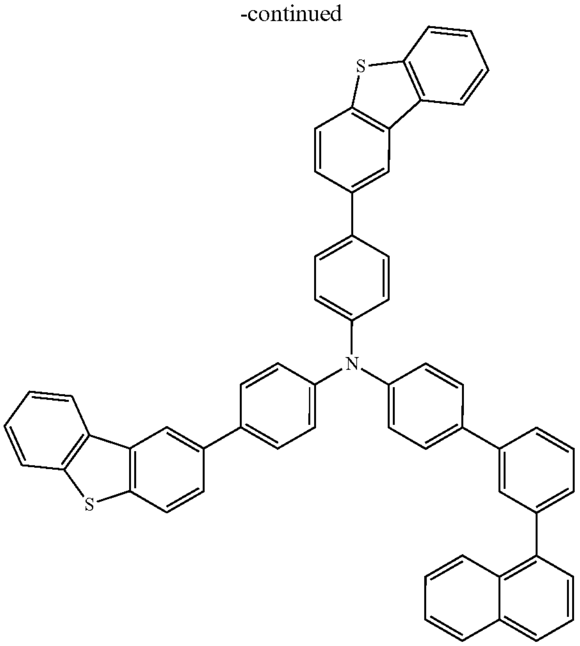
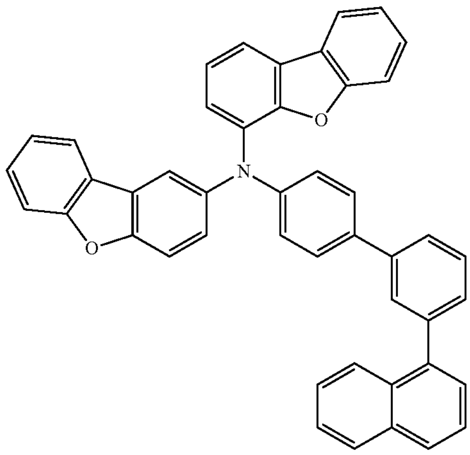
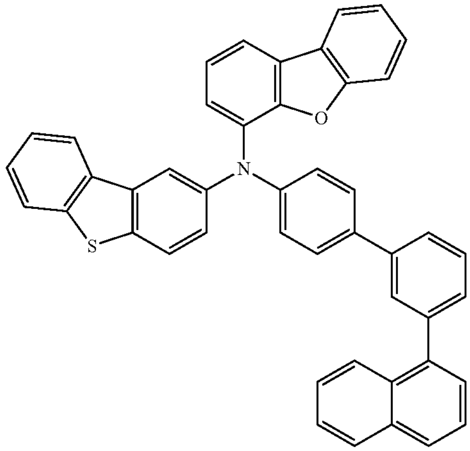

-continued
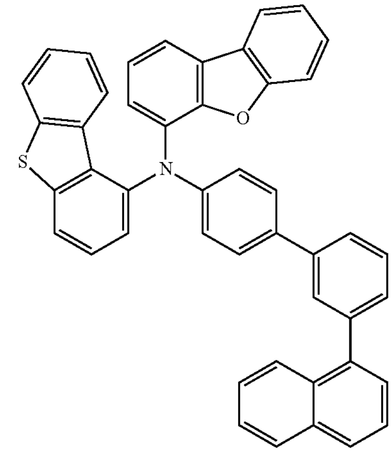
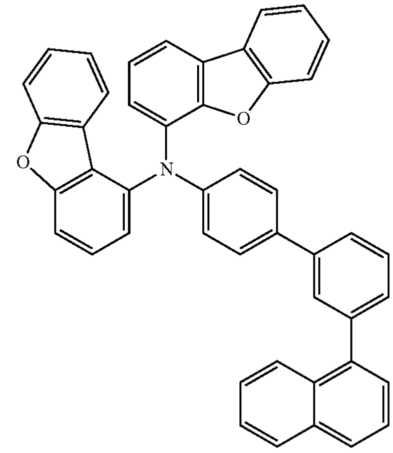
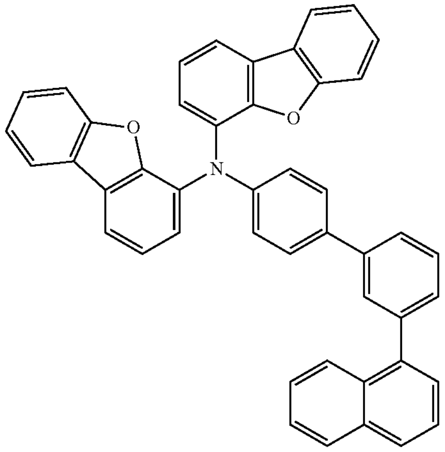
-continued
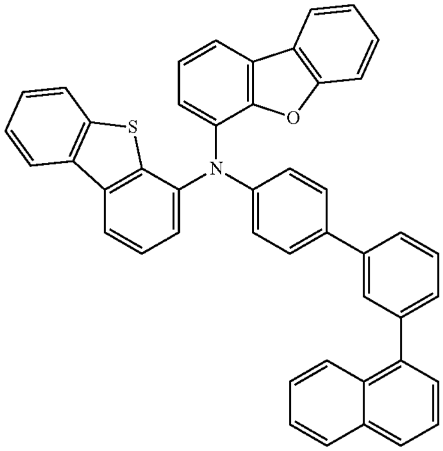
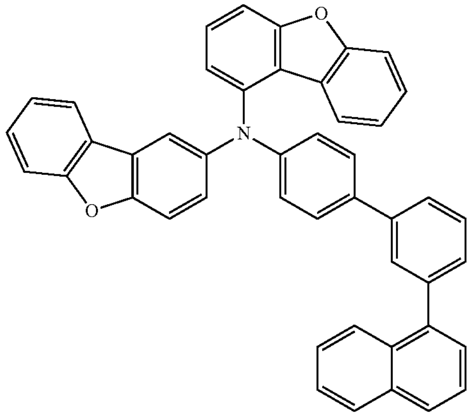
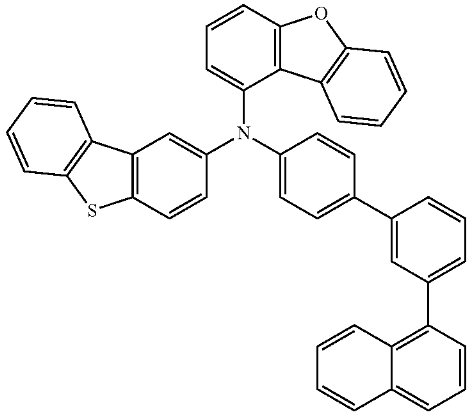
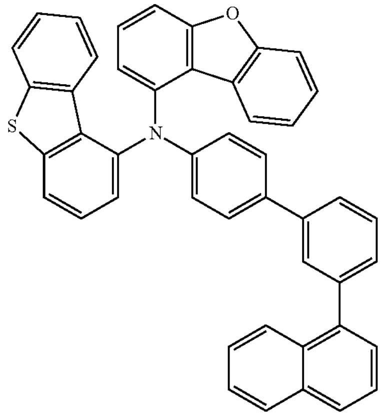

-continued
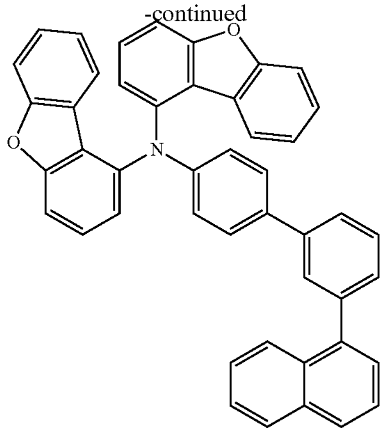
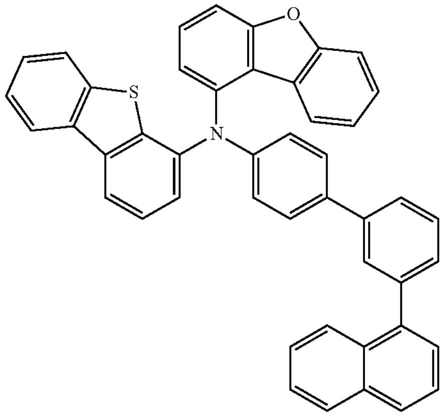
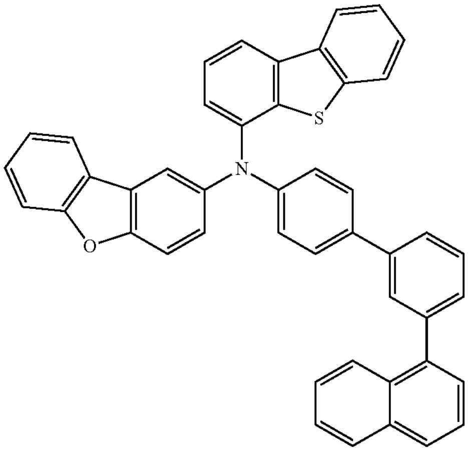
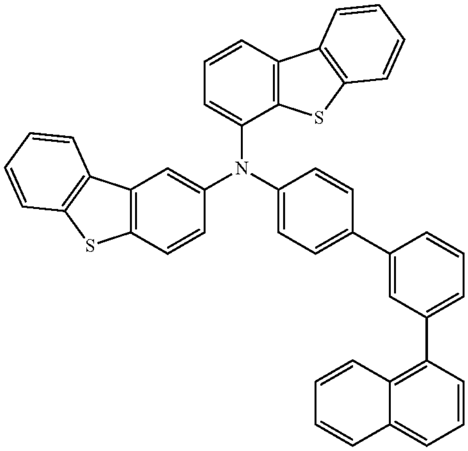
-continued
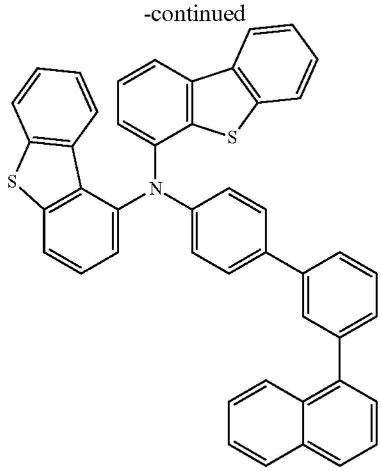
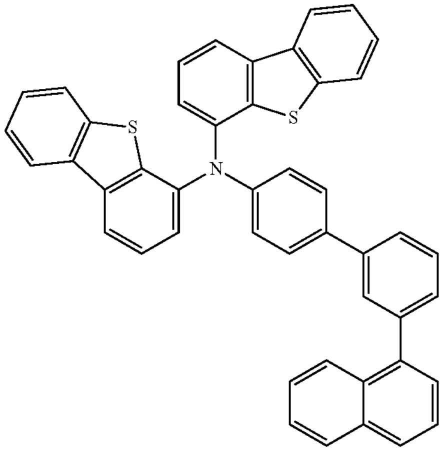
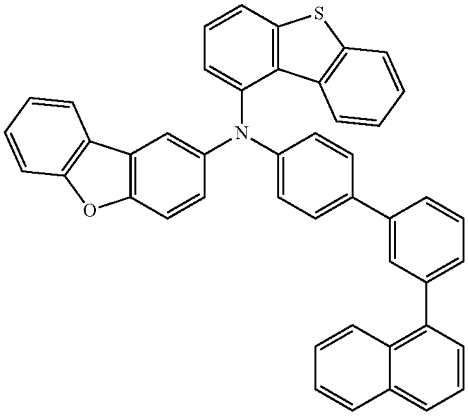
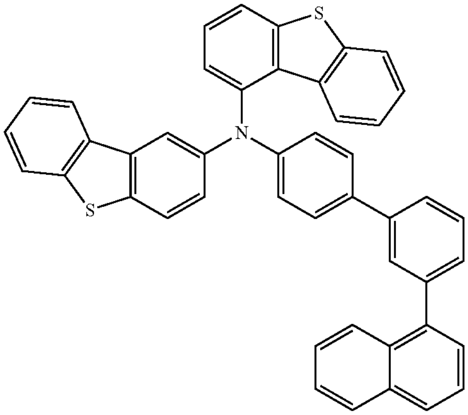

-continued
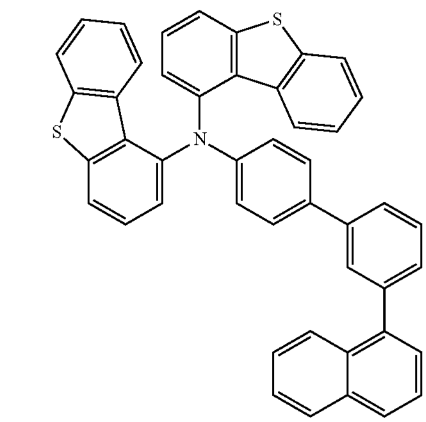
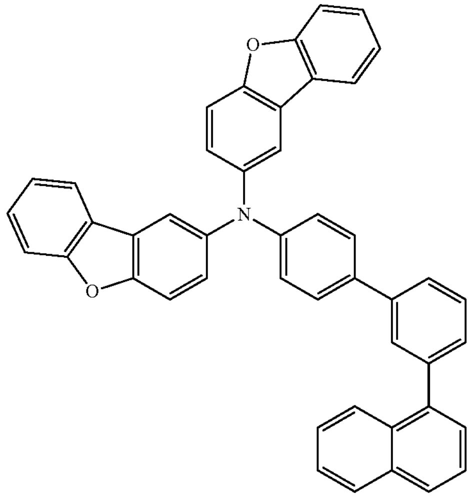
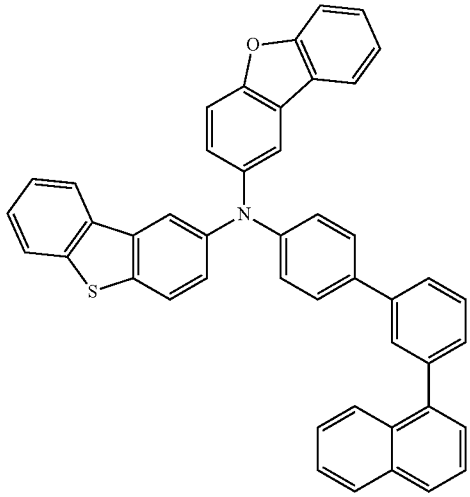
-continued
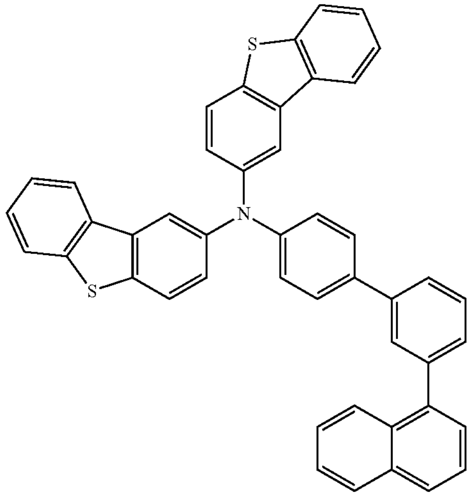
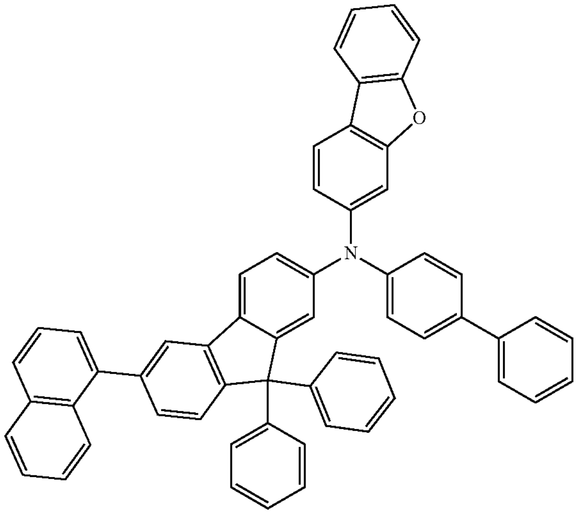
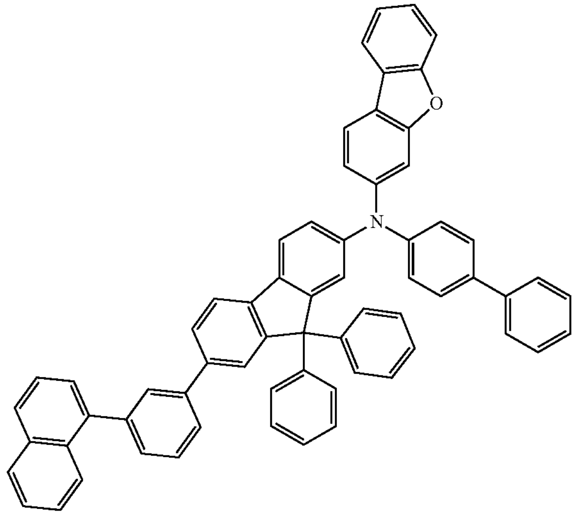

-continued
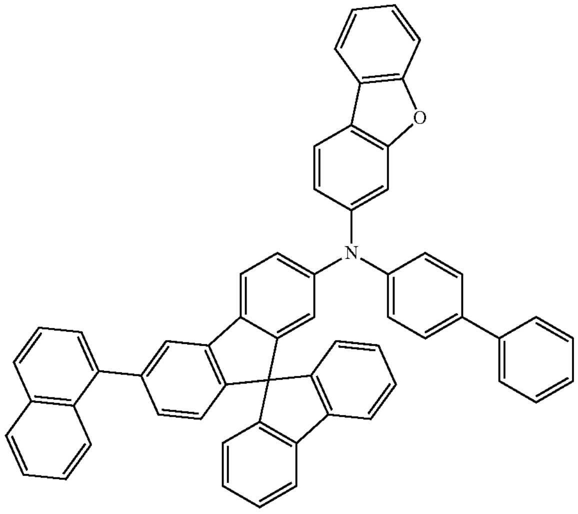
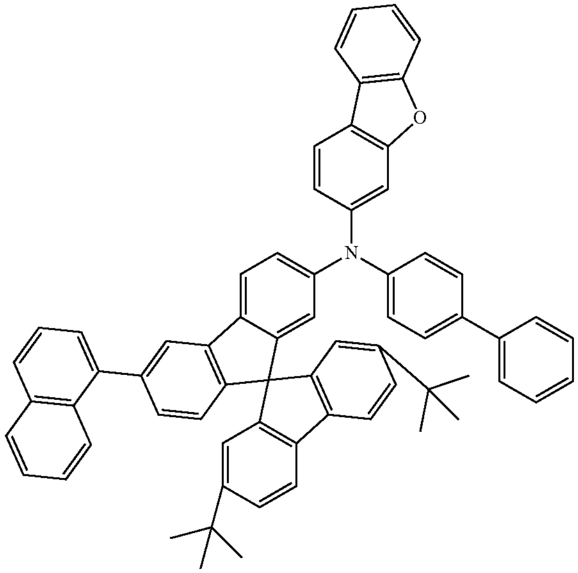
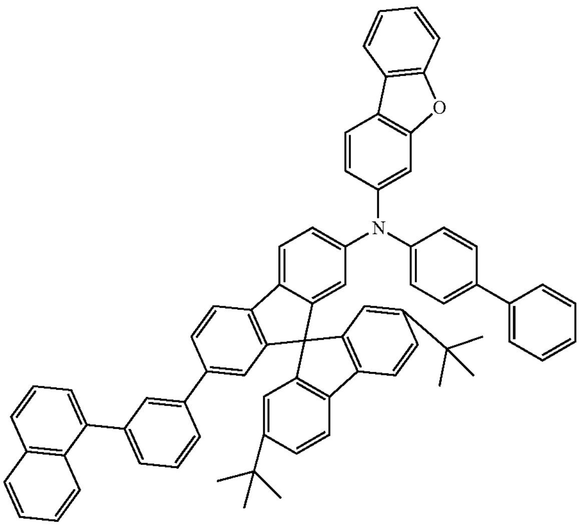
-continued
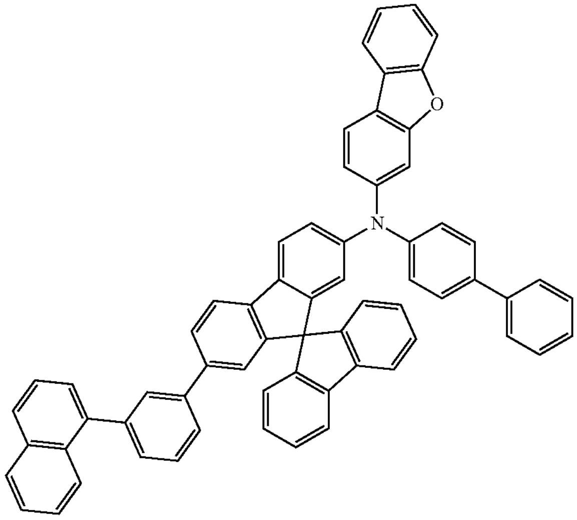
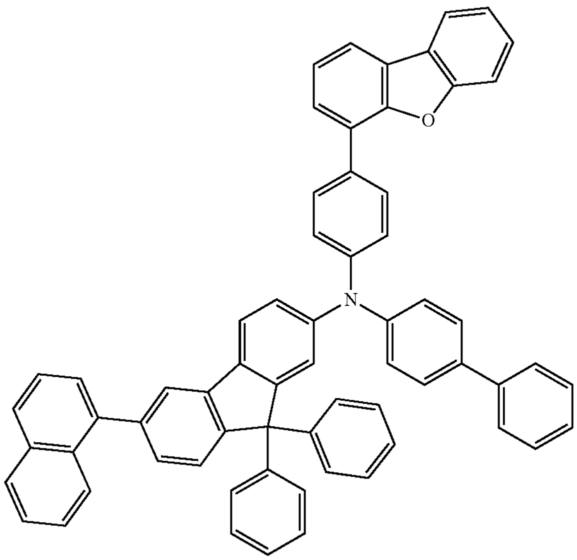
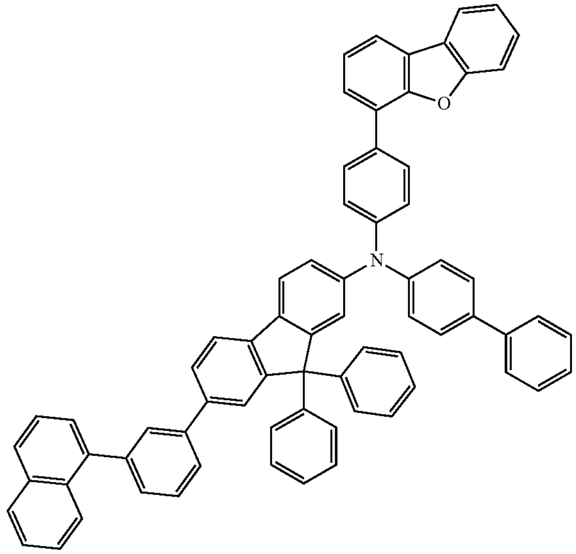

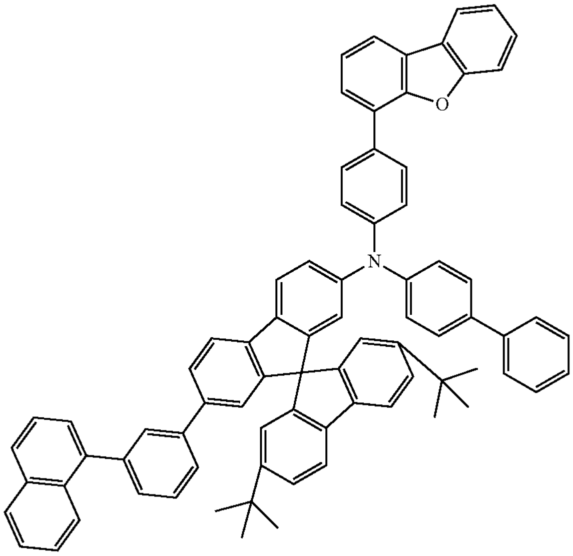
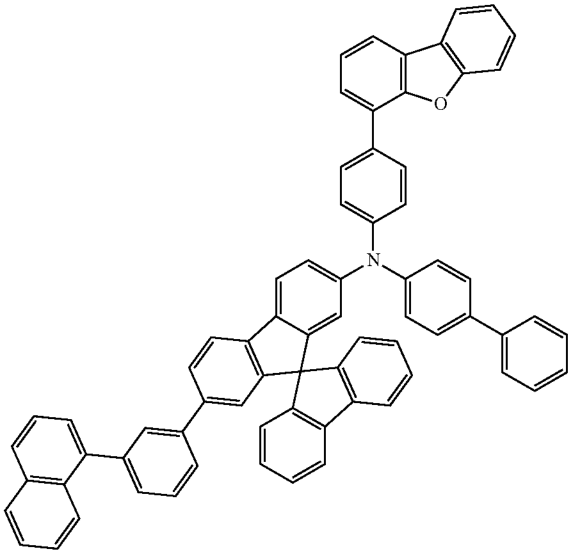
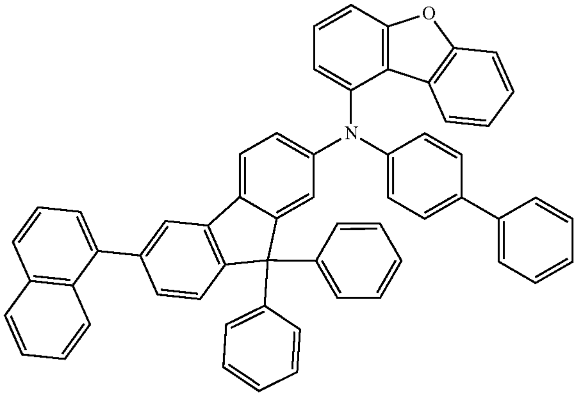
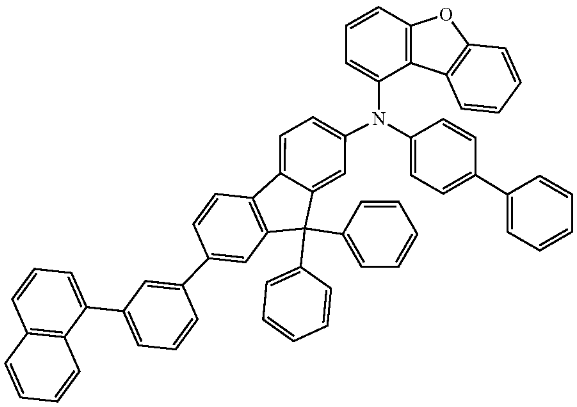
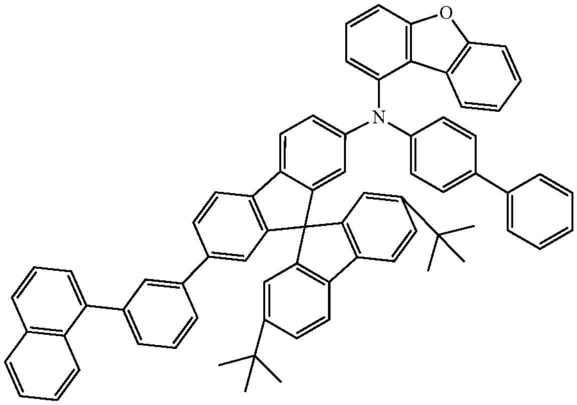
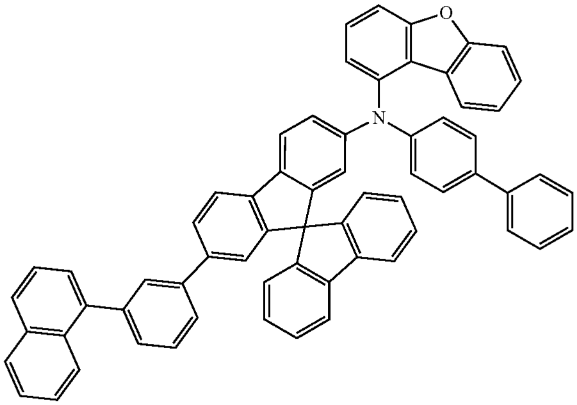
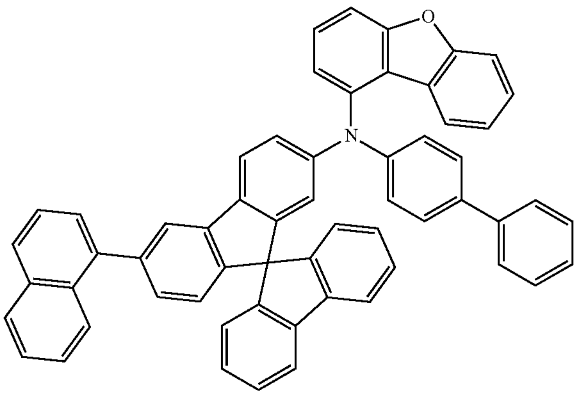

-continued
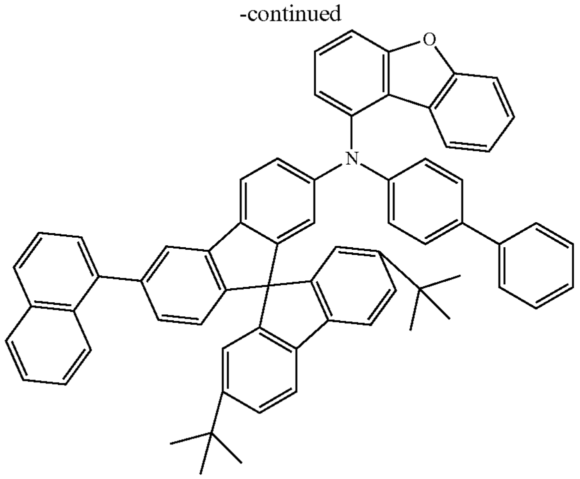
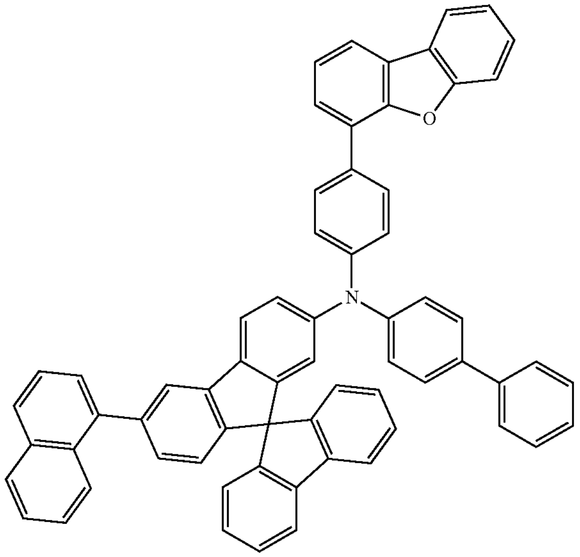
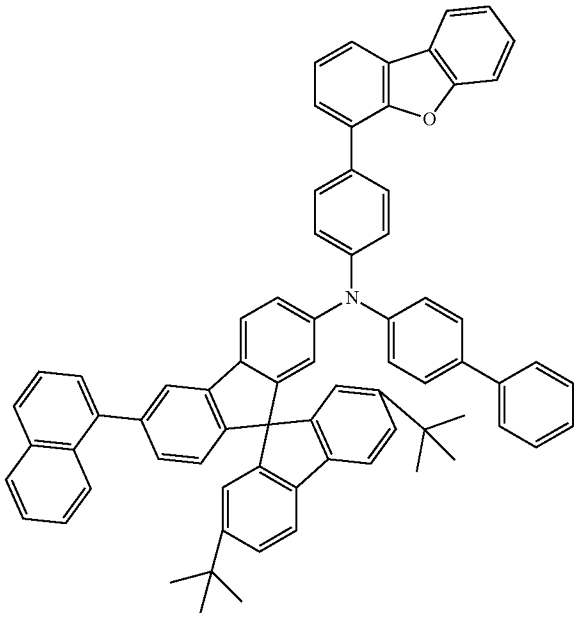 [SMILES: CC(C)(C)c1ccc2c(c1)C1(c3ccc(-c4cccc5ccccc45)cc3-c3ccc(N(c4ccc(-c5ccccc5)cc4)c4ccc(-c5cccc6c5oc5ccccc56)cc4)cc31)c1cc(C(C)(C)C)ccc1-2]
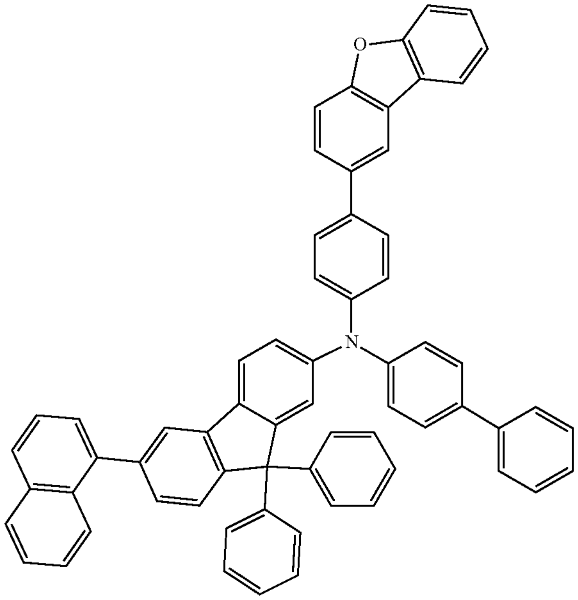
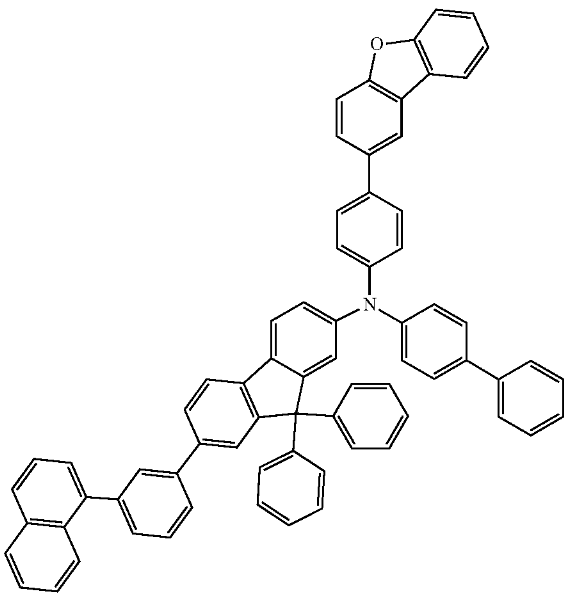

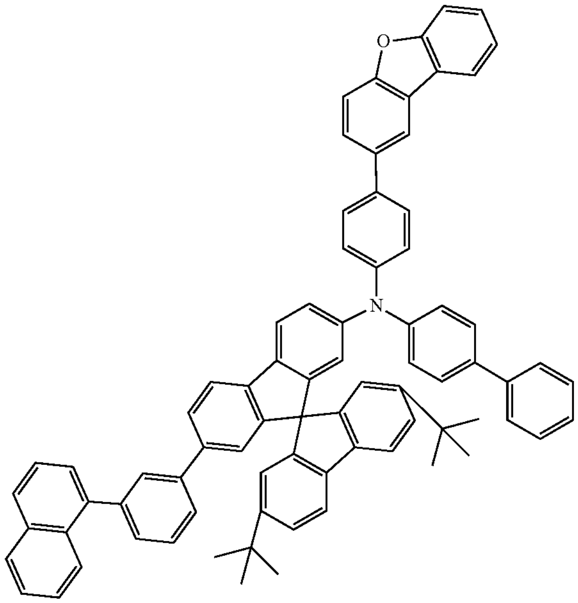
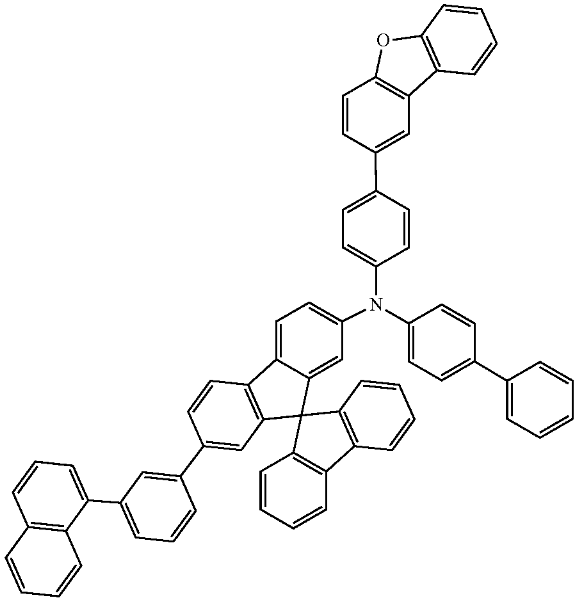
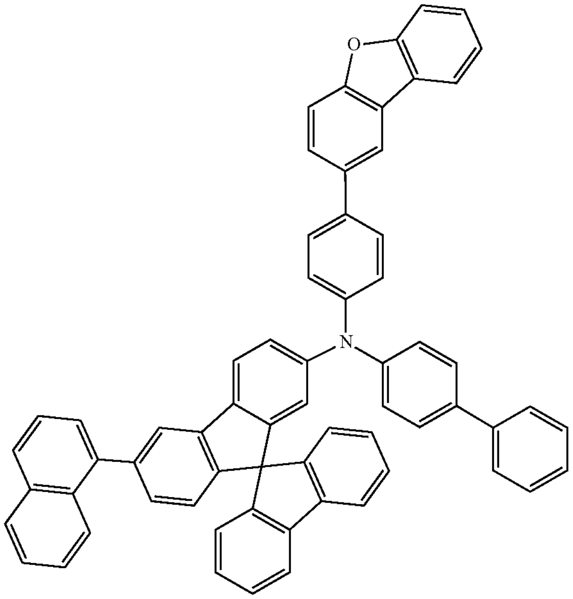
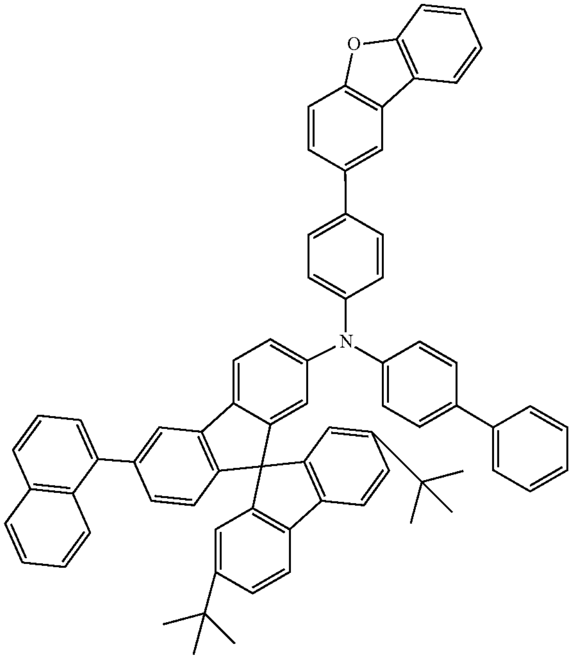

-continued
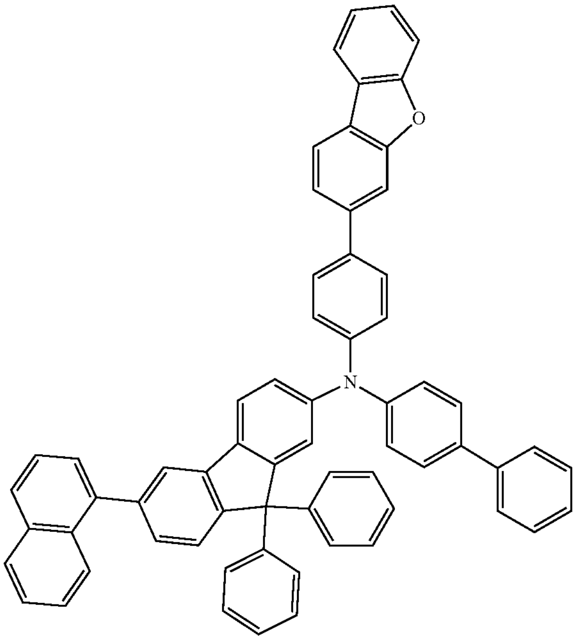
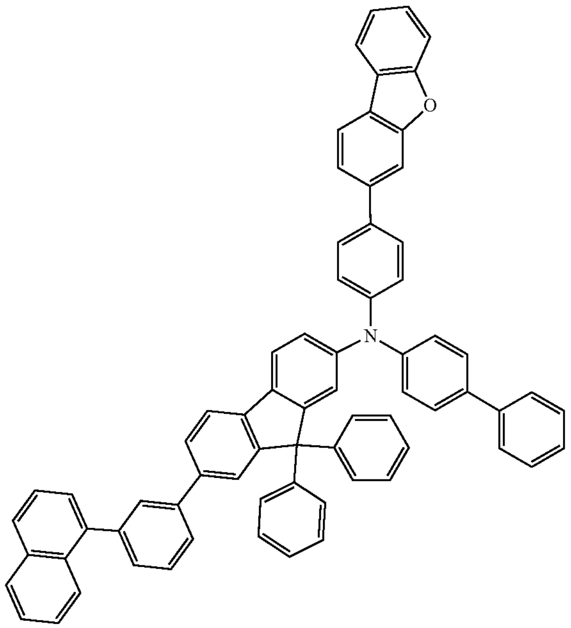
-continued
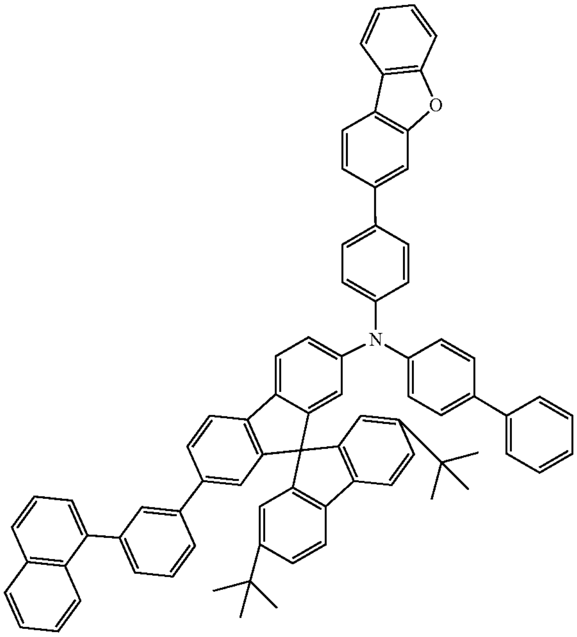
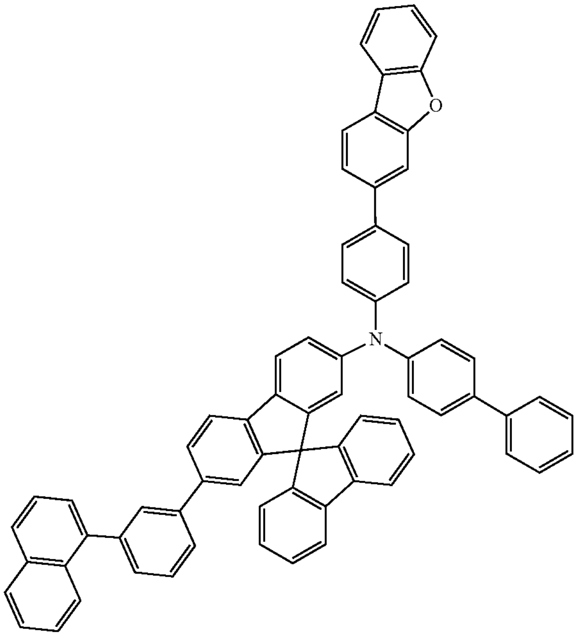

-continued
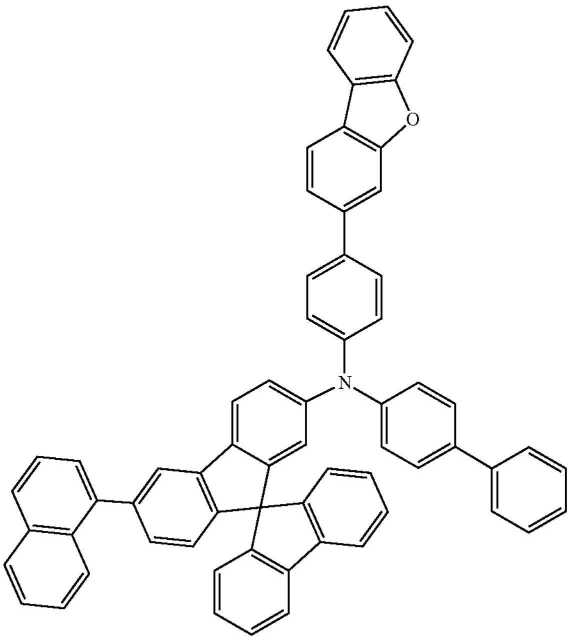
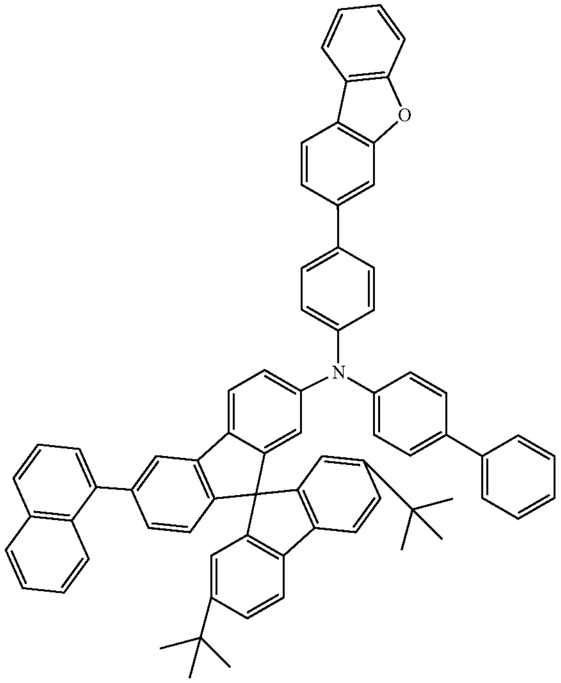
-continued
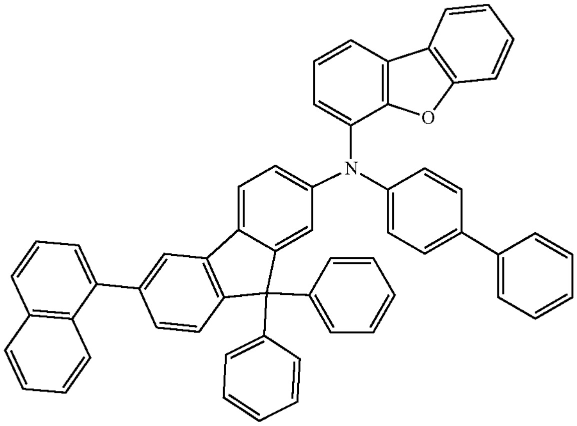
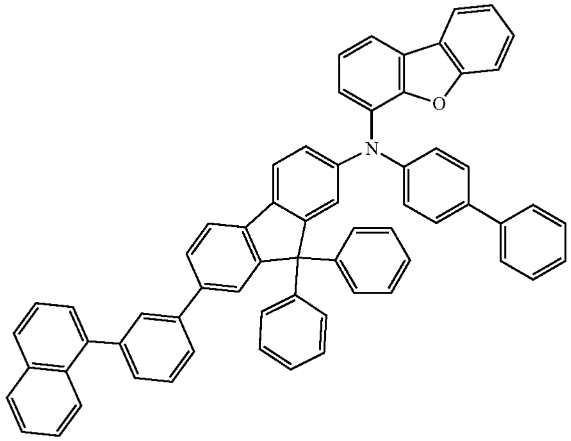
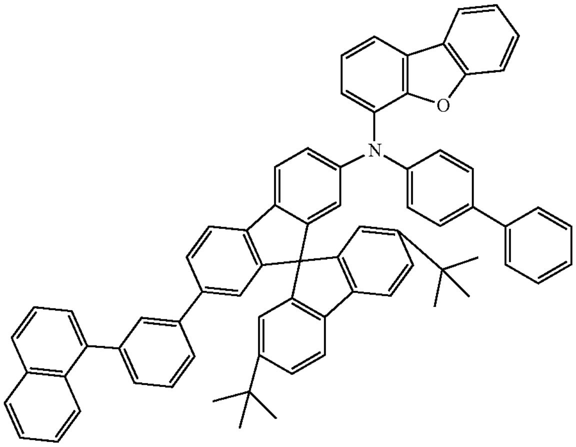

-continued
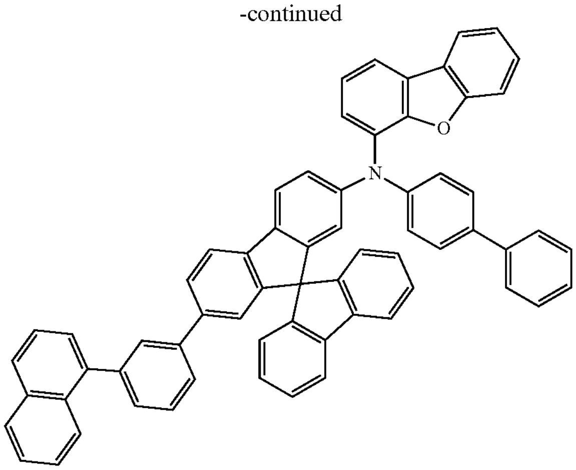
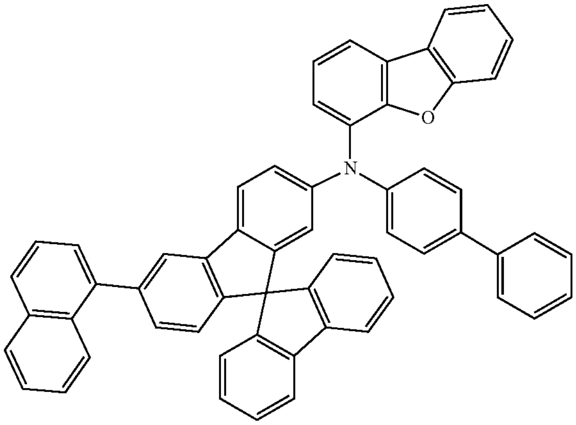
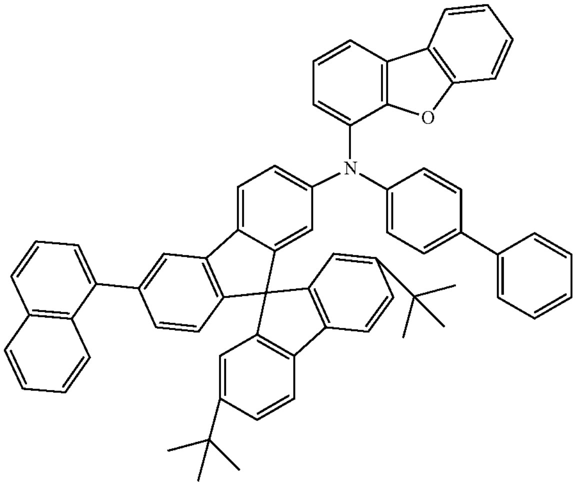
-continued
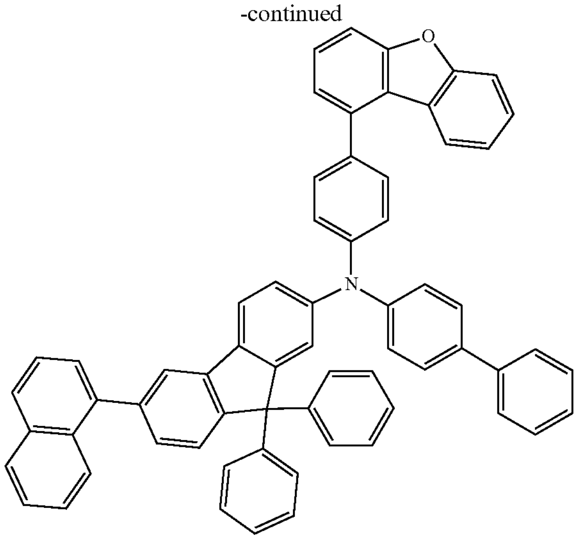
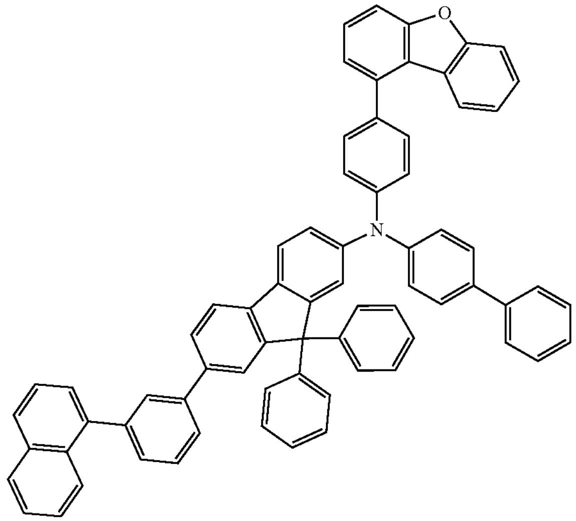
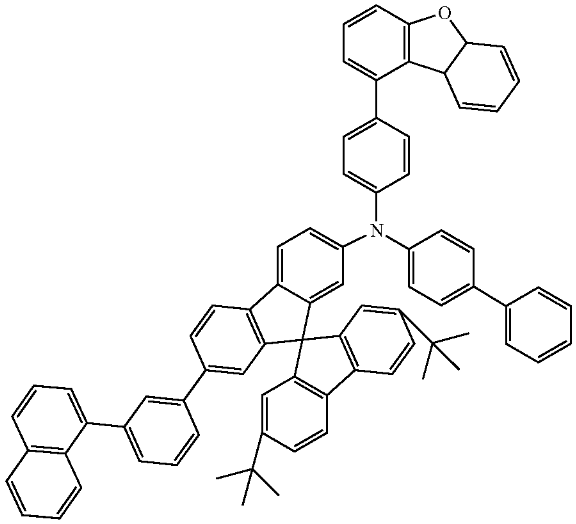

-continued
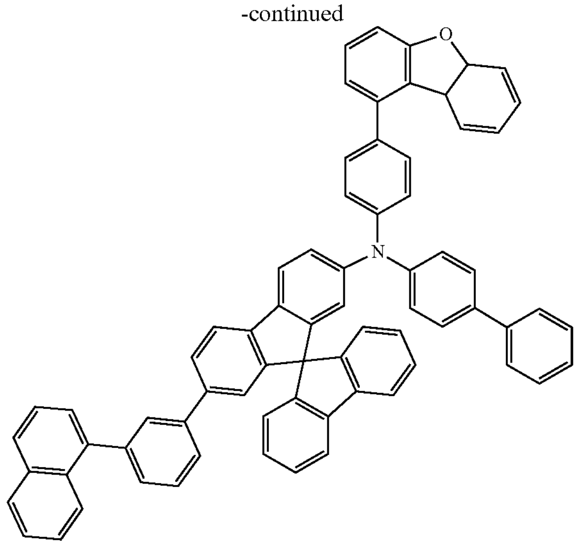
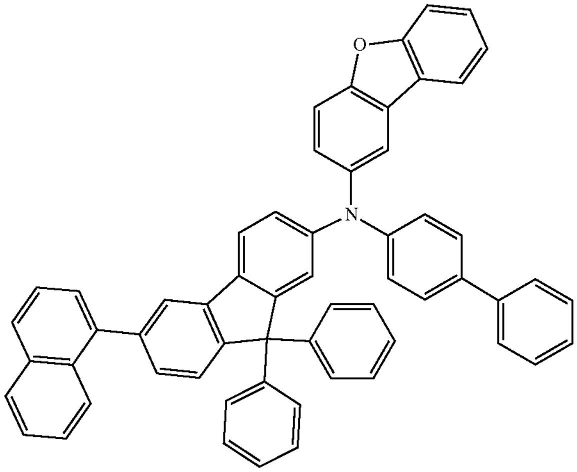
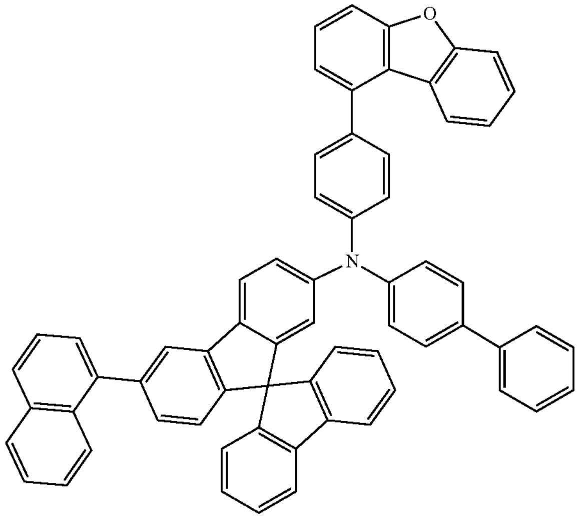
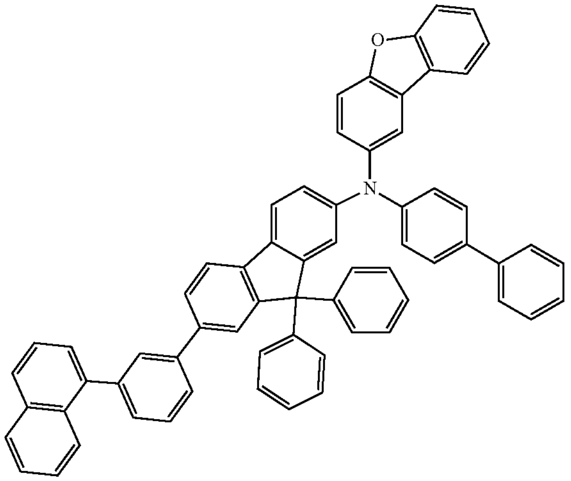
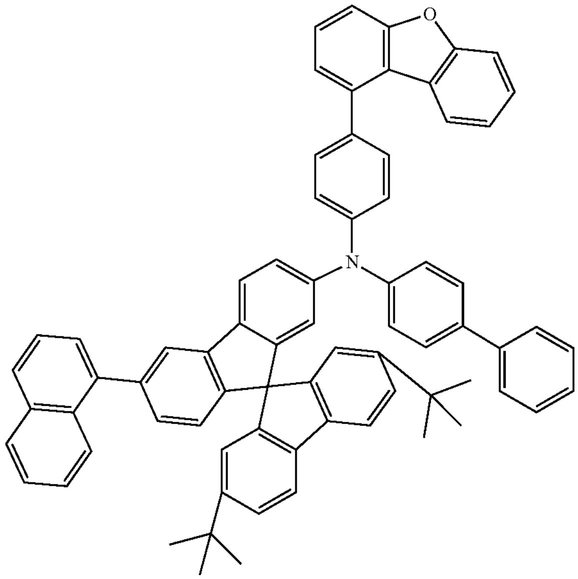
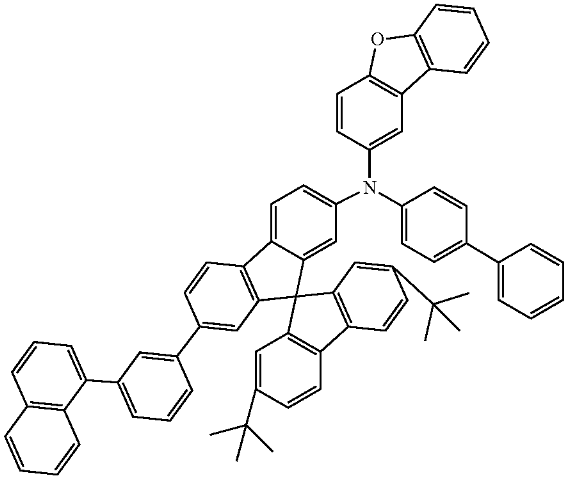
-continued -continued
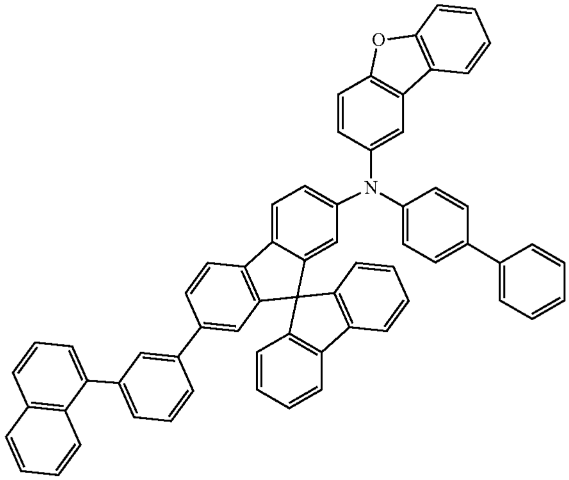
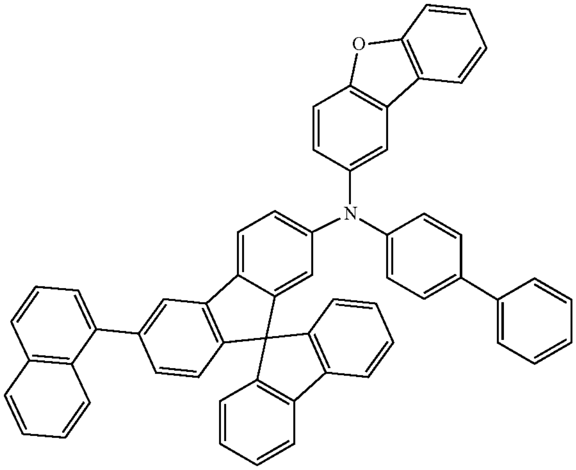
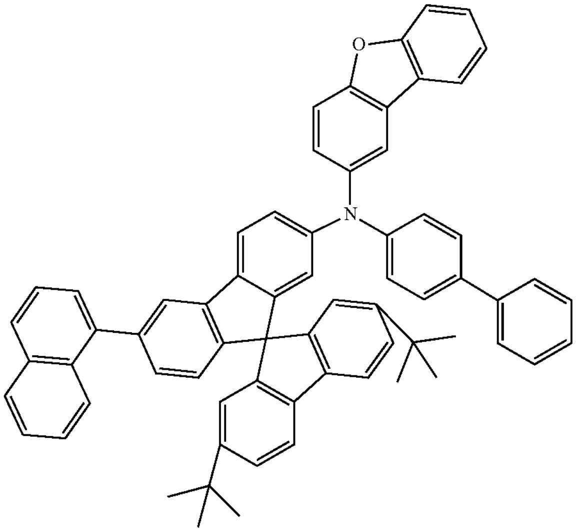
-continued
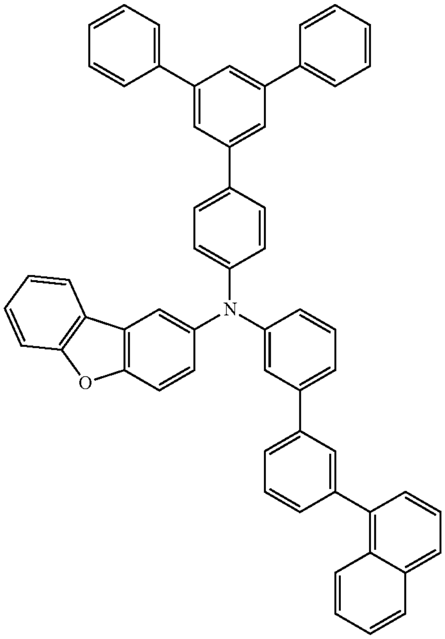
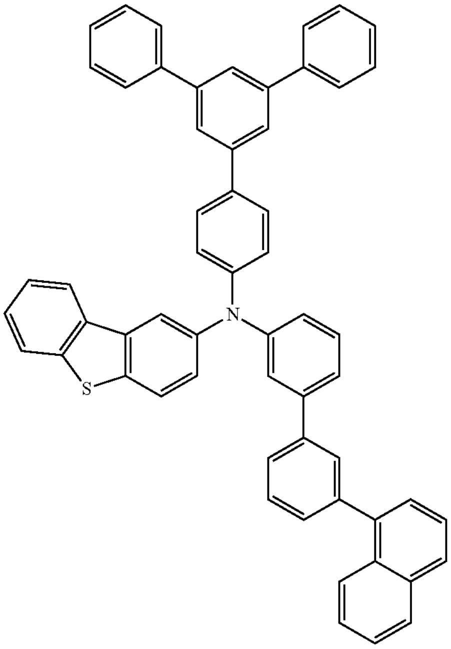

-continued
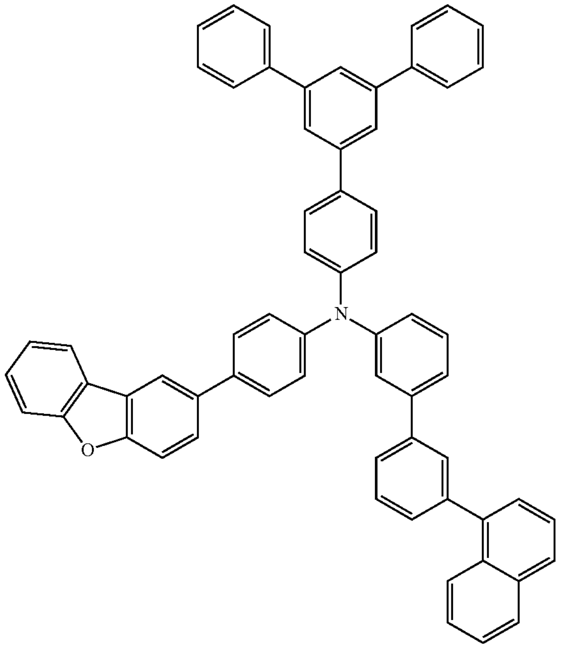
-continued
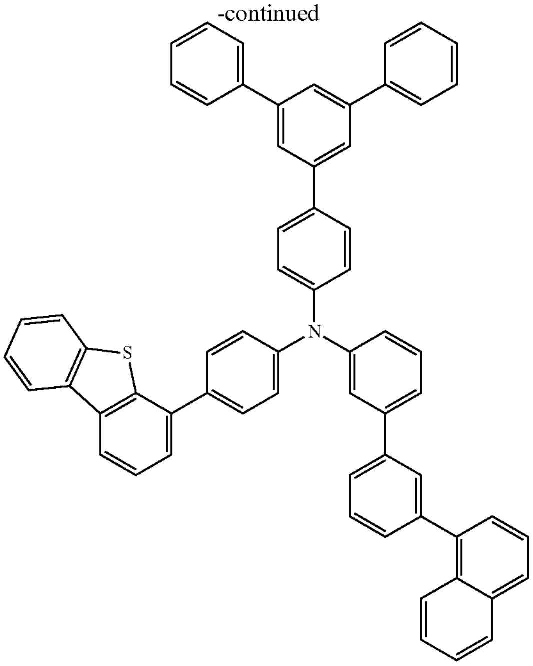
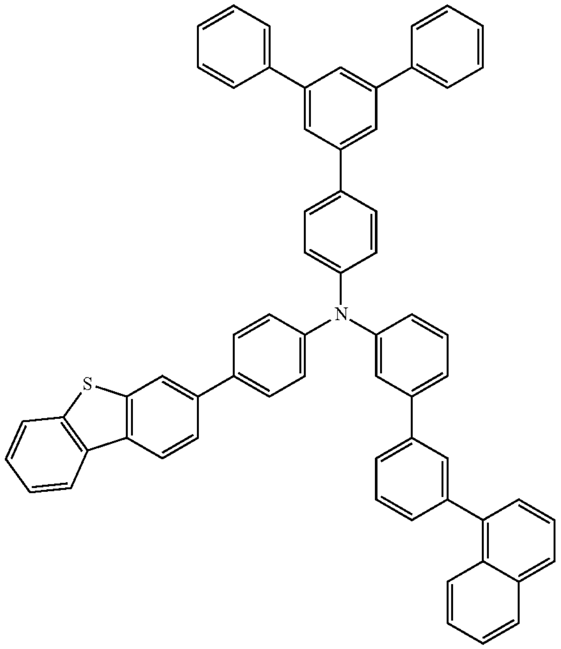
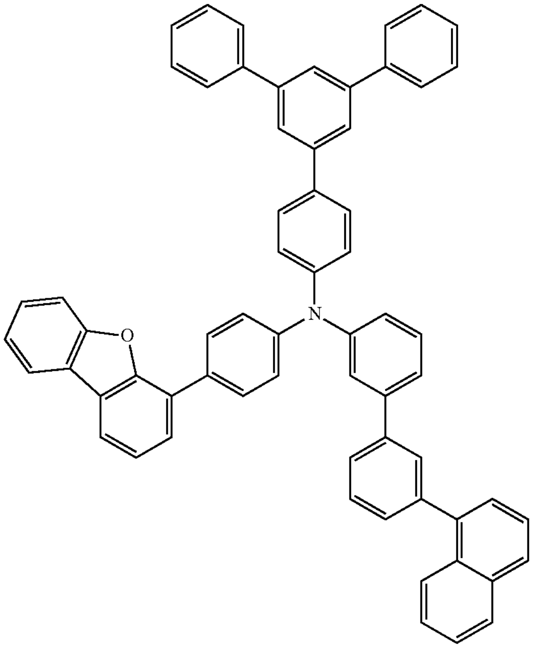

-continued
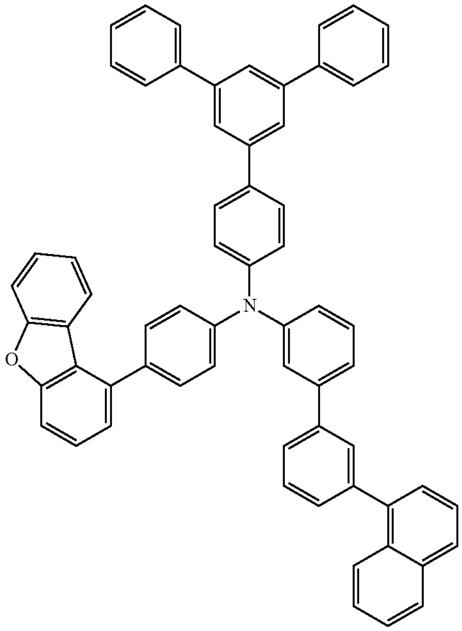
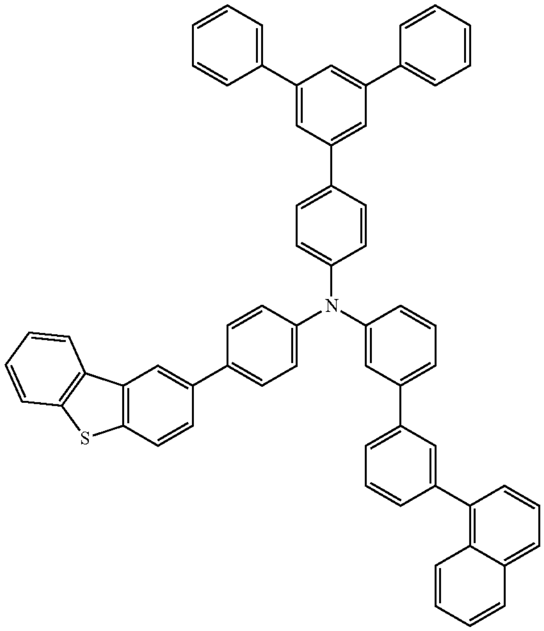
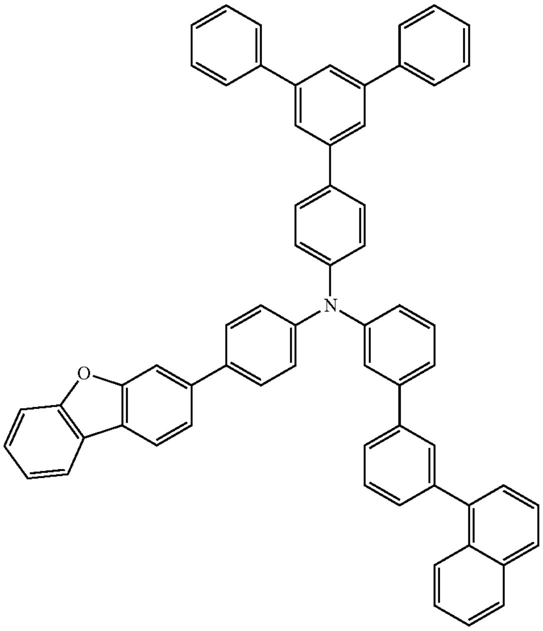
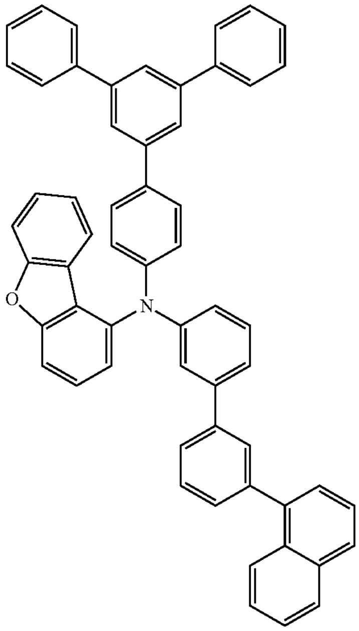

-continued
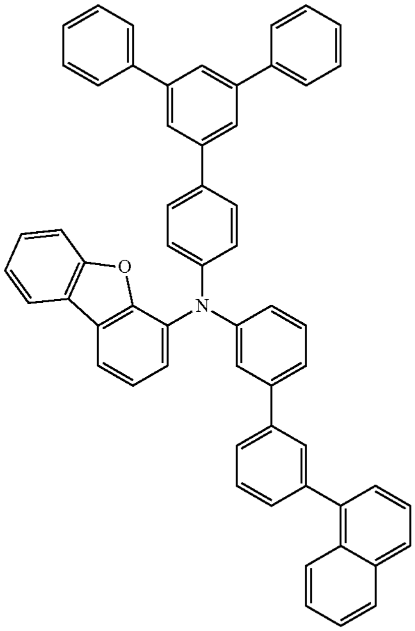
-continued
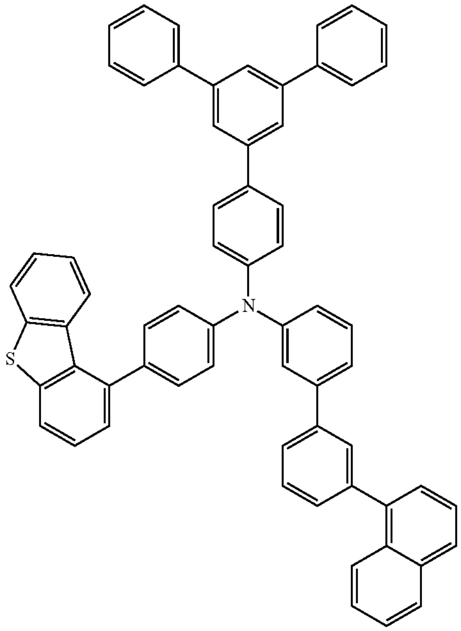
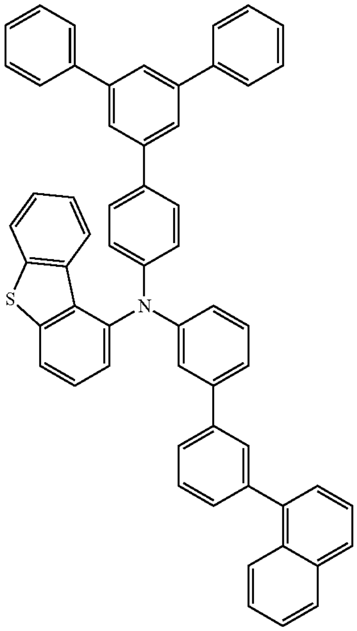
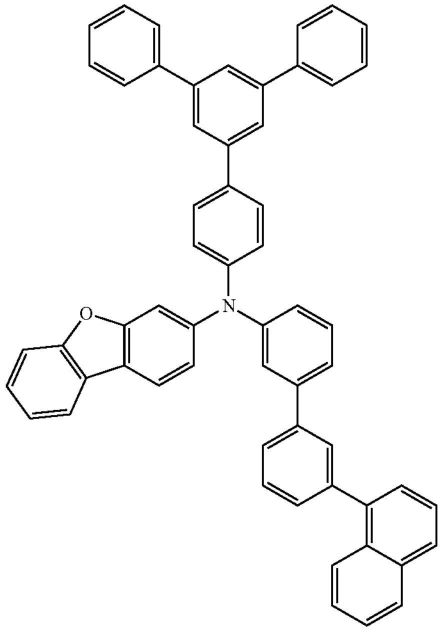

-continued
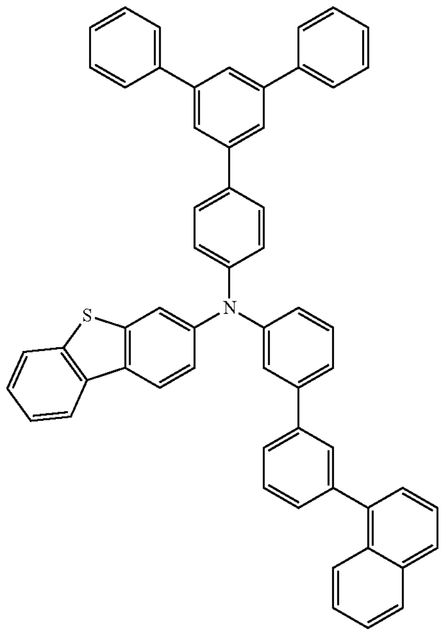
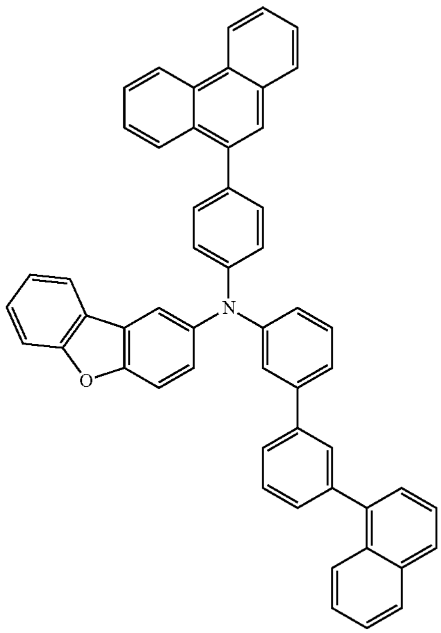
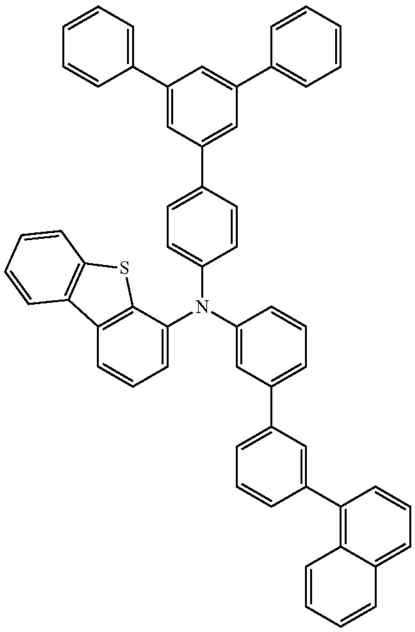
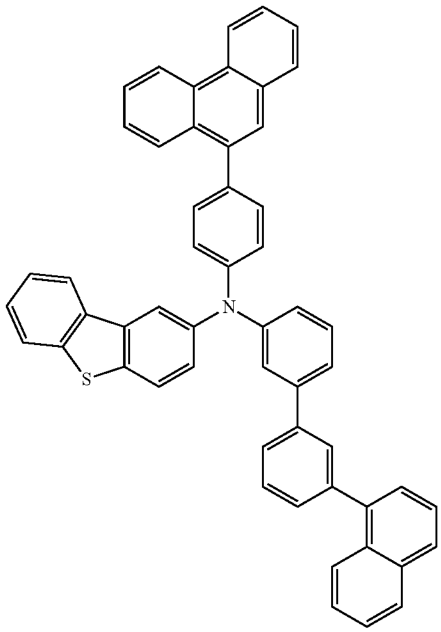
-continued

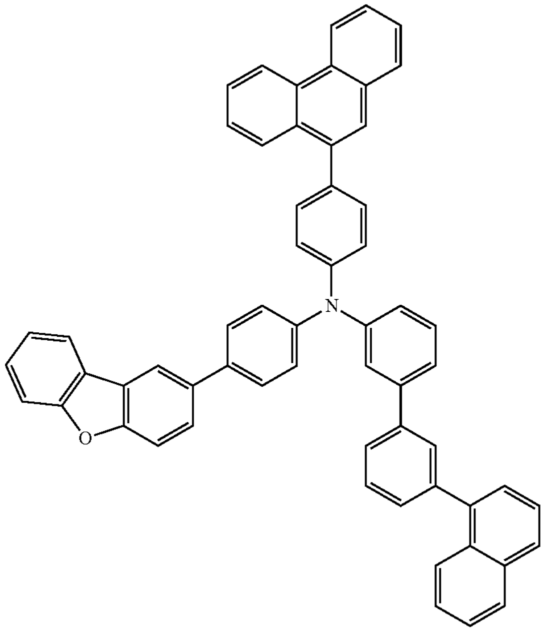
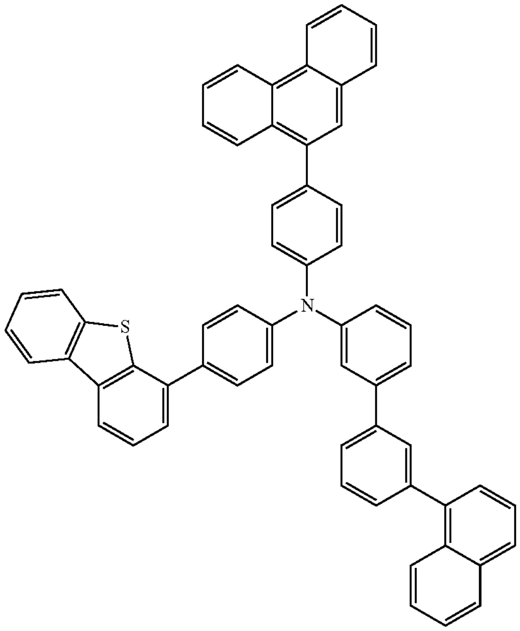
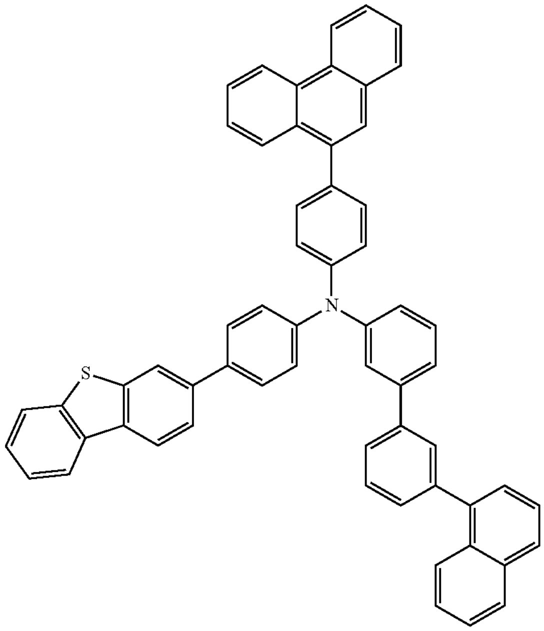
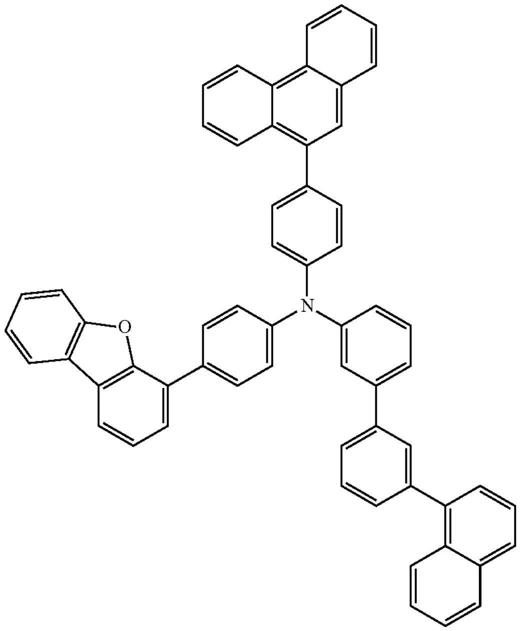 [SMILES: c1cc(-c2cccc(N(c3ccc(-c4cc5ccccc5c5ccccc45)cc3)c3ccc(-c4cccc5c4sc4ccccc45)cc3)c2)cc(-c2cccc3ccccc23)c1]

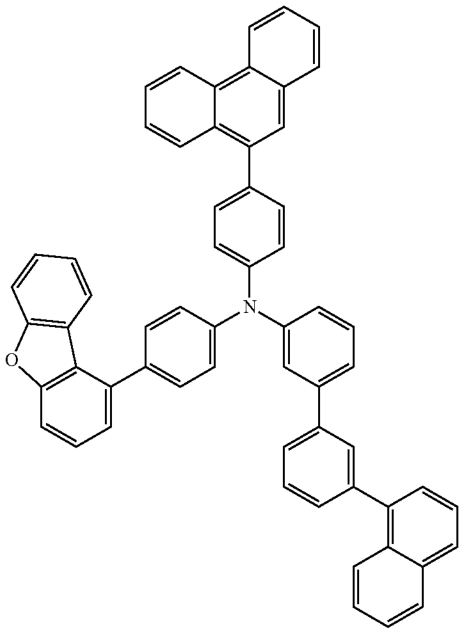
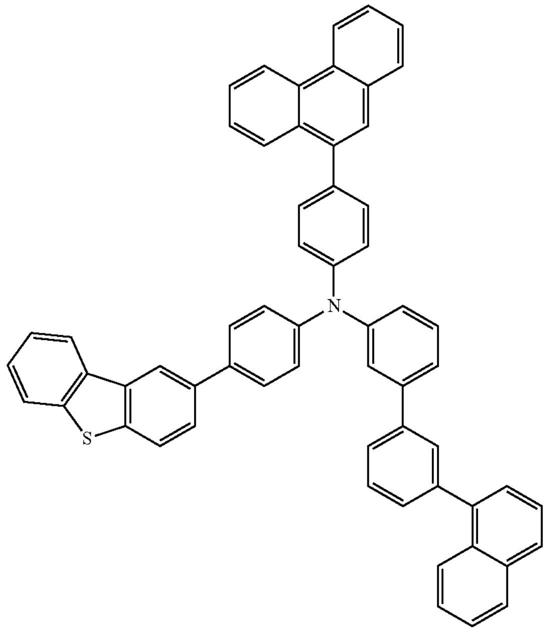
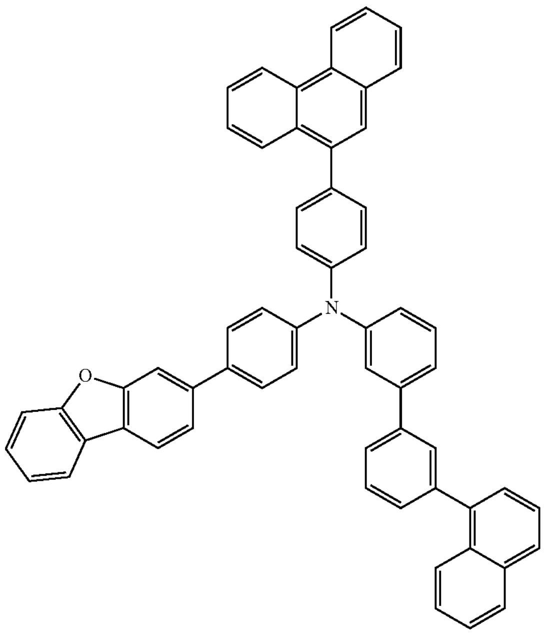
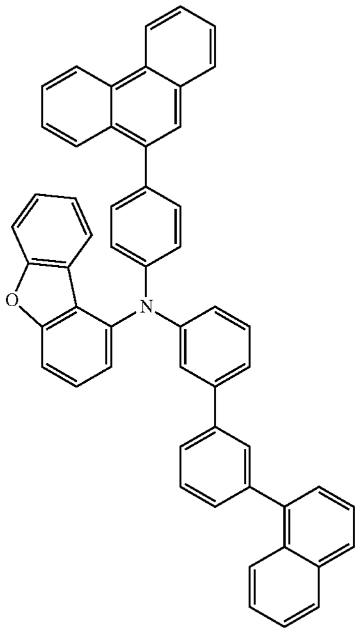

-continued
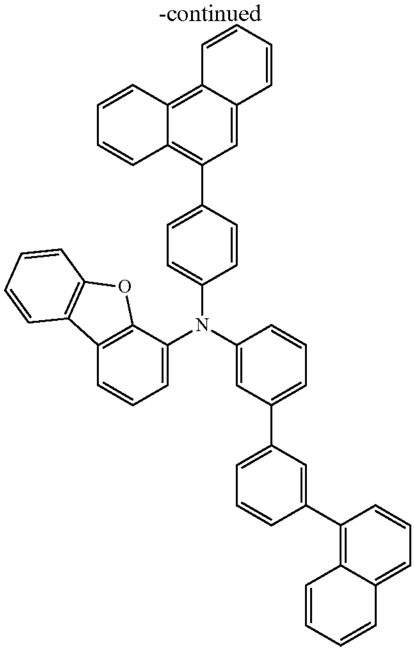
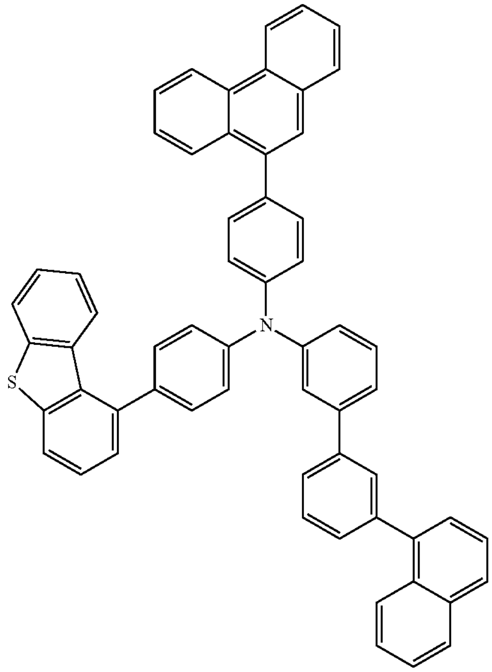
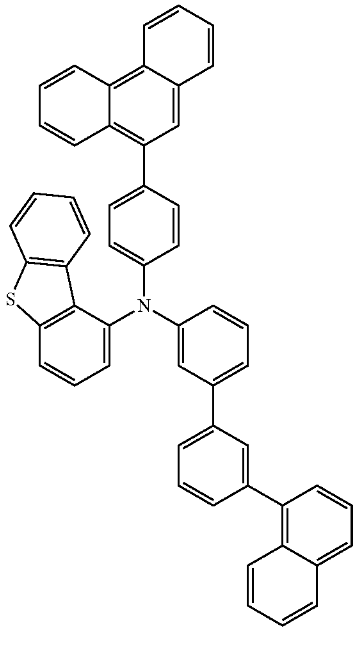 [SMILES: c1cc(-c2cccc(N(c3ccc(-c4cc5ccccc5c5ccccc45)cc3)c3cccc4sc5ccccc5c34)c2)cc(-c2cccc3ccccc23)c1]
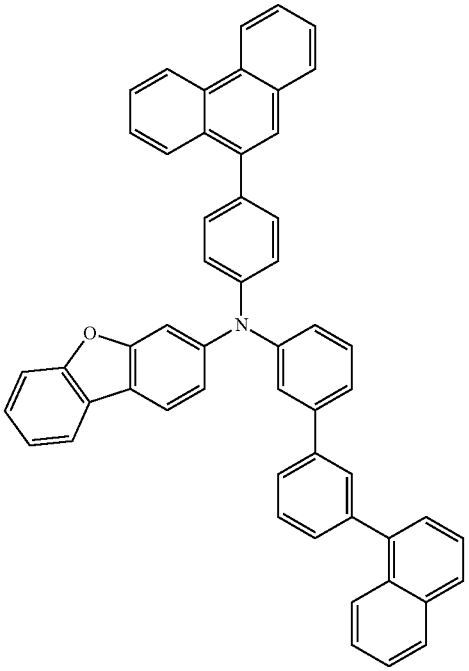

-continued
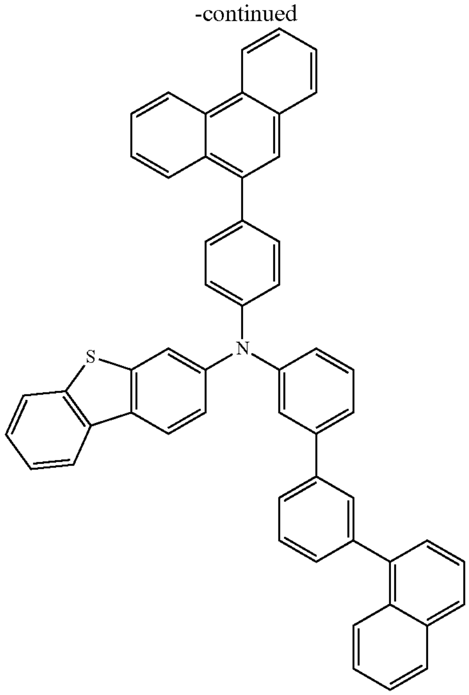
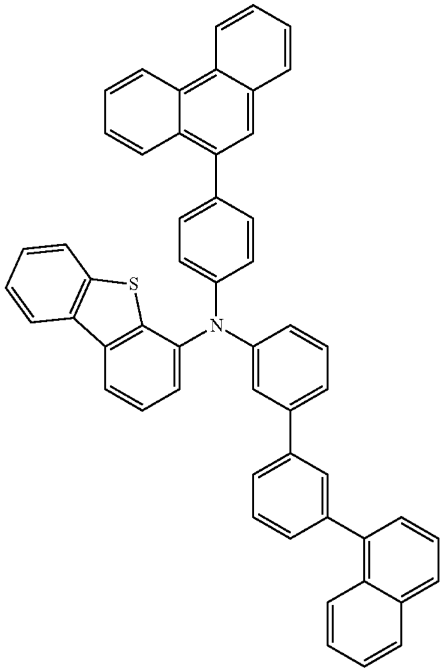
-continued
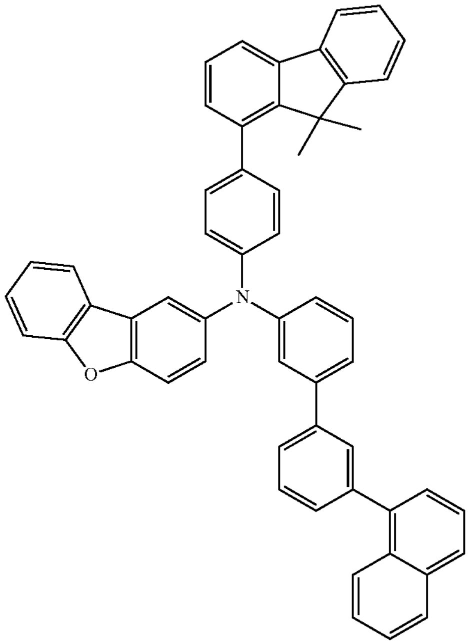
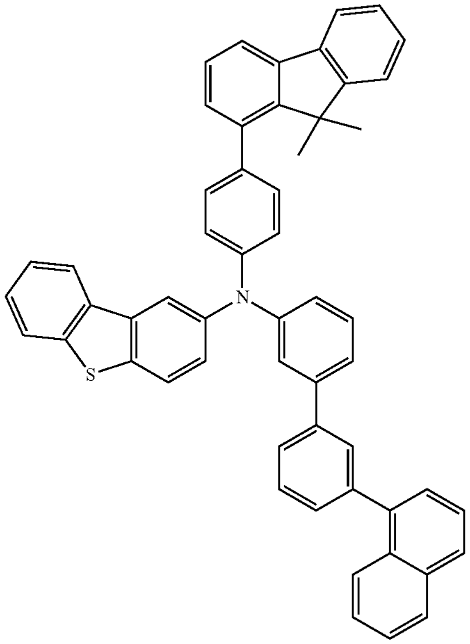

-continued
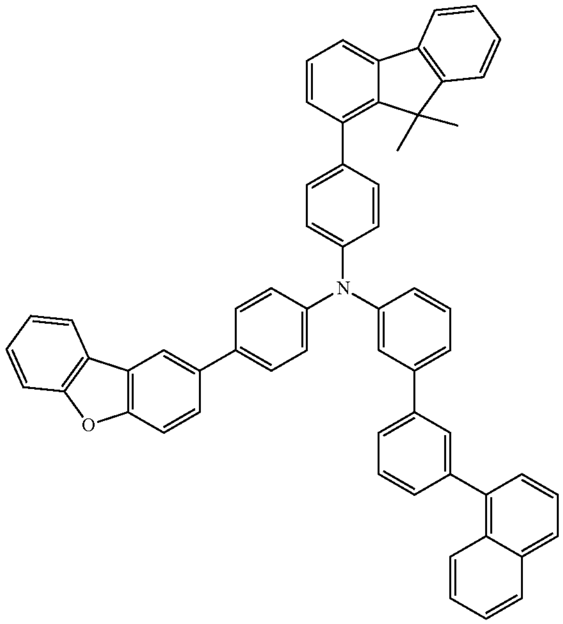
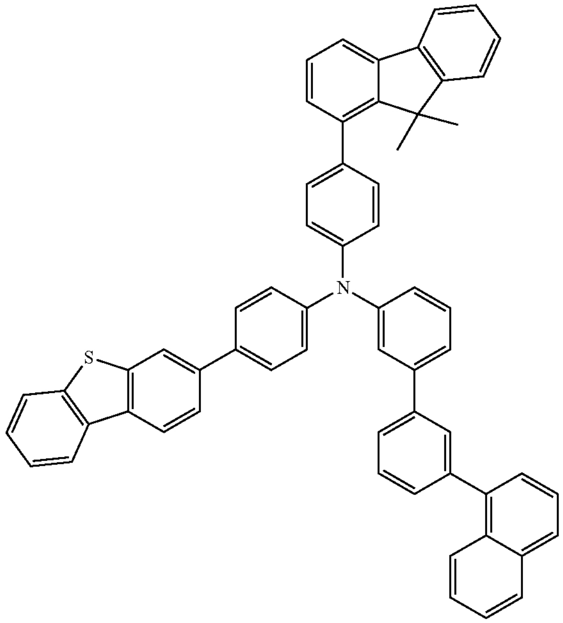
-continued
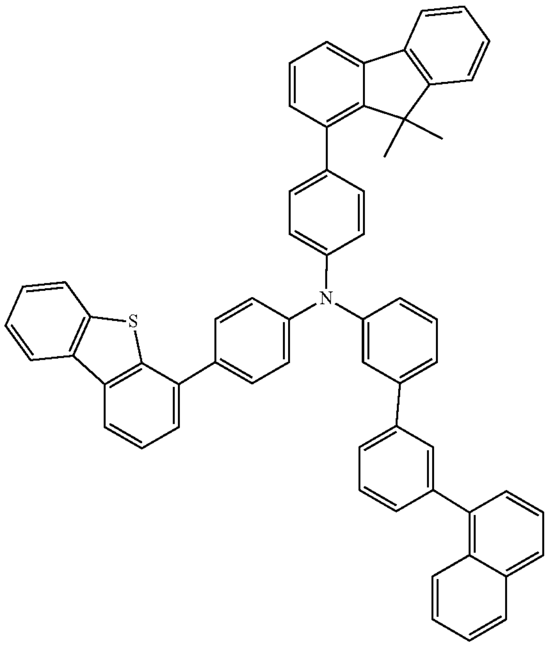
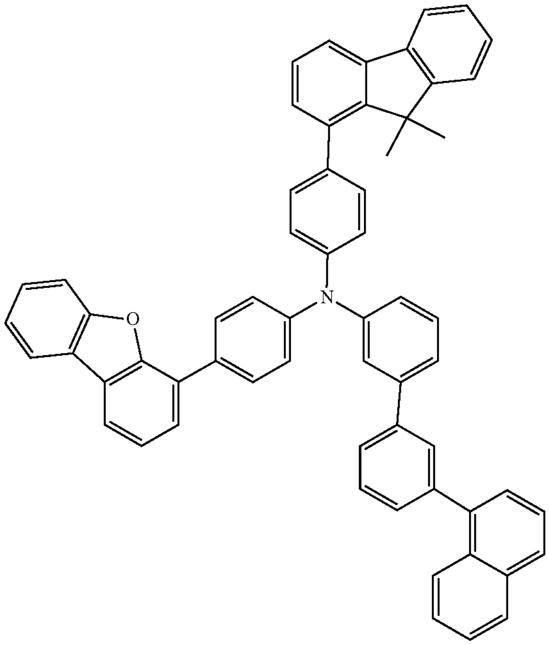

-continued
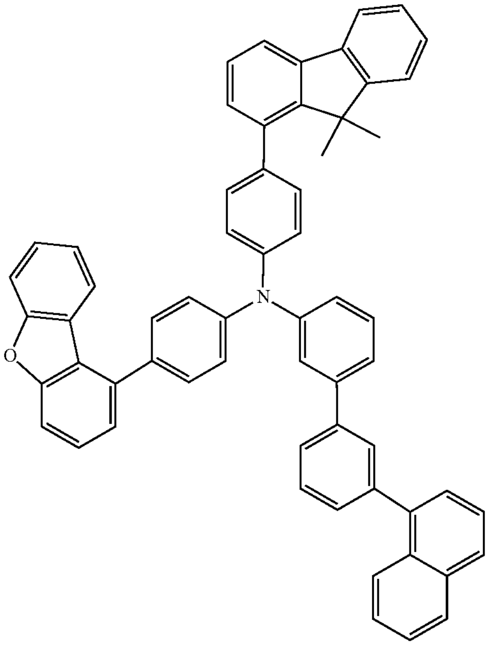
-continued
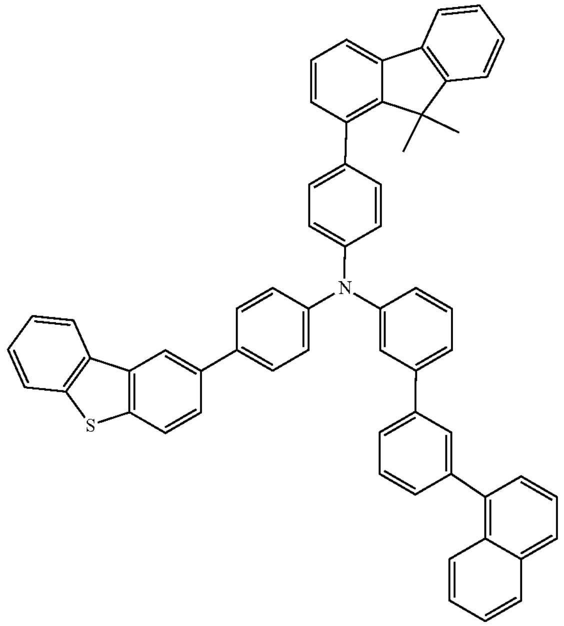
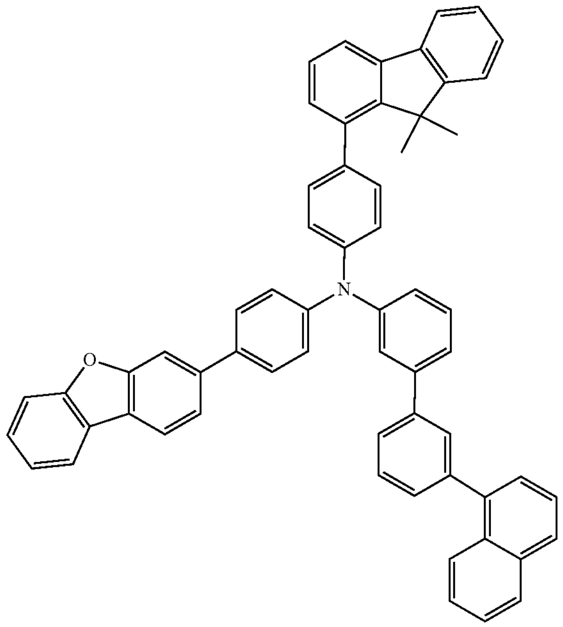
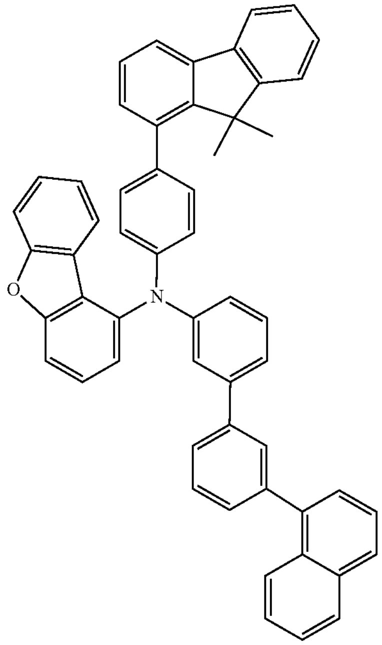

-continued
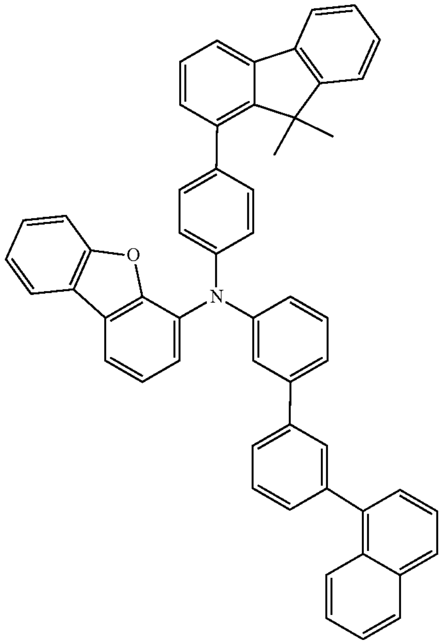
-continued
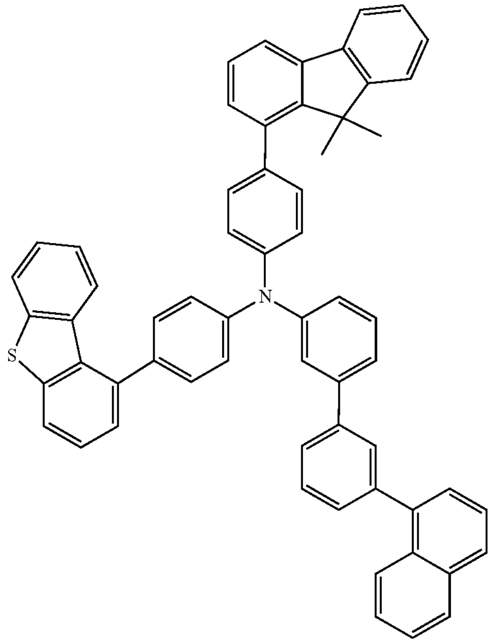
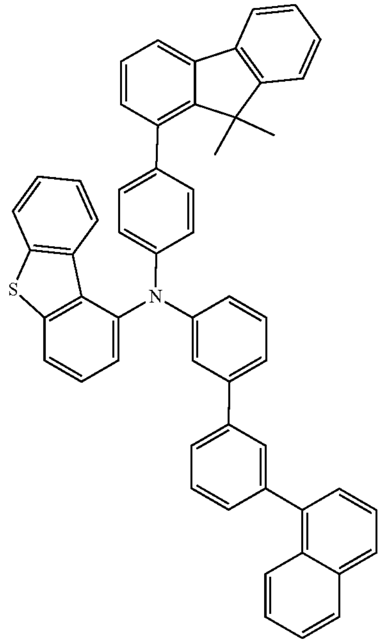
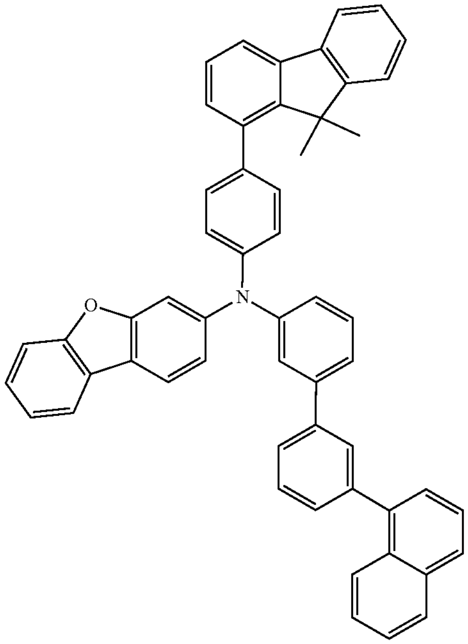

-continued
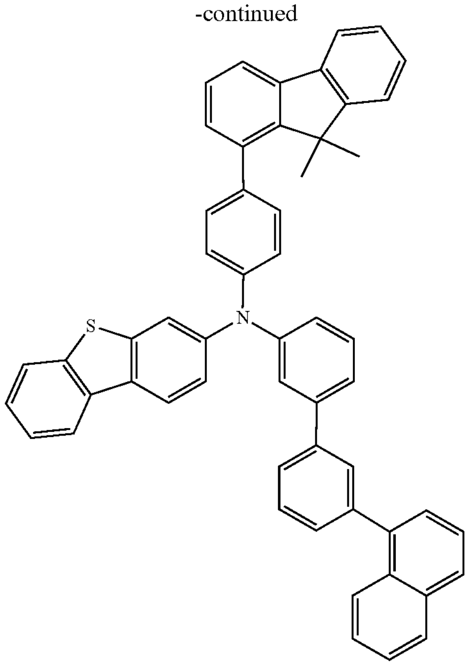
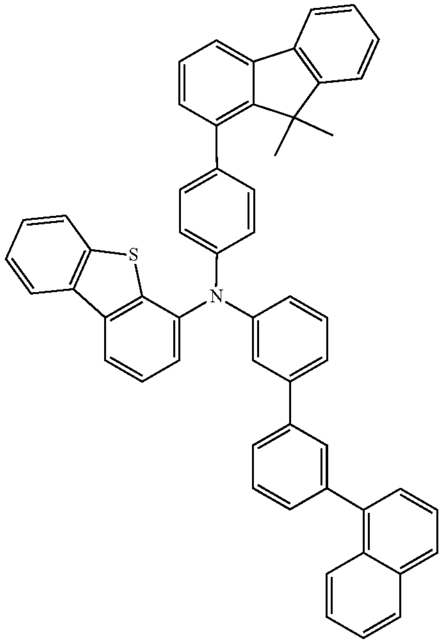
-continued
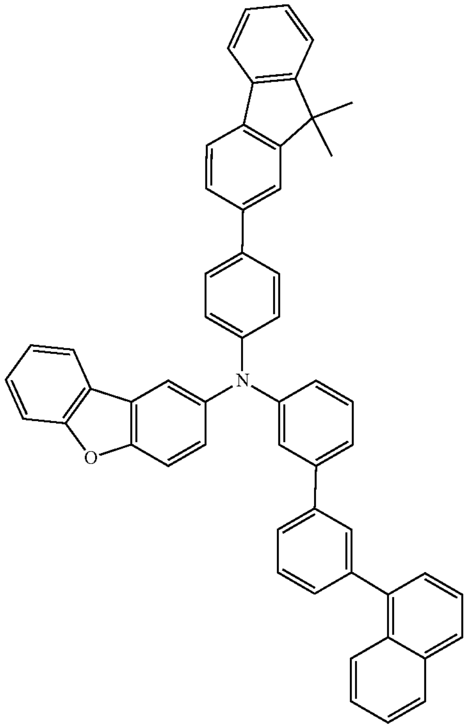
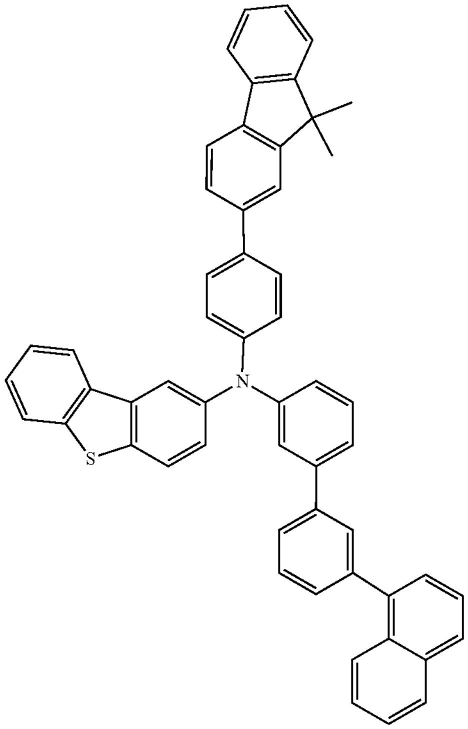

-continued
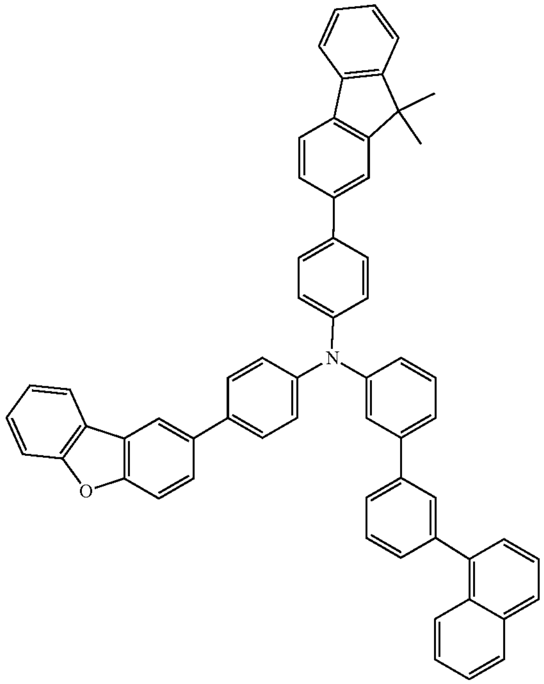
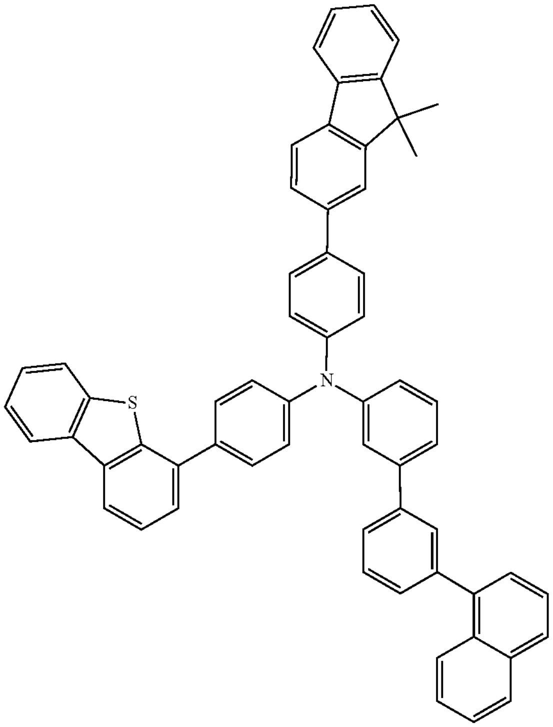
-continued
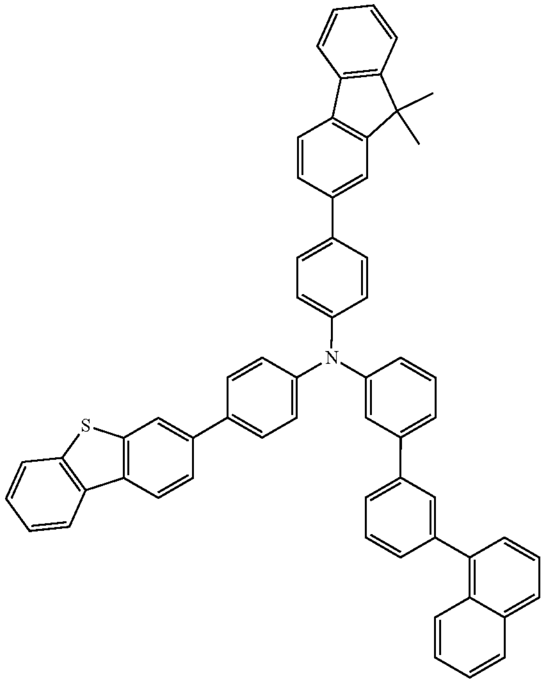
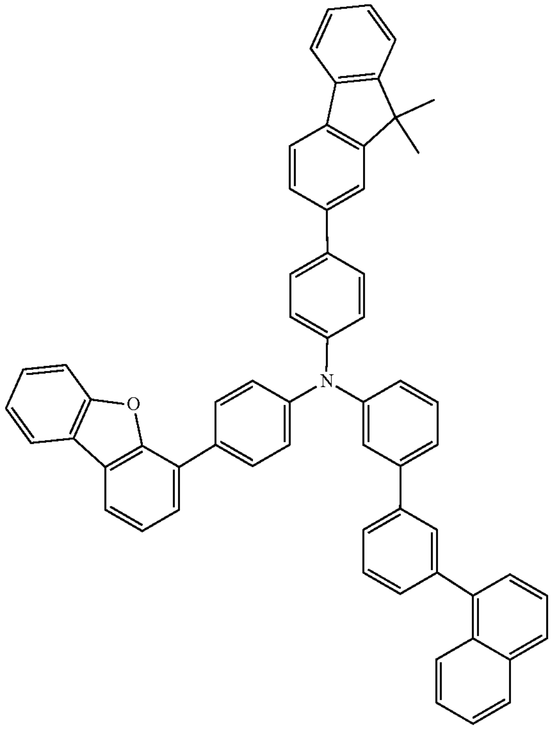

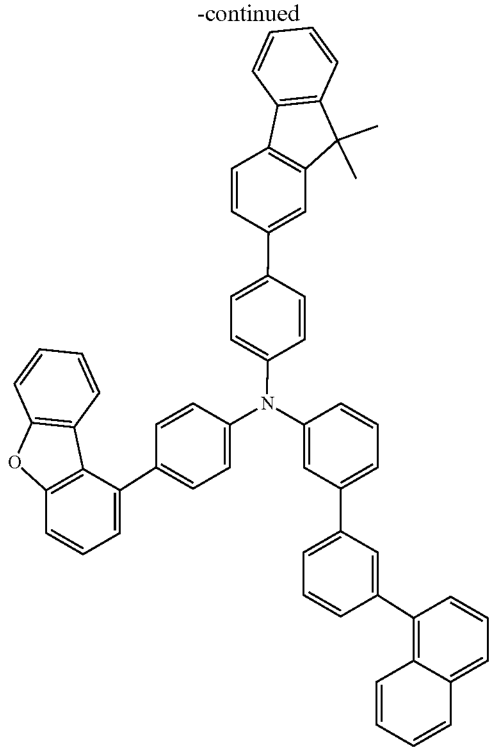
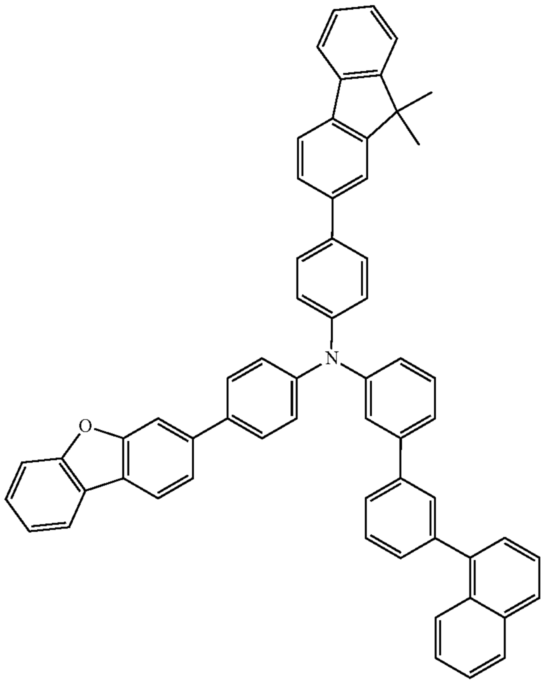
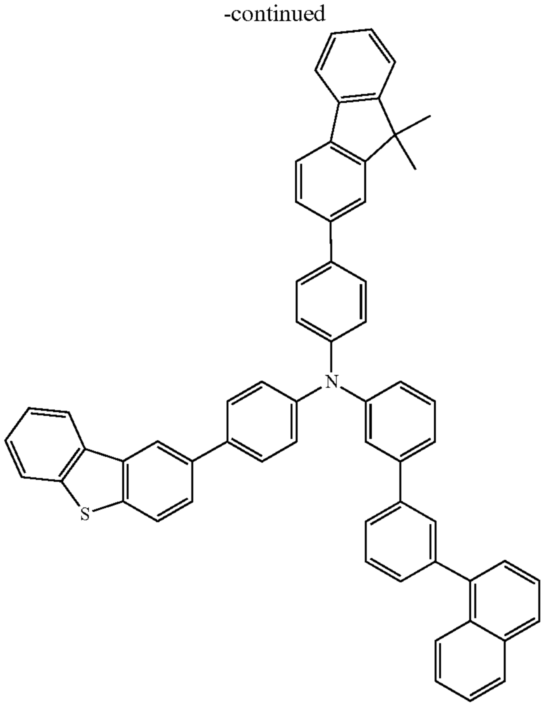
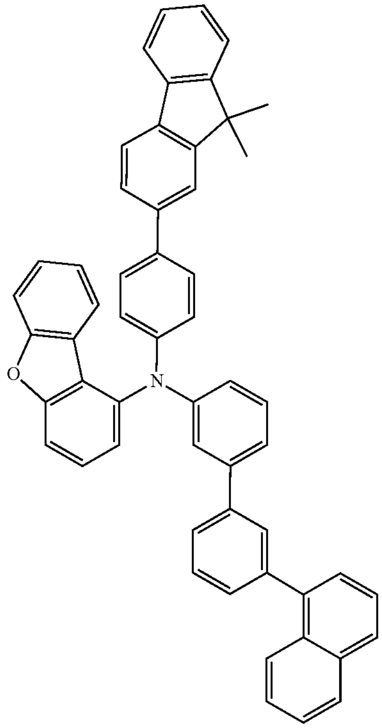

-continued
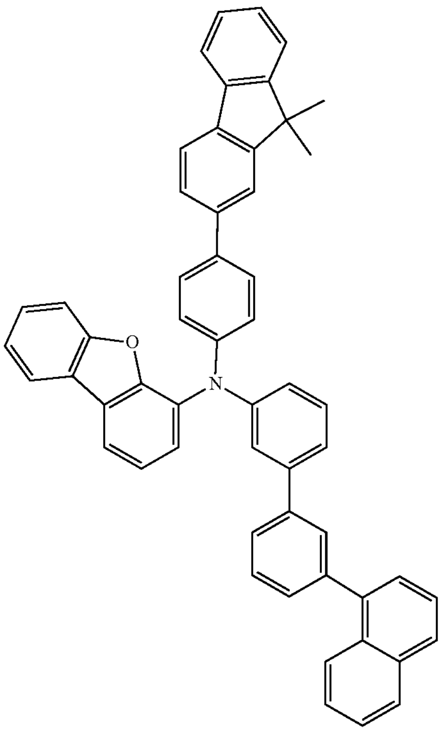
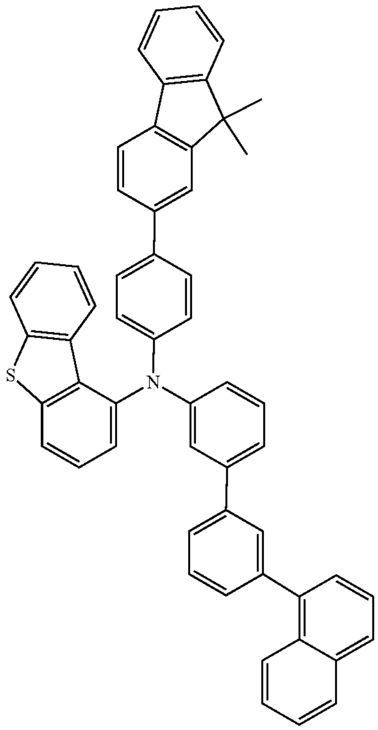
-continued
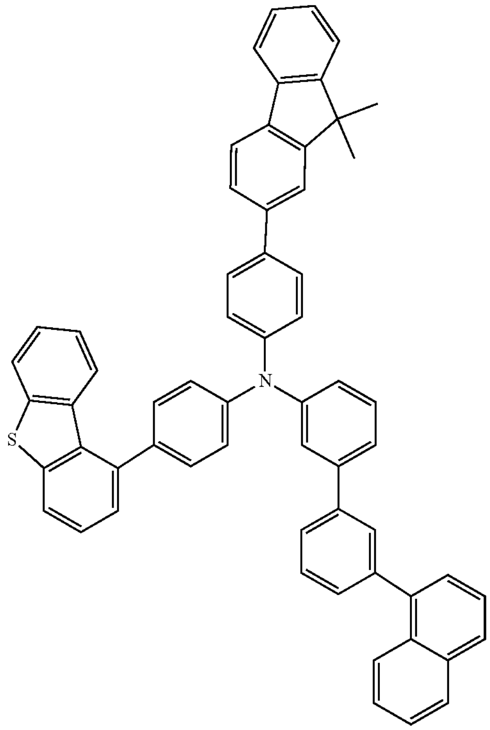
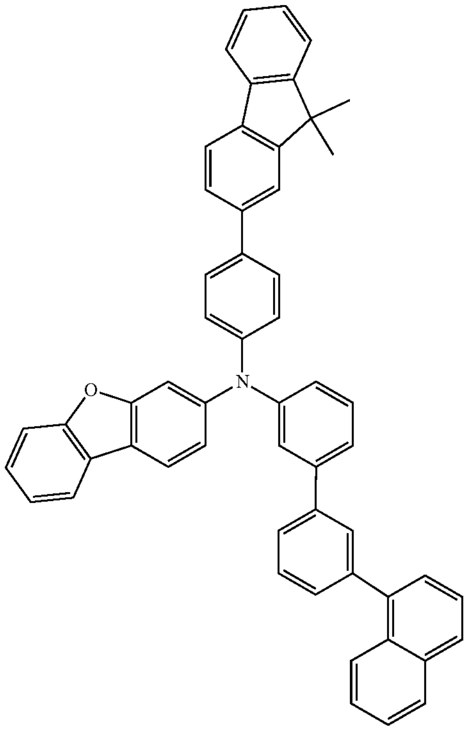

-continued
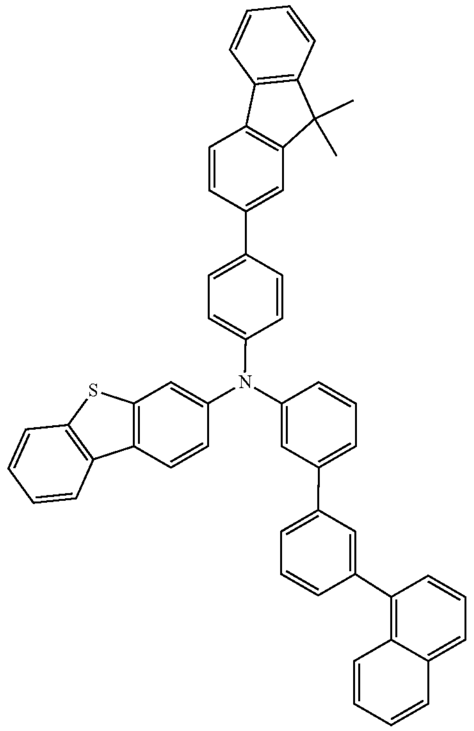
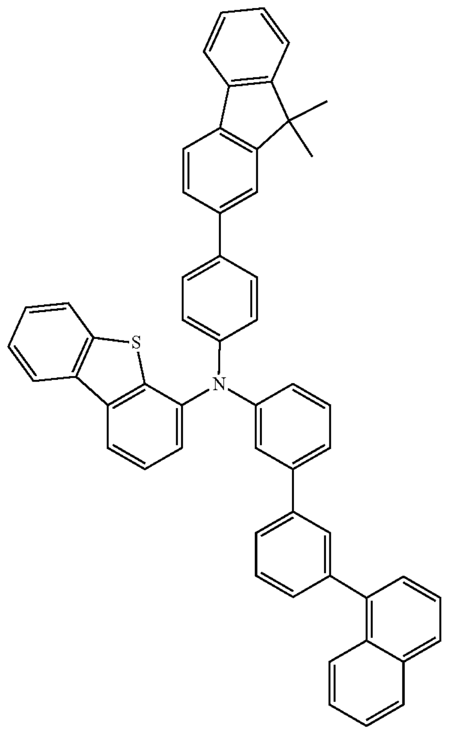
-continued
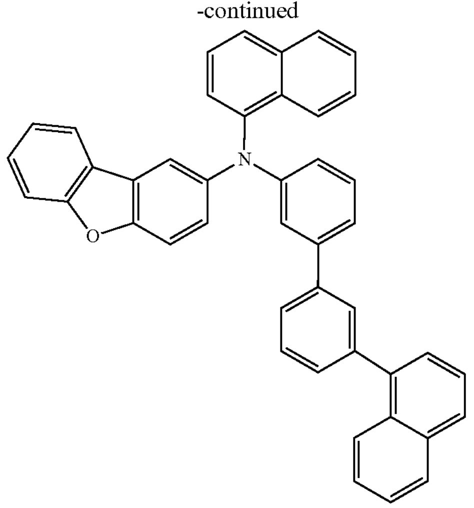
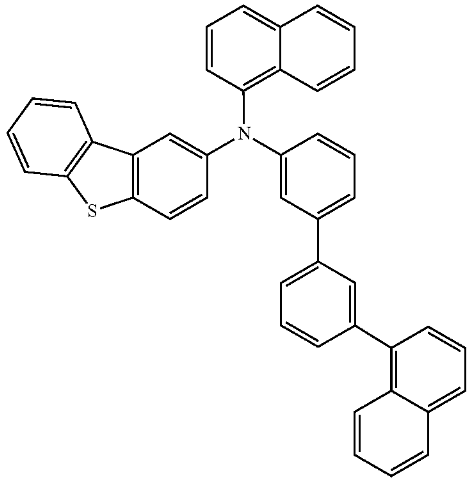
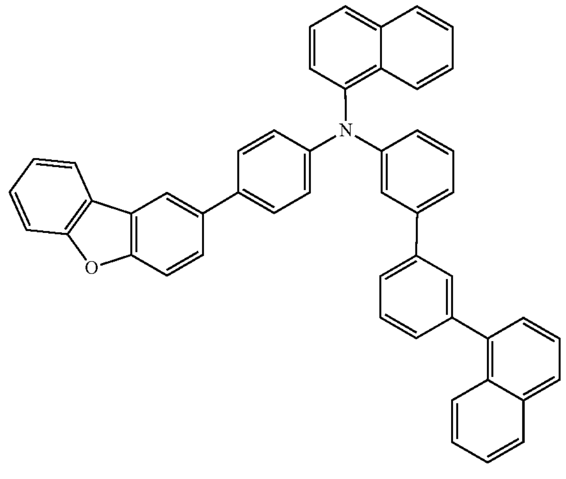

-continued
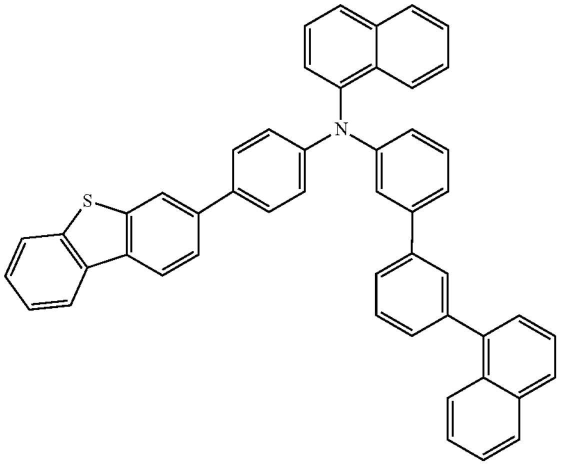
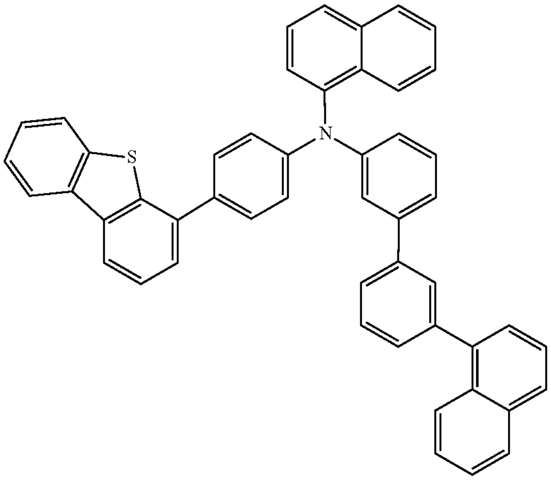
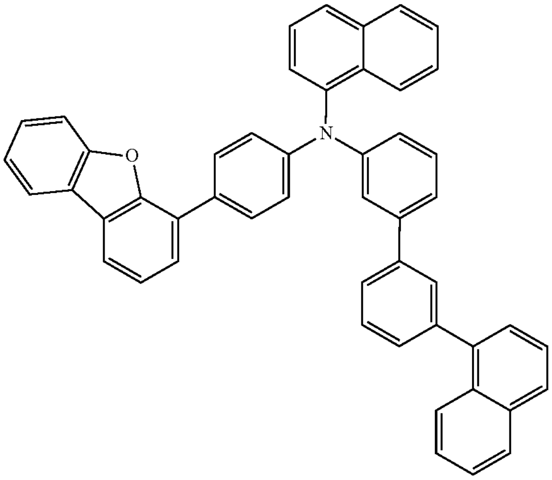
-continued
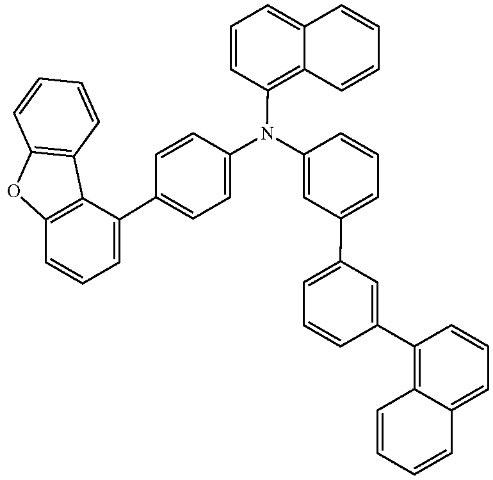
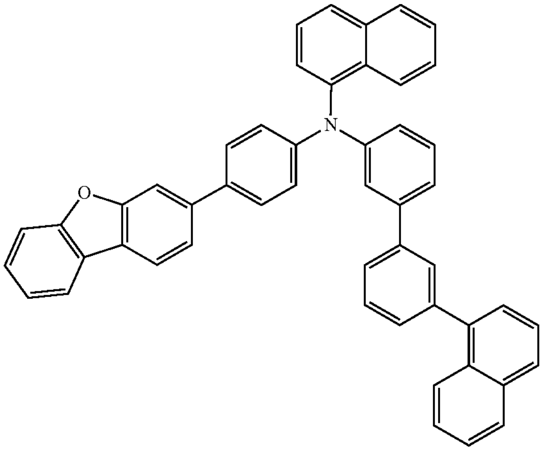
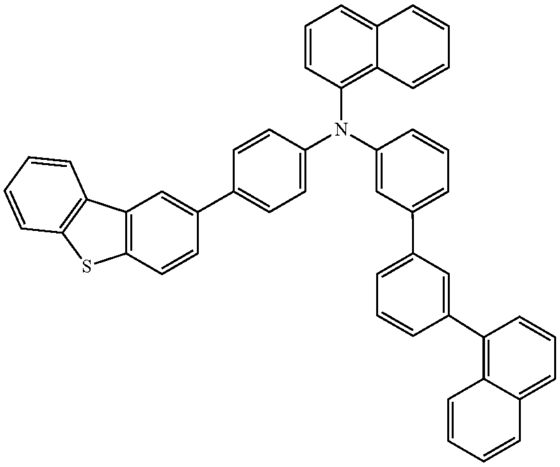

-continued
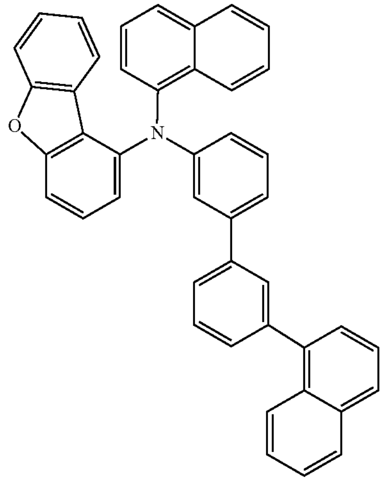
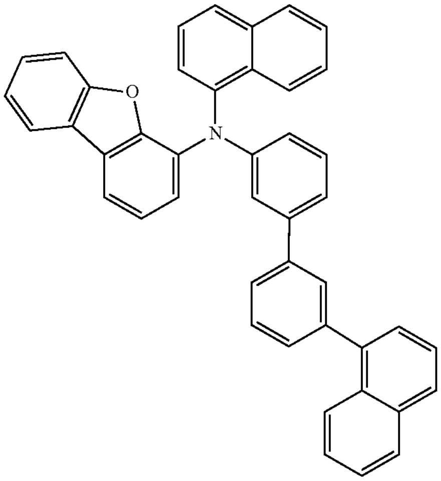
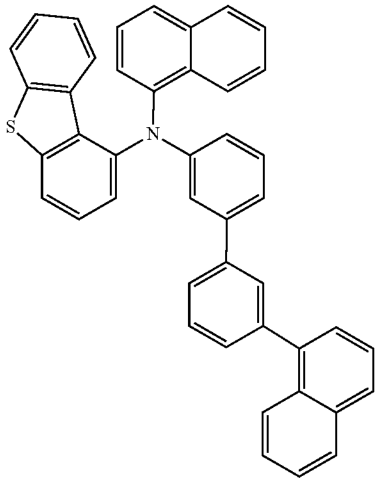
-continued
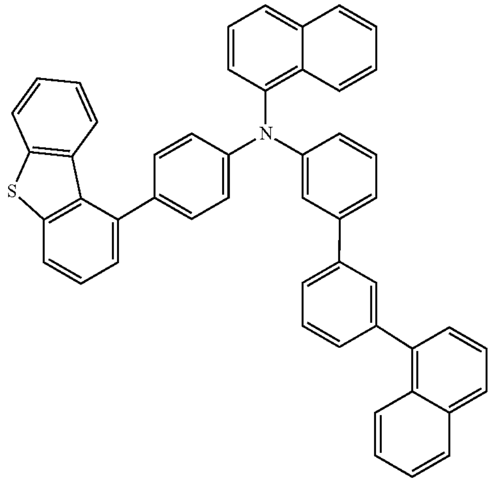
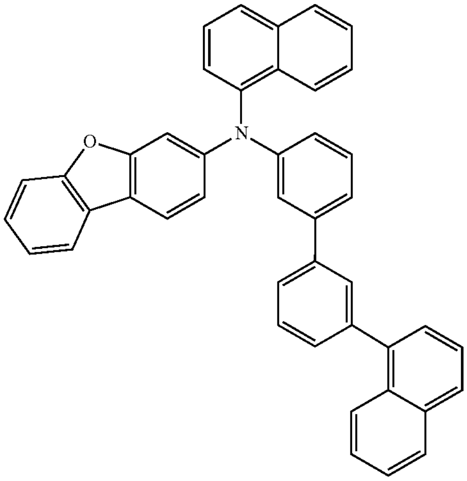
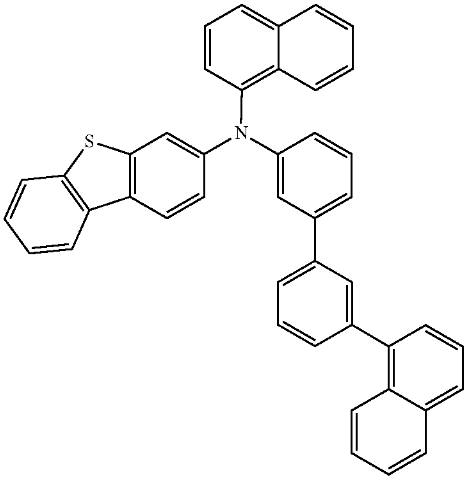

-continued
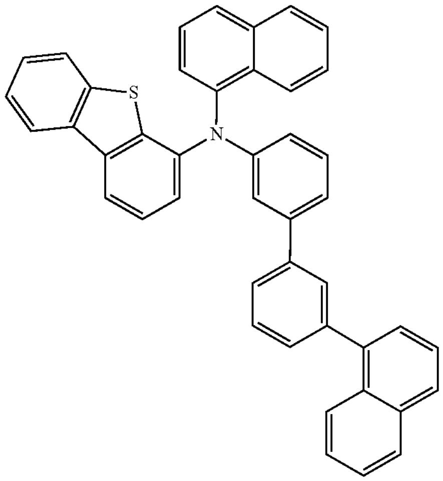
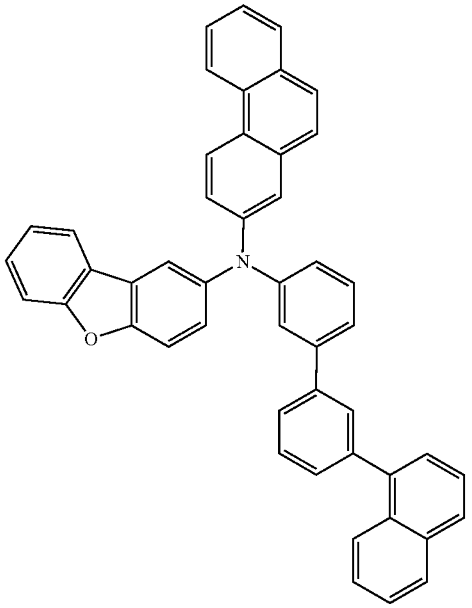
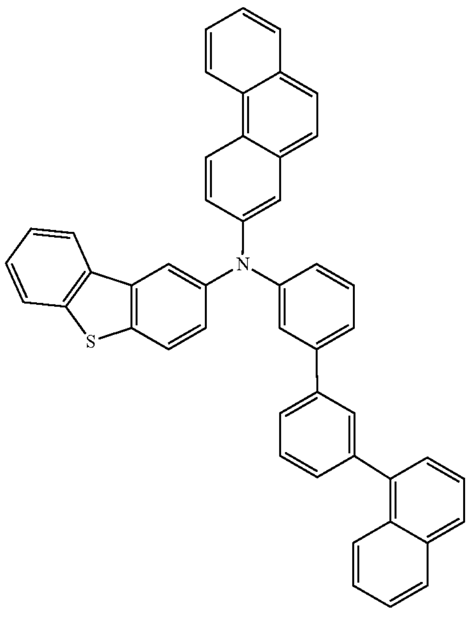
-continued
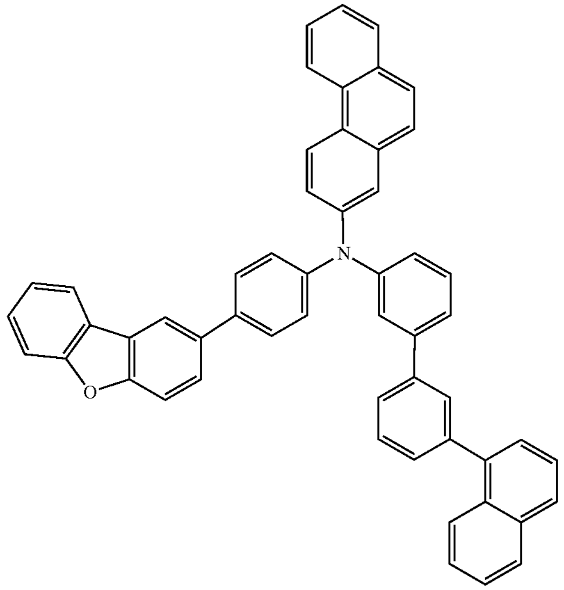
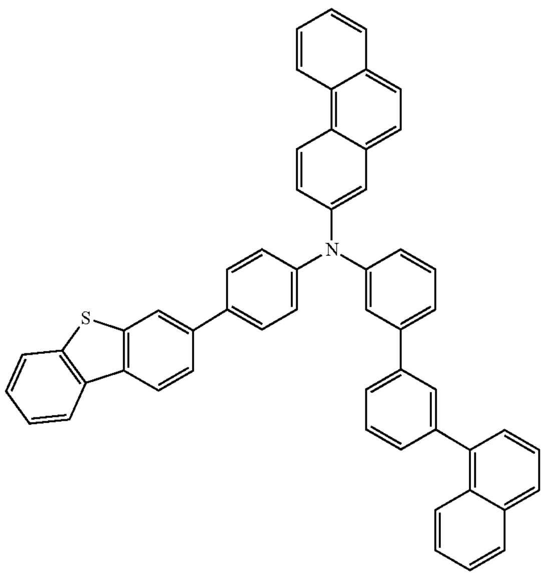

-continued
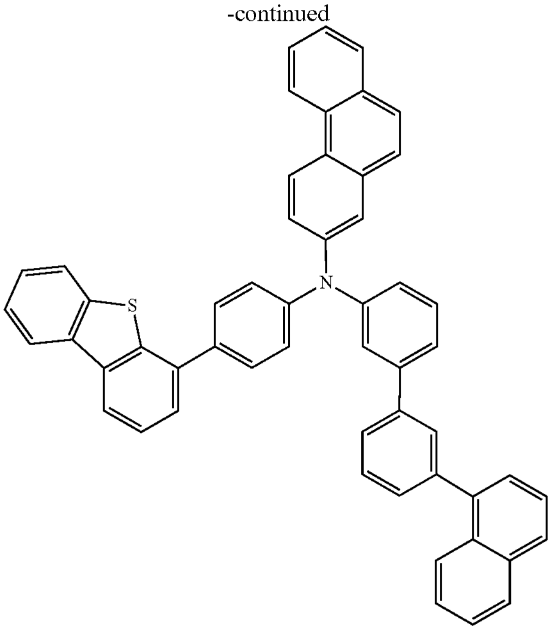
-continued
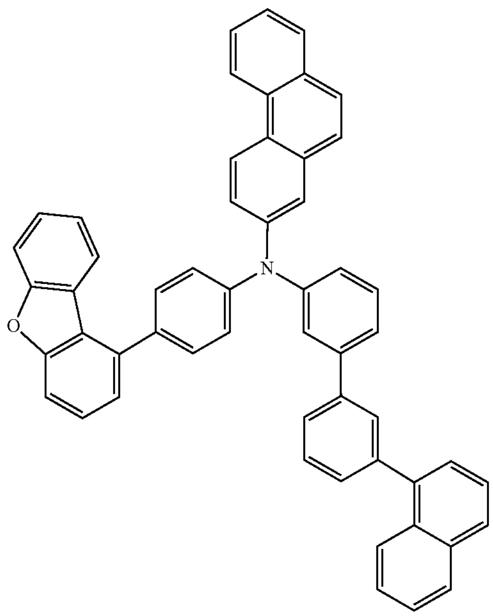
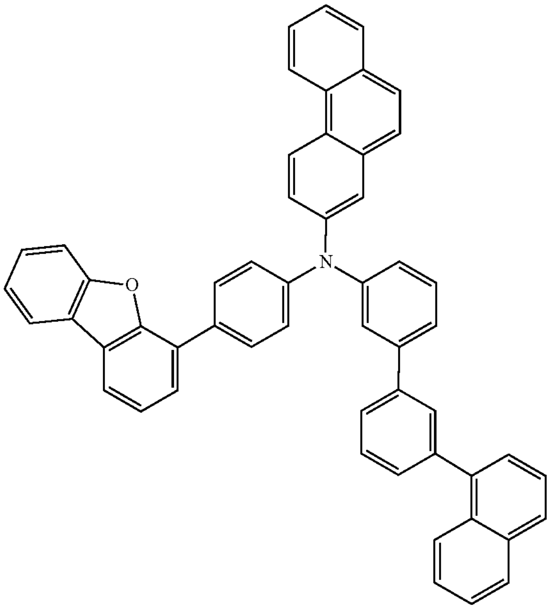
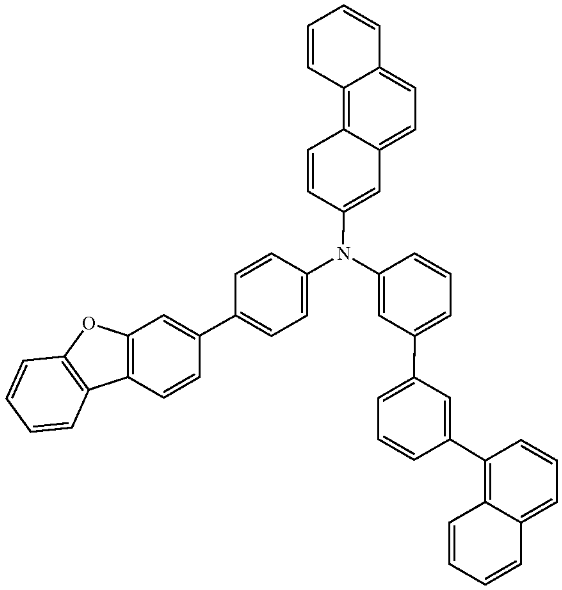

-continued
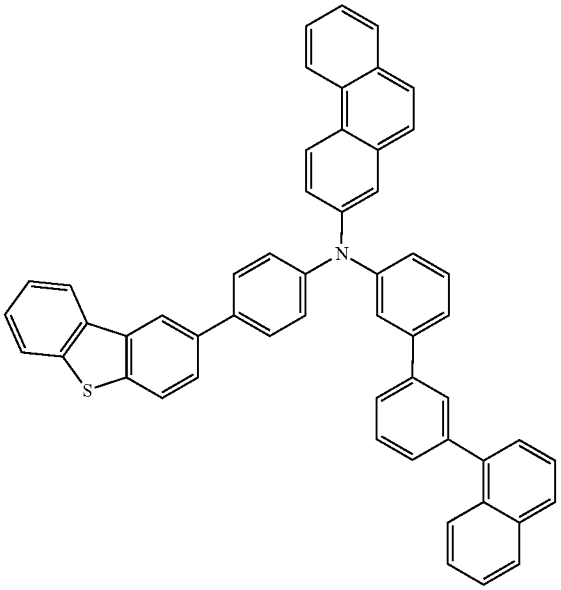
-continued
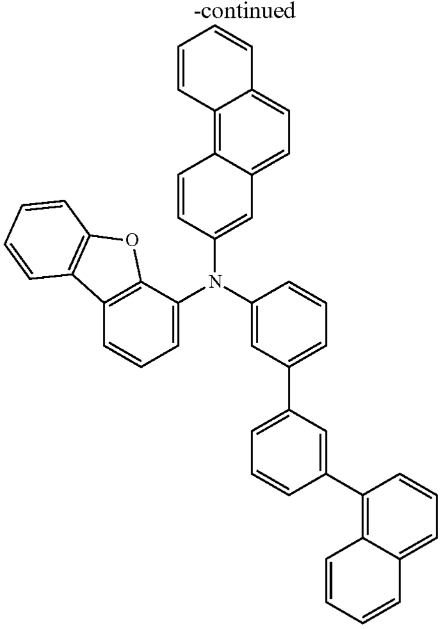
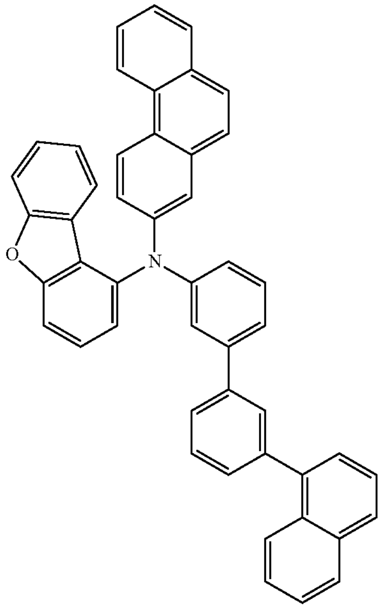
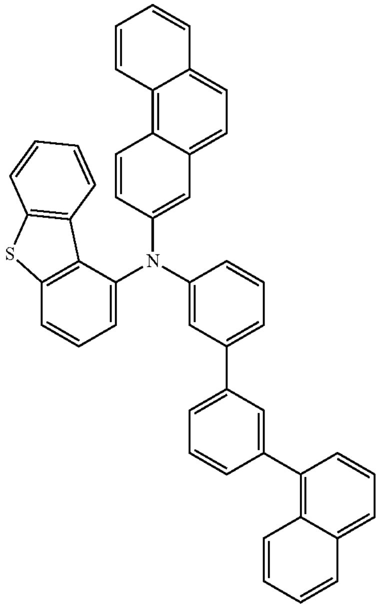

-continued
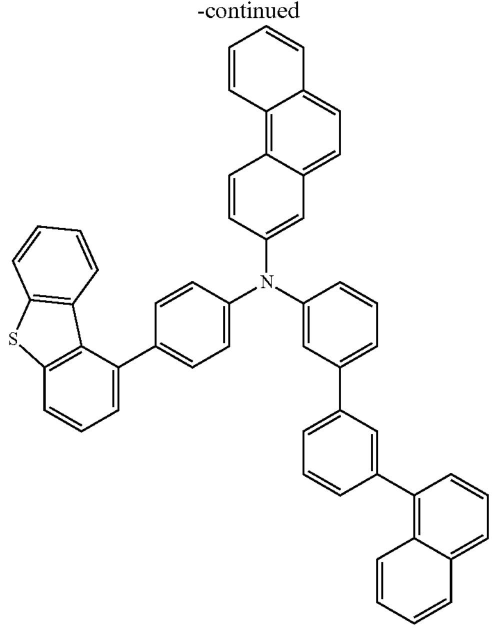
-continued
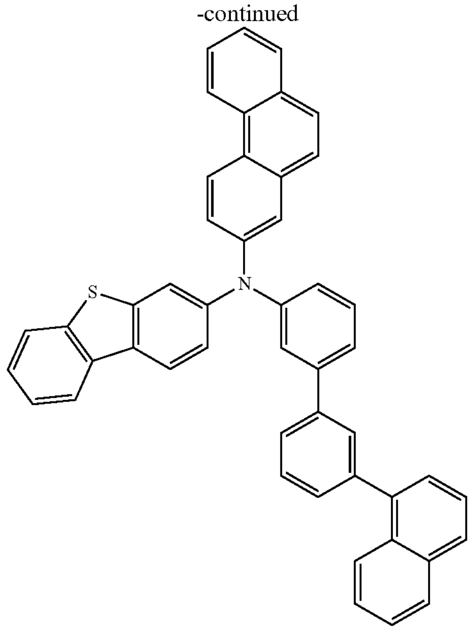
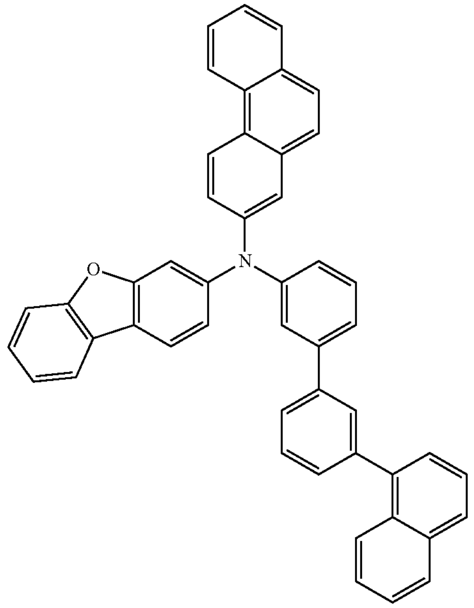
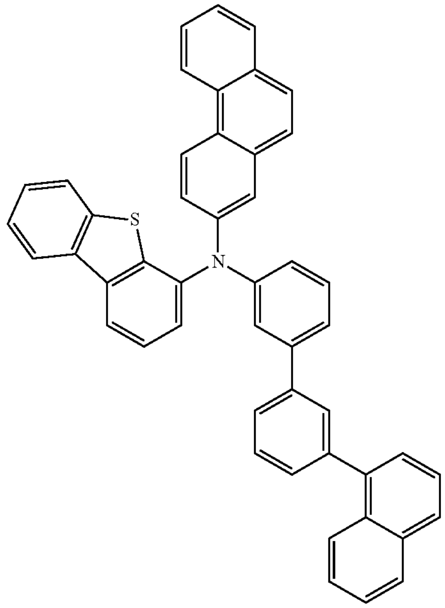

-continued
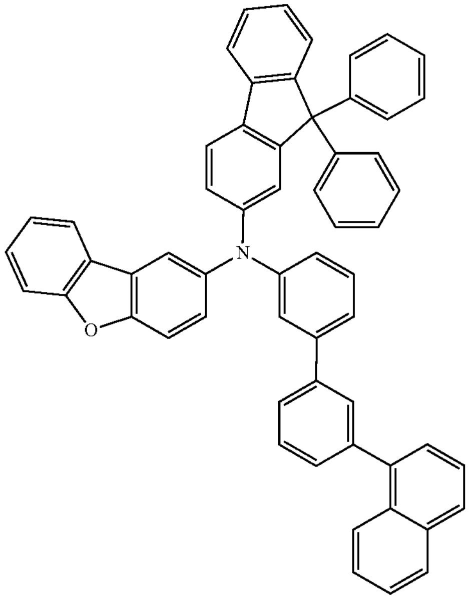
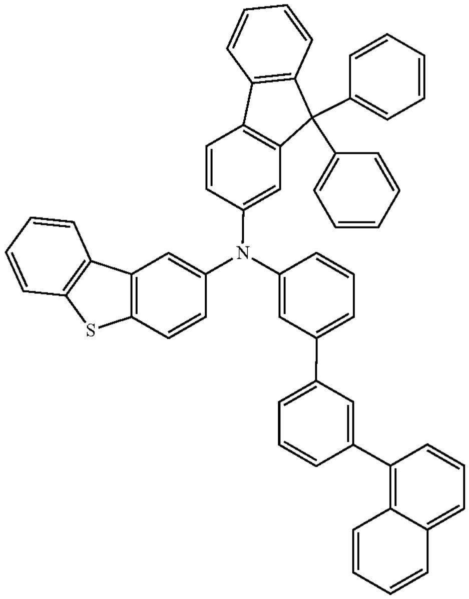
-continued
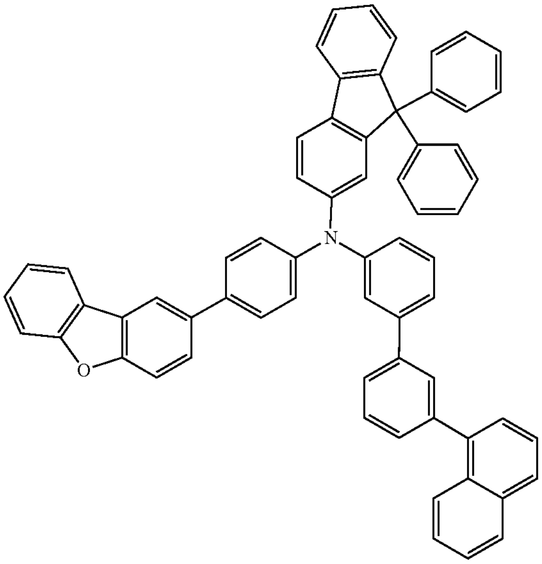
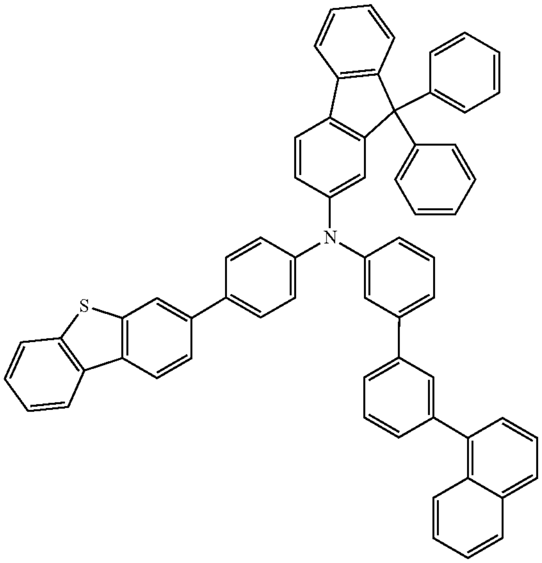
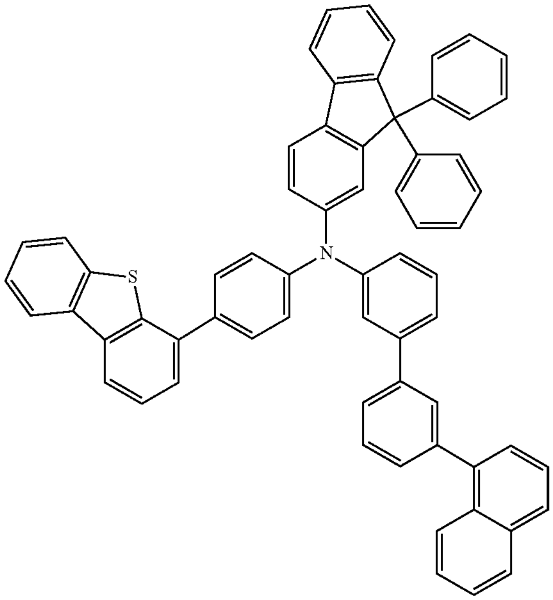

-continued
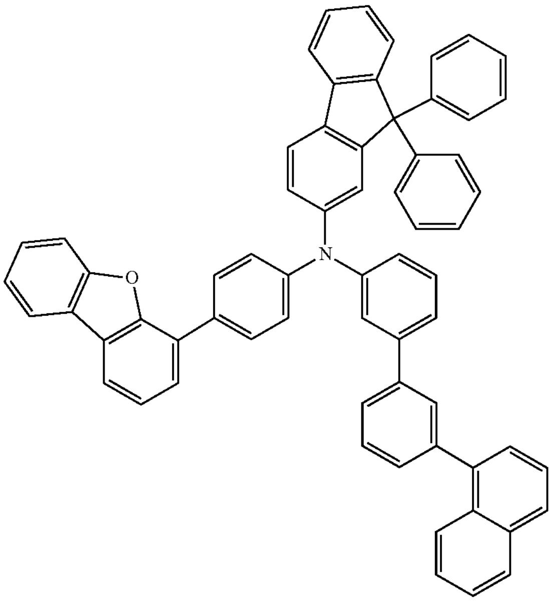
-continued
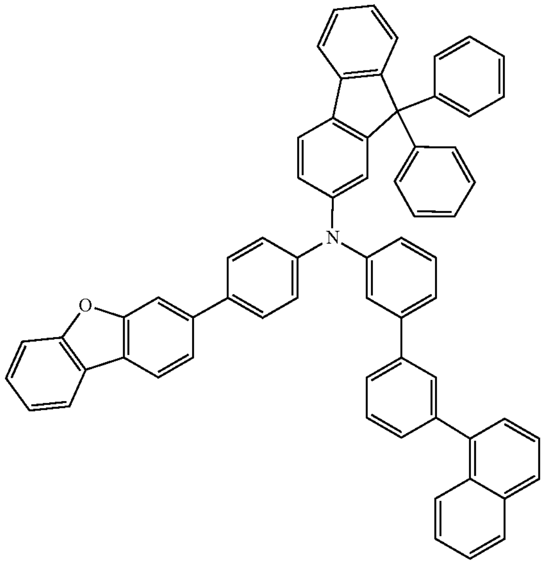
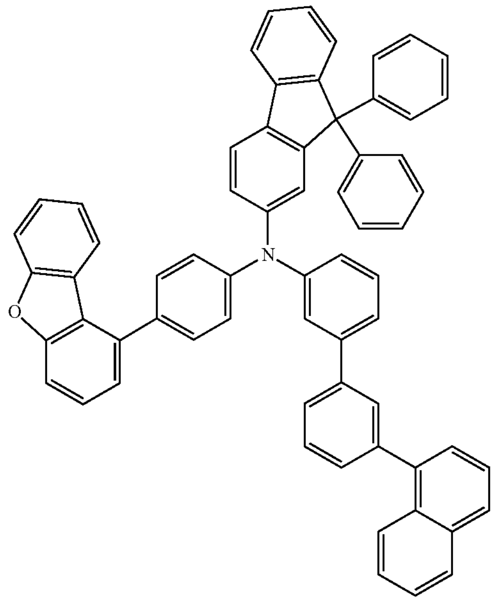
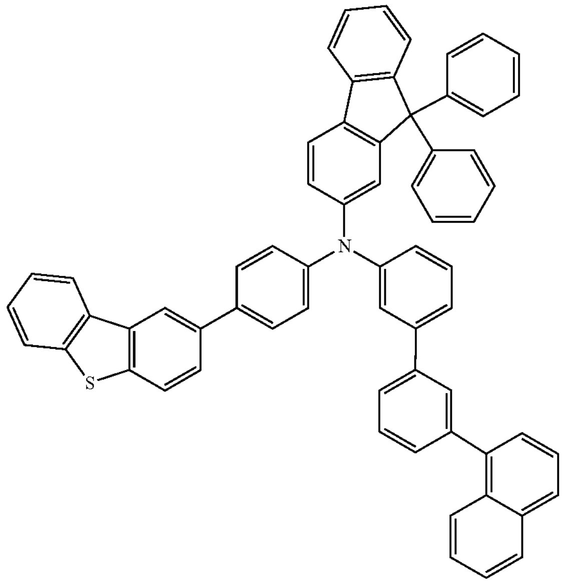

-continued
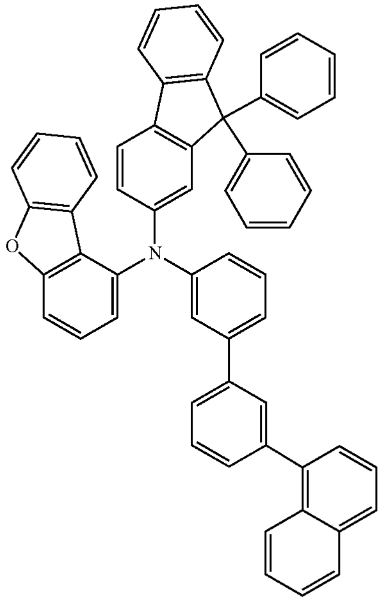
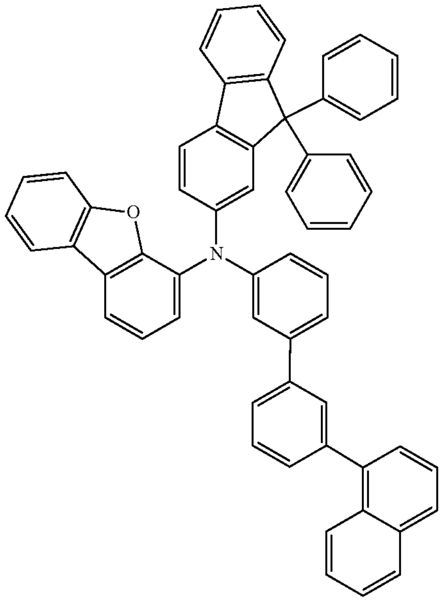
-continued
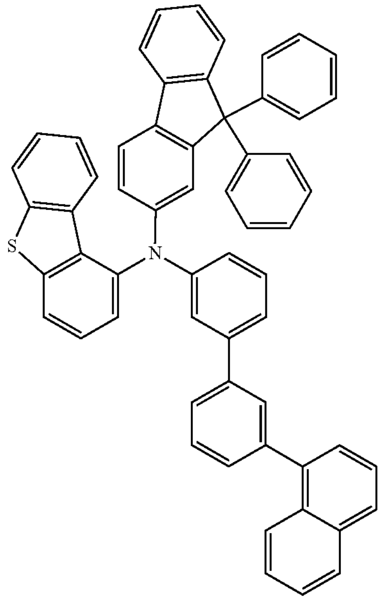
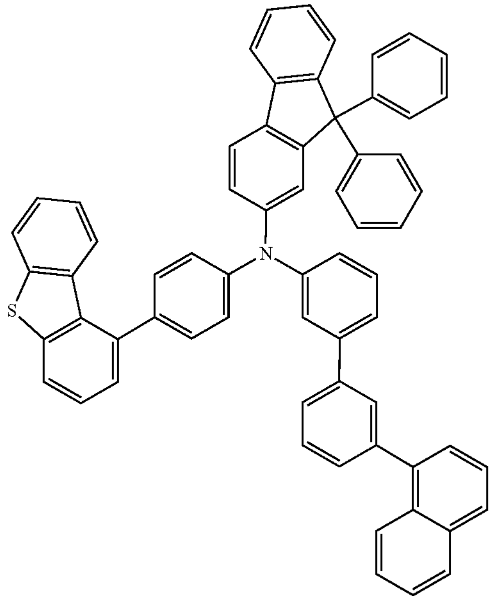

-continued
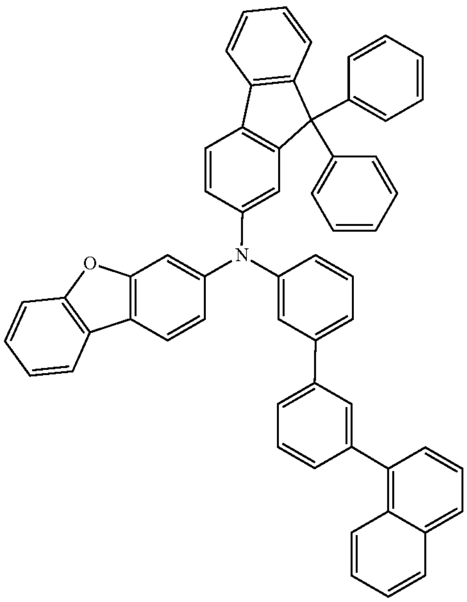
-continued
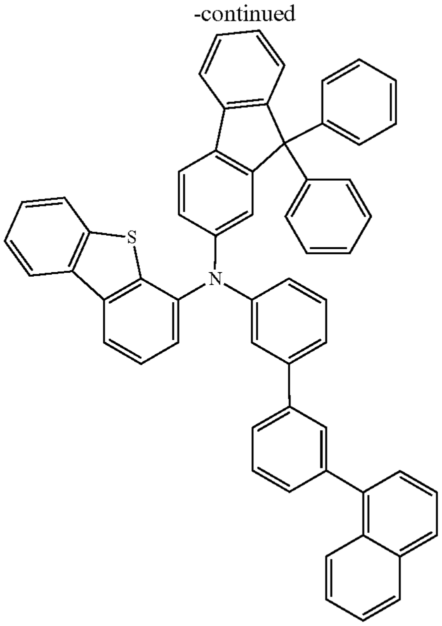
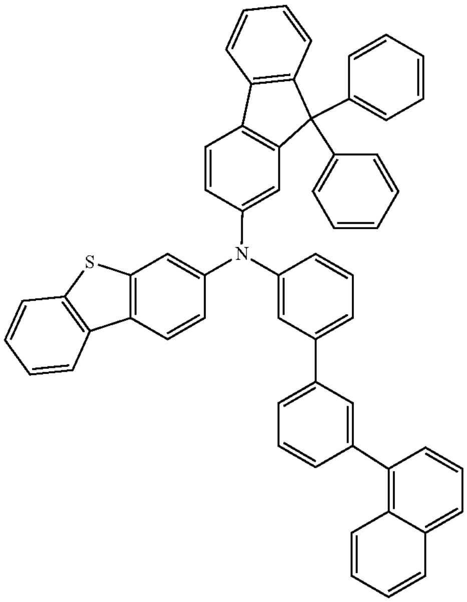
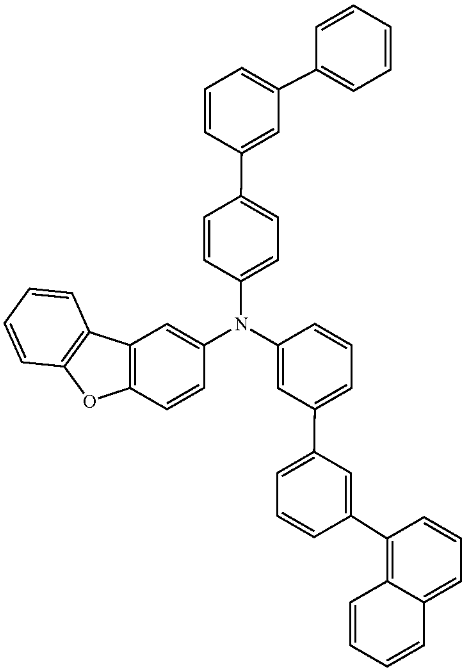

-continued
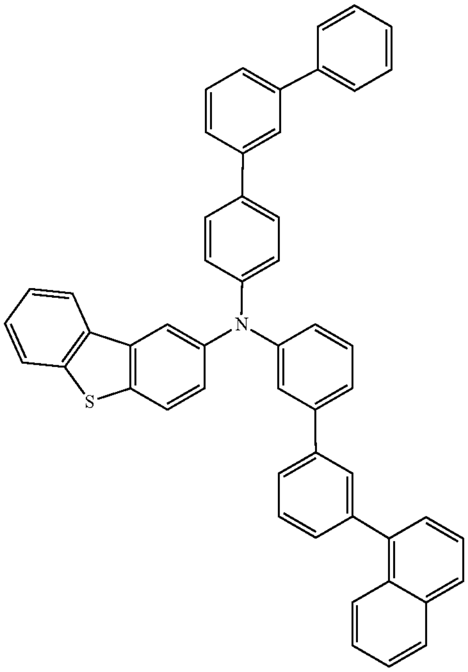
-continued
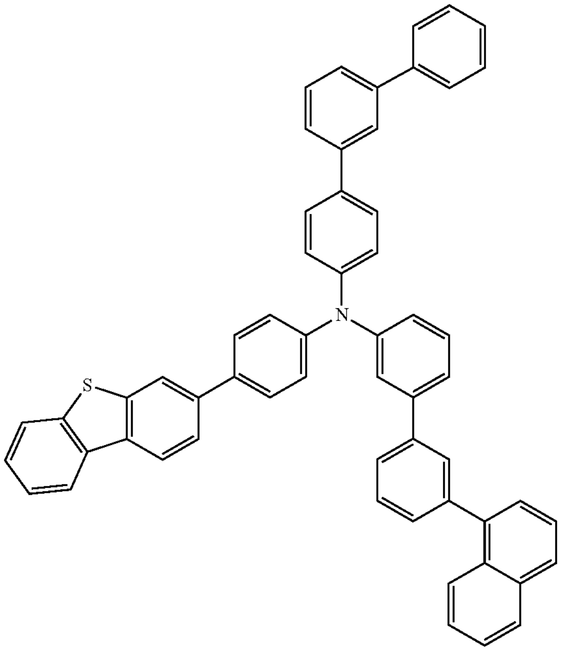
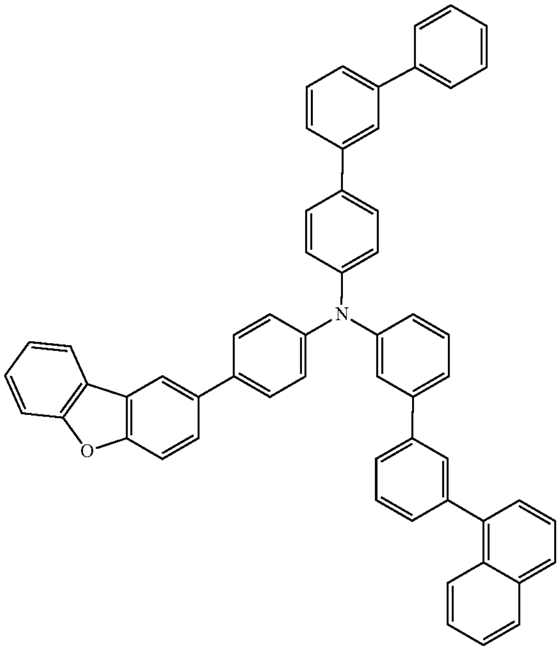
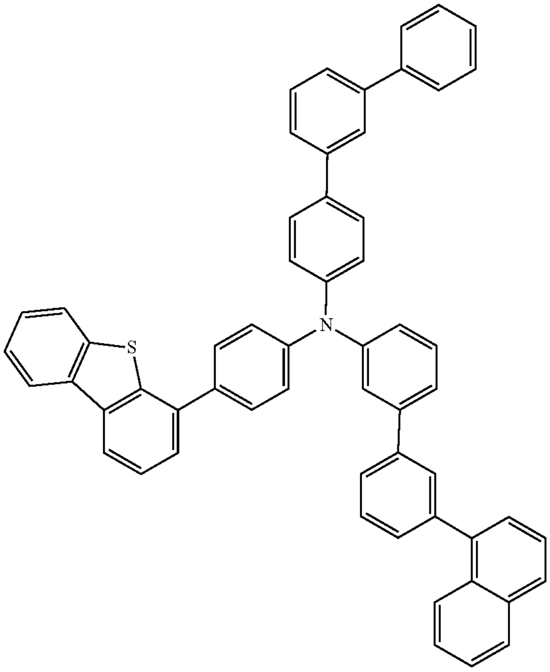

-continued
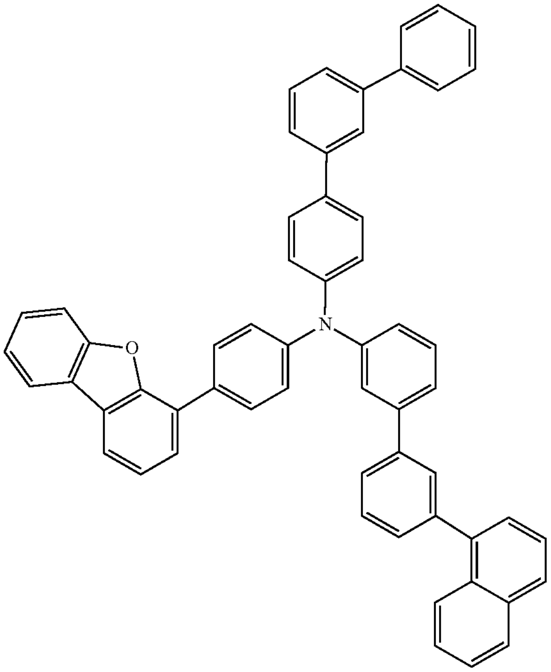
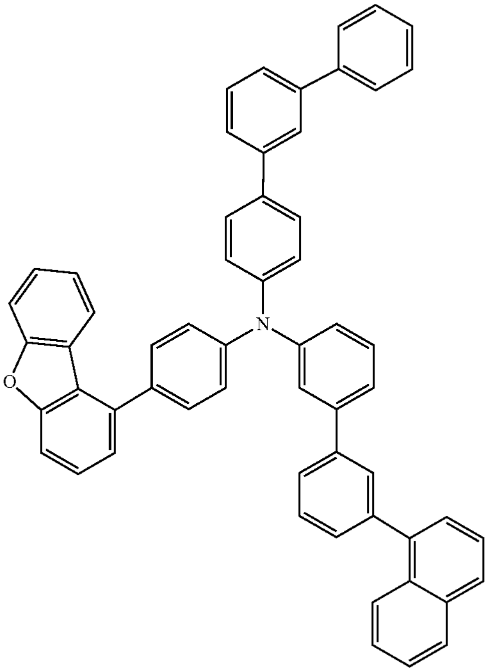
-continued
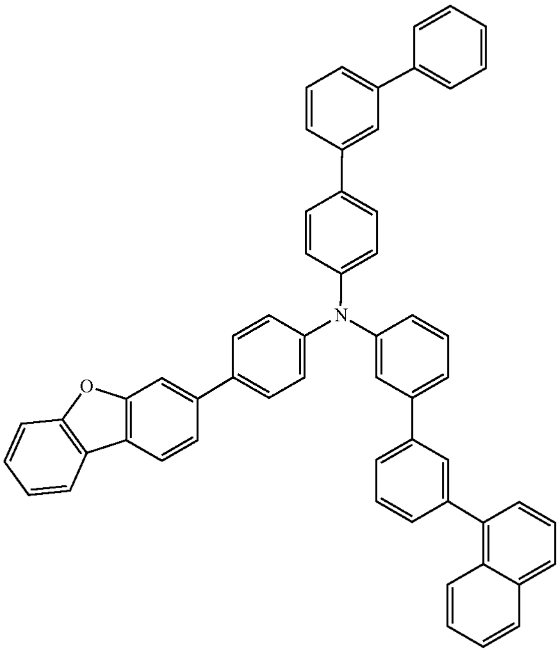
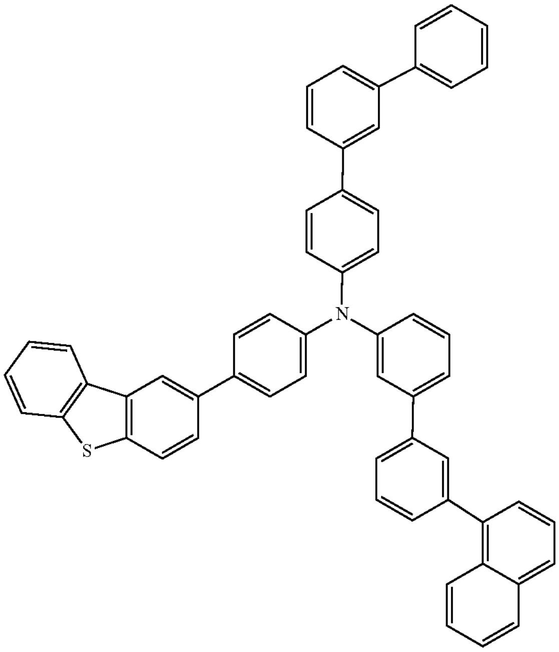

-continued
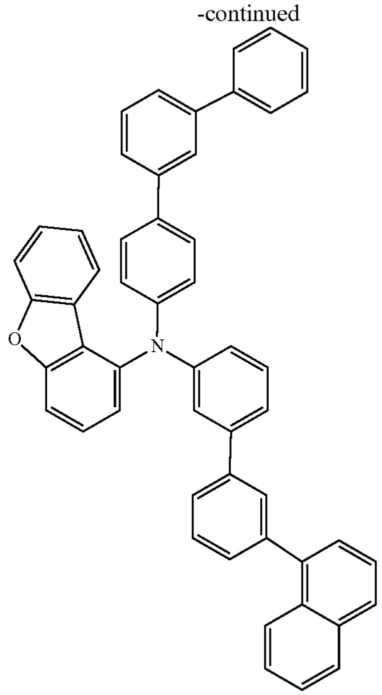
-continued
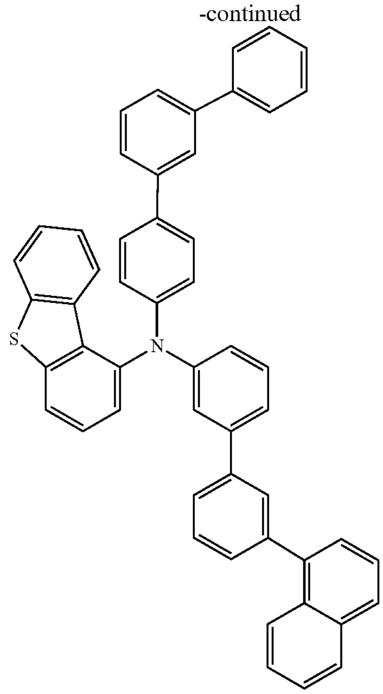
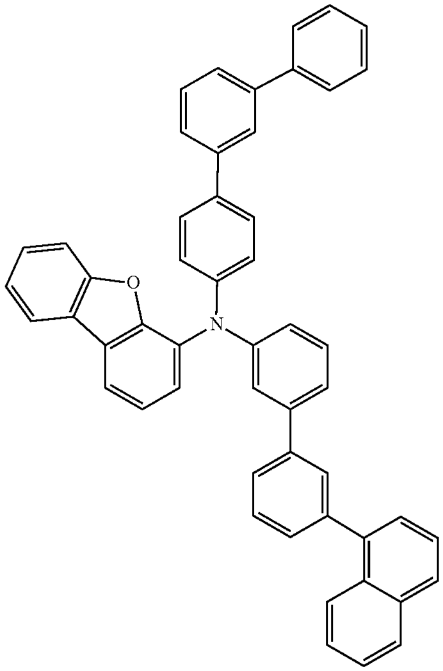
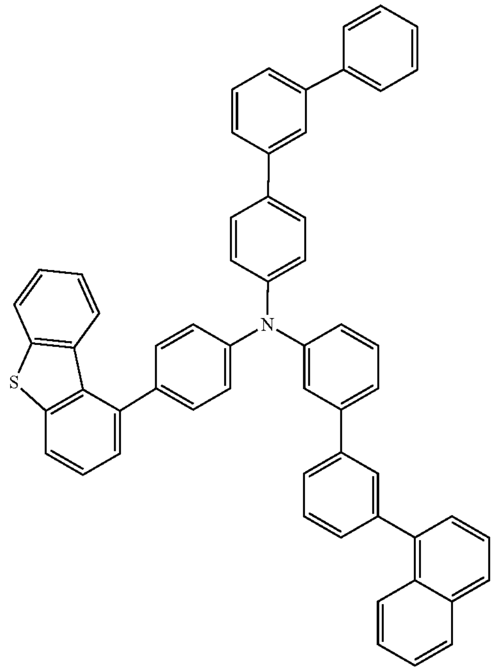

-continued
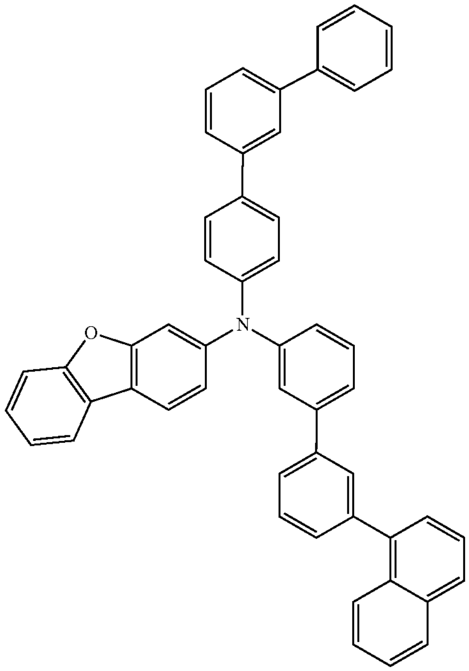
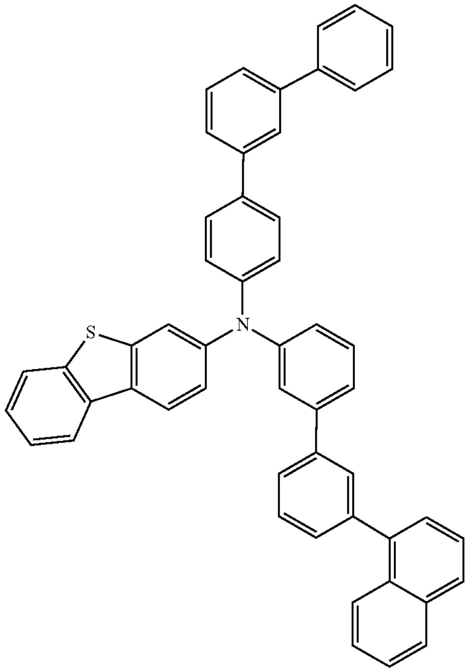
-continued
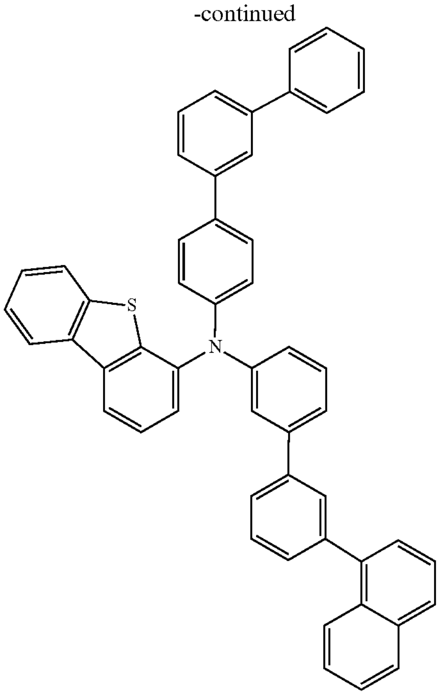
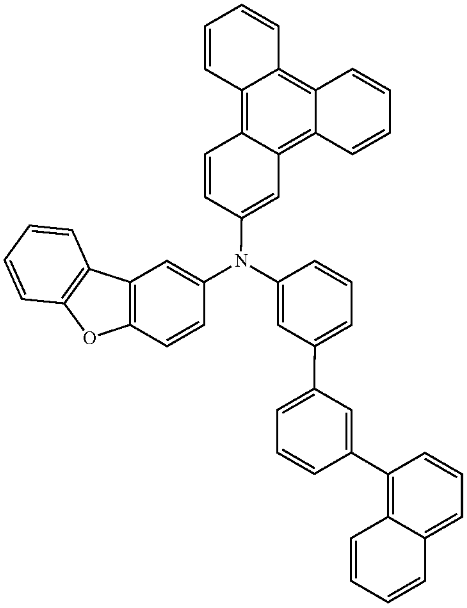

-continued
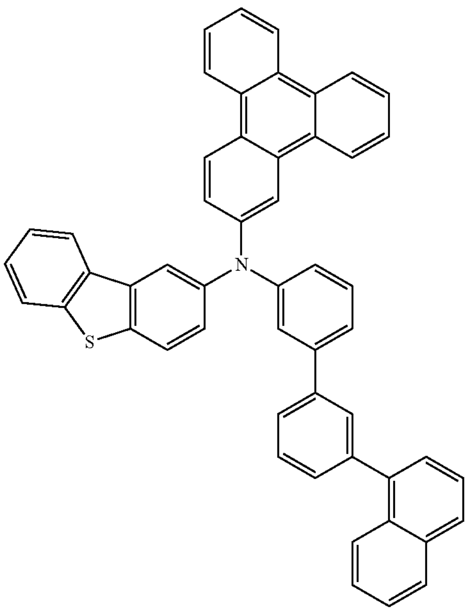
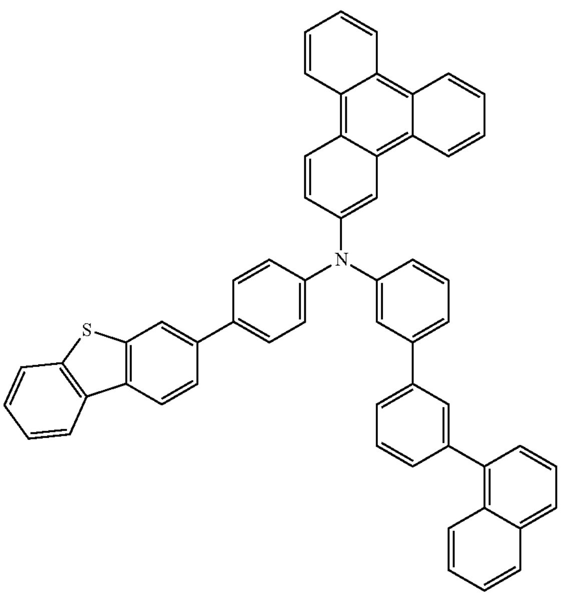
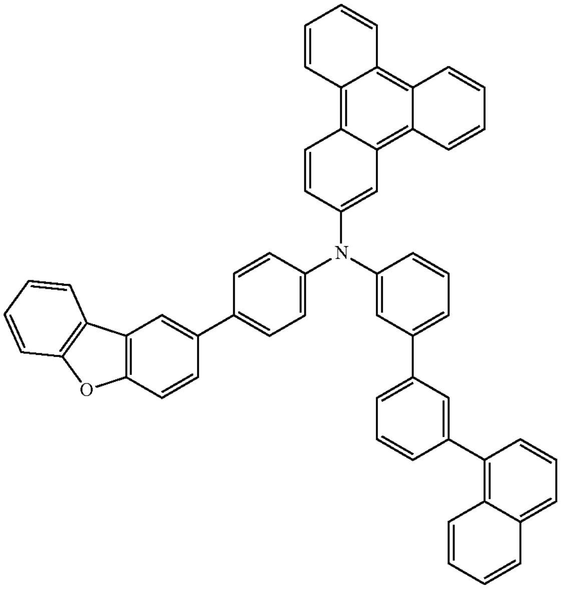
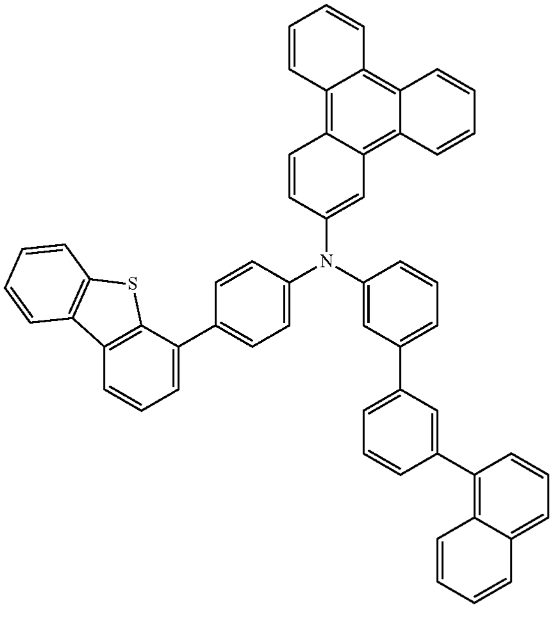
-continued

-continued
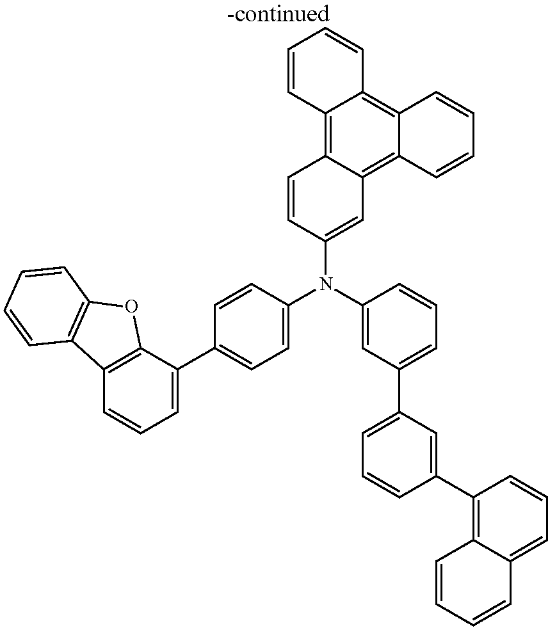
-continued
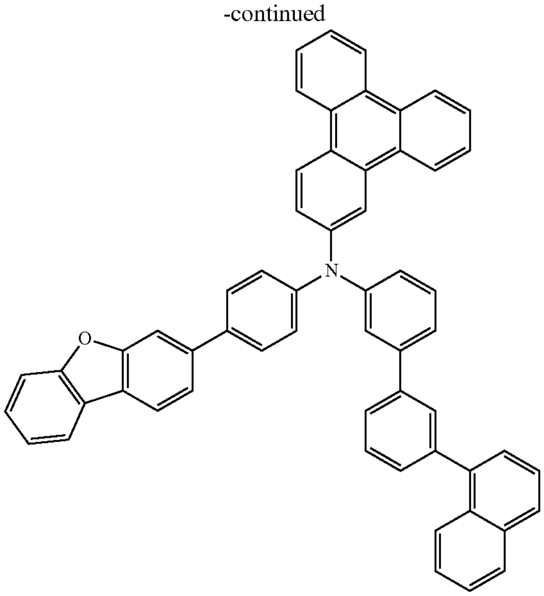
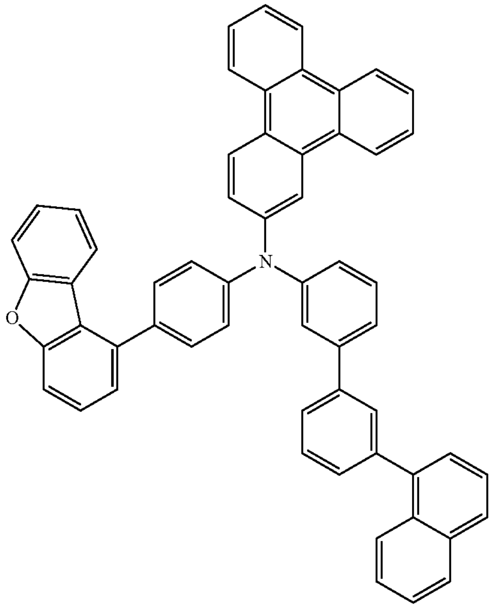
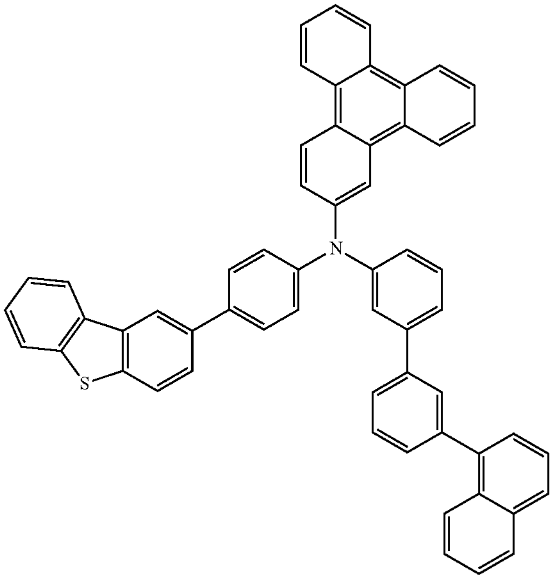

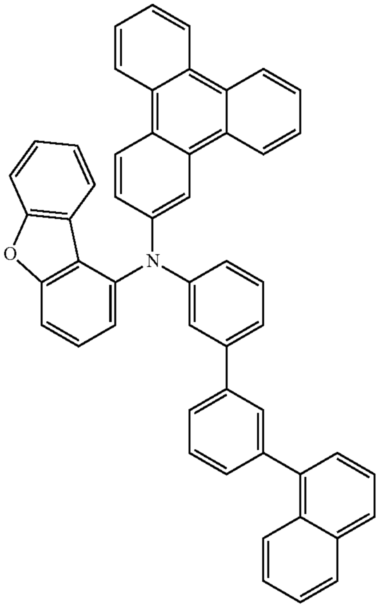
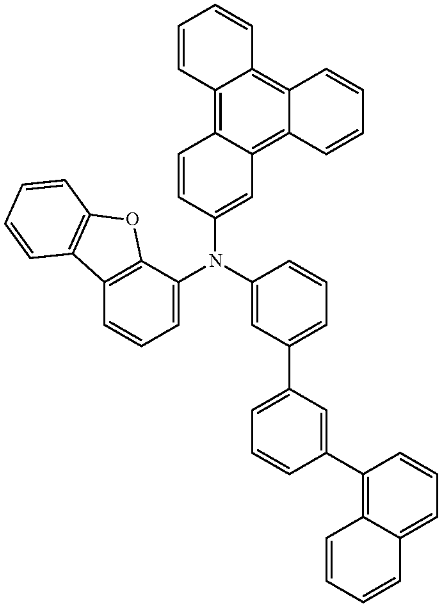
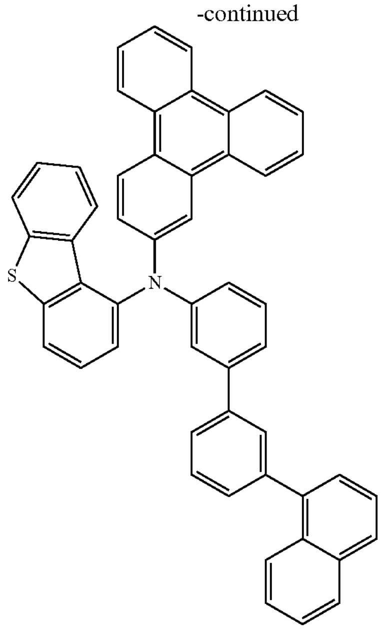
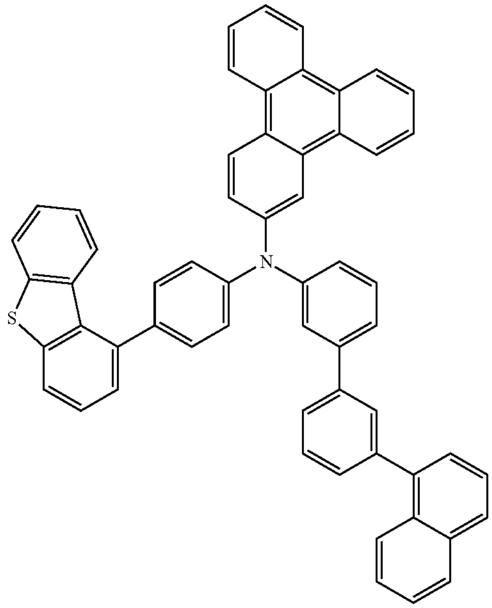

-continued
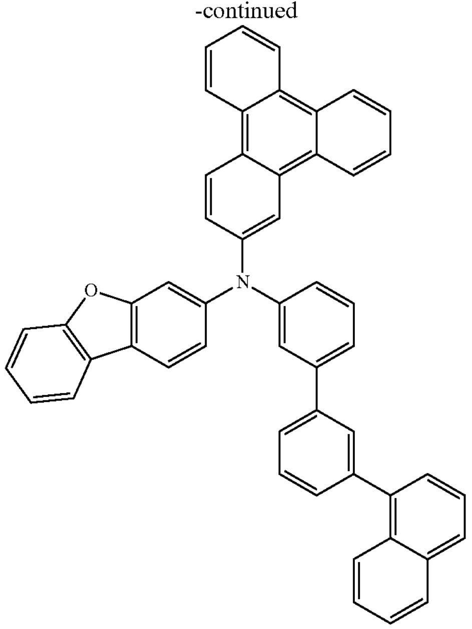
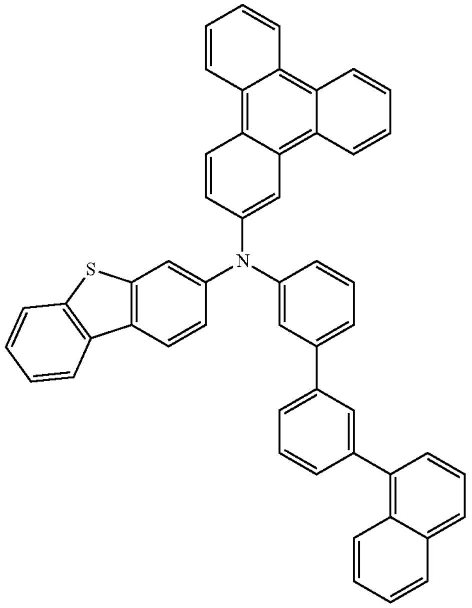
-continued
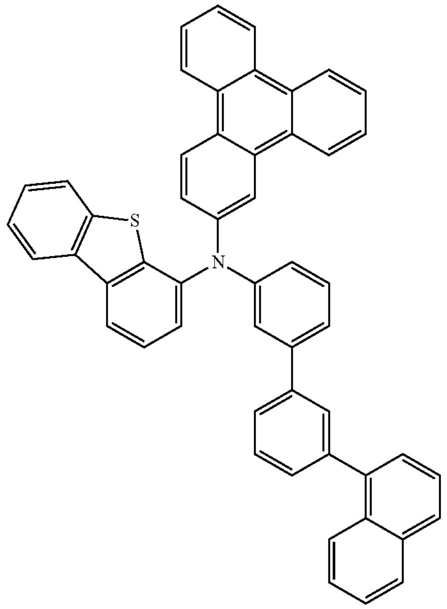
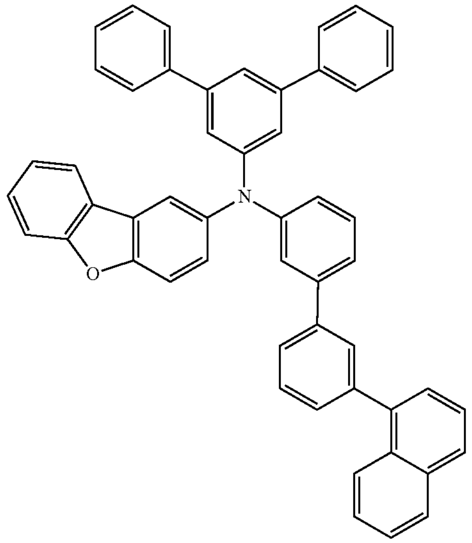
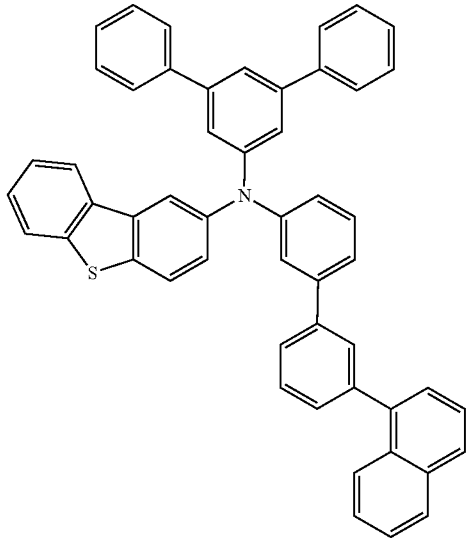

-continued
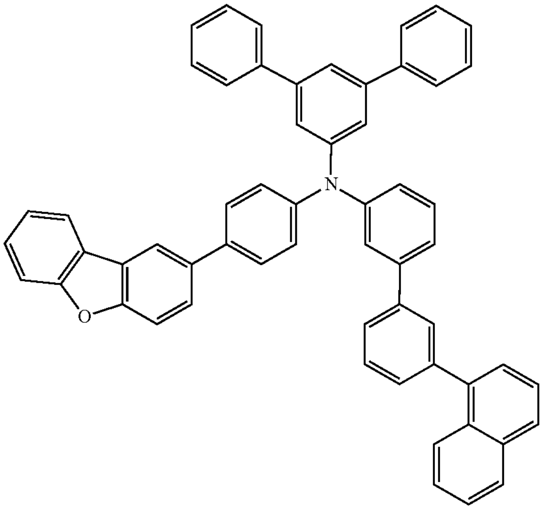
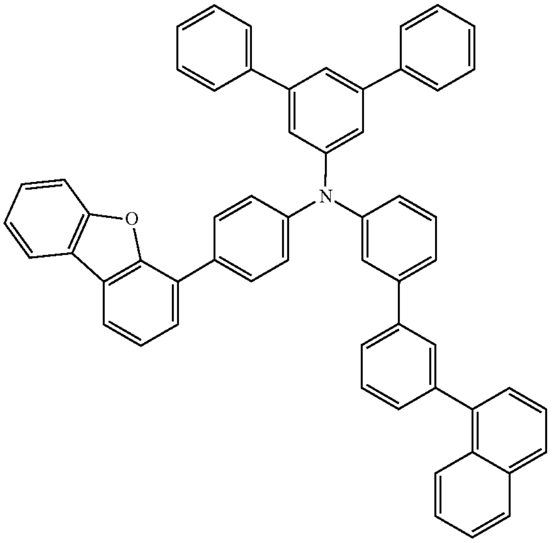
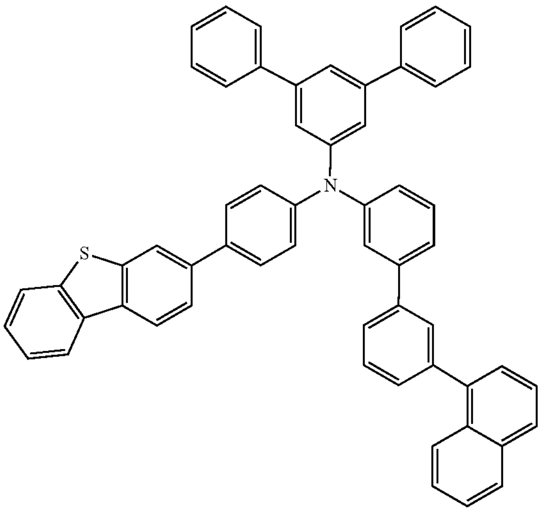
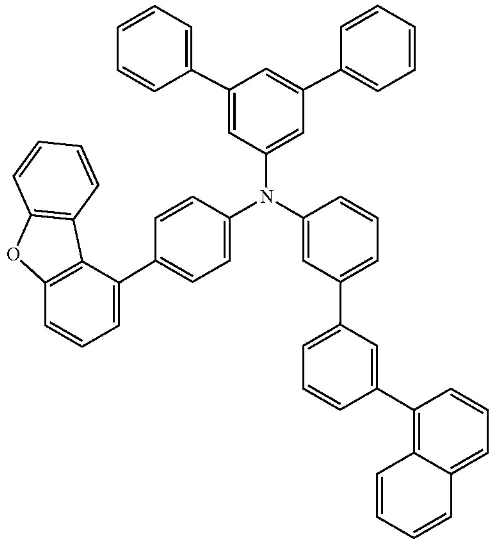
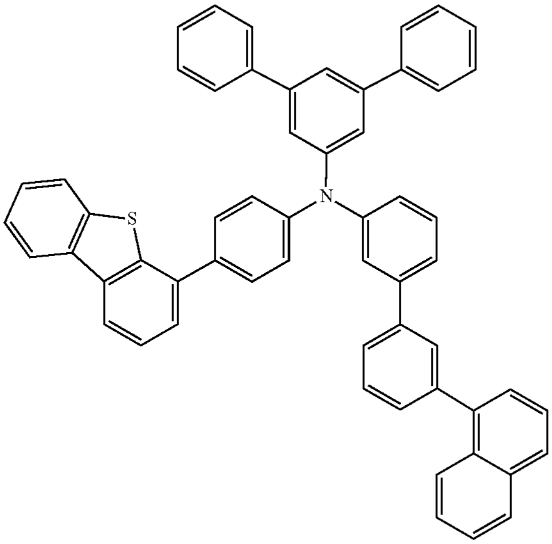
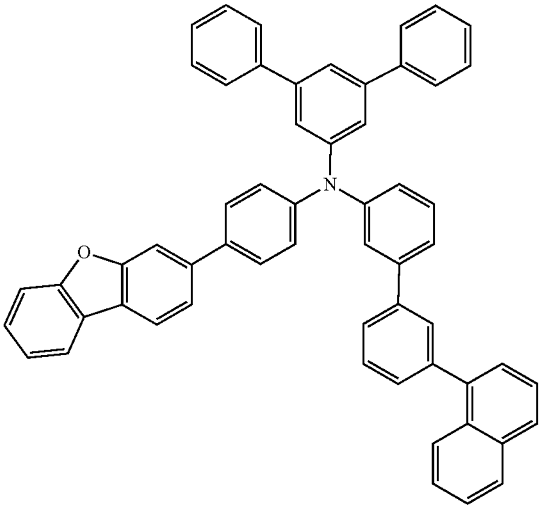
-continued -continued
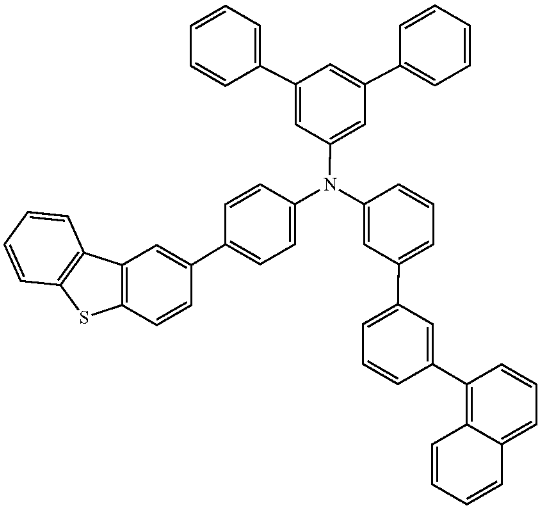
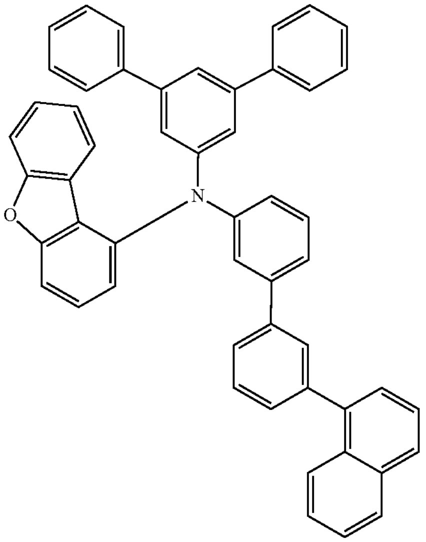
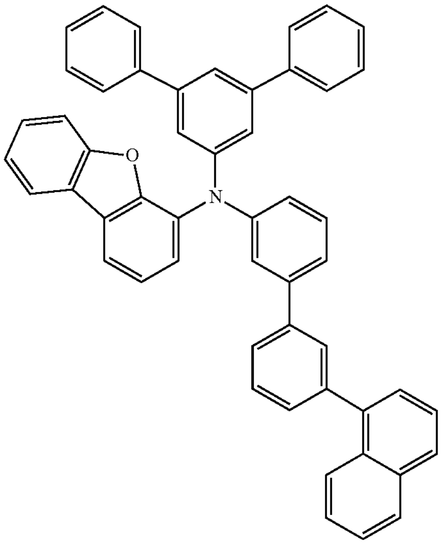
-continued
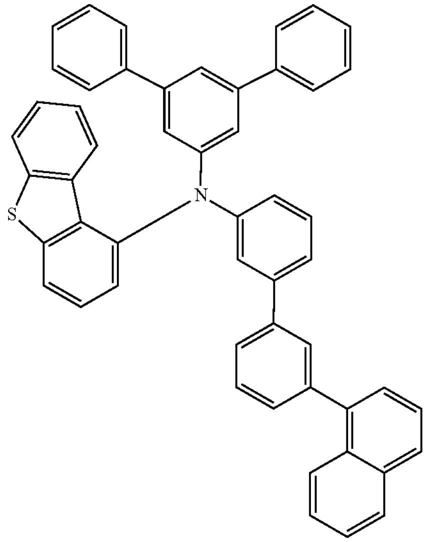
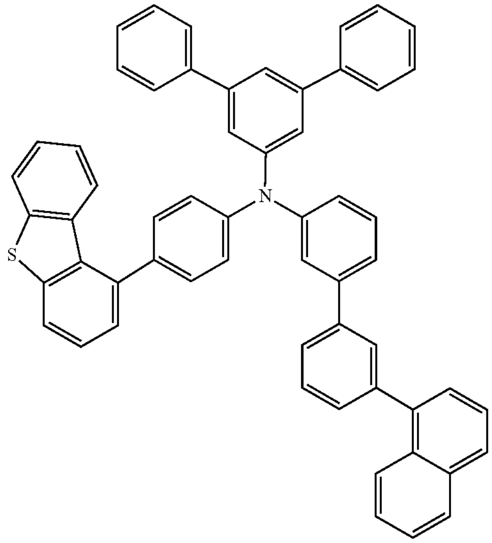
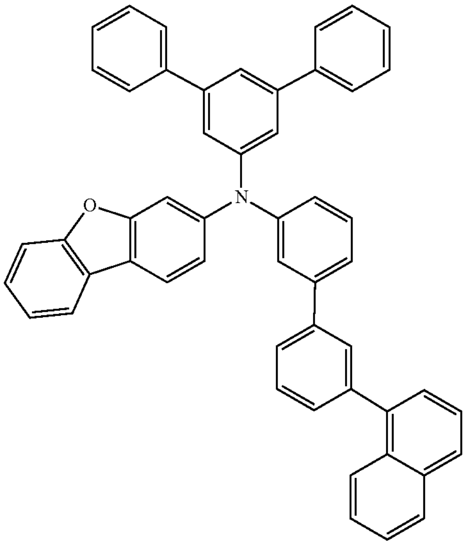

-continued
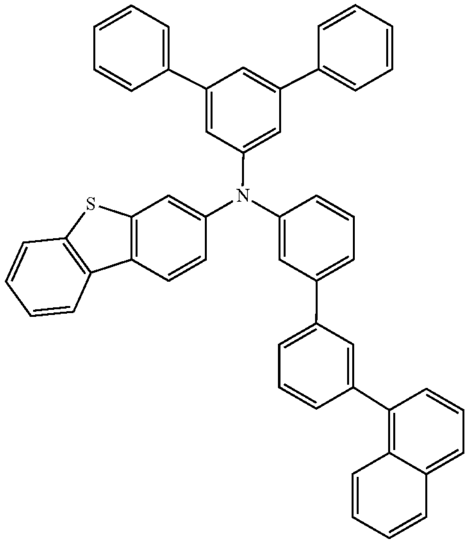
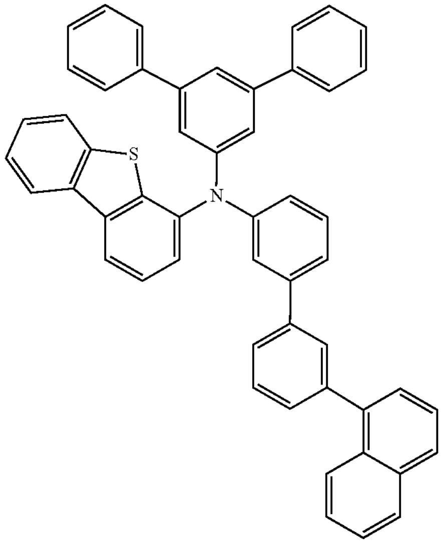
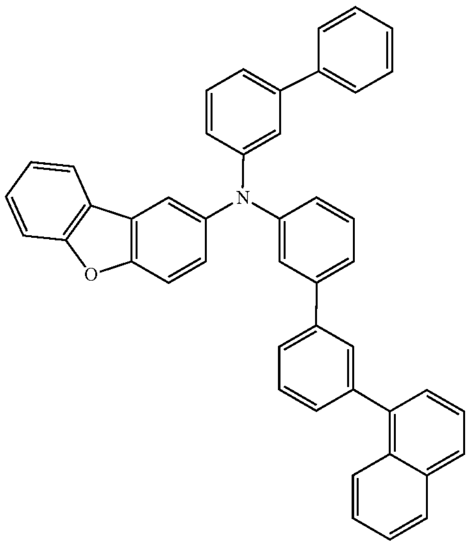
-continued
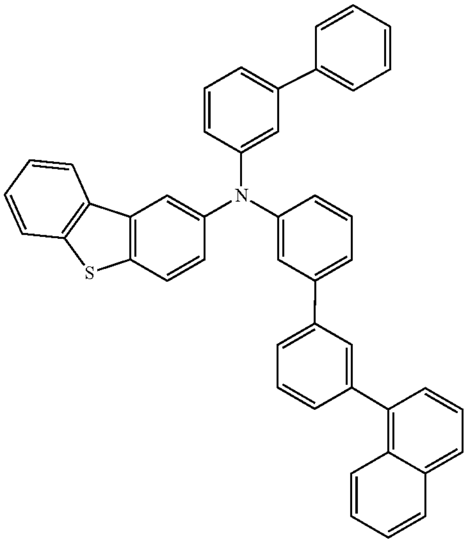
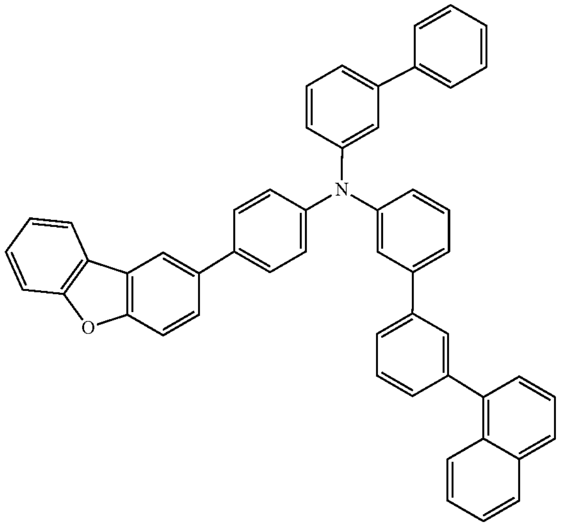
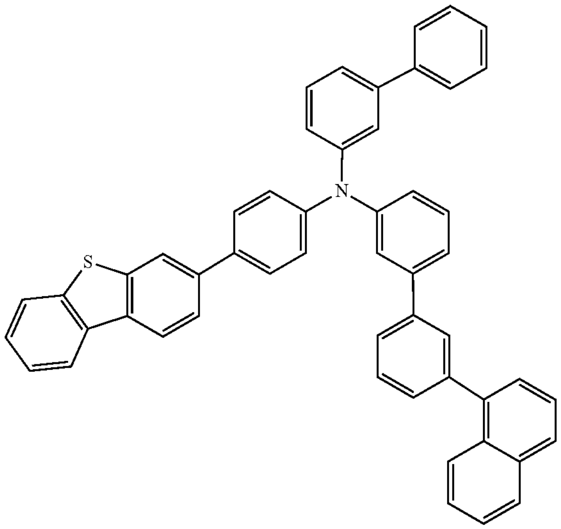

-continued
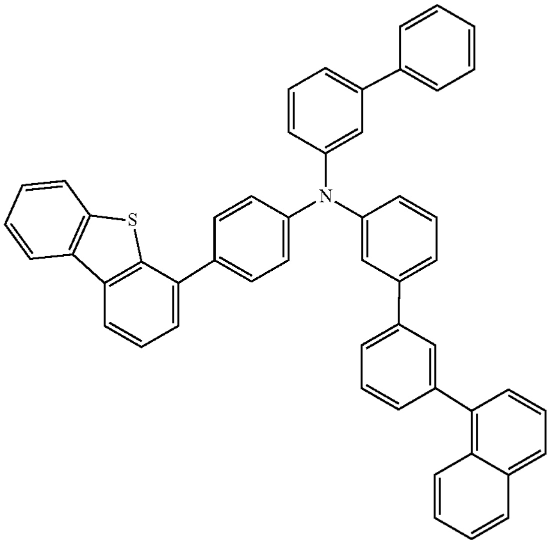
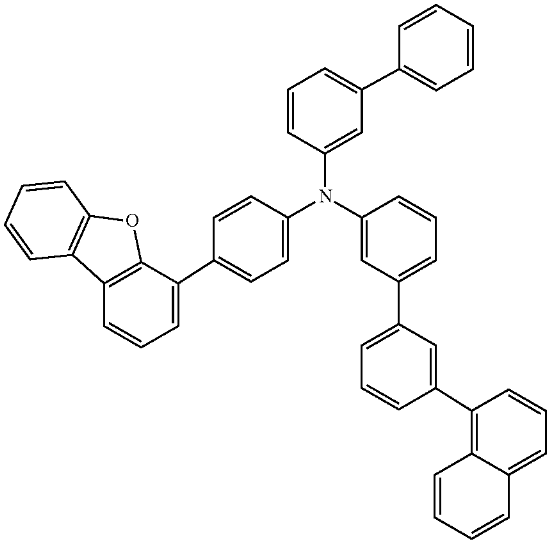
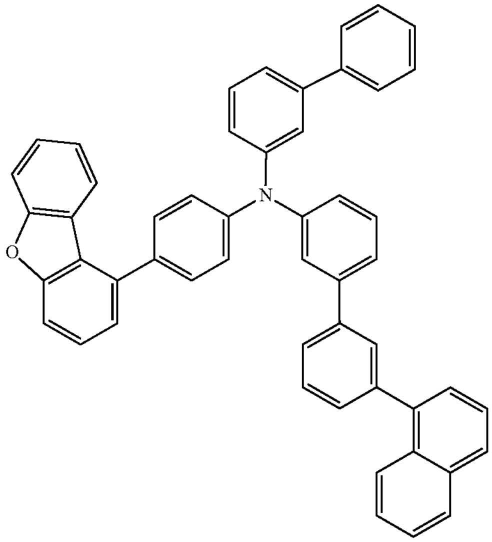
-continued
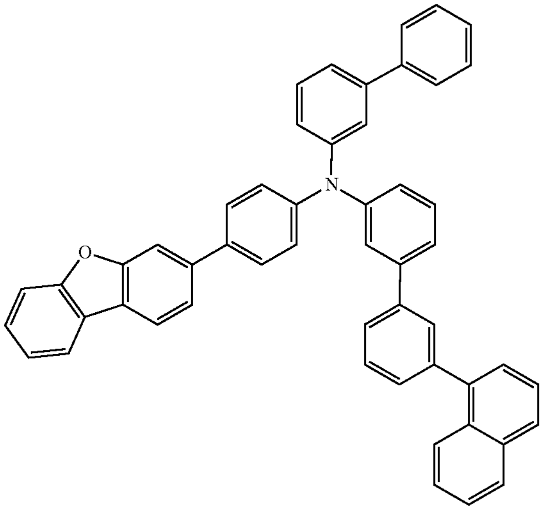
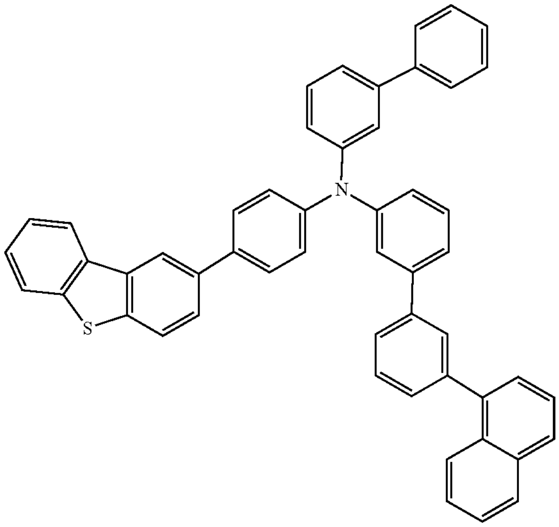
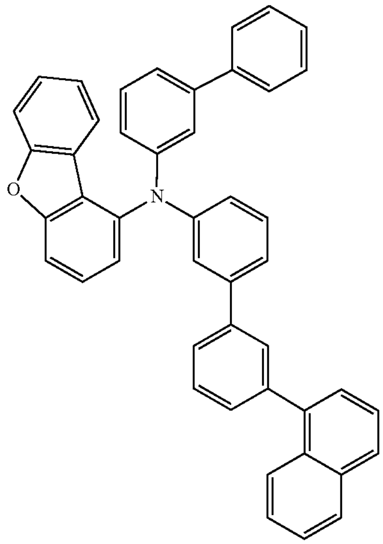

-continued
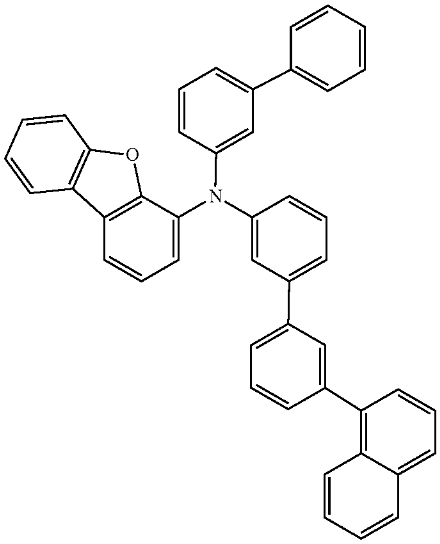
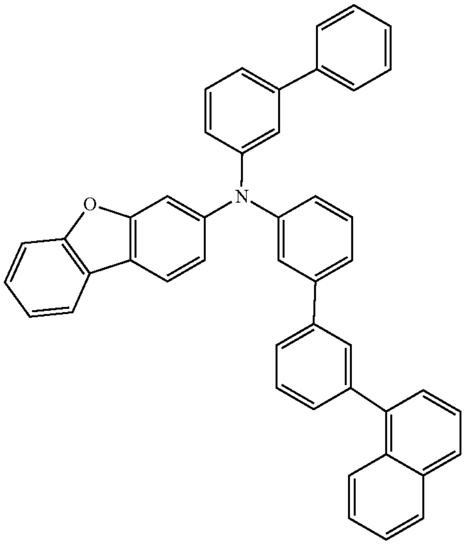
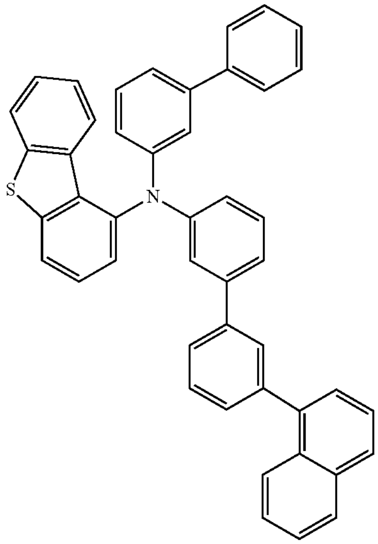
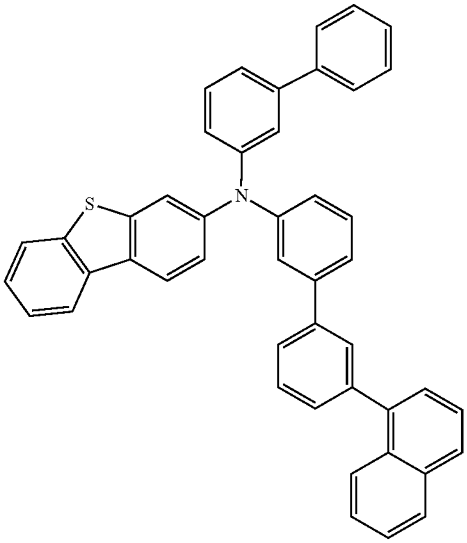
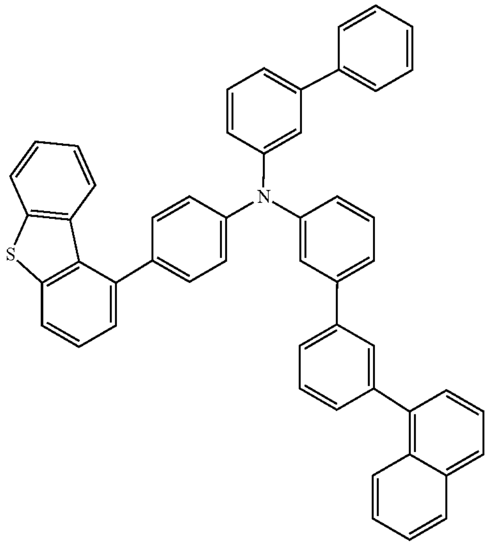
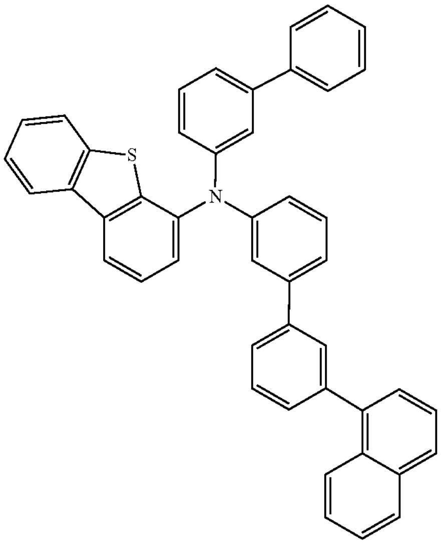

-continued
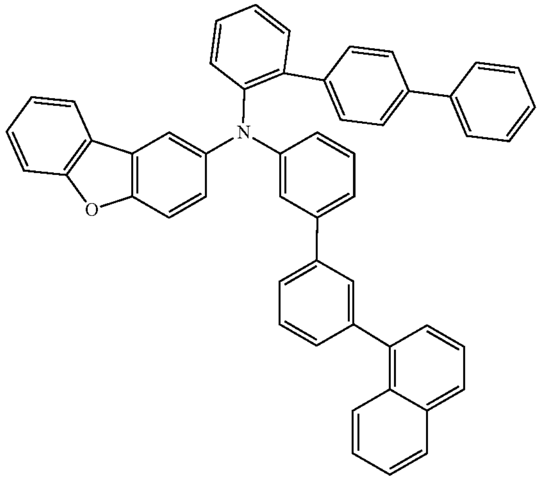
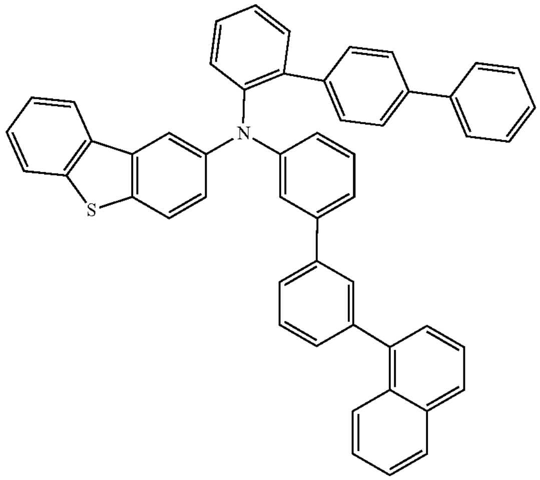
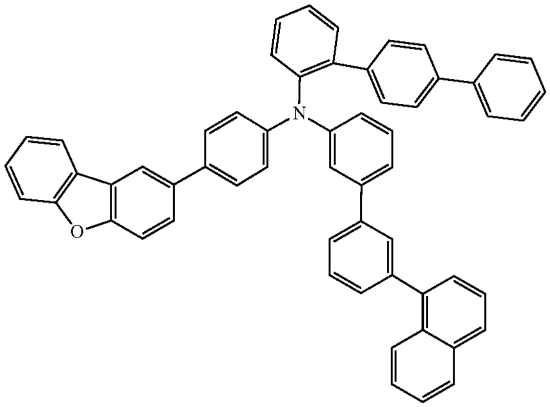
-continued
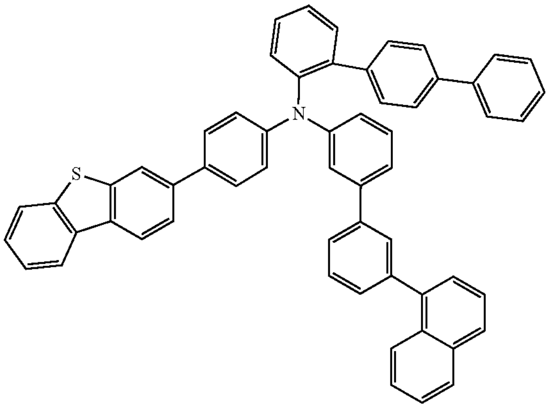
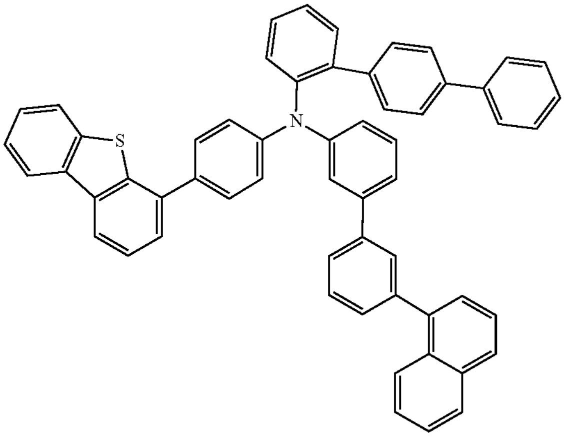
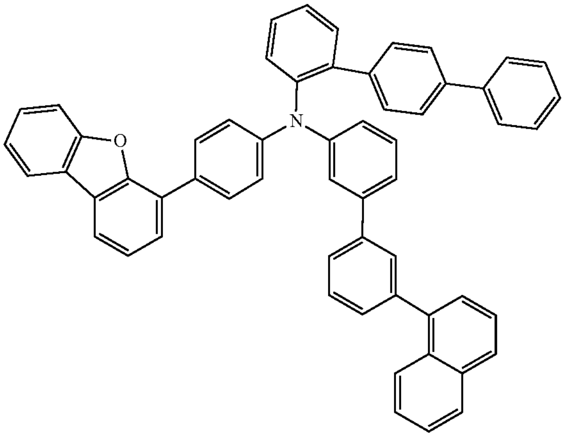

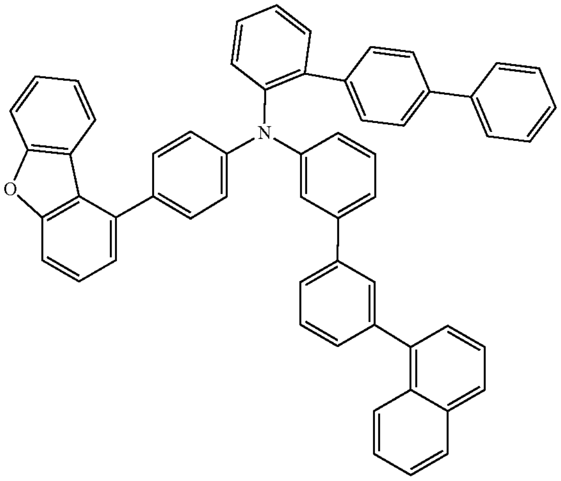
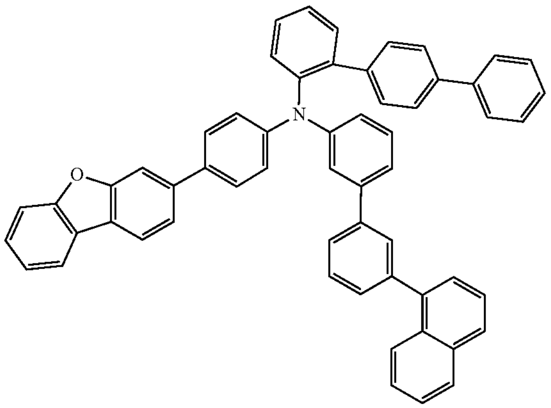
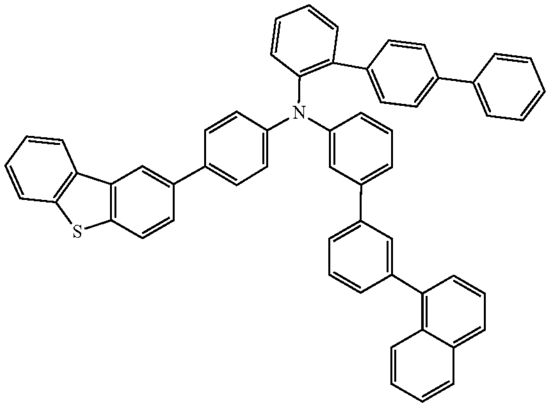
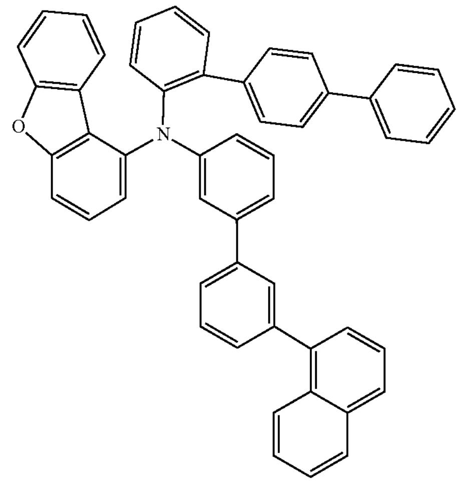
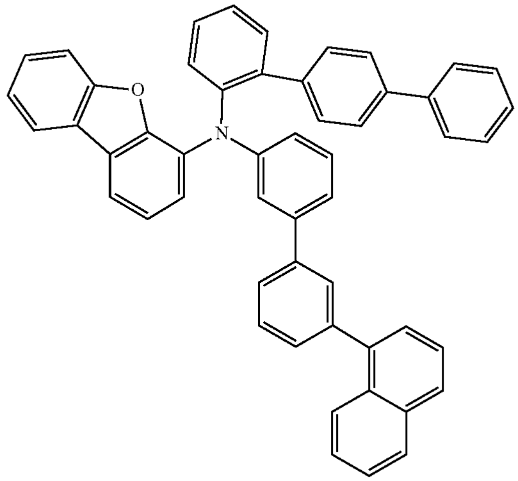
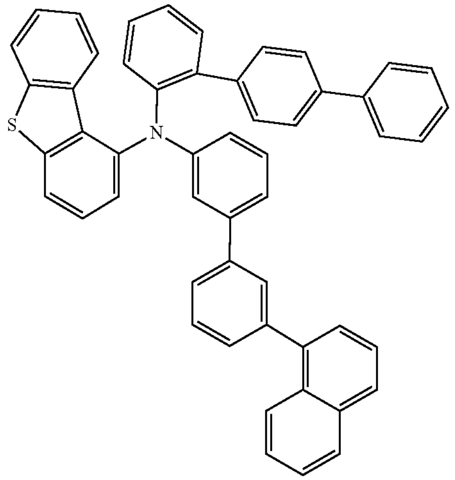

-continued
-continued
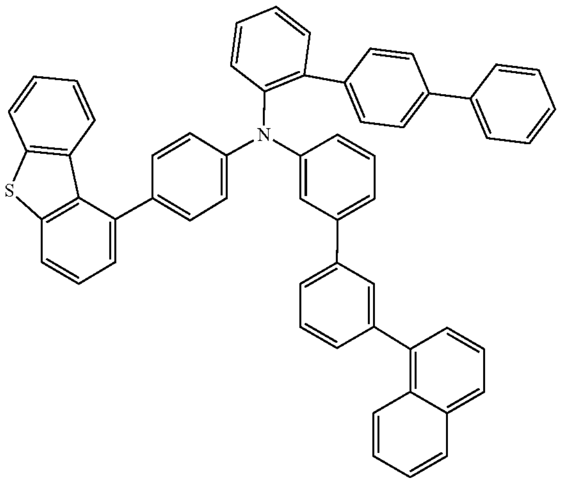
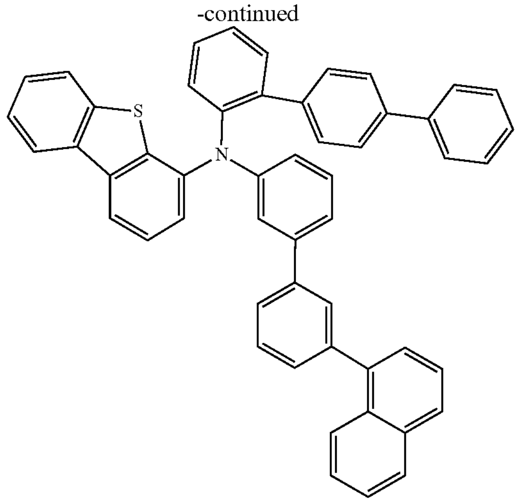
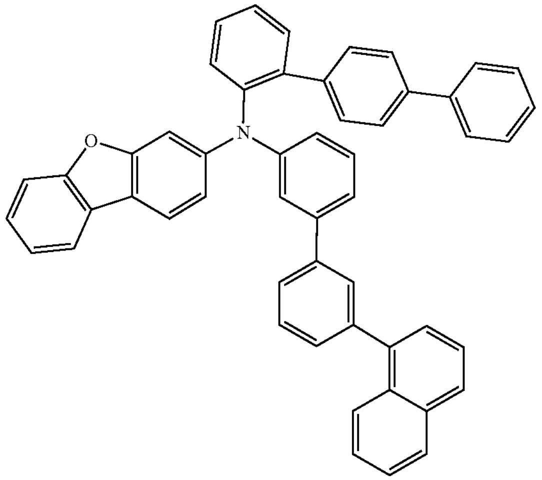
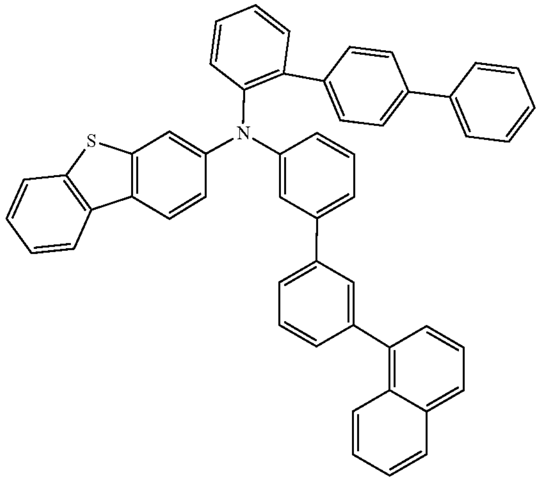
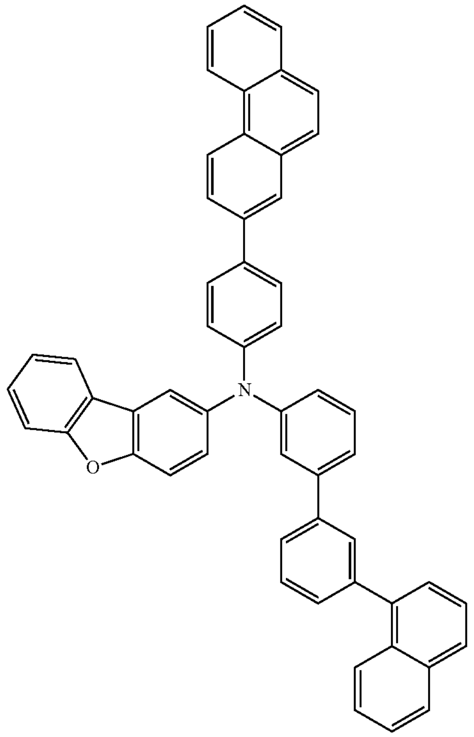

-continued
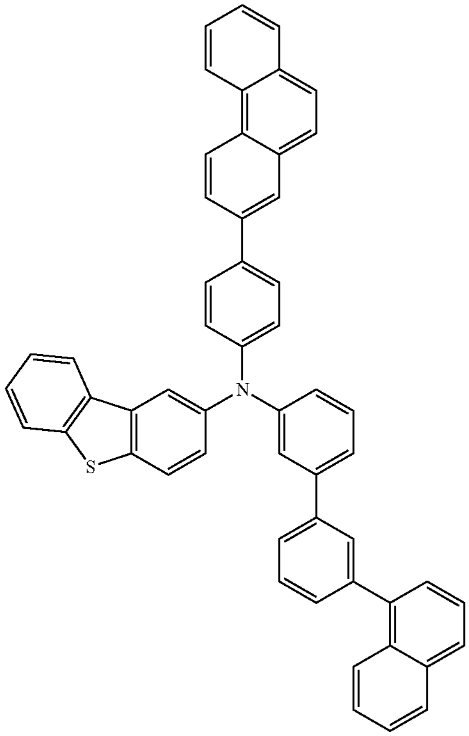
-continued
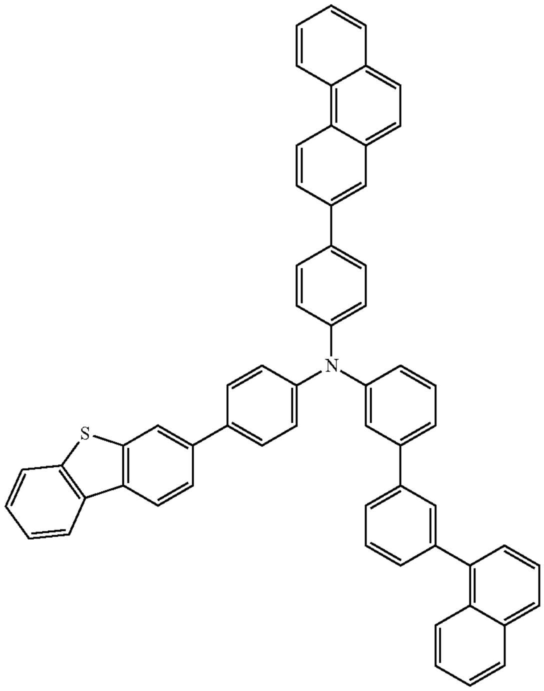
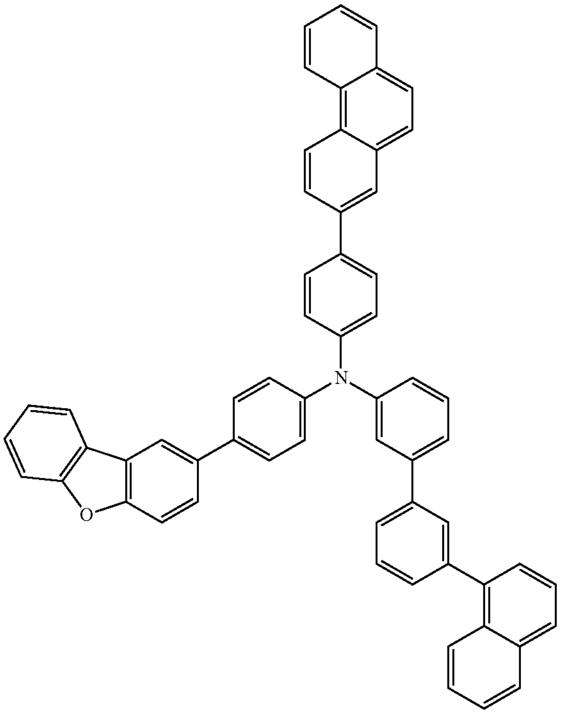
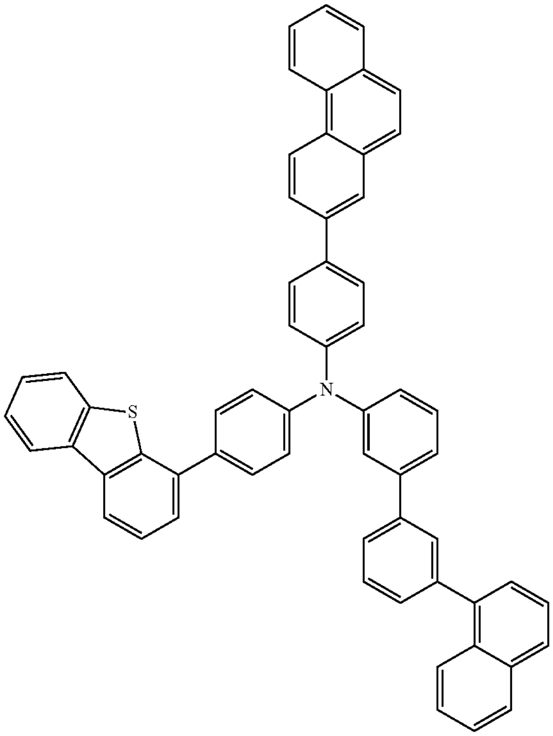

-continued
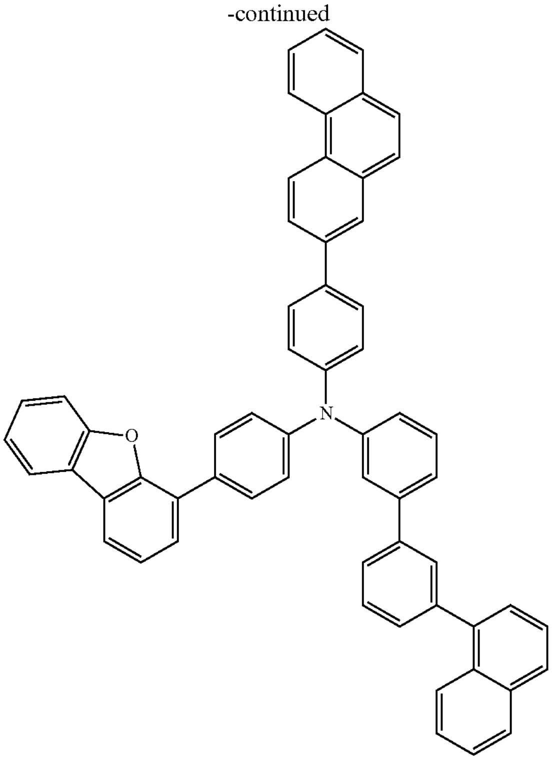
-continued
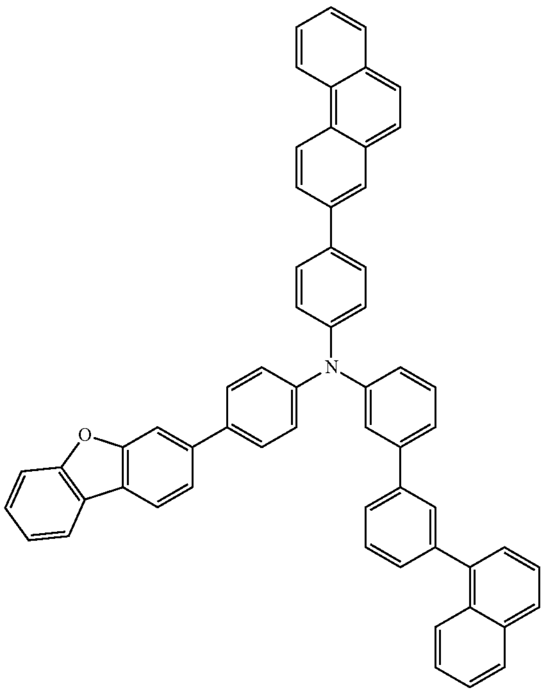
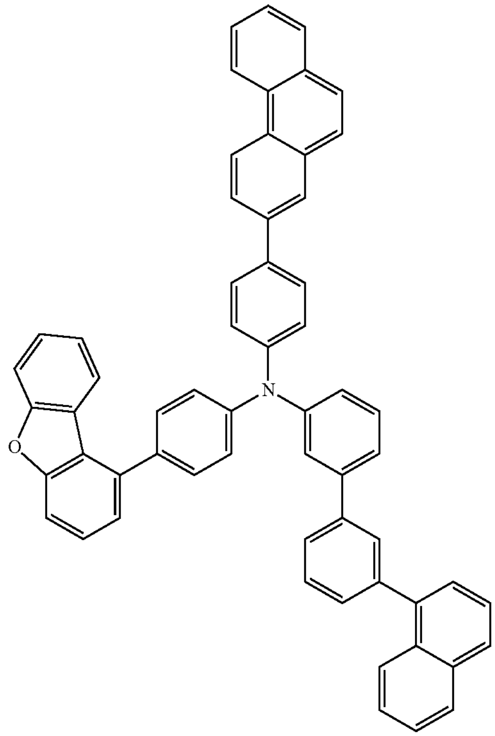
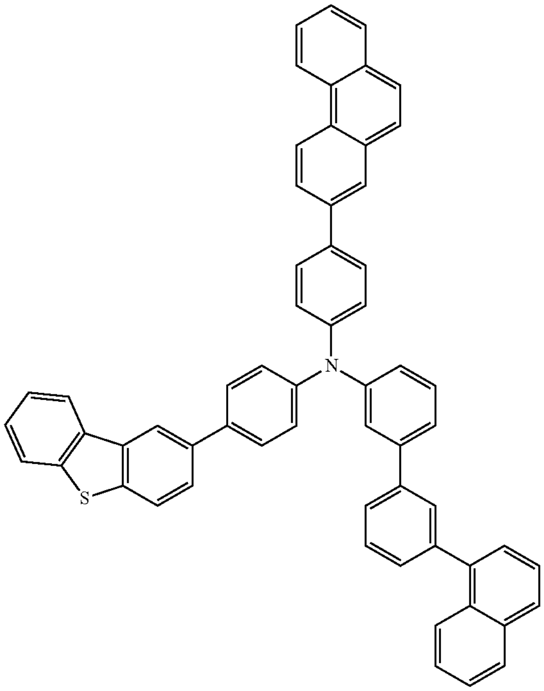

-continued
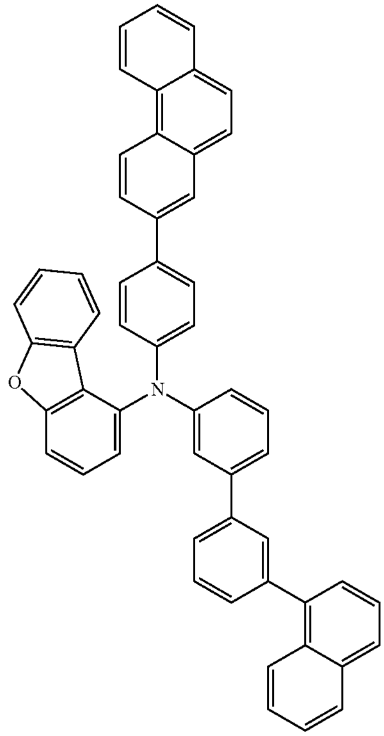
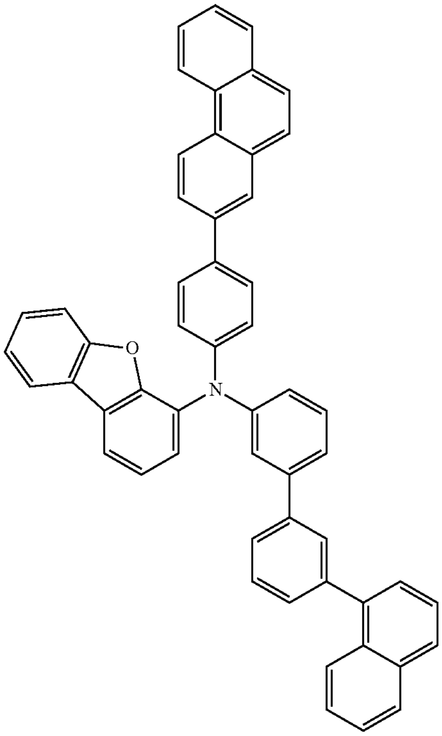
-continued
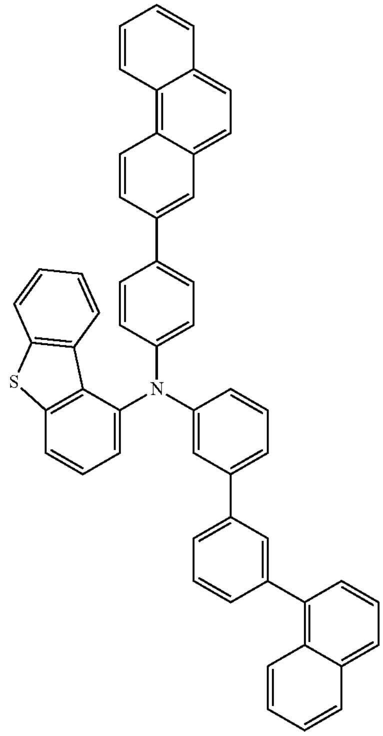
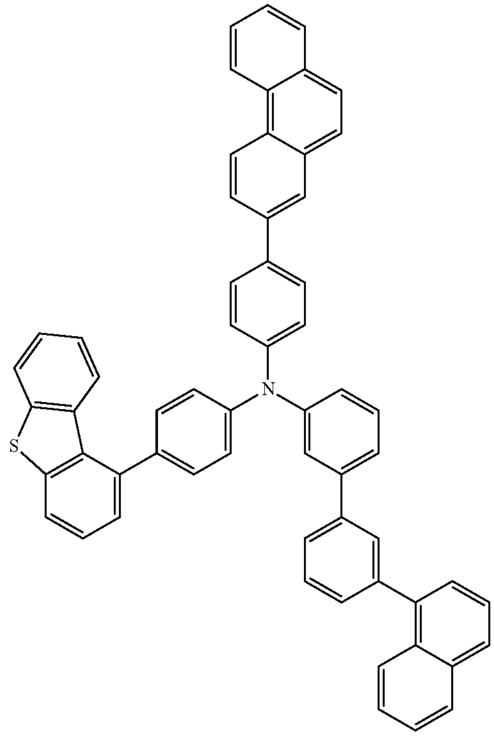

-continued
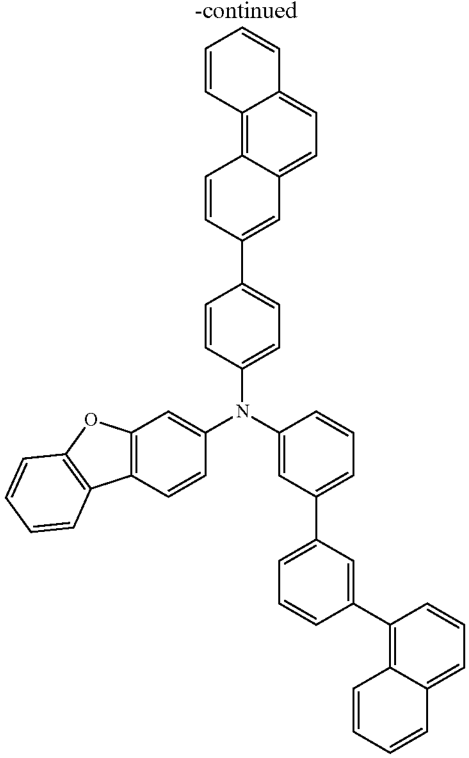
-continued
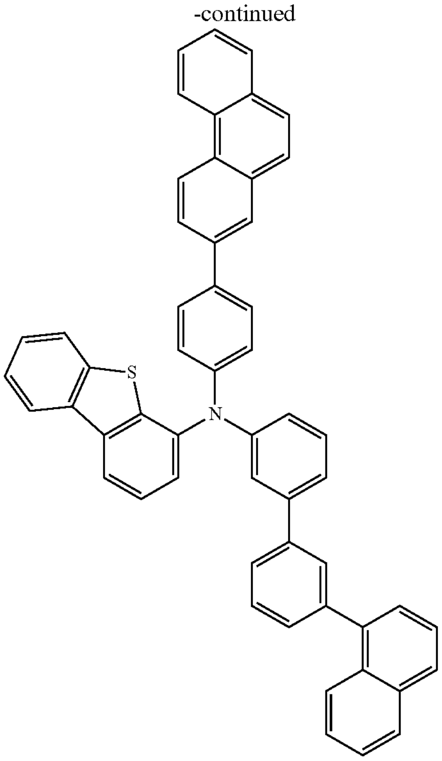
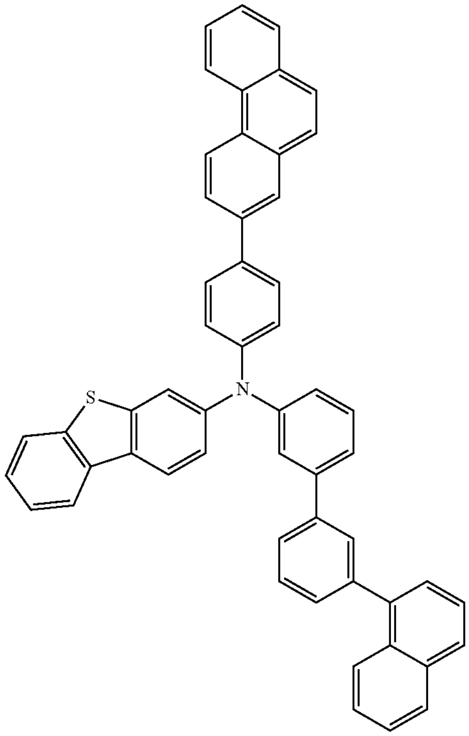
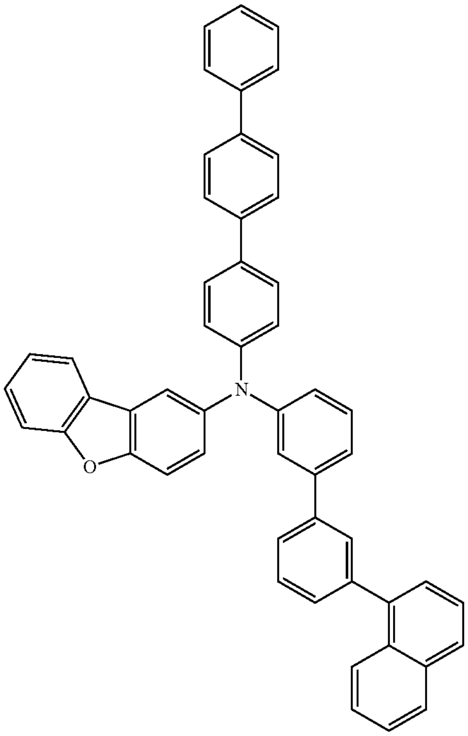

-continued
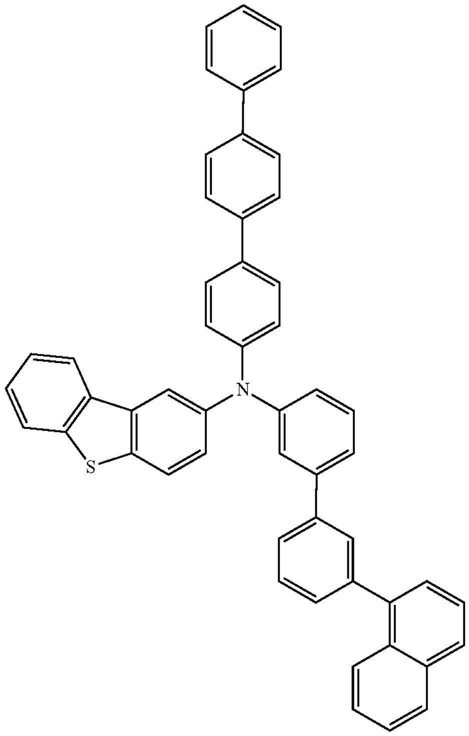
-continued
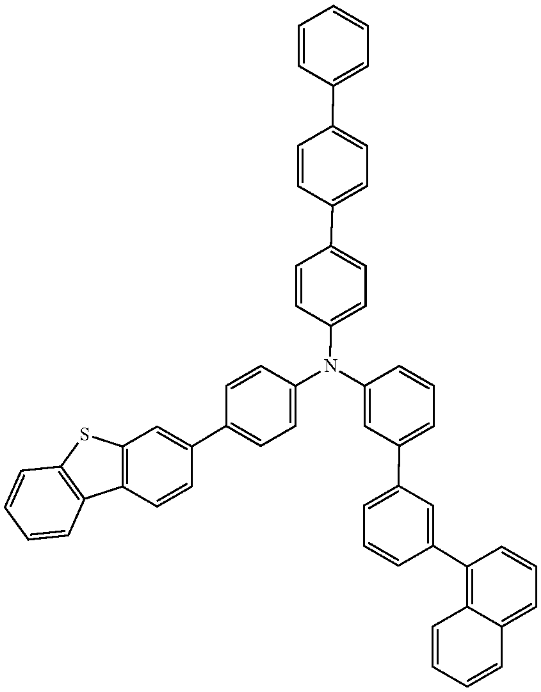
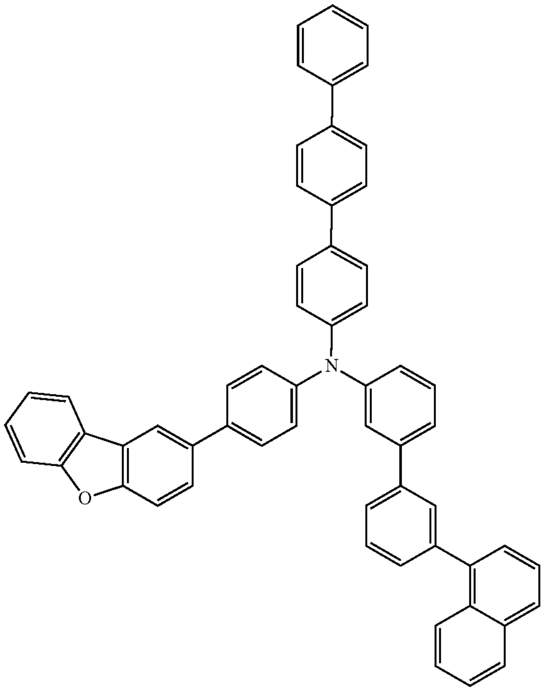
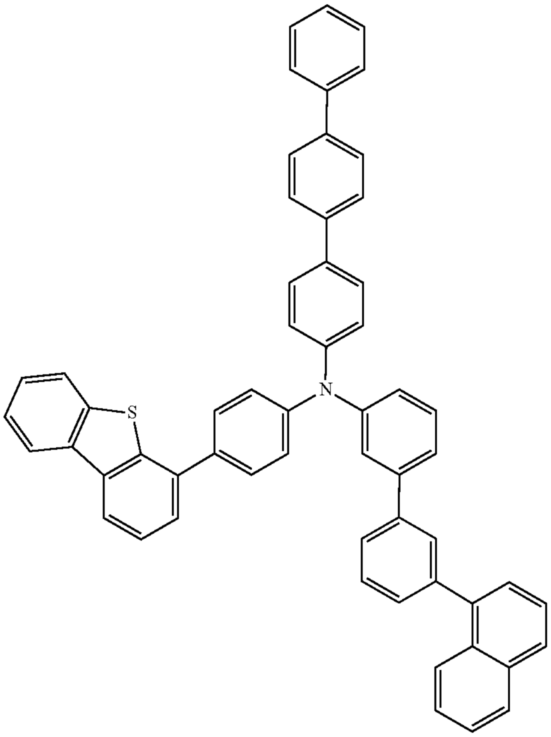

-continued
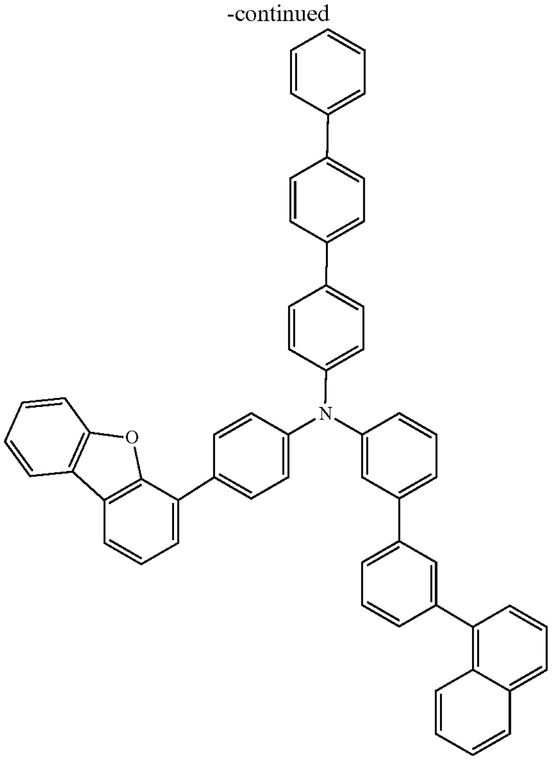
-continued
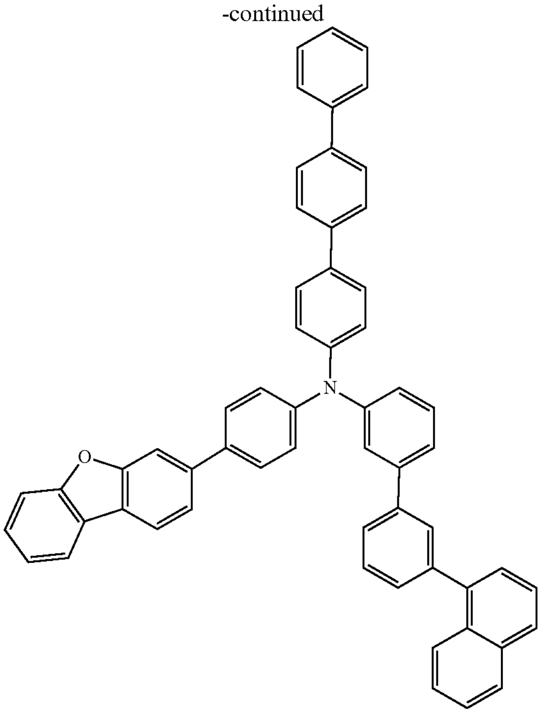
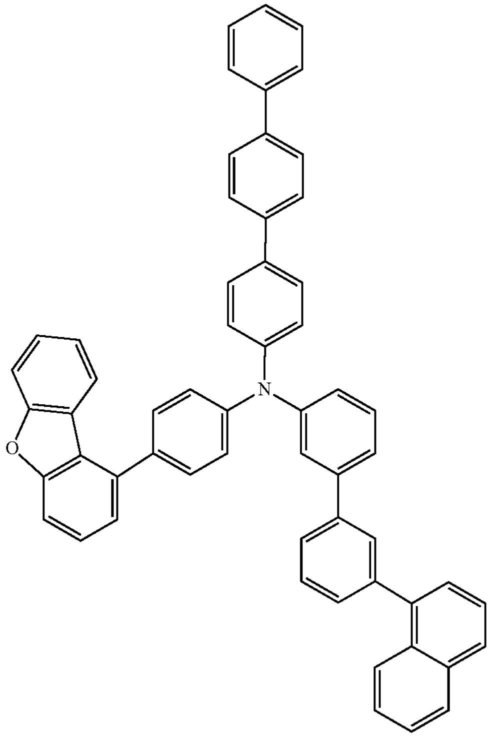
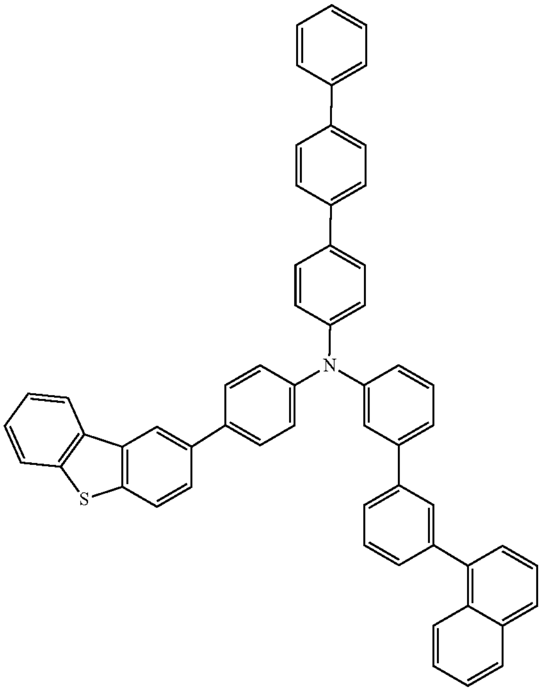

-continued
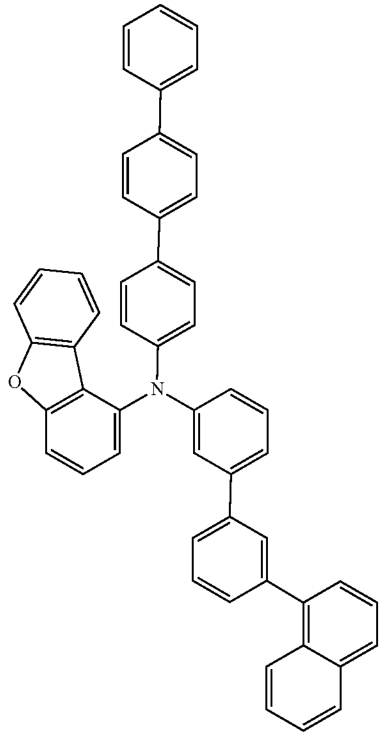
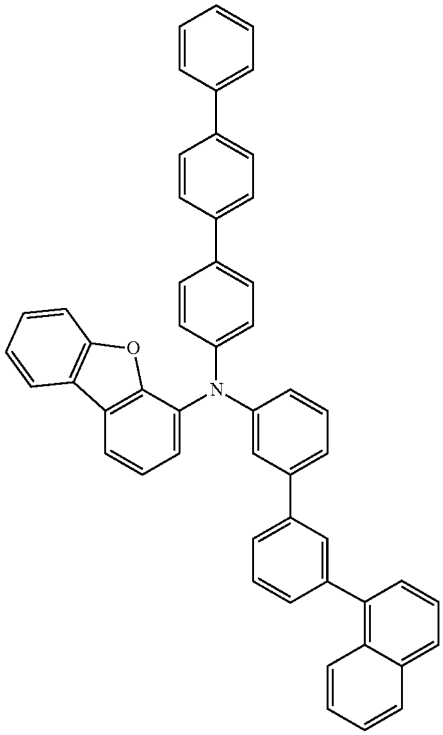
-continued
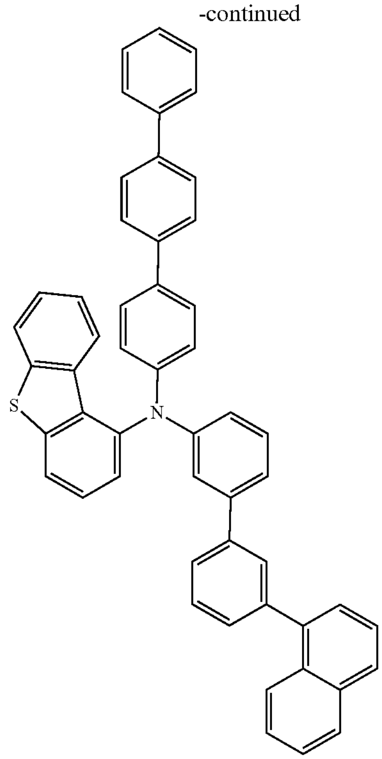
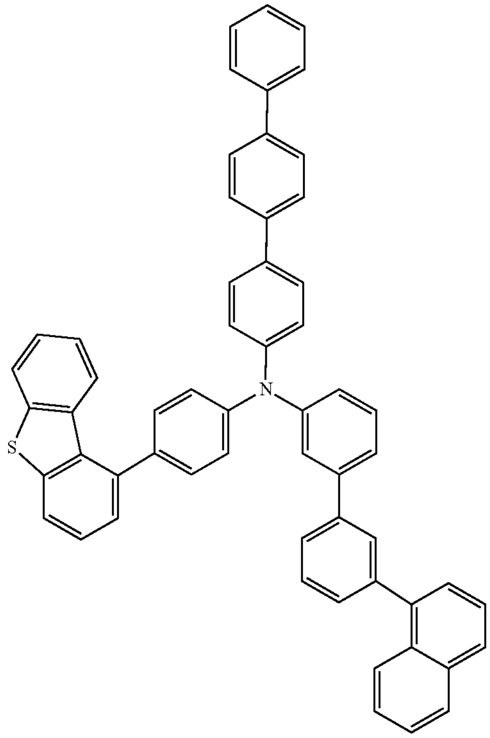

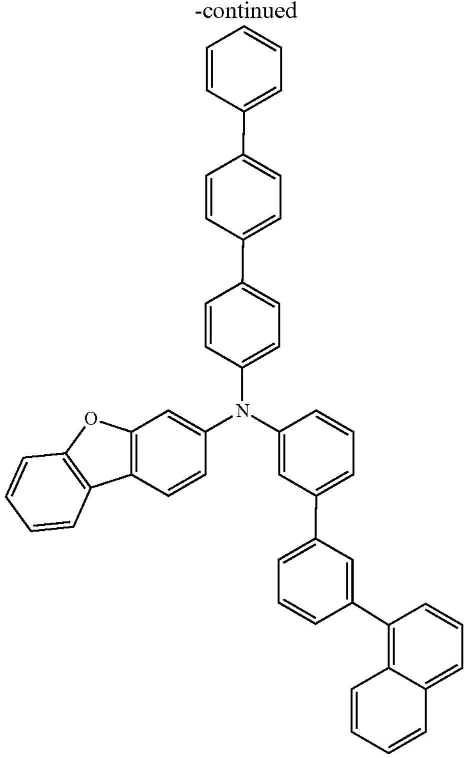
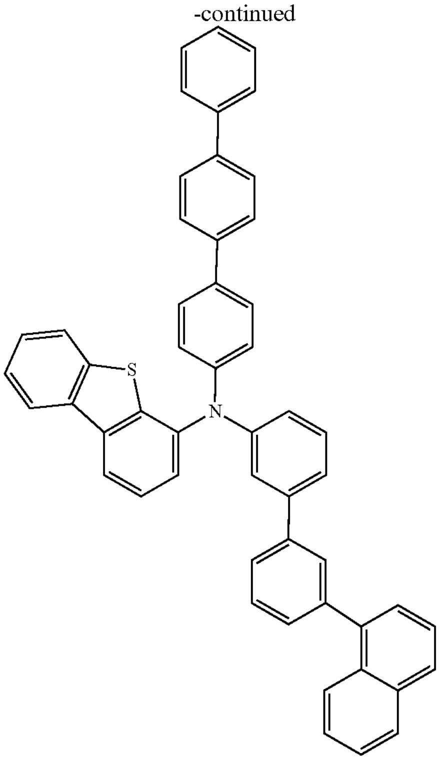
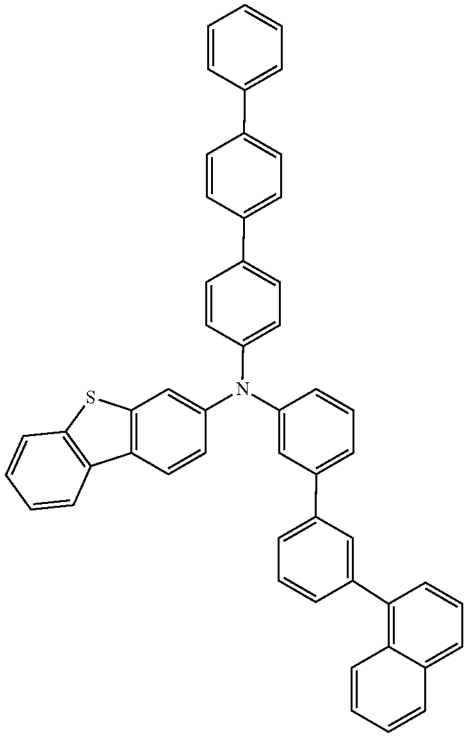
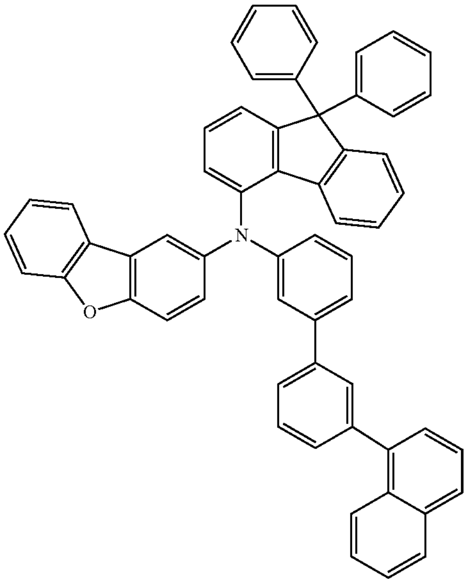

-continued
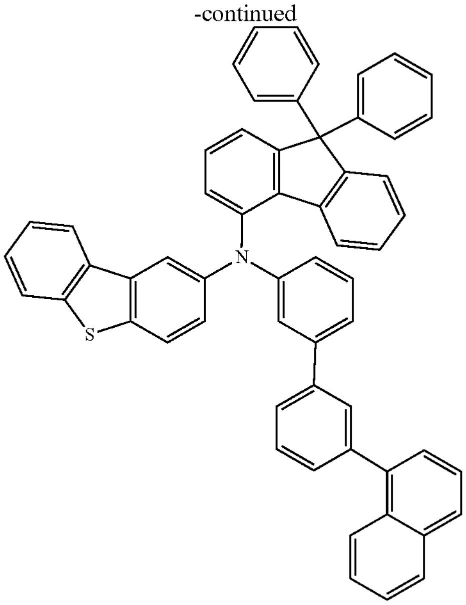
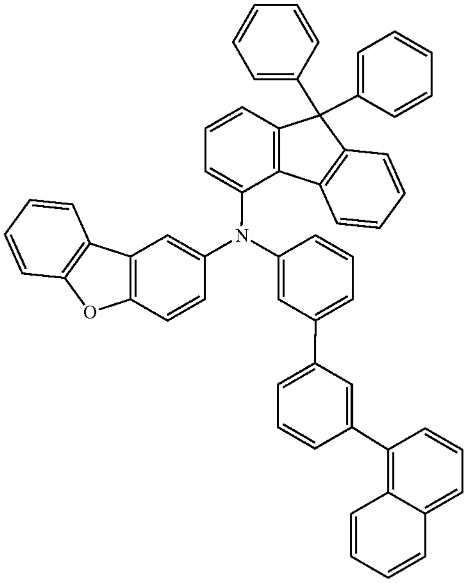
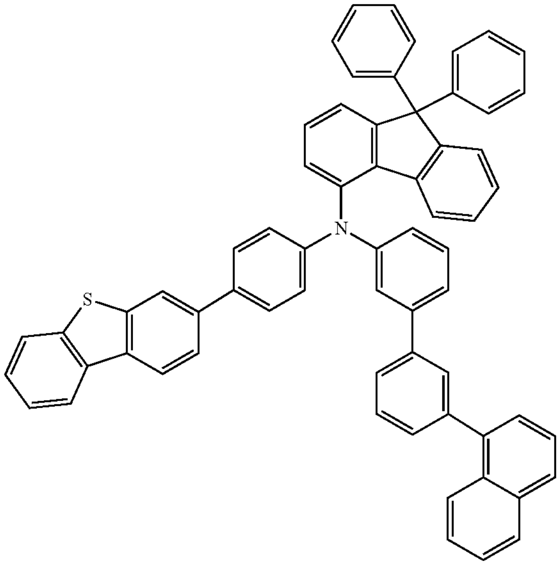
-continued
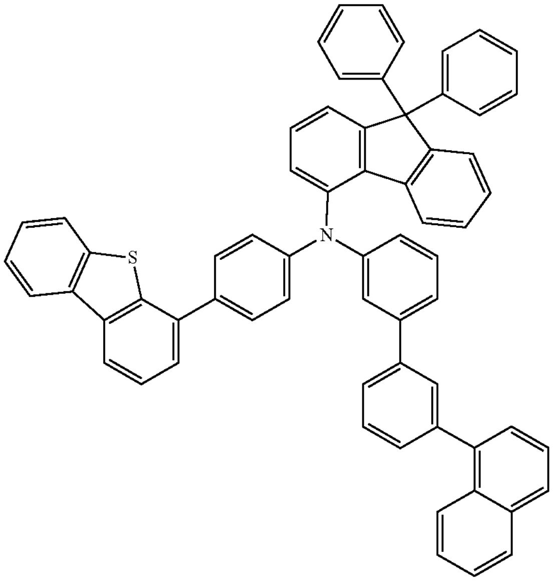
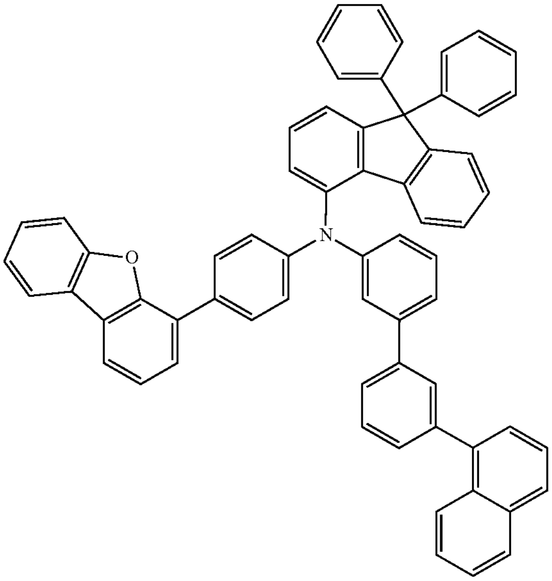

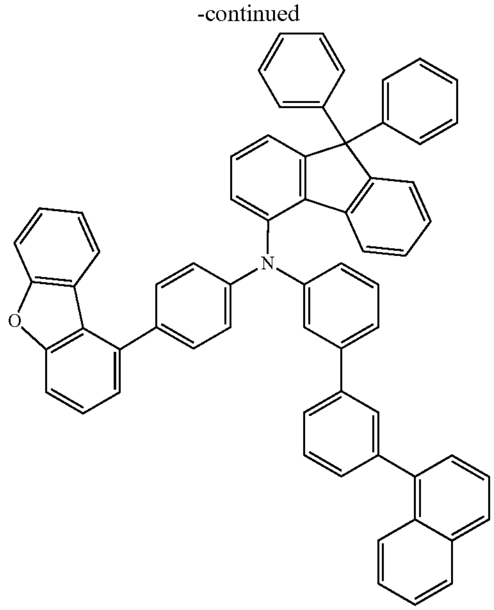
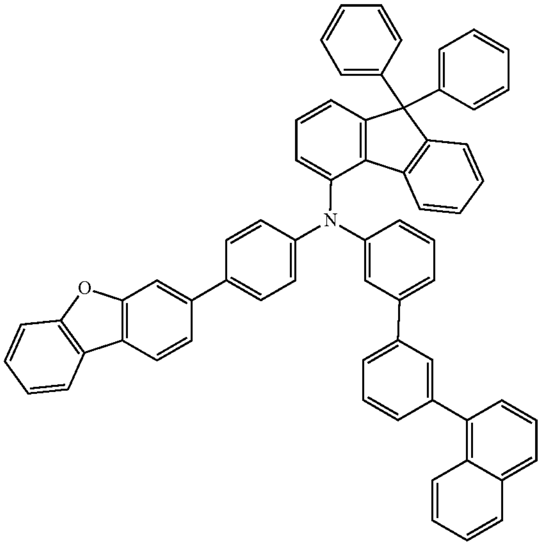
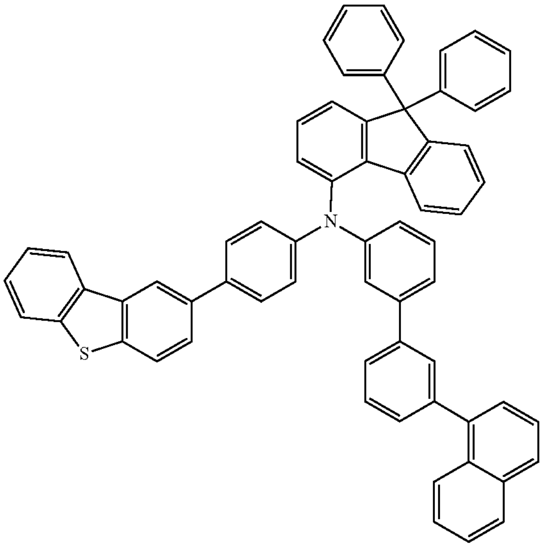
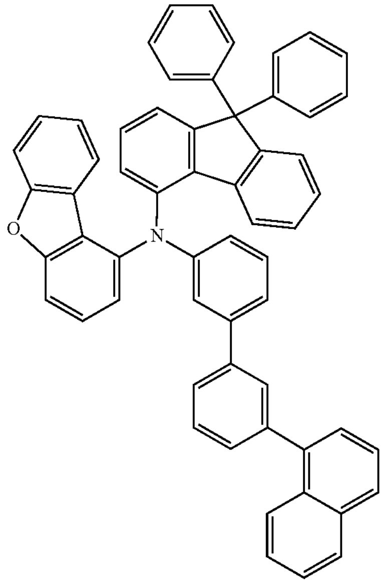
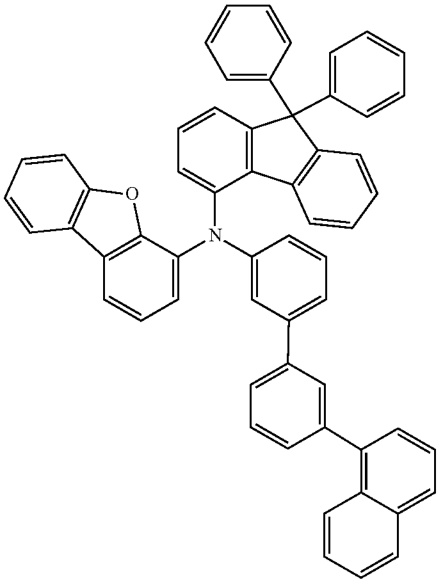

-continued
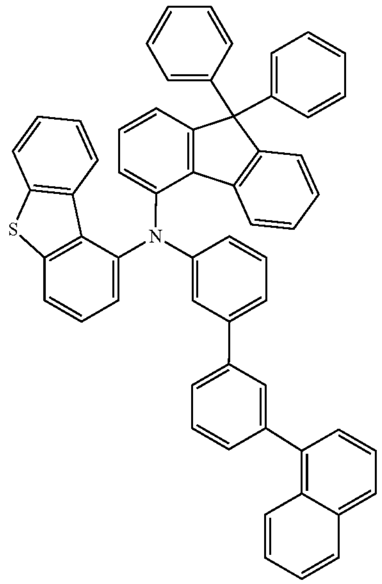
-continued
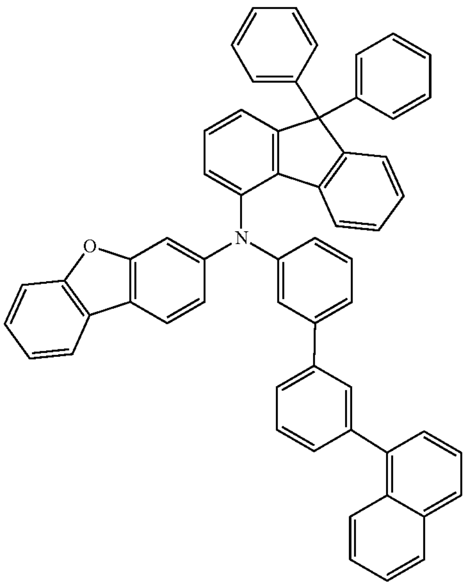
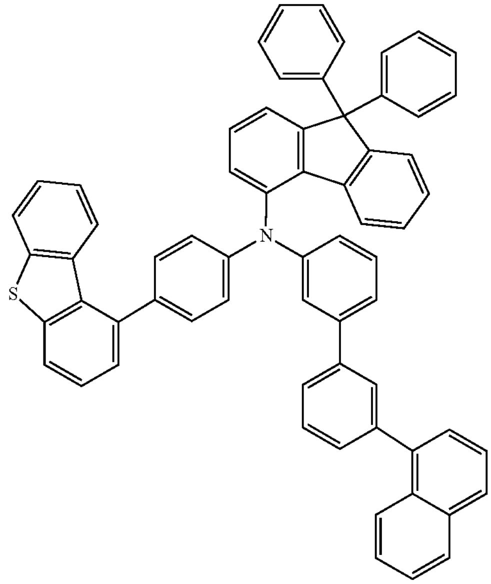
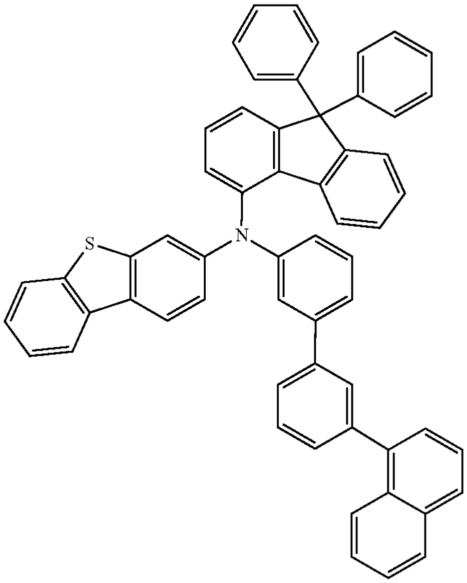

-continued
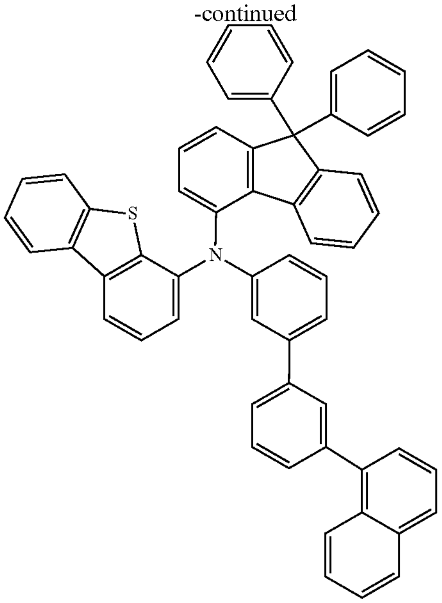
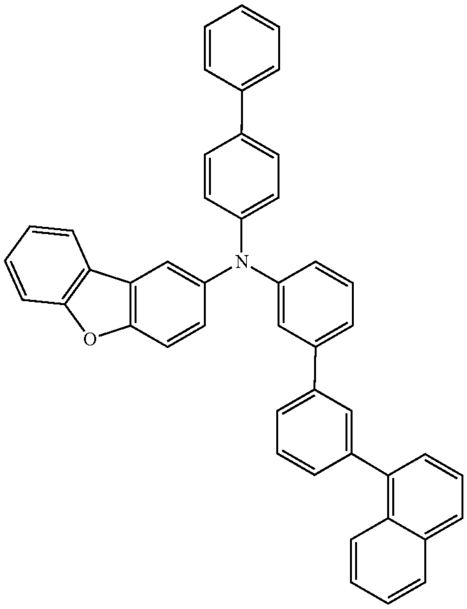
-continued
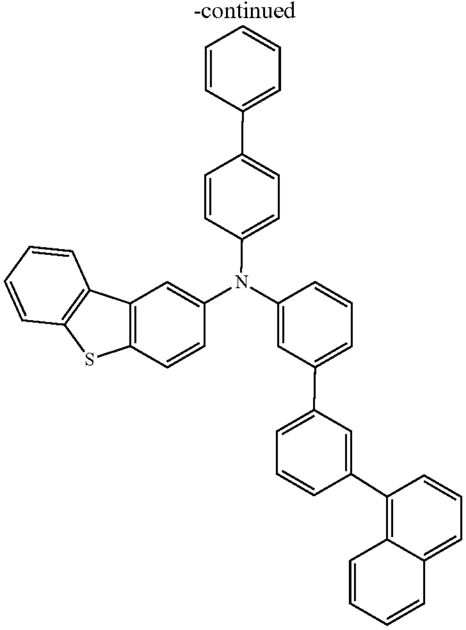
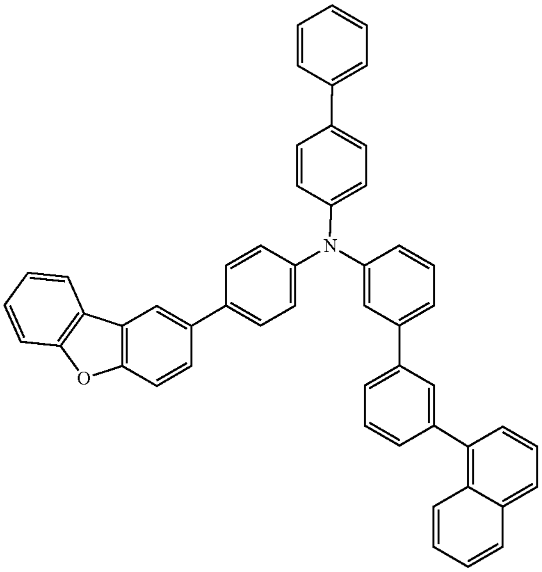

-continued
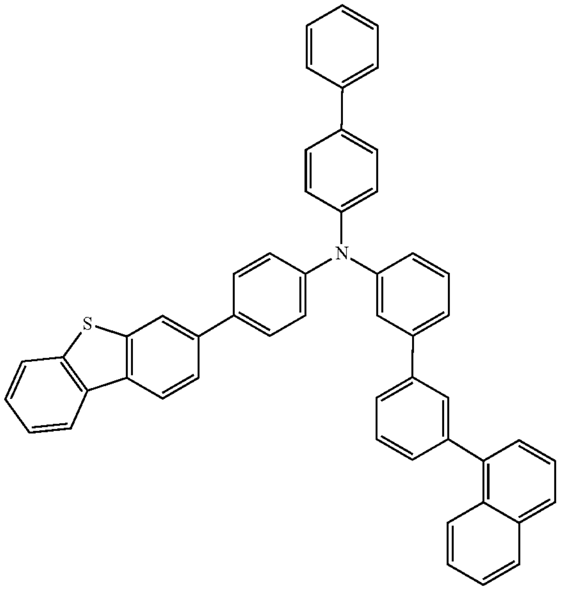
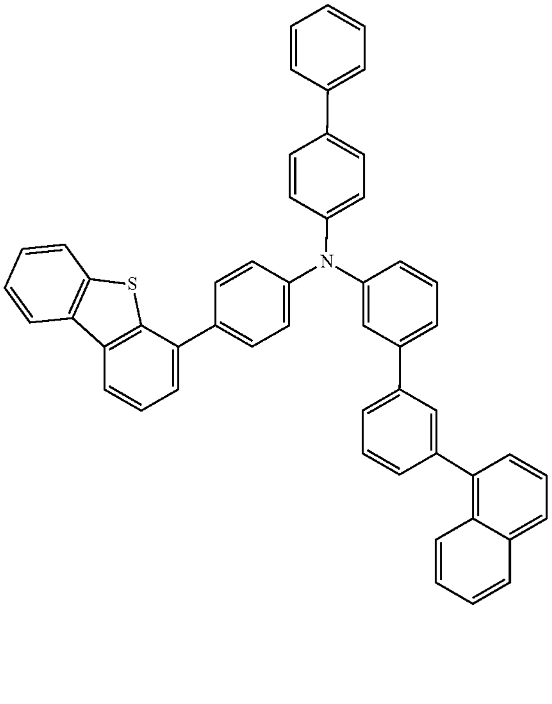
-continued
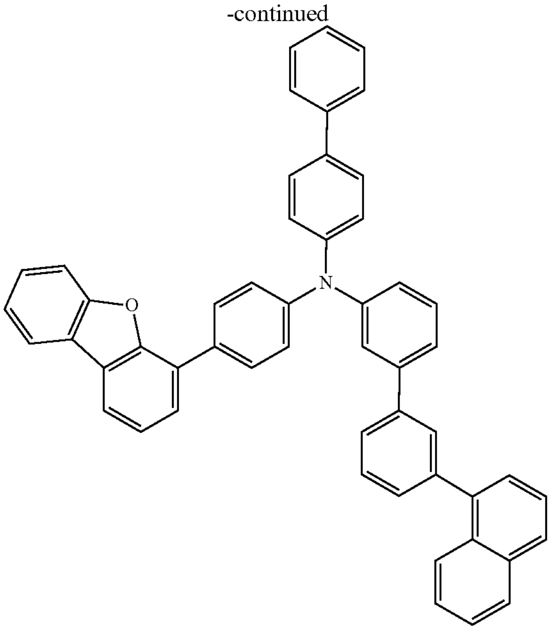
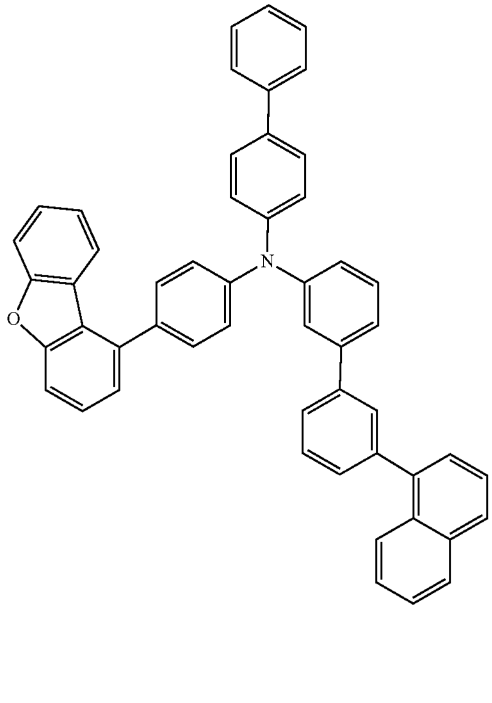

-continued
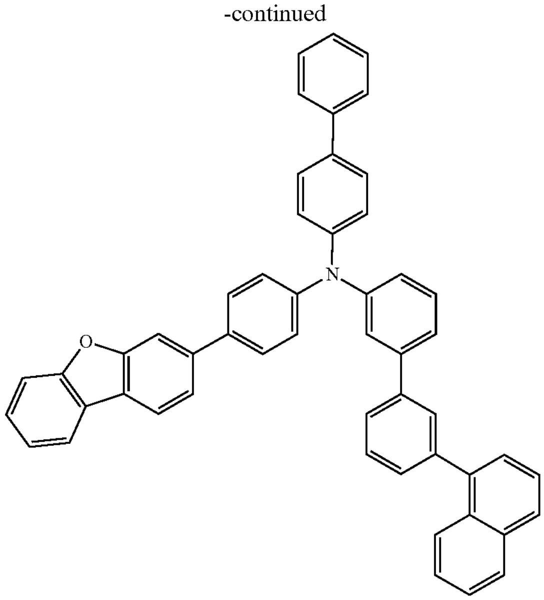
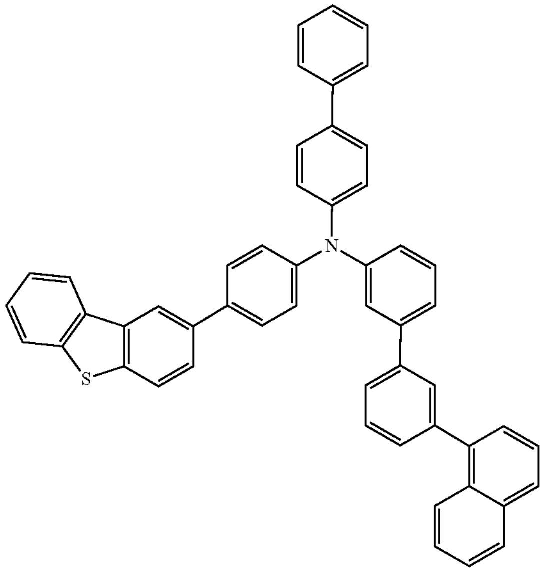
-continued
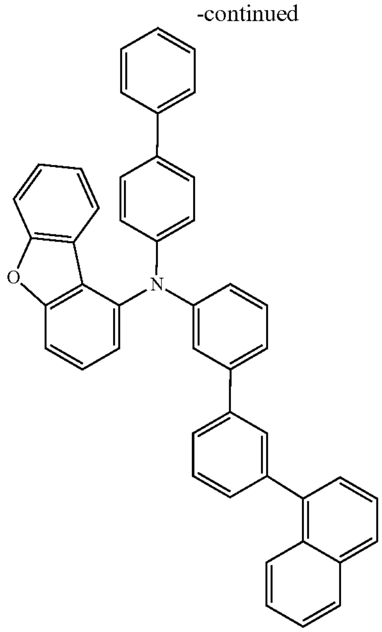
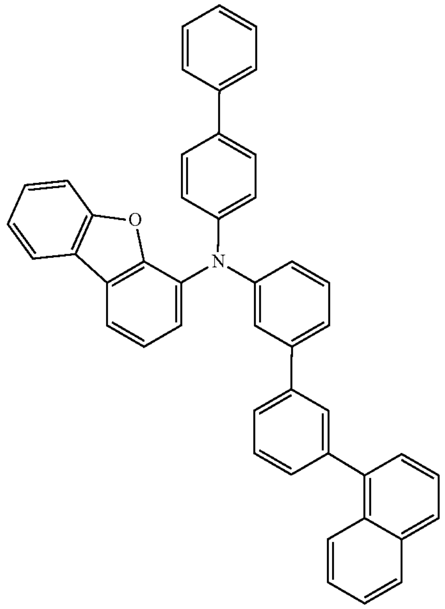

-continued
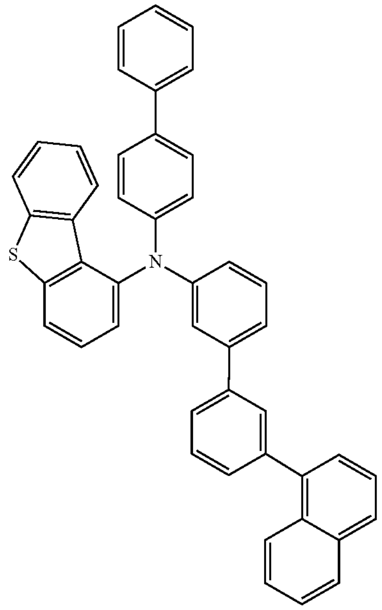
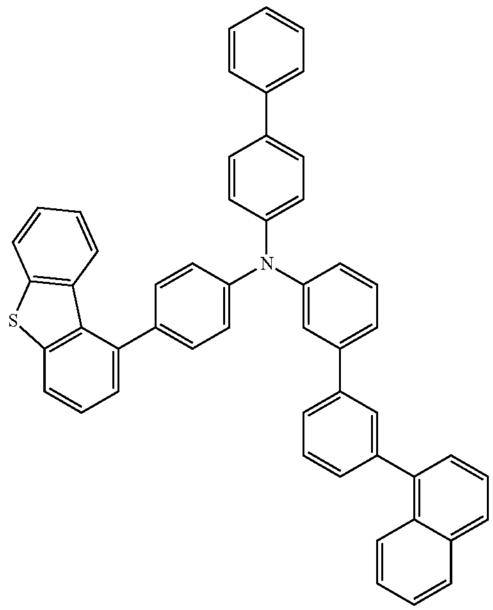
-continued
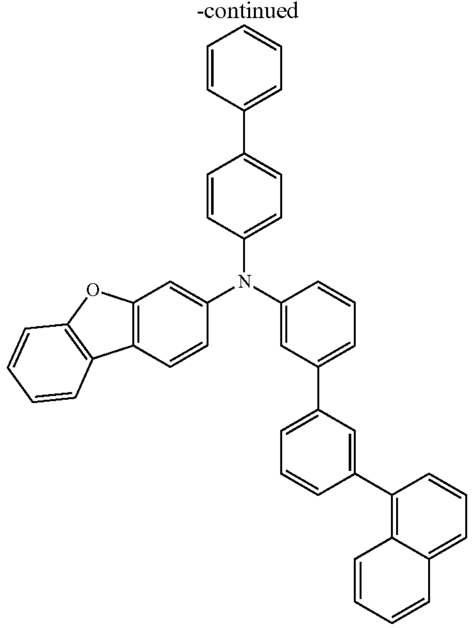
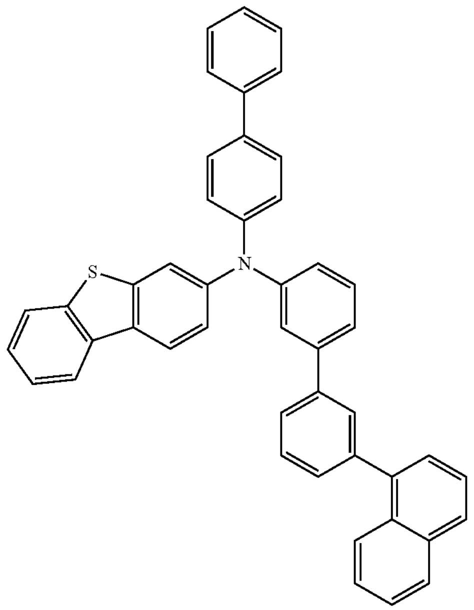

-continued
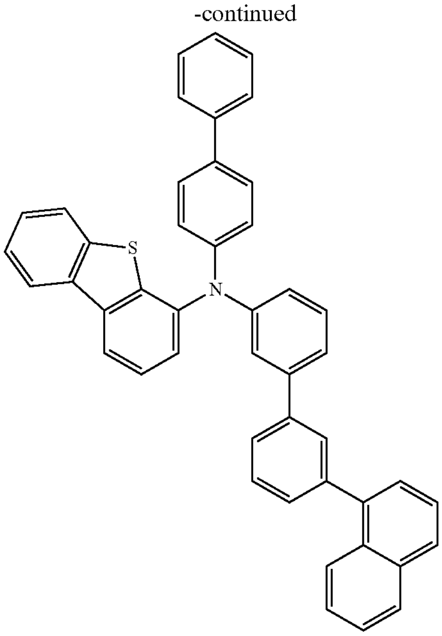
-continued
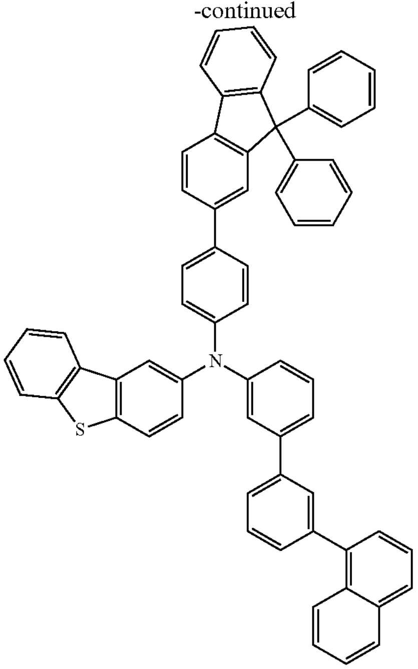
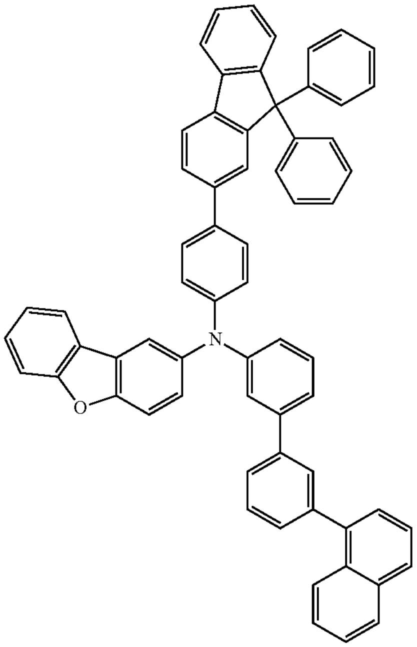
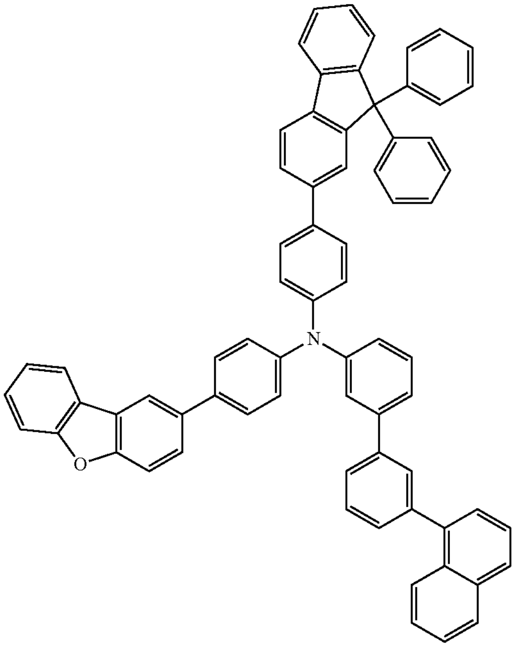

-continued
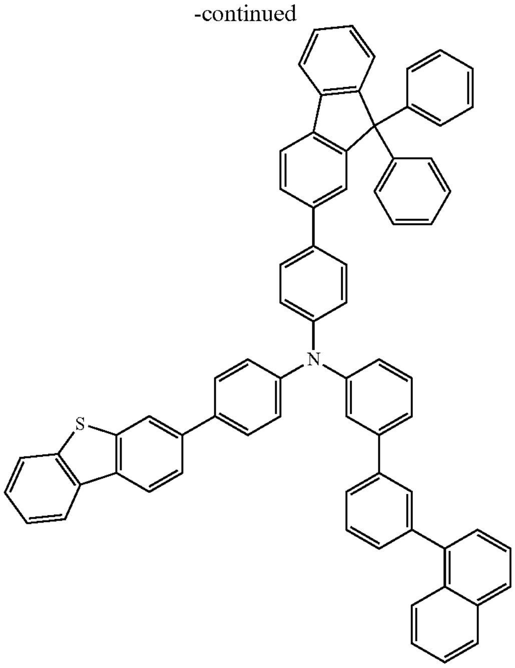
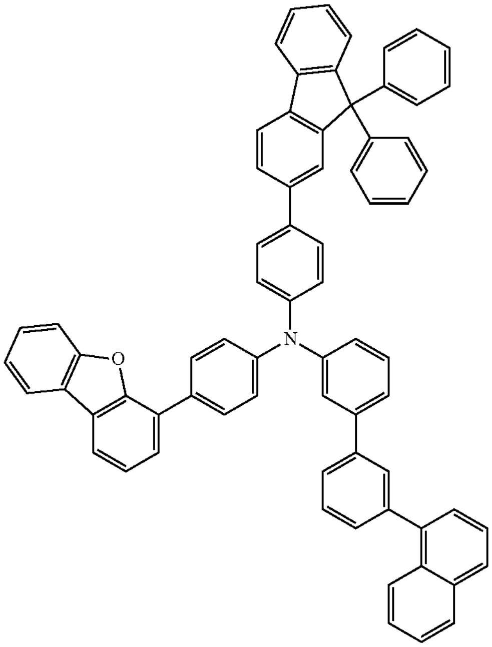
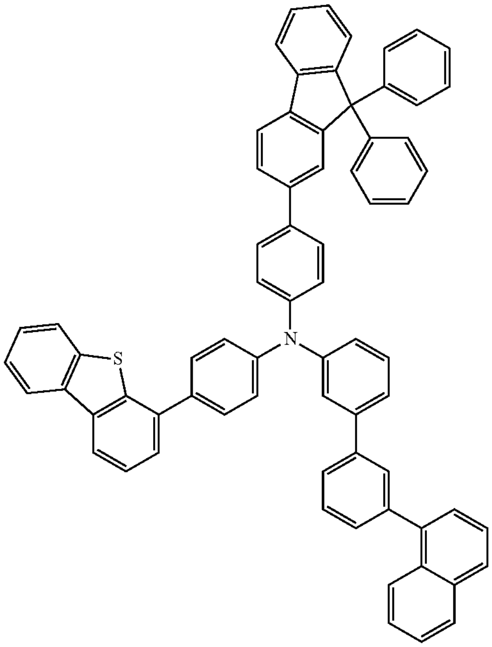
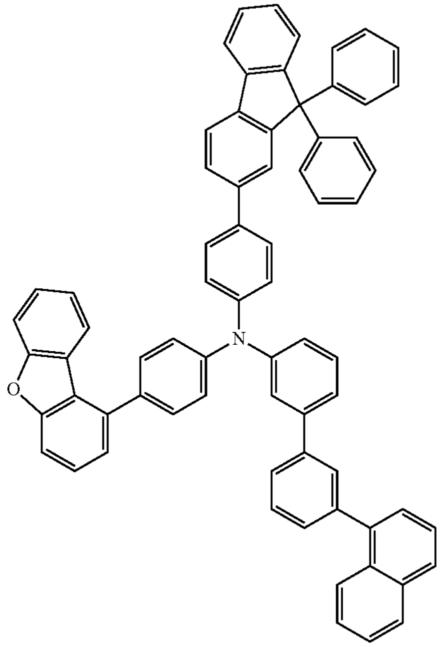
-continued

-continued
-continued
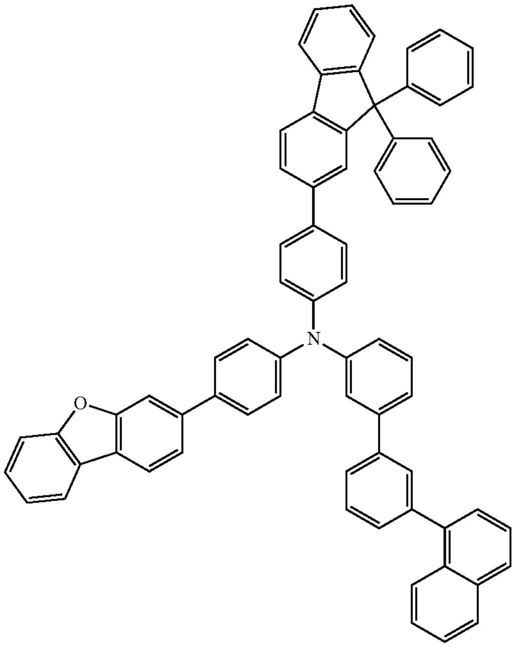
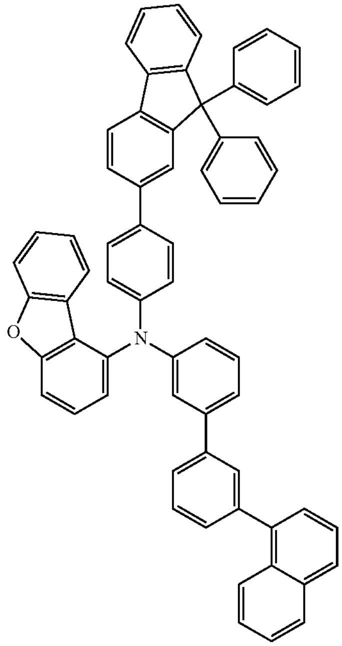
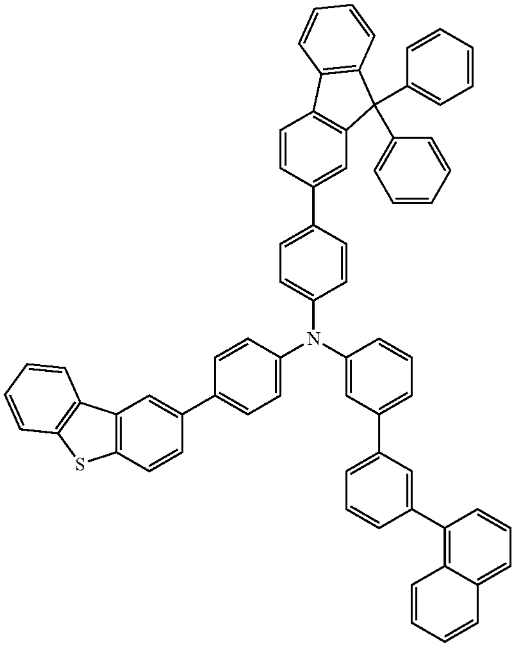
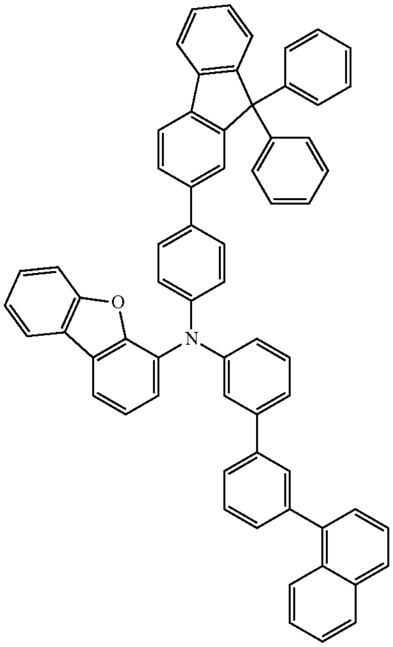

-continued
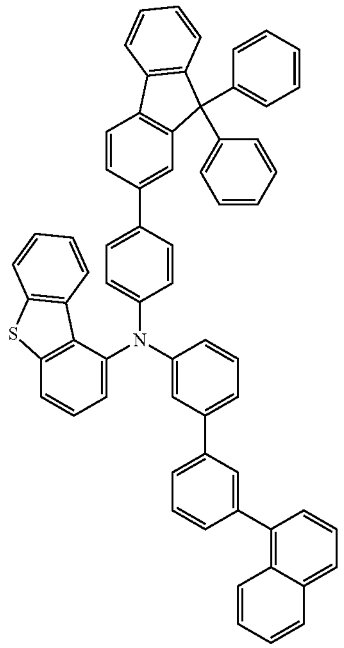
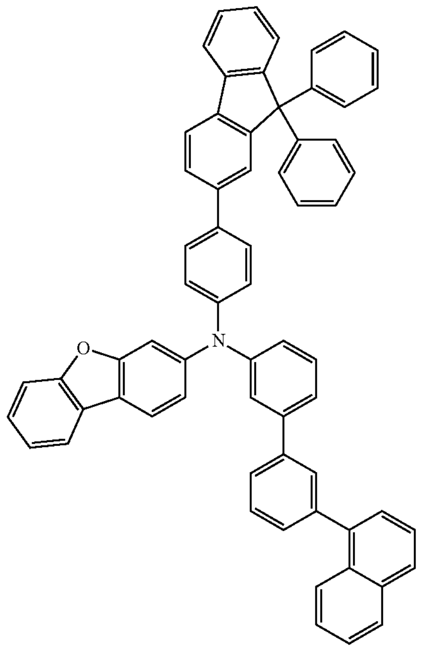
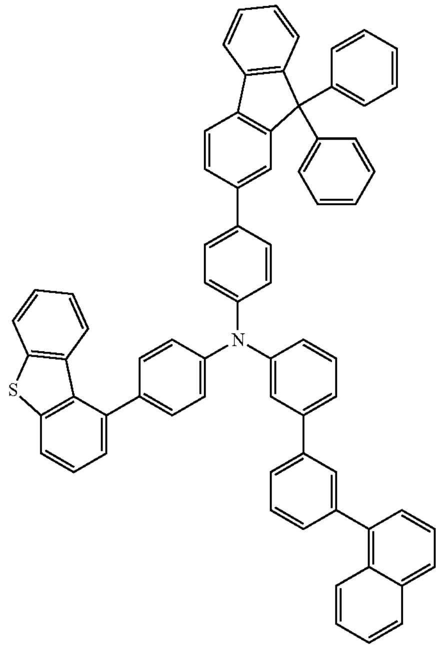
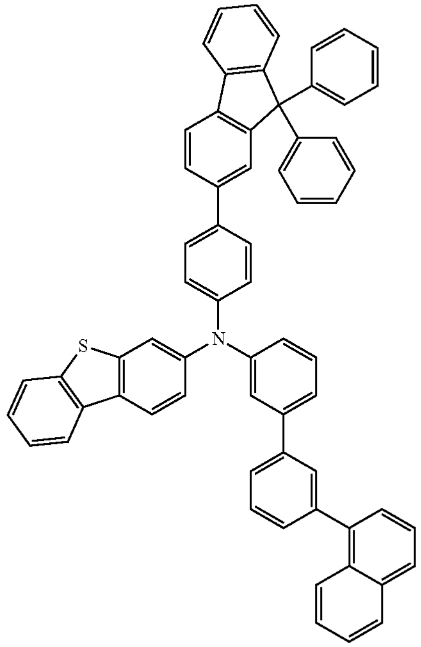
-continued

-continued
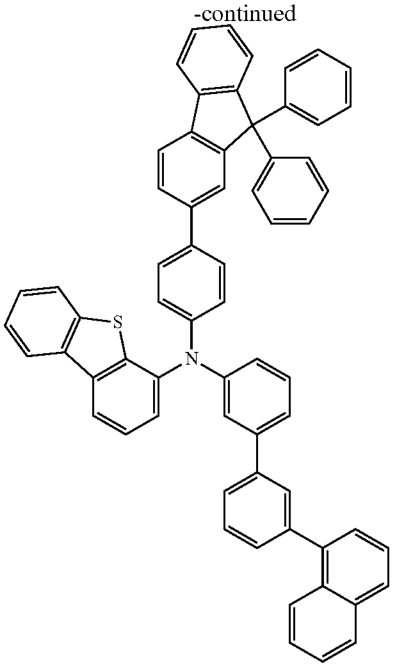
-continued
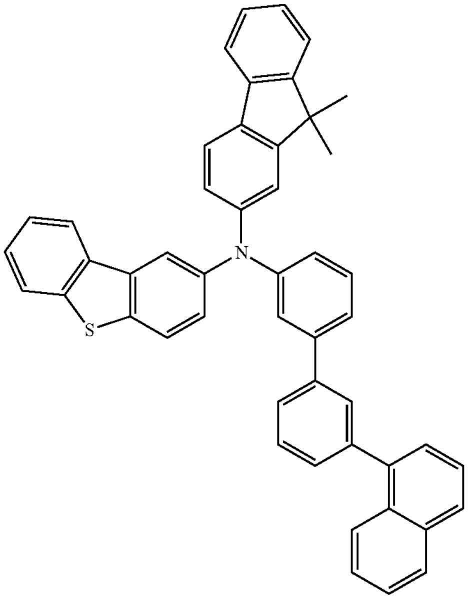
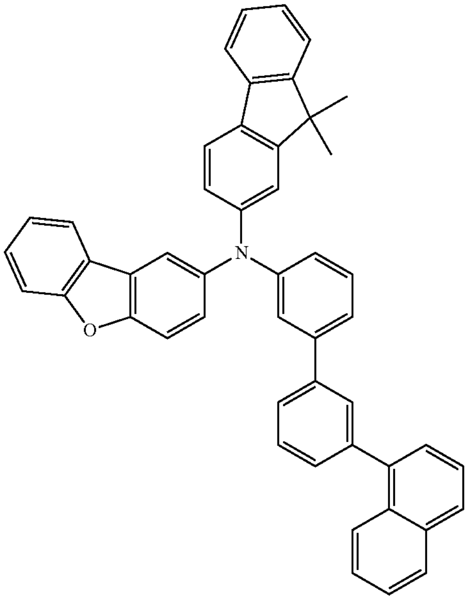
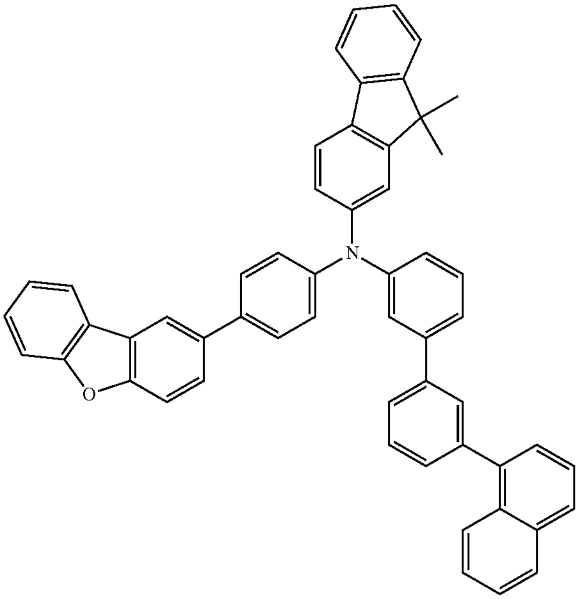

-continued
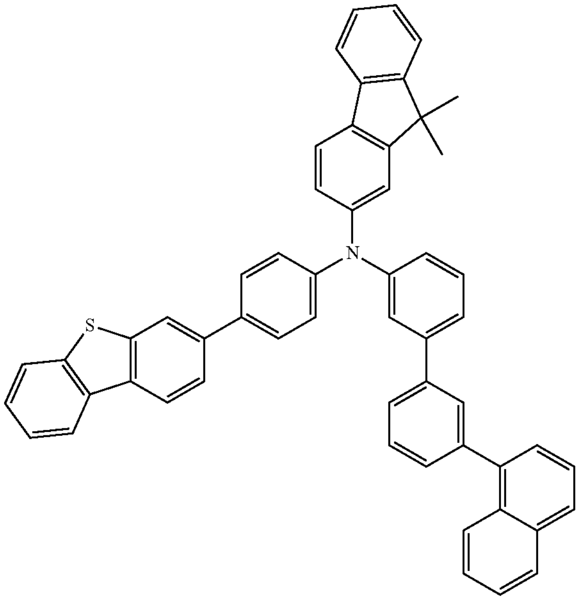
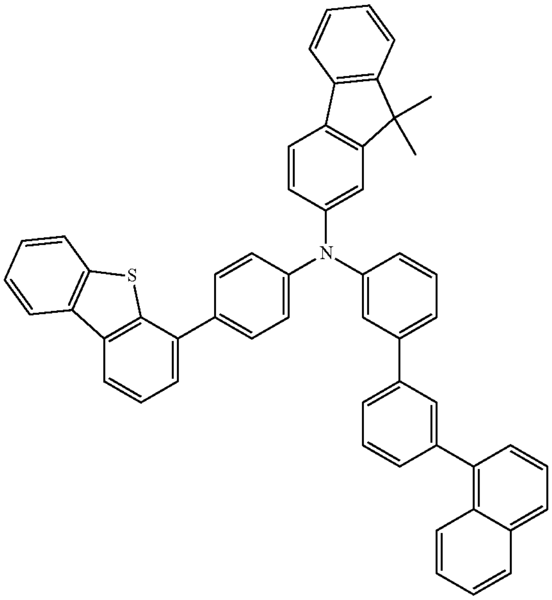
-continued
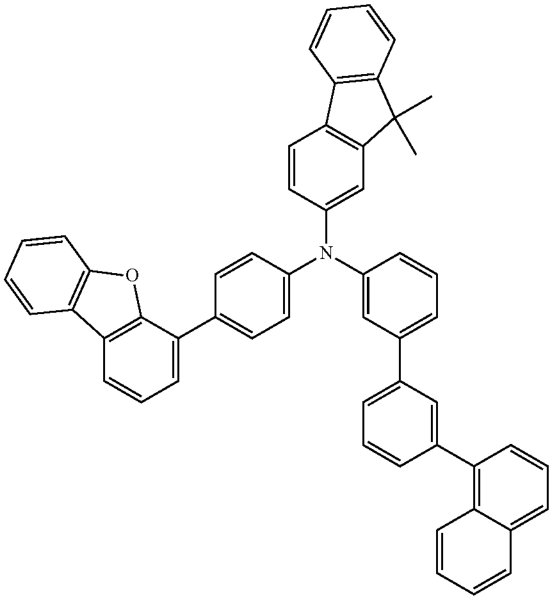
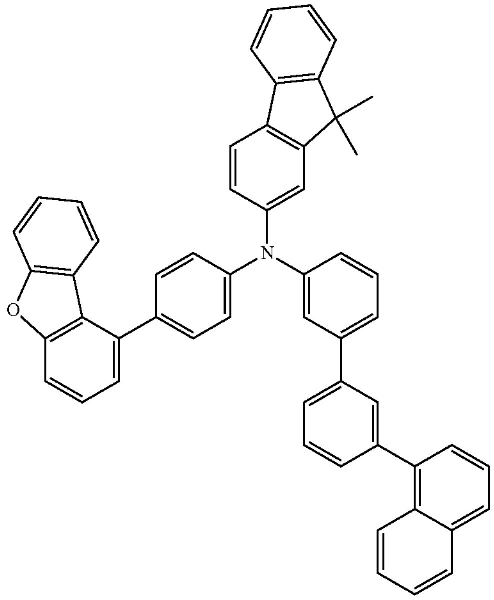

-continued
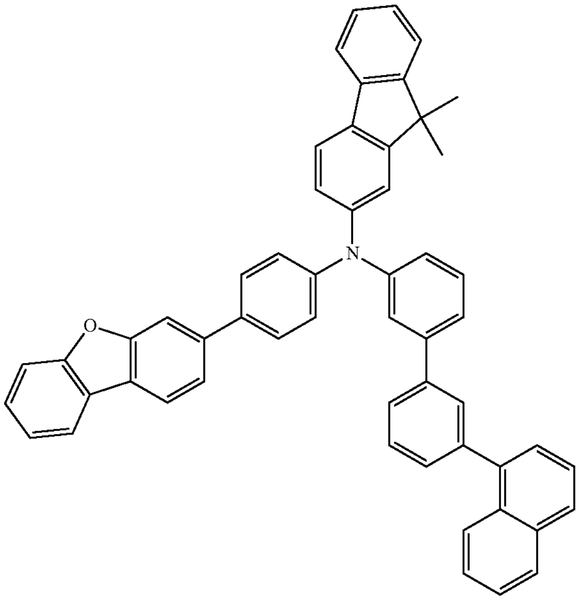
-continued
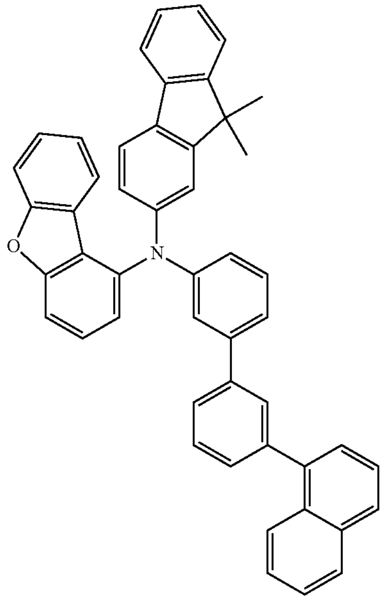
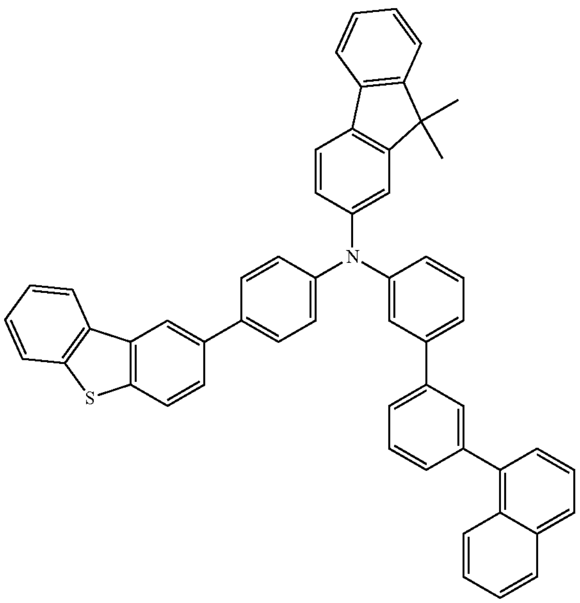
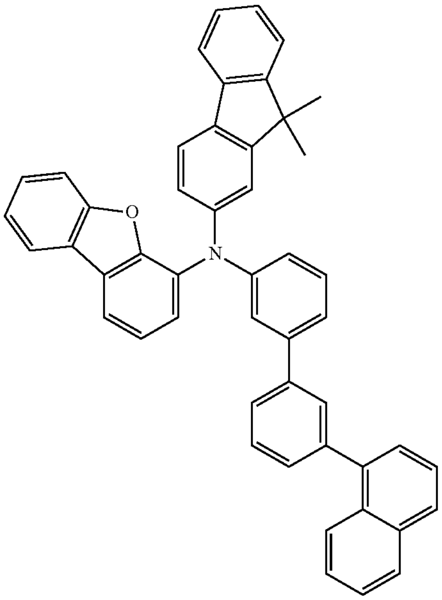

-continued
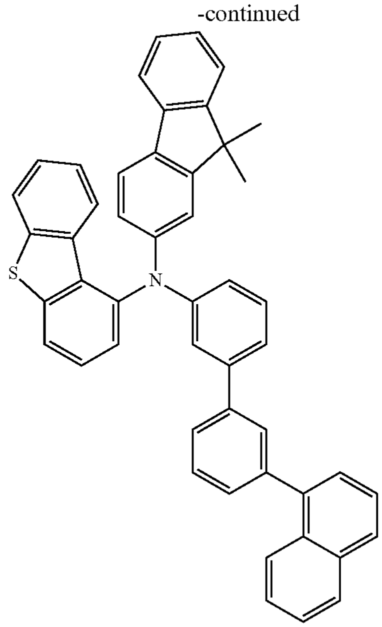
-continued
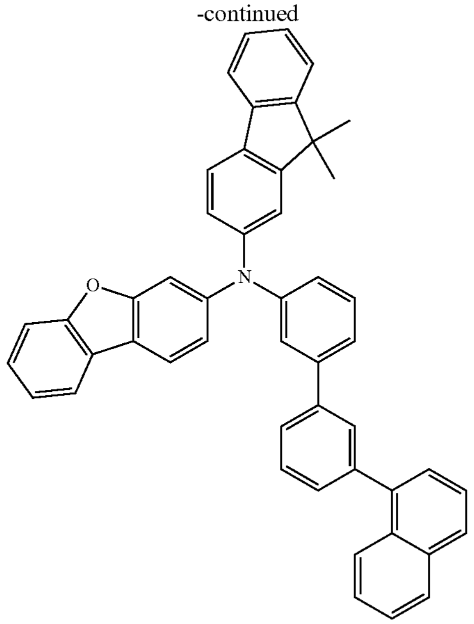
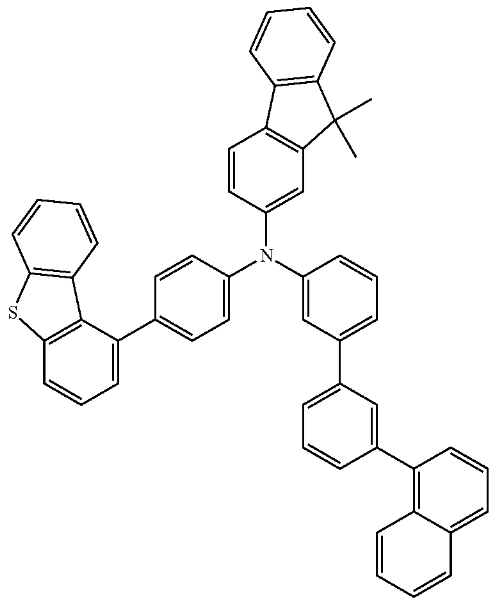
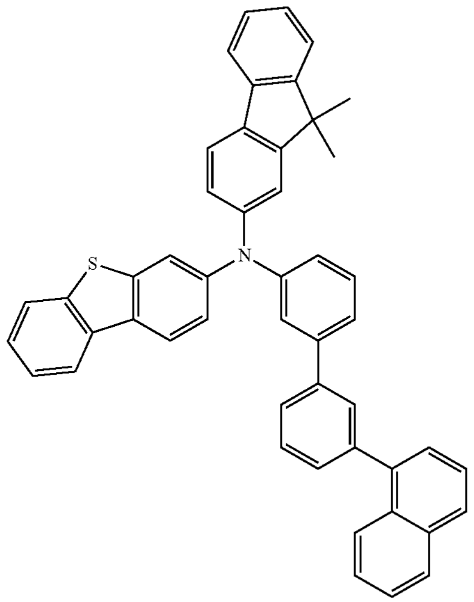

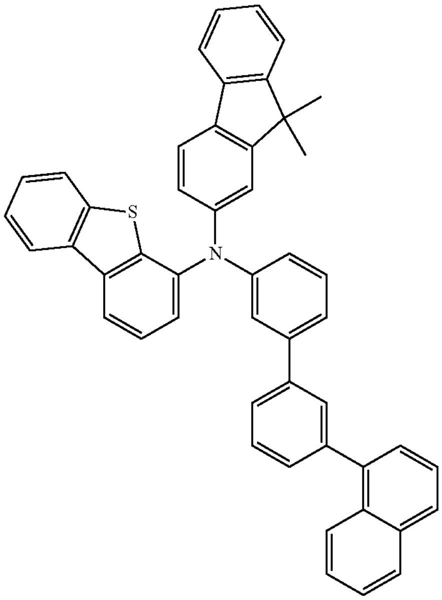
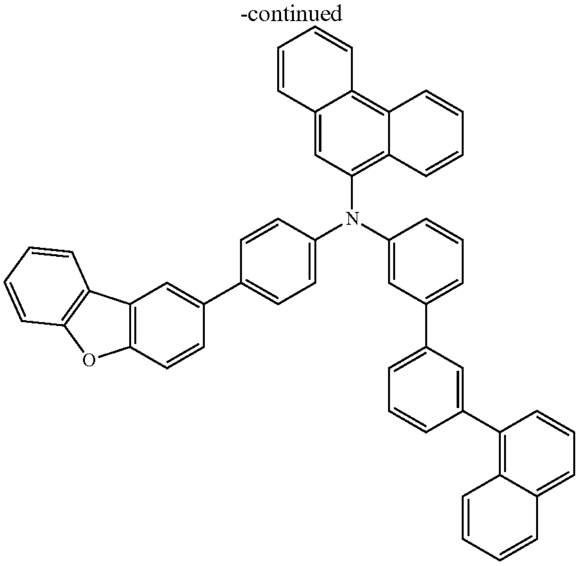
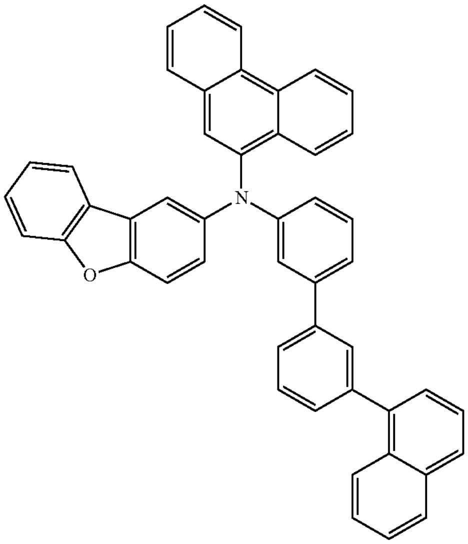
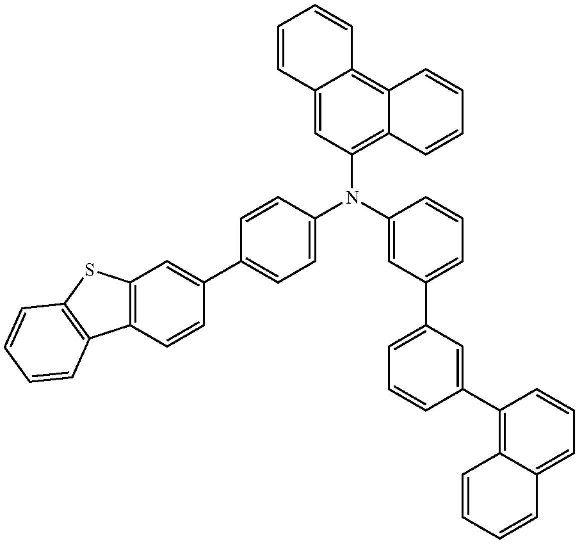
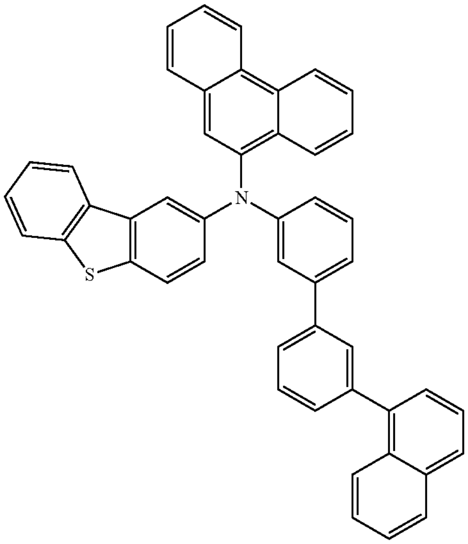
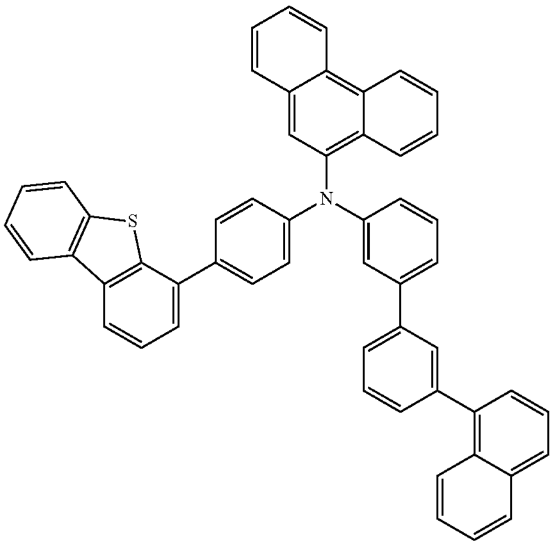

-continued
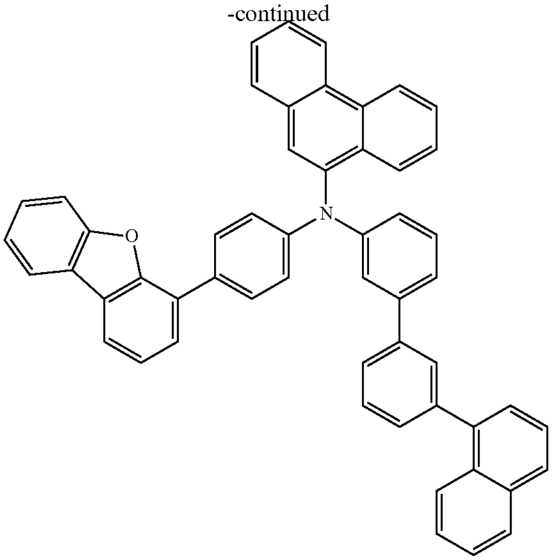
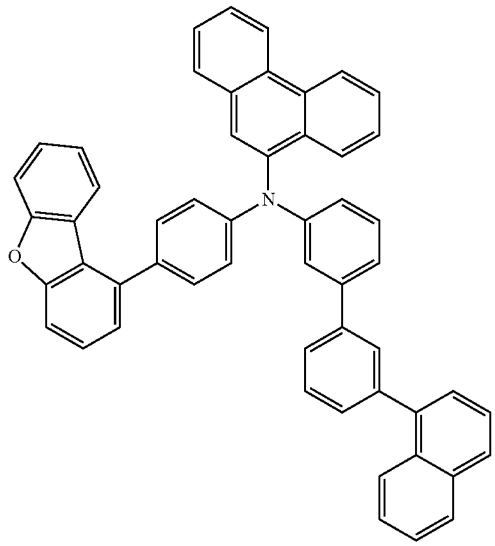
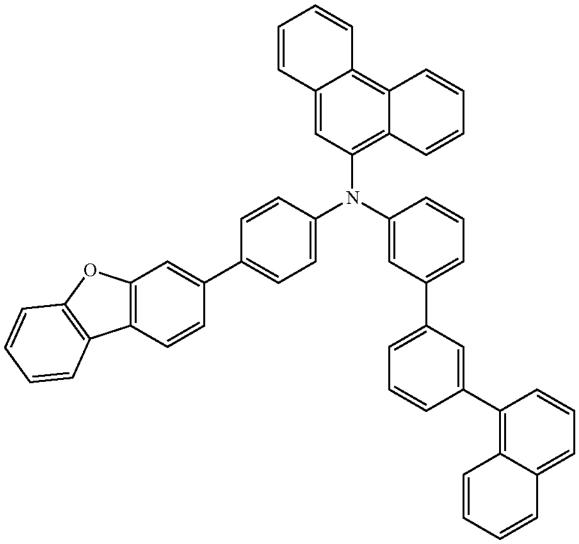
-continued
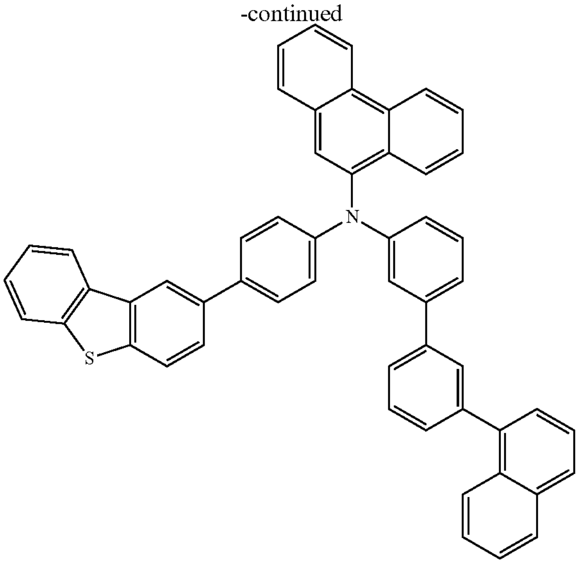
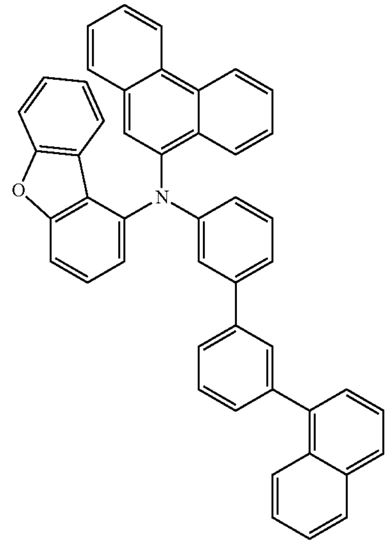
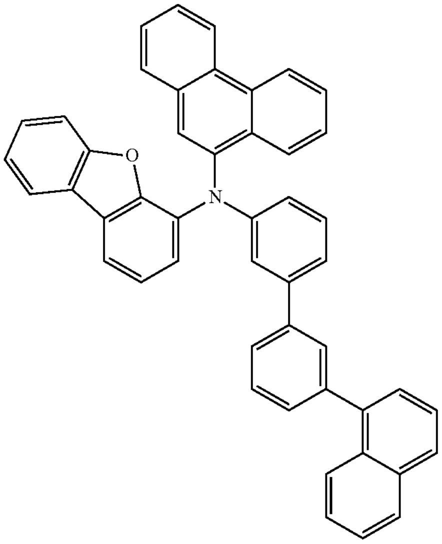

-continued
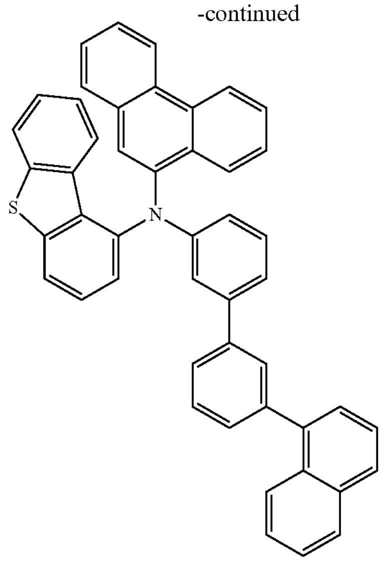
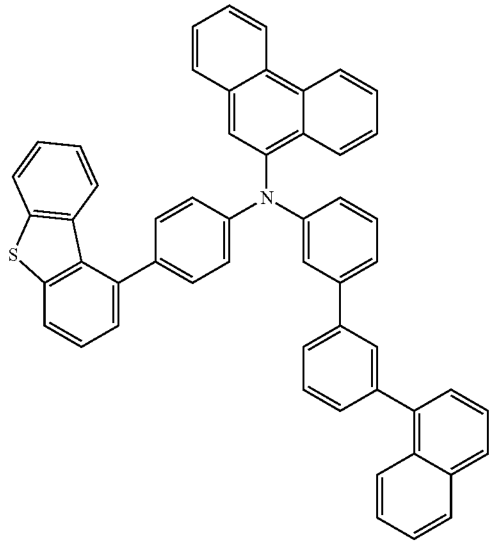
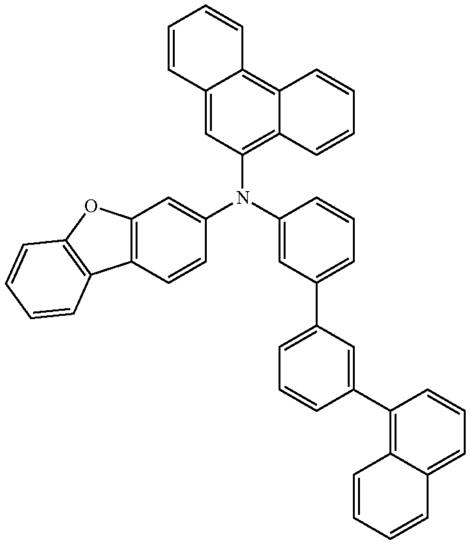
-continued
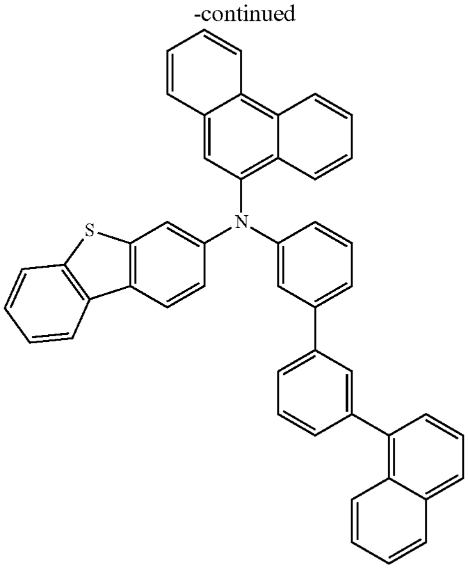
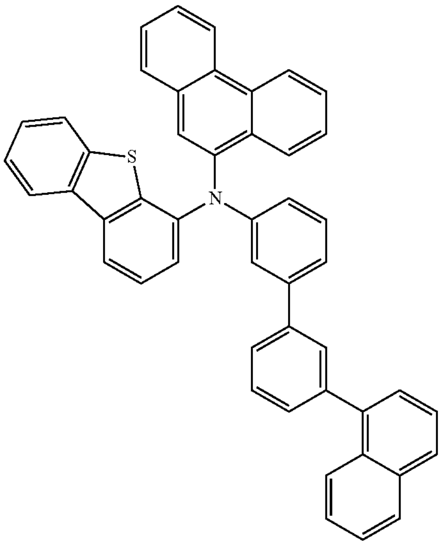

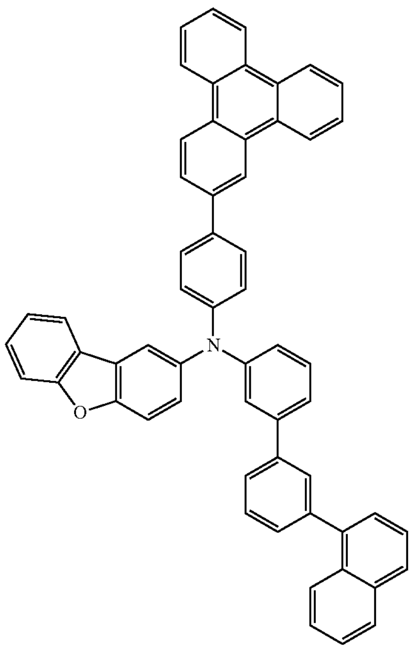
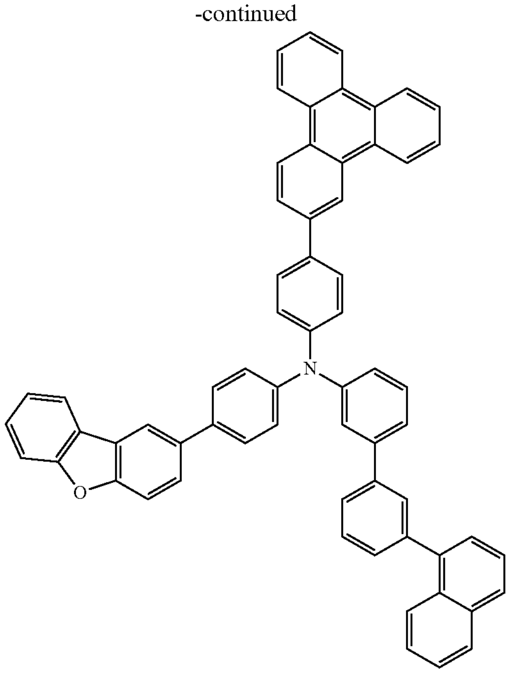
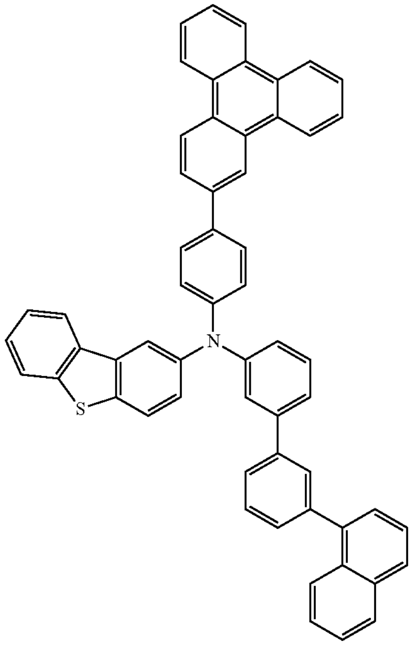
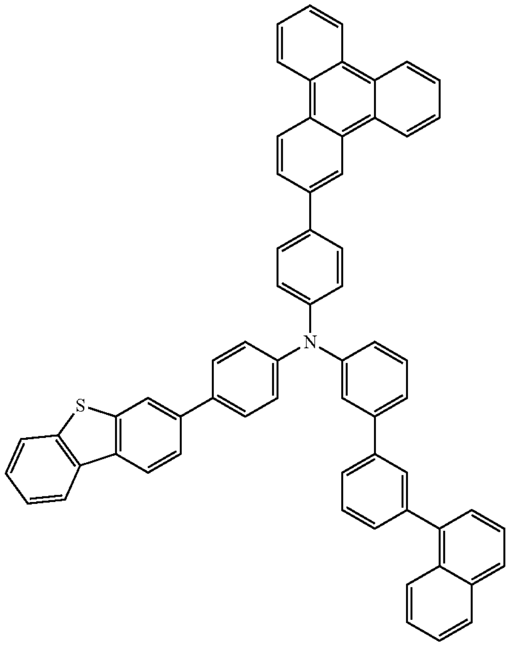

-continued
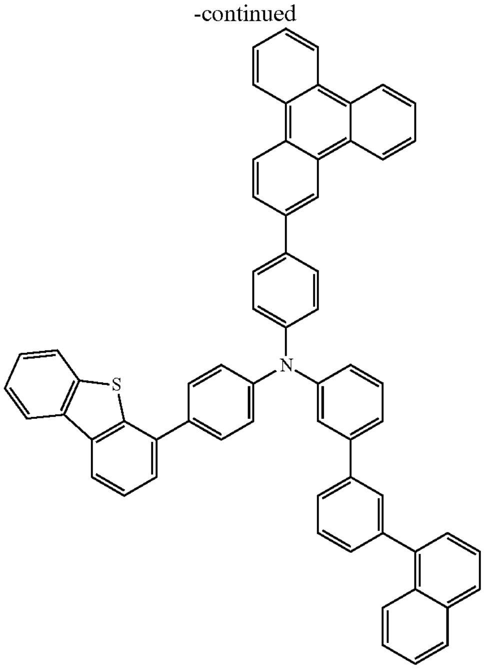
-continued
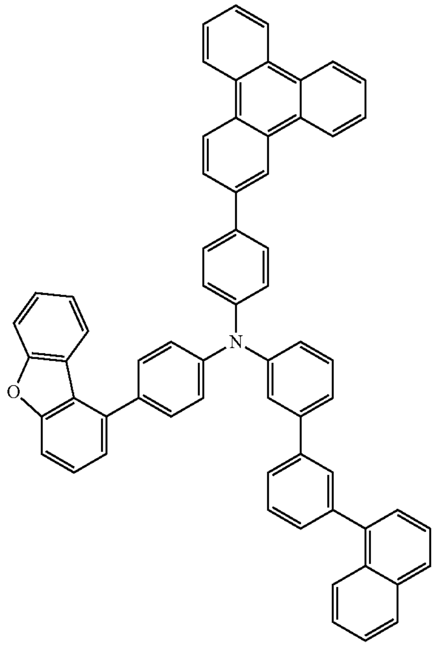
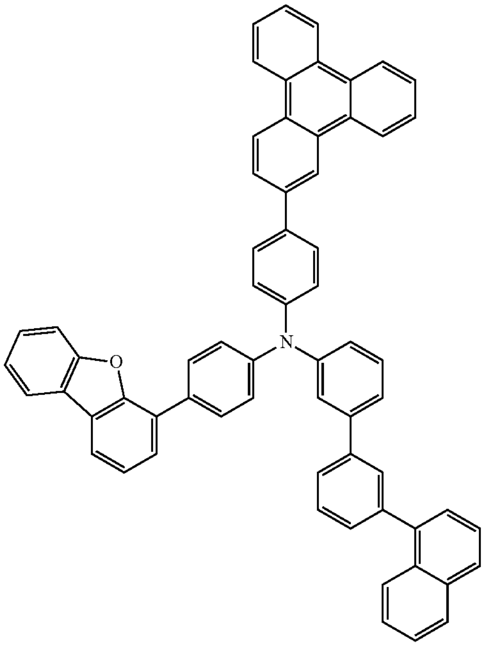
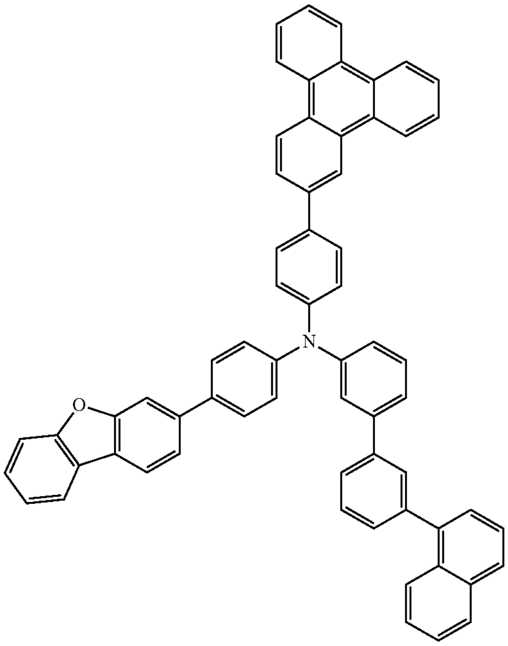

-continued
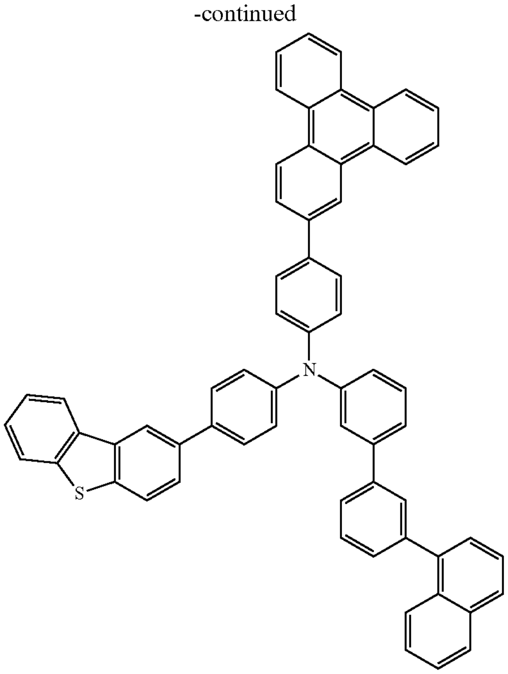
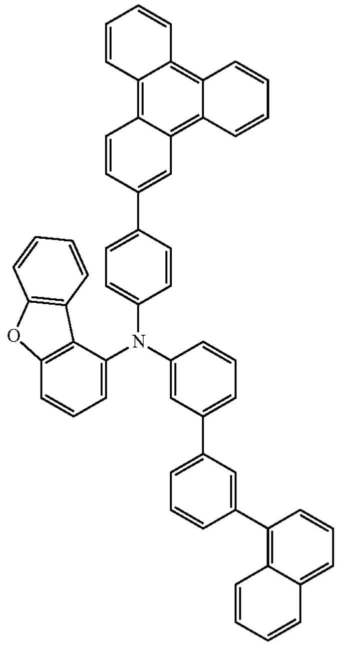
-continued
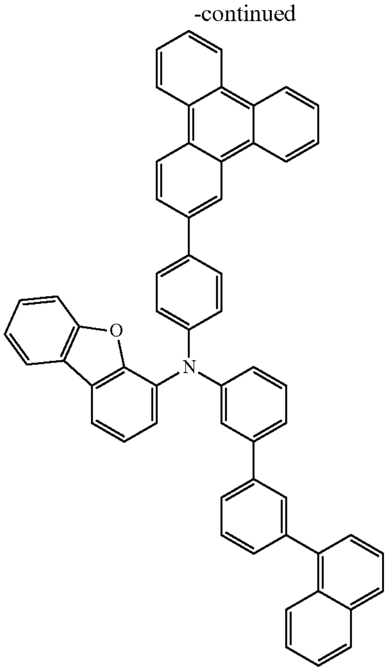
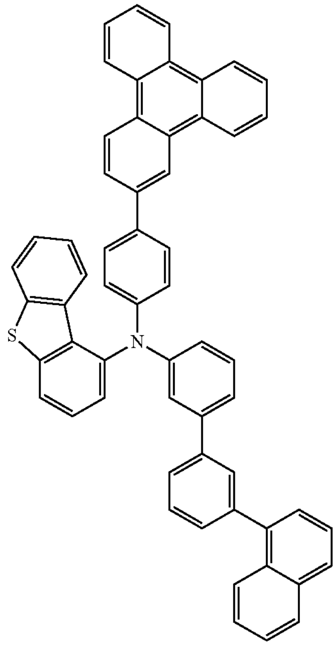

-continued
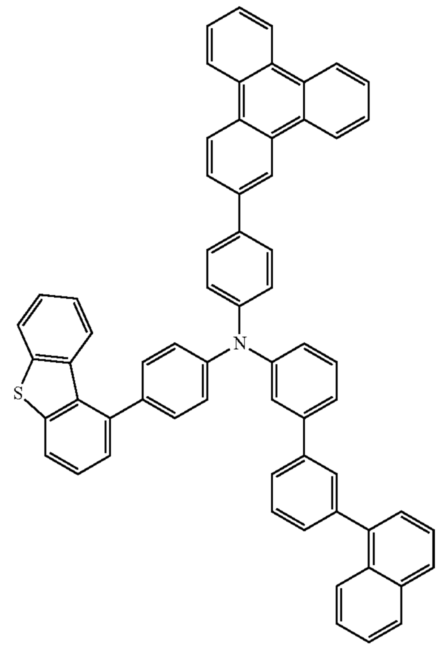
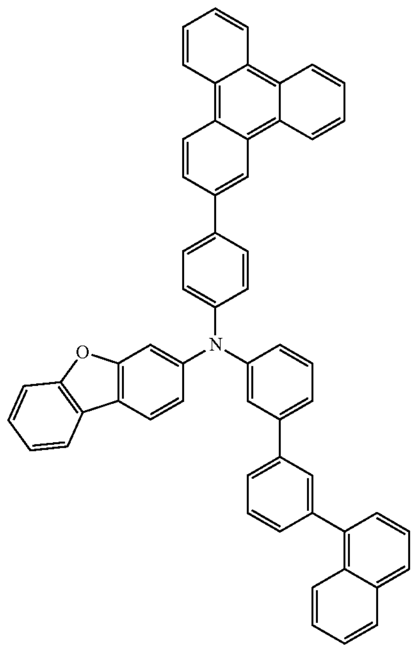
-continued
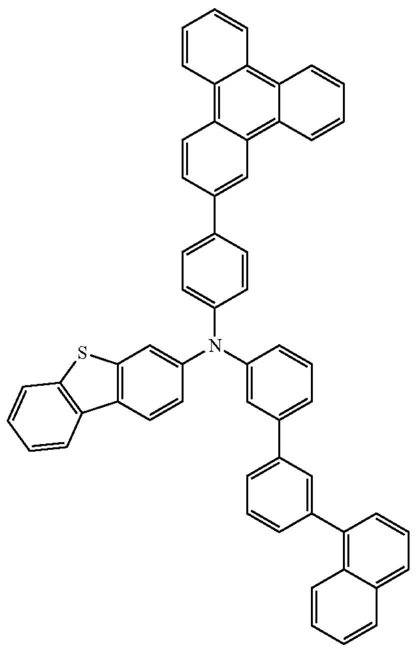
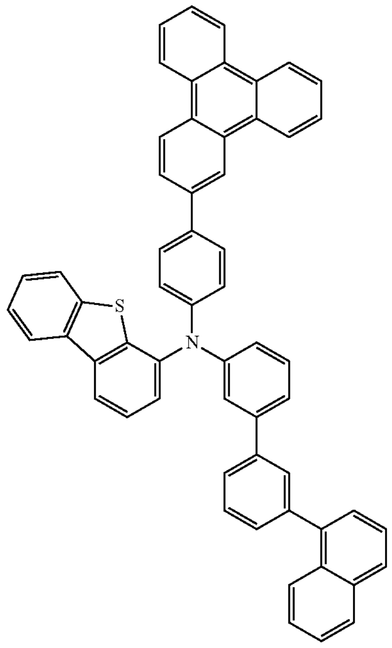

-continued
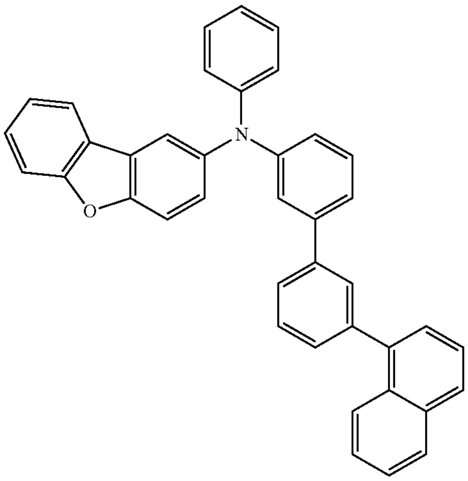
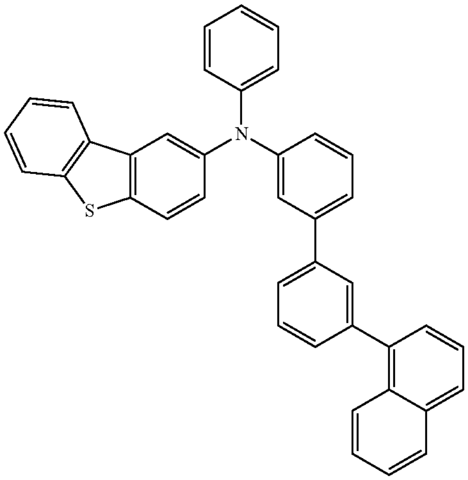
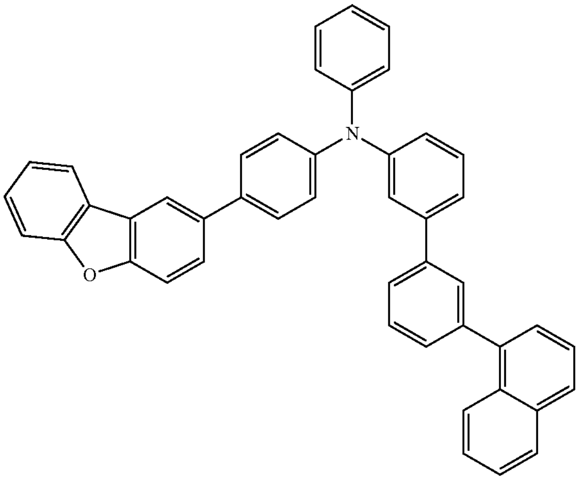
-continued
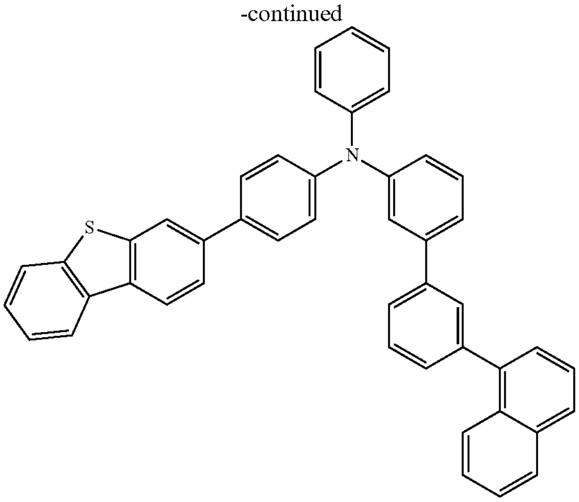
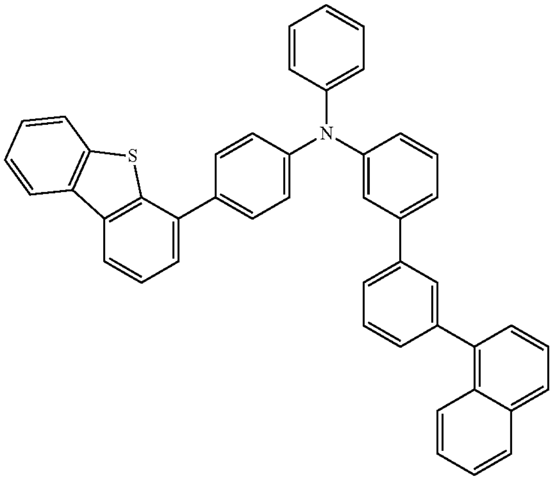
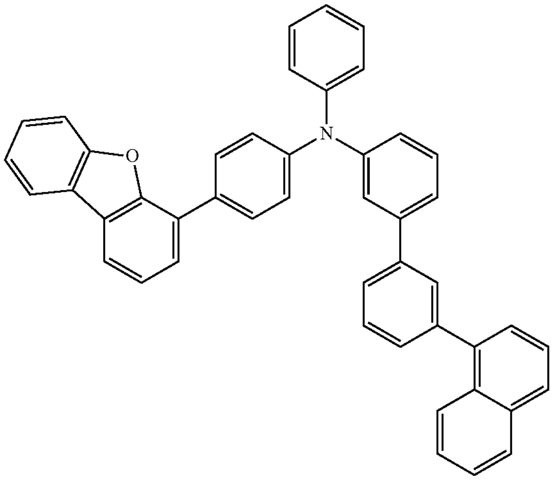

-continued
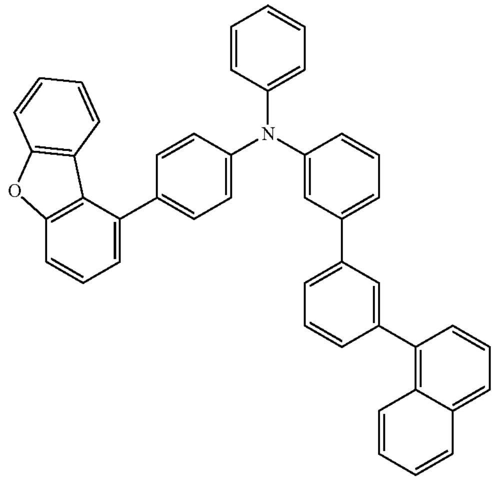
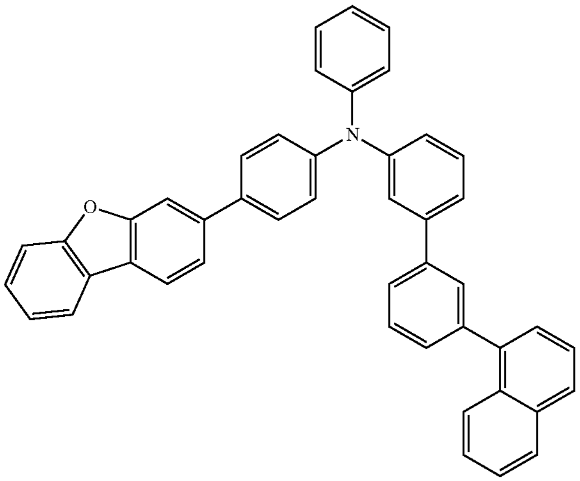
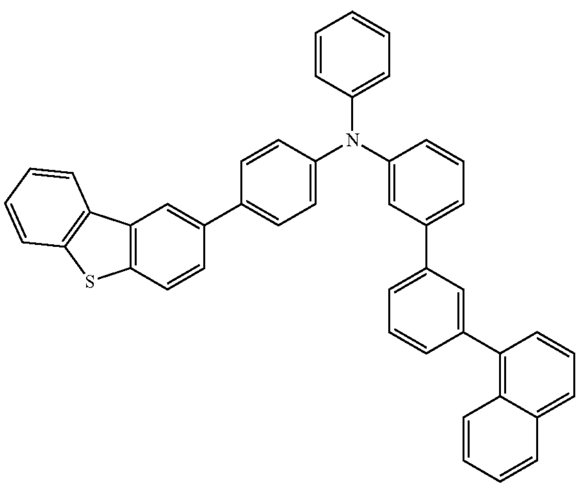
-continued
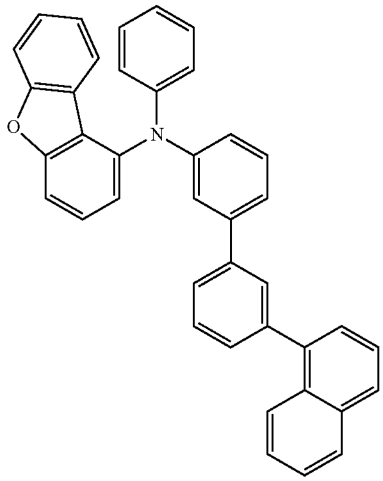
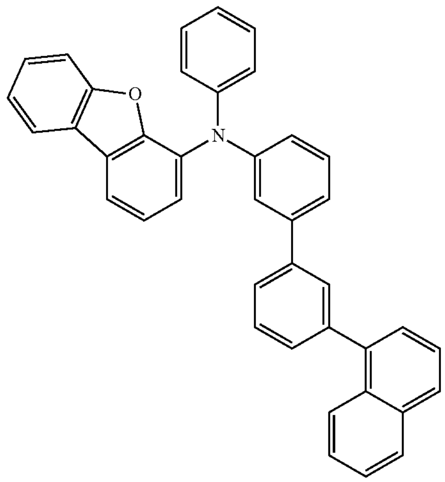
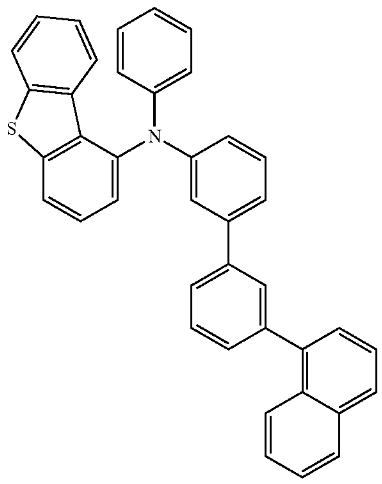

-continued
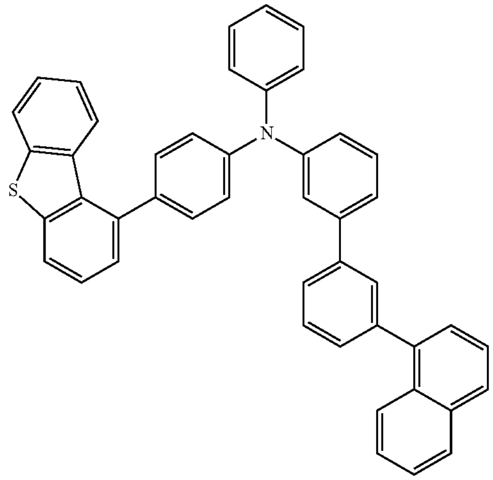
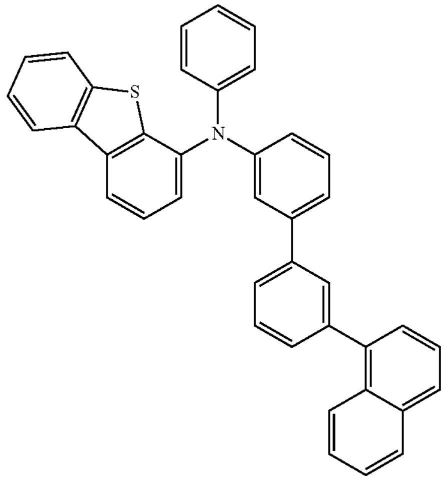
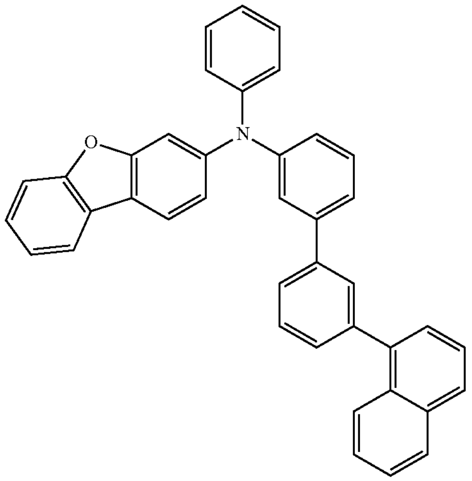
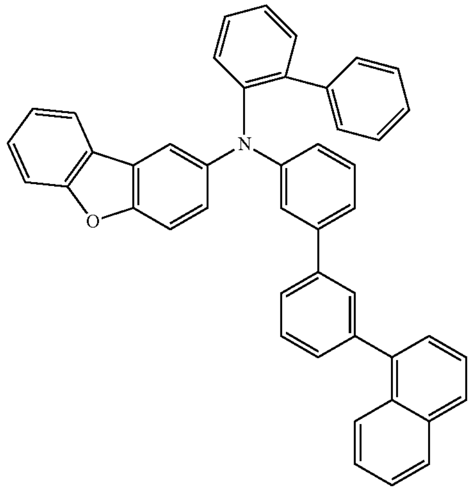
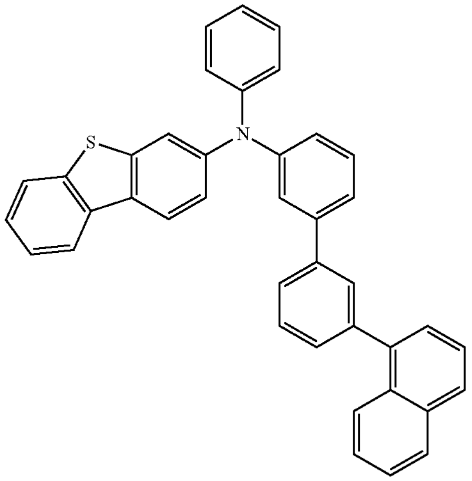
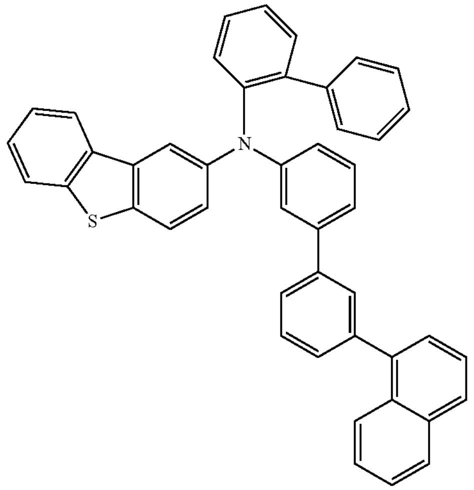
-continued -continued
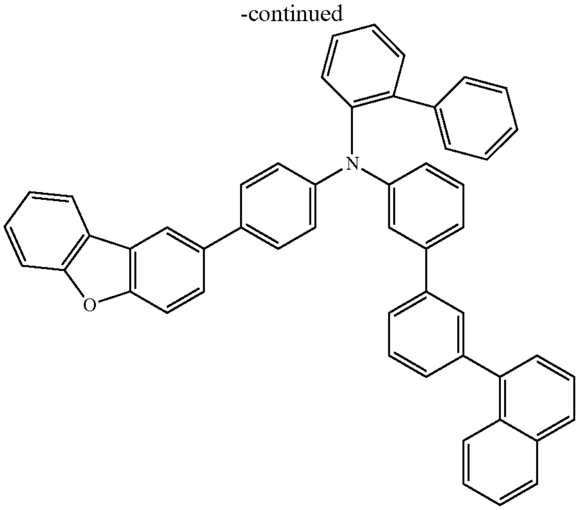
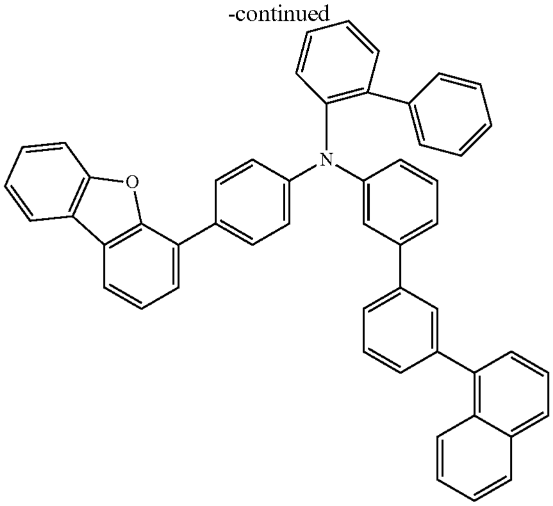
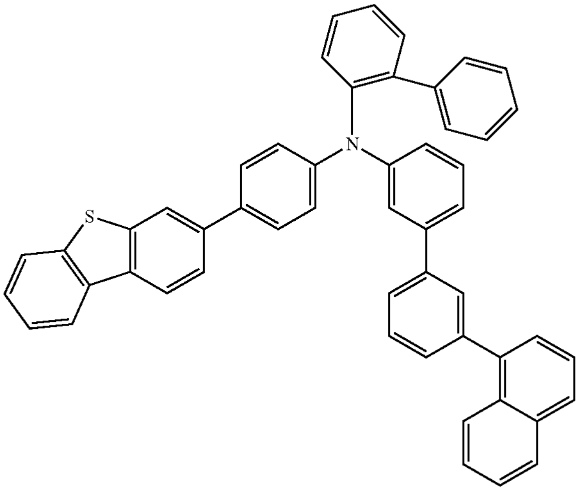
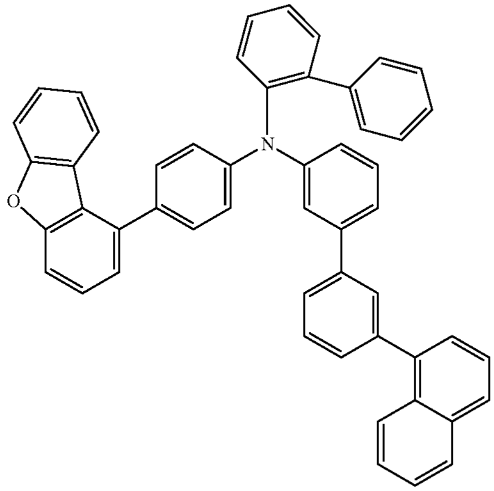
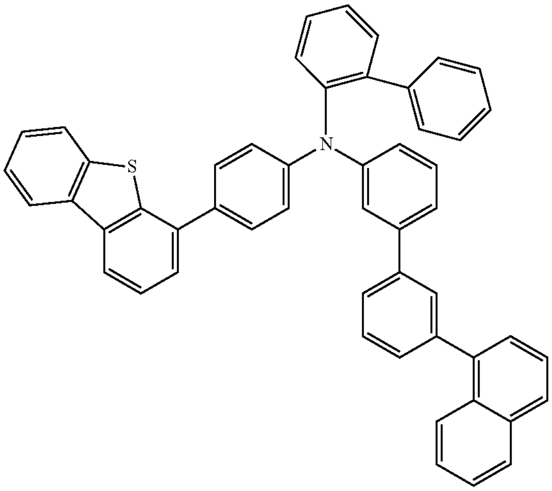
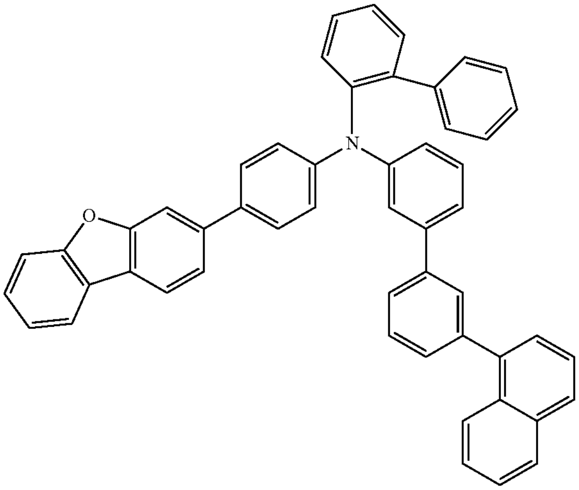

-continued
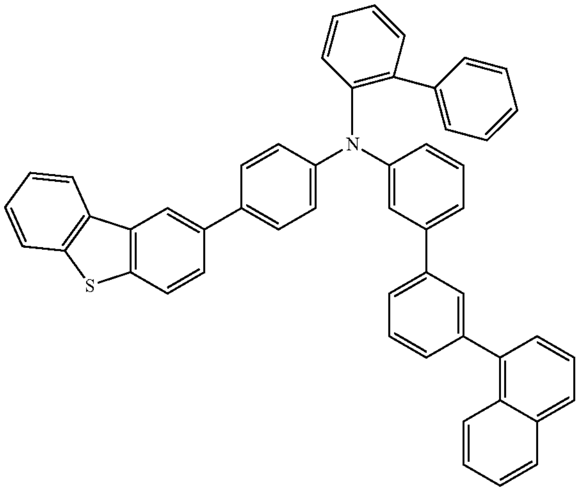
-continued
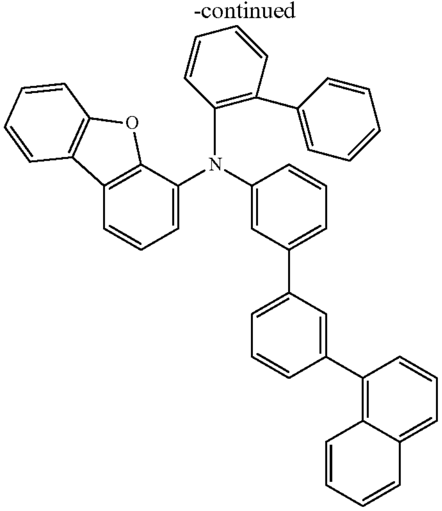
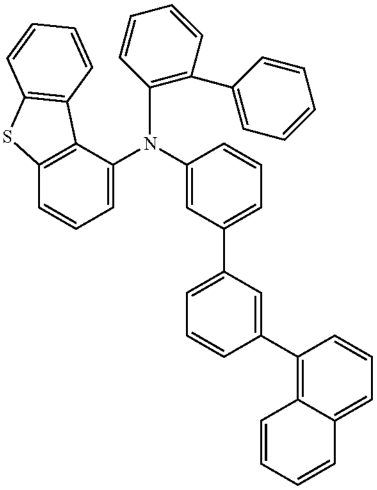
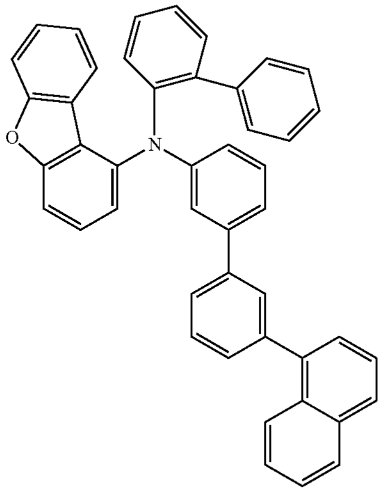
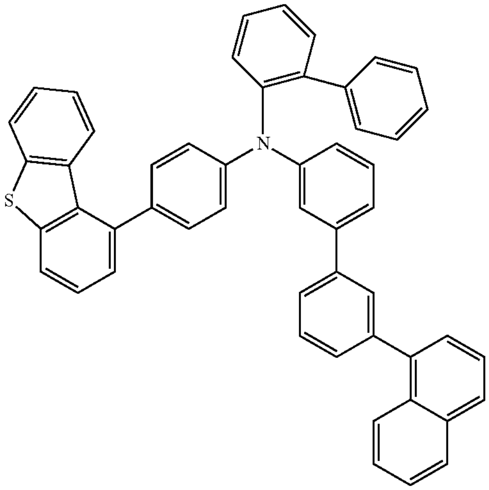

-continued
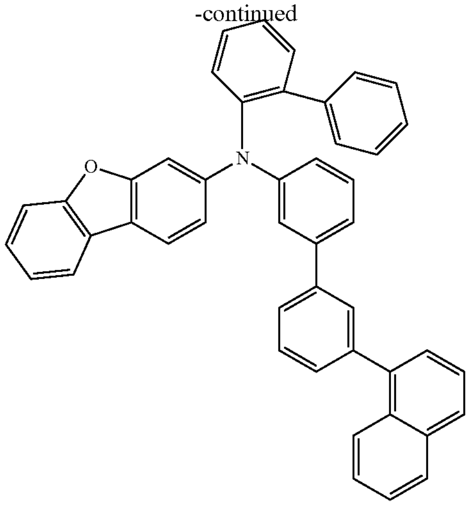
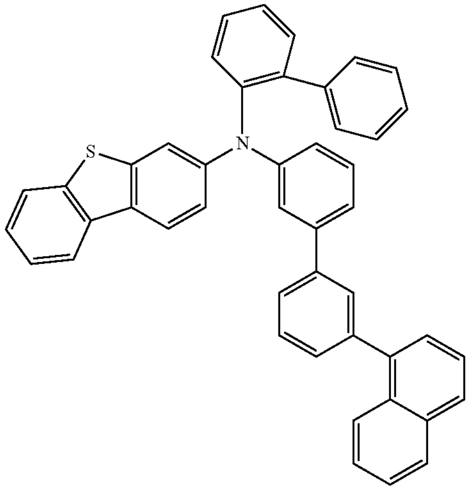
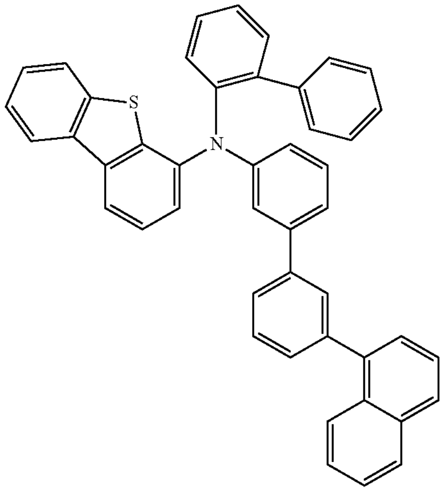
-continued
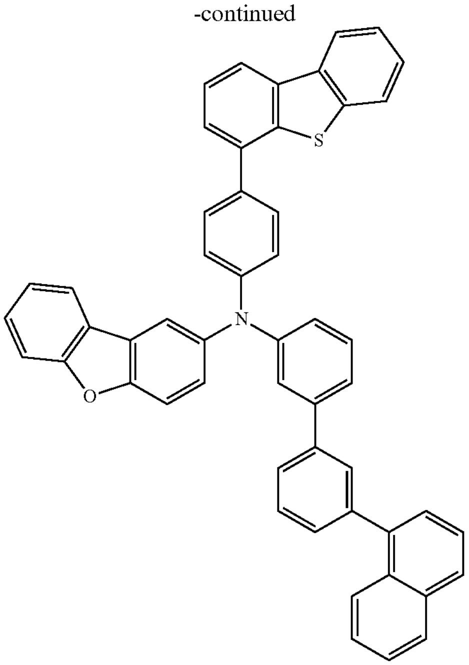
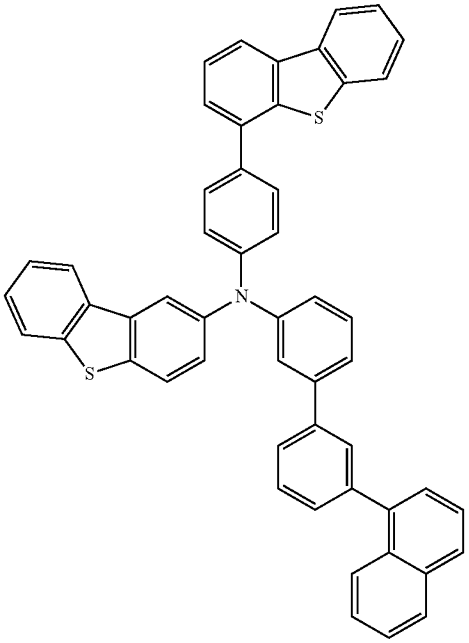

-continued
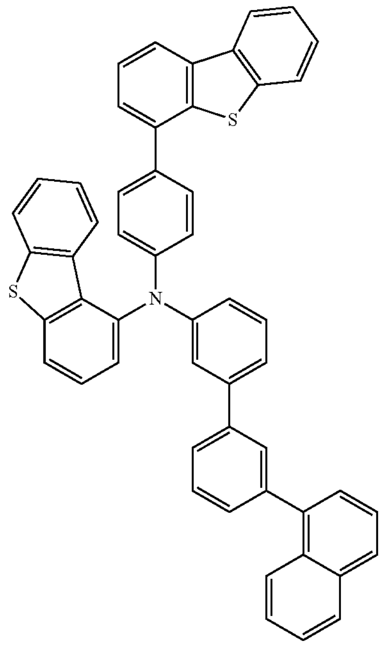
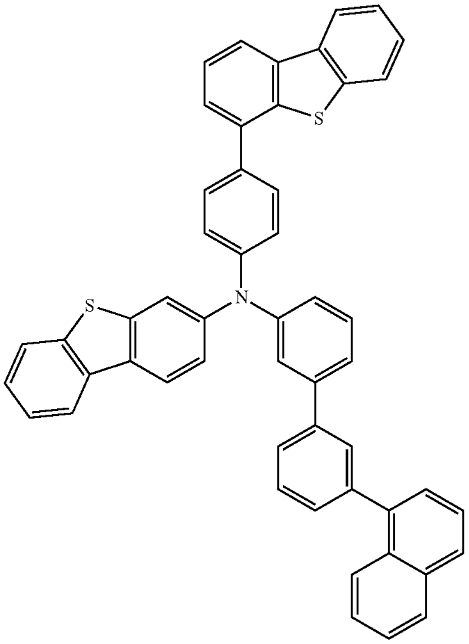
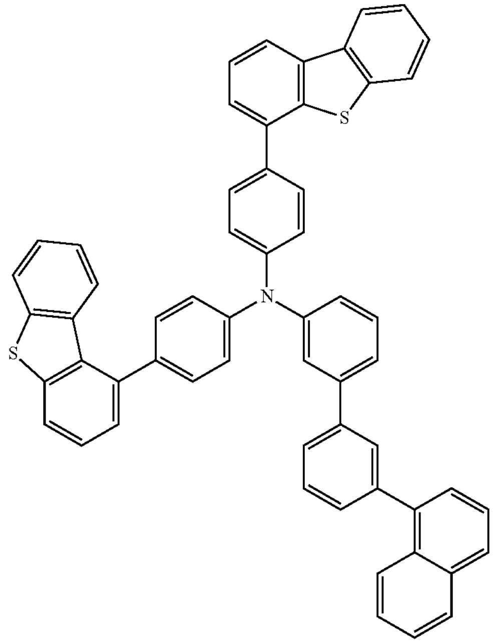
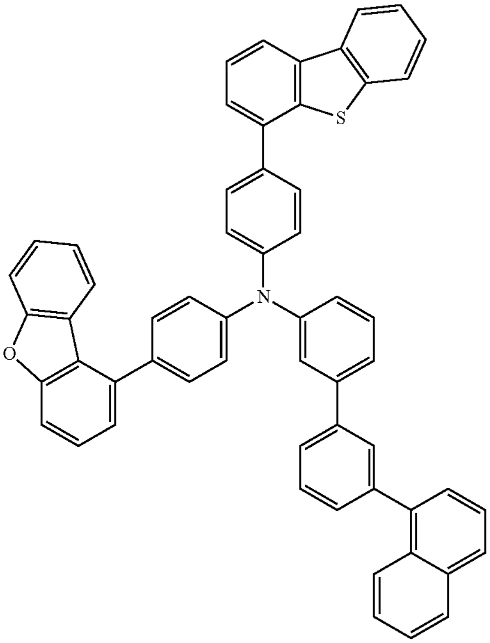
-continued

-continued
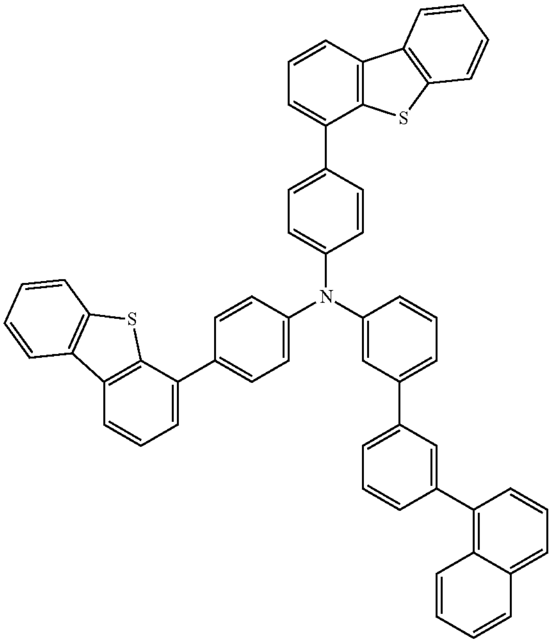
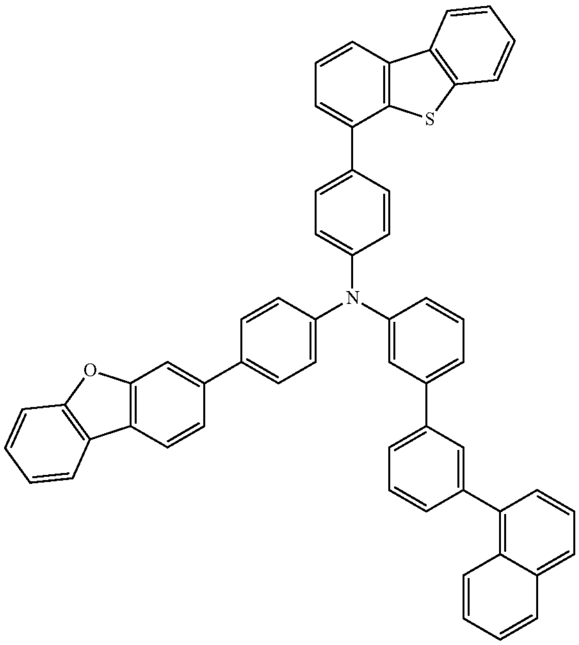
-continued
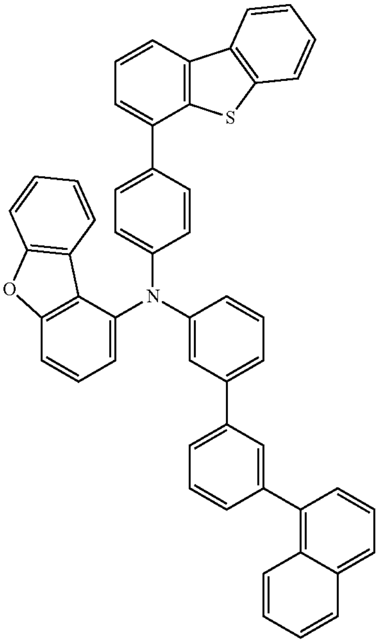
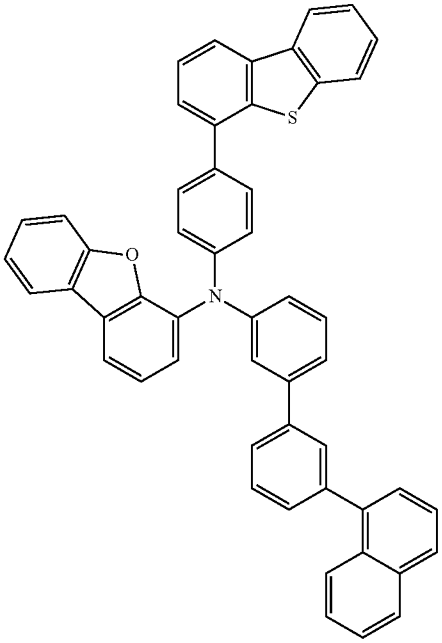

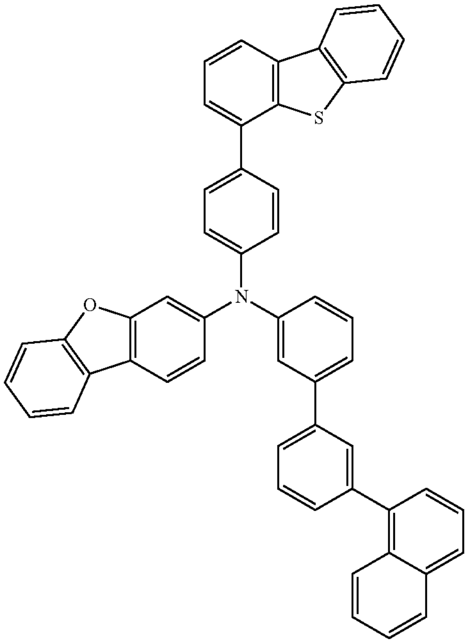
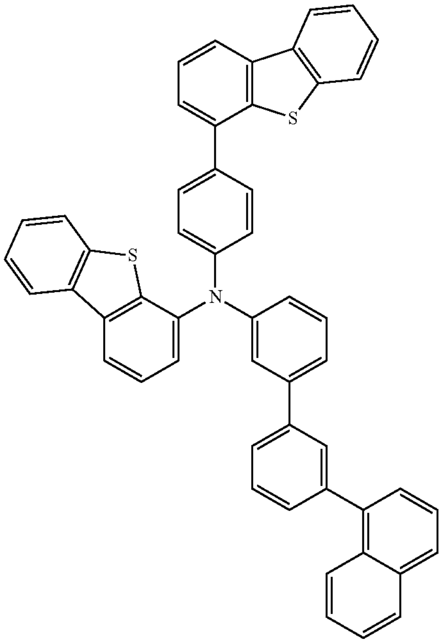
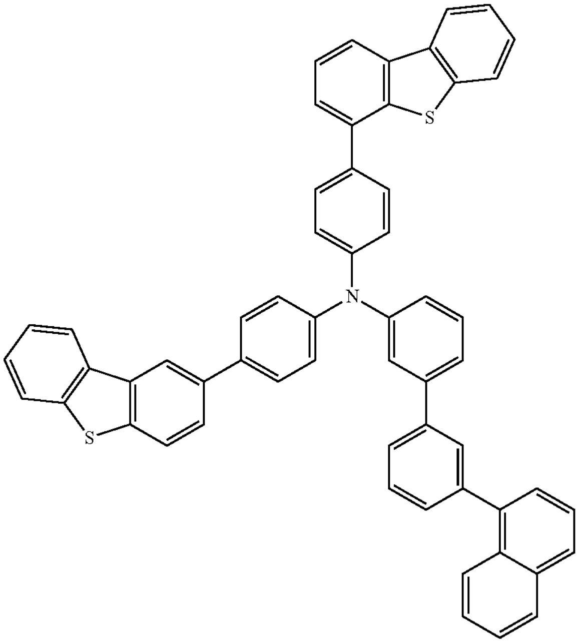
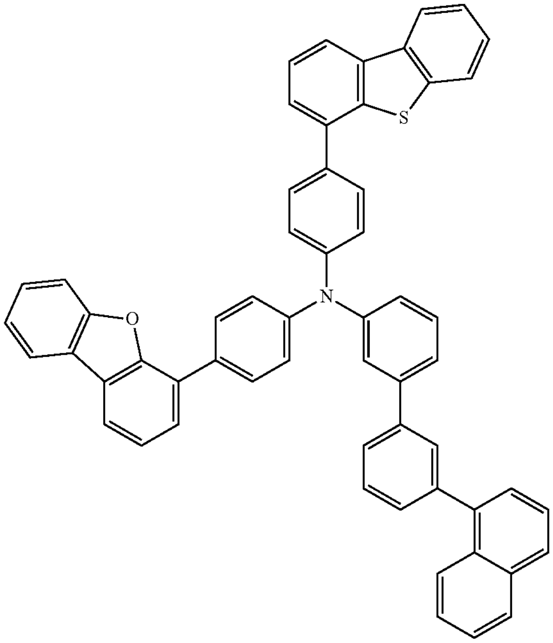

-continued
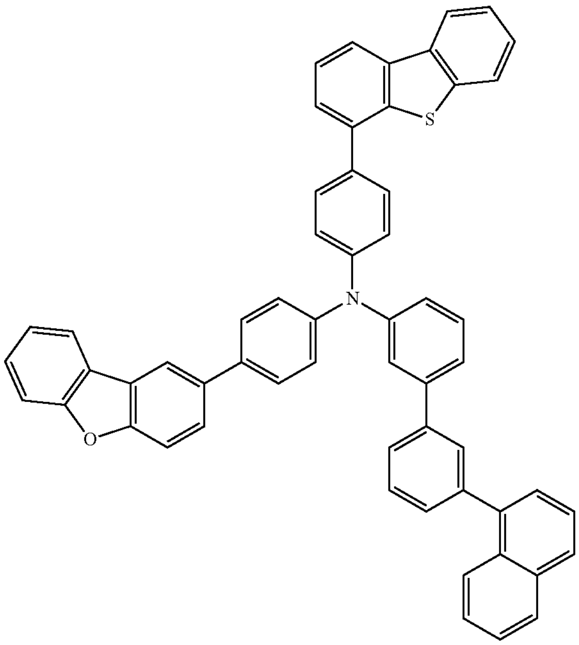
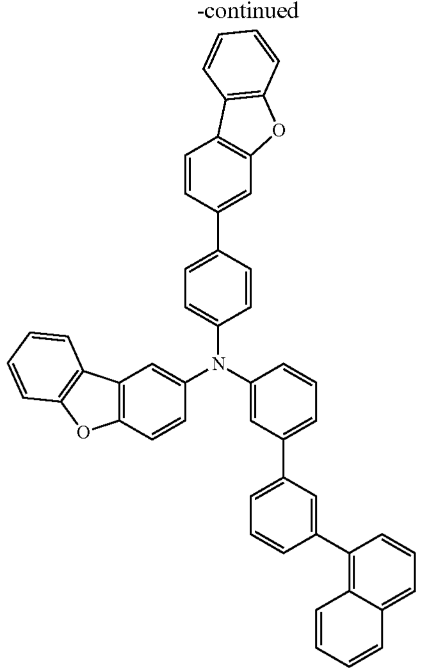
-continued
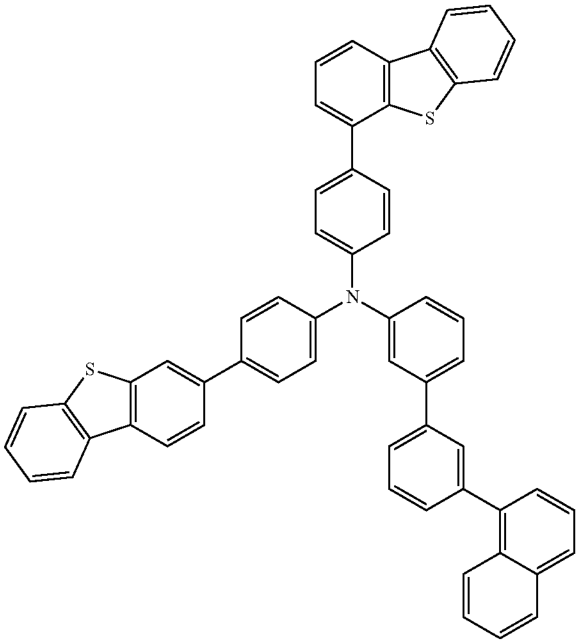
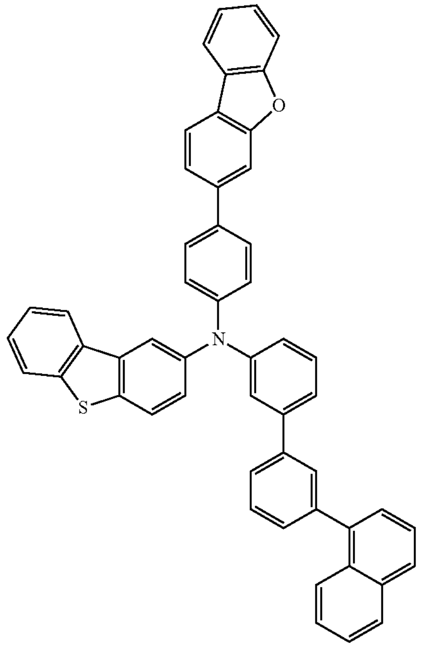

-continued
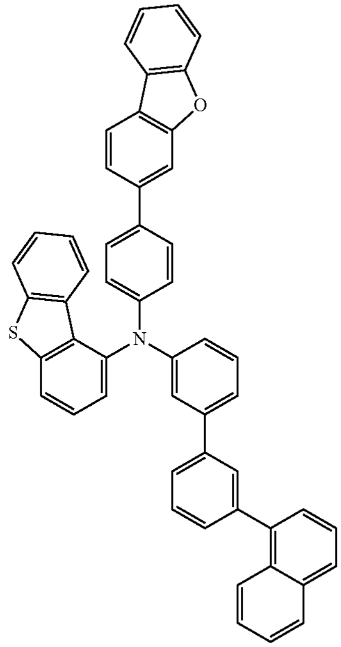
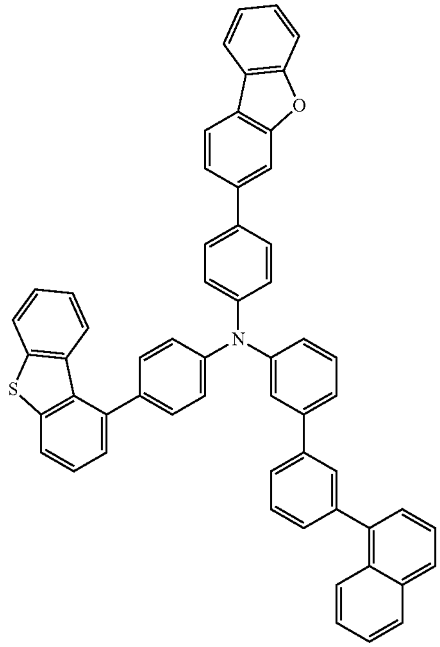
-continued
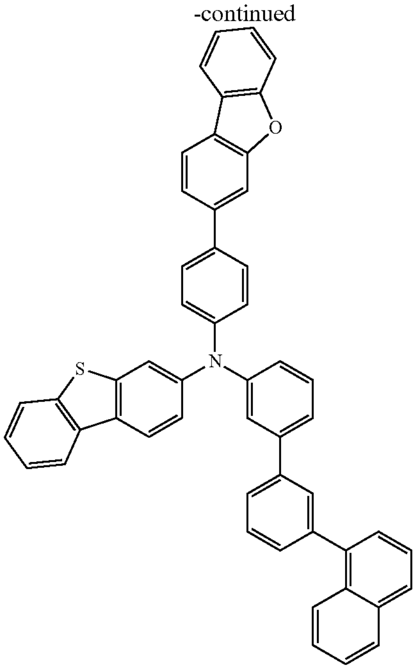
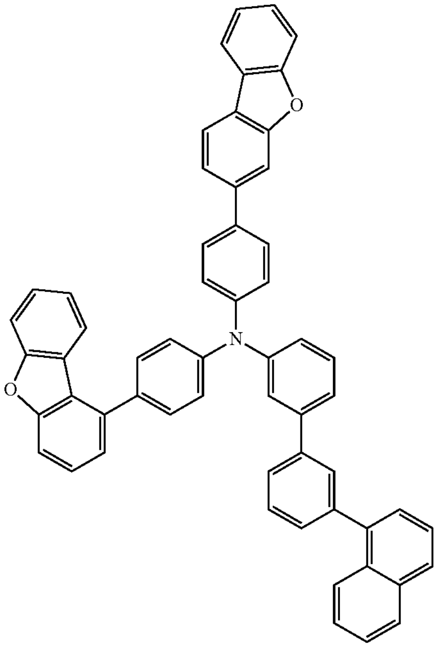

-continued
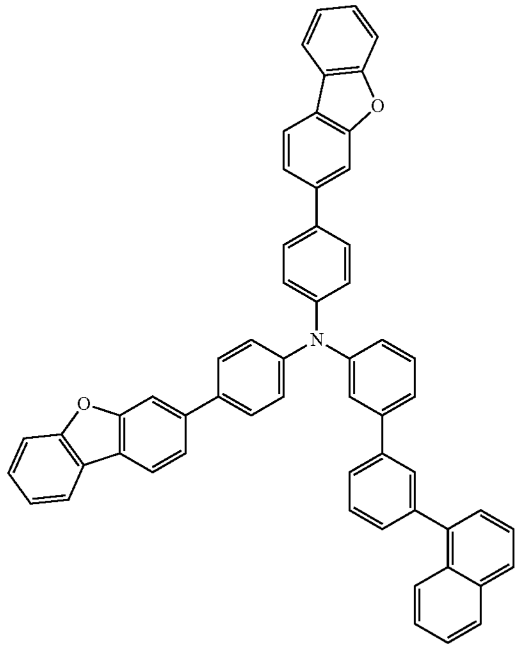
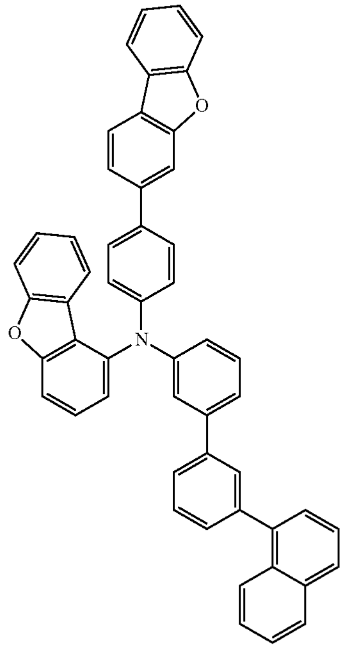
-continued
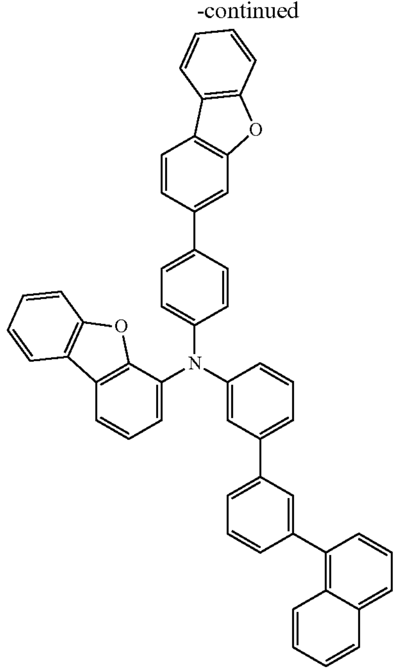
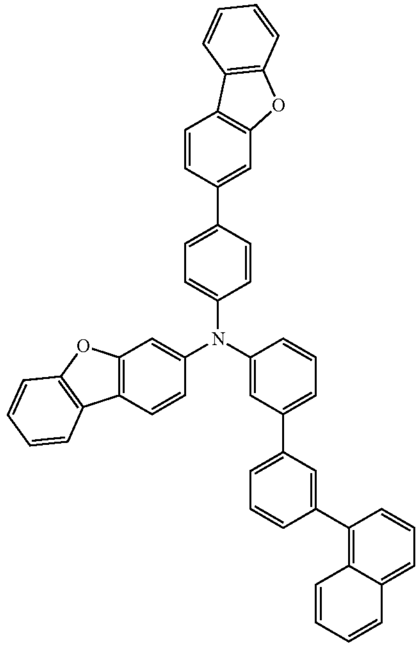

-continued
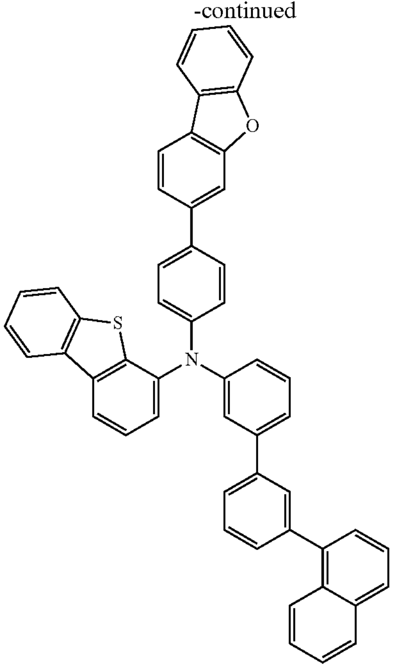
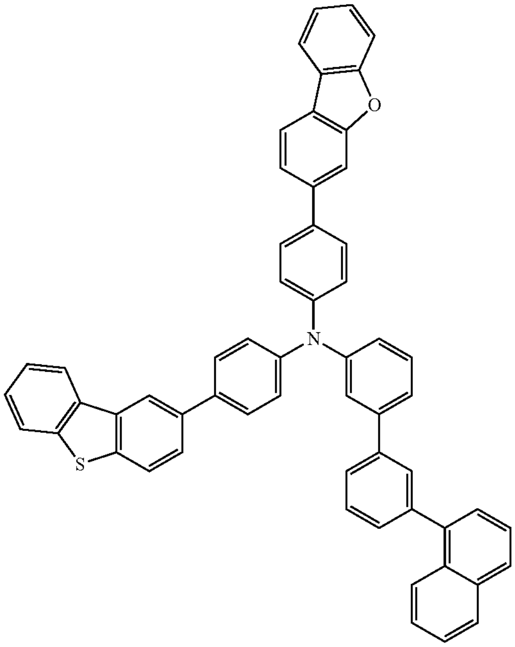
-continued
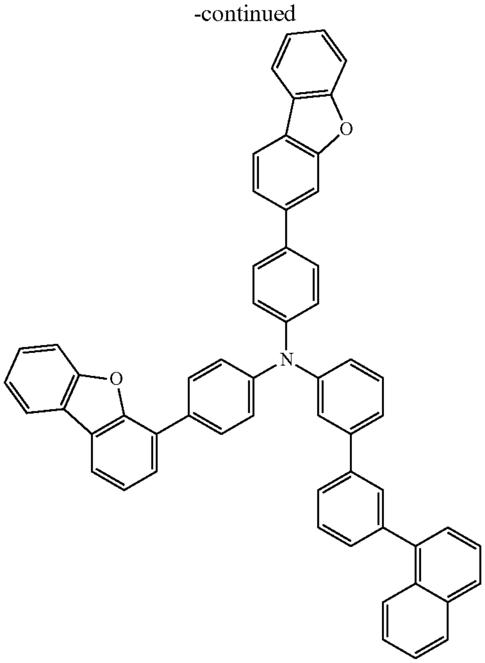
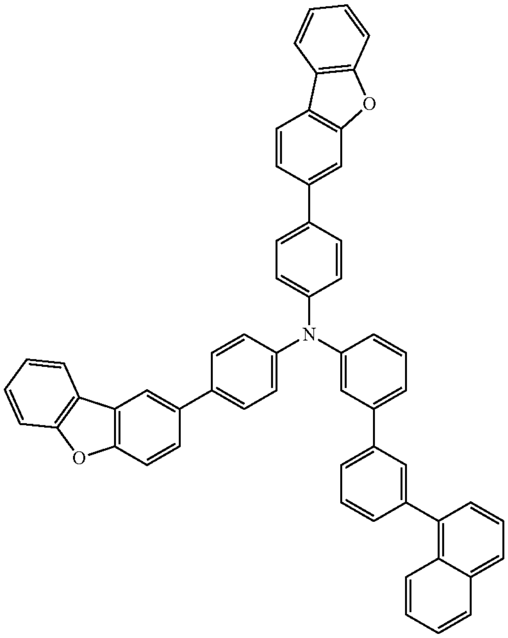

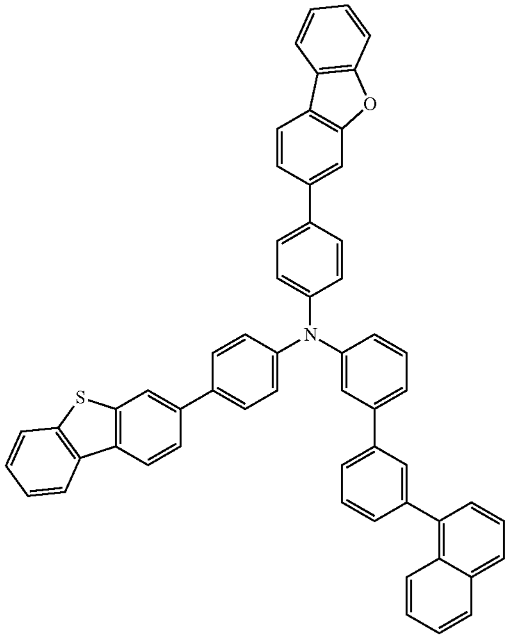
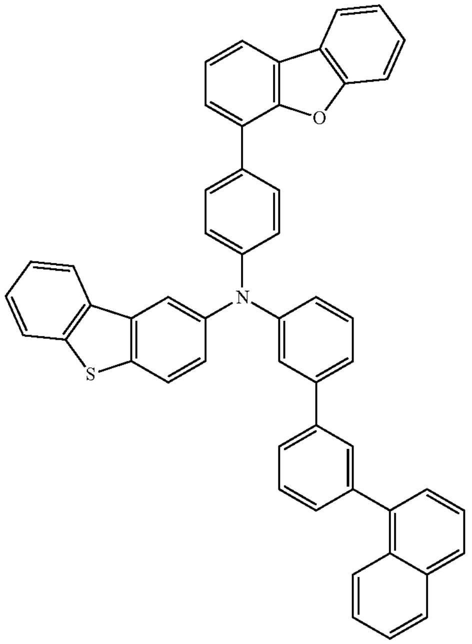
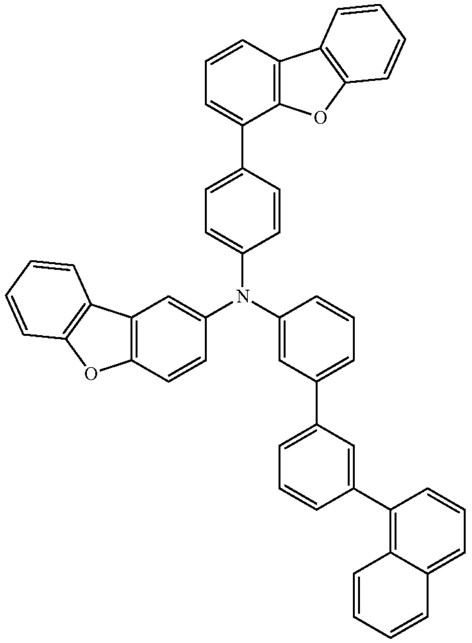
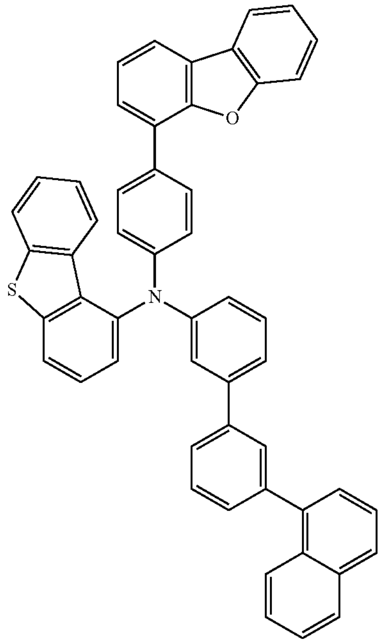

-continued
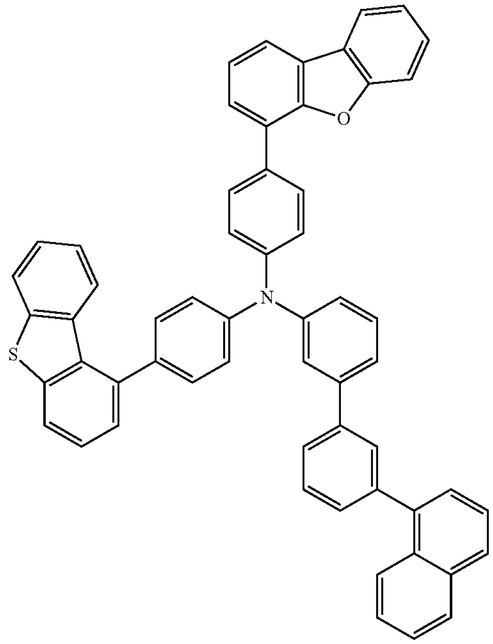
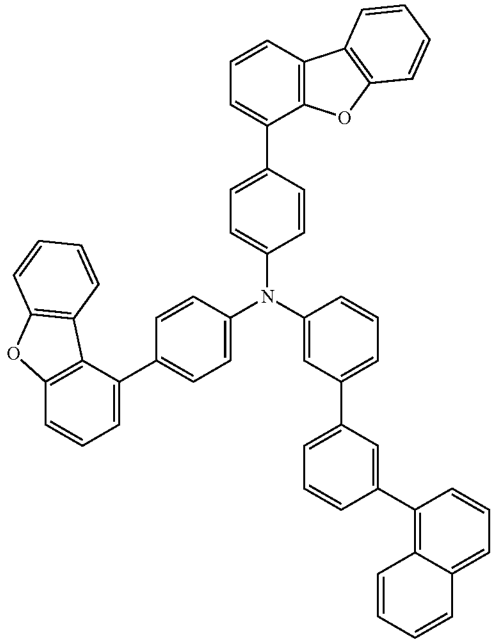
-continued
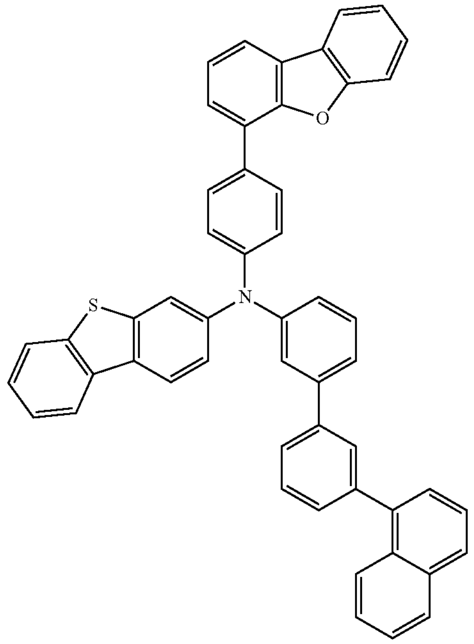
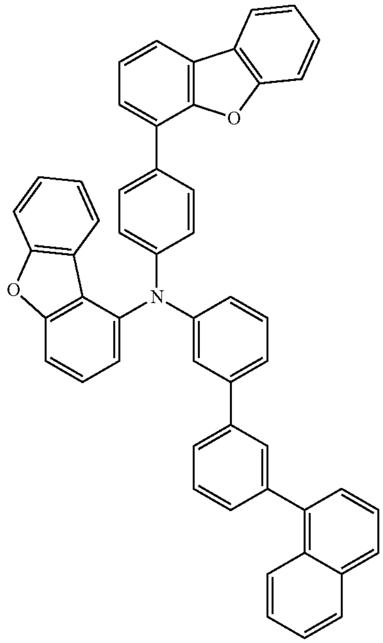

-continued
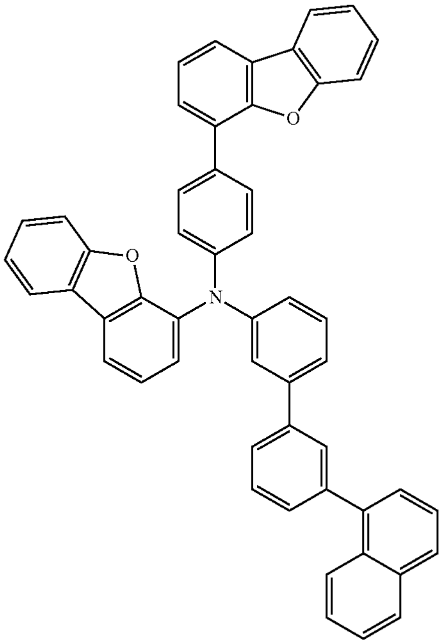
-continued
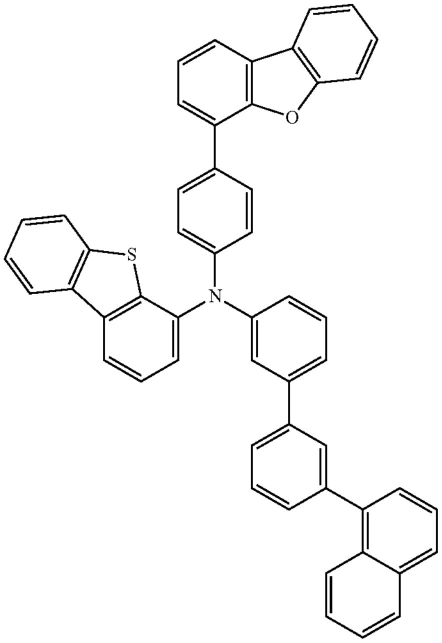
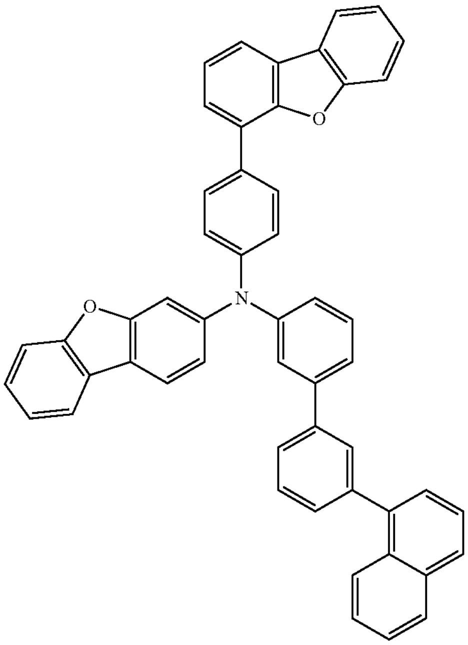
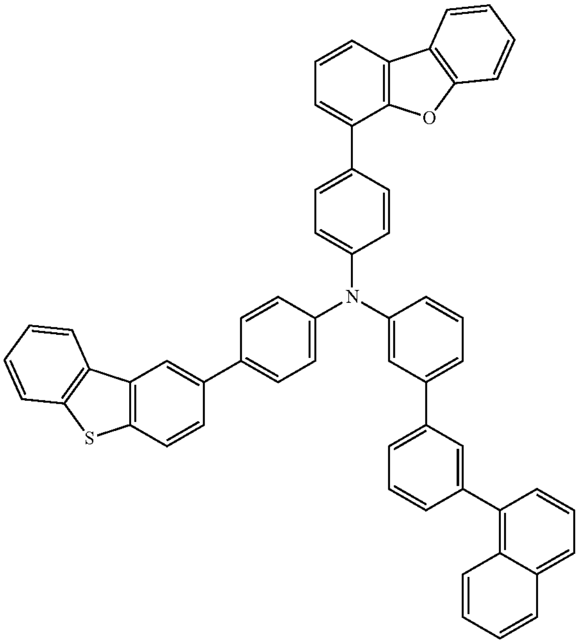

-continued
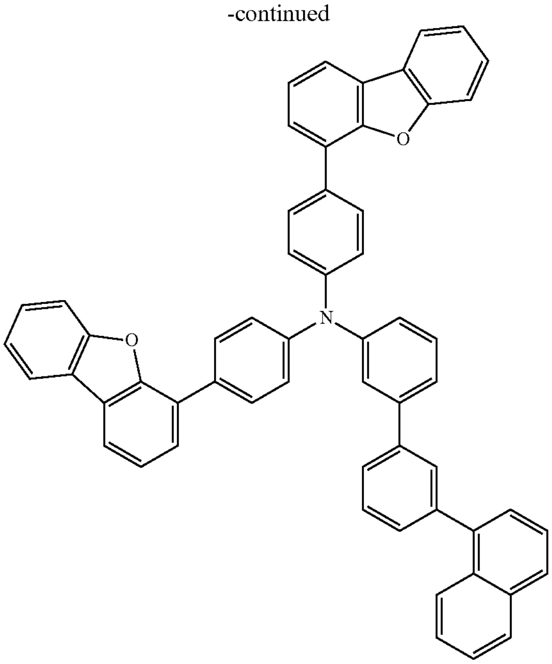
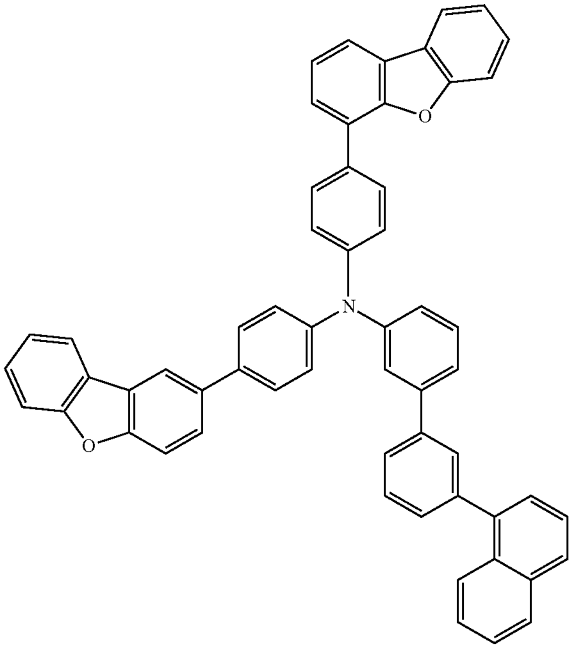
-continued
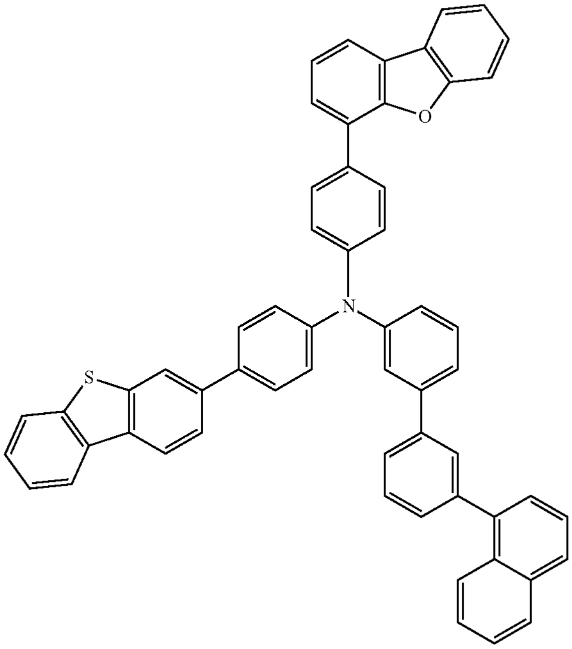
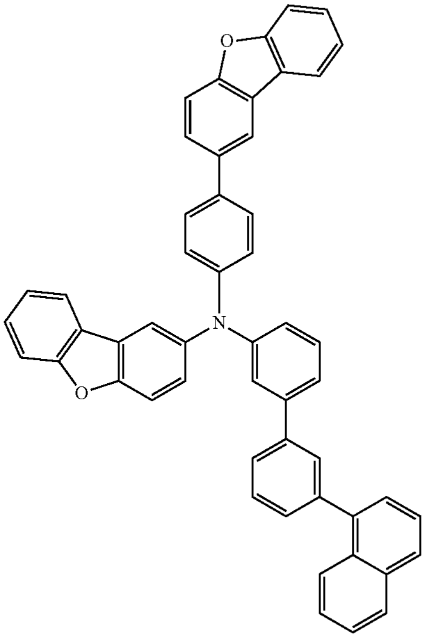

-continued
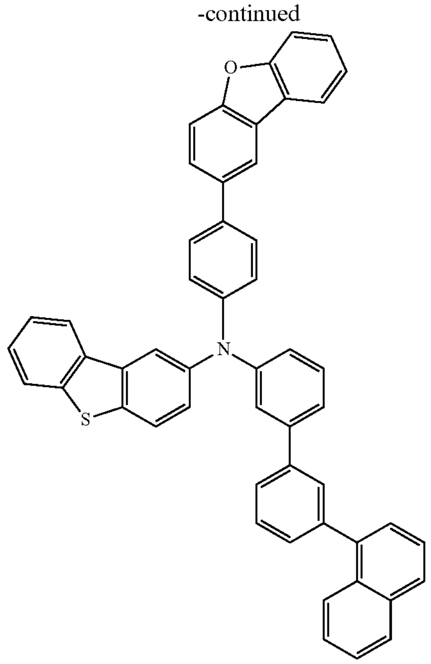
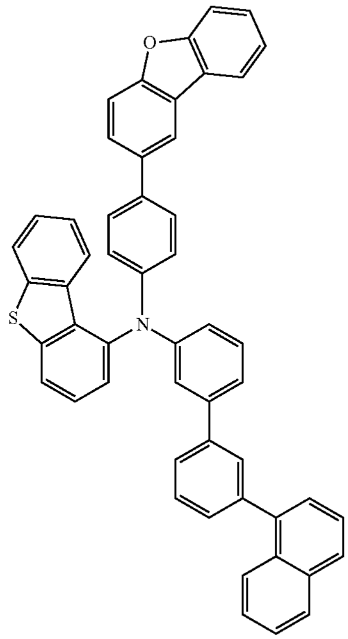
-continued
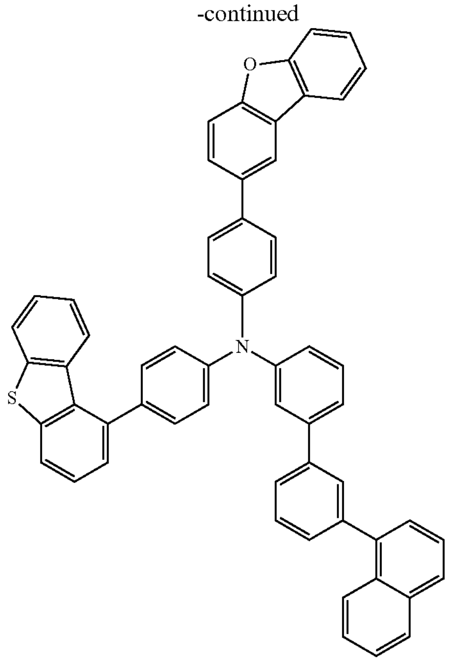
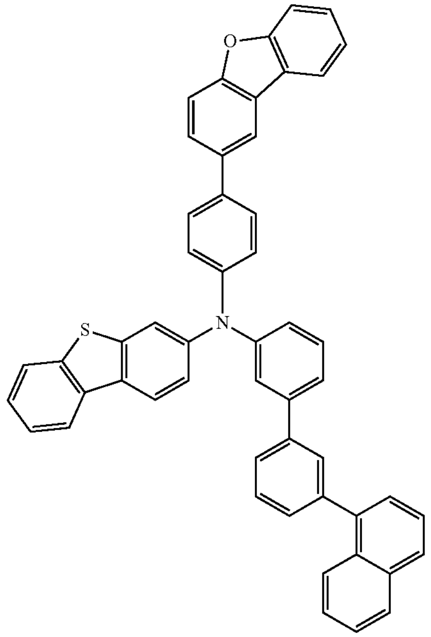

-continued
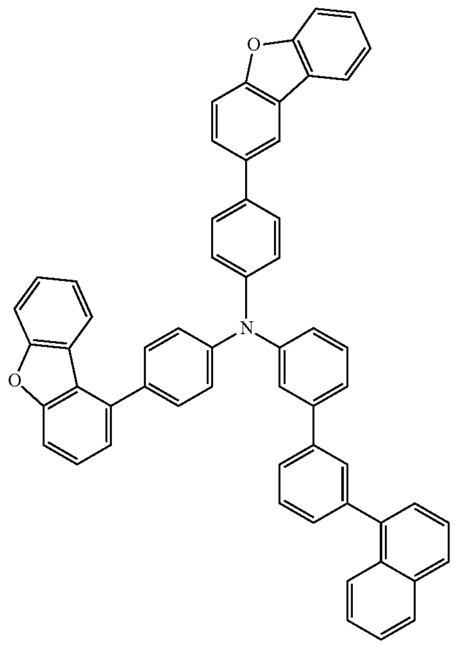
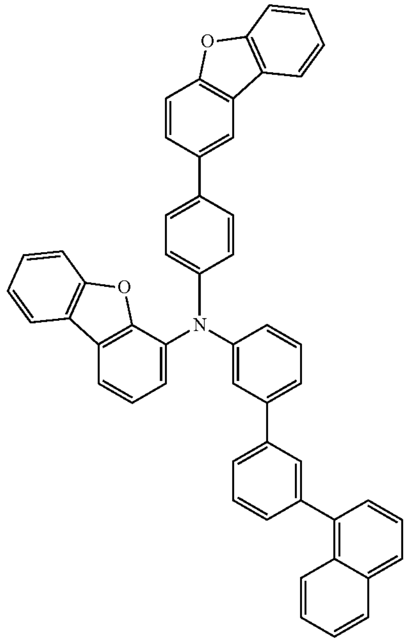
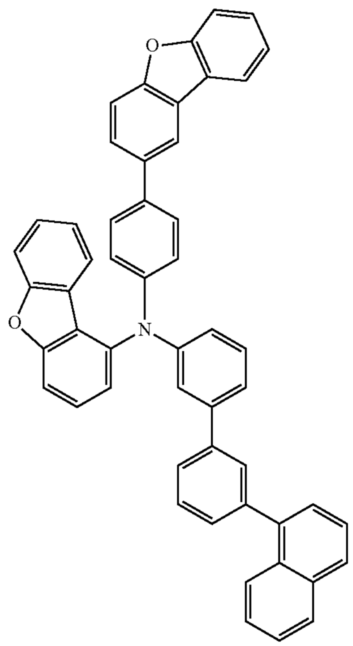
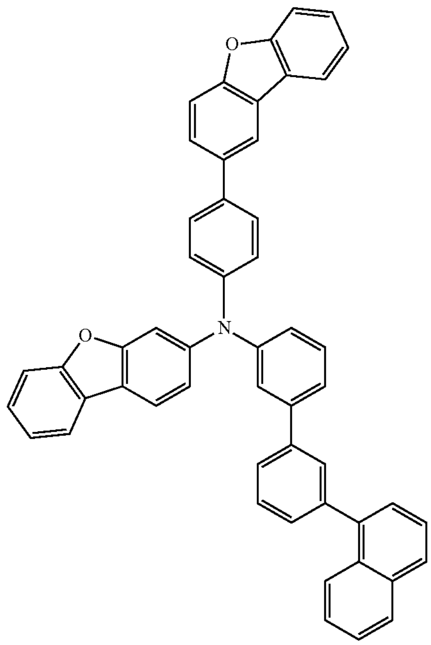
-continued

-continued
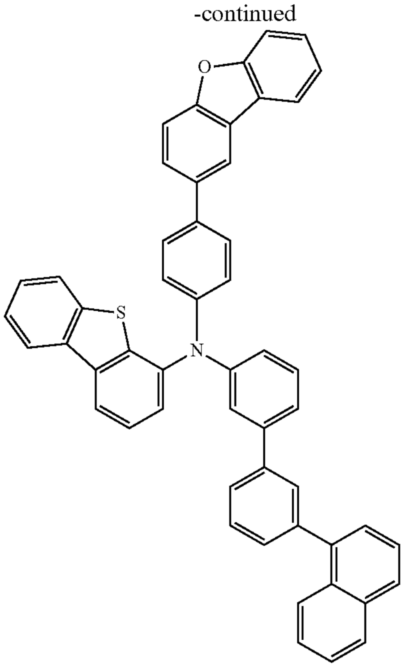
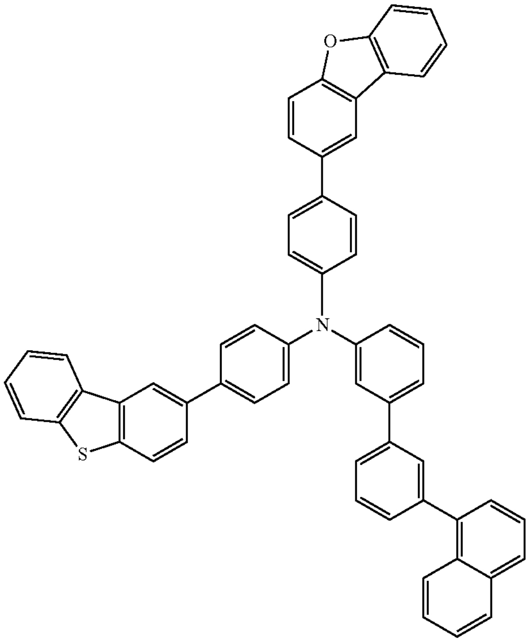
-continued
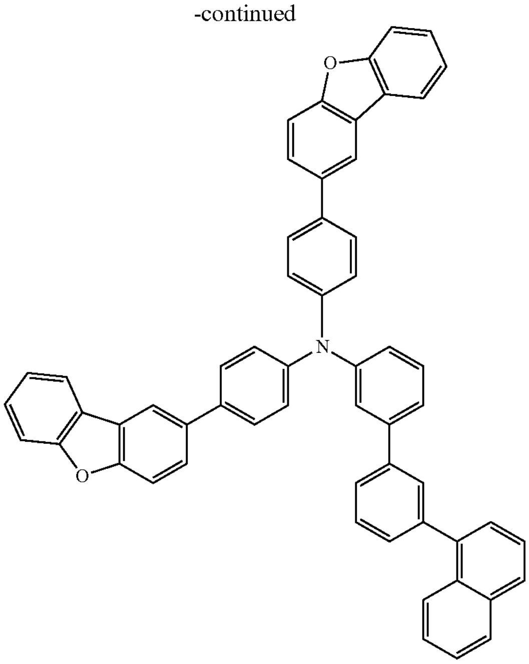
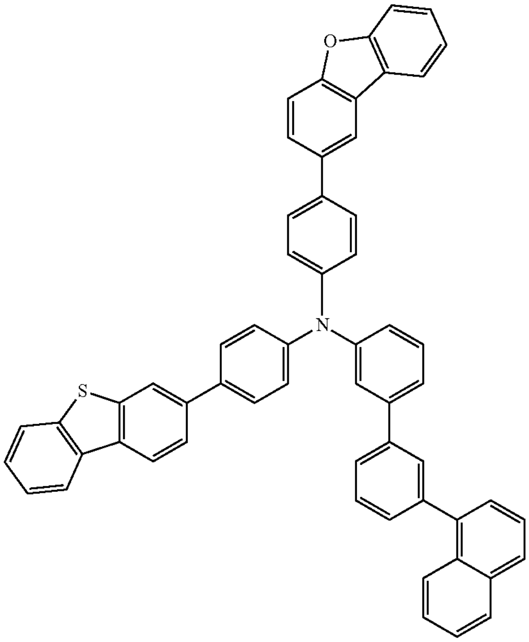

-continued
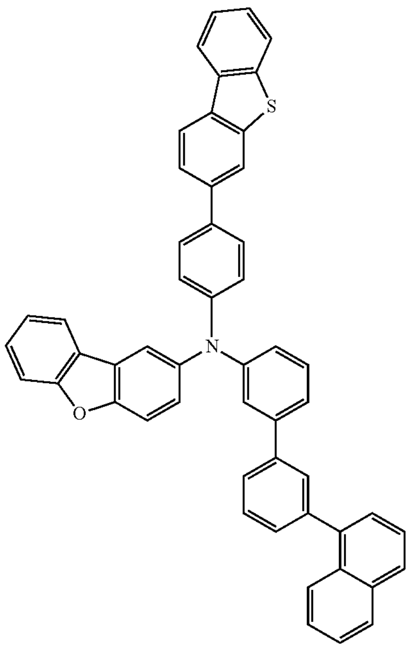
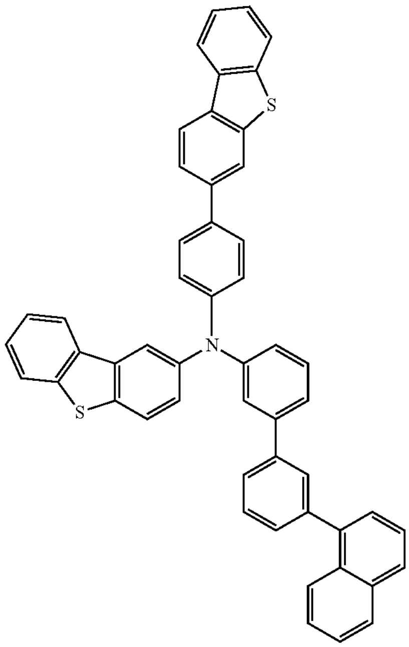
-continued
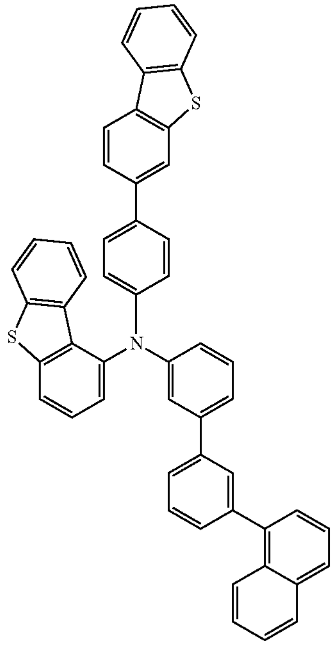
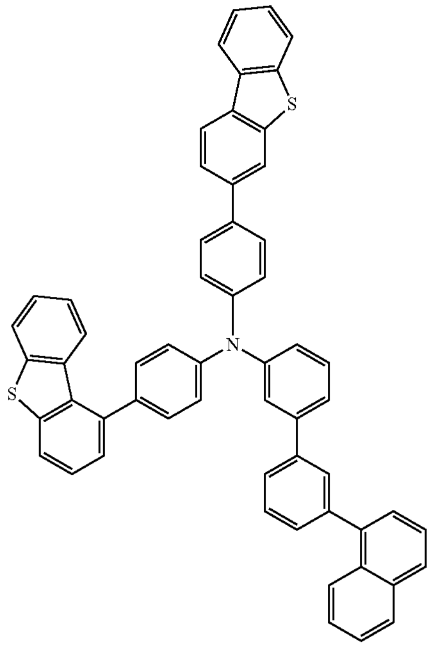

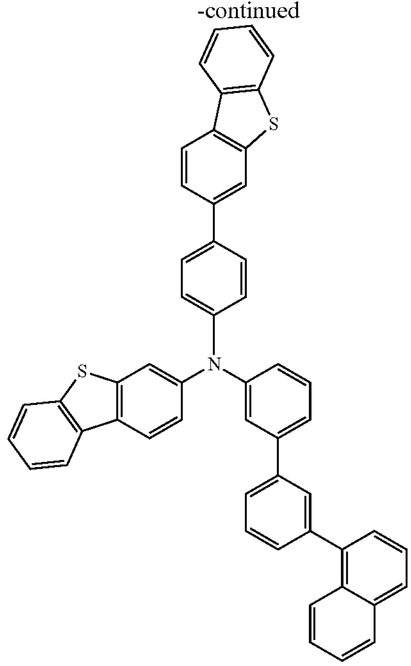
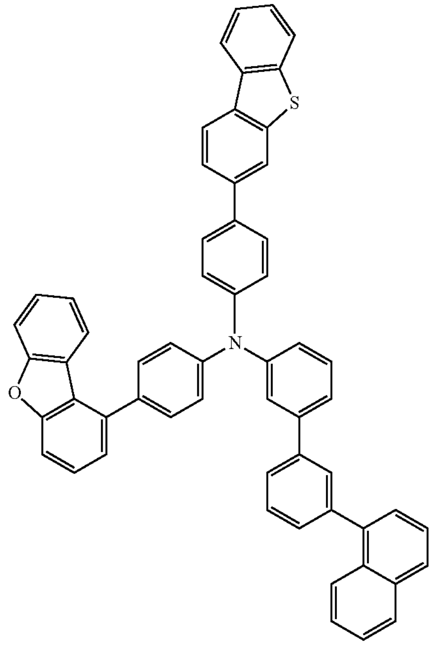
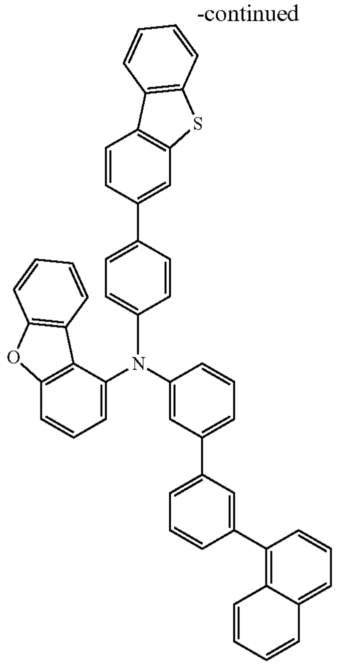
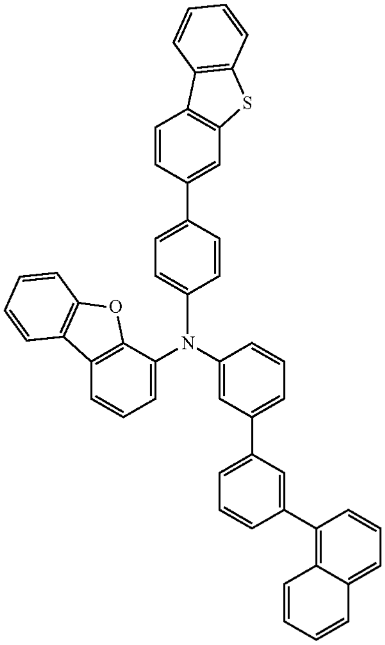

-continued
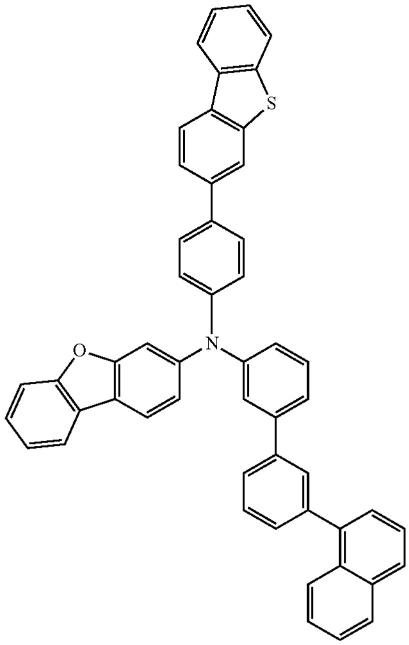
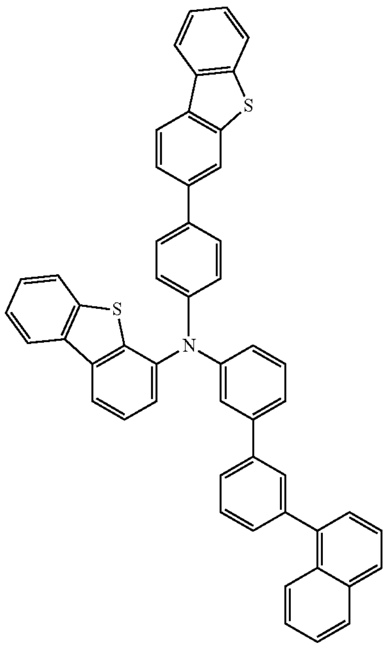
-continued
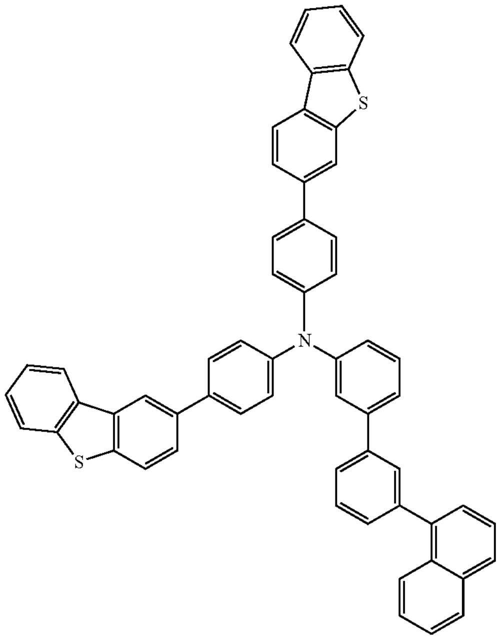
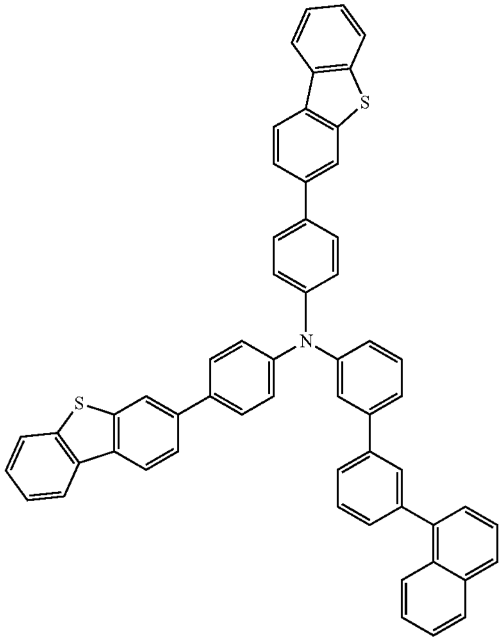

-continued
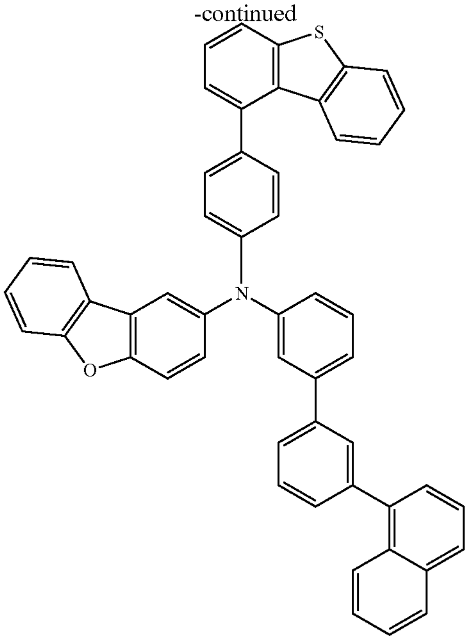
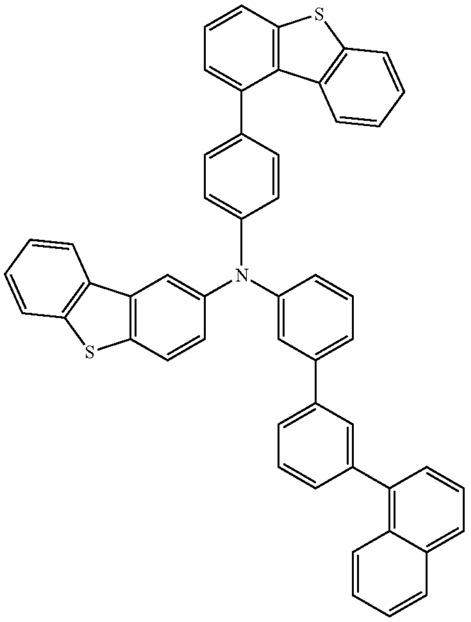
-continued
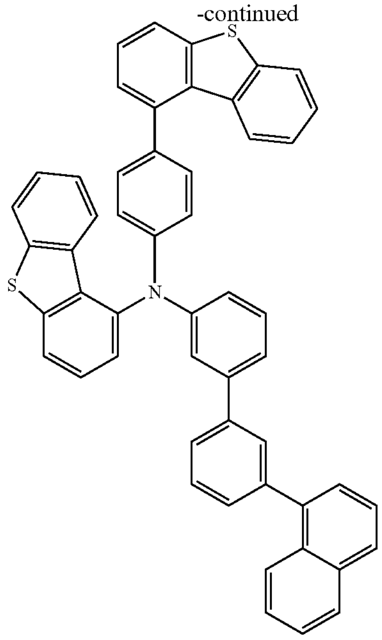
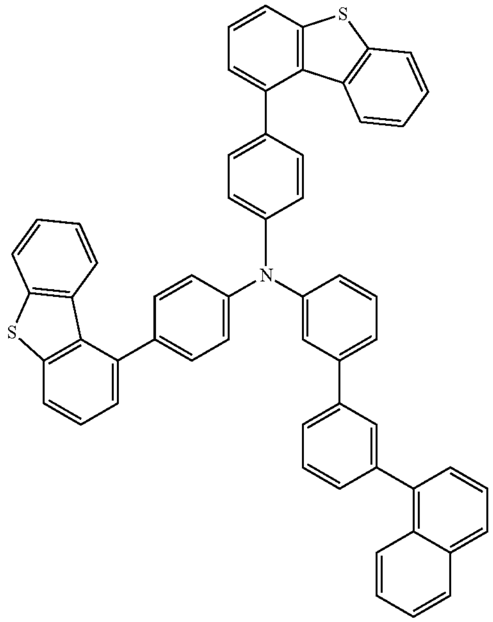

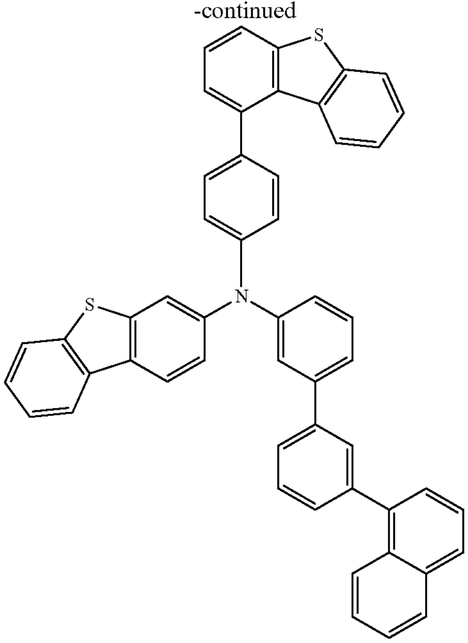
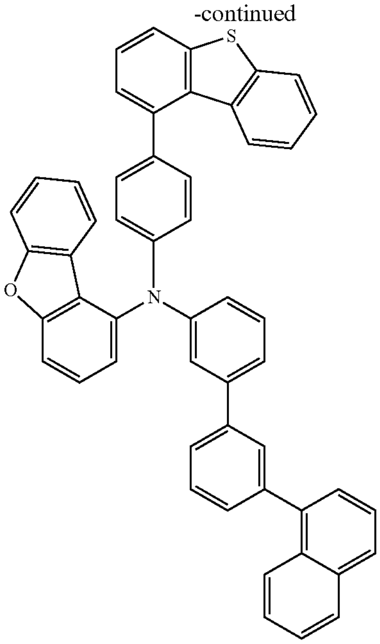
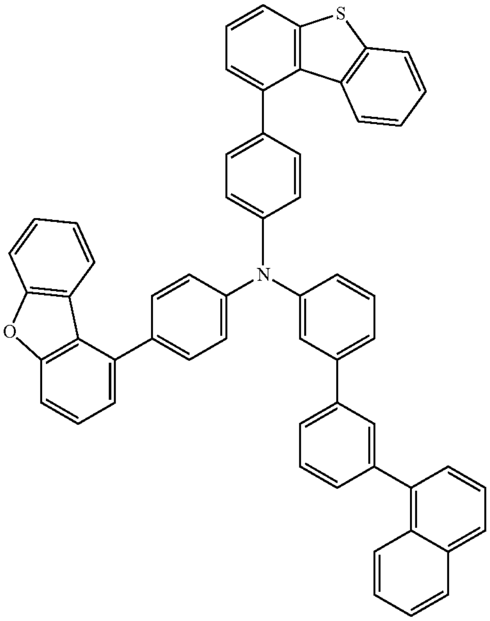
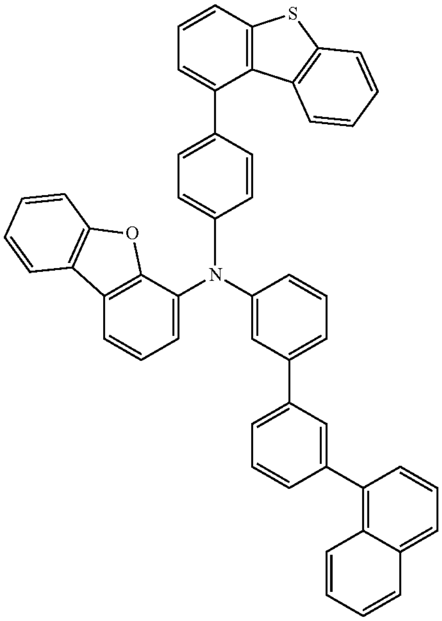

-continued
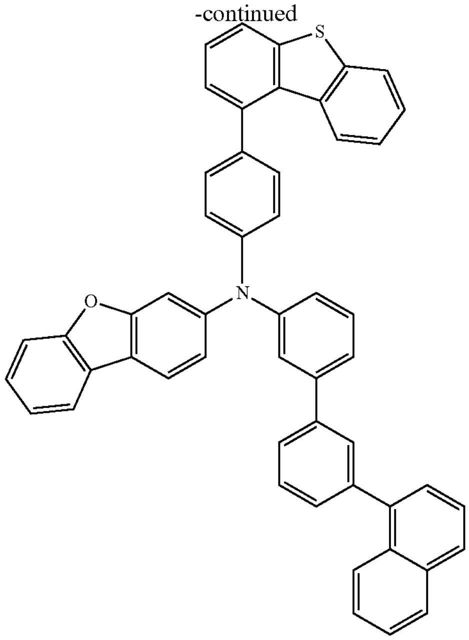
-continued
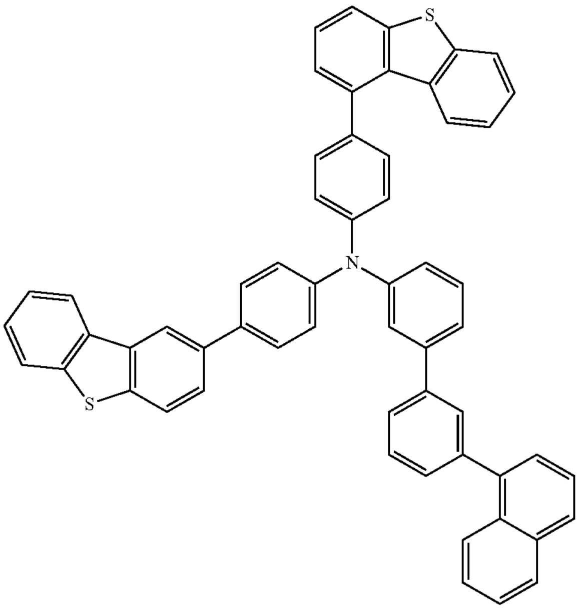
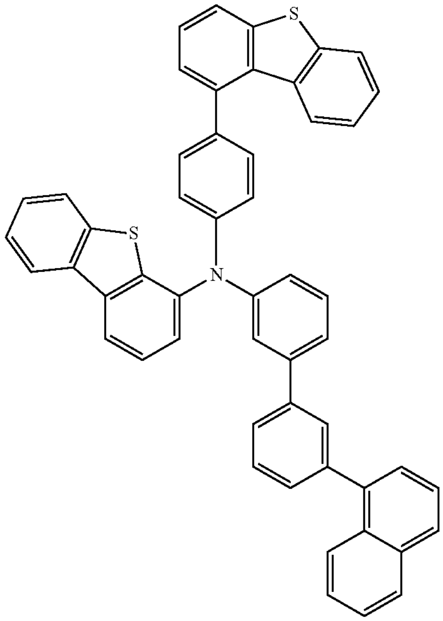
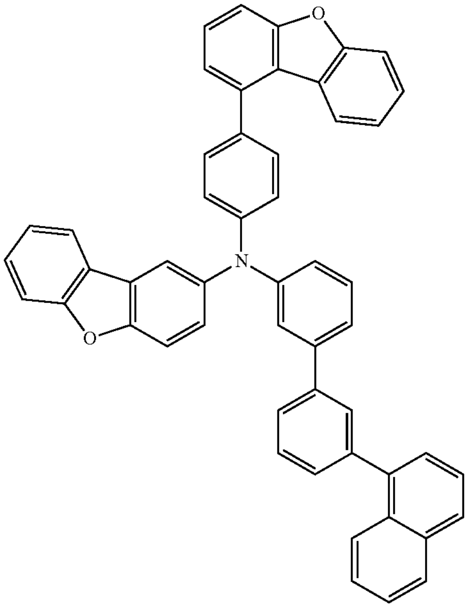

-continued
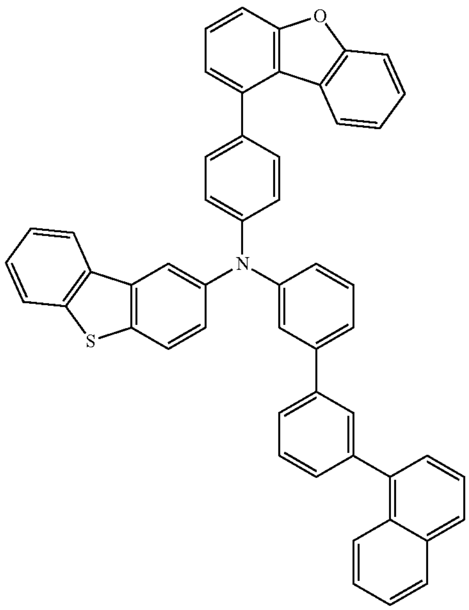
-continued
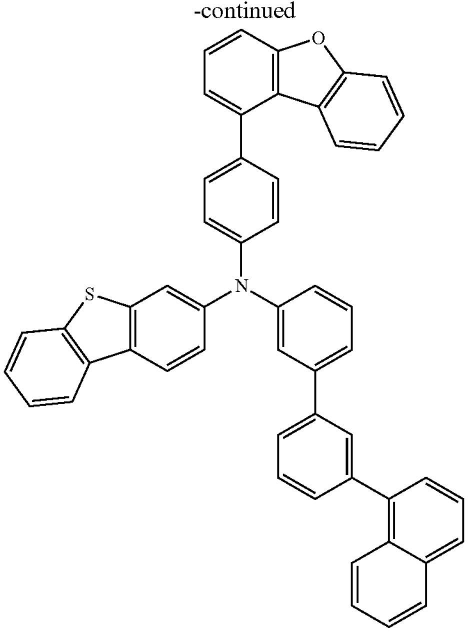
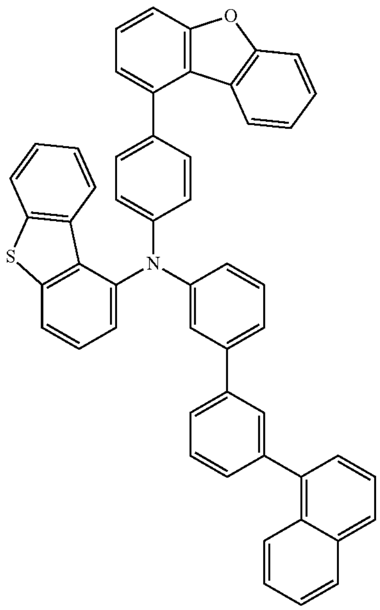
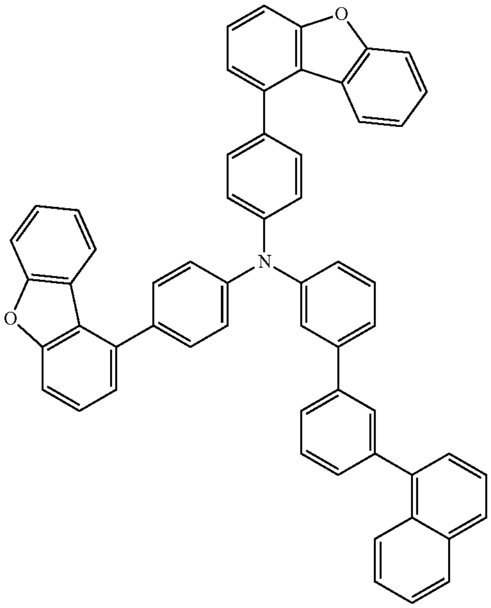

-continued
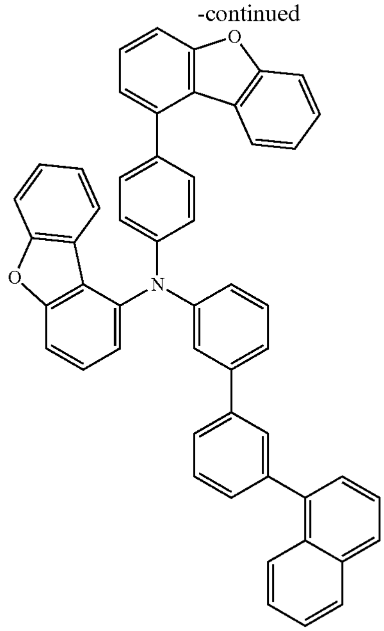
-continued
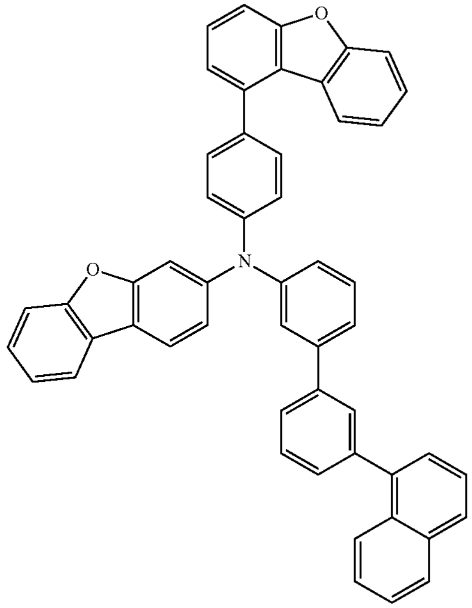
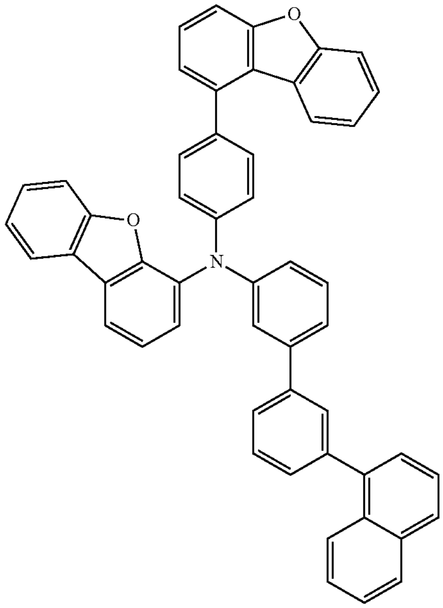
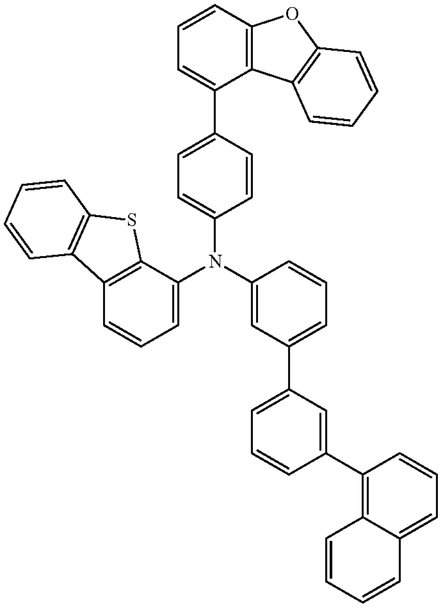

-continued
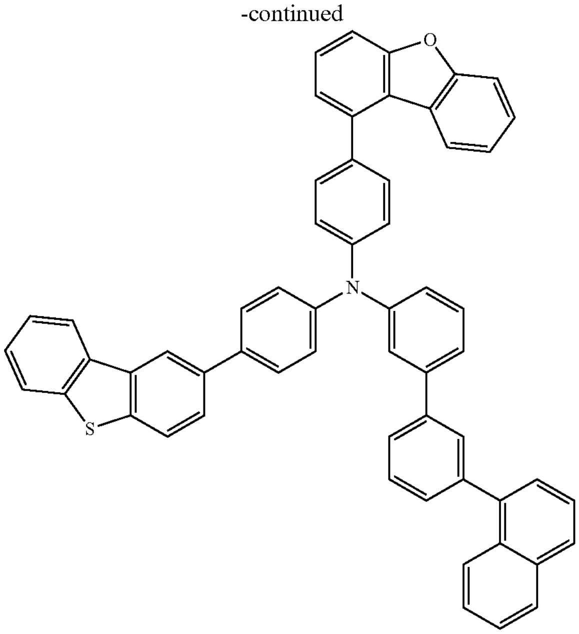
-continued
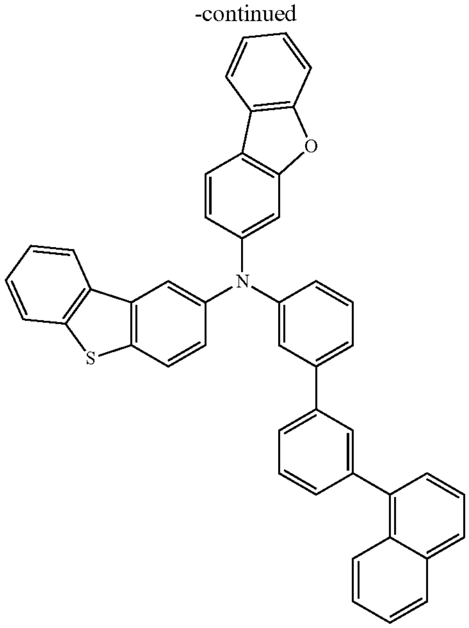
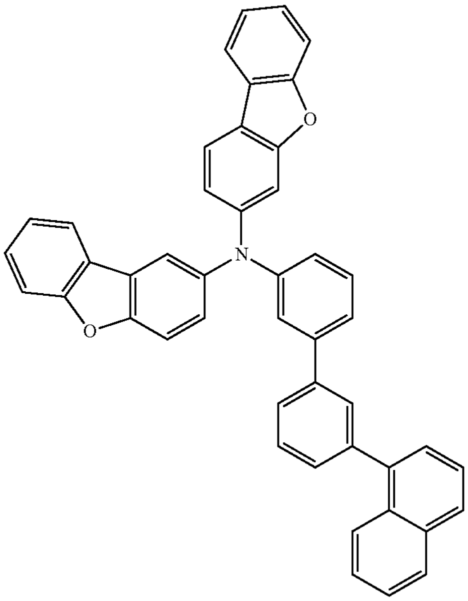
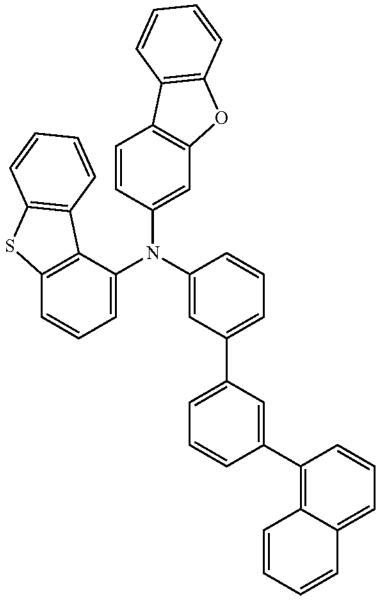

-continued
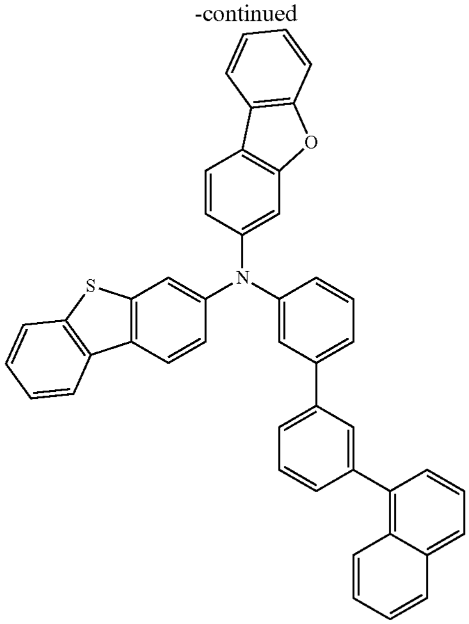
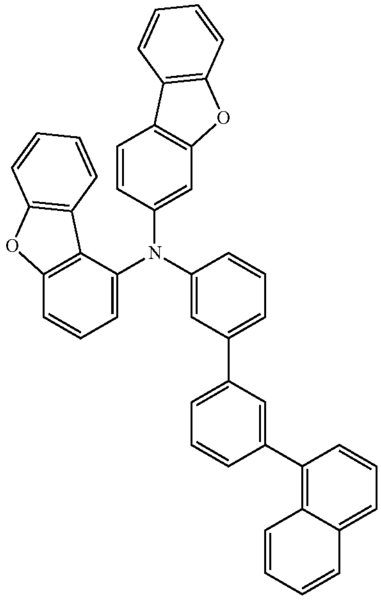
-continued
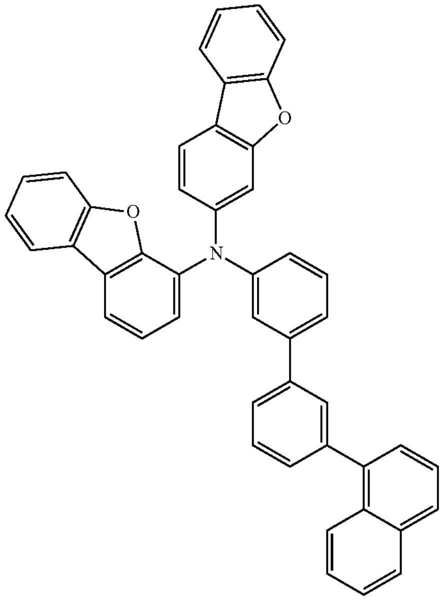
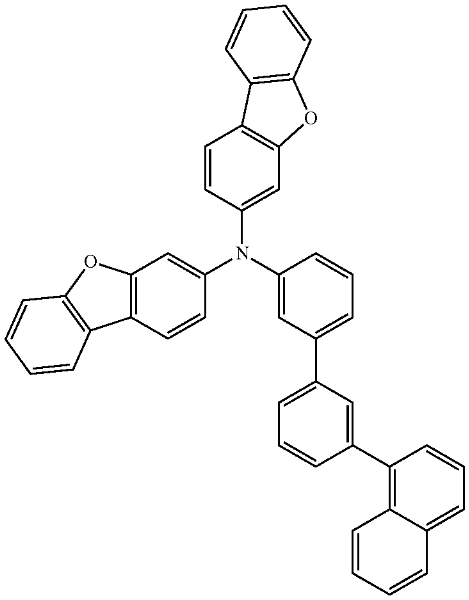

-continued
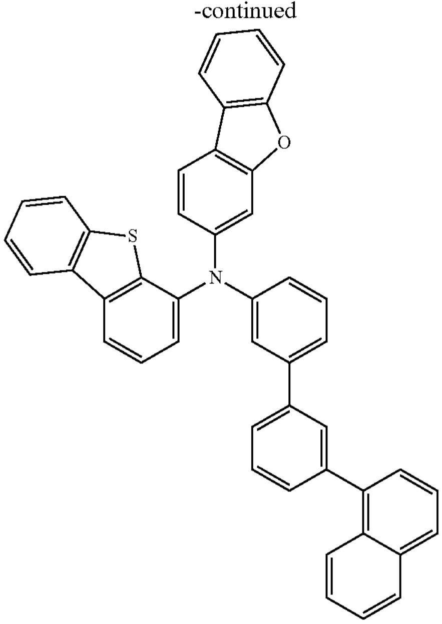
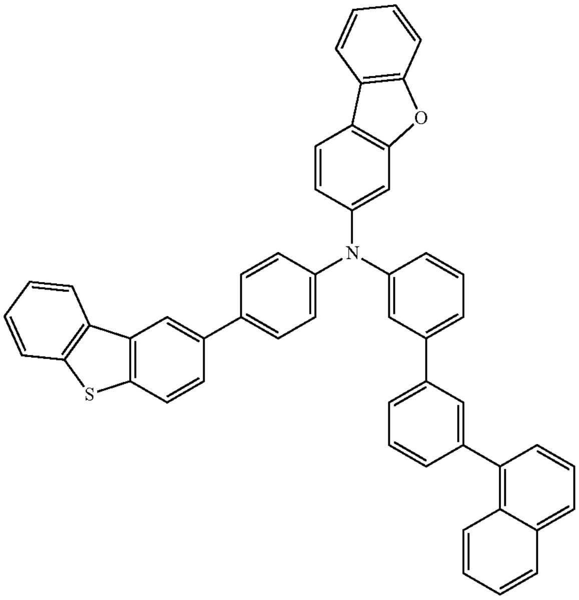
-continued
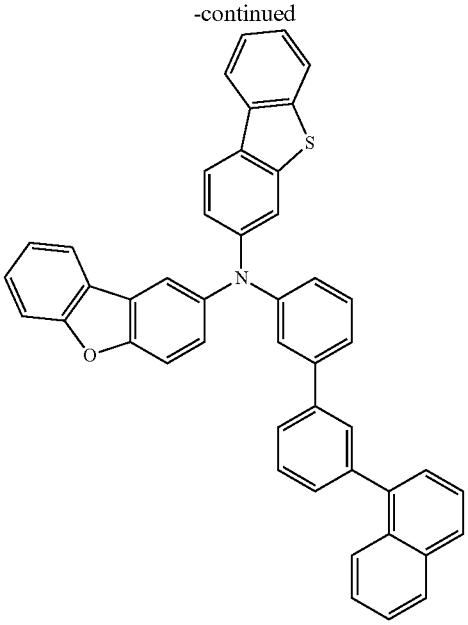
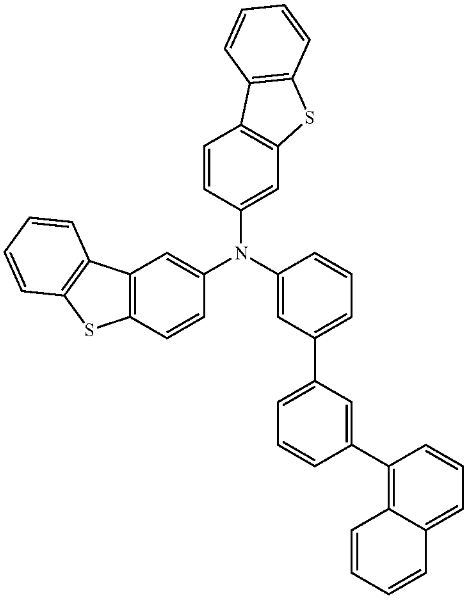

-continued
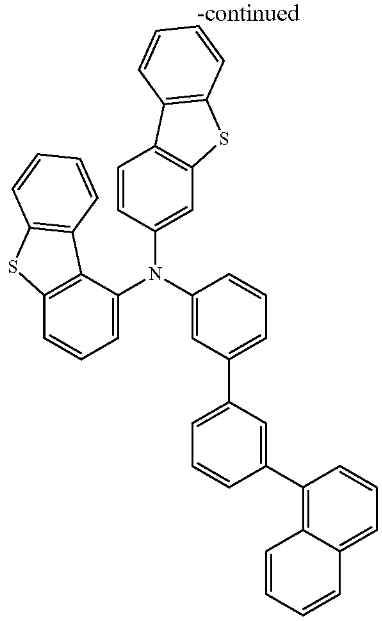
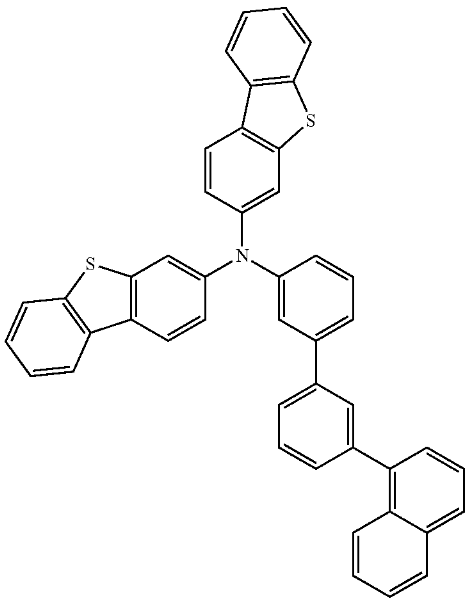
-continued
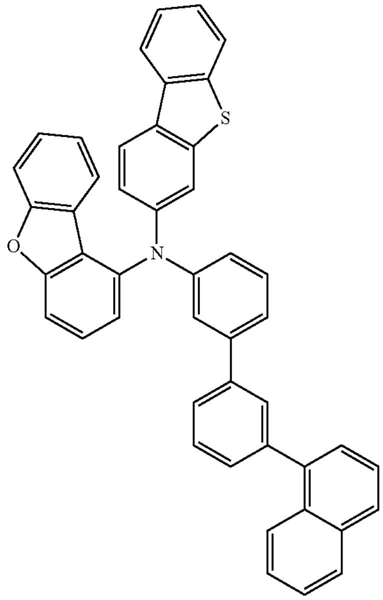
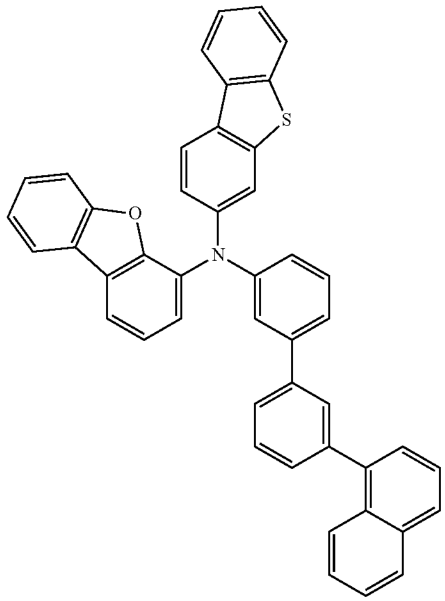

-continued
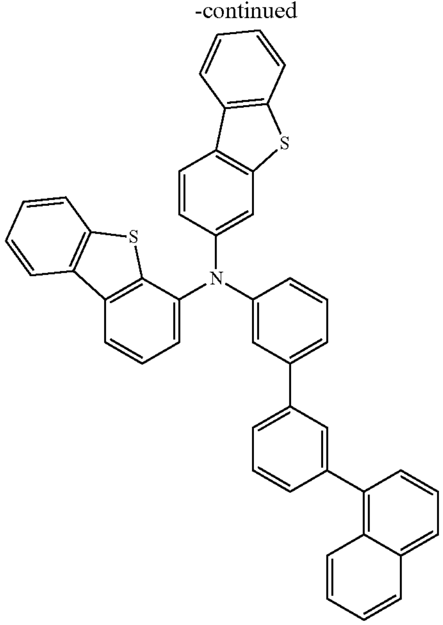
-continued
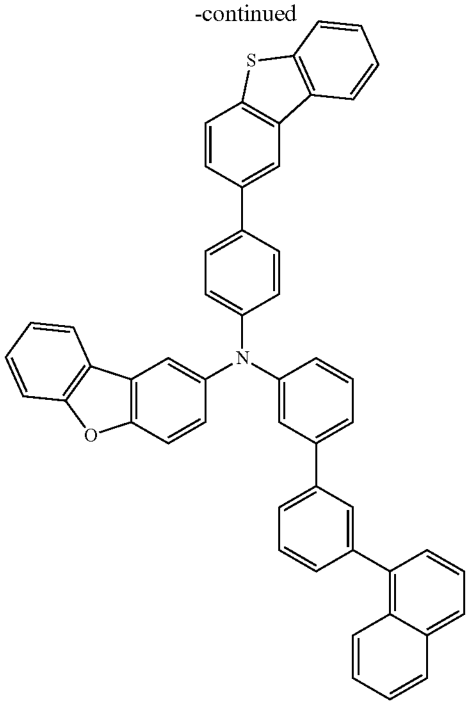
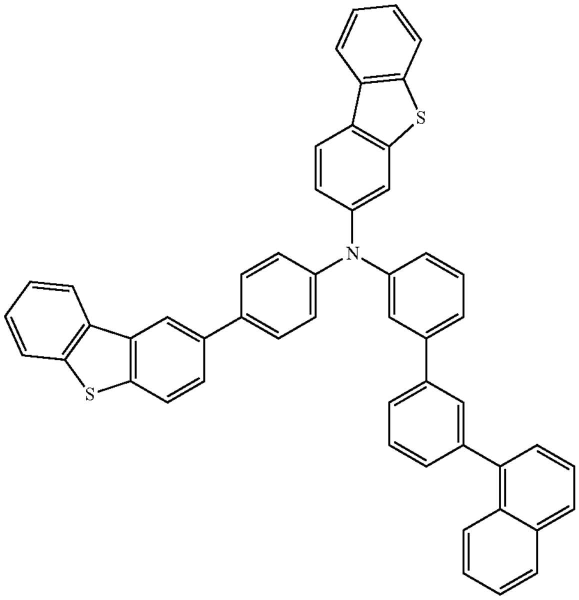
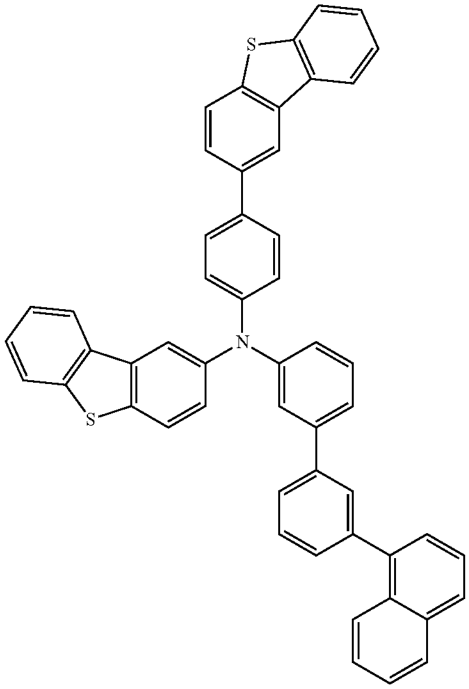

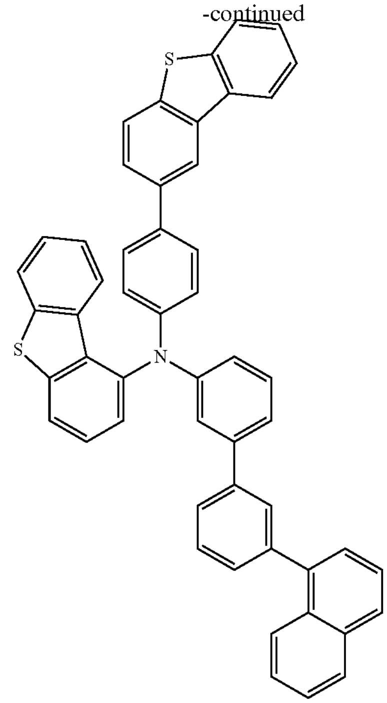
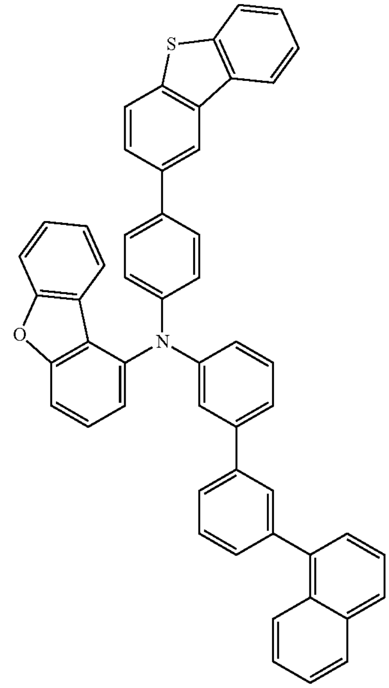
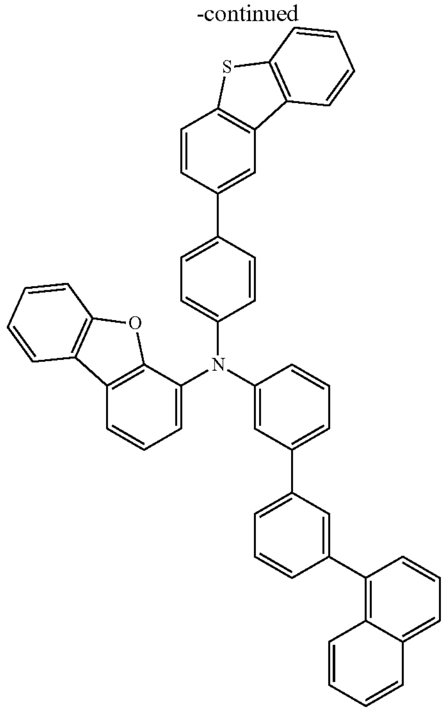
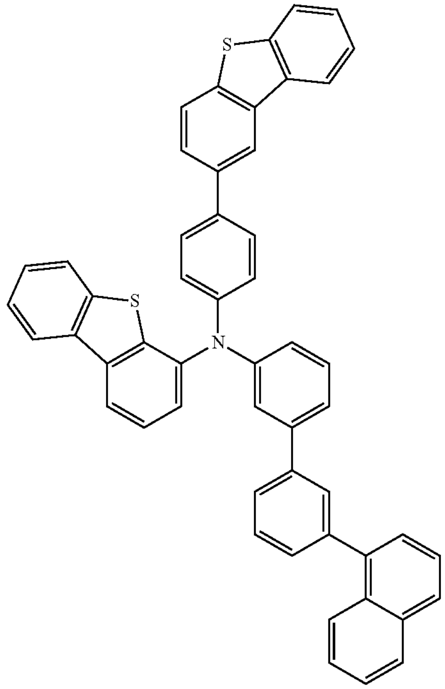

-continued
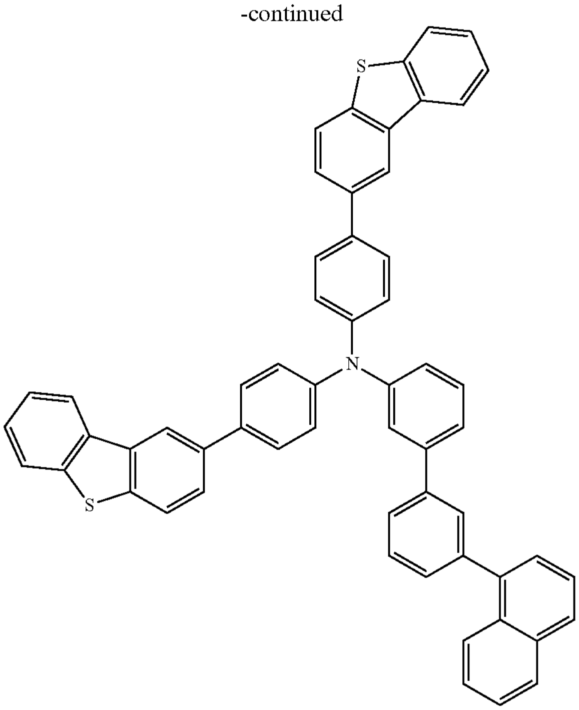
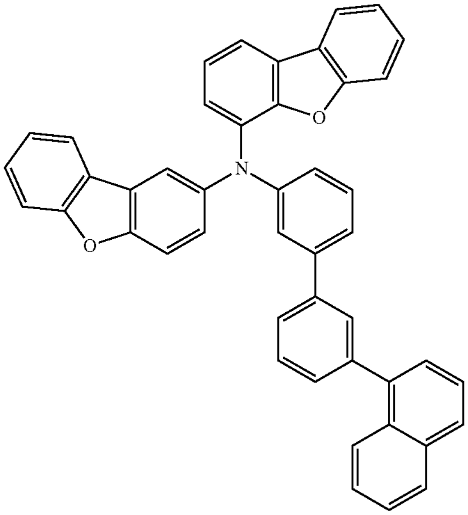
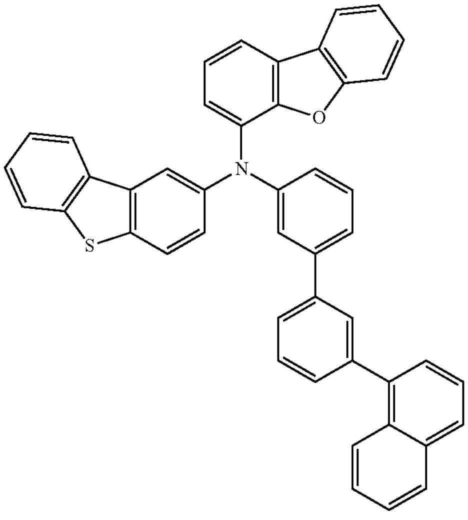
-continued
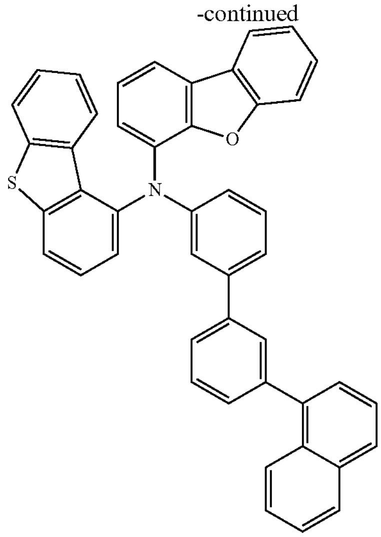
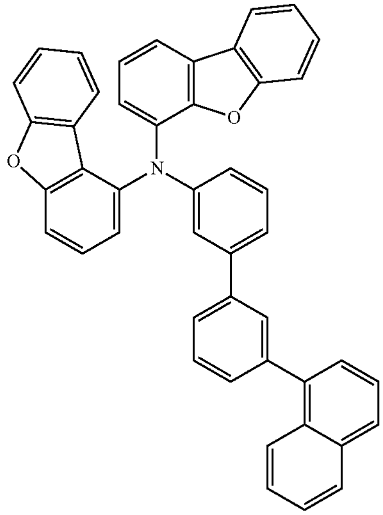
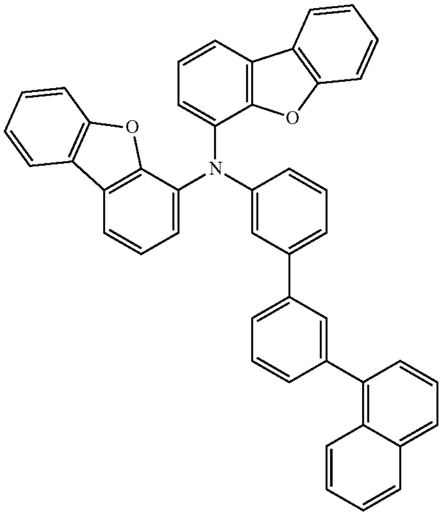

-continued
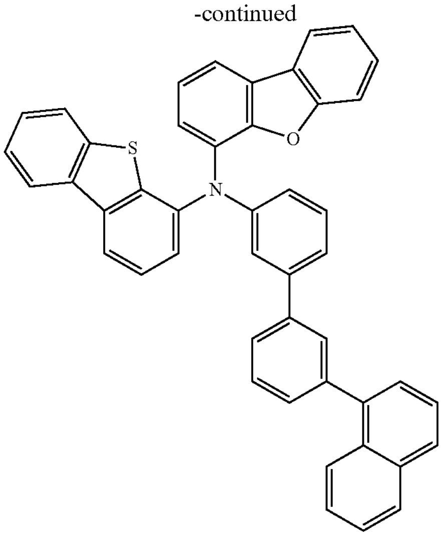
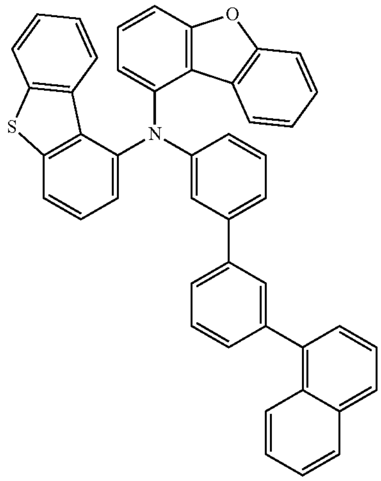
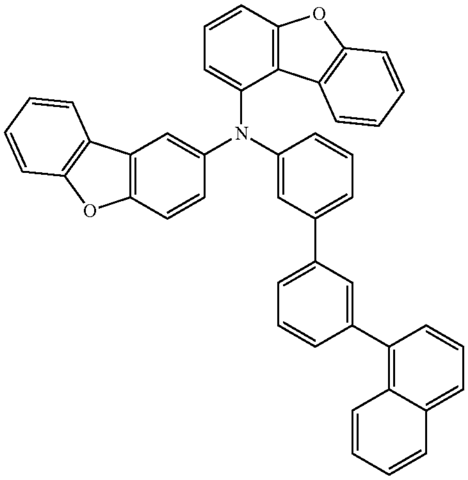
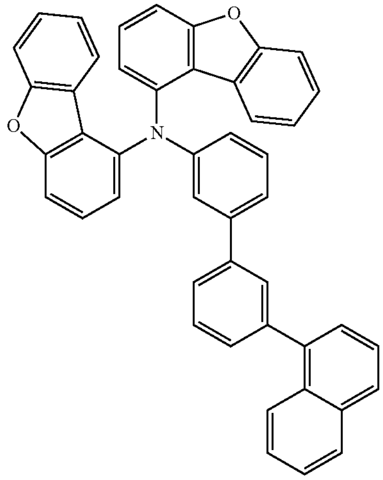
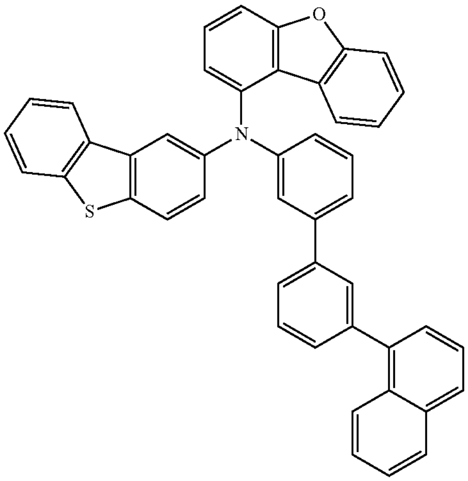
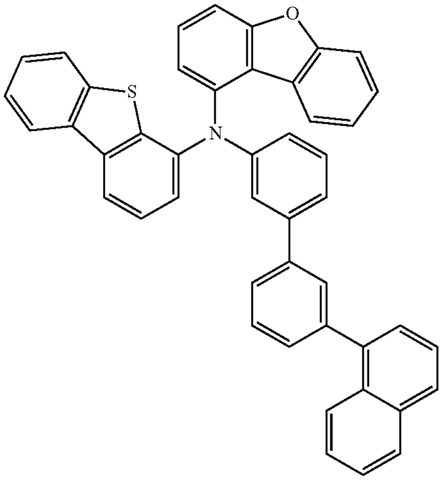
-continued -continued
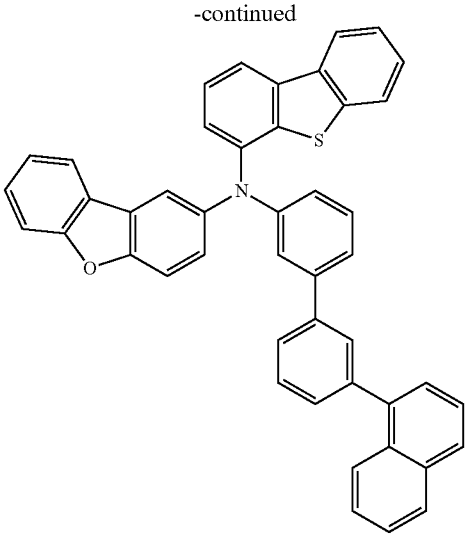
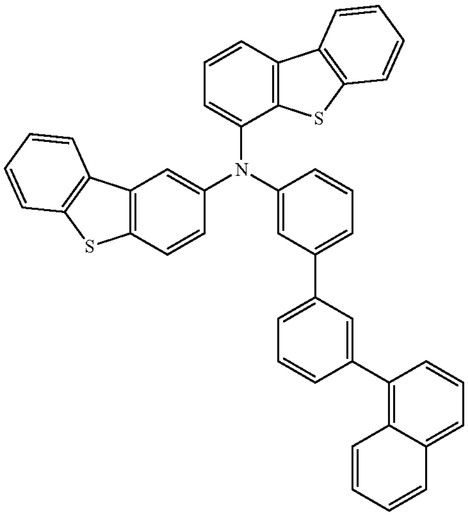
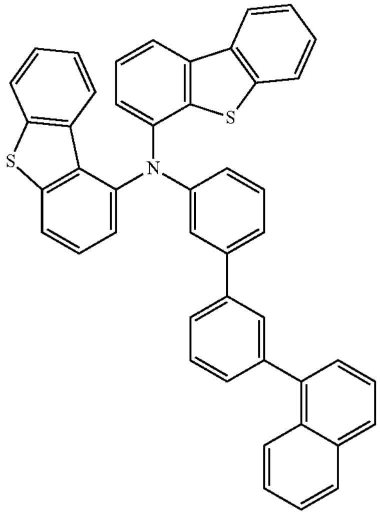
-continued
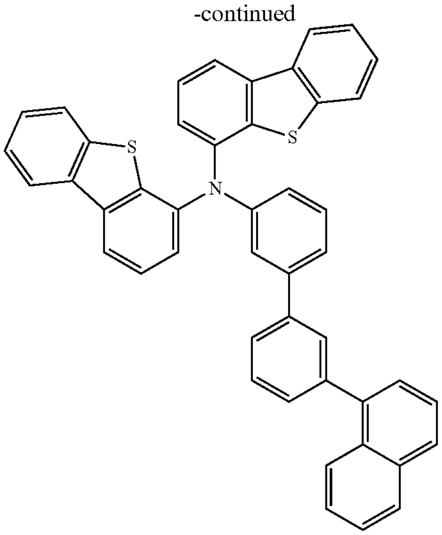
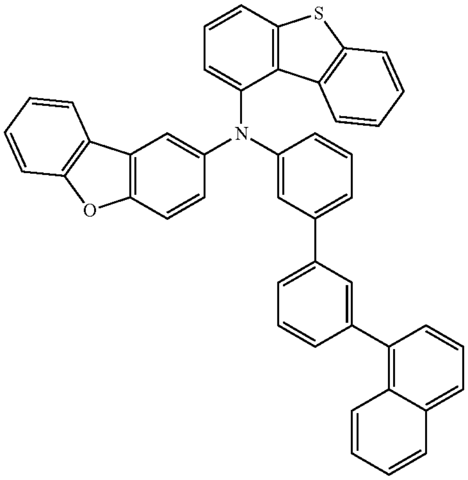
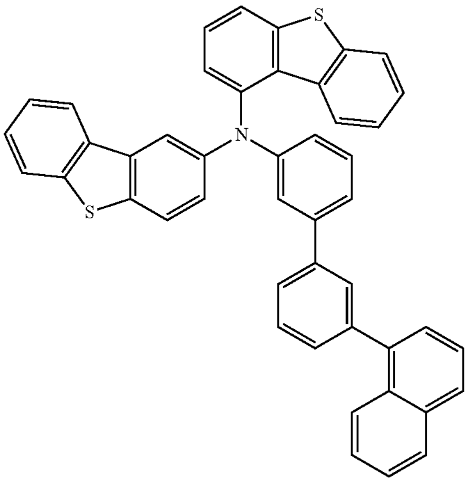

-continued

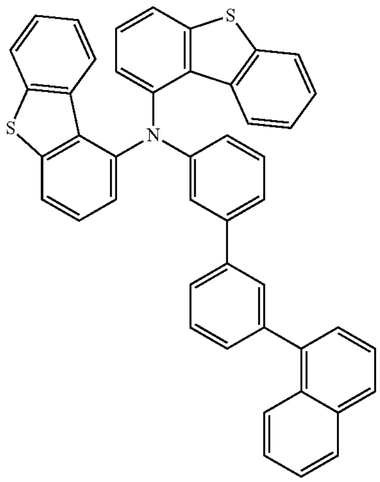

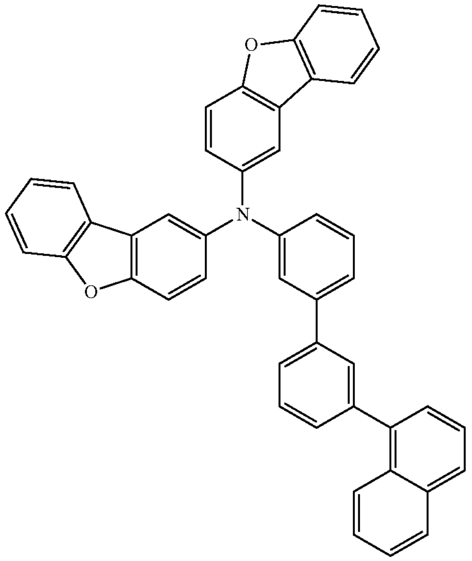

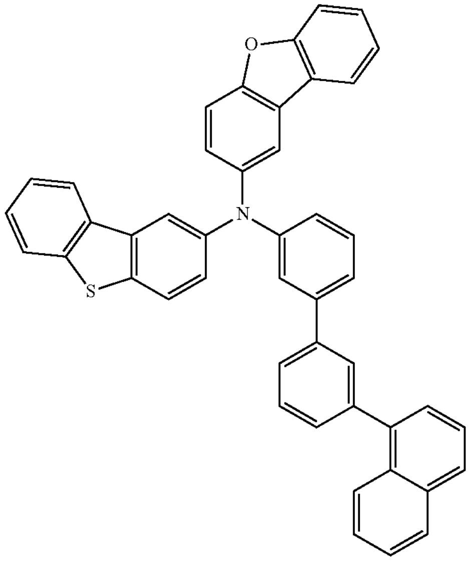

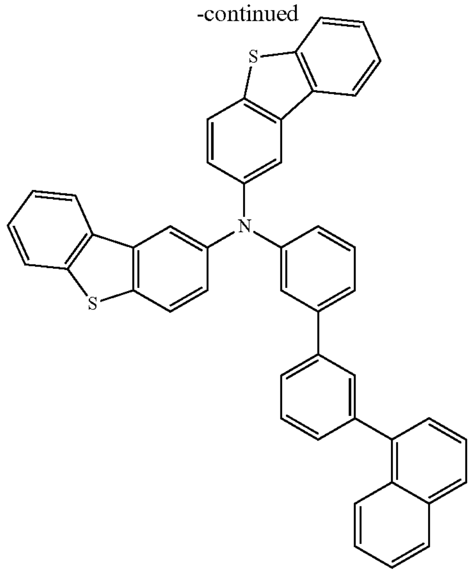

Material for Organic EL Devices

The material for organic EL devices of one embodiment of the present invention contains the inventive compound. The content of the inventive compound in the material for organic EL devices of the present invention may be 1% by mass or more (including 100%), and is preferably 10% by mass or more (including 100%), more preferably 50% by mass or more (including 100%), further preferably 80% by mass or more (including 100%), still further preferably 90% by mass or more (including 100%). The material for organic EL devices of one embodiment of the present invention is useful for the production of an organic EL device.

Organic EL Device

The organic EL device of one embodiment of the present invention includes an anode, a cathode, and organic layers intervening between the anode and the cathode. The organic layers include a light emitting layer, and at least one layer of the organic layers contains the inventive compound.

Examples of the organic layer containing the inventive compound include a hole transporting zone (such as a hole injecting layer, a hole transporting layer, an electron blocking layer, and an exciton blocking layer) intervening between the anode and the light emitting layer, the light emitting layer, a space layer, and an electron transporting zone (such as an electron injecting layer, an electron transporting layer, and a hole blocking layer) intervening between the cathode and the light emitting layer, but are not limited thereto. The inventive compound is preferably used as a material for the electron transporting zone or the light emitting layer in a fluorescent or phosphorescent EL device, more preferably as a material for the hole transporting zone, further preferably as a material for the hole injecting layer, the hole transporting layer, the electron blocking layer, or the exciton blocking layer, and particularly preferably as a material for the hole injecting layer or the hole transporting layer.

The organic EL device of one embodiment of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Above all, the fluorescent light emission-type device is preferred. The "light emitting unit" referred to herein refers to a minimum unit that emits light through recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

The light emitting unit may be a multilayer type having a plurality of phosphorescent light emitting layers or fluorescent light emitting layers. In this case, a space layer may intervene between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

(a) (hole injecting layer/) hole transporting layer/fluorescent light emitting layer/electron transporting layer (/electron injecting layer)
(b) (hole injecting layer/) hole transporting layer/phosphorescent light emitting layer/electron transporting layer (/electron injecting layer)
(c) (hole injecting layer/) hole transporting layer/first fluorescent light emitting layer/second fluorescent light emitting layer/electron transporting layer (/electron injecting layer)
(d) (hole injecting layer/) hole transporting layer/first phosphorescent light emitting layer/second phosphorescent light emitting layer/electron transporting layer (/electron injecting layer)
(e) (hole injecting layer/) hole transporting layer/phosphorescent light emitting layer/space layer/fluorescent light emitting layer/electron transporting layer (/electron injecting layer)
(f) (hole injecting layer/) hole transporting layer/first phosphorescent light emitting layer/second phosphorescent light emitting layer/space layer/fluorescent light emitting layer/electron transporting layer (/electron injecting layer)
(g) (hole injecting layer/) hole transporting layer/first phosphorescent light emitting layer/space layer/second phosphorescent light emitting layer/space layer/fluorescent light emitting layer/electron transporting layer (/electron injecting layer)
(h) (hole injecting layer/) hole transporting layer/phosphorescent light emitting layer/space layer/first fluorescent light emitting layer/second fluorescent light emitting layer/electron transporting layer (/electron injecting layer)
(i) (hole injecting layer/) hole transporting layer/electron blocking layer/fluorescent light emitting layer/electron transporting layer (/electron injecting layer)
(j) (hole injecting layer/) hole transporting layer/electron blocking layer/phosphorescent light emitting layer/electron transporting layer (/electron injecting layer)
(k) (hole injecting layer/) hole transporting layer/exciton blocking layer/fluorescent light emitting layer/electron transporting layer (/electron injecting layer)
(l) (hole injecting layer/) hole transporting layer/exciton blocking layer/phosphorescent light emitting layer/electron transporting layer (/electron injecting layer)
(m) (hole injecting layer/) first hole transporting layer/second hole transporting layer/fluorescent light emitting layer/electron transporting layer (/electron injecting layer)
(n) (hole injecting layer/) first hole transporting layer/second hole transporting layer/phosphorescent light emitting layer/electron transporting layer (/electron injecting layer)
(o) (hole injecting layer/) first hole transporting layer/second hole transporting layer/fluorescent light emitting layer/first electron transporting layer/second electron transporting layer (/electron injecting layer)
(p) (hole injecting layer/) first hole transporting layer/second hole transporting layer/phosphorescent light emitting layer/first electron transporting layer/second electron transporting layer (/electron injecting layer)
(q) (hole injecting layer/) hole transporting layer/fluorescent light emitting layer/hole blocking layer/electron transporting layer (/electron injecting layer)
(r) (hole injecting layer/) hole transporting layer/phosphorescent light emitting layer/hole blocking layer/electron transporting layer (/electron injecting layer)
(s) (hole injecting layer/) hole transporting layer/fluorescent light emitting layer/exciton blocking layer/electron transporting layer (/electron injecting layer)
(t) (hole injecting layer/) hole transporting layer/phosphorescent light emitting layer/exciton blocking layer/electron transporting layer (/electron injecting layer)

The phosphorescent and fluorescent light emitting layers may emit emission colors different from each other, respectively. Specifically, in the light emitting unit (f), a layer configuration, such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer, may be exemplified.

An electron blocking layer may be properly provided between each light emitting layer and the hole transporting layer or the space layer. A hole blocking layer may be properly provided between each light emitting layer and the electron transporting layer. The employment of the electron blocking layer or the hole blocking layer allows to improve the emission efficiency by trapping electrons or holes within the light emitting layer and increasing the probability of charge recombination in the light emitting layer.

As a representative device configuration of the tandem type organic EL device, the following device configuration may be exemplified.

(2) Anode/First Light Emitting Unit/Intermediate Layer/Second Light Emitting Unit/Cathode For example, each of the first light emitting unit and the second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration can be used, in which electrons are supplied to the first light emitting unit, and holes are supplied to the second light emitting unit.

FIG. 1 is a schematic illustration showing an example of the configuration of the organic EL device of one embodiment of the present invention. The organic EL device 1 of this example includes a substrate 2, an anode 3, a cathode 4, and a light emitting unit 10 disposed between the anode 3 and the cathode 4. The light emitting unit 10 includes a light emitting layer 5. A hole transporting zone 6 (such as a hole injecting layer and a hole transporting layer) is provided between the light emitting layer 5 and the anode 3, and an electron transporting zone 7 (such as an electron injecting layer and an electron transporting layer) is provided between the light emitting layer 5 and the cathode 4. In addition, an electron blocking layer (which is not shown in the figure) may be provided on the side of the anode 3 of the light emitting layer 5, and a hole blocking layer (which is not shown in the figure) may be provided on the side of the cathode 4 of the light emitting layer 5. According to the configuration, electrons and holes are trapped in the light emitting layer 5, thereby enabling one to further increase the production efficiency of excitons in the light emitting layer 5.

Figure 2:
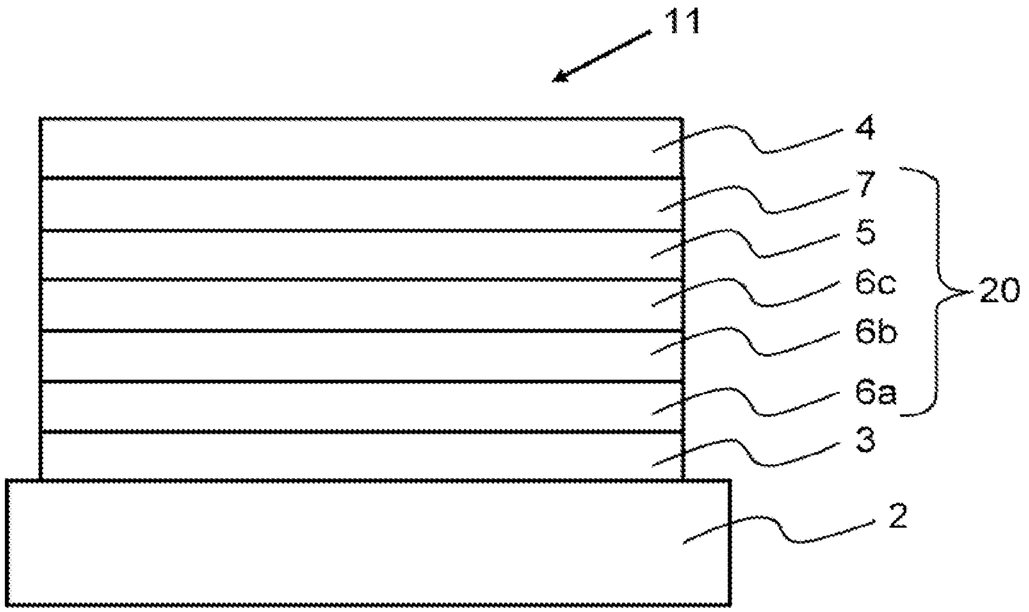
FIG. 2 is a schematic illustration showing another example of the layer configuration of the organic EL device according to one embodiment of the present invention.

FIG. 2 is a schematic illustration showing another configuration of the organic EL device of one embodiment of the present invention. An organic EL device 11 includes the substrate 2, the anode 3, the cathode 4, and a light emitting unit 20 disposed between the anode 3 and the cathode 4. The light emitting unit 20 includes the light emitting layer 5. A hole transporting zone disposed between the anode 3 and the light emitting layer 5 includes a hole injecting layer 6*a*, a first hole transporting layer 6*b* and a second hole transporting layer 6*c*. The electron transporting zone disposed between the light emitting layer 5 and the cathode 4 includes a first electron transporting layer 7*a* and a second electron transporting layer 7*b*.

In the present invention, a host combined with a fluorescent dopant (a fluorescent emitting material) is referred to as a fluorescent host, and a host combined with a phosphorescent dopant is referred to as a phosphorescent host. The fluorescent host and the phosphorescent host are not distinguished from each other merely by the molecular structures thereof. Specifically, the phosphorescent host means a material that forms a phosphorescent light emitting layer containing a phosphorescent dopant, but does not mean unavailability as a material that forms a fluorescent light emitting layer. The same also applies to the fluorescent host.

Substrate

The substrate is used as a support of the organic EL device. Examples of the substrate include a plate of glass, quartz, and plastic. In addition, a flexible substrate may be used. Examples of the flexible substrate include a plastic substrate made of polycarbonate, polyarylate, polyether sulfone, polypropylene, polyester, polyvinyl fluoride, or polyvinyl chloride. In addition, an inorganic vapor deposition film can be used.

Anode

It is preferred that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, examples there include gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride).

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, or the like.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals, such as lithium (Li) and cesium (Cs), alkaline earth metals, such as magnesium (Mg), calcium (Ca), and strontium (Sr), and alloys containing these (such as MgAg and AlLi), and rare earth metals, such as europium (Eu), and ytterbium (Yb) and alloys containing these. When the anode is formed by using the alkali metals, the alkaline earth metals, and alloys containing these, a vacuum vapor deposition method or a sputtering method can be used. Further, when a silver paste or the like is used, a coating method, an inkjet method, or the like can be used.

Hole Injecting Layer

The hole injecting layer is a layer containing a material having a high hole injection capability (a hole injecting material) and is provided between the anode and the light emitting layer, or between the hole transporting layer, if exists, and the anode.

As the hole injecting material except the inventive compound, molybdenum oxide, titanium oxide, vanadium oxide, rhenium oxide, ruthenium oxide, chromium oxide, zirconium oxide, hafnium oxide, tantalum oxide, silver oxide, tungsten oxide and manganese oxide can be used.

Examples of the hole injecting layer material also include aromatic amine compounds as low-molecular weight organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High-molecular weight compounds (such as oligomers, dendrimers, and polymers) may also be used. Examples thereof include high-molecular weight compounds, such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD). In addition, high-molecular weight compounds to which an acid is added, such as poly(3,4-ethylenedioxythiophene)/poly (styrene sulfonic acid) (PEDOT/PSS), and polyaniline/poly (styrenesulfonic acid) (PAni/PSS), can also be used.

Furthermore, it is also preferred to use an acceptor material, such as a hexaazatriphenylene (HAT) compound represented by formula (K).

(K)

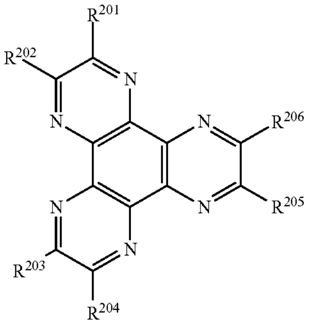

In the aforementioned formula, $R^{201}$ to $R^{206}$ each independently represent a cyano group, —$CONH_2$, a carboxy group, or —$COOR^{207}$ ($R^{207}$ represents an alkyl group having 1 to 20 carbon atoms or a cycloalkyl group having 3 to 20 carbon atoms). In addition, adjacent two selected from $R^{201}$ and $R^{202}$, $R^{203}$ and $R^{204}$, and $R^{205}$ and $R^{200}$ may be bonded to each other to form a group represented by —CO—O—CO—.

Examples of $R^{207}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting capability (a hole transporting material) and is provided between the anode and the light emitting layer, or between the hole injecting layer, if exists, and the light emitting layer. The inventive compound can be used as the hole transporting layer either singly or as combined with the compound mentioned below.

The hole transporting layer may have a single layer structure or a multilayer structure including two or more layers. For example, the hole transporting layer may have a two-layer structure including a first hole transporting layer (anode side) and a second hole transporting layer (cathode side). In one embodiment of the present invention, the hole transporting layer having a single layer structure is preferably disposed adjacent to the light emitting layer, and the hole transporting layer that is closest to the cathode in the multilayer structure, such as the second hole transporting layer in the two-layer structure, is preferably disposed adjacent to the light emitting layer. In another embodiment of the present invention, and an electron blocking layer described later may be disposed between the hole transporting layer having a single layer structure and the light emitting layer, or between the hole transporting layer that is closest to the light emitting layer in the multilayer structure and the light emitting layer.

In the hole transporting layer of a two-layer structure, the inventive compound may be in the first hole transporting layer and the second hole transporting layer, or may be in the two.

In one embodiment of the present invention, the inventive compound is preferably contained in the first hole transporting layer alone, and in another embodiment, the inventive compound is preferably contained in the second hole transporting layer alone, and in still another embodiment, the inventive compound is preferably contained in the first hole transporting layer and the second hole transporting layer.

In one embodiment of the present invention, the inventive compound contained in one or both of the first hole transporting layer and the second hole transporting layer is preferably a protium compound from the viewpoint of production cost.

The protium compound is the inventive compound where all hydrogen atoms are protium atoms.

Accordingly, the organic EL device of one embodiment of the present invention is preferably an organic EL device where one or both of the first hole transporting layer and the second hole transporting layer contain the inventive compound of substantially a protium compound alone. The "inventive compound of substantially a protium compound alone" means that the content ratio of a protium compound relative to the total amount of the inventive compound is 90 mol % or more, preferably 95 mol % or more, more preferably 99 mol % or more (each inclusive of 100%).

As the hole transporting material except the inventive compound, for example, an aromatic amine compound, a carbazole derivative, and an anthracene derivative can be used.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB). The aforementioned compounds have a hole mobility of $10^{-6}$ $cm^2/Vs$ or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High-molecular weight compounds, such as poly(N-vinylcarbazole) (abbreviation: PVK) and poly(4-vinyltriphenylamine) (abbreviation: PVTPA), can also be used.

However, compounds other than those as mentioned above can also be used so long as they are compounds high in the hole transporting capability rather than in the electron transporting capability.

Dopant Material of Light Emitting Layer

The light emitting layer is a layer containing a material having a high light emitting property (a dopant material), and various materials can be used. For example, a fluorescent emitting material or a phosphorescent emitting material can be used as the dopant material. The fluorescent emitting material is a compound that emits light from a singlet excited state, and the phosphorescent emitting material is a compound that emits from a light triplet excited state.

Examples of a blue-based fluorescent emitting material that can be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that can be used for the light emitting layer include an aromatic amine derivative. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

Examples of a red-based fluorescent emitting material that can be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

Examples of a blue-based phosphorescent emitting material that can be used for the light emitting layer include a metal complex, such as an iridium complex, an osmium complex, and a platinum complex. Specific examples thereof include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III) acetylacetonate (abbreviation: FIracac).

Examples of a green-based phosphorescent emitting material that can be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzimidazolato)iridium(III)acetylacetonate (abbreviation: Ir(pbi)2(acac)), and bis(benzo[h]quinolinato)iridium(III) acetylacetonate (abbreviation: Ir(bzq)2(acac)).

Examples of a red-based phosphorescent emitting material that can be used for the light emitting layer include a metal complex, such as an iridium complex, a platinum complex, a terbium complex, and a europium complex. Specific examples thereof include organic metal complexes, such as bis[2-(2'-benzo[4,5-α]thienyl)pyridinato-N,C3']iridium(III)acetylacetonate (abbreviation: Ir (btp) 2 (acac)), bis(1-phenylisoquinolinato-N,C2')iridium(III) acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Rare earth metal complexes, such as tris(acetylacetonate)(monophenanthroline)terbium(III) (abbreviation: Tb(acac)3 (Phen)), tris(1,3-diphenyl-1,3-propanedionate)(monophenanthroline)europium(III) (abbreviation: Eu(DBM)3 (Phen)), and tris[1-(2-thenoyl)-3,3,3-trifluoro acetonate](monophenanthroline) europium(III) (abbreviation: Eu(TTA)3(Phen)), emit light from rare earth metal ions (electron transition between different multiplicities), and thus may be used as the phosphorescent emitting material.

Host Material of Light Emitting Layer

The light emitting layer may have a configuration in which the aforementioned dopant material is dispersed in another material (a host material). The host material is preferably a material that has a higher lowest unoccupied orbital level (LUMO level) and a lower highest occupied orbital level (HOMO level) than the dopant material.

Examples of the host material include:

(1) a metal complex, such as an aluminum complex, a beryllium complex, and a zinc complex, (2) a heterocyclic compound, such as an oxadiazole derivative, a benzimidazole derivative, and a phenanthroline derivative, (3) a fused aromatic compound, such as a carbazole derivative, an anthracene derivative, a phenanthrene derivative, a pyrene derivative, and a chrysene derivative, or (4) an aromatic amine compound, such as a triarylamine derivative and a fused polycyclic aromatic amine derivative.

For example, metal complexes, such as tris(8-quinolinolato)aluminum (III) (abbreviation: Alq), tris(4-methyl-8-quinolinolato) aluminum(III) (abbreviation: Almq3), bis(10-hydroxybenzo[h]quinolinato)beryllium(H) (abbreviation: BeBq2), bis(2-methyl-8-quinolinolato) (4-phenylphenolato)aluminum (III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(H) (abbreviation: ZnBTZ);

heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), and bathophenanthroline (abbreviation: BPhen), bathocuproine (abbreviation: BCP);

fused aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl(abbreviation BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; and aromatic amine compounds, such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or a-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), and 4,4'-bis[N-(spiro-9,9'- bifluoren-2-yl)-N-phenylamino]biphenyl (abbreviation: BSPB) can be used. A plurality of host materials may be used.
In particular, in the case of a blue fluorescent device, it is preferred to use the following anthracene compounds as the host material.
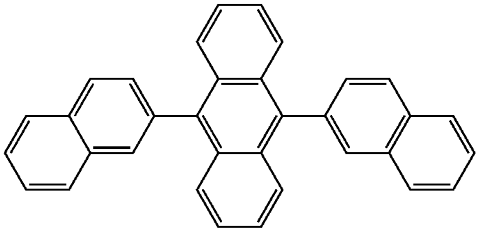
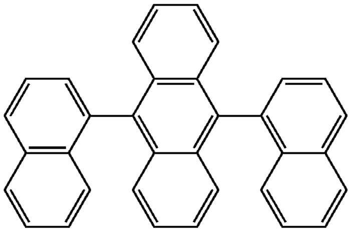
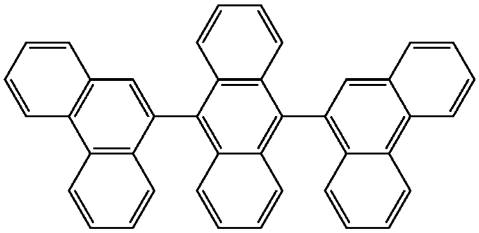
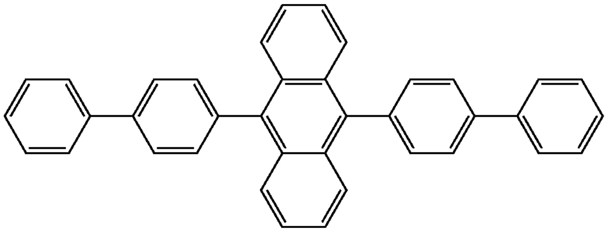
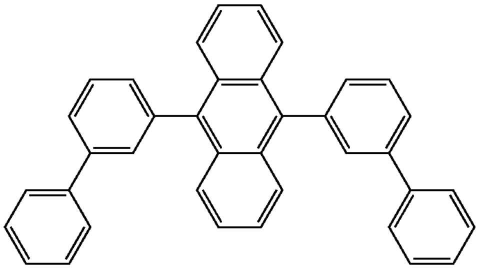
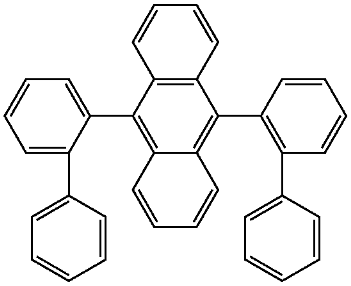
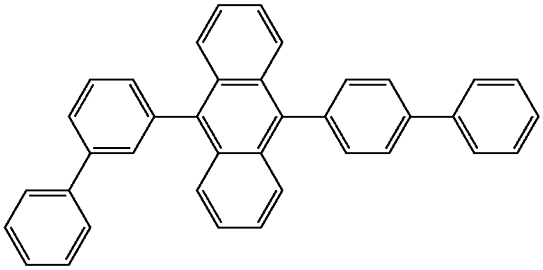
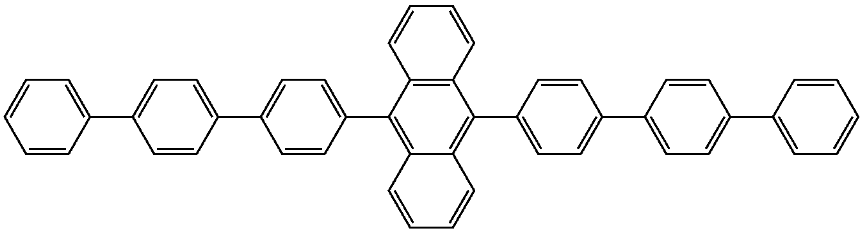
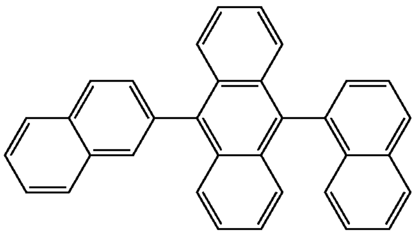
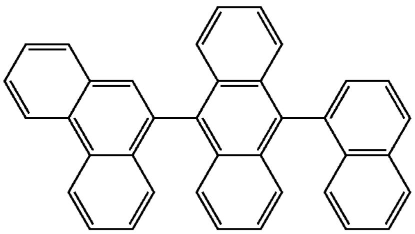

-continued
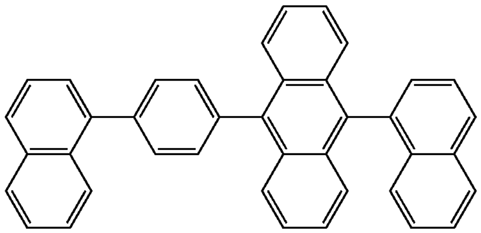
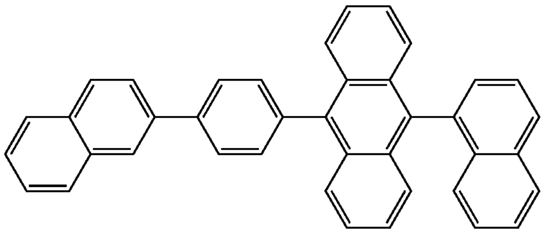
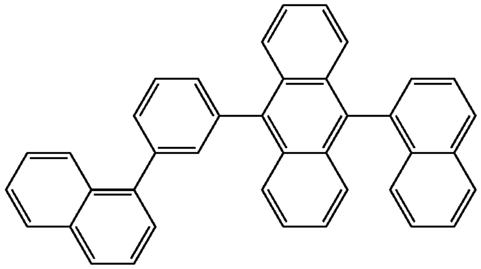
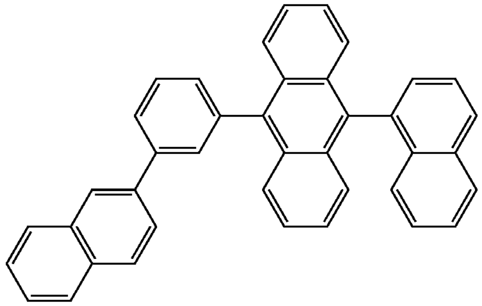
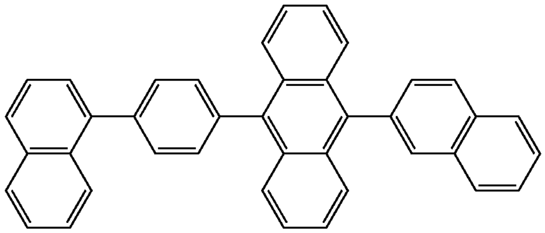
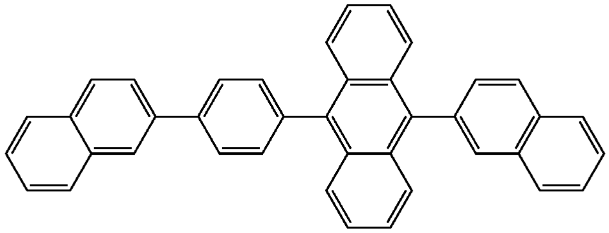
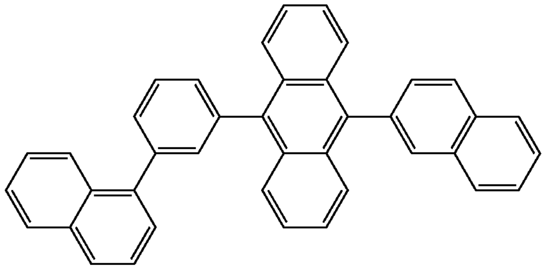
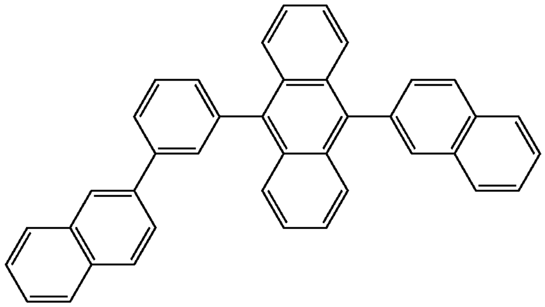

-continued
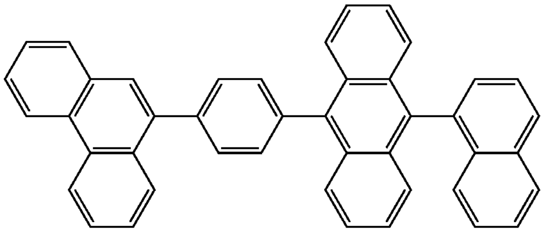
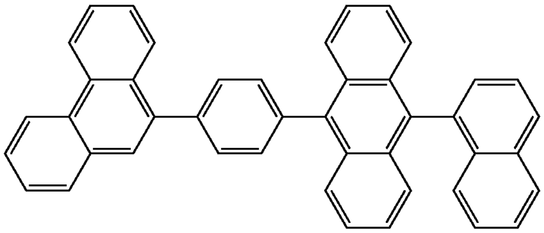
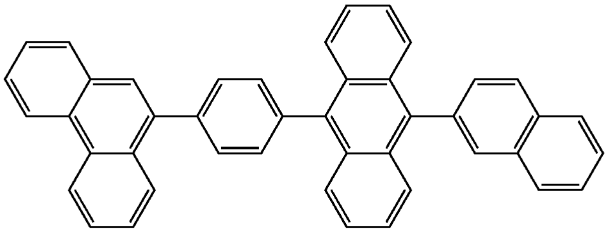
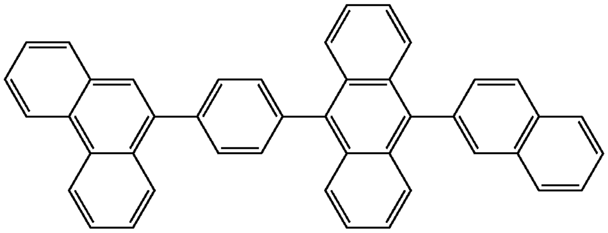
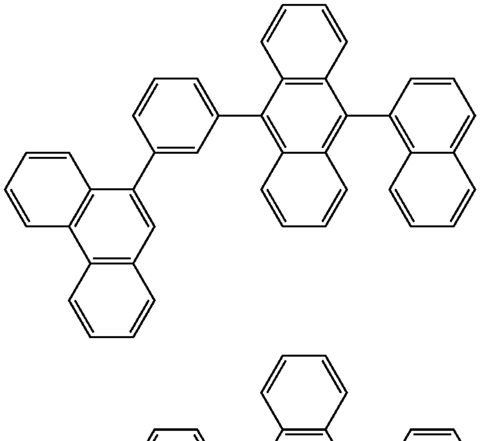
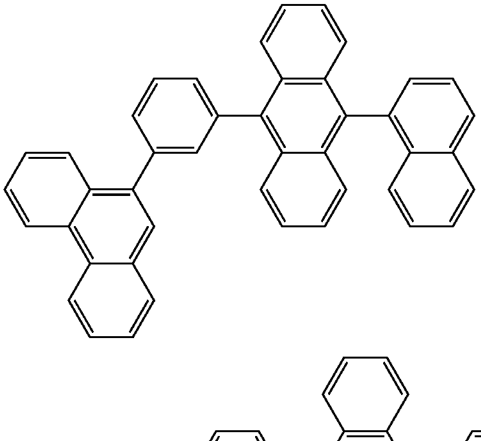
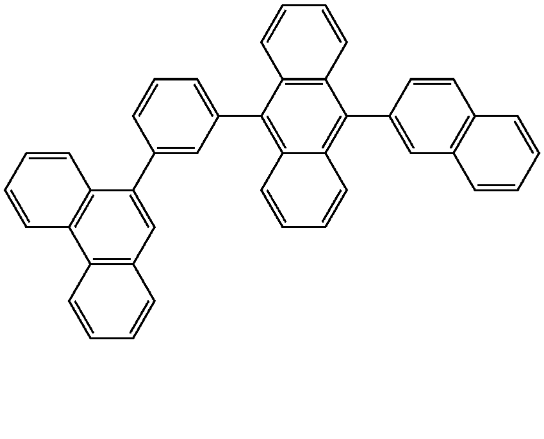
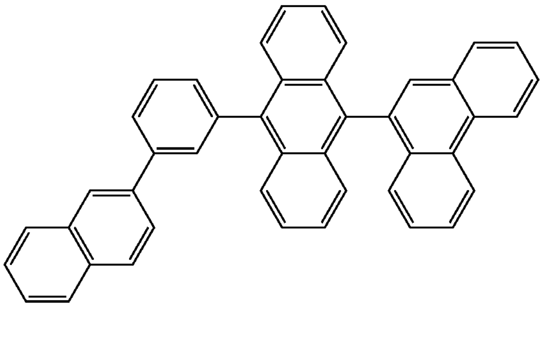

-continued
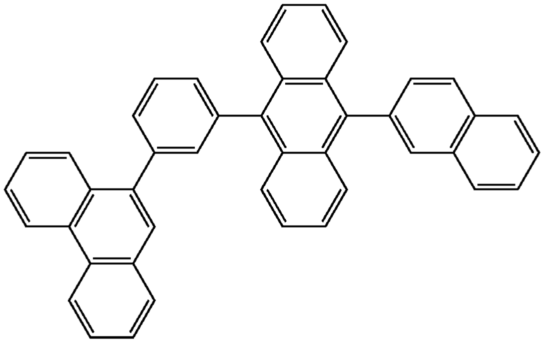
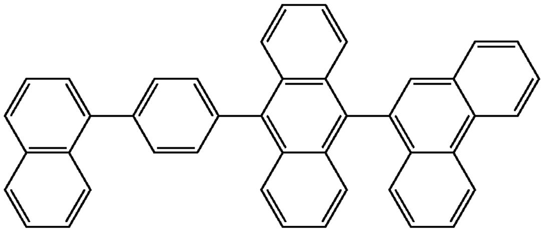
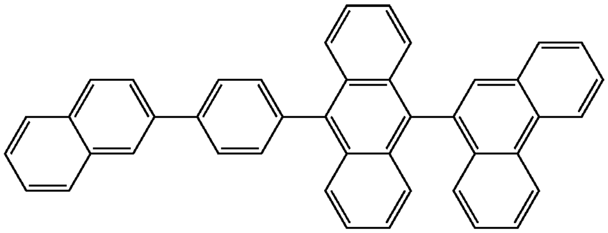
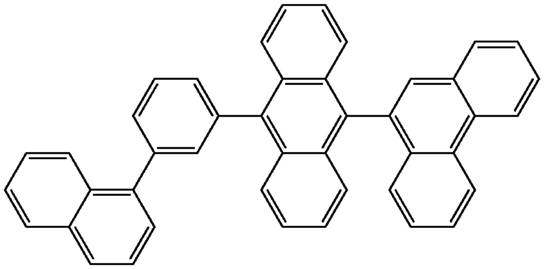
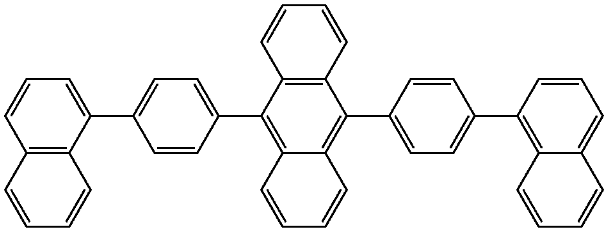
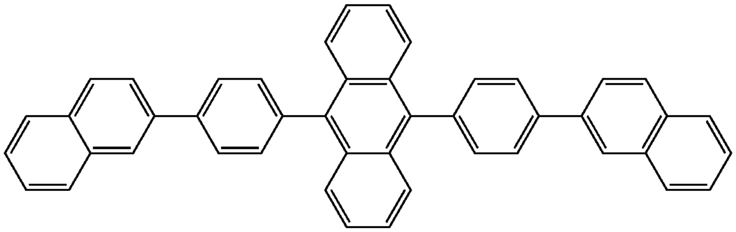

-continued
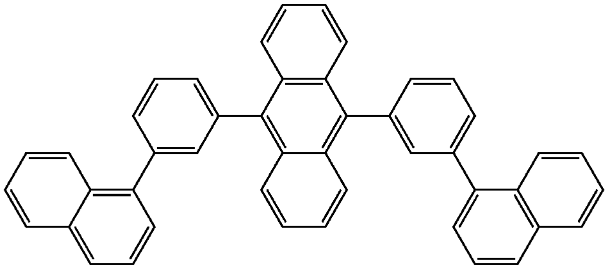
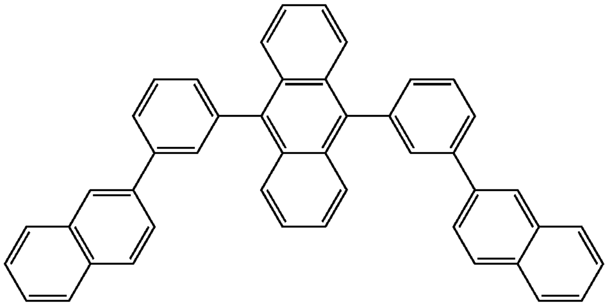
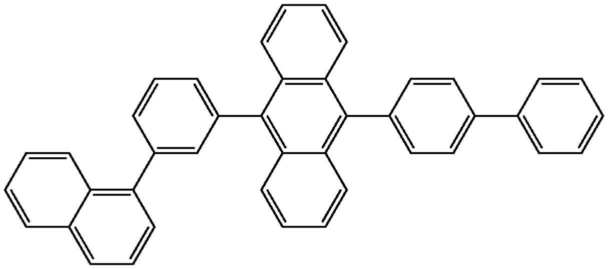
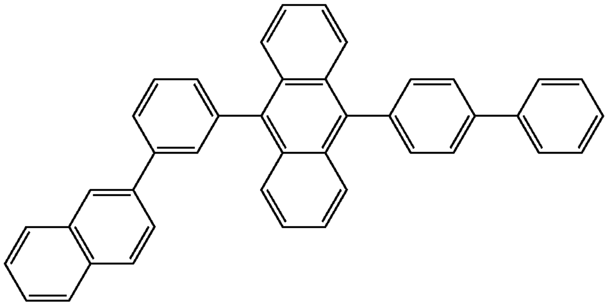
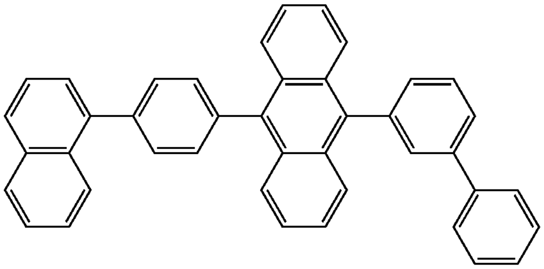
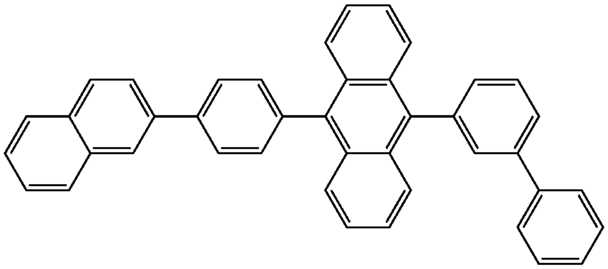
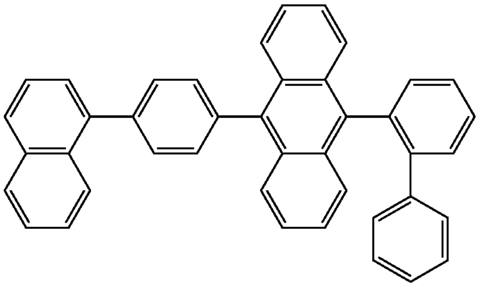

-continued
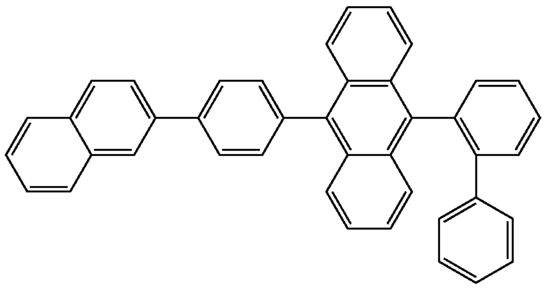
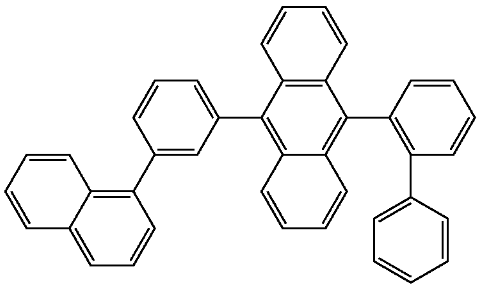
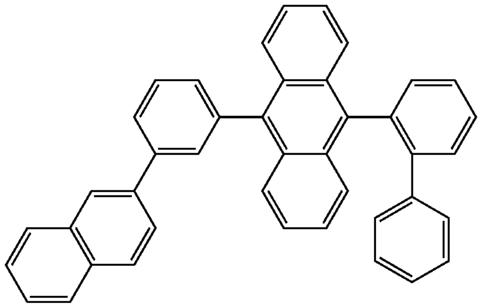
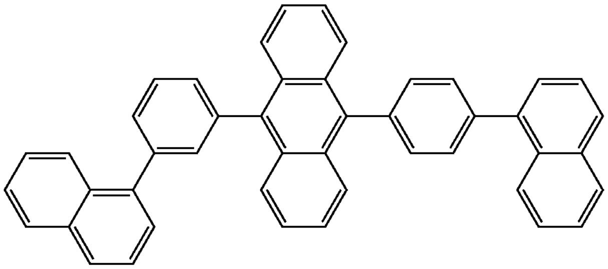
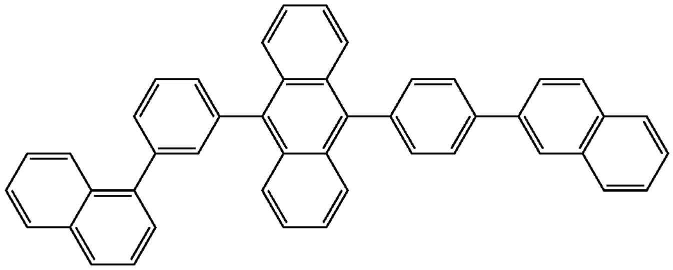
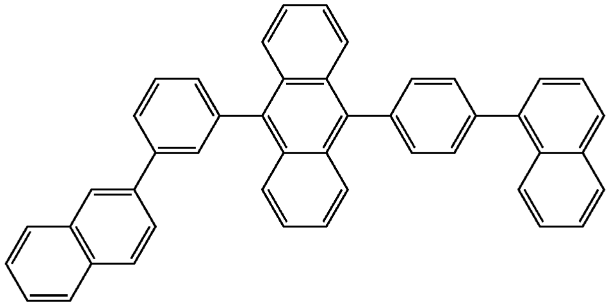
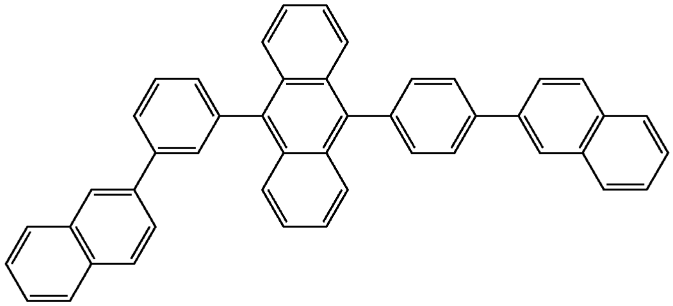
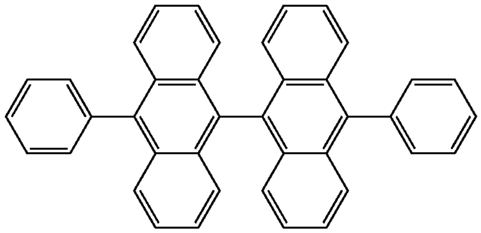

-continued
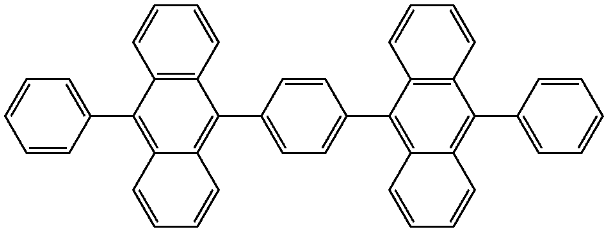
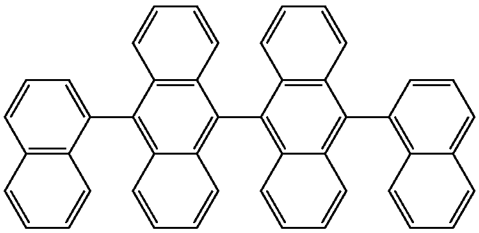
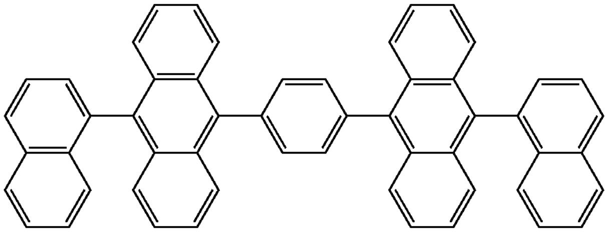
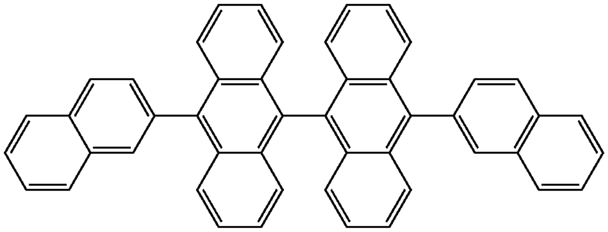
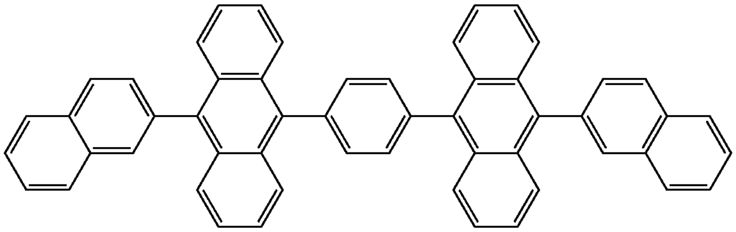
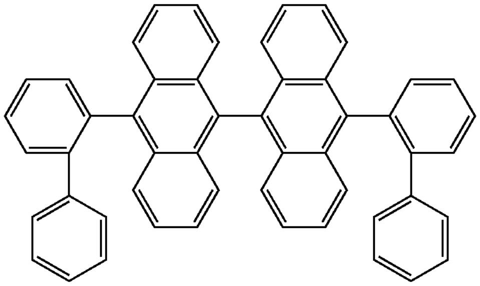
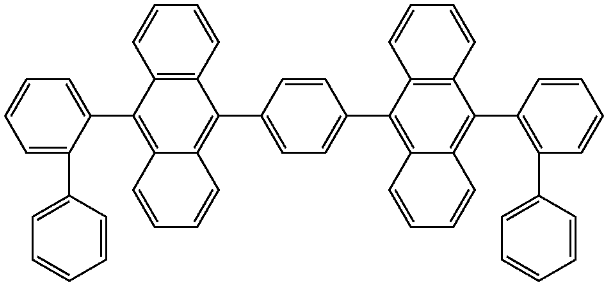
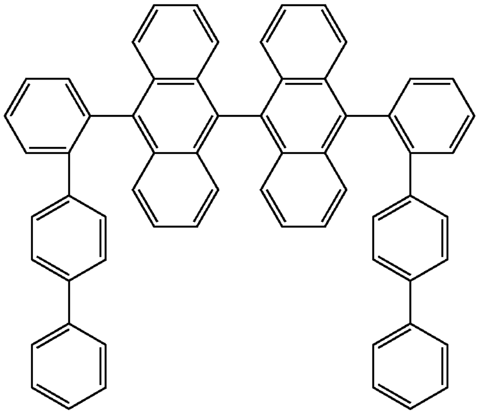

-continued
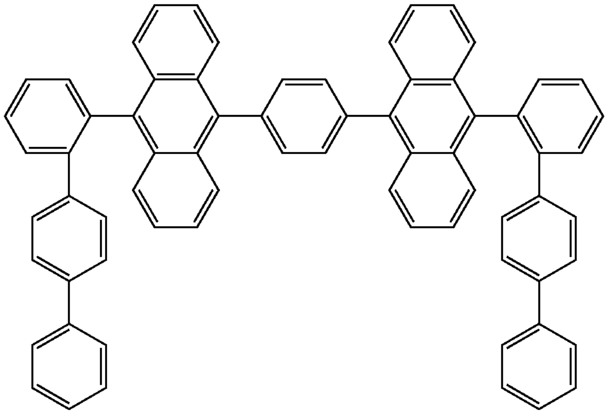
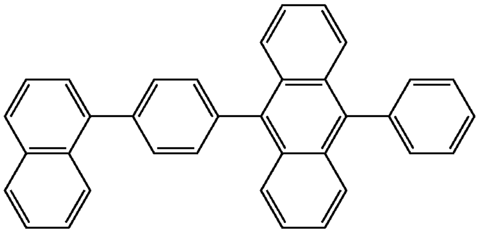
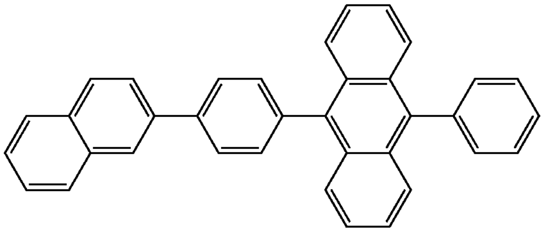
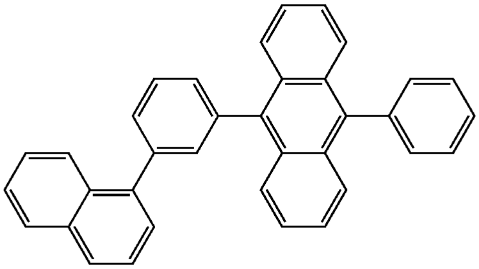
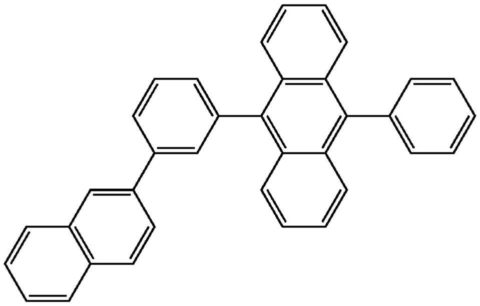
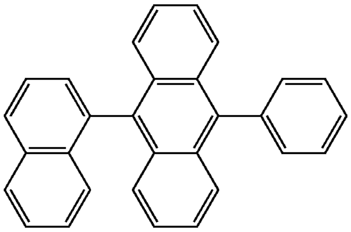
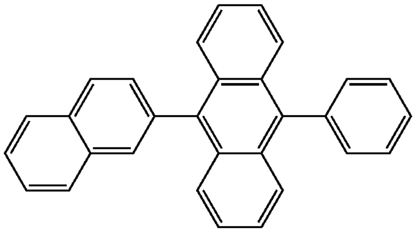
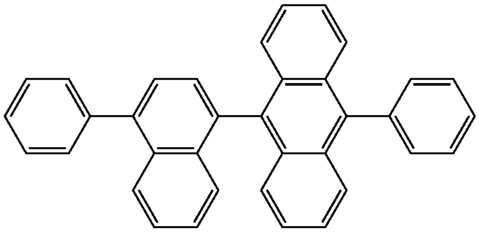
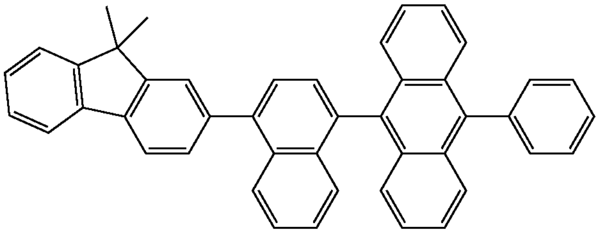
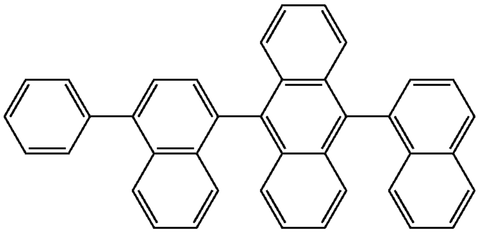
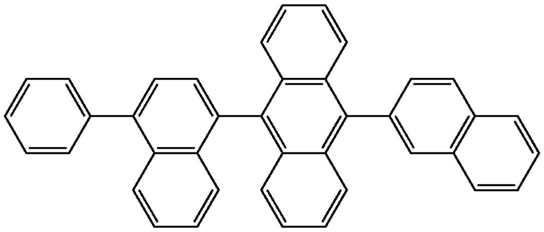

-continued
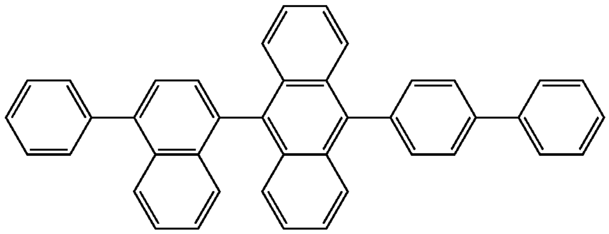
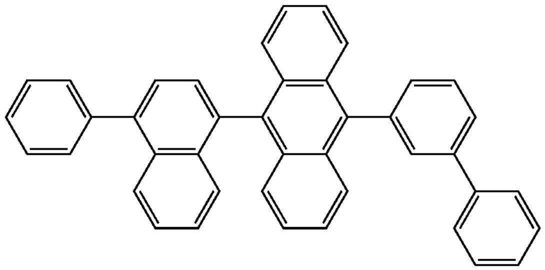
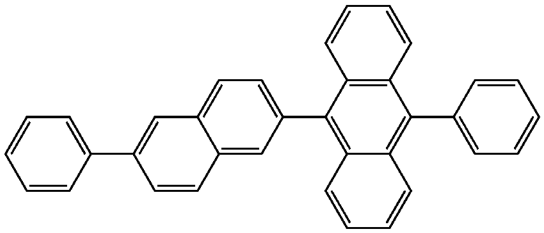
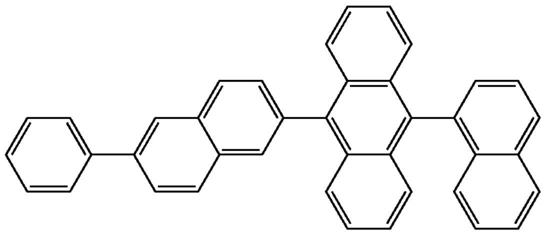
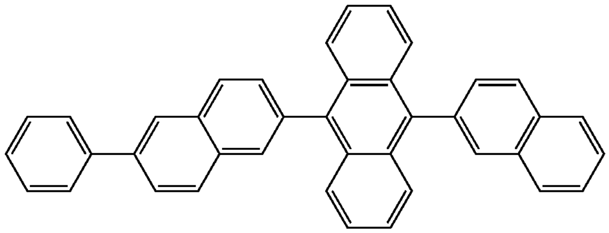
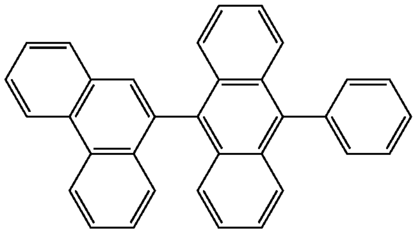
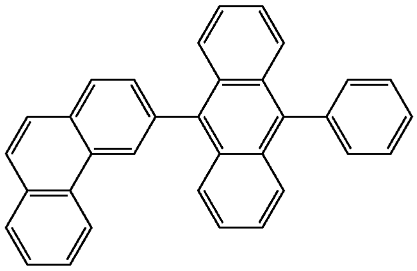
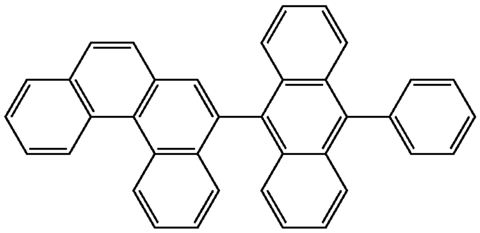
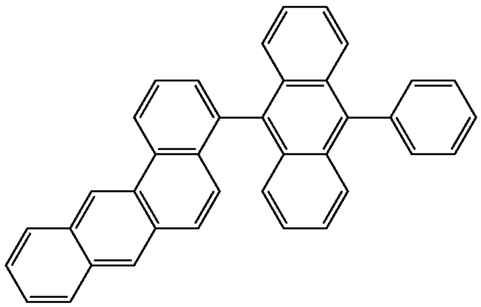
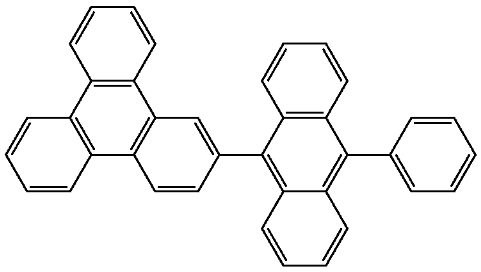

-continued
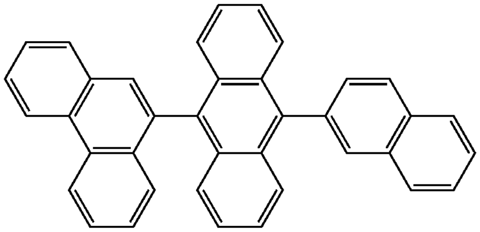
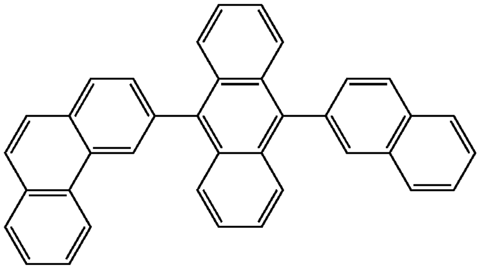
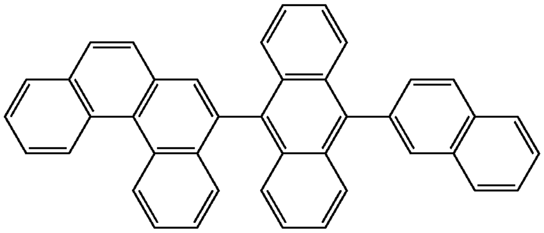
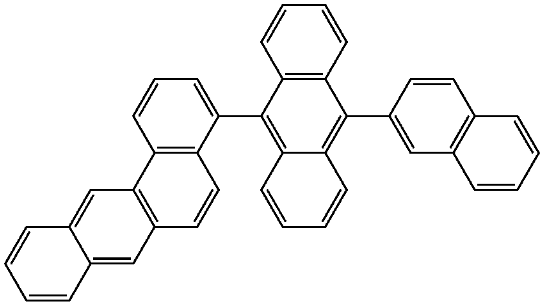
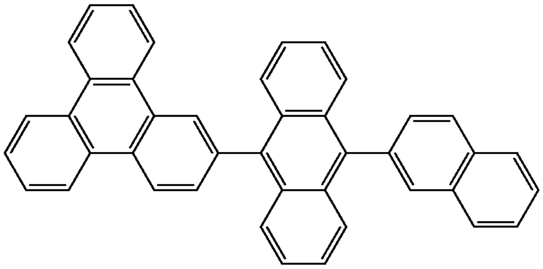
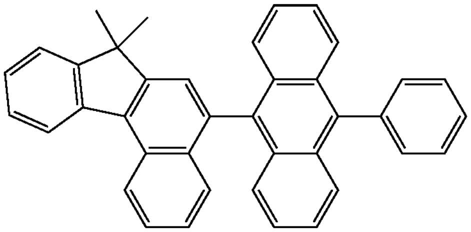
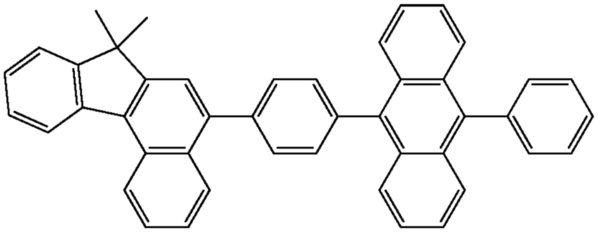
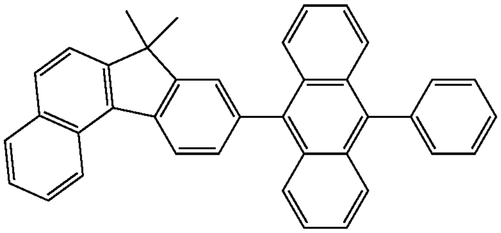
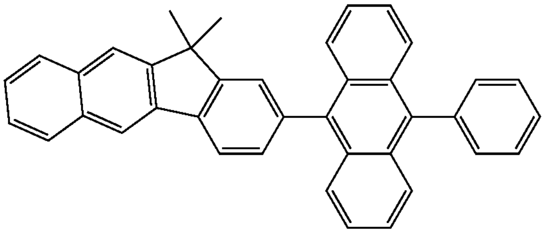
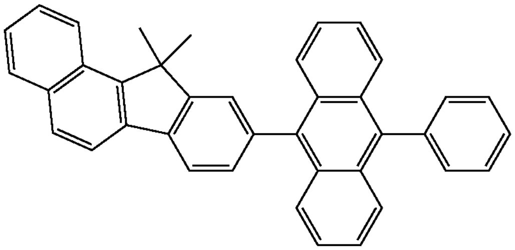
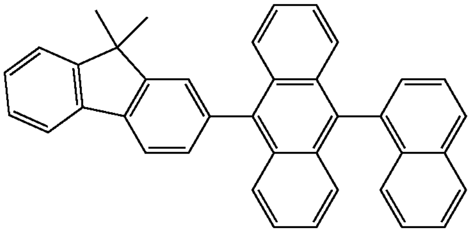

-continued
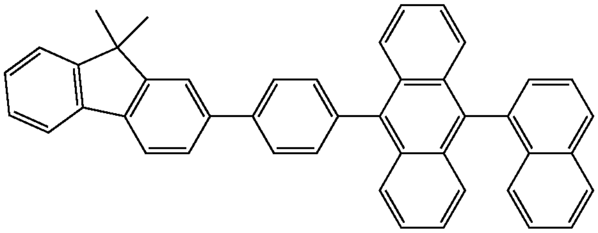
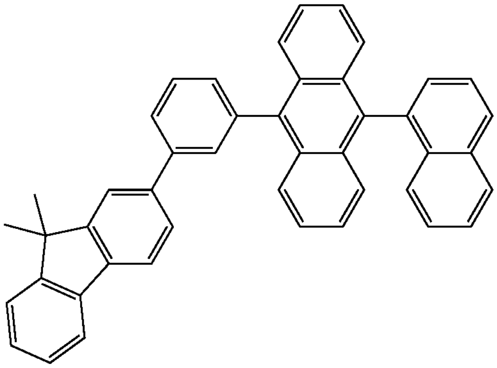
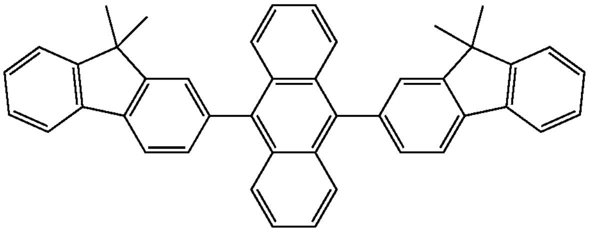
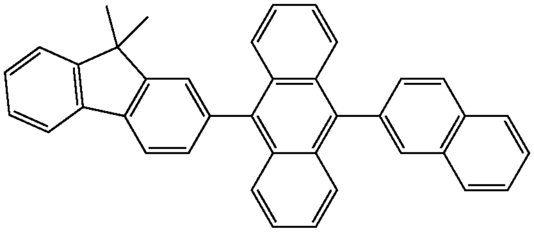
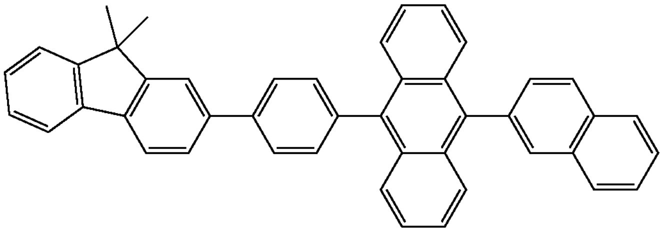
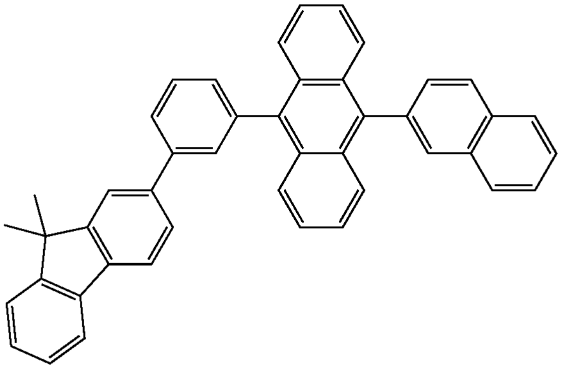
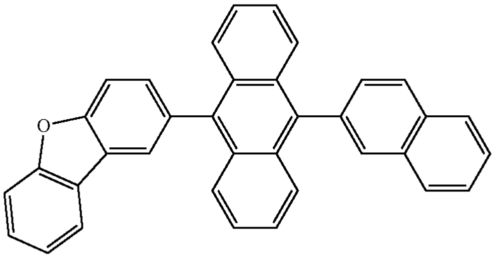
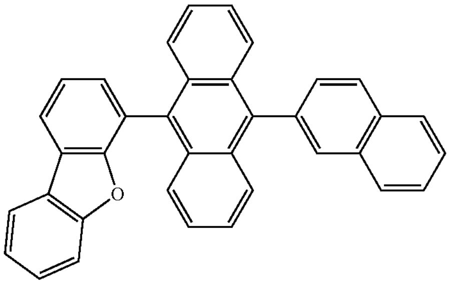

-continued
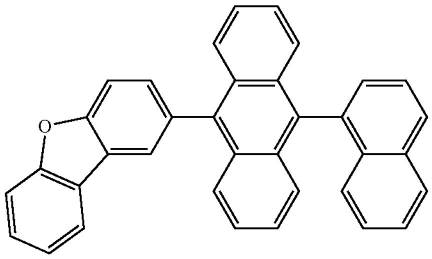
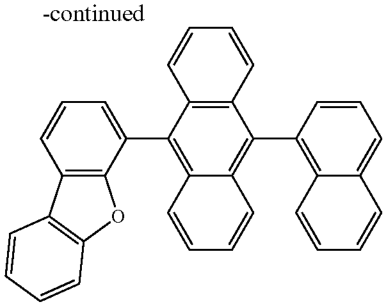
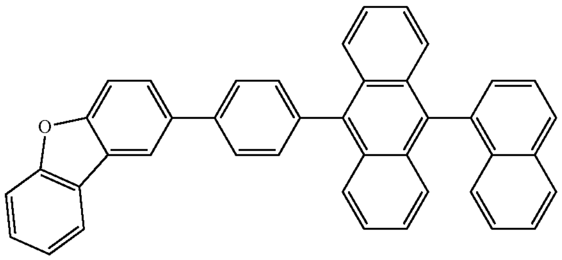
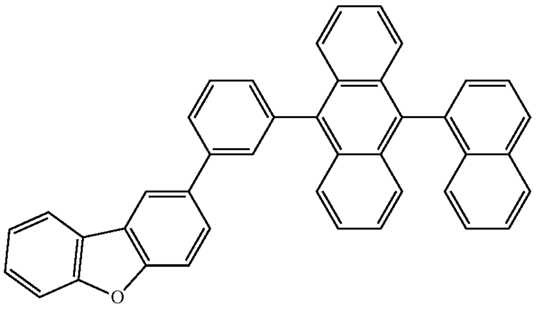
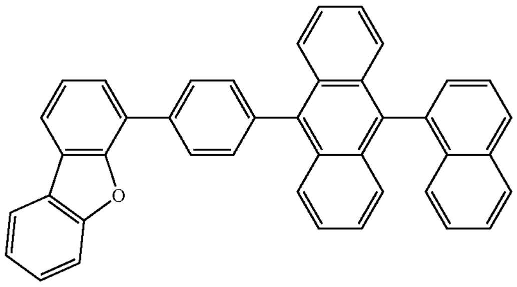
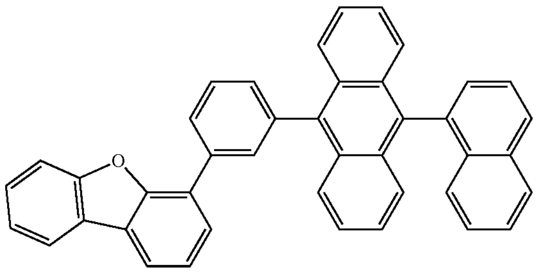
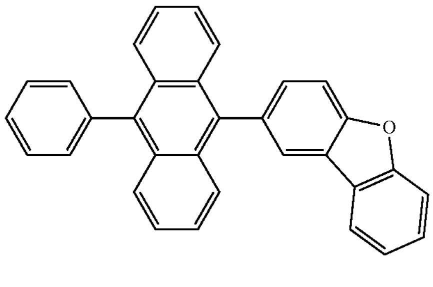
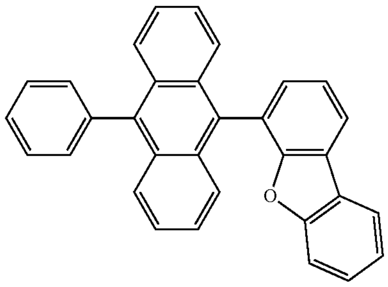
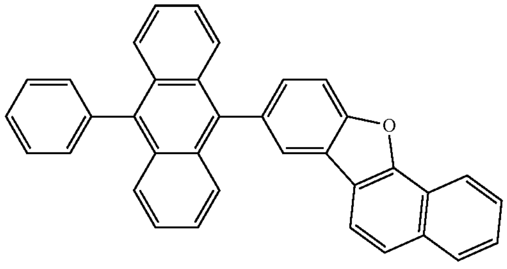
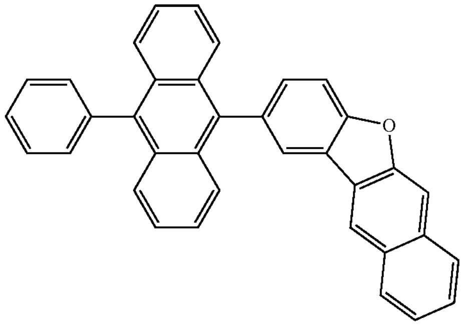

-continued
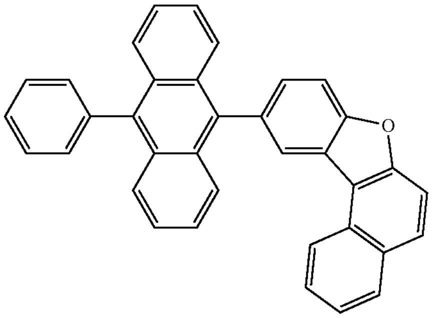
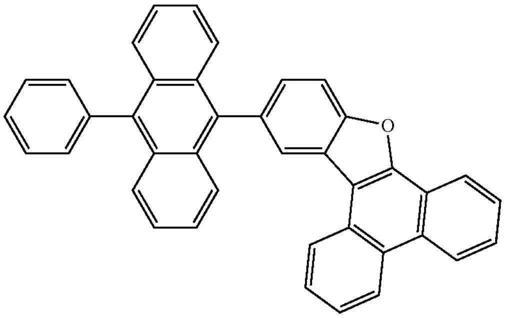
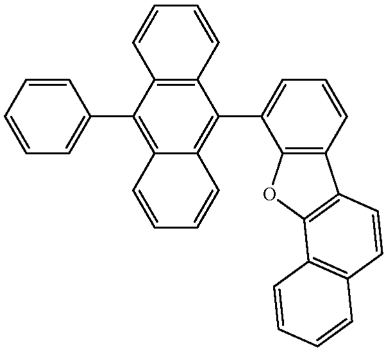
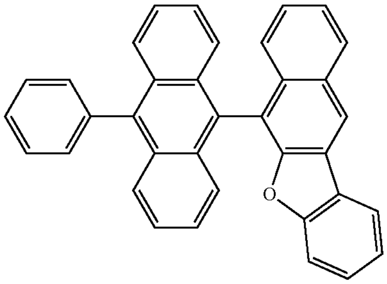
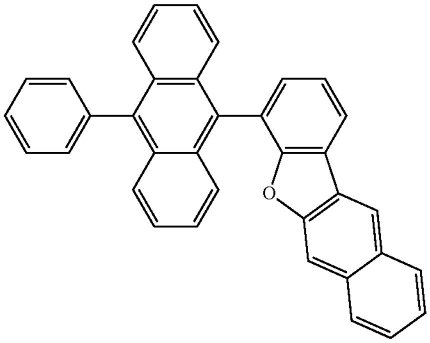
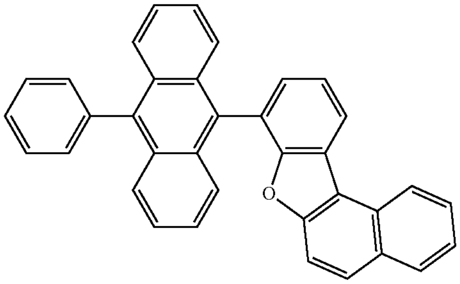
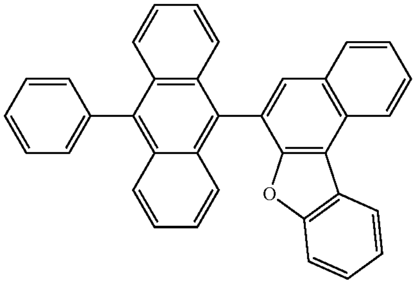
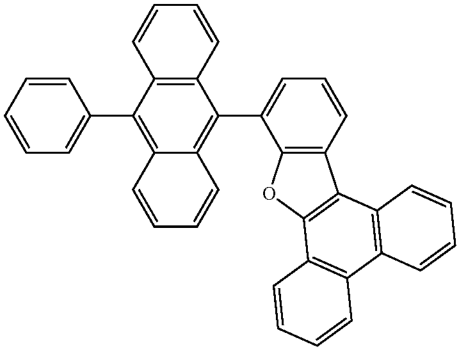
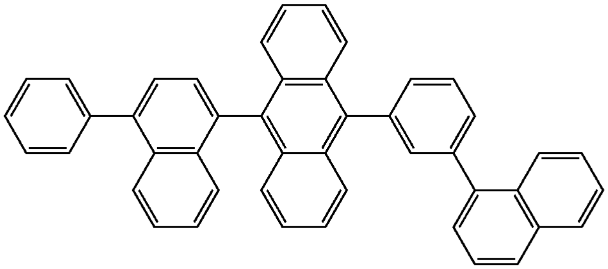

-continued
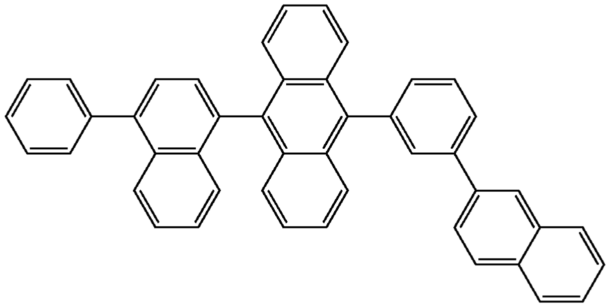
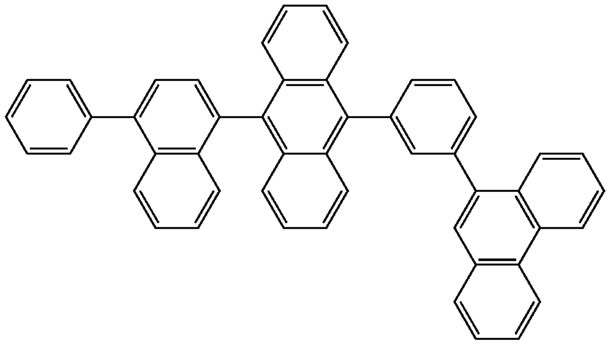
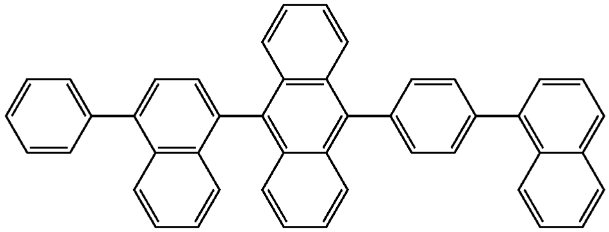
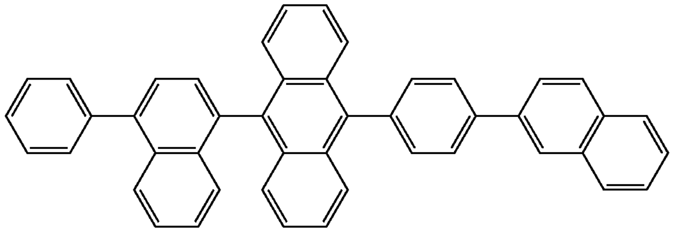
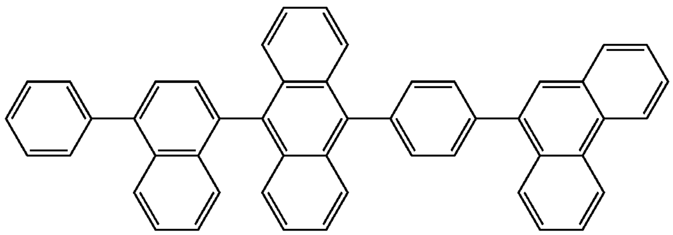
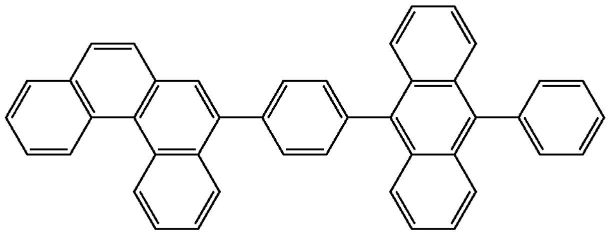

-continued

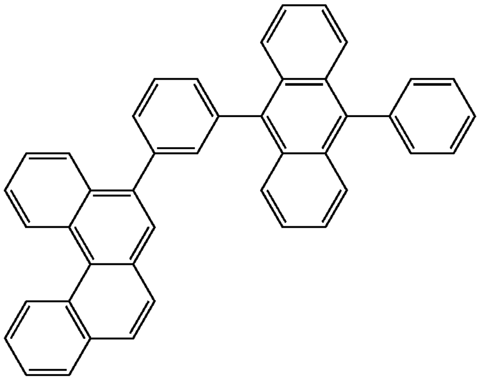

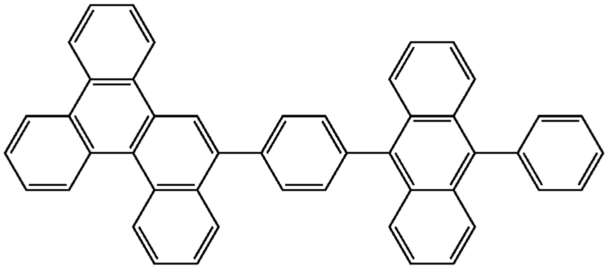

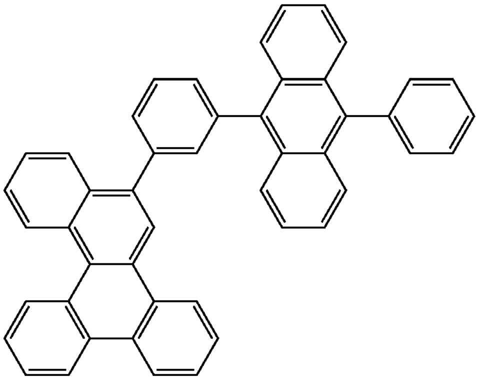

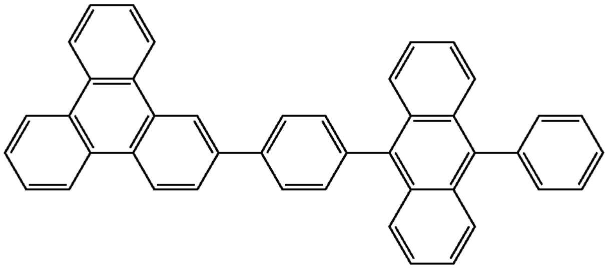

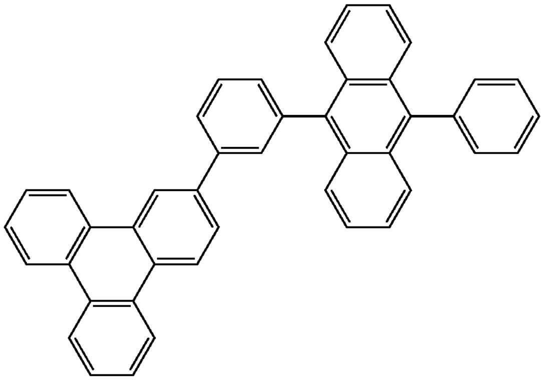

Electron Transporting Layer

The electron transporting layer is a layer containing a material having a high electron transporting capability (an electron transporting material) and is provided between the light emitting layer and the cathode, or between the electron injecting layer, if exists, and the light emitting layer.

The electron transporting layer may have a single layer structure or a multilayer structure including two or more layers. For example, the electron transporting layer may have a two-layer structure including a first electron transporting layer (anode side) and a second electron transporting layer (cathode side). In one embodiment of the present invention, the electron transporting layer having a single layer structure is preferably disposed adjacent to the light emitting layer, and the electron transporting layer that is closest to the anode in the multilayer structure, such as the first electron transporting layer in the two-layer structure, is preferably disposed adjacent to the light emitting layer. In another embodiment of the present invention, and a hole blocking layer described later may be disposed between the electron transporting layer having a single layer structure and the light emitting layer, or between the electron transporting layer that is closest to the light emitting layer in the multilayer structure and the light emitting layer.

As the electron transporting layer, for example, (1) a metal complex, such as an aluminum complex, a beryllium complex, and a zinc complex;

(2) a heteroaromatic compound, such as an imidazole derivative, a benzimidazole derivative, an azine derivative, a carbazole derivative, and a phenanthroline derivative; and (3) a high-molecular weight compound can be used.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h] quinolinato)beryllium (abbreviation: $BeBq_2$), bis(2-methyl-8-quinolinolato)(4-phenylphenolato) aluminum (III) (abbreviation: BAlq), bis(8-quinolinolato) zinc(II) (abbreviation: Znq), bis[2-(2-benzoxazolyl)phenolato]zinc(II) (abbreviation: ZnPBO), and bis[2-(2-benzothiazolyl)phenolato]zinc(ID (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzxazol-2-yl)stilbene (abbreviation: BzOs).

Examples of the high-molecular weight compound include poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The materials are materials having an electron mobility of $10^{-6}$ $cm^2/Vs$ or more. Materials other than those as mentioned above may also be used in the electron transporting layer so long as they are materials high in the electron transporting capability rather than in the hole transporting capability.

Electron Injecting Layer

The electron injecting layer is a layer containing a material having a high electron injection capability. As the electron injecting layer, alkali metals, such as lithium (Li) and cesium (Cs), alkaline earth metals, such as magnesium (Mg), calcium (Ca), and strontium (Sr), rare earth metals, such as europium (Eu) and ytterbium (Yb), and compounds containing these metals can be used. Examples of the compounds include an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. These compounds may be used as a mixture of a plurality thereof.

In addition, a material having an electron transporting capability, in which an alkali metal, an alkaline earth metal, or a compound thereof is contained, specifically Alq in which magnesium (Mg) is contained may be used. In this case, electron injection from the cathode can be more efficiently performed.

Otherwise, in the electron injecting layer, a composite material obtained by mixing an organic compound with an electron donor may be used. Such a composite material is excellent in the electron injection capability and the electron transporting capability because the organic compound receives electrons from the electron donor. In this case, the organic compound is preferably a material excellent in transporting received electrons, and specifically, examples thereof include a material constituting the aforementioned electron transporting layer (such as a metal complex and a heteroaromatic compound). As the electron donor, a material having an electron donation property for the organic compound may be used. Specifically, alkali metals, alkaline earth metals, and rare earth metals are preferred, and examples thereof include lithium, cesium, magnesium, calcium, erbium, and ytterbium. In addition, an alkali metal oxide or an alkaline earth metal oxide is preferred, and examples thereof include lithium oxide, calcium oxide, and barium oxide. In addition, a Lewis base, such as magnesium oxide, can also be used. In addition, an organic compound, such as tetrathiafulvalene (abbreviation: TTF), can also be used.

Cathode

It is preferred that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals, such as lithium (Li) and cesium (Cs), alkaline earth metals, such as magnesium (Mg), calcium (Ca), and strontium (Sr), and alloys containing these (such as MgAg, and AlLi), and rare earth metals, such as europium (Eu), and ytterbium (Yb) and alloys containing these.

When the cathode is formed by using the alkali metals, the alkaline earth metals, and the alloys containing these, a vacuum vapor deposition method or a sputtering method can be adopted. In addition, when a silver paste or the like is used, a coating method, an inkjet method, of the like can be adopted.

By providing the electron injecting layer, the cathode can be formed using various conductive materials, such as Al, Ag, ITO, graphene, and indium oxide-tin oxide containing silicon or silicon oxide regardless of the magnitude of a work function. Such a conductive material can be deposited by using a sputtering method, an inkjet method, a spin coating method, or the like.

Insulating Layer

The organic EL device applies an electric field to an ultrathin film, and thus, pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer can also be provided among the plurality of phosphorescent light emitting layers.

Since the space layer is provided between the light emitting layers, a material having both an electron transporting capability and a hole transporting capability is preferred. Also, one having a triplet energy of 2.6 eV or more is preferred in order to prevent triplet energy diffusion in the adjacent phosphorescent light emitting layer. Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and trapping the excitons within the light emitting layer.

Each layer of the organic EL device may be formed by a conventionally known vapor deposition method, a coating method, or the like. For example, formation can be performed by a known method using a vapor deposition method such as a vacuum vapor deposition method, or a molecular beam vapor deposition method (MBE method), or a coating method using a solution of a compound for forming a layer, such as a clipping method, a spin-coating method, a casting method, a bar-coating method, and a roll-coating method.

The film thickness of each layer is not particularly limited, but is typically 5 nm to 10 μm, and more preferably 10 nm to 0.2 μm because in general, when the film thickness is too small, defects such as pinholes are likely to occur, and conversely, when the film thickness is too large, a high driving voltage is required and the efficiency decreases.

The organic EL device can be used for electronic devices, such as display components of an organic EL panel module, display devices of a television, a mobile phone and a personal computer, and light emitting devices of lightings and vehicular lamps.

EXAMPLES

The present invention is hereunder described in more detail by reference to Examples, but it should be construed that the present invention is not limited to the following Examples.

Inventive Compounds Used in Production of Organic EL Devices of Examples 1 to 9

Compound 1

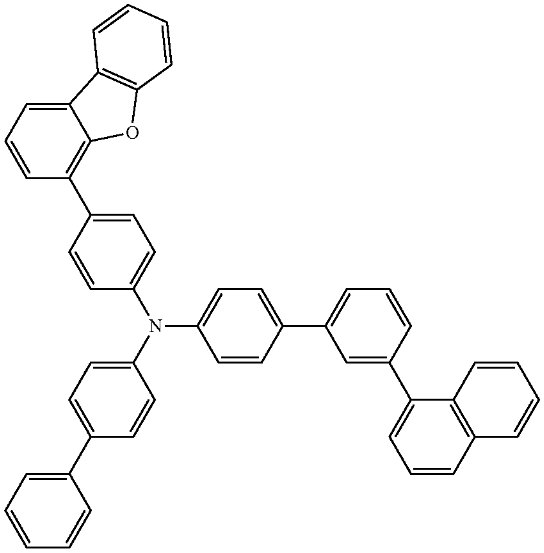

Compound 3

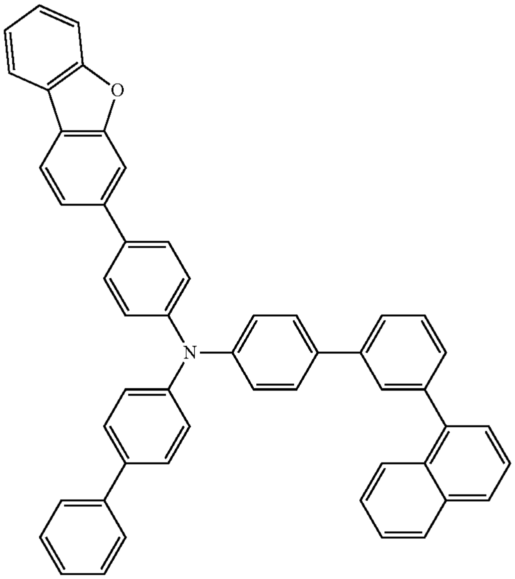

-continued
Compound 5
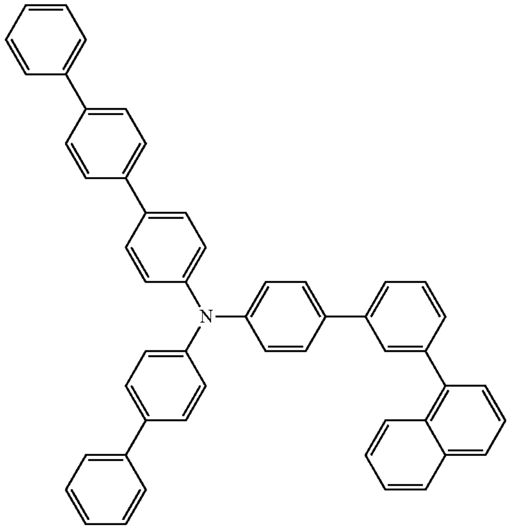
Compound 6
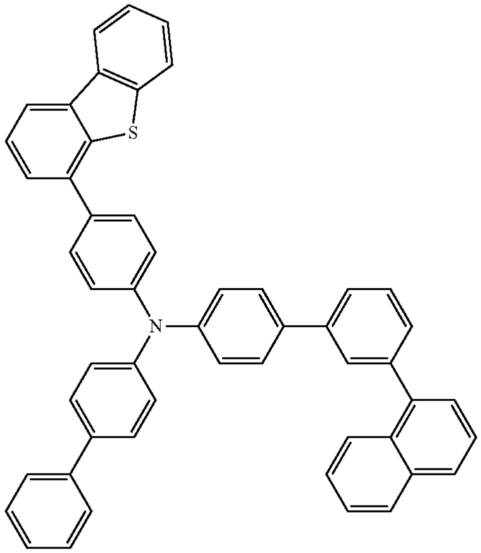
-continued
Compound 8
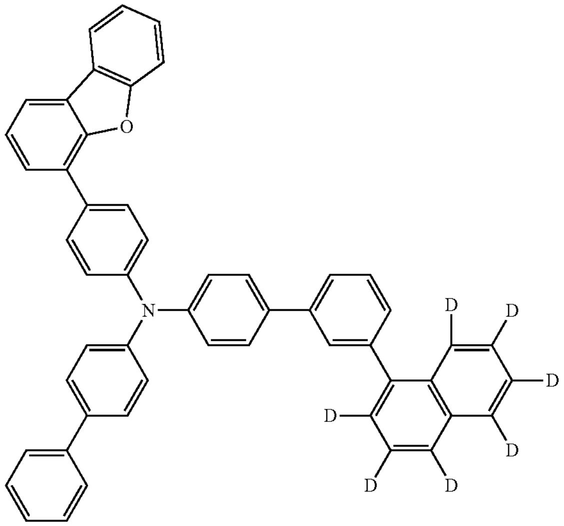
Compound 9
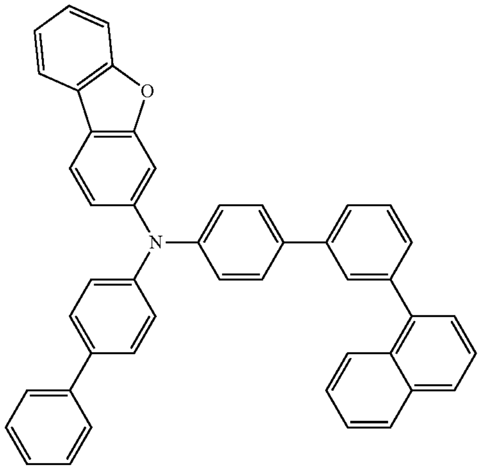
Compound 15
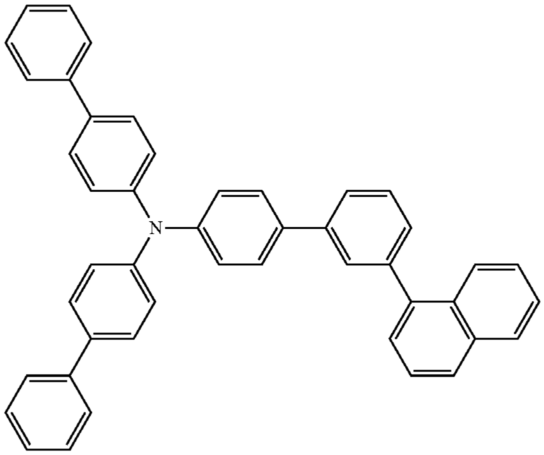

-continued
Compound 16
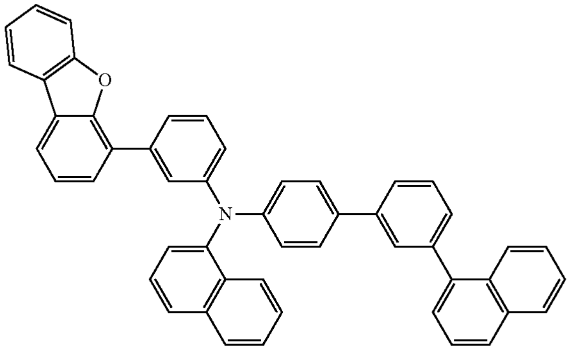
Compound 17
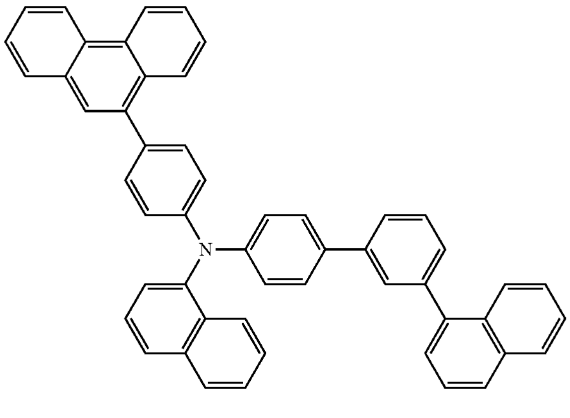
Comparative Compounds Used in Production of Organic EL Devices of Comparative Examples 1 to 3
Comparative Compound 1
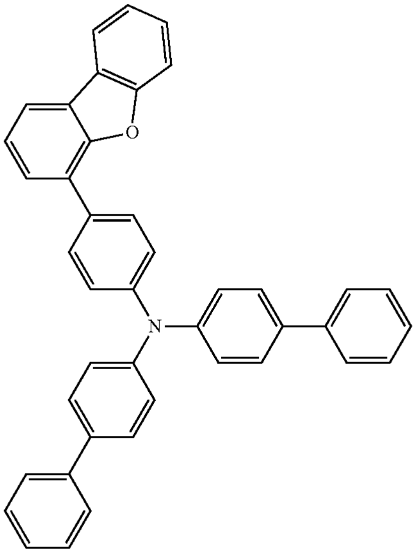
-continued
Comparative Compound 2
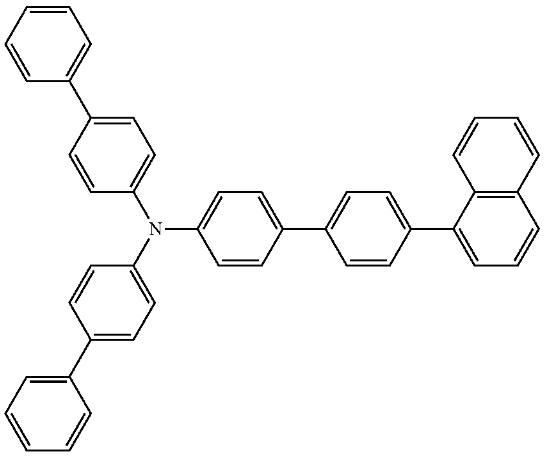
Comparative Compound 3
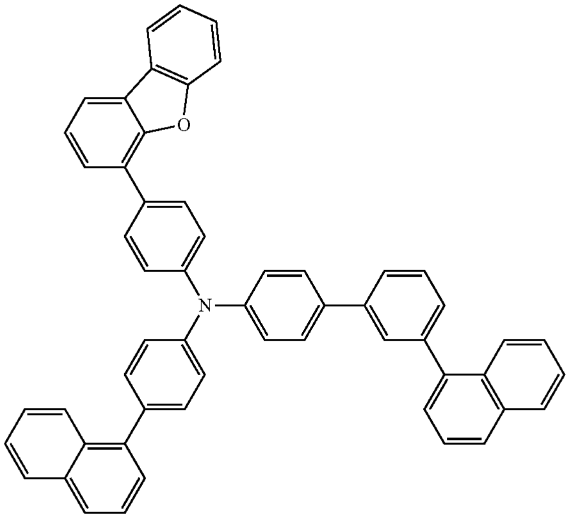
Other compounds used in production of organic EL devices of Examples 1 to 9 and Comparative Examples 1 to 3
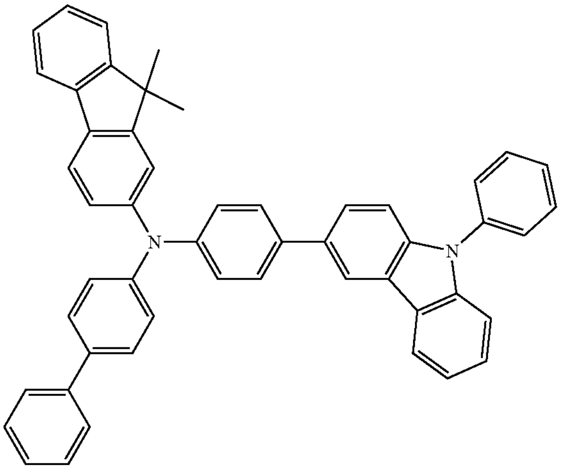
HT-1

-continued

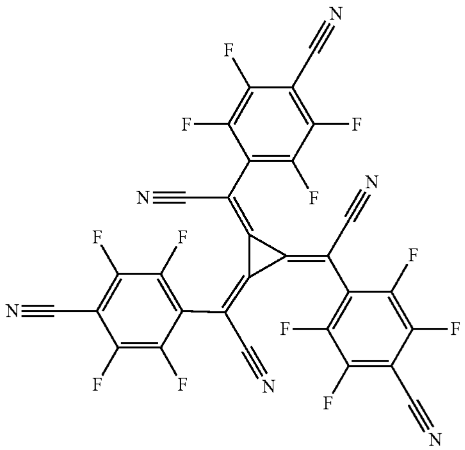

HA

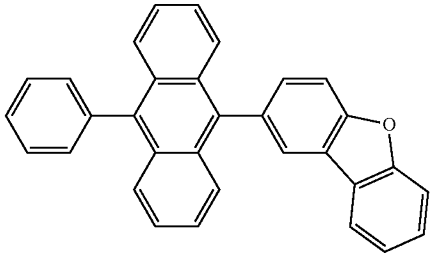

BH

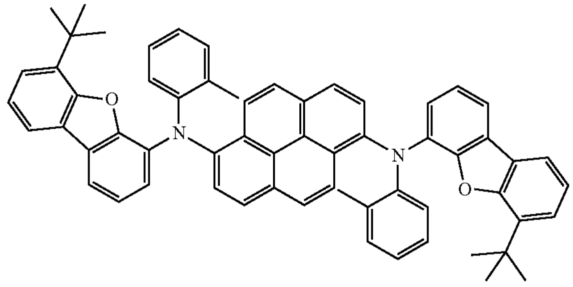

BD

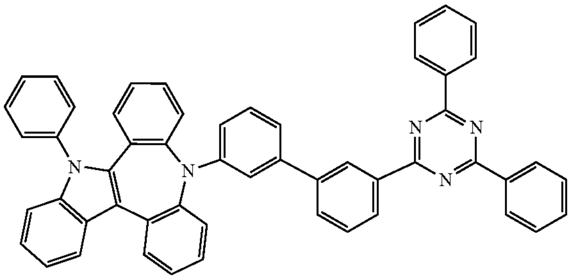

ET-1

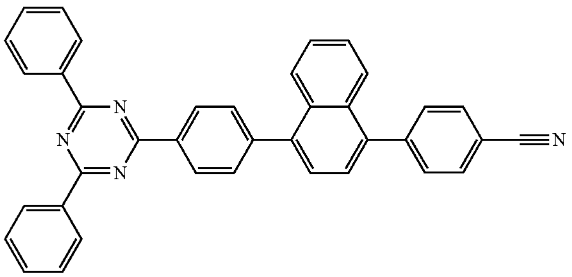

ET-2

Production of Organic EL Device

Example 1

A glass substrate of 25 mm×75 mm×1.1 mm provided with an ITO transparent electrode (anode) (manufactured by GEOMATEC Co., Ltd.) was ultrasonically cleaned in isopropyl alcohol for 5 minutes and then subjected to UV ozone cleaning for 30 minutes. The film thickness of the ITO was 130 nm.

The cleaned glass substrate provided with the transparent electrode was mounted on a substrate holder of a vacuum vapor deposition apparatus, and firstly, Compound HT-1 and Compound HA were vapor co-deposited on the surface having the transparent electrode formed thereon, so as to cover the transparent electrode, resulting in a hole injecting layer with a film thickness of 10 nm. The mass ratio of Compound HT-1 to Compound HA (HT-1/HA) was 97/3.

Subsequently, on this hole injecting layer, Compound HT-1 was vapor deposited to form a first hole transporting layer with a film thickness of 80 nm.

Subsequently, on this first hole transporting layer, Compound 1 was vapor deposited to form a second hole transporting layer with a film thickness of 10 nm.

Subsequently, on this second hole transporting layer, Compound BH (host material) and Compound BD (dopant material) were vapor co-deposited to form a light emitting layer with a film thickness of 25 nm. The mass ratio of Compound BH to Compound BD (BH/BD) was 96/4.

Subsequently, on this light emitting layer, Compound ET-1 was vapor deposited to form a first electron transporting layer with a film thickness of 5 nm.

Subsequently, on this first electron transporting layer, Compound ET-2 and Liq were vapor co-deposited to form a second electron transporting layer with a film thickness of 20 nm. The mass ratio of Compound ET-2 to Liq (ET-2/Liq) was 50/50.

Subsequently, on this second electron transporting layer, LiF was vapor deposited to form an electron injecting electrode with a film thickness of 1 nm.

Then, on this electron injecting electrode, metal Al was vapor deposited to form a metal cathode with a film thickness of 50 nm.

The layer configuration of the organic EL device of Example 1 thus obtained was as follows.

ITO (130)/HT-1/HA=97/3 (10)/HT-1 (80)/Compound 1 (10)/BH/BD=96/4 (25)/ET-1 (5)/ET-2/Liq=50/50 (20)/LiF (1)/Al (50)

In the layer configuration, the numeral in parentheses indicates the film thickness (nm), and the ratio is by mass.

Measurement of Device Lifetime (LT90)

The resulting organic EL device was emitted by driving with DC direct current at a current density of 50 mA/cm$^2$, and the period of time until the luminance was reduced to 95% of the initial luminance was measured, and was defined as 95% lifetime (LT95). The results are shown in Table 1.

Examples 2 to 9 and Comparative Examples 1 to 3

Organic EL devices were produced in the same manner as in Example 1 except that the second hole transporting layer material was changed to Compound 8 (Example 2), Compound 3 (Example 3), Compound 5 (Example 4), Compound 6 (Example 5), Compound 9 (Example 6), Compound 15 (Example 7), Compound 16 (Example 8), Compound 17 (Example 9), Comparative Compound 1 (Comparative Example 1), Comparative Compound (Comparative Example 2) or Comparative Compound (Comparative Example 3), and LT95 thereof was measured. The results are shown in Table 1.

TABLE 1

| | Second Hole Transporting Layer Material | LT95(h) @50 mA/cm$^2$ |
|---|---|---|
| Example 1 | Compound 1 | 109 |
| Example 2 | Compound 8 | 106 |
| Example 3 | Compound 3 | 111 |
| Example 4 | Compound 5 | 114 |
| Example 5 | Compound 6 | 105 |
| Example 6 | Compound 9 | 103 |
| Example 7 | Compound 15 | 107 |
| Example 8 | Compound 16 | 105 |
| Example 9 | Compound 17 | 108 |
| Comparative Example 1 | Comparative Compound 1 | 96 |
| Comparative Example 2 | Comparative Compound 2 | 93 |
| Comparative Example 3 | Comparative Compound 3 | 86 |

As obvious from the results in Table 1, a monoamine in which one having a group that has an m-(1-naphthyl)phenyl group at the terminal bonds to the central nitrogen atom, and one of the remaining two having a specific aryl group and the other having a specific heteroaryl group bond thereto, or both the remaining two each having a specific heteroaryl group bond to the central nitrogen atom (Compound 1, 3, 5, 6, 8, 9, 15) provides an organic EL device having a remarkably prolonged device lifetime, as compared with a monoamine in which a group not having an m-(1-naphthyl)phenyl group at the terminal bonds to the central nitrogen atom.

In addition, a monoamine in which one having a group that has an m-(1-naphthyl)phenyl group at the terminal bonds to the central nitrogen atom, and one of the remaining two having a specific aryl group (naphthyl group) directly bonds thereto (Compound 16, 17) provides an organic EL device having a remarkably prolonged device lifetime, as compared with a monoamine in which one having a group that has an m-(1-naphthyl)phenyl group at the terminal bonds to the central nitrogen atom but one of the remaining two having a specific aryl group (naphthyl group) does not directly bonds thereto (Comparative Compound 3).

Compounds 2, 4, 7, 10 to 14 Synthesized in Synthesis Examples 2, 4, 7, 10 to 14

Compound 2

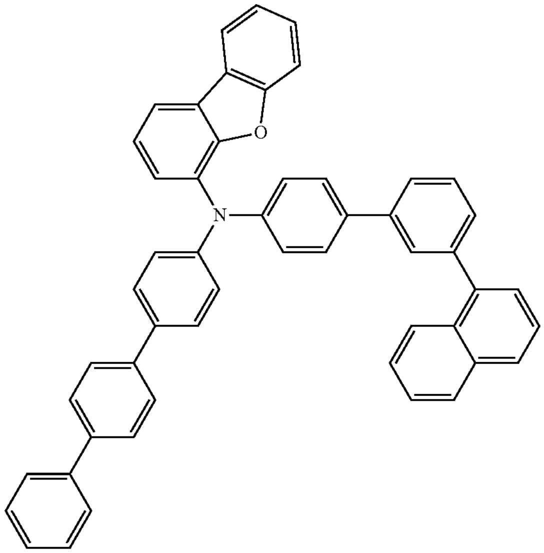

-continued

Compound 4

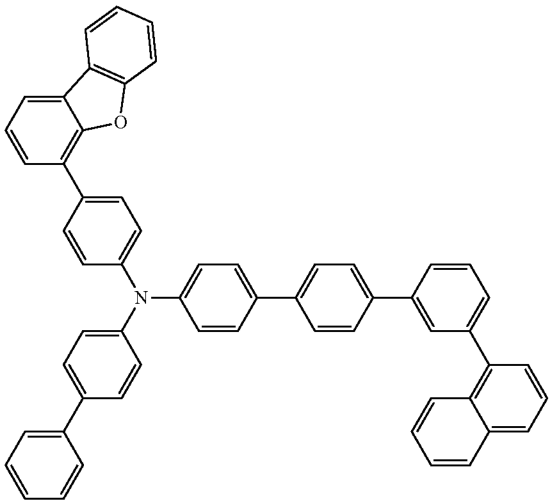

Compound 7

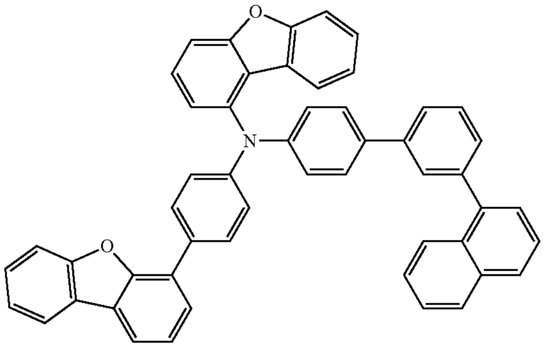

Compound 10

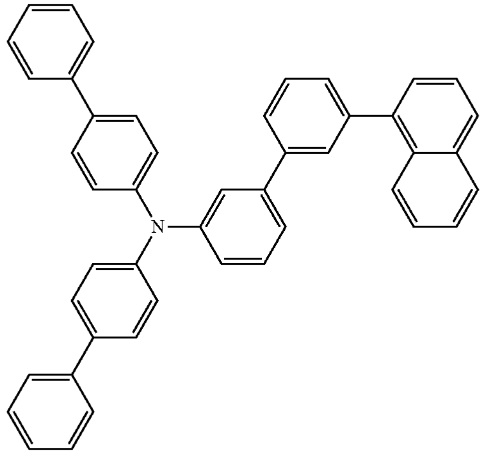

-continued

Compound 11

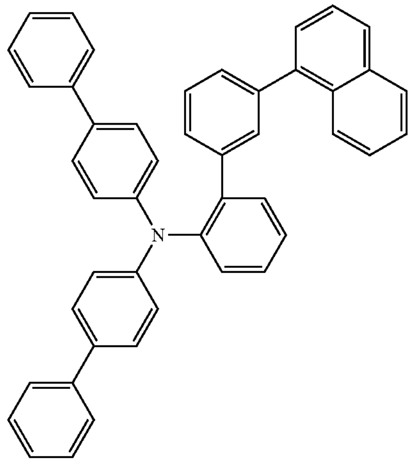

Compound 12

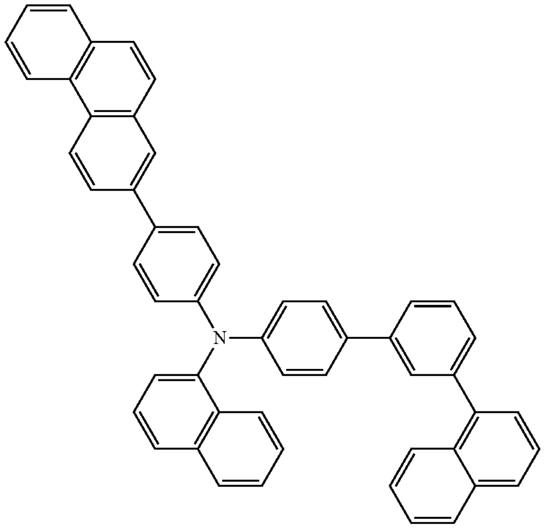

Compound 13

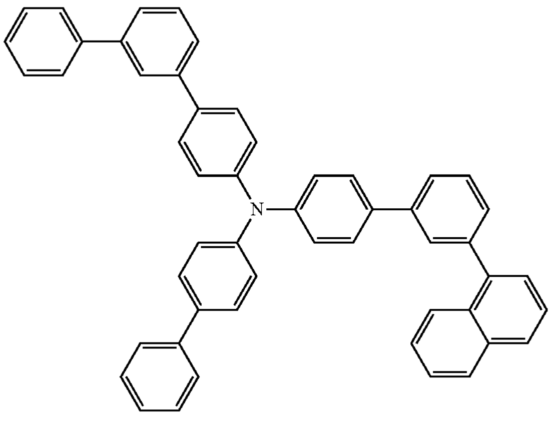

-continued

Compound 14

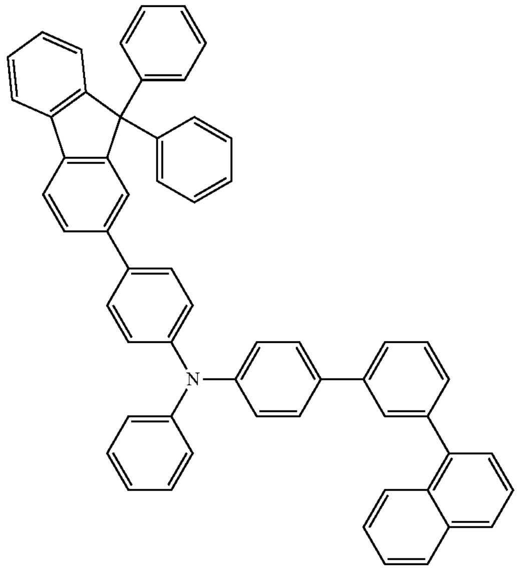

Intermediate Synthesis Example 1: Synthesis of Intermediate A

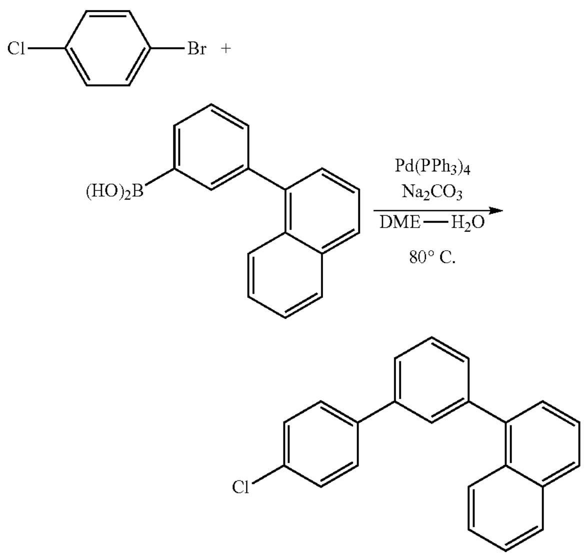

Intermediate A

In an argon atmosphere, a mixture of 3.83 g (20.0 mmol) of 1-bromo-4-chlorobenzene, 5.46 g (22.0 mmol) of 3-(naphthalen-1-yl)phenylboronic acid, 0.693 g (0.60 mmol) of tetrakis(triphenylphosphine)palladium(0), 6.36 g (60.0 mmol) of sodium carbonate, 80 mL of DME and 20 mL of water was stirred at 80° C. for 8 hours. The reaction liquid was cooled to room temperature, water was added thereto, and then filtered. The resulting residue was purified through silica gel column chromatography and recrystallization to give 5.783 g of a white solid. The yield was 92%.

Intermediate Synthesis Example 2: Synthesis of Intermediate B

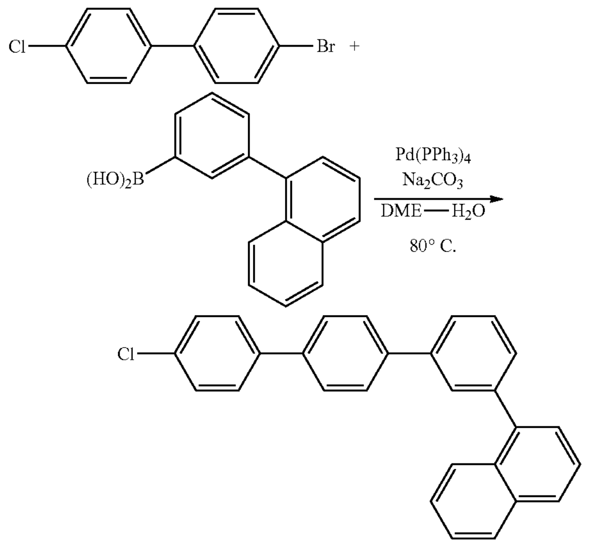

Intermediate B

Intermediate B was produced in the same manner as above except that, in Intermediate Synthesis Example 1, 4-bromo-4'-chloro-1,1'-biphenyl was used in place of 1-bromo-4-chlorobenzene. The yield was 84%.

Intermediate Synthesis Example 3: Synthesis of Intermediate C

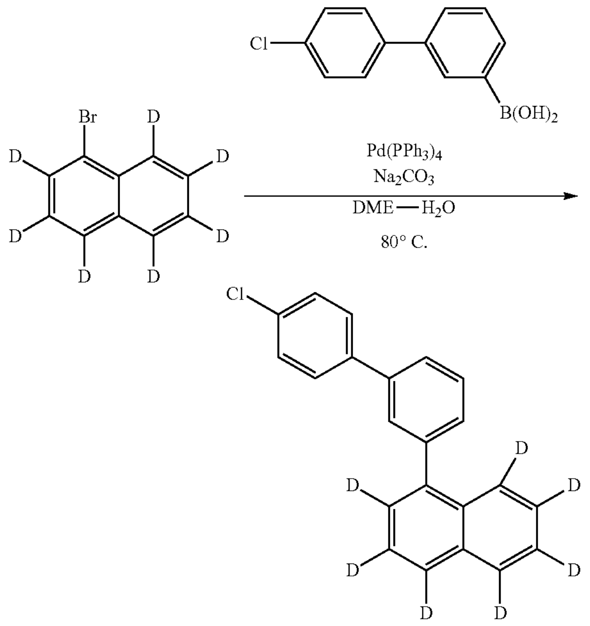

Intermediate C

Synthesis of Intermediate C

Intermediate C was produced in the same manner as above except that, in Intermediate Synthesis Example 1,1-bromonaphthalene-d7 was used in place of 1-bromo-4-chlorobenzene, and 4'-chloro(1,1'-biphenyl-3-yl)boronic acid was used in place of 3-(naphthalen-1-yl)phenylboronic acid. The yield was 79%.

Intermediate Synthesis Example 4: Synthesis of Intermediate D

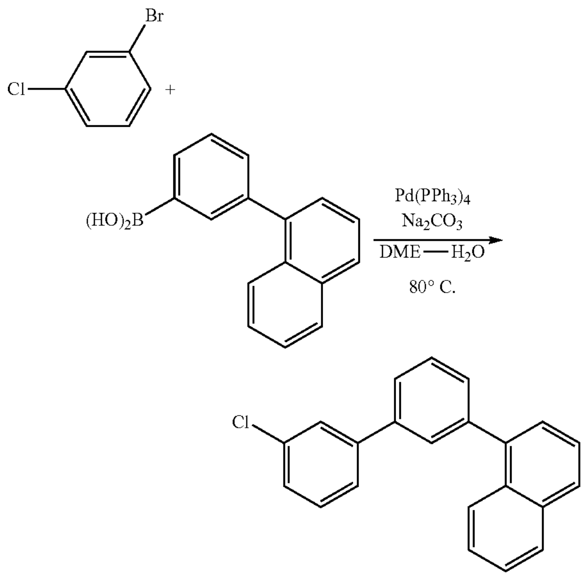

Intermediate D

Synthesis of Intermediate D

Intermediate D was produced in the same manner as above except that, in Intermediate Synthesis Example 1,1-bromo-3-chlorobenzene was used in place of 1-bromo-4-chlorobenzene. The yield was 74%.

Intermediate Synthesis Example 5: Synthesis of Intermediate E

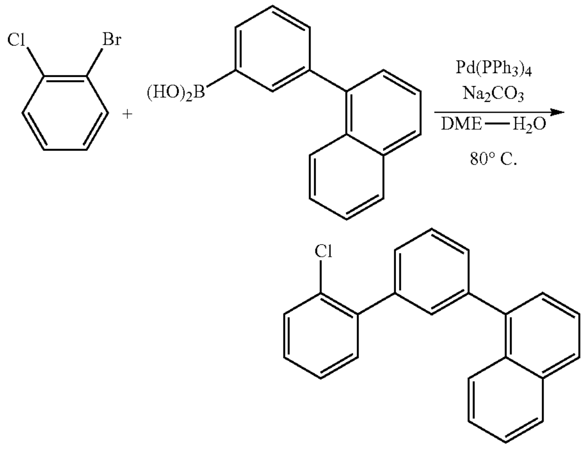

Intermediate E

Synthesis of Intermediate E

Intermediate E was produced in the same manner as above except that, in Intermediate Synthesis Example 1,1- bromo-2-chlorobenzene was used in place of 1-bromo-4-chlorobenzene. The yield was 70%.

Intermediate Synthesis Example 6: Synthesis of Intermediate F

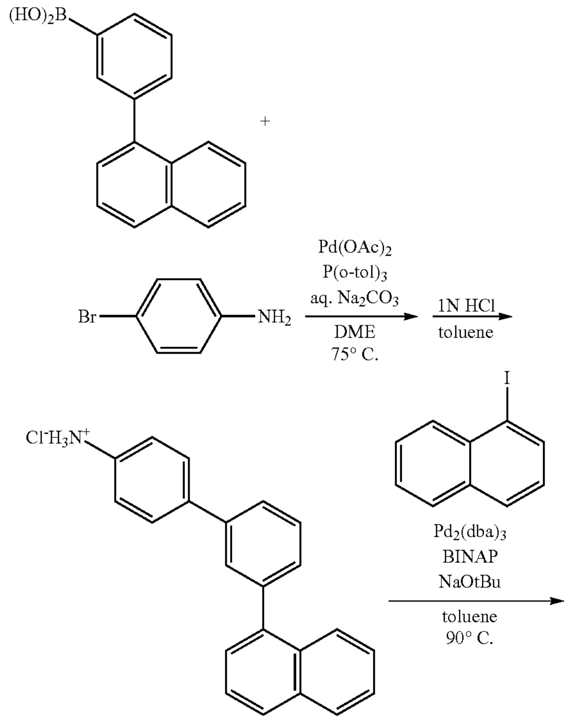

Intermediate F-1

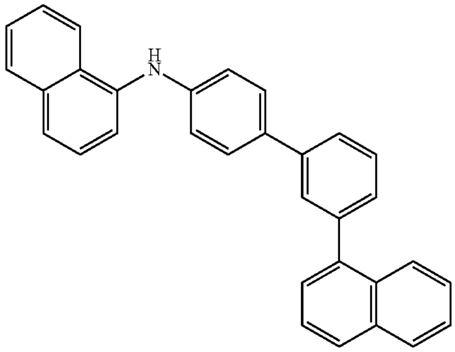

Intermediate F

Synthesis of Intermediate F-1

In an argon atmosphere, a mixture of 3.23 g (13.0 mmol) of 3-(naphthalen-1-yl)phenylboronic acid, 2.24 g (13.0 mmol) of 4-bromoaniline, 0.044 g (0.195 mmol) of palladium(II) acetate, 0.237 g (0.780 mmol) of tris(2-methylphenyl)phosphine, 19.5 mL (30.0 mmol) of an aqueous solution of 2 M sodium carbonate, and 65 mL of DME was stirred at 75° C. for 10 hours. The reaction liquid was cooled to room temperature, and then filtered using activated white earth, and the filtrate was concentrated under reduced pressure. The resulting residue was dissolved in toluene, and 40 mL of 1 N hydrochloric acid was dropwise added thereto. This was stirred at room temperature for 3 hours, and filtered to give a white solid (5.422 g). The yield was 59%.

Synthesis of Intermediate F

In an argon atmosphere, a mixture of 5.422 g (16.3 mmol) of Intermediate F-1, 4.57 g (18.0 mmol) of 1-iodonaphthalene, 0.277 g (0.302 mmol) of tris(dibenzylideneacetone) dipalladium(0), 0.433 g (0.654 mmol) of BINAP, 3.14 g (32.7 mmol) of sodium-t-butoxide, and 82 mL of xylene was stirred at 90° C. for 7 hours. The reaction liquid was cooled to room temperature, and then concentrated under reduced pressure. The resulting residue was purified through silica gel column chromatography and recrystallization to give a white solid (5.144 g). The yield was 74%.

Synthesis Example 1: Synthesis of Compound 1

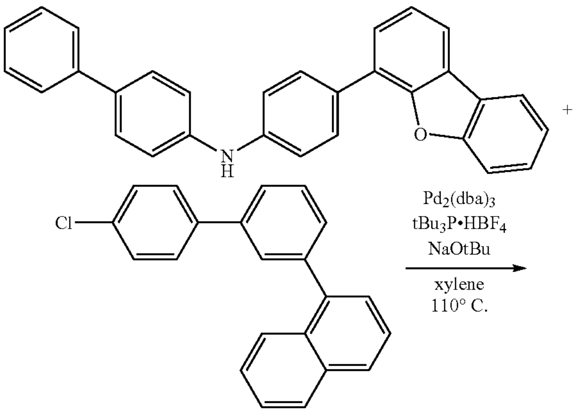

Intermediate A

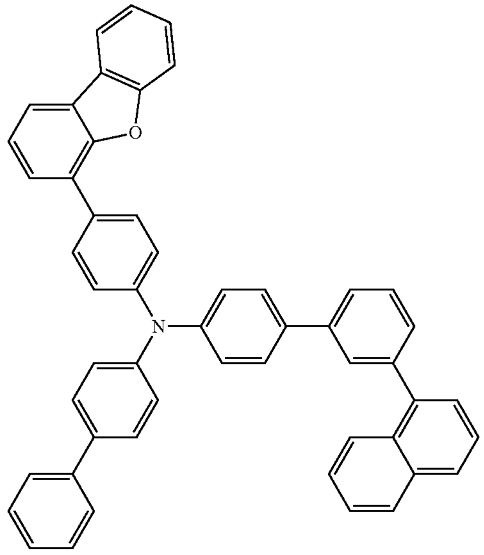

Compound 1

In an argon atmosphere, a mixture of 6.58 g (16.0 mmol) of N-[4-(dibenzo[b,d]furan-4-yl)phenyl][1,1'-biphenyl]-4-amine, 5.54 g (17.6 mmol) of Intermediate A, 0.293 g (0.32 mmol) of tris(dibenzylideneacetone)palladium(0), 0.371 g (1.28 mmol) of tri-t-butylphosphonium tetrafluoroborate, 2.31 g (24.0 mmol) of sodium-t-butoxide and 80 mL of xylene was stirred at 110° C. for 2.5 hours. The reaction liquid was cooled to room temperature, and then concentrated under reduced pressure. The resulting residue was purified through silica gel column chromatography and recrystallization to give a white solid (3.021 g). The yield was 72%.

As a result of mass spectrometry (m/e=690 relative to molecular weight 689.86), the resulting compound was Compound 1.

Synthesis Example 2: Synthesis of Compound 2

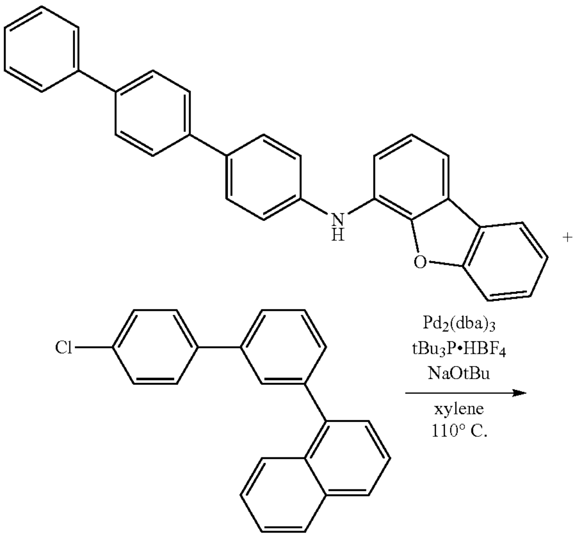

Intermediate A

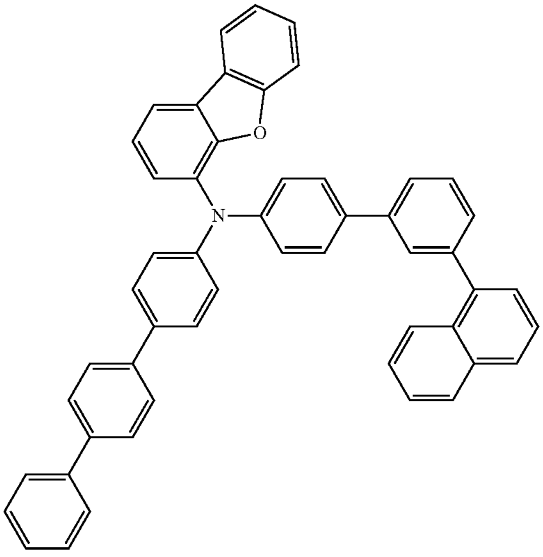

Compound 2

According to the same process as in Synthesis Example 1 but using N-([1,1':4',1"-terphenyl]-4-yl)-4-(dibenzo[b,d]furan)amine in place of N-[4-(dibenzo[b,d]furan-4-yl)phenyl][1,1'-biphenyl]-4-amine, a white solid was produced. The yield was 35%.

As a result of mass spectrometry (m/e=690 relative to molecular weight 689.86), the resulting compound was Compound 2.

Synthesis Example 3: Synthesis of Compound 3

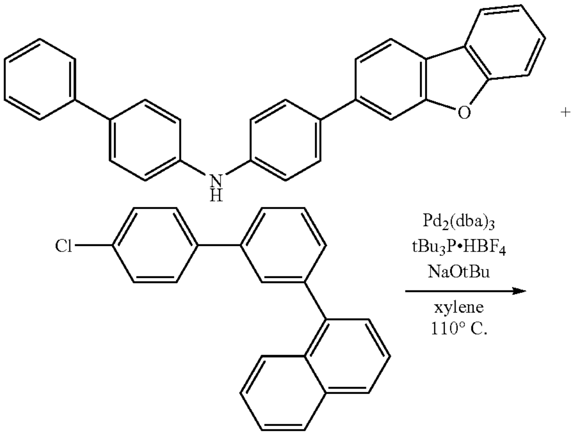

Intermediate A

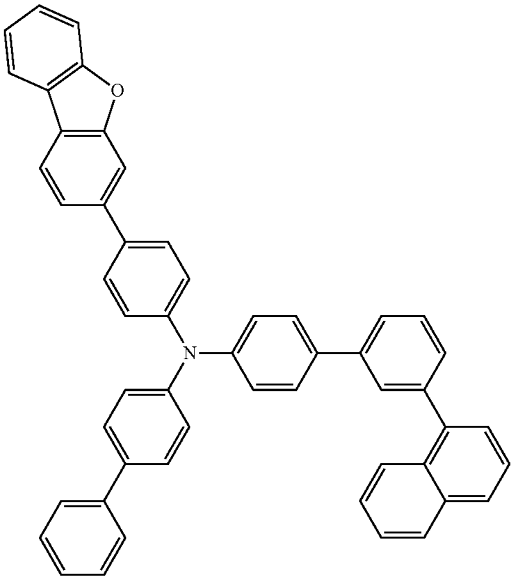

Compound 3

According to the same process as in Synthesis Example 1 but using N-[4-(dibenzo[b,d]furan-3-yl)phenyl][1,1'-biphenyl]-4-amine in place of N-[4-(dibenzo[b,d]furan-4-yl)phenyl][1,1'-biphenyl]-4-amine, a white solid was produced. The yield was 41%.

As a result of mass spectrometry (m/e=690 relative to molecular weight 689.86), the resulting compound was Compound 3.

Synthesis Example 4: Synthesis of Compound 4

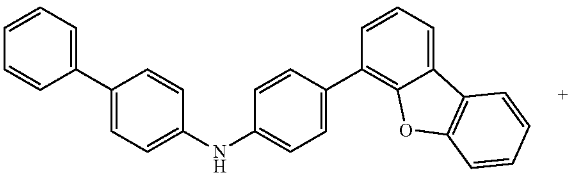

-continued

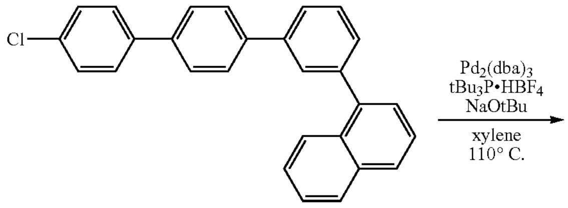

Intermediate B

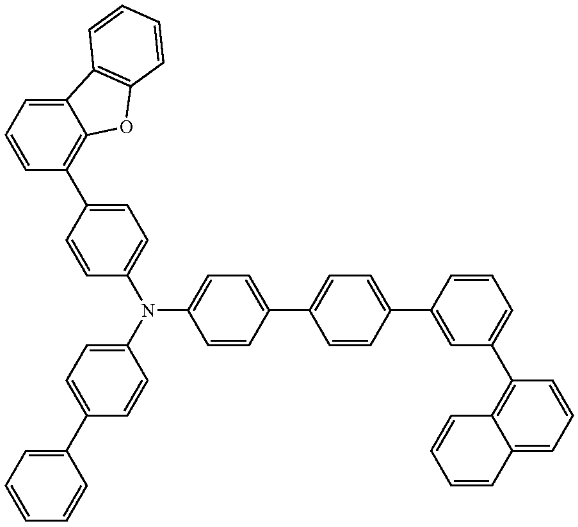

Compound 4

According to the same process as in Synthesis Example 1 but using Intermediate B in place of Intermediate A, a white solid was produced. The yield was 38%.

As a result of mass spectrometry (m/e=766 relative to molecular weight 765.96), the resulting compound was Compound 4.

Synthesis Example 5: Synthesis of Compound 5

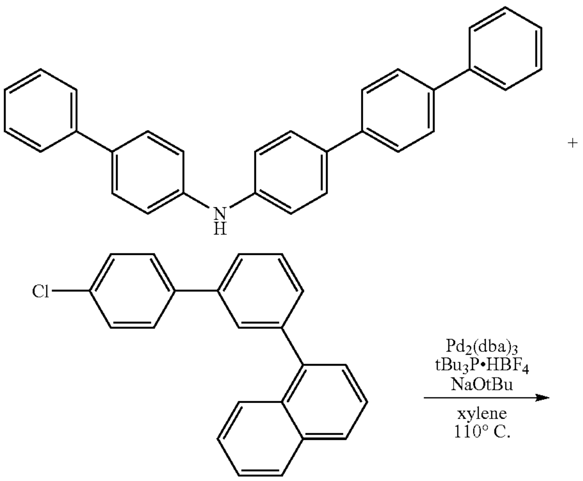

Intermediate A

-continued

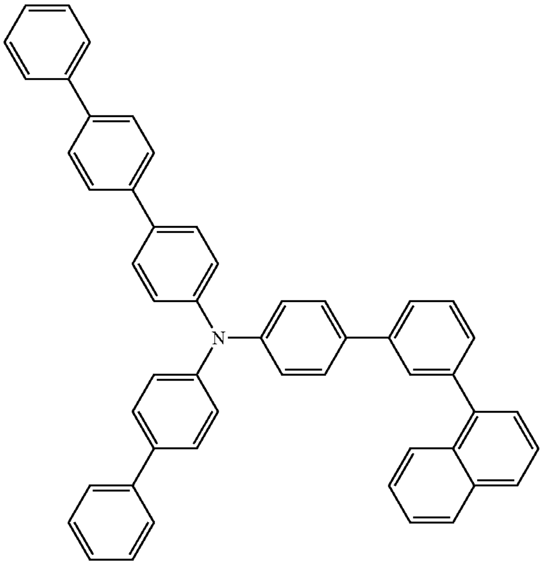

Compound 5

According to the same process as in Synthesis Example 1 but using N-[1,1'-biphenyl]-4-yl-[1,1':4',1"-terphenyl]-4-amine in place of N-[4-(dibenzo[b,d]furan-4-yl)phenyl][1,1'-biphenyl]-4-amine, a white solid was produced. The yield was 49%.

As a result of mass spectrometry (m/e=676 relative to molecular weight 675.88), the resulting compound was Compound 5.

Synthesis Example 6: Synthesis of Compound 6

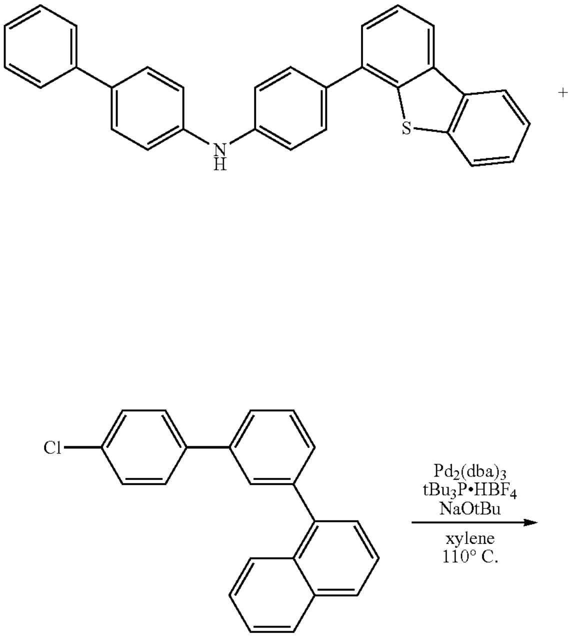

Intermediate A

-continued

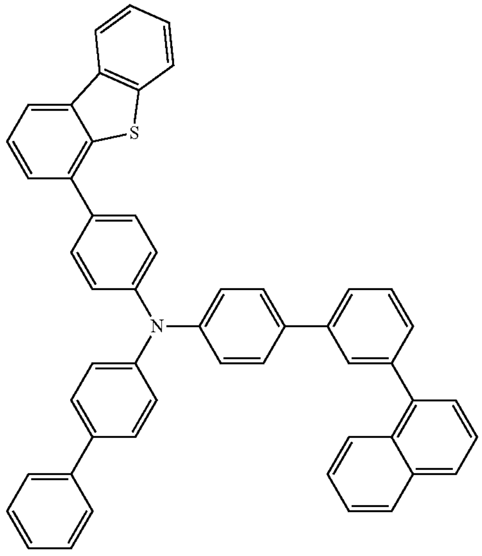

Compound 6

According to the same process as in Synthesis Example 1 but using N-[4-(dibenzo[b,d]thiophen-4-yl)phenyl][1,1'-biphenyl]-4-amine in place of N-[4-(dibenzo[b,d]furan-4-yl)phenyl][1,1'-biphenyl]-4-amine, a white solid was produced. The yield was 41%.

As a result of mass spectrometry (m/e=706 relative to molecular weight 705.92), the resulting compound was Compound 6.

Synthesis Example 7: Synthesis of Compound 7

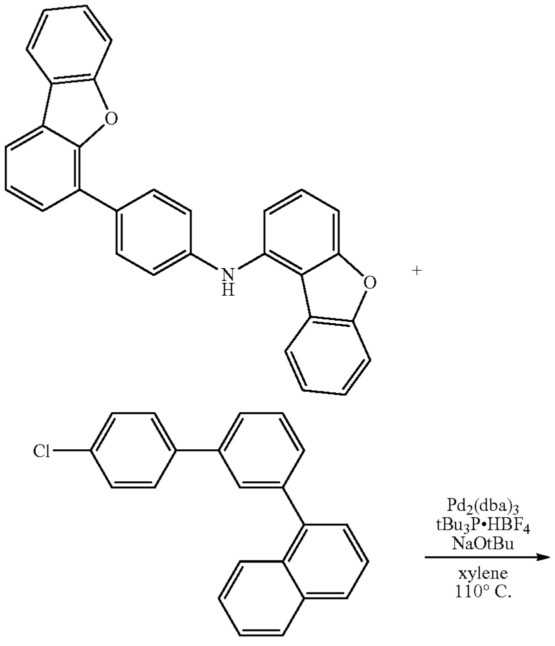

Intermediate A

-continued

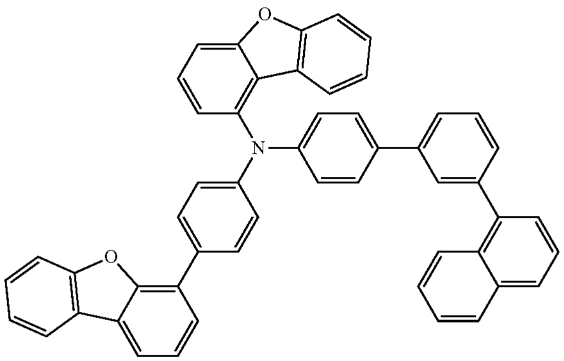

Compound 7

According to the same process as in Synthesis Example 1 but using N-[4-(dibenzo[b,d]furan-4-yl)phenyl]-1-dibenzo[b,d]furan)amine in place of N-[4-(dibenzo[b,d]furan-4-yl)phenyl][1,1'-biphenyl]-4-amine, a white solid was produced. The yield was 34%.

As a result of mass spectrometry (m/e=704 relative to molecular weight 703.81), the resulting compound was Compound 7.

Synthesis Example 8: Synthesis of Compound 8

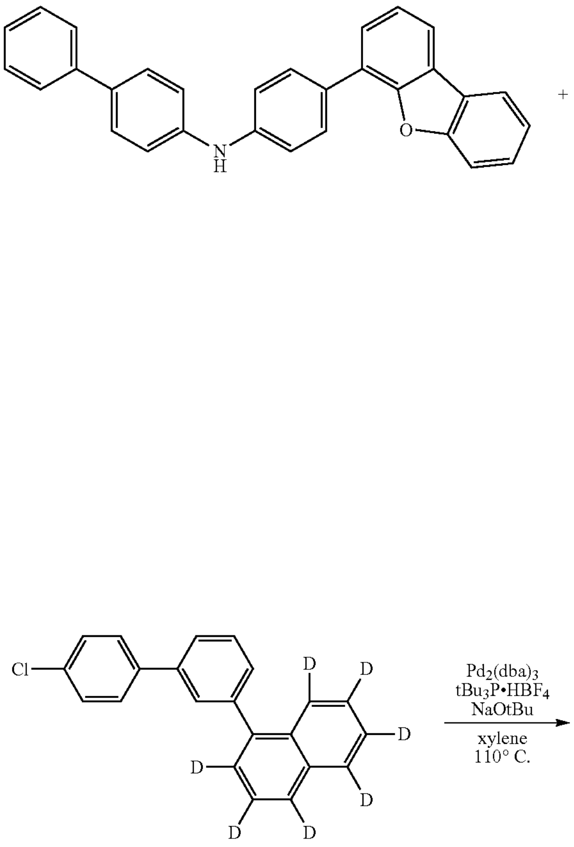

Intermediate C

-continued

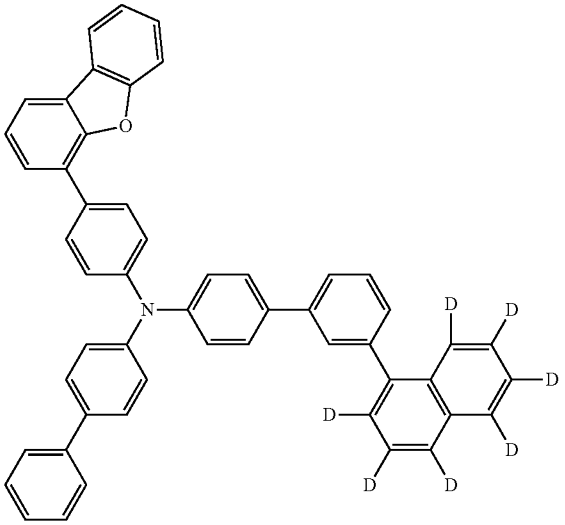

Compound 8

According to the same process as in Synthesis Example 1 but using Intermediate C in place of Intermediate 1, a white solid was produced. The yield was 46%.

As a result of mass spectrometry (m/e=697 relative to molecular weight 696.90), the resulting compound was Compound 8.

Synthesis Example 9: Synthesis of Compound 9

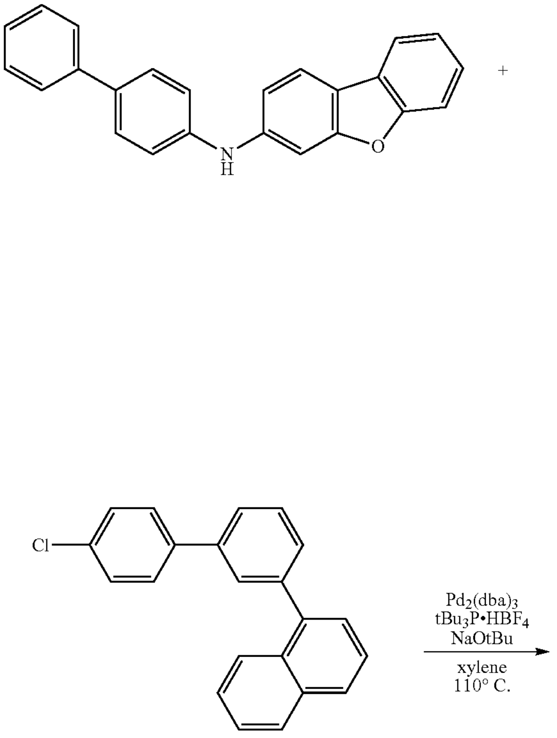

Intermediate A

-continued

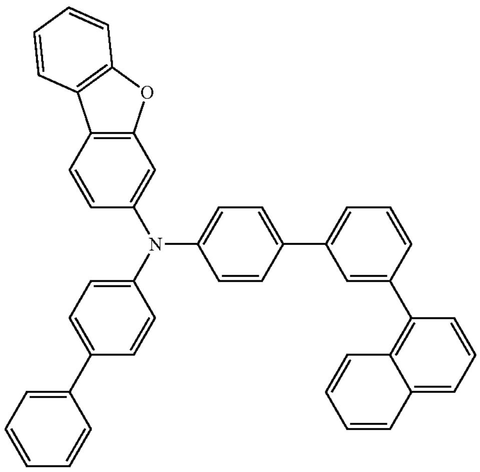

Compound 9

According to the same process as in Synthesis Example 1 but using N-([1,1'-biphenyl](dibenzo[b,d]furan)amine in place of N-[4-(dibenzo[b,d]furan-4-yl)phenyl][1,1'-biphenyl]-4-amine, a white solid was produced. The yield was 51%.

As a result of mass spectrometry (m/e=614 relative to molecular weight 613.76), the resulting compound was Compound 9.

Synthesis Example 10: Synthesis of Compound 10

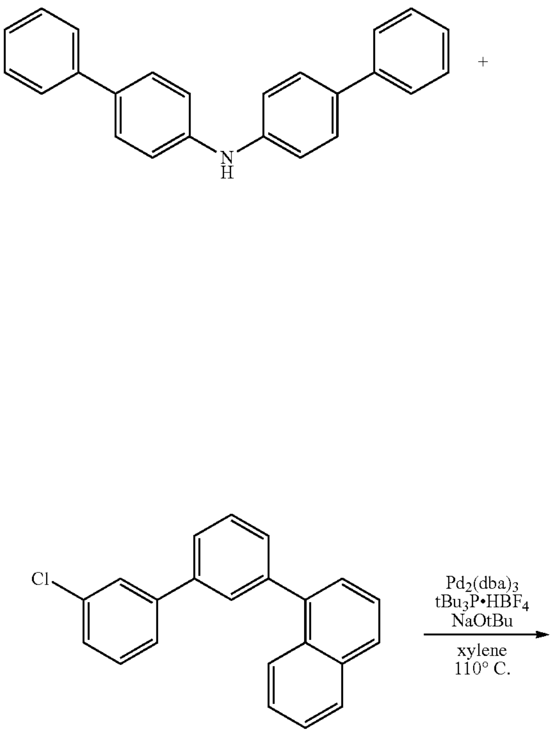

Intermediate D

-continued

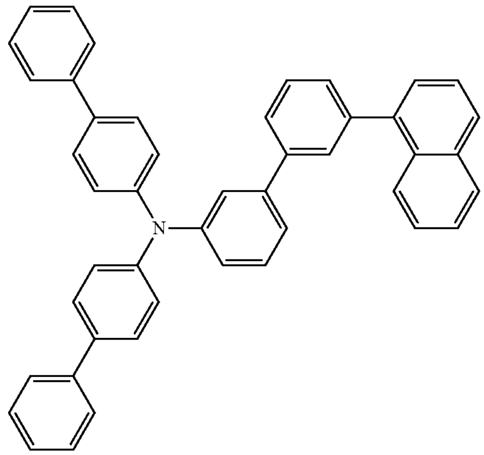

Compound 10

According to the same process as in Synthesis Example 1 but using N-[1,1'-biphenyl]-4-yl-[1,1'-biphenyl]-4-amine in place of N-[4-(dibenzo[b,d]furan-4-yl)phenyl][1,1'-biphenyl]-4-amine, a white solid was produced. The yield was 33%.

As a result of mass spectrometry (m/e=600 relative to molecular weight 599.78), the resulting compound was Compound 10.

Synthesis Example 11: Synthesis of Compound 11

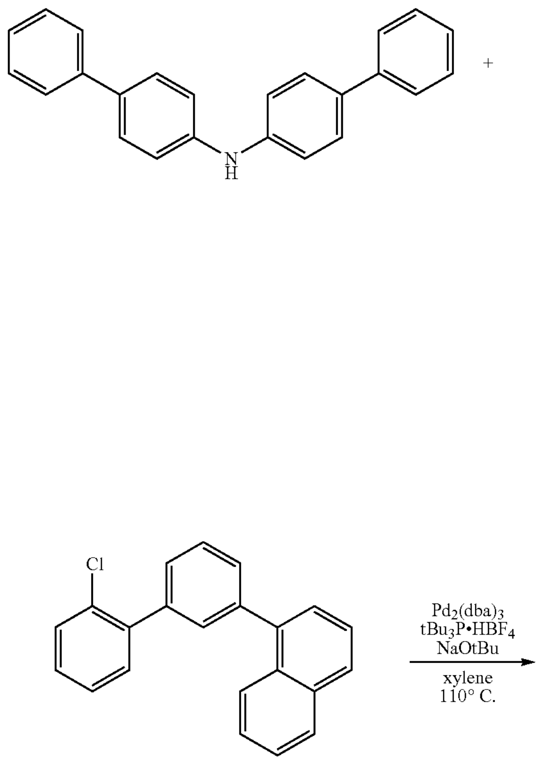

Intermediate E

-continued

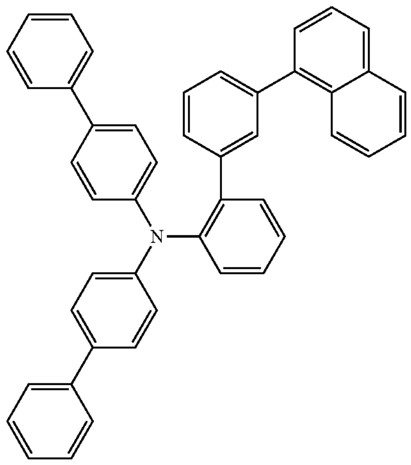

Compound 11

According to the same process as in Synthesis Example 1 but using N-[1,1'-biphenyl]-4-yl-[1,1'-biphenyl]-4-amine in place of N-[4-(dibenzo[b,d]furan-4-yl)phenyl][1,1'-biphenyl]-4-amine and using Intermediate E in place of Intermediate A, a white solid was produced. The yield was 49%.

As a result of mass spectrometry (m/e=600 relative to molecular weight 599.78), the resulting compound was Compound 11.

Synthesis Example 12: Synthesis of Compound 12

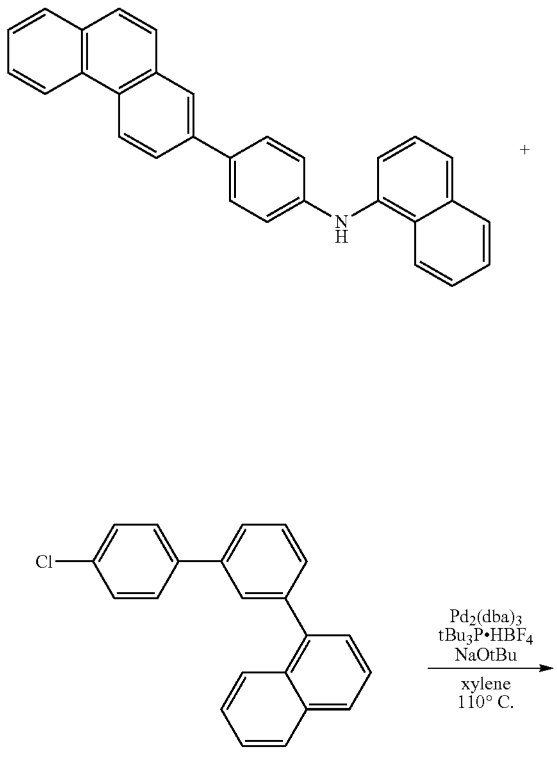

Intermediate A

-continued

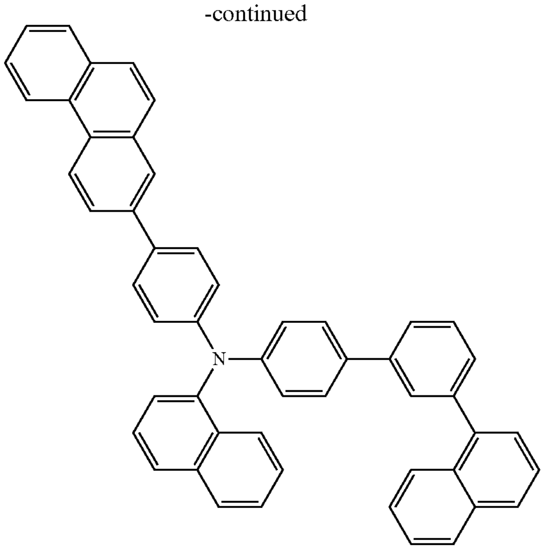

Compound 12

According to the same process as in Synthesis Example 1 but using N-[4-(phenanthren-2-yl)phenyl]naphthalene-1-amine in place of N-[4-(dibenzo[b,d]furan-4-yl)phenyl][1,1'-biphenyl]-4-amine, a white solid was produced. The yield was 54%.

As a result of mass spectrometry (m/e=674 relative to molecular weight 673.86), the resulting compound was Compound 12.

Synthesis Example 13: Synthesis of Compound 13

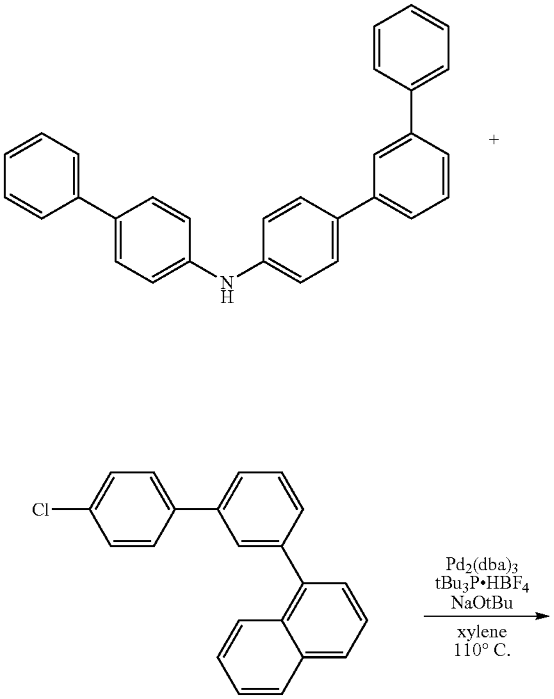

Intermediate A

-continued

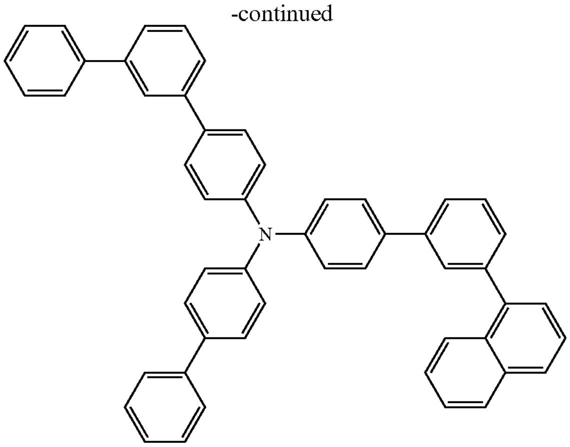

Compound 13

According to the same process as in Synthesis Example 1 but using N-[1,1'-biphenyl]-4-yl[1,1':3',1"-terphenyl]-4-amine in place of N-[4-(dibenzo[b,d]furan-4-yl)phenyl][1,1'-biphenyl]-4-amine, a white solid was produced. The yield was 62%.

As a result of mass spectrometry (m/e=676 relative to molecular weight 675.88), the resulting compound was Compound 13.

Synthesis Example 14: Synthesis of Compound 14

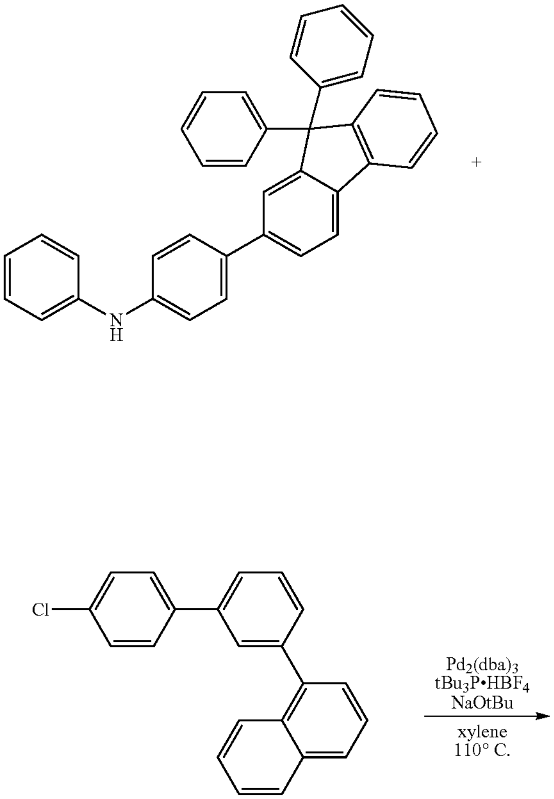

Intermediate A

-continued

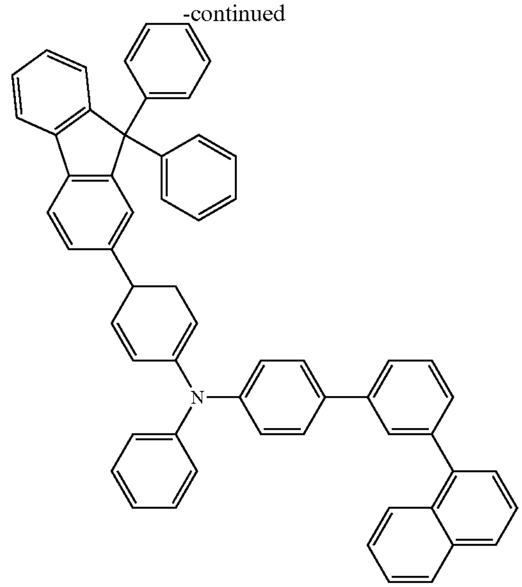

Compound 14

According to the same process as in Synthesis Example 1 but using 4-(9,9-diphenyl-9H-fluoren-2-yl)-N-phenylbenzenamine in place of N-[4-(dibenzo[b,d]furan-4-yl)phenyl][1,1'-biphenyl]-4-amine, a white solid was produced. The yield was 36%.

As a result of mass spectrometry (m/e=764 relative to molecular weight 763.98), the resulting compound was Compound 14.

Synthesis Example 15: Synthesis of Compound 15

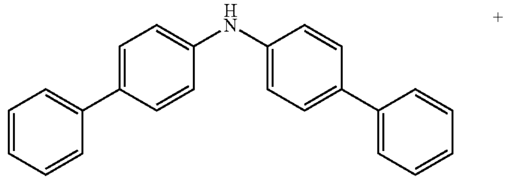

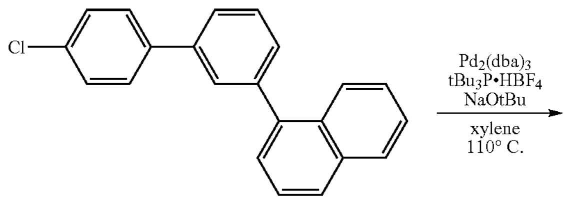

Intermediate A

-continued

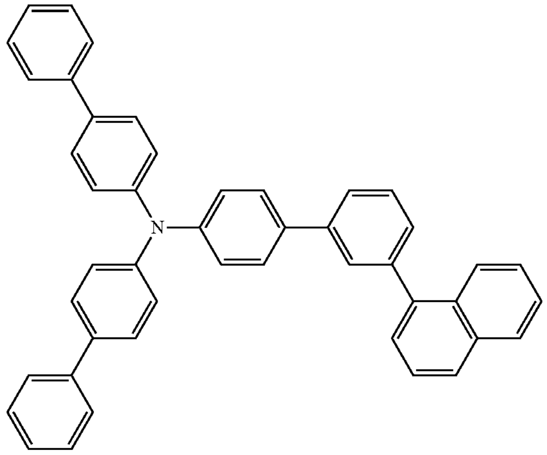

Compound 15

According to the same process as in Synthesis Example 1 but using [1,1'-biphenyl]-4-yl-[1,1'-biphenyl]-4-amine in place of N-[4-(dibenzo[b,d]furan-4-yl)phenyl][1,1'-biphenyl]-4-amine, a white solid was produced. The yield was 51%.

As a result of mass spectrometry (m/e=600 relative to molecular weight 599.78), the resulting compound was Compound 15.

Synthesis Example 16: Synthesis of Compound 16

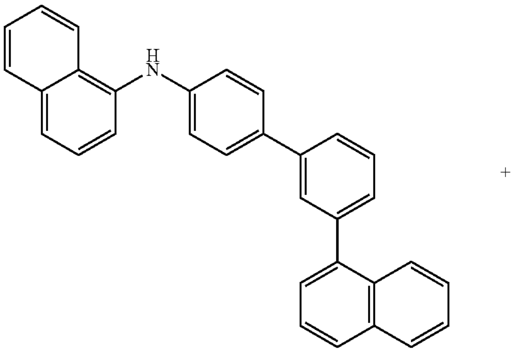

Intermediate F

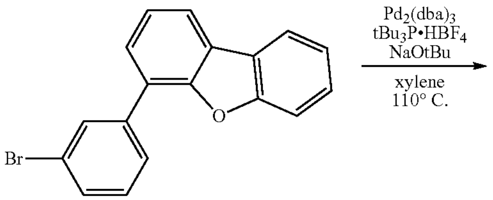

-continued

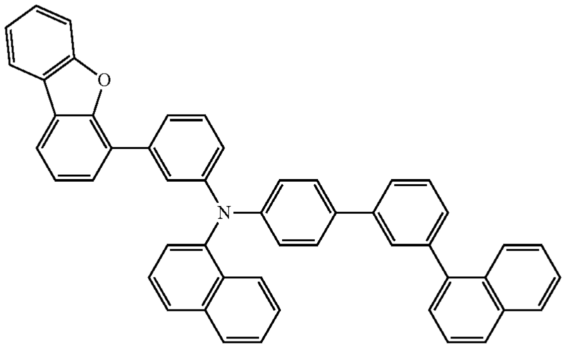

Compound 16

According to the same process as in Synthesis Example 1 but using Intermediate F in place of N-[4-(dibenzo[b,d]furan-4-yl)phenyl][1,1'-biphenyl]-4-amine and using 4-(3-bromophenyl)dibenzofuran in place of Intermediate A, a white solid was produced. The yield was 40%.

As a result of mass spectrometry (m/e=663 relative to molecular weight 663.82), the resulting compound was Compound 16.

Synthesis Example 17: Synthesis of Compound 17

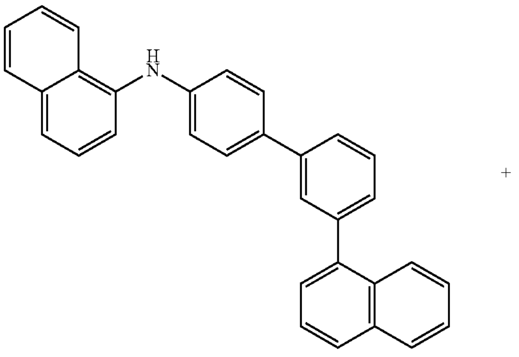

Intermediate F

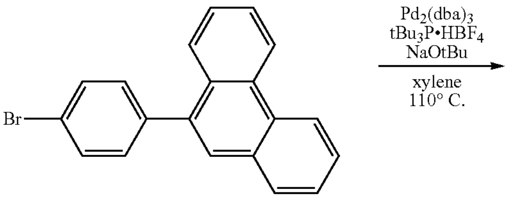

-continued

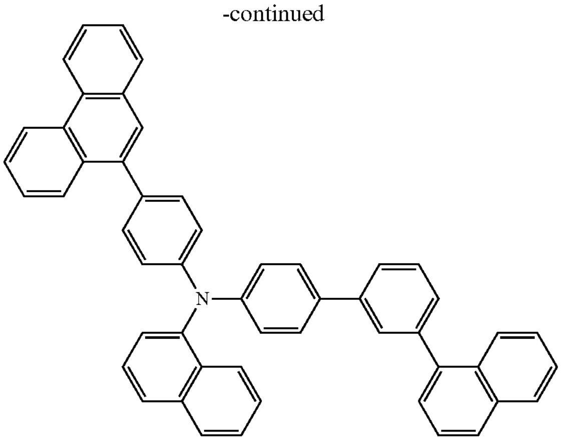

Compound 17

According to the same process as in Synthesis Example 1 but using Intermediate F in place of N-[4-(dibenzo[b,d]furan-4-yl)phenyl][1,1'-biphenyl]-4-amine and using 9-(4-bromophenyl)phenanthrene in place of Intermediate A, a white solid was produced. The yield was 47%.

As a result of mass spectrometry (m/e=674 relative to molecular weight 673.86), the resulting compound was Compound 17.

Synthesis Example 18: Synthesis of Compound 18

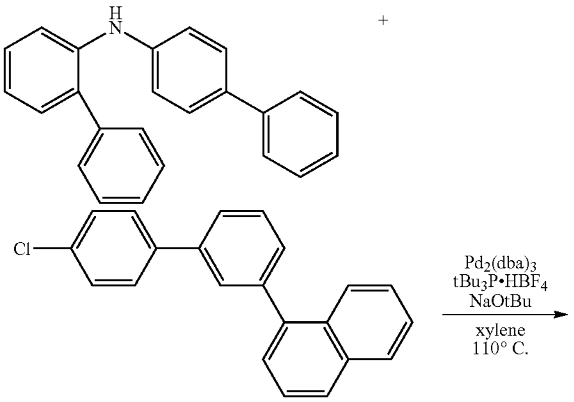

Intermediate A

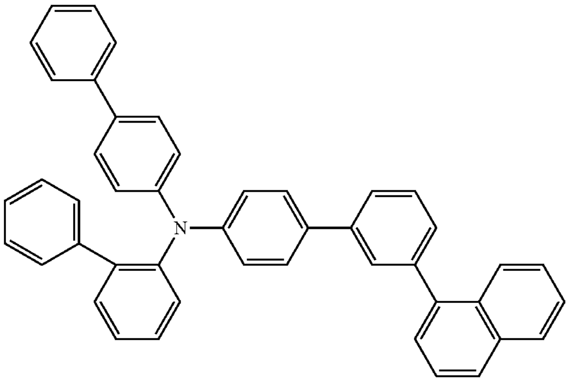

Compound 18

According to the same process as in Synthesis Example 1 but using [1,1'-biphenyl]-4-yl-[1,1'-biphenyl]-2-amine in place of N-[4-(dibenzo[b,d]furan-4-yl)phenyl][1,1'-biphenyl]-4-amine, a white solid was produced. The yield was 42%.

As a result of mass spectrometry (m/e=600 relative to molecular weight 599.78), the resulting compound was Compound 18.

REFERENCE SIGNS LIST

1, 11: Organic EL device
2: Substrate
3: Anode
4: Cathode
5: Light emitting layer
6: Hole transporting zone (hole transporting layer)
6*a*: Hole injecting layer
6*b*: First hole transporting layer
6*c*: Second hole transporting layer
7: Electron transporting zone (electron transporting layer)
7*a*: First electron transporting layer
7*b*: Second electron transporting layer
10, 20: Light emitting unit

The invention claimed is:

1. A compound represented by the following formula (1A):

(1A)

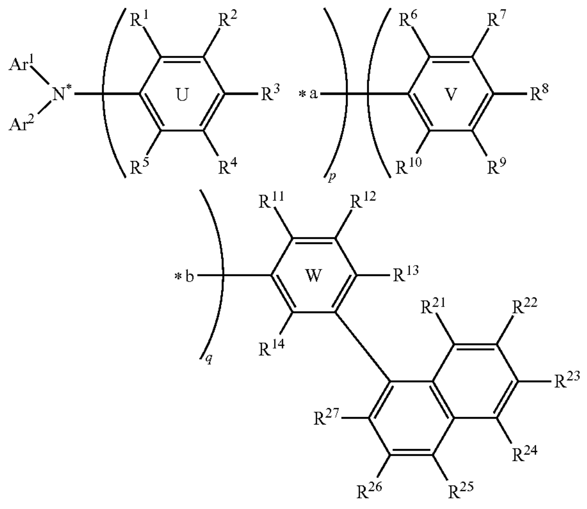

in the formula (1A),

N* is a central nitrogen atom, p represents 0 or 1, q represents 0 or 1, provided that p+q≥1, when p is 0 and q is 1, *a bonds to the nitrogen atom N*, and one selected from $R^6$ to $R^{10}$ is a single bond bonding to *b, when p is 1 and q is 0, one selected from $R^1$ to $R^5$ is a single bond bonding to *b, when p is 1 and q is 1, one selected from $R^1$ to $R^5$ is a single bond bonding to *a, and one selected from $R^6$ to $R^{10}$ is a single bond bonding to *b, $R^1$ to $R^5$ that are not a single bond bonding to *a or *b, $R^6$ to $R^{10}$ that are not a single bond bonding to *b, $R^{11}$ to $R^{14}$, and $R^{21}$ to $R^{27}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, adjacent two selected from $R^1$ to $R^5$ that are not a single bond, adjacent two selected from $R^6$ to $R^{10}$ that are not a single bond, adjacent two selected from $R^{11}$ to $R^{14}$ that are not a single bond, and adjacent two selected from $R^{21}$ to $R^{27}$ do not bond to each other and therefore do not form a cyclic structure, provided that one or more pairs of two benzene rings bonding to each other selected from the benzene ring U, the benzene ring V and the benzene ring W may be crosslinked with $CR^xR^y$ to form a substituted or unsubstituted fluorene structure, or may not be crosslinked and may not form a fluorene structure, $R^x$ and $R^y$ each independently represent a substituted or unsubstituted alkyl group having 1 to 50 carbon atoms or a substituted or unsubstituted aryl group having 6 to 50 ring carbon atoms, and $R^x$ and $R^y$ may bond via a single bond, $Ar^1$ and $Ar^2$ each are independently represented by any of the following formulae (1-a) to (1-e):

(1-a)

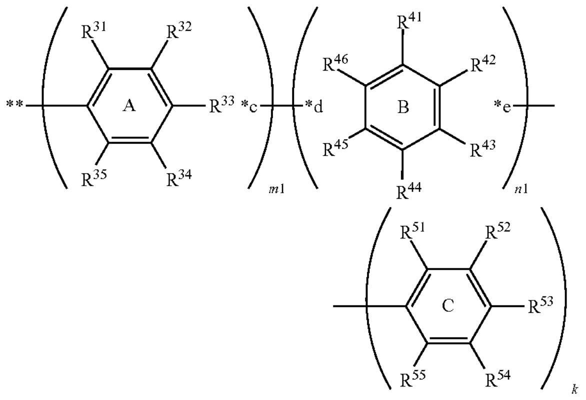

(1-b)

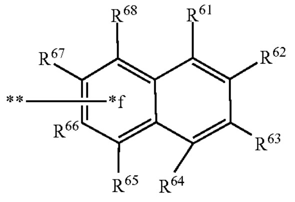

-continued (1-c)

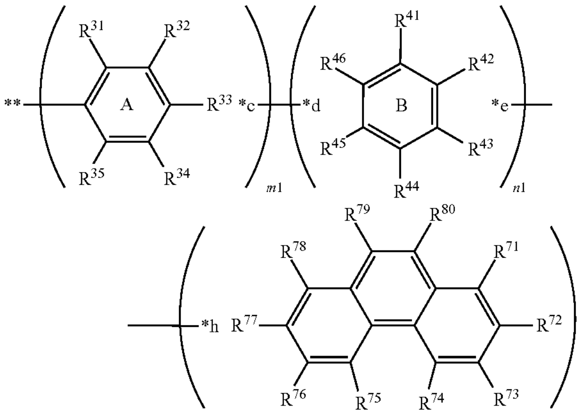

(1-d)

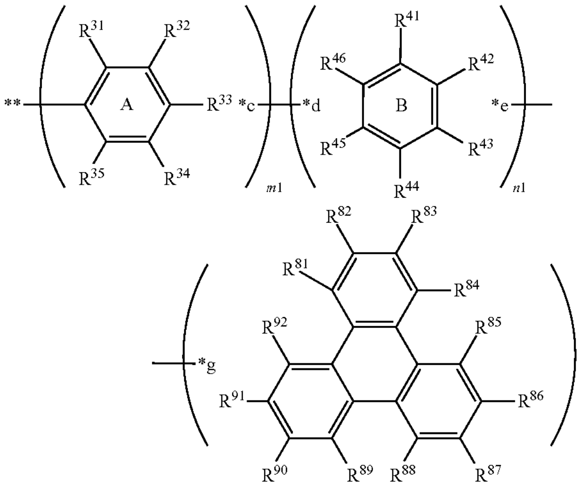

(1-e)

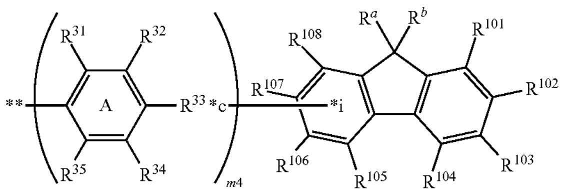

in the formula (1-a), $R^{31}$ to $R^{35}$, $R^{41}$ to $R^{46}$, and $R^{51}$ to $R^{55}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{31}$ to $R^{35}$ is a single bond bonding to *c, one selected from $R^{41}$ to $R^{46}$ is a single bond bonding to *d, and the other one selected from $R^{41}$ to $R^{46}$ is a single bond bonding to *e,

** is a bonding position to the nitrogen atom N*, m1 represents 0 or 1, and n1 represents 0 or 1, when m1 is 0 and n1 is 0, *e bonds to the nitrogen atom N* when m1 is 0 and n1 is 1, *c bonds to the nitrogen atom N*, when m1 is 1 and n1 is 0, one selected from $R^{31}$ to $R^{35}$ is a single bond bonding to *e, k represents 1 or 2, adjacent two selected from $R^{31}$ to $R^{35}$ that are not a single bond, adjacent two selected from $R^{41}$ to $R^{46}$ that are not a single bond, and adjacent two selected from $R^{51}$ to $R^{55}$ do not bond to each other and therefore do not form a cyclic structure, the benzene ring A and the benzene ring B, the benzene ring A and the benzene ring C, and the benzene ring B and the benzene ring C do not crosslink;

in the formula (1-b), $R^{61}$ to $R^{68}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{61}$ to $R^{68}$ is a single bond bonding to *f,

** represents a bonding position to the nitrogen atom N*, adjacent two selected from $R^{61}$ to $R^{68}$ that are not a single bond do not bond to each other and therefore do not form a cyclic structure;

in the formula (1-c), $R^{31}$ to $R^{35}$, $R^{41}$ to $R^{46}$, **, *c, *d, and *e are the same as above, $R^{71}$ to $R^{80}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{71}$ to $R^{80}$ is a single bond bonding to *h, m2 represents 0 or 1, n2 represents 0 or 1, when m2 is 0 and n2 is 0, *e bonds to the nitrogen atom N*, when m2 is 0 and n2 is 1, *c bonds to the nitrogen atom N*, when m2 is 1 and n2 is 0, one selected from $R^{31}$ to $R^{35}$ is a single bond bonding to *e, adjacent two selected from $R^{31}$ to $R^{35}$ that are not a single bond, adjacent two selected from $R^{41}$ to $R^{46}$ that are not a single bond, and adjacent two selected from $R^{71}$ to $R^{80}$ do not bond to each other and therefore do not form a cyclic structure, the benzene ring A and the benzene ring B do not crosslink;

in the formula (1-d), $R^{31}$ to $R^{35}$, $R^{41}$ to $R^{46}$, **, *c, *d, and *e are the same as above, $R^{81}$ to $R^{92}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{81}$ to $R^{92}$ is a single bond bonding to *g, m3 represents 0 or 1, n3 represents 0 or 1, when m3 is 0 and n3 is 0, *e bonds to the nitrogen atom N*, when m3 is 0 and n3 is 1, *c bonds to the nitrogen atom N*, when m3 is 1 and n3 is 0, one selected from $R^{31}$ to $R^{35}$ is a single bond bonding to *e, adjacent two selected from $R^{31}$ to $R^{35}$ that are not a single bond, adjacent two selected from $R^{41}$ to $R^{46}$ that are not a single bond, and adjacent two selected from $R^{81}$ to $R^{92}$ do not bond to each other and therefore do not form a cyclic structure, the benzene ring A and the benzene ring B do not crosslink;

in the formula (1-e), $R^{31}$ to $R^{35}$, **, and *c are the same as above, $R^{101}$ to $R^{108}$ each independently represent a hydrogen atom, a halogen atom, a nitro group, a cyano group, a substituted or unsubstituted alkyl group having 1 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted aryloxy group having 6 to 50 ring carbon atoms, a substituted or unsubstituted aralkyl group having 7 to 50 carbon atoms, or a mono, di or tri-substituted silyl group having substituent(s) selected from a substituted or unsubstituted alkyl group having 1 to 50 carbon atoms, a substituted or unsubstituted cycloalkyl group having 3 to 50 ring carbon atoms, and a substituted or unsubstituted aryl group having 6 to 50 ring carbon atoms, provided that, one selected from $R^{101}$ to $R^{108}$ is a single bond bonding to *i, m4 represents 0 or 1, one of $R^a$ and $R^b$ is a substituted or unsubstituted aryl group having 6 to 50 ring carbon atoms, and the other is a substituted or unsubstituted alkyl group having 1 to 50 carbon atoms, or $R^a$ and $R^b$ each are independently a substituted or unsubstituted alkyl group having 1 to 50 ring carbon atoms, or a substituted or unsubstituted aryl group having 6 to 50 ring carbon atoms, adjacent two selected from $R^{101}$ to $R^{104}$ and $R^{105}$ to $R^{108}$ that are not a single bond do not bond to each other and therefore do not form a cyclic structure, provided that when $Ar^1$ is represented by the formula (1-e), m4 is 1, and when $Ar^2$ is represented by the formula (1-e), m4 is 0 or 1,

** represents a bonding position to the nitrogen atom N*, wherein, when either one of $Ar^1$ or $Ar^2$ has formula (1-b), (1-c), or (1-d), the other of $Ar^1$ and $Ar^2$ has formula (1-a), and wherein, when $Ar^1$ or $Ar^2$ has formula (1-e), m4 is 1.

2. The compound of claim 1, represented by any of the following formulae (1A-1), (1A-2), and (1A-5) to (1A-7):
(1A-1)
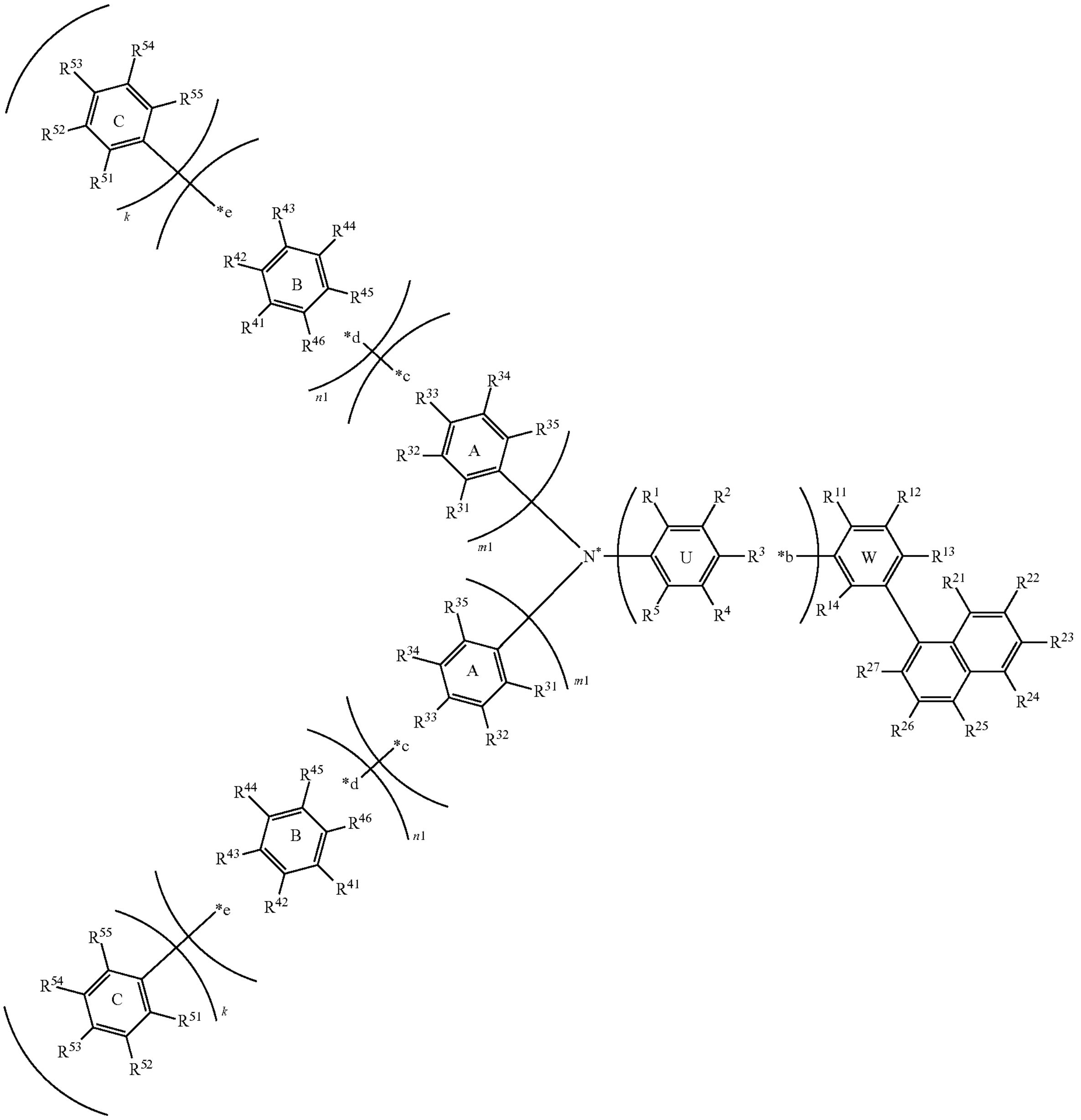

-continued
(1A-2)
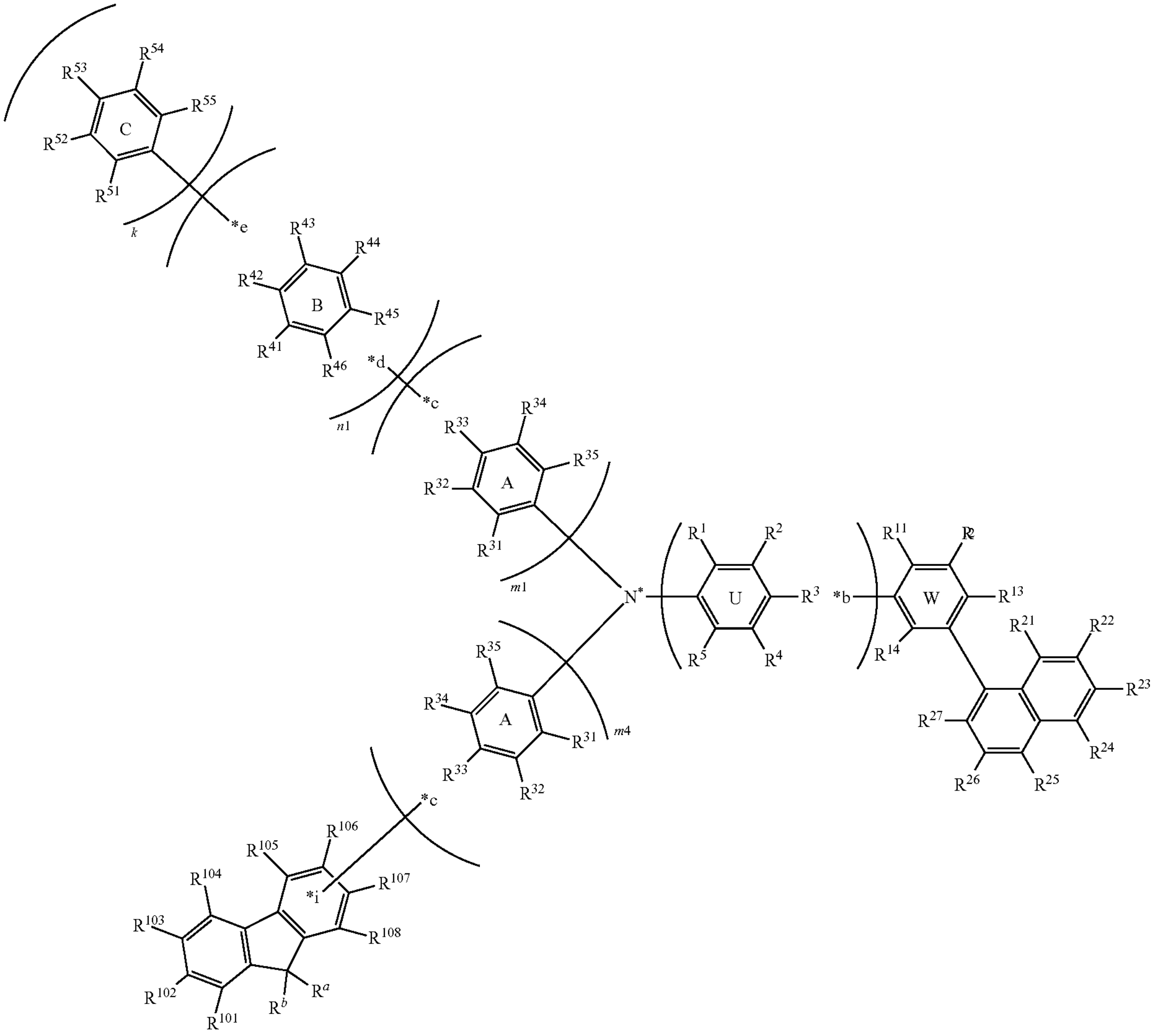

-continued
(1A-5)
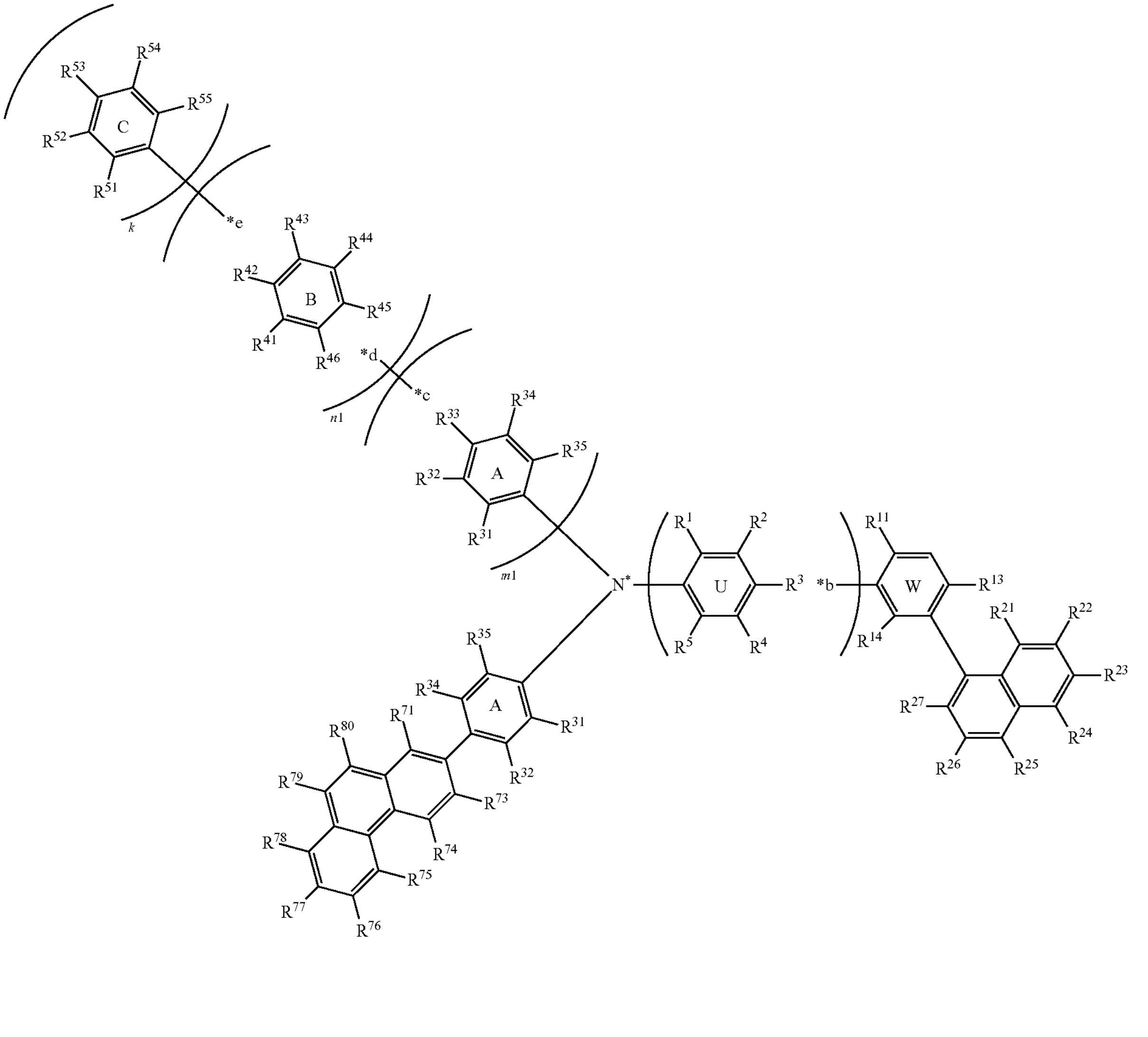

-continued
(1A-6)
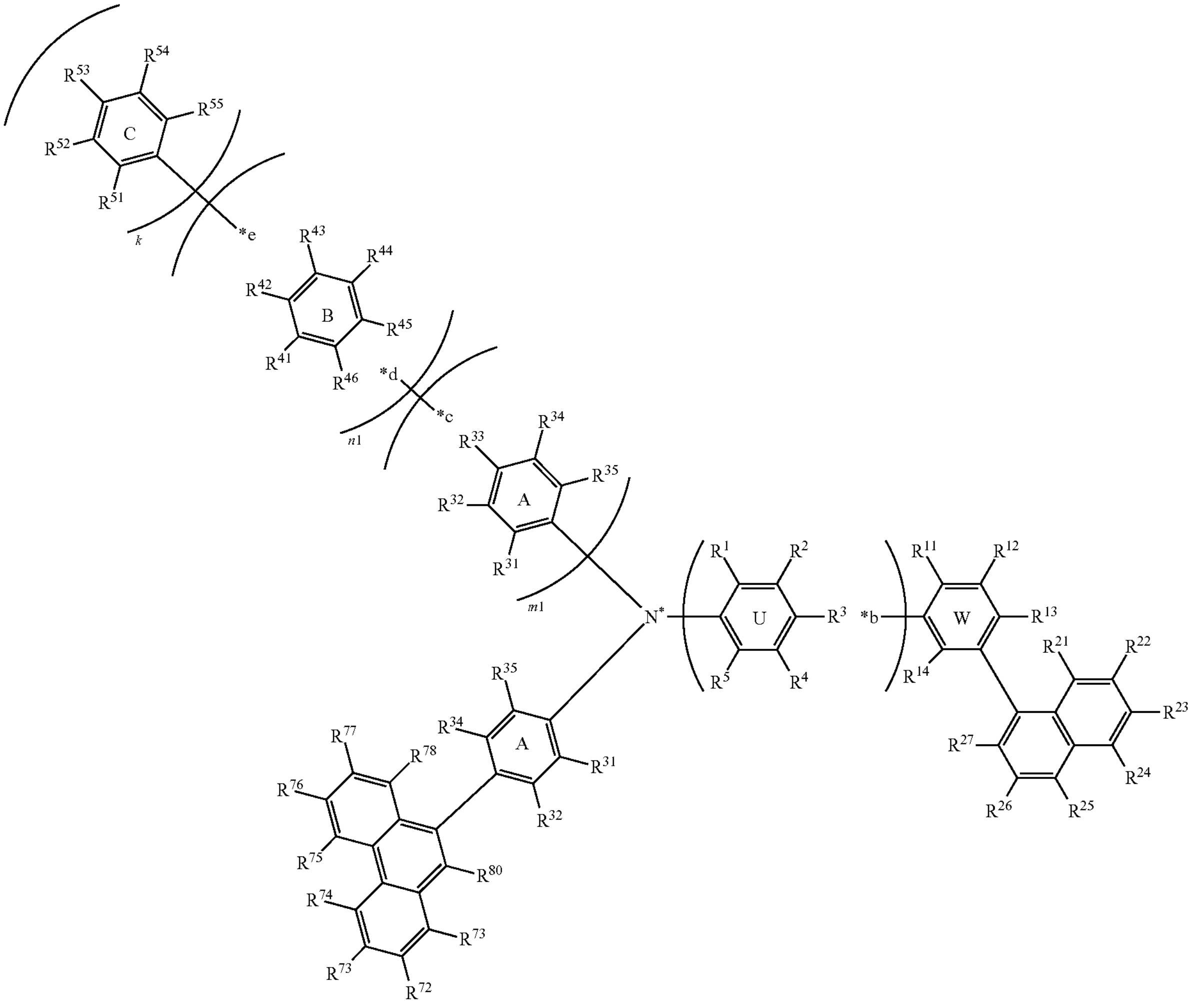

-continued
(1A-7)
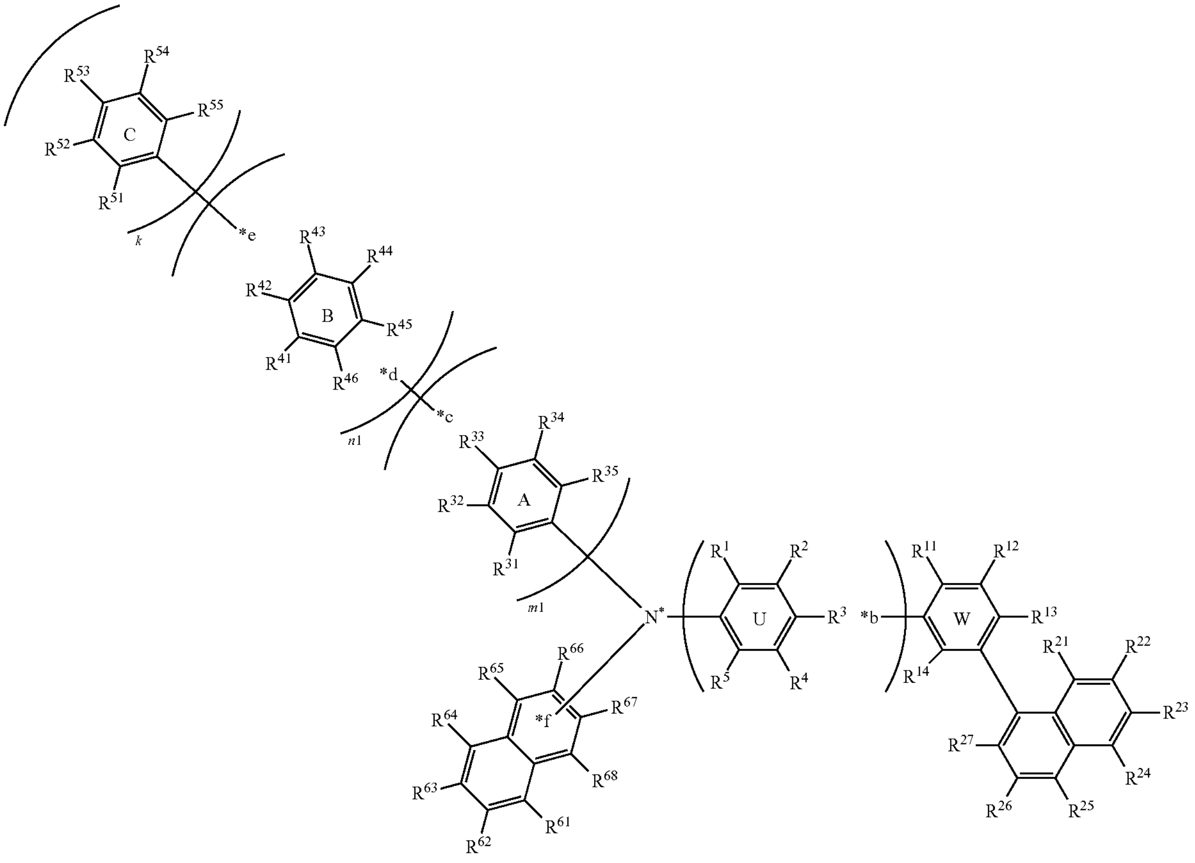
wherein N*, *b, *c, *d, *e, *f, *i, k, n1, m1, m4, $R^a$, $R^b$, $R^1$ to $R^5$, $R^{11}$ to $R^{14}$, $R^{21}$ to $R^{27}$, $R^{31}$ to $R^{35}$, $R^{41}$ to $R^{46}$, $R^{51}$ to $R^{55}$, $R^{61}$ to $R^{68}$, $R^{71}$ to $R^{80}$, and $R^{101}$ to $R^{108}$ are as defined in the formula (1A).

3. The compound of claim 1, represented by any of the following formulae (1A-2-1) to (1A-2-4),
(1A-2-1)
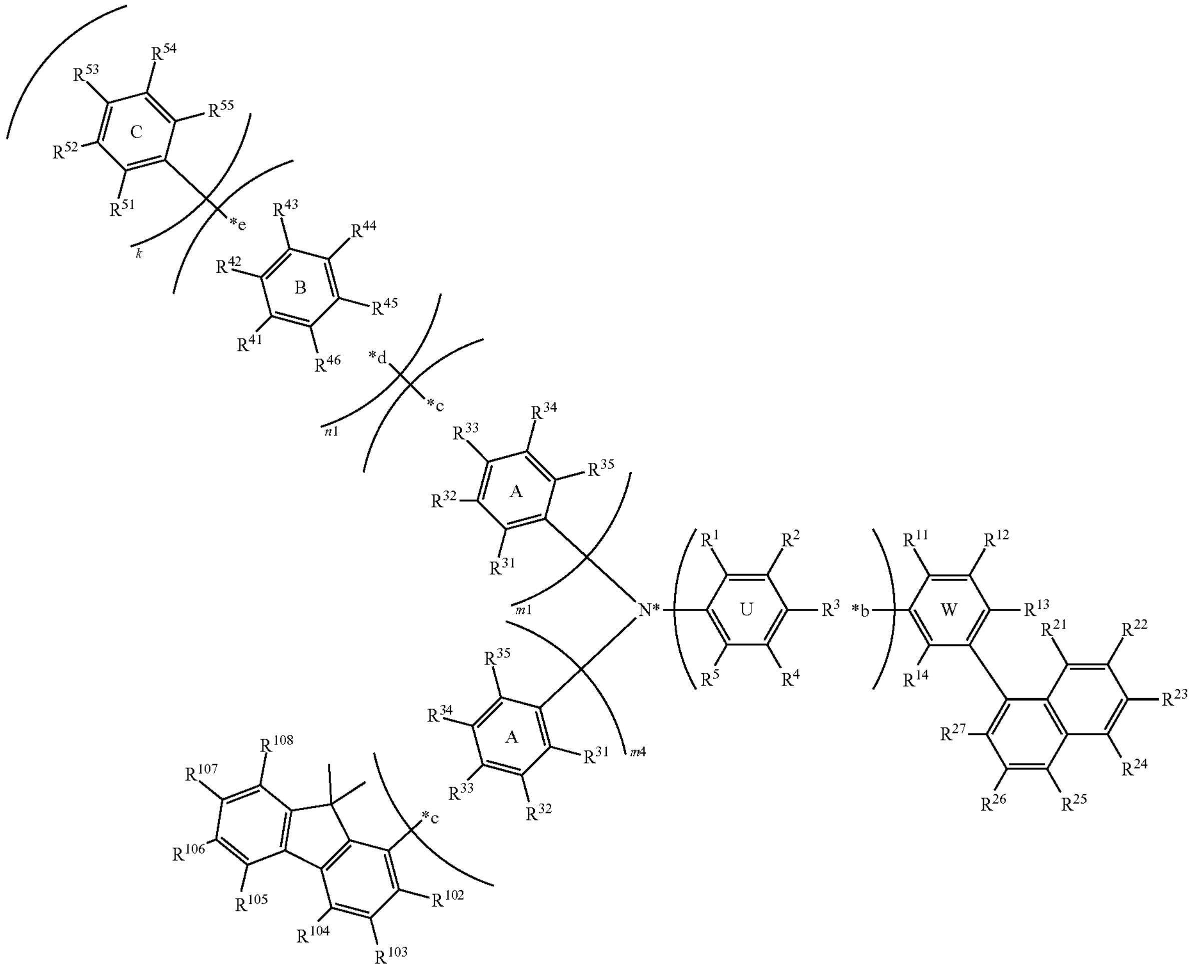

-continued
(1A-2-2)
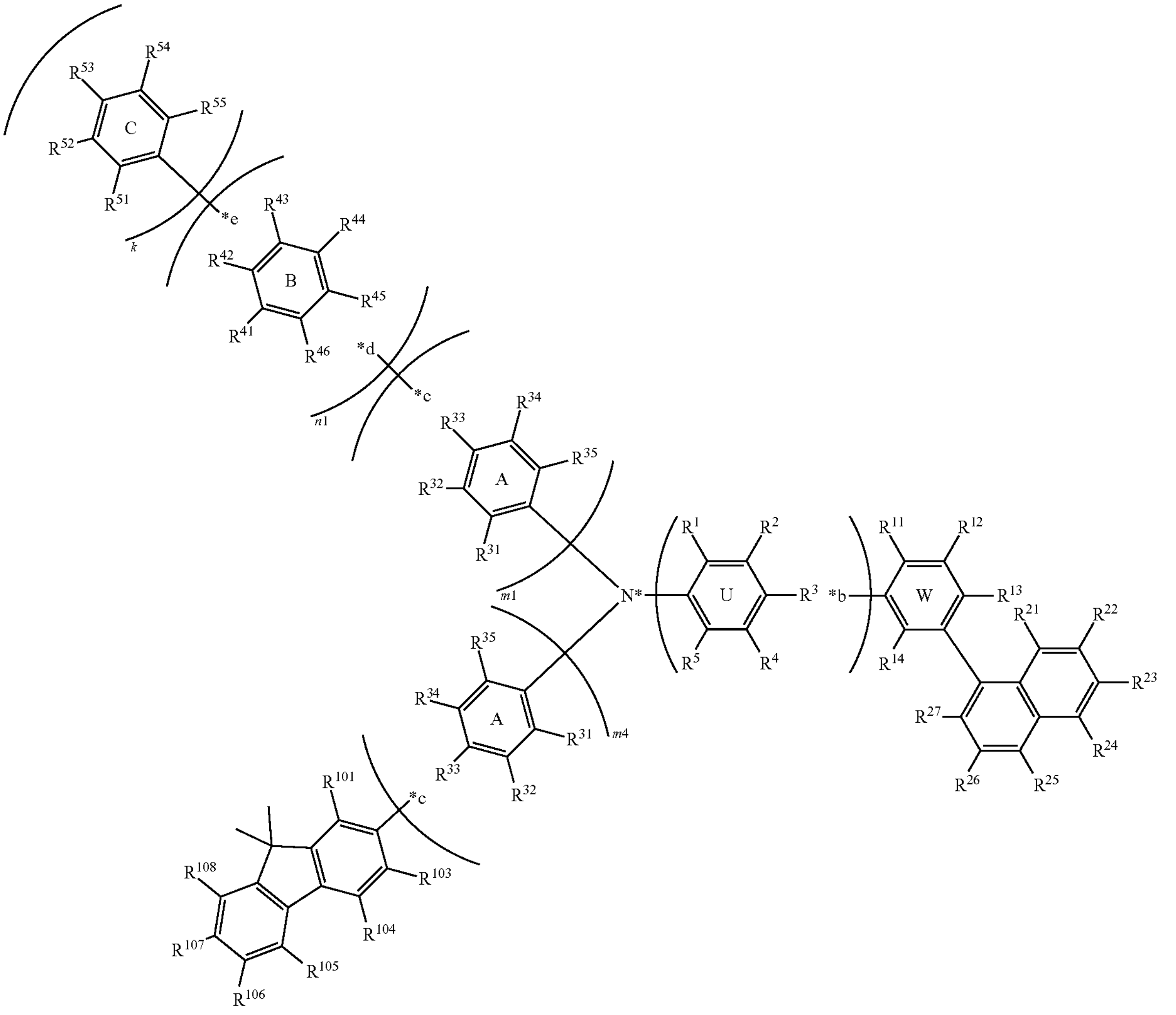

-continued
(1A-2-3)
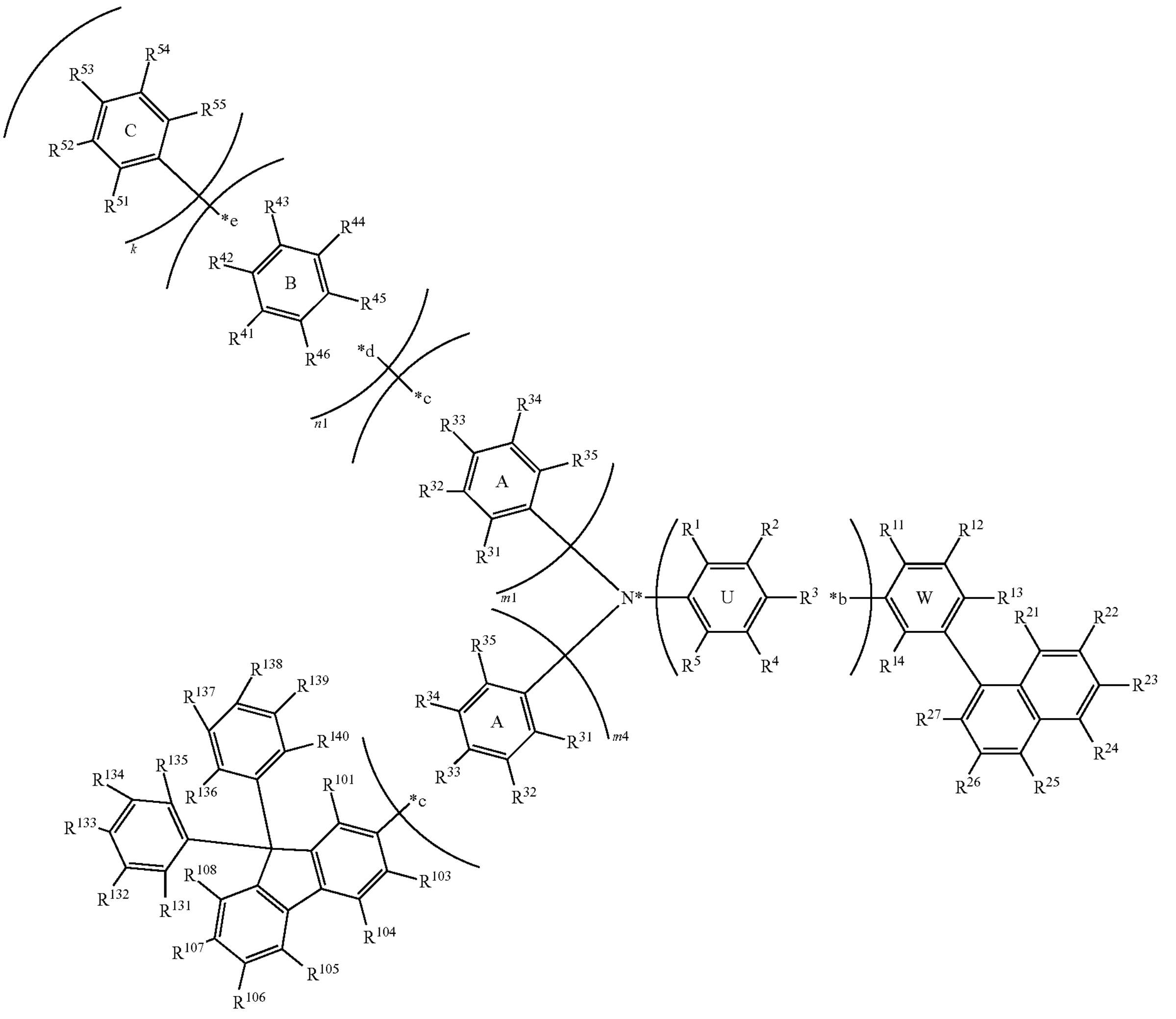

-continued (1A-2-4)

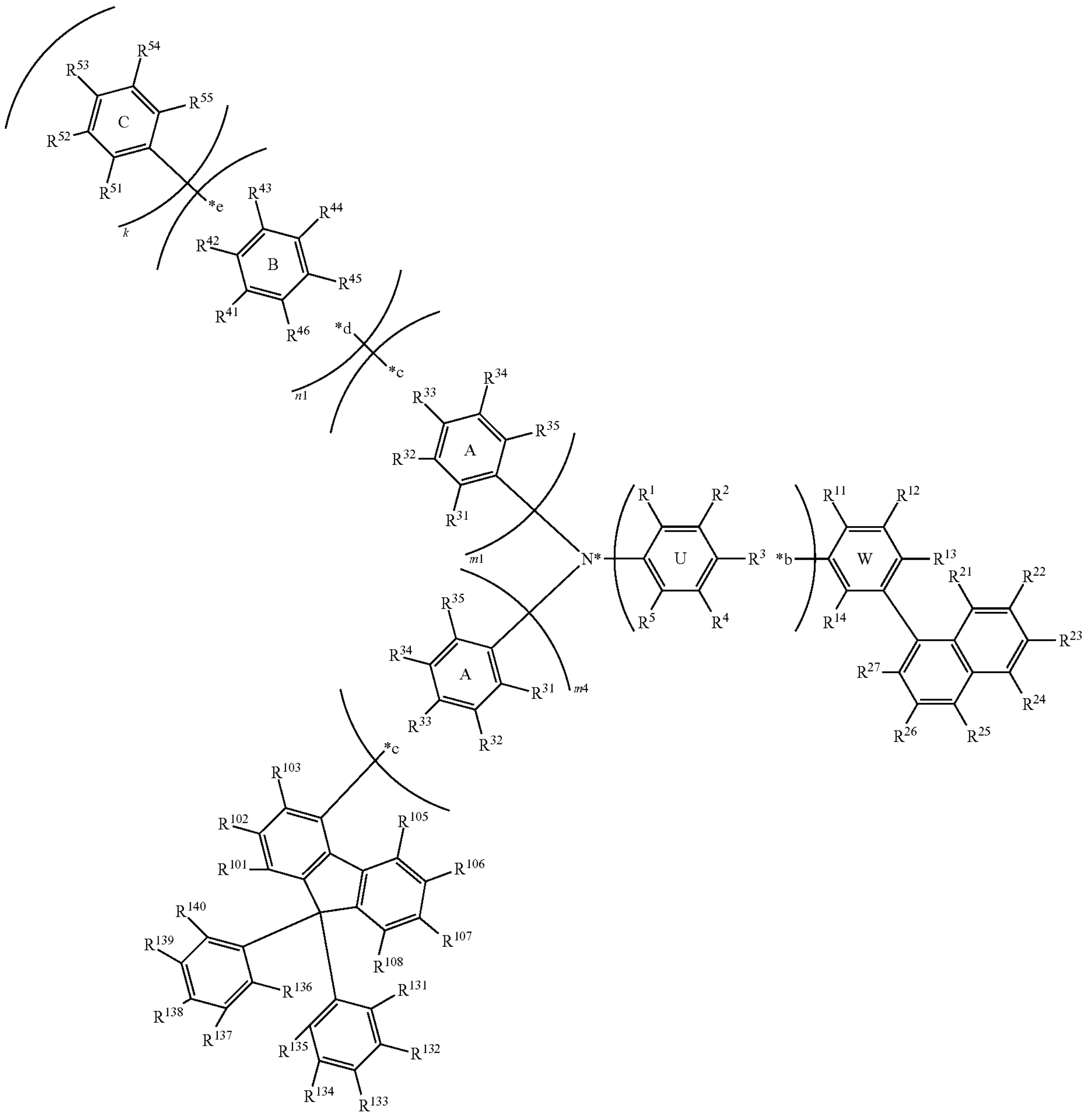

wherein N*, *b, *c, *d, *e, k, n1, m1, m4, $R^1$ to $R^5$, $R^{11}$ to $R^{14}$, $R^{21}$ to $R^{27}$, $R^{31}$ to $R^{35}$, $R^{41}$ to $R^{46}$, $R^{51}$ to $R^{55}$, and $R^{101}$ to $R^{108}$ are as defined in the formula (1A), $R^{131}$ to $R^{140}$ are the same as $R^{101}$ to $R^{108}$ defined in the formula (IA).

4. The compound of claim 1, wherein the substituted or unsubstituted alkyl group having 1 to 50 carbon atoms represented by $R^a$, $R^b$, $R^1$ to $R^5$, $R^6$ to $R^{10}$, $R^{11}$ to $R^{14}$, $R^{21}$ to $R^{27}$, $R^{31}$ to $R^{35}$, $R^{41}$ to $R^{46}$, $R^{51}$ to $R^{55}$, $R^{61}$ to $R^{68}$, $R^{71}$ to $R^{80}$, $R^{81}$ to $R^{92}$, $R^{101}$ to $R^{108}$, and $R^{131}$ to $R^{140}$ is independently selected from a methyl group, an ethyl group, an n-propyl group, an isopropyl group, an n-butyl group, an isobutyl group, an s-butyl group and a t-butyl group.

5. The compound of claim 1, wherein the substituted or unsubstituted aryl group having 6 to 50 ring carbon atoms represented by $R^a$ and $R^b$ is independently selected from a phenyl group, a biphenyl group, a naphthyl group, and a phenanthryl group.

6. The compound of claim 1, wherein the compound represented by the formula (1A) comprises a deuterium atom.

7. A material for an electroluminescent device, comprising:

the compound of claim 1.

8. An organic electroluminescent device, comprising:

an anode;

a cathode; and organic layers intervening between the anode and the cathode, the organic layers comprising a light emitting layer, wherein at least one layer of the organic layers comprises the compound of claim 1.

9. The device of claim 8, wherein the compound comprises a deuterium atom.

10. The device of claim 8, wherein the organic layer comprises a hole transporting zone between the anode and the light emitting layer, and wherein the hole transporting zone comprises the compound.

11. The device of claim 10, wherein the hole transporting zone comprises a first hole transporting layer on the anode side and a second hole transporting layer on the cathode side, and wherein the first hole transporting layer and/or the second hole transporting layer comprises the compound.

12. The device of claim 11, wherein the second hole transporting layer comprises the compound.

13. The device of claim 11, wherein the second hole transporting layer is adjacent to the light emitting layer.

14. The compound of claim 1, wherein Ar1 and/or Ar2 has the formula (1-a):

(1-a)

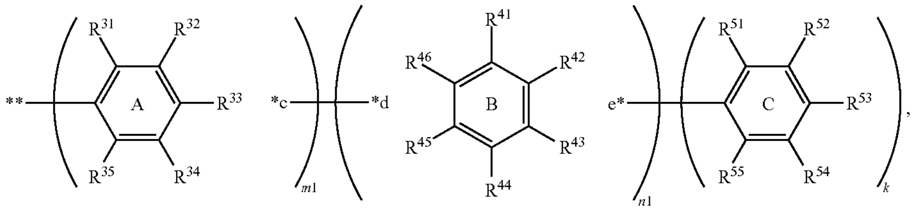

and in the formula (1-a), *c is bonded to $R^{31}$, $R^{33}$, or $R^{35}$, and *e is bonded to benzene ring B in the ortho or para position.

* * * * *